(12) United States Patent
Cottrell et al.

(10) Patent No.: US 11,986,471 B2
(45) Date of Patent: May 21, 2024

(54) COMPOUNDS AND METHODS OF USE

(71) Applicant: Tango Therapeutics, Inc., Boston, MA (US)

(72) Inventors: Kevin M. Cottrell, Arlington, MA (US); John P. Maxwell, Hingham, MA (US); Douglas A. Whittington, West Newtown, MA (US)

(73) Assignee: Tango Therapeutics, Inc., Boston, MA (US)

( * ) Notice: Subject to any disclaimer, the term of this patent is extended or adjusted under 35 U.S.C. 154(b) by 342 days.

(21) Appl. No.: 17/338,579

(22) Filed: Jun. 3, 2021

(65) Prior Publication Data

US 2023/0060499 A1 Mar. 2, 2023

Related U.S. Application Data

(62) Division of application No. 16/515,910, filed on Jul. 18, 2019, now Pat. No. 11,077,101.

(60) Provisional application No. 62/700,176, filed on Jul. 18, 2018.

(51) Int. Cl.
| | |
|---|---|
| *A61K 31/4725* | (2006.01) |
| *A61K 31/496* | (2006.01) |
| *A61K 31/5377* | (2006.01) |
| *A61K 31/5386* | (2006.01) |
| *C07D 401/14* | (2006.01) |
| *C07D 413/14* | (2006.01) |
| *C07D 498/08* | (2006.01) |

(52) U.S. Cl.
CPC ........ *A61K 31/4725* (2013.01); *A61K 31/496* (2013.01); *A61K 31/5377* (2013.01); *A61K 31/5386* (2013.01); *C07D 401/14* (2013.01); *C07D 413/14* (2013.01); *C07D 498/08* (2013.01)

(58) Field of Classification Search
None
See application file for complete search history.

(56) References Cited

U.S. PATENT DOCUMENTS

| | | |
|---|---|---|
| 5,814,631 A | 9/1998 | Fukami et al. |
| 10,278,955 B1 | 5/2019 | Yao et al. |
| 11,077,101 B1 | 8/2021 | Cottrell et al. |
| 2017/0027935 A1 | 2/2017 | Duncan et al. |
| 2017/0210751 A1 | 7/2017 | Duncan et al. |
| 2019/0071425 A1 | 3/2019 | Bergman et al. |
| 2019/0083482 A1 | 3/2019 | Duncan et al. |
| 2019/0175526 A1 | 6/2019 | Yao et al. |
| 2019/0175553 A1 | 6/2019 | Yao et al. |

FOREIGN PATENT DOCUMENTS

| | | |
|---|---|---|
| CN | 116462676 A | 7/2023 |
| CN | 116462677 A | 7/2023 |
| WO | 2004096774 A1 | 11/2004 |
| WO | WO-2014100716 A1 | 6/2014 |
| WO | WO-2014100719 A2 | 6/2014 |
| WO | WO-2016038550 A1 | 3/2016 |
| WO | WO-2016044585 A1 | 3/2016 |
| WO | WO-2016089883 A1 | 6/2016 |
| WO | 2018039972 A1 | 3/2018 |
| WO | WO-2019032859 A1 | 2/2019 |
| WO | WO-2019084470 A1 | 5/2019 |
| WO | WO-2019094311 A1 | 5/2019 |
| WO | WO-2019094312 A1 | 5/2019 |
| WO | WO-2019102494 A1 | 5/2019 |
| WO | WO-2019110734 A1 | 6/2019 |
| WO | WO-2019112719 A1 | 6/2019 |
| WO | WO-2019116302 A1 | 6/2019 |
| WO | WO-2019165189 A1 | 8/2019 |
| WO | WO-2019173804 A1 | 9/2019 |
| WO | WO-2019180628 A1 | 9/2019 |
| WO | WO-2019180631 A1 | 9/2019 |
| WO | WO-2019219805 A1 | 11/2019 |
| WO | WO-2019229614 A1 | 12/2019 |
| WO | WO-2020094712 A1 | 5/2020 |
| WO | 2020139991 A1 | 7/2020 |
| WO | WO-2020168125 A1 | 8/2020 |
| WO | WO-2020182018 A1 | 9/2020 |

(Continued)

OTHER PUBLICATIONS

Bertino et al., Cancer Biology & Therapy, vol. 11, No. 7, pp. 627-632, Apr. 1, 2011.*
U.S. Appl. No. 16/515,910, filed Jul. 18, 2019, Kevin M. Cottrell.
Chan-Penebre "A selective inhibitor of PRMT5 with in vivo and in vitro potency in MCL models," Nature: Chemical Biology, vol. 11 p. 432, 2015, DOI: 10.1038/NCHEMBIO.1810.
Duncan, et al., "Structure and Property Guided Design in the Identification of PRMT5 Tool Compound EPZ015666," ACS Med. Chem. Lett. Vol. 7, pp. 162-166, 2015, DOI: 10.1021/acsmedchemlett. 5b00380.

(Continued)

*Primary Examiner* — Zinna Northington Davis
(74) *Attorney, Agent, or Firm* — Goodwin Procter LLP

(57) ABSTRACT

Compounds are provided according to Formula (I):

(I)

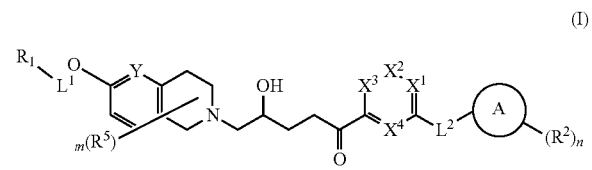

and pharmaceutically acceptable salts thereof, and pharmaceutical compositions thereof; wherein $X^1$, $X^2$, $X^3$, $X^4$, Y, A, $L^1$, $L^2$, $R^1$, $R^2$, $R^5$, m and n are as defined herein. Compounds of the present invention are contemplated useful for the prevention and treatment of a variety of conditions.

20 Claims, 1 Drawing Sheet

(56) References Cited

FOREIGN PATENT DOCUMENTS

| WO | WO-2020198323 A1 | 10/2020 |
| WO | WO-2020198601 A1 | 10/2020 |
| WO | WO-2020205660 A1 | 10/2020 |
| WO | WO-2020205867 A1 | 10/2020 |
| WO | WO-2020206289 A1 | 10/2020 |
| WO | WO-2020206299 A1 | 10/2020 |
| WO | WO-2020206308 A1 | 10/2020 |
| WO | WO-2020217070 A1 | 10/2020 |
| WO | WO-2021004547 A1 | 1/2021 |
| WO | 2021126731 A1 | 6/2021 |
| WO | 2021126999 A1 | 6/2021 |
| WO | 2021140427 A1 | 7/2021 |
| WO | 2021163344 A1 | 8/2021 |
| WO | WO-2022026892 A1 | 2/2022 |
| WO | WO-2022115377 A1 | 6/2022 |
| WO | WO-2022132914 A1 | 6/2022 |
| WO | WO-2022256806 A1 | 12/2022 |
| WO | WO-2023098439 A1 | 6/2023 |

OTHER PUBLICATIONS

Mavrakis, et al., Disordered methionine metabolism in MTAP/CDKN2A-deleted cancers leads to dependence on PRMT5, Science vol. 351, Issue 6278, 2016.

Bogolubsky et al., "2,2,2-Trifluoroethyl Chlorooxoacetate-Universal Reagent for One-Pot Parallel Synthesis of N1-Aryl-N2-alkyl-Substituted Oxamides", ACS Combinational Science, vol. 17, No. 10, Oct. 12, 2015.

Wu et al., "Protein arginine methylation: from enigmatic functions to therapeutic targeting", Nature Reviews Drug Discovery, Nature Publishing Group, GB, vol. 20, No. 7, Mar. 19, 2021, pp. 509-530.

\* cited by examiner

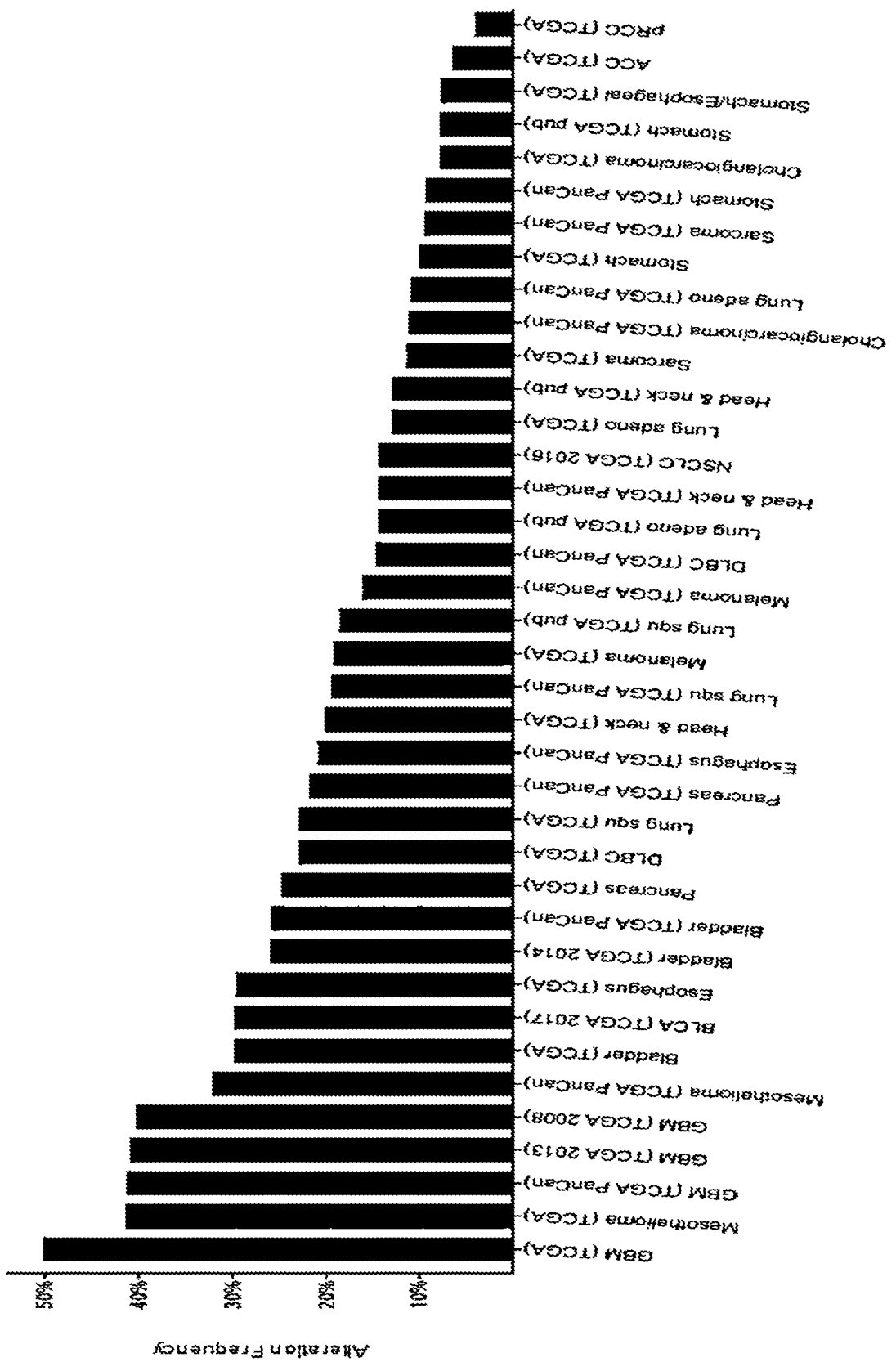

COMPOUNDS AND METHODS OF USE

CLAIM OF PRIORITY

This application is a division of U.S. application Ser. No. 16/515,910, filed Jul. 18, 2019, which claims priority to U.S. Provisional Application No. 62/700,176, filed Jul. 18, 2018, both of which are incorporated by reference in their entirety.

BACKGROUND OF THE INVENTION

Cancer therapeutics can be broadly classified into two categories, cytotoxic and targeted therapies. While cytotoxic therapies are associated with widespread toxicities, targeted therapies have the advantage of selectively targeting the tumor cells that rely on the activity of their substrates. The clinical efficacy of targeted therapies has been demonstrated with BCR/ABL and EGFR inhibitors for the treatment of CML and non-small cell lung cancer, respectively. The success of these programs has furthered development of other therapies that specifically target amplified or mutation-activated oncogenes. The greater challenge is to develop selective therapies that target those tumors with loss-of-function mutations or deletion of tumor suppressor genes, the loss of which obviate traditional strategies for molecular targeted therapeutics.

Efforts to characterize the cancer genome, led by groups like the Cancer Genome Atlas (TCGA), have made tremendous strides in elucidating the size and frequency of the deletion events that promote tumor growth by causing the loss of tumor suppressor genes. However, these events are often regional and cause the co-deletion of genes proximal to their intended targets. Though these passenger events are not known to cause a fitness advantage, they may cause collateral vulnerabilities that can be therapeutically leveraged. One example is the collateral vulnerability to PRMT5 inhibition conferred by loss of methylthioadenosine phosphorylase (MTAP), which is frequently co-deleted with the well-described tumor suppressor gene, CDKN2A (Kruykov et al., 2016; Marjon et al., 2016 and Markarov et al., 2016).

Loss of CDKN2A occurs in ~15% of all human cancers and with frequency in histologies such as malignant peripheral nerve sheath tumors, glioblastoma, mesothelioma, bladder urothelial carcinoma, esophageal squamous cell carcinoma, pancreatic adenocarcinoma, melanoma, non-small cell lung cancer, head and neck cancer and cholangiosarcoma (Gao et al. Sci. Signal. 2013 & Cerami et al. *Cancer Discov.* 2012). Because of its proximity to CDKN2A on chromosome 9p21, MTAP is frequently included in the deletion. MTAP is a critical enzyme in the methionine salvage pathway, a six-step process that recycles methionine from the product of polyamine synthesis, methylthioadenosine (MTA). Loss of MTAP causes the accumulation of its substrate, MTA, which has been demonstrated by multiple groups to function as a SAM-competitive PRMT5 inhibitor (Kruykov et al., 2016; Marjon et al., 2016 and Markarov et al., 2016).

PRMT5 is a type II arginine methyltransferase that regulates essential cellular functions, including the regulation of cell cycle progression, apoptosis and the DNA-damage response, by symmetrically dimethylating proteins involved in transcription and signaling (insert reference). However, data from genome-wide genetic perturbation screens using shRNA has revealed a selective requirement for PRMT5 activity in MTAP-deleted cancer cell lines (Kruykov et al., 2016; Marjon et al., 2016 and Markarov et al., 2016). The accumulation of MTA caused by MTAP-deletion in these cell lines partially inhibits PRMT5, rendering those cells selectively sensitive to additional PRMT5 inhibition.

PRMT5 inhibitors have been developed, yet they do not demonstrate selectivity for MTAP-deleted cancer cell lines. This lack of selectivity can be explained by the mechanisms of action of the inhibitors, as they are either SAM-uncompetitive or SAM-competitive inhibitors and therefore, MTAP-agnostic (Kruykov et al., 2016; Marjon et al., 2016 and Markarov et al., 2016) However, if a PRMT5 inhibitor were developed that leverages the accumulation of MTA by binding in an MTA-uncompetitive manner, it could demonstrate selectivity for MTAP-deleted tumor cells.

SUMMARY OF THE INVENTION

In one aspect, the invention provides a compound or a pharmaceutically acceptable salt thereof wherein the compound is of formula (I)

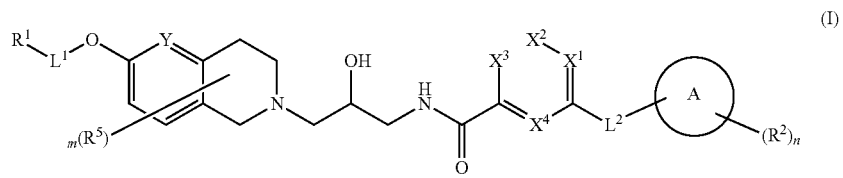

(I)

wherein $X^1$, $X^2$, $X^3$ and $X^4$ are each independently N or $CR^x$;

Y is N, CH or $CR^5$;

$L^1$ is a bond or $C_1$-$C_4$-alkylene substituted with 0-2 instances of $R^6$;

$L^2$ is a bond, —NH— or —O—;

Ring A is a carbocycle, heterocycle, 5-6 member monocyclic heteroaryl or a monocyclic aryl;

$R^1$ is a 3-7 membered carbocycle, a 4-7 membered heterocycle or a 5-6 membered heteroaryl substituted with 0-3 instances of $R^4$;

each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —$C(=O)R^3$, —$C(=O)OR^3$, —$CH_2C(=O)R^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^3$ is independently selected from H, $C_1$-$C_6$ alkyl, $C_1$-$C_6$ heteroalkyl, $C_3$-$C_7$ carbocyclyl, $C_3$-$C_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a —$C_3$-$C_9$ heterocyclyl;

each $R^6$ is independently selected from halo, —$C_1$-$C_4$ alkyl, —$C_1$-$C_4$ haloalkyl, —$OC_1$-$C_4$ alkyl, —$OC_1$-$C_4$ haloalkyl, or two $R^6$ can be taken together with the atoms to which they are attached to form a $C_3$-$C_7$ carbocycle or a $C_3$-$C_7$ heterocycle.

m is 0, 1, 2 or 3; and n is 0, 1, 2 or 3.

In certain embodiments, the compound has structure (Ia)

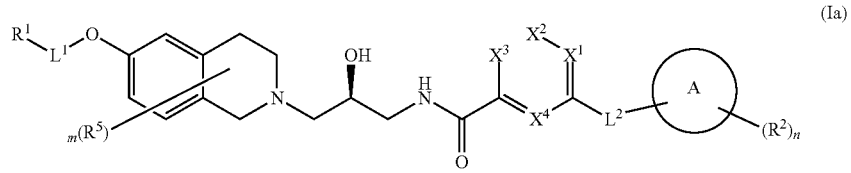

(Ia)

In other embodiments, the compound has structure (Ib)

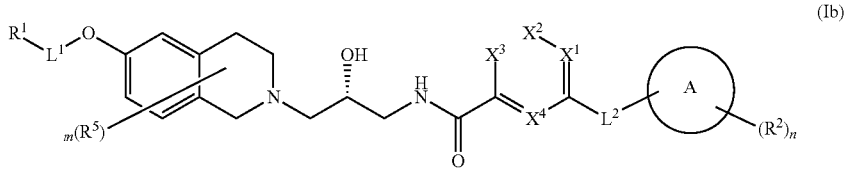

(Ib)

In some embodiments of the invention, $X^1$ is N and each of $X^2$, $X^3$ and $X^4$ are independently $CR^x$.

In further embodiments, the compound has structure (IIa)ke

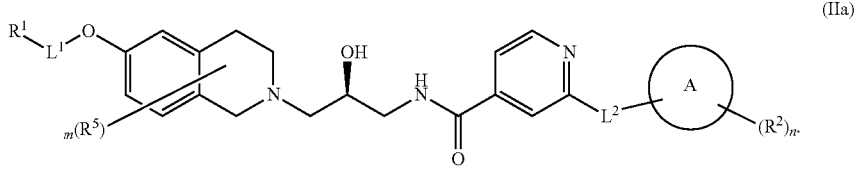

(IIa)

In alternative embodiments, the compound has structure (IIb)

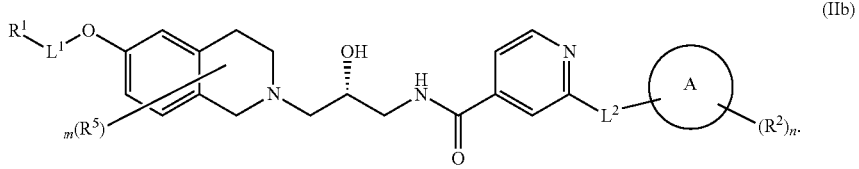

(IIb)

In some embodiments of the invention, $X^1$ and $X^3$ are N and each of $X^2$ and $X^4$ are independently $CR^x$.

In further embodiments, the compound has structure (IIIa)

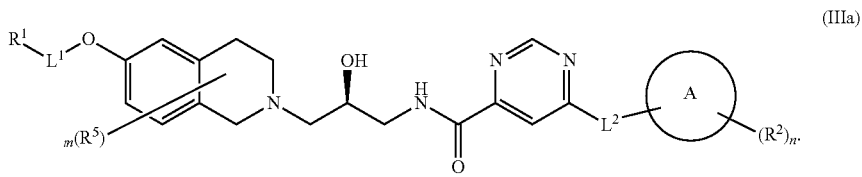

(IIIa)

In alternative embodiments, the compound has structure (IIIb)

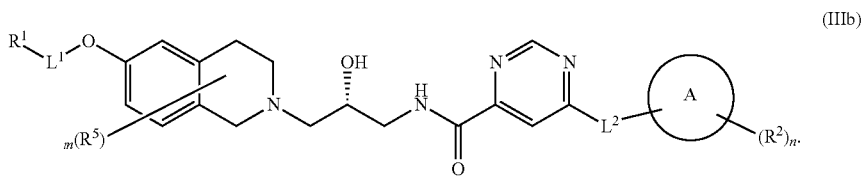

(IIIb)

In some embodiments of the invention, $X^1$, $X^2$, $X^3$ and $X^4$ are each independently $CR^x$.

In further embodiments, the compound has structure (IVa)

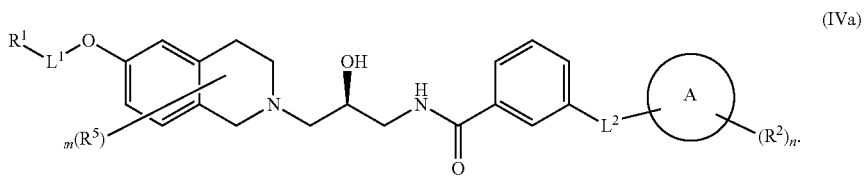

(IVa)

In alternate embodiments, the compound has structure (IVb)

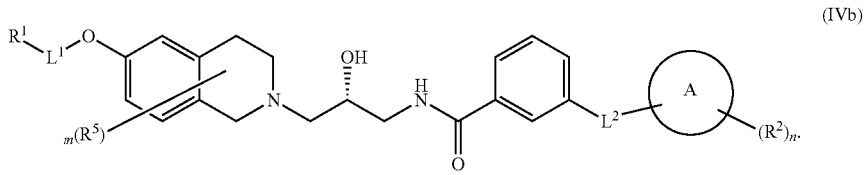

(IVb)

In some embodiments of the invention, L is a bond.

In some embodiments of the invention, $L^1$ is $C_1$-$C_4$-alkylene substituted with 0-2 instances of $R^6$. In certain embodiments, $L^1$ is substituted with 1 instance of $R^6$ and $R^6$ is $C_1$-$C_4$ alkyl.

In some embodiments of the invention, $L^1$ is —$CH_2$—.

In certain embodiments, the compound has structure (Va)

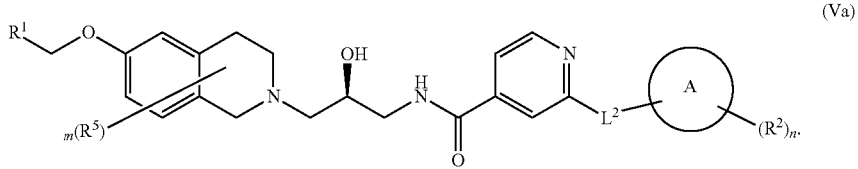

(Va)

In other embodiments, the compound has structure (Vb)
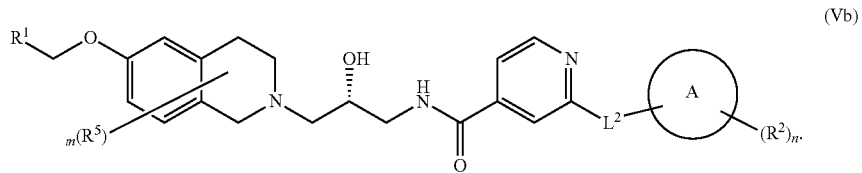
In certain embodiments, the compound has structure (VIa)
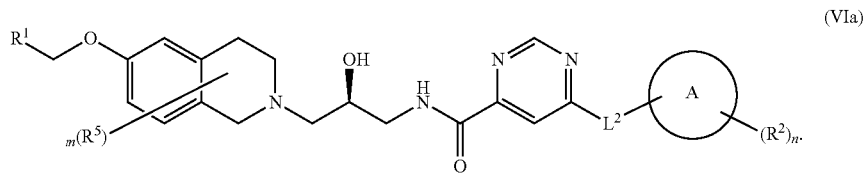
In alternate embodiments, the compound has structure (VIb)
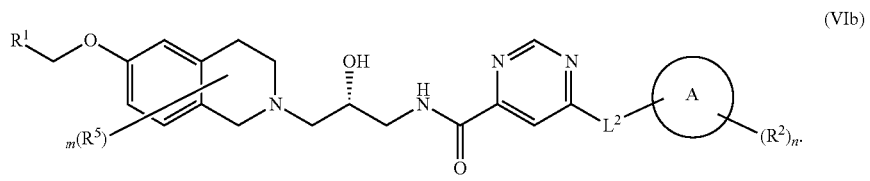
In certain embodiments, the compound has structure (VIIa)
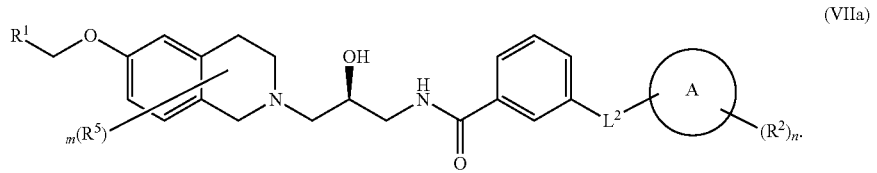
In other embodiments, the compound has structure (VIIb)
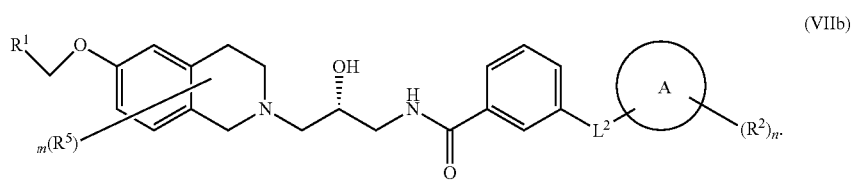

In some embodiments of the invention, L² is —NH—.
In some embodiments, the compound has structure (Va1)

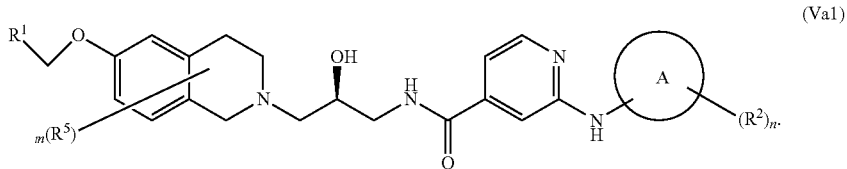

(Va1)

In other embodiments, the compound has structure (Vb1)

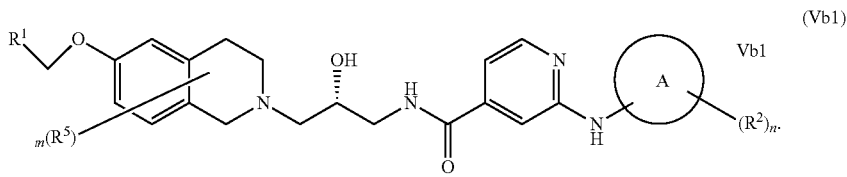

(Vb1)

In some embodiments, the compound has structure (Va1')

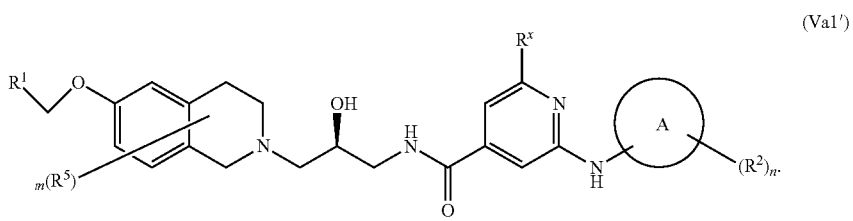

(Va1')

In some embodiments, the compound has structure (Vb1')

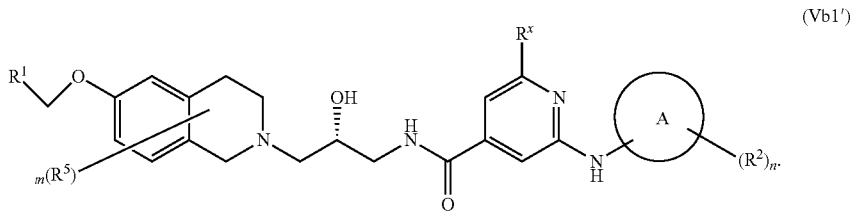

(Vb1')

In certain embodiments, $R^x$ is H, $N(R^3)_2$, $NHR^3$, $N(CH_3)R^3$, $OR^3$, $C_1$-$C_6$ alkyl, optionally substituted —$C_3$-$C_9$ carbocyclyl or optionally substituted —$C_3$-$C_9$ heterocyclyl.

In further embodiments, $R^x$ is —$C_3$-$C_9$ carbocyclyl or —$C_3$-$C_9$ heterocyclyl substituted with 0-1 instances of $R^7$, wherein $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, aryl-alkyl, heteroarylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ or —S(=O)$_2N(R^3)_2$.

In some embodiments, $R^7$ is —$C_1$-$C_6$ alkyl or —C(=O)$R^3$.

In certain embodiments, $R^3$ is $C_3$-$C_7$ carbocyclyl, $C_1$-$C_6$ alkyl or $C_1$-$C_6$ heteroalkyl In some embodiments, the compound has structure (VIa1)

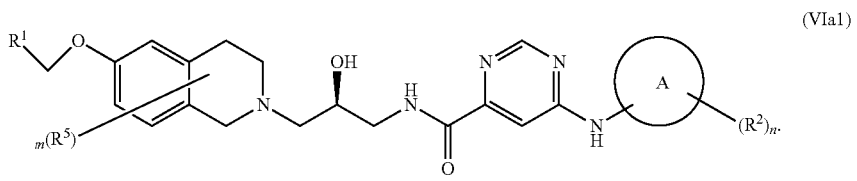

In some embodiments, the compound has structure (VIb1)

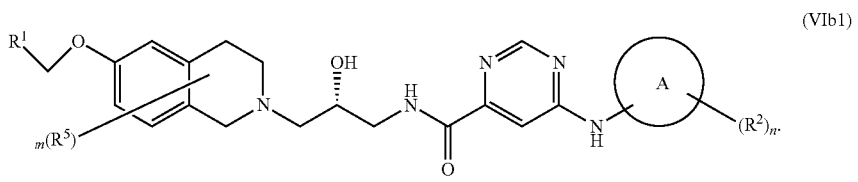

In some embodiments, the compound has structure (VIa1')

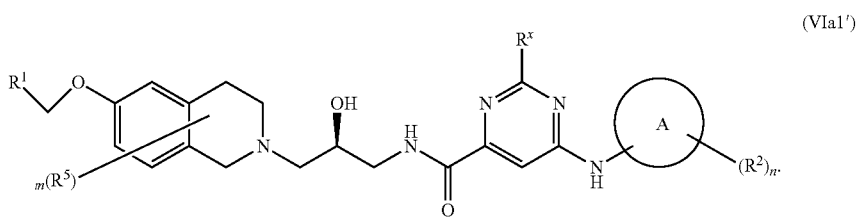

In other embodiments, the compound has structure (VIb1')

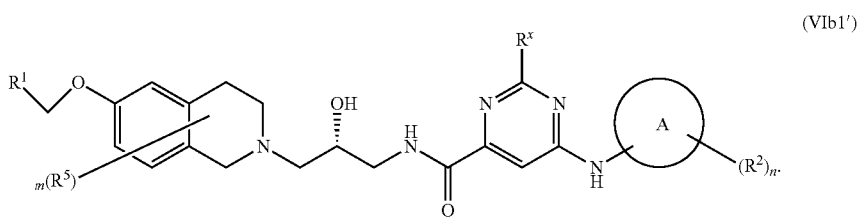

In further embodiments, $R^x$ is H, $N(R^3)_2$, $NHR^3$, $N(CH_3)R^3$, $OR^3$, $C_1$-$C_6$ alkyl, optionally substituted —$C_3$-$C_9$ carbocyclyl or optionally substituted —$C_3$-$C_9$ heterocyclyl.

In some embodiments, $R^x$ is —$C_3$-$C_9$ carbocyclyl or —$C_3$-$C_9$ heterocyclyl substituted with 0-1 instances of $R^7$, wherein $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —$OR^3$, —$N(R^3)_2$, —C(=O)$R^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ or —S(=O)$_2$N(R$^3$)$_2$.

In certain embodiments R$^7$ is —C$_1$-C$_6$ alkyl or —C(=O) R$^3$.

In some embodiments, R$^3$ is C$_3$-C$_7$ carbocyclyl, C$_1$-C$_6$ alkyl or C$_1$-C$_6$ heteroalkyl In some embodiments, the compound has structure (VIIa1)

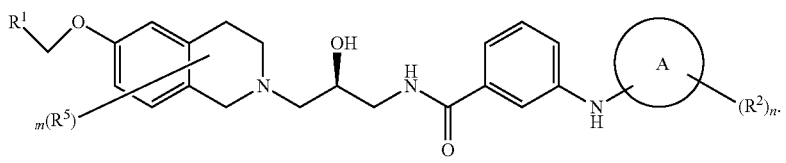

(VIIa1)

In some embodiments, the compound has structure (VIIb1)

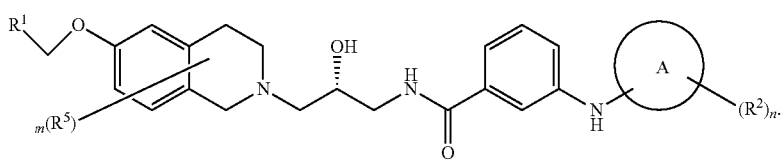

(VIIb1)

In some embodiments of the invention, L$^2$ is a bond.
In other embodiments of the invention, L$^2$ is —O—.
In one aspect of the invention, provided is a compound or pharmaceutically acceptable salts thereof according to Formula (XI)

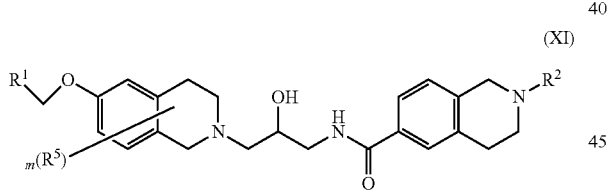

(XI)

wherein:
R$^1$ is a 3-7 membered carbocycle, a 4-7 membered heterocycle or a 5-6 membered heteroaryl substituted with 0-3 instances of R$^4$;
each R$^2$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, heterocyclylalkyl, cycloalkylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ and —S(=O)$_2$N(R$^3$)$_2$;
each R$^3$ is independently selected from H, C$_1$-C$_6$ alkyl, C$_3$-C$_7$ carbocyclyl, C$_3$-C$_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each R$^4$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, heterocyclylalkyl, cycloalkylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N (R$^3$)$_2$, —S(=O)R$^3$, —S(=O)$_2$R$^3$, —SR$^3$, —S(=O) (=NR$^3$)R$^3$, —NR$^3$S(=O)$_2$R$^3$ and —S(=O)$_2$N(R$^3$)$_2$;
each R$^5$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, C$_6$-C$_{10}$ aryl, C$_5$-C$_{10}$ heteroaryl, cycloalkylalkyl, heterocyclylalkyl, arylalkyl, heteroarylalkyl, —OR$^3$, —N(R$^3$)$_2$, —C(=O)R$^3$, —C(=O)OR$^3$, —NR$^3$C(=O) R$^3$, —NR$^3$C(=O)OR$^3$, —C(=O)N(R$^3$)$_2$, —OC(=O) N(R$^3$)$_2$, —S(=O)R$^3$, —S(=O)$_2$R$^3$, —SR$^3$, —S(=O) (=NR$^3$)R$^3$, —NR$^3$S(=O)$_2$R$^3$, —S(=O)$_2$N(R$^3$)$_2$, or two R$^5$ can be taken together with the atoms to which they are attached to form a —C$_3$-C$_9$ carbocyclyl or a —C$_3$-C$_9$ heterocyclyl; and
m is 0, 1, 2 or 3.

In one embodiment, the compound has structure (XIa)

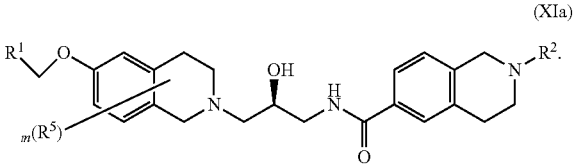

(XIa)

In another embodiment, the compound has structure (XIb)

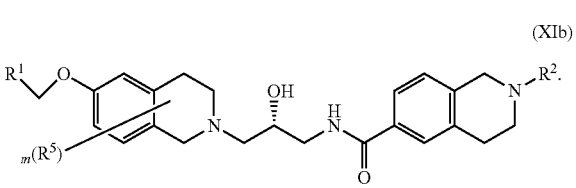

(XIb)

In one aspect of the invention, provided is a compound or pharmaceutically acceptable salts thereof according to Formula (XII)

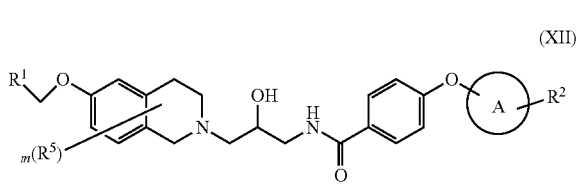

(XII)

wherein
Ring A is a carbocycle, heterocycle, 5-6 member monocyclic heteroaryl or a monocyclic aryl;
$R^1$ is a 3-7 membered carbocycle, a 4-7 membered heterocycle or a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, heteroarylalkyl, arylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)R^3$ and —$S(=O)_2N(R^3)_2$;
each $R^3$ is independently selected from H, $C_1$-$C_6$ alkyl, $C_3$-$C_7$ carbocyclyl, $C_3$-$C_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each $R^4$ is independently selected from =O, halo, —CN, —$C_1$-$C_6$ alkyl, —$C_1$-$C_6$ heteroalkyl, —$C_1$-$C_6$haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;
each $R^5$ is independently selected from =O, halo, —CN, —$C_1$-$C_6$ alkyl, —$C_1$-$C_6$ heteroalkyl, —$C_1$-$C_6$haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a —$C_3$-$C_9$ heterocyclyl; and
m is 0, 1, 2 or 3.
In one embodiment, the compound has Formula (XIIa)

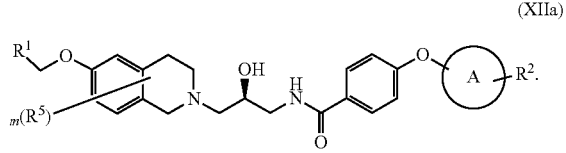

(XIIa)

In another embodiment, the compound has Formula (XIIb)

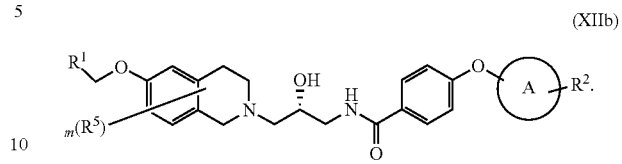

(XIIb)

In some embodiments of the invention, $R^1$ is a 3-7 membered carbocycle substituted with 0-3 instances of $R^4$.

In some embodiments of the invention, $R^1$ is a 4-7 membered heterocycle substituted with 0-3 instances of $R^4$.

In some embodiments of the invention, $R^1$ is a 5-6 membered heteroaryl substituted with 0-3 instances of $R^4$.

In some embodiments, $R^1$ is a 5-membered heteroaryl substituted with 0-3 instances of $R^4$. In some embodiments, $R^4$ is $C_1$-$C_6$ alkyl. In further embodiments $R^4$ is methyl.

In some embodiments of the invention, $R^1$ is selected from:

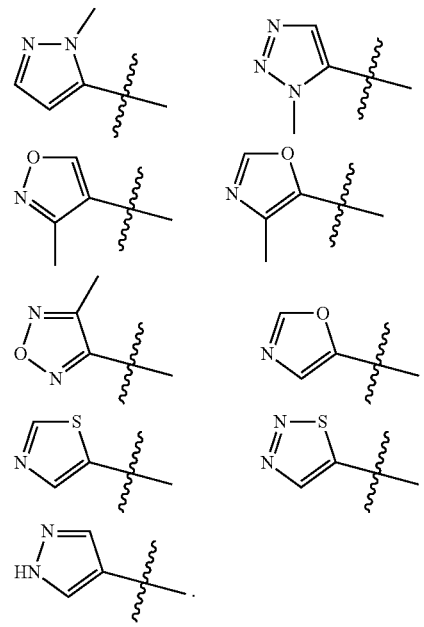

In further embodiments, $R^1$ is selected from:

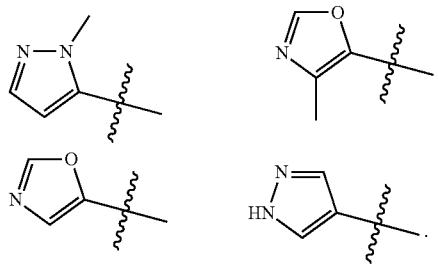

In a further embodiment, $R^1$ is selected from:

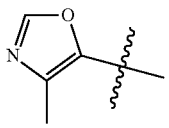 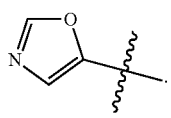

In some embodiments of the invention, ring A is a 4-7 membered monocyclic heterocycle. In further embodiments, ring A is piperidinyl, pyrrolidinyl, oxetanyl, tetrahydrofuranyl, azetidinyl, tetrahydropyranyl, 1,4-dioxan-2-yl or morpholinyl. In certain embodiments, ring A is piperidinyl. In some embodiments, ring A is oxetanyl. In certain embodiments, ring A is tetrahydropyranyl. In some embodiments, ring A is morpholinyl.

In some embodiments of the invention, ring A is a 5-6 membered monocyclic heteroaryl. In further embodiments, ring A is pyridinyl (e.g., 3-pyridinyl).

In some embodiments of the invention, ring A is aryl. In further embodiments, ring A is phenyl.

In some embodiments of the invention, ring A is a 3-8 membered carbocycle. In certain embodiments, ring A is a 6-8 membered spirocarbocycle. In further embodiments, ring A is cyclopropyl, cyclobutyl, cyclopentyl, cyclohexyl, cycloheptyl spiro[2.3]hexyl, spiro[3.3]heptyl. In certain embodiments, ring A is cyclobutyl.

In some embodiments of the invention, n is 1 and $R^2$ is —C(=O)$R^3$. In further embodiments, $R^3$ is $C_1$-$C_6$ alkyl or $C_3$-$C_7$ cycloalkyl. In yet further embodiments, $R^2$ is —C(=O)CH$_3$, —C(=O)cyclopropyl, —C(=O)cyclobutyl, —C(=O)$^t$Bu, —C(=O)$^i$Pr, —C(=O)Pr or —C(=O)$^i$Bu.

In some embodiments of the invention, n is 1, $R^2$ is —C(=O)$R^3$ and $R^3$ is optionally substituted aryl. In further embodiments, $R^3$ is phenyl substituted with 0-2 instances of —OMe or halo.

In some embodiments of the invention, n is 1 and $R^2$ is arylalkyl or heteroarylalkyl. In further embodiments, $R^2$ is benzyl or pyridinylmethyl (e.g., pyridin-4-ylmethyl)

In some embodiments of the invention, n is 0.

In some embodiments of the invention, m is 1.

In some embodiments of the invention, the moiety represented by

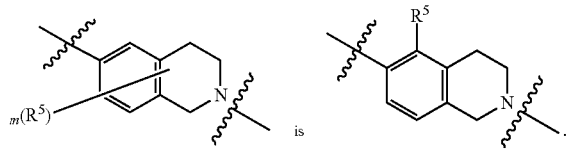

In some embodiments of the invention, m is 2.

In some embodiments of the invention, m is 0.

In some embodiments of the invention, each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, —OR$^3$, —N(R$^3$)$_2$, —CO(R$^3$), —NR$^3$(CO)R$^3$, —(CO)N(R$^3$)$_2$. In some embodiments, each $R^5$ is independently selected from halo, —CN and —$C_1$-$C_6$ alkyl. In further embodiments, each $R^5$ is independently selected from fluoro, chloro, bromo and iodo. In certain embodiments, each $R^5$ is —CN. In some embodiments, each $R^5$ is independently selected from methyl or ethyl.

In some embodiments of the invention, Y is N.

In one embodiment of the invention, the compound is selected from Table 1a.

In one aspect, the invention provides a pharmaceutical composition comprising a compound of the invention and a pharmaceutically acceptable carrier. In one embodiment, the composition further comprises a second therapeutic agent.

In one aspect, the invention provides a method of treating an MTAP-deffcient and/or an MTA-accumulating disease in a subject in need thereof by administering to the subject a therapeutically effective amount of a compound of the invention as described herein or a pharmaceutically acceptable composition comprising compounds of the invention.

In one embodiment, the compound or composition is administered in combination with a second therapeutic agent.

In one aspect, the invention provides a method of treating an MTAP-deffcient and/or an MTA-accumulating disease in a subject in need thereof by administering to the subject a therapeutically effective amount of a pharmaceutically acceptable composition comprising a compound of the invention as described herein and a second therapeutic agent.

In one embodiment, the disease is a proliferating disease.

In one embodiment, the disease is an MTAP-deficient and/or MTA-accumulating cancer. In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one aspect, the invention provides a method of treating a cancer in a subject in need thereof comprising the steps of:
  a) assessing the level of MTAP and/or MTA in a test sample obtained from said subject, wherein the MTA level can be assessed directly (e.g., by ELISA or LC-MS/MS or indirectly (e.g., by SDMA-modified protein ELISA or IHC, or by RNA splicing);
  b) comparing the test sample with a reference, wherein MTAP deficiency and/or MTA accumulation in said test sample compared to the reference indicates the cancer in said subject will respond to therapeutic treatment with a PRMT5 inhibitor; and
  c) administering a therapeutically effective amount of a compound or composition of the invention as described herein to the subject identified in step b).

Other objects and advantages will become apparent to those skilled in the art from a consideration of the ensuing Detailed Description, Examples, and Claims.

BRIEF DESCRIPTION OF THE DRAWINGS

FIG. 1. Frequency of MTAP homozygous deletion in cell lines representing exemplary cancers according to The Cancer Genome Atlas (TCGA).

DEFINITIONS

MTAP

"MTAP" as used herein refers to methylthioadenosine phosphorylase, an enzyme in the methionine salvage pathway, also known as S-methyl-5'-thioadenosine phosphorylase; also known as BDMF; DMSFH; DMSMFH; LGMBF; MSAP; and c86fus. External IDs: OMIM: 156540 MGI: 1914152 HomoloGene:1838 chEMBL: 4941 GeneCards: MTAP Gene; Entrez 4507; RefSeq (mRNA): NM_002451; location: Chr 9: 21.8-21.93 Mb. By "wild-type" MTAP is meant that encoded by NM_002451, or having the same amino acid sequence (NP_002442). (Schmid et al. Oncogene 2000, 19, pp 5747-54).

As used herein, the term "MTAP-deficient", "MTAP-deficiency", "MTAP-null" and the like refer to cells (including, but not limited to, cancer cells, cell lines, tissues, tissue types, tumors, etc.) that have a significant reduction in post-translational modification, production, expression, level, stability and/or activity of MTAP relative to that in a control, e.g., reference or normal or non-cancerous cells. The reduction can be at least about 20%, 30%, 40%, 50%, 60%, 70%, 80% or 90%. In some embodiments, the reduction is at least 20%. In some embodiments, the reduction is at least 50%. The terms "MTAP-deficient and/or MTA accumulating", "MTAP-deficient and/or MTA-accumulating", MTAP deficient and/or MTA upregulated" and the like, regarding a cell or cells, etc., indicate that the cell or cells, etc., either are deficient in MTAP and/or overproduce or accumulate MTA. MTAP-deficient cells include those wherein the MTAP gene has been mutated, deleted, or transcriptionally silenced. As a non-limiting example, MTAP-deficient cells can have a homozygous deletion. MTAP knockdown is not lethal. In some embodiments, the MTAP-deficient cells are also CDKN2A-deficient. The MTAP deficiency can be detected using any reagent or technique known in the art, for example: immunohistochemistry utilizing an antibody to MTAP, and/or genomic sequencing, and/or nucleic acid hybridization and/or amplification utilizing at least one probe or primer comprising a sequence of at least 12 contiguous nucleotides (nt) of the sequence of MTAP, wherein the primer is no longer than about 30 nt.

An "MTAP-deficiency-related" or "MTAP-deficiency" or "MTAP deficient" disease (for example, a proliferating disease, e.g., a cancer) or a disease (for example, a proliferating disease, e.g., a cancer) "associated with MTAP deficiency" or a disease (for example, a proliferating disease, e.g., a cancer) "characterized by MTAP deficiency" and the like refer to an ailment (for example, a proliferating disease, e.g., a cancer) wherein a significant number of cells are MTAP-deficient. For example, in a MTAP-deficiency-related disease, one or more disease cells can have a significantly reduced post-translational modification, production, expression, level, stability and/or activity of MTAP. Examples of MTAP-deficiency-related diseases include, but are not limited to, cancers, including but not limited to: glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma (See FIG. 1). In a patient afflicted with a MTAP-deficiency-related disease, it is possible that some disease cells (e.g., cancer cells) can be MTAP-deficient while others are not. Similarly, some disease cells may be MTA-accumulating while others are not.

Thus, the present disclosure encompasses methods of treatment involving diseases of these tissues, or any other tissues, wherein the proliferation of MTAP-deficient and/or MTA-accumulating cells can be inhibited by administration of a PRMT5 inhibitor.

Some cancer cells which are MTAP-deficient are also deficient in CDKN2A; the post-translational modification, production, expression, level, stability and/or activity of the CDKN2A gene or its product are decreased in these cells. The genes for MTAP and CDKN2A are in close proximity on chromosome 9p21; MTAP is located approximately 100 kb telomeric to CDKN2A. Many cancer cell types harbor CDKN2A/MTAP loss (loss of both genes). Thus, in some embodiments, a MTAP-deficient cell is also deficient in CDKN2A.

MTA and MTA Accumulation

By "MTA" is meant the PRMT5 inhibitor also known as methyl-thioadenosine, S-methyl-5'-thioadenosine, [5'deoxy-5'-(methylthio)-fl-D-ribofuranosyl] adenine, 5'-methyl-thio-adenosine, 5'-deoxy, 5'-methyl thioadenosine, and the like. MTA selectively inhibits PRMT5 methyltransferase activity. MTA is the sole known catabolic substrate for MTAP. The terms "MTA accumulating", "MTA overproducing", "MTA upregulated" and the like refer to cells (including, but not limited to, cancer cells, cell lines, tissues, tissue types, tumors, etc.) that have a significantly increased production, level and/or stability of MTA. MTA-accumulating cells include those wherein the cells comprise at least about 20%, 30%, 40%, 50%, 60%, 70%, 80%, 90%, 100%, or greater than 100%, higher production, level and/or stability of MTA than that in normal or non-cancerous cells. In some embodiments, MTA-accumulating cells include those wherein the cells comprise at least 20% higher production, level and/or stability of MTA than that in normal or non-cancerous cells. In some embodiments, MTA-accumulating cells include those wherein the cells comprise at least 50% higher production, level and/or stability of MTA than that in normal or non-cancerous cells. Determination of MTA accumulation in test samples (e.g., cells such as cancer cells being tested for MTA accumulation) and reference samples, and other cells, tissues, samples, etc., can be performed using any method known in the art. Such methods for detecting MTA include, as a non-limiting example, liquid chromatography-electrospray ionization-tandem mass spectrometry (LC-ESI-MS/MS), as described in Stevens et al. *J. Chromatogr. A.* 2010, 1217, pp 3282-3288; and Kirovski et al. *Am. J. Pathol.* 2011, 178, pp 1145-1152; and references cited therein. Loss of MTAP is associated with accumulation of MTA (Williams-Ashman et al. *Biochem. Pharm.* 1982, 31, pp 277-288; and Limm et al. *Eur. J. Cancer* 2013, 49, Issue 6.

An "MTA-accumulation-related", "MTA-accumulation", "MTA-accumulating", "MTA overproducing", "MTA upregulated" disease (for example, a proliferating disease, e.g., a cancer) or a disease (for example, a proliferating disease, e.g., a cancer) "associated with MTA accumulation" or a disease (for example, a proliferating disease, e.g., a cancer) "characterized by MTA accumulation" and the like refer to an ailment (for example, a proliferating disease, e.g., a cancer) wherein a significant number of cells are MTA accumulating. Examples of MTA-accumulating diseases include, but are not limited to, cancers, including but not limited to: glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma (See FIG. 1). In a patient afflicted with a MTAP-deficiency-related disease, it is possible that some disease cells (e.g., cancer cells) can be MTAP-deficient while others are not.

In a patient having or having been diagnosed with an MTA-accumulating disease, some cells may be MTA-accumulating while others are not.

An increase in therapeutic window between normal cells and MTAP-deleted/MTA accumulating cells could be achieved by using an inhibitor that binds PRMT5 uncompetitively with MTA. As used herein, "uncompetitive binding" and "uncompetitive inhibition" and "cooperative binding" and "cooperative inhibition" (e.g., MTA-uncompetitive binding, MTA-uncompetitive inhibition, MTA-cooperative binding, MTA-cooperative inhibition) refers to binding of an inhibitor to a protein (e.g., PRMT5) that is increased in the presence of a co-factor (e.g., MTA) over the binding of the same inhibitor in the absence of the co-factor. The PRMT5 inhibitors known in the art are generally either SAM (S-adenosylmethionine) uncompetitive or SAM competitive. As the concentration of SAM in wild-type and MTAP-null cells is similar, these inhibitors are expected to bind with similar potency to both cell types. By contrast, an MTA-cooperative (and either SAM competitive or showing enhanced cooperativity with MTA relative to SAM) inhibitor would bind with apparent greater potency in the presence of high concentrations of MTA and would therefore result in preferential inhibition of PRMT5 in MTA-accumulating cells relative to normal cells.

As described further herein, a cancer cell, a cancer type, or a subject with cancer, is "PRMT5 inhibitor sensitive," sensitive to treatment with PRMT5 inhibitors, "sensitive to PRMT5 therapeutic inhibition," or described in similar terms if it is amenable to treatment with a PRMT5 inhibitor, e.g., due to its MTAP deficiency and/or MTA accumulation character.

PRMT5

"PRMT5" as used herein is the gene or protein Protein Arginine Methyltransferase 5, also known as HRMTIL5; IBP72; JBP1; SKB1; or SKB1Hs External IDs: OMIM:

604045, MGI: 1351645, HomoloGene: 4454, ChEMBL: 1795116, GeneCards: PRMT5 Gene; EC number 2.1.1.125. Ensembl ENSG00000100462; UniProt 014744; Entrez Gene ID: 10419; RefSeq (mRNA): NM_001039619. The mouse homolog is NM_013768.

Methyltransferases such as PRMT5 catalyze the transfer of one to three methyl groups from the co-factor S-adenosylmethionine (also known as SAM or AdoMet) to lysine or arginine residues of histone proteins. Arginine methylation is carried out by 9 different protein arginine methyltransferases (PRMT) in humans. Three types of methylarginine species exist: (1) Monomethylarginine (MMA); (2) Asymmetric dimethyl arginine (ADMA), which is produced by Type I methyl transferases (PRMT1, PRMT2, PRMT3, CARM1, PRMT6 and PRMT8); and (3) Symmetrical dimethylarginine (SDMA), which is produced by Type II methyl transferases (PRMT5 and PRMT7). PRMT1 and PRMT5 are the major asymmetric and symmetric arginine methyltransferases, respectively. PRMT5 promotes symmetric dimethylation on histones at H3R8 and H4R3 (H4R3me2). Symmetric methylation of H4R3 is associated with transcriptional repression and can act as a binding site for DNMT3A. Loss of PRMT5 results in reduced DNMT3A binding and gene activation. Tumor suppressor gene ST7 and chemokines RNATES, IP10, CXCL11 are targeted and silenced by PRMT5. WO 2011/079236.

Additional substrates include E2F1, p53, EGFR and CRAF. PRMT5 is part of a multi-protein complex comprising the co-regulatory factor WDR77 (also known as MEP50, a CDK4 substrate) during GUS transition. Phosphorylation increases PRMT5/WDR77 activity. WDR77 is the non-catalytic component of the complex and mediates interactions with binding partners and substrates. PRMT5 can also interact with pICln or RioK1 adaptor proteins in a mutually exclusive fashion to modulate complex composition and substrate specificity.

PRMT5 has either a positive or negative effect on its substrates by arginine methylation when interacting with a number of complexes and is involved in a variety of cellular processes, including RNA processing, signal transduction, transcriptional regulation, and germ cell development. PRMT5 is a major pro-survival factor regulating eIF4E expression and p53 translation. PRMT5 triggers p53-dependent apoptosis and sensitized various cancer cells to Tumor necrosis factor (TNF)-related apoptosis-inducing ligand (TRAIL) without affecting TRAIL resistance in non-transformed cells.

The term "PRMT5 inhibitor" refers to any compound capable of inhibiting the production, level, activity, expression or presence of PRMT5. These include, as non-limiting examples, any compound inhibiting the transcription of the gene, the maturation of RNA, the translation of mRNA, the posttranslational modification of the protein, the enzymatic activity of the protein, the interaction of same with a substrate, etc. The term also refers to any agent that inhibits the cellular function of the PRMT5 protein, either by ATP-competitive inhibition of the active site, allosteric modulation of the protein structure, disruption of protein-protein interactions, or by inhibiting the transcription, translation, post-translational modification, or stability of PRMT5 protein.

In some embodiments, a PRMT5 inhibitor competes with another compound, protein or other molecule which interacts with PRMT5 and is necessary for PRMT5 function.

As a non-limiting example, a PRMT5 inhibitor can compete with the co-factor S-adenosylmethionine (also known as SAM or AdoMet).

In some embodiments, the PRMT5 inhibitor is uncompetitive with MTA. In further embodiments, the PRMT5 inhibitor is uncompetitive with MTA and competitive with SAM.

In some embodiments, the PRMT5 inhibitor is uncompetitive with MTA and uncompetitive with SAM but binds with a higher degree of potency for the MTA complex relative to the SAM complex.

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modem Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, IN 1972). The invention additionally encompasses compounds described herein as individual isomers substantially free of other isomers, and alternatively, as mixtures of various isomers.

The "enantiomeric excess" ("e.e.") or "% enantiomeric excess" ("% e.e.") of a composition as used herein refers to an excess of one enantiomer relative to the other enantiomer present in the composition. For example, a composition can contain 90% of one enantiomer, e.g., the S enantiomer, and 10% of the other enantiomer, i.e., the R enantiomer.

$$e.e.=(90-10)/100=80\%.$$

Thus, a composition containing 90% of one enantiomer and 10% of the other enantiomer is said to have an enantiomeric excess of 80%.

The "diastereomeric excess" ("d.e.") or "% diastereomeric excess" ("% d.e.") of a composition as used herein refers to an excess of one diastereomer relative to one or more different diastereomers present in the composition. For example, a composition can contain 90% of one diastereomer, and 10% of one or more different diastereomers.

$$d.e.=(90-10)/100=80\%.$$

Thus, a composition containing 90% of one diastereomers and 10% of one or more different diastereomers is said to have a diastereomeric excess of 80%.

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

In a formula, ⌇ is a single bond where the stereochemistry of the moieties immediately attached thereto is not specified.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "azido" refers to the radical —N$_3$.

"Aliphatic" refers to an alkyl, alkenyl, alkynyl, or carbocyclyl group, as defined herein.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Aralkyl" or "arylalkyl" is a subset of alkyl and aryl, as defined herein, and refers to an optionally substituted alkyl group substituted by an optionally substituted aryl group.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl (C), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-4}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl (C), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-4}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-8}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl. Exemplary heteroalkyl groups include: —CH$_2$OH, —CH$_2$OCH$_3$, —CH$_2$NH$_2$, —CH$_2$NH(CH$_3$), —CH$_2$N(CH$_3$)$_2$, —CH$_2$CH$_2$OH, —CH$_2$CH$_2$OCH$_3$, —CH$_2$CH$_2$NH$_2$, —CH$_2$CH$_2$NH(CH$_3$), —CH$_2$CH$_2$N(CH$_3$)$_2$.

"'Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group is substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

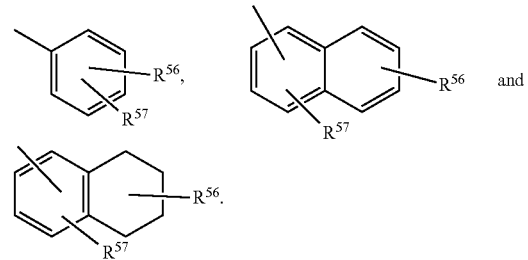

wherein one of R$^6$ and R$^{57}$ may be hydrogen and at least one of R$^6$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^9$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{56}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. In some embodiments, a heteroaryl group is a bicyclic 8-12 membered aromatic ring system having ring carbon atoms and 1-6 ring heteroatoms provided in the aromatic ring system, wherein each heteroatom is independently selected from nitrogen, oxygen, and sulfur ("8-12 membered bicyclic heteroaryl"). In some embodiments, a heteroaryl group is a 8-10 membered bicyclic aromatic ring system having ring carbon atoms and 1-6 ring heteroatoms provided in the aromatic ring system, wherein each heteroatom is independently selected from nitrogen, oxygen, and sulfur ("8-10 membered bicyclic heteroaryl"). In some embodiments, a heteroaryl group is a 9-10 membered bicyclic aromatic ring system having ring carbon atoms and 1-6 ring heteroatoms provided in the aromatic ring system, wherein each heteroatom is independently selected from nitrogen, oxygen, and sulfur ("9-10 membered bicyclic heteroaryl"). Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

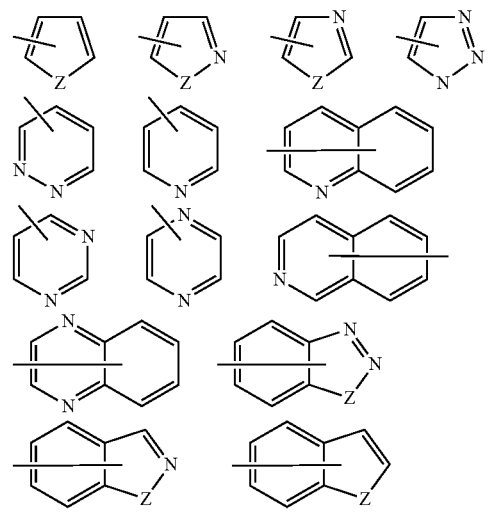

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

In the structures described herein, a substituent attached to a polycyclic (e.g., bicyclic or tricyclic) cycloalkyl, heterocycloalkyl, aryl or heteroaryl with a bond that spans two or more rings is understood to mean that the substituent can be attached at any position in each of the rings.

"Heteroaralkyl" or "heteroarylalkyl" is a subset of "alkyl" and refers to an alkyl group substituted by a heteroaryl group, wherein the point of attachment is on the alkyl moiety.

The term "carbocyclyl" or "carbocyclic" refers to a radical of a non-aromatic monocyclic, bicyclic, or tricyclic or polycyclic hydrocarbon ring system having from 3 to 14 ring carbon atoms ("C$_{3-14}$ carbocyclyl") and zero heteroatoms in the non-aromatic ring system. Carbocyclyl groups include fully saturated ring systems (e.g., cycloalkyls), and partially saturated ring systems. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_3$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like.

As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

The term "cycloalkyl" as employed herein includes saturated cyclic, bicyclic, tricyclic, or polycyclic hydrocarbon groups having 3 to 14 carbons containing the indicated number of rings and carbon atoms (for example a $C_3$-$C_{14}$ monocyclic, $C_4$-$C_{14}$ bicyclic, $C_5$-$C_{14}$ tricyclic, or $C_6$-$C_{14}$ polycyclic cycloalkyl). In some embodiments "cycloalkyl" is a monocyclic cycloalkyl. In some embodiments, a monocyclic cycloalkyl has 3-14 ring carbon atoms. ("$C_{3-14}$ monocyclic cycloalkyl"). In some embodiments, a monocyclic cycloalkyl group has 3 to 10 ring carbon atoms ("$C_{3-10}$ monocyclic cycloalkyl"). In some embodiments, a monocyclic cycloalkyl group has 3 to 8 ring carbon atoms ("$C_{3-8}$ monocyclic cycloalkyl"). In some embodiments, a monocyclic cycloalkyl group has 3 to 6 ring carbon atoms ("$C_{3-6}$ monocyclic cycloalkyl"). In some embodiments, a monocyclic cycloalkyl group has 4 to 6 ring carbon atoms ("$C_{4-6}$ monocyclic cycloalkyl"). In some embodiments, a monocyclic cycloalkyl group has 5 to 6 ring carbon atoms ("$C_{5-6}$ monocyclic cycloalkyl"). In some embodiments, a monocyclic cycloalkyl group has 5 to 10 ring carbon atoms ("$C_{5-10}$ monocyclic cycloalkyl"). Examples of monocyclic $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$).

In some embodiments "cycloalkyl" is a bicyclic cycloalkyl. In some embodiments, a bicyclic cycloalkyl has 4-14 ring carbon atoms. ("$C_{4-14}$ bicyclic cycloalkyl"). In some embodiments, a bicyclic cycloalkyl group has 4 to 12 ring carbon atoms ("$C_{4-12}$ bicyclic cycloalkyl"). In some embodiments, a bicyclic cycloalkyl group has 4 to 10 ring carbon atoms ("$C_{4-10}$ bicyclic cycloalkyl"). In some embodiments, a bicyclic cycloalkyl group has 5 to 10 ring carbon atoms ("$C_{5-10}$ bicyclic cycloalkyl"). In some embodiments, a bicyclic cycloalkyl group has 6 to 10 ring carbon atoms ("$C_{6-10}$ bicyclic cycloalkyl"). In some embodiments, a bicyclic cycloalkyl group has 8 to 10 ring carbon atoms ("$C_{5-10}$ bicyclic cycloalkyl"). In some embodiments, a bicyclic cycloalkyl group has 7 to 9 ring carbon atoms ("$C_{7-9}$ bicyclic cycloalkyl"). Examples of bicyclic cycloalkyls include bicyclo[1.1.0]butane ($C_4$), bicyclo[1.1.1]pentane ($C_5$), spiro[2.2] pentane ($C_5$), bicyclo[2.1.0]pentane ($C_5$), bicyclo[2.1.1] hexane ($C_6$), bicyclo[3.1.0]hexane ($C_6$), spiro[2.3] hexane ($C_6$), bicyclo[2.2.1]heptane (norbornane) ($C_7$), bicyclo [3.2.0]heptane ($C_7$), bicyclo[3.1.1]heptane ($C_7$), bicyclo [3.1.1]heptane ($C_7$), bicyclo[4.1.0]heptane ($C_7$), spiro[2.4] heptane ($C_7$), spiro [3.3]heptane ($C_7$), bicyclo[2.2.2]octane ($C_8$), bicyclo[4.1.1]octane ($C_8$)octahydropentalene ($C_8$), bicyclo[3.2.1]octane ($C_8$), bicyclo[4.2.0]octane ($C_8$), spiro [2.5]octane ($C_8$), spiro[3.4]octane ($C_8$), bicyclo[3.3.1] nonane ($C_9$), octahydro-1H-indene ($C_9$), bicyclo[4.2.1] nonane ($C_9$), spiro[3.5]nonane ($C_9$), spiro[4.4]nonane ($C_9$), bicyclo[3.3.2]decane ($C_{10}$), bicyclo[4.3.1]decane ($C_{10}$), spiro[4.5]decane ($C_{10}$), bicyclo[3.3.3]undecane ($C_{11}$), decahydronaphthalene ($C_{10}$), bicyclo[4.3.2]undecane ($C_{11}$), spiro[5.5]undecane ($C_{11}$) and bicyclo[4.3.3]dodecane ($C_{12}$).

In some embodiments "cycloalkyl" is a tricyclic cycloalkyl. In some embodiments, a tricyclic cycloalkyl has 6-14 ring carbon atoms. ("$C_{6-14}$ tricyclic cycloalkyl"). In some embodiments, a tricyclic cycloalkyl group has 8 to 12 ring carbon atoms ("$C_{8-12}$ tricyclic cycloalkyl"). In some embodiments, a tricyclic cycloalkyl group has 10 to 12 ring carbon atoms ("$C_{10-12}$ tricyclic cycloalkyl. Examples of tricyclic cycloalkyls include adamantine ($C_{12}$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl "Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary bicyclic heterocyclyl groups include, without limitation, indolinyl, isoindolinyl, dihydrobenzofuranyl, dihydrobenzothienyl, tetrahydrobenzo-thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g., 2-piperidinyl, 3-piperidinyl and 4-piperidinyl), pyrrolidine (e.g., 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(=O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)$CH_3$), cyclohexylcarbonyl, cyclohexylmethylcarbonyl, benzoyl (—C(=O)Ph), benzylcarbonyl (—C(=O)$CH_2$Ph), —C(=O)—$C_1$-$C_8$ alkyl, —C(=O)—$(CH_2)_t$($C_6$-$C_{10}$ aryl), —C(=O)—$(CH_2)_t$(5-10 membered heteroaryl), —C(=O)—$(CH_2)_t$($C_3$-$C_{10}$ cycloalkyl), and —C(=O)—$(CH_2)_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

The term aminoalkyl refers to a substituted alkyl group wherein one or more of the hydrogen atoms are independently replaced by an —$NH_2$ group.

The term hydroxyalkyl refers to a substituted alkyl group wherein one or more of the hydrogen atoms are independently replaced by an —OH group.

The terms "alkylamino" and "dialkylamino" refer to —NH(alkyl) and —N(alkyl)$_2$ radicals respectively. In some embodiments the alkylamino is a —NH($C_1$-$C_4$ alkyl). In some embodiments the alkylamino is methylamino, ethylamino, propylamino, isopropylamino, n-butylamino, isobutylamino, sec-butylamino or tert-butylamino. In some embodiments the dialkylamino is —N($C_1$-$C_6$ alkyl)$_2$. In some embodiments the dialkylamino is a dimethylamino, a methylethylamino, a diethylamino, a methylpropylamino, a methylisopropylamino, a methylbutylamino, a methylisobutylamino or a methyltertbutylamino.

The term "aryloxy" refers to an —O-aryl radical. In some embodiments the aryloxy group is phenoxy.

The term "haloalkoxy" refers to alkoxy structures that are substituted with one or more halo groups or with combinations thereof. For example, the term "fluoroalkoxy" includes haloalkoxy groups, in which the halo is fluorine. In some embodiments haloalkoxy groups are difluoromethoxy and trifluoromethoxy.

"Alkoxy" refers to the group —$OR^2$ where $R^2$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^2$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary "substituted amino" groups include, but are not limited to, —NR$^{39}$—C$_1$-C$_5$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —C$_{1-10}$ alkyl (e.g., aralkyl, heteroaralkyl), —C$_{2-10}$ alkenyl, —C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^d$ edition, John Wiley & Sons, 1999, incorporated herein by reference.

each instance of R$^{aa}$ is, independently, selected from —C$_{1-10}$ alkyl, —C$_{1-10}$ perhaloalkyl, —C$_{2-10}$ alkenyl, —C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, —C$_{1-10}$ alkyl, —C$_{1-10}$ perhaloalkyl, —C$_{2-10}$ alkenyl, —C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion.

each instance of R$^{cc}$ is, independently, selected from hydrogen, —C$_{1-10}$ alkyl, —C$_{1-10}$ perhaloalkyl, —C$_{2-40}$ alkenyl, —C$_{2-40}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR—, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR—, —SSR$^{ee}$, —C(=O)R$^{ee}$, —CO$_2$H, —CO$_2$R$^{ee}$, —OC(=O)R$^{ee}$, —OCO$_2$R$^{ee}$—, —C(=O)N(R$^{ff}$)$_2$, —OC(=O)N(R$^{ff}$)$_2$, —NR$^{ff}$C(=O)R$^{ee}$—, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$—, —OC(=NR$^{ff}$)OR$^{ee}$—, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$—, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, —C$_{1-6}$ alkyl, —C$_{1-6}$ perhaloalkyl, —C$_{2-6}$ alkenyl, —C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^g$ groups, or two geminal $R^{dd}$ substituents can be joined to form =O or =S; wherein X$^-$ is a counterion;

each instance of $R^1$ is, independently, selected from —C$_{1-6}$ alkyl, —C$_{1-6}$ perhaloalkyl, —C$_{2-6}$ alkenyl, —C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^9$ groups;

each instance of $R^{ff}$ is, independently, selected from hydrogen, —C$_{1-6}$ alkyl, —C$_{1-6}$ perhaloalkyl, —C$_{2-6}$ alkenyl, —C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, —C$_{1-6}$ alkyl, —C$_{1-6}$ perhaloalkyl, —C$_{2-6}$ alkenyl, —C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxy acetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxy ethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl) methyl, 4-(4'-bromophenacyloxyphenyl)diphenylmethyl, 4,4',4"-tris(4,5-dichlorophthalimidophenyl)methyl, 4,4',4"- tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-r-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In certain embodiments, the leaving group is halogen, alkanesulfonyloxy, arenesulfonyloxy, diazonium, alkyl diazenes, aryl diazenes, alkyl triazenes, aryl triazenes, nitro, alkyl nitrate, aryl nitrate, alkyl phosphate, aryl phosphate, alkyl carbonyl oxy, aryl carbonyl oxy, alkoxcarbonyl oxy, aryoxcarbonyl oxy ammonia, alkyl amines, aryl amines, hydroxyl group, alkyloxy group, or aryloxy. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —$OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

"Carboxy" refers to the radical —C(=O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl (—$CF_3$), difluoromethyl (—$CHF_2$), fluoromethyl (—$CH_2F$), chloromethyl (—$CH_2Cl$), dichloromethyl (—$CHCl_2$), tribromomethyl (—$CH_2Br$), and the like.

"Hydroxy" refers to the radical —OH.

"Nitro" refers to the radical —$NO_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —S(=O)(=NR$^{bb}$)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{aa}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_6$ m aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$)alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgous monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Detailed Description of Certain Embodiments of the Invention

As generally described herein, the present invention provides compounds (e.g., compounds of formula (I), (Ia), (Ib), (Ic), (Id), (II), (IIa), (IIb), (III), (IIIa), (IIIb), (IV), (IVa), (IVb), (V), (V1), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or compounds of Table 1a, or pharmaceutically acceptable salts thereof) that are MTA-uncompetitive PRMT5 inhibitors useful for treating proliferating disorders (e.g., cancers) associated with MTAP deficiencies and/or MTA accumulation.

Compounds

In one aspect, provided herein are compounds or pharmaceutically acceptable salts thereof according to Formula (I)

Ring A is a carbocycle, heterocycle, 5-6 member monocyclic heteroaryl or a monocyclic aryl;

$R^1$ is a 3-7 membered carbocycle, a 4-7 membered heterocycle or a 5-6 membered heteroaryl substituted with 0-3 instances of $R^4$;

each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)O$R^3$, —$CH_2$C(=O)$R^3$, —$NR^3$C(=O)$R^3$, —$NR^3$C(=O)O$R^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$;

each $R^3$ is independently selected from H, $C_1$-$C_6$ alkyl, $C_1$-$C_6$ heteroalkyl, $C_3$-$C_7$ carbocyclyl, $C_3$-$C_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)O$R^3$, —$NR^3$C(=O)$R^3$, —$NR^3$C(=O)O$R^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$;

each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)O$R^3$, —$NR^3$C(=O)$R^3$, —$NR^3$C(=O)O$R^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heteroarylalkyl, heterocyclylalkyl, arylalkyl, heteroarylalkyl, —$OR^3$, —$N(R^3)_2$, —C(=O)$R^3$, —C(=O)O$R^3$, —$NR^3$C(=O)$R^3$, —$NR^3$C(=O)O$R^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$, —S(=O)$_2$N($R^3$)$_2$, or

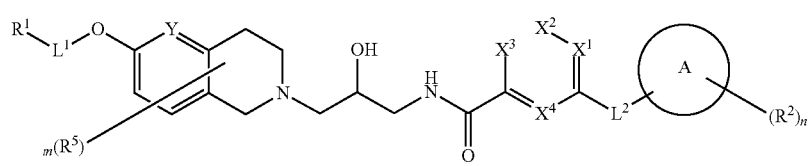

(I)

wherein
$X^1$, $X^2$, $X^3$ and $X^4$ are each independently N or $CR^x$;
Y is N, CH or $CR^5$;
$L^1$ is a bond or $C_1$-$C_4$-alkylene substituted with 0-2 instances of $R^6$;
$L^2$ is a bond, —NH— or —O—;

two $R^5$ can be taken together with the atoms to which they are attached to form a —$C_3$-$C_9$ carbocyclyl or a —$C_3$-$C_9$ heterocyclyl;

each $R^6$ is independently selected from halo, —$C_1$-$C_4$ alkyl, —$C_1$-$C_4$ haloalkyl, —O$C_1$-$C_4$ alkyl, —O$C_1$-$C_4$ haloalkyl, or two $R^6$ can be taken together with the atoms to which they are attached to form a $C_3$-$C_7$ carbocycle or a $C_3$-$C_7$ heterocycle.

m is 0, 1, 2 or 3; and n is 0, 1, 2 or 3.

In certain embodiments, Y is CH or $CR^5$. In further embodiments, Y is CH.

In certain embodiments, the compound of Formula (I) is of formula (Ia)

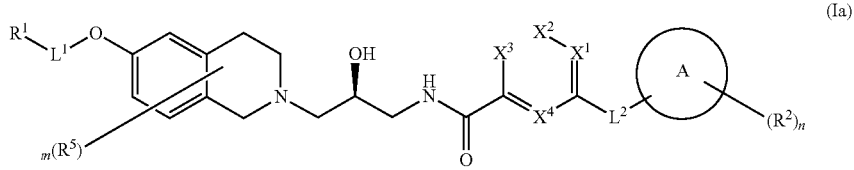

(Ia)

wherein each instance of $X^1$, $X^2$, $X^3$, $X^4$, A, $L^1$, $L^2$, $R^1$, $R^2$, $R^5$, m and n are as defined herein.

In certain embodiments, the compound of Formula (I) is of formula (Ib)

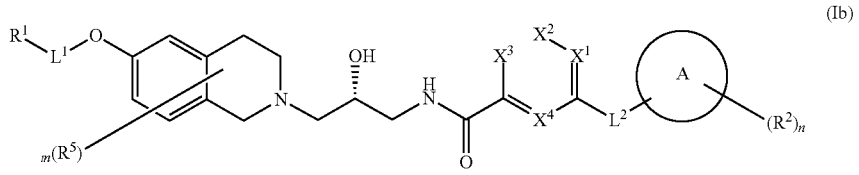

(Ib)

wherein each instance of $X^1$, $X^2$, $X^3$, $X^4$, A, $L^1$, $L^2$, $R^1$, $R^2$, $R^5$, m and n are as defined herein.

In certain embodiments, Y is CN.

In certain embodiments, the compound of Formula (I) is of formula (Ic)

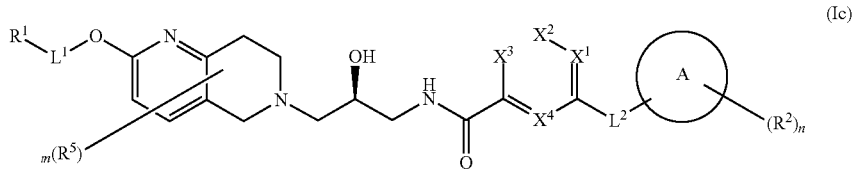

(Ic)

wherein each instance of $X^1$, $X^2$, $X^3$, $X^4$, A, $L^1$, $L^2$, $R^1$, $R^2$, $R^5$, m and n are as defined herein.

In certain embodiments, the compound of Formula (I) is of formula (Id)

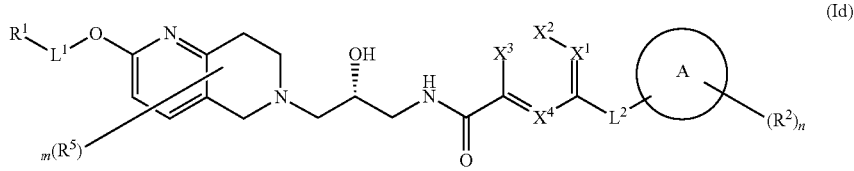

(Id)

wherein each instance of $X^1$, $X^2$, $X^3$, $X^4$, A, $L^1$, $L^2$, $R^1$, $R^2$, $R^5$, m and n are as defined herein.

As generally defined herein, $X^1$, $X^2$, $X^3$ and $X^4$ are each independently N or $CR^x$, wherein each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$, wherein each alkyl, carbocyclyl, heterocyclyl, heterocyclylalkyl, cycloalkylalkyl is optionally substituted.

In certain embodiments, $R^x$ is selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$NHR^3$, N(CH$_3$)$R^3$, —C(=O)$R^3$, —C(=O)$OR^3$, —NHC(=O)$R^3$, —N(CH$_3$)C(=O)$R^3$, —NHC(=O)$OR^3$, —N(CH$_3$)C(=O)$OR^3$, —C(=O)NH($R^3$), —C(=O)N(CH$_3$)($R^3$), —OC(=O)$NHR^3$, —OC(=O)N(CH$_3$)$R^3$—S(=O)$R^3$, —S(=O)$_2R^3$, —$SR^3$, —S(=O)(=NH)$R^3$, —S(=O)(=NCH$_3$)$R^3$, —NHS(=O)$_2R^3$, —N(CH$_3$)S(=O)$_2R^3$, —S(=O)$_2NHR^3$ and —S(=O)$_2$N(CH$^3$)$R^3$, wherein each alkyl, carbocyclyl, heterocyclyl, heterocyclylalkyl, cycloalkylalkyl is optionally substituted.

In certain embodiments, $R^x$ is H, $N(R^3)_2$, $NHR^3$, $N(CH_3)R^3$, $OR^3$, $C_1$-$C_6$ alkyl, optionally substituted —$C_3$-$C_9$ carbocyclyl or optionally substituted —$C_3$-$C_9$ heterocyclyl. In further embodiments, $R^x$ is —$C_3$-$C_9$ carbocyclyl or —$C_3$-$C_9$ heterocyclyl substituted with 0-1 instances of $R^7$, wherein $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ or —$S(=O)_2N(R^3)_2$, In certain embodiments, $R^x$ is hydrogen.

In certain embodiments, $R^x$ is halo (e.g., fluoro, chloro, bromo, iodo). In further embodiments, $R^x$ is chloro. In some embodiments, $R^x$ is fluoro. In some embodiments, $R^x$ is bromo. In some embodiments, $R^x$ is iodo.

In some embodiments, $R^x$ is —CN.

In certain embodiments, $R^x$ is optionally substituted —$C_1$-$C_6$ alkyl. In certain embodiments, $R^x$ is unsubstituted alkyl. In further embodiments, $R^x$ is methyl. In some embodiments, $R^x$ is ethyl. In some embodiments $R^x$ is propyl or isopropyl. In certain embodiments, $R^x$ is alkyl substituted with 1-2 instances of $R^7$.

In some embodiments, $R^x$ is —$C_1$-$C_6$ heteroalkyl. In further embodiments, $R^x$ is methoxymethyl (—$CH_2OCH_3$). In some embodiments, $R^x$ is aminomethyl (e.g., —$CH_2NH_2$, —$CH_2NHCH_3$, —$CH_2N(CH_3)_2$, —$CH_2CH_2N(CH_3)_2$. In certain embodiments, $R^x$ is heteroalkyl further substituted with 1-2 instances of $R^7$.

In some embodiments, $R^x$ is —$C_1$-$C_6$ haloalkyl. In further embodiments, $R^x$ is trifluoromethyl (—$CF_3$).

In some embodiments, $R^x$ is optionally substituted —$C_3$-$C_9$ carbocyclyl (e.g., cyclopropyl, cyclobutyl, cyclopentyl, cyclohexyl). In some embodiments, $R^x$ is cyclopropyl. In some embodiments $R^x$ is cyclobutyl. In some embodiments, $R^x$ is cyclopentyl. In some embodiments, $R^x$ is cyclohexyl. In certain embodiments, $R^x$ is —$C_3$-$C_9$ carbocyclyl (e.g., cyclopropyl, cyclobutyl, cyclopentyl, cyclohexyl) substituted with 1-2 instances of $R^7$. In further embodiments, the $R^7$ substituent is selected from $C_1$-$C_6$ alkyl (e.g., methyl, ethyl, propyl, isopropyl) and —$C(=O)R^3$ (e.g., —$C(=O)Me$, —$C(=O)Et$, —$C(=O)Pr$, —$C(=O)iPr$, —$C(=O)Ph$, —$C(=O)cyclopropyl$, $C(=O)heteroalkyl$).

In some embodiments, $R^x$ is optionally substituted-$C_3$-$C_9$ heterocyclyl (e.g., oxetanyl, tetrahydropyranyl, tetrahydrofuranyl, azetidinyl, pyrrolidinyl, piperidinyl, piperazinyl, morpholinyl, azepanyl, 8-oxa-3-azabicyclo[3.2.1]octanyl. In some embodiments, $R^x$ is —$C_3$-$C_9$ heterocyclyl optionally substituted with 0-2 instances of $R^7$. In some embodiments, $R^x$ is oxetanyl, optionally substituted with 0-2 instances of $R^7$. In exemplary embodiments, the $R^7$ substituent is selected from $C_1$-$C_6$ alkyl (e.g., methyl, ethyl, propyl, isopropyl) and —$C(=O)R^3$ (e.g., —$C(=O)Me$, —$C(=O)Et$, —$C(=O)Pr$, —$C(=O)iPr$, —$C(=O)Ph$, —$C(=O)cyclopropyl$, $C(=O)heteroalkyl$). In some embodiments, $R^x$ is tetrahydropyranyl, optionally substituted with 0-2 instances of $R^7$. In some embodiments, $R^x$ is tetrahydrofuranyl, optionally substituted with 0-2 instances of $R^7$. In some embodiments, $R^x$ is azetidinyl, optionally substituted with 0-2 instances of $R^7$. In some embodiments, $R^x$ is pyrrolidinyl, optionally substituted with 0-2 instances of $R^7$. In some embodiments, $R^x$ is piperidinyl, optionally substituted with 0-2 instances of $R^7$. In some embodiments, $R^x$ is piperazinyl, optionally substituted with 0-2 instances of $R^7$ (e.g., N-acetylpiperazinyl, N-methylpiperazinyl, N-ethylpiperazinyl). In some embodiments, $R^x$ is morpholinyl, optionally substituted with 0-2 instances of $R^7$. In some embodiments, $R^x$ is azepanyl. In some embodiments, $R^x$ is 8-oxa-3-azabicyclo[3.2.1]octanyl (e.g., 8-oxa-3-azabicyclo[3.2.1]octan-3-yl), optionally substituted with 0-2 instances of $R^7$.

In some embodiments $R^x$ is optionally substituted cycloalkylalkyl (e.g., cyclopropylmethyl, cyclobutylmethyl, cyclopentylmethyl, cyclohexylmethyl, cycloheptylmethyl). In some embodiments, $R^x$ is cycloalkylalkyl optionally substituted with 0-2 instances of $R^7$. In some embodiments, $R^x$ is optionally substituted heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl). In some embodiments, $R^x$ is heterocyclylalkyl optionally substituted with 0-2 instances of $R^7$.

In some embodiments, $R^x$ is —$OR^3$ (e.g., methoxy, fluoromethoxy (—$OCHF_2$), trifluoromethoxy (—$OCF_3$), ethoxy, propoxy, isopropoxy, cyclopropyloxy, cyclobutyloxy). In some embodiments, $R^x$ is methoxy. In some embodiments, $R^x$ is ethoxy. In some embodiments, $R^x$ is propoxy. In some embodiments, $R^x$ is isopropoxy. In some embodiments $R^x$ is fluoromethoxy (—$OCHF_2$). In some embodiments, $R^x$ is trifluoromethoxy (—$OCF_3$).

In some embodiments, $R^x$ is —$N(R^3)_2$ (e.g., —$NH_2$, —$NHR^3$, —$N(CH_3)R_3$). In some embodiments, $R^x$ is —$NH_2$. In some embodiments, $R^x$ is —$NHR^3$ (e.g., —NHMe, —NHEt, —NHPr, —$NH^iPr$, —NHcyclopropyl, —NHcyclobutyl). In some embodiments, $R^x$ is —$N(CH_3)R^3$ (e.g., —$NMe_2$, —$N(CH_3)Et$, —$N(CH_3)Pr$, —$N(CH_3)^iPr$, —$N(CH_3)cyclopropyl$, —$N(CH_3)cyclobutyl$).

In some embodiments, $R^x$ is —$C(=O)R^3$. In some embodiments, $R^x$ is —$C(=O)alkyl$. In some embodiments, $R^x$ is acetyl (—$C(=O)Me$). In some embodiments, $R^x$ is —$C(=O)cycloalkyl$ (e.g. —$C(=O)cyclopropyl$).

In some embodiments, $R^x$ is —$C(=O)OR^3$. In some embodiments, $R^x$ is —COOH. In some embodiments, $R^x$ is COOMe.

In some embodiments, $R^x$ is —$NR^3C(=O)R^3$. In certain embodiments, $R^x$ is —$NHC(=O)R^3$ (e.g., $NHC(=O)Me$, $NHC(=O)Et$, $NHC(=O)Pr$, $NHC(=O)^iPr$, $NHC(=O)Bu$, $NHC(=O)^tBu$, $NHC(=O)Cyclopropyl$, $NHC(=O)Cyclobutyl$). In some embodiments, $R^x$ is —$N(CH_3)C(=O)R^3$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)BU$, $N(CH_3)C(=O)^tBU$, $N(CH_3)C(=O)Cyclopropyl$, $N(CH_3)C(=O)Cyclobutyl$).

In some embodiments, $R^x$ is —$NR^3C(=O)OR^3$. In certain embodiments, $R^x$ is —$NHC(=O)OR^3$ (e.g., $NHC(=O)OMe$, $NHC(=O)OEt$, $NHC(=O)OPr$, $NHC(=O)O^iPr$, $NHC(=O)OBu$, $NHC(=O)O^tBu$, $NHC(=O)OCyclopropyl$, $NHC(=O)OCyclobutyl$). In some embodiments, $R^x$ is —$N(CH_3)C(=O)OR^3$ (e.g., $N(CH_3)C(=O)OMe$, $N(CH_3)C(=O)OEt$, $N(CH_3)C(=O)OPr$, $N(CH_3)C(=O)O^iPr$, N(CH₃)C(=O)OBu, N(CH₃)C(=O)O'Bu, N(CH₃)C(=O)OCyclopropyl, N(CH₃)C(=O)OCyclobutyl).

In some embodiments, $R^x$ is —C(=O)N(R³)₂ (e.g., —C(=O)NH₂, —C(=O)NHR³, —C(=O)N(CH₃)R₃). In some embodiments, $R^x$ is —C(=O)NH₂. In certain embodiments, $R^x$ is —C(=O)NHR³ (e.g., —C(=O)NHMe, —C(=O)NHEt, —C(=O)NHPr, —C(=O)NH'Pr, —C(=O)NHBu, —C(=O)NH'Bu, —C(=O)NHCyclopropyl, —C(=O)NHCyclobutyl). In certain embodiments, $R^x$ is —C(=O)N(CH₃)R³ (e.g., —C(=O)NMe₂, —C(=O)N(CH₃)Et, —C(=O)N(CH₃)Pr, —C(=O)N(CH₃)'Pr, —C(=O)N(CH₃)BU, —C(=O)N(CH₃)'Bu, —C(=O)N(CH₃)Cyclopropyl, —C(=O)N(CH₃)Cyclobutyl).

In some embodiments, $R^x$ is —OC(=O)N(R³)₂. In certain embodiments, $R^x$ is —OC(=O)NHR³ (e.g., —OC(=O)NHMe, —OC(=O)NHEt, —OC(=O)NHPr, —OC(=O)NH'Pr, —OC(=O)NHBu, —OC(=O)NH'Bu, —OC(=O)NHCyclopropyl, —OC(=O)NHCyclobutyl). In certain embodiments, $R^x$ is —OC(=O)N(CH₃)R³ (e.g., —OC(=O)NMe₂, —OC(=O)N(CH₃)Et, —OC(=O)N(CH₃)Pr, —OC(=O)N(CH₃)'Pr, —OC(=O)N(CH₃)Bu, —OC(=O)N(CH₃)'Bu, —OC(=O)N(CH₃)Cyclopropyl, —OC(=O)N(CH₃)Cyclobutyl).

In some embodiments, $R^x$ is —S(=O)R³. In certain embodiments, $R^x$ is —S(=O)alkyl (e.g., —S(=O)Me, —S(=O)Et, —S(=O)Pr, —S(=O)'Pr). In certain embodiments, $R^x$ is —S(=O)cycloalkyl (e.g., —S(=O)cyclopropyl, —S(=O)cyclobutyl, —S(=O)cyclopentyl, —S(=O)cyclohexyl).

In some embodiments, $R^x$ is —S(=O)₂R³. In certain embodiments, $R^x$ is —S(=O)₂alkyl (e.g., —S(=O)₂Me, —S(=O)₂Et, —S(=O)₂Pr, —S(=O)₂'Pr). In certain embodiments, $R^x$ is —S(=O)₂cycloalkyl (e.g., —S(=O)₂cyclopropyl, —S(=O)₂cyclobutyl, —S(=O)₂cyclopentyl, —S(=O)₂cyclohexyl). In some embodiments, $R^x$ is S(=O)₂aryl (e.g., S(=O)₂phenyl).

In some embodiments, $R^x$ is —SR³. In certain embodiments, $R^x$ is —Salkyl (e.g., —SMe, —SEt, —SPr, —S'Pr). In certain embodiments, $R^x$ is —Scycloalkyl (e.g., —Scyclopropyl, —Scyclobutyl, —Scyclopentyl, —Scyclohexyl). In certain embodiments, $R^x$ is —Saryl (e.g., Sphenyl).

In some embodiments, $R^x$ is —S(=O)(=NR³)R³. In certain embodiments, $R^x$ is —S(=O)(=NH)R³ (e.g., —S(=O)(=NH)Me, —S(=O)(=NH)Et, —S(=O)(=NH)Pr, —S(=O)(=NH)'Pr, —S(=O)(=NH)Bu, —S(=O)(=NH)'Bu, —S(=O)(=NH)Cyclopropyl, —S(=O)(=NH)Cyclobutyl). In some embodiments, $R^x$ is —S(=O)(=NCH₃)R³ (e.g., —S(=O)(=NCH₃)Me, —S(=O)(=NCH₃)Et, —S(=O)(=NCH₃)Pr, —S(=O)(=NCH₃)'Pr, —S(=O)(=NCH₃)Bu, —S(=O)(=NCH₃)'Bu, —S(=O)(=NCH₃)Cyclopropyl, —S(=O)(=NCH₃)Cyclobutyl).

In some embodiments, $R^x$ is —NR³S(=O)₂R³. In certain embodiments, $R^x$ is —NHS(=O)₂alkyl (e.g., —NHS(=O)₂Me, —NHS(=O)₂Et, —NHS(=O)₂Pr, —NHS(=O)₂'Pr). In certain embodiments, $R^x$ is —NHS(=O)₂cycloalkyl (e.g., —NHS(=O)₂cyclopropyl, —NHS(=O)₂cyclobutyl, —NHS(=O)₂cyclopentyl, —NHS(=O)₂cyclohexyl). In certain embodiments, $R^x$ is —N(CH₃)S(=O)₂alkyl (e.g., —N(CH₃)S(=O)₂Me, —N(CH₃)S(=O)₂Et, —N(CH₃)S(=O)₂Pr, —N(CH₃)S(=O)₂'Pr). In certain embodiments, $R^x$ is —N(CH₃)S(=O)₂cycloalkyl (e.g., —N(CH₃)S(=O)₂cyclopropyl, —N(CH₃)S(=O)₂cyclobutyl, —N(CH₃)S(=O)₂cyclopentyl, —N(CH₃)S(=O)₂cyclohexyl).

In some embodiments, $R^x$ is —S(=O)₂N(R³)₂. (e.g., —S(=O)₂NH₂, —S(=O)₂NHR³, —S(=O)₂N(CH₃)R₃). In some embodiments, $R^x$ is —S(=O)₂NH₂. In some embodiments, $R^x$ is —S(=O)₂NHR³ (e.g., —S(=O)₂NHMe, —S(=O)₂NHEt, —S(=O)₂NHPr, —S(=O)₂NH'Pr, —S(=O)₂NHcyclopropyl, —S(=O)₂NHcyclobutyl). In some embodiments, $R^x$ is —S(=O)₂N(CH₃)R³ (e.g., —S(=O)₂NMe₂, —S(=O)₂N(CH₃)Et, —S(=O)₂N(CH₃)Pr, —S(=O)₂N(CH₃)'Pr, —S(=O)₂N(CH₃)cyclopropyl, —S(=O)₂N(CH₃)cyclobutyl).

In certain embodiments, $X^1$ is N and $X^2$, $X^3$ and $X^4$ are $CR^x$. In a further embodiment, $X^1$ is N and $X^2$, $X^3$ and $X^4$ are CH. In other embodiments, $X^2$ is N and $X^1$, $X^3$ and $X^4$ are $CR^x$. In a further embodiment, $X^2$ is N and $X^1$, $X^3$ and $X^4$ are CH. In other embodiments, $X^3$ is N and $X^1$, $X^2$ and $X^4$ are $CR^x$. In a further embodiment, $X^3$ is N and $X^1$, $X^2$ and $X^4$ are CH. In other embodiments, $X^4$ is N and $X^1$, $X^2$ and $X^3$ are $CR^x$. In a further embodiment, $X^4$ is N and $X^1$, $X^2$ and $X^3$ are CH.

In certain embodiments, $X^1$ and $X^2$ are N and $X^3$ and $X^4$ are $CR^x$. In further embodiments, $X^1$ and $X^2$ are N and $X^3$ and $X^4$ are CH. In certain embodiments, $X^1$ and $X^3$ are N and $X^2$ and $X^4$ are $CR^x$. In further embodiments, $X^1$ and $X^3$ are N and $X^2$ and $X^4$ are CH. In certain embodiments, $X^1$ and $X^4$ are N and $X^2$ and $X^3$ are $CR^x$. In further embodiments, $X^1$ and $X^4$ are N and $X^2$ and $X^3$ are CH. In certain embodiments, $X^2$ and $X^3$ are N and $X^1$ and $X^4$ are $CR^x$. In further embodiments, $X^2$ and $X^3$ are N and $X^1$ and $X^4$ are CH. In certain embodiments, $X^2$ and $X^4$ are N and $X^1$ and $X^3$ are $CR^x$. In further embodiments, $X^2$ and $X^4$ are N and $X^1$ and $X^3$ are CH. In certain embodiments, $X^3$ and $X^4$ are N and $X^1$ and $X^2$ are $CR^x$. In further embodiments, $X^3$ and $X^4$ are N and $X^1$ and $X^2$ are CH. In some embodiments, $X^1$, $X^2$, $X^3$ and $X^4$ are all $CR^x$. In some embodiments, $X^1$, $X^2$, $X^3$ and $X^4$ are all CH.

In some embodiments the invention provides a compound or pharmaceutically acceptable salt thereof, wherein the compound is of Structure (II)

(II)

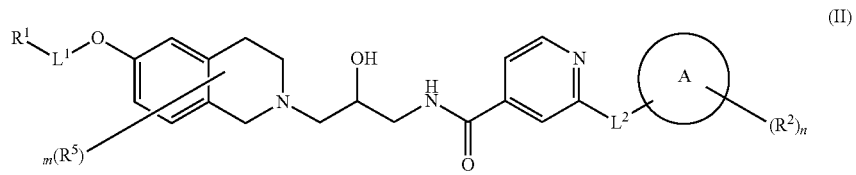

wherein L¹, L², R¹, R², R⁵, A, m and n are as described herein.

In certain embodiments, the invention provides a compound or pharmaceutically acceptable salt thereof wherein the compound is of Structure (IIa).

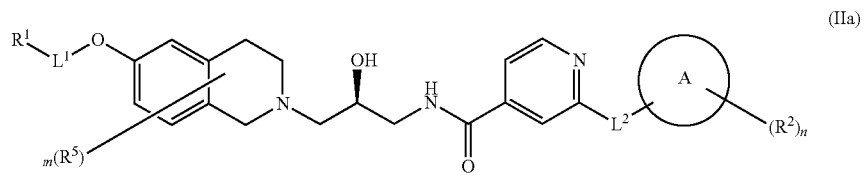
(IIa)

wherein L¹, L², R¹, R², R⁵, A, m and n are as described herein.

In certain embodiments, the invention provides a compound or pharmaceutically acceptable salt thereof wherein the compound is of Structure (IIb).

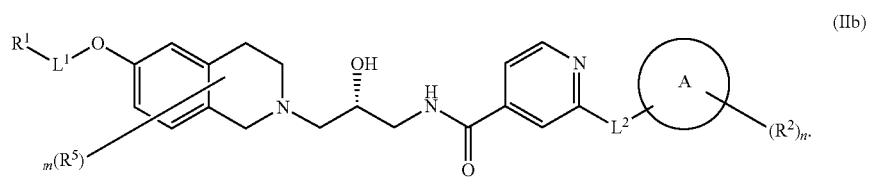
(IIb)

wherein L¹, L², R¹, R², R⁵, A, m and n are as described herein.

In some embodiments, the invention provides a compound or pharmaceutically acceptable salt thereof, wherein the compound is of Structure (III)

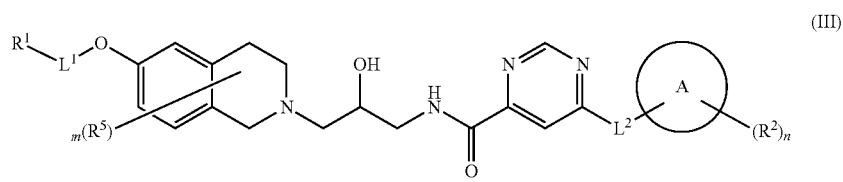
(III)

wherein L¹, L², R¹, R², R⁵, A, m and n are as described herein.

In certain embodiments, the invention provides a compound or pharmaceutically acceptable salt thereof wherein the compound is of Structure (IIIa).

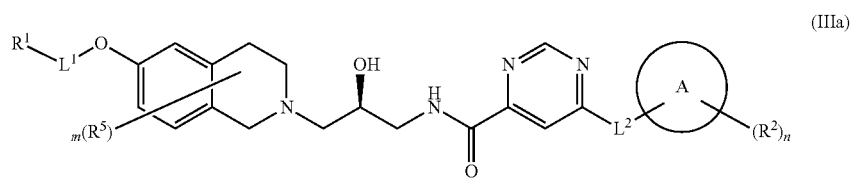
(IIIa)

wherein L¹, L², R¹, R², R⁵, A, m and n are as described herein.

In certain embodiments, the invention provides a compound or pharmaceutically acceptable salt thereof wherein the compound is of Structure (IIIb).

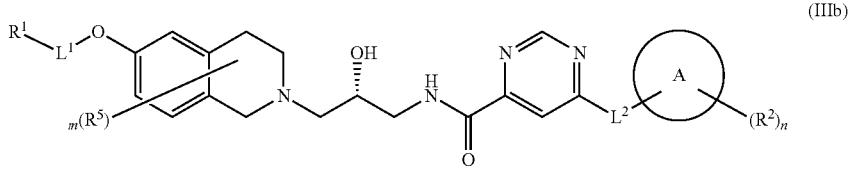

(IIIb)

wherein $L^1$, $L^2$, $R^1$, $R^2$, $R^5$, A, m and n are as described herein.

In some embodiments, the invention provides a compound or pharmaceutically acceptable salt thereof, wherein the compound is of Structure (IV)

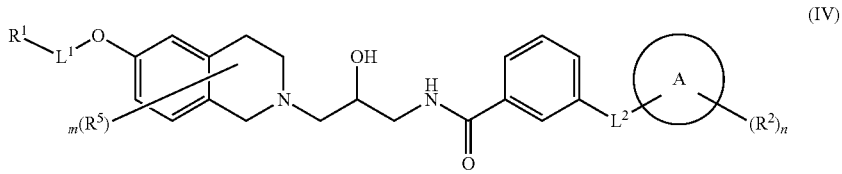

(IV)

wherein $L^1$, $L^2$, $R^1$, $R^2$, $R^5$, A, m and n are as described herein.

In certain embodiments, the invention provides a compound or pharmaceutically acceptable salt thereof wherein the compound is of Structure (IVa).

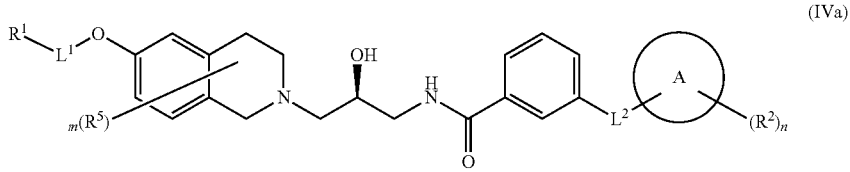

(IVa)

wherein $L^1$, $L^2$, $R^1$, $R^2$, $R^5$, A, m and n are as described herein.

In certain embodiments, the invention provides a compound or pharmaceutically acceptable salt thereof wherein the compound is of Structure (IVb).

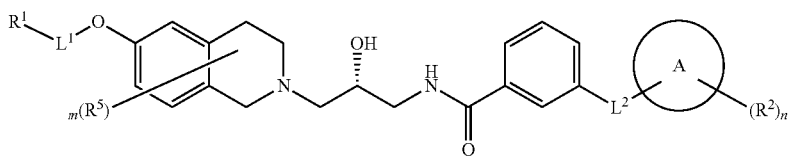

(IVb)

wherein $L^1$, $L^2$, $R^1$, $R^2$, $R^5$, A, m and n are as described herein.

As generally defined herein, $L^1$ is a bond or $C_1$-$C_4$-alkylene substituted with 0-2 instances of $R^6$, wherein each $R^6$ is independently selected from halo, —$C_1$-$C_4$ alkyl, —$C_1$-$C_4$ haloalkyl, —$OC_1$-$C_4$ alkyl, —$OC_1$-$C_4$ haloalkyl, or two $R^6$ can be taken together with the atoms to which they are attached to form a $C_3$-$C_7$ carbocycle or a $C_3$-$C_7$ heterocycle.

In certain embodiments, $L^1$ is a $C_1$-$C_4$-alkylene substituted with 0-2 instances of $R^6$. In further embodiments, $L^1$ is substituted with 0 instances of $R^6$. In some embodiments, $L^1$ is methylene. In some embodiments, $L^1$ is ethylene. In another embodiment, $L^1$ is propylene.

In some instances, $L^1$ is substituted with one instance of $R^6$. In some embodiments, $L^1$ is substituted with 2 instances of $R^6$.

In some embodiments, $R^6$ is $C_1$-$C_4$ alkyl. In further embodiments, $R^6$ is selected from methyl, ethyl, propyl or isopropyl. In further embodiments, $R^6$ is methyl or ethyl. In an exemplary embodiment, $L^1$ is methylene substituted with methyl. In another embodiment, LI is methylene substituted with ethyl.

In some embodiments, $R^6$ is halo. In an exemplary embodiment, $L^1$ is an ethylene substituted with one instance of halo.

In some embodiments of the invention, $R^6$ is haloalkyl. In a further embodiment, $R^6$ is trifluoromethyl (—$CF_3$). In an exemplary embodiment, $L^1$ is a methylene substituted with a trifluoromethyl In some embodiments of the invention, $R^6$ is $-OC_1-C_4$ alkyl (e.g., —OMe, —OEt, —O$^i$Pr, —OPr). In a further embodiment, $R^6$ is methoxy (—OMe).

In some embodiments of the invention, $R^6$—$OC_1-C_4$ haloalkyl (e.g., fluoromethoxy (—OCHF$_2$), trifluoromethoxy (—OCF$_3$))

In some embodiments of the invention, two $R^6$ can be taken together with the atoms to which they are attached to form a $C_3-C_7$ carbocycle (e.g., cyclopropyl, cyclobutyl, cyclopentyl, cyclohexyl) or a $C_3-C_7$ heterocycle (e.g., oxetanyl, azetidinyl, tetrahydropyranyl, tetrahydrofuranyl, pyrrolidinyl, piperidinyl, piperazinyl, morpholinyl, azepanyl). In some embodiments, the two $R^6$ are taken together with the atom to which they are attached to form a cyclopropyl. In some embodiments, the two $R^6$ are taken together with the atom to which they are attached to form a cyclobutyl. In some embodiments, the two $R^6$ are taken together with the atom to which they are attached to form a cyclopentyl. In some embodiments, the two $R^6$ are taken together with the atom to which they are attached to form a cyclohexyl. In some embodiments, the two $R^6$ are taken together with the atom to which they are attached to form an oxetanyl. In some embodiments, the two $R^6$ are taken together with the to which they are attached to form a tetrahydrofuranyl. In some embodiments, the two $R^6$ are taken together with the atom to which they are attached to form a tetrahydropyranyl.

In certain embodiments of the invention, $L^1$ is —CH$_2$—;

In some embodiments, the invention provides a compound or pharmaceutically acceptable salt thereof, wherein the compound is of Structure (V)

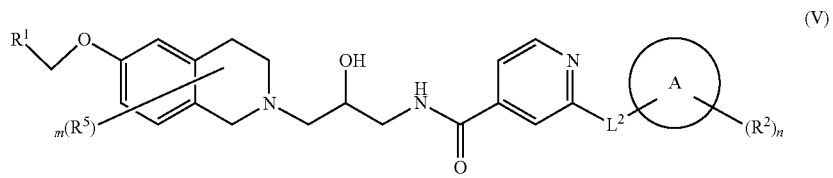

(V)

wherein $L^2$, $R^1$, $R^2$, $R^5$, A, m and n are as described herein.

In certain embodiments, the invention provides a compound or pharmaceutically acceptable salt thereof wherein the compound is of Structure (Va).

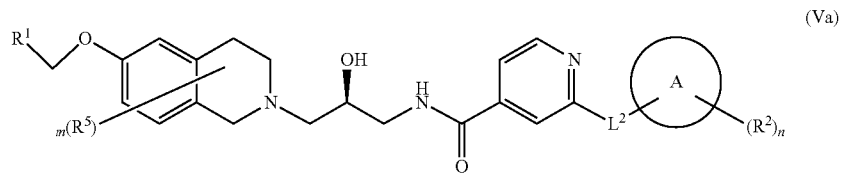

(Va)

wherein $L^2$, $R^1$, $R^2$, $R^5$, A, m and n are as described herein.

In certain embodiments, the invention provides a compound or pharmaceutically acceptable salt thereof wherein the compound is of Structure (Vb).

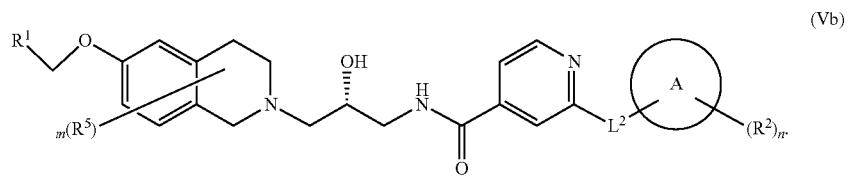

(Vb)

wherein $L^2$, $R^1$, $R^2$, $R^5$, A, m and n are as described herein.

In some embodiments the invention provides a compound or pharmaceutically acceptable salt thereof, wherein the compound is of Structure (VI)

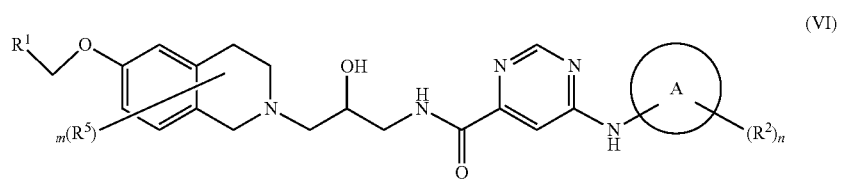

(VI)

wherein $L^2$, $R^1$, $R^2$, $R^5$, A, m and n are as described herein.

In certain embodiments, the invention provides a compound or pharmaceutically acceptable salt thereof wherein the compound is of Structure (VIa).

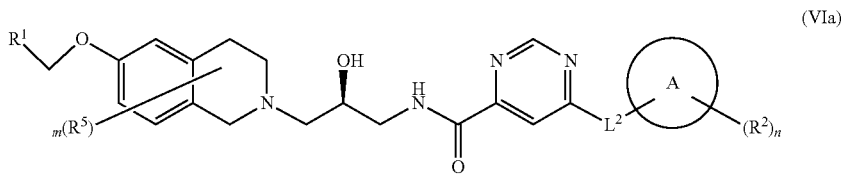

(VIa)

wherein L², R¹, R², R⁵, A, m and n are as described herein.

In certain embodiments, the invention provides a compound or pharmaceutically acceptable salt thereof wherein the compound is of Structure (VIb).

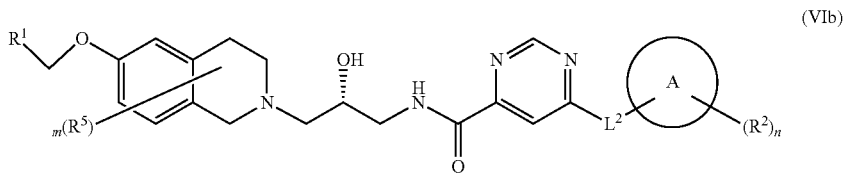

(VIb)

wherein L², R¹, R², R⁵, A, m and n are as described herein.

In some embodiments the invention provides a compound or pharmaceutically acceptable salt thereof, wherein the compound is of Structure (VII)

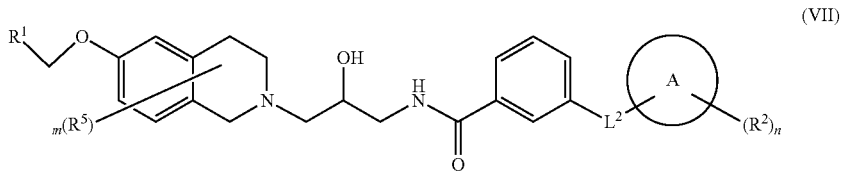

(VII)

wherein L², R¹, R², R⁵, A, m and n are as described herein.

In certain embodiments, the invention provides a compound or pharmaceutically acceptable salt thereof wherein the compound is of Structure (VIIa).

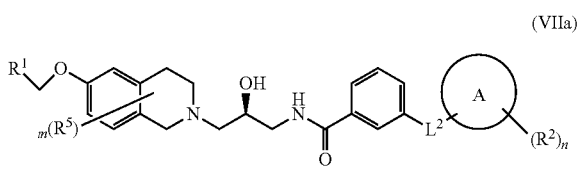

(VIIa)

wherein L², R¹, R², R⁵, A, m and n are as described herein.

In certain embodiments, the invention provides a compound or pharmaceutically acceptable salt thereof wherein the compound is of Structure (VIIb).

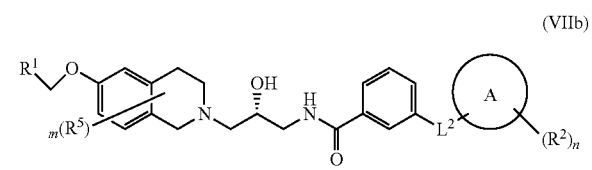

(VIIb)

wherein L², R¹, R², R⁵, A, m and n are as described herein.

In certain embodiments of the invention, $L^1$ is a bond.

In some embodiments the invention provides a compound or pharmaceutically acceptable salt thereof, wherein the compound is of Structure (VIII)

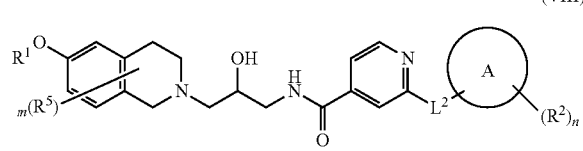

(VIII)

wherein $L^2$, $R^1$, $R^2$, $R^5$, A, m and n are as described herein.

In certain embodiments, the invention provides a compound or pharmaceutically acceptable salt thereof wherein the compound is of Structure (VIIIa).

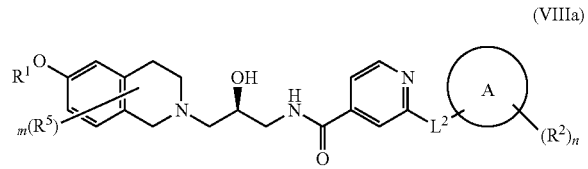

(VIIIa)

wherein $L^2$, $R^1$, $R^2$, $R^5$, A, m and n are as described herein.

In certain embodiments, the invention provides a compound or pharmaceutically acceptable salt thereof wherein the compound is of Structure (VIIIb).

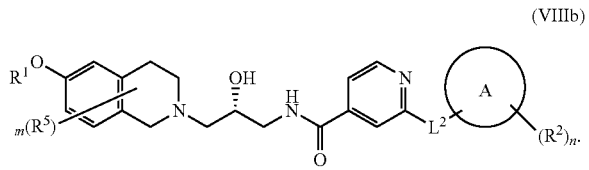

(VIIIb)

wherein $L^2$, $R^1$, $R^2$, $R^5$, A, m and n are as described herein.

In some embodiments the invention provides a compound or pharmaceutically acceptable salt thereof, wherein the compound is of Structure (IX)

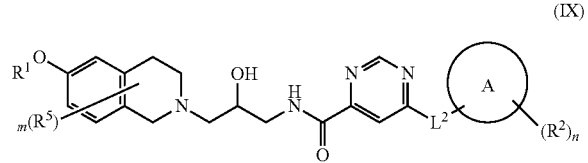

(IX)

wherein $L^2$, $R^1$, $R^2$, $R^5$, A, m and n are as described herein.

In certain embodiments, the invention provides a compound or pharmaceutically acceptable salt thereof wherein the compound is of Structure (IXa).

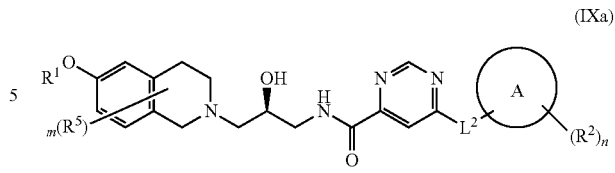

(IXa)

wherein $L^2$, $R^1$, $R^2$, $R^5$, A, m and n are as described herein.

In certain embodiments, the invention provides a compound or pharmaceutically acceptable salt thereof wherein the compound is of Structure (IXb).

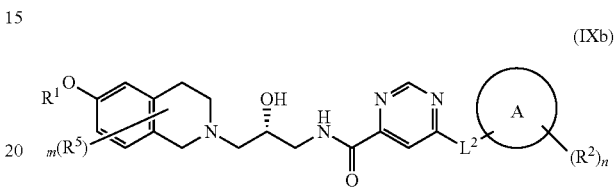

(IXb)

wherein $L^2$, $R^1$, $R^2$, $R^5$, A, m and n are as described herein.

In some embodiments the invention provides a compound or pharmaceutically acceptable salt thereof, wherein the compound is of Structure (X)

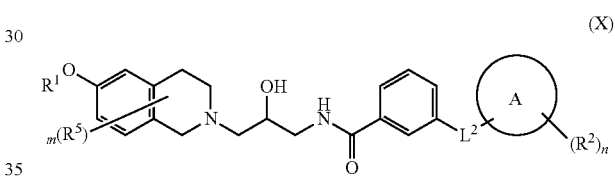

(X)

wherein $L^2$, $R^1$, $R^2$, $R^5$, A, m and n are as described herein.

In certain embodiments, the invention provides a compound or pharmaceutically acceptable salt thereof wherein the compound is of Structure (Xa).

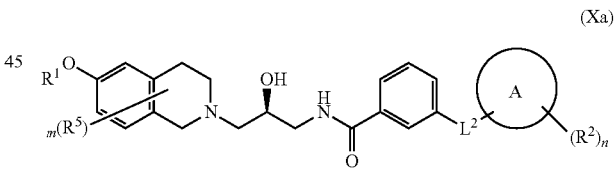

(Xa)

wherein $L^2$, $R^1$, $R^2$, $R^5$, A, m and n are as described herein.

In certain embodiments, the invention provides a compound or pharmaceutically acceptable salt thereof wherein the compound is of Structure (Xb).

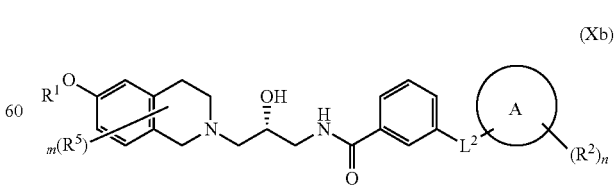

(Xb)

wherein $L^2$, $R^1$, $R^2$, $R^5$, A, m and n are as described herein.

As generally described herein, $L^2$ is a bond, —NH— or —O—.

In some embodiments, L² is —O—.

In certain embodiments of the invention, L² is —NH—.

In some embodiments the invention provides a compound or pharmaceutically acceptable salt thereof, wherein the compound is of Structure (VI)

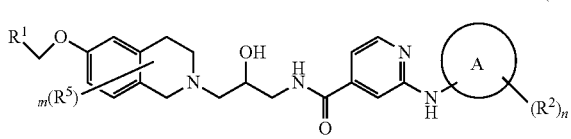
(VI)

wherein R¹, R², R⁵, A, m and n are as described herein.

In certain embodiments, the invention provides a compound or pharmaceutically acceptable salt thereof wherein the compound is of Structure (Va1).

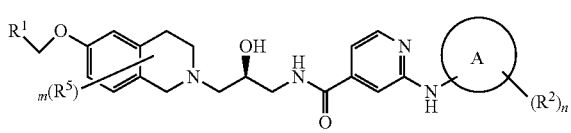
(Va1)

wherein R¹, R², R⁵, A, m and n are as described herein.

In certain embodiments, the invention provides a compound or pharmaceutically acceptable salt thereof wherein the compound is of Structure (Vb1).

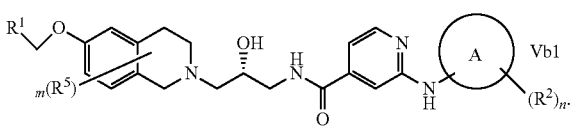
(Vb1)

wherein R¹, R², R⁵, A, m and n are as described herein.

In certain embodiments, the invention provides a compound or pharmaceutically acceptable salt thereof wherein the compound is of Structure (Va1').

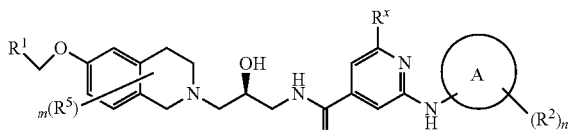
(Va1')

wherein R¹, R², R⁵, Rˣ, A, m and n are as described herein.

In certain embodiments, the invention provides a compound or pharmaceutically acceptable salt thereof wherein the compound is of Structure (Vb1').

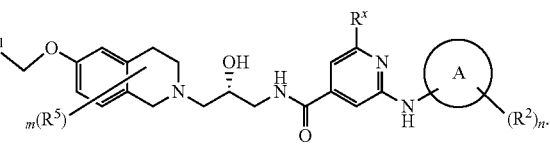
(Vb1')

wherein R¹, R², R⁵, Rˣ, A, m and n are as described herein.

In some embodiments the invention provides a compound or pharmaceutically acceptable salt thereof, wherein the compound is of Structure (VII)

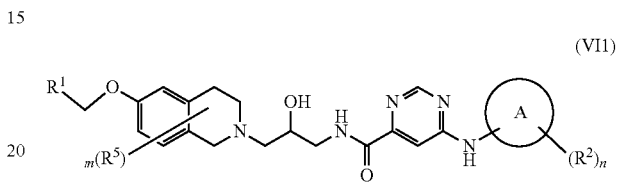
(VII)

wherein R¹, R², R⁵, A, m and n are as described herein.

In certain embodiments, the invention provides a compound or pharmaceutically acceptable salt thereof wherein the compound is of Structure (VIa1).

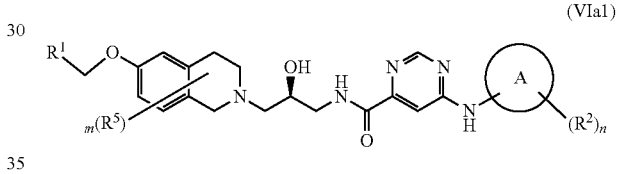
(VIa1)

wherein R¹, R², R⁵, A, m and n are as described herein.

In certain embodiments, the invention provides a compound or pharmaceutically acceptable salt thereof wherein the compound is of Structure (VIb1).

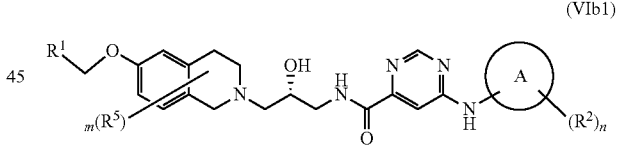
(VIb1)

wherein R¹, R², R⁵, A, m and n are as described herein.

In certain embodiments, the invention provides a compound or pharmaceutically acceptable salt thereof wherein the compound is of Structure (VIa1').

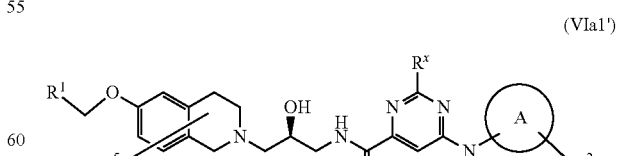
(VIa1')

wherein R¹, R², R⁵, Rˣ, A, m and n are as described herein.

In certain embodiments, the invention provides a compound or pharmaceutically acceptable salt thereof wherein the compound is of Structure (VIb1').

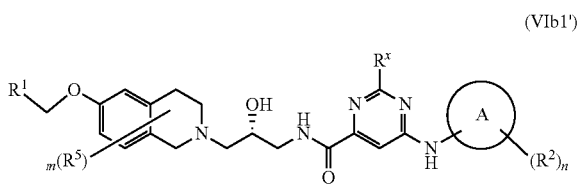

(VIb1')

wherein $R^1$, $R^2$, $R^5$, $R^x$, A, m and n are as described herein.

In some embodiments the invention provides a compound or pharmaceutically acceptable salt thereof, wherein the compound is of Structure (VII1)

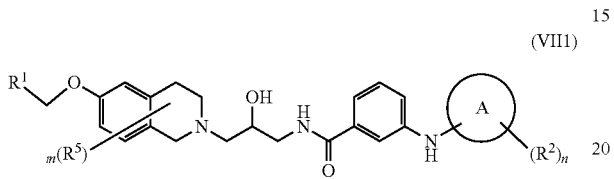

(VII1)

wherein $R^1$, $R^2$, $R^5$, A, m and n are as described herein.

In certain embodiments, the invention provides a compound or pharmaceutically acceptable salt thereof wherein the compound is of Structure (VIIa1).

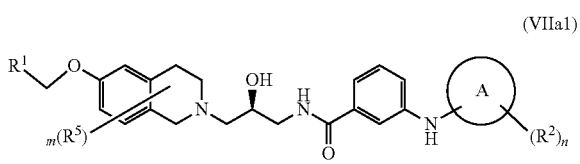

(VIIa1)

wherein $R^1$, $R^2$, $R^5$, A, m and n are as described herein.

In certain embodiments, the invention provides a compound or pharmaceutically acceptable salt thereof wherein the compound is of Structure (VIIb1).

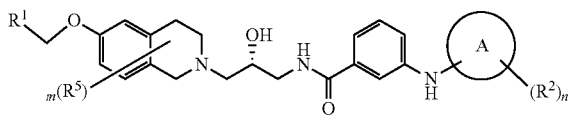

(VIIb1)

wherein $R^1$, $R^2$, $R^5$, A, m and n are as described herein.

In some embodiments, $L^2$ is a bond.

In some embodiments the invention provides a compound or pharmaceutically acceptable salt thereof, wherein the compound is of Structure (V2)

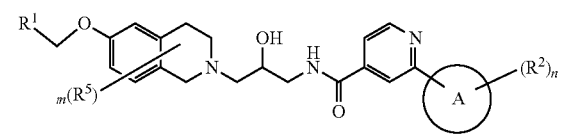

(V2)

wherein $R^1$, $R^2$, $R^5$, A, m and n are as described herein.

In certain embodiments, the invention provides a compound or pharmaceutically acceptable salt thereof wherein the compound is of Structure (Va2).

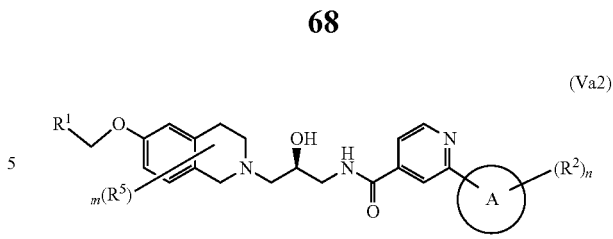

(Va2)

wherein $R^1$, $R^2$, $R^5$, A, m and n are as described herein.

In certain embodiments, the invention provides a compound or pharmaceutically acceptable salt thereof wherein the compound is of Structure (Vb2).

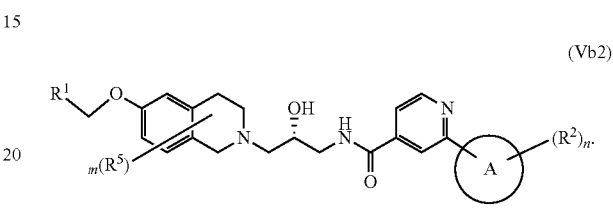

(Vb2)

wherein $R^1$, $R^2$, $R^5$, A, m and n are as described herein.

In some embodiments the invention provides a compound or pharmaceutically acceptable salt thereof, wherein the compound is of Structure (VI2)

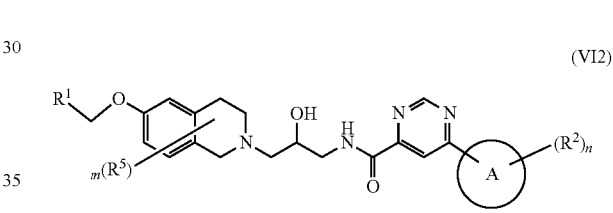

(VI2)

wherein $R^1$, $R^2$, $R^5$, A, m and n are as described herein.

In certain embodiments, the invention provides a compound or pharmaceutically acceptable salt thereof wherein the compound is of Structure (VIa2).

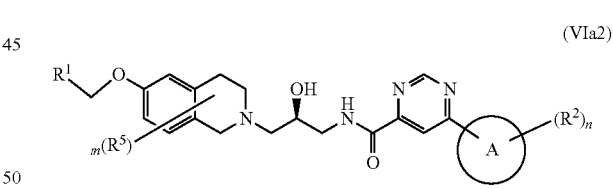

(VIa2)

wherein $R^1$, $R^2$, $R^5$, A, m and n are as described herein.

In certain embodiments, the invention provides a compound or pharmaceutically acceptable salt thereof wherein the compound is of Structure (VIb2).

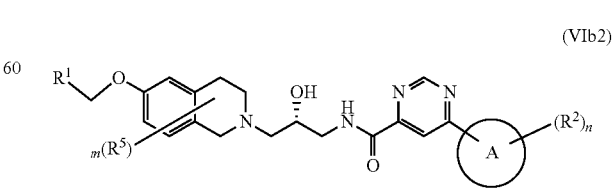

(VIb2)

wherein $R^1$, $R^2$, $R^5$, A, m and n are as described herein.

In some embodiments the invention provides a compound or pharmaceutically acceptable salt thereof, wherein the compound is of Structure (VII2)

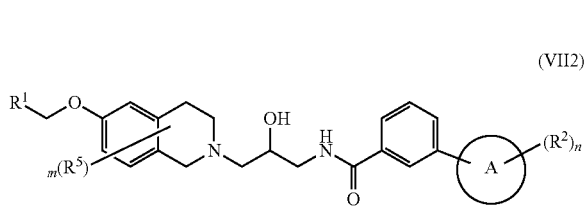

wherein $R^1$, $R^2$, $R^5$, A, m and n are as described herein.

In certain embodiments, the invention provides a compound or pharmaceutically acceptable salt thereof wherein the compound is of Structure (VIIa2).

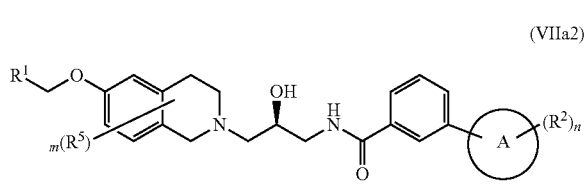

wherein $R^1$, $R^2$, $R^5$, A, m and n are as described herein.

In certain embodiments, the invention provides a compound or pharmaceutically acceptable salt thereof wherein the compound is of Structure (VIIb2).

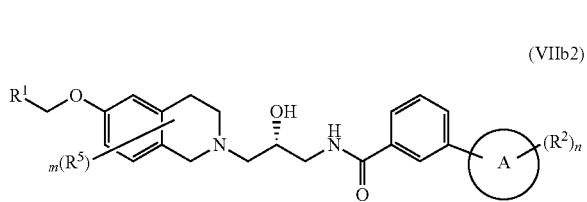

In another aspect of the invention, provided herein are compounds or pharmaceutically acceptable salts thereof according to Formula (XI)

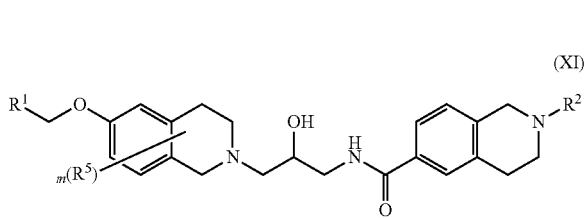

wherein $R^1$, $R^2$, $R^5$ and m are as provided herein

In some embodiments, the compound is of formula (XIa)

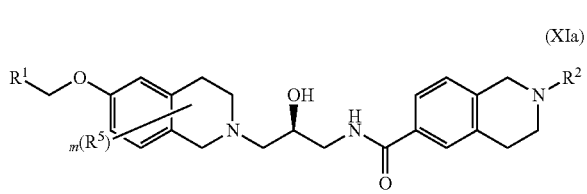

wherein $R^1$, $R^2$, $R^5$ and m are as provided herein.

In some embodiments, the compound is of formula (XIb)

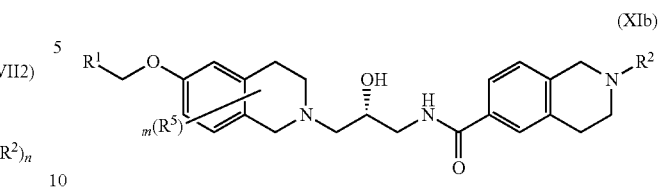

wherein $R^1$, $R^2$, $R^5$ and m are as provided herein

In another aspect of the invention, provided herein are compounds or pharmaceutically acceptable salts thereof according to Formula (XII)

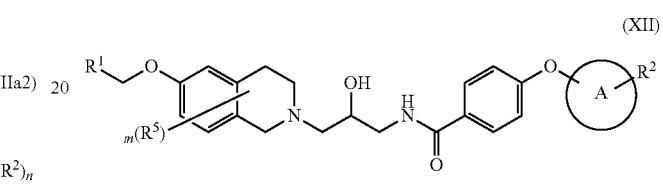

wherein A, $R^1$, $R^2$, $R^5$ and m are as provided herein

In certain embodiments, the compounds are of formula Formula (XIIa)

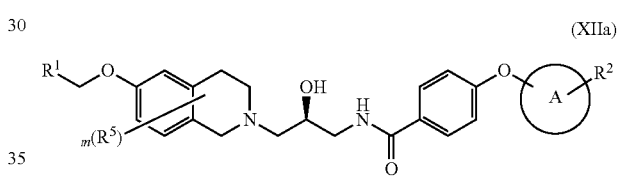

wherein A, $R^1$, $R^2$, $R^5$ and m are as provided herein

In certain embodiments, the compounds are of formula Formula (XIIb)

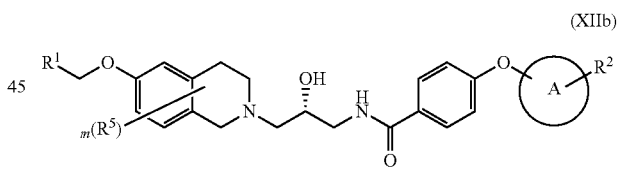

wherein A, $R^1$, $R^2$, $R^5$ and m are as provided herein.

As generally described herein, $R^1$ is a 3-7 membered carbocycle, a 4-7 membered heterocycle or a 5-6 membered heteroaryl substituted with 0-3 instances of $R^4$ (e.g., 0, 1, 2 or 3 instances of $R^4$), wherein each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$. In certain embodiments, $R^4$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$NHR^3$, $N(CH_3)R^3$, —$C(=O)R^3$, —$C(=O)OR^3$, —$NHC(=O)R^3$, —$N(CH_3)C(=O)R^3$, —$NHC(=O)OR^3$, —$N(CH_3)C(=O)OR^3$, —$C(=O)NH(R^3)$, —$C(=O)N(CH_3)(R^3)$, —$OC(=O)NHR^3$, —$OC(=O)N(CH_3)R^3$ —S (=O)R³, —S(=O)₂R³, —SR³, —S(=O)(=NH)R³, —S(=O)(=NCH₃)R³, —NHS(=O)₂R³, —N(CH₃)S(=O)₂R³, —S(=O)₂NHR³ and —S(=O)₂N(CH³)R³.

In some embodiments, R⁴ is =O.

In certain embodiments, R⁴ is halo (e.g., fluoro, chloro, bromo, iodo). In further embodiments, R⁴ is chloro. In some embodiments, R⁴ is fluoro. In some embodiments, R⁴ is bromo. In some embodiments, R⁴ is iodo.

In some embodiments, R⁴ is —CN.

In certain embodiments, R⁴ is —C₁-C₆ alkyl. In further embodiments, R⁴ is methyl. In some embodiments, R⁴ is ethyl. In some embodiments R⁴ is propyl or isopropyl.

In some embodiments, R⁴ is —C₁-C₆ heteroalkyl. In further embodiments, R⁴ is methoxymethyl (—CH₂OCH₃). In some embodiments, R⁴ is aminomethyl (e.g., —CH₂NH₂, —CH₂NHCH₃, —CH₂N(CH₃)₂.

In some embodiments, R⁴ is —C₁-C₆ haloalkyl. In further embodiments, R⁴ is trifluoromethyl (—CF₃).

In some embodiments, R⁴ is —C₃-C₉ carbocyclyl (e.g., cyclopropyl, cyclobutyl, cyclopentyl, cyclohexyl). In some embodiments, R⁴ is cyclopropyl. In some embodiments R⁴ is cyclobutyl. In some embodiments, R⁴ is cyclopentyl. In some embodiments, R⁴ is cyclohexyl, In some embodiments, R⁴ is —C₃-C₉ heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, R⁴ is oxetanyl. In some embodiments, R⁴ is tetrahydropyranyl. In some embodiments, R⁴ is tetrahydrofuranyl. In some embodiments, R⁴ is azetidinyl. In some embodiments, R⁴ is pyrrolidinyl. In some embodiments, R⁴ is piperidinyl. In some embodiments, R⁴ is piperazinyl. In some embodiments, R⁴ is morpholinyl. In some embodiments, R⁴ is azepanyl.

In some embodiments R⁴ is cycloalkylalkyl (e.g., cyclopropylmethyl, cyclobutylmethyl, cyclopentylmethyl, cyclohexylmethyl, cycloheptylmethyl). In some embodiments, R⁴ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, R⁴ is —OR³ (e.g., methoxy, fluoromethoxy (—OCHF₂), trifluoromethoxy (—OCF₃), ethoxy, propoxy, isopropoxy, cyclopropyloxy, cyclobutyloxy). In some embodiments, R⁴ is methoxy. In some embodiments, R⁴ is ethoxy. In some embodiments, R⁴ is propoxy. In some embodiments, R⁴ is isopropoxy. In some embodiments R⁴ is fluoromethoxy. (—OCHF₂). In some embodiments, R⁴ is trifluoromethoxy (—OCF₃).

In some embodiments, R⁴ is —N(R³)₂ (e.g., —NH₂, —NHR³, —N(CH₃)R₃). In some embodiments, R⁴ is —NH₂. In some embodiments, R⁴ is —NHR³ (e.g., —NHMe, —NHEt, —NHPr, —NHⁱPr, —NHcyclopropyl, —NHcyclobutyl). In some embodiments, R⁴ is —N(CH₃)R³ (e.g., —NMe₂, —N(CH₃)Et, —N(CH₃)Pr, —N(CH₃)ⁱPr, —N(CH₃)cyclopropyl, —N(CH₃)cyclobutyl).

In some embodiments, R⁴ is —C(=O)R³. In some embodiments, R⁴ is —C(=O)alkyl. In some embodiments, R⁴ is acetyl (—C(=O)Me). In some embodiments, R⁴ is —C(=O)cycloalkyl (e.g. —C(=O)cyclopropyl).

In some embodiments, R⁴ is —C(=O)OR³. In some embodiments, R⁴ is —COOH. In some embodiments, R⁴ is COOMe.

In some embodiments, R⁴ is —NR³C(=O)R³. In certain embodiments, R⁴ is —NHC(=O)R³ (e.g., NHC(=O)Me, NHC(=O)Et, NHC(=O)Pr, NHC(=O)ⁱPr, NHC(=O)Bu, NHC(=O)ⁱBu, NHC(=O)Cyclopropyl, NHC(=O)Cyclobutyl). In some embodiments, R⁴ is —N(CH₃)C(=O)R³ (e.g., N(CH₃)C(=O)Me, N(CH₃)C(=O)Et, N(CH₃)C(=O)Pr, N(CH₃)C(=O)ⁱPr, N(CH₃)C(=O)BU, N(CH₃)C(=O)ⁱBU, N(CH₃)C(=O)Cyclopropyl, N(CH₃)C(=O)Cyclobutyl).

In some embodiments, R⁴ is —NR³C(=O)OR³. In certain embodiments, R⁴ is —NHC(=O)OR³ (e.g., NHC(=O)OMe, NHC(=O)OEt, NHC(=O)OPr, NHC(=O)OⁱPr, NHC(=O)OBu, NHC(=O)OⁱBu, NHC(=O)OCyclopropyl, NHC(=O)OCyclobutyl). In some embodiments, R⁴ is —N(CH₃)C(=O)OR³ (e.g., N(CH₃)C(=O)OMe, N(CH₃)C(=O)OEt, N(CH₃)C(=O)OPr, N(CH₃)C(=O)OⁱPr, N(CH₃)C(=O)OBu, N(CH₃)C(=O)OⁱBu, N(CH₃)C(=O)OCyclopropyl, N(CH₃)C(=O)OCyclobutyl).

In some embodiments, R⁴ is —C(=O)N(R³)₂ (e.g., —C(=O)NH₂, —C(=O)NHR³, —C(=O)N(CH₃)R₃). In some embodiments, R⁴ is —C(=O)NH₂. In certain embodiments, R⁴ is —C(=O)NHR³ (e.g., —C(=O)NHMe, —C(=O)NHEt, —C(=O)NHPr, —C(=O)NHⁱPr, —C(=O)NHBu, —C(=O)NHⁱBu, —C(=O)NHCyclopropyl, —C(=O)NHCyclobutyl). In certain embodiments, R⁴ is —C(=O)N(CH₃)R³ (e.g., —C(=O)NMe₂, —C(=O)N(CH₃)Et, —C(=O)N(CH₃)Pr, —C(=O)N(CH₃)ⁱPr, —C(=O)N(CH₃)BU, —C(=O)N(CH₃)ⁱBu, —C(=O)N(CH₃)Cyclopropyl, —C(=O)N(CH₃)Cyclobutyl).

In some embodiments, R⁴ is —OC(=O)N(R³)₂. In certain embodiments, R⁴ is —OC(=O)NHR³ (e.g., —OC(=O)NHMe, —OC(=O)NHEt, —OC(=O)NHPr, —OC(=O)NHⁱPr, —OC(=O)NHBu, —OC(=O)NHⁱBu, —OC(=O)NHCyclopropyl, —OC(=O)NHCyclobutyl). In certain embodiments, R⁴ is —OC(=O)N(CH₃)R³ (e.g., —OC(=O)NMe₂, —OC(=O)N(CH₃)Et, —OC(=O)N(CH₃)Pr, —OC(=O)N(CH₃)ⁱPr, —OC(=O)N(CH₃)Bu, —OC(=O)N(CH₃)ⁱBu, —OC(=O)N(CH₃)Cyclopropyl, —OC(=O)N(CH₃)Cyclobutyl).

In some embodiments, R⁴ is —S(=O)R³. In certain embodiments, R⁴ is —S(=O)alkyl (e.g., —S(=O)Me, —S(=O)Et, —S(=O)Pr, —S(=O)ⁱPr). In certain embodiments, R⁴ is —S(=O)cycloalkyl (e.g., —S(=O)cyclopropyl, —S(=O)cyclobutyl, —S(=O)cyclopentyl, —S(=O)cyclohexyl).

In some embodiments, R⁴ is —S(=O)₂R³. In certain embodiments, R⁴ is —S(=O)₂alkyl (e.g., —S(=O)₂Me, —S(=O)₂Et, —S(=O)₂Pr, —S(=O)₂ⁱPr). In certain embodiments, R⁴ is —S(=O)₂cycloalkyl (e.g., —S(=O)₂cyclopropyl, —S(=O)₂cyclobutyl, —S(=O)₂cyclopentyl, —S(=O)₂cyclohexyl).

In some embodiments, R⁴ is S(=O)₂aryl (e.g., S(=O)₂phenyl).

In some embodiments, R⁴ is —SR³. In certain embodiments, R⁴ is —Salkyl (e.g., —SMe, —SEt, —SPr, —SⁱPr). In certain embodiments, R⁴ is —Scycloalkyl (e.g., —Scyclopropyl, —Scyclobutyl, —Scyclopentyl, —Scyclohexyl). In certain embodiments, R⁴ is —Saryl (e.g., Sphenyl).

In some embodiments, R⁴ is —S(=O)(=NR³)R³. In certain embodiments, R⁴ is —S(=O)(=NH)R³ (e.g., —S(=O)(=NH)Me, —S(=O)(=NH)Et, —S(=O)(=NH)Pr, —S(=O)(=NH)ⁱPr, —S(=O)(=NH)Bu, —S(=O)(=NH)ⁱBu, —S(=O)(=NH)Cyclopropyl, —S(=O)(=NH)Cyclobutyl). In some embodiments, R⁴ is —S(=O)(=NCH₃)R³ (e.g., —S(=O)(=NCH₃)Me, —S(=O)(=NCH₃)Et, —S(=O)(=NCH₃)Pr, —S(=O)(=NCH₃)ⁱPr, —S(=O)(=NCH₃)Bu, —S(=O)(=NCH₃)ⁱBu, —S(=O)(=NCH₃)Cyclopropyl, —S(=O)(=NCH₃)Cyclobutyl).

In some embodiments, R⁴ is —NR³S(=O)₂R³. In certain embodiments, R⁴ is —NHS(=O)₂alkyl (e.g., —NHS(=O)₂Me, —NHS(=O)₂Et, —NHS(=O)₂Pr, —NHS (=O)$_2$Tr). In certain embodiments, R$^4$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, R$^4$ is —N(CH$_3$)S(=O)$_2$alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, R$^4$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, R$^4$ is —S(=O)$_2$N(R$^3$)$_2$. (e.g., —S(=O)$_2$NH$_2$, —S(=O)$_2$NHR$^3$, —S(=O)$_2$N(CH$_3$)R$_3$). In some embodiments, R$^4$ is —S(=O)$_2$NH$_2$. In some embodiments, R$^4$ is —S(=O)$_2$NHR$^3$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, R$^4$ is —S(=O)$_2$N(CH$_3$)R$^3$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally defined herein, each R$^3$ is independently selected from H, C$_1$-C$_6$ alkyl, C$_1$-C$_6$ heteroalkyl, C$_3$-C$_7$ carbocyclyl, C$_3$-C$_7$ heterocyclyl, cycloalkylalkyl, heterocyclylalkyl, aryl, 5-6 membered heteroaryl, arylalkyl and heteroarylalkyl, wherein each alkyl, carbocyclyl, heterocyclyl, cycloalkylalkyl, heterocyclylalkyl, aryl, heteroaryl, arylalkyl and heteroarylalkyl is optionally substituted. In some embodiments, each R$^3$ is independently selected from H, C$_1$-C$_6$ alkyl (e.g., methyl, ethyl, propyl, iso-propyl, butyl, iso-butyl, sec-butyl and butyl), C$_3$-C$_7$ carbocyclyl (e.g., cyclopropyl, cyclobutyl, cyclopentyl, cyclohexyl, cycloheptyl), and C$_3$-C$_7$ heterocyclyl (e.g., oxetanyl, aziridinyl, tetrahydrofuranyl, pyrolidinyl, tetrahydropyranyl, piperidinyl, piperazinyl, morpholinyl, azepanyl). In some embodiments, each R$^3$ is independently selected from H and C$_1$-C$_6$ alkyl. In some embodiments, R$^3$ is selected from H, methyl, ethyl, propyl, iso-propyl, butyl, iso-butyl, sec-butyl and tert-butyl. In some embodiments, R$^3$ is selected from H and methyl. In some embodiments R$^3$ is optionally substituted aryl (e.g., phenyl). In some embodiments R$_3$ is aryl substituted with 0-2 instances of OMe or halo. In some embodiments, R$^3$ is C$_1$-C$_6$ heteroalkyl. In certain embodiments, R$^3$ is —(CH$_2$)$_2$N(CH$_3$)$_2$.

In some embodiments, R$^3$ is 5-6 membered heteroaryl (e.g., pyridinyl, pyrimidinyl, pyridazinyl, pyrazinyl, furanyl, thiophenyl, pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, R$^3$ is arylalkyl (e.g., benzyl). In some embodiments, R$^3$ is heteroarylalkyl (e.g., pyridinylmethyl, pyrimidinylmethyl, pyridazinylmethyl, pyrazinylmethyl, furanylmethyl, thiophenylmethyl, pyrrolylmethyl, pyrazolylmethyl, imidazolylmethyl, thiazolylmethyl, oxazolylmethyl, isoxazolylmethyl, isothiazolylmethyl, triazolylmethyl, oxadiazolylmethyl, thiadiazolylmethyl, tetrazolylmethyl). In some embodiments R$^3$ is cycloalkylalkyl (e.g., cyclopropylmethyl, cyclobutylmethyl, cyclopentylmethyl, cyclohexylmethyl, cycloheptylmethyl). In some embodiments, R$^3$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments of the invention, R$^1$ is a 3-7 membered carbocycle substituted with 0-3 instances of R$^4$ (e.g., 0, 1, 2 or 3 instances of R$^4$). In some embodiments of the invention, R$^1$ is a 3-7 membered monocyclic carbocycle (e.g., cyclopropyl, cyclobutyl, cyclopentyl, cyclohexy, cycloheptyl) substituted with 0-3 instances of R$^4$ (e.g., 0, 1, 2 or 3 instances of R$^4$). In some embodiments, R$^1$ is selected from unsubstituted cyclopropyl, unsubstituted cyclobutyl, unsubstituted cyclopentyl, unsubstituted cyclohexyl and unsubstituted cycloheptyl. In some embodiments, R$^1$ is selected from cyclopropyl, cyclobutyl, cyclopentyl, cyclohexyl and cycloheptyl substituted with one instance of R$^4$. In some embodiments, R$^1$ is selected from cyclopropyl, cyclobutyl, cyclopentyl, cyclohexyl and cycloheptyl substituted with one instance of =O, methyl, ethyl, —CN, -halo, —CF$_3$ or —OH. In some embodiments, R$^1$ is selected from cyclopropyl, cyclobutyl, cyclopentyl, cyclohexyl and cycloheptyl substituted with two instances of halo (e.g., fluoro) or methyl. In some embodiments, R$^1$ is selected from cyclopropyl, cyclobutyl, cyclopentyl, cyclohexyl and cycloheptyl substituted with one instance of halo and one instance of methyl.

In some embodiments of the invention, R$^1$ is a 4-7 membered heterocycle substituted with 0-3 instances of R$^4$ (e.g., 0, 1, 2 or 3 instances of R$^4$). In some embodiments of the invention, R$^1$ is a 4-7 membered monocyclic heterocycle (e.g., oxetanyl, tetrahydrofuranyl, tetrahydropyranyl, pyrolidinyl, piperidinyl) substituted with 0-3 instances of R$^4$ (e.g., 0, 1, 2 or 3 instances of R$^4$). In some embodiments, R$^1$ is selected from unsubstituted oxetanyl, unsubstituted tetrahydropyranyl and unsubstituted tetranhydrofuranyl. In some embodiments, R$^1$ is selected from oxetanyl, tetrahydropyranyl and tetranhydrofuranyl substituted with one instance of R$^4$. In some embodiments, R$^1$ is selected from oxetanyl, tetrahydropyranyl and tetranhydrofuranyl substituted with one instance of =O, methyl, ethyl, —CN, -halo, —CF$_3$ or —OH. In some embodiments, R$^1$ is selected from oxetanyl, tetrahydropyranyl and tetranhydrofuranyl substituted with two instances of halo (e.g., fluoro) or methyl. In some embodiments, R$^1$ is selected from oxetanyl, tetrahydropyranyl and tetranhydrofuranyl substituted with one instance of halo and one instance of methyl.

In some embodiments of the invention, R$^1$ is a 5-6 membered heteroaryl substituted with 0-3 instances of R$^4$ (e.g., 0, 1, 2 or 3 instances of R$^4$). In some embodiments, the heteroaryl is a 6-membered nitrogen containing heteroaryl (e.g., pyridinyl, pyrimidinyl, pyridazinyl, pyrazinyl, triazinyl). In certain embodiments, the heteroaryl is a 5-membered heteroaryl. In further embodiments, the heteroaryl is a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, the heteroaryl is selected from pyrazolyl, triazolyl, oxazolyl, isoxazolyl, oxadiazolyl, thiazolyl, and thiadiazolyl.

In some embodiments of the invention, R$^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl))substituted with 0-3 instances of R$^4$ (e.g., 0, 1, 2 or 3 instances of R$^4$). In some embodiments of the invention, R$^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with one instance of C$_1$-C$_6$ alkyl (e.g., methyl, ethyl, propyl, isopropyl). In some embodiments of the invention, R$^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with methyl. In some embodiments of the invention, R¹ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with two instances of $C_1$-$C_6$ alkyl (e.g., methyl, ethyl, propyl, isopropyl). In some embodiments of the invention, R¹ is a 5-membered heteroaryl (e.g., 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with two instances of methyl.

In certain embodiments of the invention, R¹ is selected from:

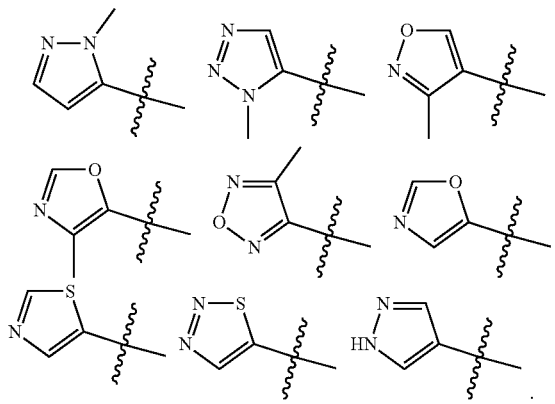

In further embodiments, R¹ is selected from:

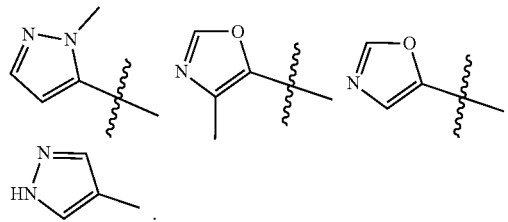

As generally described herein, ring A is selected from a carbocycle, heterocycle, 5-6 member monocyclic heteroaryl and a monocyclic aryl.

In certain embodiments of the invention, ring A is a 4-7 membered monocyclic heterocycle. In some embodiments, ring A is selected from piperidinyl, pyrrolidinyl, oxetanyl, tetrahydrofuranyl, azetidinyl, tetrahydropyranyl, 1,4-dioxan-2-yl and morpholinyl.

In some embodiments, ring A is piperidinyl. In some embodiments, ring A is oxetanyl. In some embodiments, ring A is tetrahydropyranyl. In some embodiments, ring A is morpholinyl.

In certain embodiments, ring A is a 5-6 membered monocyclic heteroaryl. In an exemplary embodiment, Ring A is pyridinyl (e.g., 3-pyridinyl).

In certain embodiments of the invention, ring A is aryl. In some embodiments, ring A is monocyclic aryl. In some embodiments, ring A is bicyclic $C_9$-$C_{10}$ aryl.

In some embodiments, ring A is phenyl.

In certain embodiments of the invention, ring A is a 3-8 membered carbocycle. In some embodiments, ring A is selected from cyclopropyl, cyclobutyl, cyclopentyl, cyclohexyl cycloheptyl, spiro[2.3]hexyl and spiro[3.3]heptyl.

In some embodiments, ring A is cyclopropyl. In some embodiments, ring A is cyclobutyl. In some embodiments, ring A is cyclopentyl. In some embodiments, ring A is cyclohexyl. In some embodiments, ring A is cycloheptyl.

In some embodiments, ring A is a 6-8 membered spirocarbocycle. In exemplary embodiments, A is spiro[2.3]hexyl or spiro[3.3]heptyl.

As generally defined herein, $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, arylalkyl, heteroarylalkyl, —$OR^3$, —$N(R^3)_2$, —$C(=O)R^3$, —$C(=O)OR^3$, $CH_2C(=O)R^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$.

In certain embodiments, $R^2$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$NHR^3$, $N(CH_3)R^3$, —$C(=O)R^3$, —$C(=O)OR^3$, —$NHC(=O)R^3$, —$N(CH_3)C(=O)R^3$, —$NHC(=O)OR^3$, —$N(CH_3)C(=O)OR^3$, —$C(=O)NH(R^3)$, —$C(=O)N(CH_3)(R^3)$, —$OC(=O)NHR^3$, —$OC(=O)N(CH_3)R^3$—$S(=O)R^3$, —$S(=O)_2R^3$, —$SR^3$, —$S(=O)(=NH)R^3$, —$S(=O)(=NCH_3)R^3$, —$NHS(=O)_2R^3$, —$N(CH_3)S(=O)_2R^3$, —$S(=O)_2NHR^3$ and —$S(=O)_2N(CH^3)R^3$.

In certain embodiments, $R^2$ is =O.

In certain embodiments, $R^2$ is halo (e.g., fluoro, chloro, bromo, iodo). In further embodiments, $R^2$ is chloro. In some embodiments, $R^2$ is fluoro. In some embodiments, $R^2$ is bromo. In some embodiments, $R^2$ is iodo.

In some embodiments, $R^2$ is —CN.

In certain embodiments, $R^2$ is —$C_1$-$C_6$ alkyl. In further embodiments, $R^2$ is methyl. In some embodiments, $R^2$ is ethyl. In some embodiments $R^2$ is propyl or isopropyl.

In some embodiments, $R^2$ is —$C_1$-$C_6$ heteroalkyl. In further embodiments, $R^2$ is methoxymethyl (—$CH_2OCH_3$). In some embodiments, $R^2$ is aminomethyl (e.g., —$CH_2NH_2$, —$CH_2NHCH_3$, —$CH_2N(CH_3)_2$.

In some embodiments, $R^2$ is —$C_1$-$C_6$ haloalkyl. In further embodiments, $R^2$ is trifluoromethyl (—$CF_3$).

In some embodiments, $R^2$ is —$C_3$-$C_9$ carbocyclyl (e.g., cyclopropyl, cyclobutyl, cyclopentyl, cyclohexyl). In some embodiments, $R^2$ is cyclopropyl. In some embodiments $R^2$ is cyclobutyl. In some embodiments, $R^2$ is cyclopentyl. In some embodiments, $R^2$ is cyclohexyl, In some embodiments, $R^2$ is —$C_3$-$C_9$ heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^2$ is oxetanyl. In some embodiments, $R^2$ is tetrahydropyranyl. In some embodiments, $R^2$ is tetrahydrofuranyl. In some embodiments, $R^2$ is azetidinyl. In some embodiments, $R^2$ is pyrrolidinyl. In some embodiments, $R^2$ is piperidinyl. In some embodiments, $R^2$ is piperazinyl. In some embodiments, $R^2$ is morpholinyl. In some embodiments, $R^2$ is azepanyl.

In some embodiments $R^2$ is cycloalkylalkyl (e.g., cyclopropylmethyl, cyclobutylmethyl, cyclopentylmethyl, cyclohexylmethyl, cycloheptylmethyl). In some embodiments, $R^2$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^2$ is arylalkyl. In some embodiments, $R^2$ is benzyl.

In some embodiments, $R^2$ is heteroarylalkyl. In some embodiments, $R^2$ is pyridinylmethyl (e.g., pyridinyl-4-methyl).

In some embodiments, $R^2$ is —$OR^3$ (e.g., methoxy, fluoromethoxy (—$OCHF_2$), trifluoromethoxy (—$OCF_3$), ethoxy, propoxy, isopropoxy, cyclopropyloxy, cyclobutyloxy). In some embodiments, $R^2$ is methoxy. In some embodiments, $R^2$ is ethoxy. In some embodiments, $R^2$ is propoxy. In some embodiments, $R^2$ is isopropoxy. In some embodiments $R^2$ is fluoromethoxy. (—$OCHF_2$). In some embodiments, $R^2$ is trifluoromethoxy (—$OCF_3$).

In some embodiments, $R^2$ is —$N(R^3)_2$ (e.g., —$NH_2$, —$NHR^3$, —$N(CH_3)R_3$). In some embodiments, $R^2$ is —$NH_2$. In some embodiments, $R^2$ is —$NHR^3$ (e.g., —NHMe, —NHEt, —NHPr, —$NH^iPr$, —NHcyclopropyl, —NHcyclobutyl). In some embodiments, $R^2$ is —$N(CH_3)R^3$ (e.g., —$NMe_2$, —$N(CH_3)Et$, —$N(CH_3)Pr$, —$N(CH_3)^iPr$, —$N(CH_3)$cyclopropyl, —$N(CH_3)$cyclobutyl).

In some embodiments, $R^2$ is —$C(=O)R^3$. In some embodiments, $R^2$ is —C(=O)alkyl. In some embodiments, $R^2$ is acetyl (—C(=O)Me). In some embodiments, $R^2$ is —C(=O)cycloalkyl (e.g. —C(=O)cyclopropyl). In some embodiments, $R^2$ is C(=O)aryl wherein the aryl is optionally substituted with 0-2 instances of $R^7$. In some embodiments $R^2$ is C(=O)phenyl, wherein the phenyl is optionally substituted with 0-2 instances of halo (e.g., bromo) or alkoxy (e.g., methoxy).

In some embodiments, $R^2$ is —$C(=O)OR^3$. In some embodiments, $R^2$ is —COOH. In some embodiments, $R^2$ is COOMe.

In some embodiments, $R^2$ is —$NR^3C(=O)R^3$. In certain embodiments, $R^2$ is —$NHC(=O)R^3$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^2$ is —$N(CH_3)C(=O)R^3$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)BU$, $N(CH_3)C(=O)^1BU$, $N(CH_3)C(=O)$Cyclopropyl, $N(CH_3)C(=O)$Cyclobutyl).

In some embodiments, $R^2$ is —$NR^3C(=O)OR^3$. In certain embodiments, $R^2$ is —$NHC(=O)OR^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^2$ is —$N(CH_3)C(=O)OR^3$ (e.g., $N(CH_3)C(=O)OMe$, $N(CH_3)C(=O)OEt$, $N(CH_3)C(=O)OPr$, $N(CH_3)C(=O)O^iPr$, $N(CH_3)C(=O)OBu$, $N(CH_3)C(=O)O^tBu$, $N(CH_3)C(=O)OCyclopropyl$, $N(CH_3)C(=O)OCyclobutyl$).

In some embodiments, $R^2$ is —$C(=O)N(R^3)_2$ (e.g., —$C(=O)NH_2$, —$C(=O)NHR^3$, —$C(=O)N(CH_3)R_3$). In some embodiments, $R^2$ is —$C(=O)NH_2$. In certain embodiments, $R^2$ is —$C(=O)NHR^3$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, $R^2$ is —$C(=O)N(CH_3)R^3$ (e.g., —$C(=O)NMe_2$, —$C(=O)N(CH_3)Et$, —$C(=O)N(CH_3)Pr$, —$C(=O)N(CH_3)^iPr$, —$C(=O)N(CH_3)BU$, —$C(=O)N(CH_3)^tBu$, —$C(=O)N(CH_3)Cyclopropyl$, —$C(=O)N(CH_3)Cyclobutyl$).

In some embodiments, $R^2$ is —$OC(=O)N(R^3)_2$. In certain embodiments, $R^2$ is —$OC(=O)NHR^3$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, $R^2$ is —$OC(=O)N(CH_3)R^3$ (e.g., —$OC(=O)NMe_2$, —$OC(=O)N(CH_3)Et$, —$OC(=O)N(CH_3)Pr$, —$OC(=O)N(CH_3)^iPr$, —$OC(=O)N(CH_3)Bu$, —$OC(=O)N(CH_3)^tBu$, —$OC(=O)N(CH_3)Cyclopropyl$, —$OC(=O)N(CH_3)Cyclobutyl$).

In some embodiments, $R^2$ is —$S(=O)R^3$. In certain embodiments, $R^2$ is —S(=O)alkyl (e.g., —S(=O)Me, —S(=O)Et, —S(=O)Pr, —S(=O)$^i$Pr). In certain embodiments, $R^2$ is —S(=O)cycloalkyl (e.g., —S(=O)cyclopropyl, —S(=O)cyclobutyl, —S(=O)cyclopentyl, —S(=O)cyclohexyl).

In some embodiments, $R^2$ is —$S(=O)_2R^3$. In certain embodiments, $R^2$ is —$S(=O)_2$alkyl (e.g., —$S(=O)_2Me$, —$S(=O)_2Et$, —$S(=O)_2Pr$, —$S(=O)_2^iPr$). In certain embodiments, $R^2$ is —$S(=O)_2$cycloalkyl (e.g., —$S(=O)_2$cyclopropyl, —$S(=O)_2$cyclobutyl, —$S(=O)_2$cyclopentyl, —$S(=O)_2$cyclohexyl). In some embodiments, $R^2$ is $S(=O)_2$aryl (e.g., $S(=O)_2$phenyl).

In some embodiments, $R^2$ is —$SR^3$. In certain embodiments, $R^2$ is —Salkyl (e.g., —SMe, —SEt, —SPr, —S$^i$Pr). In certain embodiments, $R^2$ is —Scycloalkyl (e.g., —Scyclopropyl, —Scyclobutyl, —Scyclopentyl, —Scyclohexyl). In certain embodiments, $R^2$ is —Saryl (e.g., Sphenyl).

In some embodiments, $R^2$ is —$S(=O)(=NR^3)R^3$. In certain embodiments, $R^2$ is —$S(=O)(=NH)R^3$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, $R^2$ is —$S(=O)(=NCH_3)R^3$ (e.g., —$S(=O)(=NCH_3)Me$, —$S(=O)(=NCH_3)Et$, —$S(=O)(=NCH_3)Pr$, —$S(=O)(=NCH_3)^iPr$, —$S(=O)(=NCH_3)Bu$, —$S(=O)(=NCH_3)^tBu$, —$S(=O)(=NCH_3)Cyclopropyl$, —$S(=O)(=NCH_3)Cyclobutyl$).

In some embodiments, $R^2$ is —$NR^3S(=O)_2R^3$. In certain embodiments, $R^2$ is —$NHS(=O)_2$alkyl (e.g., —$NHS(=O)_2Me$, —$NHS(=O)_2Et$, —$NHS(=O)_2Pr$, —$NHS(=O)_2Tr$). In certain embodiments, $R^2$ is —$NHS(=O)_2$cycloalkyl (e.g., —$NHS(=O)_2$cyclopropyl, —$NHS(=O)_2$cyclobutyl, —$NHS(=O)_2$cyclopentyl, —$NHS(=O)_2$cyclohexyl). In certain embodiments, $R^2$ is —$N(CH_3)S(=O)_2$alkyl (e.g., —$N(CH_3)S(=O)_2Me$, —$N(CH_3)S(=O)_2Et$, —$N(CH_3)S(=O)_2Pr$, —$N(CH_3)S(=O)_2^iPr$). In certain embodiments, $R^2$ is —$N(CH_3)S(=O)_2$cycloalkyl (e.g., —$N(CH_3)S(=O)_2$cyclopropyl, —$N(CH_3)S(=O)_2$cyclobutyl, —$N(CH_3)S(=O)_2$cyclopentyl, —$N(CH_3)S(=O)_2$cyclohexyl).

In some embodiments, $R^2$ is —$S(=O)_2N(R^3)_2$. (e.g., —$S(=O)_2NH_2$, —$S(=O)_2NHR^3$, —$S(=O)_2N(CH_3)R_3$). In some embodiments, $R^2$ is —$S(=O)_2NH_2$. In some embodiments, $R^2$ is —$S(=O)_2NHR^3$ (e.g., —$S(=O)_2NHMe$, —$S(=O)_2NHEt$, —$S(=O)_2NHPr$, —$S(=O)_2NH^iPr$, —$S(=O)_2NHcyclopropyl$, —$S(=O)_2NHcyclobutyl$). In some embodiments, $R^2$ is —$S(=O)_2N(CH_3)R^3$ (e.g., —$S(=O)_2NMe_2$, —$S(=O)_2N(CH_3)Et$, —$S(=O)_2N(CH_3)Pr$, —$S(=O)_2N(CH_3)^iPr$, —$S(=O)_2N(CH_3)$cyclopropyl, —$S(=O)_2N(CH_3)$cyclobutyl).

As generally defined herein, n is 0, 1, 2 or 3.

In certain embodiments, n is 0. In an exemplary embodiment, ring A is a carbocycle. In some embodiments, ring A is a 3-8 membered carbocycle (e.g., cyclopropyl, cyclobutyl, cyclopentyl, cyclohexyl, cycloheptyl) and n is 0. In a further embodiment, ring A is cyclobutyl and n is 0. In some embodiments, ring A is a 6-8 membered spirocarbocycle (e.g., spiro [2.3]hexyl, spiro [3.3]heptyl)

In an exemplary embodiment, ring A is a 4-7 membered monocyclic heterocycle (e.g., piperidinyl, pyrrolidinyl, oxetanyl, tetrahydrofuranyl, azetidinyl, tetrahydropyranyl, 1,4-dioxan-2-yl and morpholinyl) and n is 0.

In certain embodiments, n is 1. In an exemplary embodiment, ring A is a cycloalkyl (e.g., cyclopropyl, cyclobutyl, cyclopentyl, cyclohexyl, cycloheptyl) and n is 1. In an exemplary embodiment, ring A is a cycloalkyl (e.g., cyclopropyl, cyclobutyl, cyclopentyl, cyclohexyl, cycloheptyl), $R^2$ is selected from =O, halo (e.g., chloro, fluoro, bromo, iodo), $C_1$-$C_4$ alkyl (e.g., methyl, ethyl, propyl, isopropyl) and —OH and n is 1. In an exemplary embodiment, ring A is a 4-7 membered monocyclic heterocycle (e.g., piperidinyl, pyrrolidinyl, oxetanyl, tetrahydrofuranyl, azetidinyl, tetrahydropyranyl, 1,4-dioxan-2-yl and morpholinyl) and n is 1. In some embodiments, ring A is selected from piperidinyl, pyrrolidinyl, oxetanyl, tetrahydrofuranyl, azetidinyl, tetrahydropyranyl, 1,4-dioxan-2-yl and morpholinyl, n is 1 and $R^2$ is selected from from —C(=O)$R^3$, =O, halo (e.g., chloro, fluoro, bromo, iodo), $C_1$-$C_4$ alkyl (e.g., methyl, ethyl, propyl, isopropyl) and —OH. In one exemplary embodiment, A is piperidinyl, n is 1 and $R^2$ is —C(=O)$R^3$. For example, A is piperidinyl, n is 1 and $R^2$ is —C(=O)$CH_3$.

In certain embodiments, n is 2. In an exemplary embodiment, ring A is a cycloalkyl (e.g., cyclopropyl, cyclobutyl, cyclopentyl, cyclohexyl, cycloheptyl) and n is 2. In an exemplary embodiment, ring A is a cycloalkyl (e.g., cyclopropyl, cyclobutyl, cyclopentyl, cyclohexyl, cycloheptyl), each $R^2$ is independently selected from =O, halo (e.g., chloro, fluoro, bromo, iodo), $C_1$-$C_4$ alkyl (e.g., methyl, ethyl, propyl, isopropyl) and —OH and n is 2. In an exemplary embodiment, ring A is a 4-7 membered monocyclic heterocycle (e.g., piperidinyl, pyrrolidinyl, oxetanyl, tetrahydrofuranyl, azetidinyl, tetrahydropyranyl, 1,4-dioxan-2-yl and morpholinyl) and n is 2. In some embodiments, ring A is selected from piperidinyl, pyrrolidinyl, oxetanyl, tetrahydrofuranyl, azetidinyl, tetrahydropyranyl, 1,4-dioxan-2-yl and morpholinyl, n is 2 and each $R^2$ is independently selected from from —C(=O)$R^3$, =O, halo (e.g., chloro, fluoro, bromo, iodo), $C_1$-$C_4$ alkyl (e.g., methyl, ethyl, propyl, isopropyl) and —OH.

In certain embodiments, n is 3.

As generally described herein, each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —O$R^3$, —N($R^3$)$_2$, —C(=O)$R^3$, —C(=O)O$R^3$, —N$R^3$C(=O)$R^3$, —N$R^3$C(=O)O$R^3$, —C(=O)N($R^3$)$_2$, —OC(=O)N($R^3$)$_2$, —S(=O)$R^3$, —S(=O)$_2R^3$, —S$R^3$, —S(=O)(=N$R^3$)$R^3$, —N$R^3$S(=O)$_2R^3$, —S(=O)$_2$N($R^3$)$_2$, or two $R^5$ can be taken together with the atoms to which they are attached to form a —$C_3$-$C_9$ carbocyclyl or a —$C_3$-$C_9$ heterocyclyl;

Each instance of $R^5$ can be independently attached to any available position on either the phenyl or the tetrahydropydidine ring of the isoquinoline moiety.

In certain embodiments, $R^5$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl —O$R^3$, —NH$R^3$, N(CH$_3$)$R^3$, —C(=O)$R^3$, —C(=O)O$R^3$, —NHC(=O)$R^3$, —N(CH$_3$)C(=O)$R^3$, —NHC(=O)O$R^3$, —N(CH$_3$)C(=O)O$R^3$, —C(=O)NH($R^3$), —C(=O)N(CH$_3$)($R^3$), —OC(=O)NH$R^3$, —OC(=O)N(CH$_3$)$R^3$, —S(=O)$R^3$, —S(=O)$_2R^3$, —S$R^3$, —S(=O)(=NH)$R^3$, —S(=O)(=NCH$_3$)$R^3$, —NHS(=O)$_2R^3$, —N(CH$_3$)S(=O)$_2R^3$, —S(=O)$_2$NH$R^3$ and —S(=O)$_2$N(CH$^3$)$R^3$.

In some embodiments, each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, —O$R^3$, —N($R^3$)$_2$, —CO($R^3$), —N$R^3$(CO)$R^3$, —(CO)N($R^3$)$_2$.

In certain embodiments, each $R^5$ is independently selected from halo, —CN and —$C_1$-$C_6$ alkyl.

In certain embodiments, $R^5$ is =O.

In certain embodiments, $R^5$ is halo (e.g., fluoro, chloro, bromo, iodo). In further embodiments, $R^5$ is chloro. In some embodiments, $R^5$ is fluoro. In some embodiments, $R^5$ is bromo. In some embodiments, $R^5$ is iodo.

In some embodiments, $R^5$ is —CN.

In certain embodiments, $R^5$ is —$C_1$-$C_6$ alkyl. In further embodiments, $R^5$ is methyl. In some embodiments, $R^5$ is ethyl. In some embodiments $R^5$ is propyl or isopropyl.

In some embodiments, $R^5$ is —$C_1$-$C_6$ heteroalkyl. In further embodiments, $R^5$ is methoxymethyl (—CH$_2$OCH$_3$). In some embodiments, $R^5$ is aminomethyl (e.g., —CH$_2$NH$_2$, —CH$_2$NHCH$_3$, —CH$_2$N(CH$_3$)$_2$.

In some embodiments, $R^5$ is —$C_1$-$C_6$ haloalkyl. In further embodiments, $R^5$ is trifluoromethyl (—CF$_3$).

In some embodiments, $R^5$ is —$C_3$-$C_9$ carbocyclyl (e.g., cyclopropyl, cyclobutyl, cyclopentyl, cyclohexyl). In some embodiments, $R^5$ is cyclopropyl. In some embodiments $R^5$ is cyclobutyl. In some embodiments $R^5$ is cyclopentyl. In some embodiments, $R^5$ is cyclohexyl, In some embodiments, $R^5$ is —$C_3$-$C_9$ heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^5$ is oxetanyl. In some embodiments, $R^5$ is tetrahydropyranyl. In some embodiments, $R^5$ is tetrahydrofuranyl. In some embodiments, $R^5$ is azetidinyl. In some embodiments, $R^5$ is pyrrolidinyl. In some embodiments, $R^5$ is piperidinyl. In some embodiments, $R^5$ is piperazinyl. In some embodiments, $R^5$ is morpholinyl. In some embodiments, $R^5$ is azepanyl.

In some embodiments, $R^5$ is phenyl. In some embodiments, $R^5$ is 5-6 membered heteroaryl (e.g., pyridinyl, pyrimidinyl, pyridazinyl, pyrazinyl, furanyl, thiophenyl, pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, $R^5$ is arylalkyl (e.g., benzyl). In some embodiments, $R^5$ is heteroarylalkyl (e.g., pyridinylmethyl, pyrimidinylmethyl, pyridazinylmethyl, pyrazinylmethyl, furanylmethyl, thiophenylmethyl, pyrrolylmethyl, pyrazolylmethyl, imidazolylmethyl, thiazolylmethyl, oxazolylmethyl, isoxazolylmethyl, isothiazolylmethyl, triazolylmethyl, oxadiazolylmethyl, thiadiazolylmethyl, tetrazolylmethyl). In some embodiments $R^5$ is cycloalkylalkyl (e.g., cyclopropylmethyl, cyclobutylmethyl, cyclopentylmethyl, cyclohexylmethyl, cycloheptylmethyl). In some embodiments, $R^5$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^5$ is —O$R^3$ (e.g., methoxy, fluoromethoxy (—OCHF$_2$), trifluoromethoxy (—OCF$_3$), ethoxy, propoxy, isopropoxy, cyclopropyloxy, cyclobutyloxy). In some embodiments, $R^5$ is methoxy. In some embodiments, $R^5$ is ethoxy. In some embodiments, $R^5$ is propoxy. In some embodiments, $R^5$ is isopropoxy. In some embodiments $R^5$ is fluoromethoxy. (—OCHF$_2$). In some embodiments, $R^5$ is trifluoromethoxy (—OCF$_3$).

In some embodiments, $R^5$ is —N($R^3$)$_2$ (e.g., —NH$_2$, —NH$R^3$, —N(CH$_3$)$R_3$). In some embodiments, $R^5$ is —NH$_2$. In some embodiments, $R^5$ is —NH$R^3$ (e.g., —NHMe, —NHEt, —NHPr, —NH$^i$Pr, —NHcyclopropyl, —NHcyclobutyl). In some embodiments, $R^5$ is —N(CH$_3$)R$^3$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl).

In some embodiments, $R^5$ is —C(=O)R$^3$. In some embodiments, $R^5$ is —C(=O)alkyl. In some embodiments, $R^5$ is acetyl (—C(=O)Me). In some embodiments, $R^5$ is —C(=O)cycloalkyl (e.g. —C(=O)cyclopropyl).

In some embodiments, $R^5$ is —C(=O)OR$^3$. In some embodiments, $R^5$ is —COOH. In some embodiments, $R^5$ is COOMe.

In some embodiments, $R^5$ is —NR$^3$C(=O)R$^3$. In certain embodiments, $R^5$ is —NHC(=O)R$^3$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^5$ is —N(CH$_3$)C(=O)R$^3$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)BU, N(CH$_3$)C(=O)$^1$BU, N(CH$_3$)C(=O)Cyclopropyl, N(CH$_3$)C(=O)Cyclobutyl).

In some embodiments, $R^5$ is —NR$^3$C(=O)OR$^3$. In certain embodiments, $R^5$ is —NHC(=O)OR$^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^5$ is —N(CH$_3$)C(=O)OR$^3$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, $R^5$ is —C(=O)N(R$^3$)$_2$ (e.g., —C(=O)NH$_2$, —C(=O)NHR$^3$, —C(=O)N(CH$_3$)R$_3$). In some embodiments, $R^5$ is —C(=O)NH$_2$. In certain embodiments, $R^5$ is —C(=O)NHR$^3$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, $R^5$ is —C(=O)N(CH$_3$)R$^3$ (e.g., —C(=O)NMe$_2$, —C(=O)N(CH$_3$)Et, —C(=O)N(CH$_3$)Pr, —C(=O)N(CH$_3$)$^i$Pr, —C(=O)N(CH$_3$)BU, —C(=O)N(CH$_3$)$^t$Bu, —C(=O)N(CH$_3$)Cyclopropyl, —C(=O)N(CH$_3$)Cyclobutyl).

In some embodiments, $R^5$ is —OC(=O)N(R$^3$)$_2$. In certain embodiments, $R^5$ is —OC(=O)NHR$^3$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, $R^5$ is —OC(=O)N(CH$_3$)R$^3$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)$^t$Bu, —OC(=O)N(CH$_3$)Cyclopropyl, —OC(=O)N(CH$_3$)Cyclobutyl).

In some embodiments, $R^5$ is —S(=O)R$^3$. In certain embodiments, $R^5$ is —S(=O)alkyl (e.g., —S(=O)Me, —S(=O)Et, —S(=O)Pr, —S(=O)$^i$Pr). In certain embodiments, $R^5$ is —S(=O)cycloalkyl (e.g., —S(=O)cyclopropyl, —S(=O)cyclobutyl, —S(=O)cyclopentyl, —S(=O)cyclohexyl).

In some embodiments, $R^5$ is —S(=O)$_2$R$^3$. In certain embodiments, $R^5$ is —S(=O)$_2$alkyl (e.g., —S(=O)$_2$Me, —S(=O)$_2$Et, —S(=O)$_2$Pr, —S(=O)$_2$$^i$Pr). In certain embodiments, $R^5$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In certain embodiments, $R^5$ is S(=O)$_2$aryl (e.g., S(=O)$_2$phenyl).

In some embodiments, $R^5$ is —SR$^3$. In certain embodiments, $R^5$ is —Salkyl (e.g., —SMe, —SEt, —SPr, —S$^i$Pr). In certain embodiments, $R^5$ is —Scycloalkyl (e.g., —Scyclopropyl, —Scyclobutyl, —Scyclopentyl, —Scyclohexyl). In certain embodiments, $R^5$ is —Saryl (e.g., Sphenyl).

In some embodiments, $R^5$ is —S(=O)(=NR$^3$)R$^3$. In certain embodiments, $R^5$ is —S(=O)(=NH)R$^3$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, $R^5$ is —S(=O)(=NCH$_3$)R$^3$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, $R^5$ is —NR$^3$S(=O)$_2$R$^3$. In certain embodiments, $R^5$ is —NHS(=O)$_2$alkyl (e.g., —NHS(=O)$_2$Me, —NHS(=O)$_2$Et, —NHS(=O)$_2$Pr, —NHS(=O)$_2$Tr). In certain embodiments, $R^5$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, $R^5$ is —N(CH$_3$)S(=O)$_2$alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, $R^5$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, $R^5$ is —S(=O)$_2$N(R$^3$)$_2$. (e.g., —S(=O)$_2$NH$_2$, —S(=O)$_2$NHR$^3$, —S(=O)$_2$N(CH$_3$)R$_3$). In some embodiments, $R^5$ is —S(=O)$_2$NH$_2$. In some embodiments, $R^5$ is —S(=O)$_2$NHR$^3$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, $R^5$ is —S(=O)$_2$N(CH$_3$)R$^3$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

In some embodiments of the invention, two $R^5$ can be taken together with the atoms to which they are attached to form a $C_3$-$C_7$ carbocycle (e.g., cyclopropyl, cyclobutyl, cyclopentyl, cyclohexyl) or a $C_3$-$C_7$ heterocycle (e.g., oxetanyl, azetidinyl, tetrahydropyranyl, tetrahydrofuranyl, pyrrolidinyl, piperidinyl, piperazinyl, morpholinyl, azepanyl). In some embodiments, the two $R^5$ are taken together with the atom to which they are attached to form a cyclopropyl. In some embodiments, the two $R^5$ are taken together with the atom to which they are attached to form a cyclobutyl. In some embodiments, the two $R^5$ are taken together with the atom to which they are attached to form a cyclopentyl. In some embodiments, the two $R^5$ are taken together with the atom to which they are attached to form a cyclohexyl. In some embodiments, the two $R^5$ are taken together with the atom to which they are attached to form an oxetanyl. In some embodiments, the two $R^5$ are taken together with the atom to which they are attached to form a tetrahydrofuranyl. In some embodiments, the two $R^5$ are taken together with the atom to which they are attached to form a tetrahydropyranyl.

As generally described herein, each $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ or —S(=O)$_2$N(R$^3$)$_2$.

Each instance of $R^7$ can be independently attached to any available position of the underlying moiety.

In certain embodiments, $R^7$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl —$OR^3$, —$NHR^3$, $N(CH_3)R^3$, —$C(=O)R^3$, —$C(=O)OR^3$, —NHC$(=O)R^3$, —$N(CH_3)C(=O)R^3$, —$NHC(=O)OR^3$, —$N(CH_3)C(=O)OR^3$, —$C(=O)NH(R^3)$, —$C(=O)N(CH_3)(R^3)$, —$OC(=O)NHR^3$, —$OC(=O)N(CH_3)R^3$, —$S(=O)R^3$, —$S(=O)_2R^3$, —$SR^3$, —$S(=O)(=NH)R^3$, —$S(=O)(=NCH_3)R^3$, —$NHS(=O)_2R^3$, —$N(CH_3)S(=O)_2R^3$, —$S(=O)_2NHR^3$ and —$S(=O)_2N(CH^3)R^3$.

In some embodiments, each $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, —$OR^3$, —$N(R^3)_2$, —$CO(R^3)$, —$NR^3(CO)R^3$, —(CO)$N(R^3)_2$.

In certain embodiments, each $R^7$ is independently selected from halo, —CN and —$C_1$-$C_6$ alkyl.

In certain embodiments, $R^7$ is =O.

In certain embodiments, $R^7$ is halo (e.g., fluoro, chloro, bromo, iodo). In further embodiments, $R^7$ is chloro. In some embodiments, $R^7$ is fluoro. In some embodiments, $R^7$ is bromo. In some embodiments, $R^7$ is iodo.

In some embodiments, $R^7$ is —CN.

In certain embodiments, $R^7$ is —$C_1$-$C_6$ alkyl. In further embodiments, $R^7$ is methyl. In some embodiments, $R^7$ is ethyl. In some embodiments $R^7$ is propyl or isopropyl.

In some embodiments, $R^7$ is —$C_1$-$C_6$ heteroalkyl. In further embodiments, $R^7$ is methoxymethyl (—$CH_2OCH_3$). In some embodiments, $R^7$ is aminomethyl (e.g., —$CH_2NH_2$, —$CH_2NHCH_3$, —$CH_2N(CH_3)_2$, —$CH_2CH_2N(CH_3)_2$.

In some embodiments, $R^7$ is —$C_1$-$C_6$ haloalkyl. In further embodiments, $R^7$ is trifluoromethyl (—$CF_3$).

In some embodiments, $R^7$ is —$C_3$-$C_9$ carbocyclyl (e.g., cyclopropyl, cyclobutyl, cyclopentyl, cyclohexyl). In some embodiments, $R^7$ is cyclopropyl. In some embodiments $R^7$ is cyclobutyl. In some embodiments, $R^7$ is cyclopentyl. In some embodiments, $R^7$ is cyclohexyl, In some embodiments, $R^7$ is —$C_3$-$C_9$ heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^7$ is oxetanyl. In some embodiments, $R^7$ is tetrahydropyranyl. In some embodiments, $R^7$ is tetrahydrofuranyl. In some embodiments, $R^7$ is azetidinyl. In some embodiments, $R^7$ is pyrrolidinyl. In some embodiments, $R^7$ is piperidinyl. In some embodiments, $R^7$ is piperazinyl. In some embodiments, $R^7$ is morpholinyl. In some embodiments, $R^7$ is azepanyl.

In some embodiments, $R^7$ is phenyl. In some embodiments, $R^7$ is 5-6 membered heteroaryl (e.g., pyridinyl, pyrimidinyl, pyridazinyl, pyrazinyl, furanyl, thiophenyl, pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, $R^7$ is arylalkyl (e.g., benzyl). In some embodiments, $R^7$ is heteroarylalkyl (e.g., pyridinylmethyl, pyrimidinylmethyl, pyridazinylmethyl, pyrazinylmethyl, furanylmethyl, thiophenylmethyl, pyrrolylmethyl, pyrazolylmethyl, imidazolylmethyl, thiazolylmethyl, oxazolylmethyl, isoxazolylmethyl, isothiazolylmethyl, triazolylmethyl, oxadiazolylmethyl, thiadiazolylmethyl, tetrazolylmethyl). In some embodiments $R^7$ is cycloalkylalkyl (e.g., cyclopropylmethyl, cyclobutylmethyl, cyclopentylmethyl, cyclohexylmethyl, cycloheptylmethyl). In some embodiments, $R^7$ is heterocyclylalkyl (e.g., oxetanylmethyl, aziridinylmethyl, tetrahydrofuranylmethyl, pyrrolidinylmethyl, tetrahydropyranylmethyl, piperidinylmethyl, piperazinylmethyl, morpholinylmethyl, azepanylmethyl).

In some embodiments, $R^7$ is —$OR^3$ (e.g., methoxy, fluoromethoxy (—$OCHF_2$), trifluoromethoxy (—$OCF_3$), ethoxy, propoxy, isopropoxy, cyclopropyloxy, cyclobutyloxy). In some embodiments, $R^7$ is methoxy. In some embodiments, $R^7$ is ethoxy. In some embodiments, $R^7$ is propoxy. In some embodiments, $R^7$ is isopropoxy. In some embodiments $R^7$ is fluoromethoxy. (—$OCHF_2$). In some embodiments, $R^7$ is trifluoromethoxy (—$OCF_3$).

In some embodiments, $R^7$ is —$N(R^3)_2$ (e.g., —$NH_2$, —$NHR^3$, —$N(CH_3)R_3$). In some embodiments, $R^7$ is —$NH_2$. In some embodiments, $R^7$ is —$NHR^3$ (e.g., —NHMe, —NHEt, —NHPr, —$NH^iPr$, —NHcyclopropyl, —NHcyclobutyl). In some embodiments, $R^7$ is —$N(CH_3)R^3$ (e.g., —$NMe_2$, —$N(CH_3)Et$, —$N(CH_3)Pr$, —$N(CH_3)^iPr$, —$N(CH_3)cyclopropyl$, —$N(CH_3)cyclobutyl$).

In some embodiments, $R^7$ is —$C(=O)R^3$. In some embodiments, $R^7$ is —$C(=O)alkyl$. In some embodiments, $R^7$ is acetyl (—$C(=O)Me$). In some embodiments, $R^7$ is —$C(=O)(C_3$-$C_7)cycloalkyl$ (e.g., —$C(=O)cyclopropyl$). In some embodiments, $R^7$ is —$C(=O)heteroalkyl$.

In some embodiments, $R^7$ is —$C(=O)OR^3$. In some embodiments, $R^7$ is —COOH. In some embodiments, $R^7$ is COOMe.

In some embodiments, $R^7$ is —$NR^3C(=O)R^3$. In certain embodiments, $R^7$ is —$NHC(=O)R^3$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^7$ is —$N(CH_3)C(=O)R^3$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)BU$, $N(CH_3)C(=O)^1BU$, $N(CH_3)C(=O)Cyclopropyl$, $N(CH_3)C(=O)Cyclobutyl$).

In some embodiments, $R^7$ is —$NR^3C(=O)OR^3$. In certain embodiments, $R^7$ is —$NHC(=O)OR^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^7$ is —$N(CH_3)C(=O)OR^3$ (e.g., $N(CH_3)C(=O)OMe$, $N(CH_3)C(=O)OEt$, $N(CH_3)C(=O)OPr$, $N(CH_3)C(=O)O^iPr$, $N(CH_3)C(=O)OBu$, $N(CH_3)C(=O)O^tBu$, $N(CH_3)C(=O)OCyclopropyl$, $N(CH_3)C(=O)OCyclobutyl$).

In some embodiments, $R^7$ is —$C(=O)N(R^3)_2$ (e.g., —$C(=O)NH_2$, —$C(=O)NHR^3$, —$C(=O)N(CH_3)R_3$). In some embodiments, $R^7$ is —$C(=O)NH_2$. In certain embodiments, $R^7$ is —$C(=O)NHR^3$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, $R^7$ is —$C(=O)N(CH_3)R^3$ (e.g., —$C(=O)NMe_2$, —$C(=O)N(CH_3)Et$, —$C(=O)N(CH_3)Pr$, —$C(=O)N(CH_3)^iPr$, —$C(=O)N(CH_3)BU$, —$C(=O)N(CH_3)^tBu$, —$C(=O)N(CH_3)Cyclopropyl$, —$C(=O)N(CH_3)Cyclobutyl$).

In some embodiments, $R^7$ is —$OC(=O)N(R^3)_2$. In certain embodiments, $R^7$ is —$OC(=O)NHR^3$ (e.g., —OC(=O)NHMe, —OC(=O)NHEt, —OC(=O)NHPr, —OC(=O)NH$^i$Pr, —OC(=O)NHBu, —OC(=O)NH$^7$Bu, —OC(=O)NHCyclopropyl, —OC(=O)NHCyclobutyl). In certain embodiments, $R^7$ is —$OC(=O)N(CH_3)R^3$ (e.g., —$OC(=O)NMe_2$, —$OC(=O)N(CH_3)Et$, —$OC(=O)N(CH_3)Pr$, —$OC(=O)N(CH_3)^iPr$, —$OC(=O)N(CH_3)Bu$, —$OC(=O)N(CH_3)^tBu$, —$OC(=O)N(CH_3)Cyclopropyl$, —$OC(=O)N(CH_3)Cyclobutyl$).

In some embodiments, $R^7$ is —$S(=O)R^3$. In certain embodiments, $R^7$ is —$S(=O)alkyl$ (e.g., —$S(=O)Me$, —$S(=O)Et$, —$S(=O)Pr$, —$S(=O)^iPr$). In certain embodiments, $R^7$ is —$S(=O)cycloalkyl$ (e.g., —$S(=O)cyclopropyl$, —$S(=O)cyclobutyl$, —$S(=O)cyclopentyl$, —$S(=O)cyclohexyl$).

In some embodiments, R⁷ is —S(=O)₂R³. In certain embodiments, R⁷ is —S(=O)₂alkyl (e.g., —S(=O)₂Me, —S(=O)₂Et, —S(=O)₂Pr, —S(=O)₂ⁱPr). In certain embodiments, R⁷ is —S(=O)₂cycloalkyl (e.g., —S(=O)₂cyclopropyl, —S(=O)₂cyclobutyl, —S(=O)₂cyclopentyl, —S(=O)₂cyclohexyl). In some embodiments, R⁷ is S(=O)₂aryl (e.g., S(=O)₂phenyl).

In some embodiments, R⁷ is —SR³. In certain embodiments, R⁷ is —Salkyl (e.g., —SMe, —SEt, —SPr, —SⁱPr). In certain embodiments, R⁷ is —Scycloalkyl (e.g., —Scyclopropyl, —Scyclobutyl, —Scyclopentyl, —Scyclohexyl). In certain embodiments, R⁷ is —Saryl (e.g., Sphenyl).

In some embodiments, R⁷ is —S(=O)(=NR³)R³. In certain embodiments, R⁷ is —S(=O)(=NH)R³ (e.g., —S(=O)(=NH)Me, —S(=O)(=NH)Et, —S(=O)(=NH)Pr, —S(=O)(=NH)ⁱPr, —S(=O)(=NH)Bu, —S(=O)(=NH)ᵗBu, —S(=O)(=NH)Cyclopropyl, —S(=O)(=NH)Cyclobutyl). In some embodiments, R⁷ is —S(=O)(=NCH₃)R³ (e.g., —S(=O)(=NCH₃)Me, —S(=O)(=NCH₃)Et, —S(=O)(=NCH₃)Pr, —S(=O)(=NCH₃)ⁱPr, —S(=O)(=NCH₃)Bu, —S(=O)(=NCH₃)ᵗBu, —S(=O)(=NCH₃)Cyclopropyl, —S(=O)(=NCH₃)Cyclobutyl).

In some embodiments, R⁷ is —NR³S(=O)₂R³. In certain embodiments, R⁷ is —NHS(=O)₂alkyl (e.g., —NHS(=O)₂Me, —NHS(=O)₂Et, —NHS(=O)₂Pr, —NHS(=O)₂Tr). In certain embodiments, R⁷ is —NHS(=O)₂cycloalkyl (e.g., —NHS(=O)₂cyclopropyl, —NHS(=O)₂cyclobutyl, —NHS(=O)₂cyclopentyl, —NHS(=O)₂cyclohexyl). In certain embodiments, R⁷ is —N(CH₃)S(=O)₂alkyl (e.g., —N(CH₃)S(=O)₂Me, —N(CH₃)S(=O)₂Et, —N(CH₃)S(=O)₂Pr, —N(CH₃)S(=O)₂ⁱPr). In certain embodiments, R⁷ is —N(CH₃)S(=O)₂cycloalkyl (e.g., —N(CH₃)S(=O)₂cyclopropyl, —N(CH₃)S(=O)₂cyclobutyl, —N(CH₃)S(=O)₂cyclopentyl, —N(CH₃)S(=O)₂cyclohexyl).

In some embodiments, R⁷ is —S(=O)₂N(R³)₂. (e.g., —S(=O)₂NH₂, —S(=O)₂NHR³, —S(=O)₂N(CH₃)R₃). In some embodiments, R⁷ is —S(=O)₂NH₂. In some embodiments, R⁷ is —S(=O)₂NHR³ (e.g., —S(=O)₂NHMe, —S(=O)₂NHEt, —S(=O)₂NHPr, —S(=O)₂NHⁱPr, —S(=O)₂NHcyclopropyl, —S(=O)₂NHcyclobutyl). In some embodiments, R⁷ is —S(=O)₂N(CH₃)R³ (e.g., —S(=O)₂NMe₂, —S(=O)₂N(CH₃)Et, —S(=O)₂N(CH₃)Pr, —S(=O)₂N(CH₃)ⁱPr, —S(=O)₂N(CH₃)cyclopropyl, —S(=O)₂N(CH₃)cyclobutyl).

As generally described herein, m is 0, 1, 2 or 3.

In certain embodiments, the moiety represented by

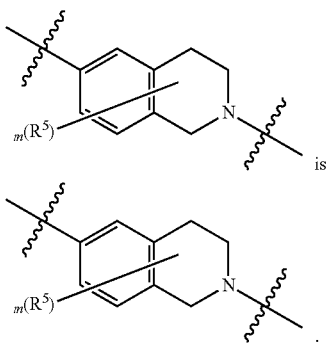

In certain embodiments, the moiety represented by

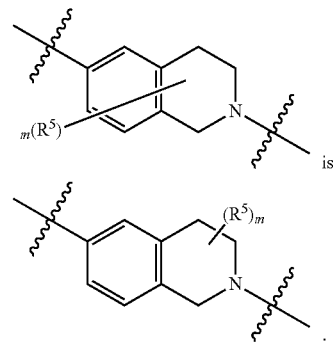

In certain embodiments, m is 0.

In certain embodiments, m is 1. In some embodiments, m is 1 and the moiety represented by

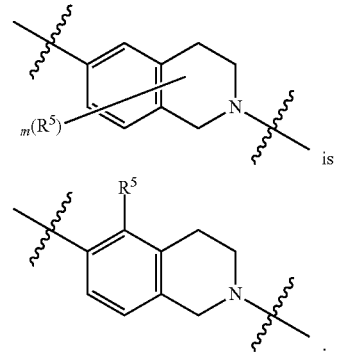

In certain embodiments, m is 2. In certain embodiments the moiety represented by

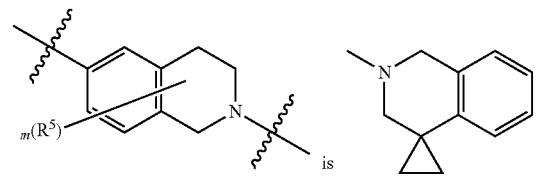

In one embodiment, the invention provides a compound selected from the compounds of Table 1a, or pharmaceutically acceptable salts thereof.

Compounds described herein (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) are useful as inhibitors of PRMT5 (e.g., MTA uncompetitive PRMT5 inhibitors).

Data in Table 1a has been obtained using different experimental conditions compared to the data in Table 1 of priority application 62/700,176. A change to the assay protocol used in the priority filing resulted in erroneous assay readings in some instances.

Table 1a indicates IC$_{50}$ values (µM) against PRMT5 for exemplary compounds in the presence of SAM as cofactor, with no cofactor and with MTA as cofactor, respectively (columns 3-5). For Table 1a, "a" "aa" and "aaa" indicates an IC$_{50}$ less than 50 nM in the assays with SAM, no cofactor and MTA respectively; "b", "bb" and "bbb" indicates an IC$_{50}$ of 50 nM to less than 500 nM in the assays with SAM, no cofactor and MTA, respectively; "c", "cc" and "ccc" indicates an IC$_{50}$ of greater than or equal to 500 nM to less than 5 µM in the assays with SAM, no cofactor and MTA, respectively; "d", "dd" and "ddd" indicates an IC$_{50}$ of greater than or equal to 5 µM in the assays with SAM, no cofactor and MTA, respectively. The Ki values can be calculated from the IC$_{50}$ values as described in the Examples section. As detailed in the Examples section, for the assay performed in the presence of SAM, IC$_{50}$=Ki×1.5 (Ki=IC$_{50}$/1.5). For the assay performed in the presence of MTA, IC$_{50}$=Ki×13.5 (Ki=IC$_{50}$/13.5). Column 6 indicates the ratio between the Ki of compounds in the presence of SAM and the Ki of compounds in the presence of MTA In column 6, "A" indicates a Ki ratio greater than or equal to 10 fold between the Ki in the presence of SAM and the Ki in the presence of MTA; "B" indicates a Ki ratio greater than or equal to 3 fold but lower than 10 fold between the Ki in the presence of SAM and the Ki in the presence of MTA; "C" indicates a Ki ratio of less than 3 fold between the IC$_{50}$ in the presence of SAM and the IC$_{50}$ in the presence of MTA; Compounds with a SAM/MTA ratio of more than 1 show greater cooperativity with MTA than with SAM.

Table 1a also indicates IC$_{50}$ values in an MTAP-isogenic cell line pair for exemplary compounds in an SDMA in-cell western assay (columns 7-8). HAP1 MTAP-intact is a cell line in which endogenous levels of MTAP are expressed, and HAP1 MTAP-deleted is an MTAP-null cell line. For Table 1a, "a*" and "aa*" indicates an IC$_{50}$ of <1 µM, "b*" and "bb*" indicates an IC$_{50}$ equal to or greater than 1 µM but less than 10 µM, and "c*" and "cc*" indicates an IC$_{50}$ of greater than or equal to 10 µM in the HAP1 MTAP-intact and the HAP1 MTAP-deleted assays, respectively. In column 9, "A*" indicates an IC$_{50}$ ratio greater than or equal to 10 fold between the IC$_{50}$ in the HAP1 MTAP-intact cell line and the HAP1 MTAP-deleted cell line; "B*" indicates an IC$_{50}$ ratio greater than or equal to 3 fold but lower than 10 fold between the IC$_{50}$ in the HAP1 MTAP-intact cell line and the HAP1 MTAP-deleted cell line; "C*" indicates an IC$_{50}$ ratio of less than 3 fold between the IC$_{50}$ in the HAP1 MTAP-intact cell line and the HAP1 MTAP-deleted cell line. Compounds with a ratio in the SDMA in-cell western assay of equal to or greater than 3 fold are considered MTAP-selective.

Unless otherwise indicated, the stereochemistry of all chiral atoms is as depicted. For compounds marked with (*) which contain a secondary alcohol stereocenter and at least one additional stereocenter, the absolute configuration of the secondary alcohol stereocenter is as indicated and was assigned based on the absolute configuration of the corresponding chiral starting material (e.g., (2S)-1-amino-3-chloro-propan-2-ol or (2R)-1-amino-3-chloro-propan-2-ol). For the second stereocenter, the configuration of the second stereocenter that is not the secondary alcohol was arbitrarily assigned based on chiral SFC elution as described in detail in the Examples section. For compounds marked with (**), the configuration at the secondary alcohol stereocenter was arbitrarily assigned based on chiral SFC elution as described in detail in the Examples section.

TABLE 1a

Exemplary compounds of the invention and biological data

| Name | Nr. | SAM IC50 | No Cofactor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| 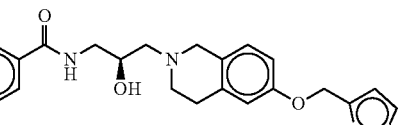 | 14 | c | dd | ccc | A | b* | cc* | C* |
| 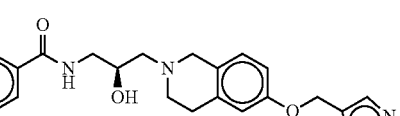 | 74 | b | dd | bbb | A | b* | bb* | C* |
| 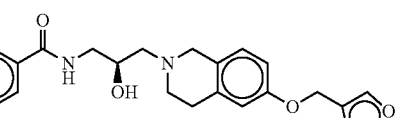 | 76 | c | dd | ccc | A | | | |
| 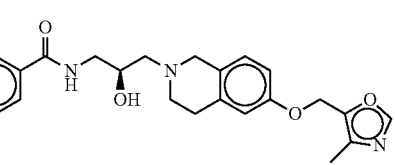 | 96 | b | dd | bbb | A | a* | aa* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact $IC_{50}$ | HAP1 MTAP Deleted $IC_{50}$ | MTAP Intact/Deleted Ratio |
|---|---|---|---|---|---|---|---|---|
| [structure] | 135 | b | dd | bbb | A | b* | bb* | C* |
| [structure] | 140 | c | dd | bbb | A | c* | cc* | C* |
| [structure] | 161 | c | dd | ccc | A | | | |
| [structure] | 163 | b | cc | bbb | A | a* | aa* | C* |
| [structure] | 179 | b | dd | bbb | A | c* | bb* | C* |
| [structure] | 194 | c | dd | bbb | A | c* | cc* | C* |
| [structure] | 198 | b | dd | bbb | A | c* | bb* | C* |
| [structure] | 201 | b | cc | bbb | A | b* | aa* | C* |
| [structure] | 203 | c | dd | ccc | A | c* | cc* | C* |
| [structure] | 207 | c | dd | ccc | A | a* | aa* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 219 | b | dd | bbb | A | b* | aa* | B* |
| | 233 | b | dd | bbb | A | c* | bb* | C* |
| | 241 | b | cc | bbb | A | c* | bb* | C* |
| | 242 | c | dd | ccc | B | c* | cc* | C* |
| | 249 | c | dd | ccc | A | c* | cc* | C* |
| | 250 | c | dd | ccc | A | c* | cc* | C* |
| | 251 | c | dd | ccc | B | c* | cc* | C* |
| | 252 | b | dd | bbb | A | c* | bb* | C* |
| | 253 | c | cc | bbb | A | b* | bb* | C* |
| | 254 | c | cc | bbb | A | b* | bb* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 255 | c | dd | bbb | A | c* | cc* | C* |
| | 256 | b | dd | bbb | A | c* | bb* | C* |
| | 257 | c | dd | bbb | A | c* | bb* | C* |
| | 258 | c | dd | ccc | A | c* | cc* | C* |
| | 259 | c | dd | ccc | A | a* | aa* | C* |
| | 260 | c | dd | ccc | A | b* | bb* | C* |
| | 261 | b | cc | bbb | A | a* | bb* | C* |
| | 262 | c | dd | bbb | A | b* | bb* | C* |
| | 263 | c | dd | ccc | A | c* | cc* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| [structure] | 264 | c | dd | bbb | A | c* | cc* | C* |
| [structure] | 265 | b | cc | aaa | A | | | |
| [structure] | 266 | b | cc | bbb | A | b* | bb* | B* |
| [structure] | 267 | c | dd | bbb | A | c* | cc* | C* |
| [structure] | 268 | c | dd | ccc | B | c* | cc* | C* |
| [structure] | 269 | c | dd | ccc | A | | | |
| [structure] | 270 | b | cc | bbb | A | a* | aa* | C* |
| [structure] | 271 | b | cc | bbb | A | a* | aa* | C* |
| [structure] | 272 | b | dd | bbb | A | c* | bb* | C* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 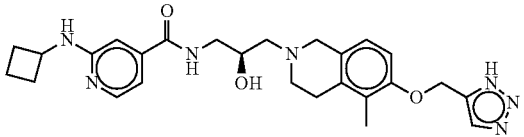 | 273 | c | dd | ccc | B | c* | bb* | C* |
| 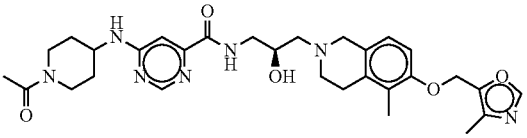 | 274 | b | dd | bbb | A | c* | bb* | C* |
| 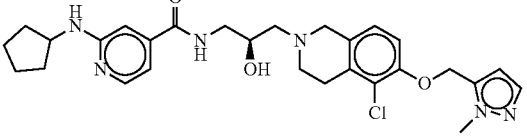 | 275 | c | dd | ccc | A | c* | cc* | C* |
| 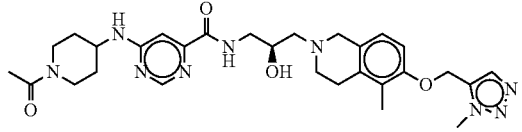 | 276 | c | dd | ccc | A | | | |
| 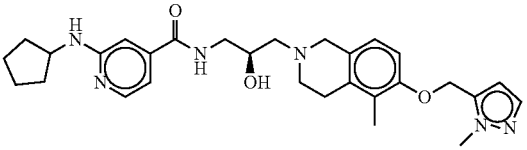 | 277 | c | dd | ccc | A | c* | cc* | C* |
| 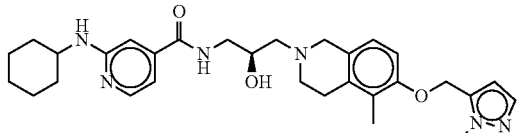 | 278 | c | dd | ccc | A | c* | cc* | C* |
| 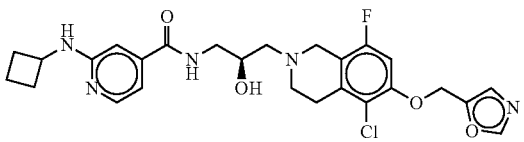 | 279 | b | dd | bbb | A | c* | bb* | C* |
| 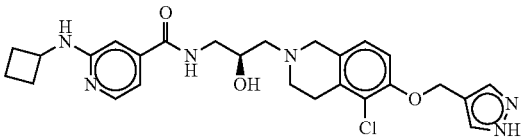 | 280 | b | dd | ccc | B | a* | aa* | C* |
| 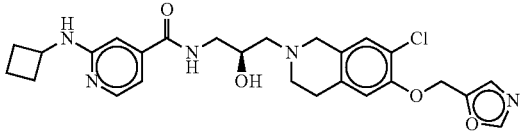 | 281 | c | dd | bbb | A | c* | bb* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact $IC_{50}$ | HAP1 MTAP Deleted $IC_{50}$ | MTAP Intact/Deleted Ratio |
|---|---|---|---|---|---|---|---|---|
| | 282 | c | dd | ccc | A | c* | cc* | C* |
| | 283 | c | dd | ccc | A | a* | aa* | C* |
| | 284 | c | dd | bbb | A | a* | aa* | C* |
| | 285 | b | cc | bbb | A | c* | bb* | C* |
| | 286 | b | cc | bbb | A | b* | bb* | B* |
| | 287 | c | dd | ccc | A | c* | cc* | C* |
| | 288 | c | dd | bbb | A | c* | bb* | C* |
| | 289 | b | cc | bbb | A | b* | bb* | B* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| [structure] | 290 | b | cc | bbb | A | b* | bb* | B* |
| [structure] | 291 | b | cc | bbb | B | b* | bb* | C* |
| [structure] | 292 | b | cc | bbb | A | c* | bb* | C* |
| [structure] | 293 | c | cc | bbb | A | c* | cc* | C* |
| [structure] | 294 | b | cc | bbb | A | b* | aa* | C* |
| [structure] | 295 | b | cc | bbb | A | a* | aa* | C* |
| [structure] | 296 | b | cc | bbb | A | c* | bb* | C* |
| [structure] | 297 | b | cc | bbb | A | c* | bb* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| (structure) | 298 | c | dd | ccc | A | c* | bb* | C* |
| (structure) | 299 | b | cc | bbb | A | c* | bb* | B* |
| (structure) | 300 | b | cc | bbb | A | c* | cc* | C* |
| (structure) | 301 | b | cc | bbb | A | c* | bb* | C* |
| (structure) | 302 | c | dd | bbb | A | c* | cc* | C* |
| (structure) | 303 | b | dd | bbb | A | c* | bb* | C* |
| (structure) | 304 | b | cc | bbb | B | b* | bb* | C* |
| (structure) | 305 | c | dd | ccc | A | c* | bb* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 306 | b | cc | bbb | A | b* | cc* | C* |
| | 307 | c | dd | bbb | A | b* | aa* | C* |
| | 308 | c | dd | ccc | A | c* | cc* | C* |
| | 309 | b | cc | bbb | A | c* | bb* | C* |
| | 310 | c | dd | bbb | A | b* | bb* | B* |
| | 311 | b | dd | bbb | A | c* | cc* | C* |
| | 312 | b | cc | bbb | A | c* | bb* | B* |
| | 313 | b | cc | bbb | A | b* | bb* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| (structure) | 314 | b | cc | bbb | A | c* | bb* | C* |
| (structure) | 315 | b | cc | aaa | A | b* | aa* | C* |
| (structure) | 316 | b | dd | bbb | A | c* | cc* | C* |
| (structure) | 317 | c | dd | bbb | A | c* | cc* | C* |
| (structure) | 318 | b | cc | bbb | A | c* | bb* | C* |
| (structure) | 319 | b | cc | bbb | A | c* | cc* | C* |
| (structure) | 320 | c | cc | ccc | B | b* | bb* | C* |
| (structure) | 321 | b | cc | bbb | A | c* | bb* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| (structure) | 322 | b | dd | bbb | A | c* | cc* | C* |
| (structure) | 323 | b | cc | bbb | A | c* | bb* | B* |
| (structure) | 324 | b | cc | bbb | A | c* | bb* | C* |
| (structure) | 325 | b | cc | bbb | A | b* | aa* | C* |
| (structure) | 326 | c | dd | bbb | A | c* | cc* | C* |
| (structure) | 327 | b | cc | bbb | A | c* | bb* | B* |
| (structure) | 328 | b | cc | bbb | A | b* | aa* | C* |
| (structure) | 329 | b | cc | aaa | A | c* | bb* | B* |
| (structure) | 330 | b | cc | bbb | A | c* | cc* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| | 331 | c | cc | ccc | A | | | |
| | 332 | c | dd | ccc | A | | | |
| | 333 | b | dd | bbb | A | a* | aa* | C* |
| | 334 | c | dd | bbb | A | a* | aa* | C* |
| | 335 | c | dd | ccc | A | c* | cc* | C* |
| | 336 | c | dd | ccc | A | c* | cc* | C* |
| | 337 | c | dd | ccc | A | c* | cc* | C* |
| | 338 | c | dd | ccc | A | c* | cc* | C* |
| | 339 | c | dd | bbb | A | c* | cc* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 340 | c | dd | bbb | A | c* | cc* | C* |
| | 341 | b | cc | bbb | A | c* | bb* | B* |
| | 342 | b | cc | bbb | A | c* | aa* | A* |
| | 343 | c | dd | ccc | A | c* | bb* | C* |
| | 344 | b | dd | bbb | A | c* | cc* | C* |
| | 345 | b | dd | bbb | A | c* | bb* | B* |
| | 346 | c | dd | bbb | A | c* | cc* | C* |
| | 347 | b | dd | bbb | A | c* | cc* | C* |
| | 348 | c | dd | ccc | A | c* | cc* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 349 | b | cc | bbb | A | a* | aa* | C* |
| | 350 | b | dd | bbb | A | c* | cc* | C* |
| | 351 | c | dd | bbb | A | c* | cc* | C* |
| | 352 | b | cc | bbb | A | c* | bb* | C* |
| | 353 | b | cc | bbb | A | b* | bb* | C* |
| | 354 | c | dd | ccc | B | c* | cc* | C* |
| | 355 | c | dd | bbb | A | c* | cc* | C* |
| | 356 | b | dd | bbb | A | c* | cc* | C* |
| | 357 | c | dd | bbb | A | c* | cc* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 358 | c | dd | ccc | A | c* | cc* | C* |
| | 359 | c | dd | ccc | A | c* | bb* | C* |
| | 360 | b | cc | bbb | A | c* | aa* | A* |
| | 361 | c | dd | ccc | A | c* | cc* | C* |
| | 362 | c | dd | bbb | A | a* | bb* | C* |
| | 363 | b | cc | bbb | A | | | |
| | 364 | b | dd | bbb | A | c* | bb* | C* |
| | 365 | b | cc | aaa | A | b* | aa* | B* |
| | 366 | b | cc | bbb | A | c* | bb* | B* |

TABLE 1a-continued
Exemplary compounds of the invention and biological data
| Name | Nr. | SAM IC50 | No Co-factor IC50 | MTA IC50 | SAM/MTA Ratio | HAP1 MTAP Intact $IC_{50}$ | HAP1 MTAP Deleted $IC_{50}$ | MTAP Intact/Deleted Ratio |
|---|---|---|---|---|---|---|---|---|
| 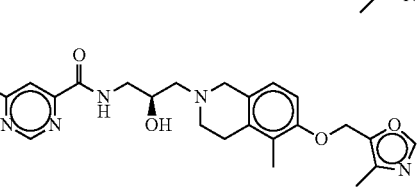 | 367 | c | dd | bbb | A | c* | cc* | C* |
| 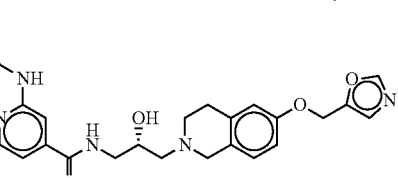 | 368 | c | dd | bbb | A | c* | cc* | C* |
| 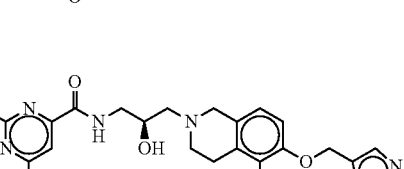 | 369 | c | cc | bbb | A | b* | cc* | C* |
| 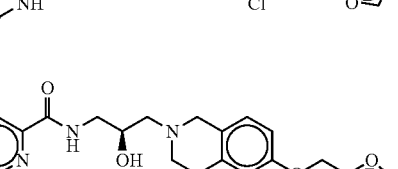 | 370 | b | dd | bbb | A | c* | bb* | C* |
| 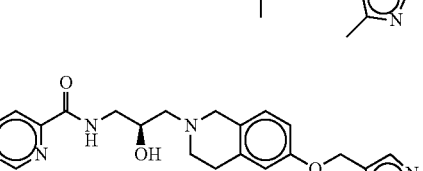 | 371 | c | dd | bbb | A | c* | aa* | A* |
| 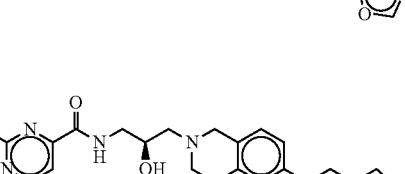 | 372 | c | dd | bbb | A | a* | aa* | C* |
| 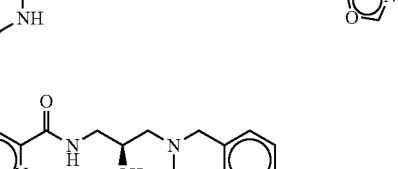 | 373 | b | cc | bbb | A | c* | bb* | B* |
|  | 374 | b | dd | bbb | A | b* | aa* | C* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 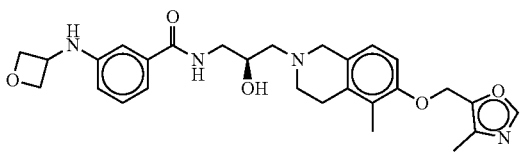 | 375 | c | dd | ccc | A | c* | cc* | C* |
| 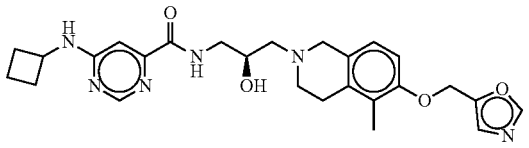 | 376 | c | dd | ccc | A | c* | cc* | C* |
| 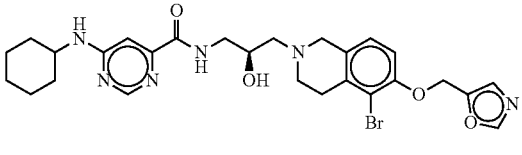 | 377 | c | dd | ccc | A | | | |
| 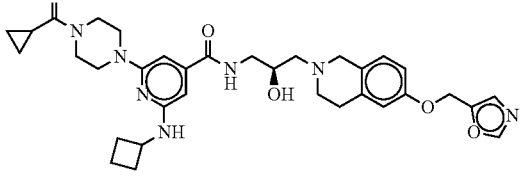 | 378 | b | cc | bbb | A | a* | aa* | C* |
| 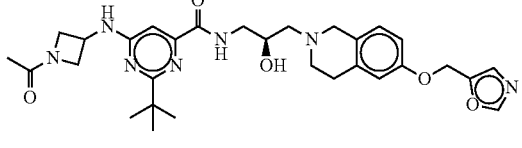 | 379 | b | cc | bbb | A | a* | aa* | C* |
| 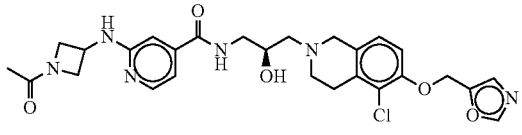 | 380 | b | cc | bbb | A | c* | cc* | C* |
| 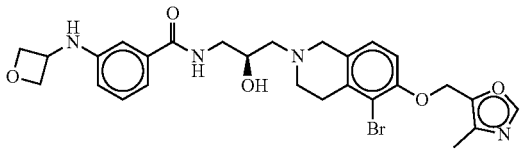 | 381 | c | dd | ccc | A | c* | cc* | C* |
| 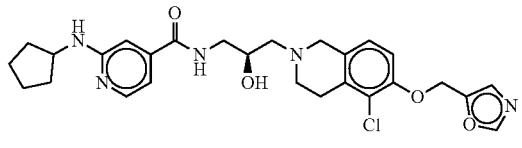 | 382 | b | cc | bbb | A | c* | cc* | C* |
| 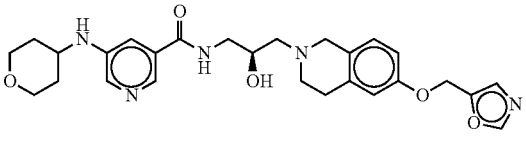 | 383 | c | dd | ccc | A | c* | cc* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| [structure] | 384 | b | cc | bbb | A | a* | aa* | B* |
| [structure] | 385 | b | dd | bbb | A | c* | bb* | C* |
| [structure] | 386 | b | cc | bbb | A | c* | bb* | C* |
| [structure] | 387 | b | cc | bbb | A | b* | aa* | B* |
| [structure] | 388 | b | dd | bbb | A | a* | aa* | B* |
| [structure] | 389 | b | cc | bbb | A | a* | aa* | B* |
| [structure] | 390 | b | cc | bbb | A | a* | aa* | C* |
| [structure] | 391 | b | dd | bbb | A | c* | aa* | A* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 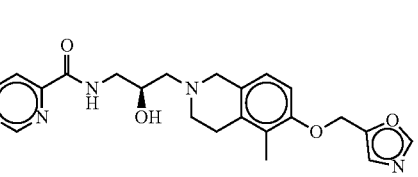 | 392 | b | cc | bbb | A | a* | aa* | C* |
| 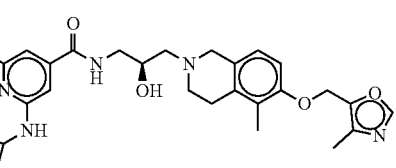 | 393 | c | dd | ccc | A | c* | cc* | C* |
| 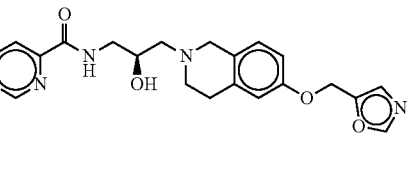 | 394 | b | cc | bbb | A | c* | aa* | A* |
| 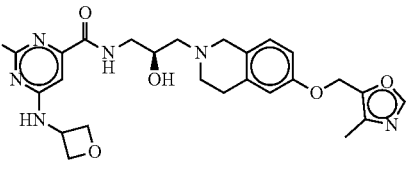 | 395 | c | dd | bbb | A | c* | bb* | B |
| 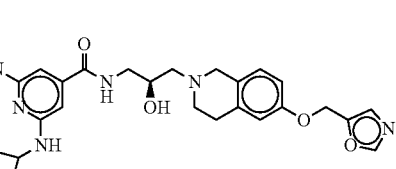 | 396 | b | cc | bbb | A | b* | aa* | C* |
| 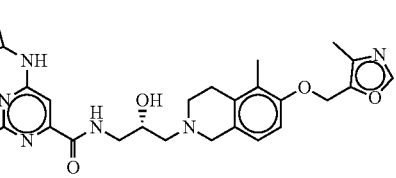 | 397 | b | cc | bbb | A | b* | aa* | C* |
| 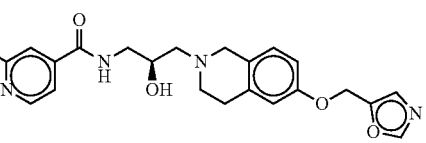 | 398 | b | dd | bbb | A | c* | bb* | B* |
|  | 399 | c | dd | bbb | A | b* | aa* | B* |

TABLE 1a-continued
Exemplary compounds of the invention and biological data
| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| 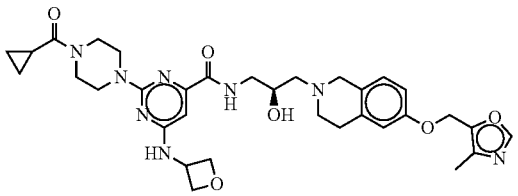 | 400 | b | cc | bbb | A | b* | aa* | B* |
| 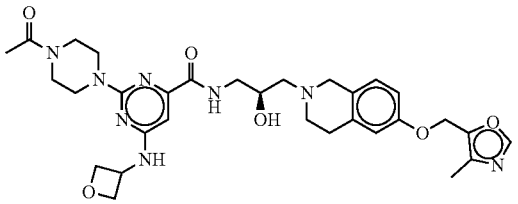 | 401 | b | cc | bbb | A | c* | bb* | B* |
| 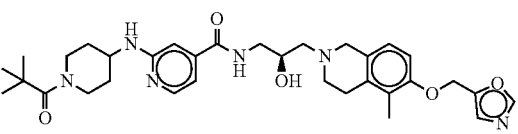 | 402 | b | cc | bbb | A | c* | bb* | B* |
| 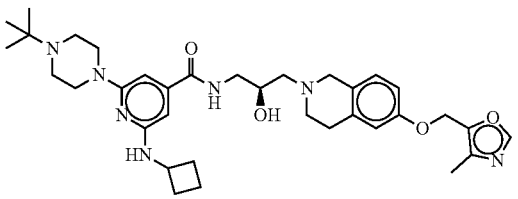 | 403 | b | cc | bbb | A | a* | cc* | C* |
| 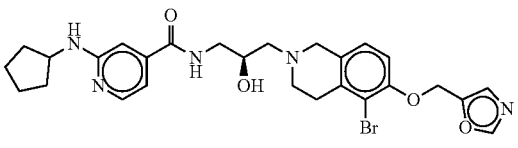 | 404 | b | dd | bbb | A | c* | cc* | C* |
| 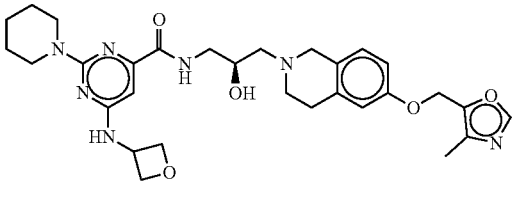 | 405 | b | cc | bbb | A | a* | aa* | B* |
| 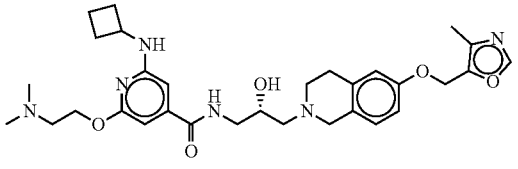 | 406 | b | cc | aaa | A | a* | aa* | B* |
| 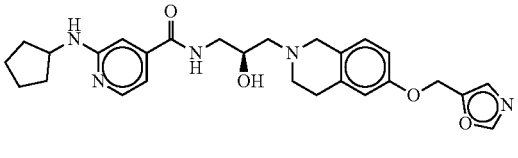 | 407 | b | dd | bbb | A | a* | aa* | B* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 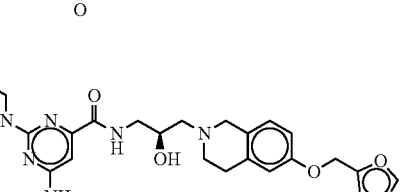 | 408 | b | cc | bbb | A | a* | aa* | C* |
| 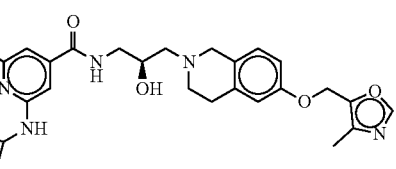 | 409 | b | cc | bbb | A | c* | bb* | B* |
| 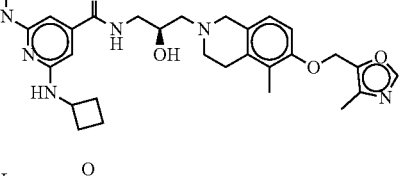 | 410 | b | cc | bbb | A | a* | aa* | B* |
| 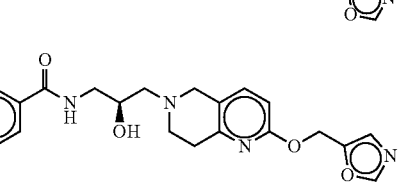 | 411 | b | cc | bbb | A | c* | aa* | A* |
| 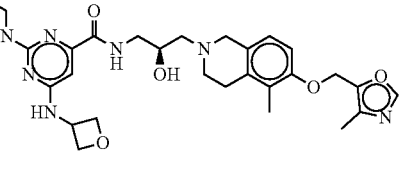 | 412 | c | dd | bbb | A | c* | cc* | C* |
| 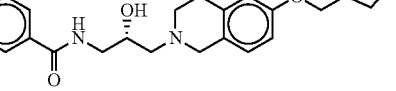 | 413 | c | dd | ccc | A | c* | cc* | C* |
|  | 414 | b | dd | bbb | A | c* | aa* | A* |
|  | 415 | b | cc | bbb | A | b* | aa* | C* |

TABLE 1a-continued
Exemplary compounds of the invention and biological data
| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
|  | 416 | b | cc | bbb | A | a* | aa* | C* |
|  | 417 | b | cc | bbb | A | c* | aa* | A* |
|  | 418 | b | dd | bbb | A | c* | bb* | C* |
|  | 419 | b | cc | bbb | A | c* | cc* | C* |
|  | 420 | b | cc | bbb | A | c* | cc* | C* |
|  | 421 | b | dd | bbb | A | c* | bb* | B* |
|  | 422 | b | cc | bbb | A | b* | bb* | C* |
|  | 423 | c | dd | bbb | A | c* | bb* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| (structure) | 424 | c | dd | ccc | A | c* | cc* | C* |
| (structure) | 425 | b | dd | bbb | A | c* | cc* | C* |
| (structure) | 426 | b | cc | bbb | A | c* | cc* | C* |
| (structure) | 427 | b | cc | bbb | A | c* | bb* | B* |
| (structure) | 428 | b | cc | aaa | A | c* | cc* | C* |
| (structure) | 429 | b | cc | bbb | A | c* | bb* | B* |
| (structure) | 430 | b | cc | bbb | A | c* | bb* | C* |
| (structure) | 431 | b | cc | bbb | A | b* | aa* | B* |
| (structure) | 432 | b | cc | bbb | A | c* | bb* | B* |
| (structure) | 433 | b | cc | bbb | A | b* | aa* | B* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| (structure) | 434 | b | dd | bbb | A | b* | aa* | C* |
| (structure) | 435 | b | dd | bbb | A | c* | cc* | C* |
| (structure) | 436 | c | dd | ccc | A | c* | cc* | C* |
| (structure) | 437 | b | dd | bbb | A | c* | bb* | B* |
| (structure) | 438 | c | dd | bbb | A | b* | bb* | C* |
| (structure) | 439 | b | dd | bbb | A | b* | aa* | C* |
| (structure) | 440 | b | cc | bbb | A | c* | bb* | B* |
| (structure) | 441 | b | cc | bbb | A | c* | bb* | C* |
| (structure) | 442 | b | cc | bbb | A | c* | aa* | A* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| [structure] | 443 | b | cc | bbb | A | c* | aa* | A* |
| [structure] | 444 | b | dd | bbb | A | c* | bb* | C* |
| [structure] | 445 | c | dd | bbb | A | c* | cc* | C* |
| [structure] | 446 | b | cc | aaa | A | b* | aa* | C* |
| [structure] | 447 | b | cc | bbb | A | c* | aa* | A* |
| [structure] | 448 | b | cc | bbb | A | a* | aa* | C* |
| [structure] | 449 | b | cc | bbb | A | b* | aa* | C* |
| [structure] | 450 | b | cc | bbb | A | c* | aa* | A* |
| [structure] | 451 | b | cc | bbb | A | c* | cc* | C* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| 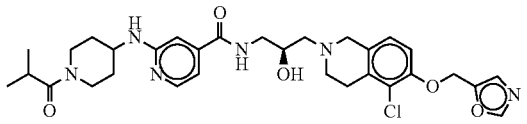 | 452 | b | cc | bbb | A | c* | bb* | B* |
| 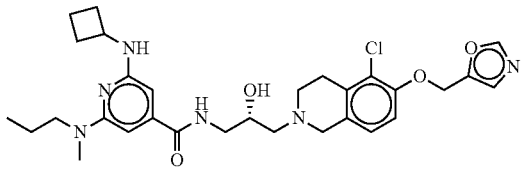 | 453 | c | dd | ccc | A | | | |
| 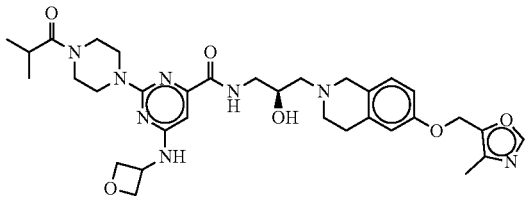 | 454 | b | cc | bbb | A | b* | aa* | B* |
| 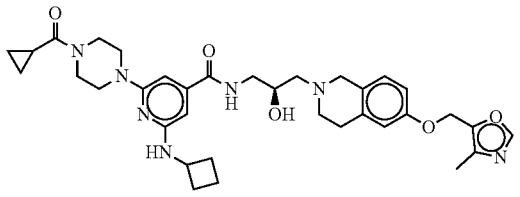 | 455 | b | bb | bbb | A | a* | aa* | B* |
| 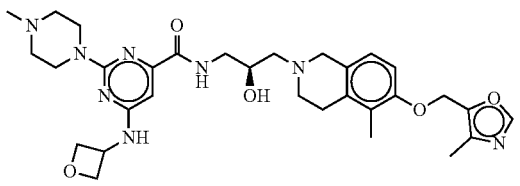 | 456 | b | dd | bbb | A | c* | bb* | C* |
| 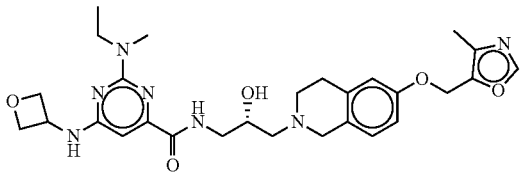 | 457 | b | cc | bbb | A | a* | aa* | C* |
| 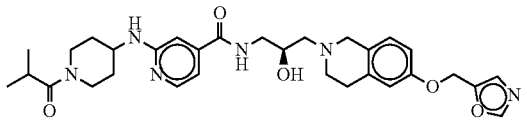 | 458 | b | cc | bbb | A | b* | aa* | C* |
| 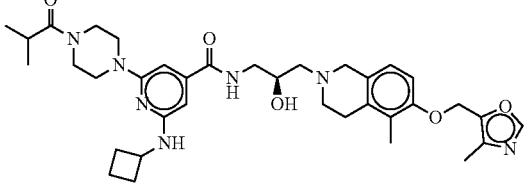 | 459 | b | cc | bbb | A | b* | aa* | A* |

TABLE 1a-continued
Exemplary compounds of the invention and biological data
| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
|  | 460 | b | cc | bbb | A | b* | aa* | B* |
|  | 461 | b | dd | bbb | B | c* | bb* | B* |
| 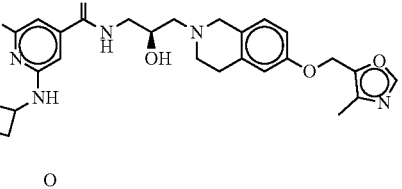 | 462 | b | cc | bbb | A | c* | cc* | C* |
|  | 463 | b | cc | bbb | A | a* | aa* | B* |
|  | 464 | b | cc | bbb | A | c* | cc* | C* |
|  | 465 | b | dd | bbb | A | c* | bb* | B* |
| 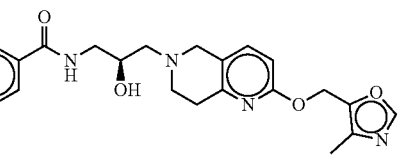 | 466 | b | cc | bbb | A | a* | aa* | C* |
|  | 467 | b | dd | bbb | A | c* | bb* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 468 | b | cc | bbb | A | b* | bb* | B* |
| | 469 | b | cc | bbb | A | b* | bb* | C* |
| | 470 | b | cc | bbb | A | c* | aa* | A* |
| | 471 | b | cc | bbb | A | b* | bb* | B* |
| | 472 | b | cc | bbb | A | c* | bb* | B* |
| | 473 | b | cc | bbb | A | c* | bb* | C* |
| | 474 | b | dd | bbb | A | b* | bb* | B* |
| | 475 | c | dd | bbb | A | b* | bb* | C* |
| | 476 | c | dd | bbb | A | c* | cc* | C* |
| | 477 | b | dd | bbb | A | c* | bb* | B* |

TABLE 1a-continued
Exemplary compounds of the invention and biological data
| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| 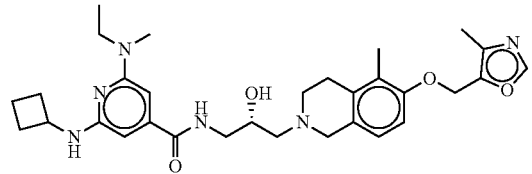 | 478 | c | dd | bbb | A | c* | cc* | C* |
| 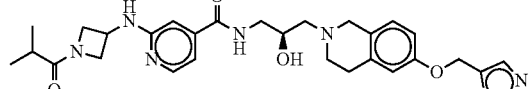 | 479 | c | dd | bbb | A | b* | bb* | C* |
| 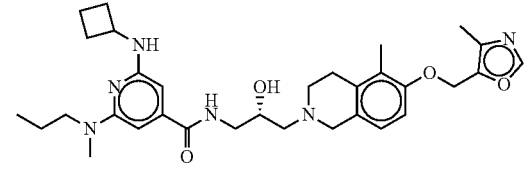 | 480 | b | dd | bbb | A | c* | cc* | C* |
| 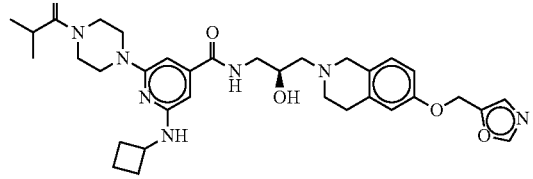 | 481 | b | cc | bbb | A | a* | aa* | C* |
| 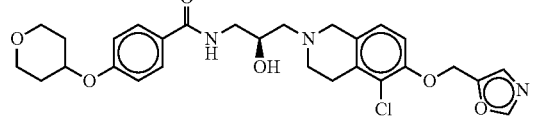 | 482 | c | dd | ccc | A | c* | cc* | C* |
| 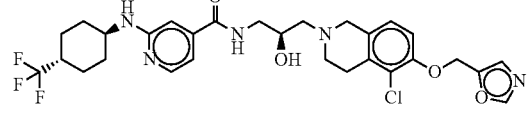 | 483 | c | dd | bbb | A | c* | bb* | C* |
| 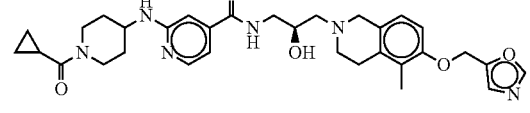 | 484 | b | cc | bbb | A | c* | bb* | B* |
| 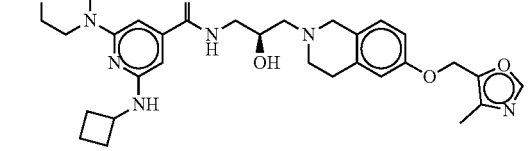 | 485 | b | cc | bbb | A | a* | aa* | C* |
| 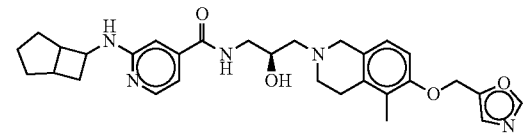 | 486 | b | dd | bbb | A | c* | bb* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 487 | b | dd | bbb | A | c* | cc* | C* |
| | 488 | c | dd | bbb | A | c* | bb* | C* |
| | 489 | c | dd | bbb | A | c* | bb* | B* |
| | 490 | c | dd | ccc | A | c* | cc* | C* |
| | 491 | b | dd | bbb | A | c* | bb* | C* |
| | 492 | b | dd | bbb | A | b* | bb* | C* |
| | 493 | b | cc | aaa | A | b* | aa* | B* |
| | 494 | b | cc | bbb | A | c* | bb* | B* |
| | 495 | b | cc | bbb | A | c* | cc* | C* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 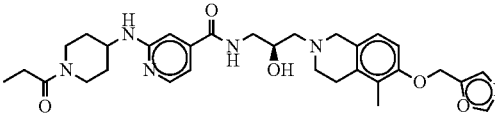 | 496 | b | cc | bbb | A | c* | bb* | B* |
| 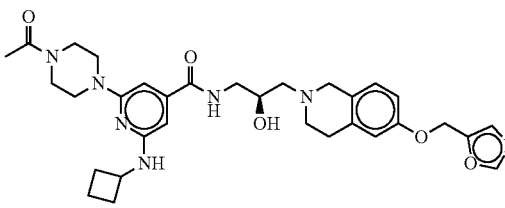 | 497 | b | cc | bbb | A | b* | aa* | C* |
| 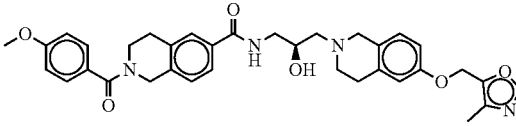 | 498 | b | cc | bbb | A | b* | aa* | B* |
| 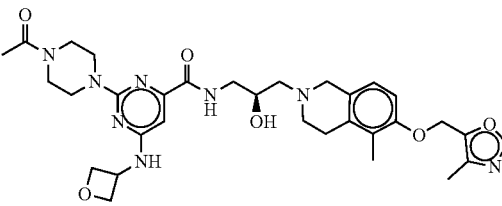 | 499 | c | dd | bbb | A | c* | cc* | C* |
| 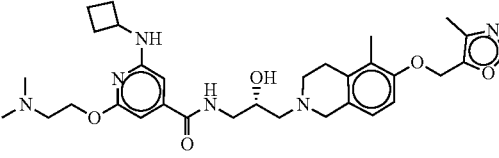 | 500 | b | cc | bbb | A | c* | aa* | A* |
| 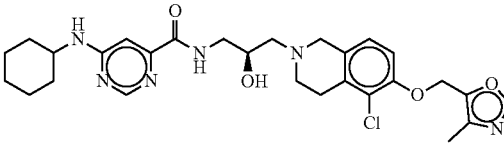 | 501 | b | dd | bbb | A | c* | cc* | C* |
| 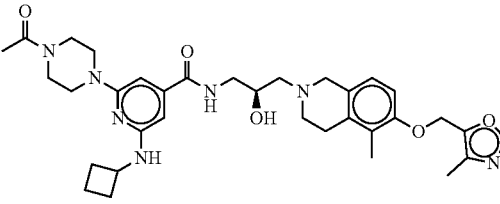 | 502 | b | cc | bbb | A | b* | aa* | A* |
| 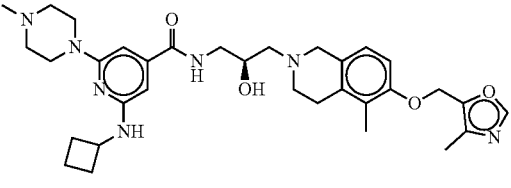 | 503 | b | cc | bbb | A | c* | aa* | A* |

TABLE 1a-continued

Exemplary compounds of the invention and biological data

| Name | Nr. | SAM IC50 | No Cofactor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| (structure) | 504 | b | dd | bbb | A | c* | cc* | C* |
| (structure) | 505* | c | dd | ccc | A | | | |
| (structure) | 506 | b | dd | bbb | A | c* | bb* | B* |
| (structure) | 507 | b | cc | bbb | A | c* | bb* | B* |
| (structure) | 508 | c | dd | bbb | A | | | |
| (structure) | 509 | c | cc | bbb | A | b* | aa* | C* |
| (structure) | 510 | c | dd | bbb | A | | | |
| (structure) | 511 | c | dd | ccc | A | | | |
| (structure) | 512 | b | dd | bbb | A | c* | cc* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 513 | c | dd | bbb | A | c* | bb* | B* |
| | 514 | c | dd | ccc | A | | | |
| | 515 | c | dd | bbb | A | b* | bb* | C* |
| | 516 | b | cc | bbb | A | a* | aa* | C* |
| | 517 | b | cc | bbb | A | c* | bb* | B* |
| | 518 | c | dd | ccc | A | | | |
| | 519 | c | dd | ccc | A | | | |
| | 520 | b | dd | bbb | A | c* | bb* | B* |
| | 521 | c | dd | ccc | A | | | |
| | 522 | b | dd | bbb | A | c* | cc* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 523 | b | dd | bbb | A | c* | cc* | C* |
| | 524 | c | dd | ccc | A | | | |
| | 525 | c | dd | ccc | A | | | |
| | 526 | c | dd | bbb | A | | | |
| | 527 | b | cc | bbb | A | c* | bb* | B* |
| | 528 | b | cc | bbb | A | c* | bb* | C* |
| | 529 | b | cc | bbb | A | c* | bb* | B* |
| | 530 | b | dd | bbb | A | c* | cc* | C* |
| | 531 | c | dd | ccc | A | | | |
| | 532 | b | cc | bbb | A | c* | aa* | A* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 533 | b | dd | bbb | A | c* | bb* | C* |
| | 534 | b | cc | aaa | A | b* | aa* | A* |
| | 535 | c | dd | bbb | A | | | |
| | 536 | b | cc | bbb | A | c* | bb* | B* |
| | 537 | c | dd | bbb | A | | | |
| | 538 | c | dd | bbb | A | | | |
| | 539 | b | cc | bbb | A | c* | cc* | C* |
| | 540 | b | cc | bbb | A | c* | bb* | C* |
| | 541 | c | dd | bbb | A | | | |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 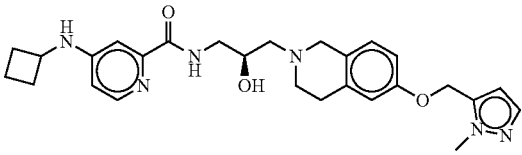 | 542 | c | dd | bbb | A | | | |
| 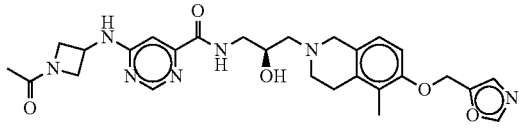 | 543 | c | dd | ccc | A | | | |
| 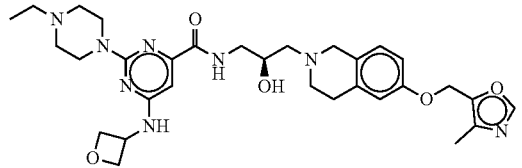 | 544 | b | cc | bbb | A | b* | bb* | B* |
| 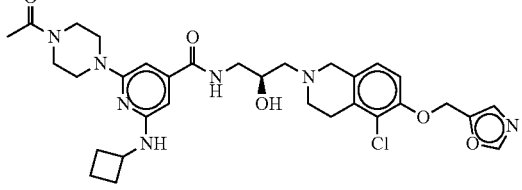 | 545 | b | cc | bbb | A | c* | bb* | B* |
| 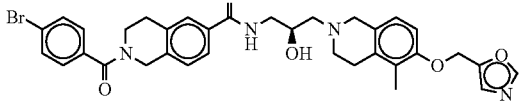 | 546 | b | cc | bbb | A | c* | cc* | C* |
| 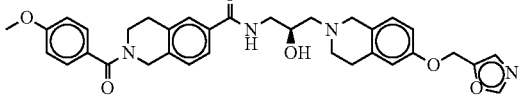 | 547 | b | cc | bbb | A | b* | bb* | C* |
| 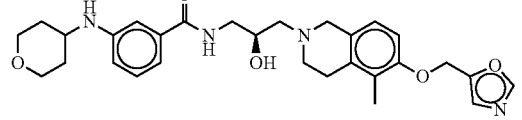 | 548 | c | dd | ccc | A | | | |
| 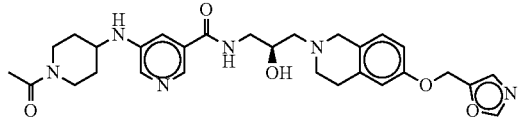 | 549 | b | cc | bbb | A | c* | cc* | C* |
| 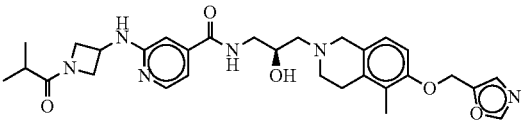 | 550 | b | dd | bbb | A | c* | cc* | C* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 551 | b | cc | bbb | A | c* | cc* | C* |
| | 552 | c | dd | ccc | A | | | |
| | 553 | c | dd | bbb | A | | | |
| | 554 | b | cc | bbb | A | a* | aa* | C* |
| | 555 | b | dd | bbb | A | c* | bb* | C* |
| | 556 | b | cc | bbb | A | a* | aa* | B* |
| | 557 | c | dd | bbb | A | | | |
| | 558 | c | dd | ccc | A | | | |
| | 559 | b | cc | bbb | A | c* | bb* | C* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| (structure) | 560 | b | cc | bbb | A | c* | bb* | B* |
| (structure) | 561 | b | cc | bbb | A | c* | bb* | B* |
| (structure) | 562 | c | dd | bbb | A | | | |
| (structure) | 563 | b | cc | bbb | A | b* | bb* | C* |
| (structure) | 564 | b | cc | bbb | A | b* | aa* | B* |
| (structure) | 565 | c | dd | ccc | A | | | |
| (structure) | 566 | b | cc | bbb | A | c* | cc* | C* |
| (structure) | 567 | b | dd | bbb | A | | | |
| (structure) | 568 | b | cc | bbb | A | b* | aa* | C* |
| (structure) | 569 | b | dd | bbb | A | c* | bb* | B* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| (structure) | 570 | b | cc | bbb | A | c* | aa* | A* |
| (structure) | 571 | b | cc | bbb | A | c* | aa* | A* |
| (structure) | 572 | c | dd | bbb | A | c* | cc* | C* |
| (structure) | 573 | c | dd | ccc | A | | | |
| (structure) | 574 | b | dd | bbb | A | c* | bb* | C* |
| (structure) | 575 | b | dd | bbb | A | c* | bb* | B* |
| (structure) | 576 | b | cc | bbb | A | b* | bb* | B* |
| (structure) | 577 | b | cc | bbb | A | b* | bb* | B* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| (structure) | 578 | b | cc | bbb | A | b* | bb* | B* |
| (structure) | 579 | b | bb | bbb | A | b* | aa* | A* |
| (structure) | 580 | | cc | | | | | |
| (structure) | 581 | b | dd | bbb | A | b* | bb* | B* |
| (structure) | 582 | b | cc | bbb | A | b* | aa* | A* |
| (structure) | 583 | b | cc | bbb | A | c* | bb* | C* |
| (structure) | 584 | b | bb | bbb | A | c* | bb* | B* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 585 | b | dd | bbb | A | | | |
| | 586 | b | cc | bbb | A | c* | bb* | B* |
| | 587 | b | cc | bbb | A | b* | aa* | A* |
| | 588 | b | cc | bbb | A | c* | bb* | C* |
| | 589 | b | cc | bbb | A | c* | aa* | A* |
| | 590 | b | cc | bbb | A | c* | bb* | C* |
| | 591 | b | dd | bbb | A | | | |
| | 592 | b | cc | bbb | A | c* | aa* | A* |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 593 | b | cc | bbb | A | c* | bb* | B* |
| | 594 | b | cc | bbb | A | c* | bb* | C* |
| | 595 | b | cc | aaa | A | b* | aa* | A* |
| | 596 | c | cc | bbb | A | | | |
| | 597 | b | bb | aaa | A | b* | aa* | B* |
| | 598 | b | cc | bbb | A | a* | aa* | C* |
| | 599 | b | cc | bbb | A | b* | aa* | A* |
| | 600 | b | dd | bbb | A | c* | bb* | B* |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 601 | b | cc | aaa | A | a* | aa* | B* |
| | 602 | b | cc | bbb | A | b* | bb* | C* |
| | 603 | b | cc | aaa | A | b* | aa* | B* |
| | 604 | b | cc | bbb | A | b* | aa* | A* |
| | 605 | b | dd | bbb | A | c* | bb* | B* |
| | 606 | b | cc | bbb | A | c* | bb* | C* |
| | 607 | b | dd | bbb | A | a* | aa* | C* |
| | 608 | c | dd | bbb | A | | | |

TABLE 1a-continued

Exemplary compounds of the invention and biological data

| Name | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| (structure) | 609 | c | cc | aaa | A | b* | aa* | B* |
| (structure) | 610 | b | bb | aaa | A | b* | bb* | C* |
| (structure) | 611 | b | bb | aaa | A | a* | aa* | B* |
| (structure) | 612 | b | bb | bbb | A | c* | aa* | A* |
| (structure) | 613 | b | dd | bbb | B | | | |
| (structure) | 614 | b | cc | bbb | A | b* | aa* | C* |
| (structure) | 615 | b | cc | bbb | A | b* | aa* | A* |
| (structure) | 616 | b | cc | aaa | A | b* | aa* | C* |

TABLE 1a-continued
Exemplary compounds of the invention and biological data
| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 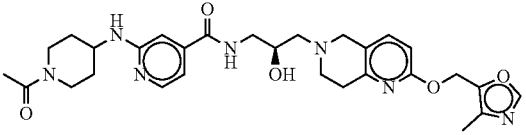 | 617 | b | cc | bbb | B | c* | bb* | C* |
| 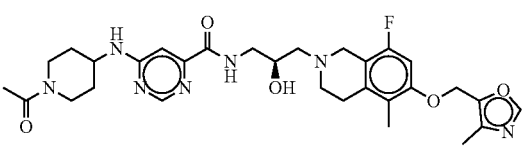 | 618 | b | cc | bbb | B | c* | bb* | B* |
| 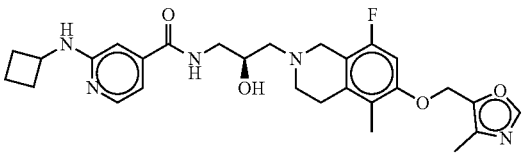 | 619 | b | cc | bbb | B | c* | bb* | C* |
| 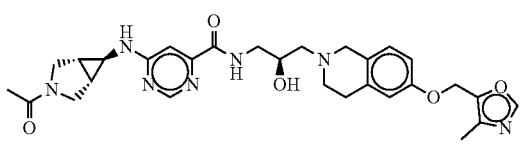 | 620 | c | dd | ccc | A | | | |
| 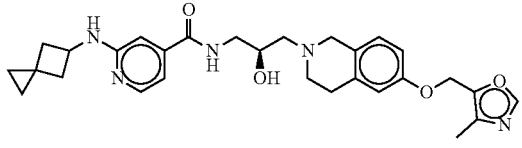 | 621 | b | cc | bbb | A | a* | aa* | B* |
| 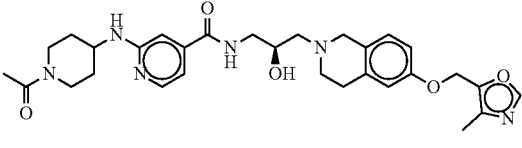 | 622 | b | cc | aaa | A | c* | aa* | A* |
| 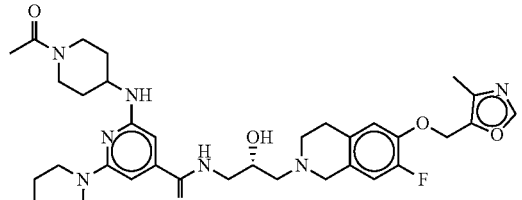 | 623 | b | bb | bbb | A | b* | aa* | A* |
| 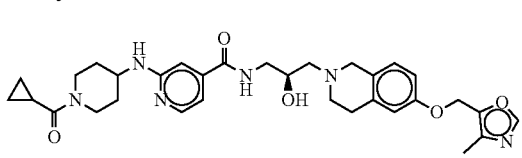 | 624 | b | cc | aaa | A | b* | aa* | A* |
| 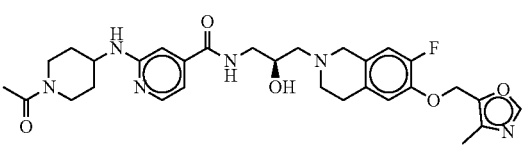 | 625 | b | cc | bbb | A | c* | aa* | A* |

TABLE 1a-continued

Exemplary compounds of the invention and biological data

| Name | Nr. | SAM IC50 | No Cofactor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 626 | b | cc | bbb | A | b* | aa* | B* |
| | 627 | b | dd | bbb | A | | | |
| | 628 | b | cc | aaa | A | b* | aa* | B* |
| | 629 | b | cc | bbb | A | b* | aa* | A* |
| | 630 | c | dd | bbb | A | | | |
| | 631 | b | dd | bbb | A | b* | aa* | B* |
| | 632 | b | dd | bbb | A | | | |
| | 633 | c | dd | bbb | A | | | |

TABLE 1a-continued

Exemplary compounds of the invention and biological data

| Name | Nr. | SAM IC50 | No Cofactor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 634 | b | bb | aaa | A | b* | bb* | B* |
| | 635 | b | dd | bbb | A | b* | aa* | A* |
| | 636 | b | cc | bbb | A | b* | aa* | B* |
| | 637 | b | dd | bbb | A | b* | bb* | B* |
| | 638 | b | bb | bbb | A | b* | | |
| | 639 | b | cc | bbb | A | a* | | |
| | 640 | b | cc | bbb | A | b* | | |

TABLE 1a-continued

Exemplary compounds of the invention and biological data

| Name | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 641 | b | cc | aaa | A | a* | | |
| | 642 | b | cc | bbb | A | c* | | |
| | 643 | b | cc | bbb | A | | | |
| | 644 | b | cc | aaa | A | b* | aa* | A* |
| | 645 | b | cc | bbb | A | c* | aa* | A* |
| | 646 | b | cc | aaa | A | | | |
| | 647 | b | bb | aaa | A | a* | aa* | B* |
| | 648** | b | dd | bbb | A | | | |

TABLE 1a-continued
Exemplary compounds of the invention and biological data
| Name | Nr. | SAM IC50 | No Co-factor IC50 | MTA IC50 | SAM/MTA Ratio | HAP1 MTAP Intact IC50 | HAP1 MTAP Deleted IC50 | MTAP Intact/Deleted Ratio |
|---|---|---|---|---|---|---|---|---|
| 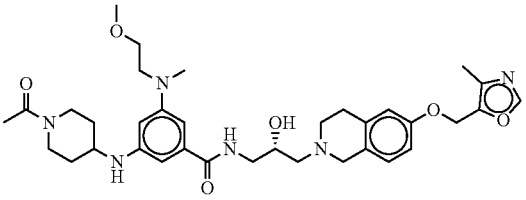 | 649** | c | dd | ccc | A | | | |
| 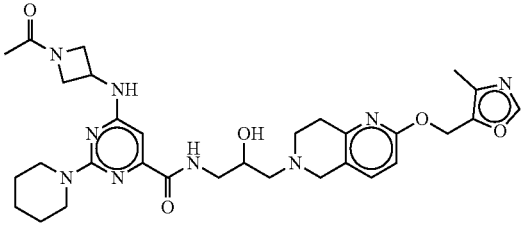 | 650 | b | cc | bbb | A | | | |
| 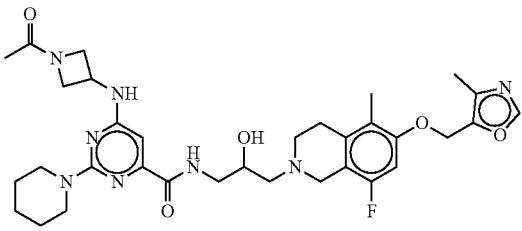 | 651 | b | cc | bbb | A | | | |
| 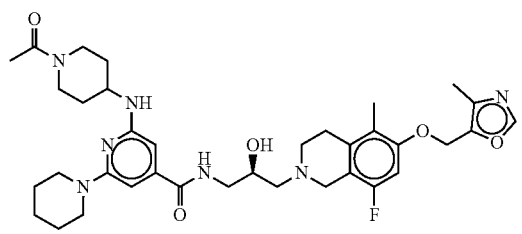 | 652 | b | cc | bbb | A | | | |
| 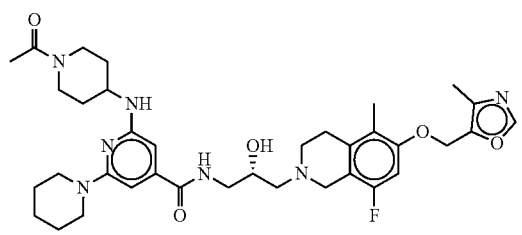 | 653 | c | dd | ccc | A | | | |
| 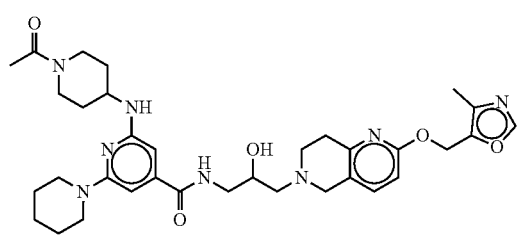 | 654 | | cc | bbb | | | | |

In some embodiments, compounds of Formula (I), (Ia), (Ib), (Ic) and (Id) as described herein can be prepared using methods illustrated in Scheme 1.

As used herein, W, $LG^1$ and $LG^2$ are each independently leaving groups as defined herein. In certain embodiments, W, $LG^1$ and $LG^2$ are each independently halogen (e.g., fluoro, chloro, bromo, iodo), alkylsulfonyl (e.g., methylsulfonyl —$SO_2CH_3$), alkanesulfonyloxy (e.g., methylsulfonyloxy-$OSO_2CH_3$), arenesulfonyloxy (e.g., p-toluenesulfonyloxy-$OSO_2C_6H_4$-pMe), hydroxyl group, alkoxy group, aryloxy group. In certain embodiments, W is halogen (e.g., fluoro, chloro, bromo, iodo). In certain embodiments, W is a boronic acid or a boronic ester. In some embodiments $LG^1$ is halogen (e.g., fluoro, chloro, bromo, iodo). In some embodiments, $LG^1$ is hydroxyl. In some embodiments, $LG^2$ is halogen (e.g., fluoro, chloro, bromo, iodo).

$PG^1$ is a nitrogen protecting group as defined herein (e.g., Boc); $PG^2$ is an oxygen protecting group as defined herein (e.g., tBu, Me).

In an alternate embodiment, W is —$NH_2$.

Protected hydroxyl-isoquinoline (A) reacts with a suitable $R^1L^1LG^1$ to give intermediates of formula B, which can be deprotected under acidic conditions (e.g., TFA, HCl (e.g., 4M HCl) in a suitable solvent (e.g., methanol, dichloromethane) to provide the isoquinoline intermediate C. In certain embodiments (e.g., wherein $LG^1$ is halogen), the reaction takes place under basic conditions (e.g., $CsCO_3$) in an appropriate solvent (e.g., DMF, MTBE). In certain embodiments, (e.g., wherein $LG^1$ is hydroxyl) the reaction takes place under mitsunobu conditions (e.g., in the presence of a phosphane (e.g., $PPh_3$) and an azodicarboxylate (e.g, azodicarbonyl dipiperidine (ADDP), diisopropyl azadicarboxylate (DIAD)) in a suitable solvent (e.g., THF).

An aryl carboxylate D, wherein W represents a leaving group (e.g., Cl, F, —$SO_2Me$) is protected (e.g., as the corresponding tBu ester) by treatment with a suitable protecting agent (e.g., $BOC_2O$) in the presence of a coupling agent (e.g., DMAP) in an acceptable solvent (e.g., THF), to provide intermediate E. Intermediate E is subjected to an aromatic substitution, aryl coupling or alternative coupling reaction in the presence of intermediate F to provide intermediate G. The reaction employed depends on the structure of F. In certain embodiments, if, for example, $L^2$ is —NH—, the reaction is an aromatic substitution reaction and can take place under basic conditions (e.g., $K_2CO_3$, DIPEA) in a suitable solvent (e.g., DMF, iPrOH). In exemplary embodiments, the reaction takes place at high temperature (e.g., temperature between 80-200° C., between 100-150° C., between 100-120° C., at about 110° C., between 40-60° C., at about 50° C.). In alternate embodiments if, for example, $L^2$ is a bond, the reaction takes place under aryl coupling conditions (e.g., Suzuki coupling conditions) in the presence of a metal catalyst (e.g., a palladium catalyst (e.g., Pd(PPh$_3$)$_2$C$_{1-2}$) and a base (e.g., Cs$_2$CO3, K$_2$CO$_3$) in an acceptable solvent (e.g., acetonitrile). In exemplary embodiments, the reaction takes place at high temperature (e.g., temperature between 80-200° C., between 100-150° C., between 100-120° C., at about 100° C.). In yet another embodiment, if, for example, $L^2$ is —NH—, W is —$NH_2$ and A is a carbocyclyl or heterocyclyl, the reaction can take place under reductive amination conditions in the presence of a reducing agent (e.g., NaBH(OAc)$_3$) in a suitable solvent (e.g., THF).

Intermediate G is deprotected under acidic conditions (e.g., HCl) in an acceptable solvent (e.g., EtOAc) to provide intermediate H. In exemplary embodiments, the reaction takes place at high temperatures (e.g., between 40-60° C., at about 50° C.). Intermediate H reacts with intermediates J, Ja or Jb or their salts (for example under amine coupling conditions, e.g., in the presence of a coupling agent (e.g., HATU) and a base (e.g., DIPEA)) in a suitable solvent (e.g., DCM, DMF) to provide intermediates K, Ka or Kb.

Intermediates K, Ka or Kb are subjected to a nucleophilic substitution reaction with intermediate C to provide compounds of formula (I), (Ia), (Ib), (Ic) or (Id). In certain embodiments, the nucleophilic substitution takes place in the presence of a base (e.g., DIPEA, TEA, DBU), in a suitable solvent (e.g., acetonitrile). Optionally, an iodine salt (e.g., NaI) is added to facilitate the reaction. In certain embodiments the reaction is conducted at high temperature (e.g., between 50-100° C., between 60-90° C., at about 75° C.).

Scheme 1.

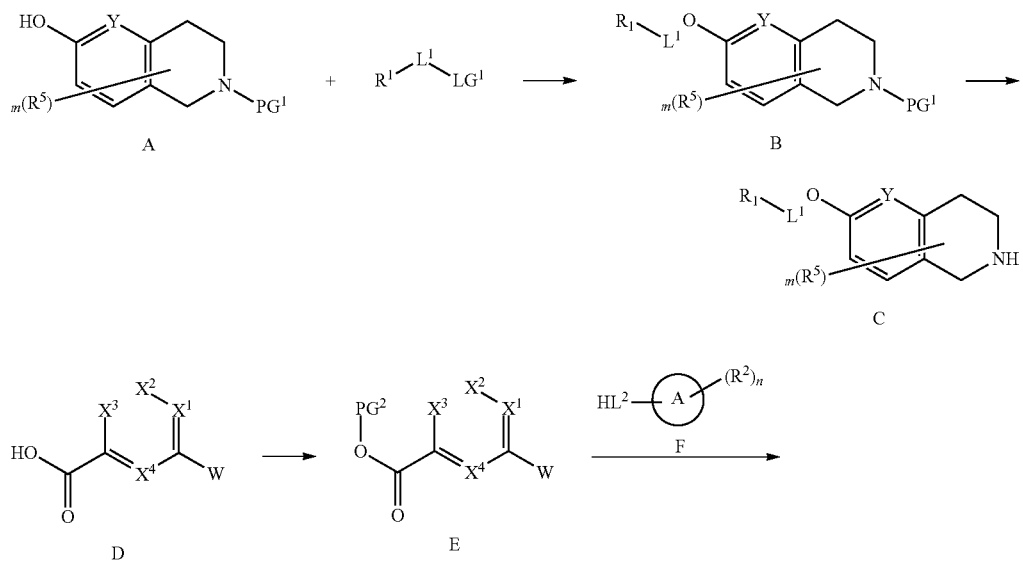

-continued
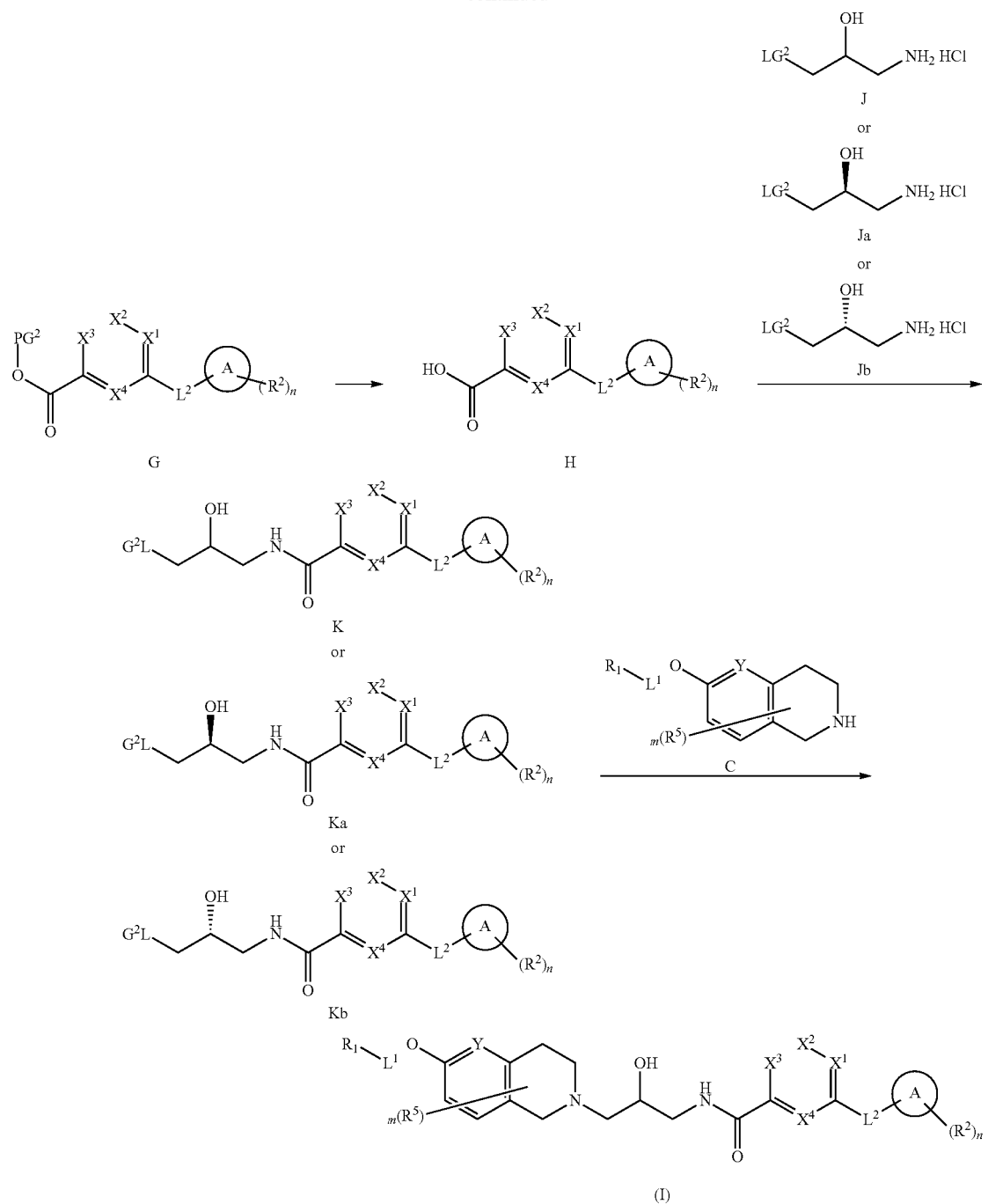
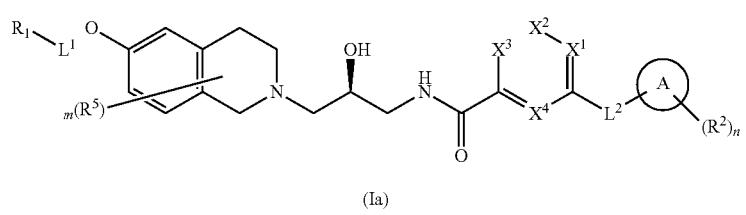

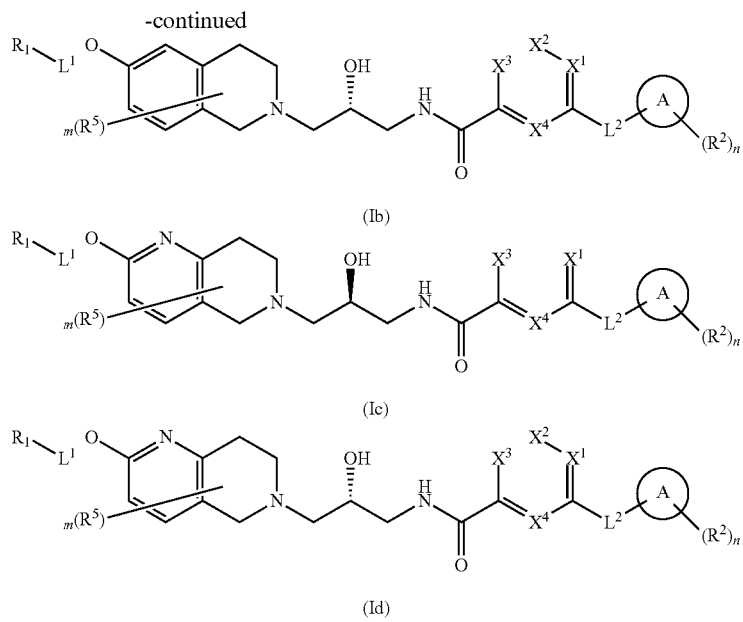

(Ib)

(Ic)

(Id)

Alternative Embodiments

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound described herein (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a), or a pharmaceutically acceptable salt thereof.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat. Cyclodextrins such as α-, β-, and γ-cyclodextrin, or chemically modified derivatives such as hydroxyalkylcyclodextrins, including 2 and 3 hydroxypropyl-β-cyclodextrins, or other solubilized derivatives may also be advantageously used to enhance delivery of compounds of the formulae described herein.

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound described herein (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) (or pharmaceutical composition thereof) for use as a pharmaceutical or a medicament (e.g., a medicament for the treatment of an MTAP-deficient and/or an MTA-accumulating disease in a subject in need thereof). In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The present invention also relates to a compound described herein (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) (or pharmaceutical composition thereof) for use in the treatment of an MTAP-deficient and/or an MTA-accumulating disease in a subject in need thereof. In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The present invention also relates to a compound described herein (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) (or pharmaceutical composition thereof) for use in the manufacturing of a medicament (e.g., a medicament for the treatment of an MTAP-deficient and/or an MTA-accumulating disease in a subject in need thereof). In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non toxic pharmaceutically acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The pharmaceutical compositions provided herewith may also be administered in the form of suppositories for rectal administration. These compositions can be prepared by mixing a compound provided herewith with a suitable non irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The above-described components for orally administrable, injectable or topically administrable, rectally administrable and nasally administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of this invention can also be administered in sustained release forms or from sustained release drug delivery systems. A description of representative sustained release materials can be found in *Remington's Pharmaceutical Sciences.*

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The present invention also relates to the pharmaceutically acceptable acid addition salt of a compound described herein (e.g., compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a).

The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long term basis upon any recurrence of disease symptoms.

Methods of Treatment and Use
Treatment of MTAP-Deficient and/or MTA-Accumulating Proliferation Disorders In one embodiment, the present invention provides methods of treating human or animal subjects having or having been diagnosed with an MTAP-deficiency-related and/or MTA-accumulating proliferative disorder (e.g. cancer) comprising administering to the subject in need thereof a therapeutically effective amount of a compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a) or a pharmaceutically acceptable salt thereof.

In one embodiment, the present invention provides methods of an MTAP-deficiency-related and/or MTA-accumulating proliferative disorder (e.g. cancer) in a subject in need thereof comprising administering to the subject a therapeutically effective amount of a compound of the present invention (e.g., compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a) or a pharmaceutically acceptable salt thereof.

In one embodiment, the present invention provides methods of treating human or animal subjects having or having been diagnosed with an MTAP-deficiency-related and/or MTA-accumulating proliferative disorder (e.g. cancer) comprising administering to the subject in need thereof a therapeutically effective amount of pharmaceutical composition of the present invention (e.g., a composition comprising a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof and a pharmaceutically acceptable carrier). In one embodiment, the compound or composition is administered in combination with a second therapeutic agent.

In one embodiment, the present invention provides methods of treating an MTAP-deficiency-related and/or MTA-accumulating proliferative disorder (e.g. cancer) in a subject in need thereof comprising administering to the subject a therapeutically effective amount of pharmaceutical composition of the present invention (e.g., a composition comprising a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof and a pharmaceutically acceptable carrier). In one embodiment, the compound or composition is administered in combination with a second therapeutic agent.

In certain embodiments, the disease is an MTAP-deficient and/or MTA-accumulating cancer.

In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one embodiment, the cancer is an MTAP-deficient and/or MTA-accumulating glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) described herein can be used in a method of inhibiting proliferation of MTAP-deficient cells in a subject in need thereof, the method comprising the step of administering to the subject, a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) in an amount that is effective to inhibit proliferation of the MTAP-deficient cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) described herein can be used in a method of inhibiting proliferation of MTA-accumulating cells in a subject in need thereof, the method comprising the step of administering to the subject, a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) in an amount that is effective to inhibit proliferation of the MTA-accumulating cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) described herein can be used in a method of inhibiting proliferation of MTAP deficient and/or MTA-accumulating cells in a subject in need thereof, the method comprising the step of administering to the subject, a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) in an amount that is effective to inhibit proliferation of the MTAP deficient and/or MTA-accumulating cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Combination Therapies

The present invention provides methods of treatment of MTAP-deficient and/or MTA accumulating proliferative disorders (e.g., cancers) with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) in combination with a second therapeutic agent.

The term "Combination" refers to either a fixed combination in one dosage unit form, or a combined administration where a compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1'), (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) and a combination partner, are both administered to a patient simultaneously in the form of a single entity or dosage. The term "non-fixed combination" means that the therapeutic agents, e.g., a compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times.

In certain embodiments, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Further compounds of particular interest for combinations with the compounds of the present invention include: EGFR-inhibitors, such as cetuximab, panitumimab, erlotinib, gefitinib and EGFRi NOS; MAPK-pathway inhibitors, such as BRAFi, panRAFi, MEKi, ERKi; PI3K-mTOR pathway inhibitors, such as alpha-specific PI3Ki, pan-class I PI3Ki and mTOR/PI3Ki, particularly everolimus and analogues thereof.

Specific compounds and classes of compounds acting via specific mechanisms can be particularly effective in conjunction with PRMT5 inhibitors (e.g., MTA-uncompetitive PRMT5 inhibitors, e.g., compounds of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or compounds of Table 1a, or pharmaceutically acceptable salts thereof). For example, PRMT5 is known to associate with SWI/SNF chromatin remodeling complexes along with other co-repressor molecules like HDAC2. PRMT5 activity on target H4R3 and H3R8 is enhanced when lysine residues become deacetylated by HD AC enzymes. Thus, HD AC inhibitors can be effective (e.g., synergistic) when used in conjunction with PRMT5 inhibitors (WO 011/079236).

Thus, PRMT5 inhibitors of the present disclosure can be used in combination with other compounds, for example: HD AC inhibitor or DNA methyltransferase inhibitor. In some embodiments, the HD AC inhibitor is Trichostatin A. In some embodiments, the DNA methyltransferase inhibitor is 5-azacytidine.

A PRMT5 inhibitor (e.g., MTA-uncompetitive PRMT5 inhibitors e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can also be administered or co-administered in any order with a MAT2A inhibitor.

A PRMT5 inhibitor (e.g., MTA-uncompetitive PRMT5 inhibitors e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can also be administered or co-administered in any order with an inhibitor of a protein which interacts with or is required for PRMT5 function, including, but not limited to, pICIN, WDR77 or RIOK1.

A PRMT5 inhibitor (e.g., MTA-uncompetitive PRMT5 inhibitors, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can be administered in combination with a HDM2 inhibitor and/or with 5-FU. The loss has been observed of wild-type p53 as a consequence of HDM2 activation resulting from CDKN2A deletion. This relates to the inability of MTAP deleted cells to salvage ATP and methionine from endogenous methyl-thioadenosine (MTA). As a consequence tumor cells become differentially sensitive towards 5-FU and other purine analogues (e.g., 6-thioguanine, 6-mercaptopurine).

Given that CDKN2A/MTAP loss also leads to deregulation of p16/CDK4/6 pathway, PRMT5 inhibitor (e.g., MTA-uncompetitive PRMT5 inhibitors, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can be administered in combination with a CDK4 inhibitor, including, but not limited to, LEE011 or a CDK 4/6 inhibitor (e.g., palbociclib (Ibrance®), ribociclib (Kisqali®), and abemaciclib (Verzenio®).

A PRMT5 inhibitor (e.g., MTA-uncompetitive PRMT5 inhibitors, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can be administered in combination with targeted treatments contingent on the dependency of individual target tumors on relevant pathways as determined by suitable predictive markers, including but not limited to: inhibitors of HDM2i, PI3K/mTOR-I, MAPKi, RTKi (EGFRi, FGFRi, METi, IGFiRi, JAKi, and WNTi.

A PRMT5 inhibitor (e.g., MTA-uncompetitive PRMT5 inhibitors, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can be administered in combination with immunotherapy.

In some embodiments, the compounds described herein are used with a cancer immunotherapy (e.g., a checkpoint blocking antibody) to treat a subject (e.g., a human subject), e.g., having a disease or disorder described herein (e.g., a cancer described herein)).

In some embodiments, the immunotherapeutic agent is an anti-CTLA-4 antibody (e.g., ipilimumab, tremelimumab).

In some embodiments, the immunotherapeutic agent is an anti-PD-1 ligand (e.g., PD-LI (e.g., B7-HI or CD274); or PD-L2 (e.g., B7-DC or CD273)). In some embodiments, the immunotherapeutic agent is an anti-PD-1 antibody (e.g., anti-PD-1 or anti-PD-L1, e.g., nivolumab (i.e., MDX-1106, BMS-936558, ONO-4538); CT-011; AMP-224; pembrolizumab; pidilizumab; or MK-3475). In some embodiments, the immunotherapeutic agent is an anti-PD-L1 antibody (e.g., BMS936559 (i.e., MDX-1105); MEDI4736; MSB0010718C (avelumab); or MPDL-3280A).

In some embodiments, the immunotherapeutic agent is a checkpoint blocking antibody (e.g., anti-TIM3, anti-LAG3, anti-TIGIT including IMP321 and MGA271).

In some embodiments, the immunotherapeutic agent is a cell-based therapy. In some embodiments, the cell-based therapy is a CAR-T therapy.

In some embodiments, the immunotherapeutic agent is a co-stimulatory antibody (e.g., anti-4-IBB, anti-OX40, anti-GITR, anti-CD27, anti-CD40).

In some embodiments, the immunotherapeutic agent is a cancer vaccine such as a neoantigen. These vaccines can be developed using peptides or RNA, e.g., In some embodiments, the immunotherapeutic agent is a oncolytic virus.

In some embodiments, the immunotherapeutic agent is a STING pathway agonist.

Exemplary STING agonists include MK-1454 and ADU-S100.

A PRMT5 inhibitor (e.g., MTA-uncompetitive PRMT5 inhibitors, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can be administered in combination with with disease-specific huMABs (e.g., an anti-HER3 huMAB)

A PRMT5 inhibitor (e.g., MTA-uncompetitive PRMT5 inhibitors e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) can be administered in combination with ADCs/ADCCs contingent on the expression of relevant surface targets on target tumors of interest.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, including, but not limited to, dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®, dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs including, but not limited to, hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g., Patents International (e.g., IMS World Publications).

The above-mentioned compounds, which can be used in combination with a compound of the present invention, can be prepared and administered as described in the art, including, but not limited to, in the documents cited above.

In one embodiment, the present invention provides pharmaceutical compositions comprising at least one compound of the present invention (e.g., a PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects having or having been diagnosed with an MTAP-deficient and/or MTA accumulating proliferative disorder (e.g. cancer) comprising administering to the subject in need thereof a therapeutically effective amount of a compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a) or a pharmaceutically acceptable salt thereof in combination with a second therapeutic agent.

In one embodiment, the present invention provides methods of an MTAP-deficient and/or MTA accumulating proliferative disorder (e.g. cancer) in a subject in need thereof comprising administering to the subject a therapeutically effective amount of a compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a) or a pharmaceutically acceptable salt thereof in combination with a second therapeutic agent.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) and a second therapeutic agent as disclosed herein are provided. Representative kits include (a) a compound of the present invention or a pharmaceutically acceptable salt thereof (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof), (b) at least one other therapeutic agent, e.g., as indicated above, whereby such kit may comprise a package insert or other labeling including directions for administration.

A compound of the present invention (e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) may also be used in combination with known therapeutic processes, for example, the administration of hormones or especially radiation. A compound of the present invention may in particular be used as a radiosensitizer, especially for the treatment of tumors which exhibit poor sensitivity to radiotherapy.

In certain instances, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

Patient Selection and Monitoring

In one aspect, the present invention provides a method of determining if a subject having or having been diagnosed with a cancer (e.g., a cancer patient) will respond to therapeutic treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof), comprising the steps of:
  a) contacting a test sample obtained from said subject with a reagent capable of detecting human cancer cells that have MTAP deficiency and/or MTA accumulation; and
  b) comparing the test sample with a reference (e.g., a reference sample taken from a non-cancerous or normal control subject),
wherein the presence of MTAP deficiency and/or MTA accumulation in said test sample indicates that the subject will respond to therapeutic treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof).

In one aspect, the present invention provides a method of determining if a cancer will respond to therapeutic treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof), comprising the steps of:
  a) contacting a test sample obtained from a subject having or having been diagnosed with said cancer with a reagent capable of detecting human cancer cells that have MTAP deficiency and/or MTA accumulation; and
  b) comparing the test sample with a reference (e.g., a reference sample taken from a non-cancerous or normal control subject),
wherein the presence of MTAP deficiency and/or MTA accumulation in said test sample indicates that the cancer will respond to therapeutic treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof). In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma. In some embodiments, the method further comprises the step of determining the level of PRMT5 in the cancer cells. The level of expression of PRMT5 can be taken into account when determining the therapeutically effective dosage of a PRMT5 inhibitor.

In one aspect, the present invention provides a method of determining the sensitivity of a cancer cell to PRMT5 inhibition (e.g., inhibition with an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof), comprising the steps of:

a) assaying the production, level, activity, expression or presence of MTAP), in said cancer cell;

b) comparing the production, level, activity, expression or presence of MTAP in the cancer cell with the production, level, activity, expression or presence of MTAP, respectively, in a non-cancerous or normal control cell, wherein a decreased level, activity or expression in the cancer cell indicates MTAP deficiency and wherein MTAP deficiency indicates that said cancer cell is sensitive to the PRMT5 inhibitor. In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one embodiment, the present invention provides a method of determining the sensitivity of a cancer cell to a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof), comprising the steps of:

a) assaying for level, activity or expression of the MTAP gene or its gene product in both the cancer cell and a normal control cell, wherein a decreased level, activity or expression in the cancer cell indicates MTAP deficiency; b) assaying for PRMT5 expression in said cancer cell; c) comparing the PRMT5 expression with PRMT5 expression in the cancer cell and a normal control cell; wherein the similarity in PRMT5 expression, and the presence of said MTAP deficiency in said cancer cell, indicates said cell is sensitive to a PRMT5 inhibitor.

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one aspect the present invention provides a therapeutic method of treating a subject having or having been diagnosed with a cancer (e.g., a cancer associated with MTAP deficiency and/or MTA accumulation) comprising the steps of:

a) assessing the level of MTAP and/or MTA in a test sample obtained from said subject (e.g., by contacting the sample with a reagent capable of detecting human MTAP-deficient and/or MTA-accumulating cancer cells in a test sample obtained from said subject), wherein the MTA level can be assessed directly (e.g., by ELISA or LC-MS/MS) or indirectly (e.g., by SDMA-modified protein ELISA or IHC, or by RNA splicing);

b) comparing the test sample with a reference (e.g., a reference sample taken from a non-cancerous or normal control subject), wherein MTAP deficiency and/or MTA accumulation in said test sample indicates said subject will respond to therapeutic treatment with a PRMT5 inhibitor; and c) administering a therapeutically effective amount of PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to the subject identified in step b).

In one aspect the present invention provides a therapeutic method of treating a cancer (e.g., a cancer associated with MTAP deficiency and/or MTA accumulation) in a subject in need thereof comprising the steps of:

a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);

b) comparing the test sample with a reference (e.g., a reference sample taken from a non-cancerous or normal control subject), wherein MTAP deficiency and/or MTA accumulation in said test sample indicates said cancer will respond to therapeutic treatment with a PRMT5 inhibitor; and c) administering a therapeutically effective amount of PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to the subject identified in step b).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

In one aspect the present invention provides a therapeutic method of treating a subject having or having been diagnosed with a cancer associated with MTAP deficiency and/or MTA accumulation comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference sample (e.g., a reference sample taken from a non-cancerous or normal control subject), wherein MTAP deficiency and/or MTA accumulation in said test sample indicates said cancer will respond to therapeutic treatment with a PRMT5 inhibitor; and
  c) administering a therapeutically effective amount of a composition comprising a PRMT5 inhibitor (e.g., an MTA-uncompetitive PRMT5 inhibitor e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to the subject identified in step b).

In one aspect the present invention provides a therapeutic method of treating cancer associated with MTAP deficiency and/or MTA accumulation in a subject in need thereof comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference sample (e.g., a reference sample taken from a non-cancerous or normal control subject), wherein MTAP deficiency and/or MTA accumulation in said test sample indicates said cancer will respond to therapeutic treatment with a PRMT5 inhibitor; and
  c) administering a therapeutically effective amount of a composition comprising a PRMT5 inhibitor (e.g., an MTA-uncompetitive PRMT5 inhibitor e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to the subject identified in step b).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

In one aspect the present invention provides a method of determining if a subject having or having been diagnosed with a cancer associated with MTAP deficiency and/or MTA accumulation will respond to treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said subject will respond to therapeutic treatment with a PRMT5 inhibitor.

In one aspect the present invention provides a method of determining if a cancer associated with MTAP deficiency and/or MTA accumulation will respond to treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) comprising the steps of:

a) assessing the level of MTAP and/or MTA in a test sample obtained from a subject having or having been diagnosed with said cancer (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);

b) comparing the test sample with a reference (e.g., a reference sample taken from a non-cancerous or normal control subject), wherein MTAP deficiency and/or MTA accumulation in said test sample indicates said cancer will respond to therapeutic treatment with a PRMT5 inhibitor.

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

Sample Preparation

The invention further provides assays for the detection of MTAP deficiency and/or MTA accumulation. They can include detecting a mutation related to MTAP deficiency and/or MTA accumulation, e.g., in a body fluid such as blood (e.g., serum or plasma) bone marrow, cerebral spinal fluid, peritoneal/pleural fluid, lymph fluid, ascite, serous fluid, sputum, lacrimal fluid, stool, and urine, or in a tissue such as a tumor tissue. The tumor tissue can be fresh tissue or preserved tissue (e.g., formalin fixed tissue, e.g. paraffin-embedded tissue).

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, a cellular DNA in a body fluid sample is separated from cells, precipitated in alcohol, and dissolved in an aqueous solution.

Detection of PRMT5 Selectivity

Samples, once prepared, can be tested for MTAP deficiency and/or MTA accumulation, either or both of which indicates that the sample is sensitive to treatment with a PRMT5 inhibitor. Cells can be determined to be MTA accumulating by techniques known in the art; methods for detecting MTA include, as a non-limiting example, liquid chromatography-electrospray ionization-tandem mass spectrometry (LC-ESI-MS/MS), as described in Stevens et al. 2010. J. Chromatogr. A. 1217: 3282-3288; and Kirovski et al. 2011 Am. J. Pathol. 178: 1145-1152; and references cited therein. The detection of MTAP deficiency can be done by any number of ways, for example: DNA sequencing, PCR based methods, including RT-PCR, microarray analysis, Southern blotting, Northern blotting, Next Generation Sequencing, and dip stick analysis. In some embodiments, MTAP deficiency is evaluated by any technique known in the art, for example, immunohistochemistry utilizing an anti-MTAP antibody or derivative thereof, and/or genomic sequencing, or nucleic acid hybridization, or amplification utilizing at least one probe or primer comprising a sequence of at least 12 contiguous nucleotides (nt) of the sequence of MTAP wherein the primer is no longer than about 30 nt.

The polymerase chain reaction (PCR) can be used to amplify and identify MTAP deficiency from either genomic DNA or RNA extracted from tumor tissue. PCR is well known in the art and is described in detail in Saiki et al., Science 1988, 239:487.

Methods of detecting MTAP deficiency by hybridization are provided. The method comprises identifying MTAP deficiency in a sample by its inability to hybridize to MTAP nucleic acid. The nucleic acid probe is detectably labeled with a label such as a radioisotope, a fluorescent agent or a chromogenic agent. Radioisotopes can include without limitation; 3H, 32P, 33P and 35S etc. Fluorescent agents can include without limitation: FITC, texas red, rhodamine, etc.

The probe used in detection that is capable of hybridizing to MTAP nucleic acid can be from about 8 nucleotides to about 100 nucleotides, from about 10 nucleotides to about 75 nucleotides, from about 15 nucleotides to about 50 nucleotides, or about 20 to about 30 nucleotides. The kit can also provide instructions for analysis of patient cancer samples, wherein the presence or absence of MTAP deficiency indicates if the subject is sensitive or insensitive to treatment with a PRMT5 inhibitor.

Single stranded conformational polymorphism (SSCP) can also be used to detect MTAP deficiency. This technique is well described in Orita et al., PNAS 1989, 86:2766-2770.

Measurement of Gene Expression

Evaluation of MTAP deficiency and measurement of MTAP gene expression, and measurement of PRMT5 gene expression can be performed using any method or reagent known in the art.

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art.

In one aspect, the expression level of a gene is determined through exposure of a nucleic acid sample to the probe-modified chip. Extracted nucleic acid is labeled, for example, with a fluorescent tag, preferably during an amplification step.

Hybridization of the labeled sample is performed at an appropriate stringency level. The degree of probe-nucleic acid hybridization is quantitatively measured using a detection device.

Alternatively, any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination. In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g., fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g., with a labeled RNA) by kinasing of the nucleic acid and subsequent attachment (ligation) of a nucleic acid linker joining the sample nucleic acid to a label (e.g., a fluorophore).

In one example, the gene expression can be measured through an in-situ hybridization protocol that can detect RNA molecules on a slide containing tissue sections or cells (e.g., through RNAscope®).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Protein levels of MTAP can be determined by examining protein expression or the protein product. Determining the protein level involves measuring the amount of any immunospecific binding that occurs between an antibody that selectively recognizes and binds to the polypeptide of the biomarker in a sample obtained from a subject and comparing this to the amount of immuno specific binding of at least one biomarker in a control sample.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS.

Adjacent Biomarkers

Near or adjacent to MTAP on chromosome 9 are several other biomarkers. CDKN2A is often, if not usually, deleted along with MTAP. Additional genes or pseudogenes in this region include: C9orf53, ERVFRD-3, TUBB8P1, KHSRPP1, MIR31, and MIR31HG.

In some embodiments of the methods, the cell that is MTAP-deficient is also deficient in CDKN2A. In some embodiments, the cell that is MTAP-deficient is also deficient in one or more of: CDKN2A, C9orf53, ERVFRD-3, TUBB8P1, KHSRPP1, MIR31, and MIR31HG.

Thus, in various methods involving a step of evaluating a cell for MTAP deficiency or determining if a cell is MTAP-deficient, this step can comprise the step of determining if the cell is deficient for one or more of these markers: CDKN2A, C9orf53, ERVFRD-3, TUBB8P1, KHSRPP1, MIR31, and MIR31HG.

Thus, in some embodiments, the disclosure encompasses: A method of determining if a subject having or having been diagnosed with a cancer will respond to therapeutic treatment with a PRMT5 inhibitor, comprising the steps of:

a) evaluating a test sample obtained from said subject for MTAP deficiency, and evaluating a reference sample from a non-cancerous or normal control subject for MTAP deficiency, wherein MTAP deficiency in the test sample relative to the reference sample indicates that the subject will respond to therapeutic treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof); wherein MTAP deficiency is evaluated by evaluating the deficiency of one or more of the following biomarkers: CDKN2A, C9orf53, ERVFRD-3, TUBB8P1, KHSRPP1, MIR31, and MIR31HG, and wherein the method can further comprise the following steps:

b) determining the level of MTAP in the subject, wherein steps a) and b) can be performed in any order;

c) administering a therapeutically effective amount of a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to the subject; and d) determining the level of PRMT5 activity in the subject following step c), wherein a decrease in the level of PRMT5 activity is correlated with the inhibition of the proliferation of the cancer, and wherein steps c) and d) are performed after steps a) and b).

In some embodiments, the disclosure encompasses: A method of determining if a cancer will respond to therapeutic treatment with a PRMT5 inhibitor, comprising the steps of:

a) evaluating a test sample obtained from a subject having or having been diagnosed with said cancer for MTAP deficiency, and evaluating a reference sample from a non-cancerous or normal control subject for MTAP deficiency, wherein MTAP deficiency in the test sample relative to the reference sample indicates that the cancer will respond to therapeutic treatment with a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof); wherein MTAP deficiency is evaluated by evaluating the deficiency of one or more of the following biomarkers: CDKN2A, C9orf53, ERVFRD-3, TUBB8P1, KHSRPP1, MIR31, and MIR31HG, and wherein the method can further comprise the following steps:

b) determining the level of MTAP in the subject, wherein steps a) and b) can be performed in any order;

c) administering a therapeutically effective amount of a PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to the subject; and d) determining the level of PRMT5 activity in the subject following step c), wherein a decrease in the level of PRMT5 activity is correlated with the inhibition of the proliferation of the cancer, and wherein steps c) and d) are performed after steps a) and b).

Assaying for Biomarkers and PRMT5 Inhibitor Treatment

A number of patient stratification strategies could be employed to find patients likely to be sensitive to PRMT5 inhibition with an MTA-uncompetitive PRMT5 inhibitor (e.g., a PRMT5 inhibitor of the present invention, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof), including but not limited to, testing for MTAP deficiency and/or MTA accumulation.

Once a patient has been assayed for MTAP deficiency and/or MTA accumulation and predicted to be sensitive to treatment with a PRMT5 inhibitor, administration of any PRMT5 inhibitor (e.g., an MTA-uncompetitive PRMT5 inhibitor, e.g., a compound of formula (I), (Ia), (Ib), (Ic), (Id), (II), (IIa), (IIb), (III), (IIIa), (IIIb), (IV), (IVa), (IVb), (V), (VI), (V2), (Va), (Va1), (Va1'), (Va2), (Vb), (Vb1), (Vb1') (Vb2), (VI), (VII), (VI2), (VIa), (VIa1), (VIa1'), (VIa2), (VIb), (VIb1), (VIb1'), (VIb2), (VII), (VIII), (VII2), (VIIa), (VIIa1), (VIIa2), (VIIb), (VIIb1), (VIIb2), (VIII), (VIIIa), (VIIIb), (IX), (IXa), (IXb), (X), (Xa), (Xb), (XI), (XIa), (XIb), (XII), (XIIa), (XIIb) or a compound of Table 1a, or pharmaceutically acceptable salts thereof) to a patient can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

Kits

In some embodiments kits related to methods of the invention are provided.

In one embodiment, a for predicting the sensitivity of a subject having or having been diagnosed with an MTAP-deficiency-related cancer for treatment with a PRMT5 inhibitor is provided. The kit comprises: i) reagents capable of detecting human MTAP-deficient and/or MTA-accumulating cancer cells; and ii) instructions for how to use said kit.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. In the synthetic examples below, the descriptions of experimental procedures within a reaction sequence are listed in numerical order.

Abbreviations

General
ADDP 1,1'-(azodicarbonyl)dipiperidine
anhy. anhydrous
aq. aqueous
satd. saturated
min(s) minute(s)
hr(s) hour(s)
mL milliliter
mmol millimole(s)
mol mole(s)
MS mass spectrometry
NMR nuclear magnetic resonance
TLC thin layer chromatography
HPLC high-performance liquid chromatography
Me methyl
i-Pr iso-propyl
t-Bu tert-butyl
'BuXPhos 2-di-tert-butylphosphino-2',4',6'-triisopropylbiphenyl
Ph phenyl
Et ethyl
Bz benzoyl
RuPhos 2-dicyclohexylphosphino-2',6'-diisopropoxybiphenyl
Spectrum
Hz hertz
δ chemical shift
J coupling constant
s singlet
d doublet
t triplet
q quartet
m multiplet
br broad
qd quartet of doublets
dquin doublet of quintets
dd doublet of doublets
dt doublet of triplets
Solvents and Reagents
DAST Diethylaminosulfurtrifluoride
$CHCl_3$ chloroform
DCM dichloromethane
DMF dimethylformamide
$Et_2O$ diethyl ether
EtOH ethyl alcohol
EtOAc ethyl acetate
MeOH methyl alcohol
MeCN acetonitrile
PE petroleum ether
THF tetrahydrofuran
DMSO dimethyl sulfoxide
t-BuOK potassium tert-butoxide
9-BBN 9-borabicyclo[3.3.1]nonane
AcOH acetic acid
HCl hydrochloric acid
$H_2SO_4$ sulfuric acid
$NH_4Cl$ ammonium chloride
KOH potassium hydroxide
NaOH sodium hydroxide
$K_2CO_3$ potassium carbonate
$Na_2CO_3$ sodium carbonate
TFA trifluoroacetic acid
$Na_2SO_4$ sodium sulfate
$NaBH_4$ sodium borohydride
$NaHCO_3$ sodium bicarbonate
LiHMDS lithium hexamethyldisilylamide
$NaBH_4$ sodium borohydride
$Et_3N$ triethylamine
Py pyridine
PCC pyridinium chlorochromate
DMAP 4-(dimethylamino)pyridine
DIPEA N,N-diisopropylethylamine
BINAP 2,2'-bis(diphenylphosphanyl)-1,1'-binaphthyl
dppf 1,1'-bis(diphenylphosphino)ferrocene
PEP Phospho(enol)pyruvic acid
LDH Lactate Dehydrogenase
DTT DL-Dithiothreitol
BSA Bovine Serum Albumin
NADH β-Nicotinamide adenine dinucleotide, reduced
$Pd(t-Bu_3P)_2$ bis(tri-tert-butylphosphine)palladium(0)
AcCl acetyl chloride
i-PrMgCl Isopropylmagnesium chloride
TBSCl tert-Butyl(chloro)dimethylsilane
$(i-PrO)_4Ti$ titanium tetraisopropoxide
BHT 2,6-di-t-butyl-4-methylphenoxide
BzCl benzoyl chloride
CsF cesium fluoride
DCC dicyclohexylcarbodiimide
DMP Dess-Martin periodinane
EtMgBr ethylmagnesium bromide
EtOAc ethyl acetate
TEA triethylamine
AlaOH alanine
TBAF tetra-n-butylammonium fluoride
TBS t-butyldimethylsilyl
TMS trimethylsilyl
$TMSCF_3$ (Trifluoromethyl)trimethylsilane
Ts p-toluenesulfonyl
Bu butyl
$Ti(OiPr)_4$ tetraisopropoxy titanium
LAH Lithium Aluminium Hydride
LDA lithium diisopropylamide
$LiOH \cdot H_2O$ lithium hydroxide hydrates
MAD methyl aluminum bis(2,6-di-t-butyl-4-methylphenoxide)
NBS N-bromosuccinimide
$Na_2SO_4$ sodium sulfate
$Na_2S_2O_3$ sodium thiosulfate
PE petroleum ether
MeCN acetonitrile
Boc t-butoxycarbonyl
MTBE methyl tert-butyl ether
DIAD diisopropyl azodicarboxylate General Experimental Notes In the following examples, the chemical reagents were purchased from commercial sources (such as Alfa, Acros, Sigma Aldrich, TCI and Shanghai Chemical Reagent Company), and used without further purification.

In some examples, purification of intermediates and final compounds was performed using HPLC ($H_2O$—MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm) The material was dissolved in 0.7 mL DMSO. Flow: 30 mL/min. Purity of the obtained fractions was checked via the analytical LCMS.

Spectra were recorded for each fraction as it was obtained straight after chromatography in the solution form. The solvent was evaporated under the $N_2$ flow upon heating to 80° C. On the basis of post-chromatography LCMS analysis fractions were united. Solid fractions were dissolved in 0.5 mL MeOH and transferred into pre-weighted marked vials. Obtained solutions were again evaporated under the $N_2$ flow upon heating to 80° C. After drying, products were subjected to lyophilization using acetonitrile-water mixtures and finally characterized by LCMS and $^1$H NMR.

Nuclear magnetic resonance (NMR) spectra were recorded using Brucker AVANCE DRX 500, Bruker 400 spectrometer or Varian UNITYplus 400. Chemical shifts for protons were reported as parts per million in δ scale using solvent residual peak ($CHCl_3$: 7.27 ppm) (methanol-$d_4$: 3.31 ppm) (DMSO-$d_6$: 2.50 ppm) or tetramethylsilane (0.00 ppm) as internal standards. Chemical shifts of $^{13}$C NMR spectra were reported in ppm from the central peak of $CDCl_3$ (77.00 ppm) (methanol-$d_4$: 49.15 ppm) (DMSO-$d_6$: 39.51 ppm) on the S scale. Data are represented as follows: chemical shift, multiplicity (s=singlet, d=doublet, t=triplet, q=quartet, qn=quintuplet, sx=sextet, sp=septuplet, m=multiplet, br=broad), coupling constant (J, Hz) and integration.

In certain examples, mass spectra were recorded on an Agilent 1100 Series LC/MSD system with DAD\ELSD and Agilent LC\MSD VL (G1956A), SL (G1956B) mass-spectrometer or an Agilent 1200 Series LC/MSD system with DAD\ELSD and Agilent LC\MSD SL (G6130A), SL (G6140A) mass-spectrometer.

All the LC/MS data were obtained using positive/negative mode switching.

Column Zorbax SB-C18 1.8 μm 4.6×15 mm Rapid Resolution cartridge (PN 821975-932)

Mobile phase A—acetonitrile, 0.1% formic acid
  B—water (0.1% formic acid)
Flow rate 3 ml/min
Gradient 0 min-100% B
0.01 min-100% B
1.5 min-0% B
1.8 min-0% B
1.81 min-100% B
Injection volume 1 μl
Ionization mode atmospheric pressure chemical ionization (APCI)
Scan range m/z 80-1000.

Other Exemplary Analytical LC/MS Instruments and Conditions are Described Below:

Instrument: Agilent LC1100-MS6100 series G1956B; Column: Xbridge Shield RP-18, 50*2.1 mm*5 μm; Mobile Phase A: $H_2O$ with 0.05% $NH_3$—$H_2O$ (v %); Mobile Phase B: MeCN; Plow rate: 1.0 mL/min; Wavelength: UV 220 nm, 254 nm; Column temperature: 30° C.; MS ionization: ESI.

0-30CD: Gradient: B from 0%~30% over 2 minutes and holding at 30% for 0.48 minutes; 0-60CD: Gradient: B from 0%~60% over 2 minutes and holding at 60% for 0.48 minutes; 10-80CD: Gradient: B from 10%~80% over 2 minutes and holding at 80% for 0.48 minutes; 30-90CD: Gradient: B from 30%~90% over 2 minutes and holding at 90% for 0.48 minutes; 50-100CD: Gradient: B from 50%~100% over 2 minutes and holding at 100% for 0.48 minutes.

Instrument: Agilent LC1100-MS6100 series G1956B; Column: Xtimate C18, 30*2.1 mm*3 μm; Mobile Phase A: $H_2O$ with 0.0375% TFA (v %); Mobile Phase B: MeCN with 0.01875% TFA (v %): Flow rate: 0.8 mL/min; Wavelength: UV 220 nm, 254 nm; Column temperature: 50° C.; MS ionization: ESI.

0-30AB: Gradient: B from 0%~30% over 3 minutes and holding at 30% for 0.5 minutes; 0-60AB: Gradient: B from 0%~60% over 3 minutes and holding at 30% for 0.5 minutes; 10-80AB: Gradient: B from 10%~80% over 3 minutes and holding at 30% for 0.5 minutes; 30-90AB: Gradient: B from 0%~30% over 3 minutes and holding at 30% for 0.5 minutes; 50-100AB: Gradient: B from 50%~100% over 3 minutes and holding at 100% for 0.5 minutes.

Instrument: Shimadzu LC20-MS2010; Column: Agilent Pursit 5 C18 20*2.0 mm; Mobile Phase A: $H_2O$ with 0.0375% of TFA (v %); Mobile Phase B: MeCN with 0.01875% of TFA (v %); Gradient: B from 5-95% over 0.7 minutes and holding at 95% for 0.4 minutes; Flow Rate: 1.5 mL/min; Wavelength: UV 220 nm, 254 nm, 215 nm; Column temperature: 50° C.; MS ionization: ESI.

Instrument: Shimadzu LC20-MS2020; Column: Agilent Pursit 5 C18 20*2.0 mm; Mobile Phase A: $H_2O$ with 0.0375% of TFA (v %); Mobile Phase B: MeCN with 0.01875% of TFA (v %); Gradient: B from 5-95% over 0.7 minutes and holding at 95% for 0.4 minutes; Flow Rate: 1.5 mL/min; Wavelength: UV 220 nm, 254 nm; Column temperature: 50° C.; MS ionization: ESI.

Exemplary HPLC Instruments and Conditions

Instrument: Shimadzu LC20; Column: YMC-Pack ODS-A 150*4.6 mm; Mobile Phase A: $H_2O$ with 0.06875% TFA (v %); Mobile Phase B: MeCN with 0.0625% TFA (v %); Flow rate: 1.5 mL/min; Wavelength: UV 220 nm, 215 nm, 254 nm; Column temperature: 40° C.

0-30: Gradient: B from 0~30% over 10 minutes and holding at 30% for 5 minutes; 0-60: Gradient: B from 0~60% over 10 minutes and holding at 60% for 5 minutes; 0-95: Gradient: B from 0~95% over 10 minutes and holding at 95% for 5 minutes; 10-80: Gradient: B from 10~80% over 10 minutes and holding at 80% for 5 minutes; 30-90: Gradient: B from 30~90% over 10 minutes and holding at 90% for 5 minutes; 50-100: Gradient: B from 50~100% over 10 minutes and holding at 100% for 5 minutes.

Instrument: Shimadzu LC20; Column: Xbridge Shield RP-18 50*2.1 mm, 5 μm; Mobile Phase A: $H_2O$ with 0.01% $NH_3$—$H_2O$; Mobile Phase B: MeCN; Flow Rate: 1.2 mL/min; Wavelength: UV 220 nm, 215 nm, 254 nm; Column temperature: 40° C.

0-30CD: Gradient: B from 0~30% over 6 minutes and holding at 30% for 2 minutes; 0-60CD: Gradient: B from 0~60% over 6 minutes and holding at 60% for 2 minutes; 10-80CD: Gradient: B from 10~80% over 6 minutes and holding at 80% for 2 minutes; 30-90CD: Gradient: B from 30~90% over 6 minutes and holding at 90% for 2 minutes; 50-100CD: Gradient: B from 10~80% over 6 minutes and holding at 100% for 2 minutes.

Instrument: Shimadzu LC20; Column: Ultimate C18 50*3 mm, 3 μm; Mobile Phase A: $H_2O$ with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C. 0-30AB: Gradient: B from 0~30% over 2.5 minutes and holding at 30% for 0.75 minutes; 0-60AB: Gradient: B from 0~60% over 2.5 minutes and holding at 60% for 0.75 minutes; 5-95AB: Gradient: B from 5~95% over 2.5 minutes and holding at 95% for 0.75 minutes.

Instrument: Shimadzu LC20; Column: Ultimate C18 50*3 mm, 3 μm; Mobile Phase A: $H_2O$ with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C. 10-80AB: Gradient: B from 10-80% over 4 minutes and holding at 80% for 2 minutes.

Exemplary TLC, Concentration and Normal Phase Chromatography.

Analytical thin layer chromatography (TLC) was performed with silica gel 60 F254 aluminum plates. Visualization was done under a UV lamp (254 nm) and by iodine or immersion in ethanolic phosphomolybdic acid (PMA) or potassium permanganate ($KMnO_4$), followed by heating using a heat gun. Organic solutions were concentrated by rotary evaporation at 20~40° C.

Purification of reaction products were generally done by flash column chromatography with 230-400 mesh silica gel or Agela flash silica column.

Exemplary Chiral SFC Analytical Methods

Column: Chiralpak AD-3 150×4.6 mm I.D., 3 µm; Mobile phase: A: supercritical $CO_2$; Mobile phase B: EtOH (0.05% DEA); Gradient: from 5% to 40% of B in 5 min and hold 40% for 2.5 min, then 5% of B for 2.5 min; Flow rate: 2.5 mL/min; Column temperature: 35° C.; ABPR: 1500 psi.

Column: Chiralpak AD-3 100×4.6 mm I.D., 3 µm; Mobile phase: A: supercritical $CO_2$ Mobile phase B: EtOH (0.1% ethanolamine); Gradient: from 5% to 40% of B in 4.5 min and hold 40% for 2.5 min, then 5% of B for 1 min; Flow rate: 2.8 mL/min; Column temperature: 40° C.

Exemplary Preparative HPLC Separation Methods

Basic condition ($NH_3$—$H_2O$): Instrument: Gilson GX-281 Liquid Handler, Gilson 322 Pump, Gilson 156 UV Detector; Column: Waters Xbridge 150×25 mm×5 µm; Mobile phase A: $H_2O$ with 0.05% $NH_3$—$H_2O$ (v %); Mobile phase B: MeCN; Gradient: B from 22% to 52% in 9.5 min, hold 100% B for 1 min; Flow Rate: 25 mL/min; Column Temperature: 30° C.; Wavelength: 220 nm, 254 nm.

Acid condition (HCOOH): Instrument: Gilson GX-281 Liquid Handler, Gilson 322 Pump, Gilson 156 UV Detector; Column: Agela Durashell C18 150*25 mm 5 µm; Mobile phase A: $H_2O$ (0.0225% HCOOH); Mobile phase B: MeCN; Gradient: B from 7% to 37% in 9 min, hold 100% B for 0 min; Flow Rate: 25 mL/min; Column Temperature: 30° C.; Wavelength: 220 nm, 254 nm.

Acid condition (HCl): Gilson GX-281 Liquid Handler, Gilson 322 Pump, Gilson 156 UV Detector; Column: Xtimate C18 150*25 mm*5 µm; Mobile phase A: $H_2O$ with 0.05% HCl (v %); Mobile phase B: MeCN; Gradient: B from 0% to 30% in 6.5 min, hold 100% B for 2.5 min; Flow Rate: 25 mL/min; Column Temperature: 30° C.; Wavelength: 220 nm, 254 nm).

Neutral condition ($NH_4HCO_3$): (Instrument: Gilson GX-281 Liquid Handler, Gilson 322 Pump, Gilson 156 UV Detector; Column: Waters Xbridge 150×25 mm×5 µm; Mobile phase A: $H_2O$ with 10 mmol $NH_4HCO_3$; Mobile phase B: MeCN; Gradient: B from 39% to 69% in 10 min, hold 100% B for 2.5 min; Flow Rate: 25 mL/min; Column Temperature: 30° C.; Wavelength: 220 nm, 254 nm).

Exemplary Large-Scale Separation

Basic condition: Instrument: Shimadzu LC-8A Pumps, Shimadzu SCL-10A VP System Controller, Shimadzu SPD-20AV UV/VIS Detector; Column: Phenomenex Gemini C18 250*50 mm*10 µm; Mobile phase A: water (0.04% $NH_3$—$H_2O$+10 mM $NH_4HCO_3$); Mobile phase B: MeCN; Gradient: B from 65% to 95% in 26 min, hold 100% B for 3 min; Flow Rate: 110 mL/min; Column Temperature: 30° C.; Wavelength: 220 nm, 254 nm.

Acid condition (TFA): Instrument: Shimadzu LC-20AP Pumps, Shimadzu CBM-20A System Controller Shimadzu SPD-20AV UV/VIS Detector; Column: Phenomenex luna C18 250×50 mm×10 µm; Mobile phase A: $H_2O$ with 0.1% TFA (v %); Mobile phase B: MeCN; Gradient: B from 0% to 25% in 15 min, hold 100% B for 4 min; Flow Rate: 120 mL/min; Column Temperature: 30° C.; Wavelength: 220 nm, 254 nm.

Exemplary Preparative Chiral SFC Method:

Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

In certain examples, the chiral separation was performed under the following conditions: Instrument: Thar 80; Column: Daicel Chiralpak AD. 250×30 mm I.D. 10 µm; Mobile phase: supercritical $CO_2$/MeOH (0.1% $NH_3$—$H_2O$, v %)=60/40; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis.

Exemplary general method for preparative HPLC: Column: Waters RBridge prep 10 µm C18, 19*250 mm. Mobile phase: acetonitrile, water ($NH_4HCO_3$) (30 L water, 24 g $NH_4HCO_3$, 30 mL $NH_3 \cdot H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 µm at 45° C.

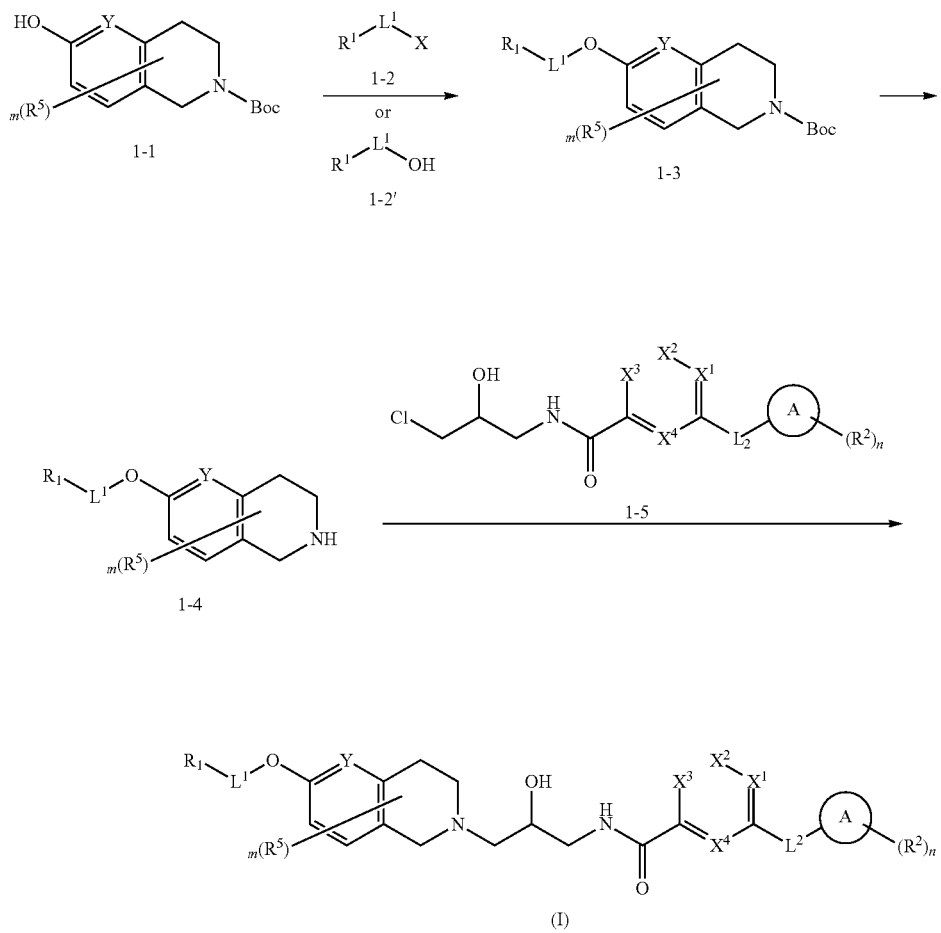

Scheme 1-1A.

As shown in Scheme 1-1A, compounds of formula (I) can be prepared from compounds of formula 1-1. Compounds of formula 1-1 be alkylated with compounds of formula 1-2 to form compounds of formula 1-3. Examples of conditions known to generate compounds of formula 1-3 from compounds of formula 1-1 and formula 1-2 include but are not limited to adding a base a such as a hydride base e.g., NaH, or KH or a carbonate base e.g. $Na_2CO_3$, $K_2CO_3$, or $CS_2CO_3$, and in one embodiment stirring the reaction at 0° C. to room temperature or another embodiment at a temperature of 70° C. or higher, for example at a temperature in a range of 70° C. to 110° C., or in a range of 70° C. to 80° C., or at 80° C. The reaction may be carried out in solvents such as but not limited to DMF, and MTBE.

Alternatively, compounds of formula 1-3 may be formed from compounds of formula 1-1 and alcohols of formula 1-2' under Mitsunobu conditions. Contemplated Mitsunobu conditions may include but are not limited to treating a solution of a compound of formula 1-1 and an alcohol of formula 1-2' with a phosphine ligand and an azodicarboxylate. Exemplary phosphine ligands include $PPh_3$, and $PBu_3$. Exemplary azodicarboxylates include ADDP, and DIAD. The reaction may be carried out in solvents such as but not limited to toluene, and THF. The reaction may be carried out at an initial temperature in the range of 0° C. to room temperature. The reaction may further comprise a subsequent heating step, for example the reaction may be heated at the reflux temperature of the solvent, or in a range of 50° C. to 110° C., or in a range of 50° C. to 95° C., or at 90° C.

Compounds of formula 1-3 can undergo boc deprotection using conditions known to one of skill in the art to give compounds of formula 1-4. For example boc deprotection may comprise treatment with an acid. Exemplary acids include TFA, and HCl, and exemplary solvents include halogenated solvents such as DCM and hexafluoroisopropanol or ether solvents such as dioxane. Compounds of formula 1-4 may be isolated as a salt or converted to the free base.

Compounds of formula 1-4 can be coupled with alkyl chlorides of formula 1-5 under A-alkylation conditions. Examples of conditions known to generate compounds of formula (I) from a mixture of compounds of formula 1-4 and an alkyl chloride of formula 1-5 include but are not limited to adding an iodide salt and one or more bases. Exemplary iodide salts include such as NaI, KI and tetra-n-butylammonium iodide. Exemplary bases include amines such as carbonate bases such as $K_2CO_3$, and amine bases such as DBU, $NEt_3$, and $NEt(iPr)_2$. The reaction may be carried out in solvents such as but not limited to acetonitrile and ethanol. The reaction may be heated at a temperature such as the reflux temperature of the solvent, or at a temperature in a range of 70° C. to 100° C., or in a range of 85° C. to 95° C., or at 90° C., or at 75° C.

Scheme 1-1B

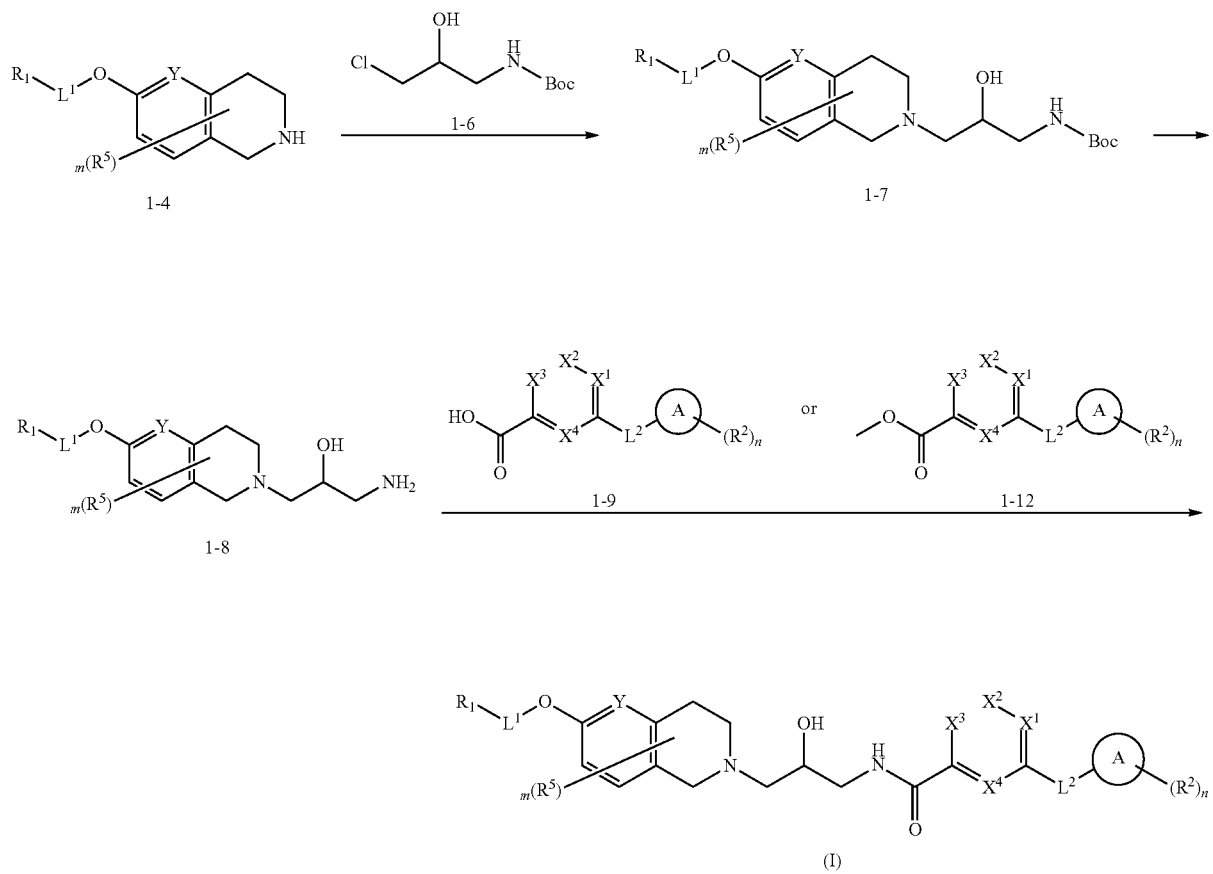

As shown in Scheme 1-1B, compounds of formula (I) can be prepared from compounds of Formula 1-4. Compounds of formula 1-4 can be alkylated with compounds of formula 1-6 to form compounds of formula 1-7. Examples of alkylation conditions include but are not limited to adding an iodide salt and one or more bases. Exemplary iodide salts include NaI, KI and tetra-n-butylammonium iodide. Exemplary bases include amines such as carbonate bases such as $K_2CO_3$, and amine bases such as DBU, $NEt_3$, and $NEt(iPr)_2$. The reaction may be carried out in solvents such as but not limited to acetonitrile and ethanol. The reaction may be heated at a temperature such as the reflux temperature of the solvent, or at a temperature in a range of 70° C. to 110° C., or in a range of 90° C. to 100° C., or at 100° C., or at 90° C., or at 75° C.

Compounds of formula 1-7 can undergo hoc deprotection using conditions known to one of skill in the art to give compounds of formula 1-8. For example hoc deprotection may comprise treatment with an acid. Exemplary acids include TFA, and HCl, and exemplary solvents include halogenated solvents such as DCM and hexafluoroisopropanol or ether solvents such as dioxane. Compounds of formula 1-8 may be isolated as a salt or converted to the free base.

Amines of formula 1-8 can be coupled with carboxylic acids of formula 1-9 under amide bond forming conditions to give amides of formula (I). Examples of amide coupling conditions that may be used to form amides of formula (I) from a carboxylic acid of formula (1-9) and an amine of formula 1-8 include but are not limited to adding a coupling reagent such as a carbodiimide coupling reagent for example, 1-ethyl-3-(3-dimethylaminopropyl)carbodiimide (EDC) or 1,3-dicyclohexylcarbodiimide (DCC), 2-(7-aza-1H-benzotriazole-1-yl)-1,1,3,3-tetramethyluronium hexafluorophosphate (HATU), 1,1'-carbonyldiimidazole (CDI), 2,4,6-tripropyl-1,3,5,2,4,6-trioxatriphosphinane 2,4,6-trioxide (T3P®). In addition to the coupling reagents, additives may be added. Exemplary additives include but are not limited to 4-(dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to dimethylformamide. The reaction may be carried out at room temperature.

Alternatively, Amines of formula 1-8 can be coupled with esters of formula 1-12 to form compounds of formula (1). Exemplary conditions, involve reacting a compound of formula 1-8 with a compound of formula 1-12 in the presence of an amine base such as TEA. The reaction may occur in a solvent, such as an alcohol solvent, for example MeOH.

Scheme 1-1C

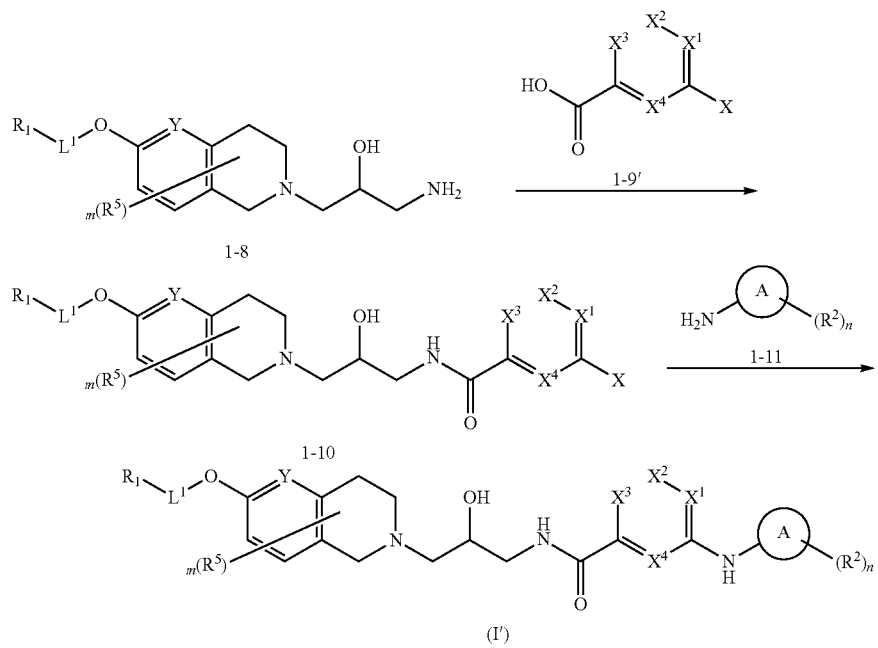

As shown in Scheme 1-1C, Compounds of formula (I') may be prepared from amines of formula 1-8. Carboxylic acids of formula 1-9' may be coupled with amines of formula 1-8 using amide coupling conditions described herein to form amides of formula 1-10. Compounds of formula 1-10 may be coupled with amines of formula 1-11 under SNAr conditions to form compounds of formula (I'). Contemplated SNAr conditions conditions include but are not limited to reacting compounds of formula (1-11) and compounds of formula 1-10 in the presence of a base. Exemplary bases include carbonate vases such as $K_2CO_3$, $Na_2CO_3$, and $Cs_2CO_3$. The reaction may be carried out in the presence of a solvent such as DMSO or DMF. The reaction may be heated at a temperature in a range of 70° C. to 150° C., or in a range of 90° C. to 120° C., or at 100 to 110° C., or at 110° C., or at 105° C.

Synthesis of Intermediate Acids

Acid—A 2-(methyl(propyl)amino)-6-(oxetan-3-ylamino)pyrimidine-4-carboxylic Acid

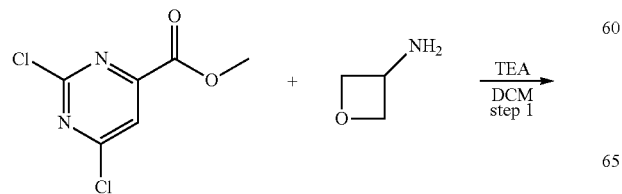

-continued

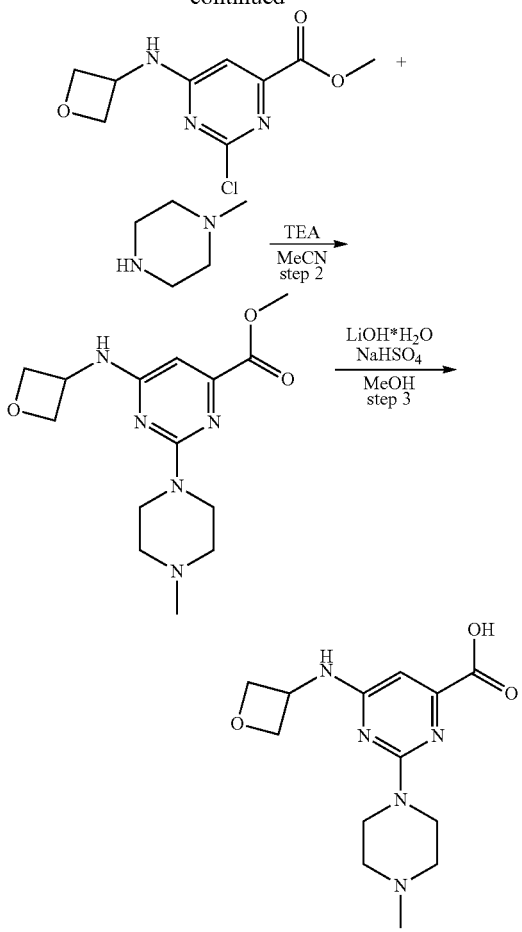

methyl 2-chloro-6-(oxetan-3-ylamino)pyrimidine-4-carboxylate. To a solution of methyl 2,6-dichloropyrimidine-4-carboxylate (31.6 g, 152.65 mmol) in DCM (500 mL) at 0° C. was added TEA (15.45 g, 152.65 mmol, 21.28 mL) followed by oxetan-3-amine (11.16 g, 152.65 mmol) and the resulting reaction mixture was stirred at 0° C. for 30 min. and allowed to warm to room temperature. After 12 hr the reaction mixture was triturated with water (200 mL). The precipitate formed was collected by filtration, washed with water and dried in vacuo to give methyl 2-chloro-6-(oxetan-3-ylamino)pyrimidine-4-carboxylate (14.3 g, 58.69 mmol, 38.45% yield). $^1$H NMR (500 MHz, DMSO-$d_6$) δ (ppm) 3.85 (s, 3H), 4.47 (m, 2H), 4.83 (m, 2H), 4.97 (m, 1H), 7.09 (s, 1H), 9.08 (bds, 1H). LCMS(ESI): [M+H]+ m/z: calcd 243.7. found 245.0; Rt=0.966 min.

methyl 2-(4-methylpiperazin-1-yl)-6-(oxetan-3-ylamino)pyrimidine-4-carboxylate. To a solution of methyl 2-chloro-6-(oxetan-3-ylamino)pyrimidine-4-carboxylate (0.6 g, 2.46 mmol) in $CH_3CN$ (30 mL) was added 1-methylpiperazine (369.98 mg, 3.69 mmol, 409.73 uL), followed by TEA (747.57 mg, 7.39 mmol, 1.03 mL). The reaction mixture was stirred at 65° C. for 48 hr. The reaction mixture was evaporated, poured into water (50 ml) and extracted with EtOAc (3×20 ml). The combined organic extracts were washed with water(2*10 ml), dried over sodium sulphate and evaporated in vacuo to afford product methyl 2-(4-methylpiperazin-1-yl)-6-(oxetan-3-ylamino)pyrimidine-4-carboxylate (0.54 g, 1.76 mmol, 71.35% yield). $^1$H NMR (500 MHz, $CDCl_3$) δ (ppm) 2.34 (s, 3H), 2.46 (m, 4H), 3.83 (m, 4H), 3.92 (s, 3H), 4.58 (m, 2H), 4.98 (m, 2H), 5.09 (m, 1H), 5.25 (m, 1H), 6.39 (s, 1H). LCMS(ESI): [M+H]+ m/z: calcd 307.4. found 308.0; Rt=0.766 min.

2-(methyl(propyl)amino)-6-(oxetan-3-ylamino)pyrimidine-4-carboxylic acid. To a solution of methyl 2-(4-methylpiperazin-1-yl)-6-(oxetan-3-ylamino)pyrimidine-4-carboxylate (0.54 g, 1.76 mmol) in methanole (5 mL) was added lithium hydroxide monohydrate, 98% (184.32 mg, 4.39 mmol, 122.07 uL) in water (2 ml). The reaction mixture was stirred at 25° C. for 24 hr. The reaction mixture was evaporated, and added sodium bisulfate (527.35 mg, 4.39 mmol) in water (10 ml) then evaporated and added hot ethanole(20 ml) the resulting precipitate was filtered off, washed with hot ethanole (3*10 ml). The filtrate was evaporated and dried to afford product 2-(4-methylpiperazin-1-yl)-6-(oxetan-3-ylamino)pyrimidine-4-carboxylic acid (0.2 g, 681.85 umol, 38.81% yield). $^1$H NMR (400 MHz, DMSO-$d_6$) δ (ppm) 2.38 (s, 3H), 2.58 (m, 4H), 3.75 (m, 4H), 4.42 (m, 2H), 4.79 (m, 2H), 4.98 (m, 1H), 6.41 (s, 1H), 8.14 (bds, 1H), 10.40 (bds, 1H). LCMS(ESI): [M+H]+ m/z: calcd 293.3. found 294.0; Rt=0.188 min.

6-(oxetan-3-ylamino)-2-(4-propionylpiperazin-1-yl)pyrimidine-4-carboxylic Acid

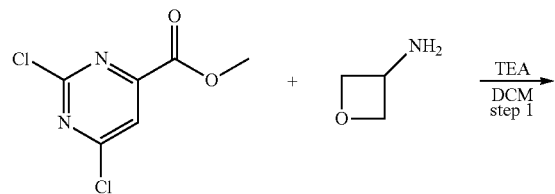

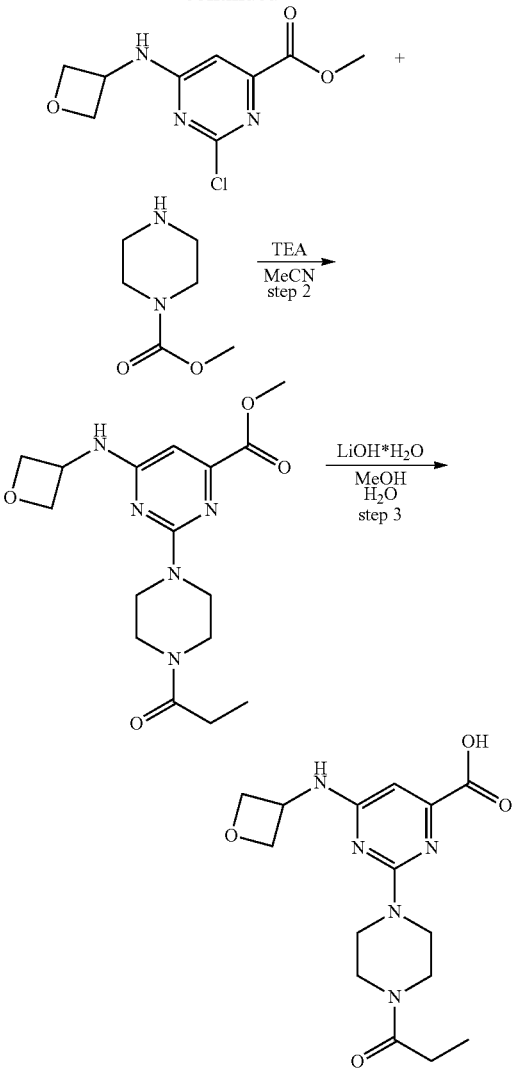

methyl 6-(oxetan-3-ylamino)-2-(4-propionylpiperazin-1-yl)pyrimidine-4-carboxylate. To a solution of methyl 2-chloro-6-(oxetan-3-ylamino)pyrimidine-4-carboxylate (0.7 g, 2.87 mmol) in ACN (25 mL) at r.t. was added TEA (639.58 mg, 6.32 mmol, 880.97 uL) followed by 1-piperazin-1-ylpropan-1-one (564.62 mg, 3.16 mmol, HCl) and the resulting reaction mixture was stirred at 80° C. for 48 hr and cooled down. The precipitate formed was collected by filtration, washed with water and dried in vacuo to give methyl 6-(oxetan-3-ylamino)-2-(4-propanoylpiperazin-1-yl)pyrimidine-4-carboxylate (0.65 g, 1.86 mmol, 64.76% yield). $^1$H NMR (400 MHz, DMSO-$d_6$) δ (ppm) 1.01 (t, 3H), 2.36 (m, 2H), 3.48 (m, 4H), 3.67 (m, 4H), 3.79 (s, 3H), 4.46 (m, 2H), 4.80 (m, 2H), 4.95 (m, 1H), 6.42 (s, 1H), 8.17 (bds, 1H). LCMS(ESI): [M+H]+ m/z: calcd 349.4. found 350.2; Rt=0.927 min.

6-(oxetan-3-ylamino)-2-(4-propionylpiperazin-1-yl)pyrimidine-4-carboxylic acid

A mixture of methyl 6-(oxetan-3-ylamino)-2-(4-propanoylpiperazin-1-yl)pyrimidine-4-carboxylate (0.65 g, 1.86 mmol) and lithium hydroxide, hydrate (171.74 mg, 4.09 mmol, 113.73 uL) in THF (10 mL)-methanol (10 mL)-water (10 mL) was stirred at r.t. for 12 hr. Then, volatile organic solvents were rotoevaporated, the aqueous phase was acidified (NaHSO₄, monohydrate) to pH 5 and the mixture was concentrated in vacuo. The residue was suspended in hot ethanol (50 mL) and filtered. The filtercake was washed with hot ethanol (2×50 mL) and discarded. The filtrate was evaporated in vacuo to leave the residue 6-(oxetan-3-ylamino)-2-(4-propanoylpiperazin-1-yl)pyrimidine-4-carboxylic acid (0.47 g, 1.40 mmol, 75.33% yield). ¹H NMR (400 MHz, DMSO-d₆) δ (ppm) 1.01 (t, 3H), 2.36 (m, 2H), 3.48 (m, 5H), 3.71 (m, 4H), 4.48 (m, 2H), 4.81 (m, 2H), 4.95 (m, 1H), 6.41 (s, 1H), 8.15 (bds, 1). LCMS(ESI): [M+H]+ m/z: calcd 335.4. found 336.2; Rt=0.753 min.

2-(4-(cyclopropanecarbonyl)piperazin-1-yl)-6-(oxetan-3-ylamino)pyrimidine-4-carboxylic Acid

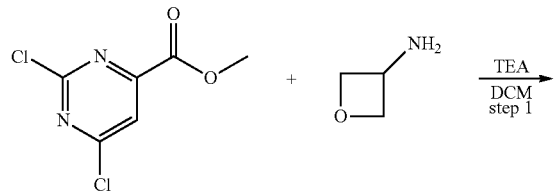

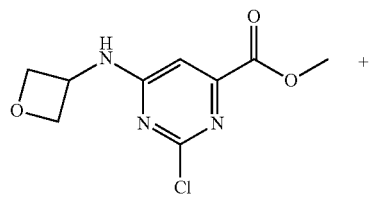

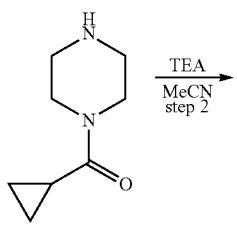

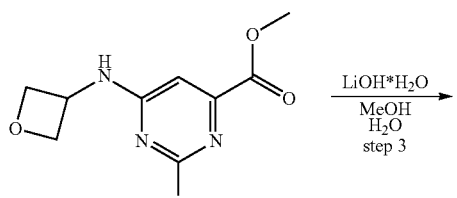

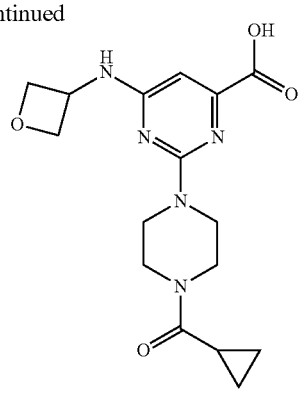

methyl 2-(4-(cyclopropanecarbonyl)piperazin-1-yl)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (35 mL) at r.t. was added TEA (639.58 mg, 6.32 mmol, 880.97 uL) followed by cyclopropyl(piperazin-1-yl)methanone (602.58 mg, 3.16 mmol, 552.82 uL, HCl) and the resulting reaction mixture was stirred at 80° C. for 48 hr, then it was diluted with water (50 mL). The aqueous layer was extracted with DCM (50 mL×2). The combined organic layers were washed with water (15 mL) and brine, dried over Na₂SO₄ and concentrated in vacuo to give methyl 2-[4-(cyclopropanecarbonyl)piperazin-1-yl]-6-(oxetan-3-ylamino)pyrimidine-4-carboxylate (0.65 g, 1.80 mmol, 62.60% yield). ¹H NMR (400 MHz, DMSO-d₆) δ (ppm) 0.75 (m, 4H), 1.99 (m, 1H), 3.51 (m, 2H), 3.79 (m, 6H), 3.81 (s, 3H), 4.48 (m, 2H), 4.80 (m, 2H), 4.95 (m, 1H), 6.43 (s, 1H), 8.15 (bds, 1H). LCMS(ESI): [M+H]+ m/z: calcd 361.4. found 362.2; Rt=0.978 min.

2-(4-(cyclopropanecarbonyl)piperazin-1-yl)-6-(oxetan-3-ylamino)pyrimidine-4-carboxylic acid. A mixture of methyl 2-[4-(cyclopropanecarbonyl)piperazin-1-yl]-6-(oxetan-3-ylamino)pyrimidine-4-carboxylate (0.65 g, 1.80 mmol) and lithium hydroxide, hydrate (166.03 mg, 3.96 mmol, 109.95 uL) in THF (10 mL)-methanol (10 mL)-water (10 mL) was stirred at r.t. for 12 hr. Then, volatile organic solvents were rotoevaporated, the aqueous phase was acidified (NaHSO₄, monohydrate) to pH 5 and the mixture was concentrated in vacuo. The residue was suspended in hot ethanol (50 mL) and filtered. The filtercake was washed with hot ethanol (2×50 mL) and discarded. The filtrate was evaporated in vacuo to leave the residue 2-[4-(cyclopropanecarbonyl)piperazin-1-yl]-6-(oxetan-3-ylamino)pyrimidine-4-carboxylic acid (0.38 g, 1.09 mmol, 60.82% yield). ¹H NMR (400 MHz, DMSO-d₆) δ (ppm) 0.75 (m, 4H), 2.01 (m, 1H), 3.51 (m, 2H), 3.74 (m, 7H), 4.47 (m, 2H), 4.81 (m, 2H), 4.95 (m, 1H), 6.41 (s, 1H), 8.16 (bds, 1H). LCMS(ESI): [M+H]+ m/z: calcd 347.4. found 348.2; Rt=0.781 min.

2-((2-methoxyethyl(methyl)amino)-6-(oxetan-3-ylamino)pyrimidine-4-carboxylic Acid

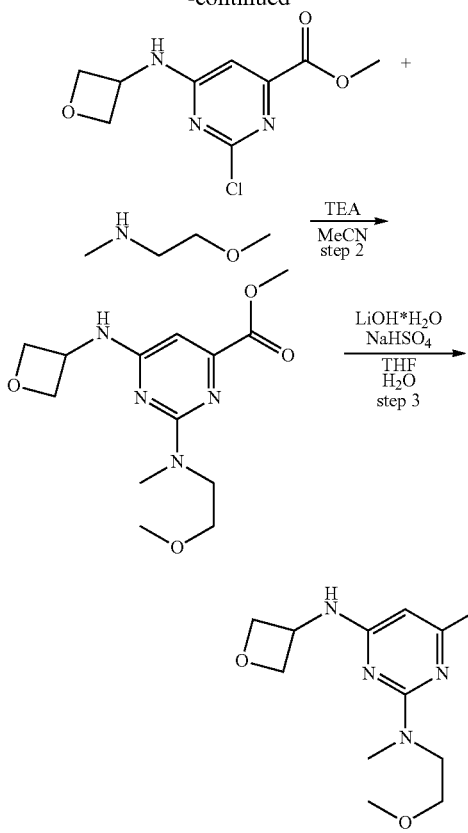

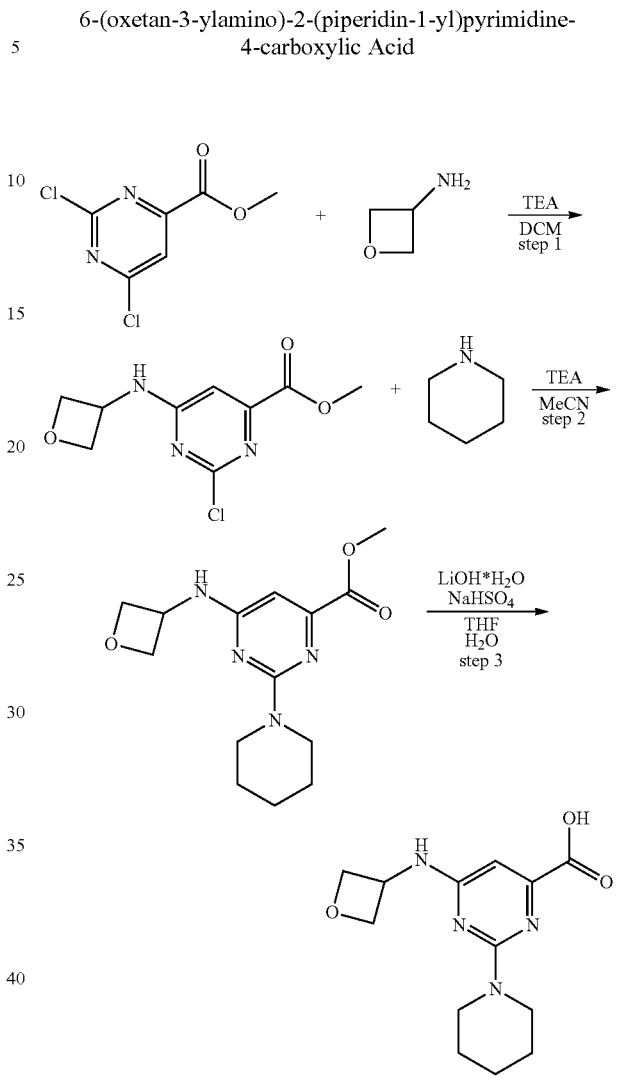

methyl 2-((2-methoxyethyl)(methyl)amino)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (30 mL), Triethylamine (581.44 mg, 5.75 mmol, 800.88 uL) and 2-methoxy-A-methyl-ethanamine (281.70 mg, 3.16 mmol, 339.39 uL) were added. The resulting mixture was heated in sealed tube at 80° C. for 48 hr and the solvent was removed in vacuo. The residue was taken up with water (80 ml) and extracted with DCM (3*50 ml). The combined organic extract was washed with brine (3*50 ml), dried over Na$_2$SO$_4$ and evaporated in vacuo to afford methyl 2-[2-methoxyethyl(methyl)amino]-6-(oxetan-3-ylamino)pyrimidine-4-carboxylate (0.78 g, 2.63 mmol, 91.62% yield) $^1$H NMR (400 MHz, DMSO-d$_6$) δ (ppm) 3.05 (s, 3H), 3.24 (s, 3H), 3.47 (m, 2H), 3.67 (m, 2H), 3.78 (s, 3H), 4.46 (m, 2H), 4.78 (m, 2H), 4.90 (m, 1H), 6.36 (s, 1H), 8.02 (bds, 1H). LCMS(ESI): [M+H]+ m/z: calcd 296.3. found 297.2; Rt=0.851 min.

2-((2-methoxyethyl)(methyl)amino)-6-(oxetan-3-ylamino)pyrimidine-4-carboxylic acid. To a solution of methyl 2-[2-methoxyethyl(methyl)amino]-6-(oxetan-3-ylamino)pyrimidine-4-carboxylate (0.78 g, 2.63 mmol) in THF (30 mL), a solution of lithium hydroxide, monohydrate (243.01 mg, 5.79 mmol, 160.93 uL) in water (15 mL) was added in one portion. The resulting mixture was stirred at 25° C. for 2 hr and the organic solvents were evaporated in vacuo. To this solution, a solution of sodium bisulfate (695.27 mg, 5.79 mmol) in water (10 mL) was added and evaporated to dryness. The residue was diluted with THF (50 ml), the precipitate was filtered, filtercake was washed with THF (3*50 ml) and discarded. The solvent was evaporated in vacuo to obtain 2-[2-methoxyethyl(methyl)amino]-6-(oxetan-3-ylamino)pyrimidine-4-carboxylic acid (0.51 g, 1.81 mmol, 68.63% yield). LCMS(ESI): [M+H]+ m/z: calcd 282.3. found 283.2; Rt=0.814 min.

6-(oxetan-3-ylamino)-2-(piperidin-1-yl)pyrimidine-4-carboxylic Acid methyl 6-(oxetan-3-ylamino)-2-(piperidin-1-yl)pyrimidine-4-carboxylate. To a solution of methyl 2-chloro-6-(oxetan-3-ylamino)pyrimidine-4-carboxylate (0.7 g, 2.87 mmol) in ACN (30 mL), triethylamine (581.44 mg, 5.75 mmol, 800.88 uL) and piperidine (269.09 mg, 3.16 mmol, 312.17 uL) were added. The resulting mixture was heated at 80° C. for 48 hr and the solvent was removed in vacuo. The residue was taken up with water (80 ml) and extracted with DCM (3*50 ml). The combined organic extract was washed with brine (3*50 ml), dried over Na$_2$SO$_4$ and evaporated in vacuo to afford methyl 6-(oxetan-3-ylamino)-2-(1-piperidyl)pyrimidine-4-carboxylate (0.8 g, 2.74 mmol, 95.25% yield). $^1$H NMR (400 MHz, DMSO-d$_6$) δ (ppm) 1.47 (m, 4H), 1.58 (m, 2H), 3.66 (m, 4H), 3.78 (s, 3H), 4.45 (m, 2H), 4.78 (m, 2H), 4.92 (m, 1H), 6.34 (s, 1H), 8.01 (bds, 1H). LCMS(ESI): [M+H]+ m/z: calcd 292.3; found 293.2; Rt=0.841 min.

6-(oxetan-3-ylamino)-2-(piperidin-1-yl)pyrimidine-4-carboxylic acid. To a solution of methyl 6-(oxetan-3-ylamino)-2-(1-piperidyl)pyrimidine-4-carboxylate (0.8 g, 2.74 mmol) in THF (15 mL) and MeOH (15 mL), a solution of lithium hydroxide, monohydrate (252.62 mg, 6.02 mmol, 167.30 uL) in water (15 mL) was added in one portion. The resulting mixture was stirred at 25° C. for 24 hr and the organic solvents were evaporated in vacuo. To this solution, a solution of sodium hydrogen sulfate (722.83 mg, 6.02 mmol) in water (10 mL) was added and evaporated to dryness. The residue was diluted with THF (50 ml), the precipitate was filtered, filtercake was washed with THF (3*50 ml) and discarded. The solvent was evaporated in vacuo to obtain 6-(oxetan-3-ylamino)-2-(1-piperidyl)pyrimidine-4-carboxylic acid (0.7 g, 2.52 mmol, 91.91% yield). $^1$H NMR (400 MHz, DMSO-d$_6$) δ (ppm) 1.45 (m, 4H), 1.57 (m, 2H), 3.64 (m, 5H), 4.46 (m, 2H), 4.76 (m, 2H), 4.78 (m, 1H), 6.30 (s, 1H), 7.97 (bds, 1H). LCMS(ESI): [M+H]+ m/z: calcd 278.3. found 279.0; Rt=0.920 min.

2-(4-acetylpiperazin-1-yl)-6-(oxetan-3-ylamino)pyrimidine-4-carboxylic Acid

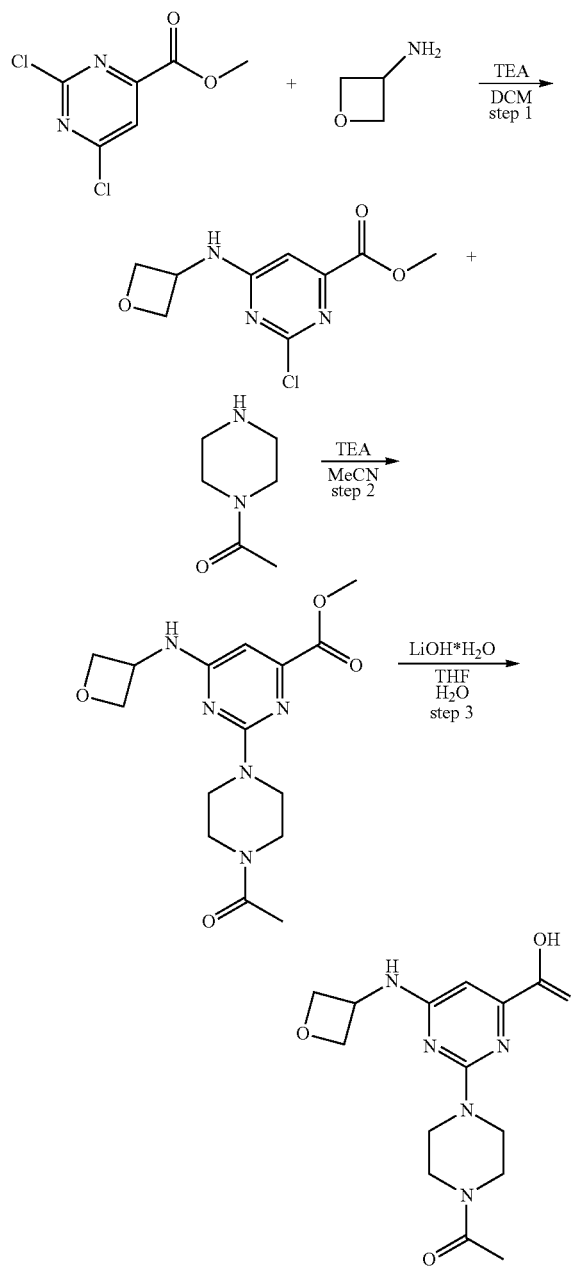

methyl 2-(4-acetylpiperazin-1-yl)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (20 mL) at r.t. was added TEA (319.79 mg, 3.16 mmol, 440.49 uL) followed by 1-piperazin-1-ylethanone (405.06 mg, 3.16 mmol, 359.00 uL) and the resulting reaction mixture was stirred at 80° C. for 48 hr and cooled down. The precipitate formed was collected by filtration, washed with ACN and dried in vacuo to give methyl 2-(4-acetylpiperazin-1-yl)-6-(oxetan-3-ylamino)pyrimidine-4-carboxylate (0.6 g, 1.79 mmol, 62.27% yield). $^1$H NMR (400 MHz, DMSO-d$_6$) δ (ppm) 2.03 (s, 3H), 3.47 (m, 4H), 3.70 (m, 4H), 3.80 (s, 3H), 4.47 (m, 2H), 4.78 (m, 2H), 4.81 (m, 1H), 6.42 (s, 1H), 8.15 (bds, 1H). LCMS(ESI): [M+H]+ m/z: calcd 335.4. found 336.2; Rt=0.877 min.

2-(4-acetylpiperazin-1-yl)-6-(oxetan-3-ylamino)pyrimidine-4-carboxylic acid. A mixture of methyl 2-(4-acetylpiperazin-1-yl)-6-(oxetan-3-ylamino)pyrimidine-4-carboxylate (0.55 g, 1.64 mmol) and lithium hydroxide, hydrate (151.40 mg, 3.61 mmol, 100.26 uL) in THF (10 mL)-methanol (10 mL)-water (10 mL) was stirred at r.t. for 12 hr. Then, volatile organic solvents were rotoevaporated, the aqueous phase was acidified (NaHSO$_4$, monohydrate) to pH 5 and the mixture was concentrated in vacuo. The residue was suspended in hot ethanol (50 mL) and filtered. The filtercake was washed with hot ethanol (2×50 mL) and discarded. The filtrate was evaporated in vacuo to leave the residue 2-(4-acetylpiperazin-1-yl)-6-(oxetan-3-ylamino)pyrimidine-4-carboxylic acid (0.46 g, 1.43 mmol, 87.29% yield). $^1$H NMR (400 MHz, DMSO-d$_6$) δ (ppm) 2.03 (s, 3H), 3.46 (m, 5H), 3.70 (m, 4H), 4.46 (m, 2H), 4.79 (m, 2H), 4.95 (m, 1H), 6.41 (s, 1H), 8.13 (bds, 1H). LCMS(ESI): [M+H]+ m/z: calcd 321.3. found 322.2; Rt=0.624 min.

2-(4-isopropylpiperazin-1-yl)-6-(oxetan-3-ylamino)pyrimidine-4-carboxylic Acid

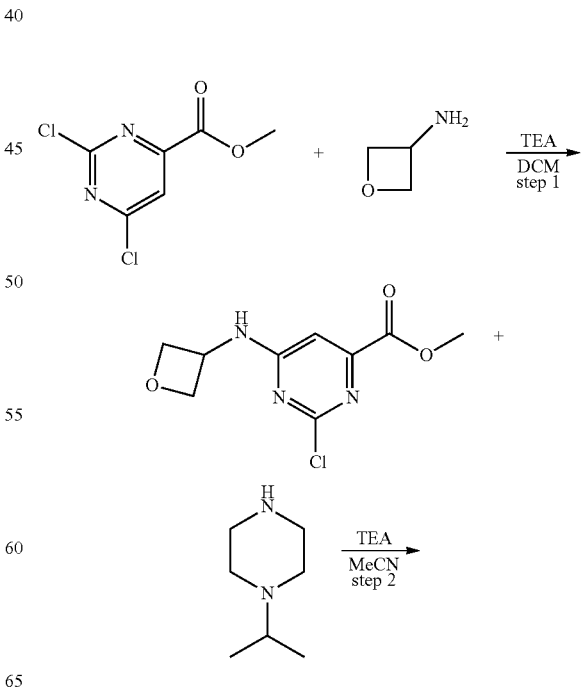

239
-continued

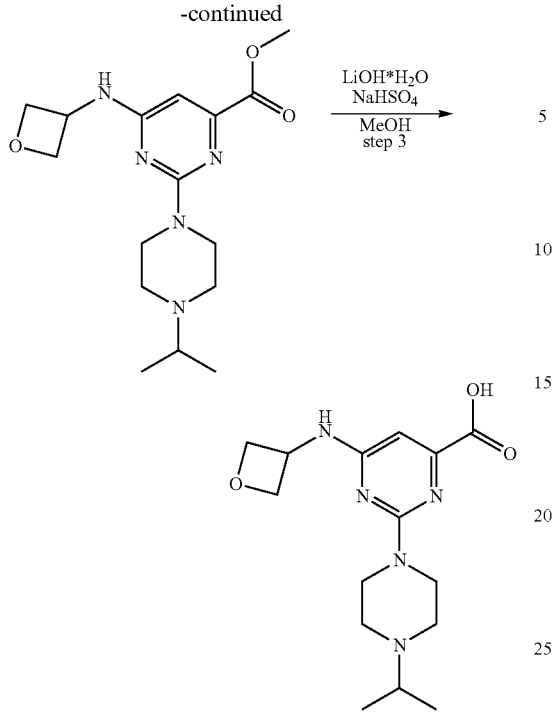

methyl 2-(4-isopropylpiperazin-1-yl)-6-(oxetan-3-ylamino)pyrimidine-4-carboxylate. To a solution of methyl 2-chloro-6-(oxetan-3-ylamino)pyrimidine-4-carboxylate (0.6 g, 2.46 mmol) in CH$_3$CN (30 mL) was added 1-isopropylpiperazine (473.61 mg, 3.69 mmol, 528.58 uL), followed by TEA (747.57 mg, 7.39 mmol, 1.03 mL). The reaction mixture was stirred at 65° C. for 48 hr. The reaction mixture was evaporated, poured into water (50 ml) and extracted with EtOAc (3×20 ml). The combined organic extracts were washed with water(2*10 ml), dried over sodium sulphate and evaporated in vacuo to afford product methyl 2-(4-isopropylpiperazin-1-yl)-6-(oxetan-3-ylamino)pyrimidine-4-carboxylate (0.54 g, 1.61 mmol, 65.38% yield). $^1$H NMR (400 MHz, CDCl$_3$) δ (ppm) 1.05 (d, 6H), 2.55 (m, 4H), 2.71 (m, 1H), 3.80 (m, 4H), 3.89 (s, 3H), 4.55 (m, 2H), 4.95 (m, 2H), 5.06 (m, 1H), 5.15 (s, 1H), 6.35 (s, 1H). LCMS(ESI): [M+H]+ m/z: calcd 335.4. found 336.2; Rt=0.694 min.

2-(4-isopropylpiperazin-1-yl)-6-(oxetan-3-ylamino)pyrimidine-4-carboxylic acid. To a solution of methyl 2-(4-isopropylpiperazin-1-yl)-6-(oxetan-3-ylamino)pyrimidine-4-carboxylate (0.6 g, 1.79 mmol) in methanole (5 mL) was added lithium hydroxide monohydrate, 98% (165.14 mg, 3.94 mmol, 109.36 uL) in water (3 ml). The reaction mixture was stirred at 25° C. for 24 hr. The reaction mixture was evaporated, and added sodium bisulfate (493.99 mg, 4.11 mmol) in water (10 ml) then evaporated and added hot ethanole(20 ml) the resulting precipitate was filtered off, washed with hot ethanole (3*10 ml). The filtrate was evaporated and dried to afford product 2-(4-isopropylpiperazin-1-yl)-6-(oxetan-3-ylamino)pyrimidine-4-carboxylic acid (0.54 g, 1.68 mmol, 93.93% yield). $^1$H NMR (400 MHz, DMSO-d$_6$) δ (ppm) 1.05 (d, 6H), 2.58 (m, 4H), 2.81 (m, 1H), 3.72 (m, 5H), 4.47 (m, 2H), 4.92 (m, 2H), 4.93 (m, 1H), 6.36 (s, 1H), 8.07 (bds, 1H). LCMS(ESI): [M+H]+ m/z: calcd 321.4. found 322.0; Rt=0.455 min.

240
2-(4-isobutyrylpiperazin-1-yl)-6-(oxetan-3-ylamino)pyrimidine-4-carboxylic Acid

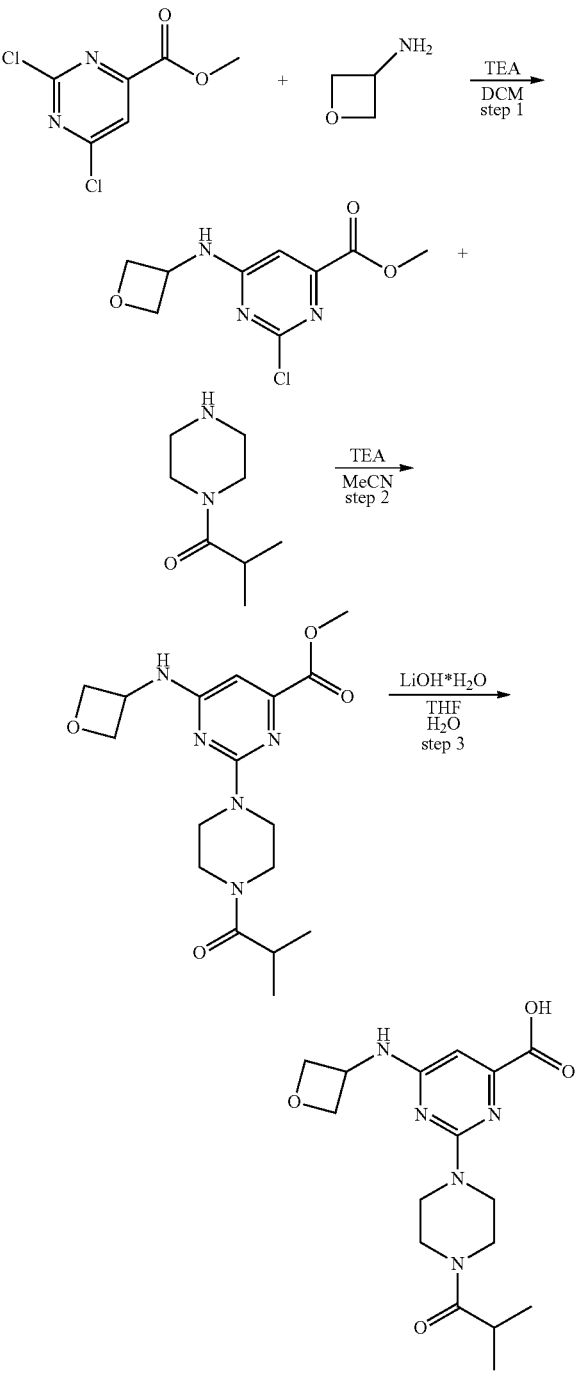

methyl 2-(4-isobutyrylpiperazin-1-yl)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (25 mL) at r.t. was added TEA (319.79 mg, 3.16 mmol, 440.49 uL) followed by 2-methyl-1-piperazin-1-yl-propan-1-one (493.72 mg, 3.16 mmol, 359.00 uL) and the resulting reaction mixture was stirred at 80° C. for 48 hr, then it was diluted with water (50 mL). The aqueous layer was extracted with DCM (50 mL×2). The combined organic layers were washed with water (15 mL) and brine, dried over Na$_2$SO$_4$ and concentrated in vacuo to give methyl 2-[4-(2-methylpropanoyl)piperazin-1-yl]-6-(oxetan-3-ylamino)pyrimidine-4-carboxylate (0.65 g, 1.79 mmol, 62.26% yield). $^1$H NMR (400 MHz, DMSO-d$_6$) δ (ppm) 1.01 (d, 6H), 2.89 (m, 1H), 3.49 (m, 4H), 3.63 (m, 4H), 3.85 (s, 3H), 4.46 (m, 2H), 4.78 (m, 2H), 4.81 (m, 1H), 6.43 (s, 1H), 8.15 (bds, 1H). LCMS(ESI): [M+H]+ m/z: calcd 363.4. found 364.2; Rt=0.696 min.

2-(4-isobutyrylpiperazin-1-yl)-6-(oxetan-3-ylamino)pyrimidine-4-carboxylic acid. A mixture of methyl 2-[4-(2-methylpropanoyl)piperazin-1-yl]-6-(oxetan-3-ylamino)pyrimidine-4-carboxylate (0.65 g, 1.79 mmol) and lithium hydroxide, hydrate (165.11 mg, 3.93 mmol, 109.34 uL) in THF (10 mL)-methanol (10 mL)-water (10 mL) was stirred at r.t. for 12 hr. Then, volatile organic solvents were evaporated, the aqueous phase was acidified (NaHSO$_4$, monohydrate) to pH 5 and the mixture was concentrated in vacuo. The residue was suspended in hot ethanol (50 mL) and filtered. The filtercake was washed with hot ethanol (2×50 mL) and discarded. The filtrate was evaporated in vacuo to leave the residue 2-[4-(2-methylpropanoyl)piperazin-1-yl]-6-(oxetan-3-ylamino)pyrimidine-4-carboxylic acid (0.46 g, 1.32 mmol, 73.61% yield). $^1$H NMR (400 MHz, DMSO-d$_6$) δ (ppm) 1.05 (d, 6H), 2.90 (m, 1H), 3.48 (m, 5H), 3.62 (m, 4H), 4.46 (m, 2H), 4.81 (m, 2H), 4.93 (m, 1H), 6.39 (s, 1H), 8.05 (bds, 1H). LCMS(ESI): [M+H]+ m/z: calcd 349.4. found 350.2; Rt=0.806 min.

2-(methyl(propyl)amino)-6-(oxetan-3-ylamino)pyrimidine-4-carboxylic Acid

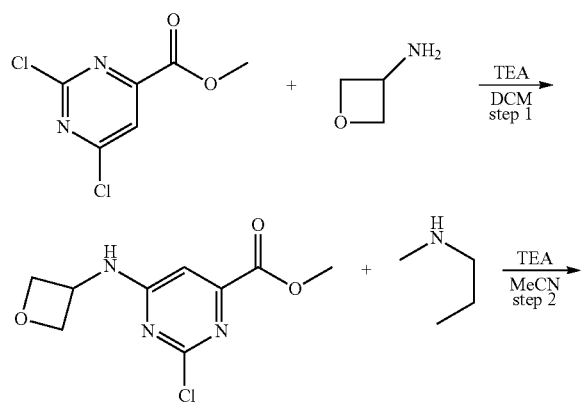

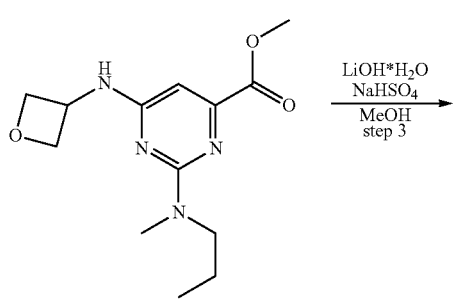

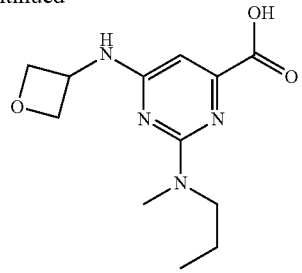

methyl 2-(methyl(propyl)amino)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (30 mL), triethylamine (581.44 mg, 5.75 mmol, 800.88 uL) and A-methy 1 propan-1-amine (231.13 mg, 3.16 mmol, 324.17 uL) were added. The resulting mixture was heated at 80° C. for 48 hr and the solvent was removed in vacuo. The residue was taken up with water (80 ml) and extracted with DCM (3*50 ml). The combined organic extract was washed with brine (3*50 ml), dried over Na$_2$SO$_4$ and evaporated in vacuo to afford methyl 2-[methyl(propyl)amino]-6-(oxetan-3-ylamino)pyrimidine-4-carboxylate (0.8 g, 2.85 mmol, 99.33% yield). $^1$H NMR (400 MHz, DMSO-d$_6$) δ (ppm) 0.83 (t, 3H), 1.52 (m, 2H), 3.01 (s, 3H), 3.46 (m, 2H), 3.78 (s, 3H), 4.46 (m, 2H), 4.78 (m, 2H), 4.88 (m, 1H), 6.33 (s, 1H), 7.97 (bds, 1H). LCMS(ESI): [M+H]+ m/z: calcd 280.3. found 281.2; Rt=0.696 min.

2-(methyl(propyl)amino)-6-(oxetan-3-ylamino)pyrimidine-4-carboxylic acid. To a solution of methyl 2-[methyl(propyl)amino]-6-(oxetan-3-ylamino)pyrimidine-4-carboxylate (0.8 g, 2.85 mmol) in THF (15 mL) and MeOH (15 mL), a solution of lithium hydroxide, monohydrate (263.45 mg, 6.28 mmol, 174.47 uL) in water (15 mL) was added in one portion. The resulting mixture was stirred at 25° C. for 24 hr and the organic solvents were evaporated in vacuo. To this solution, a solution of sodium hydrogen sulfate (753.80 mg, 6.28 mmol) in water (10 mL) was added and evaporated to dryness. The residue was diluted with THF (50 ml), the precipitate was filtered, filtercake was washed with THF (3*50 ml) and discarded. The solvent was evaporated in vacuo to obtain 2-[methyl(propyl)amino]-6-(oxetan-3-ylamino)pyrimidine-4-carboxylic acid (0.59 g, 2.22 mmol, 77.63% yield). $^1$H NMR (400 MHz, DMSO-d$_6$) δ (ppm) 0.84 (t, 3H), 1.51 (m, 2H), 3.01 (s, 3H), 3.49 (m, 2H), 4.47 (m, 2H), 4.78 (m, 2H), 4.89 (m, 1H), 6.35 (s, 1H), 8.13 (bds, 1H). LCMS(ESI): [M+H]+ m/z: calcd 266.3. found 267.2; Rt=0.804 min.

2-(ethyl(methyl)amino)-6-(oxetan-3-ylamino)pyrimidine-4-carboxylic Acid

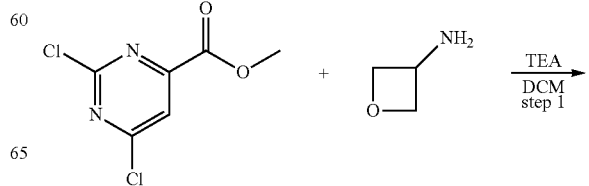

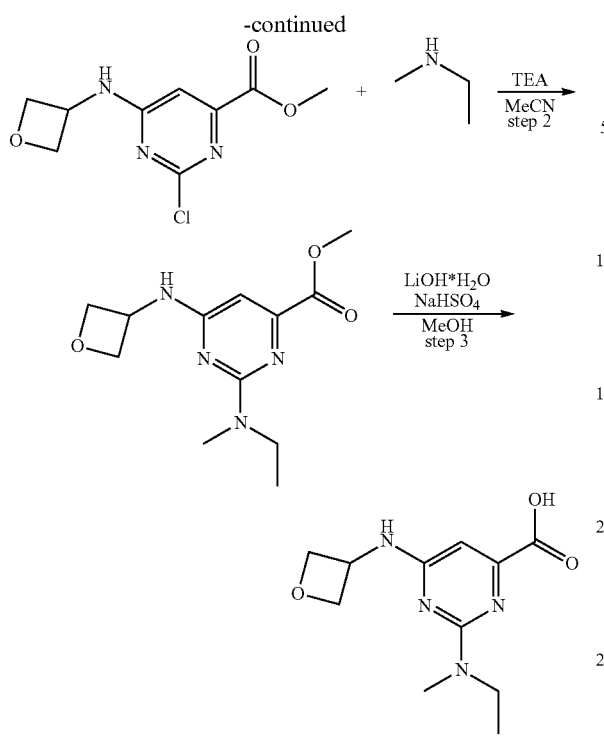

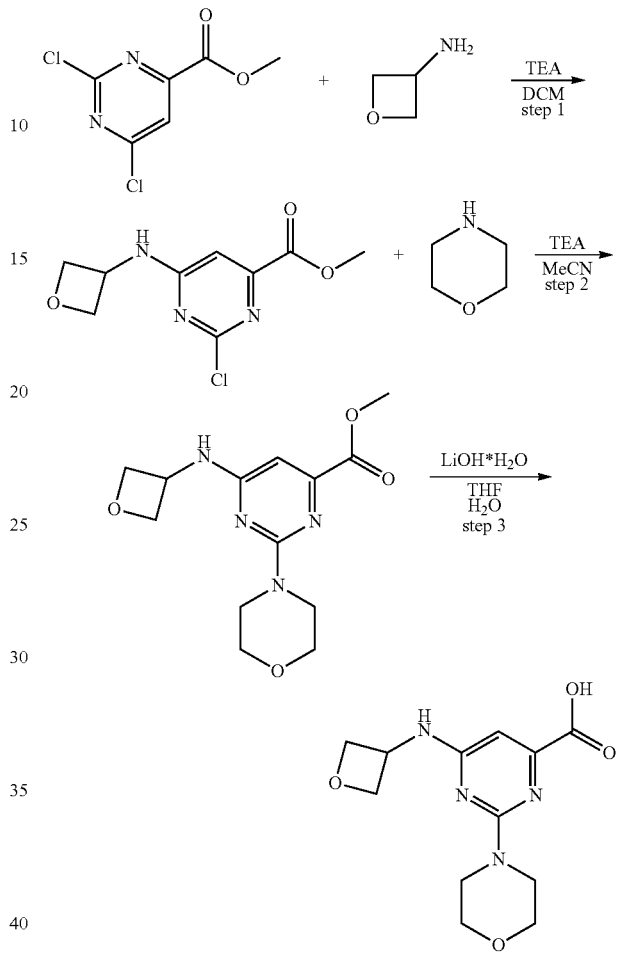

2-morpholino-6-(oxetan-3-ylamino)pyrimidine-4-carboxylic Acid methyl 2-(ethyl(methyl)amino)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (30 mL), triethylamine (581.44 mg, 5.75 mmol, 800.88 uL) and A-methylethanamine (212.28 mg, 3.59 mmol, 308.55 uL) were added. The resulting mixture was heated in sealed tube at 80° C. for 48 hr and the solvent was removed in vacuo. The residue was taken up with water (80 ml) and extracted with DCM (3*50 ml). The combined organic extract was washed with brine (3*50 ml), dried over $Na_2SO_4$ and evaporated in vacuo to afford methyl 2-[ethyl(methyl)amino]-6-(oxetan-3-ylamino)pyrimidine-4-carboxylate (0.75 g, 2.82 mmol, 98.03% yield). $^1$H NMR (400 MHz, DMSO-$d_6$) δ (ppm) 1.05 (t, 3H), 3.01 (s, 3H), 3.56 (m, 2H), 3.78 (s, 3H), 4.46 (m, 2H), 4.78 (m, 2H), 4.90 (m, 1H), 6.34 (s, 1H), 7.98 (bds, 1H). LCMS(ESI): [M+H]+ m/z: calcd 266.3. found 267.2; Rt=0.833 min.

2-(ethyl(methyl)amino)-6-(oxetan-3-ylamino)pyrimidine-4-carboxylic acid. To a solution of methyl 2-[ethyl(methyl)amino]-6-(oxetan-3-ylamino)pyrimidine-4-carboxylate (0.75 g, 2.82 mmol) in THF (30 mL), a solution of lithium hydroxide, monohydrate (259.99 mg, 6.20 mmol, 172.18 uL) in water (15 mL) was added in one portion. The resulting mixture was stirred at 25° C. for 2 hr and the organic solvents were evaporated in vacuo. To this solution, a solution of sodium bisulfate (743.91 mg, 6.20 mmol) in water (10 mL) was added and evaporated to dryness. The residue was diluted with THF (50 ml), the precipitate was filtered, filtercake was washed with THF (3*50 ml) and discarded. The solvent was evaporated in vacuo to obtain 2-[ethyl(methyl)amino]-6-(oxetan-3-ylamino)pyrimidine-4-carboxylic acid (0.4 g, 1.59 mmol, 56.30% yield). $^1$H NMR (400 MHz, DMSO-$d_6$) δ (ppm) 1.05 (t, 3H), 3.02 (s, 3H), 3.56 (m, 3H), 4.47 (m, 2H), 4.78 (m, 2H), 4.90 (m, 1H), 6.32 (s, 1H), 8.04 (bds, 1H). LCMS(ESI): [M+H]+ m/z: calcd 252.3. found 253.2; Rt=0.823 min.

methyl 2-morpholino-6-(oxetan-3-ylamino)pyrimidine-4-carboxylate. To a solution of methyl 2-chloro-6-(oxetan-3-ylamino)pyrimidine-4-carboxylate (1 g, 4.10 mmol) in ACN (20 mL) at r.t. was added TEA (415.31 mg, 4.10 mmol, 572.06 uL) followed by morpholine (357.57 mg, 4.10 mmol, 359.00 uL) and the resulting reaction mixture was stirred at 80° C. for 48 hr and cooled down. The precipitate formed was collected by filtration, washed with ACN and dried in vacuo to give methyl 2-morpholino-6-(oxetan-3-ylamino)pyrimidine-4-carboxylate (0.95 g, 3.23 mmol, 78.65% yield). $^1$H NMR (400 MHz, DMSO-$d_6$) δ (ppm) 3.32 (t, 4H), 3.62 (t, 4H), 3.79 (s, 3H), 4.46 (m, 2H), 4.95 (m, 2H), 4.96 (m, 1H), 6.44 (s, 1H), 8.14 (bds, 1H). LCMS(ESI): [M+H]+ m/z: calcd 294.3. found 295.2; Rt=0.888 min.

2-morpholino-6-(oxetan-3-ylamino)pyrimidine-4-carboxylic acid. A mixture of methyl 2-morpholino-6-(oxetan-3-ylamino)pyrimidine-4-carboxylate (0.95 g, 3.23 mmol) and lithium hydroxide, hydrate (297.98 mg, 7.10 mmol, 197.34 uL) in THF (15 mL)-methanol (15 mL)-water (15 mL) was stirred at r.t. for 12 hr. Then, volatile organic solvents were rotoevaporated, the aqueous phase was acidified ($NaHSO_4$, monohydrate) to pH 5 and the mixture was concentrated in vacuo. The residue was suspended in hot ethanol (100 mL) and filtered. The filtercake was washed with hot ethanol (2×50 mL) and discarded. The filtrate was evaporated in vacuo to leave the residue 2-morpholino-6-(oxetan-3-ylamino)pyrimidine-4-carboxylic acid (0.83 g, 2.96 mmol, 91.74% yield). $^1$H NMR (400 MHz, DMSO-$d_6$) δ (ppm) 3.63 (m, 8H), 4.45 (m, 2H), 4.78 (m, 2H), 4.94 (m, 1H), 6.41 (s, 1H), 8.13 (bds, 1H). LCMS(ESI): [M+H]+ m/z: calcd 280.3. found 281.2; Rt=0.647 min.

2-(4-ethylpiperazin-1-yl)-6-(oxetan-3-ylamino)pyrimidine-4-carboxylic Acid

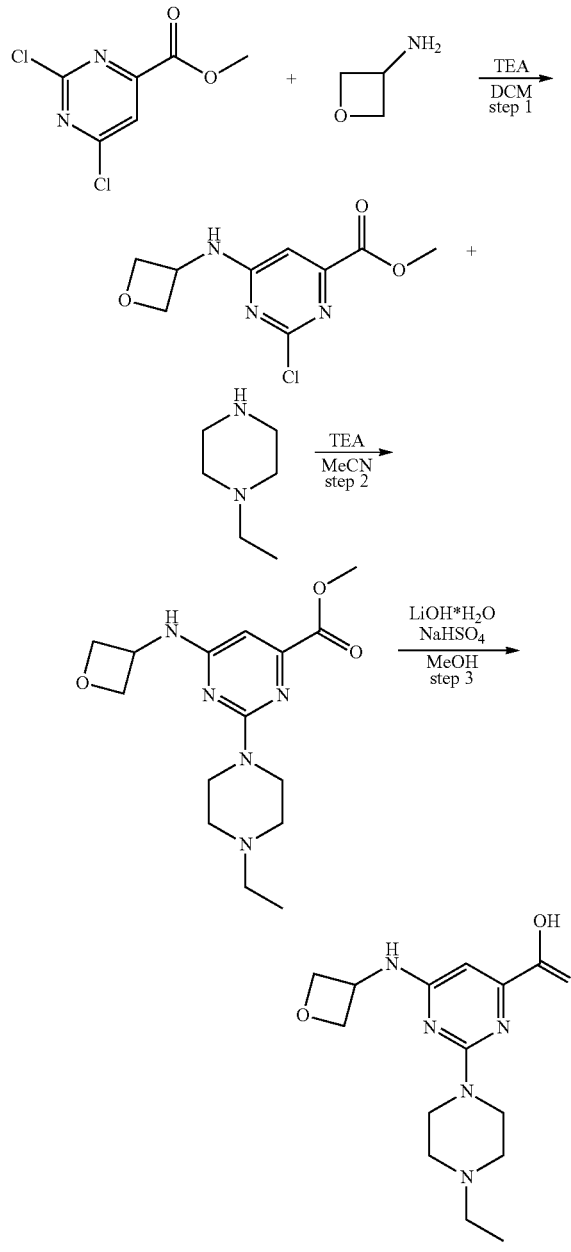

methyl 2-(4-ethylpiperazin-1-yl)-6-(oxetan-3-ylamino)pyrimidine-4-carboxylate. To a solution of methyl 2-chloro-6-(oxetan-3-ylamino)pyrimidine-4-carboxylate (0.6 g, 2.46 mmol) in CH3CN (30 mL) was added 1-ethylpiperazine (421.80 mg, 3.69 mmol, 469.18 uL), followed by TEA (747.57 mg, 7.39 mmol, 1.03 mL). The reaction mixture was stirred at 65° C. for 48 hr. The reaction mixture was evaporated, poured into water (50 ml) and extracted with EtOAc (3×20 ml). The combined organic extracts were washed with water(2*10 ml), dried over sodium sulphate and evaporated in vacuo to afford product methyl 2-(4-ethylpiperazin-1-yl)-6-(oxetan-3-ylamino)pyrimidine-4-carboxylate (0.62 g, 1.93 mmol, 78.34% yield). $^1$H NMR (500 MHZ, CDCl$_3$) δ (ppm) 1.12 (t, 3H), 2.48 (m, 6H), 3.87 (m, 4H), 3.92 (s, 3H), 4.60 (m, 2H), 4.98 (m, 2H), 5.01 (m, 1H), 5.23 (bds, 1H), 6.39 (s, 1H). LCMS(ESI): [M+H]+ m/z: calcd 321.4; found 322.2; Rt=0.726 min.

2-(4-ethylpiperazin-1-yl)-6-(oxetan-3-ylamino)pyrimidine-4-carboxylic acid. To a solution of methyl 2-(4-ethylpiperazin-1-yl)-6-(oxetan-3-ylamino)pyrimidine-4-carboxylate (0.48 g, 1.49 mmol) in methanole (5 mL) was added lithium hydroxide monohydrate, 98% (137.88 mg, 3.29 mmol, 91.31 uL) in water (2 ml). The reaction mixture was stirred at 25° C. for 24 hr. The reaction mixture was evaporated, and added Sodium bisulfate (412.44 mg, 3.44 mmol) in water (5 ml) then evaporated and added hot ethanole(20 ml) the resulting precipitate was filtered off, washed with hot ethanole (3*10 ml). The filtrate was evaporated and dried to afford product 2-(4-ethylpiperazin-1-yl)-6-(oxetan-3-ylamino)pyrimidine-4-carboxylic acid (0.3 g, 976.09 umol, 65.35% yield). $^1$H NMR (400 MHz, DMSO-$d_6$) δ (ppm) 1.06 (t, 3H), 2.55 (m, 6H), 3.75 (m, 4H), 4.46 (m, 2H), 4.94 (m, 2H), 4.96 (m, 1H), 6.39 (s, 1H), 8.10 (bds, 1H). LCMS(ESI): [M+H]+ m/z: calcd 307.4. found 308.0; Rt=0.320 min.

2-(4-(tert-butyl)piperazin-1-yl)-6-(oxetan-3-ylamino)pyrimidine-4-carboxylic acid

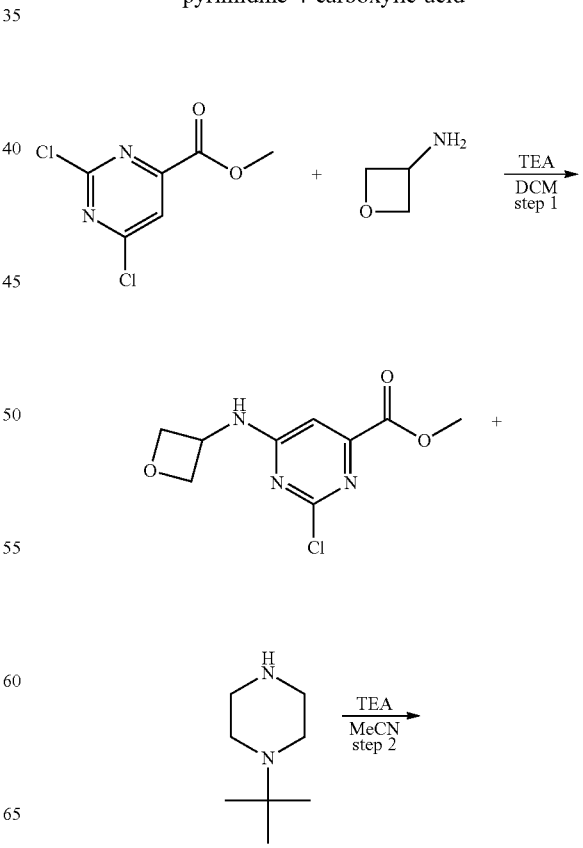

-continued

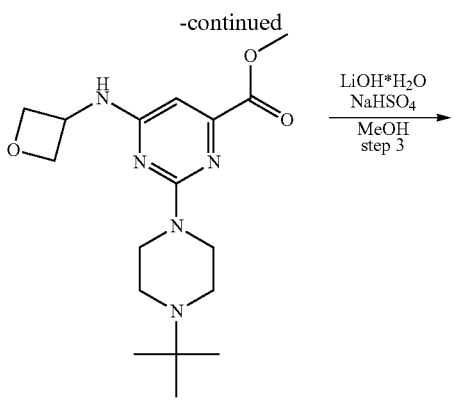

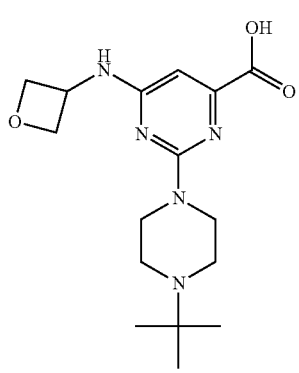

methyl 2-(4-(tert-butyl)piperazin-1-yl)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in CH3CN (30 mL) was added 1-tert-butylpiperazine (612.99 mg, 4.31 mmol, 469.18 uL), followed by TEA (872.16 mg, 8.62 mmol, 1.20 mL). The reaction mixture was stirred at 75° C. for 24 hr. The reaction mixture was evaporated, poured into water (50 ml) and extracted with EtOAc (3×20 ml). The combined organic extracts were washed with water(2*10 ml), dried over sodium sulphate and evaporated in vacuo to afford product methyl 2-(4-tert-butylpiperazine-1-yl)-6-(oxetan-3-ylamino)pyrimidine-4-carboxylate (0.72 g, 2.06 mmol, 71.72% yield). $^1$H NMR (400 MHz, CDCl$_3$) δ (ppm) 1.07 (s, 9H), 2.58 (m, 4H), 3.78 (m, 4H), 3.89 (s, 3H), 4.57 (m, 2H), 4.95 (m, 2H), 5.04 (m, 1H), 5.18 (bds, 1H), 6.34 (s, 1H). LCMS(ESI): [M+H]+ m/z: calcd 349.4. found 350.2; Rt=0.740 min.

2-(4-(tert-butyl)piperazin-1-yl)-6-(oxetan-3-ylamino)pyrimidine-4-carboxylic acid. To a solution of methyl 2-(4-tert-butylpiperazin-1-yl)-6-(oxetan-3-ylamino)pyrimidine-4-carboxylate (0.6 g, 1.72 mmol) in methanole (6 mL) was added lithium hydroxide monohydrate, 98% (158.51 mg, 3.78 mmol, 104.97 uL) in water (3 ml). The reaction mixture was stirred at 25° C. for 24 hr. The reaction mixture was evaporated, and added Sodium bisulfate (474.16 mg, 3.95 mmol) in water (10 ml) then evaporated and added hot ethanole(20 ml) the resulting precipitate was filtered off, washed with hot ethanole (3*10 ml). The filtrate was evaporated and dried to afford product 2-(4-tert-butylpiperazin-1-yl)-6-(oxetan-3-ylamino)pyrimidine-4-carboxylic acid (0.33 g). $^1$H NMR (400 MHz, DMSO-d$_6$) δ (ppm) 1.04 (s, 9H), 2.58 (m, 4H), 3.68 (m, 4H), 4.46 (m, 2H), 4.78 (m, 2H), 4.92 (m, 1H), 6.36 (s, 1H), 8.02 (bds, 1H). LCMS(ESI): [M+H]+ m/z: calcd 335.4. found 336.2; Rt=0.612 min.

3-((1-acetylpiperidin-4-yl)amino)-5-(piperidin-1-yl) benzoic Acid

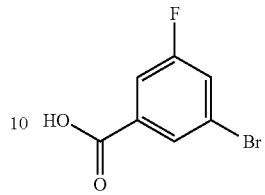

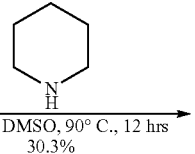

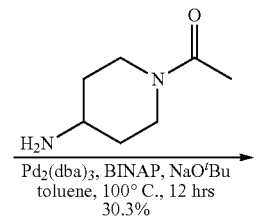

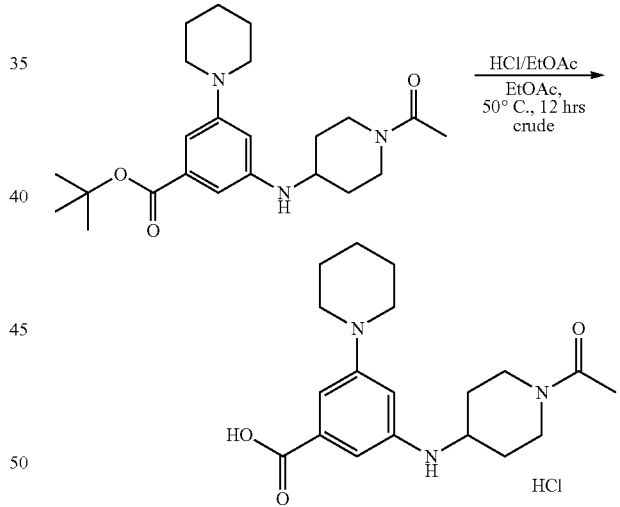

tert-butyl 3-bromo-5-fluoro-benzoate. To a solution of 3-bromo-5-fluoro-benzoic acid (10 g, 45.7 mmol), DMAP (1.12 g, 9.13 mmol) in THF (20 mL) were added tert-butoxycarbonyl tert-butyl carbonate (13.6 mL, 59.4 mmol). The mixture was stirred at 20° C. for 12 hours. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 80 g AgelaFlash® Silica Flash Column, petroleum ether/EtOAc with EtOAc from 0~3%, flow rate=50 mL/min) to afford tert-butyl 3-bromo-5-fluoro-benzoate (10.5 g, 83.6% yield)

as colorless oil. ¹H NMR (400 MHz, methanol-d₄) δ ppm 7.89-7.92 (m, 1H), 7.58-7.64 (m, 1H), 7.40 (dt, J=7.8, 2.1 Hz, 1H), 1.59 (s, 9H).

tert-butyl 3-bromo-5-(1-piperidyl) benzoate. To a solution of tert-butyl 3-bromo-5-fluoro-benzoate (2 g, 7.27 mmol), piperidine (1 mL, 10.1 mmol) in DMSO (20 mL) was added Cs₂CO₃ (7.12 g, 21.9 mmol). The mixture was stirred at 90° C. for 12 hours. The resulting mixture was quenched by addition of water (50 mL) and extracted with EtOAc (50 mL*3). The combined organic layer was washed with saturated NH₄Cl aqueous solution (50 mL*2), brine (50 mL), dried over anhydrous Na₂SO₄, filtered and concentrated under reduced pressure. The residue was purified by flash chromatography (ISCO®; 12 g AgelaFlash® Silica Flash Column, petroleum ether/EtOAc with EtOAc from 0~5%, flow rate=35 mL/min) to afford tert-butyl 3-bromo-5-(1-piperidyl)benzoate (750 mg, 30.3% yield) as colorless oil. ¹H NMR (400 MHz, methanol-d₄) δ ppm 7.44 (dd, J=2.4, 1.3 Hz, 1H), 7.40 (t, J=1.5 Hz, 1H), 7.23 (t, J=2.1 Hz, 1H), 3.17-3.22 (m, 4H), 1.66-1.73 (m, 4H), 1.60-1.63 (m, 2H), 1.58 (s, 9H).

tert-butyl 3-[(1-acetyl-4-piperidyl) amino]-5-(1-piperidyl) benzoate. To a solution of tert-butyl 3-bromo-5-(1-piperidyl)benzoate (700 mg, 2.06 mmol), 1-(4-amino-1-piperidyl)ethanone (470 mg, 3.31 mmol), Pd₂(dba)₃ (385 mg, 0.421 mmol), BINAP (280 mg, 0.450 mmol) in toluene (2 mL) was added NaO'Bu (245 mg, 2.55 mmol). The mixture was stirred at 100° C. for 12 hours. The resulting mixture was quenched by addition of water (50 mL) and extracted with EtOAc (50 mL*3). The combined organic layer was washed with saturated NH₄Cl aqueous solution (50 mL*2), brine (50 mL), dried over anhydrous Na₂SO₄, filtered and concentrated under reduced pressure. The residue was purified by flash chromatography (ISCO®; 20 g AgelaFlash® Silica Flash Column, petroleum ether/EtOAc with EtOAc from 0-100%, flow rate=35 mL/min) to afford tert-butyl 3-[(1-acetyl-4-piperidyl)amino]-5-(1-piperidyl) benzoate (250 mg, 30.3% yield) as yellow oil. ¹H NMR (400 MHz, methanol-d₄) δ ppm 6.89 (s, 1H), 6.80 (s, 1H), 6.49 (s, 1H), 4.34-4.38 (m, 1H), 3.88-3.92 (m, 1H), 3.45-3.63 (m, 1H), 3.19-3.27 (m, 2H), 3.09-3.14 (m, 4H), 2.94 (br t, J=11.0 Hz, 1H), 2.11 (s, 3H), 1.97-1.99 (m, 2H), 1.71 (br d, J=4.5 Hz, 5H), 1.58-1.63 (m, 3H), 1.57 (s, 9H).

3-[(1-acetyl-4-piperidyl) amino]-5-(1-piperidyl) benzoic acid. To a solution of tert-butyl 3-[(1-acetyl-4-piperidyl) amino]-5-(1-piperidyl)benzoate (250 mg, 0.623 mmol) in EtOAc (5 mL) was added 4M HCl/EtOAc (5 mL, 20 mmol). The mixture was stirred at 50° C. for 12 hours. The resulting mixture was concentrated under reduced pressure to give 3-[(1-acetyl-4-piperidyl)amino]-5-(1-piperidyl)benzoic acid (80 mg, crude) as white solid.

Acid—B 2-(cyclobutylamino)isonicotinic Acid

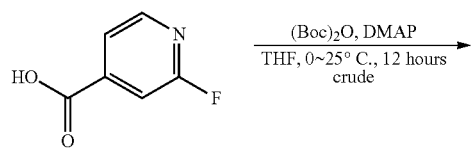

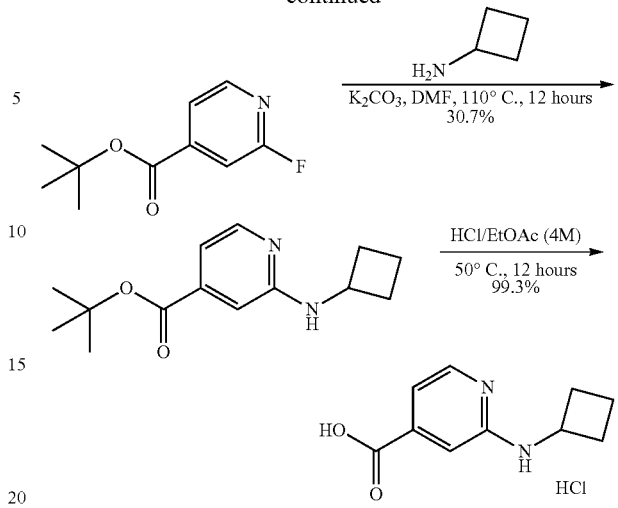

tert-Butyl 2-fluoropyridine-4-carboxylate. To a solution of 2-fluoropyridine-4-carboxylic acid (20 g, 141.74 mmol, 1 eq) and DMAP (3.46 g, 28.35 mmol, 0.2 eq) in THF (150 mL) was added (Boc)₂O (68.0 g, 311.57 mmol, 2.2 eq) at 0° C. The mixture was stirred at 25° C. for 12 hours. The resulting mixture was quenched by addition of NaHCO₃ (20 mL) and extracted with EtOAc (150 mL*3). The combined organic layer was dried over anhydrous Na₂SO₄, filtered and concentrated under reduced pressure to afford tert-butyl 2-fluoropyridine-4-carboxylate (37 g, crude) which was used in next step without further purification. ¹H NMR (400 MHz, chloroform-d) δ ppm 8.30 (d, J=5.0 Hz, 1H), 7.67 (dt, J=5.0, 1.5 Hz, 1H), 7.40 (d, J=1.0 Hz, 1H), 1.58 (s, 9H); LCMS (M+H⁺) m/z: calcd 198.1. found 198.1.

tert-butyl 2-(cyclobutylamino) pyridine-4-carboxylate. To a mixture of tert-butyl 2-fluoropyridine-4-carboxylate (70.87 mmol, crude product, 1 eq), cyclobutanamine (15 mL, 175.05 mmol, 2.5 eq) in DMF (150 mL) was added K₂CO₃ (29.38 g, 212.61 mmol, 3 eq). The mixture was stirred at 110° C. for 12 hours (2 batches in parallel). The resulting mixture was filtered and diluted with EtOAc (100 mL*3). The organic layers were washed with brine (150 mL*3), dried over anhydrous Na₂SO₄, filtered and concentrated under reduced pressure. The residue was purified by column chromatography (silica, petroleum ether/EtOAc=30:1 to 10:1) to afford tert-butyl 2-(cyclobutylamino) pyridine-4-carboxylate (12 g, 30.7% for two steps) as yellow oil. ¹H NMR (400 MHz, chloroform-d) δ ppm 8.15 (d, J=5.0 Hz, 1H), 7.03 (dd, J=5.3, 1.3 Hz, 1H), 6.84 (s, 1H), 4.85 (d, J=6.0 Hz, 1H), 4.10-4.23 (m, 1H), 2.41-2.51 (m, 2H), 1.69-1.94 (m, 4H), 1.59 (s, 9H); LCMS (M+H⁺) m/z: calcd 249.2. found 249.0.

2-(cyclobutylamino) pyridine-4-carboxylic acid. A solution of tert-butyl 2-(cyclobutylamino) pyridine-4-carboxylate (12 g, 43.49 mmol, 1 eq) in HCl/EtOAc (250 mL, 4M) was stirred at 50° C. for 12 hours. The precipitate was collected by filtration, washed with EtOAc (30 mL*3) and dried over under high vacuum to afford 2-(cyclobutylamino) pyridine-4-carboxylic acid (9.9 g, HCl salt, 99.3% yield) as yellow solid. ¹H NMR (400 MHz, DMSO-d₆) δ ppm 9.27 (br s, 1H), 7.99 (d, J=6.3 Hz, 1H), 7.41 (s, 1H), 7.06 (dd, J=6.5, 1.3 Hz, 1H), 4.29 (t, J=7.5 Hz, 1H), 2.37-2.46 (m, 2H), 1.94-2.07 (m, 2H), 1.65-1.85 (m, 2H); LCMS (M+H⁺) m/z: calcd 193.1. found 193.4.

2-(4-(tert-butyl)piperazin-1-yl)-6-(cyclobutylamino)isonicotinic Acid

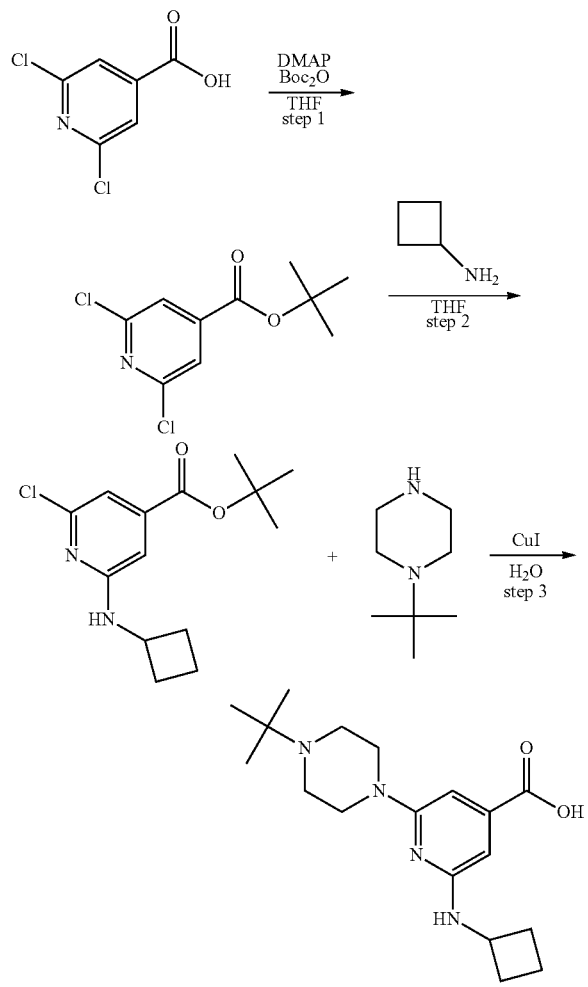

tert-butyl 2,6-dichloroisonicotinate. To a solution of 2,6-dichloroisonicotinic acid (20 g, 104.17 mmol) in THF (430 mL) at 0° C. was added di-tert-butyl dicarbonate (27.28 g, 125.00 mmol, 28.69 mL). A solution of di-tert-butyl dicarbonate (27.28 g, 125.00 mmol, 28.69 mL) in THF (40 mL) was added and the mixture was allowed to warm to ambient temperature. After 18 h, the solvent was removed and HCl (0.1 N aqueous solution) was added and the mixture was extracted with ethyl acetate (3×). The combined organic layer was washed with brine, dried over sodium sulfate, filtered and concentrated to give tert-butyl 2,6-dichloroisonicotinate (23 g, 92.70 mmol, 88.99% yield). $^1$H NMR (400 MHz, CDCl$_3$) δ (ppm) 1.58 (s, 9H), 7.72 (s, 2H). LCMS (ESI): [M-tBu]+ m/z: calcd 191.0. found 192.0; Rt=1.640 min.

tert-butyl 2-chloro-6-(cyclobutylamino)isonicotinate. tert-Butyl 2,6-dichloropyridine-4-carboxylate (20 g, 80.61 mmol) and cyclobutylamine (28.67 g, 403.05 mmol, 34.41 mL) in THF (400 mL). The resulting reaction mixture was stirred at 100° C. for 24 h and then quenched with aqueous ammonium chloride. The mixture was extracted with ethyl acetate (100 mL×2). The combined extracts were washed with brine, dried over anhydrous sodium sulfate. The filtrate was concentrated to give the tert-butyl 2-chloro-6-(cyclobutylamino)pyridine-4-carboxylate (21 g, 74.27 mmol, 92.13% yield). $^1$H NMR (500 MHZ, CDCl$_3$) δ (ppm) 1.57 (s, 9H), 1.80 (m, 2H), 1.88 (m, 2H), 2.45 (m, 2H), 4.15 (m, 1H), 5.02 (m, 1H), 6.72 (s, 1H), 7.01 (s, 1H). LCMS(ESI): [M+H]+ m/z: calcd 282.8. found 283.2; Rt=1.681 min.

2-(4-(tert-butyl)piperazin-1-yl)-6-(cyclobutylamino)isonicotinic acid. tert-Butyl 2-chloro-6-(cyclobutylamino)pyridine-4-carboxylate (1 g, 3.54 mmol), 1-tert-butylpiperazine (2.52 g, 17.68 mmol, 2.25 mL) and copper(I) iodide (67.35 mg, 353.65 umol, 11.98 uL) in H$_2$O (10 mL). The resulting reaction mixture was stirred at 120° C. for 48 h. The reaction mixture was concentrated and the residue was purified to prep-HPLC (column: Waters SunFire C18 100.19 mm, 5u; mobile phase:water—ACN; B %: 20-40%, 4 min) to obtain a 2-(4-tert-butylpiperazin-1-yl)-6-(cyclobutylamino)pyridine-4-carboxylic acid (0.243 g, 730.96 umol, 20.67% yield). $^1$H NMR (400 MHz, DMSO-d$_6$) δ (ppm) 1.04 (s, 9H), 1.68 (m, 2H), 1.86 (m, 2H), 2.25 (m, 2H), 2.61 (m, 6H), 2.95 (m, 2H), 4.18 (m, 1H), 6.18 (s, 1H), 6.25 (s, 1H), 6.43 (bds, 1H). LCMS(ESI): [M+H]+ m/z: calcd 332.4. found 333.2; Rt=0.925 min.

2-(cyclobutylamino)-6-(piperidin-1-yl)isonicotinic add

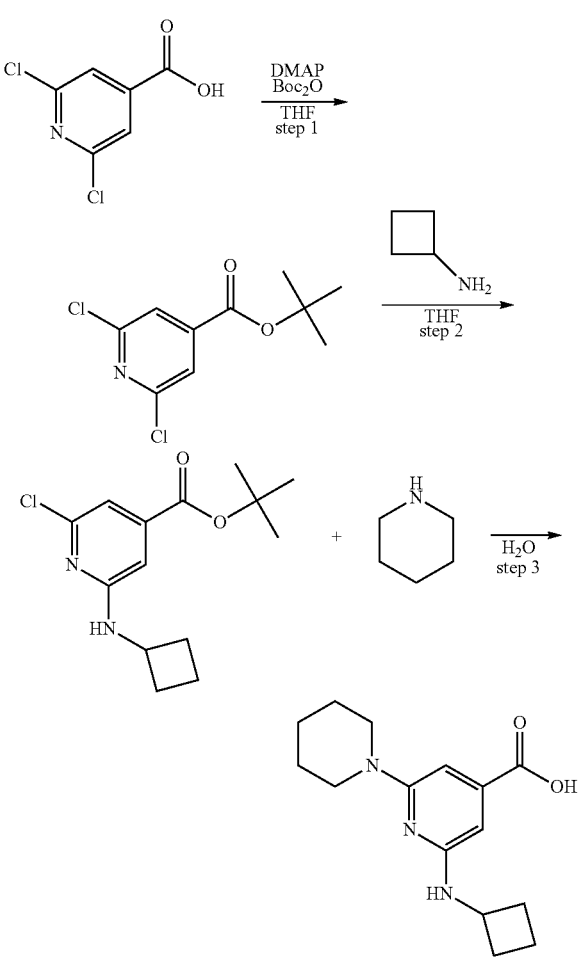

2-(cyclobutylamino)-6-(piperidin-1-yl)isonicotinic acid. tert-Butyl 2-chloro-6-(cyclobutylamino)pyridine-4-carboxylate (1 g, 3.54 mmol), and piperidine (4.52 g, 53.05 mmol, 5.24 mL) in H₂O (10 mL). The resulting reaction mixture was stirred at 120° C. for 48 h. The reaction mixture was concentrated and the residue was purified to prep-HPLC (column: Waters SunFire C18 100.19 mm, 5u; mobile phase: water-ACN; B %: 20-40%, 4 min) to obtain a 2-(cyclobutylamino)-6-(1-piperidyl)pyridine-4-carboxylic acid (0.272 g, 987.85 umol, 27.93% yield). ¹H NMR (400 MHz, DMSO-d₆) δ (ppm) 1.61 (m, 8H), 1.86 (m, 2H), 2.23 (m, 2H), 2.92 (m, 4H), 4.18 (m, 1H), 6.14 (s, 1H), 6.25 (bds, 1H), 6.34 (s, 1H). LCMS(ESI): [M+H]+ m/z: calcd 275.4. found 276.2; Rt=1.080 min.

5-(cyclobutylamino)nicotinic Acid

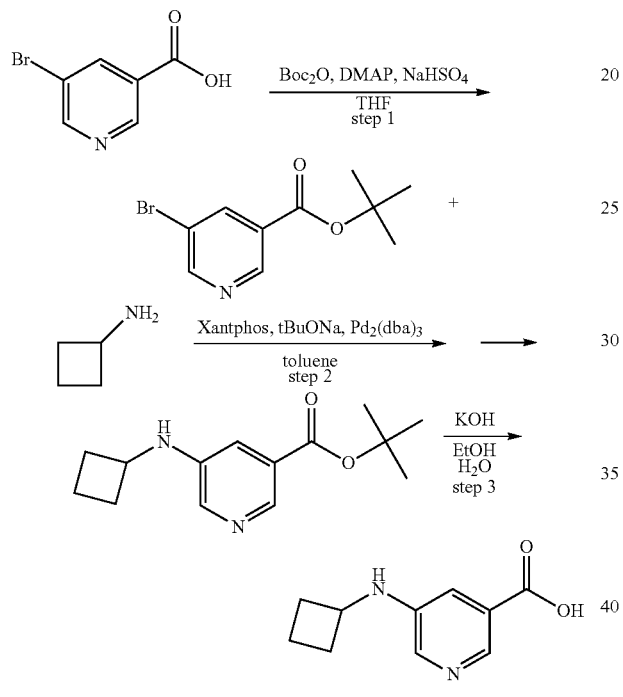

tert-butyl 5-bromonicotinate. Di-tert-butyl dicarbonate (7.72 g, 35.40 mmol, 8.12 mL) was added to a stirred mixture of 5-bromopyridine-3-carboxylic acid (5.5 g, 27.23 mmol) and N,N-dimethylpyridin-4-amine (1.66 g, 13.61 mmol) in THF (100 mL) at 25° C. The reaction mixture was stirred at 25° C. for 12 hr, and evaporated in vacuo. The residue was dissolved in dichloromethane (100 ml) and washed successively with aqueous sodium hydrogen sulphate (1.80 g, 14.97 mmol) solution (40 ml), and water (50 ml). The organic layer was separated, dried over sodium sulphate and evaporated in vacuo to afford tert-butyl-5-bromopyridine-3-carboxylate (6.4 g, 24.80 mmol, 91.07% yield) as white solid. ¹H NMR (500 MHz, CDCl₃) δ (ppm) 1.61 (s, 9H), 8.36 (t, 1H), 8.81 (d, 1H), 9.07 (d, 1H). LCMS(ESI): [M+H]⁺ m/z: 258.1 calcd. found 259.0; Rt=1.508 min.

tert-butyl 5-(cyclobutylamino)nicotinate. tert-Butyl 5-bromopyridine-3-carboxylate (2.5 g, 9.69 mmol) and sodium 2-methylpropan-2-olate (1.40 g, 14.53 mmol) were mixed together in toluene (50 mL). The resulting mixture was evacuated and then backfilled with argon, this operation was repeated three times, then cyclobutanamine (2.07 g, 29.06 mmol, 2.48 mL), [5-(diphenylphosphanyl)-9,9-dimethyl-9H-xanthen-4-yl]diphenylphosphane (280.22 mg, 484.29 umol) and tris(1,5-diphenylpenta-1,4-dien-3-one) dipalladium (221.74 mg, 242.14 umol) were added under argon. The flask was sealed, and the reaction mixture was stirred under argon at 90° C. for 12 hr, then cooled and evaporated in vacuo to leave 5 g of the crude product (85.39% purity by LCMS, approximately 2.05 g of the target compound) tert-butyl 5-(cyclobutylamino)pyridine-3-carboxylate (2.05 g, 8.26 mmol, 85.23% yield) as brown gum, which was used directly in the next step. ¹H NMR (500 MHz, CDCl₃) δ (ppm) 1.57 (s, 9H), 1.83 (m, 4H), 2.43 (m, 2H), 3.92 (m, 1H), 7.15 (m, 1H), 7.31 (m, 1H), 8.05 (m, 1H), 8.46 (m, 1H). LCMS(ESI): [M+H]⁺ m/z: 248.3 calcd. found 249.2; Rt=1.229 min.

5-(cyclobutylamino)nicotinic acid, tert-Butyl 5-(cyclobutylamino)pyridine-3-carboxylate (5 g, 20.14 mmol) (crude from previous step 85.39% purity by LCMS, approximately 2.05 g of the target compound) was dissolved in a solution of potassium hydroxide (4 g, 71.29 mmol, 1.96 mL) in a mixture of water (10 mL) and ethanol (30 mL). The resulting mixture was stirred with reflux condenser at 90° C. for 12 hr, then cooled and evaporated in vacuo. The residue was diluted with water (50 ml), stirred for 0.25 hr and filtered. The filtercake was washed with water (2*20 ml) and discarded. The filtrate was acidified to pH 5 with concentrated hydrochloric acid. The resulting clear solution was evaporated to dryness in vacuo, the residue was diluted with hot isopropanol (50° C., 100 ml) and stirred for 0.1 hr. The inorganic salts was filtered and discarded, the filtrate was evaporated and dried in vacuo to afford 5-(cyclobutylamino)pyridine-3-carboxylic acid (1.5 g, 7.80 mmol, 38.76% yield) as yellow solid, which was used in the next step without further purification. ¹H NMR (400 MHz, DMSO) δ (ppm) 1.79 (m, 4H), 2.35 (m, 2H), 3.93 (m, 1H), 6.79 (m, 1H), 7.44 (m, 1H), 8.08 (m, 1H), 8.28 (m, 1H). LCMS(ESI): [M+H]⁺ m/z: 192.2 calcd. found 193.2; Rt=0.737 min.

2-(cyclobutylamino)-6-(4-ethylpiperazin-1-yl)isonicotinic Acid

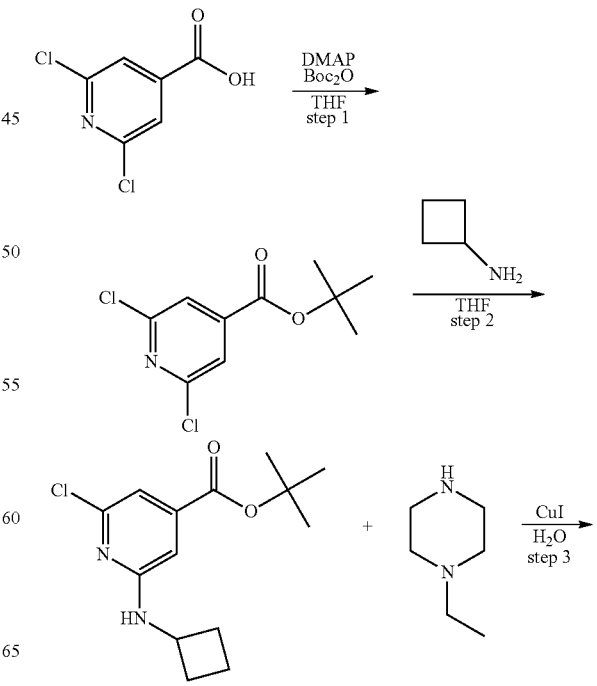

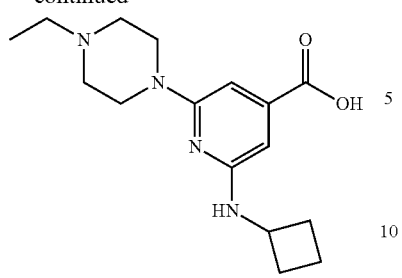

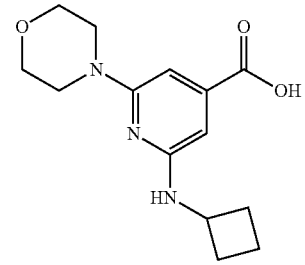

2-(cyclobutylamino)-6-(4-ethylpiperazin-1-yl)isonicotinic acid. tert-Butyl 2-chloro-6-(cyclobutylamino)pyridine-4-carboxylate (1 g, 3.54 mmol), 1-ethylpiperazine (2.02 g, 17.68 mmol, 2.25 mL) and copper(I) iodide (67.35 mg, 353.65 umol, 11.98 uL) in $H_2O$ (10 mL). The resulting reaction mixture was stirred at 120° C. for 48 h. The reaction mixture was concentrated and the residue was purified to prep-HPLC (column: Waters SunFire C18 100.19 mm, 5u; mobile phase:water-ACN; B %: 20-40%, 4 min) to obtain a 2-(cyclobutylamino)-6-(4-ethylpiperazin-1-yl)pyridine-4-carboxylic acid. $^1$H NMR (400 MHz, DMSO-cfc) δ (ppm) 1.24 (t, 3H), 1.68 (m, 2H), 1.85 (m, 2H), 2.24 (m, 2H), 3.32 (m, 6H), 3.55 (d, 2H), 4.18 (m, 1H), 4.38 (d, 2H), 6.32 (s, 1H), 6.36 (s, 1H), 9.71 (bds, 1H), 12.82 (bds, 1H). LCMS (ESI): [M+H]+ m/z: calcd 304.4. found 305.2; Rt=0.840 min.

2-(cyclobutylamino)-6-morpholinoisonicotinic Acid 2-(cyclobutylamino)-6-morpholinoisonicotinic acid. tert-Butyl 2-chloro-6-(cyclobutylamino)pyridine-4-carboxylate (1 g, 3.54 mmol), morpholin (3.08 g, 35.37 mmol, 3.09 mL) and copper(I) iodide (67.35 mg, 353.65 umol, 11.98 uL) in $H_2O$ (10 mL). The resulting reaction mixture was stirred at 120° C. for 48 h. The resulting reaction mixture was stirred at 120° C. for 48 h. The reaction mixture was concentrated and the residue was purified to prep-HPLC (column: Waters SunFire C18 100.19 mm, 5u; mobile phase:water-ACN; B %: 20-40%, 4 min) to obtain a 2-(cyclobutylamino)-6-morpholino-pyridine-4-carboxylic acid (0.326 g, 1.18 mmol, 33.24% yield). $^1$H NMR (400 MHz, DMSO-$d_6$) δ (ppm) 1.65 (m, 2H), 1.88 (m, 2H), 2.24 (m, 2H), 3.35 (m, 4H), 3.68 (m, 4H), 4.19 (m, 1H), 6.26 (s, 1H), 6.28 (s, 1H), 8.89 (bds, 2H). LCMS(ESI): [M+H]+ m/z: calcd 277.3. found 278.2; Rt=1.064 min.

2-(4-acetylpiperazin-1-yl)-6-(cyclobutylamino)pyridine-4-carboxylic Acid

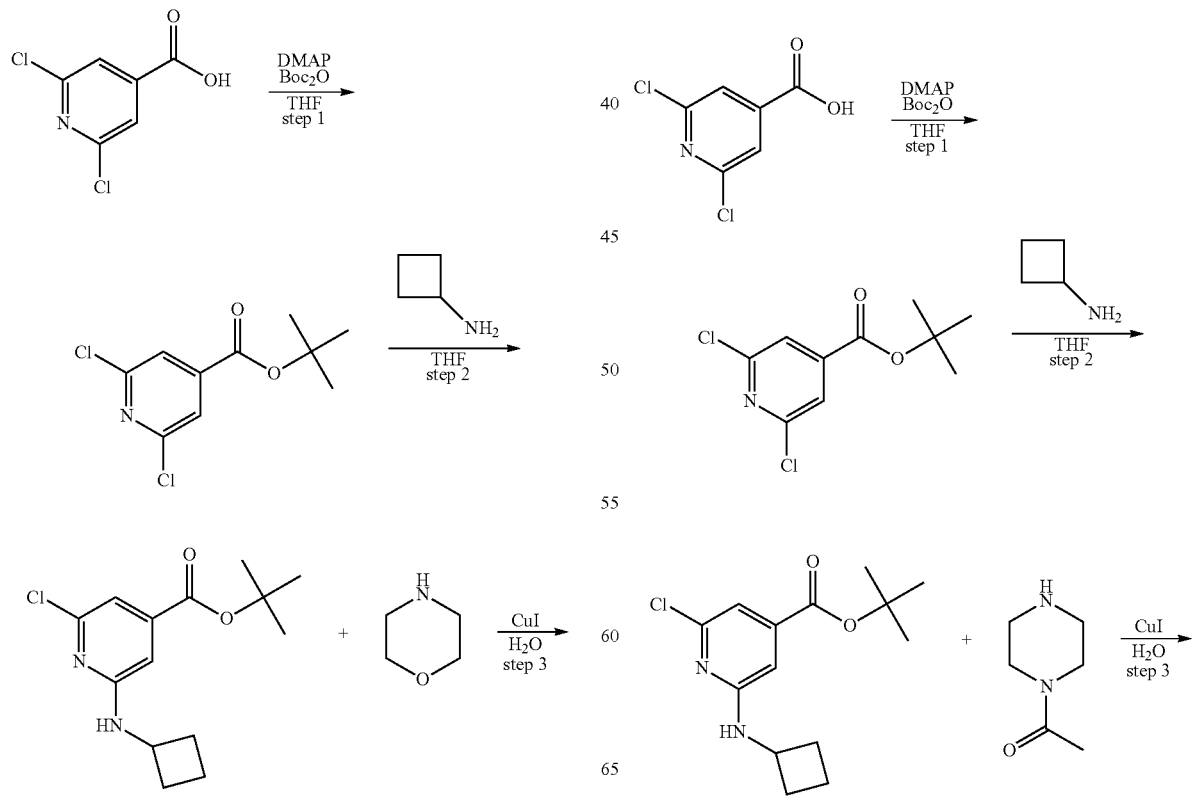

-continued

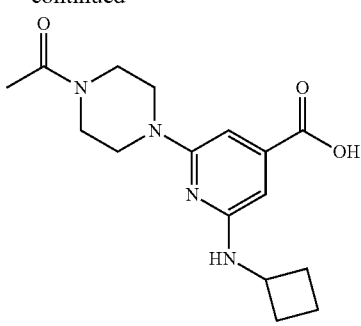

2-(4-acetylpiperazin-1-yl)-6-(cyclobutylamino)pyridine-4-carboxylic acid. tert-Butyl 2-chloro-6-(cyclobutylamino)pyridine-4-carboxylate (1 g, 3.54 mmol), 1-piperazin-1-ylethanone (4.53 g, 35.37 mmol, 5.00 mL) and copper(I) iodide (67.35 mg, 353.65 umol, 11.98 uL) in $H_2O$ (10 mL). The resulting reaction mixture was stirred at 120° C. for 48 h. The resulting reaction mixture was stirred at 120° C. for 48 h. All operations with this reaction mixture was stopped. LCMS(ESI): [M+H]+ m/z: calcd 318.4. found 319.2; Rt=1.053 min.

2-(cyclobutylamino)-6-(4-propionyl)piperazin-1-yl)isonicotinic Acid

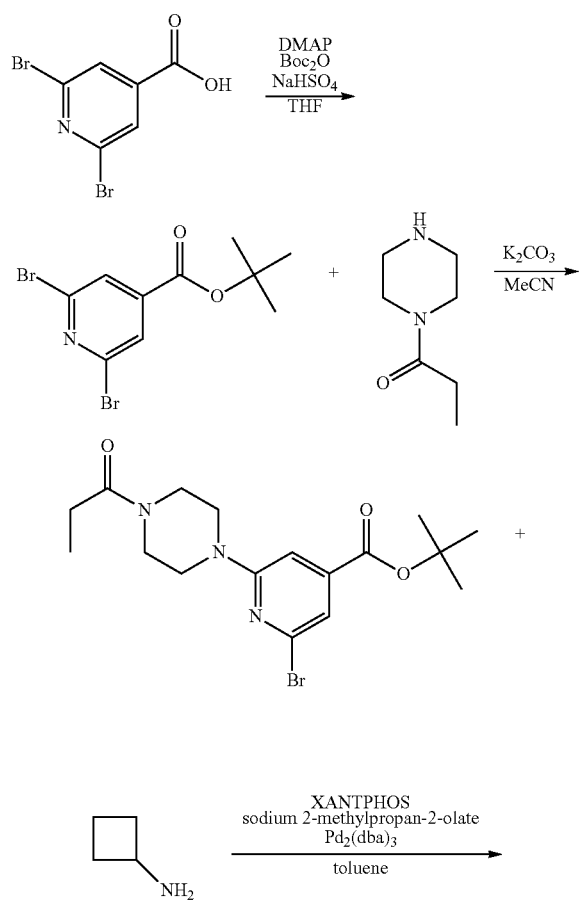

-continued

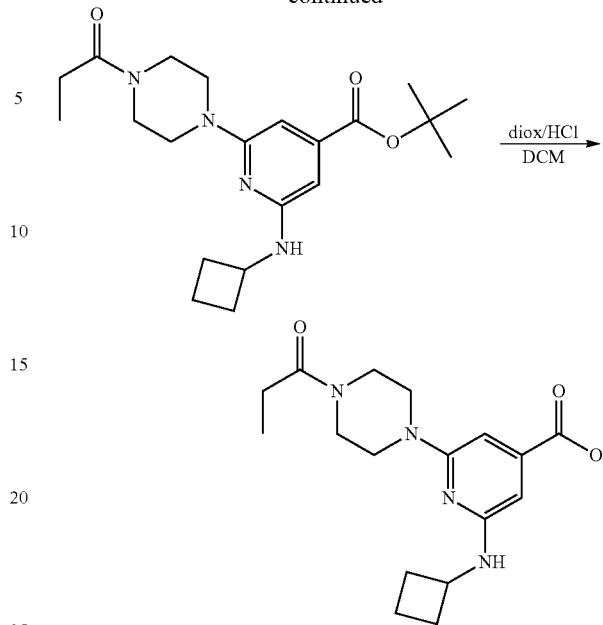

tert-butyl 2,6-dibromoisonicotinate. Di-tert-butyl dicarbonate (20.20 g, 92.56 mmol, 21.24 mL) was added to a stirred mixture of 2,6-dibromopyridine-4-carboxylic acid (20 g, 71.20 mmol) and N,N-dimethylpyridin-4-amine (4.35 g, 35.60 mmol) in THF (300 mL) at 25° C. The reaction mixture was stirred at 25° C. for 12 hr, and evaporated in vacuo. The residue was dissolved in dichloromethane (400 ml) and washed successively with aqueous sodium hydrogen sulphate (5.98 g, 49.84 mmol) solution (120 ml), and water (100 ml). The organic layer was separated, dried over sodium sulphate, filtered through short pad of silica gel and evaporated in vacuo to afford tert-butyl 2,6-dibromopyridine-4-carboxylate (21 g, 62.31 mmol, 87.52% yield) as white solid. $^1$H NMR (400 MHz, $CDCl_3$) δ (ppm) 1.60 (s, 9H), 7.92 (s, 2H). LCMS(ESI): [M+H]+ m/z: calcd 337.0. found 338.2; Rt=1.700 min.

tert-butyl 2-bromo-6-(4-propionylpiperazin-1-yl)isonicotinate. 1-Piperazin-1-ylpropan-1-one (2.23 g, 10.39 mmol, 1.47 mL, 2HCl) was added to a stirred mixture of tert-butyl 2,6-dibromopyridine-4-carboxylate (2.5 g, 7.42 mmol) and potassium carbonate, anhydrous, 99% (5.13 g, 37.09 mmol, 2.24 mL) in acetonitrile (50 mL). The resulting mixture was stirred at 80° C. for 96 hr (the reaction progress was monitored by HNMR of the aliquots), then cooled and filtered. The filtercake was washed with acetonitrile (2*20 ml) and discarded. The filtrate was evaporated in vacuo, the residue was dissolved in dichloromethane, dried over sodium sulphate and filtered through a pad of silicagel (50 g). The silica gel pad was additionally washed with THL (3*50 ml). The combined $CH_2Cl_2$-THL filtrate was evaporated in vacuo to afford tert-butyl 2-bromo-6-(4-propanoylpiperazin-1-yl)pyridine-4-carboxylate (2.7 g, 6.78 mmol, 91.38% yield) as light-yellow solid. $^1$H NMR (500 MHz, $CDCl_3$) δ (ppm) 1.18 (t, 3H), 1.58 (s, 9H), 2.41 (m, 2H), 3.57 (m, 4H), 3.67 (m, 2H), 3.76 (m, 2H), 7.08 (s, 1H), 7.23 (s, 1H). LCMS(ESI): [M+H]+m/z: calcd 398.3. found 400.2; Rt=1.585 min.

tert-butyl 2-(cyclobutylamino)-6-(4-propionylpiperazin-1-yl)isonicotinate.tert-Butyl 2-bromo-6-(4-propanoylpiperazin-1-yl)pyridine-4-carboxylate (2.7 g, 6.78 mmol) and sodium 2-methylpropan-2-olate (977.18 mg, 10.17 mmol) were mixed together in toluene (50 mL). The resulting mixture was evacuated and then backfilled with argon, this operation was repeated three times, then cyclobutanamine (964.24 mg, 13.56 mmol, 1.16 mL), [5-(diphenylphosphinyl)-9,9-dimethyl-9H-xanthen-4-yl]diphenylphosphane (196.12 mg, 338.95 umol) and tris(1,5-diphenylpenta-1,4-dien-3-one) dipalladium (155.19 mg, 169.47 umol) were added under argon. The reaction mixture was stirred under argon at 70° C. for 18 hr, then cooled, filtered and the filtrate was evaporated in vacuo to leave 2.6 g of the crude product (78.99% purity by LCMS, 13.08% of corresponding acid by LCMS (ester cleavage)) tert-butyl 2-(cyclobutylamino)-6-(4-propanoylpiperazin-1-yl)pyridine-4-carboxylate (2.6 g, 6.69 mmol, 98.72% yield) as red solid, which was directly used in the next step. $^1$H NMR (500 MHz, CDCl$_3$) δ (ppm) 1.18 (t, 3H), 1.58 (s, 9H), 1.80 (m, 2H), 1.89 (m, 2H), 2.41 (m, 4H), 3.51 (m, 2H), 3.57 (m, 4H), 3.74 (m, 2H), 4.18 (m, 1H), 6.24 (s, 1H), 6.45 (s, 1H), 7.18 (bds, 1H). LCMS(ESI): [M+H]+ m/z: calcd 388.5. found 389.2; Rt=1.532 min.

2-(cyclobutylamino)-6-(4-propionylpiperazin-1-yl)isonicotinic acid. Hydrogen chloride solution 4.0M in dioxane (52.66 g, 200.77 mmol, 50.16 mL, 13.9% purity) was added to a solution of tert-butyl 2-(cyclobutylamino)-6-(4-propanoylpiperazin-1-yl)pyridine-4-carboxylate (2.6 g, 6.69 mmol) (crude from previous step) in dichloromethane (30 mL). The reaction mixture was stirred at 25° C. for 72 hr, then filtered from tarry solid, and the filtrate was evaporated to dryness in vacuo to afford crude 2-(cyclobutylamino)-6-(4-propanoylpiperazin-1-yl)pyridine-4-carboxylic acid (1.65 g, 4.47 mmol, 66.84% yield, HCl) as yellow solid, which was used in the next step without further purification. $^1$H NMR (400 MHz, DMSO-d$_6$) δ (ppm) 1.01 (t, 3H), 1.72 (m, 3H), 1.91 (m, 2H), 2.35 (m, 4H), 3.64 (m, 9H), 4.16 (m, 1H), 6.25 (s, 1H), 6.42 (s, 1H). LCMS(ESI): [M+H]+ m/z: calcd 332.4. found 333.2; Rt=1.065 min.

2-(cyclobutylamino)-6-(4-isopropylpiperazin-1-yl) isonicotinic Acid

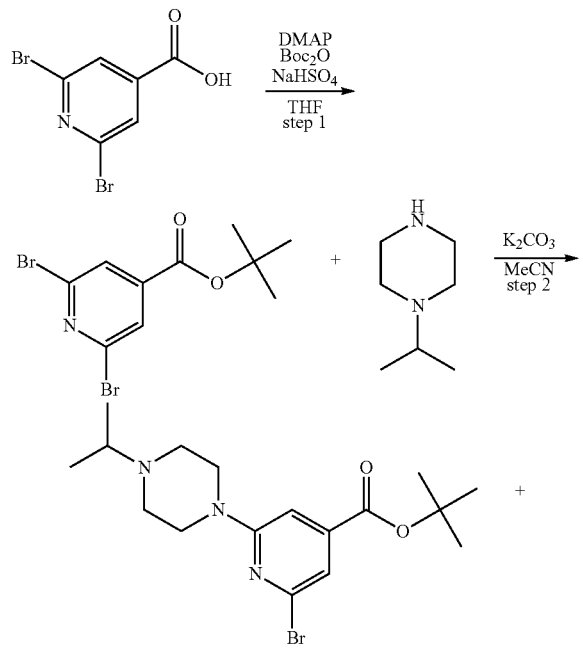

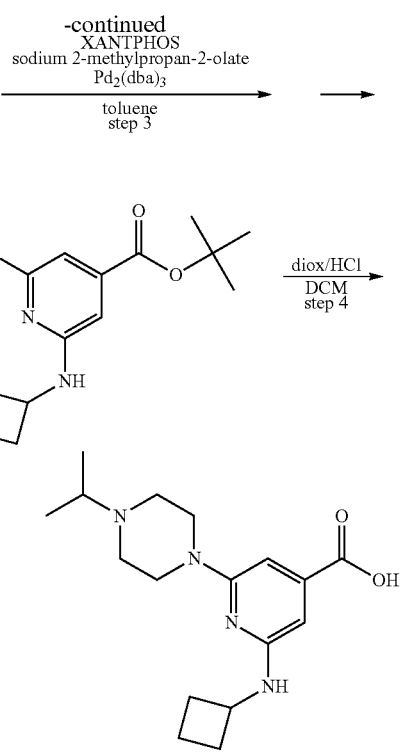

tert-butyl 2-bromo-6-(4-isopropylpiperazin-1-yl)isonicotinate. 1-Isopropylpiperazine (1.60 g, 12.46 mmol, 1.78 mL) was added to a stirred mixture of tert-butyl 2,6-dibromopyridine-4-carboxylate (3 g, 8.90 mmol) and potassium carbonate, anhydrous, 99% (2.46 g, 17.80 mmol, 1.07 mL) in acetonitrile (50 mL). The resulting mixture was stirred at 80° C. for 72 hr (the reaction progress was monitored by H-NMR of the aliquots), then cooled and filtered. The filtercake was washed with acetonitrile (2*20 ml) and discarded. The filtrate was evaporated in vacuo, the residue was dissolved in dichloromethane, dried over sodium sulphate and filtered through a pad of silicagel (50 g). The silica gel pad was additionally washed with THF (3*50 ml). The combined CH$_2$Cl$_2$-THF filtrate was evaporated in vacuo to afford tert-butyl 2-bromo-6-(4-isopropylpiperazin-1-yl)pyridine-4-carboxylate (3.1 g, 8.07 mmol, 90.61% yield) as yellow gum. $^1$H NMR (500 MHz, CDCl$_3$) δ (ppm) 1.08 (d, 6H), 1.58 (s, 9H), 2.60 (t, 4H), 2.75 (m, 1H), 3.60 (t, 4H), 7.06 (s, 1H), 7.16 (s, 1H). LCMS(ESI): [M+H]+ m/z: calcd 384.3. found 386.2; Rt=1.229 min.

tert-butyl 2-(cyclobutylamino)-6-(4-isopropylpiperazin-1-yl)isonicotinate. tert-Butyl 2-bromo-6-(4-isopropylpiperazin-1-yl)pyridine-4-carboxylate (3.1 g, 8.07 mmol) and sodium 2-methylpropan-2-olate (1.16 g, 12.10 mmol) were mixed together in toluene (50 mL). The resulting mixture was evacuated and then backfilled with argon, this operation was repeated three times, then cyclobutanamine (1.15 g, 16.13 mmol, 1.38 mL), [5-(diphenylphosphanyl)-9,9-dimethyl-9H-xanthen-4-yl]diphenylphosphane (233.37 mg, 403.32 umol) and tris(1,5-diphenylpenta-1,4-dien-3-one) dipalladium (184.66 mg, 201.66 umol) were added under argon. The reaction mixture was stirred under argon at 70° C. for 18 hr, then cooled, filtered and the filtrate was evaporated in vacuo to leave 3.7 g of the crude product (80.48% purity by LCMS, 19.52% of corresponding acid by LCMS (ester cleavage), and 90% by HNMR, approximately 3 g of the target compound), tert-butyl 2-(cyclobutylamino)-

6-(4-isopropylpiperazin-1-yl)pyridine-4-carboxylate (3 g, 8.01 mmol, 99.30% yield) as red gum, which was directly used in the next step. ¹H NMR (500 MHz, CDCl₃) δ (ppm) 1.08 (d, 6H), 1.58 (s, 9H), 1.87 (m, 5H), 2.42 (m, 2H), 2.58 (t, 4H), 2.72 (m, 1H), 3.54 (t, 4H), 4.17 (m, 1H), 6.19 (s, 1H), 6.46 (s, 1H). LCMS(ESI): [M+H]+ m/z: calcd 374.5. found 375.4; Rt=1.161 min.

2-(cyclobutylamino)-6-(4-isopropylpiperazin-1-yl)isonicotinic acid. Hydrogen chloride solution 4.0M in dioxane (77.74 g, 296.38 mmol, 74.04 mL, 13.9% purity) was added to a solution of tert-butyl 2-(cyclobutylamino)-6-(4-isopropylpiperazin-1-yl)pyridine-4-carboxylate (3.7 g, 9.88 mmol) (crude from previous step) in dichloromethane (50 mL). The reaction mixture was stirred at 25° C. for 72 hr, then evaporated to dryness in vacuo. The residue was triturated with dichloromethane (30 ml), stirred for 0.1 hr and the precipitate was filtered, washed with dichloromethane (2*20 ml) and dried in vacuo to afford crude 2-(cyclobutylamino)-6-(4-isopropylpiperazin-1-yl)pyridine-4-carboxylic acid (3 g, 7.67 mmol, 77.60% yield, 2HCl) as yellow solid, which was used in the next step without further purification. ¹H NMR (400 MHz, DMSO-d₆) δ (ppm) 1.30 (d, 6H), 1.66 (m, 2H), 1.88 (m, 2H), 2.28 (m, 2H), 3.05 (m, 2H), 3.45 (m, 5H), 4.17 (m, 1H), 4.39 (m, 2H), 6.33 (s, 1H), 6.42 (s, 1H), 11.44 (bds, 2H). LCMS(ESI): [M+H]+ m/z: calcd 318.4. found 319.2; Rt=0.893 min.

2-(cyclobutylamino)-6-(4-(cyclopropanecarbonyl)piperazin-1-yl)isonicotinic Acid

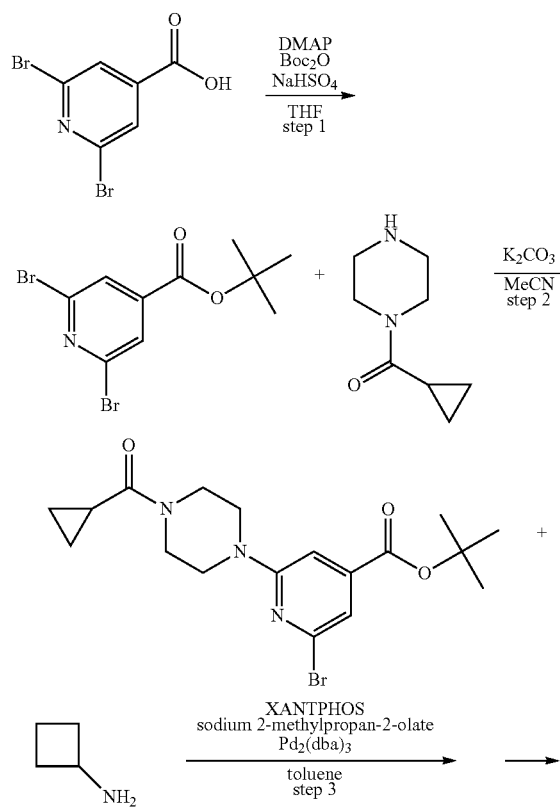

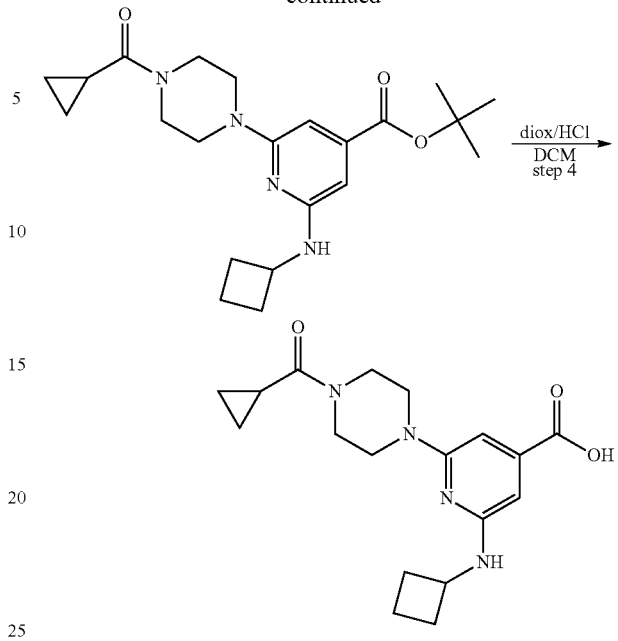

tert-butyl 2-bromo-6-(4-(cyclopropanecarbonyl)piperazin-1-yl)isonicotinate. Cyclopropyl(piperazin-1-yl)methanone (2.36 g, 10.39 mmol, 2.16 mL, 2HCl) was added to a stirred mixture of tert-butyl 2,6-dibromopyridine-4-carboxylate (2.5 g, 7.42 mmol) and potassium carbonate, anhydrous, 99% (5.13 g, 37.09 mmol, 2.24 mL) in acetonitrile (50 mL). The resulting mixture was stirred at 80° C. for 96 hr (the reaction progress was monitored by H-NMR of the aliquots), then cooled and filtered. The filtercake was washed with acetonitrile (2*20 ml) and discarded. The filtrate was evaporated in vacuo, the residue was dissolved in dichloromethane, dried over sodium sulphate and filtered through a pad of silicagel (50 g). The silica gel pad was additionally washed with THF (3*50 ml). The combined CH₂Cl₂-THF filtrate was evaporated in vacuo to afford tert-butyl 2-bromo-6-[4-(cyclopropanecarbonyl)piperazin-1-yl]pyridine-4-carboxylate (2.6 g, 6.34 mmol, 85.42% yield) as yellow solid. ¹H NMR (500 MHZ, CDCl₃) δ (ppm) 0.81 (m, 2H), 1.03 (m, 2H), 1.58 (s, 9H), 1.78 (m, 1H), 3.58 (m, 2H), 3.79 (m, 6H), 7.08 (s, 1H), 7.23 (s, 1H). LCMS (ESI): [M+H]+ m/z: calcd 410.3. found 412.2; Rt=1.518 min.

tert-butyl 2-(cyclobutylamino)-6-(4-(cyclopropanecarbonyl)piperazin-1-yl)isonicotinate. tert-Butyl 2-bromo-6-[4-(cyclopropanecarbonyl)piperazin-1-yl]pyridine-4-carboxylate (2.6 g, 6.34 mmol) and sodium 2-methylpropan-2-olate (913.44 mg, 9.51 mmol) were mixed together in toluene (50 mL). The resulting mixture was evacuated and then back-filled with argon, this operation was repeated three times, then cyclobutanamine (901.35 mg, 12.67 mmol, 1.08 mL), [5-(diphenylphosphanyl)-9,9-dimethyl-9H-xanthen-4-yl]diphenylphosphane (183.33 mg, 316.84 umol) and tris(1,5-diphenylpenta-L4-dien-3-one) dipalladium (145.07 mg, 158.42 umol) were added under argon. The reaction mixture was stirred under argon at 70° C. for 18 hr, then cooled, filtered and the filtrate was evaporated in vacuo to leave 2.5 g of the crude product (78.51% purity by LCMS, 17.12% of corresponding acid by LCMS (ester cleavage)), tert-butyl 2-(cyclobutylamino)-6-[4-(cyclopropanecarbonyl)piperazin-1-yl]pyridine-4-carboxylate (2.5 g, 6.24 mmol, 98.50% yield) as red solid, which was directly used in the next step. ¹H NMR (500 MHz, CDCl₃) δ (ppm) 0.79 (m, 2H), 1.03 (m, 2H), 1.58 (s, 9H), 1.87 (m, 5H), 2.42 (m, 2H), 3.58 (m, 4H), 3.76 (m, 4H), 4.20 (m, 1H), 6.24 (s, 1H), 6.45 (s, 1H), 7.18 (bds, 1H). LCMS(ESI): [M+H]+ m/z: calcd 400.5. found 401.2; Rt=1.550 min.

2-(cyclobutylamino)-6-(4-(cyclopropanecarbonyl)piperazin-1-yl)isonicotinic acid. Hydrogen chloride solution 4.0M in dioxane (49.12 g, 187.26 mmol, 46.78 mL, 13.9% purity) was added to a solution of tert-butyl 2-(cyclobutylamino)-6-[4-(cyclopropanecarbonyl)piperazin-1-yl]pyridine-4-carboxylate (2.5 g, 6.24 mmol) (crude from previous step) in dichloromethane (30 mL). The reaction mixture was stirred at 25° C. for 72 hr, then filtered from tarry solid, and the filtrate was evaporated to dryness in vacuo to afford crude 2-(cyclobutylamino)-6-[4-(cyclopropanecarbonyl)piperazin-1-yl]pyridine-4-carboxylic acid (1.8 g, 4.73 mmol, 75.71% yield, HCl) as light-brown solid, which was used in the next step without further purification. ¹H NMR (400 MHz, DMSO-d₆) δ (ppm) 0.72 (m, 4H), 1.68 (m, 2H), 1.88 (m, 2H), 1.99 (m, 1H), 2.32 (m, 2H), 3.65 (m, 6H), 3.81 (m, 2H), 4.19 (m, 1H), 6.25 (s, 1H), 6.41 (s, 1H). LCMS (ESI): [M+H]+ m/z: calcd 344.4. found 345.2; Rt=1.098 min.

2-(cyclobutylamino)-6-(4-isobutyrylpiperazin-1-yl) isonicotinic Acid

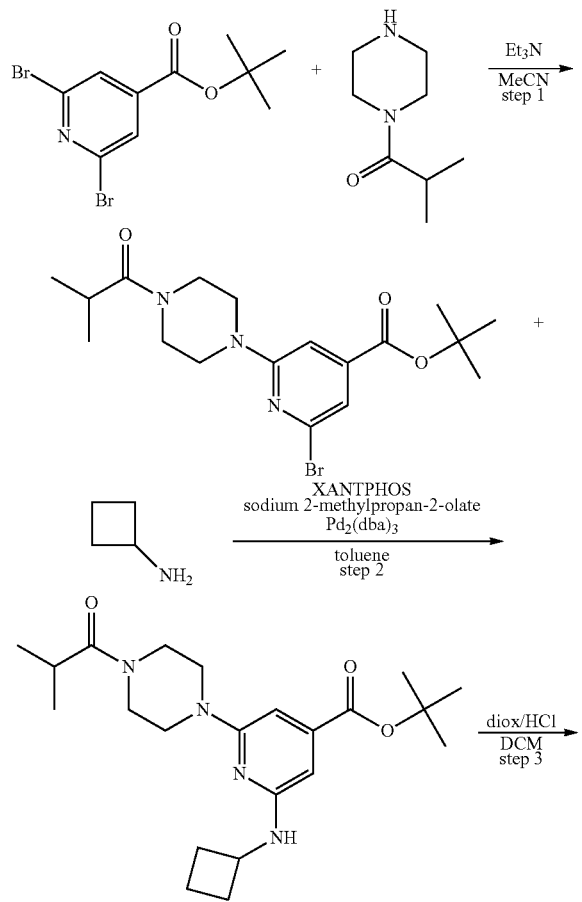

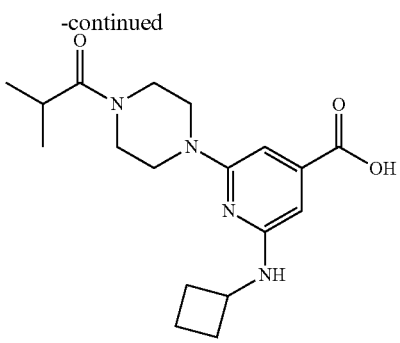

tert-butyl 2-bromo-6-(4-isobutyrylpiperazin-1-yl)isonicotinate. To a suspension of tert-butyl 2,6-dibromopyridine-4-carboxylate (2.5 g, 7.42 mmol) and 2-methyl-1-piperazin-1-yl-propan-1-one (1.57 g, 8.16 mmol, HCl) in ACN (35 mL), triethylamine (1.88 g, 18.55 mmol, 2.58 mL) was added. The resulting mixture was stirred at 80° C. for 72 hr and evaporated in vacuo. The residue was diluted with water (70 ml) and extracted with DCM (3*50 ml). The combined organic layer was washed with brine (2*50 ml), dried over Na₂SO₄ and evaporated in vacuo to give tert-butyl 2-bromo-6-[4-(2-methylpropanoyl)piperazin-1-yl]pyridine-4-carboxylate (2.9 g, 7.03 mmol, 94.81% yield). ¹H NMR (500 MHz, CDCl₃) δ (ppm) 1.13 (d, 6H), 1.56 (s, 9H), 2.81 (m, 1H), 3.54 (m, 2H), 3.62 (m, 4H), 3.71 (m, 2H), 7.05 (s, 1H), 7.21 (s, 1H). LCMS(ESI): [M+H]+ m/z: calcd 412.3. found 412.2; Rt=1.690 min.

tert-butyl 2-(cyclobutylamino)-6-(4-isobutyrylpiperazin-1-yl)isonicotinate. To a solution of tert-butyl 2-bromo-6-[4-(2-methylpropanoyl)piperazin-1-yl]pyridine-4-carboxylate (2.9 g, 7.03 mmol), cyclobutanamine (1.00 g, 14.07 mmol, 1.20 mL) and sodium tert-butoxide (1.01 g, 10.55 mmol) in toluene (50 mL), 4,5-bis(diphenylphosphino)-9,9-dimethylxanthene (203.48 mg, 351.67 umol) and tris(dibenzylideneacetone)dipalladium(0) (161.01 mg, 175.83 umol) were added under Ar atmosphere. The resulting mixture was heated at 70° C. for 18 hr, cooled and filtered through a thin layer of silicagel. Silicagel was washed with MTBE (50 ml). The solvent was evaporated in vacuo to obtain tert-butyl 2-(cyclobutylamino)-6-[4-(2-methylpropanoyl)piperazin-1-yl]pyridine-4-carboxylate (3.4 g, crude). The product was used for the next step without purification. ¹H NMR (500 MHz, CDCl₃) δ (ppm) 1.17 (d, 6H), 1.59 (s, 9H), 1.80 (m, 2H), 1.88 (m, 2H), 2.43 (m, 2H), 2.84 (m, 1H), 3.51 (m, 2H), 3.59 (m, 4H), 3.73 (m, 2H), 4.17 (m, 1H), 4.63 (m, 1H), 6.25 (s, 1H), 6.43 (s, 1H). LCMS(ESI): [M+H]+ m/z: calcd 402.5. found 403.2; Rt=1.525 min.

2-(cyclobutylamino)-6-(4-isobutyrylpiperazin-1-yl)isonicotinic acid. To a solution of tert-butyl 2-(cyclobutylamino)-6-(4-methylpiperazin-1-yl)pyridine-4-carboxylate (3 g, 7.79 mmol) in DCM (30 mL), hydrogen chloride solution, 4.0 M in dioxane (50 g, 7.79 mmol) was added. The resulting mixture was stirred at 25° C. for 72 hr. The formed precipitate was filtered and discarded. The solvent was evaporated in vacuo and residue was triturated with MTBE (50 ml). The formed precipitate was filtered, washed with MTBE (30 ml) and dried to obtain 2-(cyclobutylamino)-6-[4-(2-methylpropanoyl)piperazin-1-yl]pyridine-4-carboxylic acid (2.3 g, 6.01 mmol, 79.02% yield, HCl). This compound was used for the next step without purification. NMR (500 MHz, DMSO-d₆) δ (ppm) 0.99 (d, 6H), 1.73 (m, 2H), 1.88 (m, 2H), 2.32 (m, 2H), 2.88 (m, 1H), 3.14 (m, 1H), 3.55 (m, 4H), 3.57 (m, 2H), 3.63 (m, 2H), 3.76 (m, 1H), 4.13 (m, 1H), 6.24

(s, 1H), 6.44 (s, 1H). LCMS(ESI): [M+H]+ m/z: calcd 346.4. found 347.2; Rt=1.177 min.

2-(cyclobutylamino)-6-(methyl(propyl)amino)isonicotinic Acid

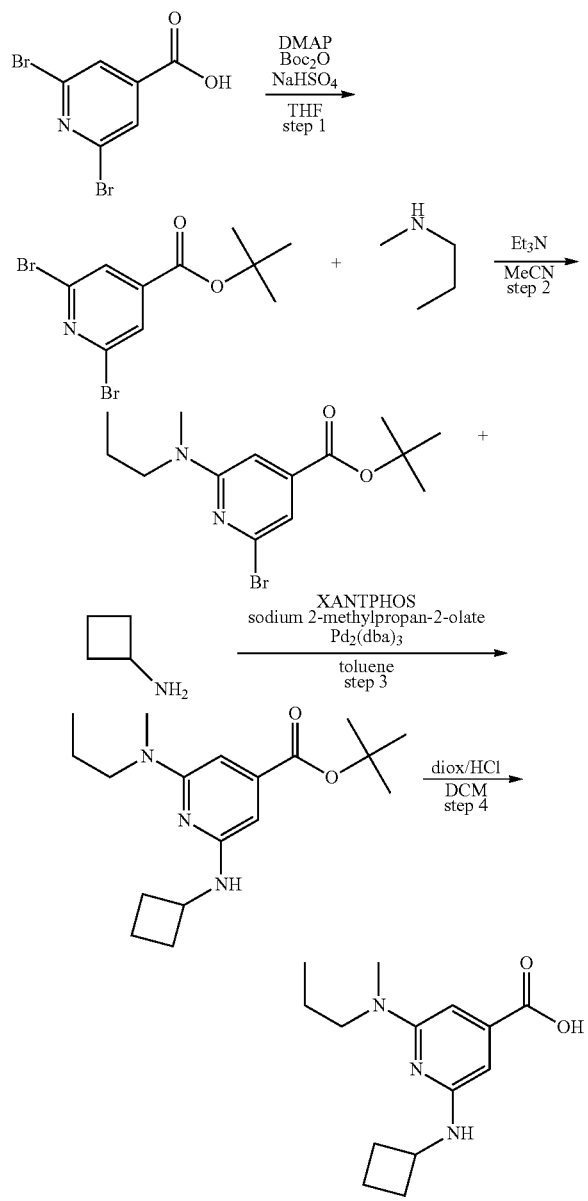

tert-butyl 2-bromo-6-(methyl(propyl)amino)isonicotinate. To a solution of tert-butyl 2,6-dibromopyridine-4-carboxylate (2.5 g, 7.42 mmol) and N-methylpropan-1-amine (651.05 mg, 8.90 mmol, 913.12 uL) in ACN (35 mL), triethylamine (1.13 g, 11.13 mmol, 1.55 mL) was added. The resulting mixture was stirred at 80° C. for 72 hr and evaporated in vacuo. The residue was diluted with water (70 ml) and extracted with DCM (3*50 ml). The combined organic layer was washed with brine (2*50 ml), dried over $Na_2SO_4$ and evaporated in vacuo to give tert-butyl 2-bromo-6-[methyl(propyl)amino]pyridine-4-carboxylate (2.25 g, 6.83 mmol, 92.13% yield). $^1$H NMR (500 MHz, $CDCl_3$) δ (ppm) 0.93 (t, 3H), 1.62 (s, 9H), 1.64 (m, 2H), 3.07 (s, 3H), 3.48 (m, 2H), 6.93 (s, 1H), 7.08 (s, 1H). LCMS(ESI): [M+H]+ m/z: calcd 329.2. found 330.2; Rt=1.793 min.

tert-butyl 2-(cyclobutylamino)-6-(methyl(propyl)amino) isonicotinate. To a solution of tert-butyl 2-bromo-6-[methyl (propyl)amino]pyridine-4-carboxylate (2.25 g, 6.83 mmol), cyclobutanamine (972.09 mg, 13.67 mmol, 1.17 mL) and sodium tert-butoxide (985.13 mg, 10.25 mmol) in toluene (50 mL), 4,5-bis(diphenylphosphino)-9,9-dimethylxanthene (197.72 mg, 341.70 umol) and tris(dibenzylideneacetone) dipalladium(0) (156.45 mg, 170.85 umol) were added under Ar atmosphere. The resulting mixture was heated at 70° C. for 18 hr, cooled and filtered through a thin layer of silicagel. Silicagel was washed with MTBE (50 ml). The solvent was evaporated in vacuo to obtain tert-butyl 2-(cyclobutylamino)-6-[methyl(propyl)amino]pyridine-4-carboxylate (2.6 g, crude). The product was used for the next step without purification. $^1$H NMR (500 MHz, $CDCl_3$) δ (ppm) 0.89 (t, 3H), 1.56 (s, 9H), 1.58 (m, 2H), 1.76 (m, 2H), 1.85 (m, 2H), 2.40 (m, 2H), 2.99 (s, 3H), 3.43 (m, 2H), 4.15 (m, 1H), 6.06 (s, 1H), 6.30 (s, 1H), 7.19 (bds, 1H). LCMS(ESI): [M+H]+ m/z: calcd 319.4. found 320.2; Rt=1.508 min.

2-(cyclobutylamino)-6-(methyl(propyl)amino)isonicotinic acid. To a solution of tert-butyl 2-(cyclobutylamino)-6-[methyl(propyl)amino]pyridine-4-carboxylate (2.6 g, 7.33 mmol) in DCM (30 mL), hydrogen chloride solution, 4.0 M in dioxane (50 g, 7.33 mmol) was added. The resulting mixture was stirred at 25° C. for 24 hr and evaporated in vacuo to obtain 2-(cyclobutylamino)-6-[methyl(propyl) amino]pyridine-4-carboxylic acid (1.9 g, 7.22 mmol, 98.50% yield). $^1$H NMR (500 MHz, DMSO-$d_6$) δ (ppm) 0.89 (t, 3H), 1.52 (m, 2H), 1.56 (m, 2H), 1.76 (m, 2H), 1.91 (m, 2H), 2.34 (m, 2H), 3.13 (s, 3H), 3.56 (m, 2H), 4.08 (m, 1H), 6.11 (s, 1H), 6.34 (s, 1H). LCMS(ESI): [M+H]+ m/z: calcd 263.3. found 264.2; Rt=0.959 min.

2-(cyclobutylamino)-6-(ethyl(methyl)amino)isonicotinic acid

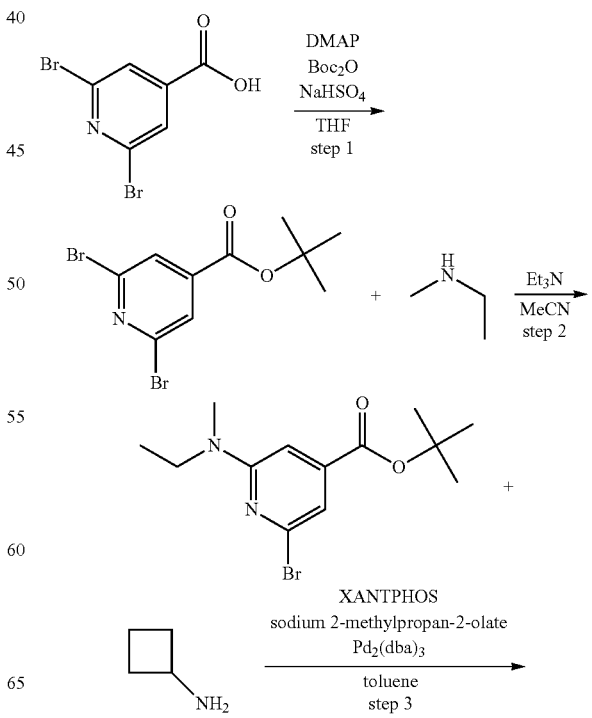

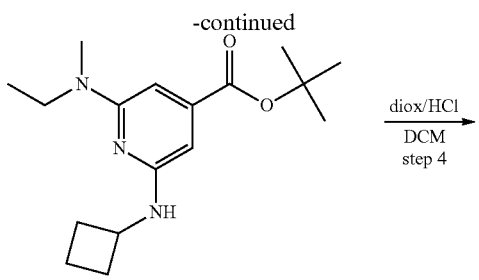

tert-butyl 2-bromo-6-(ethyl(methyl)amino)isonicotinate. To a solution of tert-butyl 2,6-dibromopyridine-4-carboxylate (2.5 g, 7.42 mmol) and N-methylethanamine (526.19 mg, 8.90 mmol, 764.82 uL) in ACN (35 mL), triethylamine (1.13 g, 11.13 mmol, 1.55 mL) was added. The resulting mixture was stirred at 80° C. for 72 hr and evaporated in vacuo. The residue was diluted with water (70 ml) and extracted with DCM (3*50 ml). The combined organic layer was washed with brine (2*50 ml), dried over $Na_2SO_4$ and evaporated in vacuo to give tert-butyl 2-bromo-6-[ethyl(methyl)amino]pyridine-4-carboxylate (2.1 g, 6.66 mmol, 89.81% yield). $^1H$ NMR (400 MHz, $CDCl_3$) δ (ppm) 1.13 (t, 3H), 1.55 (s, 9H), 3.02 (s, 3H), 3.56 (m, 2H), 6.90 (s, 1H), 7.06 (s, 1H). LCMS(ESI): [M+H]+ m/z: calcd 315.2. found 315.0; Rt=1.736 min.

tert-butyl 2-(cyclobutylamino)-6-(ethyl(methyl)amino)isonicotinate. To a solution of tert-butyl 2-bromo-6-[ethyl(methyl)amino]pyridine-4-carboxylate (2.1 g, 6.66 mmol), cyclobutanamine (947.66 mg, 13.32 mmol, 1.14 mL) and sodium tert-butoxide (960.37 mg, 9.99 mmol) in toluene (50 mL), 4,5-bis(diphenylphosphino)-9,9-dimethylxanthene (192.75 mg, 333.12 umol) and tris(dibenzylideneacetone) dipalladium(0) (152.52 mg, 166.56 umol) were added under Ar atmosphere. The resulting mixture was heated at 70° C. for 18 hr, cooled and filtered through a thin layer of silicagel. Silicagel was washed with MTBE (50 ml). The solvent was evaporated in vacuo to obtain tert-butyl 2-(cyclobutylamino)-6-[ethyl(methyl)amino]pyridine-4-carboxylate (2.0 g, crude). The product was used for the next step without purification. $^1H$ NMR (500 MHz, $CDCl_3$) δ (ppm) 1.10 (t, 3H), 1.55 (s, 9H), 1.76 (m, 2H), 1.85 (m, 2H), 2.40 (m, 2H), 2.97 (s, 3H), 3.53 (m, 2H), 4.15 (m, 1H), 4.51 (m, 1H), 6.07 (s, 1H), 6.31 (s, 1H). LCMS(ESI): [M+H]+ m/z: calcd 305.4. found 306.2; Rt=1.401 min.

2-(cyclobutylamino)-6-(ethyl(methyl)amino)isonicotinic acid. To a solution of tert-butyl 2-(cyclobutylamino)-6-[ethyl(methyl)amino]pyridine-4-carboxylate (2 g, 5.89 mmol) in DCM (30 mL), hydrogen chloride solution, 4.0 M in dioxane (50 g, 5.89 mmol) was added. The resulting mixture was stirred at 25° C. for 72 hr and evaporated in vacuo to dryness. The residue was triturated with MTBE (100 ml) and the precipitate was filtered, washed with MTBE (30 ml) and dried to obtain 2-(cyclobutylamino)-6-[ethyl(methyl)amino]pyridine-4-carboxylic acid (1.5 g, 5.25 mmol, 89.06% yield, HCl). $^1H$ NMR (500 MHz, DMSO-$d_6$) δ (ppm) 1.09 (t, 3H), 1.76 (m, 2H), 1.90 (m, 2H), 2.34 (m, 2H), 3.12 (s, 3H), 3.64 (m, 2H), 4.06 (m, 1H), 6.09 (s, 1H), 6.35 (s, 1H), 9.30 (bds, 1H), 12.85 (bds, 1H). LCMS(ESI): [M+H]+ m/z: calcd 249.3. found 250.2; Rt=0.942 min.

2-(cyclobutylamino)-6-((2-methoxyethyl)(methyl)amino)isonicotinic Acid

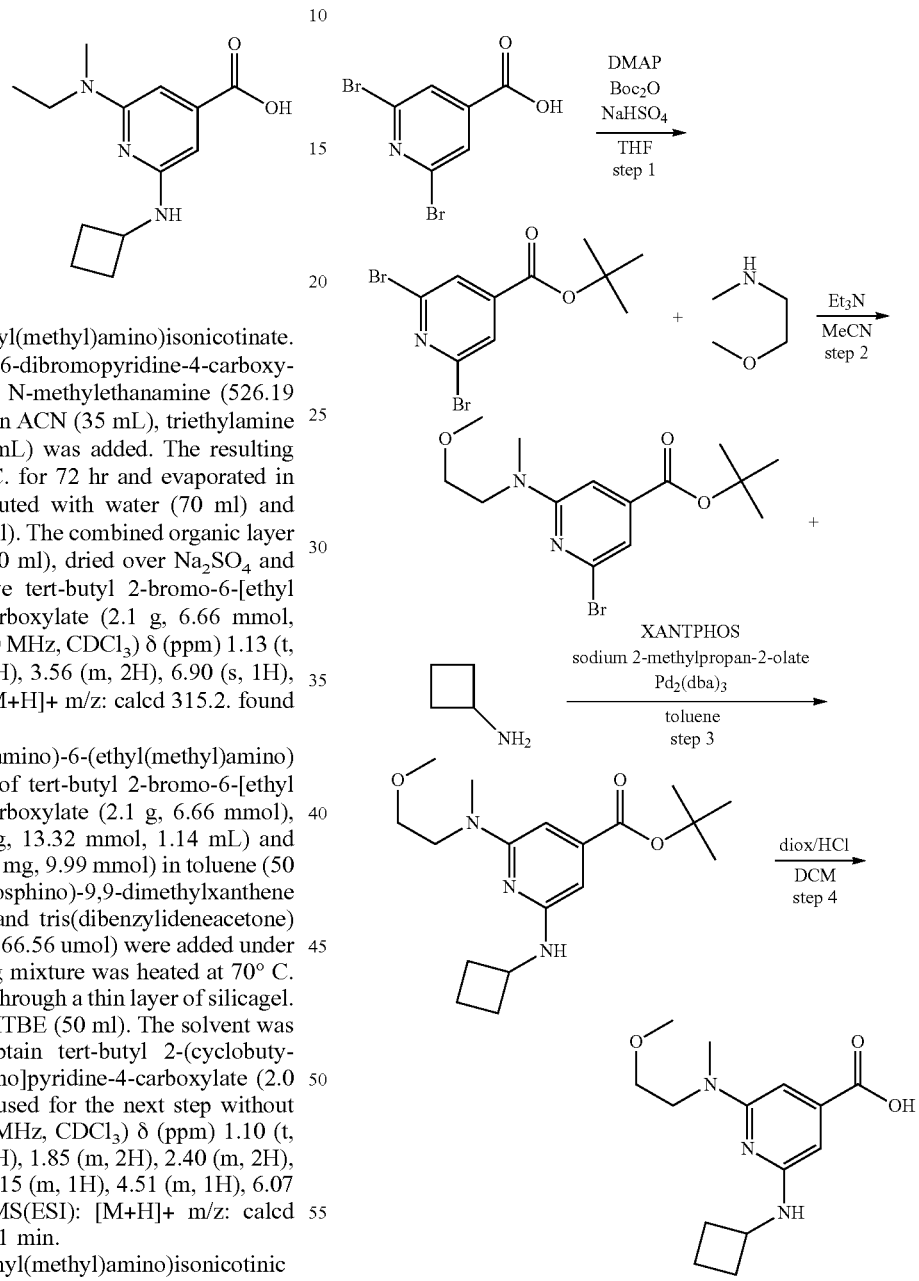

tert-butyl 2-bromo-6-((2-methoxyethyl)(methyl)amino)isonicotinate. tert-Butyl 2,6-dibromopyridine-4-carboxylate (2.4 g, 7.12 mmol), 2-methoxy-N-methylethanamine (825.22 mg, 9.26 mmol, 994.24 uL) and triethylamine (936.81 mg, 9.26 mmol, 1.29 mL) were mixed together in acetonitrile (30 mL). The flask was sealed and the reaction mixture was stirred at 80° C. for 72 hr (the reaction progress was monitored by HNMR of the aliquots, more amines can be added if necessary), then cooled and evaporated in vacuo. The residue was diluted with water (20 ml) and extracted with dichloromethane (2*30 ml). The combined organic extracts were dried over sodium sulphate and evaporated in vacuo to afford tert-butyl 2-bromo-6-[2-methoxyethyl (methyl)amino]pyridine-4-carboxylate (2.2 g, 6.37 mmol, 89.48% yield) as yellow gum. $^1$H NMR (500 MHz, CDCl$_3$) δ (ppm) 1.58 (s, 9H), 3.12 (s, 3H), 3.35 (s, 3H), 3.58 (t, 2H), 3.75 (t, 2H), 6.96 (s, 1H), 7.12 (s, 1H). LCMS(ESI): [M+H]+ m/z: calcd 345.2. found 347.0; Rt=1.586 min.

tert-butyl 2-(cyclobutylamino)-6-((2-methoxyethyl) (methyl)amino)isonicotinate. tert-Butyl 2-bromo-6-[2-methoxyethyl(methyl)amino]pyridine-4-carboxylate (1.5 g, 4.34 mmol) and sodium 2-methylpropan-2-olate (626.32 mg, 6.52 mmol) were mixed together in toluene (50 mL). The resulting mixture was evacuated and then backfilled with argon, this operation was repeated three times, then cyclobutanamine (618.03 mg, 8.69 mmol, 741.93 uL), [5-(diphenylphosphanyl)-9,9-dimethyl-9H-xanthen-4-yl]diphenylphosphane (125.70 mg, 217.25 umol) and tris(1,5-diphenylpenta-1,4-dien-3-one) dipalladium (99.47 mg, 108.62 umol) were added under argon. The reaction mixture was stirred under argon at 70° C. for 18 hr, then cooled, filtered and the filtrate was evaporated in vacuo to leave 1.9 g of the crude product (76.89% purity by LCMS, 15.02% of corresponding acid by LCMS (ester cleavage), and 90% by HNMR, approximately 1.4 g of the target compound), tert-butyl 2-(cyclobutylamino)-6-[2-methoxyethyl(methyl) amino]pyridine-4-carboxylate (1.4 g, 4.17 mmol, 96.06% yield) as red gum, which was directly used in the next step. $^1$H NMR (500 MHz, CDCl$_3$) δ (ppm) 1.61 (s, 9H), 1.76 (m, 2H), 1.88 (m, 2H), 2.41 (m, 2H), 3.06 (s, 3H), 3.36 (s, 3H), 3.57 (t, 2H), 3.72 (t, 2H), 4.19 (m, 1H), 6.12 (s, 1H), 6.34 (s, 1H), 7.19 (bds, 1H). LCMS(ESI): [M+H]+ m/z: calcd 335.4; found 336.2; Rt=1.327 min.

2-(cyclobutylamino)-6-((2-methoxyethyl)(methyl)amino) isonicotinic acid. Hydrogen chloride solution 4.0M in dioxane (44.57 g, 169.93 mmol, 42.45 mL, 13.9% purity) was added to a solution of tert-butyl 2-(cyclobutylamino)-6-[2-methoxyethyl(methyl)amino]pyridine-4-carboxylate (1.9 g, 5.66 mmol) (crude from previous step) in dichloromethane (30 mL). The reaction mixture was stirred at 25° C. for 72 hr, then evaporated to dryness in vacuo. The residue was reevaporated with MTBE (30 ml) and dried in vacuo to afford crude 2-(cyclobutylamino)-6-[2-methoxyethyl(methyl)amino]pyridine-4-carboxylic acid (1.58 g, 5.00 mmol, 88.33% yield, HCl as brown solid, which was used in the next step without further purification. $^1$H NMR (400 MHz, DMSO-d$_6$) δ (ppm) 1.82 (m, 2H), 1.98 (m, 2H), 2.28 (m, 2H), 3.06 (m, 2H), 3.22 (s, 3H), 3.42 (s, 3H), 3.89 (t, 2H), 4.02 (t, 2H), 4.19 (m, 1H), 6.13 (s, 1H), 6.34 (s, 1H). LCMS(ESI): [M+H]+ m/z: calcd 279.3. found 280.2; Rt=0.934 min.

2-(cyclobutylamino)-6-(4-methylpiperazin-1-yl) isonicotinic Acid

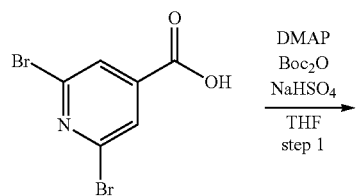

tert-butyl 2-bromo-6-(4-methylpiperazin-1-yl)isonicotinate. To a solution of tert-butyl 2,6-dibromopyridine-4-carboxylate (2.5 g, 7.42 mmol) and 1-methylpiperazine (817.33 mg, 8.16 mmol, 905.12 uL) in ACN (35 mL), triethylamine (1.13 g, 11.13 mmol, 1.55 mL) was added. The resulting mixture was stirred at 80° C. for 72 hr and evaporated in vacuo. The residue was diluted with water (70 ml) and extracted with DCM (3*50 ml). The combined organic layer was washed with brine (2*50 ml), dried over Na$_2$SO$_4$ and evaporated in vacuo to give tert-butyl 2-bromo-6-(4-methylpiperazin-1-yl)pyridine-4-carboxylate (2.55 g, 7.16 mmol, 96.49% yield). $^1$H NMR (500 MHz, CDCl$_3$) δ (ppm) 1.58 (s, 9H), 2.35 (s, 3H), 2.50 (t, 4H), 3.62 (t, 4H), 7.07 (s, 1H), 7.18 (s, 1H). LCMS(ESI): [M+H]+ m/z: calcd 356.2. found 357.2; Rt=1.188 min.

tert-butyl 2-(cyclobutylamino)-6-(4-methylpiperazin-1-yl)isonicotinate. To a solution of tert-butyl 2-bromo-6-(4-methylpiperazin-1-yl)pyridine-4-carboxylate (2.55 g, 7.16 mmol), cyclobutanamine (1.02 g, 14.32 mmol, 1.22 mL) and sodium tert-butoxide (1.03 g, 10.74 mmol) in toluene (50 mL), 4,5-bis(diphenylphosphino)-9,9-dimethylxanthene (207.08 mg, 357.89 umol) and tris(dibenzylideneacetone) dipalladium(0) (163.86 mg, 178.94 umol) were added under Ar atmosphere. The resulting mixture was heated at 70° C.

for 18 hr, cooled and filtered through a thin layer of silicagel. Silicagel was washed with MTBE (50 ml). The solvent was evaporated in vacuo to obtain tert-butyl 2-(cyclobutylamino)-6-(4-methylpiperazin-1-yl)pyridine-4-carboxylate (3.0 g, crude). The product was used for the next step without purification. $^1$H NMR (500 MHz, CDCl$_3$) δ (ppm) 1.57 (s, 9H), 1.78 (m, 2H), 1.87 (m, 2H), 2.35 (s, 3H), 2.41 (m, 2H), 2.52 (t, 4H), 3.55 (t, 4H), 4.15 (m, 1H), 4.60 (m, 1H), 6.20 (s, 1H), 6.46 (s, 1H). LCMS(ESI): [M+H]+ m/z: calcd 346.5. found 347.2; Rt=1.194 min.

2-(cyclobutylamino)-6-(4-methylpiperazin-1-yl)isonicotinic acid. To a solution of tert-butyl 2-(cyclobutylamino)-6-(4-methylpiperazin-1-yl)pyridine-4-carboxylate (3 g, 7.79 mmol) in DCM (30 mL), hydrogen chloride solution, 4.0 M in dioxane (50 g, 7.79 mmol) was added. The resulting mixture was stirred at 25° C. for 72 hr. The formed precipitate was filtered, washed with DCM (50 ml) and MTBE (30 ml) to give 2-(cyclobutylamino)-6-(4-methylpiperazin-1-yl)pyridine-4-carboxylic acid (1.9 g, 5.23 mmol, 67.11% yield, 2HCl). The product was obtained as a mixture of salt forms. $^1$H NMR (400 MHz, DMSO-d$_6$) δ (ppm) 1.68 (m, 2H), 1.86 (m, 2H), 2.25 (m, 2H), 2.75 (s, 3H), 3.09 (m, 2H), 3.26 (m, 2H), 3.76 (m, 2H), 4.20 (m, 2H), 4.31 (m, 2H), 6.24 (s, 1H), 6.38 (s, 1H), 11.41 (bds, 1H). LCMS(ESI): [M+H]+m/z: calcd 290.4. found 291.2; Rt=0.851 min.

2-(4-acetylpiperazin-1-yl)-6-(cyclobutylamino)isonicotinic Acid

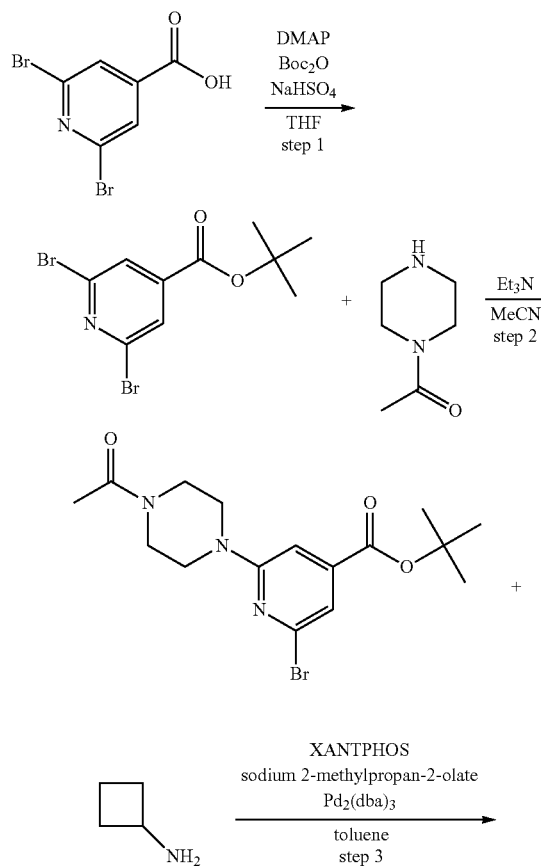

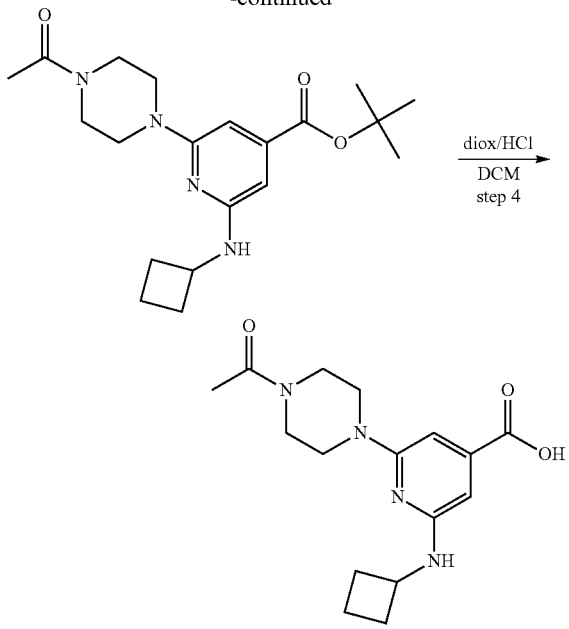

tert-butyl 2-(4-acetylpiperazin-1-yl)-6-bromoisonicotinate. 1-Piperazin-1-ylethanone (2.51 g, 12.46 mmol, 2.16 mL, 2HCl) was added to a stirred mixture of tert-butyl 2,6-dibromopyridine-4-carboxylate (3 g, 8.90 mmol) and potassium carbonate, anhydrous, 99% (6.15 g, 44.51 mmol, 2.69 mL) in acetonitrile (50 mL). The resulting mixture was stirred at 80° C. for 96 hr (the reaction progress was monitored by H-NMR of the aliquots), then cooled and filtered. The filtercake was washed with acetonitrile (2*20 ml) and discarded. The filtrate was evaporated in vacuo, the residue was dissolved in dichloromethane, dried over sodium sulphate and filtered through a pad of silicagel (50 g). The silica gel pad was additionally washed with THF (4*50 ml). The combined CH$_2$Cl$_2$-THF filtrate was evaporated in vacuo to afford tert-butyl 2-(4-acetylpiperazin-1-yl)-6-bromo-pyridine-4-carboxylate (2.6 g, 6.77 mmol, 76.01% yield) as light-yellow solid. $^1$H NMR (500 MHz, CDCl$_3$) δ (ppm) 1.59 (s, 9H), 2.15 (s, 3H), 3.58 (t, 4H), 3.69 (t, 2H), 3.74 (t, 2H), 7.08 (s, 1H), 7.24 (s, 1H). LCMS(ESI): [M+H]+ m/z: calcd 384.3; found 386.2; Rt=1.449 min.

tert-butyl 2-(4-acetylpiperazin-1-yl)-6-(cyclobutylamino)isonicotinate. tert-Butyl 2-(4-acetylpiperazin-1-yl)-6-bromo-pyridine-4-carboxylate (2.60 g, 6.78 mmol) and sodium 2-methylpropan-2-olate (977.18 mg, 10.17 mmol) were mixed together in toluene (50 mL). The resulting mixture was evacuated and then backfilled with argon, this operation was repeated three times, then cyclobutanamine (964.24 mg, 13.56 mmol, 1.16 mL), [5-(diphenylphosphanyl)-9,9-dimethyl-9H-xanthen-4-yl]diphenylphosphane (196.12 mg, 338.95 umol) and tris(1,5-diphenylpenta-1,4-dien-3-one) dipalladium (155.19 mg, 169.47 umol) were added under argon. The reaction mixture was stirred under argon at 70° C. for 18 hr, then cooled, filtered and the filtrate was evaporated in vacuo to leave the crude product tert-butyl 2-(4-acetylpiperazin-1-yl)-6-(cyclobutylamino)pyridine-4-carboxylate (2.3 g, 6.14 mmol, 90.60% yield) as red solid, which was directly used in the next step. $^1$H NMR (500 MHz, CDCl$_3$) δ (ppm) 1.56 (s, 9H), 1.78 (m, 2H), 1.87 (m, 2H), 2.13 (s, 3H), 2.41 (m, 2H), 3.48 (t, 2H), 3.56 (t, 4H), 3.71 (t, 2H), 4.16 (m, 1H), 6.23 (s, 1H), 6.44 (s, 1H), 7.12 (bds, 1H). LCMS(ESI): [M+H]+ m/z: calcd 374.5. found 375.2; Rt=1.374 min.

2-(4-acetylpiperazin-1-yl)-6-(cyclobutylamino)isonicotinic acid, tert-Butyl 2-(4-acetylpiperazin-1-yl)-6-(cyclobutylamino)pyridine-4-carboxylate (2.3 g, 6.14 mmol) was dissolved in trifluoroacetic acid (21.01 g, 184.26 mmol, 14.20 mL). The resulting mixture was stirred at 25° C. for 1 hr, then evaporated in vacuo and the residue was tritutated with MTBE (40 ml). The precipitate was filtered, washed with MTBE(2*10 ml) and dried in vacuo to afford 2-(4-acetylpiperazin-1-yl)-6-(cyclobutylamino)pyridine-4-carboxylic acid (1 g, 2.31 mmol, 37.65% yield, $CF_3COOH$) as light-brown solid, which was used in the next step without further purification. $^1H$ NMR (400 MHz, DMSO-$d_6$) δ (ppm) 1.52 (m, 2H), 1.81 (m, 2H), 1.92 (m, 2H), 2.03 (s, 3H), 2.25 (m, 2H), 3.05 (m, 1H), 3.41 (m, 7H), 4.22 (m, 1H), 6.24 (s, 1H), 6.29 (s, 1H). LCMS(ESI): [M+H]+ m/z: calcd 318.4. found 319.2; Rt=0.979 min.

2-(cyclobutylamino)-6-(2-(dimethylamino)ethoxy)isonicotinic Acid

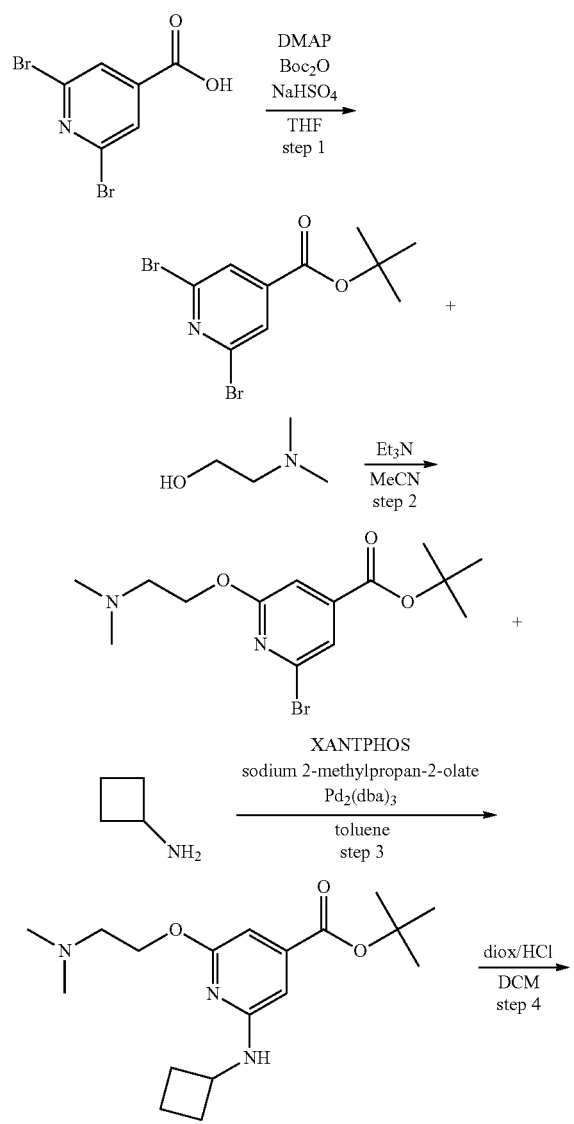

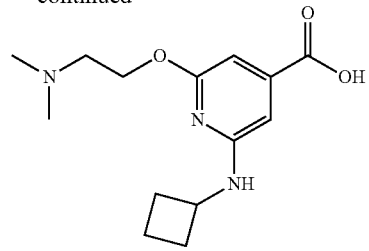

tert-butyl 2-bromo-6-(2-(dimethylamino)ethoxy)isonicotinate. Triethylamine (1.20 g, 11.87 mmol, 1.65 mL) was added at 25° C. to a stirred mixture of tert-butyl 2,6-dibromopyridine-4-carboxylate (2 g, 5.93 mmol) and 2-(dimethylamino)-ethanol (7.93 g, 89.02 mmol, 8.96 mL). The flask was sealed and the reaction mixture was stirred at 70° C. for 12 hr, then cooled and poured into ice cold water (50 ml). The precipitate was filtered, washed with water (2*10 ml) and then dissolved in dichloromethane (50 ml). The resulting solution was dried over sodium sulphate and evaporated in vacuo to afford tert-butyl 2-bromo-6-[2-(dimethylamino)ethoxy]pyridine-4-carboxylate (1.9 g, 5.50 mmol, 92.74% yield) as white solid. NMR (500 MHz, $CDCl_3$) δ (ppm) 1.58 (s, 9H), 2.33 (s, 6H), 2.71 (t, 2H), 4.43 (t, 2H), 7.27 (s, 1H), 7.53 (s, 1H). LCMS(ESI): [M+H]+ m/z: calcd 345.2. found 346.2; Rt=1.130 min.

tert-butyl 2-(cyclobutylamino)-6-(2-(dimethylamino)ethoxy)isonicotinate. tert-Butyl 2-bromo-6-[2-(dimethylamino)ethoxy]pyridine-4-carboxylate (1.9 g, 5.50 mmol) and sodium 2-methylpropan-2-olate (793.34 mg, 8.26 mmol) were mixed together in toluene (50 mL). The resulting mixture was evacuated and then backfilled with argon, this operation was repeated three times, then cyclobutanamine (1.17 g, 16.51 mmol, 1.41 mL), [5-(diphenylphosphanyl)-9,9-dimethyl-9H-xanthen-4-yl]diphenylphosphane (159.22 mg, 275.18 umol) and tris(1,5-diphenylpenta-1,4-dien-3-one) dipalladium (125.99 mg, 137.59 umol) were added under argon. The reaction mixture was stirred under argon at 70° C. for 12 hr, then cooled and evaporated in vacuo to leave 3 g of the residue (52.07% purity by LCMS), which was purified by column chromatography on silica gel using MTBE/methanol gradient (0-100% methanol) tert-butyl 2-(cyclobutylamino)-6-[2-(dimethylamino)ethoxy]pyridine-4-carboxylate (0.7 g, 2.09 mmol, 37.92% yield) as yellow oil. $^1H$ NMR (500 MHz, $CDCl_3$) δ (ppm) 1.56 (s, 9H), 1.82 (m, 4H), 2.33 (s, 6H), 2.45 (m, 2H), 2.68 (t, 2H), 4.18 (m, 1H), 4.34 (t, 2H), 4.68 (m, 1H), 6.38 (s, 1H), 6.56 (s, 1H). LCMS(ESI): [M+H]+ m/z: calcd 335.4. found 336.2; Rt=1.208 min.

2-(cyclobutylamino)-6-(2-(dimethylamino)ethoxy)isonicotinic acid. Hydrogen chloride solution 4.0M in dioxane (21.74 g, 83.47 mmol, 20.70 mL, 14% purity) was added to a stirred solution of tert-butyl 2-(cyclobutylamino)-6-[2-(dimethylamino)ethoxy]pyridine-4-carboxylate (0.7 g, 2.09 mmol) in dichloromethane (20 mL). The resulting clear solution was stirred at 25° C. for 72 hr (the reaction progress was monitored by H-NMR of the aliquots, which showed 60% conversion after 24 hr, and 85% conversion after 48 hr). The precipitate was filtered, washed with MTBE (2*5 ml) and dried in vacuo to afford 2-(cyclobutylamino)-6-[2-(dimethylamino)ethoxy]pyridine-4-carboxylic acid (330 mg, 936.82 umol, 44.89% yield, 2HCl) as white solid. $^1H$ NMR (400 MHz, DMSO-$d_6$) δ (ppm) 1.68 (m, 2H), 1.89 (m, 2H), 2.31 (m, 2H), 2.81 (s, 6H), 3.46 (m, 2H), 3.56 (m, 2H), 4.24

(m, 1H), 4.57 (m, 2H), 6.29 (s, 1H), 6.52 (s, 1H). LCMS (ESI): [M+H]+ m/z: calcd 279.3. found 280.2; Rt=0.870 min.

2-(cyclobutylamino)-6-(oxetan-3-ylamino)isonicotinic Acid

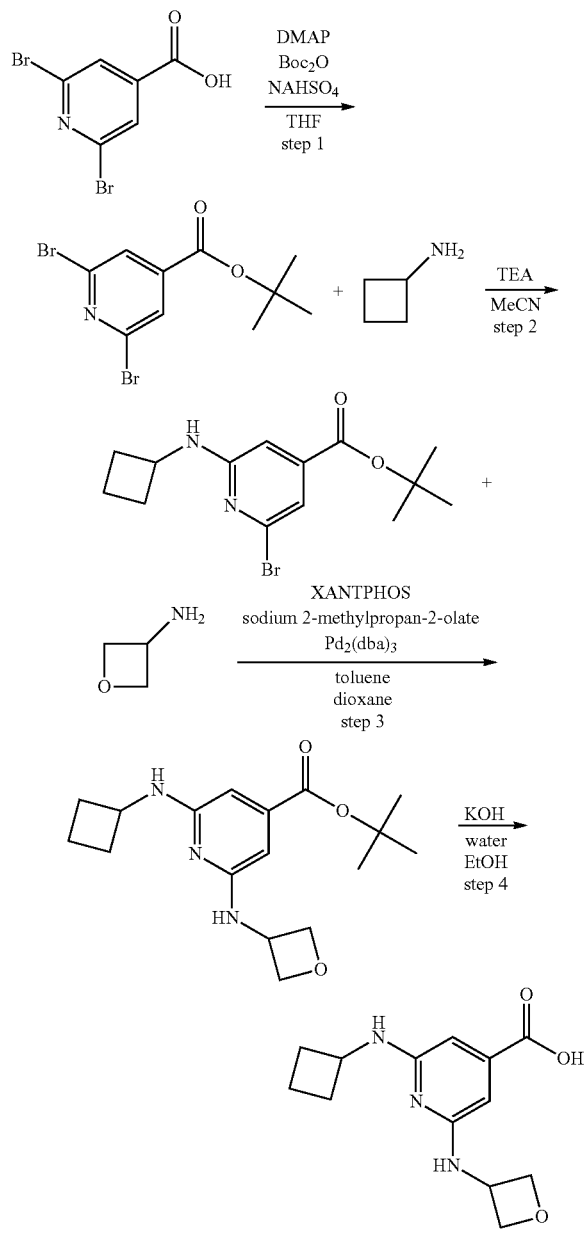

tert-butyl 2-bromo-6-(cyclobutylamino)isonicotinate. tert-Butyl 2,6-dibromopyridine-4-carboxylate (4 g, 11.87 mmol), cyclobutanamine (8.44 g, 118.69 mmol, 10.13 mL) and triethyl amine (2.40 g, 23.74 mmol, 3.31 mL) were mixed together in acetonitrile (60 mL). The reaction mixture was stirred with reflux condenser at 80° C. for 72 hr (the reaction progress was monitored by H-NMR of the aliquots, more amines can be added if necessary), then cooled and evaporated in vacuo. The residue was diluted with water (40 ml) and extracted with dichloromethane (2*40 ml). The combined organic extracts were dried over sodium sulphate and evaporated in vacuo to afford tert-butyl 2-bromo-6-(cyclobutylamino)pyridine-4-carboxylate (3.7 g, 11.31 mmol, 95.27% yield) as yellow gum. $^1$H NMR (400 MHz, CDCl$_3$) δ (ppm) 1.58 (s, 9H), 1.88 (m, 4H), 2.45 (m, 2H), 4.13 (m, 1H), 5.02 (m, 1H), 6.75 (s, 1H), 7.16 (s, 1H). LCMS(ESI): [M+H]+ m/z: calcd 327.2. found 329.2; Rt=1.731 min.

tert-butyl 2-(cyclobutylamino)-6-(oxetan-3-ylamino) isonicotinate. tert-Butyl 2-bromo-6-(cyclobutylamino)pyridine-4-carboxylate (1 g, 3.06 mmol) and sodium 2-methylpropan-2-olate (440.53 mg, 4.58 mmol) were mixed together in a mixture of toluene (50 mL) and dioxane (10 mL). The resulting mixture was evacuated and then back-filled with argon, this operation was repeated three times, then oxetan-3-amine (1.34 g, 18.34 mmol), [5-(diphenylphosphanyl)-9,9-dimethyl-9H-xanthen-4-yl]diphenylphosphane (88.42 mg, 152.80 umol) and tris(1,5-diphenylpenta-1,4-dien-3-one) dipalladium (69.96 mg, 76.40 umol) were added under argon. The reaction mixture was stirred under argon at 70° C. for 18 hr, then cooled, filtered and the filtrate was evaporated in vacuo to leave 1.4 g of the residue (48.5% purity by LCMS), which was purified by column chromatography on silica gel using hexane/MTBE gradient (5-100% MTBE) to afford tert-butyl 2-(cyclobutylamino)-6-(oxetan-3-ylamino)pyridine-4-carboxylate (200 mg, 626.18 umol, 20.49% yield) as white solid. $^1$H NMR (400 MHz, CDCl$_3$) δ (ppm) 1.57 (s, 9H), 1.86 (m, 4H), 2.42 (m, 2H), 4.13 (m, 1H), 4.53 (m, 2H), 4.55 (m, 1H), 4.76 (m, 1H), 4.98 (m, 3H), 6.15 (s, 1H), 6.19 (s, 1H). LCMS(ESI): [M+H]+ m/z: calcd 319.4. found 320.2; Rt=1.288 min.

2-(cyclobutylamino)-6-(oxetan-3-ylamino)isonicotinic acid, tert-Butyl 2-(cyclobutylamino)-6-(oxetan-3-ylamino) pyridine-4-carboxylate (270 mg, 845.34 umol) was added to a solution of potassium hydroxide (189.71 mg, 3.38 mmol, 93.00 uL) in a mixture of water (1 mL) and ethanol (4 mL). The resulting mixture was stirred at 50° C. for 48 hr, then cooled and evaporated in vacuo. The residue was dissolved in water (5 ml), and the pH was adjusted to 7 with 5% aqueous sodium hydrogen sulphate solution. The resulting clear solution was evaporated to dryness in vacuo, the residue was diluted with hot isopropanol (50° C. 1-20 ml) and stirred for 0.1 hr. The inorganic salts was filtered and discarded, the filtrate was evaporated in vacuo. The residue was triturated with MTBE (10 ml), the precipitate was isolated by filtration and dried in vacuo to afford 2-(cyclobutylamino)-6-(oxetan-3-ylamino)pyridine-4-carboxylic acid (100 mg, 379.81 umol, 44.93% yield) as light-brown solid, which was used in the next step without further purification. $^1$H NMR (400 MHz, DMSO-d$_6$) δ (ppm) 1.82 (m, 4H), 2.02 (m, 2H), 2.15 (m, 2H), 4.03 (m, 1H), 4.17 (m, 3H), 6.17 (s, 1H), 6.27 (s, 1H). LCMS(ESI): [M+H]+m/z: calcd 263.3. found 264.2; Rt=0.739 min.

2-((1-acetylpiperidin-4-yl)amino)-6-(4-methylpiperazin-1-yl)isonicotinic Acid

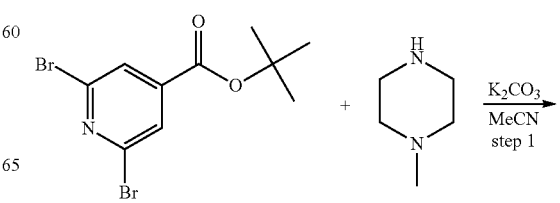

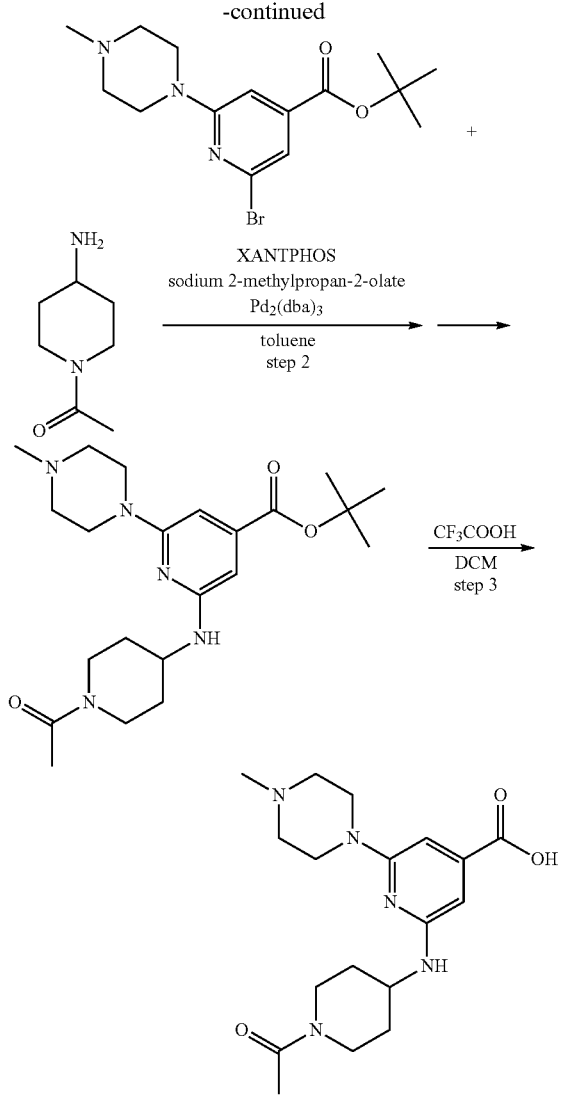

argon, this operation was repeated three times, then [5-(diphenylphosphanyl)-9,9-dimethyl-9H-xanthen-4-yl]diphenylphosphane (194.90 mg, 336.84 umol) and tris(1,5-diphenylpenta-1,4-dien-3-one) dipalladium (154.22 mg, 168.42 umol) were added under argon. The reaction mixture was stirred under argon at 75° C. for 18 hr, then cooled and evaporated in vacuo. The residue was purified by column chromatography on silica gel using MTBE/methanol gradient (5-100% methanol) to afford tert-butyl 2-(4-methylpiperazin-1-yl)-6-[(1-methyl-4-piperidyl)amino]pyridine-4-carboxylate (1.8 g, 4.31 mmol, 63.99% yield) as light-yellow solid. $^1$H NMR (400 MHz, CDCl$_3$) δ (ppm) 1.38 (m, 2H), 1.58 (s, 9H), 2.12 (m, 2H), 2.28 (s, 3H), 2.49 (t, 4H), 2.88 (m, 1H), 3.22 (m, 1H), 3.48 (s, 3H), 3.56 (t, 4H), 3.88 (m, 2H), 4.30 (m, 1H), 4.49 (m, 1H), 6.27 (s, 1H), 6.46 (s, 1H). LCMS(ESI): [M+H]+ m/z: calcd 417.5. found 418.2; Rt=1.081 min.

2-((1-acetylpiperidin-4-yl)amino)-6-(4-methylpiperazin-1-yl)isonicotinic acid, tert-Butyl 2-[(1-acetyl-4-piperidyl)amino]-6-(4-methylpiperazin-1-yl)pyridine-4-carboxylate (1.8 g, 4.31 mmol) was dissolved in trifluoroacetic acid (24.58 g, 215.55 mmol, 16.61 mL). The reaction mixture was stirred at 25° C. for 1 hr, and then evaporated in vacuo. The residue was triturated with MTBE (50 ml), stirred for 0.1 hr and the precipitate was filtered, washed with MTBE (2*10 ml) and dried in vacuo to afford 2-[(1-acetyl-4-piperidyl)amino]-6-(4-methylpiperazin-1-yl)pyridine-4-carboxylic acid (2.54 g, 4.31 mmol, 100.00% yield, 2CF$_3$COOH) as yellow solid, which was used directly in the next step. $^1$H NMR (400 MHz, DMSO-d$_6$) δ (ppm) 1.20 (m, 1H), 1.34 (m, 1H), 1.88 (m, 2H), 1.99 (s, 3H), 2.82 (t, 4H), 3.05 (s, 3H), 3.18 (m, 3H), 3.44 (m, 2H), 3.72 (m, 1H), 3.84 (m, 1H), 4.17 (m, 1H), 4.33 (m, 2H), 6.37 (s, 1H), 6.41 (s, 1H), 10.12 (bds, 1H). LCMS(ESI): [M+H]+ m/z: calcd 361.4. found 362.2; Rt=0.762 min.

2-(4-acetylpiperazin-1-yl)-6-((1-acetylpiperidin-4-yl)amino)isonicotinic Acid

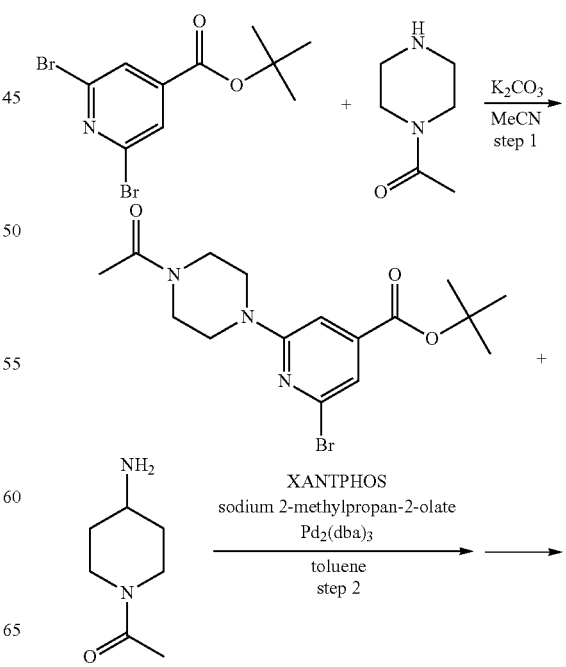

tert-butyl 2-bromo-6-(4-methylpiperazin-1-yl)isonicotinate. 1-Methylpiperazine (1.25 g, 12.46 mmol, 1.38 mL) was added to a stirred mixture of tert-butyl 2,6-dibromopyridine-4-carboxylate (3 g, 8.90 mmol) and potassium carbonate, anhydrous, 99% (2.46 g, 17.80 mmol, 1.07 mL) in acetonitrile (50 mL). The resulting mixture was stirred at 80° C. for 72 hr (the reaction progress was monitored by H-NMR of the aliquots), then cooled and filtered. The filtercake was washed with acetonitrile (2*20 ml) and discarded. The filtrate was concentrated to 25 ml in vacuo, the precipitate was filtered, washed with acetonitrile (2*5 ml) an dried in vacuo to afford tert-butyl 2-bromo-6-(4-methylpiperazin-1-yl)pyridine-4-carboxylate (2.4 g, 6.74 mmol, 75.68% yield) as yellow solid. $^1$H NMR (500 MHz, CDCl$_3$) δ (ppm) 1.58 (s, 9H), 2.37 (s, 3H), 2.52 (t, 4H), 3.63 (t, 4H), 7.08 (s, 1H), 7.19 (s, 1H). LCMS(ESI): [M+H]+ m/z: calcd 356.3. found 357.2; Rt=1.152 min.

tert-butyl 2-((1-acetylpiperidin-4-yl)amino)-6-(4-methylpiperazin-1-yl)isonicotinate. tert-Butyl 2-bromo-6-(4-methylpiperazin-1-yl)pyridine-4-carboxylate (2.4 g, 6.74 mmol), 1-(4-amino-1-piperidyl)ethanone (1.15 g, 8.08 mmol) and sodium 2-methylpropan-2-olate (971.10 mg, 10.11 mmol) were mixed together in toluene (50 mL). The resulting mixture was evacuated and then backfilled with

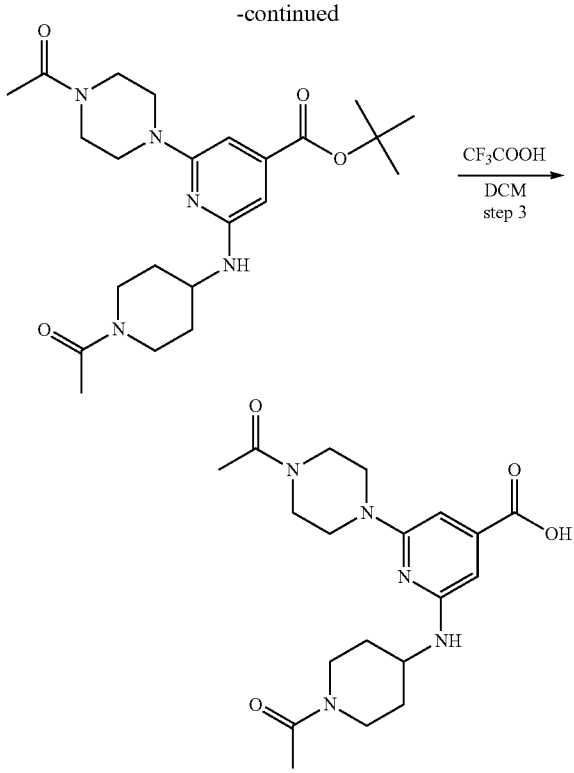

3.14 mmol, 49.28% yield) as light-yellow gum, which was used directly in the next step. $^1$H NMR (500 MHz, CDCl$_3$) δ (ppm) 1.38 (m, 2H), 1.54 (s, 9H), 2.02 (m, 1H), 2.12 (m, 7H), 2.85 (m, 1H), 3.18 (m, 1H), 3.58 (m, 6H), 3.72 (m, 2H), 3.88 (m, 2H), 4.35 (m, 1H), 4.50 (m, 1H), 6. (s, 1H), 6.46 (s, 1H). LCMS(ESI): [M+H]+ m/z: calcd 445.5. found 446.2; Rt=1.321 min.

2-(4-acetylpiperazin-1-yl)-6-((1-acetylpiperidin-4-yl) amino)isonicotinic acid, tert-Butyl 2-(4-acetylpiperazin-1-yl)-6-[(1-acetyl-4-piperidyl)amino]pyridine-4-carboxylate (1.4 g, 3.14 mmol) was dissolved in trifluoroacetic acid (17.91 g, 157.11 mmol, 12.10 mF). The reaction mixture was stirred at 25° C. for 1 hr, and then evaporated in vacuo. The residue was triturated with hexane/MTBE mixture (1/1, 60 ml), stirred for 0.1 hr and the precipitate was filtered, washed with hexane (2*10 ml) and dried in vacuo to afford 2-(4-acetylpiperazin-1-yl)-6-[(1-acetyl-4-piperidyl)amino] pyridine-4-carboxylic acid (1.2 g, 2.38 mmol, 75.85% yield, CF$_3$COOH) as yellow solid, which was used directly in the next step. $^1$H NMR (400 MHz, DMSO-d$_6$) δ (ppm) 1.22 (m, 1H), 1.34 (m, 1H), 1.85 (m, 2H), 2.01 (s, 3H), 2.05 (s, 3H), 2.79 (m, 1H), 3.06 (m, 1H), 3.28 (m, 1H), 3.38 (m, 2H), 3.50 (m, 6H), 3.81 (m, 1H), 3.85 (m, 1H), 4.19 (m, 1H), 6.30 (s, 1H), 6.34 (s, 1H), 7.12 (bds, 1H). LCMS(ESI): [M+H]+ m/z: calcd 389.5; found 390.2; Rt=0.857 min.

2-((1-acetylpiperidin-4-yl)amino)-6-((2-methoxyethyl)(methyl)amino)isonicotinic Acid

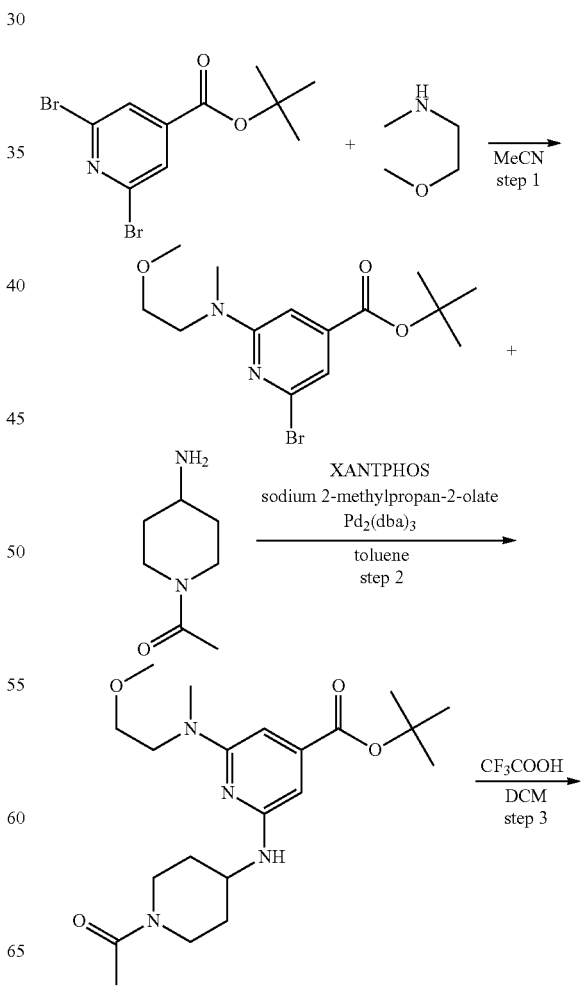

tert-butyl 2-(4-acetylpiperazin-1-yl)-6-bromoisonicotinate. 1-Piperazin-1-ylethanone (2.51 g, 12.46 mmol, 2.16 mL, 2HCl) was added to a stirred mixture of tert-butyl 2,6-dibromopyridine-4-carboxylate (3 g, 8.90 mmol) and potassium carbonate, anhydrous, 99% (6.15 g, 44.51 mmol, 2.69 mL) in acetonitrile (50 mL). The resulting mixture was stirred at 80° C. for 96 hr (the reaction progress was monitored by H-NMR of the aliquots), then cooled and filtered. The filtercake was washed with acetonitrile (2*20 ml) and discarded. The filtrate was evaporated in vacuo, and the residue was purified by column chromatography on silica gel using hexane/ethyl acetate gradient (5-100% ethyl acetate) to afford tert-butyl 2-(4-acetylpiperazin-1-yl)-6-bromo-pyridine-4-carboxylate (2.45 g, 6.38 mmol, 71.62% yield) as white solid. $^1$H NMR (500 MHz, CDCl$_3$) δ (ppm) 1.59 (s, 9H), 2.16 (s, 3H), 3.58 (t, 4H), 3.70 (t, 2H), 3.75 (t, 2H), 7.09 (s, 1H), 7.24 (s, 1H). LCMS(ESI): [M+H]+ m/z: calcd 384.3. found 385.0; Rt=1.584 min.

tert-butyl 2-(4-acetylpiperazin-1-yl)-6-((1-acetylpiperidin-4-yl)amino)isonicotinate. tert-Butyl 2-(4-acetylpiperazin-1-yl)-6-bromo-pyridine-4-carboxylate (2.45 g, 6.38 mmol), 1-(4-amino-1-piperidyl)ethanone (951.95 mg, 6.69 mmol) and sodium 2-methylpropan-2-olate (919.07 mg, 9.56 mmol) were mixed together in toluene (50 mL). The resulting mixture was evacuated and then backfilled with argon, this operation was repeated three times, then [5-(diphenylphosphanyl)-9,9-dimethyl-9H-xanthen-4-yl]diphenylphosphane (184.46 mg, 318.79 umol) and tris(1,5-diphenylpenta-1,4-dien-3-one) dipalladium (145.96 mg, 159.39 umol) were added under argon. The reaction mixture was stirred under argon at 75° C. for 4 hr, then cooled and filtered through a pad of silica gel (40 g). The toluene filtrate was discarded and the silica gel pad was additionally washed with THF (2*50 ml). The THF filtrate was evaporated in vacuo to afford tert-butyl 2-(4-acetylpiperazin-1-yl)-6-[(1-acetyl-4-piperidyl)amino]pyridine-4-carboxylate (1.4 g, -continued

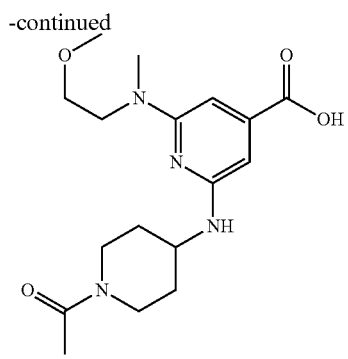

tert-butyl 2-bromo-6-((2-methoxyethyl)(methyl)amino) isonicotinate. tert-Butyl 2,6-dibromopyridine-4-carboxylate (2 g, 5.93 mmol) and 2-methoxy-N-methylethanamine (2.64 g, 29.67 mmol, 3.19 mL) were mixed together in acetonitrile (30 mL). The flask was sealed and the reaction mixture was stirred at 80° C. for 72 hr (the reaction progress was monitored by H-NMR of the aliquots, more amines can be added if necessary), then cooled and evaporated in vacuo. The residue was diluted with water (20 ml) and extracted with dichloromethane (2*30 ml). The combined organic extracts were dried over sodium sulphate and evaporated in vacuo to afford tert-butyl 2-bromo-6-[2-methoxyethyl (methyl)amino]pyridine-4-carboxylate (2.05 g, 5.94 mmol, 100.00% yield) as yellow solid. $^1$H NMR (500 MHz, CDCl$_3$) δ (ppm) 1.57 (s, 9H), 3.11 (s, 3H), 3.34 (s, 3H), 3.57 (t, 2H), 3.74 (t, 2H), 6.95 (s, 1H), 7.11 (s, 1H). LCMS(ESI): [M+H]+m/z: calcd 345.2. found 346.2; Rt=1.662 min.

tert-butyl 2-((1-acetylpiperidin-4-yl)amino)-6-((2-methoxyethyl)(methyl)amino)isonicotinate. tert-Butyl 2-bromo-6-[2-methoxyethyl(methyl)amino]pyridine-4-carboxylate (2.05 g, 5.94 mmol), 1-(4-amino-1-piperidyl)ethanone (1.01 g, 7.13 mmol) and sodium 2-methylpropan-2-olate (855.97 mg, 8.91 mmol) were mixed together in toluene (40 mL). The resulting mixture was evacuated and then backfilled with argon, this operation was repeated three times, then [5-(diphenylphosphanyl)-9,9-dimethyl-9H-xanthen-4-yl]diphenylphosphane (171.79 mg, 296.90 umol) and tris(1,5-diphenylpenta-1,4-dien-3-one) dipalladium (135.94 mg, 148.45 umol) were added under argon. The reaction mixture was stirred under argon at 75° C. for 18 hr, then cooled and evaporated in vacuo. The residue was purified by column chromatography on silica gel using hexane-ethyl acetate gradient (5-100% ethyl acetate) to afford tert-butyl 2-[(1-acetyl-4-piperidyl)amino]-6-[2-methoxyethyl(methyl) amino]pyridine-4-carboxylate (1 g, 2.46 mmol, 41.43% yield) as grey solid. $^1$H NMR (500 MHz, CDCl$_3$) δ (ppm) 1.38 (m, 2H), 1.54 (s, 9H), 2.05 (m, 1H), 2.12 (m, 4H), 2.82 (t, 1H), 3.08 (s, 3H), 3.21 (t, 1H), 3.36 (s, 3H), 3.56 (t, 2H), 3.71 (t, 2H), 3.79 (m, 1H), 3.88 (m, 1H), 4.22 (m, 1H), 4.50 (m, 1H), 6.19 (s, 1H), 6.34 (s, 1H). LCMS(ESI): [M+H]+ m/z: calcd 406.5. found 407.2; Rt=1.327 min.

2-((1-acetylpiperidin-4-yl)amino)-6-((2-methoxyethyl) (methyl)amino)isonicotinic acid, tert-Butyl 2-[(1-acetyl-4-piperidyl)amino]-6-[2-methoxyethyl(methyl)amino]pyridine-4-carboxylate (1 g, 2.46 mmol) was dissolved in trifluoroacetic acid (14.02 g, 123.00 mmol, 9.48 mL). The reaction mixture was stirred at 25° C. for 1 hr, and then evaporated in vacuo. The residue was triturated with hexane/MTBE mixture (2/1, 70 ml), stirred for 1 hr and the precipitate was filtered, washed with hexane (2*10 ml) and dried in vacuo to afford 2-[(1-acetyl-4-piperidyl)amino]-6-[2-methoxyethyl(methyl)amino]pyridine-4-carboxylic acid (0.92 g, 1.98 mmol, 80.53% yield, CF$_3$COOH) as yellow solid, which was used directly in the next step. $^1$H NMR (400 MHz, DMSO-d$_6$) δ (ppm) 1.22 (m, 1H), 1.34 (m, 1H), 1.85 (m, 2H), 2.01 (s, 3H), 2.88 (m, 1H), 3.07 (m, 3H), 3.14 (m, 1H), 3.18 (s, 3H), 3.48 (m, 2H), 3.64 (m, 2H), 3.82 (m, 2H), 4.20 (m, 1H), 6.18 (s, 1H), 6.27 (s, 1H), 7.18 (bds, 2H). LCMS(ESI): [M+H]+ m/z: calcd 350.4. found 351.2; Rt=0.876 min.

2-((1-acetylpiperidin-4-yl)amino)-6-(piperidin-1-yl) isonicotinic Acid

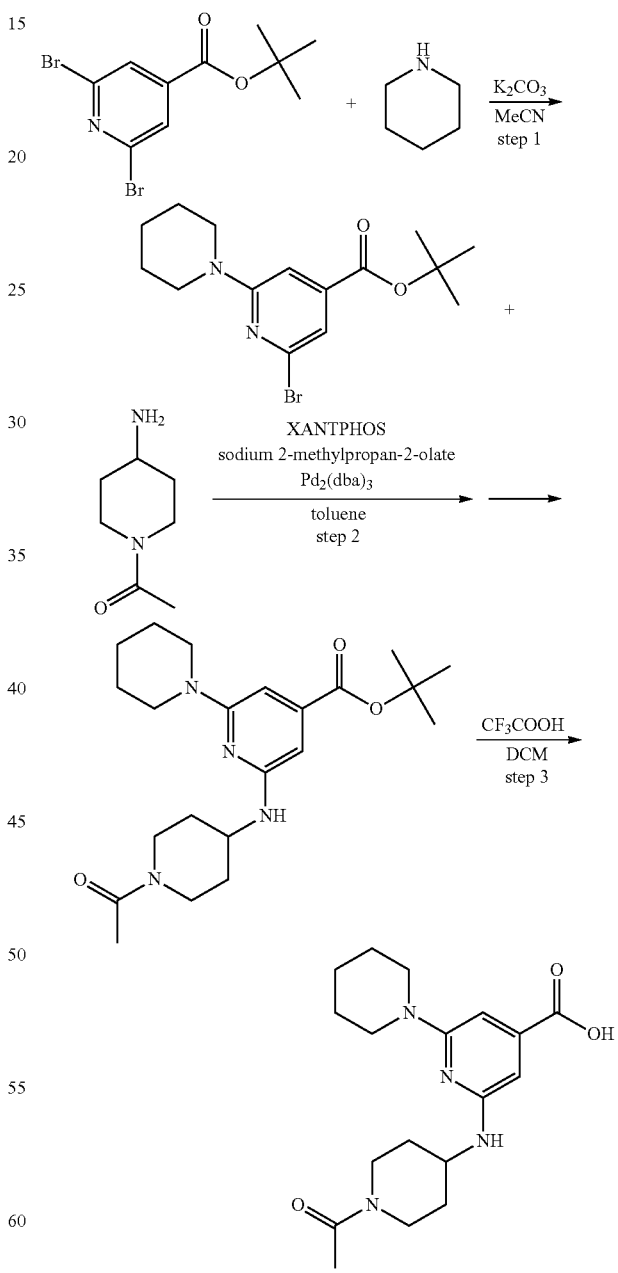

tert-butyl 2-bromo-6-(piperidin-1-yl)isonicotinate. Piperidine (947.46 mg, 11.13 mmol, 1.10 mL) was added to a stirred mixture of tert-butyl 2,6-dibromopyridine-4-carboxylate (2.5 g, 7.42 mmol) and potassium carbonate, anhydrous, 99% (2.05 g, 14.84 mmol, 895.44 uL) in acetonitrile (50 mL). The resulting mixture was stirred at 80° C. for 72 hr (the reaction progress was monitored by H-NMR of the aliquots), then cooled and filtered. The filtercake was washed with acetonitrile (2*20 ml) and discarded. The filtrate was evaporated in vacuo, the residue was diluted with water (30 ml) and extracted with dichloromethane (2*30 ml). The combined organic extracts were dried over sodium sulphate and evaporated in vacuo to afford tert-butyl 2-bromo-6-(1-piperidyl)pyridine-4-carboxylate (2.1 g, 6.15 mmol, 82.96% yield) as yellow gum. $^1$H NMR (500 MHz, CDCl$_3$) δ (ppm) 1.58 (s, 9H), 1.65 (m, 6H), 3.58 (m, 4H), 7.07 (s, 1H), 7.10 (s, 1H). LCMS(ESI): [M+H]+ m/z: calcd 341.2. found 343.0; Rt=1.734 min.

tert-butyl 2-((1-acetylpiperidin-4-yl)amino)-6-(piperidin-1-yl)isonicotinate. tert-Butyl 2-bromo-6-(1-piperidyl)pyridine-4-carboxylate (2.1 g, 6.15 mmol), 1-(4-amino-1-piperidyl)ethanone (1.05 g, 7.38 mmol) and sodium 2-methylpropan-2-olate (887.10 mg, 9.23 mmol) were mixed together in toluene (40 mL). The resulting mixture was evacuated and then backfilled with argon, this operation was repeated three times, then [5-(diphenylphosphanyl)-9,9-dimethyl-9H-xanthen-4-yl]diphenylphosphane (178.04 mg, 307.70 umol) and tris(1,5-diphenylpenta-1,4-dien-3-one) dipalladium (140.88 mg, 153.85 umol) were added under argon. The reaction mixture was stirred under argon at 75° C. for 18 hr, then cooled and evaporated in vacuo. The residue was purified by column chromatography on silica gel using hexane-ethyl acetate gradient (5-100% ethyl acetate) to afford tert-butyl 2-[(1-acetyl-4-piperidyl)amino]-6-(1-piperidyl)pyridine-4-carboxylate (1.5 g, 3.73 mmol, 60.55% yield) as yellow solid. $^1$H NMR (500 MHz, CDCl$_3$) δ (ppm) 1.38 (m, 2H), 1.58 (s, 9H), 1.62 (m, 6H), 2.02 (m, 2H), 2.12 (s, 3H), 2.82 (m, 1H), 3.24 (m, 1H), 3.50 (m, 4H), 3.85 (m, 2H), 4.24 (m, 1H), 4.49 (m, 1H), 6.20 (s, 1H), 6.47 (s, 1H). LCMS(ESI): [M+H]+ m/z: calcd 402.5. found 403.2; Rt=1.494 min.

2-((1-acetylpiperidin-4-yl)amino)-6-(piperidin-1-yl) isonicotinic acid, tert-Butyl 2-[(1-acetyl-4-piperidyl)amino]-6-(1-piperidyl)pyridine-4-carboxylate (1.5 g, 3.73 mmol) was dissolved in trifluoroacetic acid (21.24 g, 186.32 mmol, 14.35 mL). The reaction mixture was stirred at 25° C. for 1 hr, and then evaporated in vacuo. The residue was triturated with hexane/MTBE mixture (2/1, 70 ml), stirred for 0.1 hr and the precipitate was filtered, washed with hexane (2*10 ml) and dried in vacuo to afford 2-[(1-acetyl-4-piperidyl)amino]-6-(1-piperidyl)pyridine-4-carboxylic acid (1 g, 2.17 mmol, 58.28% yield, CF$_3$COOH) as yellow solid, which was used directly in the next step. $^1$H NMR (400 MHz, DMSO-d$_6$) δ (ppm) 1.28 (m, 1H), 1.42 (m, 1H), 1.53 (m, 6H), 1.82 (m, 1H), 1.89 (m, 1H), 1.99 (s, 3H), 2.82 (m, 1H), 3.15 (m, 1H), 3.46 (m, 4H), 3.76 (m, 1H), 3.85 (m, 1H), 4.17 (m, 1H), 6.29 (s, 1H), 6.33 (s, 1H). LCMS(ESI): [M+H]+ m/z: calcd 346.4. found 347.2; Rt=0.996 min.

2-(cyclobutylamino)-6-methoxyisonicotinic Acid

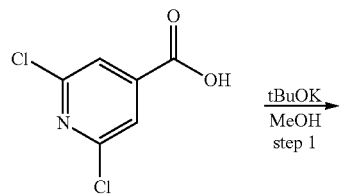

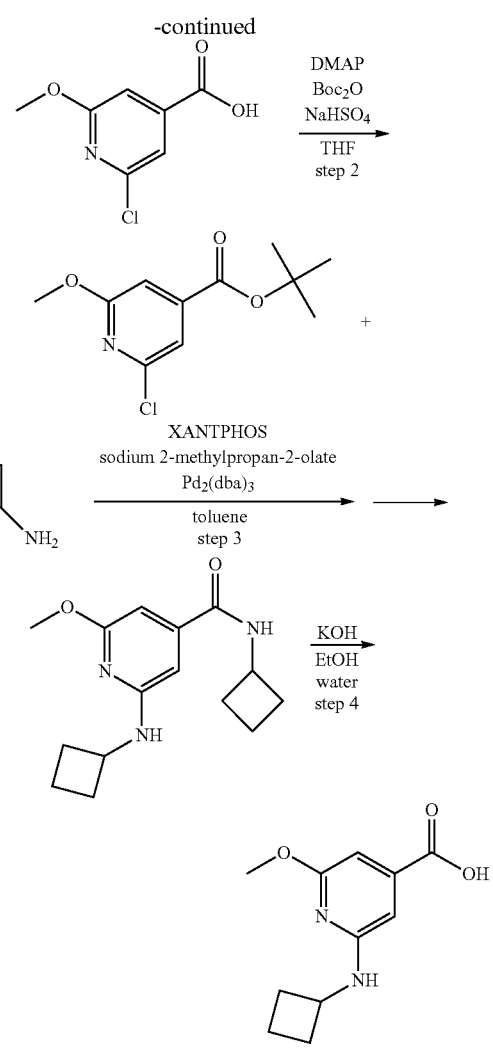

2-chloro-6-methoxyisonicotinic acid. 2,6-Dichloropyridine-4-carboxylic acid (5 g, 26.04 mmol) was added to solution of potassium 2-methylpropan-2-olate (9.64 g, 85.94 mmol) in methanol (100 mL). The resulting mixture was stirred with a reflux condenser at 65° C. for 24 hr, then cooled down and evaporated in vacuo. The residue was dissolved in water (50 ml) and acidified with concentrated hydrochloric acid to pH 5. The resulting precipitate was filtered, washed with water (2*10 ml) and dried in vacuo to afford 2-chloro-6-methoxy-pyridine-4-carboxylic acid (4.6 g, 24.52 mmol, 94.17% yield) as white solid. $^1$H NMR (400 MHz, DMSO-d$_6$) δ (ppm) 3.89 (s, 3H), 7.17 (s, 1H), 7.39 (s, 1H), 13.92 (bds, 1H). LCMS(ESI): [M+H]+ m/z: calcd 187.6. found 188.2; Rt=1.097 min.

tert-butyl 2-chloro-6-methoxyisonicotinate. Di-tert-butyl dicarbonate (6.42 g, 29.43 mmol, 6.75 mL) was added to a stirred mixture of 2-chloro-6-methoxy-pyridine-4-carboxylic acid (4.6 g, 24.52 mmol) and A/N-dimethylpyridin-4-amine (1.50 g, 12.26 mmol) in THF (50 mL) at 25° C. The reaction mixture was stirred at 25° C. for 12 hr, and evaporated in vacuo. The residue was dissolved in dichloromethane (100 ml) and washed with aqueous sodium hydrogen sulphate (2.06 g, 17.17 mmol) solution (40 ml). The organic layer was separated, dried over sodium sulphate and evaporated in vacuo to afford tert-butyl 2-chloro-6-methoxy-pyridine-4-carboxylate (5.5 g, 22.57

92.04% yield) as white solid. ¹H NMR (400 MHz, CDCl₃) δ (ppm) 1.59 (s, 9H), 3.97 (s, 3H), 7.17 (s, 1H), 7.38 (s, 1H). LCMS(ESI): [M-tBu]+ m/z: calcd 187.2. found 188.2; Rt=1.673 min.

N-cyclobutyl-2-(cyclobutylamino)-6-methoxyisonicotinamide. tert-Butyl 2-chloro-6-methoxy-pyridine-4-carboxylate (1 g, 4.10 mmol) and sodium 2-methylpropan-2-olate (591.54 mg, 6.16 mmol) were mixed together in toluene (50 mL). The resulting mixture was evacuated and then backfilled with argon, this operation was repeated three times, then cyclobutanamine (875.56 mg, 12.31 mmol, 1.05 mL), [5-(diphenylphosphanyl)-9,9-dimethyl-9H-xanthen-4-yl]diphenylphosphane (118.72 mg, 205.18 umol) and tris(1,5-diphenylpenta-1,4-dien-3-one) dipalladium (93.94 mg, 102.59 umol) were added under argon. The flask was sealed, and the reaction mixture was stirred under argon at 110° C. for 48 hr, then cooled, filtered through short pad of silicagel and the filtrate was evaporated in vacuo to leave 1.4 g of the crude product (63.9% purity by LCMS, 0.89 g of the target compound)N-cyclobutyl-2-(cyclobutylamino)-6-methoxy-pyridine-4-carboxamide (0.89 g, 3.23 mmol, 78.77% yield) as brown gum, which was used in the next step without further purification. ¹H NMR (400 MHz, CDCl₃) δ (ppm) 1.72 (m, 5H), 1.91 (m, 5H), 2.40 (m, 4H), 3.83 (s, 3H), 4.14 (m, 1H), 4.54 (m, 1H), 6.16 (s, 1H), 6.19 (s, 1H). LCMS (ESI): [M+H]+ m/z: calcd 275.3. found 276.2; Rt=1.339 min.

2-(cyclobutylamino)-6-methoxyisonicotinic acid. N-Cyclobutyl-2-(cyclobutylamino)-6-methoxy-pyridine-4-carboxamide (1.4 g, 5.08 mmol) was dissolved in a solution of potassium hydroxide (855.88 mg, 15.25 mmol, 419.55 uL) in a mixture of water (5 mL) and ethanol (11 mL). The resulting mixture was stirred with reflux condenser at 90° C. for 48 hr, then cooled and evaporated in vacuo. The residue was diluted with water (20 ml), stirred for 0.25 hr and filtered. The filtercake was washed with water (2*5 ml) and discarded. The filtrate was acidified to pH 5 with concentrated hydrochloric acid. The precipitate was filtered, washed successively with water (2*5 ml) and MTBE (2*10 ml), and dried in vacuo to afford 2-(cyclobutylamino)-6-methoxy-pyridine-4-carboxylic acid (0.44 g, 1.98 mmol, 38.94% yield) as brown solid. ¹H NMR (400 MHz, DMSO-d₆) δ (ppm) 1.67 (m, 2H), 1.88 (m, 2H), 2.26 (m, 2H), 3.77 (s, 3H), 4.20 (m, 1H), 6.22 (s, 1H), 6.44 (s, 1H), 7.08 (bds, 1H), 13.01 (bds, 1H). LCMS(ESI): [M+H]+ m/z: calcd 222.2. found 223.1; Rt=1.222 min.

4-((1-acetylpiperidin-4-yl)amino)picolinic Acid

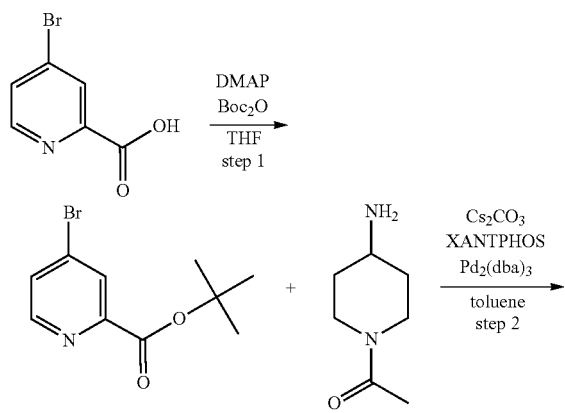

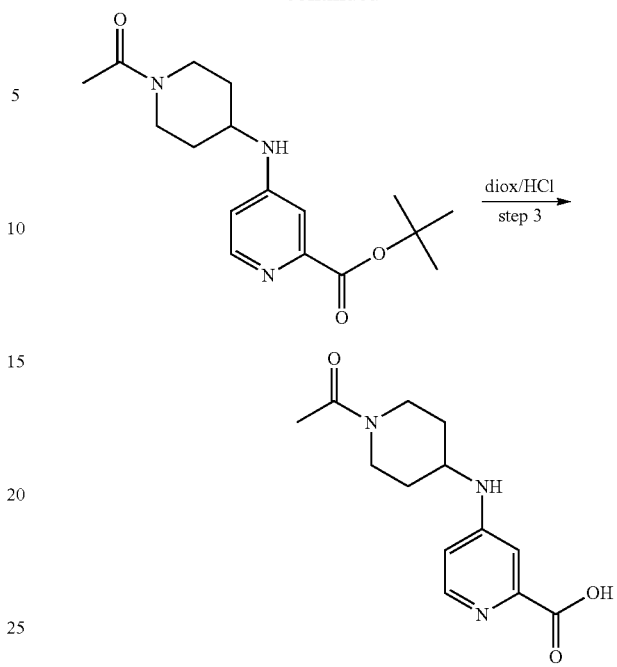

tert-butyl 4-((1-acetylpiperidin-4-yl)amino)picolinate. tert-Butyl 4-bromopyridine-2-carboxylate (5 g, 19.37 mmol) tert-butyl 4-bromopyridine-2-carboxylate (5 g, 19.37 mmol) and tris(dibenzylideneacetone)dipalladium (0) (443.47 mg, 484.29 umol), cesium carbonate (9.47 g, 29.06 mmol) were mixed together in toluene (50 mL). The resulting mixture was evacuated and then backfilled with argon, this operation was repeated three times, then 1-(4-amino-1-piperidyl)ethanone (2.75 g, 19.37 mmol), cesium carbonate (9.47 g, 29.06 mmol) and 4,5-bis(diphenylphosphino)-9,9-dimethylxanthene (112.09 mg, 193.71 umol) were added under argon. The resulting mixture was stirred under argon at 90° C. for 12 hr. The reaction mixture was cooled to r.t. and diluted with water. The resulting mixture was extracted twice with 20 ml EtOAc. The combined organic extracts were dried over sodium sulfate and evaporated. The residue was subjected to column chromatography (companion combiflash; 120 g SiO₂; chloroform/acetonitrile with acetonitrile from 0 to 100%, flow rate=85 ml/min, Rv=16 cv.) to obtain tert-butyl 4-[(1-acetyl-4-piperidyl)amino]pyridine-2-carboxylate (3 g, 9.39 mmol, 48.49% yield). ¹H NMR (500 MHz, DMSO-d₆) δ (ppm) 1.17 (m, 1H), 1.22 (m, 1H), 1.42 (s, 9H), 1.76 (m, 2H), 1.86 (s, 3H), 2.72 (m, 1H), 3.09 (m, 1H), 3.43 (m, 1H), 3.63 (m, 1H), 4.05 (m, 1H), 6.45 (d, 1H), 6.56 (d, 1H), 7.00 (s, 1H), 7.88 (d, 1H). LCMS(ESI): [M+H]+ m/z: calcd 319.4; found 320.2; Rt=0.821 min.

4-((1-acetylpiperidin-4-yl)amino)picolinic acid. The solution of tert-butyl 4-[(1-acetyl-4-piperidyl)amino]pyridine-2-carboxylate (3 g, 9.39 mmol) in dioxane/HCl (30 mL) with 5 drops of water was stirred at 20° C. for 12 hr. The resulting mixture was evaporated to dryness to obtain 4-[(1-acetyl-4-piperidyl)amino]pyridine-2-carboxylic acid (3.2 g, crude, HCl). NMR (400 MHz, DMSO-d₆) δ (ppm) 1.42 (m, 2H), 1.85 (m, 2H), 2.02 (s, 3H), 2.81 (m, 1H), 3.22 (m, 1H), 3.85 (m, 2H), 4.29 (m, 1H), 7.12 (m, 1H), 7.62 (m, 1H), 8.17 (m, 1H), 9.48 (m, 1H), 13.62 (bds, 1H). LCMS(ESI): [M+H]+ m/z: calcd 263.3. found 264.2; Rt=0.673 min.

5-((tetrahydro-2H-pyran-4-yl)aminonicotinic Acid

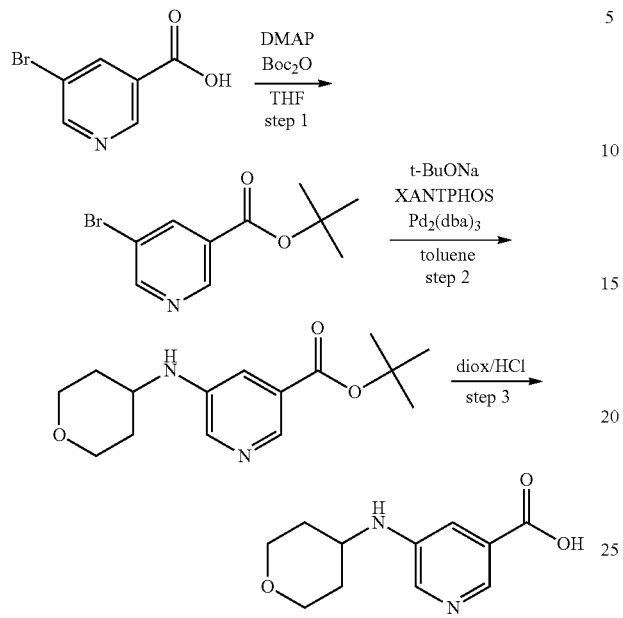

tert-butyl 5-((tetrahydro-2H-pyran-4-yl)amino)nicotinate. tert-Butyl 5-bromopyridine-3-carboxylate (2.5 g, 9.69 mmol) and sodium tert-butoxide (1.40 g, 14.53 mmol) were mixed together in toluene (30 mL). The resulting mixture was evacuated and then backfilled with argon, this operation was repeated three times, then tetrahydropyran-4-amine (1.08 g, 10.65 mmol), 4,5-bis(diphenylphospheno)-9,9-dimethyl xanthene (280.22 mg, 484.29 umol) and tris(dibenzylideneacetone)dipalladium (0) (221.74 mg, 242.14 umol) were added under argon. The resulting mixture was stirred under argon at 90° C. for 12 hr. The reaction was controlled by LCMS and H-NMR. HNMR and LCMS of reaction mixture shoved partial tert-butyl ester cleavage of starting bromonicotinic acid and approx. 42% conversion into desired product. The reaction mixture was cooled to r.t., diluted with water and extracted with EtOAc (2×20 ml). The combined organic extracts were dried over sodium sulfate and evaporated to dryness. The residue (1.1 g) was subjected to column chromatography (companion combiflash; 40 g SiO$_2$, chloroform/acetonitrile with acetonitrile from 0-70%, flow rate=40 mL/min, Rv=13 CV) to obtain tert-butyl 5-(tetrahydropyran-4-ylamino)pyridine-3-carboxylate (0.5 g, 1.80 mmol, 18.55% yield). $^1$H NMR (400 MHz, DMSO-d$_6$) δ (ppm) 1.42 (m, 2H), 1.55 (s, 9H), 1.89 (m, 2H), 3.48 (m, 3H), 3.88 (m, 2H), 6.02 (d, 1H), 7.30 (s, 1H), 8.10 (s, 1H), 8.17 (s, 1H). LCMS(ESI): [M+H]+ m/z: calcd 278.3. found 279.2; Rt=1.120 min.

5-((tetrahydro-2H-pyran-4-yl)amino)nicotinic acid. The solution of tert-butyl 5-(tetrahydropyran-4-ylamino)pyridine-3-carboxylate (0.5 g, 1.80 mmol) in dioxane/HCl (20 mL) with 5 drops of water was stirred at 20° C. for 24 hr. The resulting mixture was evaporated to dryness to obtain 5-(tetrahydropyran-4-ylamino)pyridine-3-carboxylic acid (0.45 g, 1.74 mmol, 96.83% yield, HCl). $^1$H NMR (500 MHz, DMSO-d$_6$) δ (ppm) 1.43 (m, 2H), 1.89 (m, 2H), 3.46 (m, 2H), 3.68 (m, 1H), 3.88 (m, 2H), 7.14 (bds, 1H), 7.92 (s, 1H), 8.27 (s, 1H), 8.30 (s, 1H), 12.52 (bds, 1H). LCMS (ESI): [M+H]+ m/z: calcd 222.2. found 223.0; Rt=0.629 min.

4-((tetrahydro-2H-pyran-4-yl)amino)picolinic Acid

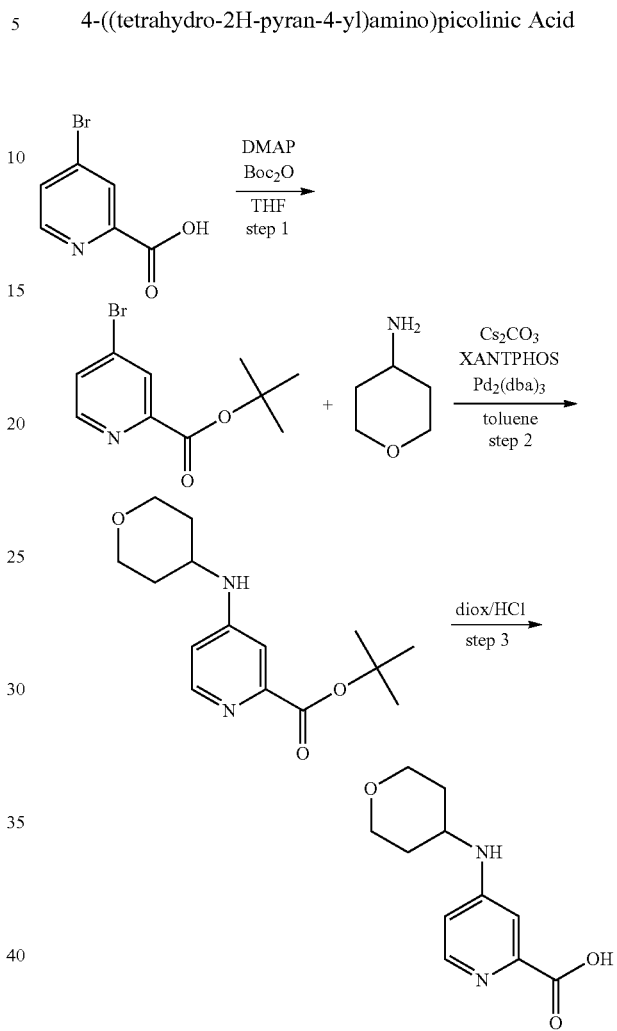

tert-butyl 4-((tetrahydro-2H-pyran-4-yl)amino)picolinate. tert-Butyl-4-bromopyridine-2-carboxylate (5 g, 19.37 mmol) and tris(dibenzylideneacetone)dipalladium (0) (443.47 mg, 484.29 umol) were mixed together in toluene (50 mL). The resulting mixture was evacuated and then backfilled with argon, this operation was repeated three times, then tetrahydropyran-4-amine (2.93 g, 21.31 mmol, HCl), tris(dibenzylideneacetone)dipalladium (0) (443.47 mg, 484.29 umol) and 4,5-bis(diphenylphosphino)-9,9-dimethylxanthene (560.44 mg, 968.58 umol) were added under argon. The resulting mixture was stirred under argon at 90° C. for 12 hr. The reaction was controlled by LCMS and H-NMR. The reaction mixture was cooled to r.t. and diluted with water. The resulting mixture was extracted twice with 20 ml EtOAc. The combined organic extracts were dried over sodium sulfate and evaporated. The residue (7 g) was subjected to column chromatography (companion combiflash; 120 g SiO$_2$; chloroform/acetonitrile with acetonitrile from 0 to 70%, flow rate=85 ml/min, Rv=14 cv.) to obtain tert-butyl 4-(tetrahydropyran-4-ylamino)pyridine-2-carboxylate (1.86 g, 6.68 mmol, 34.50% yield). $^1$H NMR (500 MHz, DMSO) δ (ppm) 1.44 (m, 2H), 1.56 (s, 9H), 1.88 (m, 2H), 3.45 (m, 2H), 3.52 (m, 1H), 3.87 (m, 2H), 6.58 (m, 2H), 7.13 (s, 1H), 8.03 (d, 1H). LCMS(ESI): [M+H]+ m/z: calcd 278.3. found 279.2; Rt=0.863 min.

4-((tetrahydro-2H-pyran-4-yl)amino)picolinic acid. The solution of tert-butyl 4-(tetrahydropyran-4-ylamino)pyridine-2-carboxylate (1.86 g, 6.68 mmol) in dioxane/HCl (30 mL) with 5 drops of water was stirred at 20° C. for 24 hr. The resulting mixture was evaporated to dryness to obtain 4-(tetrahydropyran-4-ylamino)pyridine-2-carboxylic acid (1.45 g, 5.60 mmol, 83.88% yield, HCl). $^1$H NMR (500 MHz, DMSO) δ (ppm) 1.52 (m, 2H), 1.84 (m, 2H), 3.45 (m, 2H), 3.87 (m, 3H), 7.12 (m, 1H), 7.60 (m, 1H), 8.17 (m, 1H), 9.33 (d, 1H), 13.60 (bds, 1H). LCMS(ESI): [M+H]+ m/z: calcd 222.2. found 223.0; Rt=0.655 min.

5-((1-acetylpiperidin-4-yl)amino)nicotinic Acid

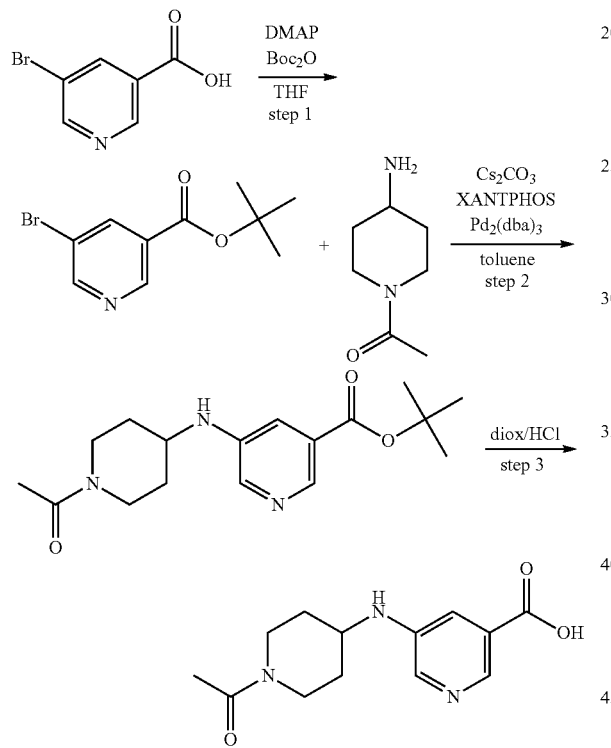

tert-butyl 5-((1-acetylpiperidin-4-yl)amino)nicotinate. tert-Butyl-5-bromopyridine-3-carboxylate (5 g, 19.37 mmol) and tris(dibenzylideneacetone)dipalladium (0) (443.47 mg, 484.29 umol) cesium carbonate (9.47 g, 29.06 mmol) were mixed together in toluene (50 mL). The resulting mixture was evacuated and then backfilled with argon, this operation was repeated three times, then 1-(4-amino-1-piperidyl)ethanone (2.75 g, 19.37 mmol), 4,5-bis(diphenylphospheno)-9,9-dimethyl xanthene (560.43 mg, 968.57 umol) and cesium carbonate (9.47 g, 29.06 mmol) tris (dibenzylideneacetone)dipalladium (0) (443.47 mg, 484.29 umol) were added under argon. The resulting mixture was stirred under argon at 90° C. for 48 hr. The reaction was controlled by LCMS and HNMR. The reaction mixture was cooled to r.t. and diluted with water. The resulting mixture was extracted twice with 40 ml EtOAc. The combined organic extracts were dried over sodium sulfate and evaporated. The residue (7 g) was subjected to column chromatography (1st run: chloroform/acetonitrile/methanol. 2nd run: Interchim, 80 g C18, water/methanol with methanol from 10-55%, flow rate=60 mL/min, Rv=13.5 CV) to obtain tert-butyl 5-[(1-acetyl-4-piperidyl)amino]pyridine-3-carboxylate (0.6 g, 1.88 mmol, 9.70% yield). $^1$H NMR (500 MHz, DMSO) δ (ppm) 1.33 (m, 2H), 1.56 (s, 9H), 1.97 (m, 2H), 2.02 (s, 3H), 2.87 (m, 1H), 3.25 (m, 1H), 3.54 (m, 1H), 3.77 (m, 1H), 4.21 (m, 1H), 6.97 (d, 1H), 7.30 (s, 1H), 8.09 (s, 1H), 8.17 (s, 1H). LCMS(ESI): [M+H]+ m/z: calcd 319.4. found 320.2; Rt=1.036 min.

5-((1-acetylpiperidin-4-yl)amino)nicotinic acid. The solution of tert-butyl 5-[(1-acetyl-4-piperidyl)amino]pyridine-3-carboxylate (0.6 g, 1.88 mmol) in dioxane/HCl (50 mL) with 5 drops of water was stirred at 20° C. for 24 hr. The resulting mixture was evaporated to dryness to obtain 5-[(1-acetyl-4-piperidyl)amino]pyridine-3-carboxylic acid (0.497 g, 1.66 mmol, 88.26% yield, HCl). $^1$H NMR (500 MHz, DMSO) δ (ppm) 1.28 (m, 2H), 1.91 (m, 2H), 2.01 (s, 3H), 2.86 (m, 1H), 3.22 (m, 1H), 3.78 (m, 2H), 4.21 (m, 1H), 7.20 (bds, 1H), 7.99 (s, 1H), 8.29 (s, 1H), 8.33 (s, 1H), 12.56 (bds, 1H). LCMS(ESI): [M+H]+ m/z: calcd 263.3. found 264.2; Rt=0.667 min.

2-(pyridin-3-ylamino)isonicotinic Acid

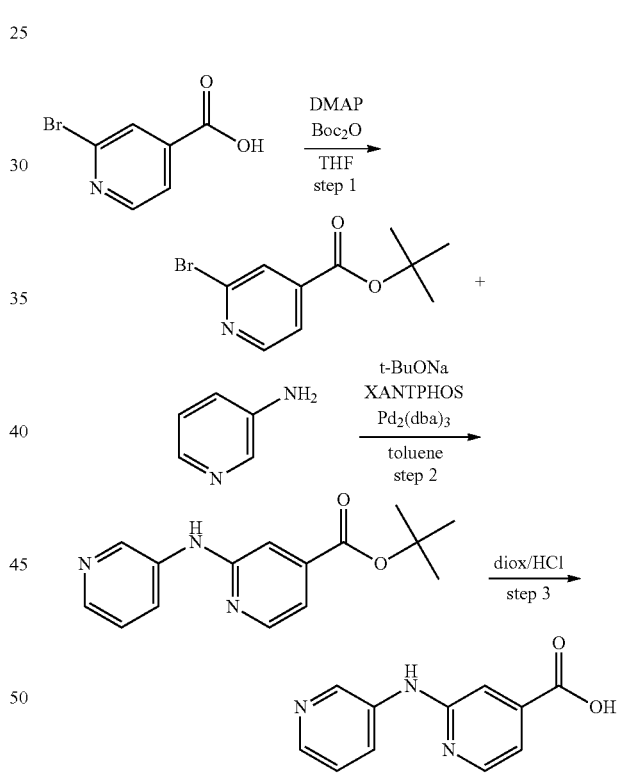

tert-butyl 2-bromoisonicotinate. tert-Butoxycarbonyl tert-butyl carbonate (9.51 g, 43.56 mmol, 10.00 mL) was added dropwise to the solution of 2-bromopyridine-4-carboxylic acid (8 g, 39.60 mmol) and 4-dimethylaminopyridine (2.42 g, 19.80 mmol) in THF (150 mL) at 0° C. The resulting mixture was left to warm slowly to r.t. and stirred for 17 hr. After consumption of the starting material (H-NMR control) the reaction mixture was evaporated. The residue was subjected to column chromatography (Companion combiflash; 220 g SiO$_2$; petroleum ether/MtBE with MtBE from 0 to 15%, flow rate=85 ml/min, Rv=5cv). To obtain tert-butyl 2-bromopyridine-4-carboxylate (7.81 g, 30.26 mmol, 76.40% yield) tert-butyl 2-bromopyridine-4-carboxylate (7.81 g, 30.26 mmol, 76.40% yield). ¹H NMR (400 MHz, DMSO) δ (ppm) 1.57 (s, 9H), 7.79 (d, 1H), 7.88 (s, 1H), 8.55 (d, 1H). LCMS(ESI): [M+H]+m/z: calcd 201.0. found 202.0; Rt=1.543 min.

tert-butyl 2-(pyridin-3-ylamino)isonicotinate. tert-Butyl 2-bromopyridine-4-carboxylate (8.3 g, 32.16 mmol) and sodium tert-butoxide (4.64 g, 48.24 mmol) sodium tert-butoxide (4.64 g, 48.24 mmol) were mixed together in toluene (100 mL). The resulting mixture was evacuated and then backfilled with argon, this operation was repeated three times, then pyridin-3-amine (3.03 g, 32.16 mmol), 4,5-bis(diphenylphosphino)-9,9-dimethylxanthene (930.32 mg, 1.61 mmol) and tris(dibenzylideneacetone)dipalladium (0) (736.16 mg, 803.92 umol) were added under argon. The resulting mixture was stirred under argon at 90° C. for 12 hr. The reaction was controlled by LCMS and HNMR. After consumption of the starting material the reaction mixture was cooled to r.t. and diluted with water. The resulting mixture was extracted twice with 20 ml EtOAc. The combined organic extracts were dried over sodium sulfate and evaporated. The residue was subjected to column chromatography (Ok. Companion combiflash; 120 g SiO₂; MtBE/methanol with methanol from 0 to 1%, flow rate=85 ml/min, Rv=8cv) to obtain tert-butyl 2-(3-pyridylamino)pyridine-4-carboxylate (3.87 g, 14.26 mmol, 44.36% yield). ¹H NMR (500 MHz, DMSO) δ (ppm) 1.54 (s, 9H), 7.08 (m, 1H), 7.20 (m, 1H), 7.28 (m, 1H), 8.04 (m, 1H), 8.21 (m, 1H), 8.24 (m, 1H), 8.73 (m, 1H), 9.40 (m, 1H). LCMS(ESI): [M+H]+ m/z: calcd 271.3. found 272.2; Rt=1.116 min.

2-(pyridin-3-ylamino)isonicotinic acid. The solution of tert-butyl 2-(3-pyridylamino)pyridine-4-carboxylate (3.87 g, 14.26 mmol) in dioxane/HCl (50 mL) with 5 drops of water was stirred at 20° C. for 24 hr. The resulting mixture was evaporated to dryness to obtain 2-(3-pyridylamino)pyridine-4-carboxylic acid (2.7 g, 10.73 mmol, 75.21% yield, HCl). NMR (500 MHz, DMSO) δ (ppm) 7.37 (m, 1H), 7.57 (m, 1H), 7.98 (m, 1H), 8.45 (m, 2H), 8.63 (m, 1H), 9.52 (m, 1H), 10.84 (m, 1H). LCMS(ESI): [M+H]+ m/z: calcd 215.3. found 216.2; Rt=0.720 min.

2-((1-acetylpiperidin-4-yl)amino)-6-(cyclobutyl) methyl)amino)isonicotinic Acid

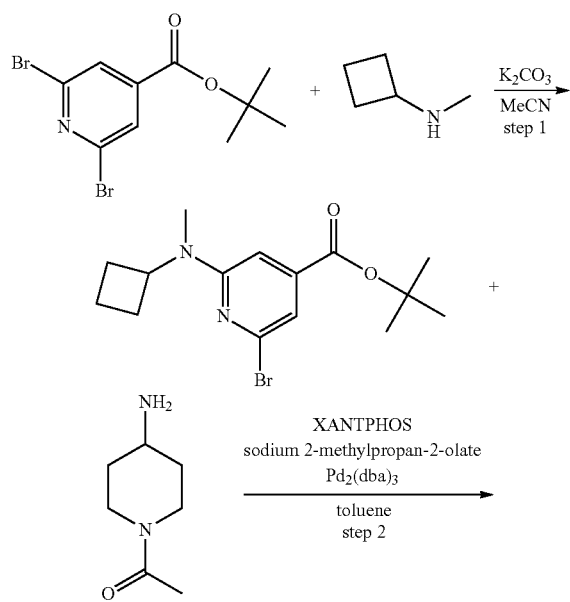

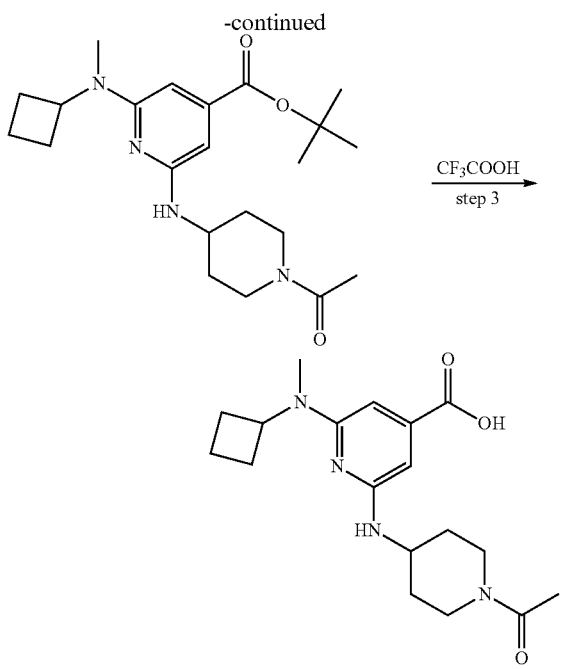

tert-butyl 2-bromo-6-(cyclobutyl(methyl)amino)isonicotinate. N-Methylcyclobutanamine (14.53 g, 119.46 mmol, 7.33 mL, HCl) was added to a stirred mixture of tert-butyl 2,6-dibromopyridine-4-carboxylate (11.5 g, 34.12 mmol) in acetonitrile (300 mL). The resulting mixture was stirred with reflux condenser at 85° C. for 24 hr (the reaction progress was monitored by HNMR of the aliquots), then cooled and evaporated in vacuo, the residue was diluted with water (300 ml) and extracted with dichloromethane (2*150 ml). The combined organic extracts were dried over sodium sulphate and evaporated in vacuo to afford tert-butyl 2-bromo-6-[cyclobutyl(methyl)amino]pyridine-4-carboxylate (11 g, 32.24 mmol, 94.47% yield) as light-brown solid. ¹H NMR (400 MHz, CDCl₃) δ (ppm) 1.58 (s, 9H), 1.73 (m, 2H), 2.16 (m, 2H), 2.26 (m, 2H), 3.02 (s, 3H), 4.69 (m, 1H), 6.94 (s, 1H), 7.11 (s, 1H). LCMS(ESI): [M+H]+m/z: calcd 341.2. found 342.2; Rt=1.886 min.

tert-butyl 2-((1-acetylpiperidin-4-yl)amino)-6-(cyclobutyl(methyl)amino)isonicotinate. tert-Butyl 2-bromo-6-[cyclobutyl(methyl)amino]pyridine-4-carboxylate (4 g, 11.72 mmol) and sodium 2-methylpropan-2-olate (1.69 g, 17.58 mmol) were mixed together in toluene (40 mL). The resulting mixture was evacuated and then backfilled with argon, this operation was repeated three times, then 1-(4-amino-1-piperidyl)ethanone (2.00 g, 14.07 mmol), [5-(diphenylphosphanyl)-9,9-dimethyl-9H-xanthen-4-yl]diphenylphosphane (339.13 mg, 586.09 umol) and tris(1,5-diphenylpenta-1,4-dien-3-one) dipalladium (268.35 mg, 293.05 umol) were added under argon. The reaction mixture was stirred under argon at 70° C. for 2 hr, then cooled and evaporated in vacuo. The residue was purified by column chromatography on silica gel (40 g pre-column, 40 g column, tubes 60-70 were combined and evaporated) using hexane/ethyl acetate gradient (0-100% ethyl acetate) to afford tert-butyl 2-[(1-acetyl-4-piperidyl)amino]-6-[cyclobutyl(methyl)amino]pyridine-4-carboxylate (1.3 g, 3.23 mmol, 27.55% yield) as yellow solid. ¹H NMR (400 MHz, CDCl₃) δ (ppm) 1.39 (m, 2H), 1.58 (s, 9H), 1.71 (m, 3H), 2.12 (s, 3H), 2.23 (m, 5H), 2.82 (m, 1H), 3.01 (s, 3H), 3.21 (m, 1H), 3.82 (m, 1H), 3.90 (m, 1H), 4.11 (m, 1H), 4.49 (m, 1H), 4.67 (m, 1H), 6.19 (s, 1H), 6.34 (s, 1H). LCMS(ESI): [M+H]+ m/z: calcd 402.5. found 403.2; Rt=1.442 min.

2-((1-acetylpiperidin-4-yl)amino)-6-(cyclobutyl(methyl) amino)isonicotinic acid, tert-Butyl 2-[(1-acetyl-4-piperidyl) amino]-6-[cyclobutyl(methyl)amino]pyridine-4-carboxylate (1.3 g, 3.23 mmol) was dissolved in trifluoroacetic acid (18.41 g, 161.48 mmol, 12.44 mL). The reaction mixture was stirred at 25° C. for 1 hr, and then evaporated in vacuo. The residue was triturated with hexane/MTBE mixture (4/1, 60 ml), stirred for 1 hr and the precipitate was filtered, washed with hexane (2*10 ml) and dried in vacuo to afford 2-[(1-acetyl-4-piperidyl)amino]-6-[cyclobutyl(methyl) amino]pyridine-4-carboxylic acid (1.1 g, 2.39 mmol, 73.97% yield, CF$_3$COOH) as yellow solid, which was used directly in the next step. $^1$H NMR (400 MHz, DMSO-d$_6$) δ (ppm) 1.35 (m, 2H), 1.63 (m, 2H), 1.99 (m, 6H), 2.19 (s, 3H), 2.79 (m, 1H), 2.95 (s, 3H), 3.19 (m, 1H), 3.85 (m, 2H), 4.20 (m, 1H), 4.57 (m, 1H), 6.22 (s, 1H), 6.30 (s, 1H). LCMS(ESI): [M+H]+ m/z: calcd 346.4. found 347.2; Rt=0.993 min.

2-((1-acetylpiperidin-4-yl)amino)-6-(dimethylamino) isonicotinic Acid

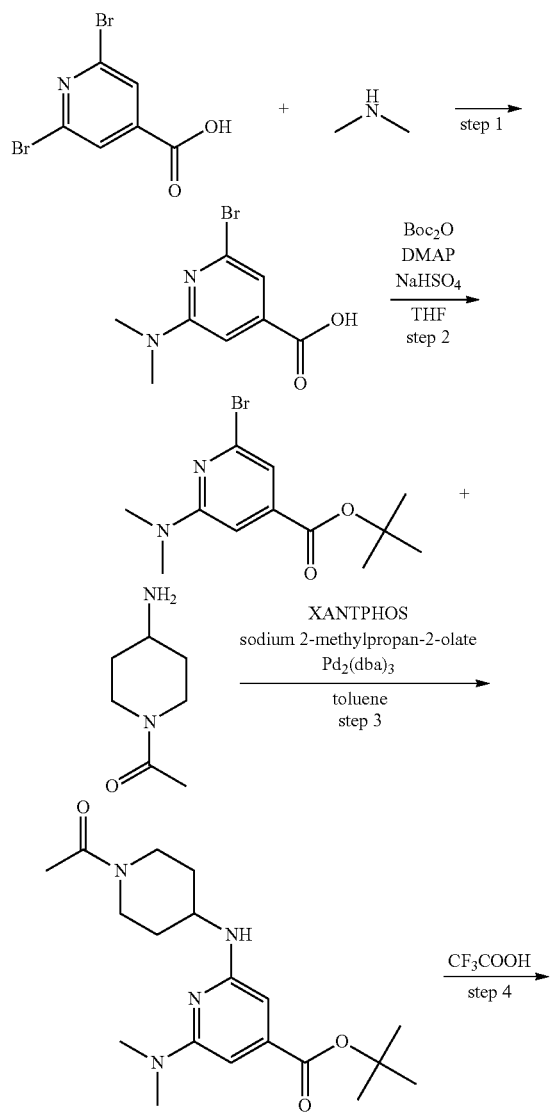

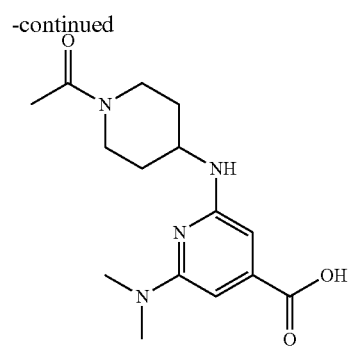

2-bromo-6-(dimethylamino)isonicotinic acid. 2,6-Dibromopyridine-4-carboxylic acid (5 g, 17.80 mmol) was dissolved in 40% aqueous solution of N-methylmethanamine (75 g, 665.43 mmol, 96.77 mL). The reaction mixture was stirred at 50° C. for 24 hr, and then evaporated in vacuo. The residue was dissolved in water (50 ml) and acidified to pH4 with concentrated aqueous hydrochloric acid. The precipitate was filtered, washed with water (2*15 ml) and dried in vacuo to afford 2-bromo-6-(dimethylamino)pyridine-4-carboxylic acid (3.2 g, 13.06 mmol, 73.36% yield) as light-brown solid. $^1$H NMR (400 MHz, DMSO-d$_6$) δ (ppm) 3.03 (s, 6H), 6.96 (s, 1H), 7.00 (s, 1H). LCMS(ESI): [M+H]+ m/z: calcd 245.1. found 246.2; Rt=1.178 min.

tert-butyl 2-bromo-6-(dimethylamino)isonicotinate. Di-tert-butyl dicarbonate (3.70 g, 16.97 mmol, 3.90 mL) was added to a stirred mixture of 2-bromo-6-(dimethylamino)pyridine-4-carboxylic acid (3.2 g, 13.06 mmol) and N,N-dimethylpyridin-4-amine (797.61 mg, 6.53 mmol) in THF (60 mL) at 25° C. The reaction mixture was stirred at 45° C. for 2 hr, and then evaporated in vacuo. The residue was dissolved in dichloromethane (100 ml) and washed successively with aqueous sodium hydrogen sulphate (783.83 mg, 6.53 mmol) solution (20 ml), and water (20 ml). The organic layer was separated, dried over sodium sulphate, filtered through short pad of silica gel and evaporated in vacuo to afford tert-butyl 2-bromo-6-(dimethylamino) pyridine-4-carboxylate (3.6 g, 11.95 mmol, 91.54% yield) as light-brown solid, which was used directly in the next step. $^1$H NMR (400 MHz, CDCl$_3$) δ (ppm) 1.58 (s, 9H), 3.11 (s, 6H), 6.95 (s, 1H), 7.11 (s, 1H). LCMS(ESI): [M+H]+ m/z: calcd 301.2. found 302.2; Rt=1.713 min.

tert-butyl 2-((1-acetylpiperidin-4-yl)amino)-6-(dimethylamino)isonicotinate. tert-Butyl 2-bromo-6-(dimethylamino) pyridine-4-carboxylate (3.6 g, 11.95 mmol) and sodium 2-methylpropan-2-olate (1.72 g, 17.93 mmol) were mixed together in toluene (50 mL). The resulting mixture was evacuated and then backfilled with argon, this operation was repeated three times, then 1-(4-amino-1-piperidyl)ethanone (2.04 g, 14.34 mmol), [5-(diphenylphosphanyl)-9,9-dimethyl-9H-xanthen-4-yl]diphenylphosphane (345.81 mg, 597.65 umol) and tris(1,5-diphenylpenta-1,4-dien-3-one) dipalladium (273.64 mg, 298.83 umol) were added under argon. The reaction mixture was stirred under argon at 70° C. for 2 hr, then cooled and evaporated in vacuo. The residue was purified by column chromatography on silica gel (40 g pre-column, 40 g column, tubes 70-93 were combined and evaporated) using hexane/ethyl acetate gradient (0-100% ethyl acetate) to afford tert-butyl 2-[(1-acetyl-4-piperidyl) amino]-6-(dimethylamino) pyridine-4-carboxylate (1.65 g, 4.55 mmol, 38.08% yield) as yellow solid. $^1$H NMR (400 MHz, CDCl$_3$) δ (ppm) 1.38 (m, 2H), 1.58 (m, 9H), 2.08 (m, 2H), 2.18 (s, 3H), 2.83 (m, 1H), 3.04 (s, 6H), 3.20 (m, 1H), 3.89 (m, 2H), 4.11 (m, 1H), 4.49 (m, 1H), 6.18 (s, 1H), 6.35 (s, 1H). LCMS(ESI): [M+H]+ m/z: calcd 362.5. found 363.2; Rt=1.249 min.

2-((1-acetylpiperidin-4-yl)amino)-6-(dimethylamino) isonicotinic acid, tert-Butyl 2-[(1-acetyl-4-piperidyl) amino]-6-(dimethylamino)pyridine-4-carboxylate (1.65 g, 4.55 mmol) was dissolved in trifluoroacetic acid (25.95 g, 227.61 mmol, 17.54 mL). The reaction mixture was stirred at 25° C. for 1 hr, and then evaporated in vacuo. The residue was triturated with hexane/MTBE mixture (4/1, 60 ml), stirred for 0.1 hr and the precipitate was filtered, washed with hexane (2*10 ml) and dried in vacuo to afford 2-[(1-acetyl-4-piperidyl)amino]-6-(dimethylamino)pyridine-4-carboxylic acid (1.71 g, 4.07 mmol, 89.36% yield, CF$_3$COOH) as yellow solid, which was used directly in the next step. $^1$H NMR (400 MHz, CDCl$_3$) δ (ppm) 1.35 (m, 2H), 1.85 (m, 2H), 1.99 (s, 3H), 2.84 (m, 1H), 3.02 (s, 6H), 3.20 (m, 1H), 3.80 (m, 2H), 4.18 (m, 1H), 6.22 (s, 1H), 6.28 (s, 1H). LCMS(ESI): [M+H]+ m/z: calcd 306.4. found 307.2; Rt=0.795 min.

2-(cyclobutyl)methyl)amino)-6-(cyclobutylamino) isonicotinic Acid

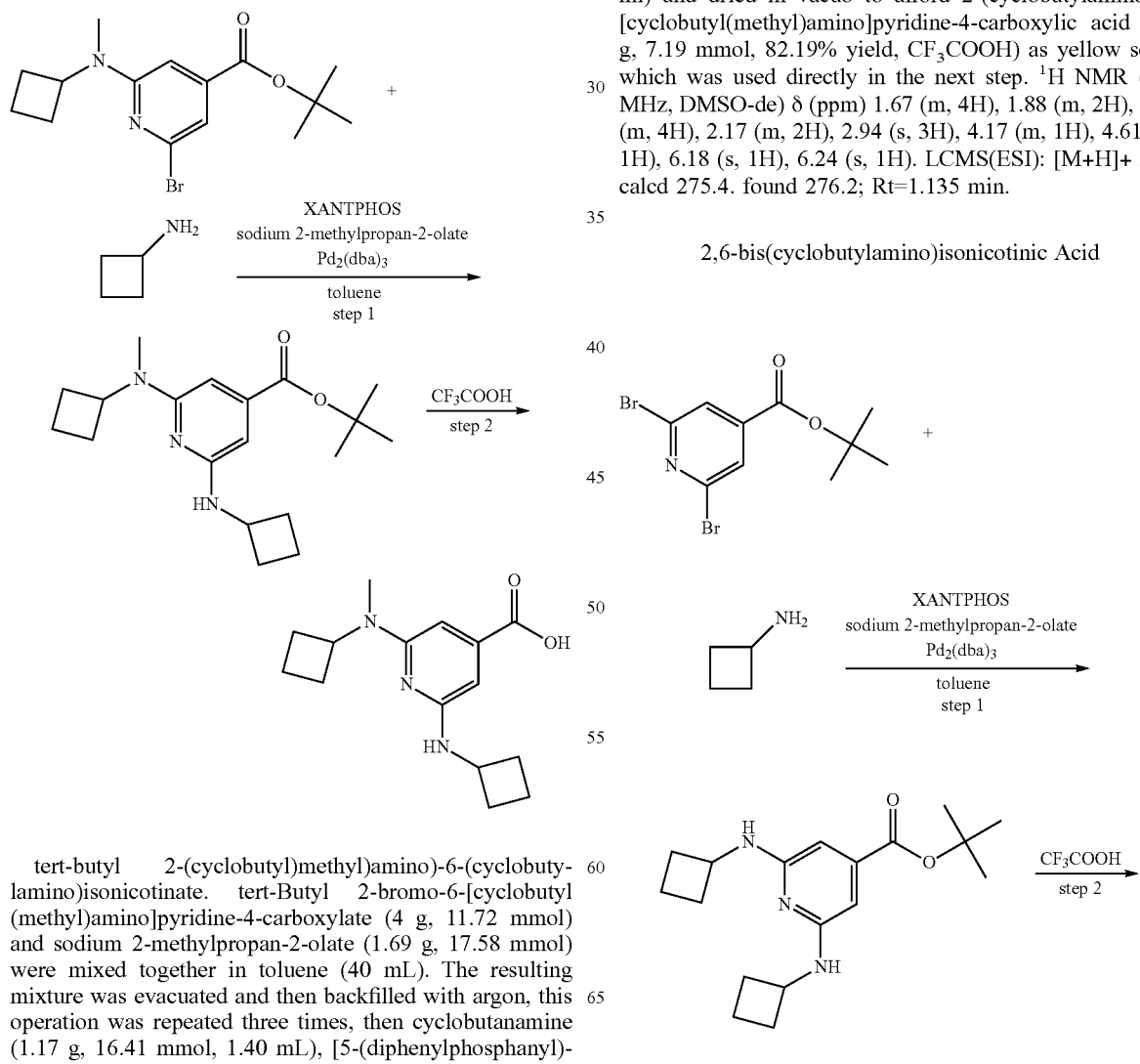

tert-butyl 2-(cyclobutyl)methyl)amino)-6-(cyclobutylamino)isonicotinate. tert-Butyl 2-bromo-6-[cyclobutyl(methyl)amino]pyridine-4-carboxylate (4 g, 11.72 mmol) and sodium 2-methylpropan-2-olate (1.69 g, 17.58 mmol) were mixed together in toluene (40 mL). The resulting mixture was evacuated and then backfilled with argon, this operation was repeated three times, then cyclobutanamine (1.17 g, 16.41 mmol, 1.40 mL), [5-(diphenylphosphanyl)-9,9-dimethyl-9H-xanthen-4-yl]diphenylphosphane (339.13 mg, 586.09 umol) and tris(1,5-diphenylpenta-1,4-dien-3-one) dipalladium (268.35 mg, 293.05 umol) were added under argon. The reaction mixture was stirred under argon at 70° C. for 2 hr, then cooled and evaporated in vacuo. The residue was purified by column chromatography on silica gel (40 g pre-column, 40 g column, tubes 20-30 were combined and evaporated) using hexane/ethyl acetate gradient (0-100% ethyl acetate) to afford tert-butyl 2-(cyclobutylamino)-6-[cyclobutyl(methyl)amino]pyridine-4-carboxylate (2.9 g, 8.75 mmol, 74.64% yield) as yellow gum. $^1$H NMR (500 MHz, CDCl$_3$) δ (ppm) 1.58 (s, 9H), 1.68 (m, 2H), 1.78 (m, 2H), 1.88 (m, 2H), 2.10 (m, 4H), 2.42 (m, 2H), 2.96 (s, 3H), 4.16 (m, 1H), 4.55 (m, 1H), 4.70 (m, 1H), 6.12 (s, 1H), 6.35 (s, 1H). LCMS(ESI): [M+H]+ m/z: calcd 331.4. found 332.4; Rt=1.611 min.

2-(cyclobutyl(methyl)amino)-6-(cyclobutylamino)isonicotinic acid. tert-Butyl 2-(cyclobutylamino)-6-[cyclobutyl(methyl)amino]pyridine-4-carboxylate (2.9 g, 8.75 mmol) was dissolved in trifluoroacetic acid (49.88 g, 437.47 mmol, 33.70 mL). The reaction mixture was stirred at 25° C. for 1 hr, and then evaporated in vacuo. The residue was triturated with hexane/MTBE mixture (5/1, 180 ml), stirred for 1 hr and the precipitate was filtered, washed with hexane (2*10 ml) and dried in vacuo to afford 2-(cyclobutylamino)-6-[cyclobutyl(methyl)amino]pyridine-4-carboxylic acid (2.8 g, 7.19 mmol, 82.19% yield, CF$_3$COOH) as yellow solid, which was used directly in the next step. $^1$H NMR (400 MHz, DMSO-de) δ (ppm) 1.67 (m, 4H), 1.88 (m, 2H), 2.12 (m, 4H), 2.17 (m, 2H), 2.94 (s, 3H), 4.17 (m, 1H), 4.61 (m, 1H), 6.18 (s, 1H), 6.24 (s, 1H). LCMS(ESI): [M+H]+ m/z: calcd 275.4. found 276.2; Rt=1.135 min.

2,6-bis(cyclobutylamino)isonicotinic Acid

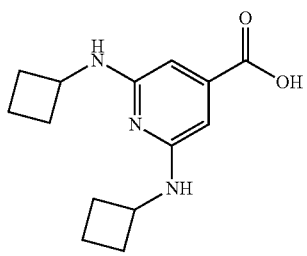

tert-butyl 2,6-bis(cyclobutylamino)isonicotinate. tert-Butyl 2,6-dibromopyridine-4-carboxylate (4 g, 11.87 mmol) and sodium 2-methylpropan-2-olate (3.42 g, 35.61 mmol) were mixed together in toluene (50 mL). The resulting mixture was evacuated and then backfilled with argon, this operation was repeated three times, then cyclobutanamine (2.36 g, 33.23 mmol, 2.84 mL), [5-(diphenylphosphanyl)-9,9-dimethyl-9H-xanthen-4-yl]diphenylphosphane (343.39 mg, 593.46 umol) and tris(1,5-diphenylpenta-1,4-dien-3-one) dipalladium (271.72 mg, 296.73 umol) were added under argon. The reaction mixture was stirred under argon at 70° C. for 3 hr, then cooled and evaporated in vacuo. The residue was purified by column chromatography on silica gel (40 g pre-column, 40 g column, 3rd peak was collected, tubes 20-34 were combined) using hexane/ethyl acetate gradient (0-100% ethyl acetate) to afford tert-butyl 2,6-bis(cyclobutylamino)pyridine-4-carboxylate (2 g, 6.30 mmol, 53.08% yield) as yellow gum, which was used directly in the next step. $^1$H NMR (400 MHz, CDCl$_3$) δ (ppm) 1.57 (s, 9H), 1.85 (m, 7H), 2.41 (m, 5H), 4.12 (m, 2H), 4.54 (m, 2H), 6.14 (s, 2H). LCMS(ESI): [M+H]+ m/z: calcd 317.4. found 318.2; Rt=1.358 min.

2,6-bis(cyclobutylamino)isonicotinic acid, tert-Butyl 2,6-bis(cyclobutylamino)pyridine-4-carboxylate (2 g, 6.30 mmol) was dissolved in trifluoroacetic acid (35.92 g, 315.04 mmol, 24.27 mL). The reaction mixture was stirred at 25° C. for 1 hr, and then evaporated in vacuo. The residue was triturated with hexane/MTBE mixture (4/1, 75 ml), stirred for 1 hr and the precipitate was filtered, washed with hexane (2*10 ml) and dried in vacuo to afford 2,6-bis(cyclobutylamino)pyridine-4-carboxylic acid (1.7 g, 4.53 mmol, 71.88% yield, CF$_3$COOH) as yellow solid, which was used directly in the next step. $^1$H NMR (400 MHz, DMSO-d$_6$) δ (ppm) 1.72 (m, 5H), 1.92 (m, 5H), 2.32 (m, 5H), 4.11 (m, 2H), 6.16 (s, 2H). LCMS(ESI): [M+H]+ m/z: calcd 261.3. found 262.2; Rt=0.873 min.

2-((1-acetylazetidin-3-yl)amino)-6-(piperidin-1-yl) isonicotinic Acid

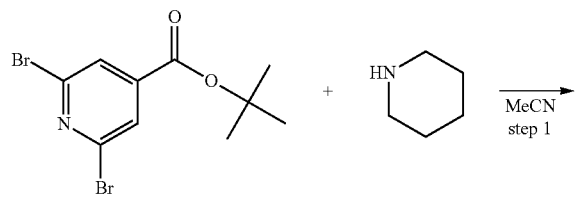

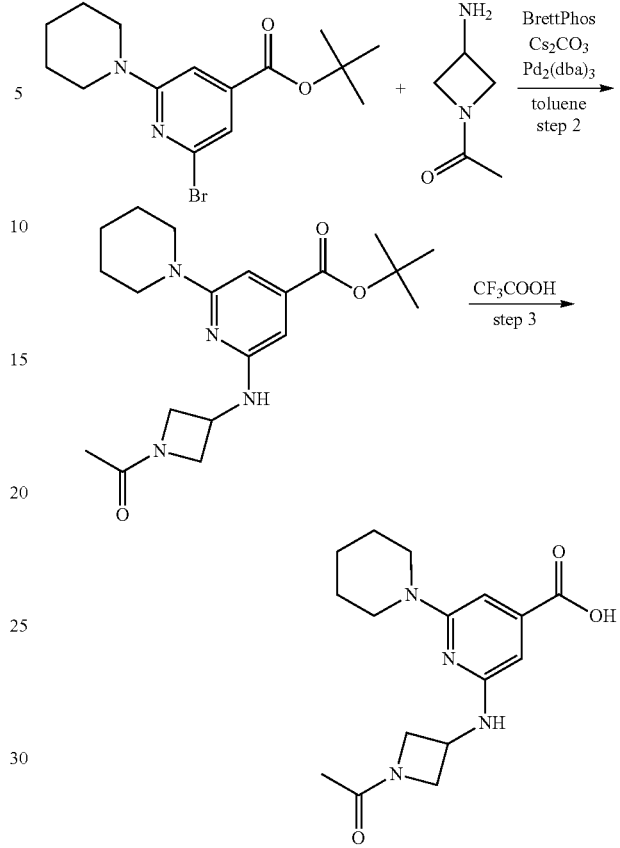

tert-butyl 2-bromo-6-(piperidin-1-yl)isonicotinate. Piperidine (7.58 g, 89.02 mmol, 8.79 mL) was added to a stirred mixture of tert-butyl 2,6-dibromopyridine-4-carboxylate (6 g, 17.80 mmol) in acetonitrile (100 mL). The resulting mixture was stirred at 80° C. for 7 hr (the reaction progress was monitored by HNMR of the aliquots), then cooled and evaporated in vacuo, the residue was diluted with water (100 mL) and extracted with dichloromethane (2*75 mL). The combined organic extracts were dried over sodium sulphate and evaporated in vacuo to afford tert-butyl 2-bromo-6-(1-piperidyl)pyridine-4-carboxylate (6 g, 17.58 mmol, 98.76% yield) as light-brown solid. $^1$H NMR (400 MHz, DMSO-d$_6$) δ (ppm) 1.56 (m, 15H), 3.54 (m, 4H), 6.95 (s, 1H), 7.08 (s, 1H). LCMS(ESI): [M+H]+ m/z: calcd 341.2. found 342.2; Rt=1.865 min.

tert-butyl 2-((1-acetylazetidin-3-yl)amino)-6-(piperidin-1-yl)isonicotinate. tert-Butyl 2-bromo-6-(1-piperidyl)pyridine-4-carboxylate (5.2 g, 15.24 mmol), 1-(3-aminoazetidin-1-yl)ethanone (4.17 g, 18.29 mmol, CF$_3$CO$_2$H) and cesium carbonate (14.89 g, 45.72 mmol) were mixed together in toluene (150 mL). The resulting mixture was evacuated and then backfilled with argon, this operation was repeated three times, then tris(1,5-diphenylpenta-1,4-dien-3-one) dipalladium (348.85 mg, 380.96 umol) and 2-(dicyclohexylphosphino)3,6-dimethoxy-2',4',6'-triisopropyl-1,1-biphenyl (817.95 mg, 1.52 mmol) were added under argon. The reaction mixture was stirred under argon at 100° C. for 120 hr, then it was diluted with water (150 mL). The layers were separated and the organic layer was washed with brine, dried over Na$_2$SO$_4$ and concentrated in vacuo. The residue was triturated with hexane (60 mL). The precipitate was filtered, washed with hexane (2×20 mL) and dried in vacuo to afford tert-butyl 2-[(1-acetylazetidin-3-yl)amino]-6-(1-piperidyl)pyridine-4-carboxylate (5.7 g, 15.22 mmol, 99.89% yield). $^1$H NMR (500 MHz, DMSO-d$_6$) δ (ppm) 1.13 (m, 1H), 1.56 (m, 12H), 1.75 (m, 4H), 3.44 (m, 5H), 3.49 (m, 1H), 3.89 (m, 1H), 4.08 (m, 1H), 4.36 (m, 1H), 4.43 (m, 1H), 6.18 (s, 1H), 6.29 (s, 1H), 7.13 (m, 1H). LCMS(ESI): [M+H]+ m/z: calcd 374.5. found 375.2; Rt=1.505 min.

2-((1-acetylazetidin-3-yl)amino)-6-(piperidin-1-yl)isonicotinic acid, tert-Butyl 2-[(1-acetylazetidin-3-yl)amino]-6-(1-piperidyl)pyridine-4-carboxylate (5.7 g, 15.22 mmol) was dissolved in TFA (173.55 g, 1.52 mol, 117.27 mL). The resulting solution was stirred at 20° C. for 3 hr, and then evaporated in vacuo. The residue was triturated with MTBE/hexane mixture (1/1, 100 mL). The precipitate was filtered, washed with hexane (2*30 mL) and dried in vacuo to afford 2-[(1-acetylazetidin-3-yl)amino]-6-(1-piperidyl)pyridine-4-carboxylic acid (6 g, 13.88 mmol, 91.16% yield, CF$_3$CO$_2$H) as yellow solid. $^1$H NMR (400 MHz, DMSO-d$_6$) δ (ppm) 1.58 (m, 9H), 3.45 (m, 4H), 3.70 (m, 1H), 3.91 (m, 1H), 4.09 (m, 1H), 4.40 (m, 2H), 6.23 (s, 1H), 6.36 (s, 1H), 7.28 (m, 2H). LCMS(ESI): [M+H]+ m/z: calcd 318.4. found 319.2; Rt=1.025 min.

Acid—C 2-(tert-butyl)-6-(cyclobutylamino)isonicotinic Acid

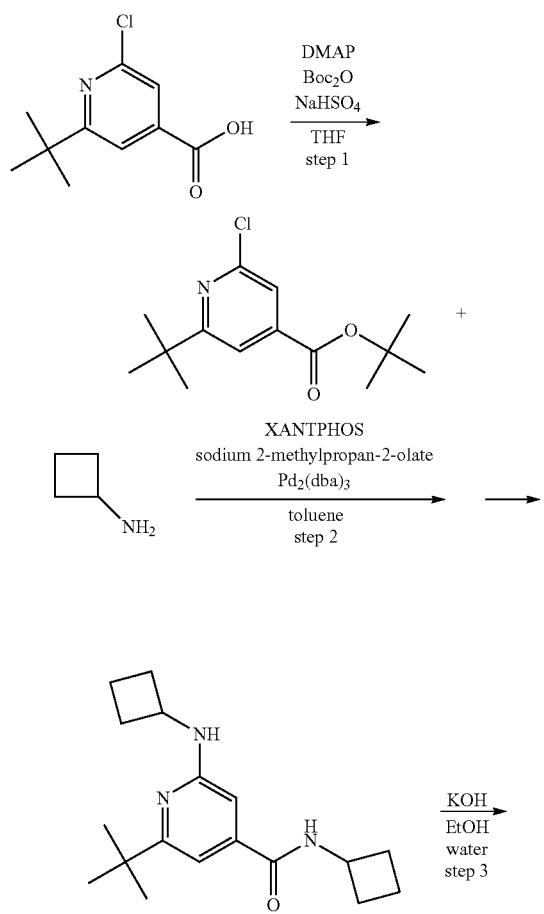

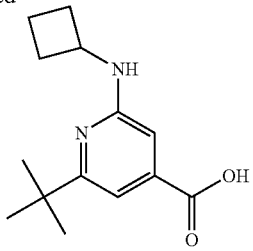

tert-butyl 2-(tert-butyl)-6-chloroisonicotinate. Di-tert-butyl dicarbonate (4.54 g, 20.78 mmol, 4.77 mL) was added to a stirred mixture of 2-tert-butyl-6-chloro-pyridine-4-carboxylic acid (3.7 g, 17.32 mmol) and N,N-dimethylpyridin-4-amine (1.06 g, 8.66 mmol) in THF (50 mL) at 25° C. The reaction mixture was stirred at 25° C. for 12 hr, and evaporated in vacuo. The residue was dissolved in dichloromethane (100 ml) and washed with aqueous sodium hydrogen sulphate (1.46 g, 12.12 mmol) solution (30 ml). The organic layer was separated, dried over sodium sulphate and evaporated in vacuo to afford tert-butyl 2-tert-butyl-6-chloro-pyridine-4-carboxylate (4.4 g, 16.31 mmol, 94.19% yield) as yellow oil. $^1$H NMR (400 MHz, CDCl$_3$) δ (ppm) 1.37 (s, 9H), 1.60 (s, 9H), 7.59 (s, 1H), 7.75 (s, 1H). LCMS(ESI): [M+H]+ m/z: calcd 269.8. found 270.2; Rt=1.826 min.

2-(tert-butyl)-N-cyclobutyl-6-(cyclobutylamino)isonicotinamide. tert-Butyl 2-tert-butyl-6-chloro-pyridine-4-carboxylate (2.50 g, 9.27 mmol) and sodium 2-methylpropan-2-olate (1.34 g, 13.90 mmol) were mixed together in toluene (50 mL). The resulting mixture was evacuated and then backfilled with argon, this operation was repeated three times, then cyclobutanamine (1.98 g, 27.80 mmol, 2.37 mL), [5-(diphenylphosphanyl)-9,9-dimethyl-9H-xanthen-4-yl]diphenylphosphane (268.11 mg, 463.36 umol) and tris(1,5-diphenylpenta-1,4-dien-3-one) dipalladium (212.16 mg, 231.68 umol) were added under argon. The resulting mixture was stirred under argon at 85° C. for 24 hr, then cooled, filtered through short pad of silicagel and the filtrate was evaporated in vacuo to leave 3 g of the crude product (66% purity by LCMS, 2 g of the target compound, and 26% of corresponding acid by LCMS) 2-tert-butyl-N-cyclobutyl-6-(cyclobutylamino)pyridine-4-carboxamide (2 g, 6.64 mmol, 71.60% yield) as brown gum, which was used in the next step without further purification. $^1$H NMR (400 MHz, CDCl$_3$) δ (ppm) 1.28 (s, 9H), 1.75 (m, 6H), 1.90 (m, 2H), 2.43 (m, 6H), 4.15 (m, 1H), 4.53 (m, 1H), 6.40 (s, 1H), 6.75 (s, 1H). LCMS(ESI): [M+H]+ m/z: calcd 301.4. found 302.2; Rt=1.171 min.

2-(tert-butyl)-6-(cyclobutylamino)isonicotinic acid. 2-tert-Butyl-N-cyclobutyl-6-(cyclobutylamino)pyridine-4-carboxamide (3 g, 9.95 mmol) was dissolved in a solution of potassium hydroxide (1.68 g, 29.86 mmol, 821.25 uL) in a mixture of water (5 mL) and ethanol (11 mL). The resulting mixture was stirred with reflux condenser at 90° C. for 48 hr, then cooled and evaporated in vacuo. The residue was diluted with water (50 ml), stirred for 0.25 hr and filtered. The filtercake was washed with water (2*10 ml) and discarded. The filtrate was acidified to pH 5 with concentrated hydrochloric acid. The precipitate was filtered, washed successively with water (2*15 ml) and MTBE (2*20 ml), and dried in vacuo to afford 2-tert-butyl-6-(cyclobutylamino)pyridine-4-carboxylic acid (1.9 g, 7.65 mmol, 76.88% yield) as beige solid. $^1$H NMR (500 MHz, DMSO-d$_6$) δ (ppm) 1.26 (s, 9H), 1.69 (m, 2H), 1.90 (m, 2H), 2.28

(m, 2H), 4.28 (m, 1H), 6.74 (s, 1H), 6.88 (s, 1H), 13.49 (bds, 1H). LCMS(ESI): [M+H]+ m/z: calcd 248.3. found 249.1; Rt=1.018 min.

2-(cyclobutylamino)-6-isobutylisonicotinic Acid

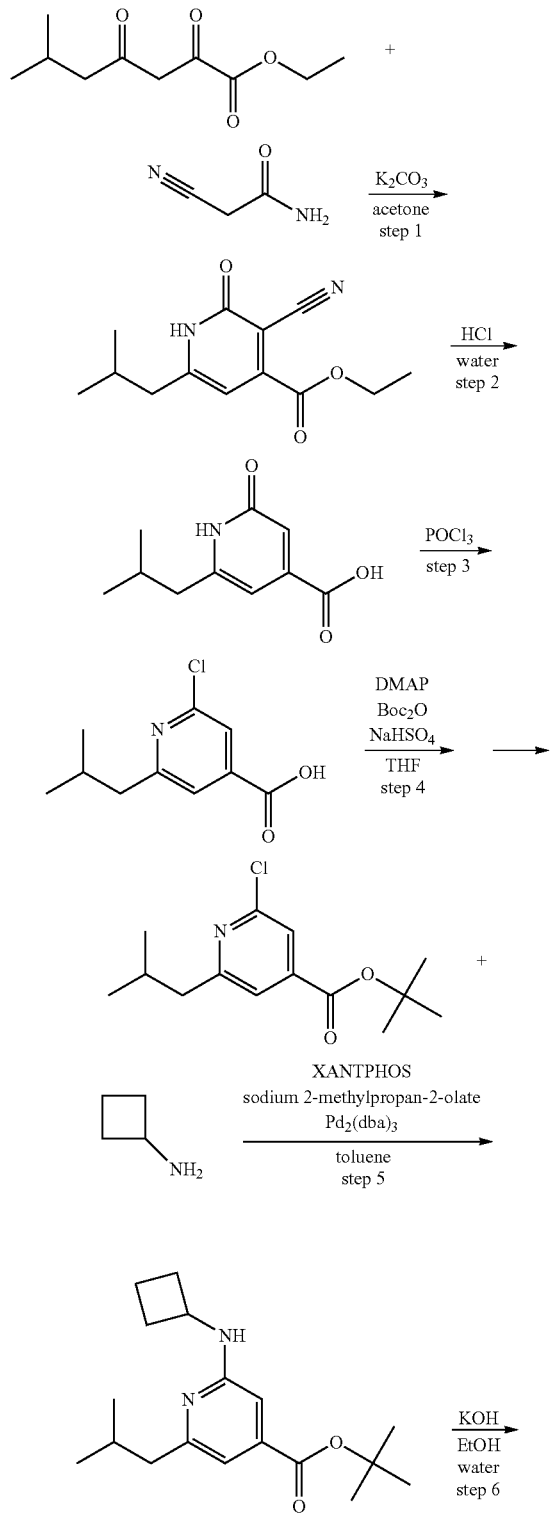

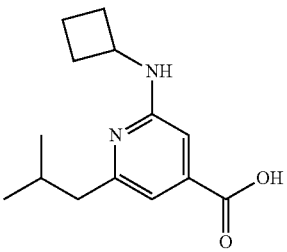

ethyl 3-cyano-6-isobutyl-2-oxo-1,2-dihydropyridine-4-carboxylate. Ethyl 6-methyl-2,4-dioxo-heptanoate (20 g, 99.88 mmol), 2-cyanoacetamide (9.24 g, 109.87 mmol) and potassium carbonate, anhydrous, 99% (20.71 g, 149.83 mmol, 9.04 mL) were mixed together in acetone (400 mL). The resulting mixture was stirred at 55° C. for 12 hr, then cooled down and evaporated in vacuo. The residue was dissolved in water (200 ml) and acidified with concentrated hydrochloric acid to pH 4 (carefully, foaming!). The precipitate was isolated by filtration, washed successively with water (2*50 ml) and MTBE (2*30 ml), and dried in vacuo to afford ethyl 3-cyano-6-isobutyl-2-oxo-1H-pyridine-4-carboxylate (11.5 g, 46.32 mmol, 46.37% yield) as yellow solid. $^1$H NMR (400 MHz, DMSO-$d_6$) δ (ppm) 0.86 (d, 6H), 1.32 (t, 3H), 1.99 (m, 1H), 2.46 (m, 2H), 4.36 (m, 2H), 6.53 (s, 1H), 12.96 (bds, 1H). LCMS(ESI): [M+H]+ m/z: calcd 248.3. found 249.2; Rt=1.140 min.

6-isobutyl-2-oxo-1,2-dihydropyridine-4-carboxylic acid. Ethyl 3-cyano-6-isobutyl-2-oxo-1H-pyridine-4-carboxylate (11.5 g, 46.32 mmol) was added to a mixture of hydrochloric acid, 36% w/w aq. soln. (59.00 g, 582.56 mmol, 50 mL, 36% purity) and water (50 mL). The resulting suspension was stirred at 120° C. for 24 hr, then cooled to 25° C. and diluted with water (100 ml). The precipitate was filtered, washed with water (3*20 ml) and dried in vacuo to afford 2-isobutyl-6-oxo-1H-pyridine-4-carboxylic acid (7.8 g, 39.96 mmol, 86.26% yield) as yellow solid. $^1$H NMR (400 MHz, DMSO-$d_6$) δ (ppm) 0.86 (d, 6H), 1.96 (m, 1H), 2.35 (d, 2H), 6.32 (s, 1H), 6.61 (s, 1H), 12.84 (bds, 2H). LCMS(ESI): [M+H]+ m/z: calcd 195.2. found 196.2; Rt=0.886 min.

2-chloro-6-isobutylisonicotinic acid. 2-isoButyl-6-oxo-1H-pyridine-4-carboxylic acid (7.8 g, 39.96 mmol) was added to phosphoryl chloride (61.26 g, 399.56 mmol, 37.13 mL) and the resulting mixture was stirred at 100° C. for 2 hr, then cooled down and evaporated in vacuo. The residue was diluted with a mixture of crushed ice and water (50/50, 100 g), and the resulting mixture was stirred at 25° C. for 12 hr (over this period of time oily product gradually solidified). The precipitate was filtered, washed with water and dried in vacuo to afford 2-chloro-6-isobutyl-pyridine-4-carboxylic acid (7.5 g, 35.10 mmol, 87.85% yield) as brown solid. $^1$H NMR (500 MHz, DMSO-$d_6$) δ (ppm) 0.86 (d, 6H), 2.05 (m, 1H), 2.66 (d, 2H), 6.63 (s, 1H), 6.64 (s, 1H). LCMS(ESI): [M+H]+ m/z: calcd 213.6. found 214.2; Rt=1.308 min.

tert-butyl 2-chloro-6-isobutylisonicotinate. 2-isoButyl-6-oxo-1H-pyridine-4-carboxylic acid (7.8 g, 39.96 mmol) was added to phosphoryl chloride (61.26 g, 399.56 mmol, 37.13 mL) and the resulting mixture was stirred at 100° C. for 2 hr, then cooled down and evaporated in vacuo. The residue was diluted with a mixture of crushed ice and water (50/50, 100 g), and the resulting mixture was stirred at 25° C. for 12 hr (over this period of time oily product gradually solidified). The precipitate was filtered, washed with water and dried in vacuo to afford 2-chloro-6-isobutyl-pyridine-4-carboxylic acid (7.5 g, 35.10 mmol, 87.85% yield) as brown solid. $^1$H NMR (400 MHz, CDCl₃) δ (ppm) 0.86 (d, 6H), 2.11 (s, 9H), 2.17 (m, 1H), 2.68 (d, 2H), 7.52 (s, 1H), 7.62 (s, 1H). LCMS(ESI): [M+H]+ m/z: calcd 269.8. found 270.2; Rt=1.795 min.

tert-butyl 2-(cyclobutylamino)-6-isobutylisonicotinate. tert-Butyl 2-chloro-6-isobutyl-pyridine-4-carboxylate (2.5 g, 9.27 mmol) and sodium 2-methylpropan-2-olate (1.34 g, 13.90 mmol) were mixed together in toluene (50 mL). The resulting mixture was evacuated and then backfilled with argon, this operation was repeated three times, then cyclobutanamine (1.98 g, 27.80 mmol, 2.37 mL), [5-(diphenylphosphanyl)-9,9-dimethyl-9H-xanthen-4-yl]diphenylphosphane (268.11 mg, 463.36 umol) and tris(1,5-diphenylpenta-1,4-dien-3-one) dipalladium (212.16 mg, 231.68 umol) were added under argon. The resulting mixture was stirred under argon at 85° C. for 24 hr, then cooled, filtered through short pad of silicagel and the filtrate was evaporated in vacuo to leave 3 g of the crude product 70% purity by HNMR (2.1 g of the target compound) tert-butyl 2-(cyclobutylamino)-6-isobutyl-pyridine-4-carboxylate (2.1 g, 6.90 mmol, 74.44% yield), which was used in the next step without further purification. ¹H NMR (400 MHz, CDCl₃) δ (ppm) 0.92 (d, 6H), 1.55 (m, 7H), 1.88 (m, 7H), 2.45 (m, 5H), 4.08 (m, 1H), 6.63 (s, 1H), 6.86 (s, 1H). LCMS(ESI): [M+H]+ m/z: calcd 304.4. found 305.2; Rt=1.433 min.

2-(cyclobutylamino)-6-isobutylisonicotinic acid, tert-Butyl 2-(cyclobutylamino)-6-isobutyl-pyridine-4-carboxylate (3 g, 9.85 mmol) was dissolved in a solution of potassium hydroxide (1.66 g, 29.56 mmol, 813.15 uL) in a mixture of water (5 mL) and ethanol (11 mL). The resulting mixture was stirred with reflux condenser at 90° C. for 48 hr, then cooled and evaporated in vacuo. The residue was diluted with water (50 ml), stirred for 0.25 hr and filtered. The filtercake was washed with water (2*10 ml) and discarded. The filtrate was acidified to pH 5 with concentrated hydrochloric acid. The precipitate was filtered, washed successively with water (2*15 ml) and MTBE (2*20 ml), and dried in vacuo to afford 2-(cyclobutylamino)-6-isobutyl-pyridine-4-carboxylic acid (2 g, 8.05 mmol, 81.73% yield) as beige solid. ¹H NMR (400 MHz, DMSO-d₆) δ (ppm) 0.86 (d, 6H), 1.65 (m, 2H), 1.84 (m, 2H), 1.99 (m, 1H), 2.02 (m, 2H), 2.41 (d, 2H), 4.26 (m, 1H), 6.69 (m, 2H), 6.95 (bds, 1H), 13.11 (bds, 1H). LCMS(ESI): [M+H]+ m/z: calcd 248.2. found 249.2; Rt=0.856 min.

Acid—D 3-(cyclobutylamino)benzoic Acid

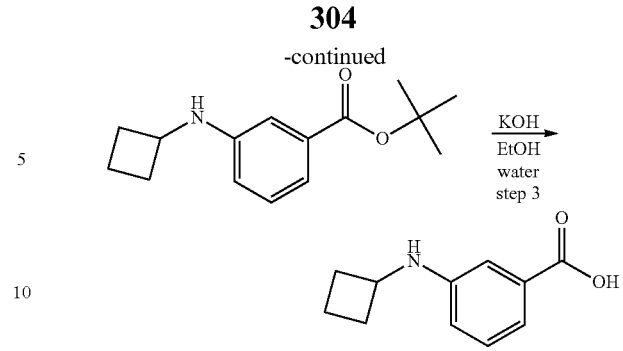

tert-butyl 3-(cyclobutylamino)benzoate. To a solution of tert-butyl 3-bromobenzoate (5 g, 19.45 mmol), cyclobutanamine (5.53 g, 77.78 mmol, 6.64 mL) and sodium tert-butoxide (5.61 g, 58.34 mmol) in toluene (150 mL), 4,5-bis(diphenylphosphino)-9,9-dimethylxanthene (562.59 mg, 972.30 umol) and tris(dibenzylideneacetone)dipalladium (0) (445.17 mg, 486.15 umol) were added under Ar atmosphere. The resulting mixture was heated at 90° C. for 72 hr and evaporated to dryness to obtain tert-butyl 3-(cyclobutylamino)benzoate (10 g, crude), which was used for the next step without purification. ¹H NMR (500 MHz, DMSO-d₆) δ (ppm) 1.15 (s, 9H), 1.50 (m, 1H), 1.69 (m, 3H), 1.80 (m, 2H), 3.81 (m, 1H), 6.47 (d, 1H), 6.96 (t, 1H), 7.14 (m, 2H), 7.23 (m, 1H). LCMS(ESI): [M-tBu]+ m/z: calcd 191.2. found 192.2; Rt=1.129 min.

3-(cyclobutylamino)benzoic acid. To a solution of tert-butyl 3-(cyclobutylamino)benzoate (10 g, 20.22 mmol) in EtOH (70 mL), a solution of potassium hydroxide (3.40 g, 60.65 mmol, 1.67 mL) in water (30 mL) was added. The resulting mixture was heated at 90° C. for 12 hr and evaporated in vacuo. The residue was taken up with water (50 ml) and extracted with DCM (3*50 ml). The pH of aqueous layer was adjusted to 7 with NaHSO₄ and oextracted with DCM (3*50 ml). The combined organic layer was washed with brine (50 ml), dried over Na₂SO₄ and evaporated in vacuo to obtain crude product (1.7 g). The crude product was purified by gradient chromatography using MTBE-DCM as eluent to obtain 3-(cyclobutylamino)benzoic acid (0.62 g, 3.24 mmol, 16.04% yield). ¹H NMR (500 MHz, DMSO-d₆) δ (ppm) 1.83 (m, 4H), 2.34 (m, 2H), 3.84 (m, 1H), 6.00 (bds, 1H), 6.67 (d, 1H), 7.10 (m, 3H), 12.44 (bds, 1H). LCMS(ESI): [M+H]+ m/z: calcd 191.2. found 192.2; Rt=1.152 min.

3-(oxetan-3-ylamino)benzoic Acid

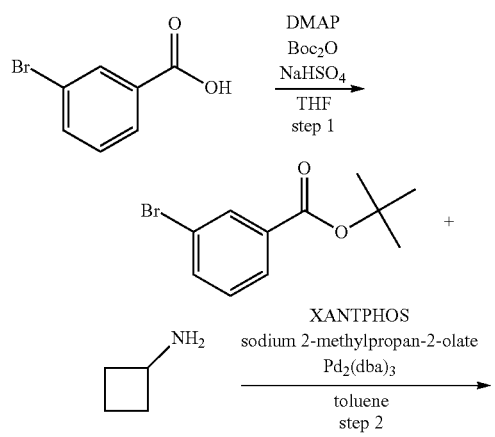

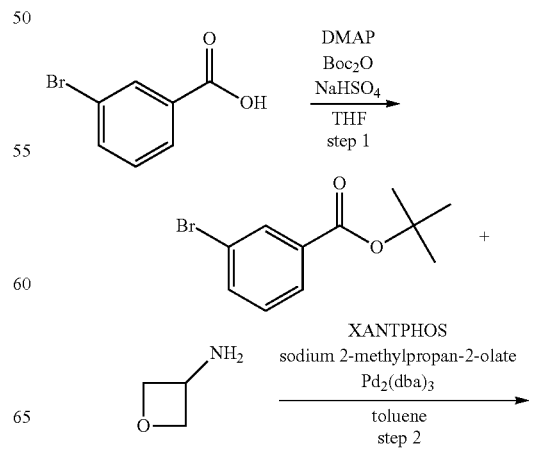

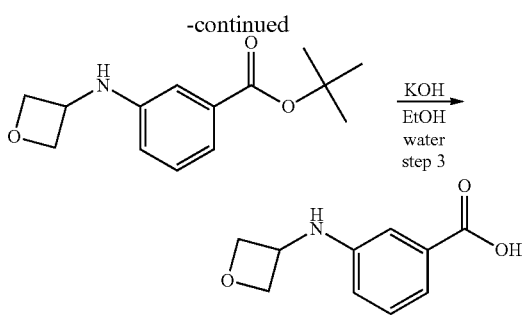

tert-butyl 3-(oxetan-3-ylamino)benzoate. To a solution of tert-butyl 3-bromobenzoate (5 g, 19.45 mmol), oxetan-3-amine (4.26 g, 58.34 mmol) and sodium tert-butoxide (5.61 g, 58.34 mmol) in toluene (100 mL), 4,5-bis(diphenylphosphino)-9,9-dimethylxanthene (562.59 mg, 972.30 umol) and tris(dibenzylideneacetone)dipalladium (0) (445.17 mg, 486.15 umol) were added under Ar atmosphere. The resulting mixture was heated at 75° C. for 24 hr and evaporated to dryness to obtain tert-butyl 3-(oxetan-3-ylamino)benzoate (10 g, crude), which was used for the next step without purification. $^1$H NMR (500 MHz, DMSO-$d_6$) δ (ppm) 1.51 (s, 9H), 4.41 (d, 2H), 4.52 (m, 1H), 4.83 (d, 2H), 6.67 (d, 1H), 7.03 (m, 1H), 7.18 (m, 2H), 7.46 (d, 1H). LCMS(ESI): [M-tBu]+ m/z: calcd 193.1. found 194.2; Rt=1.214 min.

3-(oxetan-3-ylamino)benzoic acid. To a solution of tert-butyl 3-(oxetan-3-ylamino)benzoate (10 g, 12.03 mmol) in EtOH (70 mL), a solution of potassium hydroxide (2.03 g, 36.10 mmol, 992.94 uL) in water (30 mL) was added. The resulting mixture was heated at 70° C. for 3 hr and evaporated in vacuo. The residue was taken up with water (50 ml) and extracted with DCM (3*50 ml). The pH of aqueous layer was adjusted to 7 with NaHSO$_4$ and extracted with DCM (3*50 ml). The combined organic layer was washed with brine (50 ml), dried over Na$_2$SO$_4$ and evaporated in vacuo to obtain crude product (2.5 g). The crude product was purified by gradient chromatography using MTBE-DCM as eluent to obtain 3-(oxetan-3-ylamino)benzoic acid (0.64 g, 3.31 mmol, 27.53% yield). $^1$H NMR (500 MHz, DMSO-$d_6$) δ (ppm) 4.42 (d, 2H), 4.55 (m, 1H), 4.85 (d, 2H), 6.53 (d, 1H), 6.65 (m, 1H), 7.02 (s, 1H), 7.15 (m, 2H), 12.52 (bds, 1H). LCMS(ESI): [M+H]+ m/z: calcd 193.2. found 194.2; Rt=0.842 min.

Acid—E 6-(cycloheptylamino)pyrimidine-4-carboxylic Acid

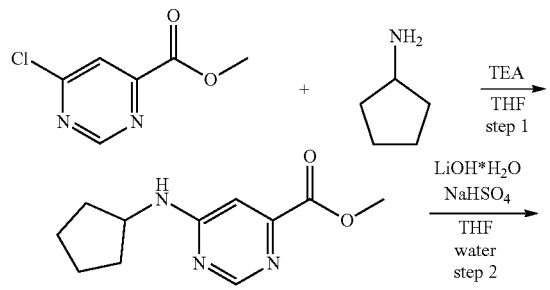

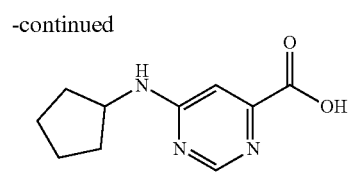

methyl 6-(cyclopentylamino)pyrimidine-4-carboxylate. A solution of methyl 6-chloropyrimidine-4-carboxylate (2.5 g, 14.49 mmol), cyclopentylamine (1.36 g, 15.94 mmol, 1.57 mL) and triethylamine (4.40 g, 43.46 mmol, 6.06 mL) in THF (50 mL) was heated at 66° C. for 72 hr. The resulting mixture was evaporated in vacuo, the residue was taken up with water (70 ml) and extracted with DCM (2*50 ml). The combined organic layer was washed with brine (2*50 ml), dried over Na$_2$SO$_4$ and evaporated in vacuo to give methyl 6-(cyclopentylamino)pyrimidine-4-carboxylate (3.1 g, 14.01 mmol, 96.71% yield). $^1$H NMR (500 MHz, CDCl$_3$) δ (ppm) 1.50 (m, 2H), 1.70 (m, 4H), 2.06 (m, 2H), 3.95 (s, 3H), 5.56 (m, 1H), 7.07 (s, 1H), 8.61 (s, 1H). LCMS(ESI): [M+H]+ m/z: calcd 221.3. found 222.2; Rt=0.923 min.

6-(cxclopentylamino)pyrimidine-4-carboxylic acid. To a solution of methyl 6-(cyclopentylamino)pyrimidine-4-carboxylate (3.1 g, 14.01 mmol) in THF (50 mL) was added a solution of lithium hydroxide, monohydrate (1.29 g, 30.82 mmol, 856.62 uL) in water (50 mL). The resulting mixture was stirred at 25° C. for 3 hr and THF was evaporated in vacuo. Aqueous solution was washed with DCM (2*50 ml) and pH was adjusted to 6 with sodium bisulfate (3.87 g, 32.23 mmol). The formed precipitate was filtered, washed with cold water (10 ml) and dried to obtain 6-(cyclopentylamino)pyrimidine-4-carboxylic acid (1.7 g, 8.20 mmol, 58.55% yield). NMR (500 MHz, DMSO-A δ (ppm) 1.46 (m, 2H), 1.55 (m, 2H), 1.68 (m, 2H), 1.93 (m, 2H), 4.30 (m, 1H), 7.02 (s, 1H), 8.28 (bds, 1H), 8.49 (s, 1H), 12.43 (bds, 1H). LCMS(ESI): [M+H]+ m/z: calcd 207.2. found 208.2; Rt=0.854 min.

6-(cyclohexylamino)pyrimidine-4-carboxylic Acid

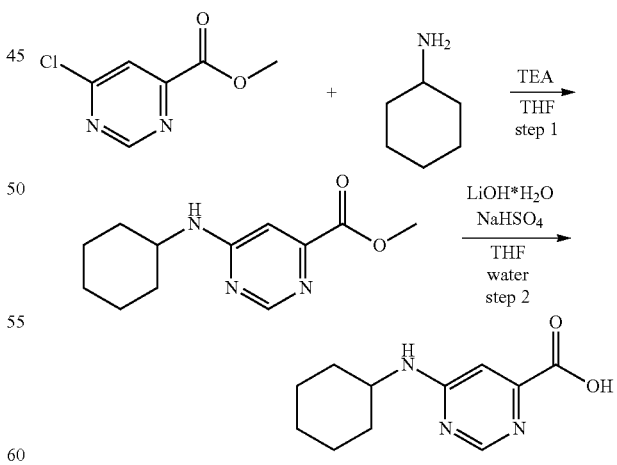

methyl 6-(cyclohexylamino)pyrimidine-4-carboxylate. A solution of methyl 6-chloropyrimidine-4-carboxylate (2.5 g, 14.49 mmol), cyclohexylamine (1.51 g, 15.21 mmol, 1.74 mL) and triethylamine (2.93 g, 28.97 mmol, 4.04 mL) in THF (50 mL) was heated at 65° C. for 48 hr. The resulting mixture was evaporated in vacuo, the residue was taken up with water (70 ml) and extracted with DCM (2*50 ml). The combined organic layer was washed with brine (2*50 ml), dried over Na₂SO₄ and evaporated in vacuo to give methyl 6-(cyclohexylamino)pyrimidine-4-carboxylate (3.4 g, 14.45 mmol, 99.75% yield). ¹H NMR (400 MHz, CDCl₃) δ (ppm) 1.22 (m, 4H), 1.39 (m, 2H), 1.62 (m, 1H), 1.73 (m, 2H), 2.01 (m, 2H), 3.95 (s, 3H), 5.22 (m, 1H), 7.02 (s, 1H), 8.60 (s, 1H). LCMS(ESI): [M+H]+ m/z: calcd 235.3; found 236.2; Rt=0.939 min.

6-(cyclohexylamino)pyrimidine-4-carboxylic acid. To a solution of methyl 6-(cyclohexylamino)pyrimidine-4-carboxylate (3.4 g, 14.45 mmol) in THF (50 mL) was added a solution of lithium hydroxide, monohydrate (1.33 g, 31.79 mmol, 883.51 uL) in water (50 mL). The resulting mixture was stirred at 25° C. for 3 hr and THF was evaporated in vacuo. Aqueous solution was washed with DCM (2*50 ml) and pH was adjusted to 6 with sodium bisulfate monohydrate (4.59 g, 33.24 mmol). The formed precipitate was filtered, washed with cold water (10 ml) and dried to obtain 6-(cyclohexylamino)pyrimidine-4-carboxylic acid (2.33 g, 10.53 mmol, 72.87% yield). ¹H NMR (400 MHz, DMSO-d₆) δ (ppm) 1.30 (m, 5H), 1.59 (m, 1H), 1.71 (m, 2H), 1.88 (m, 2H), 3.89 (m, 1H), 7.03 (s, 1H), 8.16 (bds, 1H), 8.48 (s, 1H), 12.44 (bds, 1H). LCMS(ESI): [M+H]+ m/z: calcd 221.3. found 222.2; Rt=0.927 min.

6-(cyclobutylamino)pyrimidine-4-carboxylic Acid

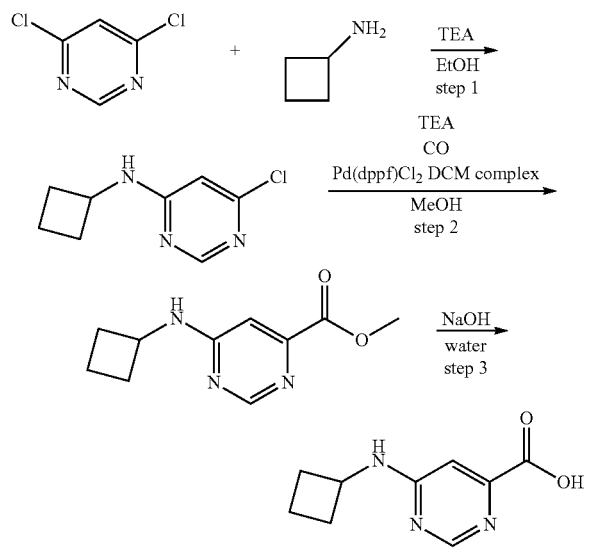

6-chloro-N-cyclobutylpyrimidin-4-amine. 4,6-Dichloropyrimidine (50 g, 335.62 mmol), TEA (50.94 g, 503.43 mmol, 70.17 mL) were dissolved in EtOH (500 mL) and cyclobutanamine (26.26 g, 369.18 mmol, 31.52 mL) was added. The mixture was stirred for 30 min (spontaneous heating was observed) and then for 3 hr at 80° C. The reaction mixture was cooled to r.t. and evaporated in vacuo at 50° C. The residue was triturated with H₂O (0.5 L). The precipitate was filtered, washed with H₂O (3*300 mL) and dried at 40° C. to give 6-chloro-A-cyclobutyl-pyrimidin-4-amine (56 g, 304.95 mmol, 90.86% yield). ¹H NMR (400 MHz, DMSO-d₆) δ (ppm) 1.68 (m, 2H), 1.89 (m, 2H), 2.25 (m, 2H), 4.40 (m, 1H), 6.43 (s, 1H), 7.98 (bds, 1H), 8.23 (s, 1H). LCMS(ESI): [M+H]+ m/z: calcd 183.6. found 184.2; Rt=1.161 min.

methyl 6-(cyclobutylamino)pyrimidine-4-carboxylate. 6-Chloro-A-cyclobutyl-pyrimidin-4-amine (5 g, 27.23 mmol), TEA (8.27 g, 81.68 mmol, 11.38 mL), [1,1'-bis(diphenylphosphino)ferrocene]dichloropalladium(II), complex with dichloromethane (222.34 mg, 272.28 umol) were dissolved in methanol (250 mL). The mixture was stirred in autoclave at 115° C. in atmosphere of CO (872.42 mg, 27.23 mmol) (40 atm) for 40 hr. Then the reaction mixture was cooled to r.t. and the solvent was evaporated in vacuo at 40° C. EtOAc (200 mL) was added and the mixture was extracted with H₂O (3*50 mL). The organic phase was separated, dried with Na₂SO₄ and evaporated in vacuo to give methyl 6-(cyclobutylamino)pyrimidine-4-carboxylate (4.55 g, 21.96 mmol, 80.64% yield). ¹H NMR (400 MHz, DMSO-d₆) δ (ppm) 1.70 (m, 2H), 1.90 (m, 2H), 2.28 (m, 2H), 3.83 (s, 3H), 4.42 (m, 1H), 7.03 (s, 1H), 8.07 (bds, 1H), 8.48 (s, 1H). LCMS(ESI): [M+H]+ m/z: calcd 207.2. found 208.2; Rt=0.797 min.

6-(cyclobutylamino)pyrimidine-4-carboxylic acid. Methyl 6-(cyclobutylamino)pyrimidine-4-carboxylate (1 g, 4.83 mmol) was added to the solution of sodium hydroxide (212.31 mg, 5.31 mmol, 99.68 uL) in H₂O (5 mL). The mixture was stirred at 50° C. for 1 hr. Then the mixture was cooled to r.t. The insoluble materials were filtered off. The filtrate was acidified to pH=3. The solid formed was filtered, washed with H₂O (3*5 mL) and dried in vacuo at 45° C. to give 6-(cyclobutylamino)pyrimidine-4-carboxylic acid (0.7 g, 3.05 mmol, 63.16% yield, HCl). ¹H NMR (500 MHz, DMSO-d₆) δ (ppm) 1.72 (m, 2H), 1.94 (m, 2H), 2.28 (m, 2H), 4.46 (m, 1H), 6.99 (s, 1H), 8.49 (m, 2H), 12.12 (bds, 1H). LCMS(ESI): [M+H]+ m/z: calcd 193.2. found 194.2; Rt=0.790 min.

6-((1-acetylpiperidin-4-yl)amino)pyrimidine-4-carboxylic Acid

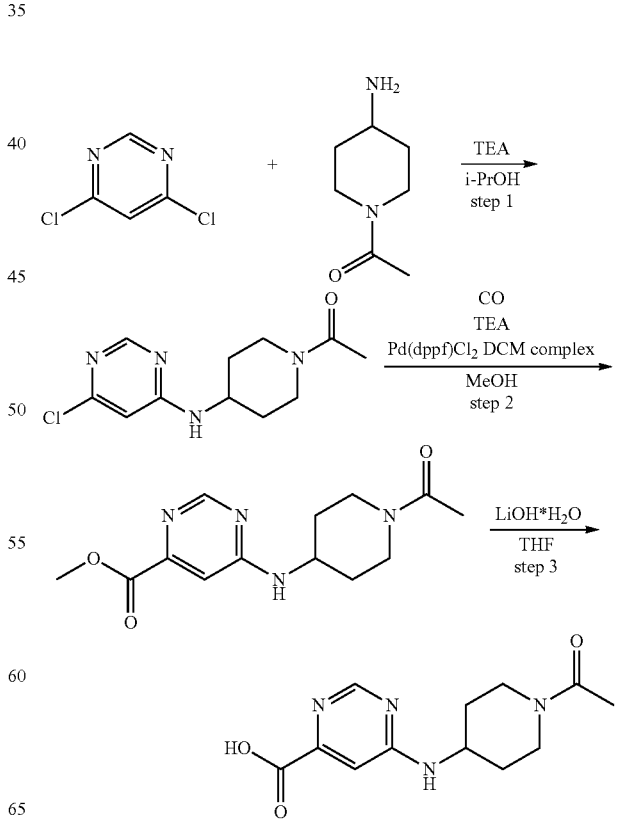

1-(4-((6-chloropyrimidin-4-yl)amino)piperidin-1-yl)ethenone. 4,6-Dichloropyrimidine (26.2 g, 175.86 mmol), 1-(4-amino-1-piperidyl)ethanone (25.01 g, 175.86 mmol), triethylamine (21.35 g, 211.04 mmol, 29.41 mL) were mixed in isopopanol (300 mL) and refluxed for 10 hr. Then the mixture was cooled to r.t. and evaporated in vacuo. EtOAc (300 mL) was added to the residue and the mixture was extracted with aqueous NaCl (5*100 mL). The organic phase was separated, dried with $Na_2SO_4$ and evaporated in vacuo at 45° C. to give 1-[4-[(6-chloropyrimidin-4-yl)amino]-1-piperidyl]ethanone (41.3 g, 162.14 mmol, 92.20% yield). NMR (500 MHz, $CDCl_3$) δ 1.42 (m, 2H), 2.03 (m, 1H), 2.12 (m, 4H), 2.83 (m, 1H), 3.23 (m, 1H), 3.82 (m, 1H), 4.01 (bds, 1H), 4.55 (m, 1H), 5.26 (m, 1H), 6.37 (s, 1H), 8.35 (s, 1H). LCMS(ESI): [M+H]+ m/z: calcd 254.7. found 255.2; Rt=0.924 min.

methyl 6-((1-acetylpiperidin-4-yl)amino)pyrimidine-4-carboxylate. i-[4-[(6-Chloropyrimidin-4-yl)amino]-1-piperidyl]ethanone (41 g, 160.96 mmol), triethylamine (48.86 g, 482.89 mmol, 67.31 mL), [1,1'-bis(diphenylphosphino)ferrocene]dichloropalladium(II), complex with dichloromethane (6.57 g, 8.05 mmol) were dissolved in methanol (500 mL). The mixture was stirred in autoclave at 110° C. in atmosphere of carbon monoxide (40 atm) for 20 hr. Then the reaction mixture was cooled to r.t. and the solvent was evaporated in vacuo at 40° C. to give the mixture of methyl 6-[(1-acetyl-4-piperidyl)amino]pyrimidine-4-carboxylate and triethylamine hydrochloride, which was purified by column chromatography to give methyl 6-[(1-acetyl-4-piperidyl)amino]pyrimidine-4-carboxylate (18.7 g, 67.19 mmol, 41.74% yield). $^1$H NMR (500 MHz, $CDCl_3$) δ 1.43 (m, 2H), 2.03 (m, 1H), 2.11 (s, 3H), 2.17 (m, 1H), 2.82 (t, 1H), 3.24 (t, 1H), 3.85 (m, 1H), 3.96 (s, 3H), 4.12 (bds, 1H), 4.57 (m, 1H), 5.47 (m, 1H), 7.08 (s, 1H), 8.65 (s, 1H). LCMS(ESI): [M+H]+ m/z: calcd 278.3. found 279.2; Rt=0.788 min.

6-((1-acetylpiperidin-4-yl)amino)pyrimidine-4-carboxylic acid. Methyl 6-[(1-acetyl-4-piperidyl)amino]pyrimidine-4-carboxylate (18.7 g, 67.19 mmol) was dissolved in THF (200 mL). The solution was cooled to 0° C. and lithium hydroxide, monohydrate (2.82 g, 67.19 mmol, 1.87 mL) was added. The mixture was warmed to 20° C. and stirred for 2 hr. The mixture was cooled to 0° C. and conc. HCl was added to pH 2-3. The solvents were evaporated in vacuo at 45° C. The residue was triturated with MeCN (100 mL). The solid formed was filtered, washed with MeCN (100 mL) and dried in vacuo at 45° C. to give 6-[(1-acetyl-4-piperidyl)amino]pyrimidine-4-carboxylic acid (16.5 g, 62.43 mmol, 92.92% yield). $^1$H NMR (500 MHz, DMSO-$d_6$) δ 1.28 (m, 1H), 1.42 (m, 1H), 1.87 (m, 2H), 2.00 (s, 3H), 2.79 (t, 1H), 3.17 (t, 1H), 3.80 (m, 1H), 4.12 (m, 1H), 4.20 (m, 1H), 7.09 (s, 1H), 8.40 (bds, 1H), 8.49 (s, 1H). LCMS(ESI): [M+H]+ m/z: calcd 264.3. found 265.0; Rt=0.574 min.

Acid—F 2-(cyclohexylamino)isonicotinic Acid

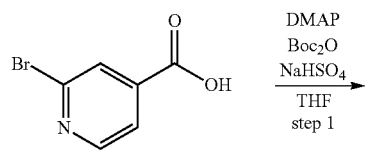

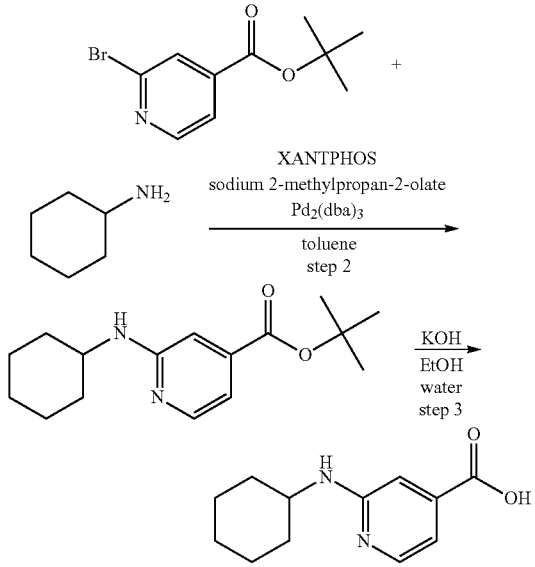

tert-butyl 2-bromoisonicotinate. Di-tert-butyl dicarbonate (7.13 g, 32.67 mmol, 7.50 mL) was added to a stirred mixture of 2-bromopyridine-4-carboxylic acid (5.5 g, 27.23 mmol) and N,N-dimethylpyridin-4-amine (1.66 g, 13.61 mmol) in THF (100 mL) at 25° C. The reaction mixture was stirred at 25° C. for 12 hr, and evaporated in vacuo. The residue was dissolved in dichloromethane (100 ml) and washed successively with aqueous sodium hydrogen sulphate (2.29 g, 19.06 mmol) solution (40 ml) and water (50 ml). The organic layer was separated, dried over sodium sulphate and evaporated in vacuo to afford tert-butyl 2-bromopyridine-4-carboxylate (6.6 g, 25.57 mmol, 93.92% yield) as light-yellow oil. $^1$H NMR (500 MHz, $CDCl_3$) δ (ppm) 1.60 (s, 9H), 7.27 (d, 1H), 7.97 (s, 1H), 8.50 (d, 1H). LCMS(ESI): [M+H]+ m/z: calcd 258.1. found 258.0; Rt=1.513 min.

tert-butyl 2-(cyclohexylamino)isonicotinate. tert-Butyl 2-bromopyridine-4-carboxylate (3.5 g, 13.56 mmol) and sodium 2-methylpropan-2-olate (1.95 g, 20.34 mmol) were mixed together in toluene (50 mL). The resulting mixture was evacuated and then backfilled with argon, this operation was repeated three times, then cyclohexane amine (4.03 g, 40.68 mmol, 4.65 mL), [5-(diphenylphosphanyl)-9,9-dimethyl-9H-xanthen-4-yl]diphenylphosphane (392.31 mg, 678.00 umol) and tris(1,5-diphenylpenta-1,4-dien-3-one) dipalladium (310.43 mg, 339.00 umol) were added under argon. The reaction mixture was stirred under argon at 90° C. for 12 hr, then cooled and evaporated in vacuo to leave 7 g of the crude product (67.31% purity by LCMS, approximately 2.5 g of the target compound) tert-butyl 2-(cyclohexylamino)pyridine-4-carboxylate (2.5 g, 9.05 mmol, 66.71% yield) as brown gum, which was used directly in the next step. $^1$H NMR (500 MHz, $CDCl_3$) δ (ppm) 1.24 (m, 3H), 1.40 (m, 2H), 1.56 (s, 9H), 1.72 (m, 3H), 2.01 (m, 2H), 3.59 (m, 1H), 6.86 (d, 1H), 6.96 (s, 1H), 7.16 (bds, 1H), 8.11 (d, 1H). LCMS(ESI): [M+H]+ m/z: calcd 276.4. found 277.2; Rt=1.227 min.

2-(cyclohexylamino)isonicotinic acid, tert-Butyl 2-(cyclohexylamino)pyridine-4-carboxylate (7 g, 25.33 mmol) (crude from previous step, 67.31% purity by LCMS, approximately 2.5 g of the target compound) was dissolved in a solution of potassium hydroxide (4.00 g, 71.29 mmol, 1.96 mL) in a mixture of water (10 mL) and ethanol (30 mL).

The resulting mixture was stirred with reflux condenser at 90° C. for 12 hr, then cooled and evaporated in vacuo. The residue was diluted with water (50 ml), stirred for 0.25 hr and filtered. The filtercake was washed with water (2*20 ml) and discarded. The filtrate was acidified to pH 5 with 6N aqueous hydrochloric acid. The precipitate was filtered, washed successively with water (2*10 ml) and MTBE (2*10 ml), and dried in vacuo at 70° C. to afford 2-(cyclohexylamino)pyridine-4-carboxylic acid (2.1 g, 9.53 mmol, 37.64% yield) as brown solid. NMR (400 MHz, DMSO-$d_6$) δ (ppm) 1.54 (m, 3H), 1.65 (m, 2H), 1.74 (m, 1H), 1.88 (m, 2H), 1.90 (m, 2H), 3.70 (m, 1H), 6.68 (d, 1H), 6.79 (bds, 1H), 6.95 (s, 1H), 8.05 (d, 1H), 12.58 (bds, 1H). LCMS (ESI): [M+H]+ m/z: calcd 220.3. found 221.2; Rt=0.824 min.

4-(cyclobutylamino)picolinic Acid

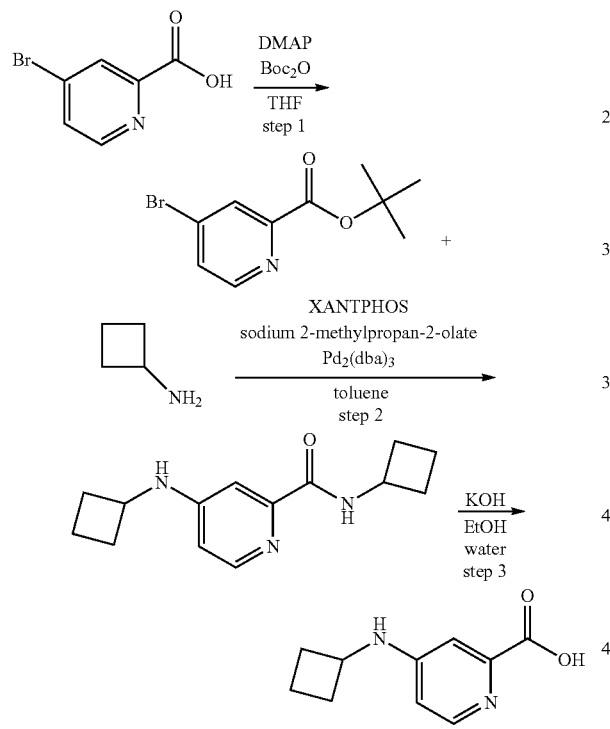

tert-butyl 4-bromopicolinate. 4-Bromopyridine-2-carboxylic acid (6.26 g, 31.01 mmol) and 4-dimethylaminopyridine (1.89 g, 15.50 mmol) were dissolved in THF (120 mL). Di-tert-butyl dicarbonate (8.80 g, 40.31 mmol, 9.25 mL) was added dropwise during 10 minutes. Solution was stirred at 20° C. for 16 hr. After that, excess of boc$_2$O was destroyed with few ml of water. When CO$_2$ evolution ceased, the solvent was distilled off under reduced pressure. Residue was dissolved in MTBE (150 ml) and washed successively with 5-% NaHSO$_4$ (100 ml), water (100 ml), 5-% NaHCO$_3$ (50 ml) and brine. Then it was dried over Na$_2$SO$_4$ end evaporated in vacuo affording tert-butyl 4-bromopyridine-2-carboxylate (7.78 g, 30.16 mmol, 97.25% yield). $^1$H NMR (500 MHz, DMSO-$d_6$) δ (ppm) 1.64 (s, 9H), 7.61 (d, 1H), 8.20 (s, 1H), 8.56 (d, 1H). GCMS: [M]: calcd 258.1. found 258.0; Rt=8.149 min.

N-cyclobutyl-4-(cyclobutylamino)picolinamide. tert-Butyl 4-bromopyridine-2-carboxylate (6.78 g, 26.27 mmol) and sodium tert-butoxide (3.79 g, 39.40 mmol) was dissolved in toluene (120 mL). Reaction flask was evacuated and refilled with argon 3 times. Then, cyclobutylamine (5.60 g, 78.80 mmol, 6.73 mL) and tris(dibenzylideneacetone) dipalladium(0) (601.34 mg, 656.69 umol) with 4,5-bis(diphenylphosphino)-9,9-dimethylxanthene (759.95 mg, 1.31 mmol) were added under stream of argon. Obtained mixture was stirred at 110° C. for 72 hr. After that, reaction mixture was diluted with benzene (150 ml) and washed with water (150 ml). Then, dioxane-HCl was added dropwise, until strongly acidic media formed. When gummy precipitate settled down, supernatant solution was decanted and residue was rinsed with benzene. Obtained crude hydrochloride was dissolved in water (150 ml) and filtered through pad of cotton wool. Then, solution was basified with solid potassium carbonate to pH-9 and extracted with DCM(2×50 ml). After drying over Na$_2$SO$_4$, it was evaporated in vacuo affording A-cyclobutyl-4-(cyclobutylamino)pyridine-2-carboxamide (3.56 g, crude). $^1$H NMR (400 MHz, CDCl$_3$) δ (ppm) 1.82 (m, 6H), 2.01 (m, 2H), 2.40 (m, 4H), 3.98 (m, 1H), 4.55 (m, 2H), 6.40 (m, 1H), 7.28 (s, 1H), 8.07 (d, 1H), 8.14 (m, 1H). LCMS(ESI): [M+H]+ m/z: calcd 245.3. found 246.2; Rt=0.927 min.

4-(cyclobutylamino)picolinic acid. A-cyclobutyl-4-(cyclobutylamino)pyridine-2-carboxamide (3.56 g, 14.51 mmol) was dissolved in ethanol (30 mL) and solution of potassium hydroxide (12.21 g, 217.68 mmol, 5.99 mL) in water (20 mL) was added. The mixture was stirred at 90° C. during 120 hr. Most of ethanol was distilled off under redused pressure. Residue was diluted with water (100 ml) and all insoluble stuff was filtered off. Then 6N hydrochloric acid was added dropwise until ph become 2-3. Solution was evaporated to dryness under reduced pressure, and washed out from inorganic salt by hot isopropyl alcohol (100 ml). Solvent was removed in vacuo and residue was subjected to column chromatography affording 4-(cyclobutylamino)pyridine-2-carboxylic acid (1.1 g, 5.72 mmol, 39.44% yield) as a mixture of freebase and hydrochloride. $^1$H NMR (400 MHz, DMSO-$d_6$) δ (ppm) 1.78 (m, 2H), 2.03 (m, 2H), 2.37 (m, 2H), 4.19 (m, 1H), 6.82 (d, 1H), 7.53 (s, 1H), 8.12 (m, 1H), 9.65 (d, 1H), 13.34 (bds, 1H). LCMS(ESI): [M+H]+ m/z: calcd 192.2. found 193.2; Rt=0.729 min.

5-((tetrahydrofuran-3-yl)amino)nicotinic Acid

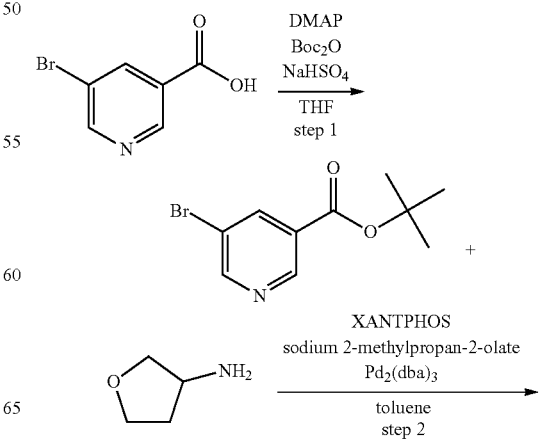

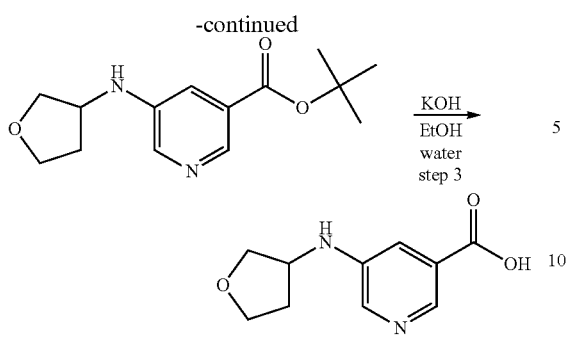

tert-butyl 5-bromonicotinate. Di-tert-butyl dicarbonate (7.72 g, 35.40 mmol, 8.12 mL) was added to a stirred mixture of 5-bromopyridine-3-carboxylic acid (5.5 g, 27.23 mmol) and N,N-dimethylpyridin-4-amine (1.66 g, 13.61 mmol) in THF (100 mL) at 25° C. The reaction mixture was stirred at 25° C. for 12 hr, and evaporated in vacuo. The residue was dissolved in dichloromethane (100 ml) and washed successively with aqueous sodium hydrogen sulphate (1.80 g, 14.97 mmol) solution (40 ml), and water (50 ml). The organic layer was separated, dried over sodium sulphate and evaporated in vacuo to afford tert-butyl 5-bromopyridine-3-carboxylate (6.4 g, 24.80 mmol, 91.07% yield) as white solid. $^1$H NMR (500 MHz, CDCl$_3$) δ (ppm) 1.61 (s, 9H), 8.36 (s, 1H), 8.81 (s, 1H), 9.07 (s, 1H). LCMS(ESI): [M+H]+ m/z: calcd 258.1. found 258.0; Rt=1.508 min.

tert-butyl 5-(((tetrahydrofuran-3-yl)amino)nicotinate. tert-Butyl 5-bromopyridine-3-carboxylate (2.5 g, 9.69 mmol) and sodium 2-methylpropan-2-olate (1.40 g, 14.53 mmol) were mixed together in toluene (50 mL). The resulting mixture was evacuated and then backfilled with argon, this operation was repeated three times, then tetrahydrofuran-3-amine (2.53 g, 29.06 mmol, 2.48 mL), [5-(diphenylphosphanyl)-9,9-dimethyl-9H-xanthen-4-yl]diphenylphosphane (280.22 mg, 484.29 umol) and tris(1,5-diphenylpenta-1,4-dien-3-one) dipalladium (221.74 mg, 242.14 umol) were added under argon. The reaction mixture was stirred under argon at 90° C. for 12 hr, then cooled and evaporated in vacuo to leave 5.6 g of the crude product (90% purity by HNMR, 48.45% by LCMS, and 36.22% of corresponding acid by LCMS, approximately 2.3 g of the target compound) tert-butyl 5-(tetrahydrofuran-3-ylamino)pyridine-3-carboxylate (2.3 g, 8.70 mmol, 89.84% yield) as yellow solid, which was used directly in the next step. $^1$H NMR (500 MHz, CDCl$_3$) δ (ppm) 1.58 (s, 9H), 1.89 (m, 1H), 2.35 (m, 1H), 3.75 (m, 1H), 3.88 (m, 1H), 3.99 (m, 3H), 4.14 (m, 1H), 7.41 (s, 1H), 8.14 (s, 1H), 8.53 (s, 1H). LCMS(ESI): [M+H]+ m/z: calcd 264.3. found 265.2; Rt=1.041 min.

5-((tetrahydrofuran-3-yl)amino)nicotinic acid. tert-Butyl 5-(tetrahydrofuran-3-ylamino)pyridine-3-carboxylate (5.6 g, 21.19 mmol) (crude from previous step 85.39% purity by LCMS, approximately 2.05 g of the target compound) was dissolved in a solution of potassium hydroxide (4 g, 71.29 mmol, 1.96 mL) in a mixture of water (10 mL) and ethanol (30 mL). The resulting mixture was stirred with reflux condenser at 80° C. for 5 hr, then cooled and evaporated in vacuo. The residue was diluted with water (50 ml), stirred for 0.25 hr and filtered. The filtercake was washed with water (2*20 ml) and discarded. The filtrate was acidified to pH 5 with concentrated hydrochloric acid. The resulting clear solution was evaporated to dryness in vacuo, the residue was diluted with hot isopropanol (50° C., 100 ml) and stirred for 0.1 hr. The inorganic salts was filtered and discarded, the filtrate was evaporated and dried in vacuo to afford 5-(tetrahydrofuran-3-ylamino)pyridine-3-carboxylic acid (1.1 g, 5.28 mmol, 24.94% yield) as light-brown solid, which was used in the next step without further purification. $^1$H NMR (500 MHz, DMSO-d$_6$) δ (ppm) 1.78 (m, 1H), 2.21 (m, 1H), 3.59 (m, 1H), 3.74 (m, 1H), 3.87 (m, 2H), 4.14 (m, 1H), 7.12 (bds, 1H), 7.76 (s, 1H), 8.21 (s, 1H), 8.34 (s, 1H), 13.35 (bds, 1H). LCMS(ESI): [M+H]+ m/z: calcd 208.2. found 209.2; Rt=0.517 min.

2-(cyclobutylamino)-5-fluoroisonicotinic Acid

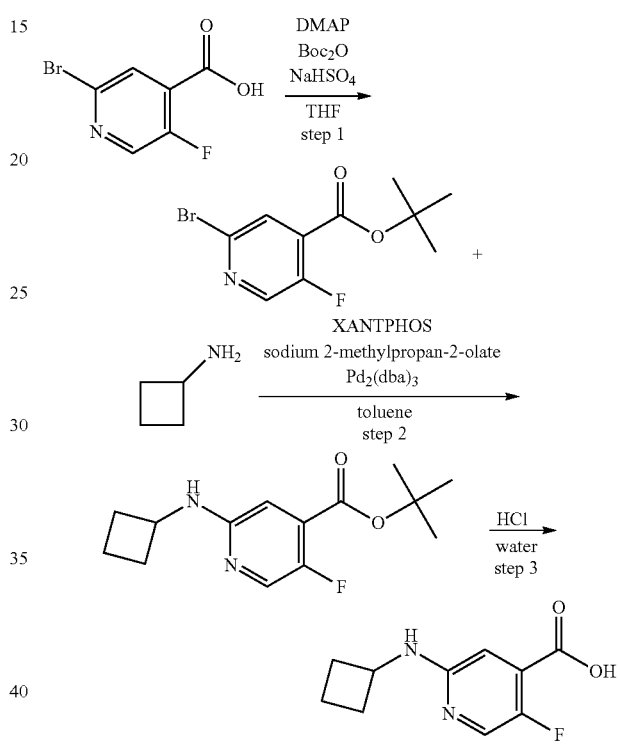

tert-butyl 2-bromo-5-fluoroisonicotinate. Di-tert-butyl dicarbonate (8.10 g, 37.09 mmol, 8.51 mL) was added to a stirred mixture of 2-bromo-5-fluoro-pyridine-4-carboxylic acid (6.8 g, 30.91 mmol) and N,N-dimethylpyridin-4-amine (1.89 g, 15.45 mmol) in THF (100 mL) at 25° C. The reaction mixture was stirred at 40° C. for 1 hr, and evaporated in vacuo. The residue was dissolved in dichloromethane (100 ml) and washed successively with aqueous sodium hydrogen sulphate (2.60 g, 21.64 mmol) solution (40 ml) and water (50 ml). The organic layer was separated, dried over sodium sulphate and evaporated in vacuo to afford tert-butyl 2-bromo-5-fluoro-pyridine-4-carboxylate (8.2 g, 29.70 mmol, 96.08% yield) as light-brown solid. $^1$H NMR (500 MHz, CDCl$_3$) δ (ppm) 1.61 (s, 9H), 7.85 (s, 1H), 8.35 (s, 1H). LCMS(ESI): [M+H]+ m/z: calcd 219.0. found 221.2; Rt=1.559 min.

tert-butyl 2-(cyclobutylamino)-5-fluoroisonicotinate. tert-Butyl 2-bromo-5-fluoro-pyridine-4-carboxylate (3.74 g, 13.56 mmol) and sodium 2-methylpropan-2-olate (1.95 g, 20.34 mmol) were mixed together in toluene (50 mL). The resulting mixture was evacuated and then backfilled with argon, this operation was repeated three times, then cyclobutanamine (1.93 g, 27.12 mmol, 2.32 mL), [5-(diphenylphosphanyl)-9,9-dimethyl-9H-xanthen-4-yl]diphenylphosphane (392.31 mg, 678.00 umol) and tris(1,5-diphenylpenta-1,4-dien-3-one) dipalladium (310.43 mg, 339.00 umol) were added under argon. The reaction mixture was stirred under argon at 70° C. for 12 hr, then cooled and evaporated in vacuo to leave 5.4 g of the crude product (67.9% purity by LCMS), which was purified by column chromatography on silica gel using hexane/ethyl acetate gradient (5-100% ethyl acetate) to afford tert-butyl 2-(cyclobutylamino)-5-fluoro-pyridine-4-carboxylate (1.1 g, 4.13 mmol, 30.46% yield) as yellow oil. $^1$H NMR (500 MHz, CDCl$_3$) δ (ppm) 1.80 (s, 9H), 1.86 (m, 4H), 2.45 (m, 2H), 4.12 (m, 1H), 4.73 (m, 1H), 6.66 (s, 1H), 8.01 (s, 1H). LCMS(ESI): [M+H]+ m/z: calcd 266.3. found 267.2; Rt=1.430 min.

2-(cyclobutylamino)-5-fluoroisonicotinic acid. tert-Butyl 2-(cyclobutylamino)-5-fluoro-pyridine-4-carboxylate (1.1 g, 4.13 mmol) was diluted with a mixture of hydrochloric acid, 36% w/w aq. soln. (5 g, 137.13 mmol, 4.24 mL) and water (10 mL). The suspension of hydrochloride salt of the ester formed immediately. It was stirred at 70° C. for 0.5 hr, then cooled and the resulting solution was decanted from the oily residue, evaporated and dried in vacuo to afford 2-(cyclobutylamino)-5-fluoro-pyridine-4-carboxylic acid (0.8 g, 3.24 mmol, 78.52% yield, HCl) as yellow solid. $^1$H NMR (500 MHz, DMSO-d$_6$) δ (ppm) 1.76 (m, 2H), 1.96 (m, 2H), 2.35 (m, 2H), 4.28 (m, 1H), 7.11 (s, 1H), 8.06 (s, 1H). LCMS(ESI): [M+H]+ m/z: calcd 210.2; found 211.2; Rt=0.618 min.

3-((1-acetylpiperidin-4-yl)amino)benzoic Acid

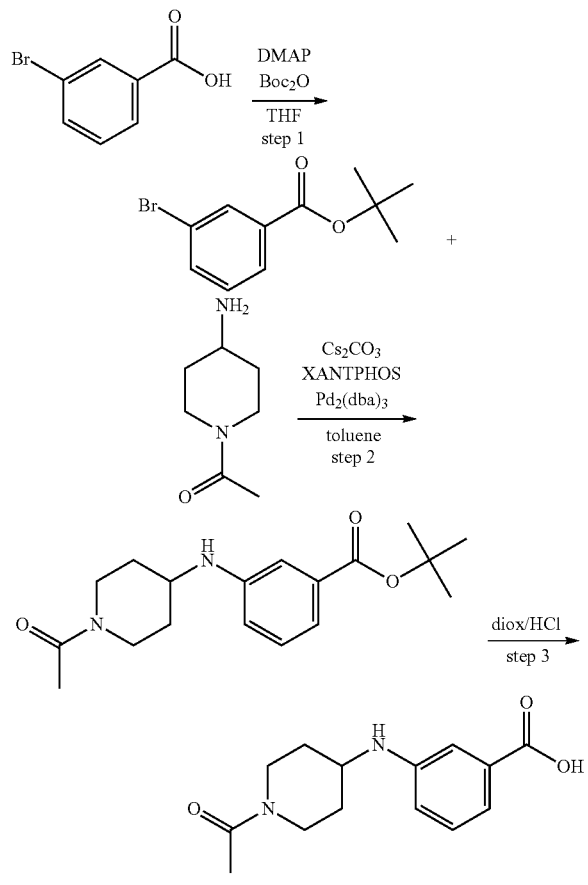

tert-butyl 3-bromobenzoate. tert-Butoxycarbonyl tert-butyl carbonate (5.97 g, 27.36 mmol, 6.28 mL) was added dropwise to the solution of 3-bromobenzoic acid (5 g, 24.87 mmol) and 4-dimethylaminopyridine (1.52 g, 12.44 mmol) in THF (50 mL). The resulting mixture was stirred at room temperature for 16 hr. After consumption of the starting material the resulting mixture was evaporated. The residue was subjected to column chromatography (companion combiflash; 120 g SiO$_2$; petroleum ether/MtBE with MtBE from 0 to 25%, flow rate=85 ml/min, Rv=7 cv.) to obtain tert-butyl 3-bromobenzoate (4.51 g, 17.54 mmol, 70.52% yield). $^1$H NMR (400 MHz, DMSO) δ (ppm) 1.55 (s, 9H), 7.43 (t, 1H), 7.77 (d, 1H), 7.87 (d, 1H), 97 (s, 1H). LCMS(ESI): [M+H]+ m/z: calcd 257.1. found 258.0; Rt=1.651 min.

tert-butyl 3-((1-acetylpiperidin-4-yl)amino)benzoate. tert-Butyl 3-bromobenzoate (1.75 g, 6.81 mmol) and cesium carbonate (3.33 g, 10.21 mmol) were mixed together in toluene (30 mL). The resulting mixture was evacuated and then backfilled with argon, this operation was repeated three times, then 1-(4-amino-1-piperidyl)ethanone (1.06 g, 7.49 mmol), tris(dibenzylideneacetone)dipalladium (0) (155.81 mg, 170.15 umol) and 4,5-bis(diphenylphosphino)-9,9-dimethylxanthene (196.91 mg, 340.30 umol) were added under argon. The resulting mixture was stirred under argon at 90° C. for 12 hr. The reaction was controlled by LCMS and HNMR. The reaction mixture was cooled to r.t. and diluted with water. The resulting mixture was extracted twice with 20 ml EtOAc. The combined organic extracts were dried over sodium sulfate and evaporated. The residue (7 g) was subjected to column chromatography (companion combiflash; 120 g SiO$_2$; chloroform/acetonitrile with acetonitrile from 0 to 70%, flow rate=85 ml/min, Rv=14 cv.) to obtain tert-butyl 3-[(1-acetyl-4-piperidyl)amino]benzoate (0.7 g, 2.20 mmol, 32.30% yield) tert-butyl 3-[(1-acetyl-4-piperidyl)amino]benzoate (0.7 g, 2.20 mmol, 32.30% yield). $^1$H NMR (400 MHz, DMSO) δ (ppm) 1.35 (m, 2H), 1.55 (s, 9H), 1.95 (m, 2H), 2.00 (s, 3H), 2.88 (m, 1H), 3.22 (m, 1H), 3.48 (m, 1H), 3.78 (m, 1H), 4.20 (m, 1H), 5.55 (m, 1H), 6.75 (m, 1H), 7.10 (m, 3H). LCMS(ESI): [M+H]+ m/z: calcd 318.4. found 263.2; Rt=1.415 min.

3-((1-acetylpiperidin-4-yl)amino)benzoic acid. The solution of tert-butyl 3-[(1-acetyl-4-piperidyl)amino]benzoate (0.7 g, 2.20 mmol) in dioxane/HCl (50 mL) with 5 drops of water was stirred at 20° C. for 12 hr. The resulting mixture was evaporated to dryness to obtain 3-[(1-acetyl-4-piperidyl)amino]benzoic acid (0.58 g, 1.94 mmol, 88.31% yield, HCl). $^1$H NMR (400 MHz, DMSO) δ (ppm) 1.34 (m, 1H), 1.44 (m, 1H), 1.91 (m, 2H), 2.00 (s, 3H), 2.73 (m, 1H), 3.22 (m, 1H), 3.60 (m, 1H), 3.82 (m, 1H), 4.30 (m, 1H), 5.18 (m, 3H), 7.43 (m, 4H) LCMS(ESI): [M+H]+ m/z: calcd 262.3. found 263.2; Rt=0.875 min.

3-((tetrahydro-2H-pyran-4-yl)methyl)benzoic Acid

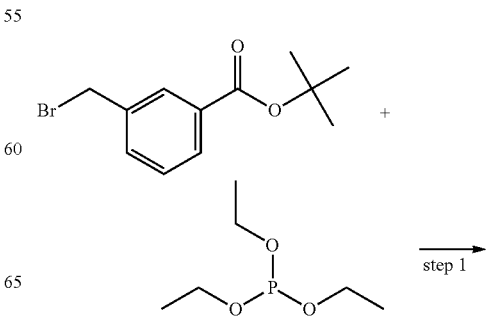

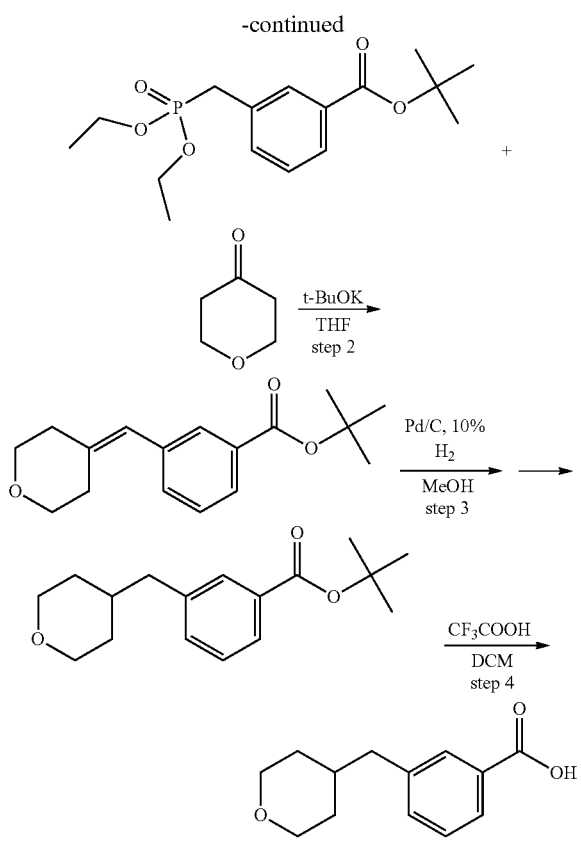

tert-butyl 3-((diethoxyphosphoryl)methyl)benzoate. tert-Butyl 3-(bromomethyl)benzoate (3 g, 11.06 mmol) and tetrahydropyran-4-one (1.66 g, 16.60 mmol, 1.54 mL) were placed in a round-bottom flask and stirred at 145° C. for 18 hr. Then, temperature was reduced to 100° C. and excessive triethyl phosphite was removed under residual pressure≤1 mbar leaving tert-butyl 3-(tetrahydropyran-4-ylidenemethyl)benzoate (3.5 g, 10.66 mmol, 96.35% yield). ¹H NMR (500 MHz, CDCl₃) δ (ppm) 1.24 (t, 6H), 1.57 (s, 9H), 3.15 (s, 1H), 3.20 (s, 1H), 4.02 (m, 4H), 7.35 (t, 1H), 7.47 (d, 1H), 7.87 (m, 2H). LCMS(ESI): [M+H]+ m/z: calcd 272.08; found 273.2; Rt=1.425 min.

tert-butyl 3-((dihydro-2H-pyran-4(3H)-ylidene)methyl)benzoate. tert-Butyl 3-(diethoxyphosphorylmethyl)benzoate (3.5 g, 10.66 mmol) and tetrahydropyran-4-one (1.17 g, 11.73 mmol, 1.09 mL) were dissolved in THF (50 mL). Solution was cooled in an ice bath and potassium tert-butoxide (2.39 g, 21.32 mmol) was added portionwise during 25 minutes. Then, cooling bath was removed and mixture was stirred at 20° C. for 16 hr. Solvent was distilled off under reduced pressure and residue partitioned between H₂O (50 ml) and MTBE (50 ml). Organic layer was separated, dried over Na₂SO₄ and evaporated in vacuo affording tert-butyl 3-(tetrahydropyran-4-ylidenemethyl)benzoate (1.5 g, 5.47 mmol, 51.29% yield) as a mixture of rotamers. ¹H NMR (500 MHz, CDCl₃) δ (ppm) 1.61 (s, 9H), 2.39 (m, 1H), 2.50 (m, 1H), 3.32 (m, 1H), 3.65 (m, 1H), 3.73 (m, 1H), 3.77 (m, 2H), 4.35 (m, 1H), 6.33 (m, 1H), 7.33 (m, 2H), 7.80 (m, 2H). LCMS(ESI): [M+H]+ m/z: calcd 218.1. found 219.2; Rt=1.590 min.

tert-butyl 3-((tetrahydro-2H-pyran-4-yl)methyl)benzoate. tert-Butyl 3-(tetrahydropyran-4-ylidenemethyl)benzoate (1.5 g, 5.47 mmol) was dissolved in methanol (30 mL) and Pd/C (10%) (290.92 mg, 273.37 umol, 10% purity) was added there to. Flask was evacuated and refilled with hydrogen (110.21 mg, 54.67 mmol). Mixture was stirred in an atmosphere of hydrogen at 20° C. during 15 hr. Then, catalyst was filtered off and filtrate was concentrated under reduced pressure affording tert-butyl 3-(tetrahydropyran-4-ylmethyl)benzoate (1.5 g, 5.43 mmol, 99.27% yield). ¹H NMR (500 MHz, CDCl₃) δ (ppm) 1.34 (m, 3H), 1.52 (m, 1H), 1.58 (s, 9H), 1.76 (m, 1H), 2.57 (m, 2H), 3.46 (m, 2H), 3.91 (m, 2H), 7.29 (m, 2H), 7.79 (m, 2H). LCMS(ESI): [M+H]+ m/z: calcd 276.4. found 277.2; Rt=1.530 min.

3-((tetrahydro-2H-pyran-4-yl)methyl)benzoic acid, tert-Butyl 3-(tetrahydropyran-4-ylmethyl)benzoate (1.5 g, 5.43 mmol) was dissolved in dichloromethane (20 mL) and trifluoroacetic acid (7.43 g, 65.13 mmol, 5.02 mL) was added. Mixture was stirred at 20° C. for 4 hr. Volatiles was removed under reduced pressure. Residue was dissolved in 5% ammonia solution (50 ml) and washed with MTBE (2×30 ml). Then, it was acidified to ph≈3 with 6N HCl and extracted with chloroform (2×30 ml). After drying over Na₂SO₄, solvent was evaporated in vacuo affording 3-(tetrahydropyran-4-ylmethyl)benzoic acid (1.05 g, 4.77 mmol, 87.83% yield). NMR (500 MHz, CDCl₃) δ (ppm) 1.36 (m, 2H), 1.55 (m, 2H), 1.78 (m, 1H), 2.61 (m, 2H), 3.34 (m, 2H), 3.97 (m, 2H), 7.38 (m, 2H), 7.94 (m, 2H), 10.55 (bds, 1H). LCMS(ESI): [M+H]+m/z: calcd 220.3. found 221.2; Rt=1.111 min.

Acid—G 6-((1-acetylazetidin-3-yl)amino)-2-morpholinopyrimidine-4-carboxylic Acid

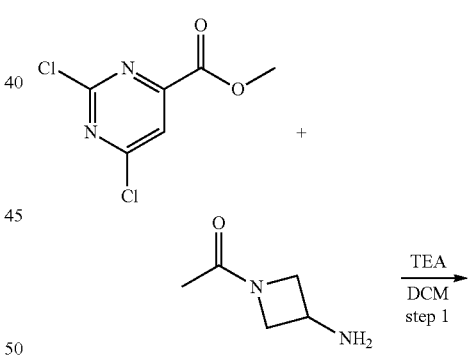

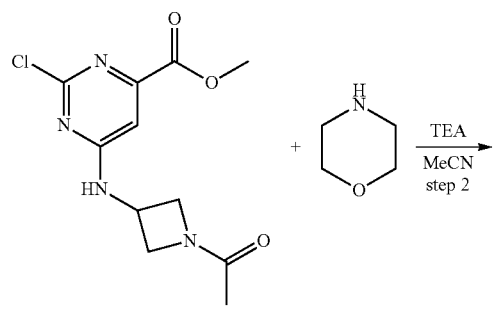

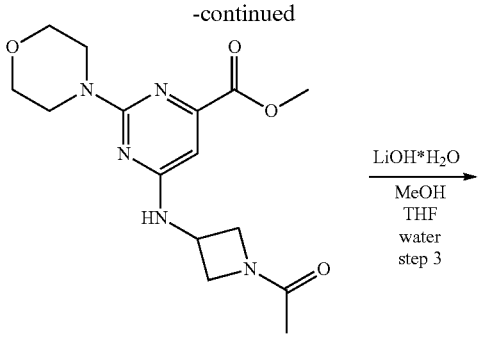

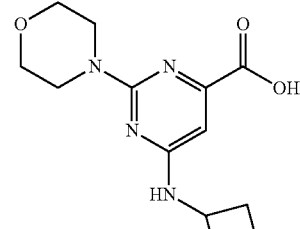

methyl 6-((1-acetylazetidin-3-yl)amino)-2-chloropyrimidine-4-carboxylate. To a solution of methyl 2,6-dichloropyrimidine-4-carboxylate (3 g, 14.49 mmol) in DCM (50 mL) at 0° C. was added TEA (2.93 g, 28.98 mmol, 4.04 mL) followed by 1-(3-aminoazetidin-1-yl)ethanone (3.31 g, 14.49 mmol, $CF_3CO_2H$) and the resulting reaction mixture was stirred at 0° C. for 30 min. and allowed to warm to room temperature. After 12 hr the reaction mixture was triturated with water (30 mL). The layers were separated and the aqueous layer was extracted with DCM (30 mL). The combined organic layers were washed with water (25 mL) and brine, dried over $Na_2SO_4$ and concentrated in vacuo to give methyl 6-[(1-acetylazetidin-3-yl)amino]-2-chloro-pyrimidine-4-carboxylate (2.95 g, crude). $^1$H NMR (500 MHz, DMSO-$d_4$) δ (ppm) 1.75 (s, 3H), 3.85 (s, 3H), 3.93 (m, 2H), 4.17 (m, 1H), 4.56 (m, 2H), 7.07 (s, 1H), 8.97 (bds, 1H). LCMS(ESI): [M+H]+ m/z: calcd 284.7. found 286.0; Rt=0.817 min.

methyl 6-((1-acetylazetidin-3-yl)amino)-2-morpholino-pyrimidine-4-carboxylate. To a solution of methyl 6-[(1-acetylazetidin-3-yl)amino]-2-chloro-pyrimidine-4-carboxylate (1.5 g, 5.27 mmol) in ACN (20 mL) at r.t. was added TEA (586.46 mg, 5.80 mmol, 807.79 uL) followed by morpholine (504.92 mg, 5.80 mmol, 506.94 uL) and the resulting reaction mixture was stirred at 80° C. for 32 hr and cooled down. The precipitate formed was collected by filtration, washed with water and dried in vacuo to give methyl 6-[(1-acetylazetidin-3-yl)amino]-2-morpholino-pyrimidine-4-carboxylate (1 g, 2.98 mmol, 56.60% yield). $^1$H NMR (500 MHz, DMSO-$d_6$) δ (ppm) 1.75 (s, 3H), 3.63 (m, 8H), 3.74 (m, 4H), 3.95 (m, 1H), 4.13 (m, 1H), 4.41 (m, 1H), 4.43 (m, 1H), 6.42 (s, 1H), 8.05 (bds, 1H). LCMS(ESI): [M+H]+ m/z: calcd 335.4; found 336.2; Rt=0.886 min.

6-((1-acetylazetidin-3-yl)amino)-2-morpholinopyrimidine-4-carboxylic acid. A mixture of methyl 6-[(1-acetylazetidin-3-yl)amino]-2-morpholino-pyrimidine-4-carboxylate (1 g, 2.98 mmol) and lithium hydroxide, hydrate (275.26 mg, 6.56 mmol, 182.29 uL) in THF (10 mL)-methanol (10 mL)-water (10 mL) was stirred at r.t. for 12 hr. Then, volatile organic solvents were rotoevaporated, the aqueous phase was acidified (NaHSO$_4$, monohydrate) to pH 5 and the mixture was concentrated in vacuo. The residue was suspended in hot ethanol (100 mL) and filtered. The filtercake was washed with hot ethanol (2×50 mL) and discarded. The filtrate was evaporated in vacuo to leave the residue 6-[(1-acetylazetidin-3-yl)amino]-2-morpholino-pyrimidine-4-carboxylic acid (0.5 g, 1.56 mmol, 52.18% yield). $^1$H NMR (500 MHz, DMSO-$d_6$) δ (ppm) 1.76 (s, 3H), 3.45 (m, 2H), 3.67 (m, 8H), 3.96 (m, 1H), 4.13 (m, 1H), 4.41 (m, 1H), 4.56 (m, 1H), 6.40 (s, 1H), 8.00 (bds, 1H). LCMS(ESI): [M+H]+ m/z: calcd 321.3. found 322.2; Rt=0.768 min.

6-((1-acetylazetidin-3-yl)amino)-2-(piperidin-1-yl)pyrimidine-4-carboxylic Acid

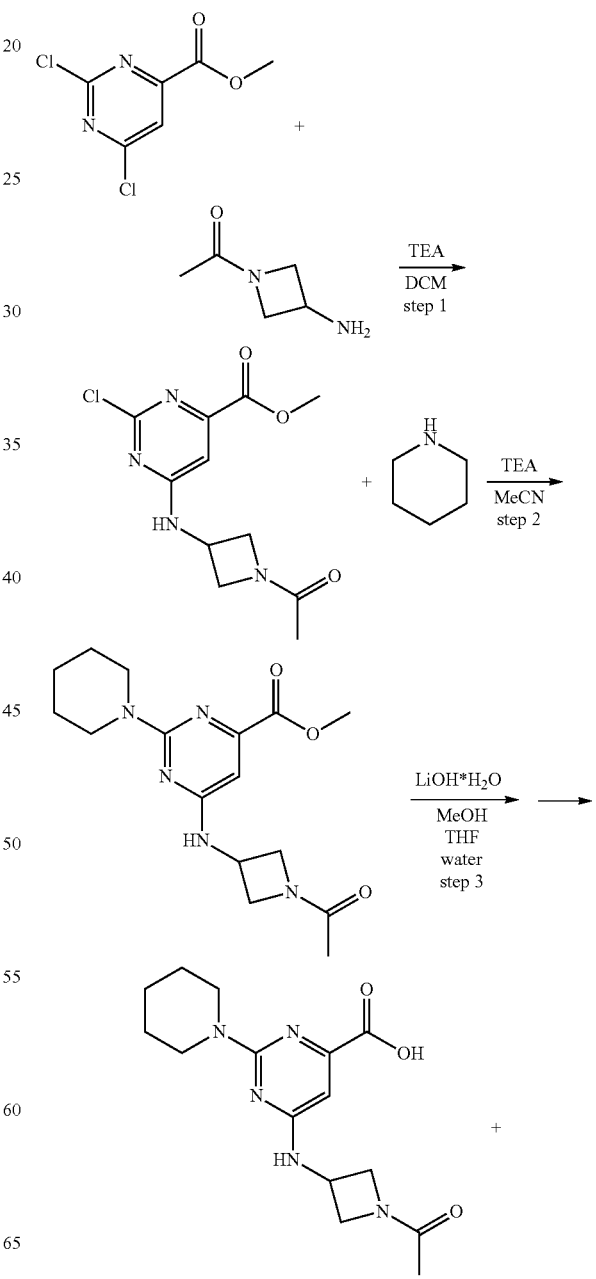

-continued

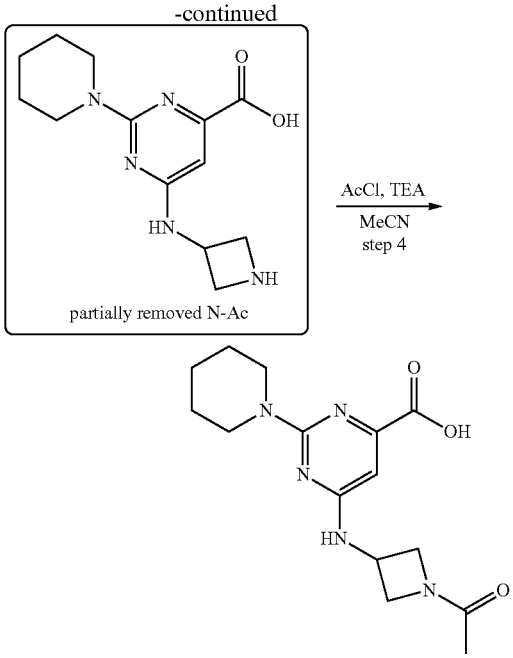

partially removed N-Ac methyl 6-((1-acetylazetidin-3-yl)amino)-2-chloropyrimidine-4-carboxylate. To a solution of methyl 2,6-dichloropyrimidine-4-carboxylate (3 g, 14.49 mmol) in DCM (50 mL) at 0° C. was added TEA (2.93 g, 28.98 mmol, 4.04 mL) followed by 1-(3-aminoazetidin-1-yl)ethanone (3.31 g, 14.49 mmol, CF$_3$CO$_2$H) and the resulting reaction mixture was stirred at 0° C. for 30 min. and allowed to warm to room temperature. After 12 hr the reaction mixture was triturated with water (30 mL). The layers were separated and the aqueous layer was extracted with DCM (30 mL). The combined organic layers were washed with water (25 mL) and brine, dried over Na$_2$SO$_4$ and concentrated in vacuo to give methyl 6-[(1-acetylazetidin-3-yl)amino]-2-chloro-pyrimidine-4-carboxylate (2.95 g, crude). $^1$H NMR (500 MHz, DMSO-d$_6$) δ (ppm) 1.75 (s, 3H), 3.85 (s, 3H), 3.93 (m, 2H), 4.17 (m, 1H), 4.56 (m, 2H), 7.07 (s, 1H), 8.97 (bds, 1H) LCMS(ESI): [M+H]+ m/z: calcd 284.7. found 286.0; Rt=0.817 min.

methyl 6-((1-acetylazetidin-3-yl)amino)-2-(piperidin-1-yl)pyrimidine-4-carboxylate. To a solution of methyl 6-[(1-acetylazetidin-3-yl)amino]-2-chloro-pyrimidine-4-carboxylate (1.5 g, 5.27 mmol) in ACN (20 mL) at r.t. was added TEA (586.46 mg, 5.80 mmol, 807.79 uL) followed by piperidine (493.48 mg, 5.80 mmol, 572.48 uL) and the resulting reaction mixture was stirred at 80° C. for 32 hr, then it was diluted with water (40 mL). The aqueous layer was extracted with DCM (40 mL×2). The combined organic layers were washed with water (15 mL) and brine, dried over Na$_2$SO$_4$ and concentrated in vacuo to give methyl 6-[(1-acetylazetidin-3-yl)amino]-2-(1-piperidyl)pyrimidine-4-carboxylate (1.1 g, crude). $^1$H NMR (500 MHz, DMSO-d$_6$) δ (ppm) 1.49 (m, 6H), 1.75 (s, 3H), 3.58 (m, 3H), 3.68 (m, 5H), 3.95 (m, 1H), 4.12 (m, 1H), 4.39 (m, 1H), 4.53 (m, 1H), 6.53 (s, 1H), 8.31 (bds, 1H). LCMS(ESI): [M+H]+ m/z: calcd 333.4. found 334.2; Rt=0.951 min.

6-(azetidin-3-ylamino)-2-(piperidin-1-yl)pyrimidine-4-carboxylic acid as a crude mixture with deacylated byproduct. A mixture of methyl 6-[(1-acetylazetidin-3-yl)amino]-2-(1-piperidyl)pyrimidine-4-carboxylate (1.1 g, 3.30 mmol) and lithium hydroxide, hydrate (304.58 mg, 7.26 mmol, 201.71 uL) in THF (10 mL)-methanol (10 mL)-water (15 mL) was stirred at r.t. for 12 hr. Then, volatile organic solvents were rotoevaporated. The aqueous phase was washed with DCM (10 mL), then acidified (NaHSO$_4$, monohydrate) to pH 5 and the mixture was concentrated in vacuo. The residue was suspended in hot ethanol (100 mL) and filtered. The filtercake was washed with hot ethanol (2×50 mL) and discarded. The filtrate was evaporated in vacuo to leave the residue 6-(azetidin-3-ylamino)-2-(piperidin-1-yl)pyrimidine-4-carboxylic acid (1 g, crude, contains 37% of deacylated byproduct). $^1$H NMR (400 MHz, DMSO-d$_6$) δ (ppm) 1.60 (m, 6H), 3.69 (m, 4H), 4.18 (m, 2H), 4.39 (m, 1H), 4.53 (m, 1H), 4.78 (m, 1H), 6.32 (s, 1H), 8.02 (bds, 1H), 8.73 (bds, 1H), 10.45 (bds, 1H). LCMS(ESI): [M+H]+ m/z: calcd 277.3; found 278.2; Rt=0.644 min.

Acid—H 4-((1-(pyridin-4-ylmethyl)piperidin-4-yl)oxy)benzoic Acid

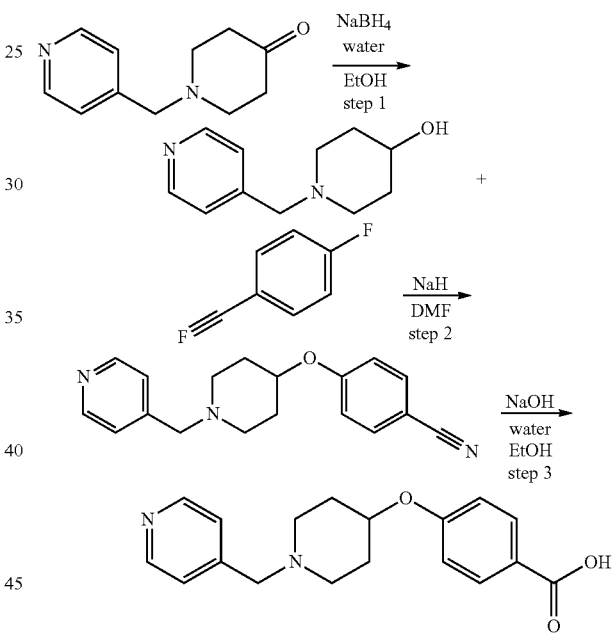

1-(pyridin-4-ylmethyl)piperidin-4-ol. 1-(4-Pyridylmethyl)piperidin-4-one (1 g, 5.26 mmol) was dissolved in ethanol (30 mL). The mixture was cooled to 0° C. and was added sodium borohydride (198.85 mg, 5.26 mmol, 185.84 uL). The mixture was stirred for 10 hr at 20° C. Water (3.79 g, 210.26 mmol, 3.79 mL) was added. The mixture was stirred for 30 min at 20° C. The mixture was evaporated in vacuo at 35° C. DCM (50 mL) was added. The organic phase was dried with Na$_2$SO$_4$ and evaporated in vacuo at 35° C. to obtain 1-(4-pyridylmethyl)piperidin-4-ol (0.82 g, 4.27 mmol, 81.14% yield). $^1$H NMR (500 MHz, CDCl$_3$) δ (ppm) 1.62 (m, 2H), 1.75 (m, 1H), 1.90 (m, 2H), 2.19 (m, 2H), 2.74 (m, 2H), 3.50 (s, 2H), 3.74 (m, 1H), 7.28 (d, 2H), 8.54 (d, 2H). LCMS(ESI): [M+H]+ m/z: calcd 192.3. found 193.2; Rt=0.159 min.

4-((1-(pyridin-4-ylmethyl)piperidin-4-yl)oxy)benzonitrile. 1-(4-Pyridylmethyl)piperidin-4-ol (0.57 g, 2.96 mmol) was dissolved in DMF (2 mL). Sodium hydride (in oil dispersion) 60% dispersion in mineral oil (85.20 mg, 3.71 mmol) was added. The mixture was stirred for 30 min at 20° C. 4-Fluorobenzonitrile (359.07 mg, 2.96 mmol) was added. The mixture was stirred for 10 hr at 20° C. Aqueous NaCl (50 mF) was added. The mixture was extracted with EtOAc (3*30 mF). The organic layer was extracted with aqueous NaCl (5*10 mF). The organic phase was dried with $Na_2SO_4$ and evaporated in vacuo at 35° C. The residue was purified by HPFC to obtain 4-[[1-(4-pyridylmethyl)-4-piperidyl]oxy]benzonitrile (297 mg, 1.01 mmol, 34.15% yield). $^1$H NMR (400 MHz, $CDCl_3$) δ (ppm) 1.85 (m, 2H), 1.98 (m, 2H), 2.32 (m, 2H), 2.67 (m, 2H), 3.50 (s, 2H), 4.40 (m, 1H), 6.91 (d, 2H), 7.24 (d, 2H), 7.53 (d, 2H), 8.51 (d, 2H). LCMS(ESI): [M+H]+ m/z: calcd 293.4. found 294.2; Rt=0.763 min.

4-((1-(pyridin-4-ylmethyl)piperidin-4-yl)oxy)benzoic acid. Solution of sodium hydroxide (121.48 mg, 3.04 mmol, 57.03 uL) in $H_2O$ (1 mF) was added to the solution of 4-[[1-(4-pyridylmethyl)-4-piperidyl]oxy]benzonitrile (297 mg, 1.01 mmol) in ethanol (1.5 mF). The mixture was stirred for 10 hr at 80° C. HCl (1 mF, 18%) was added. The mixture was evaporated in vacuo at 50° C. to obtain 4-[[1-(4-pyridylmethyl)-4-piperidyl]oxy]benzoic acid (385 mg, 999.26 umol, 98.70% yield, 2HCl). $^1$H NMR (400 MHz, $D_2O$) δ (ppm) 2.12 (m, 4H), 3.33 (m, 2H), 3.47 (m, 2H), 4.58 (s, 2H), 4.82 (m, 1H), 7.02 (d, 2H), 7.91 (d, 2H), 8.08 (d, 2H), 8.80 (d, 2H). LCMS(ESI): [M+H]+ m/z: calcd 312.4. found 313.0; Rt=0.749 min.

The synthesis of
4-((1-benzylpiperidin-4-yl)oxy)benzoic Acid

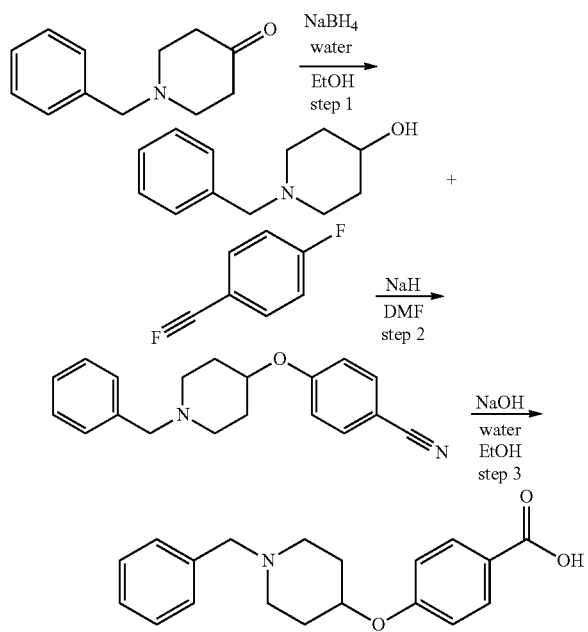

1-benzylpiperidin-4-ol. 1-Benzylpiperidin-4-one (1 g, 5.28 mmol, 943.40 uL) was dissolved in ethanol (30 mL). The mixture was cooled to 0° C. and was added sodium borohydride (199.89 mg, 5.28 mmol, 186.81 uL). The mixture was stirred for 10 hr at 20° C. Water (3.81 g, 211.36 mmol, 3.81 mL) was added. The mixture was stirred for 30 min at 20° C. The mixture was evaporated in vacuo at 35° C. DCM (50 mL) was added. The organic phase was dried with $Na_2SO_4$ and evaporated in vacuo at 35° C. to obtain 1-benzylpiperidin-4-ol (0.98 g, 5.12 mmol, 96.97% yield). $^1$H NMR (500 MHz, $CDCl_3$) δ (ppm) 1.43 (m, 1H), 1.61 (m, 2H), 1.89 (m, 2H), 2.16 (m, 2H), 2.75 (m, 2H), 3.51 (s, 2H), 3.71 (m, 1H), 7.27 (m, 2H), 7.32 (m, 3H). LCMS(ESI): [M+H]+ m/z: calcd 191.3. found 192.2; Rt=0.606 min.

4-((1-benzylpiperidin-4-yl)oxy)benzonitrile. 1-Benzylpiperidin-4-ol (0.25 g, 1.31 mmol) was dissolved in DMF (2 mL). Sodium hydride (in oil dispersion) 60% dispersion in mineral oil (37.56 mg, 1.63 mmol) was added. The mixture was stirred for 30 min at 20° C. 4-Fluorobenzonitrile (158.30 mg, 1.31 mmol) was added. The mixture was stirred for 10 hr at 20° C. Aqueous NaCl (50 mF) was added. The mixture was extracted with EtOAc (3*30 mF). The organic layer was extracted with aqueous NaCl (5*10 mF). The organic phase was dried with $Na_2SO_4$ and evaporated in vacuo at 35° C. The residue was purified by HPFC to obtain 4-[(1-benzyl-4-piperidyl)oxy]benzonitrile (131.6 mg, 450.11 umol, 34.44% yield). $^1$H NMR (400 MHz, DMSO) δ (ppm) 1.64 (m, 2H), 1.93 (m, 2H), 2.23 (m, 2H), 2.65 (m, 2H), 3.48 (s, 2H), 4.52 (m, 1H), 7.11 (d, 2H), 7.31 (m, 5H), 7.74 (d, 2H). LCMS(ESI): [M+H]+ m/z: calcd 292.4; found 293.2; Rt=0.908 min.

4-((1-benzylpiperidin-4-yl)oxy)benzoic acid. Solution of sodium hydroxide (54.17 mg, 1.35 mmol, 25.43 uF) in $H_2O$ (1 mF) was added to the solution of 4-[(1-benzyl-4-piperidyl)oxy]benzonitrile (132 mg, 451.48 umol) in ethanol (1.5 mF). The mixture was stirred for 10 hr at 80° C. HCl (0.5 mF, 185) was added. The mixture was evaporated in vacuo at 50° C. to obtain 4-[(1-benzyl-4-piperidyl)oxy]benzoic acid (150 mg, 431.24 umol, 95.52% yield, HCl. NMR (400 MHz, $D_2O$) δ (ppm) 1.76 (m, 1H), 1.97 (m, 1H), 2.17 (m, 1H), 2.33 (m, 1H), 3.11 (m, 1H), 3.29 (m, 3H), 3.51 (m, 1H), 4.25 (s, 2H), 4.82 (bds, 1H), 7.00 (d, 2H), 7.41 (m, 5H), 7.72 (m, 1H), 7.89 (m, 1H). LCMS(ESI): [M+H]+ m/z: calcd 311.4. found 312.2; Rt=0.905 min.

Acid—J 2-(4-methoxybenzyl)-1,2,3,4-tetrahydroisoquinoline-6-carboxylic Acid

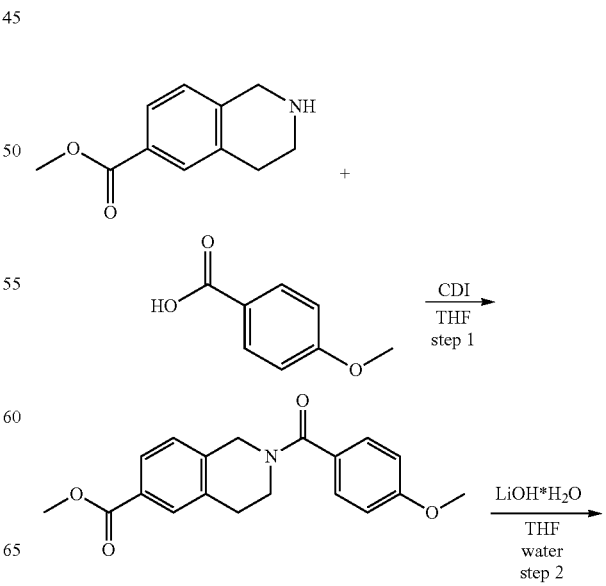

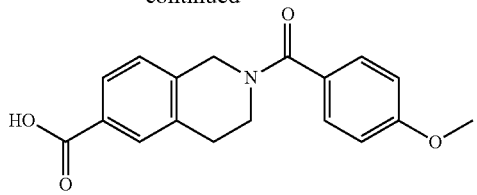

methyl 2-(4-methoxybenzoyl)-1,2,3,4-tetrahydroisoquinoline-6-carboxylate. CDI (1.51 g, 9.32 mmol) was added in one portion to a solution of 4-methoxybenzoic acid (1.35 g, 8.87 mmol, 971.22 uL) in THF (50 mL). The resulting solution was warmed to 55° C. and stirred until carbon dioxide evolution was completed, then methyl 1,2,3,4-tetrahydroisoquinoline-6-carboxylate (1.70 g, 8.87 mmol) was added and the reaction mixture was stirred at 55° C. for 2 hr, then cooled and evaporated in vacuo. The residue was diluted with 5% aqueous sodium hydrogen sulphate solution (50 ml) and the oily product was extracted with dichloromethane (2*40 ml). The combined organic extracts were washed with water (40 ml), dried over sodium sulphate and evaporated in vacuo to afford methyl 2-(4-methoxybenzoyl)-3,4-dihydro-1H-isoquinoline-6-carboxylate (2.6 g, 7.99 mmol, 90.06% yield) as yellow gum, which slowly crystallized into yellow solid. $^1$H NMR (400 MHz, DMSO) δ (ppm) 2.92 (m, 2H), 3.68 (m, 2H), 3.80 (s, 3H), 3.83 (s, 3H), 4.76 (m, 2H), 7.01 (d, 2H), 7.42 (m, 3H), 7.77 (d, 2H). LCMS(ESI): [M+H]+ m/z: calcd 325.4. found 326.2; Rt=1.315 min.

2-(4-methoxybenzoyl)-1,2,3,4-tetrahydroisoquinoline-6-carboxylic acid. Lithium hydroxide, monohydrate (1.01 g, 23.97 mmol, 666.24 uL) was added in one portion to a stirred solution of methyl 2-(4-methoxybenzoyl)-3,4-dihydro-1H-isoquinoline-6-carboxylate (2.6 g, 7.99 mmol) in a mixture of water (10 mL) and THF (30 mL). The resulting mixture was stirred at 25° C. for 12 hr, and then evaporated in vacuo. The residue was diluted with water (30 ml) and acidified with concentrated aqueous hydrochloric acid to pH 4. The oily product was extracted with dichloromethane (2*40 ml). The combined organic extracts were dried over sodium sulphate and evaporated in vacuo to afford 2-(4-methoxybenzoyl)-3,4-dihydro-1H-isoquinoline-h-carboxylic acid (2.05 g, 6.58 mmol, 82.40% yield) as light-yellow solid. $^1$H NMR (400 MHz, DMSO) δ (ppm) 2.92 (m, 2H), 3.69 (m, 2H), 3.80 (s, 3H), 4.75 (m, 2H), 7.01 (d, 2H), 7.29 (m, 1H), 7.30 (m, 2H), 7.75 (m, 2H), 12.83 (bds, 1H). LCMS(ESI): [M+H]+ m/z: calcd 311.3; found 312.2; Rt=1.114 min.

2-(4-bromobenzoyl)-1,2,3,4-tetrahydroisoquinoline-6-carboxylic Acid

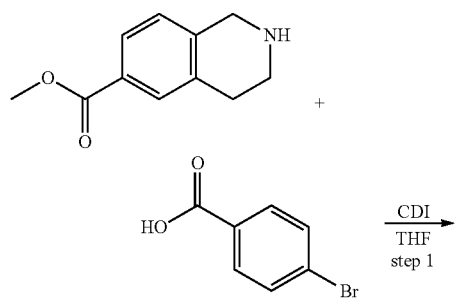

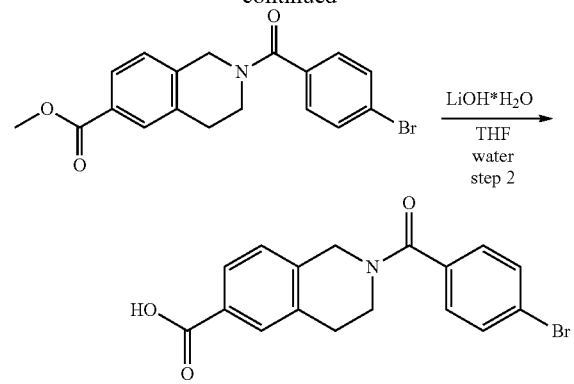

methyl 2-(4-bromobenzoyl)-1,2,3,4-tetrahydroisoquinoline-6-carboxylate. CDI (1.19 g, 7.31 mmol) was added in one portion to a solution of 4-bromobenzoic acid (1.4 g, 6.96 mmol, 359.71 uL) in THF (50 mL). The resulting solution was warmed to 55° C. and stirred until carbon dioxide evolution was completed, then methyl 1,2,3,4-tetrahydroisoquinoline-6-carboxylate (1.33 g, 6.96 mmol) was added and the reaction mixture was stirred at 55° C. for 2 hr, then cooled and evaporated in vacuo. The residue was diluted water (50 ml), the precipitate was filtered, washed with water (2*20 ml) and air dried to afford methyl 2-(4-bromobenzoyl)-3,4-dihydro-1H-isoquinoline-6-carboxylate (2.4 g, 6.41 mmol, 92.08% yield) as light-yellow solid. NMR (400 MHz, DMSO) δ (ppm) 2.92 (m, 2H), 3.56 (m, 1H), 3.80 (m, 1H), 3.83 (s, 3H), 4.82 (m, 2H), 7.20 (m, 3H), 7.67 (m, 2H), 7.78 (m, 2H). LCMS(ESI): [M+H]+ m/z: calcd 374.2. found 376.0; Rt=1.425 min.

2-(4-bromobenzoyl)-1,2,3,4-tetrahydroisoquinoline-6-carboxylic acid. Lithium hydroxide, monohydrate (807.29 mg, 19.24 mmol, 534.63 uL) was added in one portion to a stirred solution of methyl 2-(4-bromobenzoyl)-3,4-dihydro-1H-isoquinoline-6-carboxylate (2.4 g, 6.41 mmol) in a mixture of water (10 mL) and THF (30 mL). The resulting mixture was stirred at 25° C. for 12 hr, and then evaporated in vacuo. The residue was diluted with water (50 ml) and acidified with concentrated aqueous hydrochloric acid to pH 4. The precipitate was filtered, washed with water (2*20 ml) and dried in vacuo to afford 2-(4-bromobenzoyl)-3,4-dihydro-1H-isoquinoline-6-carboxylic acid (1.95 g, 5.41 mmol, 84.41% yield) as light-yellow solid. $^1$H NMR (400 MHz, DMSO) δ (ppm) 2.91 (m, 2H), 3.83 (m, 2H), 4.81 (m, 2H), 7.42 (m, 3H), 7.75 (m, 4H), 12.88 (bds, 1H). LCMS(ESI): [M+H]+ m/z: calcd 360.2. found 361.0; Rt=1.228 min.

Acid—L 3-((1-acetylpyrrolidin-3-yl)amino)benzoic Acid

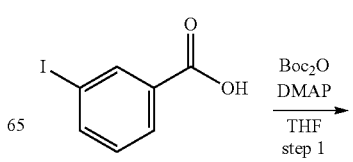

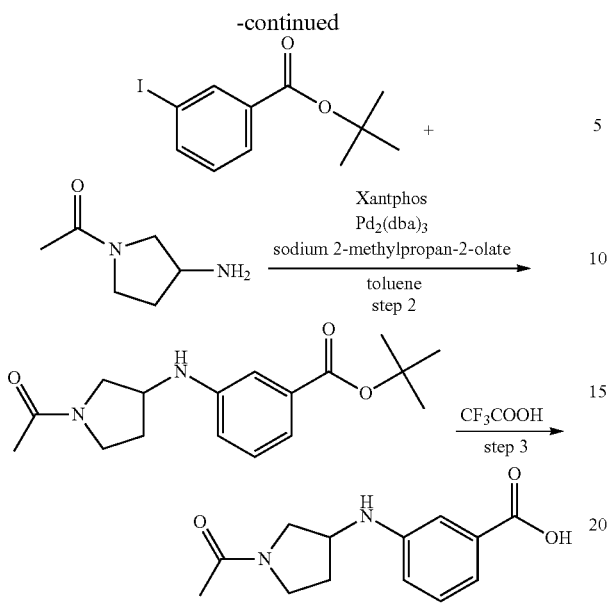

tert-butyl 3-iodobenzoate. 3-Iodobenzoic acid (11.25 g, 45.36 mmol) and 4-dimethylaminopyridine (2.77 g, 22.68 mmol) were dissolved in dry THF (100 mL). Di-tert-butyl dicarbonate (14.85 g, 68.04 mmol, 15.61 mL) was added portionwise during 20 min. The mixture was stirred at 40° C. for 15 hr. Then, solution was cooled to room temperature and few ml of water was added to destroy excess boc$_2$O. When CO$_2$ evolution ceased, solvent was removed in vacuo. Residue was dissolved in MTBE (150 ml) and washed successively with 5-% NaHCO$_3$ (50 ml), water (50 ml), 5-% NaHSO$_4$ (100 ml) and brine (50 ml). After drying over Na$_2$SO$_4$ solvent was evaporated under reduced pressure affording tert-butyl 3-iodobenzoate (13.06 g, 42.94 mmol, 94.67% yield). NMR(CDCl$_3$, 500 MHz): δ 1.60 (s, 9H), 7.17 (t, 1H), 7.85 (d, 1H), 7.96 (d, 1H), 8.32 (s, 1H). GCMS: [M]: calcd 304.1. found 304.1; Rt=7.436 min.

tert-butyl 3-((1-acetylpyrrolidin-3-yl)amino)benzoate. tert-Butyl 3-iodobenzoate (2.5 g, 8.22 mmol), 1-(3-aminopyrrolidin-1-yl)ethanone (1.62 g, 9.86 mmol, HCl) and sodium 2-methylpropan-2-olate (2.13 g, 22.19 mmol) were mixed together in toluene (50 mL). The resulting mixture was evacuated and then backfilled with argon, this operation was repeated three times, then [5-(diphenylphosphanyl)-9,9-dimethyl-9H-xanthen-4-yl]diphenylphosphane (237.82 mg, 411.02 umol) and tris(1,5-diphenylpenta-1,4-dien-3-one) dipalladium (188.19 mg, 205.51 umol) were added under argon. The reaction mixture was stirred under argon at 75° C. for 18 hr, then cooled and filtered through a short pad of silica gel. The silica gel pad was additionally washed with THF (2*30 ml) and the combined THF-toluene filtrate was evaporated in vacuo to leave 2.9 g of the residue as red gum (87.81% by LCMS), approximately 2.1 g of the product tert-butyl 3-[(1-acetylpyrrolidin-3-yl)amino]benzoate (2.1 g, 6.90 mmol, 83.93% yield), which was used directly in the next step. $^1$H NMR (CDCl$_3$, 500 MHz): δ 1.55 (s, 9H), 2.19 (s, 3H), 2.28 (m, 1H), 2.52 (m, 1H), 3.61 (m, 2H), 3.82 (m, 1H), 4.06 (m, 1H), 4.37 (m, 1H), 5.54 (m, 1H), 6.75 (m, 1H), 7.27 (m, 2H), 7.38 (m, 1H). LCMS(ESI): [M+H]$^+$ m/z: calcd 304.4; found 249.2; Rt=1.342 min.

3-((1-acetylpyrrolidin-3-yl)amino)benzoic acid, tert-Butyl 3-[(1-acetylpyrrolidin-3-yl)amino]benzoate (2.9 g, 9.53 mmol) (crude from previous step) was dissolved in trifluoroacetic acid (32.59 g, 285.82 mmol, 22.02 mL). The resulting mixture was stirred at 25° C. for 1 hr, then evaporated in vacuo and the residue was tritutated with MTBE (40 ml). The precipitate was filtered, washed with MTBE(2*20 ml) and dried in vacuo to afford 3-[(1-acetylpyrrolidin-3-yl)amino]benzoic acid (1.35 g, 3.73 mmol, 39.11% yield, CF$_3$COOH) as light-brown solid, which was used in the next step without further purification. $^1$H NMR (DMSO-d$_6$, 500 MHz): δ 1.95 (s, 3H), 2.16 (m, 1H), 3.11 (m, 1H), 3.21 (m, 1H), 3.38 (m, 1H), 3.48 (m, 1H), 3.68 (m, 1H), 4.02 (m, 2H), 6.82 (m, 1H), 7.21 (m, 3H), 12.62 (bds, 1H). LCMS(ESI): [M+H]$^+$ m/z: calcd 248.3. found 249.2; Rt=0.905 min.

Acid—M 2-(4-bromobenzoyl)-1,2,3,4-tetrahydroisoquinoline-6-carboxylic Acid

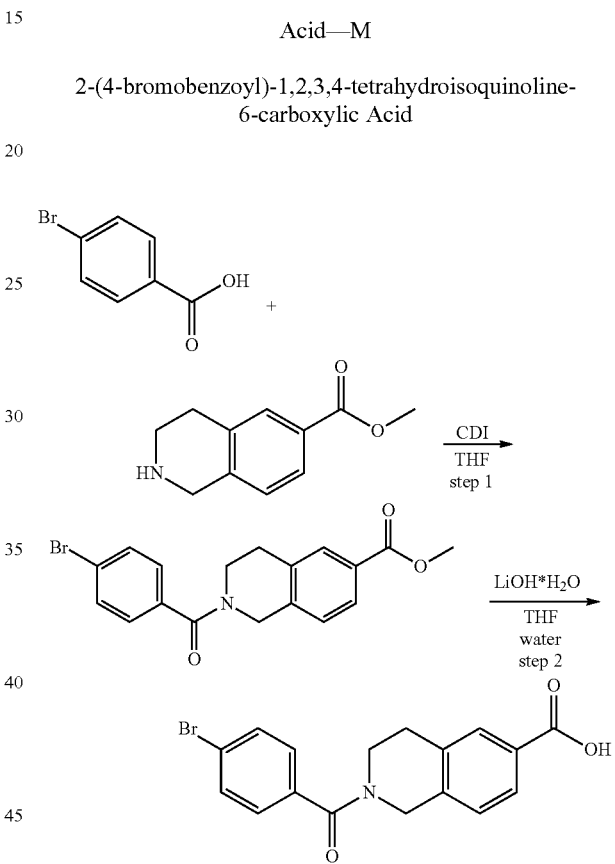

methyl 2-(4-bromobenzoyl)-1,2,3,4-tetrahydroisoquinoline-6-carboxylate. CDI (423.49 mg, 2.61 mmol) was added in one portion to a solution of 4-bromobenzoic acid (0.5 g, 2.49 mmol, 359.71 uL) in THF (20 mL). The resulting solution was warmed to 50° C. and stirred until carbon dioxide evolution was completed, then methyl 1,2,3,4-tetrahydroisoquinoline-6-carboxylate (475.65 mg, 2.49 mmol) was added and the reaction mixture was stirred at 50° C. for 12 hr, then cooled and evaporated in vacuo. The residue was diluted water (20 ml), the precipitate was filtered, washed with water (2*10 ml) and air dried to afford methyl 2-(4-bromobenzoyl)-3,4-dihydro-1H-isoquinoline-6-carboxylate (800 mg, 2.14 mmol, 85.94% yield) as light-yellow solid. $^1$H NMR (500 MHz, DMSO-d$_6$) δ (ppm) 2.96 (m, 2H), 3.59 (m, 1H), 3.84 (s, 3H), 4.82 (m, 3H), 7.41 (m, 3H), 7.66 (d, 2H), 7.78 (d, 2H). LCMS(ESI): [M+H]+ m/z: calcd 374.2. found 375.2; Rt=E439 min.

2-(4-bromobenzoyl)-1,2,3,4-tetrahydroisoquinoline-6-carboxylic acid. Lithium hydroxide, monohydrate (179.41 mg, 4.28 mmol, 118.82 uL) was added in one portion to a stirred solution of methyl 2-(4-bromobenzoyl)-3,4-dihydro-1H-isoquinoline-6-carboxylate (800 mg, 2.14 mmol) in a mixture of water (3 mL) and THF (10 mL). The resulting mixture was stirred at 25° C. for 12 hr, and then evaporated in vacuo. The residue was diluted with water (10 ml) and acidified with concentrated aqueous hydrochloric acid to pH 4. The precipitate was filtered, washed with water (2*10 ml) and dried in vacuo to afford 2-(4-bromobenzoyl)-3,4-dihydro-1H-isoquinoline-6-carboxylic acid (600 mg, 1.67 mmol, 77.92% yield) as light-yellow solid. $^1$H NMR (500 MHz, DMSO-$d_6$) δ (ppm) 2.92 (m, 2H), 3.65 (m, 2H), 4.78 (m, 2H), 7.41 (m, 3H), 7.75 (m, 4H), 12.79 (bds, 1H). LCMS(ESI): [M+H]+ m/z: calcd 360.2. found 361.2; Rt=1.244 min.

2-(4-methoxybenzoyl-1,2,3,4-tetrahydroisoquinoline-6-carboxylic Acid

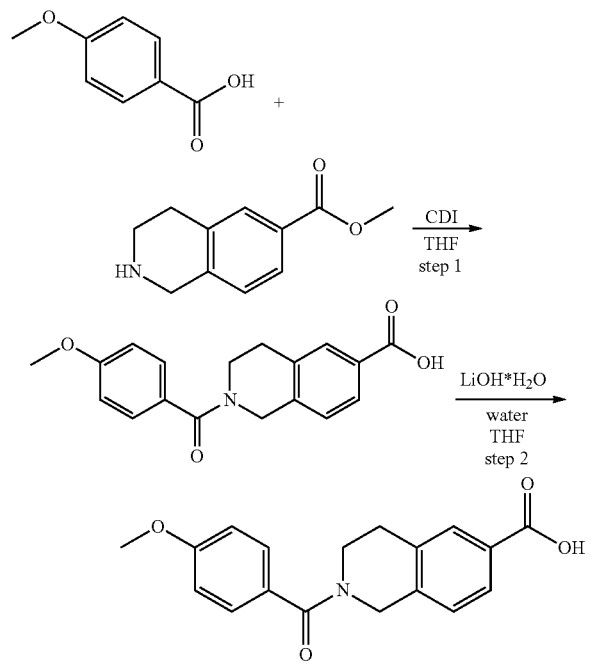

methyl 2-(4-methoxybenzoyl)-1,2,3,4-tetrahydroisoquinoline-6-carboxylate. CDI (559.51 mg, 3.45 mmol) was added in one portion to a solution of 4-methoxybenzoic acid (0.5 g, 3.29 mmol, 359.71 uL) in THF (20 mL). The resulting solution was warmed to 50° C. and stirred until carbon dioxide evolution was completed, then methyl 1,2,3,4-tetrahydroisoquinoline-6-carboxylate (628.42 mg, 3.29 mmol) was added and the reaction mixture was stirred at 50° C. for 12 hr, then cooled and evaporated in vacuo. The residue was diluted with 5% aqueous sodium hydrogen sulphate solution (30 ml) and the oily product was extracted with dichloromethane (2*20 ml). The combined organic extracts were washed with water (20 ml), dried over sodium sulphate and evaporated in vacuo to afford methyl 2-(4-methoxybenzoyl)-3,4-dihydro-1H-isoquinoline-6-carboxylate (1 g, 3.07 mmol, 93.53% yield) as yellow gum, which slowly crystallized into yellow solid. $^1$H NMR (500 MHz, DMSO-$d_6$) δ (ppm) 2.92 (m, 2H), 3.69 (m, 2H), 3.81 (s, 3H), 3.84 (s, 3H), 4.75 (m, 2H), 7.01 (m, 2H), 7.31 (s, 1H), 7.42 (m, 2H), 7.76 (m, 2H). LCMS(ESI): [M+H]+ m/z: calcd 325.4. found 326.2; Rt=1.318 min.

2-(4-methoxybenzoyl)-1,2,3,4-tetrahydroisoquinoline-6-carboxylic acid. Lithium hydroxide, monohydrate (257.95 mg, 6.15 mmol, 170.83 uL) was added in one portion to a stirred solution of methyl 2-(4-methoxybenzoyl)-3,4-dihydro-1H-isoquinoline-6-carboxylate (1 g, 3.07 mmol) in a mixture of water (3 mL) and THF (10 mL). The resulting mixture was stirred at 25° C. for 12 hr, and then evaporated in vacuo. The residue was diluted with water (10 ml) and acidified with concentrated aqueous hydrochloric acid to pH 4. The oily product was extracted with dichloromethane (2*20 ml). The combined organic extracts were dried over sodium sulphate and evaporated in vacuo to afford 2-(4-methoxybenzoyl)-3,4-dihydro-1H-isoquinoline-6-carboxylic acid (650 mg, 2.09 mmol, 67.93% yield) as light-yellow solid. $^1$H NMR (500 MHz, DMSO-$d_6$) δ (ppm) 2.92 (m, 2H), 3.70 (m, 2H), 3.81 (s, 3H), 4.75 (m, 2H), 7.01 (m, 2H), 7.28 (s, 1H), 7.42 (m, 2H), 7.88 (m, 2H), 12.72 (bds, 1H). LCMS(ESI): [M+H]+m/z: calcd 311.3. found 312.2; Rt=1.115 min.

2-((1-acetylpiperidin-4-yl)amino)-6-methoxyisonicotinic Acid

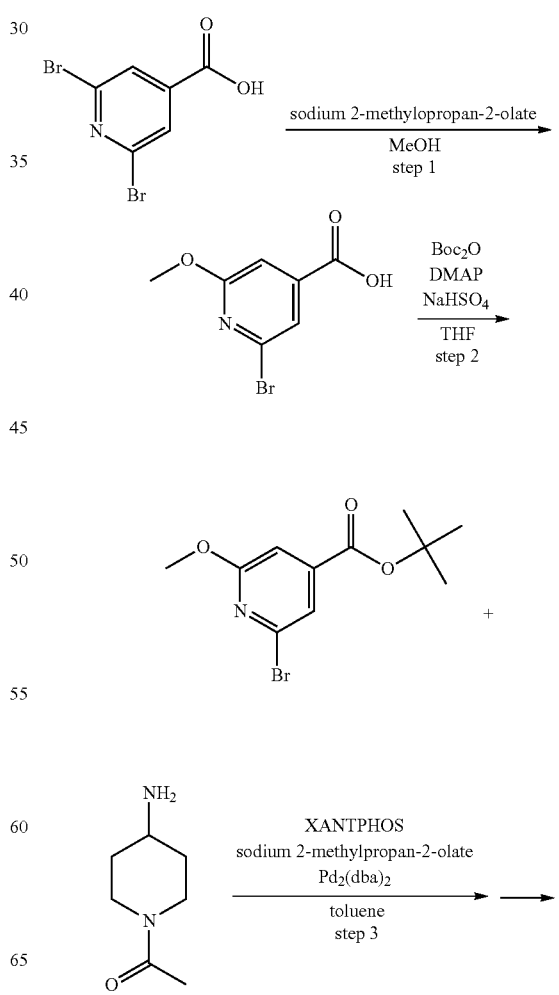

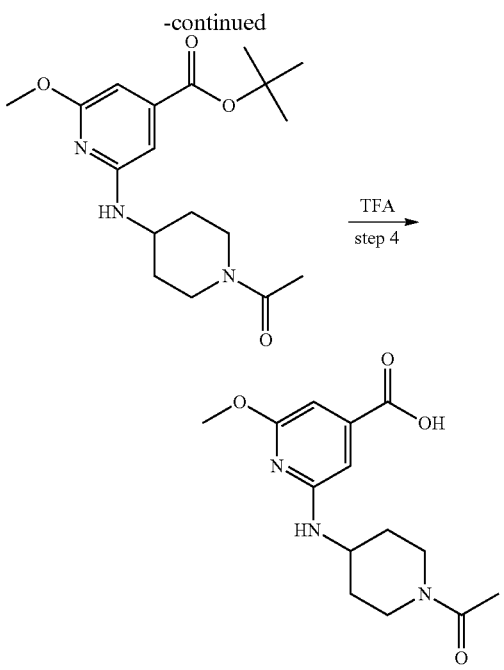

2-bromo-6-methoxyisonicotinic acid. 2,6-Dibromopyridine-4-carboxylic acid (5 g, 17.80 mmol) was added to a solution of sodium 2-methylpropan-2-olate (8.55 g, 89.00 mmol) in methanol (100 mL). The resulting mixture was stirred with reflux condenser at 70° C. for 12 hr, then cooled and evaporated to dryness in vacuo. The residue was dissolved in water (120 ml) and acidified to pH 4 with concentrated aqueous hydrochloric acid. The precipitate was filtered, washed with water (2*20 ml) and dried in vacuo to afford 2-bromo-6-methoxy-pyridine-4-carboxylic acid (3.42 g, 14.74 mmol, 82.81% yield) as beige solid. $^1$H NMR (400 MHz, DMSO-de) δ (ppm) 3.89 (s, 3H), 7.20 (s, 1H), 7.53 (s, 1H), 13.99 (bds, 1H). LCMS(ESI): [M+H]+ m/z: calcd 232.0. found 233.2; Rt=1.156 min.

tert-butyl 2-bromo-6-methoxyisonicotinate. Di-tert-butyl dicarbonate (4.18 g, 19.16 mmol, 4.40 mL) was added to a stirred mixture of 2-bromo-6-methoxy-pyridine-4-carboxylic acid (3.42 g, 14.74 mmol) and N,N-dimethylpyridin-4-amine (900.36 mg, 7.37 mmol) in THF (100 mL) at 25° C. The reaction mixture was stirred at 45° C. for 2 hr, and evaporated in vacuo. The residue was dissolved in dichloromethane (100 ml) and washed successively with aqueous sodium hydrogen sulphate (1.24 g, 10.32 mmol) solution (30 ml), and water (30 ml). The organic layer was separated, dried over sodium sulphate, filtered through short pad of silica gel and evaporated in vacuo to afford tert-butyl 2-bromo-6-methoxy-pyridine-4-carboxylate (3.65 g, 12.67 mmol, 85.94% yield) as light-yellow solid. $^1$H NMR (400 MHz, CDCl$_3$) δ (ppm) 1.59 (s, 9H), 3.97 (s, 3H), 7.20 (s, 1H), 7.53 (s, 1H). LCMS(ESI): [M+H]+ m/z: calcd 288.1. found 289.2; Rt=1.618 min.

tert-butyl 2-((1-acetylpiperidin-4-yl)amino)-6-methoxyisonicotinate. tert-Butyl 2-bromo-6-methoxy-pyridine-4-carboxylate (2 g, 6.94 mmol), 1-(4-amino-1-piperidyl)ethanone (1.09 g, 7.64 mmol) and sodium 2-methylpropan-2-olate (1.00 g, 10.41 mmol) were mixed together in toluene (40 mL). The resulting mixture was evacuated and then back-filled with argon, this operation was repeated three times, then [5-(diphenylphosphanyl)-9,9-dimethyl-9H-xanthen-4-yl]diphenylphosphane (200.81 mg, 347.06 umol) and tris(1,5-diphenylpenta-1,4-dien-3-one) dipalladium (158.90 mg, 173.53 umol) were added under argon. The reaction mixture was stirred under argon at 75° C. for 18 hr, then cooled and evaporated in vacuo. The residue was purified by column chromatography on silica gel using MTBE/methanol gradient (0-100% methanol) to afford tert-butyl 2-[(1-acetyl-4-piperidyl)amino]-6-methoxy-pyridine-4-carboxylate (1.1 g, 3.15 mmol, 45.35% yield) as yellow gum. $^1$H NMR (400 MHz, CDCl$_3$) δ (ppm) 1.38 (m, 2H), 1.56 (s, 9H), 2.09 (m, 2H), 2.17 (s, 3H), 2.88 (m, 1H), 3.25 (m, 1H), 3.83 (m, 2H), 3.91 (s, 3H), 4.49 (m, 2H), 6.48 (s, 1H), 6.50 (s, 1H). LCMS(ESI): [M+H]+ m/z: calcd 349.4. found 350.2; Rt=1.279 min.

2-((1-acetylpiperidin-4-yl)amino)-6-methoxyisonicotinic acid, tert-Butyl 2-[(1-acetyl-4-piperidyl)amino]-6-methoxy-pyridine-4-carboxylate (1.1 g, 3.15 mmol) was dissolved in trifluoroacetic acid (17.95 g, 157.40 mmol, 12.13 mL). The resulting solution was stirred at 25° C. for 1 hr, and then evaporated in vacuo. The residue was triturated with MTBE/hexane mixture (2/1, 60 ml). The precipitate was filtered, washed with hexane (2*10 ml) and dried in vacuo to afford 2-[(1-acetyl-4-piperidyl)amino]-6-methoxy-pyridine-4-carboxylic acid (0.97 g, 2.38 mmol, 75.64% yield, CF$_3$COOH) as light-yellow solid. $^1$H NMR (500 MHz, DMSO-d$_6$) δ (ppm) 1.25 (m, 1H), 1.38 (m, 1H), 1.97 (m, 2H), 1.99 (s, 3H), 2.83 (m, 1H), 3.17 (m, 1H), 3.88 (s, 3H), 3.89 (m, 2H), 4.21 (m, 1H), 6.23 (s, 1H), 6.55 (s, 1H). LCMS(ESI): [M+H]+ m/z: calcd 293.3. found 294.2; Rt=0.971 min.

2-((1-acetylpiperidin-4-yl)amino)-5-methoxyisonicotinic Acid

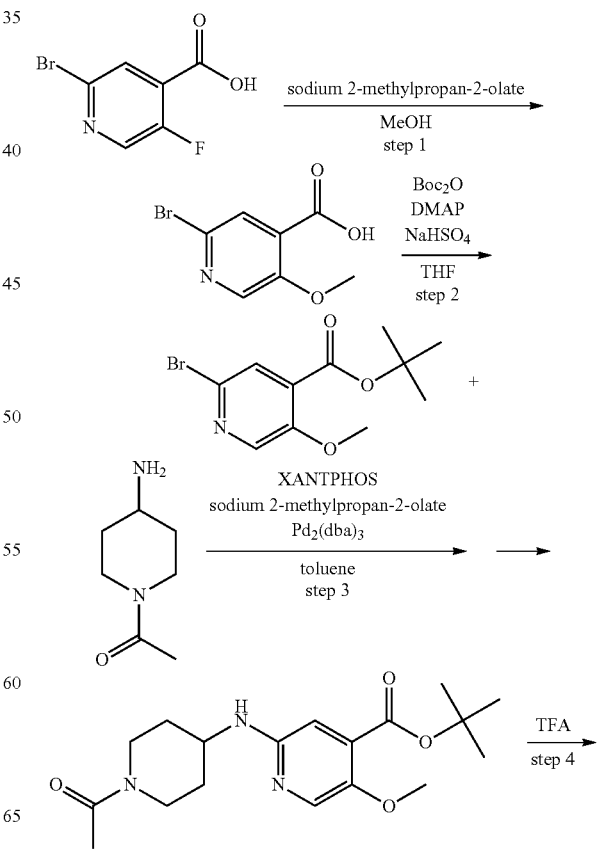

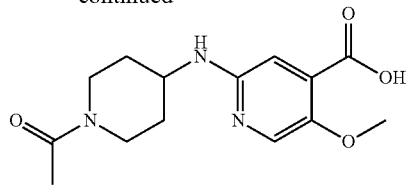

2-bromo-5-methoxyisonicotinic acid. 2-Bromo-5-fluoropyridine-4-carboxylic acid (6 g, 27.27 mmol) was added to a solution of sodium 2-methylpropan-2-olate (13.11 g, 136.37 mmol) in methanol (150 mL). The resulting mixture was stirred with reflux condenser at 70° C. for 12 hr, then cooled and evaporated to dryness in vacuo. The residue was dissolved in water (120 ml) and acidified to pH 4 with concentrated aqueous hydrochloric acid. The precipitate was filtered, washed with water (2*20 ml) and dried in vacuo to afford 2-bromo-5-methoxy-pyridine-4-carboxylic acid (5.6 g, 24.13 mmol, 88.49% yield) as white solid. $^1$H NMR (500 MHz, DMSO-$d_6$) δ (ppm) 3.92 (s, 3H), 7.69 (s, 1H), 8.34 (s, 1H), 13.75 (bds, 1H). LCMS(ESI): [M+H]+ m/z: calcd 232.0. found 233.2; Rt=0.778 min.

tert-butyl 2-bromo-5-methoxyisonicotinate. Di-tert-butyl dicarbonate (8.93 g, 40.90 mmol, 9.39 mL) was added to a stirred mixture of 2-bromo-5-methoxy-pyridine-4-carboxylic acid (7.3 g, 31.46 mmol) and N,N-dimethylpyridin-4-amine (1.92 g, 15.73 mmol) in THF (100 mL) at 25° C. The reaction mixture was stirred at 50° C. for 1 hr, and then evaporated in vacuo. The residue was dissolved in dichloromethane (100 ml) and washed successively with aqueous sodium hydrogen sulphate (2.64 g, 22.02 mmol) solution (60 ml), and water (50 ml). The organic layer was separated, dried over sodium sulphate and evaporated in vacuo to afford tert-butyl 2-bromo-5-methoxy-pyridine-4-carboxylate (7 g, 24.29 mmol, 77.22% yield) as yellow solid. $^1$H NMR (500 MHz, CDCl$_3$) δ (ppm) 1.59 (s, 9H), 3.97 (s, 3H), 7.63 (s, 1H), 8.15 (s, 1H). LCMS(ESI): [M+H]+ m/z: calcd 288.1. found 289.2; Rt=1.447 min.

tert-butyl 2-((1-acetylpiperidin-4-yl)amino)-5-methoxyisonicotinate. tert-Butyl 2-bromo-5-methoxy-pyridine-4-carboxylate (2.6 g, 9.02 mmol), 1-(4-amino-1-piperidyl)ethanone (1.48 g, 10.38 mmol) and sodium 2-methylpropan-2-olate (1.30 g, 13.54 mmol) were mixed together in toluene (50 mL). The resulting mixture was evacuated and then backfilled with argon, this operation was repeated three times, then [5-(diphenylphosphanyl)-9,9-dimethyl-9H-xanthen-4-yl]diphenylphosphane (261.06 mg, 451.17 umol) and tris(1,5-diphenylpenta-1,4-dien-3-one) dipalladium (206.57 mg, 225.59 umol) were added under argon. The reaction mixture was stirred under argon at 75° C. for 18 hr, then cooled and evaporated in vacuo. The residue was purified by column chromatography on silica gel using MTBE/methanol gradient (0-100% methanol) to afford tert-butyl 2-[(1-acetyl-4-piperidyl)amino]-5-methoxy-pyridine-4-carboxylate (1.2 g, 3.43 mmol, 38.06% yield) as yellow gum. $^1$H NMR (400 MHz, CDCl$_3$) δ (ppm) 1.35 (m, 2H), 1.56 (s, 9H), 2.08 (m, 2H), 2.15 (s, 3H), 2.84 (m, 1H), 3.19 (m, 1H), 3.83 (m, 2H), 3.88 (s, 3H), 4.22 (m, 1H), 4.51 (m, 1H), 6.63 (s, 1H), 7.89 (s, 1H). LCMS(ESI): [M+H]+ m/z: calcd 349.4; found 350.2; Rt=1.031 min.

2-((1-acetylpiperidin-4-yl)amino)-5-methoxyisonicotinic acid. tert-Butyl 2-[(1-acetyl-4-piperidyl)amino]-5-methoxy-pyridine-4-carboxylate (1.2 g, 3.43 mmol) was dissolved in trifluoroacetic acid (19.58 g, 171.71 mmol, 13.23 mL). The resulting solution was stirred at 25° C. for 1 hr, and then evaporated in vacuo. The residue was triturated with MTBE/hexane mixture (1/1, 30 ml). The precipitate was filtered, washed with hexane (2*10 ml) and dried in vacuo to afford 2-[(1-acetyl-4-piperidyl)amino]-5-methoxy-pyridine-4-carboxylic acid (0.81 g, 1.99 mmol, 57.90% yield, CF$_3$COOH) as light-yellow solid. $^1$H NMR (500 MHz, DMSO-$d_6$) δ (ppm) 1.25 (m, 1H), 1.38 (m, 1H), 1.97 (m, 2H), 1.99 (s, 3H), 2.73 (m, 1H), 3.07 (m, 1H), 3.77 (s, 3H), 3.78 (m, 2H), 4.26 (m, 1H), 7.02 (s, 1H), 7.71 (s, 1H). LCMS(ESI): [M+H]+ m/z: calcd 293.3. found 294.2; Rt=0.554 min.

2-((1R,5S)-3-oxa-8-azabicyclo[3.2.1]octan-8-yl)-6-(pyridin-3-ylamino)isonicotinic Acid

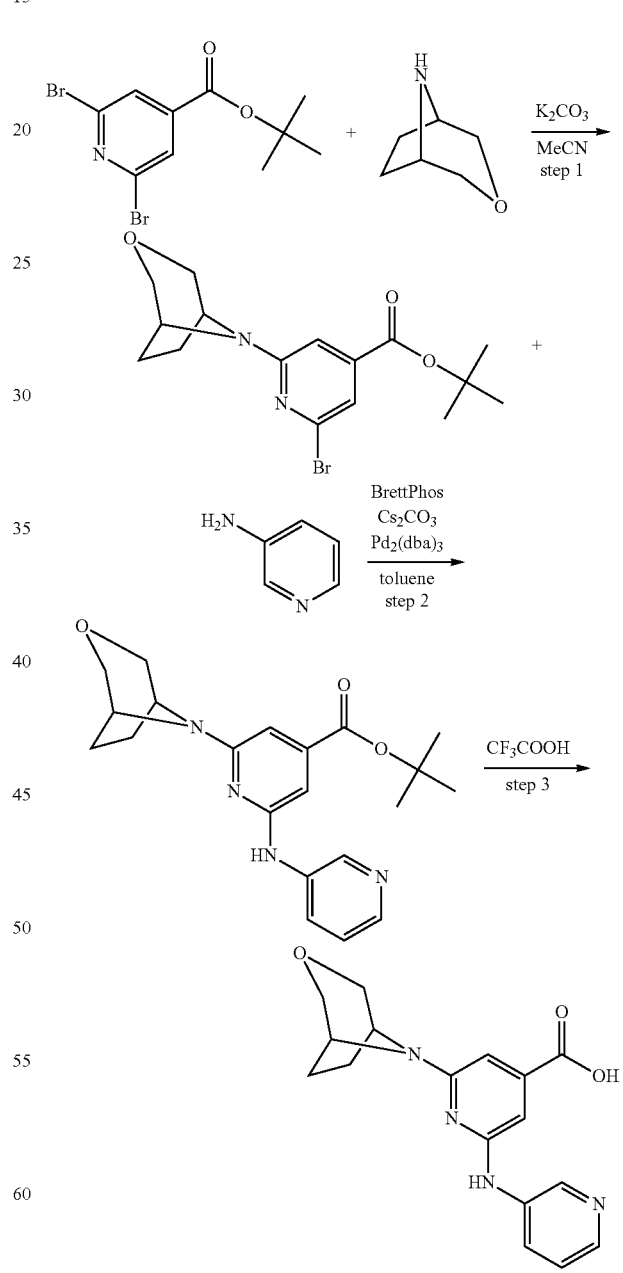

tert-butyl 2-(3-oxa-8-azabicyclo[3.2.1]octan-8-yl)-6-bromoisonicotinate. 3-Oxa-8-azabicyclo[3.2.1]octane (6.22 g, 41.54 mmol, 1.38 mL, HCl) was added to a stirred mixture of tert-butyl 2,6-dibromopyridine-4-carboxylate (5 g, 14.84 mmol) and potassium carbonate, anhydrous, 99% (14.35 g, 103.86 mmol, 6.27 mL) in acetonitrile (120 mL). The resulting mixture was stirred with reflux condenser at 80° C. for 120 hr (the reaction progress was monitored by HNMR of the aliquots), the cooled and filtered. The filtercake was washed with acetonitrile (2*50 ml) and discarded. The filtrate was evaporated in vacuo to leave 5.7 g of the residue, which was purified by column chromatography on silica gel using hexane/ethyl acetate gradient (5-100% ethyl acetate) to afford tert-butyl 2-bromo-6-(3-oxa-8-azabicyclo[3.2.1] octan-8-yl)pyridine-4-carboxylate (4 g, 10.83 mmol, 73.01% yield) as light-yellow solid. $^1$H NMR (400 MHz, CDCl$_3$) δ (ppm) 1.58 (m, 9H), 2.01 (m, 2H), 2.11 (m, 2H), 3.61 (m, 2H), 3.79 (m, 2H), 4.45 (m, 2H), 6.97 (s, 1H), 7.17 (s, 1H). LCMS(ESI): [M+H]+ m/z: calcd 369.2. found 370.2; Rt=1.772 min.

tert-butyl 2-(3-oxa-8-azabicyclo[3.2.1]octan-8-yl)-6-(pyridin-3-ylamino)isonicotinate. tert-Butyl 2-bromo-6-(3-oxa-8-azabicyclo[3.2.1]octan-8-yl)pyridine-4-carboxylate (2.2 g, 5.96 mmol), pyridin-3-amine (616.80 mg, 6.55 mmol) and cesium carbonate (2.91 g, 8.94 mmol) were mixed together in toluene (50 mL). The resulting mixture was evacuated and then backfilled with argon, this operation was repeated three times, then tris(1,5-diphenylpenta-1,4-dien-3-one) dipalladium (136.40 mg, 148.95 umol) and 2-(dicyclohexylphosphino)3,6-dimethoxy-2',4',6'-triisopropyl-1,1'-biphenyl (319.81 mg, 595.80 umol) were added under argon. The reaction mixture was stirred under argon at 100° C. for 48 hr, then cooled and evaporated in vacuo. The residue was purified by column chromatography on silica gel using hexane/ethyl acetate gradient (5-100% ethyl acetate) to afford tert-butyl 2-(3-oxa-8-azabicyclo[3.2.1]octan-8-yl)-6-(3-pyridylamino)pyridine-4-carboxylate (1.05 g, 2.75 mmol, 46.08% yield) as beige solid. $^1$H NMR (500 MHz, CDCl$_3$) δ (ppm) 1.59 (s, 9H), 2.06 (m, 4H), 3.61 (m, 2H), 3.86 (m, 2H), 4.42 (m, 2H), 6.44 (s, 1H), 6.57 (d, 2H), 7.23 (t, 1H), 7.84 (d, 1H), 8.24 (d, 1H), 8.72 (s, 1H). LCMS(ESI): [M+H]+ m/z: calcd 382.5. found 383.2; Rt=1.104 min.

2-((1R,5S)-3-oxa-8-azabicyclo[3.2.1]octan-8-yl)-6-(pyridin-3-ylamino)isonicotinic acid tert-Butyl 2-(3-oxa-8-azabicyclo[3.2.1]octan-8-yl)-6-(3-pyridylamino)pyridine-4-carboxylate (1.05 g, 2.75 mmol) was dissolved in trifluoroacetic acid (15.65 g, 137.27 mmol, 10.58 mL). The reaction mixture was stirred at 25° C. for 1 hr, and then evaporated in vacuo. The residue was triturated with hexane/MTBE mixture (1/1, 50 ml), stirred for 0.1 hr and the precipitate was filtered, washed with MTBE (2*10 ml) and dried in vacuo to afford 2-(3-oxa-8-azabicyclo[3.2.1]octan-8-yl)-6-(3-pyridylamino)pyridine-4-carboxylic acid (0.93 g, 1.68 mmol, 61.10% yield, 2CF$_3$COOH) as yellow solid. $^1$H NMR (400 MHz, DMSO-d$_6$) δ (ppm) 1.99 (m, 4H), 3.55 (m, 2H), 3.68 (m, 2H), 4.45 (m, 2H), 6.68 (m, 2H), 7.80 (t, 1H), 8.28 (d, 1H), 8.35 (d, 1H), 9.25 (s, 1H), 9.98 (s, 1H), 13.56 (bds, 1H). LCMS(ESI): [M+H]+ m/z: calcd 326.4. found 327.2; Rt=0.804 min.

2-(3-oxa-8-azabicyclo[3.2.1]octane-8-carbonyl) isonicotinic Acid

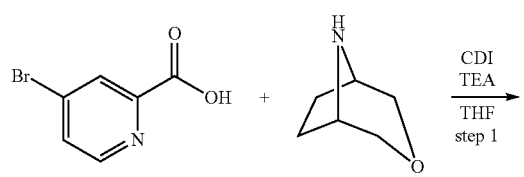

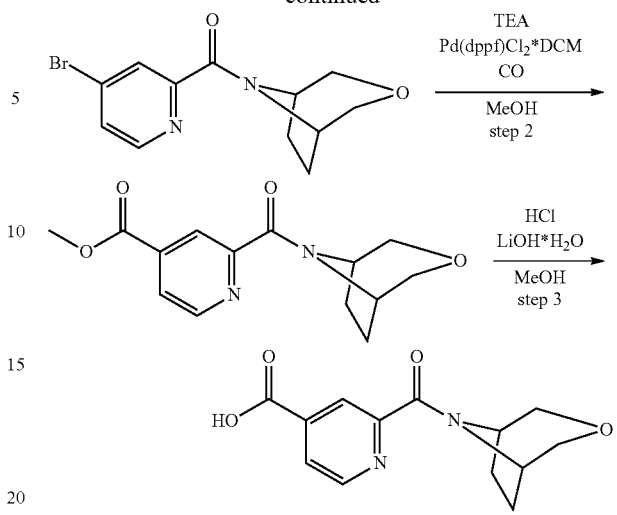

3-oxa-8-azabicyclo[3.2H]octan-8-yl(4-bromopyridin-2-yl)methanone. CDI (1.93 g, 11.88 mmol) was added to a solution 4-bromopyridine-2-carboxylic acid (2 g, 9.90 mmol) in THF (30 mL). The resulting mixture was stirred at 50° C. 1 hr, then cooled to 20° C. and 3-oxa-8-azabicyclo [3.2.1]octane (1.12 g, 7.49 mmol, HCl) was added followed by triethyl amine (1.50 g, 14.85 mmol, 2.07 mL). The reaction mixture was allowed to warm to 50° C. and stirred for 12 hr. The reaction mixture was poured into water (100 ml) and extracted with EtOAc (3×35 ml). The combined organic extracts were washed with water(2*20 ml), dried over sodium sulphate and evaporated in vacuo to afford crude product (4-bromo-2-pyridyl)-(3-oxa-8-azabicyclo [3.2.1]octan-8-yl)methanone (2.44 g, 8.21 mmol, 82.94% yield). $^1$H NMR (500 MHz, CDCl$_3$) δ (ppm) 2.07 (m, 4H), 3.72 (m, 2H), 3.88 (m, 2H), 4.83 (m, 2H), 7.54 (m, 1H), 8.09 (s, 1H), 8.38 (s, 1H). LCMS(ESI): [M+H]+ m/z: calcd 297.2. found 298.2; Rt=1.131 min.

methyl 2-(3-oxa-8-azabicyclo[3.2.1]octane-8-carbonyl) isonicotinate. (4-Bromo-2-pyridyl)-(3-oxa-8-azabicyclo [3.2.1]octan-8-yl)methanone (2.44 g, 8.21 mmol), triethyl amine (997.10 mg, 9.85 mmol, 1.37 mL) and Pd(dppf)C$_{1-2}$ DCM (201.17 mg, 246.34 umol) were dissolved in dry methanole (60 mL). The reaction mixture was heated at 120° C. in high pressure vessel at 40 atm carbon monoxide (4.60 g, 164.23 mmol, 4.26 mL) pressure for 16 hr. The solvent was evaporated and the mixture was poured into water(50 ml). The mixture was extracted with EtOAc (2*50) and the organic extracts were washed with water (2*20 ml), dried over sodium sulphate and evaporated in vacuo to leave 2.02 g of crude product, 2.02 g of which was purification by column chromatography on silica gel using CHCl$_3$/CH$_3$CN gradient (10-100% CH$_3$CN) to afford pure product methyl 2-(3-oxa-8-azabicyclo[3.2.1]octane-8-carbonyl)pyridine-4-carboxylate (1.25 g, 4.52 mmol, 55.10% yield). $^1$H NMR (500 MHz, CDCl$_3$) δ (ppm) 2.07 (m, 4H), 3.65 (m, 1H), 3.73 (m, 1H), 3.90 (m, 2H), 3.99 (s, 3H), 4.82 (m, 2H), 7.93 (d, 1H), 8.44 (s, 1H), 8.73 (d, 1H). LCMS(ESI): [M+H]+ m/z: calcd 276.3. found 277.2; Rt=0.897 min.

2-(3-oxa-8-azabicyclo[3.2.1]octane-8-carbonyl)isonicotinic acid. To a solution of methyl 2-(3-oxa-8-azabicyclo [3.2.1]octane-8-carbonyl)pyridine-4-carboxylate (0.25 g, 904.86 umol) in methanole (5 mL) was added lithium hydroxide monohydrate, 98% (94.92 mg, 2.26 mmol, 62.86 uL) in water (2 ml). The reaction mixture was stirred at 20°

C. for 5 hr. The reaction mixture was evaporated, and added hydrochloric acid, 36% w/w aq. soln. (296.93 mg, 8.14 mmol, 371.16 uL) in water (5 ml) then extracted with EtOAc (3×10 ml). The combined organic extracts were washed with brine(2*10 ml), dried over sodium sulphate and evaporated in vacuo to afford product 2-(3-oxa-8-azabicyclo[3.2.1]octane-8-carbonyl)pyridine-4-carboxylic acid (0.14 g, 533.82 umol, 59.00% yield). $^1$H NMR (500 MHz, DMSO-$d_6$) δ (ppm) 1.89 (m, 4H), 3.66 (m, 4H), 4.61 (m, 2H), 7.92 (d, 1H), 8.14 (s, 1H), 8.79 (d, 1H), 13.89 (bds, 1H). LCMS (ESI): [M+H]+ m/z: calcd 262.3. found 263.2; Rt=0.754 min.

2-(3-oxa-8-azabicyclo[3.2.1]octan-8-yl)isonicotinic Acid

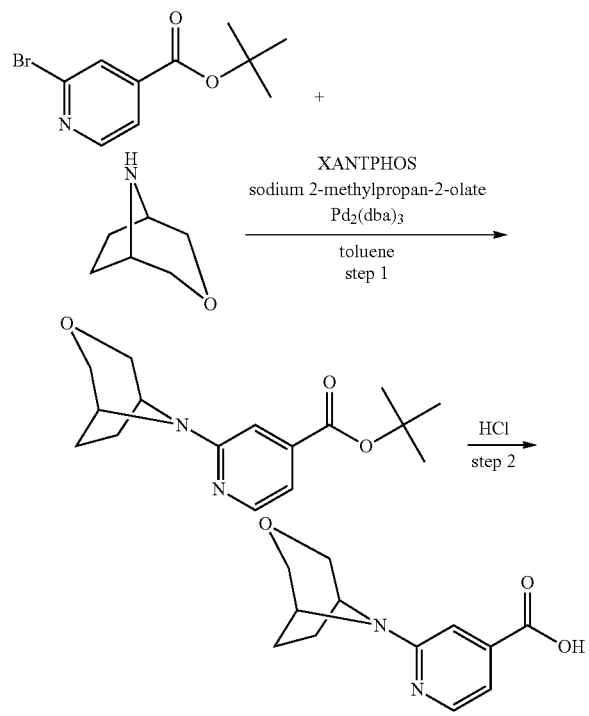

tert-butyl 2-(3-oxa-8-azabicyclo[3.2.1]octan-8-yl)isonicotinate. tert-Butyl 2-bromopyridine-4-carboxylate (2.7 g, 10.46 mmol), 3-oxa-8-azabicyclo[3.2.1]octane (1.72 g, 11.51 mmol, 4.65 mL, HCl) and sodium 2-methylpropan-2-olate (2.61 g, 27.20 mmol) were mixed together in toluene (50 mL). The resulting mixture was evacuated and then backfilled with argon, this operation was repeated three times, then [5-(diphenylphosphanyl)-9,9-dimethyl-9H-xanthen-4-yl]diphenylphosphane (302.64 mg, 523.03 umol) and tris(1,5-diphenylpenta-1,4-dien-3-one) dipalladium (239.47 mg, 261.52 umol) were added under argon. The reaction mixture was stirred under argon at 70° C. for 12 hr, then cooled and evaporated in vacuo. The residue was purified by column chromatography on silica gel using hexane-ethyl acetate gradient (5-100% ethyl acetate) to afford tert-butyl 2-(3-oxa-8-azabicyclo[3.2.1]octan-8-yl)pyridine-4-carboxylate (100 mg, 344.40 umol, 3.29% yield) as yellow gum. $^1$H NMR (400 MHz, CDCl$_3$) δ (ppm) 1.59 (s, 9H), 2.10 (m, 4H), 3.61 (m, 2H), 3.84 (m, 2H), 4.47 (m, 2H), 7.08 (m, 2H), 8.25 (d, 1H). LCMS(ESI): [M+H]+ m/z: calcd 290.4. found 291.2; Rt=1.289 min.

2-(3-oxa-8-azabicyclo[3.2.1]octan-8-yl)isonicotinic acid, tert-Butyl 2-(3-oxa-8-azabicyclo[3.2.1]octan-8-yl)pyridine-4-carboxylate (100 mg, 344.40 umol) was diluted with hydrochloric acid (5.30 g, 145.36 mmol, 5 mL). The resulting mixture was stirred at 75° C. for 0.5 hr, then cooled and the resulting solution was evaporated to dryness in vacuo. The residue was dried in vacuo to afford 2-(3-oxa-8-azabicyclo[3.2.1]octan-8-yl)pyridine-4-carboxylic acid (80 mg, 295.52 umol, 85.81% yield, HCl) as yellow solid. $^1$H NMR (500 MHz, DMSO-$d_6$) δ (ppm) 2.02 (m, 4H), 3.62 (m, 2H), 3.67 (m, 2H), 4.87 (m, 2H), 7.12 (d, 1H), 7.56 (s, 1H), 8.11 (d, 1H). LCMS(ESI): [M+H]+ m/z: calcd 234.2. found 235.2; Rt=0.679 min.

2-(piperidin-1-yl)-6-(pyridin-3-ylamino)isonicotinic Acid

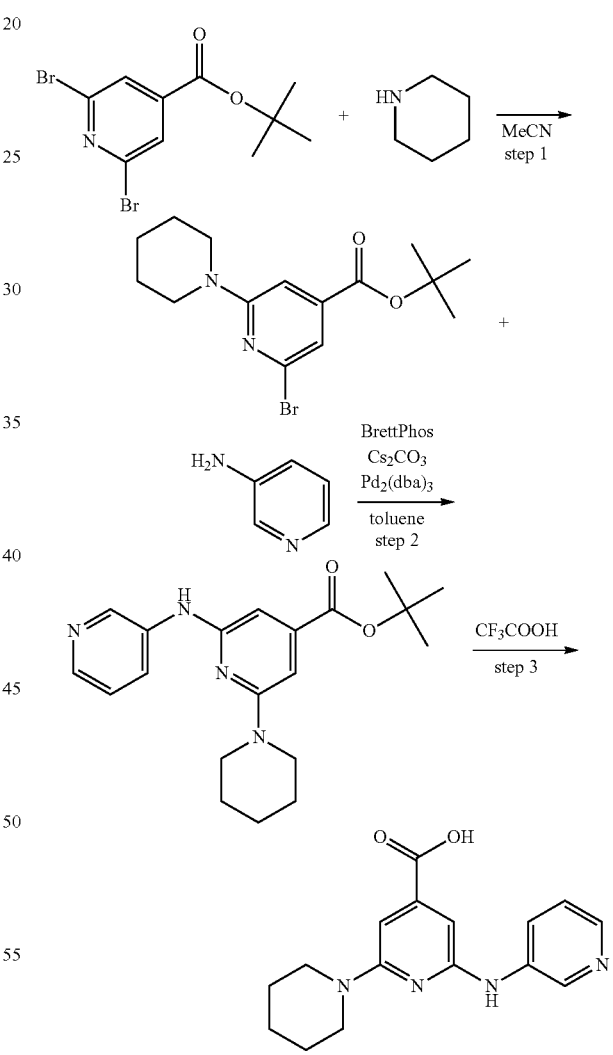

tert-butyl 2-bromo-6-(piperidin-1-yl)isonicotinate. Piperidine (6.32 g, 74.18 mmol, 7.33 mL) was added to a stirred mixture of tert-butyl 2,6-dibromopyridine-4-carboxylate (5 g, 14.84 mmol) in acetonitrile (100 mL). The resulting mixture was stirred at 80° C. for 8 hr (the reaction progress was monitored by HNMR of the aliquots), then cooled and evaporated in vacuo, the residue was diluted with water (100 ml) and extracted with dichloromethane (2*75 ml). The combined organic extracts were dried over sodium sulphate and evaporated in vacuo to afford tert-butyl 2-bromo-6-(1-piperidyl)pyridine-4-carboxylate (4.5 g, 13.19 mmol, 88.88% yield) as light-brown solid. $^1$H NMR (400 MHz, CDCl$_3$) δ (ppm) 1.58 (m, 9H), 1.64 (m, 6H), 3.58 (m, 4H), 7.07 (s, 1H), 7.10 (s, 1H). LCMS(ESI): [M+H]+ m/z: calcd 341.2. found 342.2; Rt=1.848 min.

tert-butyl 2-(piperidin-1-yl)-6-(pyridin-3-ylamino)isonicotinate. tert-Butyl 2-bromo-6-(1-piperidyl)pyridine-4-carboxylate (3 g, 8.79 mmol), pyridin-3-amine (910.14 mg, 9.67 mmol) and cesium carbonate (4.30 g, 13.19 mmol) were mixed together in toluene (50 mL). The resulting mixture was evacuated and then backfilled with argon, this operation was repeated three times, then tris(1,5-diphenylpenta-1,4-dien-3-one) dipalladium (201.26 mg, 219.78 umol) and 2-(dicyclohexylphosphino)3,6-dimethoxy-2',4',6'-triisopropyl-1,1'-biphenyl (471.89 mg, 879.14 umol) were added under argon. The reaction mixture was stirred under argon at 100° C. for 48 hr, then cooled and evaporated in vacuo. The residue was purified by column chromatography on silica gel using hexane/ethyl acetate gradient (0-100% ethyl acetate) to afford tert-butyl 2-(1-piperidyl)-6-(3-pyridylamino)pyridine-4-carboxylate (1.6 g, 4.51 mmol, 51.35% yield) as yellow solid. $^1$H NMR (500 MHz, CDCl$_3$) δ (ppm) 1.58 (s, 9H), 1.65 (m, 6H), 3.57 (m, 4H), 6.45 (s, 1H), 6.53 (d, 1H), 6.69 (s, 1H), 7.23 (m, 1H), 7.90 (m, 1H), 8.23 (d, 1H), 8.68 (s, 1H). LCMS(ESI): [M+H]+ m/z: calcd 354.5. found 355.2; Rt=1.301 min.

2-(piperidin-1-yl)-6-(pyridin-3-ylamino)isonicotinic acid, tert-Butyl 2-(1-piperidyl)-6-(3-pyridylamino)pyridine-4-carboxylate (1.6 g, 4.51 mmol) was dissolved in trifluoroacetic acid (25.73 g, 225.70 mmol, 17.39 mL). The reaction mixture was stirred at 25° C. for 1 hr, and then evaporated in vacuo. The residue was triturated with hexane/MTBE mixture (1/1, 70 ml), stirred for 0.1 hr and the precipitate was filtered, washed with MTBE (2*10 ml) and dried in vacuo to afford 2-(1-piperidyl)-6-(3-pyridylamino)pyridine-4-carboxylic acid (1.59 g, 3.02 mmol, 66.91% yield, 2CF$_3$COOH) as yellow solid. $^1$H NMR (400 MHz, DMSO-d$_6$) δ (ppm) 1.59 (m, 6H), 3.53 (m, 4H), 6.63 (d, 1H), 6.71 (s, 1H), 7.83 (m, 1H), 8.34 (m, 2H), 9.26 (s, 1H), 9.95 (s, 1H). LCMS(ESI): [M+H]+ m/z: calcd 298.3. found 299.2; Rt=0.952 min.

2-(cyclobutylamino)-5-methoxyisonicotinic Acid

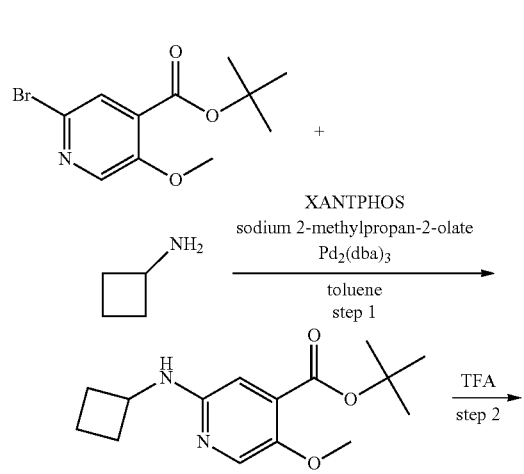

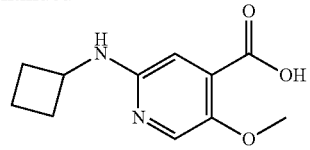

tert-butyl 2-(cyclobutylamino)-5-methoxyisonicotinate. tert-Butyl 2-bromo-5-methoxy-pyridine-4-carboxylate (2.6 g, 9.02 mmol) and sodium 2-methylpropan-2-olate (1.30 g, 13.54 mmol) were mixed together in toluene (50 mL). The resulting mixture was evacuated and then backfilled with argon, this operation was repeated three times, then cyclobutanamine (1.28 g, 18.05 mmol, 1.54 mL), [5-(diphenylphosphanyl)-9,9-dimethyl-9H-xanthen-4-yl]diphenylphosphane (261.06 mg, 451.17 umol) and tris(1,5-diphenylpenta-1,4-dien-3-one) dipalladium (206.57 mg, 225.59 umol) were added under argon. The reaction mixture was stirred under argon at 75° C. for 18 hr, then cooled, evaporated in vacuo, and the residue was purified by column chromatography on silica gel using hexane/ethyl acetate gradient (5-100% ethyl acetate) to afford tert-butyl 2-(cyclobutylamino)-5-methoxy-pyridine-4-carboxylate (0.9 g, 3.23 mmol, 35.83% yield) as light-yellow gum. $^1$H NMR (400 MHz, CDCl$_3$) δ (ppm) 1.59 (s, 9H), 1.81 (m, 4H), 2.43 (m, 2H), 3.85 (s, 3H), 4.11 (m, 1H), 4.54 (m, 1H), 6.56 (s, 1H), 7.89 (s, 1H). LCMS(ESI): [M+H]+ m/z: calcd 278.3. found 279.2; Rt=1.122 min.

2-(cyclobutylamino)-5-methoxyisonicotinic acid. tert-Butyl 2-(cyclobutylamino)-5-methoxy-pyridine-4-carboxylate (0.9 g, 3.23 mmol) was dissolved in trifluoroacetic acid (18.43 g, 161.67 mmol, 12.46 mL). The resulting solution was stirred at 25° C. for 1 hr, and then evaporated in vacuo. The residue was triturated with MTBE/hexane mixture (1/1, 30 ml). The precipitate was filtered, washed with hexane (2*10 ml) and dried in vacuo to afford 2-(cyclobutylamino)-5-methoxy-pyridine-4-carboxylic acid (0.65 g, 1.93 mmol, 59.78% yield, CF$_3$COOH) as light-yellow solid. $^1$H NMR (500 MHz, DMSO-d$_6$) δ (ppm) 1.74 (m, 2H), 1.88 (m, 2H), 2.34 (m, 2H), 3.76 (s, 3H), 4.17 (m, 2H), 6.89 (s, 1H), 7.68 (s, 1H). LCMS(ESI): [M+H]+ m/z: calcd 222.2. found 223.2; Rt=0.602 min.

2-(4-(cyclopropanecarbonyl)piperazin-1-yl)-6-(spiro[3.3]heptan-2-ylamino)isonicotinic Acid

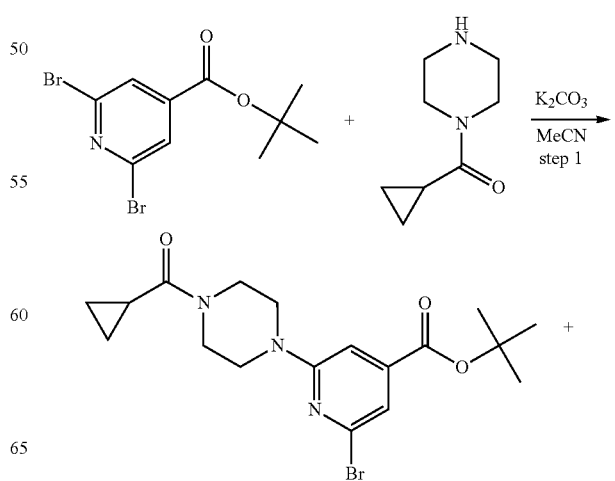

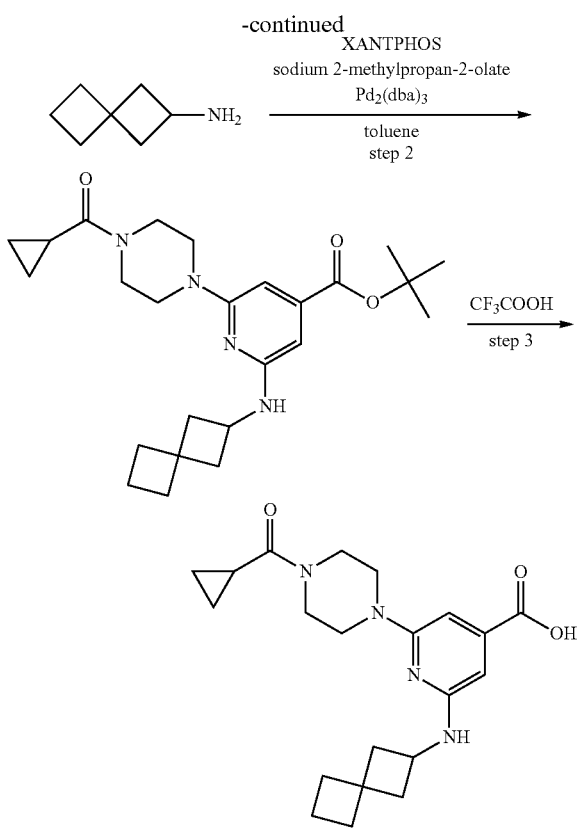

tert-butyl 2-bromo-6-(4-(cyclopropanecarbonyl)piperazin-1-yl)isonicotinate. Cyclopropyl(piperazin-1-yl)methanone (7.58 g, 33.38 mmol, 6.96 mL, 2HCl) was added to a stirred mixture of tert-butyl 2,6-dibromopyridine-4-carboxylate (7.5 g, 22.25 mmol) and potassium carbonate, anhydrous, 99% (12.30 g, 89.02 mmol, 5.37 mL) in acetonitrile (150 mL). The resulting mixture was stirred at 80° C. for 72 hr (the reaction progress was monitored by HNMR of the aliquots), then cooled and filtered. The filtercake was washed with acetonitrile (2*20 ml) and discarded. The filtrate was evaporated in vacuo to leave 11 g of the residue, which was purified by column chromatography on silica gel (80 g pre-column, 80 g column) using hexane/ethyl acetate gradient (5-100% ethyl acetate) to afford tert-butyl 2-bromo-6-[4-(cyclopropanecarbonyl)piperazin-1-yl]pyridine-4-carboxylate (5.2 g, 12.67 mmol, 56.95% yield) as light-yellow solid. $^1$H NMR (400 MHz, CDCl$_3$) δ (ppm) 0.82 (m, 2H), 1.02 (m, 2H), 1.58 (m, 9H), 1.77 (m, 1H), 3.58 (m, 2H), 3.77 (m, 6H), 7.08 (s, 1H), 7.25 (s, 1H). LCMS(ESI): [M+H]+ m/z: calcd 410.3. found 411.2; Rt=1.585 min.

tert-butyl 2-(4-(cyclopropanecarbonyl)piperazin-1-yl)-6-(spiro[3.3]heptan-2-ylamino)isonicotinate. tert-Butyl 2-bromo-6-[4-(cyclopropanecarbonyl)piperazin-1-yl]pyridine-4-carboxylate (2.6 g, 6.34 mmol) and sodium 2-methylpropan-2-olate (1.58 g, 16.48 mmol) were mixed together in toluene (50 mL). The resulting mixture was evacuated and then backfilled with argon, this operation was repeated three times, then spiro[3.3]heptan-2-amine (1.12 g, 7.60 mmol, HCl), [5-(diphenylphosphanyl)-9,9-dimethyl-9H-xanthen-4-yl]diphenylphosphane (183.33 mg, 316.84 umol) and tris(1,5-diphenylpenta-1,4-dien-3-one) dipalladium (145.07 mg, 158.42 umol) were added under argon. The reaction mixture was stirred under argon at 70° C. for 2 hr, then cooled and evaporated in vacuo. The residue was purified by column chromatography on silica gel (40 g pre-column, 40 g column, 5th peak was collected, tubes 41-62)) using hexane/ethyl acetate gradient (0-100% ethyl acetate) to afford tert-butyl 2-[4-(cyclopropanecarbonyl) piperazin-1-yl]-6-(spiro[3.3]heptan-2-ylamino)pyridine-4-carboxylate (1.6 g, 3.63 mmol, 57.31% yield) as yellow solid, which was used directly in the next step. $^1$H NMR (500 MHz, CDCl$_3$) δ (ppm) 0.78 (m, 2H), 1.01 (m, 2H), 1.58 (m, 9H), 1.78 (m, 5H), 1.96 (m, 2H), 2.08 (m, 2H), 2.52 (m, 2H), 3.62 (m, 4H), 3.75 (m, 4H), 3.98 (m, 1H), 4.56 (m, 1H), 6.22 (s, 1H), 6.45 (s, 1H). LCMS(ESI): [M+H]+ m/z: calcd 440.6. found 441.2; Rt=1.647 min.

2-(4-(cyclopropanecarbonyl)piperazin-1-yl)-6-(spiro[3.3]heptan-2-ylamino)isonicotinic acid, tert-Butyl 2-[4-(cyclopropanecarbonyl)piperazin-1-yl]-6-(spiro[3.3]heptan-2-ylamino)pyridine-4-carboxylate (1.6 g, 3.63 mmol) was dissolved in trifluoroacetic acid (20.70 g, 181.58 mmol, 13.99 mL). The reaction mixture was stirred at 25° C. for 1 hr, and then evaporated in vacuo. The residue was triturated with hexane/MTBE mixture (4/1, 60 ml), stirred for 0.1 hr and the precipitate was filtered, washed with hexane (2*10 ml) and dried in vacuo to afford 2-[4-(cyclopropanecarbonyl)piperazin-1-yl]-6-(spiro[3.3]heptan-2-ylamino)pyridine-4-carboxylic acid (1.51 g, 3.04 mmol, 83.58% yield, TFA) as yellow solid, which was used directly in the next step. $^1$H NMR (400 MHz, DMSO-d$_6$) δ (ppm) 0.73 (m, 4H), 1.88 (m, 5H), 2.03 (m, 3H), 2.40 (m, 2H), 3.50 (m, 6H), 3.77 (m, 2H), 4.02 (m, 2H), 6.23 (s, 1H), 6.32 (s, 1H). LCMS (ESI): [M+H]+ m/z: calcd 384.5. found 385.2; Rt=1.294 min.

2-((1-acetylpiperidin-4-yl)amino)-6-cyclohexlisonicotinic Acid

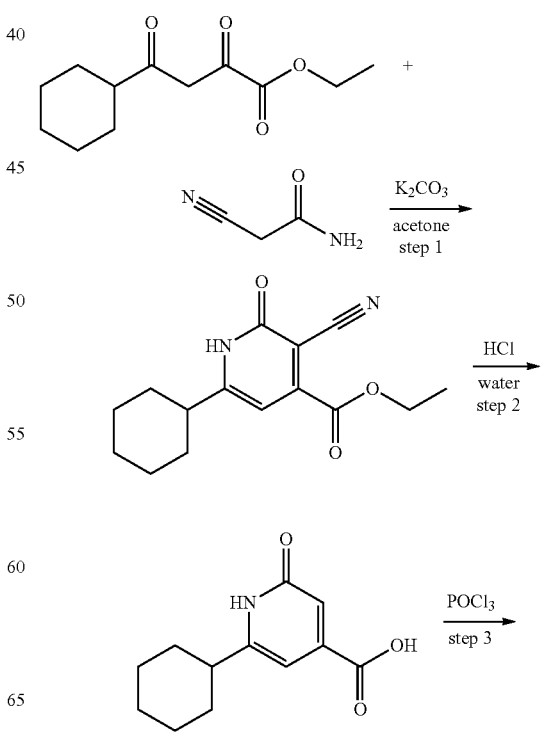

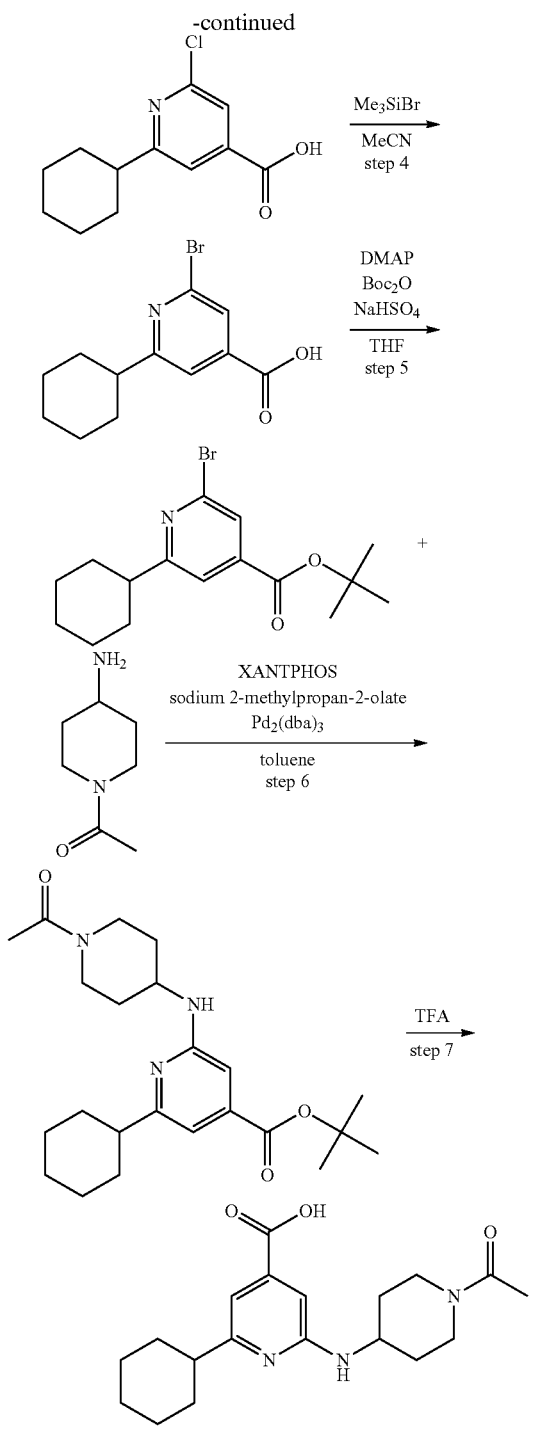

ethyl 3-cyano-6-cyclohexyl-2-oxo-1,2-dihydropyridine-4-carboxylate. Ethyl 4-cyclohexyl-2,4-dioxo-butanoate (5 g, 22.10 mmol), 2-cyanoacetamide (2.04 g, 24.31 mmol) and potassium carbonate, anhydrous, 99% (4.58 g, 33.15 mmol, 2.00 mL) were mixed together in acetone (100 mL). The resulting mixture was stirred with reflux condenser at 60° C. for 48 hr, then cooled down and evaporated in vacuo. The residue was dissolved in water (50 ml) and acidified with concentrated hydrochloric acid to pH 4 (carefully, foaming!). The precipitate was isolated by filtration, washed with water (2*50 ml) and dried in vacuo to afford ethyl 3-cyano-6-cyclohexyl-2-oxo-1H-pyridine-4-carboxylate (4.9 g, 17.86 mmol, 80.84% yield) as yellow solid, which was used directly in the next step. $^1$H NMR (500 MHz, DMSO-A) δ (ppm) 1.25 (m, 5H), 1.41 (m, 3H), 1.80 (m, 5H), 2.58 (m, 1H), 4.36 (m, 2H), 6.50 (s, 1H), 12.93 (bds, 1H). LCMS (ESI): [M+H]+ m/z: calcd 274.3. found 275.2; Rt=1.251 min.

6-cyclohexyl-2-oxo-1,2-dihydropyridine-4-carboxylic acid. Ethyl 3-cyano-6-cyclohexyl-2-oxo-1H-pyridine-4-carboxylate (4.9 g, 17.86 mmol) was added to Hydrochloric acid, 36% w/w aq. soln. (59.00 g, 582.56 mmol, 50 mL, 36% purity). The resulting suspension was stirred at 120° C. for 48 hr, then cooled to 25° C. and diluted with water (100 ml). The precipitate was filtered, washed with water (3*20 ml) and dried in vacuo to afford 2-cyclohexyl-6-oxo-1H-pyridine-4-carboxylic acid (3.2 g, 14.46 mmol, 80.97% yield) as brown solid. $^1$H NMR (500 MHz, DMSO-d$_6$) δ (ppm) 1.19 (m, 3H), 1.37 (m, 2H), 1.65 (m, 1H), 1.79 (m, 4H), 2.44 (m, 1H), 6.32 (s, 1H), 6.61 (s, 1H), 12.56 (bds, 2H). LCMS (ESI): [M+H]+ m/z: calcd 221.2. found 222.2; Rt=1.010 min.

2-chloro-6-cyclohexylisonicotinic acid. 2-Cyclohexyl-6-oxo-1H-pyridine-4-carboxylic acid (3.2 g, 14.46 mmol) was added to phosphoryl chloride (30 g, 195.66 mmol, 18.18 mL) and the resulting mixture was stirred at 100° C. for 2 hr, then cooled down and evaporated in vacuo. The residue was diluted with a mixture of crushed ice and water (50/50, 50 g), and the resulting mixture was stirred at 25° C. for 2 hr (over this period of time oily product gradually solidified). The precipitate was filtered, washed with water and dried in vacuo to afford 2-chloro-6-cyclohexyl-pyridine-4-carboxylic acid (3 g, 12.52 mmol, 86.54% yield) as brown solid. $^1$H NMR (500 MHz, DMSO-d$_6$) δ (ppm) 1.50 (m, 5H), 1.81 (m, 5H), 2.77 (m, 1H), 7.62 (s, 1H), 7.65 (s, 1H), 13.86 (bds, 1H). LCMS(ESI): [M+H]+ m/z: calcd 239.7. found 240.2; Rt=1.465 min.

2-bromo-6-cyclohexylisonicotinic acid. Bromotrimethylsilane (22.99 g, 150.19 mmol) was added in one portion to a stirred solution of 2-chloro-6-cyclohexyl-pyridine-4-carboxylic acid (3 g, 12.52 mmol) in acetonitrile (50 mL). The reaction mixture was stirred with reflux condenser at 80° C. for 36 hr, then cooled and evaporated in vacuo. The residue was diluted with water (50 ml) and hexane (20 ml), stirred for 0.5 hr and then hexane was removed in vacuo. The precipitate was filtered, washed with water (2*10 ml) and dried in vacuo to afford 2-bromo-6-cyclohexyl-pyridine-4-carboxylic acid (3.2 g, 11.26 mmol, 89.98% yield) as brown solid. $^1$H NMR (500 MHz, DMSO-d$_6$) δ (ppm) 1.78 (m, 5H), 1.85 (m, 5H), 2.76 (m, 1H), 7.67 (s, 1H), 7.75 (s, 1H), 13.86 (bds, 1H). LCMS(ESI): [M+H]+ m/z: calcd 284.5. found 285.2; Rt=1.449 min.

tert-butyl 2-bromo-6-cyclohexylisonicotinate. Di-tert-butyl dicarbonate (3.20 g, 14.64 mmol, 3.36 mL) was added to a stirred mixture of 2-bromo-6-cyclohexyl-pyridine-4-carboxylic acid (3.2 g, 11.26 mmol) and N,N-dimethylpyridin-4-amine (687.92 mg, 5.63 mmol) in THF (50 mL) at 25° C. The reaction mixture was stirred at 45° C. for 2 hr, and then evaporated in vacuo. The residue was dissolved in dichloromethane (100 ml) and washed with aqueous sodium hydrogen sulphate (1 g, 8.33 mmol) solution (20 ml). The organic layer was separated, dried over sodium sulphate, filtered through a short pad of silica gel and evaporated in vacuo to afford tert-butyl 2-bromo-6-cyclohexyl-pyridine-4-carboxylate (3.5 g, 10.29 mmol, 91.34% yield) as yellow oil. $^1$H NMR (500 MHz, CDCl$_3$) δ (ppm) 1.74 (m, 5H), 1.86 (s, 9H), 1.95 (m, 5H), 2.77 (m, 1H), 7.60 (s, 1H), 7.76 (s, 1H). LCMS(ESI): [M+H]+ m/z: calcd 340.2. found 341.2; Rt=1.813 min.

tert-butyl 2-((1-acetylpiperidin-4-yl)amino)-6-cyclohexylisonicotinate. tert-Butyl 2-bromo-6-cyclohexyl-pyridine-4-carboxylate (3.5 g, 10.29 mmol) and sodium 2-methyl-propan-2-olate (1.48 g, 15.43 mmol) were mixed together in toluene (50 mL). The resulting mixture was evacuated and then backfilled with argon, this operation was repeated three times, then 1-(4-amino-1-piperidyl)ethanone (1.76 g, 12.34 mmol), [5-(diphenylphosphanyl)-9,9-dimethyl-9H-xanthen-4-yl] diphenylphosphane (297.60 mg, 514.32 umol) and tris(1,5-diphenylpenta-1,4-dien-3-one) dipalladium (235.49 mg, 257.16 umol) were added under argon. The resulting mixture was stirred under argon at 70° C. for 2 hr, then cooled and evaporated in vacuo. The residue was purified by column chromatography on silica gel (40 g pre-column, 40 g column, tubes 51-62 were combined and evaporated) using hexane/ethyl acetate gradient (0-100% ethyl acetate) to afford tert-butyl 2-[(1-acetyl-4-piperidyl)amino]-6-cyclohexyl-pyridine-4-carboxylate (1.2 g, 2.99 mmol, 29.05% yield) as yellow gum. $^1$H NMR (500 MHz, CDCl$_3$) δ (ppm) 1.45 (m, 6H), 1.58 (s, 9H), 1.75 (m, 6H), 2.12 (m, 5H), 2.54 (m, 1H), 2.92 (m, 1H), 3.22 (m, 1H), 3.88 (m, 2H), 4.49 (m, 2H), 6.72 (s, 1H), 6.92 (s, 1H). LCMS(ESI): [M+H]+ m/z: calcd 401.5. found 402.2; Rt=1.448 min.

2-((1-acetylpiperidin-4-yl)amino)-6-cyclohexylisonicotinic acid. tert-Butyl 2-[(1-acetyl-4-piperidyl)amino]-6-cyclohexyl-pyridine-4-carboxylate (1.2 g, 2.99 mmol) was dissolved in trifluoroacetic acid (17.04 g, 149.42 mmol, 11.51 mL). The reaction mixture was stirred at 25° C. for 1 hr, and then evaporated in vacuo. The residue was triturated with hexane/MTBE mixture (4/1, 75 ml), stirred for 1 hr and the precipitate was filtered, washed with hexane (2*10 ml) and dried in vacuo to afford 2-[(1-acetyl-4-piperidyl)amino]-6-cyclohexyl-pyridine-4-carboxylic acid (0.66 g, 1.44 mmol, 48.07% yield, CF$_3$COOH) as yellow solid, which was used directly in the next step. $^1$H NMR (400 MHz, DMSO-d$_6$) δ (ppm) 1.38 (m, 7H), 1.82 (m, 10H), 2.68 (m, 1H), 2.82 (m, 1H), 3.21 (m, 1H), 3.81 (m, 1H), 4.06 (m, 1H), 4.24 (m, 1H), 6.85 (s, 1H), 7.14 (s, 1H). LCMS(ESI): [M+H]+ m/z: calcd 345.4. found 346.2; Rt=0.936 min.

6-(cyclobutylamino)-2-(piperidin-1-yl)pyrimidine-4-carboxylic Acid

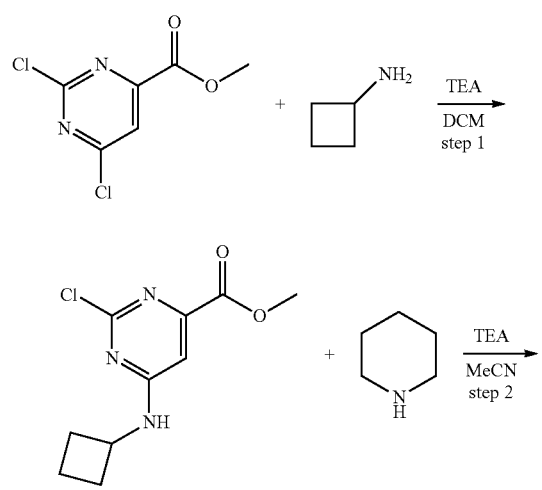

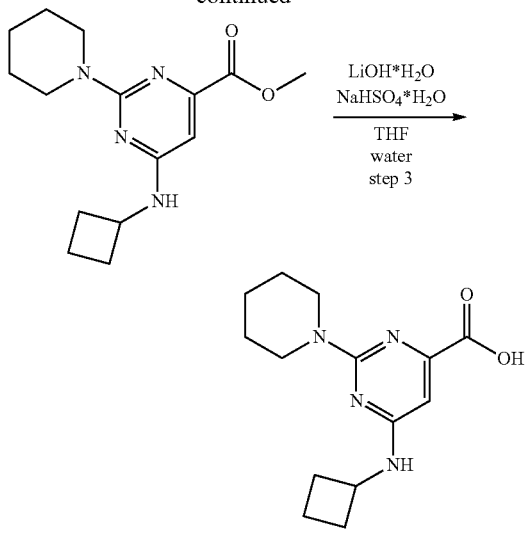

methyl 2-chloro-6-(cyclobutylamino)pyrimidine-4-carboxylate. To a solution of methyl 2,6-dichloropyrimidine-4-carboxylate (5 g, 24.15 mmol) in DCM (150 mL) at 0° C. was added triethylamine (2.69 g, 26.57 mmol, 3.70 mL) followed by cyclobutanamine (1.72 g, 24.15 mmol, 2.06 mL) and the resulting reaction mixture was stirred at 0° C. for 30 min and allowed to warm to room temperature and stirred for 12 hr. The resulting solution was taken up with water (150 ml). The organic layer was separated, washed with brine (3*50 ml), dried over Na$_2$SO$_4$ and evaporated in vacuo to obtain crude product (6 g). This compound was purified by gradient chromatography (hexane-EtOAc tubes 20-34 contain the title compound) to give methyl 2-chloro-6-(cyclobutylamino)pyrimidine-4-carboxylate (3.5 g, 14.48 mmol, 59.96% yield). $^1$H NMR (500 MHz, DMSO-d$_6$) δ (ppm) 1.70 (m, 2H), 1.91 (m, 2H), 2.27 (m, 2H), 3.83 (s, 3H), 4.36 (m, 1H), 7.00 (s, 1H), 8.59 (d, 1H). LCMS(ESI): [M+H]+ m/z: calcd 241.7. found 242.2; Rt=1.229 min.

methyl 6-(cyclobutylamino)-2-(piperidin-1-yl)pyrimidine-4-carboxylate. To a solution of methyl 2-chloro-6-(cyclobutylamino)pyrimidine-4-carboxylate (2 g, 8.28 mmol) and piperidine (739.88 mg, 8.69 mmol, 858.33 uL) in ACN (80 mL), triethylamine (1.67 g, 16.55 mmol, 2.31 mL) was added. The resulting mixture was stirred at 80° C. for 48 hr and evaporated. The residue was taken up with water (100 ml) and extracted with DCM (3*50 ml). The combined organic layer was washed with brine (2*70 ml), dried over Na$_2$SO$_4$ and evaporated in vacuo to give methyl 6-(cyclobutylamino)-2-(1-piperidyl)pyrimidine-4-carboxylate (2.3 g, 7.92 mmol, 95.72% yield). $^1$H NMR (500 MHz, DMSO-d$_6$) δ (ppm) 1.46 (m, 4H), 1.63 (m, 4H), 1.88 (m, 2H), 2.25 (m, 2H), 3.67 (m, 4H), 3.77 (s, 3H), 4.36 (m, 1H), 6.28 (s, 1H), 7.58 (d, 1H). LCMS(ESI): [M+H]+ m/z: calcd 290.4. found 291.2; Rt=1.065 min.

6-(cyclobutylamino)-2-(piperidin-1-yl)pyrimidine-4-carboxylic acid. To a solution of methyl 6-(cyclobutylamino)-2-(1-piperidyl)pyrimidine-4-carboxylate (2.3 g, 7.92 mmol) in THF (50 mL) was added a solution of Lithium hydroxide, monohydrate (731.28 mg, 17.43 mmol, 484.29 uL) in water (50 mL). The resulting mixture was stirred at 25° C. for 3 hr and THF was evaporated in vacuo. pH was adjusted to 6 with solution of sodium bisulfate monohydrate (2.52 g, 18.22 mmol) in water(20 ml). The formed precipitate was filtered, washed with cold water (10 ml), MTBE (10 ml) and dried to obtain 6-(cyclobutylamino)-2-(1-piperidyl)pyrimidine-4-carboxylic acid (1.6 g, 5.79 mmol, 73.10% yield). $^1$H NMR (500 MHz, DMSO-$d_6$) δ (ppm) 1.47 (m, 4H), 1.58 (m, 2H), 1.68 (m, 2H), 1.89 (m, 2H), 2.25 (m, 2H), 3.69 (m, 4H), 4.36 (m, 1H), 6.27 (s, 1H), 7.68 (d, 1H). LCMS(ESI): [M+H]+ m/z: calcd 276.3. found 277.2; Rt=1.059 min.

Synthesis of Intermediate Amines (3-aminocyclobutyl)-(1-piperidyl)methanone

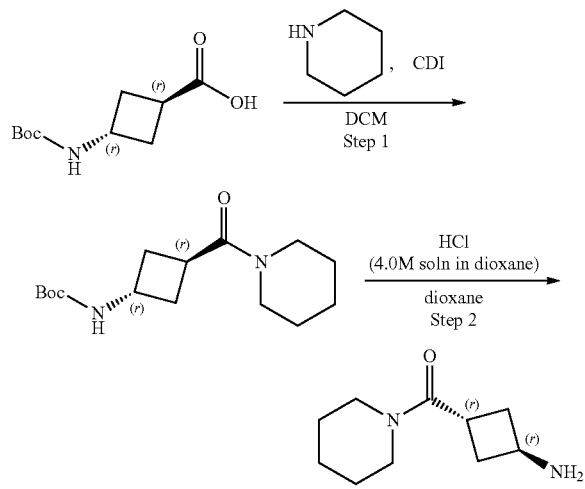

tert-butyl N-[3-(piperidine-1-carbonyl)cyclobutyl]carbamate. To a suspension of 3-(tert-butoxycarbonylamino)cyclobutanecarboxylic acid (1 g, 4.65 mmol) in dichloromethane (25 mL) was added carbonyldiimidazole (903.98 mg, 5.58 mmol) portionwise at 21° C. After gas evolution ceased piperidine (593.37 mg, 6.97 mmol, 688.37 uL, HCl) was added in one portion. The resulting mixture was left to stir overnight at 21° C. The reaction progress was monitored by $^1$H NMR and LCMS. The resulting mixture was quenched with 10% aqueous solution of citric acid, washed with brine, dried over $Na_2SO_4$ and evaporated to give tert-butyl N-[3-(piperidine-1-carbonyl)-cyclobutyl]carbamate (1.1 g, 3.90 mmol, 83.85% yield) as a white solid. $^1$H NMR (CDCl$_3$, 500 MHz): δ 1.44 (s, 9H), 1.52 (m, 4H), 1.63 (m, 2H), 2.16 (m, 2H), 2.67 (m, 2H), 3.20 (m, 2H), 3.55 (m, 2H), 4.09 (m, 1H), 4.78 (m, 1H). LCMS(ESI): [M+H]$^+$ m/z: calcd 282.2. found 283.2; Rt=1.26 min.

(3-aminocyclobutyl)-(1-piperidyl)methanone. To a solution of tert-butyl N-[3-(piperidine-1-carbonyl)cyclobutyl]carbamate (1.1 g, 3.90 mmol) in dioxane (5 mL) was added hydrogen chloride solution 4.0M in dioxane (4.00 g, 109.71 mmol, 5 mL) at 21° C. The resulting mixture was stirred for 18 h. The reaction progress was monitored by HNMR. The precipitate was filtered off, washed with MTBE and dried under high vacuum (0.3 mbar) to give (3-aminocyclobutyl)-(1-piperidyl)methanone (810 mg, 3.70 mmol, 95.07% yield, HCl) as a white solid. NMR(DMSO-$d_6$, 500 MHz): δ 1.43 (m, 4H), 1.57 (m, 2H), 2.28 (m, 2H), 2.43 (m, 2H), 3.23 (m, 2H), 3.43 (m, 3H), 3.60 (m, 1H), 8.17 (m, 3H). LCMS(ESI): [M+H]$^+$ m/z: calcd 182.1; found 183.2; Rt=0.67 min.

4-methoxycyclohexanamine

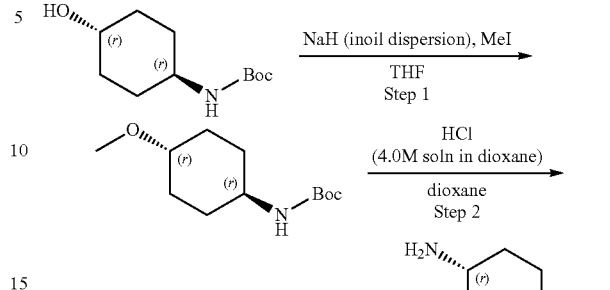

tert-butyl N-(4-methoxycyclohexyl)carbamate. tert-Butyl N-(4-hydroxycyclohexyl)carbamate (6.36 g, 29.54 mmol) was dissolved in THF (50 mL) and the mixture was cooled to 0° C. Sodium hydride (in oil dispersion) 60% dispersion in mineral oil (1.70 g, 42.45 mmol, 60% purity) was added in portions under an inert atmosphere. After stirring for 15 min, iodomethane (4.19 g, 29.54 mmol, 1.84 mL) was added dropwise and the reaction mixture was allowed to stir at room temperature for 4 hours. The reaction progress was monitored by LCMS and $^1$H NMR. The resulting mixture was quenched with a saturated aqueous solution of $NH_4Cl$, extracted with EtOAc (3*10 mL). Combined organics were washed with brine, dried over $Na_2SO_4$ and evaporated. The residue was purified by column chromatography (companion combiflash; 120 g $SiO_2$; petroleum ether/MtBE with MtBE from 0 to 25%, flow rate=85 mL/min, Rv=10 cv.) to give tert-butyl N-(4-methoxycyclohexyl)carbamate (2.4 g, 10.47 mmol, 35.43% yield) as a white solid. NMR(CDCl$_3$, 400 MHz): δ 1.10 (m, 2H), 1.27 (m, 2H), 1.42 (s, 9H), 2.00 (m, 4H), 3.09 (m, 1H), 3.31 (s, 3H), 3.42 (m, 1H), 4.34 (m, 1H). LCMS(ESI): [M-Boc-OMe]$^+$ m/z: calcd 112.2. found 113.2; Rt=1.26 min.

4-methoxycyclohexanamine. To a solution of tert-butyl N-(4-methoxycyclohexyl)carbamate (2.39 g, 10.42 mmol) in dioxane (10 mL) was added hydrogen chloride solution 4.0M in dioxane (8.00 g, 219.41 mmol, 10 mL) at 21° C. The resulting mixture was left to stir for 18 hr. The reaction progress was monitored by $^1$H NMR. The precipitate was filtered off, washed with MTBE and dried under high vacuum (0.3 mbar) to give 4-methoxycyclohexanamine (1.46 g, 8.81 mmol, 84.56% yield, HCl) as a white solid. $^1$H NMR (DMSO-$d_6$, 500 MHz): δ 1.15 (q, 2H), 1.35 (q, 2H), 1.97 (m, 4H), 2.94 (m, 1H), 3.07 (m, 1H), 3.22 (s, 3H), 8.13 (s, 3H). LCMS(ESI): [M+H]$^+$ m/z: calcd 129.1. found 130.2; Rt=0.27 min.

4-methoxycyclohexanamine

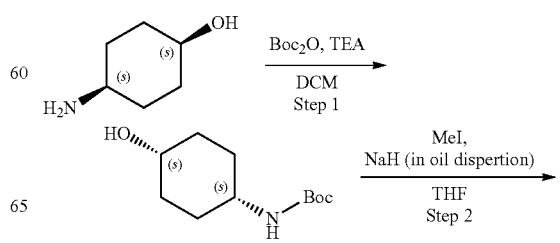

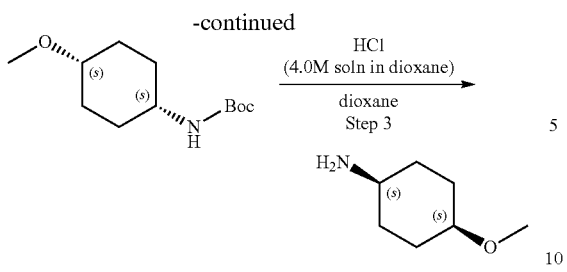

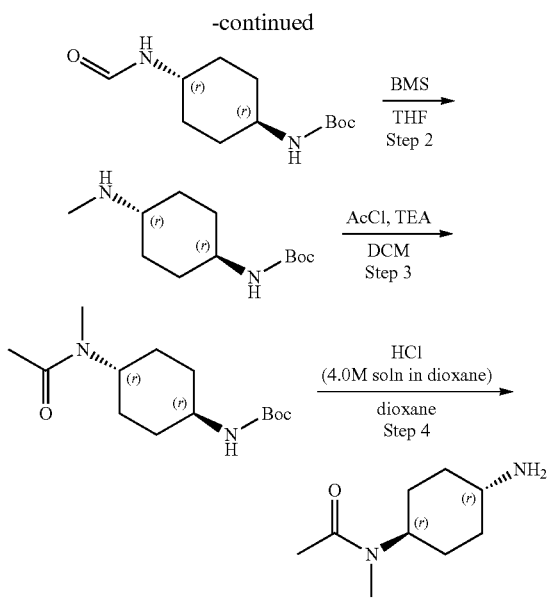

tert-butyl N-(4-hydroxycyclohexyl)carbamate. To a suspension of 4-aminocyclohexanol (3 g, 19.78 mmol, HCl) in dichloromethane (50 mL) was added triethylamine (6.01 g, 59.35 mmol, 8.27 mL) followed by tert-butoxycarbonyl tert-butyl carbonate (4.75 g, 21.76 mmol, 4.99 mL) at 21° C. The reaction mixture was left to stir at room temperature for 16 h. The resulting mixture was washed with 10% aqueous solution of citric acid, brine, dried over Na$_2$SO$_4$ and evaporated to give tert-butyl N-(4-hydroxycyclohexyl)carbamate (4.1 g, 19.04 mmol, 96.26% yield) $^1$H NMR (CDCl$_3$, 400 MHz): δ 1.42 (s, 9H), 1.64 (m, 8H), 3.51 (m, 1H), 3.87 (m, 1H), 4.51 (m, 1H). LCMS(ESI): [M+H]$^+$ m/z: calcd 215.1. found 216.1; Rt=1.08 min.

tert-butyl N-(4-methoxycyclohexyl)carbamate. tert-Butyl N-(4-hydroxycyclohexyl)carbamate (3.6 g, 16.72 mmol) was dissolved in THF (50 mL) and the mixture was cooled to 0° C. Sodium hydride (in oil dispersion) 60% dispersion in mineral oil (1.00 g, 25.08 mmol, 60% purity) was added in portions under an inert atmosphere. After stirring for 15 min, iodomethane (2.37 g, 16.72 mmol, 1.04 mL) was added dropwise and the reaction mixture was allowed to stir at room temperature for 4 hours. The reaction progress was monitored by LCMS and $^1$H NMR. The resulting mixture was quenched with a saturated aqueous solution of NH$_4$Cl, extracted with EtOAc (3*10 mL). Combined organics were washed with brine, dried over Na$_2$SO$_4$ and evaporated. The residue was purified by column chromatography (companion combiflash; 120 g SiO$_2$; petroleum ether/MtBE with MtBE from 0 to 40%, flow rate=85 mL/min, Rv=11 cv) to give tert-butyl N-(4-methoxycyclohexyl)carbamate (1.11 g, 4.84 mmol, 28.95% yield) as a light-yellow solid. $^1$H NMR (CDCl$_3$, 400 MHz): δ 1.42 (s, 9H), 1.49 (m, 4H), 1.67 (m, 2H), 1.77 (m, 2H), 3.28 (s, 3H), 3.31 (m, 1H), 3.50 (m, 1H), 4.45 (m, 1H). LCMS(ESI): [M-Boc]$^+$ m/z: calcd 129.2. found 130.2; Rt=1.28 min.

4-methoxycyclohexanamine. To a solution of tert-butyl N-(4-methoxycyclohexyl)carbamate (1.11 g, 4.84 mmol) in dioxane (10 mL) was added hydrogen chloride, 4M in 1,4-dioxane, 99% (8.00 g, 219.41 mmol, 10 mL) at 21° C. The resulting mixture was left to stir for 18 h. The reaction progress was monitored by HNMR. The precipitate was filtered off, washed with MTBE and dried under high vacuum (0.3 mbar) to give 4-methoxycyclohexanamine (0.69 g, 4.17 mmol, 86.05% yield, HCl) as a white solid. $^1$H NMR (DMSO-d$_6$, 500 MHz): δ 1.39 (m, 2H), 1.52 (m, 2H), 1.66 (m, 2H), 1.84 (m, 2H), 2.99 (m, 1H), 3.19 (s, 2H), 3.35 (m, 1H), 7.97 (m, 3H). LCMS(ESI): [M+H]$^+$ m/z: calcd 129.1. found 130.2; Rt=0.40 min.

N-(4-aminocyclohexyl)-N-methyl-acetamide

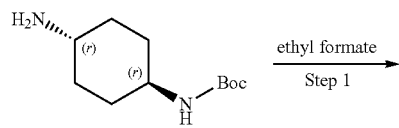

tert-butyl N-(4-formamidocyclohexyl)carbamate. tert-Butyl N-(4-aminocyclohexyl)carbamate (5 g, 23.33 mmol) was dissolved in ethyl formate (43.21 g, 583.28 mmol, 46.92 mL) and refluxed for 72 hr. The reaction progress was monitored by $^1$H NMR and LCMS. The resulting mixture was evaporated to dryness to give tert-butyl N-(4-formamidocyclohexyl)carbamate (5.5 g, 22.70 mmol, 97.28% yield). $^1$H NMR (DMSO-d$_6$, 400 MHz): δ 1.18 (m, 4H), 1.36 (s, 9H), 1.74 (m, 4H), 3.16 (m, 1H), 3.49 (m, 1H), 6.70 (d, 1H), 7.90 (s, 1H). LCMS(ESI): [M-Boc]$^+$ m/z: calcd 142.6. found 143.6; Rt=1.02 min.

tert-butyl N-[4-(methylamino)cyclohexyl]carbamate. To a solution of tert-butyl N-(4-formamidocyclohexyl)carbamate (5.93 g, 24.47 mmol) in THF (100 mL) at 0° C. was added borane dimethyl sulfide complex (5.58 g, 73.42 mmol, 6.96 mL) dropwise under Ar atmosphere. The resulting mixture was left to stir overnight at ambient temperature. The reaction progress was monitored by LCMS. The reaction mixture was poured into MeOH and refluxed for 2 hours. The resulting mixture was evaporated to dryness and re-evaporated with chloroform to give tert-butyl N-[4-(methylamino)cyclohexyl]carbamate (7 g, crude) as an off-white solid. The crude product was used in the next step without further purification. $^1$H NMR (DMSO-d$_6$, 400 MHz): δ 1.12 (m, 4H), 1.36 (s, 9H), 1.77 (m, 4H), 2.21 (s, 3H), 2.41 (m, 1H), 3.13 (m, 1H), 5.85 (m, 1H), 6.65 (m, 1H). LCMS(ESI): [M+H]$^+$ m/z: calcd 228.3. found 229.2; Rt=0.17 min.

tert-butyl N-[4-[acetyl(methyl)amino]cyclohexyl]carbamate. To a solution of acetyl chloride (1.65 g, 21.02 mmol, 1.28 mL) and triethylamine (2.66 g, 26.28 mmol, 3.66 mL) in DCM (100 mL) was added tert-butyl N-[4-(methylamino) cyclohexyl]carbamate (4 g, 17.52 mmol) at 0° C. Then, it was left for stirring at room temperature overnight. The reaction progress was monitored by LCMS and $^1$H NMR. The resulting mixture was washed with a saturated aqueous solution of NaHCO$_3$, brine, dried over anhydrous Na$_2$SO$_4$ and evaporated to give a yellowish gum. The residue was purified by column chromatography (Companion combiflash; 80 g SiO$_2$, acetonitrile/methanol with methanol from 0-15%, flow rate=60 mL/min, Rv=7 CV) to give tert-butyl N-[4-[acetyl(methyl)-amino]cyclohexyl]carbamate (1.38 g, crude) as yellowish solid. NMR(DMSO-d$_6$, 400 MHz): δ

1.27 (m, 3H), 1.39 (s, 9H), 1.63 (m, 4H), 1.85 (m, 2H), 2.00 (m, 2H), 2.70 (s, 3H), 3.49 (m, 1H), 4.19 (m, 1H), 6.42 (m, 1H). LCMS(ESI): [M+H]+ m/z: calcd 270.2. found 271.2; Rt=1.08 min.

N-(4-aminocyclohexyl)-N-methyl-acetamide. To a solution of tert-butyl N-[4-[acetyl(methyl)amino]cyclohexyl] carbamate (1.38 g, 5.10 mmol) in dioxane (10 mL) was added hydrogen chloride solution 4.0M in dioxane (186.10 mg, 5.10 mmol, 232.63 uL) at 21° C. The resulting mixture was left to stir for 18 hr. The reaction progress was monitored by ¹H NMR. The precipitate was filtered off, washed with MTBE and dried under high vacuum (0.3 mbar) to give N-(4-aminocyclohexyl)-N-methyl-acetamide (1.03 g, crude, HCl) as a yellowish solid. LCMS(ESI): [M+H]+ m/z: calcd. found; Rt=min.

Tetrahydroisoquinoline Intermediates (S)-1-amino-3-(5-chloro-6-((4-methyloxazol-5-yl)methoxy)-3N-dihydroisoquinolin-2(1H)-yl)propan-2-ol

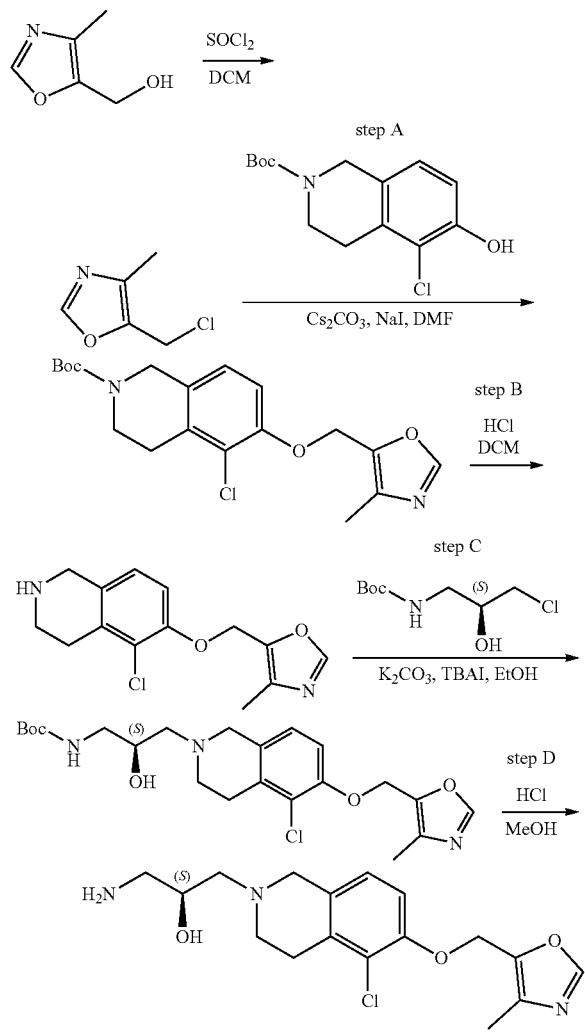

Synthesis of 5-(chloromethyl)-4-methyloxazole. To a suspension of (4-methyloxazol-5-yl)methanol (1.5 g, 13.26 mmol) in DCM (25 mL), cooled to 0° C. was added thionyl chloride (1.89 g, 15.91 mmol). The reaction mixture was stirred at room temperature for 12 hr. Then, the resulting mixture was evaporated and added to MTBE (5 mL). The formed precipitate was filtered, washed with MTBE (3 mL) and dried to afford 5-(chloromethyl)-4-methyl-oxazole (2.2 g, 13.09 mmol, 98.74% yield, HCl). ¹H NMR (500 MHz, DMSO-d₆) δ 4.89 (s, 2H), 5.32 (s, 3H), 7.23 (s, 1H), 8.39 (s, 1H). LCMS(ESI): [M+H]+ m/z: calcd 132.0. found; Rt=0.75 min.

Example 1C1, Step A. Synthesis of tert-butyl 5-chloro-6-((4-methyloxazol-5-yl)methoxy)-3,4-dihydroisoquinoline-2(1H)-carboxylate. To a solution of tert-butyl 5-chloro-6-hydroxy-3,4-dihydro-1H-isoquinoline-2-carboxylate (1.5 g, 5.29 mmol) in dimethylformamide (25 mL) was added cesium carbonate (5.68 g, 17.44 mmol) and sodium iodide (158.48 mg, 1.06 mmol, 43.18 uL), followed by 5-(chloromethyl)-4-methyl-oxazole (834.57 mg, 4.97 mmol, HCl). The reaction mixture was stirred at 45° C. for 12 hr. Then, the resulting mixture was, poured into water (50 mL) and extracted with EtOAc (3*20 mL). The combined organic extracts were washed with brine(2*10 mL), dried over sodium sulphate and evaporated in vacuo to afford product tert-butyl 5-chloro-6-[(4-methyloxazol-5-yl)methoxy]-3,4-dihydro-1H-isoquinoline-2-carboxylate (1.8 g, 4.75 mmol, 89.88% yield). ¹H NMR (400 MHz, CDCl₃) δ 1.48 (s, 9H), 2.18 (s, 3H), 2.85 (m, 2H), 3.62 (m, 2H), 4.49 (m, 2H), 5.05 (s, 2H), 6.87 (d, 1H), 6.94 (d, 1H), 7.78 (s, 1H). LCMS(ESI): [M-Boc]+ m/z: calcd 280.1. found 280.0; Rt=1.50 min.

Example 1C1, Step B: Synthesis of 5-(((5-chloro-1,2,3,4-tetrahydroisoquinolin-6-yl)oxy)methyl)-4-methyloxazole. Hydrogen chloride solution 4.0M in dioxane (4.00 g, 109.71 mmol, 5 mL) was added to a solution of tert-butyl 5-chloro-6-[(4-methyloxazol-5-yl)methoxy]-3,4-dihydro-1H-isoquinoline-2-carboxylate (1.8 g, 4.75 mmol) in DCM (30 mL). The reaction mixture was stirred at 25° C. for 12 hr. After the completion of the reaction, the solvent was removed in vacuo and the residue was suspended in MTBE (15 mL). The formed precipitate was filtered, washed with MTBE (30 mL) and air-dried to afford 5-[(5-chloro-1,2,3,4-tetrahydroisoquinolin-6-yl)oxymethyl]-4-methyl-oxazole (1.6 g, 4.55 mmol, 95.76% yield, 2HCl). ¹H NMR (500 MHz, DMSO-d₆) 5 2.14 (s, 3H), 2.94 (t, 2H), 3.34 (m, 2H), 4.18 (m, 2H), 5.24 (s, 2H), 7.23 (m, 2H), 8.29 (s, 1H), 9.75 (m, 2H). LCMS(ESI): [M+H]+ m/z: calcd 279.1; found 279.2; Rt=0.82 min.

Example 1C1, Step C. Synthesis of(S)-tert-butyl (3-(5-chloro-6-((4-methyloxazol-5-yl)methoxy)-3,4-dihydroisoquinolin-2(1H)-yl)-2-hydroxypropyl)carbamate. A mixture of tert-butyl A-[(2S)-3-chloro-2-hydroxy-propyl]carbamate (1.14 g, 5.46 mmol), 5-[(5-chloro-1,2,3,4-tetrahydroisoquinolin-6-yl)oxymethyl]-4-methyl-oxazole (1.6 g, 4.55 mmol, 2HCl), potassium carbonate, anhydrous, 99% (1.51 g, 10.92 mmol, 659.03 uL), tetra-n-butylammonium iodide (336.12 mg, 909.98 umol) in ethanole (40 mL) was stirred at 40° C. for 24 hr in sealed tube. When LCMS showed no starting material, the reaction mixture was evaporated and suspended in MTBE (70 mL). The formed precipitate was filtered off, washed with MTBE (2*30 mL) and organic filtrate was concentrated in vacuo to leave 3.3 g of crude product. The obtained solid was purified by column chromatography on silica gel using MTBE/Methanole gradient (10-100% MTBE) to afford pure product tert-butyl (V-[(2S)-3-[5-chloro-6-[(4-methyloxazol-5-yl)methoxy]-3,4-dihydro-1H-isoquinolin-2-yl]-2-hydroxy-propyl]carbamate (1.5 g, 3.32 mmol, 72.95% yield). $^1$H NMR (500 MHz, CDCl$_3$) δ 1.42 (s, 9H), 1.62 (m, 2H), 2.21 (s, 3H), 2.41 (m, 2H), 2.51 (m, 1H), 2.81 (m, 2H), 3.12 (m, 1H), 3.21 (m, 1H), 3.68 (m, 3H), 3.84 (m, 1H), 5.05 (m, 2H), 6.86 (m, 2H), 7.81 (s, 1H). LCMS(ESI): [M+H]$^+$ m/z: calcd 452.0. found 452.2; Rt=1.07 min.

Example 1C1, Step D. Synthesis of(S)-1-amino-3-(5-chloro-6-((4-methyloxazol-5-yl)methoxy)-3,4-dihydroisoquinolin-2(1H)-yl)propan-2-ol. Hydrogen chloride solution 4.0M in dioxane (4.00 g, 109.71 mmol, 5 mL) was added to a solution of tert-butyl N-[(2S)-3-[5-chloro-6-[(4-methyloxazol-5-yl)methoxy]-3,4-dihydro-1H-isoquinolin-2-yl]-2-hydroxy-propyl]carbamate (1.5 g, 3.32 mmol) in methanole (25 mL). The reaction mixture was stirred at 25° C. for 12 hr, then evaporated and added to CH$_3$CN (15 mL). The formed precipitate was filtered, washed with CH$_3$CN (20 mL) and air-dried to afford product (2S)-1-amino-3-[5-chloro-6-[(4-methyloxazol-5-yl)methoxy]-3,4-dihydro-1H-isoquinolin-2-yl]propan-2-ol (1.02 g, 2.21 mmol, 66.63% yield, 3HCl). $^1$H NMR (500 MHz, DMSO-d$_6$) δ 2.12 (m, 3H), 3.01 (m, 5H), 4.35 (m, 3H), 4.61 (m, 2H), 3.46 (s, 3H), 7.41 (m, 2H), 8.19 (m, 3H), 10.86 (s, 1H). LCMS(ESI): [M+H]$^+$ m/z: calcd 352.1. found 352.2; Rt=0.72 min.

(S)-1-amino-3-(7-fluoro-6-((4-methyloxazol-T5-yl)methoxy)-3,4-dihydroisoquinolin-2(1H)-yl)propan-2-ol tion mixture was stirred at 50° C. for 24 h. EtOH was evaporated. The residue was diluted MTBE (600 mL), precipitate was filtered and washed on filter with MTBE (3*150 mL). Filtrate was evaporated to give 26 g of crude product which was purified by column chromatography to give tert-butyl N-[(2S)-3-[7-fluoro-6-[(4-methyloxazol-5-yl)methoxy]-3,4-dihydro-1H-isoquinolin-2-yl]-2-hydroxy-propyl]carbamate (15.6 g, 35.82 mmol, 59.77% yield) as yellow oil. NMR(CDCl$_3$, 400 MHz): δ 1.45 (s, 9H), 2.17 (s, 3H), 2.51 (m, 2H), 2.68 (m, 1H), 2.82 (m, 2H), 2.90 (m, 1H), 3.06 (m 1H), 3.37 (m, 1H), 3.70 (m, 3H), 3.88 (m, 1H), 5.04 (s, 3H), 6.75 (m, 2H), 7.81 (s, 1H). LCMS(ESI): [M+H]$^+$ m/z: calcd 435.3. found 436.2; Rt=0.98 min.

To the solution of tert-butyl N-[(2S)-3-[7-fluoro-6-[(4-methyloxazol-5-yl)methoxy]-3,4-dihydro-1H-isoquinolin-2-yl]-2-hydroxy-propyl]carbamate (15.6 g, 35.82 mmol) in MeOH (200 mL) hydrogen chloride solution 4.0M in dioxane (13.06 g, 358.22 mmol, 16.33 mL) was added and the reaction mixture was stirred at 25° C. for 2 h. The reaction mixture was evaporated and the residue was dried in vacuo to give (2S)-1-amino-3-[7-fluoro-6-[(4-methyloxazol-5-yl)methoxy]-3,4-dihydro-1H-isoquinolin-2-yl]propan-2-ol (15.9 g, 35.75 mmol, 99.80% yield, 3HCl) as slightly yellow solid. NMR(DMSO-d$_6$, 500 MHz): δ 2.12 (s, 3H), 2.78 (m, 1H), 2.89 (m, 2H), 2.21 (m, 2H), 3.42 (m, 2H), 3.1 (m, 1H), 5.15 (s, 2H), 6.02 (m, 5H), 7.18 (d, 1H), 7.21

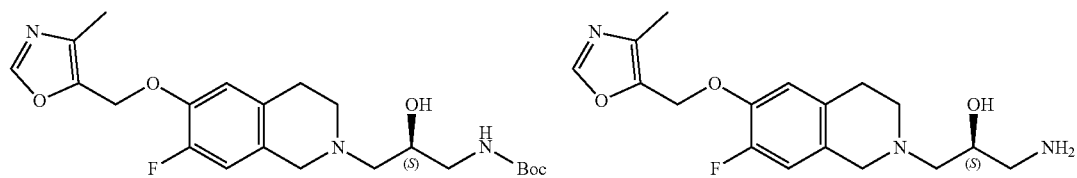

To the solution of 5-[(7-fluoro-1,2,3,4-tetrahydroisoquinolin-6-yl)oxymethyl]-4-methyl-oxazole (20.09 g, 59.93 mmol, 2HCl) in EtOH (500 mL) potassium carbonate, anhydrous, 99% (66.27 g, 479.47 mmol, 28.94 mL) and sodium iodide (1.80 g, 11.99 mmol, 489.57 uL) was added followed by addition of tert-butyl N-[(2S)-3-chloro-2-hydroxy-propyl]carbamate (18.85 g, 89.90 mmol). The reac- (d, 1H), 8.23 (m, 4H), 11.03 (s, 1H). LCMS(ESI): [M+H]$^+$ m/z: calcd 335.2. found 336.2; Rt=0.63 min.

S)-2-fluoro-N-(3-(7-fluoro-6-((4-methyloxazol-5-yl)methoxy)-3,4-dihydroisoquinolin-2(1H)-yl-2-hydroxypropyl)isonicotinamide

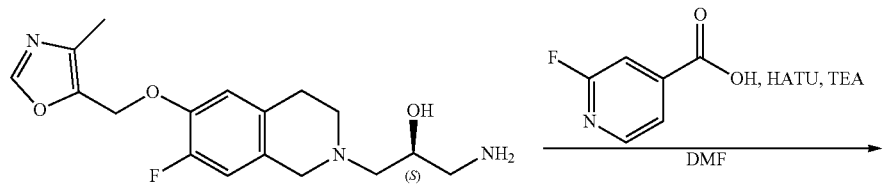

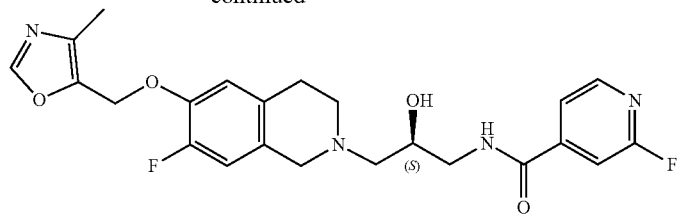

To the solution of (2S)-1-amino-3-[7-fluoro-6-[(4-methyloxazol-5-yl)methoxy]-3,4-dihydro-1H-isoquinolin-2-yl]propan-2-ol (0.5 g, 1.12 mmol, 3HCl), 2-fluoropyridine-4-carboxylic acid (158.63 mg, 1.12 mmol) and HATU (470.21 mg, 1.24 mmol) in DMF (1 mL) triethylamine (796.31 mg, 7.87 mmol, 1.10 mL) was added dropwise. The mixture was stirred at 25° C. for 2 h. After the completion of the reaction, the solvent was removed in vacuo. The residue was diluted with water (10 mL) and product was extracted with EtOAc (2*15 mL). The combined organic layers were dried over $Na_2SO_4$. Solvent was evaporated in vacuo to give 2-fluoro-N-[(2S)-3-[7-fluoro-6-[(4-methyloxazol-5-yl)methoxy]-3,4-dihydro-1H-isoquinolin-2-yl]-2-hydroxy-propyl]pyridine-4-carboxamide (0.4 g, 872.49 umol, 77.61% yield) which was used in the next step without further purification. $^1$H NMR (DMSO-$d_6$, 500 MHz): δ 1.17 (t, 2H), 1.98 (s, 2H), 2.14 (s, 2H), 2.73 (s, 2H), 2.82 (s, 1H), 2.89 (m, 1H), 3.54 (m, 3H), 3.92 (m, 1H), 4.02 (m, 1H), 5.14 (s, 2H), 6.91 (d, 1H), 7.00 (m, 1H), 7.50 (s, 1H), 7.70 (d, 1H), 8.34 (m, 2H), 8.86 (m, 1H). LCMS(ESI): [M+H]$^+$ m/z: calcd 458.2. found 459.2; Rt=0.88 min.

(S)-1-amino-3-(5-chloro-6-(oxazol-5-yl)methoxy)-3,4-dihydroisoquinolin-2(1H)-yl)propan-2-ol

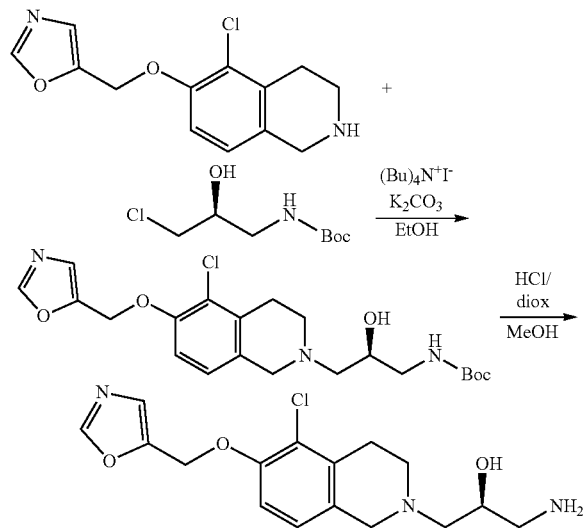

(S)-tert-butyl (3-(5-chloro-6-(oxazol-5-ylmethoxy)-3,4-dihydroisoquinolin-2(1H)-yl)-2-hydroxypropyl)carbamate. 5-[(5-Chloro-1,2,3,4-tetrahydroisoquinolin-6-yl)oxymethyl]oxazole (2.5 g, 9.44 mmol, 2HCl), tetrabutylammonium iodide (697.70 mg, 1.89 mmol) and potassium carbonate, anhydrous, 99% (4.31 g, 31.17 mmol, 1.88 mL) were mixed together in ethanol (75 mL). The resulting suspension was stirred at 25° C. for 0.1 hr, then tert-butyl A-[(2S)-3-chloro-2-hydroxy-propyl]carbamate (2.77 g, 13.22 mmol) was added and the reaction mixture was stirred at 50° C. for 12 hr, cooled down and evaporated in vacuo. The residue was diluted with MTBE (100 ml) and filtered. The filtercake was washed with MTBE (2*25 ml) and discarded. The filtrate was evaporated in vacuo to leave 5.5 g of the residue, which was purified by column chromatography on silica gel using MTBE/methanol gradient (0-100% methanol) to afford tert-butyl N-[(2S)-3-[5-chloro-6-(oxazol-5-ylmethoxy)-3,4-dihydro-1H-isoquinolin-2-yl]-2-hydroxy-propyl]carbamate (2.1 g, 4.80 mmol, 50.78% yield) as white solid. NMR (500 MHz, CDCl$_3$) δ (ppm) 1.47 (s, 9H), 1.74 (m, 1H), 2.49 (m, 2H), 2.76 (m, 1H), 2.88 (m, 3H), 3.07 (m, 1H), 3.38 (m, 1H), 3.56 (d, 1H), 3.89 (d, 1H), 3.90 (m, 1H), 5.07 (m, 1H), 5.12 (s, 2H), 6.85 (d, 1H), 6.90 (d, 1H), 7.16 (s, 1H), 7.92 (s, 1H). LCMS(ESI): [M-Boc]$^+$ m/z: calcd 437.9. found 438.2; Rt=1.042 min.

(S)-1-amino-3-(5-chloro-6-(oxazol-5-ylmethoxy)-3,4-dihydroisoquinolin-2(1H)-yl)propan-2-ol. Hydrogen chloride solution 4.0M in dioxane (20.36 g, 81.52 mmol, 19.39 mL, 14.6% purity) was added to a solution of tert-butyl N-[(2 S)-3-[5-chloro-6-(oxazol-5-ylmethoxy)-3,4-dihydro-1H-isoquinolin-2-yl]-2-hydroxy-propyl]carbamate (2.1 g, 4.08 mmol) in methanol (200 mL). The resulting mixture was stirred at 45° C. for 0.5 hr and then evaporated in vacuo. The residue was diluted with water (15 ml), reevaporated and dried in vacuo to afford (2S)-1-amino-3-[5-chloro-6-(oxazol-5-ylmethoxy)-3,4-dihydro-1H-isoquinolin-2-yl]propan-2-ol (1.6 g, 3.58 mmol, 87.78% yield, 3HCl) as white solid. $^1$H NMR (400 MHz, DMSO-$d_6$) δ (ppm) 2.81 (m, 1H), 2.99 (m, 1H), 3.07 (m, 2H), 3.23 (m, 1H), 3.39 (m, 1H), 3.47 (m, 1H), 3.74 (m, 1H), 4.37 (m, 2H), 4.56 (m, 1H), 5.32 (s, 2H), 7.21 (d, 1H), 7.31 (d, 1H), 7.36 (s, 1H), 8.27 (br.s, 3H), 8.43 (s, 1H), 11.12 (s, 1H). LCMS(ESI): [M-Boc]$^+$ m/z: calcd 337.8. found 339.2; Rt=1.271 min.

(S)—N-(3-(5-chloro-6-(oxazol-5-ylmethoxy)-3,4-dihydroisoquinolin-2(1H)-yl)-2-hydroxypropyl-2-fluoroisonicotinamide

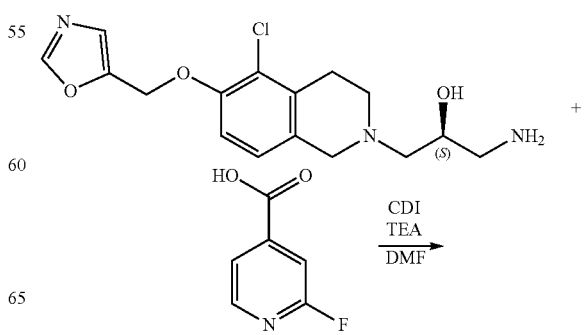

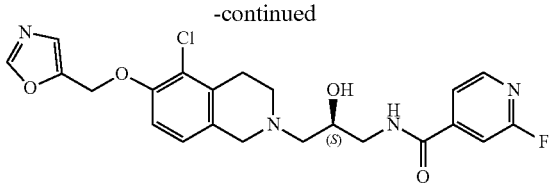

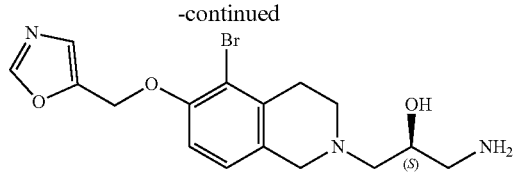

CDI (4.35 g, 26.83 mmol) was added in one portion to a stirred solution of 2-fluoroisonicotinic acid (3.16 g, 22.36 mmol) in DMF (50 mL) at 25° C. The resulting solution was stirred at 25° C. for 0.5 hr, then cooled to 0° C., and (2S)-1-amino-3-[5-chloro-6-(oxazol-5-ylmethoxy)-3,4-dihydro-1H-isoquinolin-2-yl]propan-2-ol (10 g, 22.36 mmol, 3HCl) was added followed by triethyl amine (6.79 g, 67.09 mmol, 9.35 mL). The reaction mixture was stirred at 0° C. for 3 hr, then diluted with water (200 ml) and extracted with ethyl acetate (3*150 ml). The combined organic extracts were washed with water (3*100 ml), dried over sodium sulphate and evaporated in vacuo to afford N-[(2S)-3-[5-chloro-6-(oxazol-5-ylmethoxy)-3,4-dihydro-1H-isoquinolin-2-yl]-2-hydroxy-propyl]-2-fluoro-pyridine-4-carboxamide (9.4 g, 20.40 mmol, 91.21% yield) as yellow gum, which was used in the next step without further purification. $^1$H NMR (500 MHz, CDCl$_3$-d) δ 2.58 (m, 1H), 2.89 (m, 5H), 3.39 (m, 1H), 3.56 (m, 1H), 3.76 (m, 2H), 4.03 (m, 1H), 4.09 (m, 1H), 5.11 (s, 2H), 6.86 (m, 2H), 7.15 (m, 1H), 7.27 (m, 1H), 7.45 (m, 2H), 7.91 (s, 1H), 8.24 (m, 1H). LCMS(ESI) [M+H]$^+$ m/z: calcd 460.9. found 461.2; Rt=0.890 min.

(S)-1-amino-3-(5-bromo-6-(oxazol-5-ylmethoxy)-3,4-dihydroisoquinolin-2(1H)-yl)propan-2-ol

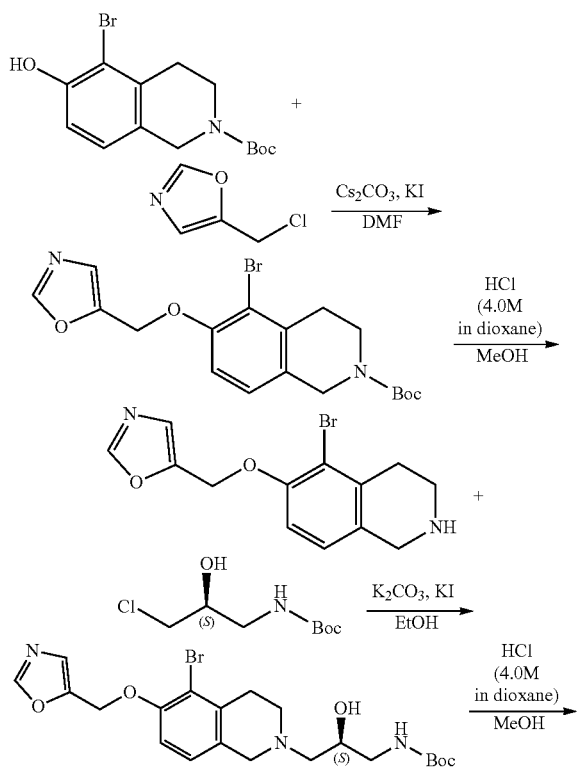

tert-butyl 5-bromo-6-(oxazol-5-ylmethoxy)-3,4-dihydroisoquinoline-2(1H)-carboxylate. To a solution of tert-butyl 5-bromo-6-hydroxy-3,4-dihydro-1H-isoquinoline-2-carboxylate (20 g, 60.94 mmol) in DMF (200 mL), cesium carbonate (69.49 g, 213.28 mmol) and potassium iodide (2.02 g, 12.19 mmol, 648.45 uL) were added. The resulting mixture was stirred for 30 min and 5-(chloromethyl)oxazole (14.08 g, 91.41 mmol, HCl) was added. The reaction mixture was stirred at 45° C. for 18 h. After the completion of the reaction, the resulting mixture was allowed to cool to 20° C., taken up with water (1000 mL) and extracted with MTBE (4*300 mL). The combined organic extract was washed with brine (3*200 mL), dried over Na$_2$SO$_4$ and evaporated in vacuo to afford tert-butyl 5-bromo-6-(oxazol-5-ylmethoxy)-3,4-dihydro-1H-isoquinoline-2-carboxylate (24.5 g, 59.86 mmol, 98.23% yield). $^1$H NMR (DMSO-de, 500 MHz): δ 1.41 (s, 9H), 2.72 (t, 2H), 3.55 (t, 2H), 4.45 (s, 2H), 5.25 (s, 2H), 7.17 (m, 2H), 7.33 (s, 1H), 8.41 (s, 1H). LCMS(ESI): [M-Boc]$^+$ m/z: calcd 309.0. found 311.0; Rt=1.42 min.

5-(((5-bromo-1,2,3,4-tetrahydroisoquinolin-6-yl)oxy)methyl)oxazole. To a solution of tert-butyl 5-bromo-6-(oxazol-5-ylmethoxy)-3,4-dihydro-1H-isoquinoline-2-carboxylate (24.5 g, 59.86 mmol) in MeOH (400 mL) was added hydrogen chloride solution, 4.0 M in dioxane (59.86 mmol, 100 mL). The resulting mixture was stirred at 25° C. for 24 h and evaporated in vacuo. The residue was triturated with MeCN (100 mL), the formed precipitate was filtered on, washed with MTBE (100 mL) and air-dried to obtain 5-[(5-bromo-1,2,3,4-tetrahydroisoquinolin-6-yl)oxymethyl]oxazole (21.5 g, 56.27 mmol, 94.00% yield, 2HCl). $^1$H NMR (DMSO-d$_6$, 400 MHz): δ 2.91 (t, 2H), 3.34 (t, 2H), 4.19 (s, 2H), 5.30 (s, 2H), 7.25 (s, 2H), 7.34 (s, 1H), 8.42 (s, 1H), 9.75 (m, 2H). LCMS(ESI): [M+3H]$^+$ m/z: calcd 308.0. found 311.0; Rt=0.78 min.

(S)-tert-butyl (3-(5-bromo-6-(oxazol-5-ylmethoxy)-3,4-dihydroisoquinolin-2(1H)-yl)-2-hydroxypropyl)carbamate. To a suspension of 5-[(5-bromo-1,2,3,4-tetrahydroisoquinolin-6-yl)oxymethyl]oxazole (14.85 g, 38.86 mmol, 2HCl), potassium carbonate, anhydrous, 99% (21.48 g, 155.45 mmol, 9.38 mL) and potassium iodide (1.29 g, 7.77 mmol, 413.53 uL) in EtOH (500 mL), tert-butyl N-[(2S)-3-chloro-2-hydroxy-propyl]carbamate (11 g, 52.46 mmol) was added. The resulting suspension was heated at 50° C. for 12 h and cooled down. The formed precipitate was filtered off, the filter cake washed with EtOH (2*50 mL) and discarded. The solvent was evaporated in vacuo to obtain crude product (25 g), which was purified by gradient chromatography (MTBE-MeOH) to give tert-butyl N-[(2S)-3-[5-bromo-6-(oxazol-5-ylmethoxy)-3,4-dihydro-1H-isoquinolin-2-yl]-2-hydroxypropyl]carbamate (18 g, 37.32 mmol, 96.02% yield). NMR (CDCl$_3$, 500 MHz): δ 1.46 (s, 9H), 2.53 (m, 2H), 3.75 (m, 1H), 2.87 (m, 2H), 2.89 (m, 1H), 3.09 (m, 1H), 3.39 (m, 1H), 3.56 (m, 1H), 3.78 (m, 1H), 3.90 (m, 1H), 5.04 (m, 1H), 5.13 (s, 2H), 6.83 (d, 1H), 6.95 (d, 1H), 7.17 (s, 1H), 7.92 (s, 1H). LCMS(ESI): [M+H]$^+$ m/z: calcd 481.1. found 482.2; Rt=0.98 min.

(S)-1-amino-3-(5-bromo-6-(oxazol-5-ylmethoxy)-3,4-dihydroisoquinolin-2(1H)-yl)propan-2-ol. To a solution of tert-butyl N-[(2S)-3-[5-bromo-6-(oxazol-5-ylmethoxy)-3,4-dihydro-1H-isoquinolin-2-yl]-2-hydroxy-propyl]carbamate (18 g, 37.32 mmol) in MeOH (500 mL), hydrogen chloride solution, 4.0 M in dioxane (37.32 mmol, 100 mL) was added. The resulting mixture was stirred at 25° C. for 24 h and evaporated to give (2S)-1-amino-3-[5-bromo-6-(oxazol-5-ylmethoxy)-3,4-dihydro-1H-isoquinolin-2-yl]propan-2-ol (17 g, 34.58 mmol, 92.66% yield, 3HCl). $^1$H NMR(DMSO-$d_6$, 400 MHz): δ 2.81 (m, 1H), 3.03 (m, 3H), 3.26 (m, 1H), 3.44 (m, 2H), 4.40 (m, 2H), 4.57 (m, 1H), 5.30 (s, 2H), 7.02 (m, 3H), 7.25 (m, 2H), 7.35 (s, 1H), 8.33 (m, 3H), 8.42 (s, 1H), 11.17 (m, 1H). LCMS(ESI): [M+H]$^+$ m/z: calcd 381.1; found 382.0; Rt=0.62 min.

(S)-1-amino-3-(5-bromo-6-((4-methyloxazol-5-yl)methoxy)-3,4-dihydroisoquinolin-2(1H)-yl)propan-2-ol

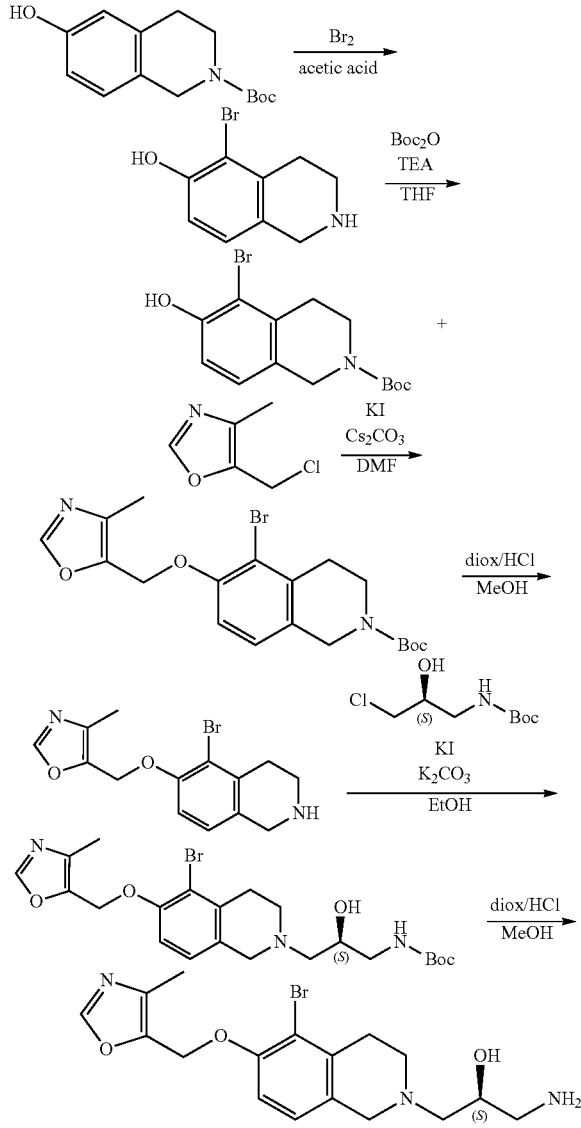

5-bromo-1,2,3,4-tetrahydroisoquinolin-6-ol. To a solution of tert-butyl 6-hydroxy-3,4-dihydro-1H-isoquinoline-2-carboxylate (45 g, 180.50 mmol) in acetic acid (250 mL), a solution of BrBr (30.29 g, 189.53 mmol, 9.80 mL) in acetic acid (50 mL) was added dropwise. The resulting mixture was stirred at 25° C. for 2 hr and precipitate was filtered, washed with MTBE and dried. The crude product was crystallized from EtOH (250 ml), the pricipitate was filtered, washed with mixture EtOH-MTBE (50:50) (50 ml), then MTBE (50 ml) to give 25 g crude product. The second crystalization from MeOH (220 ml) afforded 5-bromo-1,2,3,4-tetrahydroisoquinolin-6-ol (15 g, 48.54 mmol, 26.89% yield, HBr). $^1$H NMR (DMSO-$d_6$, 500 MHz): δ 2.89 (t, 2H), 3.39 (t, 2H), 4.19 (s, 2H), 6.90 (d, 1H), 7.07 (d, 1H), 9.07 (bds, 2H), 10.32 (s, 1H). LCMS(ESI): [M+H]$^+$ m/z: calcd 228.1. found 230.0; Rt=0.530 min.

tert-butyl 5-bromo-6-hydroxy-3,4-dihydroisoquinoline-2(1H)-carboxylate. To a suspension of 5-bromo-1,2,3,4-tetrahydroisoquinolin-6-ol (28 g, 90.62 mmol, HBr) and triethylamine (13.75 g, 135.92 mmol, 18.95 mL) in THF (300 mL), di-tert-butyl dicarbonate (20.77 g, 95.15 mmol, 21.84 mL) was added. The resulting mixture was stirred at 45° C. for 12 hr and evaporated in vacuo. The residue was taken up with water (100 ml) and extracted with DCM (3*50 ml). The organic layer was washed with NaHSO$_4$, brine, dried over Na$_2$SO$_4$ and evaporated in vacuo. The residue was taken up with hexane (100 ml) and triturated. The precipitate was filtered, washed with hexane (50 ml) and dried to obtain tert-butyl 5-bromo-6-hydroxy-3,4-dihydro-1H-isoquinoline-2-carboxylate (27.5 g, 83.79 mmol, 92.47% yield). $^1$H NMR (DMSO-$d_6$, 400 MHz): δ 1.41 (s, 9H), 2.70 (t, 2H), 3.54 (t, 2H), 4.39 (s, 2H), 6.81 (d, 1H), 6.99 (d, 1H), 10.04 (bds, 1H). LCMS(ESI): [M+H]$^+$ m/z: calcd 328.2. found 274.0; Rt=1.472 min.

tert-butyl 5-bromo-6-((4-methyloxazol-5-yl)methoxy)-3,4-dihydroisoquinoline-2(1H)-carboxylate. To a stirred solution of tert-butyl 5-bromo-6-hydroxy-3,4-dihydro-1H-isoquinoline-2-carboxylate (2 g, 6.09 mmol) in DMF (25 mL), cesium carbonate (5.96 g, 18.28 mmol) and potassium iodide (202.32 mg, 1.22 mmol, 64.85 uL) were added. The resulting mixture was stirred at 25° C. for 0.5 hour and 5-(chloromethyl)-4-methyl-oxazole (1.54 g, 9.14 mmol, HCl) was added. The mixture was stirred at 50° C. for 24 hr, taken up with water (200 ml) and extracted with MTBE (3*50 ml). The organic layer was washed with brine (3*50 ml), dried over Na$_2$SO$_4$ and evaporated in vacuo to give tert-butyl 5-bromo-6-[(4-methyloxazol-5-yl)methoxy]-3,4-dihydro-1H-isoquinoline-2-carboxy late (2.4 g, 5.67 mmol, 93.04% yield). $^1$H NMR (DMSO-$d_6$, 400 MHz): δ 1.41 (s, 9H), 2.15 (s, 3H), 2.72 (t, 2H), 3.55 (t, 2H), 4.45 (s, 2H), 5.21 (s, 2H), 7.12 (d, 1H), 7.20 (d, 1H), 8.29 (s, 1H). LCMS(ESI): [M+H]$^+$ m/z: calcd 423.3; found 369.0; Rt=1.528 min.

5-(((5-bromo-1,2,3,4-tetrahydroisoquinolin-6-yl)oxy)methyl)-4-methyloxazole. To a solution of tert-butyl 5-bromo-6-[(4-methyloxazol-5-yl)methoxy]-3,4-dihydro-1H-isoquinoline-2-carboxylate (2.4 g, 5.67 mmol) in MeOH, hydrogen chloride solution, 4.0 M in dioxane (15 g, 5.67 mmol) was added. The resulting mixture was stirred at 25° C. for 12 hr. The solvent was evaporated in vacuo and the residue was triturated with CH$_3$CN (20 ml). The precipitate was filtered and washed with CH$_3$CN (10 ml), MTBE (2*20 ml) and dried in vacuo to give 5-[(5-bromo-1,2,3,4-tetrahydroisoquinolin-6-yl)oxymethyl]-4-methyl-oxazole (2.1 g, 5.30 mmol, 93.51% yield, 2HCl). NMR (DMSO-$d_6$, 400 MHz): δ 2.15 (s, 3H), 2.92 (t, 2H), 3.33 (t, 2H), 4.18 (s, 2H), 5.25 (s, 2H), 7.21 (d, 1H), 7.25 (d, 1H), 8.30 (s, 1H), 9.83 (bds, 2H). LCMS(ESI): [M+H]⁺ m/z: calcd 323.2. found 324.0; Rt=0.848 min.

(S)-tert-butyl (3-(5-bromo-6-((4-methyloxazol-5-yl) methoxy)-3,4-dihydroisoquinolin-2(1H)-yl)-2-hydroxypropyl)carbamate. To a suspension of 5-[(5-bromo-1,2,3,4-tetrahydroisoquinolin-6-yl)oxy methyl]-4-methyl-oxazole (2.1 g, 5.30 mmol, 2HCl), potassium carbonate (2.93 g, 21.21 mmol, 1.28 mL) and potassium iodide (176.02 mg, 1.06 mmol, 56.42 uL) in EtOH (70 mL), tert-butyl A-[(2S)-3-chloro-2-hydroxy-propyl]carbamate (1.56 g, 7.42 mmol) was added. The resulting suspension was heated at 50° C. for 12 hr, filtered and the filtercake was washed with EtOH (2*35 ml) and discarded. The filtrate was evaporated in vacuo to obtain crude product 5 g. Purification by gradient chromatography (MTBE-MeOH) gave tert-butyl N-[(2S)-3-[5-bromo-6-[(4-methyloxazol-5-yl)methoxy]-3,4-dihydro-1H-isoquinolin-2-yl]-2-hydroxy-propyl]carbamate (1.9 g, 3.83 mmol, 72.20% yield). ¹H NMR (DMSO-d₆, 500 MHz): δ 1.38 (s, 9H), 2.16 (s, 3H), 2.43 (m, 2H), 2.75 (m, 4H), 2.92 (m, 1H), 3.05 (m, 1H), 3.61 (m, 2H), 3.72 (m, 1H), 4.56 (m, 1H), 5.13 (s, 2H), 6.46 (m, 1H), 7.02 (m, 2H), 8.20 (m, 1H). LCMS(ESI): [M+H]⁺ m/z: calcd 496.4. found 498.2; Rt=1.076 min.

(S)-1-amino-3-(5-bromo-6-((4-methyloxazol-5-yl) methoxy)-3,4-dihydroisoquinolin-2(1H)-yl)propan-2-ol. To a solution of tert-butyl N-[(2S)-3-[5-bromo-6-[(4-methyloxazol-5-yl)methoxy]-3,4-dihydro-1H-isoquinolin-2-yl]-2-hydroxy-propyl]carbamate (1.9 g, 3.83 mmol) in MeOH (100 mL), hydrogen chloride solution, 4.0 M in dioxane (15 g, 3.83 mmol) was added. The resulting mixture was stirred at 25° C. for 12 hr and the solvent was evaporated in vacuo to obtain (2S)-1-amino-3-[5-bromo-6-[(4-methyloxazol-5-yl)methoxy]-3,4-dihydro-1H-isoquinolin-2-yl]propan-2-ol (1.4 g, 2.77 mmol, 72.33% yield, 3HCl). NMR(DMSO-d₆, 500 MHz): δ 2.16 (s, 3H), 2.80 (m, 1H), 3.03 (m, 3H), 3.39 (m, 1H), 3.46 (m, 2H), 3.71 (m, 1H), 4.39 (m, 2H), 4.59 (m, 1H), 5.15 (m, 2H), 5.26 (s, 2H), 7.24 (m, 2H), 8.29 (m, 4H), 11.07 (m, 1H). LCMS(ESI): [M+H]⁺ m/z: calcd 396.3. found 397.2; Rt=0.721 min.

(S)-1-amino-3-(5-methyl-6-(oxazol-5-ylmethoxy)-3N-dihydroisoquinolin-2(1H)-yl)propan-2-ol

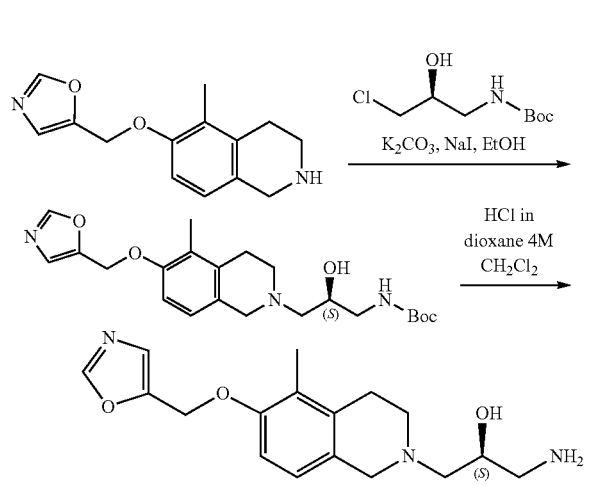

(S)-tert-butyl (2-hydroxy-3-(5-methyl-6-(oxazol-5-yl-methoxy)-3,4-dihydroisoquinolin-2(1H)-yl)propyl)carbamate. A mixture of tert-butyl N-[(2S)-3-chloro-2-hydroxy-propyl]carbamate (3.20 g, 15.28 mmol), 5-[(5-methyl-1,2, 3,4-tetrahydroisoquinolin-6-yl)oxymethyl]oxazole (4.04 g, 12.74 mmol, 2HCl), Potassium carbonate, anhydrous, 99% (5.28 g, 38.21 mmol, 2.31 mL), Sodium iodide (381.80 mg, 2.55 mmol, 104.03 uL) in Ethanole (40 mL) was stirred at 45° C. for 12 hr in sealed tube. The reaction mixture was evaporated and added MTBE (70 ml) the precipitate was filtered off, washed with MTBE (2*30 ml) and organic filtrate was evaporated in vacuo to leave 6 g of crude product, 6 g of which was purification by column chromatography on silica gel using MTBE/CH₃OH gradient (10-100% CH₃OH) to afford pure product tert-butyl N-[(2S)-2-hydroxy-3-[5-methyl-6-(oxazol-5-ylmethoxy)-3,4-dihydro-1H-isoquinolin-2-yl]propyl]carbamate (2.7 g, 6.47 mmol, 50.78% yield). NMR(CDCl₃, 400 MHz): δ (ppm) 1.50 (s, 9H), 2.05 (s, 3H), 2.50 (d, 2H), 2.60-2.80 (m, 3H), 2.90 (m, 1H), 3.05 (m, 1H), 3.30-3.40 (m, 1H), 3.50 (d, 1H), 3.70 (d, 2H), 3.80-3.90 (m, 1H), 5.00 (brs, 3H), 6.70 (d, 1H), 6.80 (d, 1H), 7.25 (s, 1H), 7.90 (s, 1H). LCMS(ESI): [M+H]⁺ m/z: calcd 417.2. found 418.2; Rt=0.978 min.

(S)-1-amino-3-(5-methyl-6-(oxazol-5-ylmethoxy)-3,4-dihydroisoquinolin-2(1H)-yl)propan-2-ol. Hydrogen chloride solution 4.0M in dioxane (6.40 g, 175.53 mmol, 8 mL) was added to a solution of tert-butyl N-[(2S)-2-hydroxy-3-[5-methyl-6-(oxazol-5-ylmethoxy)-3,4-dihydro-1H-isoquinolin-2-yl]propyl]carbamate (2.7 g, 6.47 mmol) in DCM (40 mL). The reaction mixture was stirred at 25° C. for 12 hr, then evaporated and added to MTBE (30 ml) the resulting precipitate was filtered off, washed with MTBE (10 ml) and dried to afford product (2S)-1-amino-3-[5-methyl-6-(oxazol-5-ylmethoxy)-3,4-dihydro-1H-isoquinolin-2-yl]propan-2-ol (2.7 g, 6.33 mmol, 97.83% yield, 3HCl). NMR(DMSO-d6, 500 MHz): δ (ppm) 2.05 (s, 3H), 2.70 (m, 1H), 2.80-3.00 (m, 3H), 3.10-3.20 (m, 1H), 3.30-3.50 (m, 2H), 3.70 (d, 1H), 4.20-4.50 (m, 3H), 5.15 (s, 2H), 6.20-6.50 (m, 2H), 6.90 (d, 1H), 7.10 (d, 1H), 7.30 (s, 1H), 8.10-8.30 (brs, 3H), 8.40 (s, 1H), 10.90 (brs, 1H). LCMS(ESI): [M+H]⁺ m/z: calcd 317.2. found 318.2; Rt=0.658 min.

(S)-1-amino-3-(6-((4-methyloxazol-5-yl)methoxy)-3N-dihydroisoquinolin-2(1H)-yl)propan-2-ol

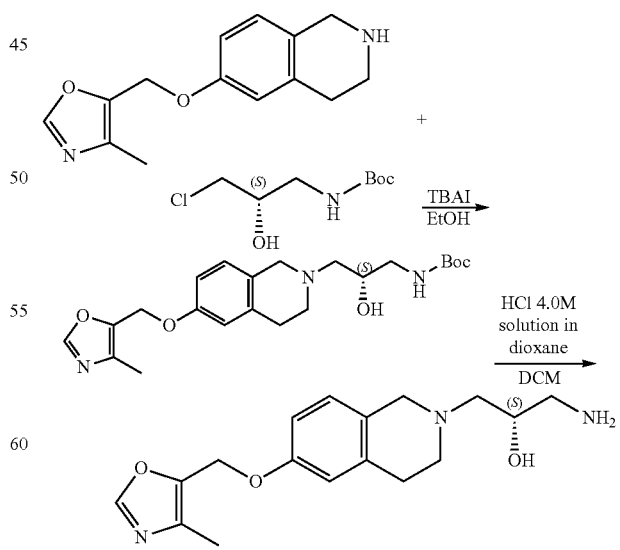

ate. The mixture of 4-methyl-5-(1,2,3,4-tetrahydroisoquinolin-6-yloxymethyl)oxazole (3.46 g, 14.16 mmol, 2HCl), tert-butyl N-[(2S)-3-chloro-2-hydroxy-propyl]carbamate (4.45 g, 21.24 mmol), potassium carbonate, anhydrous, 99% (1.96 g, 14.16 mmol, 854.54 uL), tetra-n-butylammonium iodide (5.23 g, 14.16 mmol) in EtOH (50 mL) was stirred at 65° C. for 12 hr in sealed tube. Afret the completion of the reaction, the resulting mixture was concentrated in vacuo, poured into water (50 mL) and extracted with DCM (2*50 mL). The combined organic extracts were washed with water (2*20 mL), dried over sodium sulphate, concentrated under reduced pressure to leave 7.2 g of crude product. The obtained product was purified by column chromatography on silica gel using MTBE/Methanole gradient (10-100% MTBE) to afford pure tert-butyl N-[(2S)-2-hydroxy-3-[6-[(4-methyloxazol-5-yl)methoxy]-3,4-dihydro-1H-isoquinolin-2-yl]propyl]carbamate (4.4 g, 10.54 mmol, 74.43% yield). $^1$H NMR (500 MHz, CDCl$_3$) δ (ppm) 1.46 (s, 9H), 2.23 (s, 3H), 2.56 (m, 2H), 2.69 (m, 1H), 2.90 (m, 3H), 3.10 (m, 1H), 3.22 (m, 1H), 3.78 (m, 2H), 3.90 (m, 1H), 5.02 (m, 3H), 6.72 (s, 1H), 6.76 (d, 1H), 6.94 (d, 1H), 7.81 (s, 1H). LCMS(ESI): [M+H]$^+$ m/z: calcd 418.2. found 418.2; Rt=0.95 min.

(S)-1-amino-3-(6-((4-methyloxazol-5-yl)methoxy)-3,4-dihydroisoquinolin-2(1H)-yl)propan-2-ol. Hydrogen chloride solution 4.0M in dioxane (4.00 g, 109.71 mmol, 5 mL) was added to a solution of tert-butyl N-[(2S)-2-hydroxy-3-[6-[(4-methyloxazol-5-yl)methoxy]-3,4-dihydro-1H-isoquinolin-2-yl]propyl]carbamate (2.29 g, 5.48 mmol) in methanole (25 mL). The reaction mixture was stirred at 25° C. for 12 hr. After the completion of the reaction, the solvent was removed under reduced pressure and suspended in MeCN (15 mL). The obtained precipitate was filtered, washed with MeCN (2*10 mL) and air-dried to afford (2S)-1-amino-3-[6-[(4-methyloxazol-5-yl)methoxy]-3,4-dihydro-1H-isoquinolin-2-yl]propan-2-ol (1.64 g, 3.84 mmol, 70.09% yield, 3HCl). $^1$H NMR (500 MHz, DMSO-d$_6$) δ (ppm) 2.22 (s, 3H), 2.76 (m, 1H), 2.89 (m, 2H), 3.12 (m, 2H), 3.34 (m, 2H), 3.45 (m, 2H), 3.75 (m, 1H), 4.32 (m, 5H), 5.01 (s, 3H), 6.76 (m, 2H), 7.21 (d, 1H), 8.32 (m, 1H), 11.03 (s, 1H). LCMS (ESI): [M+H]$^+$ m/z: calcd 318.2; found 318.2; Rt=0.61 min.

(S)-2-fluoro-N-(2-hydroxy-3-(6-((4-methyloxazol-5-yl)methoxy)-3,4-dihydroisoquinolin-2(1H)-yl)propyl)isonicotinamide

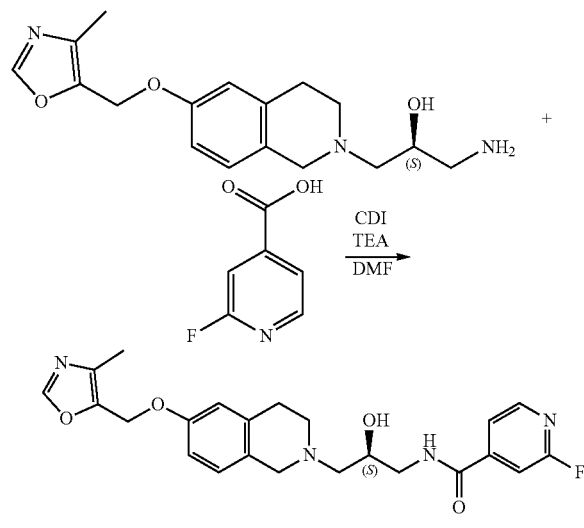

CDI (1.67 g, 10.31 mmol) was added to a solution (2S)-1-amino-3-[6-[(4-methyloxazol-5-yl) methoxy]-3,4-dihydro-1H-isoquinolin-2-yl]propan-2-ol (4 g, 9.37 mmol, 3HCl) in DMF (30 mL). The resulting mixture was stirred at 20° C. 1 hr, then cooled to 0° C. and 2-fluoropyridine-4-carboxylic acid (1.32 g, 9.37 mmol) was added followed by triethyl amine (3.13 g, 30.93 mmol, 4.31 mL). The reaction mixture was allowed to warm to 25° C. and stirred for 3 hr. The reaction mixture was poured into water (50 ml) and extracted with EtOAc (3×20 ml). The combined organic extracts were washed with water(2*15 ml), dried over sodium sulphate and evaporated in vacuo to afford product 2-fluoro-N-[(2S)-2-hydroxy-3-[6-[(4-methyloxazol-5-yl) methoxy]-3,4-dihydro-1H-isoquinolin-2-yl]propyl]pyridine-4-carboxamide (3.1 g, 7.04 mmol, 75.09% yield). NMR(500 MHz, CDCl$_3$): δ 2.24 (s, 3H), 2.59 (m, 1H), 2.67 (m, 1H), 2.75 (m, 1H), 2.97 (m, 3H), 3.43 (m, 1H), 3.58 (m, 1H), 3.75 (m, 2H), 4.05 (m, 1H), 5.01 (s, 2H), 6.77 (m, 2H), 6.93 (m, 1H), 7.28 (m, 3H), 7.47 (m, 1H), 7.82 (s, 1H), 8.28 (m, 1H). LCMS(ESI): [M+H]$^+$ m/z: calcd 440.5. found 441.2; Rt=0.924 min.

(S)-1-amino-3-(5-methyl-6-((4-methyloxazol-5-yl)methoxy)-3,4-dihydroisoquinolin-2(1H)-yl)propan-2-ol

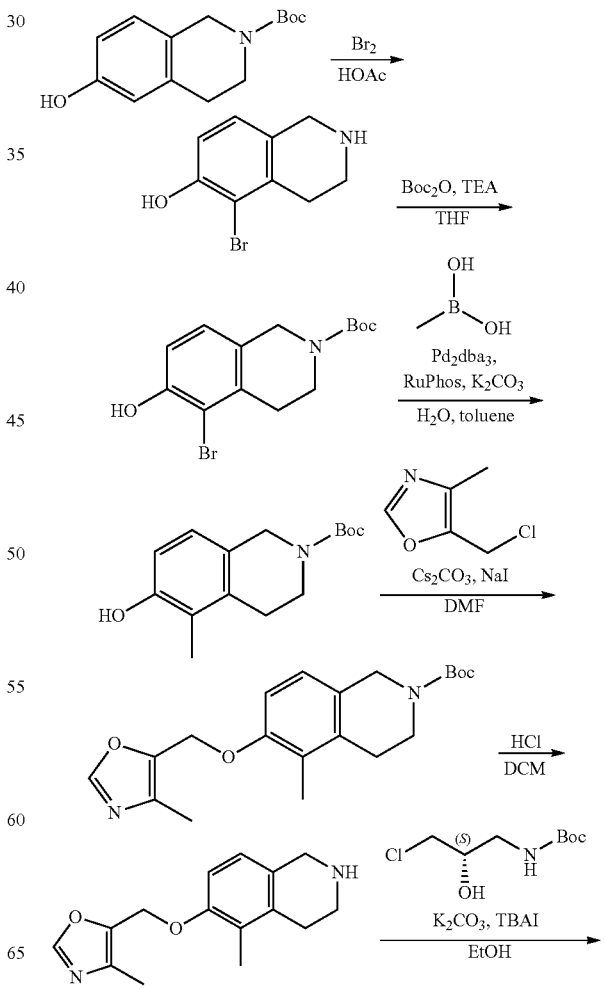

-continued

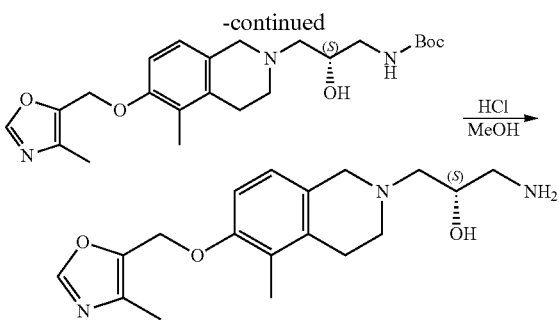

HCl / MeOH 5-bromo-1,2,3,4-tetrahydroisoquinolin-6-ol. To a solution of tert-butyl 6-hydroxy-3,4-dihydro-1H-isoquinoline-2-carboxylate (50 g, 200.56 mmol) in acetic acid (300 mL), a solution of bromine (33.65 g, 210.59 mmol, 22.59 mL) in acetic acid (50 mL) was added dropwise. The resulting mixture was stirred at 25° C. for 2 hr and precipitate was filtered, washed with MTBE and dried. The crude product was crystallized from EtOH (20 mL), the precipitate was filtered, washed with mixture EtOH-MTBE (50:50) (20 mL), then MTBE (10 mL) and dried to obtain 5-bromo-1,2,3,4-tetrahydroisoquinolin-6-ol (30 g, 97.09 mmol, 48.41% yield, HBr). $^1$H NMR (400 MHz, DMSO-$d_6$) δ (ppm) 2.88 (m, 2H), 3.38 (m, 2H), 4.17 (m, 2H), 6.89 (d, 1H), 7.06 (d, 1H), 9.02 (m, 2H), 10.32 (s, 1H). LCMS(ESI): [M+H]$^+$ m/z: calcd 227.1. found 228.0; Rt=0.50 min.

tert-butyl 5-bromo-6-hydroxy-3,4-dihydroisoquinoline-2(1H)-carboxylate. To a suspension of 5-bromo-1,2,3,4-tetrahydroisoquinolin-6-ol (10 g, 32.36 mmol, HBr) and triethylamine (4.91 g, 48.54 mmol, 6.77 mL) in THF (200 mL), di-tert-butyl dicarbonate (7.42 g, 33.98 mmol, 7.80 mL) was added. The resulting mixture was stirred at 45° C. for 12 hr and evaporated in vacuo. The residue was taken up with water (100 mL) and extracted with DCM (3*50 mL). The organic layer was washed with NaHSO$_4$, brine, dried over Na$_2$SO$_4$ and evaporated in vacuo. The residue was taken up with hexane (100 mL) and triturated. The precipitate was filtered, washed with hexane (50 mL) and dried to obtain tert-butyl 5-bromo-6-hydroxy-3,4-dihydro-1H-isoquinoline-2-carboxylate (7 g, 21.33 mmol, 65.90% yield). $^1$H NMR (400 MHz, DMSO-$d_6$) δ (ppm) 1.40 (s, 9H), 2.69 (t, 2H), 3.54 (t, 2H), 4.39 (s, 2H), 6.81 (d, 1H), 6.98 (d, 1H), 10.04 (s, 1H). LCMS(ESI): [M+H]$^+$ m/z: calcd 327.0. found 328.0; Rt=1.43 min.

tert-butyl 6-hydroxy-5-methyl-3,4-dihydroisoquinoline-2(1H)-carboxylate. tert-Butyl 5-bromo-6-hydroxy-3,4-dihydro-1H-isoquinoline-2-carboxylate (10.5 g, 31.99 mmol), methylboronic acid (8.04 g, 134.37 mmol) and potassium carbonate (13.26 g, 95.98 mmol) were mixed together in toluene (150 mL) and wather (4.00 mL). The resulting mixture was evacuated and then backfilled with argon, this operation was repeated three times, then tris(dibenzylideneacetone)dipalladium(0) (1.46 g, 1.60 mmol) and RuPhos (1.49 g, 3.20 mmol) were added under argon. The resulting mixture was stirred under argon at 90° C. for 18 hr, then volatiles were evaporated in vacuo. The residue was treated with water (600 mL) and extracted with DCM (2*400 mL). The combined organic layers were dried over Na$_2$SO$_4$ and evaporated in vacuo to give tert-butyl 6-hydroxy-5-methyl-3,4-dihydroisoquinoline-2-carboxylate (13.5 g, crude). $^1$H NMR (400 MHz, CDCl$_3$) δ (ppm) 1.46 (s, 9H), 2.12 (s, 3H), 2.70 (t, 2H), 3.62 (t, 2H), 4.47 (s, 2H), 6.66 (d, 1H), 6.78 (d, 1H). LCMS(ESI): [M-Boc]$^+$ m/z: calcd 163.1. found 164.1; Rt=1.34 min.

tert-butyl 5-methyl-6-((4-methyloxazol-5-yl)methoxy)-3,4-dihydroisoquinoline-2(1H)-carboxylate. 5-(Chloromethyl)-4-methyl-oxazole (1.53 g, 9.11 mmol, HCl) was added to the mixture of tert-butyl 6-hydroxy-5-methyl-3,4-dihydro-1H-isoquinoline-2-carboxylate (2 g, 6.08 mmol), cesium carbonate (5.94 g, 18.23 mmol) and sodium iodide (182.15 mg, 1.22 mmol) in DML (25 mL). The reaction was stirred at 45° C. for 12 hr. The mixture was quenching with H$_2$O (100 mL). The aqueous layer was extracted with MTBE (2*100 mL). The combined organic layers were washed with water (2*30 mL) and brine, dried over Na$_2$SO$_4$ and concentrated in vacuo to afford tert-butyl 5-methyl-6-[(4-methyloxazol-5-yl)methoxy]-3,4-dihydro-1H-isoquinoline-2-carboxylate (2.7 g, crude) which was used without purification. $^1$H NMR (400 MHz, CDCl$_3$) δ (ppm) 1.50 (s, 9H), 2.10 (s, 3H), 2.20 (s, 3H), 2.73 (t, 2H), 3.64 (t, 2H), 4.52 (s, 2H), 4.99 (s, 2H), 6.84 (d, 1H), 6.94 (d, 1H), 7.81 (s, 1H). LCMS(ESI): [M-Boc]$^+$ m/z: calcd 258.2. found 259.0; Rt=1.54 min.

4-methyl-5-(((5-methyl-1,2,3,4-tetrahydroisoquinolin-6-yl)oxy)methyl)oxazole. Hydrogen chloride solution 4.0M in dioxane (15.69 g, 60.26 mmol, 14.95 mL, 14% purity) was carefully added at r.t. to a solution of tert-butyl 5-methyl-6-[(4-methyloxazol-5-yl)methoxy]-3,4-dihydro-1H-isoquinoline-2-carboxylate (2.7 g, 6.03 mmol) in DCM (35 mL). The reaction mixture was then stirred for 12 hr at r.t. and the solvents were evaporated in vacuo to give 4-methyl-5-[(5-methyl-1,2,3,4-tetrahydroisoquinolin-6-yl)oxymethyl]oxazole (2.2 g, crude, 2HCl) which was used without purification. $^1$H NMR (500 MHz, DMSO-$d_6$) δ (ppm) 2.00 (s, 3H), 2.12 (s, 3H), 2.83 (m, 2H), 3.15 (m, 2H), 4.15 (m, 2H), 5.13 (s, 2H), 7.05 (m, 2H), 8.27 (m, 1H), 9.46 (m, 2H). LCMS (ESI): [M+H]$^+$ m/z: calcd 258.2. found 259.0; Rt=0.84 min.

(S)-tert-butyl (2-hydroxy-3-[5-methyl-6-((4-methyloxazol-5-yl)methoxy)-3,4-dihydroisoquinolin-2(1H)-yl)propyl)carbamate. 4-Methyl-5-[(5-methyl-1,2,3,4-tetrahydroisoquinolin-6-yl)oxymethyl]oxazole (1 g, 2.42 mmol, 2HCl), potassium carbonate (1.17 g, 8.45 mmol, 510.18 uL) and tetrabutylammonium iodide (89.21 mg, 241.52 umol) were mixed together in EtOH (15 mL). The resulting suspension was stirred at r.t. for 10 min., then tert-butyl N-[(2S)-3-chloro-2-hydroxy-propyl]carbamate (708.95 mg, 3.38 mmol) was added in one portion and the reaction mixture was stirred at 50° C. for 24 hr, cooled down and concentrated in vacuo. The residue was suspended in MTBE (100 mL) and filtered. The filtercake was washed with MTBE (3*100 mL) and discarded. The filtrate was evaporated in vacuo to leave the residue tert-butyl N-[(2S)-2-hydroxy-3-[5-methyl-6-[(4-methyloxazol-5-yl)methoxy]-3,4-dihydro-1H-isoquinolin-2-yl]propyl]carbamate (1.5 g, crude). $^1$H NMR (500 MHz, DMSO-$d_6$) δ 1.36 (s, 9H), 1.41 (m, 1H), 2.11 (s, 3H), 2.49 (s, 3H), 2.63 (m, 3H), 2.66 (m, 2H), 3.29 (m, 3H), 3.69 (m, 2H), 3.70 (m, 1H), 5.06 (s, 2H), 6.33 (s, 1H), 6.84 (d, 1H), 6.89 (d, 1H), 8.26 (s, 1H). LCMS(ESI): [M+H]$^+$ m/z: calcd 431.2. found 432.2; Rt=1.06 min.

(S)-1-amino-3-(5-methyl-6-((4-methyloxazol-5-yl)methoxy)-3,4-dihydroisoquinolin-2(1H)-yl)propan-2-ol. Hydrogen chloride solution 4.0M in dioxane (6.34 g, 24.33 mmol, 6.04 mL, 14% purity) was carefully added at r.t. to a solution of tert-butyl N-[(2S)-2-hydroxy-3-[5-methyl-6-[(4-methyloxazol-5-yl)methoxy]-3,4-dihydro-1H-isoquinolin-2-yl]propyl]carbamate (1.5 g, 2.43 mmol) in MeOH (20 mL). The reaction mixture was then stirred for 12 hr at r.t. and the solvents were evaporated in vacuo to give (2S)-1-amino-3-[5-methyl-6-[(4-methyloxazol-5-yl)methoxy]-3,4-dihydro-1H-isoquinolin-2-yl]propan-2-ol (1.5 g, crude, 3HCl). $^1$H NMR (400 MHz, DMSO-$d_6$) δ 2.04 (s, 3H), 2.99

(m, 1H), 3.15 (m, 3H), 3.17 (m, 1H), 3.83 (s, 3H), 4.46 (m, 5H), 5.18 (s, 2H), 6.36 (m, 1H), 7.05 (d, 1H), 7.09 (d, 1H), 7.36 (s, 1H), 8.23 (m, 2H), 10.84 (m, 1H). LCMS(ESI): [M+H]⁺ m/z: calcd 331.2. found 332.2; Rt=0.64 min.

(S)—N-(3-(5-bromo-6-(oxazol-5-ylmethoxy)-3,4-dihydroisoquinolin-2(1H)-yl)-2-hydroxypropyl)-2-fluoroisonicotinamide

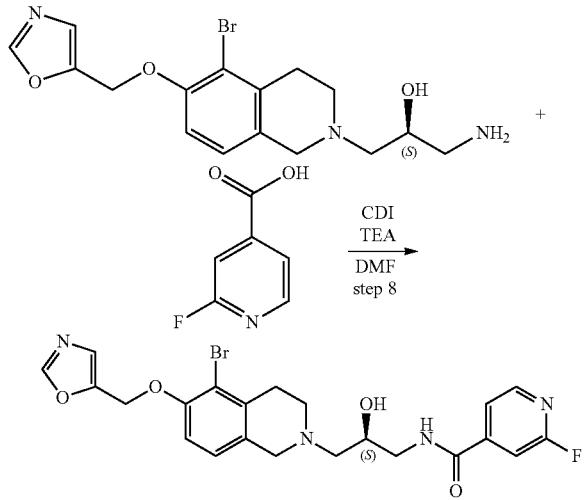

CDI (3.96 g, 24.41 mmol) was added to a solution of 2-fluoropyridine-4-carboxylic acid (2.87 g, 20.34 mmol) in DMF (60 mL). The resulting mixture was stirred at 25° C. for 0.25 hr, then cooled to −10° C. and (2S)-1-amino-3-[5-bromo-6-(oxazol-5-ylmethoxy)-3,4-dihydro-1H-isoquinolin-2-yl]propan-2-ol (10 g, 20.34 mmol, 3HCl) was added followed by Triethylamine (8.23 g, 81.36 mmol, 11.34 mL). The reaction mixture was allowed to warm to 25° C. and stirred for 1 hr. The reaction mixture was diluted with water (200 ml) and extracted with ethyl acetate (3*100 ml). The combined organic extract was washed with water (2*50 ml), dried over sodium sulphate and evaporated in vacuo to afford N-[(2S)-3-[5-bromo-6-(oxazol-5-ylmethoxy)-3,4-dihydro-1H-isoquinolin-2-yl]-2-hydroxy-propyl]-2-fluoro-pyridine-4-carboxamide (7.8 g, 15.44 mmol, 75.89% yield), which was used in the next step without further purification.

¹H NMR(DMSO-d₆, 500 MHz): δ 2.53 (m, 3H), 2.72 (m, 2H), 2.88 (m, 1H), 3.22 (m, 1H), 3.46 (m, 1H), 3.58 (m, 2H), 3.91 (m, 1H), 4.89 (m, 1H), 5.23 (s, 2H), 7.07 (m, 2H), 7.32 (s, 1H), 7.49 (s, 1H), 7.68 (d, 1H), 8.33 (d, 1H), 8.41 (s, 1H), 8.85 (m, 1H).

LCMS(ESI): [M+H]⁺ m/z: calcd 505.3. found 506.2; Rt=0.920 min.

(S)-2-fluoro-N-(2-hydroxy-3-[5-methyl-6-(oxazol-5-ylmethoxy)-3,4-dihydroisoquinolin-2(1H)-yl)propyl)isonicotinamide

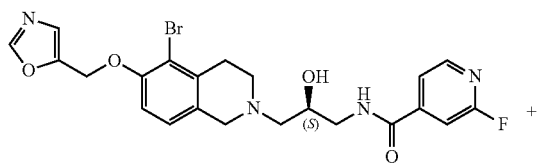

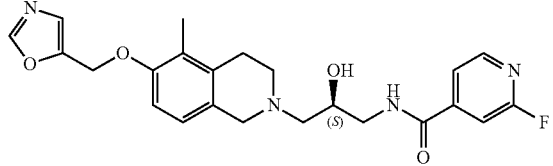

N-[(2S)-3-[5-Bromo-6-(oxazol-5-ylmethoxy)-3,4-dihydro-1H-isoquinolin-2-yl]-2-hydroxy-propyl]-2-fluoro-pyridine-4-carboxamide (3.30 g, 6.54 mmol), methylboronic acid (1.57 g, 26.16 mmol) were mixed together in toluene (30 mL) and water (0.3 mL). The resulting mixture was evacuated and then backfilled with argon, this operation was repeated three times, then potassium carbonate (2.98 g, 21.58 mmol, 1.30 mL) and Pd(dppf)C12 DCM (267.02 mg, 326.97 umol) were added under argon. The resulting mixture was stirred under argon at 100° C. for 2 hr, then it was diluted with water (50 mL). The layers were separated and the organic layer was washed with water (2*30 mL). The organic layer was dried over Na₂SO₄ and evaporated in vacuo to leave 2.68 g of crude product, 2.68 g of which was purification by column chromatography on silica gel using MTBE/methanol gradient (10-100% methanol) to afford pure product 2-fluoro-N-[(2S)-2-hydroxy-3-[5-methyl-6-(oxa/ol-5-ylmethoxy)-3,4-dihydro-1H-isoquinolin-2-yl]propyl]pyridine-4-carboxamide (0.8 g, 1.82 mmol, 27.77% yield).

¹H NMR(DMSO-d₆, 400 MHz): δ 1.99 (s, 3H), 2.48 (m, 3H), 2.64 (m, 2H), 2.74 (m, 2H), 3.23 (m, 1H), 3.55 (m, 3H), 3.92 (m, 1H), 4.89 (m, 1H), 5.11 (s, 2H), 6.83 (d, 1H), 6.91 (d, 1H), 7.49 (s, 1H), 7.68 (d, 1H), 8.31 (d, 1H), 8.39 (s, 1H), 8.88 (m, 1H).

LCMS(ESI): [M+H]⁺ m/z: calcd 440.5. found 441.2; Rt=0.862 min.

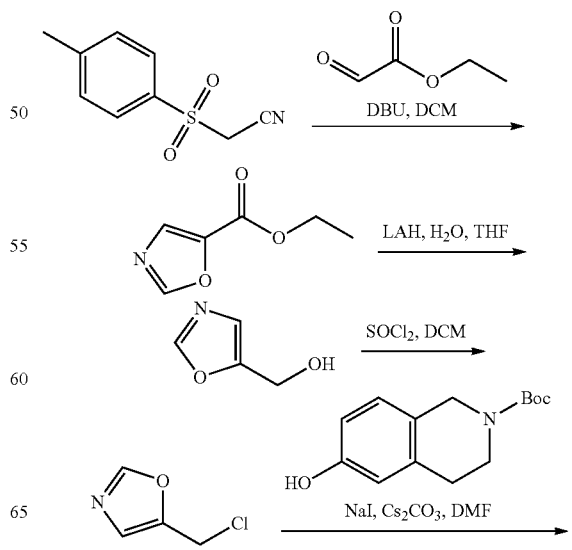

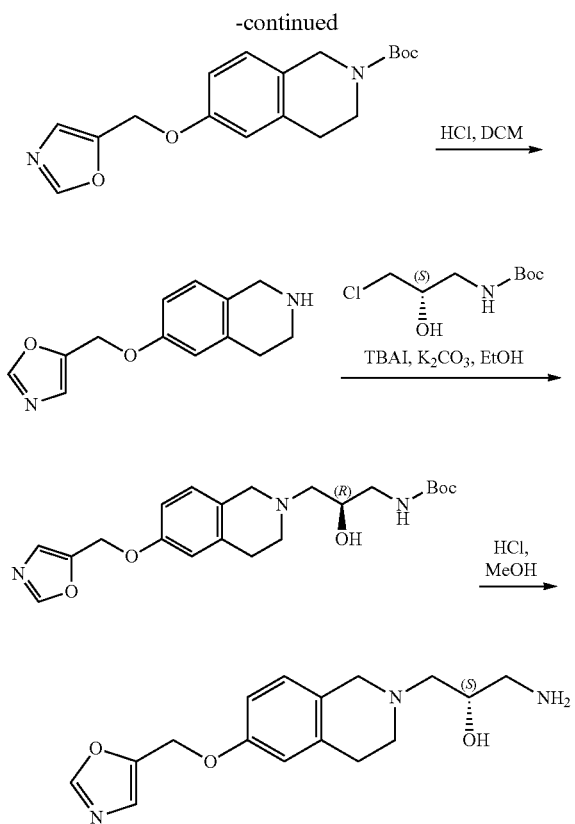

Ethyl oxazole-5-carboxylate. 1-Isocyanomethanesulfonyl-4-methylbenzene (95.62 g, 489.77 mmol) was dissolved in dry dichloromethane (900 mL) under an argon atmosphere. The reaction mixture was cooled to 0° C. and 1,8-Diazabicyclo(5.4.0)undec-7-ene (74.56 g, 489.77 mmol, 73.10 mL) and ethyl 2-oxoacetate (130 g, 636.70 mmol, 126.21 mL) solution in dichloromethane was added simultaneously over a period of 2 hr. Then, second portion of 1,8-Diazabicyclo(5.4.0)undec-7-ene (37.28 g, 244.89 mmol, 36.55 mL) was added slowly. The resulting suspension was allowed to warm to room temperature and stirred overnight. The organic layer was washed with aqueous 1.5 N HCl (450 ml) and sat. aqueous $Na_2CO_3$ (450 ml), dried over sodium sulphate and evaporated in vacuo to leave 98 g of the residue, which was purified by column chromatography on silicagel using n-hexane/dichloromethane gradient (20-100% dichloromethane) to afford ethyl oxazole-5-carboxylate (62 g, 439.33 mmol, 89.70% yield) as yellow oil. $^1$H NMR (500 MHz, $CDCl_3$) δ (ppm) 1.37 (q, 3H), 4.38 (t, 2H), 7.75 (s, 1H), 7.99 (s, 1H). LCMS(ESI): [M+H]$^+$ m/z: calcd 142.0. found 142.0; Rt=0.94 min.

oxazol-5-ylmethanol. Ethyl oxazole-5-carboxylate (20 g, 141.72 mmol) was added dropwise. to a stirred suspension of lithium aluminum hydride (2.96 g, 77.95 mmol) in THF (200 mL) at −10° C. under argon. The reaction mixture was stirred at −10° C. for 0.5 hr and, then, quenched by dropwise addition of water (25.53 g, 1.42 mol, 25.53 mL) in THF (100 ml). The resulting mixture was stirred for 0.5 hr and filtered off. The filtercake was washed with THF (3*100 mL) and discarded. The filtrate was concentrated in vacuo to afford oxazol-5-ylmethanol (10.5 g, 105.97 mmol, 74.77% yield) as red oil, which was used in the next step without further purification. $^1$H NMR (500 MHz, $CDCl_3$) δ (ppm) 3.01 (s, 1H), 4.68 (s, 2H), 7.00 (s, 1H), 7.85 (s, 1H). LCMS(ESI): [M+H]$^+$ m/z: calcd 100.0. found 100; Rt=0.94 min.

5-(chloromethyl)oxazole. Thionyl chloride (13.87 g, 116.56 mmol) was added dropwise to a solution of oxazol-5-ylmethanol (10.5 g, 105.97 mmol) in dichloromethane (150 mL) at 0° C. The reaction mixture was warmed to 25° C., stirred for 0.25 hr and evaporated in vacuo. The residue was dried in vacuo to afford 5-(chloromethyl)oxazole (16.3 g, 105.85 mmol, 99.89% yield, HCl) as brown solid. $^1$H NMR (500 MHz, DMSO-$d_6$) δ (ppm) 4.91 (s, 2H), 7.25 (s, 1H), 8.41 (s, 1H). GCMS: [M+H]$^+$ m/z: calcd 117.0. found 117.0; Rt=2.79 min.

tert-butyl 6-(oxazol-5-ylmethoxy)-3,4-dihydroisoquinoline-2(1H)-carboxylate. tert-Butyl 6-hydroxy-3,4-dihydro-1H-isoquinoline-2-carboxylate (14 g, 56.16 mmol), sodium iodide (1.68 g, 11.23 mmol, 458.71 uL) and cesium carbonate (91.48 g, 280.78 mmol) were mixed together in DMF (350 mL). The resulting suspension was stirred at 25° C. for 0.5 hr, then 5-(chloromethyl)oxazole (16.3 g, 105.85 mmol, HCl) was added and the reaction mixture was stirred at 50° C. for 24 hr, cooled down, poured in water (1000 mL) and extracted with MTBE (2*250 mL). The combined organic extracts were washed with water (2*100 mL), dried over sodium sulphate and concentrated in vacuo to afford tert-butyl 6-(oxazol-5-ylmethoxy)-3,4-dihydro-1H-isoquinoline-2-carboxylate (18 g, 54.48 mmol, 97.02% yield) as yellow oil. $^1$H NMR (500 MHz, $CDCl_3$) δ (ppm) 1.46 (s, 9H), 2.77 (t, 2H), 3.60 (t, 2H), 4.48 (s, 2H), 5.03 (s, 2H), 6.71 (s, 1H), 6.79 (dd, 1H), 7.01 (dd, 1H), 7.12 (s, 1H), 7.87 (s, 1H). LCMS(ESI): [M-Boc]$^+$ m/z: calcd 231.0. found 231.0; Rt=1.44 min.

5-(((1,2,3,4-tetrahydroisoquinolin-6-yl)oxy)methyl)oxazole. Hydrogen chloride solution 4.0M in dioxane (272.12 g, 1.09 mol, 259.16 mL, 14.6% purity) was added to a solution of tert-butyl 6-(oxazol-5-ylmethoxy)-3,4-dihydro-1H-isoquinoline-2-carboxylate (18 g, 54.48 mmol) in dichloromethane (300 mL). The resulting mixture was stirred at 25° C. for 12 hr. The formed precipitate was isolated by filtration, washed with dichloromethane (3*10 mL) and dried in vacuo to afford 5-(1,2,3,4-tetrahydroisoquinolin-6-yloxymethyl)oxazole (16.5 g, 54.42 mmol, 99.89% yield, 2HCl) as beige solid. $^1$H NMR (500 MHz, DMSO-$d_6$) δ (ppm) 2.96 (t, 2H), 3.29 (t, 2H), 4.13 (s, 2H), 5.16 (s, 2H), 6.90 (m, 2H), 7.13 (d, 1H), 7.32 (s, 1H), 8.40 (s, 1H), 9.64 (s, 2H). LCMS(ESI): [M+H]$^+$ m/z: calcd 231.1. found 231.1; Rt=0.74 min.

(S)-tert-butyl (2-hydroxy-3-(6-(oxazol-5-ylmethoxy)-3,4-dihydroisoquinolin-2(1H)-yl)propyl)carbamate. 5-(1,2,3,4-Tetrahydroisoquinolin-6-yloxymethyl)oxazole (7.4 g, 24.41 mmol, 2HCl), tetrabutylammonium iodide (1.80 g, 4.88 mmol) and potassium carbonate, anhydrous, 99% (11.13 g, 80.55 mmol, 4.86 mL) were mixed together in ethanol (250 mL). The resulting suspension was stirred at 25° C. for 0.1 hr, then tert-butyl N-[(2S)-3-chloro-2-hydroxy-propyl]carbamate (7.16 g, 34.17 mmol) was added and the reaction mixture was stirred at 50° C. for 12 hr, cooled down and evaporated in vacuo. The residue was diluted with MTBE (200 mL) and filtered. The filtercake was washed with MTBE (3*50 mL) and discarded. The filtrate was evaporated in vacuo to leave 12.5 g of the residue, which was purified by column chromatography on silicagel using MTBE/methanol gradient (0-100% methanol) to afford tert-butyl N-[(2S)-2-hydroxy-3-[6-(oxazol-5-ylmethoxy)-3,4-dihydro-1H-isoquinolin-2-yl]propyl]carbamate (8 g, 19.83 mmol, 81.24% yield) as yellow oil. $^1$H NMR (500 MHz, $CDCl_3$) δ (ppm) 1.38 (s, 9H), 2.48 (m, 2H), 2.63 (m, 1H), 2.90 (m, 3H), 3.10 (m, 1H), 3.40 (m, 1H), 3.52 (m, 1H), 3.76

(m, 1H), 3.89 (m, 1H), 5.05 (s, 3H), 6.72 (s, 1H), 6.78 (d, 1H), 6.95 (d, 1H), 7.15 (s, 1H), 7.90 (s, 1H). LCMS(ESI): [M+H]$^+$ m/z: calcd 404.2. found 404.2; Rt=0.94 min.

(S)-1-amino-3-(6-(oxazol-5-ylmethoxy)-3,4-dihydroisoquinolin-2(1H)-yl)propan-2-ol. Hydrogen chloride solution 4.0M in dioxane (99.03 g, 396.56 mmol, 94.32 mL, 14.6% purity) was added to a solution of tert-butyl-[(2S)-2-hydroxy-3-[6-(oxazol-5-ylmethoxy)-3,4-dihydro-1H-isoquinolin-2-yl]propyl]carbamate (8.00 g, 19.83 mmol) in methanol (200 mL). The resulting mixture was stirred at 45° C. for 0.5 hr, evaporated and dried in vacuo to afford (2S)-1-amino-3-[6-(oxazol-5-ylmethoxy)-3,4-dihydro-1H-isoquinolin-2-yl]propan-2-ol (8.1 g, 19.63 mmol, 98.98% yield, 3HCl) as white solid. $^1$H NMR (500 MHz, DMSO-d$_6$) δ (ppm) 2.87 (m, 1H), 2.98 (m, 2H), 3.21 (m, 2H), 3.62 (m, 3H), 3.73 (m, 2H), 4.31 (m, 3H), 5.16 (s, 2H), 6.41 (m, 1H), 6.93 (m, 2H), 7.13 (m, 1H), 7.33 (m, 1H), 10.95 (m, 1H). LCMS(ESI): [M+H]$^+$ m/z: calcd 304.2. found 304.2; Rt=0.54 min.

(S)-2-fluoro-N-(2-hydroxy-3-(6-(oxazol-5-ylmethoxy)-3N-dihydroisoquinolin-2(1H)-yl)propyl) isonicotinamide

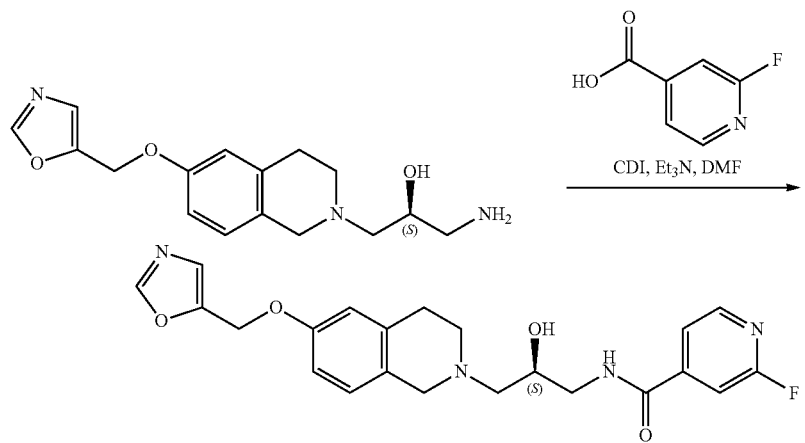

1,1'-Carbonyldiimidazole (2.36 g, 14.54 mmol) was added to a solution of 2-fluoropyridine-4-carboxylic acid (1.71 g, 12.11 mmol) in DMF (40 mL). The resulting mixture was stirred at 25° C. for 0.25 hr, then cooled to −10° C. and (2S)-1-amino-3-[6-(oxazol-5-ylmethoxy)-3,4-dihydro-1H-isoquinolin-2-yl]propan-2-ol (5 g, 12.11 mmol, 3HCl) was added followed by Triethylamine (4.90 g, 48.46 mmol, 6.75 mL). The reaction mixture was allowed to warm to 25° C. and stirred for 1 hr. The reaction mixture was diluted with water (200 ml) and extracted with ethyl acetate (3*100 ml). The combined organic extract was washed with water (2*50 ml), dried over sodium sulphate and evaporated in vacuo to afford 2-fluoro-N-[(2S)-2-hydroxy-3-[6-(oxazol-5-ylmethoxy)-3,4-dihydro-1H-isoquinolin-2-yl]propyl]pyridine-4-carboxamide (3.2 g, 7.50 mmol, 61.94% yield). $^1$H NMR (DMSO-d$_6$, 500 MHz): δ (ppm) 2.59-2.80 (m, 4H), 3.15 (m, 1H), 3.30 (s, 2H), 3.48-3.54 (m, 3H), 4.00 (brs, 1H), 4.87 (d, 1H), 5.11 (s, 2H), 6.75 (s, 1H), 6.77 (d, 1H), 6.94 (d, 1H), 7.30 (s, 1H), 7.50 (s, 1H), 7.69 (d, 1H), 8.32 (d, 1H), 8.38 (s, 1H), 8.85 (t, 1H). LCMS(ESI): [M+H]$^+$ m/z: calcd 426.17. found 427.2; Rt=0.767 min.

(S)-1-amino-3-(5-chloro-6-((1-methyl-1H-pyrazol-5-yl)methoxy)-3,4-dihydroisoquinolin-2(1H)-yl)propan-2-ol and (S)—N-(3-(5-chloro-6-((1-methyl-1H-pyrazol-5-yl)methoxy)-3,4-dihydroisoquinolin-2(1H)-yl)-2-hydroxypropyl)-2-fluoroisonicotinamide

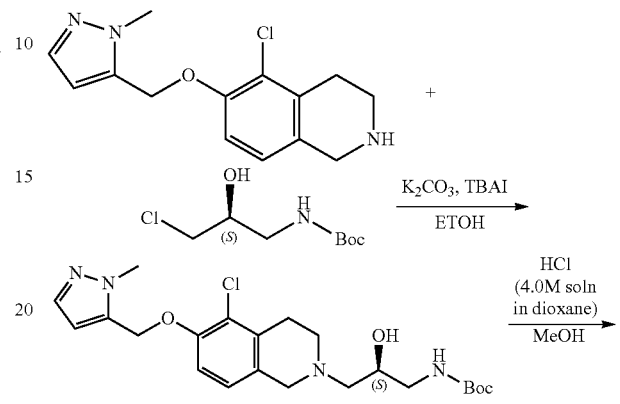

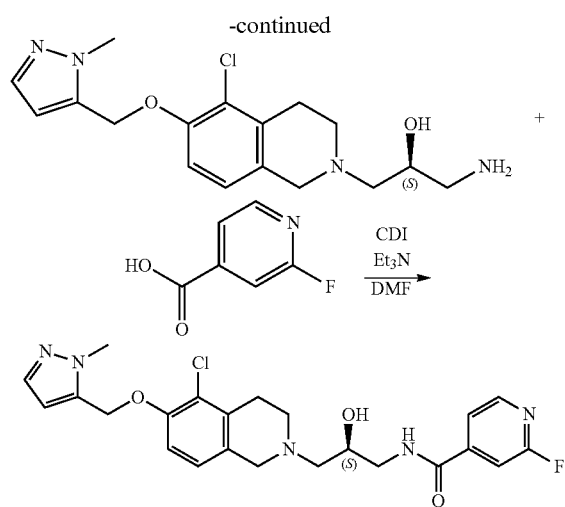

tert-butyl N-[(2S)-3-[5-chloro-6-[(2-methylpyrazol-3-yl)methoxy]-3,4-dihydro-1H-isoquinolin-2-yl]-2-hydroxypropyl]carbamate. The mixture of tert-butyl N-[(2S)-3-chloro-2-hydroxy-propyl]carbamate (2.15 g, 10.27 mmol), 5-chloro-6-[(2-methylpyrazol-3-yl)methoxy]-1,2,3,4-tetrahydroisoquinoline (3 g, 8.56 mmol, 2HCl), potassium carbonate, anhydrous, 99% (3.55 g, 25.67 mmol, 1.55 mL), tetra-n-butylammonium iodide (631.99 mg, 1.71 mmol) in ethanole (50 mL) was stirred at 40° C. for 24 hr in sealed tube. Then, the reaction mixture was concentrated in vacuo and diluted MTBE (70 mL). The formed precipitate was filtered off, washed with MTBE (2*30 mL) and organic filtrate was evaporated in vacuo to leave 4.42 g of crude product. The obtained product was purified using column chromatography on silica gel using hexan/MTBE gradient (10-100% MTBE) to afford pure tert-butyl N-[(2S)-3-[5-chloro-6-[(2-methylpyrazol-3-yl)methoxy]-3,4-dihydro-1H-isoquinolin-2-yl]-2-hydroxy-propyl]carbamate (2.3 g, 5.10 mmol, 59.62% yield). $^1$H NMR (500 MHz, CDCl$_3$) δ (ppm) 1.44 (s, 9H), 2.73 (m, 2H), 2.88 (m, 1H), 2.93 (m, 3H), 3.07 (m, 1H), 3.45 (m, 1H), 3.72 (m, 3H), 3.96 (s, 3H), 5.09 (s, 3H), 6.29 (s, 1H), 6.83 (d, 1H), 6.88 (d, 1H), 7.27 (s, 1H), 7.42 (s, 1H). LCMS(ESI): [M+H]$^+$ m/z: calcd 450.2. found 451.2; Rt=1.07 min.

(S)-1-amino-3-(5-chloro-6-((1-methyl-1H-pyrazol-5-yl)methoxy)-3,4-dihydroisoquinolin-2(1H)-yl)propan-2-ol. Hydrogen chloride 4.0M solution in dioxane (4.80 g, 131.65 mmol, 6 mL) was added to the solution of tert-butyl N-[(2S)-3-[5-chloro-6-[(2-methylpyrazol-3-yl)methoxy]-3,4-dihydro-1H-isoquinolin-2-yl]-2-hydroxy-propyl]carbamate (2.3 g, 5.10 mmol) in MeOH (25 mL). The reaction mixture was stirred at 25° C. for 12 hr, then evaporated and added to CH$_3$CN (15 mL). The obtained precipitate was filtered on, washed with CH$_3$CN (20 mL) and dried to afford product (2S)-1-amino-3-[5-chloro-6-[(2-methylpyrazol-3-yl)methoxy]-3,4-dihydro-1H-isoquinolin-2-yl]propan-2-ol (1.7 g, 3.69 mmol, 72.42% yield, 3HCl). $^1$H NMR (500 MHz, DMSO-d$_6$) δ (ppm) 2.74 (m, 1H), 2.98 (m, 4H), 3.28 (m, 3H), 2.89 (m, 3H), 4.21 (m, 3H), 4.59 (m, 1H), 5.30 (s, 2H), 6.38 (s, 1H), 7.21 (d, 1H), 7.33 (d, 1H), 7.36 (s, 1H), 8.23 (m, 1H), 11.00 (s, 1H). LCMS(ESI): [M+H]$^+$ m/z: calcd 350.1. found 351.0; Rt=0.73 min.

(S)—N-(3-(5-chloro-6-((1-methyl-1H-pyrazol-5-yl)methoxy)-3,4-dihydroisoquinolin-2(1H)-yl)-2-hydroxypropyl)-2-fluoroisonicotinamide. 1,1'-Carbonyldiimidazole (736.36 mg, 4.54 mmol) was added to a solution (2S)-1-amino-3-[5-chloro-6-[(2-methylpyrazol-3-yl)methoxy]-3,4-dihydro-1H-isoquinolin-2-yl]propan-2-ol (1.9 g, 4.13 mmol, 3HCl) in DMF (20 mL). The resulting mixture was stirred at 20° C. 1 hr, then cooled to 25° C. and 2-fluoropyridine-4-carboxylic acid (582.52 mg, 4.13 mmol) was added followed by triethyl amine (1.38 g, 13.62 mmol, 1.90 mL). The reaction mixture was allowed to warm to 25° C. and stirred for 3 hr. The reaction mixture was poured into water (80 ml) and extracted with EtOAc (3×20 ml). The combined organic extracts were washed with water(2*10 ml), dried over sodium sulphate and evaporated in vacuo to afford product N-[(2S)-3-[5-chloro-6-[(2-methylpyrazol-3-yl)methoxy]-3,4-dihydro-1H-isoquinolin-2-yl]-2-hydroxy-propyl]-2-fluoro-pyridine-4-carboxamide (1.85 g, 3.90 mmol, 94.55% yield). $^1$H NMR (400 MHz, CDCl$_3$) δ (ppm) 2.55 (m, 2H), 2.75 (m, 1H), 2.85 (m, 3H), 3.40 (m, 1H), 3.55 (m, 1H), 3.76 (m, 2H), 3.99 (s, 3H), 4.07 (m, 1H), 5.08 (s, 2H), 6.28 (s, 1H), 6.84 (m, 2H), 7.04 (m, 1H), 7.24 (m, 2H), 7.45 (m, 2H), 8.27 (d, 1H). LCMS(ESI): [M+H]$^+$ m/z: calcd 473.9. found 474.8; Rt=0.990 min.

(S)-1-amino-3-(5-methyl-6-((1-methyl-1H-pyrazol-5-yl)methoxy)-3,4-dihydroisoquinolin-2(1H)-yl)propan-2-ol and (S)—N-(2-hydroxy-3-[5-methyl-6-((1-methyl-1H-pyrazol-5-yl)methoxy)-3,4-dihydroisoquinolin-2(1H)-yl)propyl)-2-(methylamino)isonicotinamide

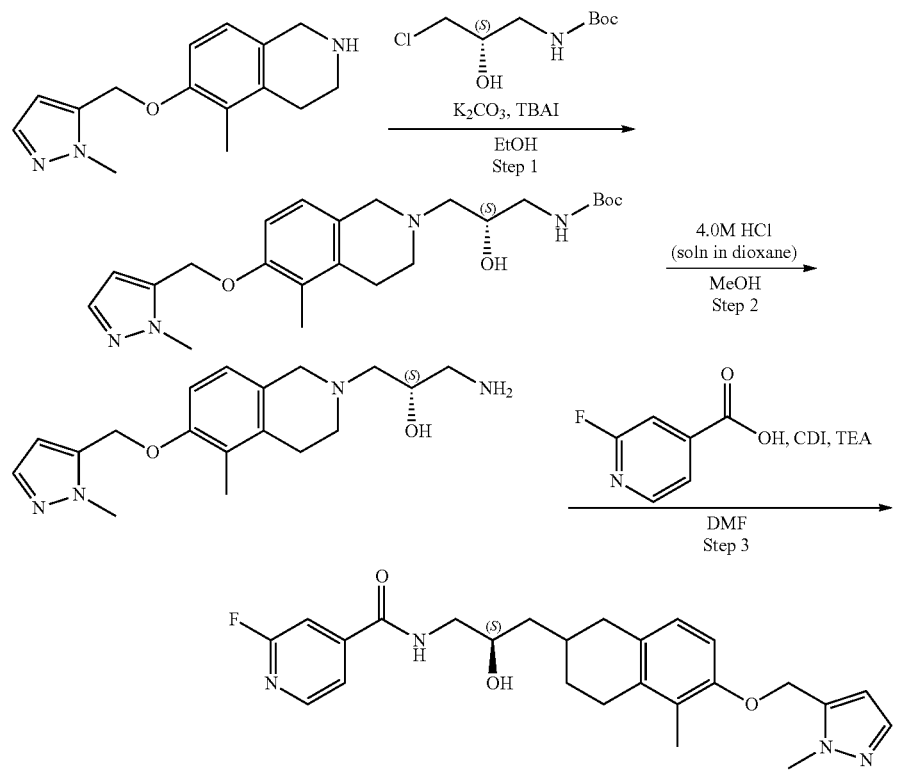

(S)-tert-butyl (2-hydroxy-3-(5-methyl-6-((1-methyl-1H-pyrazol-5-yl)methoxy)-3,4-dihydroisoquinolin-2(1H)-yl)propyl)carbamate. The mixture of 5-methyl-6-[(2-methylpyrazol-3-yl)methoxy]-1,2,3,4-tetrahydroisoquinoline (5.42 g, 16.41 mmol, 2HCl), tert-butyl N-[(2S)-3-chloro-2-hydroxy-propyl]carbamate (4.13 g, 19.69 mmol), potassium carbonate, anhydrous, 99% (7.49 g, 54.16 mmol, 3.27 mL), tetra-n-butylammonium iodide (1.21 g, 3.28 mmol) in ethanole (40 mL) was stirred at 45° C. for 12 hr in sealed tube. The reaction mixture was evaporated and mixed with MTBE (70 ml). The obtained precipitate was filtered off and washed with MTBE (2*30 mL). The organic filtrate was concentrated in vacuo to leave 6.92 g of crude product, 6.92 g of which was purification by column chromatography on silica gel using CHCl$_3$/CH$_3$CN gradient (10-100% CH$_3$CN) to afford pure product tert-butyl N-[(2S)-2-hydroxy-3-[5-methyl-6-[(2-methylpyrazol-3-yl)methoxy]-3,4-dihydro-1H-isoquinolin-2-yl]propyl]carbamate (3.1 g, 7.20 mmol, 43.87% yield). $^1$H NMR (500 MHz, CDCl$_3$) δ (ppm) 1.45 (s, 9H), 2.01 (s, 3H), 2.67 (m, 2H), 2.87 (m, 2H), 3.13 (m, 2H), 3.43 (m, 1H), 3.40 (m, 1H), 3.68 (m, 3H), 3.98 (m, 4H), 5.07 (m, 3H), 6.30 (m, 1H), 6.80 (d, 1H), 6.87 (d, 1H), 7.45 (s, 1H). LCMS(ESI): [M+H]$^+$ m/z: calcd 430.2. found 431.2; Rt=1.06 min.

(S)-1-amino-3-(5-methyl-6-((1-methyl-1H-pyrazol-5-yl)methoxy)-3,4-dihydroisoquinolin-2(1H)-yl)propan-2-ol. Hydrogen chloride solution 4.0M in dioxane (6.40 g, 175.53 mmol, 8 mL) was added to a solution of tert-butyl N-[(2S)-2-hydroxy-3-[5-methyl-6-[(2-methylpyrazol-3-yl)methoxy]-3,4-dihydro-1H-isoquinolin-2-yl]propyl]carbamate (3.1 g, 7.20 mmol) in MeOH (25 mL). The reaction mixture was stirred at 25° C. for 12 hr, then evaporated and added to CH$_3$CN (15 mL). The resulting precipitate was filtered, washed with CH$_3$CN (10 mL) and air-dried to afford product (2S)-1-amino-3-[5-methyl-6-[(2-methylpyrazol-3-yl)methoxy]-3,4-dihydro-1H-isoquinolin-2-yl]propan-2-ol (2.1 g, 4.77 mmol, 66.31% yield, 3HCl). $^1$H NMR (400 MHz, DMSO-d$_6$) δ (ppm) 2.01 (s, 3H), 2.98 (m, 4H), 3.38 (m, 6H), 3.83 (m, 2H), 4.39 (m, 3H), 5.18 (s, 2H), 6.36 (s, 1H), 7.02 (d, 1H), 7.07 (d, 1H), 7.36 (s, 1H), 8.32 (m, 2H), 10.90 (m, 1H). LCMS(ESI): [M+H]$^+$ m/z: calcd 330.2. found 331.2; Rt=0.74 min.

(S)-2-fluoro-N-(2-hydroxy-3-(5-methyl-6-((1-methyl-1H-pyrazol-5-yl)methoxy)-3,4-dihydroisoquinolin-2(1H)-yl)propyl)isonicotinamide. 1,1'-Carbonyldiimidazole (720.78 mg, 4.45 mmol) was added to a solution (2S)-1-amino-3-[5-methyl-6-[(2-methylpyrazol-3-yl)methoxy]-3,4-dihydro-1H-isoquinolin-2-yl]propan-2-ol (1.7 g, 3.87 mmol, 3HCl) in DMF (22 mL). The resulting mixture was stirred at 20° C. 1 hr, then cooled to 0° C. and 2-fluoropyridine-4-carboxylic acid (599.94 mg, 4.25 mmol) was added followed by triethyl amine (1.29 g, 12.76 mmol, 1.78 mL). The reaction mixture was allowed to warm to 25° C. and stirred for 3 hr. The reaction mixture was poured into water (100 ml) and extracted with EtOAc (3×25 ml). The combined organic extracts were washed with water(2*20 ml), dried over sodium sulphate and evaporated in vacuo to afford product 2-fluoro-N-[(2S)-2-hydroxy-3-[5-methyl-6-[(2-methylpyrazol-3-yl)methoxy]-3,4-dihydro-1H-isoquinolin-2-yl]propyl]pyridine-4-carboxamide (1.2 g, 2.65 mmol, 68.46% yield). $^1$H NMR (400 MHz, DMSO-d$_6$) δ (ppm) 2.01 (m, 3H), 2.62 (m, 2H), 2.78 (m, 3H), 3.01 (m, 2H), 3.48 (m, 1H), 3.56 (m, 1H), 3.72 (s, 2H), 4.03 (s, 3H), 4.11 (m, 1H), 5.00 (s, 2H), 6.28 (d, 1H), 6.77 (d, 2H), 6.84 (d, 2H), 7.13 (brs, 1H), 7.43 (s, 1H), 8.25 (d, 1H). LCMS(ESI): [M+H]$^+$ m/z: calcd 453.2. found 454.2; Rt=0.909 min.

6-chloro-N-[(2S)-2-hydroxy-3-[6-[(4-methyloxazol-5-yl)methoxy]-3,4-dihydro-1H-isoquinolin-2-yl]propyl]pyrimidine-4-carboxamide

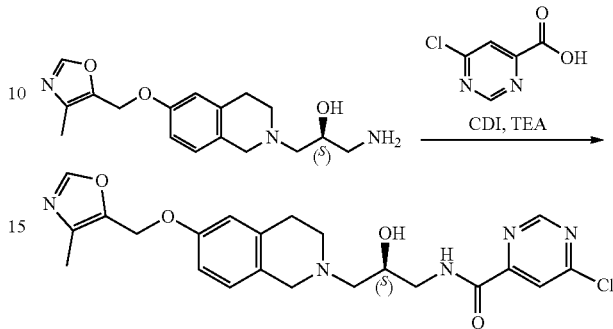

1,1'-Carbonyldiimidazole (1.25 g, 7.73 mmol) was added to a solution (2S)-1-amino-3-[6-[(4-methyloxazol-5-yl)methoxy]-3,4-dihydro-1H-isoquinolin-2-yl]propan-2-ol (3 g, 7.03 mmol, 3HCl) in DMF (25 mL). The resulting mixture was stirred at 20° C. 1 hr, then cooled to 0° C. and 6-chloropyrimidine-4-carboxylic acid (1.11 g, 7.03 mmol) was added followed by triethyl amine (2.35 g, 23.20 mmol, 3.23 mL). The reaction mixture was allowed to warm to 25° C. and stirred for 3 hr. The reaction mixture was poured into water (40 ml) and extracted with EtOAc (3×20 ml). The combined organic extracts were washed with water(2*15 ml), dried over sodium sulphate and evaporated in vacuo to afford product 6-chloro-N-[(2S)-2-hydroxy-3-[6-[(4-methyloxazol-5-yl)methoxy]-3,4-dihydro-1H-isoquinolin-2-yl]propyl]pyrimidine-4-carboxamide (1.78 g, 3.89 mmol, 55.30% yield). NMR(CDCl$_3$, 500 MHz): δ 2.21 (s,3H), 2.55 (m, 2H), 2.74 (m, 1H), 2.87-2.89 (m, 3H), 3.42 (m, 1H), 3.50 (d, 1H), 3.78 (m, 1H), 3.50 (d, 1H), 4.03 (m, 1H), 5.03 (s, 2H), 6.69 (s, 1H), 6.70 (d, 1H), 6.91 (d, 1H), 7.79 (s, 1H), 8.12 (s, 1H), 8.40 (brs, 1H), 8.95 (s, 1H), OH is broaden. LCMS(ESI): [M+H]$^+$ m/z: calcd 457.1. found 458.2; Rt=1.026 min.

(S)-1-amino-3-(6-((1-methyl-1H-1,2,3-triazol-5-yl)methoxy)-3N-dihydroisoquinolin-2(1H)-yl)propan-2-ol

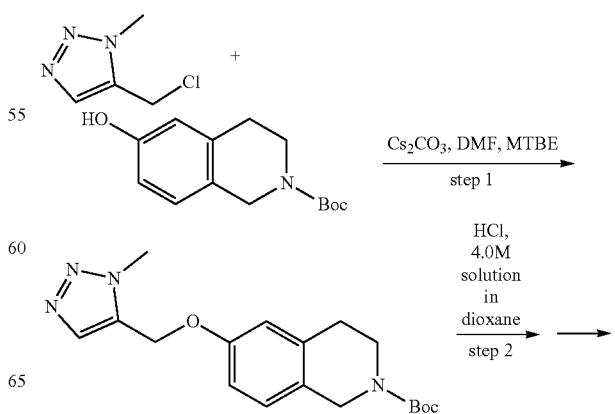

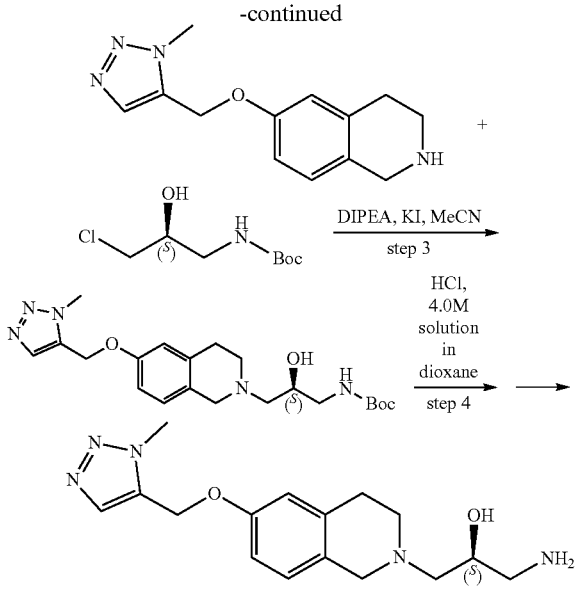

tert-butyl 6-((1-methyl-1H-1,2,3-triazol-5-yl)methoxy)-3,4-dihydroisoquinoline-2(1H)-carboxylate. tert-Butyl 6-hydroxy-3,4-dihydro-1H-isoquinoline-2-carboxylate (6.31 g, 25.32 mmol), cesium carbonate (20.60 g, 63.23 mmol) were mixed in DMF (30 ml). 5-(Chloromethyl)-1-methyl-triazole (5.1 g, 30.35 mmol, HCl) was added. The mixture was stirred 10 hr at 80° C. and then cooled to r.t. MTBE (300 ml) was added. The mixture was extracted with $H_2O$ (5*100 ml). The organic phase was separated, dried with $Na_2SO_4$ and evaporated in vacuo at 35° C. to obtain crude product which was purified by column chromatography to give tert-butyl 6-[(3-methyltriazol-4-yl)methoxy]-3,4-dihydro-1H-isoquinoline-2-carboxylate (5.8 g, 16.84 mmol, 66.58% yield). $^1$H NMR (500 MHz, CDCl$_3$) δ (ppm) 1.48 (s, 9H), 2.80 (t, 2H), 3.62 (t, 2H), 4.10 (s, 3H), 4.51 (s, 2H), 5.09 (s, 2H), 6.71 (s, 1H), 6.79 (d, 1H), 7.04 (d, 1H), 7.70 (s, 1H). LCMS(ESI): [M+H]$^+$ m/z: calcd 344.1. found 345.2; Rt=1.33 min.

6-((1-methyl-1H-1,2,3-triazol-5-yl)methoxy)-1,2,3,4-tetrahydroisoquinoline. tert-Butyl 6-[(3-methyltriazol-4-yl)methoxy]-3,4-dihydro-1H-isoquinoline-2-carboxylate (5.8 g, 16.84 mmol) was dissolved in dioxane (10 ml) and hydrogen chloride solution 4.0M in dioxane (80.00 g, 2.19 mol, 100 ml) was added. The mixture was stirred at 20° C. for 10 hr. The solid formed was filtered and dried in vacuo at 35° C. to obtain 6-[(3-methyltriazol-4-yl)methoxy]-1,2,3,4-tetrahydroisoquinoline (4.9 g, 15.45 mmol, 91.73% yield, 2HCl). $^1$H NMR (500 MHz, DMSO-d$_6$) δ (ppm) 2.97 (t, 2H), 3.29 (t, 2H), 4.03 (s, 3H), 4.14 (s, 2H), 5.27 (s, 2H), 6.93 (s, 1H), 6.94 (d, 1H), 7.80 (d, 1H), 9.59 (s, 2H). LCMS(ESI): [M+H]$^+$ m/z: calcd 244.1. found 245.2; Rt=0.67 min.

(S)-tert-butyl (2-hydroxy-3-(6-((1-methyl-1H-P2,3-triazol-5-yl)methoxy)-3,4-dihydroisoquinolin-2(1H)-yl)propyl)carbamate. tert-Butyl N-[(2 S)-3-chloro-2-hydroxy-propyl]carbamate (1.59 g, 7.57 mmol), 6-[(3-methyltriazol-4-yl)methoxy]-1,2,3,4-tetrahydroisoquinoline (2 g, 6.30 mmol, 2HCl), N,N-diisopropylethylamine (3.26 g, 25.22 mmol, 4.39 ml), potassium iodide (1.57 g, 9.46 mmol, 503.18 ul) were mixed in MeCN (30 mL) and heated at 80° C. for 10 hr. Then the mixture was cooled to r.t. and the solvent was evaporated in vacuo at 35° C. The residue was purified by column chromatography to give tert-butyl N-[(2S)-2-hydroxy-3-[6-[(3-methyltriazol-4-yl) methoxy]-3,4-dihydro-1H-isoquinolin-2-yl]propyl]carbamate (0.5 g, 1.20 mmol, 18.99% yield). $^1$H NMR (500 MHz, DMSO-d$_6$) δ (ppm) 1.36 (s, 9H), 2.39 (m, 2H), 2.69 (m, 2H), 2.76 (t, 2H), 2.88 (m, 2H), 3.07 (m, 1H), 3.51 (m, 2H), 4.02 (s, 3H), 4.61 (m, 1H), 5.22 (s, 2H), 6.63 (m, 1H), 6.79 (s, 1H), 6.81 (d, 1H), 6.95 (d, 1H), 7.77 (s, 1H). LCMS(ESI): [M+H]$^+$ m/z: calcd 417.2. found 418.2; Rt=0.90 min.

(S)-1-amino-3-(6-((1-methyl-1H-1,2,3-triazol-5-yl)methoxy)-3,4-dihydroisoquinolin-2(1H)-yl)propan-2-ol. Hydrogen chloride, 4M in 1,4-dioxane, 99% (2.40 g, 65.82 mmol, 3 ml) was added to tert-butyl N-[(2S)-2-hydroxy-3-[6-[(3-methyltriazol-4-yl) methoxy]-3,4-dihydro-1H-isoquinolin-2-yl]propyl]carbamate (60.00 mg, 143.71 umol) and the mixture was stirred for 10 hr at 25° C. The solid was filtered and dried in vacuo at 35° C. to give (2S)-1-amino-3-[6-[(3-methyltriazol-4-yl)methoxy]-3,4-dihydro-1H-isoquinolin-2-yl]propan-2-ol (13 mg, 30.46 umol, 21.20% yield, 3HCl). $^1$H NMR (500 MHz, D$_2$O) δ (ppm) 3.08 (m, 2H), 3.28 (m, 4H), 3.47 (m, 2H), 4.14 (s, 3H), 4.55 (m, 3H), 5.36 (s, 2H), 7.02 (s, 1H), 7.04 (d, 1H), 7.20 (d, 1H), 7.92 (s, 1H). LCMS(ESI): [M+H]$^+$ m/z: calcd 317.2. found 318.2; Rt=0.43 min.

R)-1-amino-3-(6-((4-methyloxazol-5-yl)methoxy)-3,4-dihydroisoquinolin-2(1H)-yl)propan-2-ol

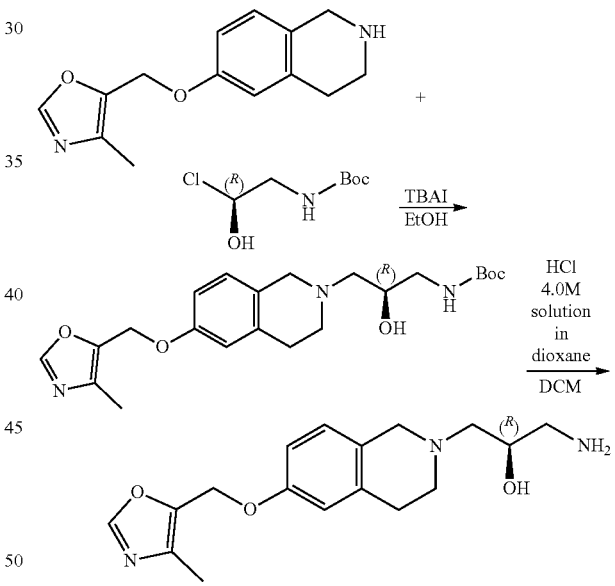

tert-butyl N-[(2R)-2-hydroxy-3-[6-[(4-methyloxazol-5-yl)methoxy]-3,4-dihydro-1H-isoquinolin-2-yl]propyl]carbamate. A mixture of 4-methyl-5-(1,2,3,4-tetrahydroisoquinolin-6-yloxymethyl)oxazole (125.27 mg, 512.79 umol, HCl), tert-butyl A-[(2R)-3-chloro-2-hydroxy-propyl]carbamate (161.28 mg, 769.19 umol), potassium carbonate, anhydrous, 99% (141.75 mg, 1.03 mmol, 61.90 uL), tetra-n-butylammonium iodide (37.88 mg, 102.56 umol) in EtOH (5 mL) was stirred at 65° C. for 15 hr in sealed tube. After the completion of the reaction, the resulting mixture was concentrated in vacuo, poured into water (50 mL) and extracted with DCM (2*50 mL). The combined organic extracts were washed with water (2*20 mL), dried over sodium sulphate and concentrated under reduced pressure to afford butyl A-[(2R)-2-hydroxy-3-[6-[(4-methyloxazol-5- yl)methoxy]-3,4-dihydro-1H-isoquinolin-2-yl]propyl]carbamate (0.2 g, 479.05 umol, 93.42% yield). $^1$H NMR (500 MHz, CDCl$_3$) δ (ppm) 1.47 (s, 9H), 2.22 (s, 3H), 2.51 (m, 2H), 2.69 (m, 1H), 2.88 (m, 3H), 3.50 (m, 5H), 3.74 (m, 1H), 4.97 (m, 3H), 6.71 (s, 1H), 6.76 (d, 1H), 6.94 (d, 1H), 7.81 (s, 1H). LCMS(ESI): [M-Boc]$^+$ m/z: calcd 318.2. found 318.2; Rt=0.65 min.

(R)-1-amino-3-(6-((4-methyloxazol-5-yl)methoxy)-3,4-dihydroisoquinolin-2(1H)-yl)propan-2-ol. Hydrogen chloride solution 4.0M in dioxane (800.00 mg, 21.94 mmol, 1 mL) was added to a solution of tert-butyl A-[(2R)-2-hydroxy-3-[6-[(4-methyloxazol-5-yl)methoxy]-3,4-dihydro-1H-isoquinolin-2-yl]propyl]carbamate (268.70 mg, 643.60 umol) in DCM (5 mL). The reaction mixture was stirred at 25° C. for 12 hr. After the completion of the reaction, the solvent was removed in vacuo and the residue was suspended in MeCN (5 mL). The obtained precipitate was filtered through a glass filter, washed with MeCN (2*2 mL) and air-dried to afford (2R)-amino-3-[6-[(4-methyloxazol-5-yl)methoxy]-3,4-dihydro-1H-isoquinolin-2-yl]propan-2-ol (0.11 g, 257.75 umol, 40.05% yield, 3HCl). $^1$H NMR (500 MHz, DMSO-d$_6$) 5 (ppm) 2.23 (s, 3H), 2.76 (m, 1H), 2.89 (m, 2H), 3.12 (m, 2H), 3.24 (m, 2H), 3.41 (m, 2H), 3.75 (m, 1H), 4.32 (m, 5H), 5.03 (s, 3H), 6.76 (m, 2H), 7.21 (d, 1H), 8.32 (m, 1H), 11.03 (s, 1H). LCMS(ESI): [M+H]$^+$ m/z: calcd 318.2. found 318.2; Rt=0.61 min.

Example 1—Synthesis of Compounds of Formula (Va1' and Vb1')

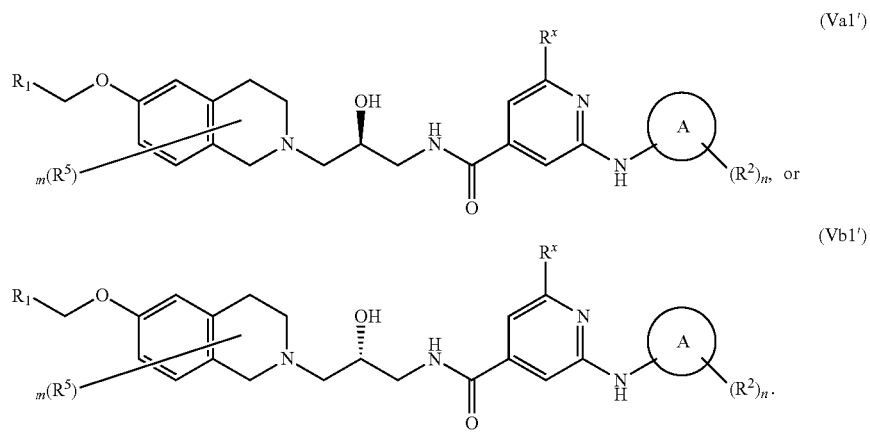

Scheme 1A

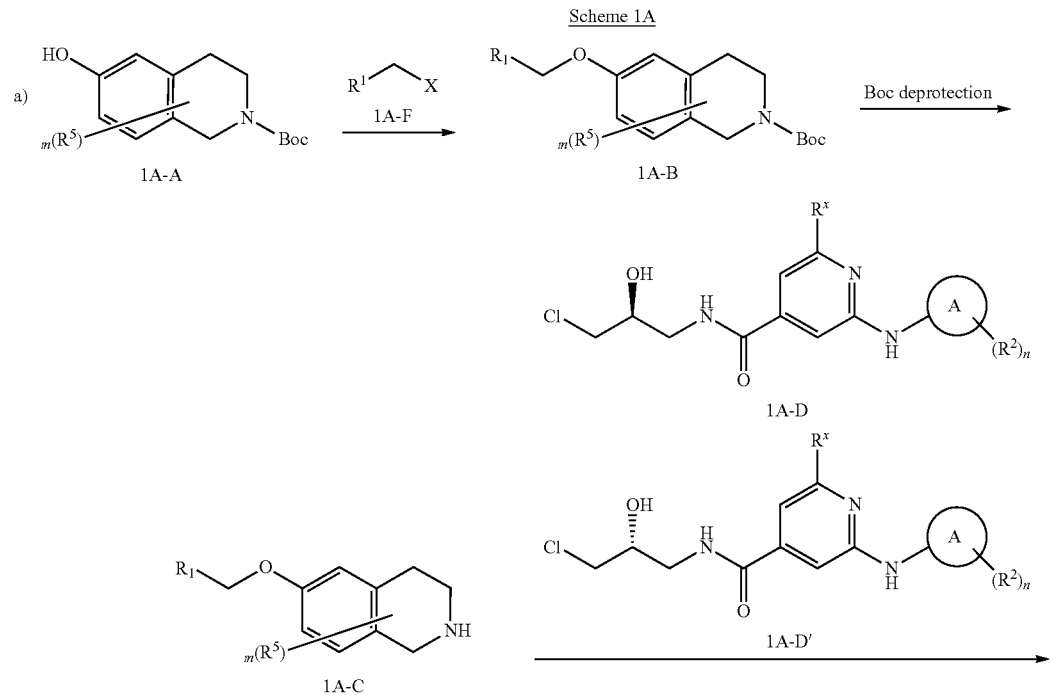

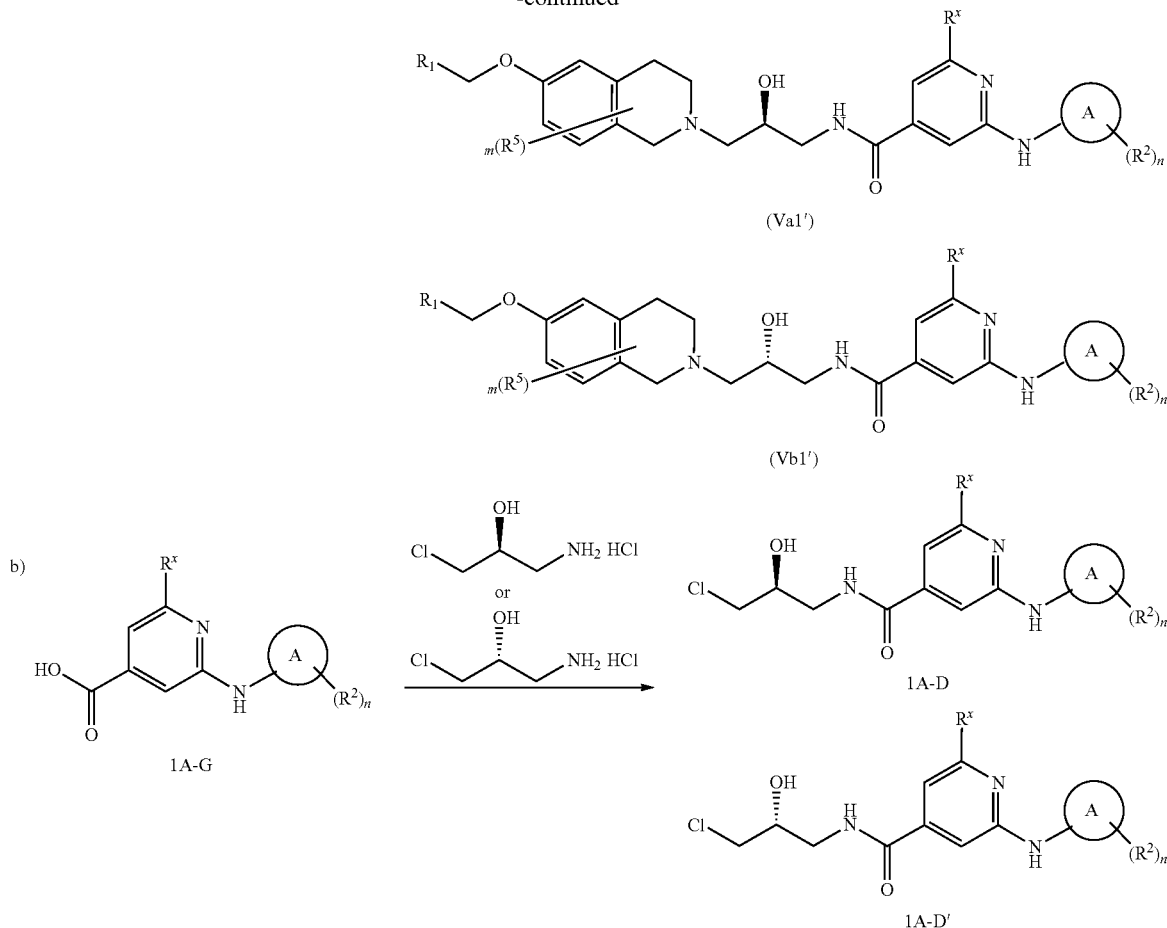

wherein X is a leaving group and variables $R^5$, $R^x$, $R^1$, $R^2$, m, and n are defined herein. In some embodiments, X is selected from Cl, Br, and I. In some embodiments X is Cl or Br.

Example 1A. General Procedure A (for Salts of the Amines)

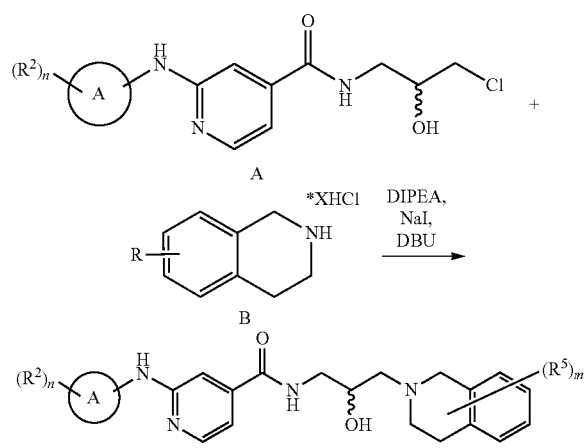

To a vial was added alkyl chloride A (1 eq, 0.5-1M soln. in DMF), amine B (1.2 eq, 0.5-1M soln. in DMF), NaI (1 eq, 0.5-1M soln. in ACN), DIPEA (3 eq), DBU (X eq, 0.5-1M soln. in DMF). The mixture heated for 12 hours at 90° C. The resulting mixture was concentrated under reduced pressure, dissolved in DMSO, filtered and subjected to HPLC purification. Scale was calculated on 70 mg of the final compound.

1) The scale was calculated on 70 mg of the final compound
2) Amount of DBU (X eq) that used for the reaction is equal to multiplicity of salt of the starting amine Example 1A. General Procedure B (for Free Bases of the Amines)

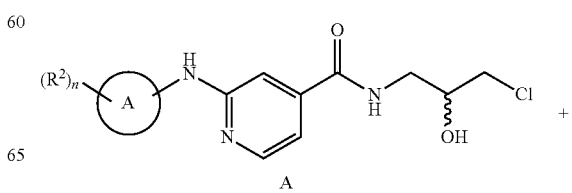

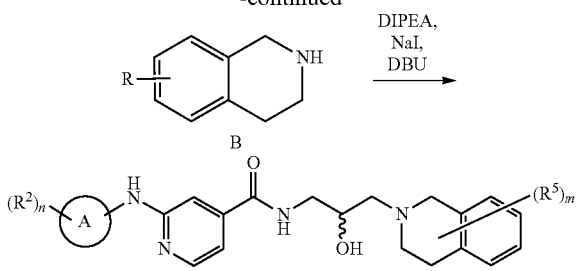

To a vial was added alkyl chloride A(1 eq, 0.5-1M soln. in DMF), amine B (1.2 eq, 0.5-1M soln. in DMF), NaI (1 eq, 0.5-1M soln. in ACN), DIPEA (3 eq). The mixture heated for 12 hours at 90° C. The resulting mixture was concentrated under reduced pressure, dissolved in DMSO, filtered and subjected to HPLC purification. Scale was calculated on 70 mg of the final compound.

Example 1A1. Synthesis of (S)-2-(cyclobutylamino)-N-(2-hydroxy-3-(6-((1-methyl-1H-pyrazol-5-yl)methoxy)-3N-dihydroisoquinolin-2(1H)-yl)propyl)isonicotinamide (Compound 14)

Example 1A1, Step A. tert-butyl 6-((1-methyl-1H-pyrazol-5-yl)methoxy)-3,4-dihydroisoquinoline-2(1H)-carboxylate. tert-Butyl 6-hydroxy-3,4-dihydro-1H-isoquinoline-2-carboxylate (16.7 g, 66.99 mmol), 5-(chloromethyl)-1-methyl-pyrazole (10.50 g, 80.38 mmol), cesium carbonate (32.74 g, 100.48 mmol) were added to DMF (100 mL). The mixture was stirred at 80° C. for 10 hr and cooled to r.t. MTBE (500 mL) was added and the mixture was extracted with H₂O (5*100 ml). The organic phase was dried with Na₂SO₄ and evaporated in vacuo at 35° C. to obtain tert-butyl 6-[(2-methylpyrazol-3-yl)methoxy]-3,4-dihydro-1H-isoquinoline-2-carboxylate (21.3 g, 62.02 mmol, 92.59% yield). ¹H NMR (400 MHz, CDCl₃) δ (ppm) 1.48 (s, 9H), 2.80 (t, 2H), 3.63 (t, 2H), 3.91 (s, 3H), 4.51 (s, 2H), 5.02 (s, 2H), 6.30 (s, 1H), 6.74 (d, 1H), 6.81 (d, 1H), 7.03 (d, 1H), 7.03 (d, 1H), 7.43 (d, 1H). LCMS(ESI): [M+H]⁺ m/z: calcd 343.1. found 344.2; Rt=1.49 min.

Example 1A1, Step B. 6-((1-methyl-1H-pyrazol-5-yl)methoxy)-1,2,3,4-tetrahydroisoquinoline*2HCl. tert-Butyl 6-[(2-methylpyrazol-3-yl)methoxy]-3,4-dihydro-1H-isoquinoline-2-carboxylate (21.3 g, 62.02 mmol) was dissolved in dioxane (50 ml) and hydrogen chloride solution 4.0M in dioxane (400.00 g, 10.97 mol, 500 ml) was added. The mixture was stirred at 20° C. for 10 hr. The solid was filtered, washed with dioxane (50 ml) and dried in vacuo at 50° C.

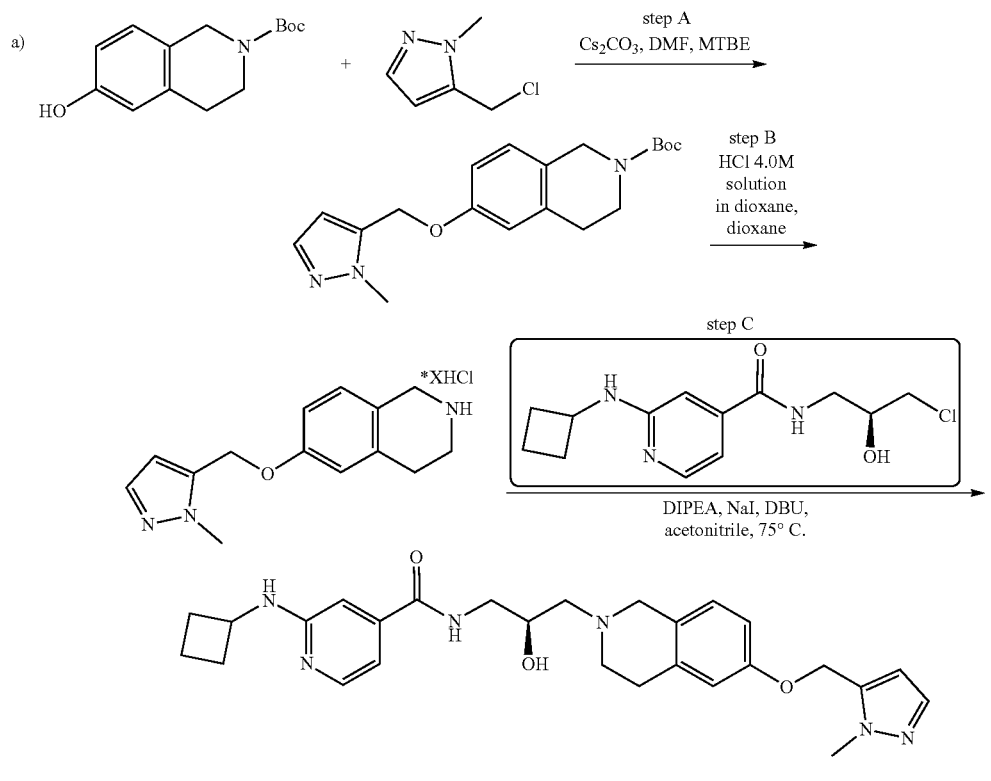

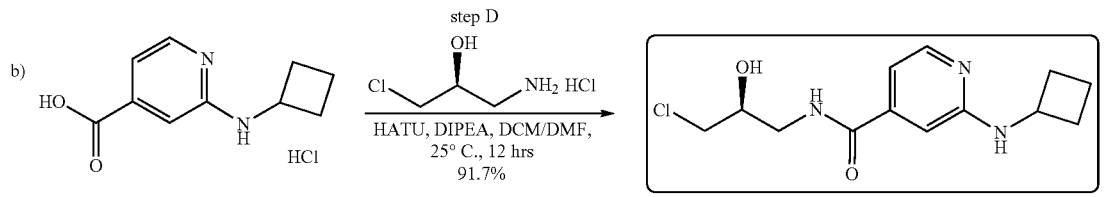

to give 6-[(2-methylpyrazol-3-yl)methoxy]-1,2,3,4-tetrahydroisoquinoline (18.6 g, 58.82 mmol, 94.83% yield, 2HCl). $^1$H NMR (400 MHz, DMSO-d$_6$) δ (ppm) 2.97 (t, 2H), 3.30 (t, 2H), 3.81 (s, 3H), 4.14 (3, 2H), 5.16 (d, 2H), 6.37 (s, 1H), 6.92 (m, 2H), 7.13 (d, 1H), 7.37 (s, 1H), 9.63 (m, 2H). LCMS(ESI): [M+H]$^+$ m/z: calcd 243.1. found 244.2; Rt=0.69 min.

Example 1A1, Step C. (S)-2-(cyclobutylamino)-N-(2-hydroxy-3-(6-((1-methyl-1H-pyrazol-5-yl)methoxy)-3,4-dihydroisoquinolin-2(1H)-yl)propyl)isonicotinamide (Compound 14). Prepared by general procedure A. Yield ~ 15% $^1$H NMR (DMSO-d$_6$, 500 MHz) δ (ppm) 1.64 (m, 2H), 1.84 (m, 2H), 2.24 (m, 2H), 2.44 (m, 2H), 2.70 (m, 3H), 3.18 (m, 1H), 3.37 (m, 2H), 3.52 (m, 2H), 3.80 (s, 3H), 3.87 (m, 1H), 4.24 (m, 1H), 4.80 (d, 1H), 5.09 (s, 2H), 6.33 (s, 1H), 6.73 (d, 2H), 6.78 (d, 2H), 6.92 (d, 1H), 6.94 (d, 1H), 7.34 (s, 1H), 7.94 (d, 1H), 8.45 (t, 1H). LCMS(ESI): [M+H]$^+$ m/z: calcd 490.3. found 491.2; Rt=0.83 min.

Example 1A1, Step D. (S)—N-(3-Chloro-2-hydroxypropyl)-2-(cyclobutylamino)isonicotinamide. To a mixture of 2-(cyclobutylamino)pyridine-4-carboxyli acid (8.5 g, 37.17 mmol, 1 eq, HCl) in DCM (130 mL) and DMF (35 mL) were added HATU (21.20 g, 55.76 mmol, 1.5 eq) and DIPEA (24.02 g, 185.85 mmol, 32.37 mL, 5 eq) sequentially. After stirring 15 minutes, (2S)-1-amino-3-chloro-propan-2-ol (5.97 g, 40.89 mmol, 1.1 eq, HCl) was added and the mixture was stirred for 12 hours at 25° C. The reaction mixture was concentrated under reduced pressure to remove DCM. The residue was diluted with H$_2$O (150 mL) and extracted with EtOAc (70 mL*4). The combined organic layers were washed with saturated NH$_4$Cl aqueous solution (100 mL), brine (100 mL), dried over anhydrous Na$_2$SO$_4$, filtered and concentrated under reduced pressure. The residue was purified by flash chromatography (ISCO®; 40 g SepaFlash® Silica Flash Column, petroleum ether/EtOAc with EtOAc from 0-95%, flow rate=35 mL/min) to afford N-[(2S)-3-chloro-2-hydroxy-propyl]-2-(cyclobutylamino) pyridine-4-carboxamide (12.1 g, 91.7% yield) as yellow solid. $^1$H NMR (400 MHz, methanol-d$_4$) δ ppm 7.98-8.05 (m, 1H), 6.79-6.88 (m, 2H), 4.25 (quin, J=7.8 Hz, 1H), 3.95-4.04 (m, 1H), 3.53-3.70 (m, 3H), 3.41-3.48 (m, 1H), 2.35-2.45 (m, 2H), 1.89-1.98 (m, 2H), 1.76-1.85 (m, 2H); LCMS (ESI) [M+H]$^+$ calcd 284.1. found 284.4.

(R)—N-(3-chloro-2-hydroxypropyl)-2-(cyclobutylamino)isonicotinamide

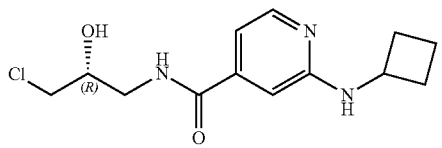

The procedure set forth in step D above was used to produce the following compound using appropriate starting materials. $^1$H NMR (400 MHz, methanol-d$_4$) δ ppm 8.01-8.04 (m, 1 H), 6.83-6.88 (m, 2H), 4.27 (quin, J=7.9 Hz, 1H), 3.98-4.06 (m, 1H), 3.55-3.68 (m, 3H), 3.34-3.48 (m, 1H), 2.39-2.48 (m, 2H), 1.90-2.00 (m, 2H), 1.76-1.84 (m, 2H); LCMS (ESI) [M+H]$^+$ m/z: calcd 284.1. found 284.1; HPLC 96.42% @ 220 nm; 94.9% ee.

Example 1A2. (S)-2-(cyclobutylamino)-N-(2-hydroxy-3-(6-((3-methylisoxazol-4-yl)methoxy)-3A-dihydroisoquinolin-2(1H)-yl)propyl)isonicotinamide (Compound 76)

tert-butyl 6-((3-methylisoxazol-4-yl)methoxy)-3,4-dihydroisoquinoline-2(1H)-carboxylate.

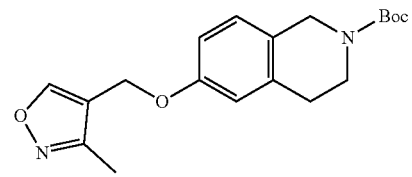 [SMILES: Cc1nocc1COc1ccc2c(c1)CCN(C(=O)OC(C)(C)C)C2]

tert-Butyl 6-hydroxy-3,4-dihydro-1H-isoquinoline-2-carboxylate (0.5 g, 2.01 mmol), cesium carbonate (980.18 mg, 3.01 mmol) were dissolved in DMF (5 mL). 4-(chloromethyl)-3-methyl-isoxazole (316.62 mg, 2.41 mmol) was added. The mixture was stirred 10 hr at 80° C. and cooled to r.t. MTBE (100 mL) was added. The mixture was extracted with H$_2$O (5*30 mL). The organic phase was dried with Na$_2$SO$_4$ and evaporated in vacuo at 35° C. The residue was purified by HPLC to obtain tert-butyl 6-[(3-methylisoxazol-4-yl)methoxy]-3,4-dihydro-1H-isoquinoline-2-carboxylate (434.40 mg, 1.26 mmol, 62.89% yield). $^1$H NMR (400 MHz, CDCl$_3$) δ (ppm) 1.48 (s, 9H), 2.34 (s, 3H), 2.80 (t, 2H), 3.62 (t, 2H), 4.51 (s, 2H), 4.87 (s, 2H), 6.71 (s, 1H), 6.79 (d, 1H), 7.05 (d, 1H), 8.63 (s, 1H). LCMS(ESI): [M+H]$^+$ m/z: calcd 344.1. found 345.2; Rt=1.35 min.

(S)-2-(cyclobutylamino)-N-(2-hydroxy-3-(6-((3-methylisoxazol-4-yl)methoxy)-3,4-dihydroisoquinolin-2(1H)-yl)propyl)isonicotinamide (Compound 76)

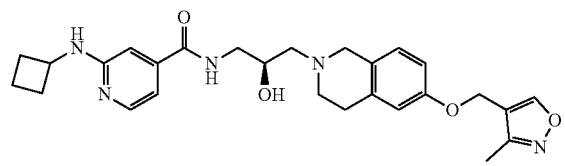 [SMILES: Cc1nocc1COc1ccc2c(c1)CCN(C[C@@H](O)CNC(=O)c1ccnc(NC3CCC3)c1)C2]

tert-butyl 6-((3-methylisoxazol-4-yl)methoxy)-3,4-dihydroisoquinoline-2(1H)-carboxylate was converted to (S)-2-(cyclobutylamino)-N-(2-hydroxy-3-(6-((3-methylisoxazol-4-yl)methoxy)-3,4-dihydroisoquinolin-2(1H)-yl)propyl) isonicotinamide using reaction conditions outlined in Steps B and Step C (general procedure A) from Example 1A. Yield ~ 13.4%. LCMS(ESI): [M+H]$^+$ m/z: calcd 491.2. found 492.2; Rt=0.81 min. $^1$H NMR (400 MHz, CDCl$_3$) δ (ppm) 1.83 (m, 4H), 2.34 (s, 3H), 2.43 (m, 2H), 2.56 (m, 2H), 2.72 (m, 1H), 2.88 (m, 3H), 3.41 (m, 2H), 3.56 (d, 1H), 3.74 (m, 2H), 4.01 (m, 1H), 4.17 (h, 1H), 4.86 (s, 2H), 4.89 (m, 1H), 6.69 (m, 2H), 6.74 (m, 2H), 6.88 (m, 1H), 6.94 (d, 1H), 8.08 (d, 1H), 8.35 (s, 1H).

Example 1A3. (S)-2-(cyclobutylamino)-N-(2-hydroxy-3-(6-((4-methyloxazol-5-yl)methoxy)-3,4-dihydroisoquinolin-2(1H)-yl)propyl)isonicotinamide (Compound 96)

Step A. tert-butyl 6-((4-methyloxazol-5-yl)methoxy)-3,4-dihydroisoquinoline-2(1H)-carboxylate

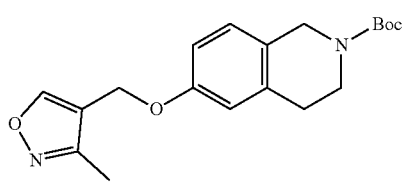 [SMILES: Cc1nocc1COc1ccc2c(c1)CCN(C(=O)OC(C)(C)C)C2]

To a solution of tert-butyl 6-hydroxy-3,4-dihydro-1H-isoquinoline-2-carboxylate (1.17 g, 4.69 mmol) in dimethylformamide (15 mL) was added cesium carbonate (5.05 g, 15.49 mmol), followed by 5-(chloromethyl)-4-methyl-oxazole (926.13 mg, 7.04 mmol). The reaction mixture was stirred at 80° C. for 48 hr. The reaction mixture was cooled down, poured into water (50 ml) and extracted with EtOAc (3*20 ml). The combined organic extracts were washed with brine (2*10 ml), dried over sodium sulphate and evaporated in vacuo to afford tert-butyl 6-[(4-methyloxazol-5-yl)methoxy]-3,4-dihydro-1H-isoquinoline-2-carboxylate (1.4 g, 4.06 mmol, 86.62% yield). $^1$H NMR (400 MHz, CDCl$_3$) δ (ppm) 1.48 (s, 9H), 2.23 (s, 3H), 2.88 (m, 2H), 3.62 (m, 2H), 4.51 (s, 2H), 4.99 (s, 2H), 6.73 (m, 1H), 6.80 (m, 1H), 7.19 (m, 1H), 8.02 (s, 1H). LCMS(ESI): [M+H]$^+$ m/z: calcd 344.1. found 345.2; Rt=1.52 min.

(S)-2-(cyclobutylamino)-N-(2-hydroxy-3-(6-((4-methyloxazol-5-yl)methoxy)-3,4-dihydroisoquinolin-2(1H)-yl)propyl)isonicotinamide (Compound 96)

tert-butyl 6-[(4-methyloxazol-5-yl)methoxy]-3,4-dihydro-1H-isoquinoline-2-carboxylate was converted to 4-methyl-5-(1,2,3,4-tetrahydroisoquinolin-6-yloxymethyl)oxazole using reaction conditions outlined in Step B from Example 1A.

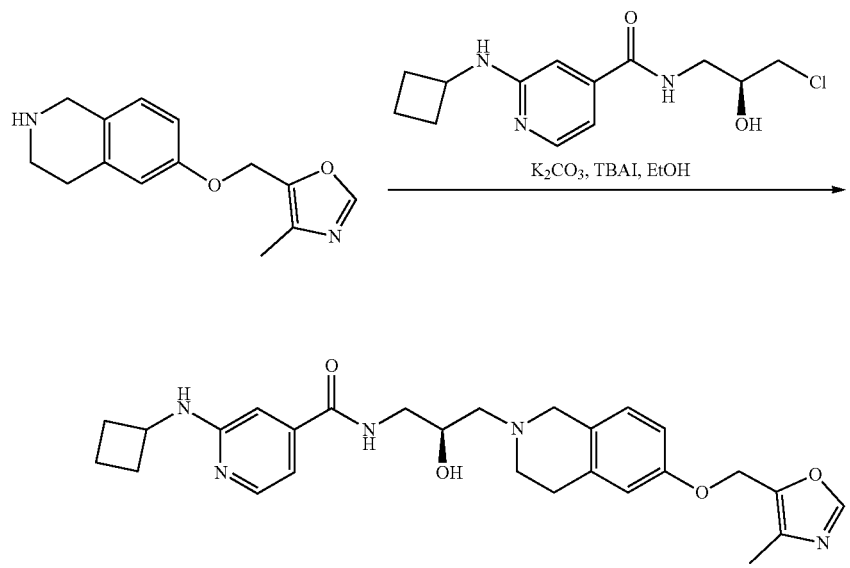

A mixture of N-[(2S)-3-chloro-2-hydroxy-propyl]-2-(cyclobutylamino)pyridine-4-carboxamide (243.93 mg, 859.64 umol), 4-methyl-5-(1,2,3,4-tetrahydroisoquinolin-6-yloxymethyl)oxazole (0.14 g, 573.09 umol), potassium carbonate, anhydrous, 99% (79.20 mg, 573.09 umol, 34.59 uL), tetra-n-butylammonium iodide (42.34 mg, 114.62 umol) in EtOH (5 mL) was stirred at 77° C. for 12 hr in sealed tube. The reaction mixture evaporated, poured into water (10 ml) and extracted with DCM (2*10 ml). The combined organic extracts were washed with water(2*10 ml), dried over sodium sulphate, evaporated in vacuo and obtained crude product 0.3 g was purified by preparative RP-HPLC with CH$_3$CN as mobile phase to afford product 2-(cyclobutylamino)-N-[(2S)-2-hydroxy-3-[6-[(4-methyloxazol-5-yl)methoxy]-3,4-dihydro-1H-isoquinolin-2-yl]propyl]pyridine-4-carboxamide (80.20 mg, 163.15 umol, 28.47% yield). $^1$H NMR (500 MHz, DMSO-d$_6$) δ (ppm) 1.66 (m, 2H), 1.85 (m, 2H), 2.15 (s, 3H), 2.26 (m, 2H), 2.43 (m, 2H), 2.7 (m, 4H), 3.03 (s, 1H), 3.19 (dd, 6.4 Hz, 1H), 3.39 (m, 1H), 3.55 (q, 2H), 3.88 (s, 1H), 4.24 (m, 1H), 4.81 (s, 1H), 5.07 (m, 2H), 6.76 (m, 3H), 6.92 (d, 1H), 6.95 (d, 1H), 7.95 (d, 1H), 8.27 (s, 1H), 8.46 (t, 1H). LCMS(ESI): [M+H]$^+$ m/z: calcd 491.2. found 492.2; Rt=0.73 min.

Example 1A4. 2-(cyclobutylamino)-N-[(2S)-2-hydroxy-3-[8-methyl-6-(oxazol-5-ylmethoxy)-3A-dihydro-1H-isoquinolin-2-yl]propyl]pyridine-4-carboxamide (Compound 260)

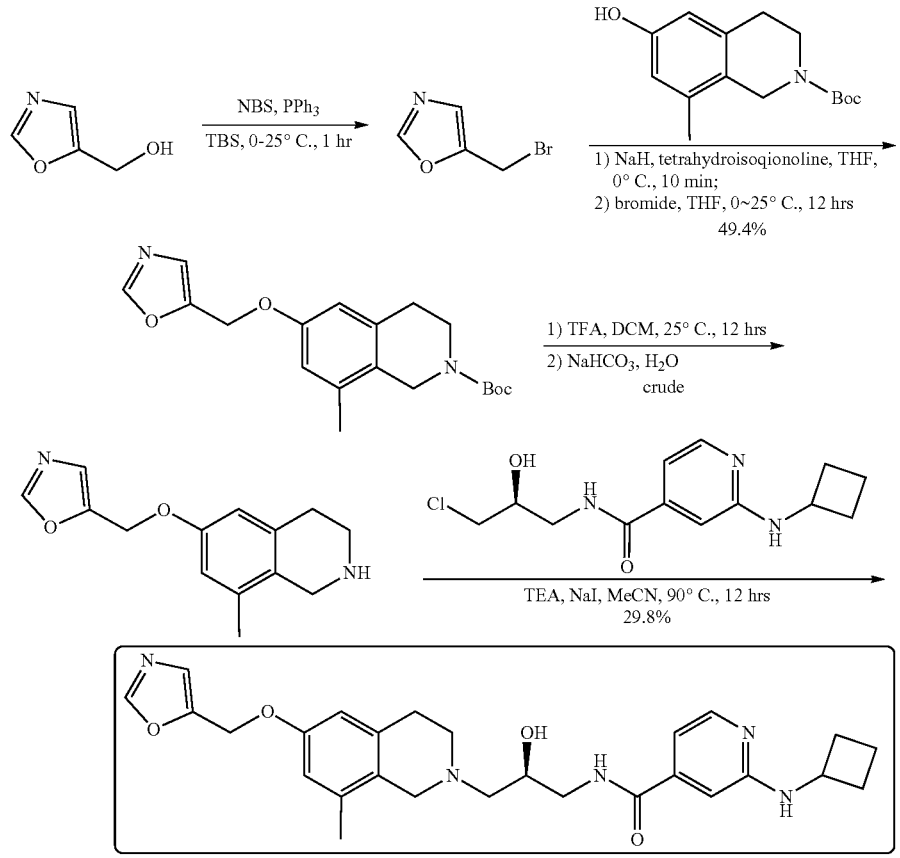

Synthesis of 5-(bromomethyl)oxazole. To a solution of oxazol-5-ylmethanol (100 mg, 1.01 mmol) and triphenylphosphine (290 mg, 1.11 mmol) in THF (5 mL) was added and NBS (180 mg, 1.01 mmol) at 0° C. The mixture was stirred at 25° C. for 1 hour and the mixture was used in next step directly without concentrated and purification.

tert-butyl 8-methyl-6-(oxazol-5-ylmethoxy)-3,4-dihydro-1H-isoquinoline-2-carboxylate. To a solution of tert-butyl 6-hydroxy-8-methyl-3,4-dihydro-1H-isoquinoline-2-carboxylate (100 mg, 0.380 mmol) in THF (5 mL) was added NaH (25 mg, 1.04 mmol, 60% in mineral oil, wt %) at 0° C. and then stirred at 0° C. for 10 minutes. Then 5-(bromomethyl)oxazole (150 mg, 0.926 mmol, dissolved in THF) was added into the mixture and the mixture was stirred at 25° C. for 12 hours. The mixture was concentrated under reduced pressure, diluted with $H_2O$ (10 mL), and then extracted with EtOAc (10 mL*2). The combined organic layers were dried over anhydrous $Na_2SO_4$, filtered and concentrated under reduced pressure. The residue was purified by flash chromatography (ISCO®; 4 g AgelaFlash® Silica Flash Column, petroleum ether/EtOAc with EtOAc from 0~30%, flow rate=20 mL/min) to afford tert-butyl 8-methyl-6-(oxazol-5-ylmethoxy)-3,4-dihydro-1H-isoquinoline-2-carboxylate (70 mg, 49.4% yield) as colorless oil. $^1$H NMR (400 MHz, methanol-$d_4$) δ ppm 8.21 (s, 1H), 7.21 (s, 1H), 6.71 (d, J=2.3 Hz, 1H), 6.65 (d, J=2.0 Hz, 1H), 5.09 (s, 2H), 4.40 (s, 2H), 3.60 (t, J=5.5 Hz, 2H), 2.79 (t, J=5.8 Hz, 2H), 2.20 (s, 3H), 1.49 (s, 9H); LCMS (ESI) [M+H−100]$^+$ m/z: calcd 245.2. found 245.1.

5-[(8-methyl-1,2,3,4-tetrahydroisoquinolin-6-yl)oxymethyl]oxazole. To a solution of tert-butyl 8-methyl-6-(oxazol-5-ylmethoxy)-3,4-dihydro-1H-isoquinoline-2-carboxylate (70 mg, 0.203 mmol) in DCM (5 mL) was added TFA (13.0 mmol, 1 mL), and then the mixture was stirred at 25° C. for 12 hours. The mixture was concentrated under reduced pressure to remove DCM, diluted with $H_2O$ (10 mL), adjusted to pH=8 with saturated aqueous solution of $NaHCO_3$, and then extracted with DCM (10 mL*2). The combined organic layers were dried over anhydrous $Na_2SO_4$, filtered and concentrated under reduced pressure to afford 5-[(8-methyl-1,2,3,4-tetrahydroisoquinolin-6-yl)oxymethyl]oxazole (40 mg, crude) as yellow oil.

2-(cyclobutylamino)-N-[(2S)-2-hydroxy-3-[8-methyl-6-(oxazol-5-ylmethoxy)-3,4-dihydro-1H-isoquinolin-2-yl]propyl]pyridine-4-carboxamide (Compound 260). To a solution of 5-[(8-methyl-1,2,3,4-tetrahydroisoquinolin-6-yl)oxymethyl]oxazole (20 mg, 0.819 mmol), N-[(2S)-3-chloro-2-hydroxy-propyl]-2-(cyclobutylamino)pyridine-4-carboxamide (25 mg, 0.881 mmol) in MeCN (1.5 mL) were added NaI (20 mg, 0.133 mmol) and TEA (0.287 mmol, 40 uL). Then the mixture was stirred at 90° C. for 12 hours in sealed tube. The mixture was concentrated under reduced pressure and the residue was purified with preparative HPLC (Instrument: Gilson GX-281 Liquid Handler, Gilson 322

Pump, Gilson 156 UV Detector; Column: Waters Xbridge 150×25 mm×5 μm; Mobile phase A: H$_2$O with 0.05% NH$_3$—H$_2$O (v %); Mobile phase B: MeCN; Gradient: B from 30% to 60% in 7.8 min, hold 100% B for 1 min; Flow Rate: 25 mL/min; Column Temperature: 30° C.; Wavelength: 220 nm, 254 nm) to afford 2-(cyclobutylamino)-N-[(2S)-2-hydroxy-3-[8-methyl-6-(oxazol-5-ylmethoxy)-3,4-dihydro-1H-isoquinolin-2-yl]propyl]pyridine-4-carboxamide (12 mg, 29.8% yield) as off-white solid. $^1$H NMR (400 MHz, methanol-d$_4$) δ ppm 8.23 (s, 1H), 7.89 (d, J=5.3 Hz, 1H), 7.22 (s, 1H), 6.78 (s, 1H), 6.74 (dd, J=5.5, 1.5 Hz, 1H), 6.65 (s, 1H), 6.62 (s, 1H), 5.09 (s, 2H), 4.18-4.26 (m, 1H), 4.08-4.14 (m, 1H), 3.61 (s, 2H), 3.48 (qd, J=13.5, 6.0 Hz, 2H), 2.88 (br d, J=5.5 Hz, 2H), 2.83 (br d, J=4.3 Hz, 2H), 2.66-2.76 (m, 2H), 2.38-2.42 (m, 2H), 2.16 (s, 3H), 1.87-1.97 (m, 2H), 1.73-1.81 (m, 2H); LCMS (ESI) [M+H]$^+$ m/z: calcd 492.3. found 492.1; HPLC: 100% @254 nm; 99.5% ee.

Example 1A5. N-[(2S)-3-[5-chloro-8-fluoro-6-(oxazol-5-ylmethoxy)-3,4-dihydro-1H-isoquinolin-2-yl]-2-hydroxy-propyl]-2-(cyclobutylamino)pyridine-4-carboxamide (Compound 279)

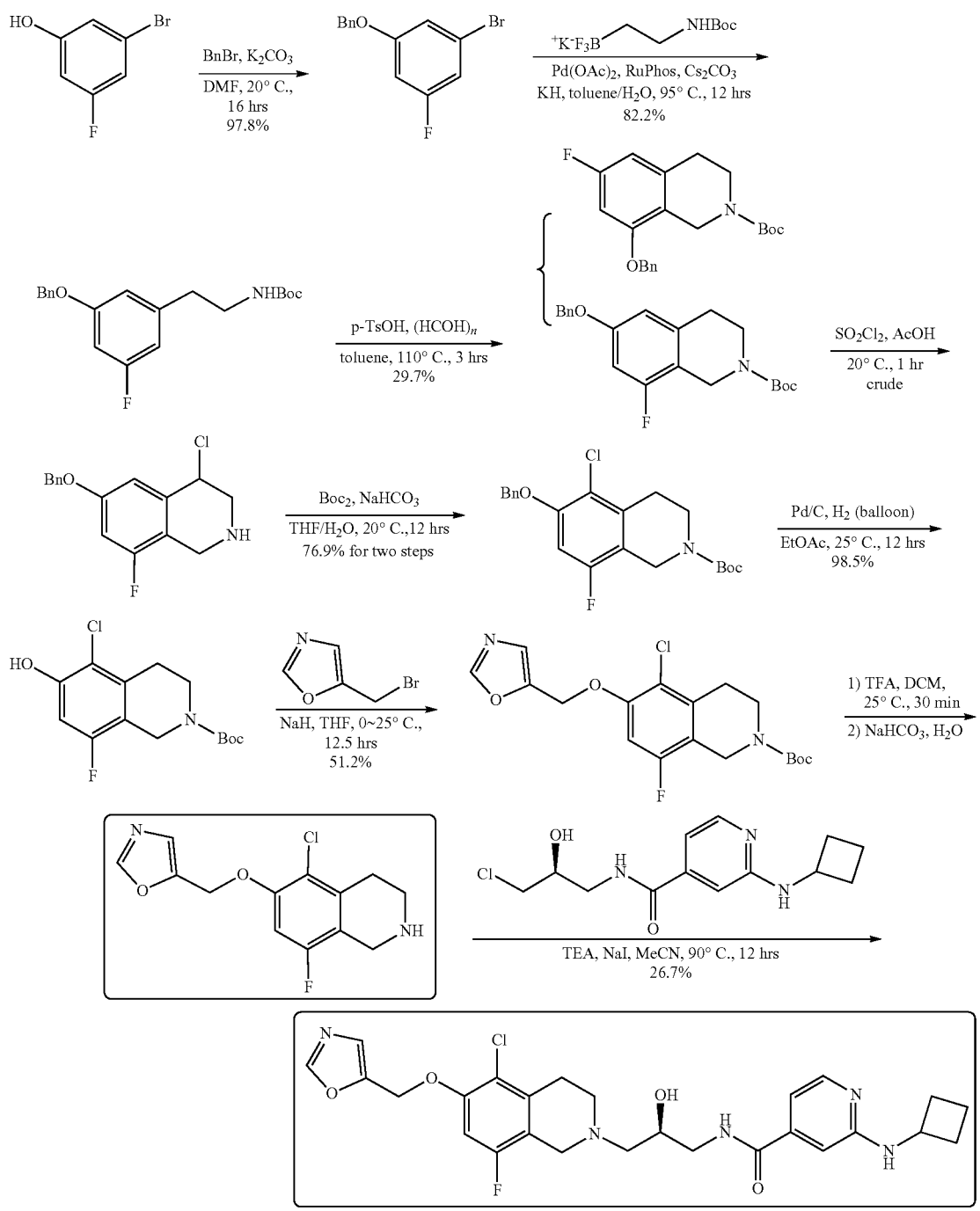

1-benzyloxy-3-bromo-5-fluoro-benzene. A mixture of 3-bromo-5-fluoro-phenol (5 g, 26.2 mmol), potassium carbonate (4.4 g, 31.8 mmol) and bromomethylbenzene (5.2 g, 30.4 mmol) in DMF (50 mL) was stirred at 20° C. for 16 hours. The resulting mixture was quenched by addition of water (100 mL) and extracted with EtOAc (100 mL*3). The combined organic layer was washed with brine (100 mL*2), dried over anhydrous $Na_2SO_4$, filtered and concentrated under reduced pressure. The residue was purified by flash chromatography (ISCO®; 20 g of AgelaFlash® Silica Flash Column, petroleum ether/EtOAc with EtOAc from 0~10%, Flow Rate: 30 mL/min) to afford 1-benzyloxy-3-bromo-5-fluoro-benzene (7.2 g, 97.8% yield) as a light-yellow oil. $^1$H NMR (400 MHz, methanol-$d_4$) δ ppm 7.24-7.41 (m, 5H), 6.97 (s, 1H), 6.87 (dt, J=8.2, 1.9 Hz, 1H), 6.72 (dt, J=10.8, 2.3 Hz, 1H), 5.01 (s, 2H).

tert-butyl N-[2-(3-benzyloxy-5-fluoro-phenyl)ethyl]carbamate. A mixture of 1-benzyloxy-3-bromo-5-fluoro-benzene (2.5 g, 8.89 mmol), 2-(tert-butoxycarbonylamino) ethyl-trifluoro-boranuide, potassium hydride (2.3 g, 9.16 mmol), RuPhos (446 mg, 0.96 mmol), $Cs_2CO_3$ (9.0 g, 27.6 mmol) and diacetoxypalladium (137 mg, 0.61 mmol) in toluene (30 mL) and $H_2O$ (6 mL) was sealed and stirred at 95° C. for 12 hours under nitrogen. The mixture was filtered and concentrated under reduced pressure. The residue was purified by flash chromatography (ISCO®; 12 g AgelaFlash® Silica Flash Column, petroleum ether/EtOAc with EtOAc from 0~20%, flow rate=30 mL/min) to afford tert-butyl N-[2-(3-benzyloxy-5-fluoro-phenyl)ethyl]carbamate (2.6 g, 82.2% yield) as yellow oil. $^1$H NMR (400 MHz, methanol-$d_4$) δ ppm 7.27-7.49 (m, 5H), 6.52-6.77 (m, 3H), 5.061 (s, 2H), 3.26 (t, J=7.2 Hz, 2H), 2.73 (t, J=7.3 Hz, 2H), 1.43 (s, 9H); LCMS (ESI) [M+H−56]$^+$ m/z: calcd 290.2. found 290.1.

tert-butyl 6-benzyloxy-8-fluoro-3,4-dihydro-1H-isoquinoline-2-carboxylate. To a solution of tert-butyl N-[2-(3-benzyloxy-5-fluoro-phenyl)ethyl]carbamate (1.3 g, 3.76 mmol) in toluene (60 mL) were added paraformaldehyde (357 mg, 11.9 mmol) and methyl 4-methylbenzenesulfonate (104 mg, 0.56 mmol), then the mixture was stirred at 110° C. for 3 hours. The mixture was concentrated under reduced pressure and the residue was purified by flash chromatography (ISCO®; 12 g AgelaFlash® Silica Flash Column, petroleum ether/EtOAc with EtOAc from 0~20%, flow rate=30 mL/min) to afford PI and P2.

PI: tert-butyl 8-benzyloxy-6-fluoro-3,4-dihydro-1H-isoquinoline-2-carboxylate (350 mg, 26.0% yield, yellow oil). $^1$H NMR (400 MHz, methanol-$d_4$) δ ppm 7.30-7.49 (m, 5H), 6.62-6.73 (m, 1H), 6.53 (dd, J=9.2, 2.1 Hz, 1H), 5.06-5.12 (m 2H), 4.49 (s, 2H), 3.63 (br s, 2H), 2.79 (t, J=5.6 Hz, 2H), 1.50 (s, 9H); $^{19}$F NMR (376 MHz, methanol-$d_4$) δ ppm −116.410; LCMS (ESI) [M+H−100]$^+$ m/z: calcd 258.2. found 258.1.

P2: tert-butyl 6-benzyloxy-8-fluoro-3,4-dihydro-1H-isoquinoline-2-carboxylate (400 mg, 29.7% yield, yellow oil). $^1$H NMR (400 MHz, methanol-$d_4$) δ ppm 7.30-7.46 (m, 5H), 6.62-6.66 (m, 2H), 5.06 (s, 2H), 4.48 (s, 2H), 3.63 (t, J=5.2 Hz, 2H), 2.80 (t, J=5.9 Hz, 2H), 1.51 (s, 9H); $^{19}$F NMR (376 MHz, methanol-$d_4$) δ ppm −120.877, −121.043; LCMS (ESI) [M+H−−100]$^+$ m/z: calcd 258.2. found 258.1.

6-benzyloxy-5-chloro-8-fluoro-1,2,3,4-tetrahydroisoquinoline. To a solution of tert-butyl 6-benzyloxy-8-fluoro-3,4-dihydro-1H-isoquinoline-2-carboxylate (380 mg, 1.06 mmol) in AcOH (10 mL) was added sulfuryl chloride (144 mg, 1.07 mmol) and the mixture was stirred at 25° C. for 1 hour. The mixture was concentrated under reduced pressure to give 6-benzyloxy-5-chloro-8-fluoro-1,2,3,4-tetrahydroisoquinoline (300 mg, crude) as a white solid which was used next step without further purification. LCMS (ESI) [M+H]$^+$ m/z: calcd 292.1, found 292.0.

tert-butyl 6-benz]oxy-5-chloro-8-fluoro-3,4-dihydro-1H-isoquinoline-2-carboxylate. To a solution of 6-benzyloxy-5-chloro-8-fluoro-1,2,3,4-tetrahydroisoquinoline (300 mg, 1.03 mmol) in THF (10 mL)/$H_2O$ (5 mL) were added $NaHCO_3$ (518 mg, 6.17 mmol) and $Boc_2O$ (493 mg, 2.26 mmol). The reaction mixture was stirred at 20° C. for 12 hours. The resulting mixture was quenched by addition of water (50 mL) and extracted with EtOAc (50 mL*3). The combined organic layer was washed with brine (100 mL), dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc from 0~20%, flow rate=30 mL/min) to afford tert-butyl 6-benzyloxy-5-chloro-8-fluoro-3,4-dihydro-1H-isoquinoline-2-carboxylate (310 mg, 76.9% yield for two steps) as colorless oil. $^1$H NMR (400 MHz, methanol-$d_4$) δ ppm 7.24-7.52 (m, 5H), 6.89 (d, J=11.3 Hz, 1H), 5.17 (s, 2H), 4.51 (s, 2H), 3.68 (t, J=5.5 Hz, 2H), 2.86 (t, J=5.9 Hz, 2H), 1.44-1.56 (m, 9H); $^{19}$F NMR (376 MHz, methanol-$d_4$) δ ppm −121.328, −121.494; LCMS (ESI) [M+H−100]$^+$ m/z: calcd 292.1, found 292.0; regio-chemistry was confirmed by 2D NMR.

tert-butyl 5-chloro-8-fluoro-6-hydroxy-3,4-dihydro-1H-isoquinoline-2-carboxylate. To a solution of tert-butyl 6-benzyloxy-5-chloro-8-fluoro-3,4-dihydro-1H-isoquinoline-2-carboxylate (290 mg, 0.74 mmol) in EtOAc (3 mL) was added Pd/C (80 mg, 10% of Pd with 50% of water, wt %). The mixture was degassed and backfilled with hydrogen for three times and then stirred at 25° C. for 12 hours under hydrogen (~15 psi, in a balloon). The mixture was filtered and concentrated under reduced pressure to give tert-butyl 5-chloro-8-fluoro-6-hydroxy-3,4-dihydro-1H-isoquinoline-2-carboxylate (220 mg, 98.5% yield) as a yellow solid. $^1$H NMR (400 MHz, methanol-$d_4$) δ ppm 6.59 (d, J=11.0 Hz, 1H), 4.46 (s, 2H), 3.65 (t, J=5.5 Hz, 2H), 2.81 (t, J=5.9 Hz, 2H), 1.49 (s, 9H).

tert-butyl 5-chloro-8-fluoro-6-(oxazol-5-ylmethoxy)-3,4-dihydro-1H-isoquinoline-2-carboxylate. To a solution of tert-butyl 5-chloro-8-fluoro-6-hydroxy-3,4-dihydro-1H-isoquinoline-2-carboxylate (200 mg, 0.66 mmol) in THF (5 mL) was added NaH (115 mg, 3.0 mmol, 60% wt in mineral oil) at 0° C. and then stirred at 0° C. for 30 minutes. 5-(bromomethyl)oxazole (1.01 mmol in 3 mL of THF) was added and the mixture was stirred at 25° C. for 12 hours. The mixture was quenched by addition of water (10 mL) and extracted with EtOAc (10 mL*2). The combined organic layers were dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~30%, flow rate=30 mL/min) to afford tert-butyl 5-chloro-8-fluoro-6-(oxazol-5-ylmethoxy)-3,4-dihydro-1H-isoquinoline-2-carboxylate (130 mg, 51.3% yield) as a yellow oil NMR (400 MHz, methanol-d$_4$) δ ppm 8.27 (s, 1H), 7.30 (s, 1H), 7.03 (d, J=11.1 Hz, 1H), 5.20 (s, 2H), 4.53 (s, 2H), 3.63-3.73 (m, 2H), 2.85 (t, J=5.9 Hz, 2H), 1.45-1.52 (m, 9H); LCMS (ESI) [M+H−100]$^+$ m/z: calcd 283.1. found 283.0.

5-[(5-chloro-8-fluoro-1,2,3,4-tetrahydroisoquinolin-6-yl)oxymethyl]oxazole. A mixture of tert-butyl 5-chloro-8-fluoro-6-(oxazol-5-ylmethoxy)-3,4-dihydro-1H-isoquinoline-2-carboxylate (130 mg, 0.34 mmol), TFA (3.89 mmol, 0.3 mL) in DCM (2 mL) was stirred at 25° C. for 30 minutes. The mixture was filtered and concentrated under reduced pressure. The residue was quenched by addition of water (20 mL) and washed with DCM (20 mL*3). The aqueous layer was adjusted to pH=7-8 by saturated NaHCO$_3$ aqueous solution, extracted with DCM(20 mL*3), washed with saturated NH$_4$Cl aqueous solution (10 mL*2), dried over anhydrous Na2SO4, filtered and concentrated under reduced pressure to afford 5-[(5-chloro-8-fluoro-1,2,3,4-tetrahydroisoquinolin-6-yl)oxymethyl]oxazole (90 mg, crude) as a yellow oil. 40 mg of this crude product was used in next step directly and the rest 50 mg was further purified by preparative HPLC (Instrument: Gilson GX-281 Liquid Handler, Gilson 322 Pump, Gilson 156 UV Detector; Column: Waters Xbridge 150 mm*50 mm, 10 μm; Mobile phase A: water (0.05% ammonia hydroxide v/v); Mobile phase B: MeCN; Gradient: B from 27% to 57% in 7.8 min, hold 100% B for 2 min; Flow Rate: 25 mL/min; Column Temperature: 30° C.; Wavelength: 220 nm, 254 nm) to afford 5-[(5-chloro-8-fluoro-1,2,3,4-tetrahydroisoquinolin-6-yl)oxymethyl]oxazole (36 mg) as a white solid. $^1$H NMR (400 MHz, methanol-d$_4$) δ ppm 8.27 (s, 1H), 7.29 (s, 1H), 6.97 (d, J=11.0 Hz, 1H), 5.23 (s, 2H), 3.90 (s, 2H), 3.10 (t, J=6.1 Hz, 2H), 2.80 (t, J=6.0 Hz, 2H); $^{19}$F NMR (376 MHz, methanol-d$_4$) δ ppm −121.632; LCMS (ESI) [M+H]$^+$ m/z: calcd 283.1. found 283.0; HPLC: 92.27%@220 nm.

N-[(2S)-3-[5-chloro-8-fluoro-6-(oxazol-5-ylmethoxy)-3,4-dihydro-1H-isoquinolin-2-yl]-2-hydroxy-propyl]-2-(cyclobutylamino)pyridine-4-carboxamide

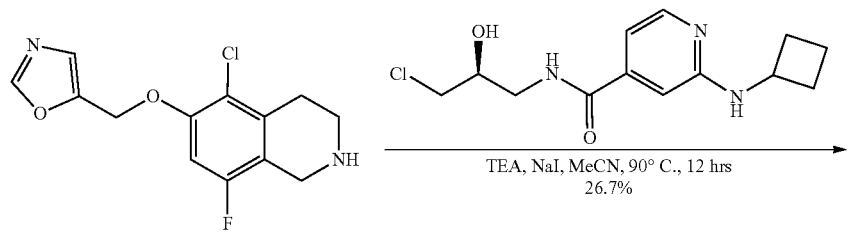

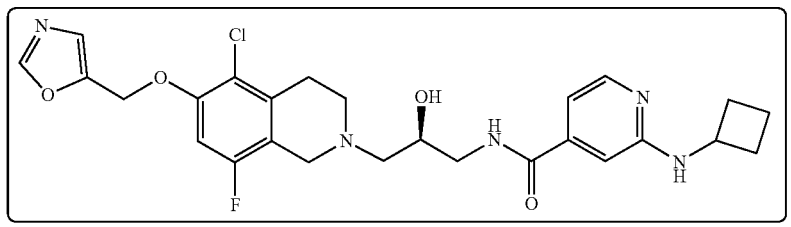

A mixture of 5-[(5-chloro-8-fluoro-1,2,3,4-tetrahydroisoquinolin-6-yl)oxymethyl]oxazole (20 mg, 0.0708 mmol), N-[(2S)-3-chloro-2-hydroxy-propyl]-2-(cyclobutylamino)pyridine-4-carboxamide (24 mg, 0.0846 mmol), TEA (22 mg, 0.217 mmol) and NaI (13 mg, 0.0867 mmol) in MeCN (2 mL) was stirred at 90° C. for 12 hours in a sealed tube. The mixture was concentrated under reduced pressure to give a crude product, which was purified by preparative HPLC (Instrument: Gilson GX-281 Liquid Handler, Gilson 322 Pump, Gilson 156 UV Detector; Column: Waters Xbridge 150×50 mm×10 μm; Mobile phase A: H$_2$O with 0.05% NH$_3$—H$_2$O (v %); Mobile phase B: MeCN; Gradient: B from 29% to 59% in 7.8 min, hold 100% B for 2 min; Flow Rate: 25 mL/min; Column Temperature: 30° C.; Wavelength: 220 nm, 254 nm) to give N-[(2S)-3-[5-chloro-8-fluoro-6-(oxazol-5-ylmethoxy)-3,4-dihydro-1H-isoquinolin-2-yl]-2-hydroxy-propyl]-2-(cyclobutylamino)pyridine-4-carboxamide (10 mg, 26.7% yield) as a white dry powder. $^1$H NMR (400 MHz, methanol-d$_4$) δ ppm 8.26 (s, 1H), 7.92 (d, J=5.4 Hz, 1H), 7.28 (s, 1H), 6.93 (d, J=11.0 Hz, 1H), 6.79 (s, 1H), 6.75 (d, J=5.5 Hz, 1H), 5.20 (s, 2H), 4.19-4.27 (m, 1H), 4.04-4.11 (m, 1H), 3.67 (s, 2H), 3.39-3.56 (m, 2H), 2.86 (s, 4H), 2.63-2.72 (m, 2H), 2.40 (d, J=8.0 Hz, 2H), 1.87-1.98 (m, 2H), 1.72-1.82 (m, 2H); $^{19}$F NMR (376 MHz, methanol-d$_4$) δ −121.393; LCMS (ESI) [M+H]$^+$ m/z: calcd 530.2. found 530.1; HPLC: 99.82% @ 254 nm; 99.6% ee.

Example 1A7. N-[(2S)-3-[5-chloro-8-fluoro-6-[(2-methylpyrazol-3-yl)methoxy]-3,4-dihydro-1H-isoquinolin-2-yl]-2-hydroxy-propyl]-2-(cyclobutylamino)pyridine-4-carboxamide (Compound 282)
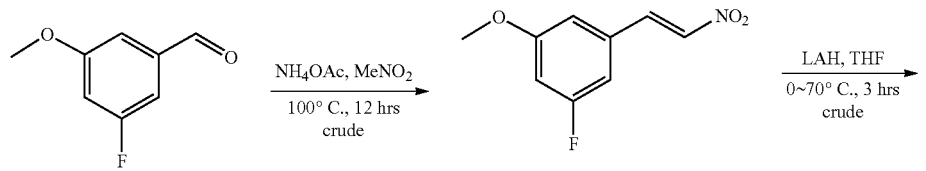
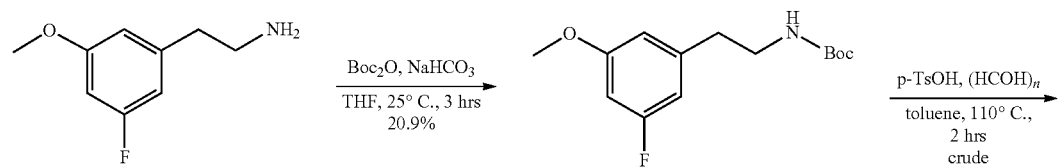
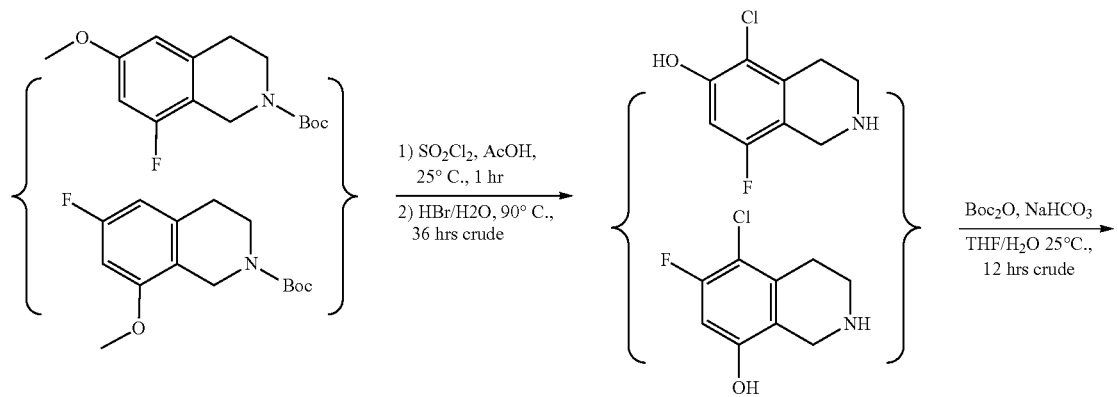
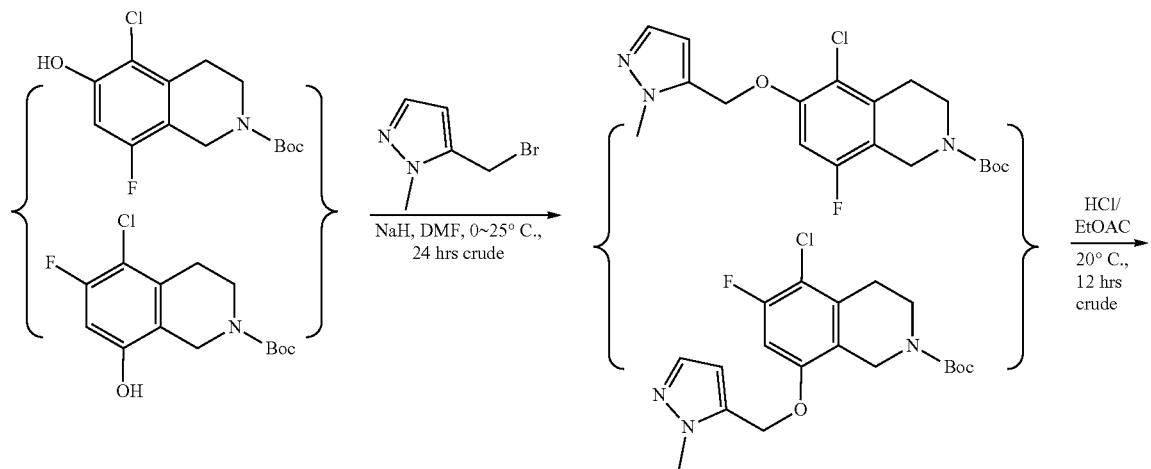

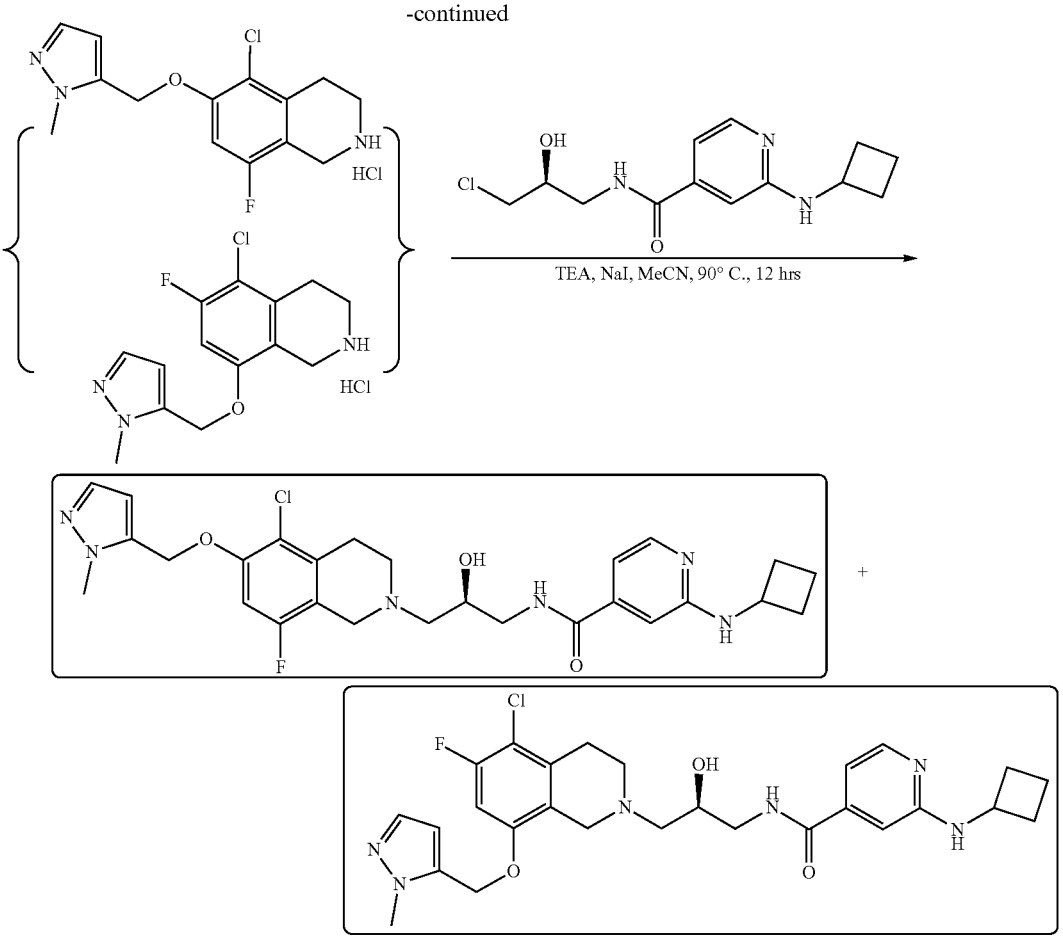

1-methoxy-3-methyl-5-[(E)-2-nitrovinyl]benzene. To a solution of 3-methoxy-5-methyl-benzaldehyde (10 g, 66.6 mmol) in MeNO$_2$ (100 mL) was added NH$_4$OAc (2.0 g, 26.0 mmol) and the reaction mixture was stirred at 100° C. for 12 hours. The reaction mixture was concentrated under reduced pressure and the residue was quenched by addition of water (50 mL) and extracted with EtOAc (50 mL*3). The combined organic layer was washed with brine (100 mL), dried over anhydrous Na$_2$SO$_4$, filtered and concentrated under reduced pressure to give 1-methoxy-3-methyl-5-[(E)-2-nitrovinyl]benzene (15 g, crude) as red solid.

2-(3-fluoro-5-methoxy-phenyl)ethanamine. To a solution of LiAlH$_4$ (3 g, 79.0 mmol) in THF (20 mL) was added a solution of 1-fluoro-3-methoxy-5-[(E)-2-nitrovinyl]benzene (5 g, 25.4 mmol) in THF (30 mL) drop-wise at 0° C. and after the addition was complete, the reaction mixture was stirred at 70° C. for 3 hours. The resulting mixture was quenched by addition of water (3 mL), NaOH/H$_2$O (3 mL, 15% wt), water (9 mL), dried over anhydrous Na$_2$SO$_4$, filtered and the filtrate was concentrated under reduced pressure to give 2-(3-fluoro-5-methoxy-phenyl)ethanamine (3 g, crude) as brown oil. $^1$H NMR (400 MHz, methanol-d$_4$) δ ppm 6.49-6.56 (m, 3H), 3.78 (s, 3H), 2.83-2.89 (m, 2H), 2.69-2.74 (m, 2H); LCMS (ESI) [M+H]$^+$ m/z: calcd 170.1. found 170.1.

tert-butyl N-[2-(3-fluoro-5-methoxy-phenyl)ethyl]carbamate. To a solution of 2-(3-fluoro-5-methoxy-phenyl) ethanamine (3 g, 17.7 mmol) in THF (30 mL) were added NaHCO$_3$ (2 g, 23.81 mmol) and tert-butoxycarbonyl tert-butyl carbonate (4.28 g, 19.6 mmol), then the mixture was stirred at 25° C. for 3 hours. The resulting mixture was quenched by addition of water (50 mL) and extracted with EtOAc (50 mL*3). The combined organic layer was washed with brine (50 mL), dried over anhydrous Na$_2$SO$_4$, filtered and concentrated under reduced pressure. The residue was purified by flash chromatography (ISCO®; 40 g Agela-Flash® Silica Flash Column, petroleum ether/EtOAc with EtOAc from 0~10%, flow rate=30 mL/min) to afford tert-butyl N-[2-(3-fluoro-5-methoxy-phenyl)ethyl]carbamate (1 g, 20.9% yield) as colorless oil. $^1$H NMR (400 MHz, methanol-d$_4$) δ ppm 6.48-6.56 (m, 3H), 3.79 (s, 3H), 2.71 (t, J=7.2 Hz, 2H), 1.38-1.42 (m, 9H); LCMS (ESI) [M+H−56]$^+$ m/z: calcd 214.1. found 214.1.

tert-butyl 8-fluoro-6-methoxy-3,4-dihydro-1H-isoquinoline-2-carboxylate and tert-butyl 6-fluoro-8-methoxy-3,4-dihydro-1H-isoquinoline-2-carboxylate. To a solution of tert-butyl N-[2-(3-fluoro-5-methoxy-phenyl)ethyl]carbamate (3.5 g, 10.4 mmol) in toluene (30 mL) were added paraformaldehyde (1 g, 33.3 mmol) and methyl 4-methylbenzenesulfonate (300 mg, 1.61 mmol). The reaction mixture was stirred at 110° C. for 2 hours. The resulting mixture was quenched by addition of water (50 mL) and extracted with EtOAc (50 mL*3). The combined organic layer was washed with saturated NH$_4$Cl aqueous solution (50 mL*2), brine (50 mL), dried over anhydrous Na$_2$SO$_4$, filtered and concentrated under reduced pressure to give a mixture (1.7 g, crude) of tert-butyl 8-fluoro-6-methoxy-3,4-dihydro-1H-isoquinoline-2-carboxylate and tert-butyl 6-fluoro-8- methoxy-3,4-dihydro-1H-isoquinoline-2-carboxylate as brown oil. LCMS (ESI) [M+H−56]+ m/z: calcd 226.1. found 226.1.

5-chloro-8-fluoro-1,2,3,4-tetrahydroisoquinolin-6-ol and 5-chloro-6-fluoro-1,2,3,4-tetrahydroisoquinolin-8-ol. To a solution of the mixture (1 g, 3.55 mmol) of tert-butyl 8-fluoro-6-methoxy-3,4-dihydro-1H-isoquinoline-2-carboxylate and tert-butyl 6-fluoro-8-methoxy-3,4-dihydro-1H-isoquinoline-2-carboxylate in AcOH (5 mL) was added drop-wise SO$_2$Cl$_2$ (0.55 g, 4.07 mmol) in portions slowly at 25° C. After addition was complete, the mixture was stirred at 25° C. for 1 hour. The reaction mixture was concentrated under reduced pressure to give a crude intermediate as brown oil which was used next step without further purification. The intermediate was dissolved in HBr/H$_2$O (10 mL, 40% wt) and stirred at 90° C. for 36 hr. The reaction mixture was concentrated under reduced pressure to give a mixture (1 g, crude) of 5-chloro-8-fluoro-1,2,3,4-tetrahydroisoquinolin-6-ol and 5-chloro-6-fluoro-1,2,3,4-tetrahydroisoquinolin-8-ol as brown oil which was used next step without further purification. LCMS (ESI) [M+H−56]+ m/z: calcd 202.0. found 202.0.

tert-butyl 5-chloro-8-fluoro-6-hydroxy-3,4-dihydro-1H-isoquinoline-2-carboxylate and tert-butyl 5-chloro-6-fluoro-8-hydroxy-3,4-dihydro-/H-isoquinoline-2-carboxylate. To a solution of a mixture (1 g, crude) of 5-chloro-8-fluoro-1,2,3,4-tetrahydroisoquinolin-6-ol and 5-chloro-6-fluoro-1,2,3,4-tetrahydroisoquinolin-8-olin THF (10 mL)/H$_2$O (5 mL) were added NaHCO$_3$ (2.50 g, 29.8 mmol) and Boc$_2$O (2.38 g, 10.9 mmol). The reaction mixture was stirred at 20° C. for 12 hours. The resulting mixture was quenched by addition of water (50 mL) and extracted with EtOAc (50 mL*3). The combined organic layer was washed with brine (100 mL), dried over anhydrous Na$_2$SO$_4$, filtered and concentrated under reduced pressure to give a residue. The residue was purified by flash chromatography (ISCO®; 40 g AgelaFlash® Silica Flash Column, petroleum ether/EtOAc with EtOAc from 0~30%, flow rate=30 mL/min) to afford a mixture (1.2 g, crude) of tert-butyl 5-chloro-8-fluoro-6-hydroxy-3,4-dihydro-1H-isoquinoline-2-carboxylate and tert-butyl 5-chloro-6-fluoro-8-hydroxy-3,4-dihydro-1H-isoquinoline-2-carboxylate as colorless oil.

tert-butyl 5-chloro-8-fluoro-6-[(2-methylpyrazol-3-yl)methoxy]-3,4-dihydro-1H-isoquinoline-2-carboxylate and tert-butyl 5-chloro-6-fluoro-8-[(2-methylpyrazol-3-yl)methoxy]-3,4-dihydro-1H-isoquinoline-2-carboxylate. To a solution of the mixture (600 mg, crude) of tert-butyl 5-chloro-8-fluoro-6-hydroxy-3,4-dihydro-1H-isoquinoline-2-carboxylate and tert-butyl 5-chloro-6-fluoro-8-hydroxy-3,4-dihydro-1H-isoquinoline-2-carboxylate in DMF (10 mL) was added NaH (0.3 g, 60% wt in mineral oil) at 0° C. and then the mixture was stirred at 0° C. for 15 minutes. The a solution of 5-(bromomethyl)-1-methyl-pyrazole (5.05 mmol, crude) in THF (10 mL) was added and the mixture was stirred at 25° C. for 24 hours. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 40 g AgelaFlash® Silica Flash Column, petroleum ether/EtOAc with EtOAc from 0~50%, flow rate=30 mL/min) to afford a mixture (80 mg, crude) of tert-butyl 5-chloro-8-fluoro-6-[(2-methylpyrazol-3-yl)methoxy]-3,4-dihydro-1H-isoquinoline-2-carboxylate and tert-butyl 5-chloro-6-fluoro-8-[(2-methylpyrazol-3-yl)methoxy]-3,4-dihydro-1H-isoquinoline-2-carboxylate as brown oil. LCMS (ESI) [M+H−56]+ m/z: calcd 340.1. found 340.0.

5-chloro-8-fluoro-6-[(2-methylpyrazol-3-yl)methoxy]-1,2,3,4-tetrahydroisoquinolin and 5-chloro-6-fluoro-8-[(2-methylpyrazol-3-yl)methoxy]-1,2,3,4-tetrahydroisoquinoline. The mixture (70 mg, crude) of tert-butyl 5-chloro-8-fluoro-6-[(2-methylpyrazol-3-yl)methoxy]-3,4-dihydro-1H-isoquinoline-2-carboxylate and tert-butyl 5-chloro-6-fluoro-8-[(2-methylpyrazol-3-yl)methoxy]-3,4-dihydro-1H-isoquinoline-2-carboxylate in HCl/EtOAc (5 mL) was stirred at 20° C. for 12 hours. The reaction mixture was concentrated under reduced pressure to give a mixture (70 mg) of 5-chloro-8-fluoro-6-[(2-methylpyrazol-3-yl)methoxy]-1,2,3,4-tetrahydroisoquinoline and 5-chloro-6-fluoro-8-[(2-methylpyrazol-3-yl)methoxy]-1,2,3,4-tetrahydroisoquinoline as a white solid which was used next step without any purification. LCMS (ESI) [M+H]+ m/z: calcd 296.1. found 296.0.

N-[(2S)-3-[5-chloro-8-fluoro-6-[(2-methylpyrazol-3-yl)methoxy]-3,4-dihydro-1H-isoquinolin-2-yl]-2-hydroxy-propyl]-2-(cyclobutylamino)pyridine-4-carboxamide (Compound 282) and N-[(2S)-3-[5-chloro-6-fluoro-8-[(2-methylpyrazol-3-yl)methoxy]-3,4-dihydro-1H-isoquinolin-2-yl]-2-hydroxy-propyl]-2-(cyclobutylamino)pyridine-4-carboxamide

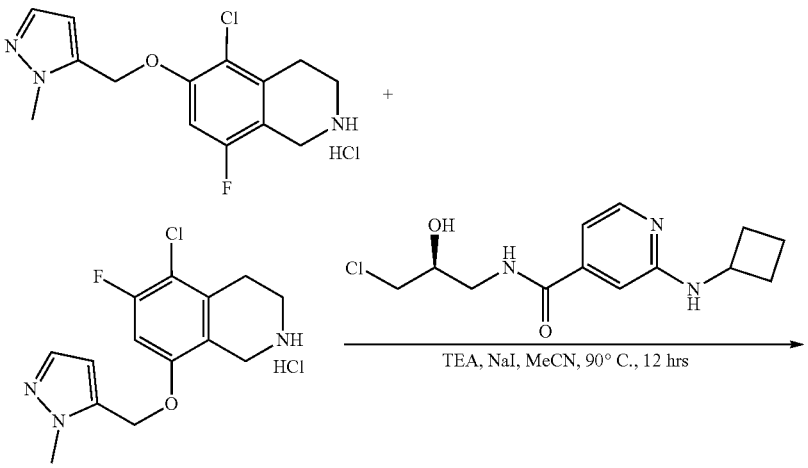

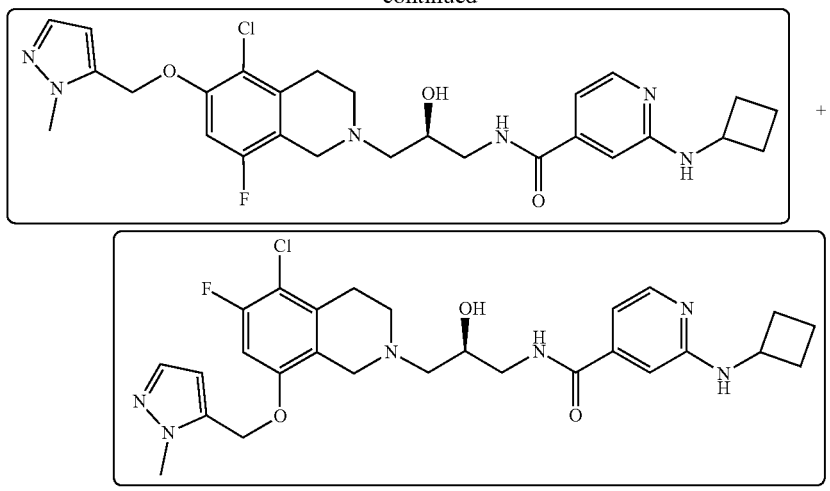

To a solution of the mixture (30 mg, crude) of 5-chloro-8-fluoro-6-[(2-methylpyrazol-3-yl)methoxy]-1,2,3,4-tetrahydroisoquinoline and 5-chloro-6-fluoro-8-[(2-methylpyrazol-3-yl)methoxy]-1,2,3,4-tetrahydroisoquinoline in MeCN (2 mL) were added N-[(2S)-3-chloro-2-hydroxy-propyl]-2-(cyclobutylamino)pyridine-4-carboxamide (30 mg, 0.11 mmol), TEA (0.10 mmol, 50 uL) and NaI (20 mg, 0.13 mmol). The reaction mixture was stirred at 90° C. for 12 hours. The reaction mixture was concentrated under reduced pressure and the residue was purified by preparative HPLC (Instrument: Gilson GX-281 Liquid Handler, Gilson 322 Pump, Gilson 156 UV Detector; Column: Durashell 150×25 mm×5 μm; Mobile phase A:water (0.05% ammonia hydroxide v/v); Mobile phase B: MeCN; Gradient: B from 33% to 63% in 8 min, hold 100% B for 2 min; Flow Rate: 25 mL/min; Column Temperature: 30° C.; Wavelength: 220 nm, 254 nm) to afford PI.

PI N-[(2S)-3-[5-chloro-8-fluoro-6-[(2-methylpyrazol-3-yl)methoxy]-3,4-dihydro-1H-isoquinolin-2-yl]-2-hydroxy-propyl]-2-(cyclobutylamino)pyridine-4-carboxamide (3.8 mg, white solid). $^1$H NMR (400 MHz, methanol-$d_4$) δ ppm 7.92 (d, J=5.5 Hz, 1H), 7.42 (d, J=2.0 Hz, 1H), 6.93 (d, J=11.3 Hz, 1H), 6.79 (s, 1H), 6.74 (dd, J=5.5, 1.5 Hz, 1H), 6.40 (d, J=2.0 Hz, 1H), 5.21 (s, 2H), 4.23 (quin, J=7.8 Hz, 1H), 4.07 (quin, J=6.0 Hz, 1H), 3.94 (s, 3H), 3.66 (s, 2H), 3.48-3.57 (m, 1H), 3.36-3.45 (m, 1H), 2.86 (s, 4H), 2.62-2.70 (m, 2H), 2.35-2.43 (m, 2H), 1.86-1.97 (m, 2H), 1.72-1.81 (m, 2H); $^{19}$F NMR (376 MHz, methanol-$d_4$) δ ppm −121.39; LCMS (ESI) [M+H]$^+$ m/z: calcd 543.2. found 543.1; HPLC: 99.17% @ 254 nm; 99.6% ee; regio-chemistry was confirmed by 2D NMR.

P2: N-[(2S)-3-[5-chloro-6-fluoro-8-[(2-methylpyrazol-3-yl)methoxy]-3,4-dihydro-1H-isoquinolin-2-yl]-2-hydroxy-propyl]-2-(cyclobutylamino)pyridine-4-carboxamide (2.0 mg, white solid). $^1$H NMR (400 MHz, methanol-$d_4$) δ ppm 7.90 (d, J=6.4 Hz, 1H), 7.90 (d, J=5.5 Hz, 1H), 7.43 (d, J=2.0 Hz, 1H), 6.96 (d, J=11.0 Hz, 1H), 6.78 (s, 1H), 6.72 (dd, J=5.4, F4 Hz, 1H), 6.40 (d, J=F8 Hz, 1H), 5.15 (s, 2H), 4.23 (quin, J=7.9 Hz, 1H), 4.04 (quin, J=5.9 Hz, 1H), 3.89 (s, 3H), 3.60 (s, 2H), 3.38-3.53 (m, 2H), 2.82-2.89 (m, 4H), 2.61-2.81 (m, 2H), 2.37-2.45 (m, 2H), F87-F98 (m, 2H), F73-1.82 (m, 2H); $^{19}$F NMR (376 MHz, methanol-$d_4$) δ ppm −117.13; LCMS (ESI) [M+H]$^+$ m/z: calcd 543.2. found 543.1; HPLC: 96.58% @254 nm; 99.3% ee; regio-chemistry was confirmed by 2D NMR.

Example 1A8. 2-(cyclobutylamino)-N-[(2R)-3-[8-fluoro-5-methyl-6-(oxazol-5-ylmethoxy)-3N-dihydro-1H-isoquinolin-2-yl]-2-hydroxy-propyl]pyridine-4-carboxamide (Compound 332) and 2-(cyclobutylamino)-N-[(2S)-3-[8-fluoro-5-methyl-6-(oxazol-5-ylmethoxy)-3,4-dihydro-1H-isoquinolin-2-yl]-2-hydroxy-propyl]pyridine-4-carboxamide (Compound 341)

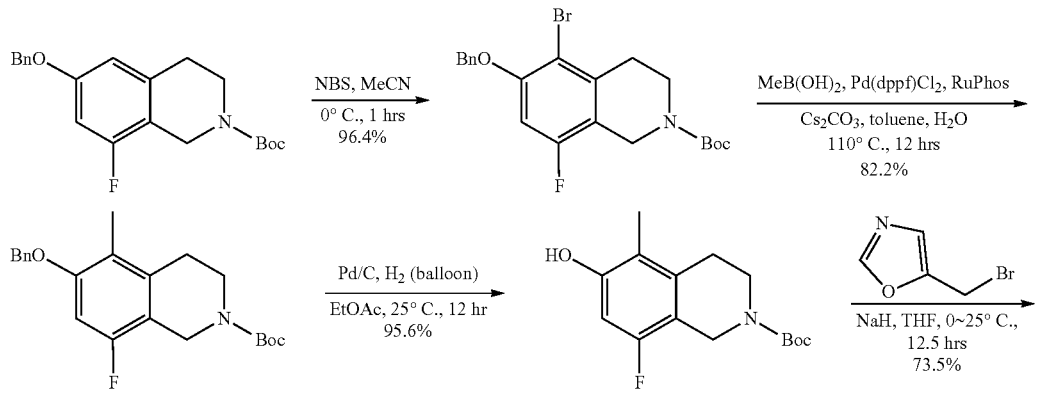

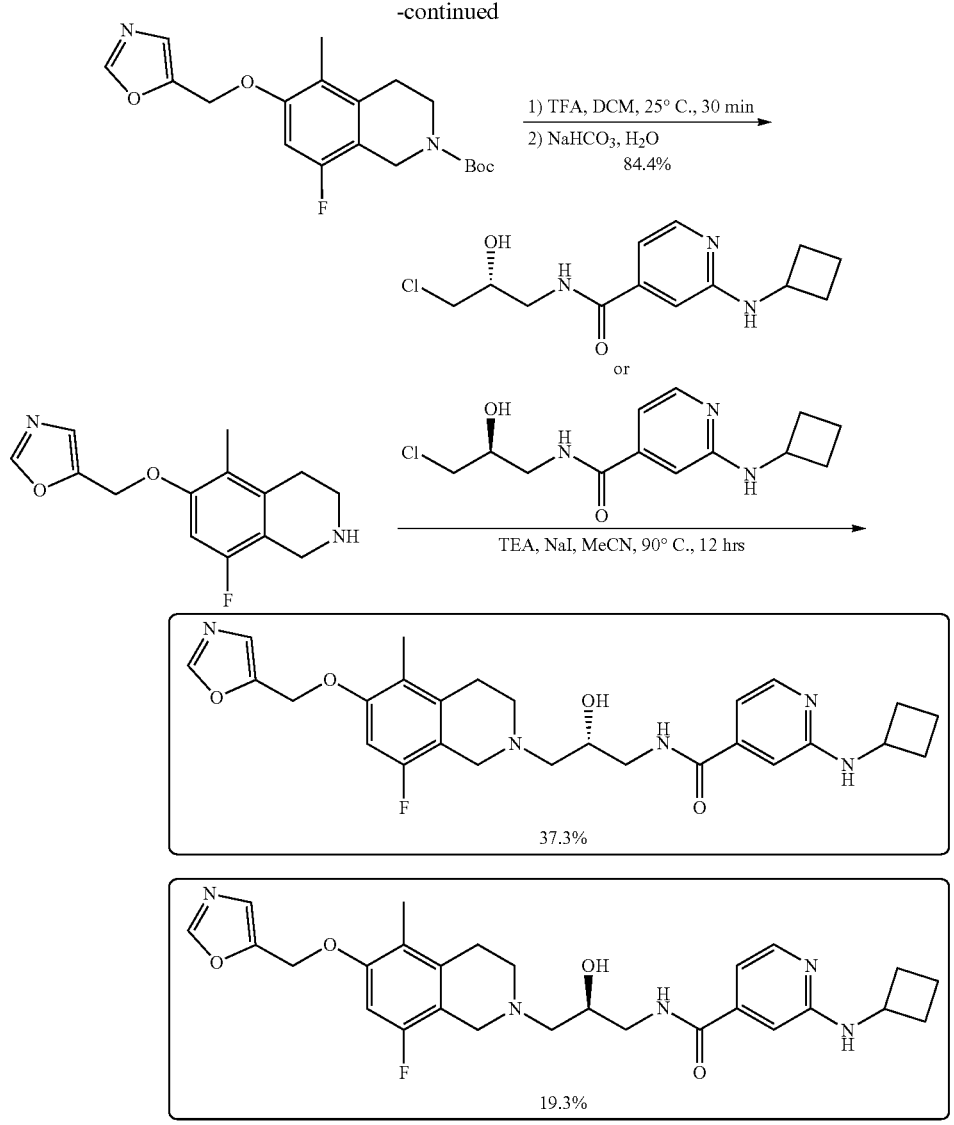

tert-butyl 6-benzyloxy-5-bromo-8-fluoro-3,4-dihydro-1H-isoquinoline-2-carboxylate. To a solution of tert-butyl 6-benzyloxy-8-fluoro-3,4-dihydro-1H-isoquinoline-2-carboxylate (340 mg, 0.95 mmol) in MeCN (3 mL) was added NBS (170 mg, 0.95 mmol). The mixture was stirred at 0° C. for 1 hour. The mixture was concentrated under reduced pressure and the residue was purified by flash chromatography (ISCO®; 20 g AgelaFlash® Silica Flash Column, petroleum ether/EtOAc with EtOAc from 0~20%, Flow Rate: 30 mL/min) to afford tert-butyl 6-benzyloxy-5-bromo-8-fluoro-3,4-dihydro-1H-isoquinoline-2-carboxylate (400 mg, 96.4% yield) as white solid. $^1$H NMR (400 MHz, methanol-$d_4$) δ ppm 7.29-7.46 (m, 5H), 6.69 (d, J=11.8 Hz, 1H), 5.05 (s, 2H), 4.47 (s, 2H), 3.64 (s, 2H), 2.73 (t, J=5.8 Hz, 2H), 2.11 (s, 3H), 1.49 (s, 9H); LCMS (ESI) [M+H−100]$^+$ m/z: calcd 336.1. found 335.9; the regio-chemistry was confirmed by 2D NMR.

tert-butyl 6-benzyloxy-8-fluoro-5-methyl-3,4-dihydro-1H-isoquinoline-2-carboxylate. A mixture of tert-butyl 6-benzyloxy-5-bromo-8-fluoro-3,4-dihydro-1H-isoquinoline-2-carboxylate (400 mg, 0.92 mmol), methylboronic acid (275 mg, 4.59 mmol), Cs$_2$CO$_3$ (896 mg, 2.75 mmol), Pd(dppf)Cl$_2$ (27 mg, 0.034 mmol) and RuPhos (120 mg, 0.26 mmol) in H$_2$O (2 mL) and dioxane (10 mL) was sealed and stirred at 110° C. for 12 hours. The mixture was filtered and concentrated under reduced pressure. The residue was purified by flash chromatography (ISCO®; 20 g of AgelaFlash® Silica Flash Column, petroleum ether/EtOAc with EtOAc from 0~50%, Flow Rate: 30 mL/min) to afford tert-butyl 6-benzyloxy-8-fluoro-5-methyl-3,4-dihydro-1H-isoquinoline-2-carboxylate (280 mg, 82.2% yield) as white solid. $^1$H NMR (400 MHz, methanol-$d_4$) δ ppm 7.29-7.46 (m, 5H), 6.69 (d, J=11.8 Hz, 1H), 5.05 (s, 2H), 4.47 (s, 2H), 3.64 (br s, 2H), 2.73 (t, J=5.8 Hz, 2H), 2.11 (s, 3H), 1.49 (s, 9H); LCMS (ESI) [M+H−100]$^+$ m/z: calcd 272.2. found 272.1.

tert-butyl 8-fluoro-6-hydroxy-5-methyl-3,4-dihydro-1H-isoquinoline-2-carboxylate. To a solution of tert-butyl 6-benzyloxy-8-fluoro-5-methyl-3,4-dihydro-1H-isoquinoline-2-carboxylate (290 mg, 0.78 mmol) in EtOAc (3 mL) was added Pd/C (20 mg, 10% wt of Pd with 50% wt of water). The mixture was degassed and backfilled with hydrogen for three times. The mixture was stirred at 25° C. for 12 hours under hydrogen (~15 psi, in a balloon). The resulting mixture was filtered and concentrated under reduced pressure to give tert-butyl 8-fluoro-6-hydroxy-5-methyl-3,4-dihydro-1H-isoquinoline-2-carboxylate (210 mg, 95.6% yield) as a white solid. NMR (400 MHz, methanol-$d_4$) δ ppm 6.41 (d, J=11.3 Hz, 1H), 4.44 (s, 2H), 3.63 (t, J=5.4 Hz, 2H), 2.70 (t, J=5.9 Hz, 2H), 2.04 (s, 3H), 1.49 (s, 9H); LCMS (ESI) [M+H+MeCN−56]$^+$ m/z: calcd 267.1. found 267.0.

tert-butyl 8-fluoro-5-methyl-6-(oxazol-5-ylmethoxy)-3,4-dihydro-1H-isoquinoline-2-carboxylate. To a solution of tert-butyl 8-fluoro-6-hydroxy-5-methyl-3,4-dihydro-1H-isoquinoline-2-carboxylate (190 mg, 0.68 mmol) in THF (5 mL) was added NaH (120 mg, 3.13 mmol, 60% wt in mineral oil) at 0° C. and then the mixture was stirred at 0° C. for 30 minutes. Then 5-(bromomethyl)oxazole (1.51 mmol in 4 mL of THF) was added and the mixture was stirred at 25° C. for 12 hours. The mixture was quenched by addition of water (10 mL), and then extracted with EtOAc (10 mL*2). The combined organic layers were dried over anhydrous $Na_2SO_4$, filtered and concentrated under reduced pressure. The residue was purified by flash chromatography (ISCO®; 20 g of AgelaFlash® Silica Flash Column, petroleum ether/EtOAc with EtOAc from 0~30%, flow rate=30 mL/min) to afford tert-butyl 8-fluoro-5-methyl-6-(oxazol-5-ylmethoxy)-3,4-dihydro-1H-isoquinoline-2-carboxylate (180 mg, 73.5% yield) as a yellow oil. NMR (400 MHz, methanol-$d_4$) δ ppm 8.24 (s, 1H), 7.24 (s, 1H), 6.80 (d, J=11.5 Hz, 1H), 5.13 (s, 2H), 4.49 (s, 2H), 3.64 (t, J=5.6 Hz, 2H), 2.72 (t, J=6.0 Hz, 2H), 2.04 (s, 3H), 1.49 (s, 9H); LCMS (ESI) [M+H−100]$^+$ m/z: calcd 263.2. found 263.1.

5-[(8-fluoro-5-methyl-1,2,3,4-tetrahydroisoquinolin-6-yl)oxymethyl]oxazole. A mixture of tert-butyl 8-fluoro-5-methyl-6-(oxazol-5-ylmethoxy)-3,4-dihydro-1H-isoquinoline-2-carboxylate (180 mg, 0.50 mmol) and TFA (0.4 mL, 5.0 mmol) in DCM (3 mL) was stirred at 25° C. for 30 minutes. The mixture was filtered and concentrated under reduced pressure. The residue was quenched by addition of water (20 mL) and washed with DCM (20 mL*3). The aqueous layer was adjusted to pH=7~8 by saturated $NaHCO_3$ aqueous solution and extracted with DCM (20 mL*3). The combined organic layer was washed with saturated $NH_4Cl$ aqueous solution (10 mL*2), dried over anhydrous $Na_2SO_4$, filtered and concentrated under reduced pressure to afford 5-[(8-fluoro-5-methyl-1,2,3,4-tetrahydroisoquinolin-6-yl)oxymethyl]oxazole (110 mg, 84.4% yield, crude) as a yellow oil. 90 mg of this crude product was used in next step directly and the rest 20 mg was further purified by preparative HPLC (Instrument: Gilson GX-281 Liquid Handler, Gilson 322 Pump, Gilson 156 UV Detector; Column: Waters Xbridge 150 mm*50 mm, 10 μm; Mobile phase A: water (0.05% ammonia hydroxide v/v); Mobile phase B: MeCN; Gradient: B from 30% to 60% in 7.8 min, hold 100% B for 3 min; Flow Rate: 25 mL/min; Column Temperature: 30° C.; Wavelength: 220 nm, 254 nm) to afford 5-[(8-fluoro-5-methyl-1,2,3,4-tetrahydroisoquinolin-6-yl)oxymethyl]oxazole (4 mg) as a white solid. $^1$H NMR (400 MHz, methanol-$d_4$) δ ppm 8.24 (s, 1H), 7.23 (s, 1H), 6.76 (d, J=11.5 Hz, 1H), 5.12 (s, 2H), 3.90 (s, 2H), 3.09 (t, J=6.0 Hz, 2H), 2.69 (t, J=6.0 Hz, 2H), 2.02 (s, 3H); $^{19}$F NMR (400 MHz, methanol-$d_4$) δ ppm −124.230; LCMS (ESI) [M+H]$^+$ m/z: calcd 263.1. found 263.0; HPLC: 97.85% @ 220 nm.

Step 8: Synthesis of 2-(cyclobutylamino)-N-[(2R)-3-[8-fluoro-5-methyl-6-(oxazol-5-ylmethoxy)-3,4-dihydro-1H-isoquinolin-2-yl]-2-hydroxy-propyl]pyridine-4-carboxamide (Compound 332)

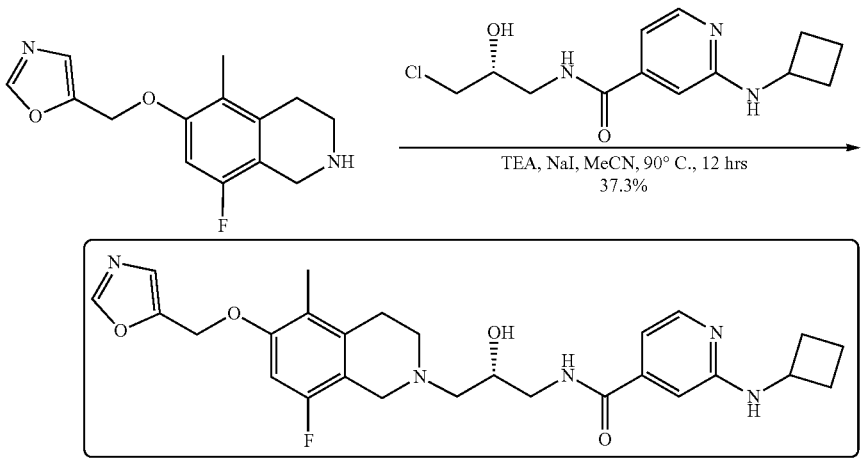

A mixture of 5-[(8-fluoro-5-methyl-1,2,3,4-tetrahydroisoquinolin-6-yl)oxymethyl]oxazole (40 mg, 0.15 mmol), N-[(2R)-3-chloro-2-hydroxy-propyl]-2-(cyclobutylamino)pyridine-4-carboxamide (52 mg, 0.18 mmol), TEA (47 mg, 0.46 mmol) and NaI (28 mg, 0.19 mmol) in MeCN (2 mL) was stirred at 90° C. for 12 hours in a sealed tube. The mixture was filtered and concentrated under reduced pressure. The residue was purified by preparative HPLC (Instrument: Gilson GX-281 Liquid Handler, Gilson 322 Pump, Gilson 156 UV Detector; Column: Waters Xbridge 150 mm*50 mm, 10 μm; Mobile phase A: water (0.05% ammonia hydroxide v/v); Mobile phase B: MeCN; Gradient: B from 29% to 59% in 9.5 min, hold 100% B for 3 min; Flow Rate: 25 mL/min; Column Temperature: 30° C.; Wavelength: 220 nm, 254 nm) to afford 2-(cyclobutylamino)-N-[(2R)-3-[8-fluoro-5-methyl-6-(oxazol-5-ylmethoxy)-3,4-dihydro-1H-isoquinolin-2-yl]-2-hydroxy-propyl]pyridine-4-carboxamide (29 mg, 37.3% yield) as a white solid. $^1$H NMR (400 MHz, methanol-$d_4$) δ ppm 8.24 (s, 1H), 7.89 (d, J=5.3 Hz, 1H), 7.24 (s, 1H), 6.78 (s, 1H), 6.70-6.77 (m, 1H), 5.12 (s, 2H), 4.22 (quin, J=7.8 Hz, 1H), 4.08 (quin, J=6.0 Hz, 1H), 3.67 (s, 2H), 3.41-3.53 (m, 2H), 2.85 (dd, J=5.5, 2.3 Hz, 2H), 2.73-2.79 (m, 2H), 2.67 (t, J=5.6 Hz, 2H), 2.35-2.47

(m, 2H), 2.01 (s, 3H), 1.86-1.95 (m, 2H), 1.71-1.82 (m, 2H); $^{19}$F NMR (400 MHz, methanol-d$_4$) δ ppm −123.981; LCMS (ESI) [M+H]$^+$ m/z: calcd 510.2. found 510.1; HPLC: 100% @ 254 nm; 99.5% ee.

2-(cyclobutylamino)-N-[(2S)-3-[8-fluoro-5-methyl-6-(oxazol-5-ylmethoxy)-3,4-dihydro-1H-isoquinolin-2-yl]-2-hydroxy-propyl]pyridine-4-carboxamide (Compound 341)

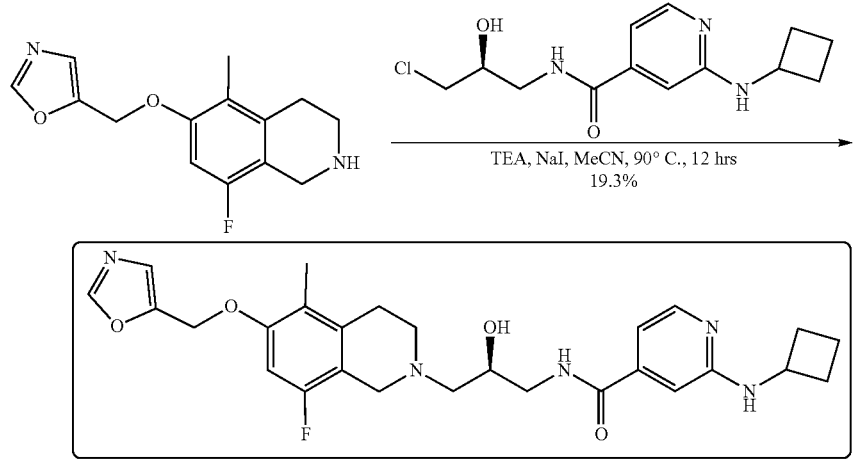

A mixture of 5-[(8-fluoro-5-methyl-1,2,3,4-tetrahydroisoquinolin-6-yl)oxymethyl]oxazole (40 mg, 0.153 mmol), N-[(2S)-3-chloro-2-hydroxy-propyl]-2-(cyclobutylamino) pyridine-4-carboxamide (52 mg, 0.183 mmol), TEA (47 mg, 0.464 mmol) and NaI (28 mg, 0.187 mmol) in MeCN (2 mL) was stirred at 90° C. for 12 hours in a sealed tube. The mixture was concentrated under reduced pressure to give a crude product, which was purified by preparative HPLC (Instrument: Gilson GX-281 Liquid Handler, Gilson 322 Pump, Gilson 156 UV Detector; Column: Waters Xbridge 150×50 mm×10 µm; Mobile phase A: H$_2$O with 0.05% NH$_3$—H$_2$O (v %); Mobile phase B: MeCN; Gradient: B from 25% to 55% in 10.5 min, hold 100% B for 2 min; Flow Rate: 25 mL/min; Column Temperature: 30° C.; Wavelength: 220 nm, 254 nm) to give a crude product (~20 mg) which was further purified by preparative HPLC (Instrument: Gilson GX-281 Liquid Handler, Gilson 322 Pump, Gilson 156 UV Detector; Column: Xtimate C18 150×25 mm×5 µm; Mobile phase A: H$_2$O with 10 mmol NH$_4$HCO$_3$ (v %); Mobile phase B: MeCN; Gradient: B from 32% to 62% in 8.5 min, hold 100% B for 2 min; Flow Rate: 25 mL/min; Column Temperature: 30° C.; Wavelength: 220 nm, 254 nm) to give 2-(cyclobutylamino)-N-[(2S)-3-[8-fluoro-5-methyl-6-(oxazol-5-ylmethoxy)-3,4-dihydro-1H-isoquinolin-2-yl]-2-hydroxy-propyl]pyridine-4-carboxamide (15 mg, 19.3% yield) as a white dry powder. $^1$H NMR (400 MHz, methanol-d$_4$) δ ppm 8.25 (s, 1H), 7.89 (d, J=5.1 Hz, 1H), 7.24 (s, 1H), 6.78 (s, 1H), 6.71-6.77 (m, 2H), 5.12 (s, 2H), 4.22 (quin, J=7.8 Hz, 1H), 4.08 (quin, J=6.0 Hz, 1H), 3.67 (s, 2H), 3.43-3.49 (m, 2H), 2.80-2.91 (m, 2H), 2.73-2.79 (m, 2H), 2.62-2.72 (m, 2H), 2.35-2.45 (m, 2H), 2.01 (s, 3H), 1.87-1.98 (m, 2H), 1.72-1.83 (m, 2H); $^{19}$F NMR (376 MHz, methanol-d$_4$) δ ppm −123.965; LCMS (ESI) [M+H]$^+$ m/z: calcd 510.2. found 510.2; HPLC: 98.98% @ 254 nm; 99.6% ee.

Example 1A9. 2-(cyclobutylamino)-N-[(2S)-3-[8-fluoro-6-(oxazol-5-ylmethoxy)-3N-dihydro-1H-isoquinolin-2-yl]-2-hydroxy-propyl]pyridine-4-carboxamide (Compound 362)

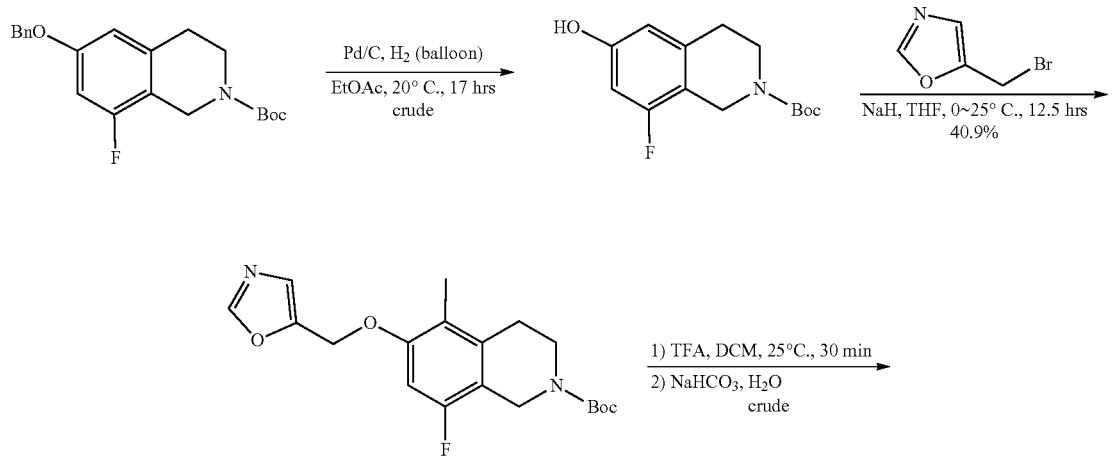

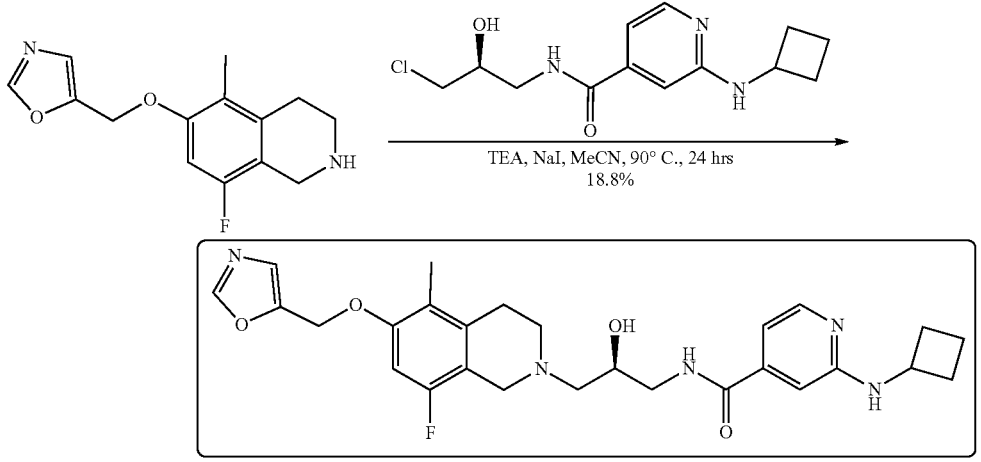

tert-butyl 8-fluoro-6-hydroxy-3,4-dihydro-1H-isoquinoline-2-carboxylate. To a solution of tert-butyl 6-benzyloxy-8-fluoro-3,4-dihydro-1H-isoquinoline-2-carboxylate (250 mg, 0.699 mmol) in EtOAc (5 mL) was added Pd/C (120 mg, 10% wt of Pd with 50% wt of water). The mixture was degassed and backfilled with hydrogen for three times. Then the mixture was stirred at 25° C. for 17 hours under hydrogen (~15 psi, in balloon). The mixture was filtered and concentrated under reduced pressure to give tert-butyl 8-fluoro-6-hydroxy-3,4-dihydro-1H-isoquinoline-2-carboxylate (200 mg, crude) as a yellow oil. $^1$H NMR (400 MHz, methanol-$d_4$) δ ppm 6.35-6.43 (m, 2H), 4.44 (s, 2H), 3.59 (t, J=5.0 Hz, 2H), 2.74 (t, J=5.9 Hz, 2H), 1.49 (s, 9H); LCMS (ESI) [M+H+MeCN-56]$^+$ m/z: calcd 253.1. found 253.0.

tert-butyl 8-fluoro-6-(oxazol-5-ylmethoxy)-3,4-dihydro-1H-isoquinoline-2-carboxylate. To a solution of tert-butyl 8-fluoro-6-hydroxy-3,4-dihydro-1H-isoquinoline-2-carboxylate (150 mg, 0.561 mmol) in THF (5 mL) was added NaH (100 mg, 2.61 mmol, 60% wt in mineral oil) at 0° C. and the mixture was stirred at 0° C. for 30 minutes. Then a solution of 5-(bromomethyl)oxazole in THF (4 mF) was added and the mixture was stirred at 25° C. for 12 hours. The mixture was quenched by addition of water (10 mF), and extracted with EtOAc (10 mF*2). The combined organic layers were dried over anhydrous $Na_2SO_4$, filtered and concentrated under reduced pressure to give a crude product which was purified by flash chromatography (ISCO®; 20 g AgelaFlash® Silica Flash Column, petroleum ether/EtOAc with EtOAc from 0~40%, flow rate=30 mF/min) to afford tert-butyl 8-fluoro-6-(oxazol-5-ylmethoxy)-3,4-dihydro-1H-isoquinoline-2-carboxylate (80 mg, 40.9% yield) as a yellow oil. LCMS(ESI) [M+H+MeCN-56]$^+$ m/z: calcd 334.1. found 334.0.

5-[(8-fluoro-1,2,3,4-tetrahydroisoquinolin-6-yl)oxymethyl]oxazole. A mixture of tert-butyl 8-fluoro-6-(oxazol-5-ylmethoxy)-3,4-dihydro-1H-isoquinoline-2-carboxylate (80 mg, 0.23 mmol) and TFA (264 mg, 2.31 mmol) in DCM (3 mF) was stirred at 25° C. for 30 minutes. The mixture was filtered and concentrated under reduced pressure. The residue was quenched by addition of water (20 mF) and washed with DCM (20 mF*3). The aqueous layer was adjusted to pH=7-8 by saturated $NaHCO_3$ aqueous solution, and then extracted with DCM (20 mF*3). The combined organic phase was washed with saturated $NH_4Cl$ aqueous solution (10 mF*2), dried over anhydrous $Na_2SO_4$, filtered and concentrated under reduced pressure to afford 5-[(8-fluoro-1,2,3,4-tetrahydroisoquinolin-6-yl)oxymethyl]oxazole (60 mg, crude) as a yellow oil. 40 mg of this crude product was used in next step directly. The rest 20 mg was further purified by preparative HPFC (Instrument: Gilson GX-281 Liquid Handler, Gilson 322 Pump, Gilson 156 UV Detector; Column: Waters Xtimate 150*50 mm*5 μm; Mobile phase A: water (10 mM $NH_4HCO_3$); Mobile phase B: MeCN; Gradient: B from 30% to 60% in 8.5 min, hold 100% B for 2 min; Flow Rate: 25 mF/min; Column Temperature: 30° C.; Wavelength: 220 nm, 254 nm) to afford 5-[(8-fluoro-1,2,3,4-tetrahydroisoquinolin-6-yl)oxymethyl]oxazole (4 mg) as a yellow oil. $^1$H NMR (400 MHz, methanol-$d_4$) δ ppm 8.23 (s, 1H), 7.24 (s, 1H), 6.54-6.69 (m, 2H), 5.11 (s, 2H), 3.88 (s, 2H), 3.05 (t, J=5.9 Hz, 2H), 2.81 (t, J=6.0 Hz, 2H); $^{19}$F NMR (376 MHz, methanol-$d_4$) δ ppm −120.997; LCMS (ESI) [M+H]$^+$ m/z: calcd 249.1. found 249.1; HPLC: 91.85%@220 nm.

2-(cyclobutylamino)-N-[(2S)-3-[8-fluoro-6-(oxazol-5-ylmethoxy)-3,4-dihydro-1H-isoquinolin-2-yl]-2-hydroxypropyl]pyridine-4-carboxamide. A mixture of 5-[(8-fluoro-1,2,3,4-tetrahydroisoquinolin-6-yl)oxymethyl]oxazole (20 mg, 80.6 umol), N-[(2S)-3-chloro-2-hydroxy-propyl]-2-(cyclobutylamino)pyridine-4-carboxamide (27 mg, 95.2 umol), TEA (25 mg, 0.247 mmol), NaI (15 mg, 0.10 mmol) in MeCN (2 mL) was stirred at 90° C. for 12 hours in a sealed tube. Another batch of N-[(2S)-3-chloro-2-hydroxy-propyl]-2-(cyclobutylamino)pyridine-4-carboxamide (27 mg, 95.2 umol) was added and the mixture was stirred at 90° C. for 12 hours. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: $H_2O$ with 0.04% $NH_3$—$H_2O$ (v %); Mobile phase B: MeCN; Gradient: B from 30% to 60% in 8 min, hold 100% B for 2 min; Flow Rate: 25 mL/min; Column Temperature: 30° C.; Wavelength: 220 nm, 254 nm) to afford 2-(cyclobutylamino)-N-[(2S)-3-[8-fluoro-6-(oxazol-5-ylmethoxy)-3,4-dihydro-1H-isoquinolin-2-yl]-2-hydroxy-propyl]pyridine-4-carboxamide (7.5 mg, 18.8% yield) as off-white solid. $^1$H NMR (400 MHz, methanol-$d_4$) δ ppm 8.26 (s, 1H), 7.94 (d, J=5.5 Hz, 1H), 7.27 (s, 1H), 6.81 (s, 1H), 6.78 (dd, J=5.5, 1.5 Hz, 1H), 6.58-6.68 (m, 2H), 5.13 (s, 2H), 4.25 (quin, J=7.8 Hz, 1H), 4.10 (quin, J=6.0 Hz, 1H), 3.68 (s, 2H), 3.51-3.57 (m, 1H), 3.41-3.48 (m, 1H), 2.82-2.95 (m, 4H), 2.64-2.74

(m, 2H), 2.38-2.47 (m, 2H), 1.89-2.01 (m, 2H), 1.74-1.85 (m, 2H); LCMS (ESI) [M+H]+ m/z calcd 496.2. found 496.1; HPLC: 100% @ 254 nm; 99.5% ee.

Example 1A10. 2-(cyclobutylamino)-N-[(2S)-3-[7,8-difluoro-6-(oxazol-5-ylmethoxy)-3N-dihydro-1H-isoquinolin-2-yl]-2-hydroxy-propyl]pyridine-4-carboxamide (Compound 364)

organic layer was washed with brine (30 mL), dried over anhydrous Na$_2$SO$_4$, filtered and concentrated under reduced pressure to a crude product which was purified by flash chromatography (ISCO®; 20 g AgelaFlash® Silica Flash Column, petroleum ether/EtOAc with EtOAc from 0~10%, 30 mL/min) to afford tert-butyl N-[2-(3,4-difluoro-5-methoxy-phenyl)ethyl]carbamate (1.45 g, crude) as a yellow solid. $^1$H NMR (400 MHz, methanol-d$_4$) δ ppm 6.77 (d, J=6.8 Hz, 1H), 6.64-6.73 (m, 1H), 3.89 (s, 3H), 3.25 (t, J=7.2

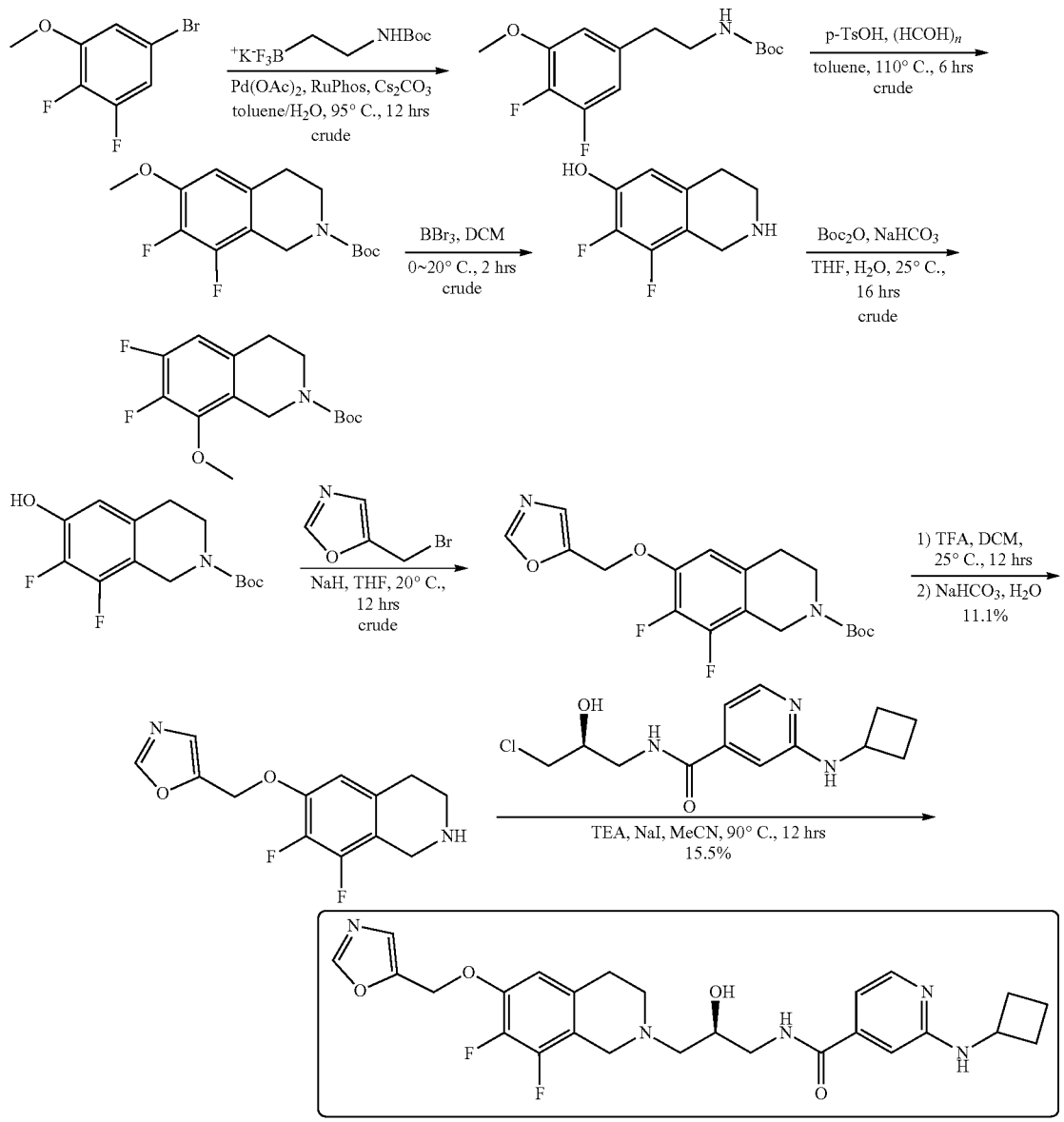

tert-butyl N-[2-(3,4-difluoro-5-methoxy-phenyl)ethyl]carbamate. A mixture of 5-bromo-1,2-difluoro-3-methoxybenzene (1.5 g, 6.73 mmol), potassium; tert-butyl N-(2-difluoroboranylethyl)carbamate fluoride (1.72 g, 6.86 mmol), Pd(OAc)$_2$ (76.5 mg, 0.341 mmol), RuPhos (315 mg, 0.675 mmol), Cs$_2$CO$_3$ (6.57 g, 0.202 mol), toluene (30 mL) and H$_2$O (10 mL) was degassed and purged with nitrogen for 3 times and stirred at 95° C. for 12 hours under nitrogen. The resulting mixture was quenched by addition of water (30 mL) and extracted with EtOAc (30 mL*3). The combined Hz, 2H), 2.71 (t, J=7.2 Hz, 2H), 1.41 (s, 9H); LCMS (ESI) [M+H−56]+ m/z: calcd 232.1, found 232.0.

tert-butyl 7,8-difluoro-6-methoxy-3,4-dihydro-1H-isoquinoline-2-carboxylate. To a solution of tert-butyl N-[2-(3,4-difluoro-5-methoxy-phenyl)ethyl]carbamate (1.45 g, 5.05 mmol) in toluene (20 mL) was added p-TsOH (130 mg, 0.755 mmol) and paraformaldehyde (517 mg, 0.152 mol), then the mixture was stirred at 110° C. for 6 hours. The mixture was concentrated under reduced pressure to give a crude product which was purified by flash chromatography (ISCO®; 40 g AgelaFlash® Silica Flash Column, petroleum ether/EtOAc with EtOAc from 0-13%, 30 mL/min) to afford P1 and P2.

- P1: tert-butyl 7,8-difluoro-6-methoxy-3,4-dihydro-1H-isoquinoline-2-carboxylate (400 mg, crude) was obtained as a white solid. $^1$H NMR (400 MHz, methanol-$d_4$) δ ppm 6.72 (d, J=7.0 Hz, 1H), 4.50 (s, 2H), 3.86 (s, 3H), 3.55-3.68 (m, 2H), 2.78 (t, J=5.8 Hz, 2H), 1.49 (s, 9H); LCMS (ESI) [M+H−56]$^+$ m/z: calcd 244.1. found 244.0.
- P2: tert-butyl 6,7-difluoro-8-methoxy-3,4-dihydro-1H-isoquinoline-2-carboxylate (500 mg, crude) was obtained as a white solid. LCMS (ESI) [M+H−56]$^+$ m/z: calcd 244.1. found 244.0.

7,8-difluoro-1,2,3,4-tetrahydroisoquinolin-6-ol. To a solution of tert-butyl 7,8-difluoro-6-methoxy-3,4-dihydro-1H-isoquinoline-2-carboxylate (200 mg, 0.668 mmol) in DCM (10 mL) was added BBr$_3$ (0.20 mL, 2.12 mmol) slowly at 0° C., then the mixture was stirred at 20° C. for 2 hours. The reaction mixture was concentrated under reduced pressure to give 7,8-difluoro-1,2,3,4-tetrahydroisoquinolin-6-ol (150 mg, crude, HBr salt) as a yellow solid. LCMS (ESI) [M+H]$^+$ m/z: calcd 186.1. found 186.1.

tert-butyl 7,8-difluoro-6-hydroxy-3,4-dihydro-1H-isoquinoline-2-carboxylate. To a mixture of 7,8-difluoro-1,2,3,4-tetrahydroisoquinolin-6-ol (150 mg, 0.564 mmol, HBr salt) in THF (5 mL) were added NaHCO$_3$ (142 mg, 1.69 mmol) and (Boc)$_2$O (0.153 mL, 0.667 mmol). The resulting mixture was stirred at 25° C. for 16 hours. The resulting mixture was quenched by addition of water (10 mL) and extracted with EtOAc (10 mL*3). The combined organic layer was washed with brine (10 mL), dried over anhydrous Na$_2$SO$_4$, filtered and concentrated under reduced pressure. The residue was purified by flash chromatography (ISCO®; 12 g Agela-Flash® Silica Flash Column, petroleum ether/EtOAc with EtOAc from 0~25%, flow rate=30 mL/min) to afford tert-butyl 7,8-difluoro-6-hydroxy-3,4-dihydro-1H-isoquinoline-2-carboxylate (160 mg, crude) as white solid. $^1$H NMR (400 MHz, methanol-$d_4$) δ ppm 6.53 (d, J=7.6 Hz, 1H), 4.47 (s, 2H), 3.55-3.60 (m, 2H), 2.70 (t, J=5.8 Hz, 2H), 1.49 (s, 9H); LCMS (ESI) [M+H+MeCN−56]$^+$ m/z: calcd 271.1. found 271.0.

tert-butyl 7,8-difluoro-6-(oxazol-5-ylmethoxy)-3,4-dihydro-1H-isoquinoline-2-carboxylate. To a solution of tert-butyl 7,8-difluoro-6-hydroxy-3,4-dihydro-1H-isoquinoline-2-carboxylate (160 mg, 0.561 mmol) in THF (5 mL) was added NaH (99 mg, 2.58 mmol, 60% wt in mineral oil) at 0° C. and the mixture was stirred at 0° C. for 30 minutes, then a solution of 5-(bromomethyl)oxazole in THF (4 mL) was added and the mixture was stirred at 25° C. for 12 hours. The mixture was quenched by addition of water (10 mL), and then extracted with EtOAc (10 mL*2). The combined organic layers were dried over anhydrous Na$_2$SO$_4$, filtered and concentrated under reduced pressure. The residue was purified by flash chromatography (ISCO®; 20 g Agela-Flash® Silica Flash Column, petroleum ether/EtOAc with EtOAc from 0~40%, flow rate=35 mL/min) to afford tert-butyl 7,8-difluoro-6-(oxazol-5-ylmethoxy)-3,4-dihydro-1H-isoquinoline-2-carboxylate (150 mg, crude) as a white solid. $^1$H NMR (400 MHz, methanol-$d_4$) δ ppm 8.25 (s, 1H), 7.27 (s, 1H), 6.87 (d, J=7.5 Hz, 1H), 5.21 (s, 2H), 4.51 (s, 2H), 3.63 (m, 2H), 2.79 (t, J=5.4 Hz, 2H), 1.49 (s, 9H); LCMS (ESI) [M+H−100]$^+$ m/z: calcd 267.1. found 267.1.

5-[(7′,8-difluoro-1,2,3,4-tetrahydroisoquinolin-6-yl)oxymethyl]oxazole. A mixture of tert-butyl 7,8-difluoro-6-(oxazol-5-ylmethoxy)-3,4-dihydro-1H-isoquinoline-2-carboxylate (150 mg, 0.409 mmol), TFA (0.013 mol, 1 mL) and DCM (5 mL) was stirred at 25° C. for 12 hours. The mixture was filtered and concentrated under reduced pressure. The residue was quenched by addition of water (20 mL) and adjusted to pH=8 by saturated NaHCO$_3$ aqueous solution, then extracted with DCM (50 mL*3). The combined organic layer was washed with saturated NH$_4$Cl aqueous solution (10 mL*2), dried over anhydrous Na$_2$SO$_4$, filtered and concentrated under reduced pressure to afford a crude product (190 mg) as yellow oil. 160 mg of this crude product was used in next step directly. The rest 30 mg was further purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% NH$_3$—H$_2$O (v %); Mobile phase B: MeCN; Gradient: B from 26% to 56% in 7.8 min, hold 100% B for 5 min; Flow Rate: 25 mL/min; Column Temperature: 30° C.; Wavelength: 220 nm, 254 nm) to give 5-[(7,8-difluoro-1,2,3,4-tetrahydroisoquinolin-6-yl)oxymethyl]oxazole (12.1 mg) as a white dry powder. $^1$H NMR (400 MHz, methanol-$d_4$) δ ppm 8.25 (s, 1H), 7.26 (s, 1H), 6.80 (d, J=6.8 Hz, 1H), 5.20 (s, 2H), 3.89 (s, 2H), 3.00-3.06 (m, 2H), 2.76 (t, J=5.9 Hz, 2H); $^{19}$F NMR (376 MHz, methanol-$d_4$) δ ppm −146.885, −146.936, −164.552; LCMS (ESI) [M+H]$^+$ m/z: calcd 267.1, found 267.0; HPLC: 98.27% @ 220 nm.

2-(cyclobutylamino)-N-[(2S)-3-[7,8-difluoro-6-(oxazol-5-ylmethoxy)-3,4-dihydro-1H-isoquinolin-2-yl]-2-hydroxy-propyl]pyridine-4-carboxamide (Compound 364)

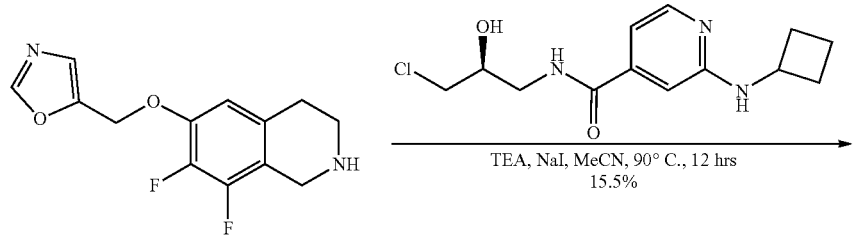

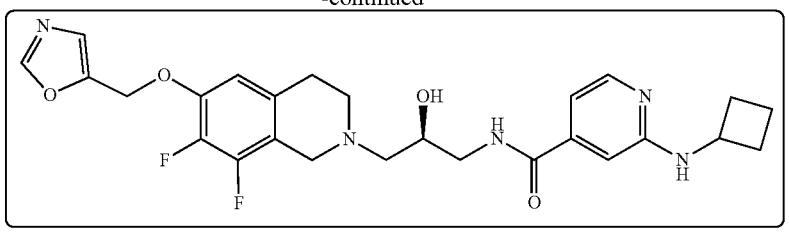

To a solution of 5-[(7,8-difluoro-1,2,3,4-tetrahydroisoquinolin-6-yl)oxymethyl]oxazole (60 mg, 0.188 mmol) and N-[(2S)-3-chloro-2-hydroxy-propyl]-2-(cyclobutylamino)pyridine-4-carboxamide (60 mg, 0.211 mmol) in MeCN (2 mL) were added TEA (0.574 mmol, 80 uL) and NaI (45 mg, 0.30 mmol) and the mixture was stirred for 12 hours at 90° C. The mixture was concentrated under reduced pressure and the residue was purified with preparative HPLC (Instrument: Gilson GX-281 Liquid Handler, Gilson 322 Pump, Gilson 156 UV Detector; Column: Xtimate C18 150×25 mm×5 μm; Mobile phase A: H$_2$O with 0.10% NH$_4$HCO$_3$ (v %); Mobile phase B: MeCN; Gradient: B from 26% to 56% in 8.5 min, hold 100% B for 2 min; Flow Rate: 25 mL/min; Column Temperature: 30° C.; Wavelength: 220 nm, 254 nm) to afford 2-(cyclobutylamino)-N-[(2S)-3-[7,8-difluoro-6-(oxazol-5-ylmethoxy)-3,4-dihydro-1H-isoquinolin-2-yl]-2-hydroxy-propyl]pyridine-4-carboxamide (15 mg, 15.5% yield) as white solid. $^1$H NMR (400 MHz, methanol-d$_4$) δ ppm 8.25 (s, 1H), 7.94 (dd, J=5.4, 0.7 Hz, 1H), 7.26 (s, 1H), 6.76-6.82 (m, 3H), 5.20 (s, 2H), 4.19-4.23 (m, 1H), 4.04-4.10 (m 1H), 3.68 (s, 2H), 3.50-3.56 (m, 1H), 3.38-3.44 (m, 1H), 2.79-2.88 (m, 4H), 2.61-2.71 (m, 2H), 2.36-2.46 (m, 2H), 1.87-1.99 (m, 2H), 1.72-1.83 (m, 2H); $^{19}$F NMR (376 MHz, methanol-d$_4$) δ ppm −146.648, −146.704, −164.794; LCMS (ESI) [M+H]$^+$ m/z: calcd 514.2. found 514.2; HPLC: 100%@254 nm; 99.5% ee.

Example 1A11. 2-(cyclobutylamino)-N-[(2S)-3-[8-fluoro-5-methyl-6-[(4-methyloxazol-5-yl)methoxy]-3N-dihydro-1H-isoquinolin-2-yl]-2-hydroxy-propyl]pyridine-4-carboxamide Compound 619

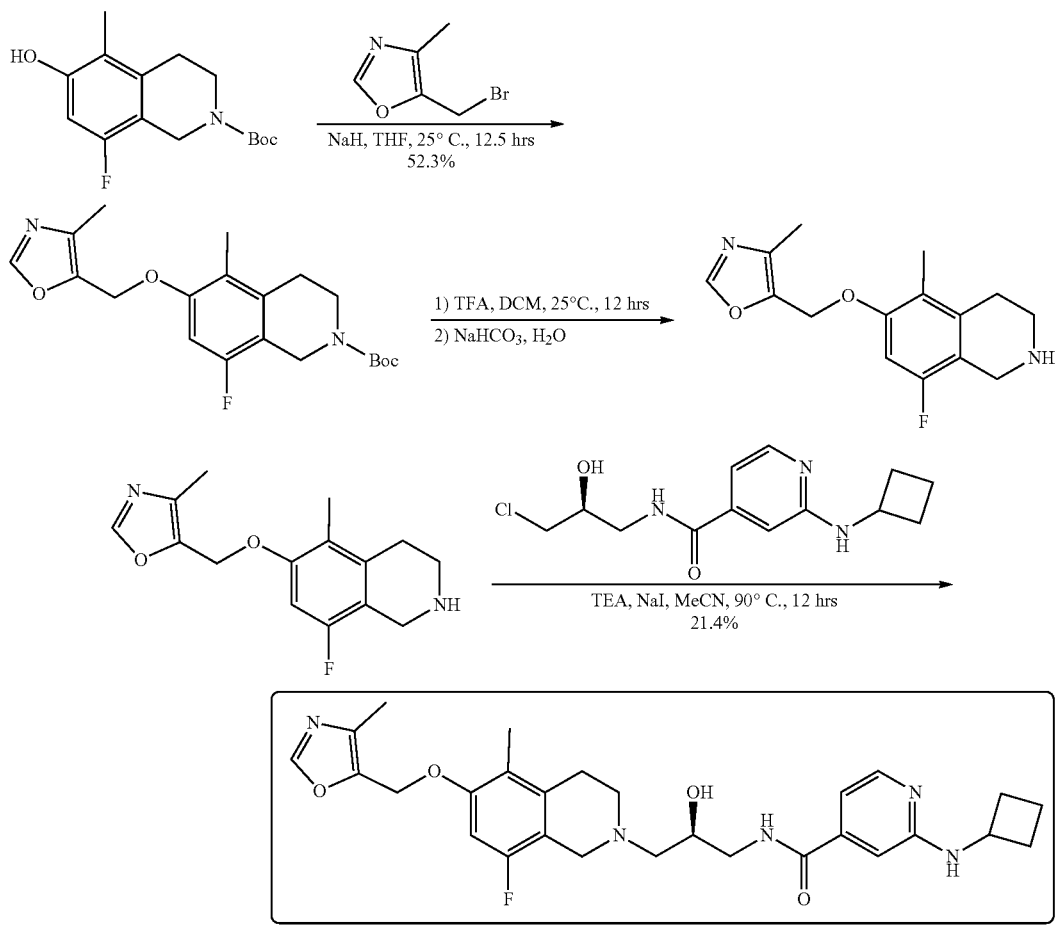

(4-methyloxazol-5-yl)methanol. To a solution of ethyl 4-methyloxazole-5-carboxylate (5 g, 32.2 mmol) in THF (30 mL) was added LAH (1.50 g, 39.5 mmol) at 0° C. in portions. The mixture was stirred at 0° C. for 30 minutes. The resulting mixture was quenched by addition of water (1.5 mL), NaOH aqueous solution (1.5 mL, 15% wt) and water (4.5 mL). The mixture was dried over anhydrous $Na_2SO_4$, filtered and concentrated under reduced pressure to afford (4-methyloxazol-5-yl)methanol (2.9 g, 79.6% yield) as yellow oil. $^1$H NMR (400 MHz, methanol-$d_4$) δ ppm 8.09 (s, 1H), 4.58 (s, 2H), 2.20 (s, 3H).

5-(bromomethyl)-4-methyl-oxazole. To a solution of (4-methyloxazol-5-yl)methanol (1 g, 8.84 mmol) in DCM (10 mL) were added NBS (1.60 g, 8.99 mmol) and triphenylphosphine (2.40 g, 9.15 mmol) at 0° C. The mixture was stirred at 25° C. for 1 hour. The resulting mixture was concentrated under reduced pressure and the residue was purified by flash chromatography (ISCO®; 40 g AgelaFlash® Silica Flash Column, petroleum ether/EtOAc with EtOAc from 0~20%, Flow rate: 30 mL/min) to afford 5-(bromomethyl)-4-methyl-oxazole (1.4 g, 90.0% yield) as colorless oil. LCMS (ESI) [M+H]$^+$ m/z: calcd 176.0. found 175.9.

tert-butyl 8-fluoro-5-methyl-6-[(4-methyloxazol-5-yl)methoxy]-3,4-dihydro-1H-isoquinoline-2-carboxylate. To a solution of tert-butyl 8-fluoro-6-hydroxy-5-methyl-3,4-dihydro-1H-isoquinoline-2-carboxylate (1 g, 3.55 mmol) in THF (5 mL) was added NaH (450 mg, 11.6 mmol, 60% wt in mineral oil). The mixture was stirred at 25° C. for 30 minutes. Then 5-(bromomethyl)-4-methyl-oxazole (1.6 g, 9.09 mmol) was added and the mixture was stirred at 25° C. for 12 hours. The resulting mixture was quenched by addition of saturated $NH_4Cl$ aqueous solution (20 mL) and extracted with EtOAc (50 mL*3), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~20%, Flow rate: 30 mL/min) to afford tert-butyl 8-fluoro-5-methyl-6-[(4-methyloxazol-5-yl)methoxy]-3,4-dihydro-1H-isoquinoline-2-carboxylate (700 mg, 52.3% yield) as yellow oil and recover tert-butyl 8-fluoro-6-hydroxy-5-methyl-3,4-dihydro-1H-isoquinoline-2-carboxylate was recycled (500 mg) as white solid. $^1$H NMR (400 MHz, methanol-$d_4$) δ ppm 8.16 (s, 1H), 6.82 (d, J=11.5 Hz, 1H), 5.10 (s, 2H), 4.51 (s, 2H), 3.66 (br s, 2H), 2.74 (t, J=6.0 Hz, 2H), 2.21 (s, 3H), 2.05 (s, 3H), 1.51 (s, 9H); $^{19}$F NMR (376 MHz, methanol-$d_4$) δ ppm −123.809, −123.966; LCMS (ESI) [M+H−56]$^+$ m/z: calcd 321.2. found 321.0.

5-[(8-fluoro-5-methyl-1,2,3,4-tetrahydroisoquinolin-6-yl)oxymethyl]-4-methyl-oxazole. To a solution of tert-butyl 8-fluoro-5-methyl-6-[(4-methyloxazol-5-yl)methoxy]-3,4-dihydro-1H-isoquinoline-2-carboxylate (700 mg, 1.86 mmol) in DCM (10 mL) was added TFA (1.5 mL, 19.5 mmol). The mixture was stirred at 25° C. for 12 hours. The resulting mixture was quenched by addition of saturated $NaHCO_3$ aqueous solution (15 mL) and extracted with a mixture of DCM/MeOH (30 mL*4, 10:1, v/v). The combined organic layer was dried over anhydrous $Na_2SO_4$, filtered and concentrated under reduced pressure to afford 5-[(8-fluoro-5-methyl-1,2,3,4-tetrahydroisoquinolin-6-yl)oxymethyl]-4-methyl-oxazole (500 mg, 97.3% yield) as yellow oil. 15 mg of this crude product was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: $H_2O$ with 0.225 FA(v %); Mobile phase B: MeCN; Gradient: B from 35% to 51% in 7.8 min, hold 100% B for 2.5 min; Flow Rate: 25 mL/min; Column Temperature: 30° C.; Wavelength: 220 nm, 254 nm) to afford 5-[(8-fluoro-5-methyl-1,2,3,4-tetrahydroisoquinolin-6-yl)oxymethyl]-4-methyl-oxazole (4.5 mg, 0.75 HCOOH) as a off white solid. $^1$H NMR (400 MHz, methanol-$d_4$) δ ppm 8.52 (br s, 0.75 H), 8.15 (s, 1H), 6.91 (br d, J=11.8 Hz, 1H), 5.12 (s, 2H), 4.22 (s, 2H), 3.43 (brt, J=6.1 Hz, 2H), 2.93 (br t, J=5.8 Hz, 2H), 2.20 (s, 3H), 2.05 (s, 3H); $^{19}$F NMR (376 MHz, methanol-$d_4$) δ ppm −122.823; LCMS (ESI) [M+H]$^+$ m/z: calcd 277.1. found 277.1; HPLC: 100% @220 nm.

2-(cyclobutylamino)-N-[(2S)-3-[8-fluoro-5-methyl-6-[(4-methyloxazol-5-yl)methoxy]-3,4-dihydro-1H-isoquinolin-2-yl]-2-hydroxy-propyl]pyridine-4-carboxamide

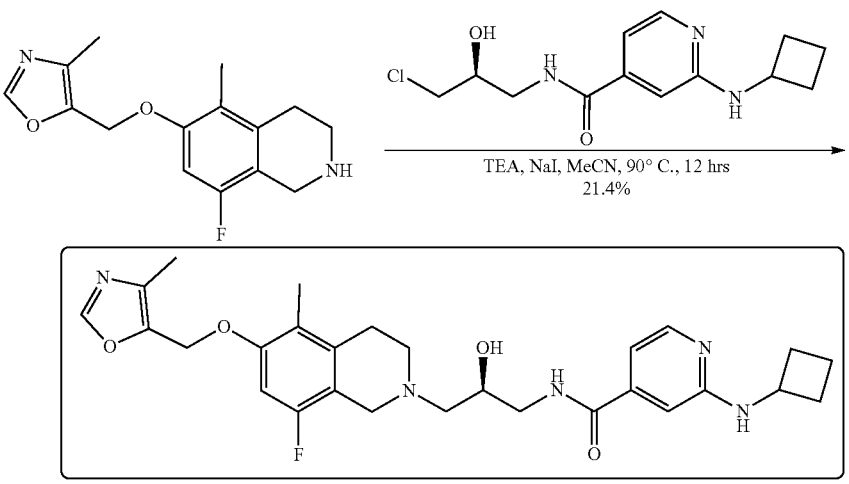

To a solution of 5-[(8-fluoro-5-methyl-1,2,3,4-tetrahydroisoquinolin-6-yl)oxymethyl]-4-methyl-oxazole (40 mg, 0.145 mmol) and N-[(2S)-3-chloro-2-hydroxy-propyl]-2-(cyclobutylamino)pyridine-4-carboxamide (50 mg, 0.176 mmol) in MeCN (2 mL) were added NaI (24 mg, 0.160 mmol) and TEA (44 mg, 0.434 mmol). The mixture was stirred at 90° C. for 12 hours. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% ammonia hydroxide (v %); Mobile phase B: MeCN; Gradient: B from 25% to 55% in 7.8 min, hold 100% B for 2.5 min; Flow Rate: 25 mL/min; Column Temperature: 30° C.; Wavelength: 220 nm, 254 nm) to afford 2-(cyclobutylamino)-N-[(2S)-3-[8-fluoro-5-methyl-6-[(4-methyloxazol-5-yl)methoxy]-3,4-dihydro-1H-isoquinolin-2-yl]-2-hydroxy-propyl]pyridine-4-carboxamide (16.2 mg, 21.4% yield) as yellow solid. $^1$H NMR (400 MHz, methanol-d$_4$) δ ppm 8.14 (s, 1H), 7.89 (d, J=5.0 Hz, 1H), 6.79 (s, 1H), 6.71-6.76 (m, 2H), 5.07 (s, 2H), 4.22 (quin, J=7.9 Hz, 1H), 4.08 (quin, J=6.0 Hz, 1H), 3.67 (s, 2H), 3.42-3.51 (m, 2H), 2.80-2.91 (m, 2H), 2.73-2.78 (m, 2H), 2.61-2.71 (m, 2H), 2.34-2.45 (m, 2H), 2.19 (s, 3H), 1.99 (s, 3H), 1.87-1.95 (m, 2H), 1.73-1.82 (m, 2H); $^{19}$F NMR (376 MHz, methanol-d$_4$) δ ppm −124.068; LCMS (ESI) [M+H]$^+$ m/z: calcd 524.3. found 524.2; HPLC: 98.89% @ 254 nm; 100% ee.

Example 1A12. (S)-2-(cyclobutylamino)-N-(3-(7-fluoro-6-((4-methyloxazol-5-yl)methoxy)-3N-dihydroisoquinolin-2(1H)-yl)-2-hydroxypropyl)isonicotinamide (Compound 266)

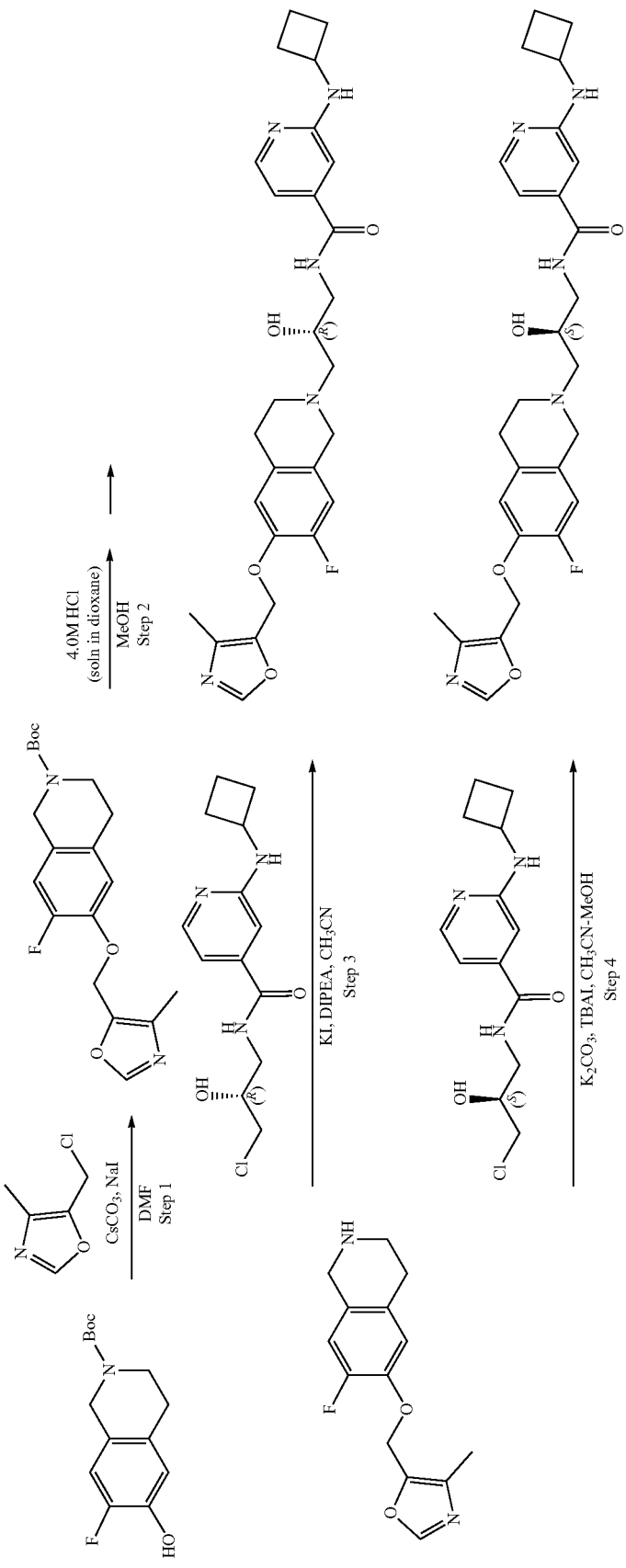

7-fluoro-1,2,3,4-tetrahydroisoquinolin-6-ol. A solution of 7-fluoro-6-methoxy-1,2,3,4-tetrahydroisoquinoline (0.3 g, 1.38 mmol, HCl) in hydrobromic acid, 48% (5 g, 61.80 mmol, 3.36 mL) was stirred at 140° C. for 12 hr and evaporated in vacuo. The residue was triturated with EtOAc and filtered to obtain 7-fluoro-1,2,3,4-tetrahydroisoquinolin-6-ol (0.25 g, 1.01 mmol, 73.11% yield, HBr). $^1$H NMR (500 MHz, DMSO-$d_6$) δ (ppm) 2.87 (t, 2H), 3.31 (t, 2H), 4.13 (s, 2H), 6.77 (d, 1H), 7.04 (d, 1H), 9.01 (s, 1H), 9.90 (s, 1H). LCMS(ESI): [M+H]$^+$ m/z: calcd 167.1. found 168.2; Rt=0.56 min.

tert-butyl 7-fluoro-6-hydroxy-3,4-dihydroisoquinoline-2(1H)-carboxylate. To a suspension of 7-fluoro-1,2,3,4-tetrahydroisoquinolin-6-ol (1.9 g, 7.66 mmol, HBr) in THF (50 mL), triethylamine (1.55 g, 15.32 mmol, 2.13 mL) and di-tert-butyl dicarbonate (1.84 g, 8.42 mmol, 1.93 mL) were added. The reaction mixture was stirred at 25° C. for 12 hr, filtered and evaporated. The residue was taken up with water and extracted with DCM. The organic extract was dried over Na$_2$SO$_4$ and evaporated. The residue was triturated with hexane, filtered and dried to obtain tert-butyl 7-fluoro-6-hydroxy-3,4-dihydro-1H-isoquinoline-2-carboxylate (1.8 g, 6.73 mmol, 87.93% yield). $^1$H NMR (400 MHz, DMSO-$d_6$) δ (ppm) 1.40 (s, 9H), 2.62 (t, 2H), 3.47 (t, 2H), 4.34 (s, 2H), 6.69 (d, 1H), 6.95 (d, 1H), 9.63 (s, 1H). LCMS(ESI): [M-Boc]$^+$ m/z: calcd 167.1. found 168.2; Rt=1.37 min.

tert-butyl 7-fluoro-6-((4-methyloxazol-5-yl)methoxy)-3,4-dihydroisoquinoline-2(1H)-carboxylate. To the solution tert-butyl 7-fluoro-6-hydroxy-3,4-dihydro-1H-isoquinoline-2-carboxylate (0.7 g, 2.62 mmol), cesium carbonate (2.56 g, 7.86 mmol) and sodium iodide (78.51 mg, 523.77 umol, 21.39 uL) in DMF (10 mL), 5-(chloromethyl)-4-methyl-oxazole (660.03 mg, 3.93 mmol, HCl) was added. The resulting mixture was stirred at 45° C. for 12 h, taken up with water (80 mL) and extracted with MTBE (3*30 mL). The combined organic extract was washed with brine (2*50 mL), dried over Na$_2$SO$_4$ and evaporated in vacuo to obtain tert-butyl 7-fluoro-6-[(4-methyloxazol-5-yl)methoxy]-3,4-dihydro-1H-isoquinoline-2-carboxy late (0.9 g, 2.48 mmol, 94.83% yield). NMR(400 MHz, CDCl$_3$): δ (ppm) 1.46 (s, 9H), 2.23 (s, 3H), 2.72 (t, 2H), 3.59 (t, 2H), 4.44 (s, 2H), 5.02 (s, 2H), 6.79 (m, 2H), 7.78 (s, 1H). LCMS(ESI): [M-t-Bu]$^+$ m/z: calcd 306.1. found 306.2; Rt=1.52 min.

5-(((7-fluoro-1,2,3,4-tetrahydroisoquinolin-6-yl)oxy)methyl)-4-methyloxazole. tert-butyl 7-fluoro-6-[(4-methyloxazol-5-yl) methoxy]-3,4-dihydro-1H-isoquinoline-2-carboxy late was converted to 5-[(7-fluoro-1,2,3,4-tetrahydroisoquinolin-6-yl)oxymethyl]-4-methyl-oxazole (0.7 g, 2.09 mmol, 84.09% yield, 2HCl) using reaction conditions outlined in Step B from Example 1A. NMR(500 MHz, DMSO-$d_6$): δ (ppm) 2.14 (s, 3H), 2.95 (t, 2H), 3.30 (t, 2H), 4.12 (s, 2H), 5.19 (s, 2H), 7.14 (m, 2H), 8.31 (s, 1H), 9.70 (s, 2H). LCMS(ESI): [M+H]$^+$ m/z: calcd 262.1. found 263.2; Rt=0.84 min.

(S)-2-(cyclobutylamino)-N-(3-(7-fluoro-6-((4-methyloxazol-5-yl)methoxy)-3,4-dihydroisoquinolin-2(1H)-yl)-2-hydroxypropyl)isonicotinamide (Compound 266)

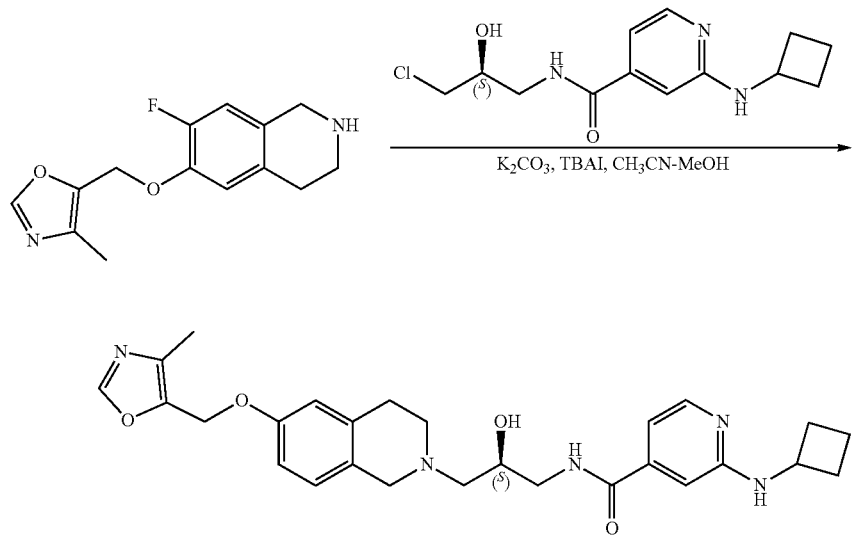

5-[(7-Fluoro-1,2,3,4-tetrahydroisoquinolin-6-yl)oxymethyl]-4-methyl-oxazole (100 mg, 298.33 umol, 2HCl) and A-[(2S)-3-chloro-2-hydroxy-propyl]-2-(cyclobutylamino) pyridine-4-carboxamide (76.96 mg, 271.21 umol) were dissolved in the mixture of methanol (2 mL) and acetonitrile (2 mL). Then, potassium carbonate-granular (123.70 mg, 894.99 umol) and tetrabutylammonium iodide (15.03 mg, 40.68 umol) were added and the reaction mixture was allowed to stir at 80° C. for 18 h. After the completion of the reaction (monitored by LCMS), the solvent was removed under reduced pressure and the obtained crude product was purified by preparative HPLC (Sunfire C18 100 mm A 9 mm, 5 um; mobile phase: water-ACN; B %: 0-1.9 min: 23%, 2-9 min: 30%-40%; stop time: 6 min; flow: 30 ml/min; loading pump: 4 ml/min.), affording 2-(cyclobutylamino)-N-[(2S)-3-[7-fluoro-6-[(4-methyloxazol-5-yl)methoxy]-3,4-dihydro-1H-isoquinolin-2-yl]-2-hydroxy-propyl]pyridine-4-carboxamide (19.4 mg, 38.07 umol, 14.04% yield). NMR(DMF-$d_7$, 500 MHz): δ (ppm) 1.79 (m, 2H), 1.88 (m, 2H), 2.21 (s, 3H), 2.46 (m, 2H), 2.54 (m, 1H), 2.62 (d, 1H), 2.73 (m, 2H), 2.84 (m, 2H), 2.95 (m, 1H), 3.41 (m, 2H), 3.55 (d, 1H), 3.75 (m, 2H), 4.03 (m, 1H), 4.18 (m, 1H), 4.90 (m, 1H), 5.06 (s, 2H), 6.71 (s, 1H), 6.76 (m, 3H), 7.82 (s, 1H), 8.12 (d, 1H). LCMS(ESI): [M+H]$^+$ m/z: calcd 509.2. found 510.2; Rt=0.82 min.

Example 1A13 (S)—N-(3-(6-((1H-1,2,3-triazol-4-yl)methoxy)-3,4-dihydroisoquinolin-2(1H)-yl)-2-hydroxypropyl)-2-(cyclobutylamino)isonicotinamide (Compound 207)

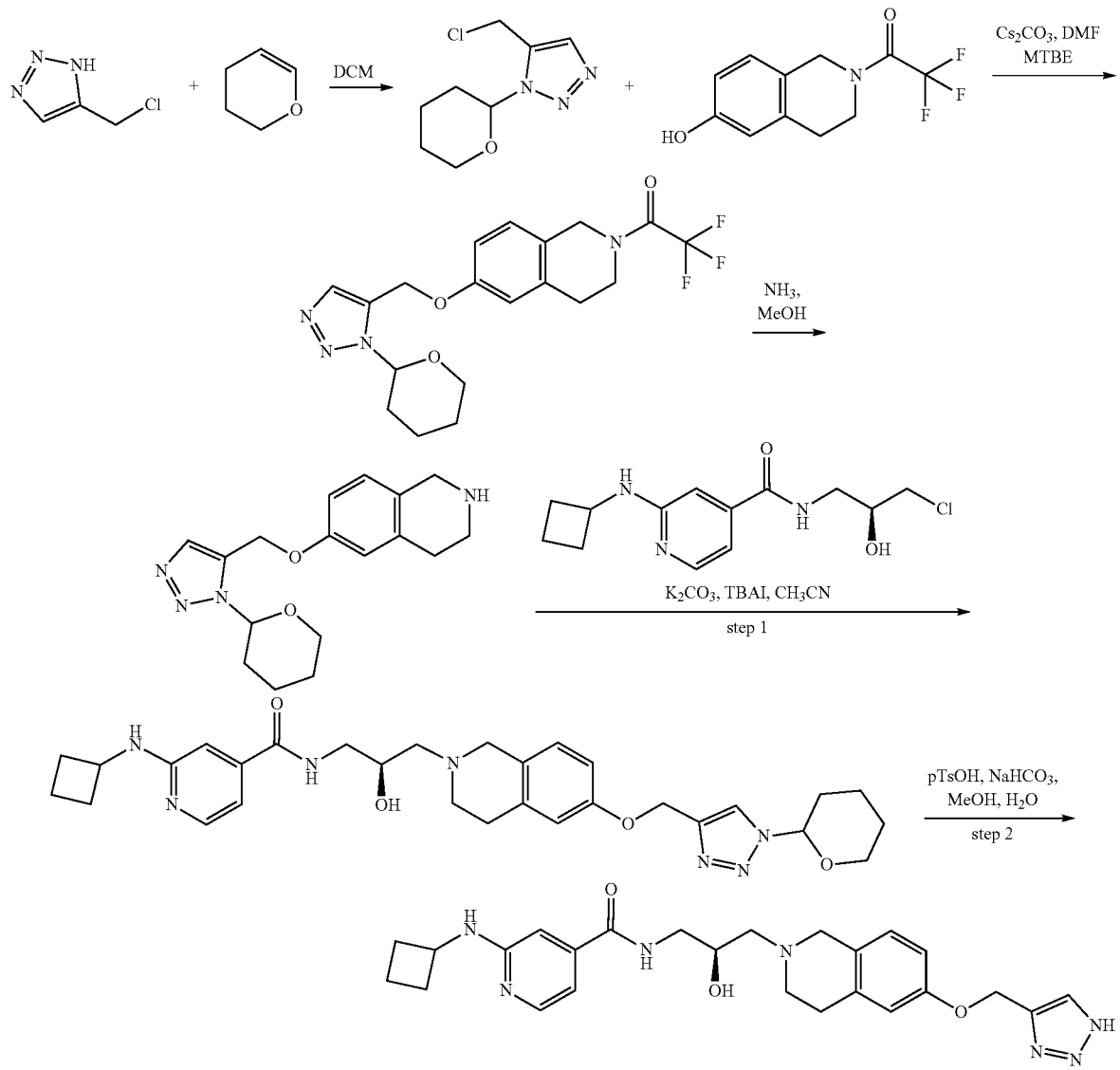

5-(chloromethyl)-1-(tetrahydro-2H-pyran-2-yl)-1H-1,2,3-triazole. To the stirred mixture of 5-(chloromethyl)-1H-triazole (0.5 g, 3.25 mmol, HCl) in DCM (10 mL) 3,4-dihydro-2H-pyran (819.32 mg, 9.74 mmol, 884.80 uL) was added. The mixture was stirred for 10 hr at 20° C. and evaporated in vacuo at 35° C. to give crude product, which was purified by column chromatography to give 5-(chloromethyl)-1-tetrahydropyran-2-yl-triazole (0.53 g, 2.63 mmol, 80.95% yield). $^1$H NMR (500 MHz, CDCl$_3$) δ (ppm) 1.64 (m, 1H), 1.73 (m, 2H), 2.08 (m, 2H), 2.38 (m, 1H), 3.73 (m, 1H), 4.04 (d, 1H), 4.67 (s, 2H), 5.68 (d, 1H), 7.69 (s, 1H). GCMS: [M+H]$^+$ m/z: calcd 201.1. found 202.1; Rt=2.32 min.

2,2,2-trifluoro-1-(6-((1-(tetrahydro-2H-pyran-2-yl)-1H-1,2,3-triazol-5-yl)methoxy)-3,4-dihydroisoquinolin-2(1H)-yl)ethanone. 2,2,2-Trifluoro-1-(6-hydroxy-3,4-dihydroiso- quinolin-2(1H)-yl)ethanone (585.86 mg, 2.39 mmol), 5-(chloromethyl)-1-(tetrahydro-2H-pyran-2-yl)-1H-1,2,3-triazole (0.53 g, 2.63 mmol) and cesium carbonate (1.17 g, 3.58 mmol) were mixed in DMF (10 mL) and the mixture was heated at 80° C. for 10 hr while stirring. Then the mixture was cooled to r.t. MTBE (100 mL) was added and the organic solution was washed with H$_2$O (5*30 mL). The organic layer was separated, dried with Na$_2$SO$_4$ and evaporated in vacuo at 35° C. to obtain crude 2,2,2-trifluoro-1-(6-((1-(tetrahydro-2H-pyran-2-yl)-1H-1,2,3-triazol-5-yl)methoxy)-3,4-dihydroisoquinolin-2(1H)-yl)ethanone (0.950 g, 2.31 mmol, 96.88% yield) which was used as is. $^1$H NMR (400 MHz, CDCl$_3$) δ (ppm) 1.64 (m, 2H), 2.10 (m, 2H), 2.77 (m, 2H), 2.84 (m, 1H), 3.13 (t, 2H), 3.80 (m, 2H), 3.96 (s, 2H), 4.05 (m, 1H), 4.72 (m, 1H), 5.14 (s, 2H), 5.70 (d, 1H), 6.66 (s, 1H), 6.79 (m, 1H), 7.01 (m, 1H), 7.71 (s, 1H). LCMS(ESI): [M+H]$^+$ m/z: calcd 410.1. found 411.1; Rt=0.93 min.

6-((1-(tetrahydro-2H-pyran-2-yl)-1H-1,2,3-triazol-5-yl)methoxy)-1,2,3,4-tetrahydroisoquinoline. 2,2,2-Trifluoro-1-[6-[(3-tetrahydropyran-2-yltriazol-4-yl)methoxy]-3,4-dihydro-1H-isoquinolin-2-yl]ethanone (0.95 g, 2.31 mmol) was dissolved in saturated methanolic ammonia (50 mL) and stirred at 20° C. for 10 hr. The solvent was evaporated in vacuo at 35° C. to obtain crude 6-[(3-tetrahydropyran-2-yltriazol-4-yl)methoxy]-1,2,3,4-tetrahydroisoquinoline (0.47 g, 1.49 mmol, 64.58% yield) which was used as is on the next step. $^1$H NMR (500 MHz, CDCl$_3$) δ (ppm) 1.64 (m, 1H), 1.72 (m, 2H), 2.09 (m, 2H), 2.42 (m, 1H), 2.72 (m, 1H), 2.77 (m, 2H), 3.12 (m, 2H), 3.73 (m, 1H), 3.96 (m, 2H), 4.05 (m, 1H), 5.14 (s, 2H), 5.69 (d, 1H), 6.71 (s, 1H), 6.77 (d, 1H), 6.85 (d, 1H), 6.93 (d, 1H), 7.71 (s, 1H). LCMS(ESI): [M+H]$^+$ m/z: calcd 314.1. found 315.2; Rt=0.96 min.

2-(cyclobutylamino)-N-((2S)-2-hydroxy-3-(6-((1-(tetrahydro-2H-pyran-2-yl)-1H-1,2,3-triazol-4-yl)methoxy)-3,4-dihydroisoquinolin-2(1H)-yl)propyl)isonicotinamide. 6-[(1-Tetrahydropyran-2-yltriazol-4-yl)methoxy]-1,2,3,4-tetrahydroisoquinoline (160 mg, 508.94 umol) and N-[(2S)-3-chloro-2-hydroxy-propyl]-2-(cyclobutylamino)pyridine-4-carboxamide (120.34 mg, 424.11 umol) were dissolved in acetonitrile (2.8 mL). Potassium carbonate (76.20 mg, 551.35 umol) and tetrabutylammonium iodide (23.50 mg, 63.62 umol) were added and the reaction mixture was allowed to stir at 80° C. for 18 hr. Then, the solvent was removed under reduced pressure and obtained 2-(cyclobutylamino)-N-[(2S)-2-hydroxy-3-[6-[(1-tetrahydropyran-2-yl-triazol-4-yl)methoxy]-3,4-dihydro-1H-isoquinolin-2-yl]propyl]pyridine-4-carboxamide (263 mg, crude) was used as is in the next step. LCMS(ESI): [M+2H]$^+$ m/z: calcd 561.3. found 563.2; Rt=0.94 min.

(S)—N-(3-(6-((1H-1,2,3-triazol-4-yl)methoxy)-3,4-dihydroisoquinolin-2(1H)-yl)-2-hydroxypropyl)-2-(cyclobutylamino)isonicotinamide. 2-(Cyclobutylamino)-N-[(2S)-2-hydroxy-3-[6-[(1-tetrahydropyran-2-yltriazol-4-yl)methoxy]-3,4-dihydro-1H-isoquinolin-2-yl]propyl] pyridine-4-carboxamide (22.7 mg, 40.41 umol) was dissolved in methanol (0.3 mL) and water (0.2 mL) was added, followed by the addition of p-Toluenesulfonic acid monohydrate (23.83 mg, 125.29 umol). The reaction mixture was heated to 65° C. and stirred for 18 hr. Then, it was cooled to 25° C. and Sodium hydrogen carbonate, 99% (10.52 mg, 125.29 umol) was added. The volatiles were removed in vacuo and th residue was purified by preparative HPLC, affording 2-(cyclobutylamino)-N-[(2S)-2-hydroxy-3-[6-(1H-triazol-4-ylmethoxy)-3,4-dihydro-1H-isoquinolin-2-yl]propyl]pyridine-4-carboxamide (3 mg, 6.28 umol, 15.54% yield). $^1$H NMR (500 MHz, CDCl$_3$) δ (ppm) 1.74 (m, 4H), 2.15 (m, 2H), 2.38 (m, 2H), 2.69 (m, 1H), 2.89 (m, 3H), 3.40 (m, 1H), 3.51 (m, 1H), 3.66 (m, 1H), 3.70 (m, 1H), 3.96 (m, 1H), 4.11 (m, 1H), 4.99 (m, 1H), 5.20 (s, 2H), 6.73 (m, 4H), 6.94 (d, 1H), 6.96 (m, 1H), 7.78 (s, 1H), 8.06 (t, 1H). LCMS(ESI): [M+H]$^+$ m/z: calcd 477.2. found 478.2; Rt=0.73 min.

Example 1A14. 2-(cyclobutylamino)-N-[(2S)-3-[7-fluoro-6-(oxazol-5-ylmethoxy)-3N-dihydro-1H-isoquinolin-2-yl]-2-hydroxy-propyl]pyridine-4-carboxamide (Compound 513)

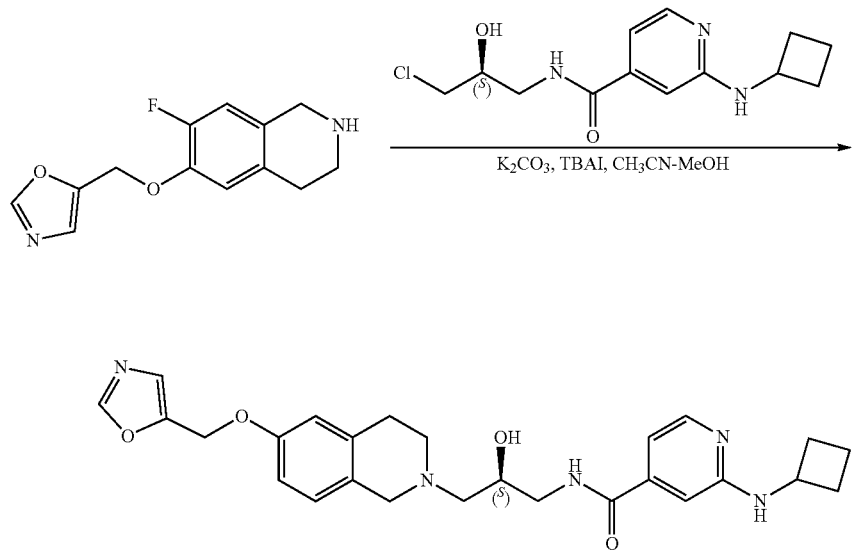

To the solution of 5-[(7-fluoro-1,2,3,4-tetrahydroisoquinolin-6-yl)oxymethyl]oxazole (100 mg, 351.23 umol, HCl) in EtOH (10 mL) Potassium carbonate, anhydrous, 99% (194.17 mg, 1.40 mmol, 84.79 uL) and Sodium iodide (10.53 mg, 70.25 umol, 2.87 uL) was added followed by addition of N-[(2S)-3-chloro-2-hydroxy-propyl]-2-(cyclobutylamino)pyridine-4-carboxamide (149.49 mg, 526.85 umol). The reaction mixture was stirred at 50° C. for 15 hr. EtOH was evaporated. The residue was purified by reverse phase HPLC (LC 11 Sample Info: 50-55% 0-5 min water-methanol, flow: 30 ml/min (loading pump 4 ml/min methanol), target mass 496.56; column: SunFire C18 100×19 mm, 5 um) to give 2-(cyclobutylamino)-N-[(2S)-3-[7-fluoro-6-(oxazol-5-ylmethoxy)-3,4-dihydro-1H-isoquinolin-2-yl]-2-hydroxy-propyl]pyridine-4-carboxamide (45 mg, 90.81 umol, 25.85% yield).

$^1$H NMR (400 MHz, DMSO-d$_6$) δ 1.66 (td, 2H), E85 (m, 2H), 2.26 (m, 2H), 2.44 (m, 1H), 2.72 (m, 4H), 3.16 (m, 1H), 3.38 (m, 1H), 3.53 (m, 2H), 3.85 (m, 1H), 4.25 (m, 1H), 4.82 (d, 1H), 5.19 (s, 2H), 6.76 (m, 2H), 6.94 (m, 2H), 7.03 (d, 1H), 7.33 (s, 1H), 7.96 (d, 1H), 8.31 (s, 1H), 8.42 (s, 1H), 8.45 (t, 1H).

LCMS(ESI): [M+H]$^+$ m/z: calcd 495.26. found 496.2; Rt=0.781 min.

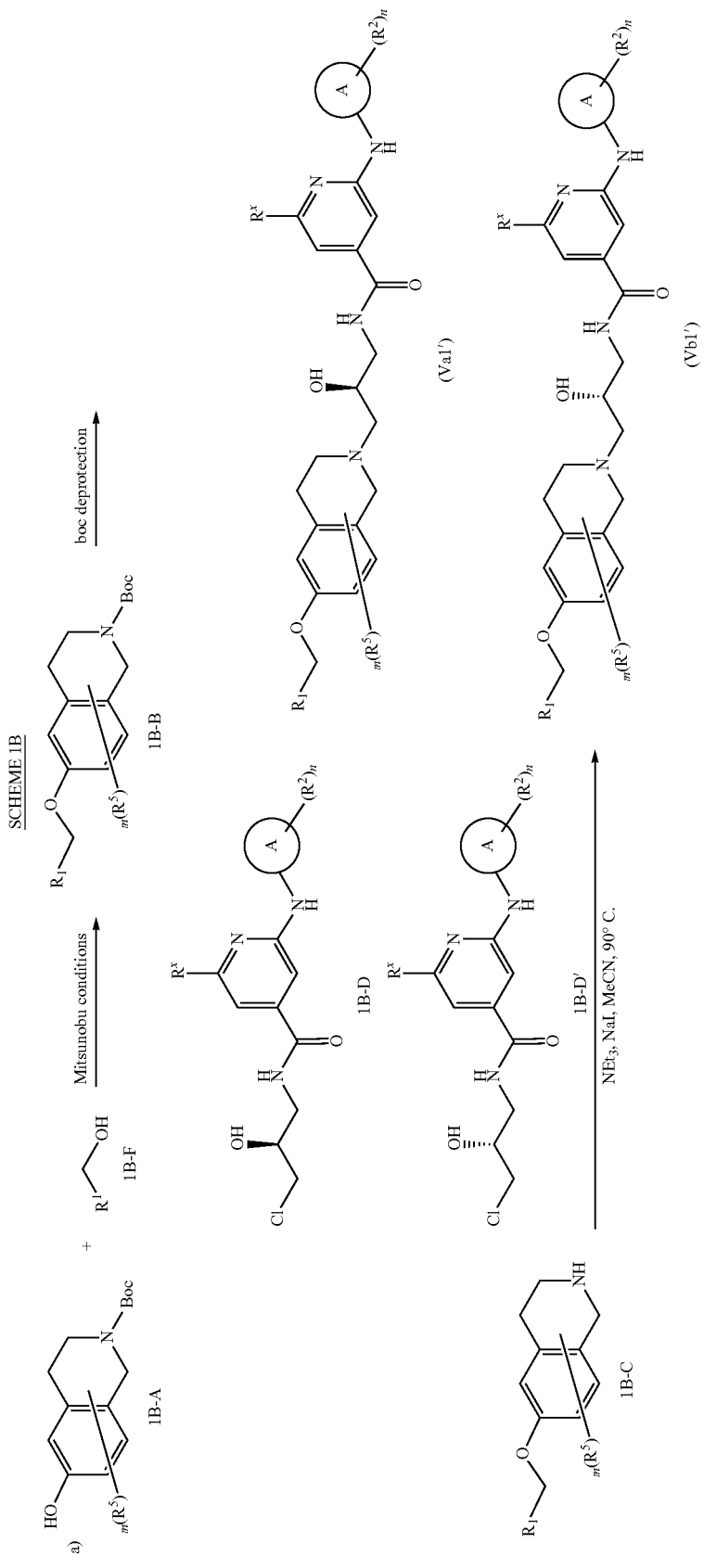

wherein variables $R^5$, $R^x$, $R^1$, $R^2$, m, and n are defined herein.

Example 1B1. Synthesis of 2-(cyclobutylamino)-N-[(2S)-2-hydroxy-3-[6-(oxazol-5-ylmethoxy)-3,4-dihydro-1H-isoquinolin-2-yl]propyl]benzamide (Compound 74)

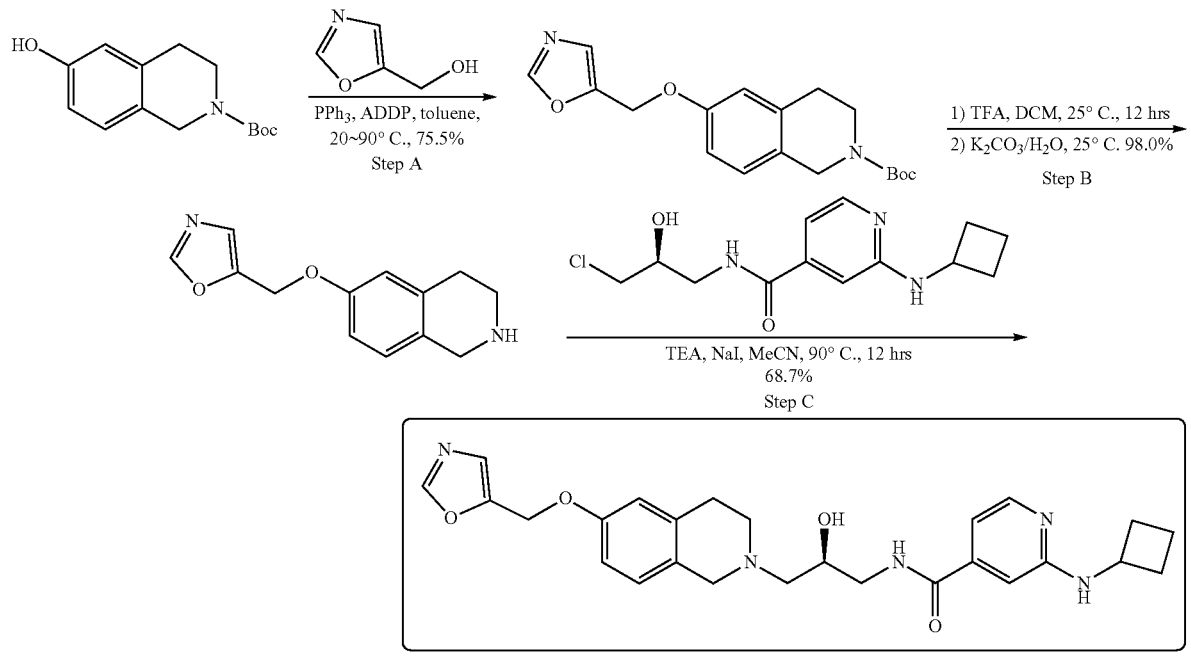

Example IBP Step A: Synthesis of tert-butyl 6-(oxazol-5-ylmethoxy)-3,4-dihydro-1H-isoquinoline-2-carboxylate.
To a solution of tert-butyl 6-hydroxy-3,4-dihydro-1H-isoquinoline-2-carboxylate (3 g, 12.03 mmol) and oxazol-5-ylmethanol (1.43 g, 14.45 mmol) in toluene (20 mL) was added triphenylphosphine (4.73 g, 18.05 mmol). Then the mixture was degassed and backfilled with nitrogen for three times. A solution of (NE)-N-(piperidine-1-carbonylimino)piperidine-1-carboxamide (4.55 g, 18.05 mmol) in toluene (10 mL) was added to the mixture drop-wise at 20° C. The mixture was stirred at 90° C. for 12 hours. The resulting mixture was concentrated under reduced pressure and the residue was purified by flash chromatography (ISCO®; 40 g*2 AgelaFlash® Silica Flash Column, petroleum ether/EtOAc with EtOAc from 0~50%, Flow rate: 30 mL/min) to afford tert-butyl 6-(oxazol-5-ylmethoxy)-3,4-dihydro-1H-isoquinoline-2-carboxylate (3 g, 75.5% yield) as colorless oil. $^1$H NMR (400 MHz, methanol-$d_4$) δ ppm 8.23 (s, 1H), 7.23 (s, 1H), 7.05 (d, J=8.3 Hz, 1H), 6.77-6.86 (m, 2H), 5.11 (s, 2H), 4.48 (br s, 2H), 3.60 (t, J=5.5 Hz, 2H), 2.72-2.82 (m, 2H), 1.49 (s, 9H); LCMS (ESI) [M–100+H]$^+$ m/z: calcd 231.1. found 231.1.

Example 1B1, Step B: Synthesis of 5-(1,2,3,4-tetrahydroisoquinolin-6-yloxymethyl)oxazole. To a solution of tert-butyl 6-(oxazol-5-ylmethoxy)-3,4-dihydro-1H-isoquinoline-2-carboxylate (3 g, 9.08 mmol) in DCM (20 mL) was added TFA (0.130 mol, 10 mL) drop-wise at 25° C. The mixture was stirred at 25° C. for 12 hours. Saturated $K_2CO_3$ aqueous solution (15 mL) was added to the resulting mixture drop-wise (adjust pH=8). The mixture was separated and the aqueous solution was extracted with a mixture of DCM and MeOH (100 mL*3, 10:1, v/v). The combine organic layer was dried over anhydrous $Na_2SO_4$, filtered and concentrated under reduced pressure to afford 5-(1,2,3,4-tetrahydroisoquinolin-6-yloxymethyl)oxazole (2.05 g, 98.0% yield) as yellow solid. $^1$H NMR (400 MHz, methanol-$d_4$) δ ppm 8.22 (s, 1H), 7.21 (s, 1H), 6.96 (d, J=8.4 Hz, 1H), 6.76-6.80 (m, 1H), 6.75 (s, 1H), 5.09 (s, 2H), 3.88 (s, 2H), 3.01-3.07 (m, 2H), 2.80 (t, J=6.0 Hz, 2H); LCMS (ESI) [M+H]$^+$ m/z: calcd 231.1. found 231.1; HPLC: 97.46% @ 254 nm.

Example IBP Step C: Synthesis of 2-(cyclobutylamino)-N-[(2S)-2-hydroxy-3-[6-(oxazol-5-ylmethoxy)-3,4-dihydro-1H-isoquinolin-2-yl]propyl]pyridine-4-carboxamide (Compound 74). To a solution of 5-(1,2,3,4-tetrahydroisoquinolin-6-yloxymethyl)oxazole (80 mg, 0.35 mmol) and N-[(2S)-3-chloro-2-hydroxy-propyl]-2-(cyclobutylamino)pyridine-4-carboxamide (84.3 mg, 0.30 mmol) in MeCN (3 mL) were added NaI (72.0 mg, 0.48 mmol) and triethylamine (TEA) (88.0 mg, 0.87 mmol). The mixture was stirred at 90° C. for 12 hours. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 µm; Mobile phase A: $H_2O$ with 0.05% ammonia hydroxide (v %); Mobile phase B: MeCN; Gradient: B from 26% to 56% in 7.8 min, hold 100% B for 2.5 min; Flow Rate: 25 mL/min; Column Temperature: 30° C.; Wavelength: 220 nm, 254 nm) to afford 2-(cyclobutylamino)-N-[(2S)-2-hydroxy-3-[6-(oxazol-5-ylmethoxy)-3,4-dihydro-1H-isoquinolin-2-yl]propyl]pyridine-4-carboxamide (95 mg, 68.7% yield) as a yellow solid. $^1$H NMR (400 MHz, methanol-$d_4$) δ ppm 8.23 (s, 1H), 7.89 (d, J=5.4 Hz, 1H), 7.23 (s, 1H), 6.97 (d, J=8.1 Hz, 1H), 6.76-6.80 (m, 3H), 6.73 (dd, J=5.4, 1.4 Hz, 1H), 5.10 (s, 2H), 4.22 (quin, J=7.8 Hz, 1H), 4.08 (quin, J=6.0 Hz, 1H), 3.67 (s, 2H), 3.47 (qd, J=13.3, 5.9 Hz, 2H), 2.88 (br d, J=5.8 Hz, 2H), 2.78-2.85 (m, 2H), 2.58-2.70 (m, 2H), 2.36-2.44 (m, 2H), 1.86-1.99 (m, 2H), 1.70-1.83 (m, 2H); LCMS (ESI) [M+H]+ m/z: calcd 478.2. found 478.2; HPLC: 99.63% @254 nm; 100% ee.

Example 1B2. 2-(cyclobutylamino)-N-[(2S)-2-hydroxy-3-(5-methyl-6-(oxazol-5-ylmethoxy)-3A-dihydro-1H-isoquinolin-2-yl]propyl]pyridine-4-carboxamide (Compound 179)

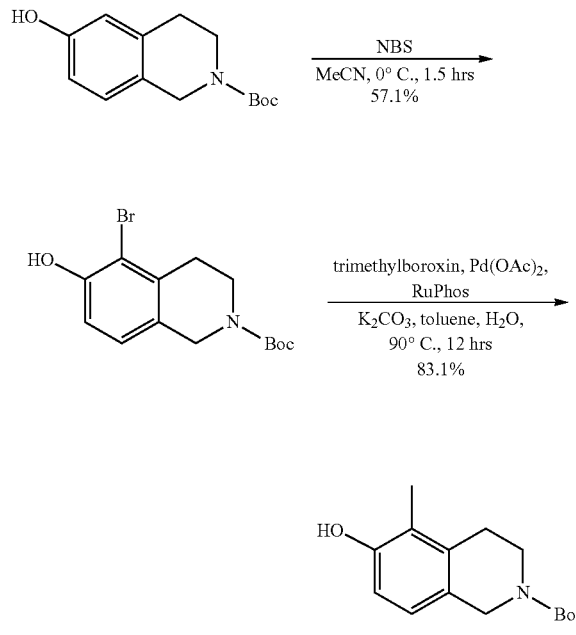

tert-butyl 5-bromo-6-hydroxy-3,4-dihydro-/H-isoquinoline-2-carboxylate. The solution of tert-butyl 6-hydroxy-3,4-dihydro-1H-isoquinoline-2-carboxylate (4 g, 16.04 mmol) in MeCN (40 mL) was cooled to 0° C. and then NBS (4 g, 22.46 mmol) was added in portions over 0.5 hour and the mixture was stirred for 1 hour at 0° C. TLC (petroleum ether/EtOAc=3:1, UV254 nm/I$_2$) showed that starting material was almost consumed and two new spots formed. The resulting mixture was quenched by addition of water (30 mL) and extracted with EtOAc (30 mL*3). The combined organic layers were washed with brine (30 mL), dried over anhydrous Na$_2$SO$_4$, filtered and concentrated under reduced pressure. The residue was purified by flash chromatography (ISCO®; 40 g AgelaFlash® Silica Flash Column, petroleum ether/EtOAc with EtOAc from 0~10%, Flow Rate: 30 mL/min) to afford a crude product which was further purified by flash chromatography (ISCO®; 40 g AgelaFlash® Silica Flash Column, petroleum ether/DCM with DCM from 0-100%, Flow Rate: 30 mL/min) to afford P1 and P2.

P1: tert-butyl 5-bromo-6-hydroxy-3,4-dihydro-1H-isoquinoline-2-carboxylate (3 g, 57.0% yield) as yellow solid. $^1$H NMR (400 MHz, methanol-d$_4$) δ ppm 6.96 (d, J=8.3 Hz, 1H), 6.79 (d, J=8.3 Hz, 1H), 4.48 (s, 2H), 3.64 (t, J=5.9 Hz, 2H), 2.83 (t, J=6.0 Hz, 2H), 1.45-1.56 (m, 9H); LCMS (ESI) [M+H−56]+ m/z: calcd 274.1. found 274.0.

P2: tert-butyl 5,7-dibromo-6-hydroxy-3,4-dihydro-1H-isoquinoline-2-carboxylate (1 g, 15.3% yield) as yellow solid. $^1$H NMR (400 MHz, DMSO-d$_6$) δ ppm 9.72 (s, 1H), 7.45 (s, 1H), 4.43 (br s, 2H), 3.55 (t, J=5.9 Hz, 2H), 2.67 (t, J=5.9 Hz, 2H), 1.42 (s, 9H). (regioselectivity was confirmed by NOE)

tert-butyl 6-hydroxy-5-methyl-3,4-dihydro-1H-isoquinoline-2-carboxylate. To a solution of tert-butyl 5-bromo-6-hydroxy-3,4-dihydro-1H-isoquinoline-2-carboxylate (1.5 g, 4.57 mmol), Pd(OAc)$_2$ (120.00 mg, 0.53 mmol), RuPhos (240 mg, 0.51 mmol), K$_2$CO$_3$ (1.89 g, 13.7 mmol) in H$_2$O (0.5 mL) and toluene (10 mL) was added 2,4,6-trimethyl-1,3,5,2,4,6-trioxatriborinane (1.6 g, 6.37 mmol). The mixture was stirred at 90° C. for 12 hours in a sealed tube under nitrogen. The resulting mixture was diluted with EtOAc (50 mL), filtered and concentrated under reduced pressure to afford crude product which was purified by flash chromatography (ISCO®; 20 g AgelaFlash® Silica Flash Column, petroleum ether/EtOAc with EtOAc from 0~30%, Flow Rate: 30 mL/min) to afford tert-butyl 6-hydroxy-5-methyl-3,4-dihydro-1H-isoquinoline-2-carboxylate (1 g, 83.1% yield) as off white solid. $^1$H NMR (400 MHz, methanol-d$_4$) δ ppm 6.70-6.83 (m, 1H), 6.65 (d, J=8.3 Hz, 1H), 4.48 (s, 2H), 3.63 (t, J=5.5 Hz, 2H), 2.73 (t, J=5.9 Hz, 2H), 2.11 (s, 3H), 1.46-1.56 (m, 9H); LCMS (ESI) [M+H−56]+ m/z calcd 208.2. found 208.1.

Step A. tert-butyl 5-methyl-6-(oxazol-5-ylmethoxy)-3,4-dihydro-1H-isoquinoline-2-carboxylate

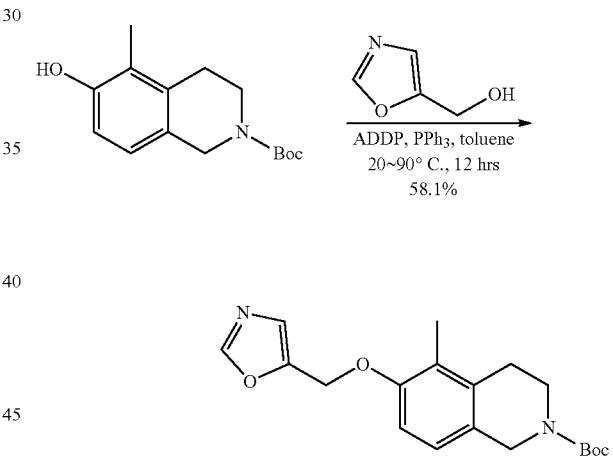

To a solution of tert-butyl 6-hydroxy-5-methyl-3,4-dihydro-1H-isoquinoline-2-carboxylate (200 mg, 0.76 mmol), oxazol-5-ylmethanol (92 mg, 0.93 mmol), triphenylphosphine (300 mg, 1.14 mmol) in toluene (3 mL) was added a solution of ADDP (288 mg, 1.14 mmol) in toluene (3 mL) slowly at 20° C. under nitrogen and after addition was complete, the mixture was allowed to warm to 90° C. and stir for 12 hours in a sealed tube. The resulting mixture was concentrated under reduced pressure to give a crude product which was purified by flash chromatography (ISCO®; 12 g AgelaFlash® Silica Flash Column, petroleum ether/EtOAc with EtOAc from 0~30%, Flow Rate: 30 mL/min) to afford tert-butyl 5-methyl-6-(oxazol-5-ylmethoxy)-3,4-dihydro-1H-isoquinoline-2-carboxylate (152 mg, 58.1% yield) as light yellow solid. $^1$H NMR (400 MHz, methanol-d$_4$) δ ppm 8.25 (s, 1H), 7.23 (s, 1H), 6.95 (s, 2H), 5.14 (s, 2H), 4.50 (s, 2H), 3.65 (t, J=5.6 Hz, 2H), 2.75 (t, J=6.0 Hz, 2H), 2.11 (s, 3H), 1.50 (s, 9H); LCMS (ESI) [M+H−100]+ m/z: calcd 245.2. found 245.1.

2-(cyclobutylamino)-N-[(2S)-2-hydroxy-3-[5-methyl-6-(oxazol-5-ylmethoxy)-3,4-dihydro-1H-isoquinolin-2-yl]propyl]pyridine-4-carboxamide (Compound 179)

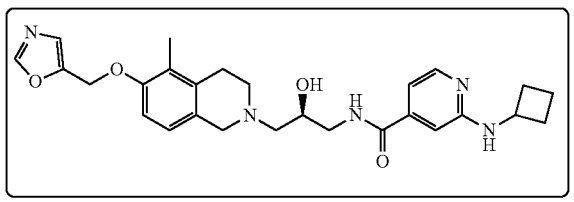 [SMILES: Cc1c(OCc2cnco2)ccc2c1CCN(C[C@@H](O)CNC(=O)c1ccnc(NC3CCC3)c1)C2]

tert-butyl 5-methyl-6-(oxazol-5-ylmethoxy)-3,4-dihydro-1H-isoquinoline-2-carboxylate was converted to N-[(2S)-3-chloro-2-hydroxy-propyl]-2-(cyclobutylamino)pyridine-4-carboxamide using reaction conditions outlined in Steps B and Step C from Example 1B. The mixture was concentrated under reduced pressure and the residue was purified by preparative HPLC purification (Instrument: Gilson GX-281 Liquid Handler, Gilson 322 Pump, Gilson 156 UV Detector; Column:Waters Xbridge 150×25 mm×5 μm; Mobile phase A: H$_2$O with 0.05% NH$_3$—H$_2$O (v %); Mobile phase B: MeCN; Gradient: B from 45% to 75% in 7.8 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[5-methyl-6-(oxazol-5-ylmethoxy)-3,4-dihydro-1H-isoquinolin-2-yl]propyl]pyridine-4-carboxamide (40 mg, 39.8%) as yellow solid. $^1$H NMR (400 MHz, methanol-d$_4$) δ ppm 8.24 (s, 1H), 7.85 (d, J=5.4 Hz, 1H), 7.20 (s, 1H), 6.88 (s, 2H), 6.78 (s, 1H), 6.69 (d, J=4.8 Hz, 1H), 5.11 (s, 2H), 4.18-4.26 (m, 1H), 4.04-4.12 (m, 1H), 3.68 (s, 2H), 3.47 (d, J=4.5 Hz, 2H), 2.82-2.91 (m, 2H), 2.76 (d, J=5.8 Hz, 2H), 2.59-2.69 (m, 2H), 2.40 (d, J=7.6 Hz, 2H), 2.05 (s, 3H), 1.86-1.98 (m, 2H), 1.71-1.82 (m, 2H); LCMS (ESI) [M+H]$^+$ m/z: calcd 492.3. found 492.2; HPLC: 96.88%@254 nm; 99.4% ee.

Example 1B3. (S)—N-(3-(5-chloro-6-((1-methyl-1H-pyrazol-5-yl)methoxy)-3N-dihydroisoquinolin-2(1H)-yl)-2-hydroxypropyl-2-(cyclobutylamino)isonicotinamide (Compound 194)

tert-butyl 5-chloro-6-hydroxy-3,4-dihydro-1H-isoquinoline-2-carboxylate

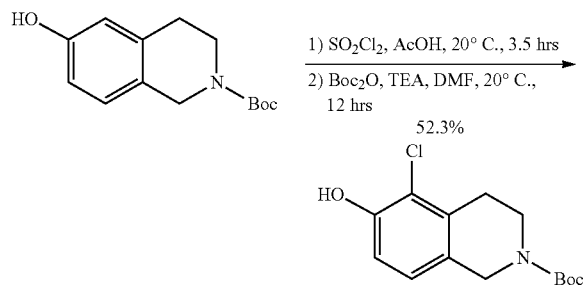

To a solution of tert-butyl 6-hydroxy-3,4-dihydro-1H-isoquinoline-2-carboxylate (4.7 g, 18.85 mmol) in AcOH (20 mL) was added SO$_2$Cl$_2$ (3.05 g, 22.62 mmol) in portions (509 mg dissolved in 1 mL of AcOH) every 20 minutes (2 hours in total) slowly at 20° C. After addition was complete, the mixture was stirred at 20° C. for 1 hour. LCMS showed that the peak with de-Boc MS was observed, and also the peaks with di-Cl substituted, and starting material remaining (de-Boc form). Another batch of SO$_2$Cl$_2$ (255 mg, 1.89 mmol) in AcOH (1 mL) was added, and the mixture was stirred at 20° C. for 0.5 hour. No change was observed on LCMS. The mixture was concentrated under reduced pressure to give a residue, which was dissolved in DMF (30 mL) and followed by addition of TEA (75.41 mmol, 10.51 mL) and (Boc)$_2$O (4.93 g, 22.62 mmol). The mixture was stirred at 20° C. for 12 hours and the resulting mixture was quenched by addition of water (50 mL) and extracted with EtOAc (30 mL*3). The combined organic layer was washed with saturated NH$_4$Cl aqueous solution (60 mL*2), brine (60 mL*2), dried over anhydrous Na$_2$SO$_4$, filtered and concentrated under reduced pressure to give a crude product, which was was purified by flash chromatography (ISCO®; 80 g AgelaFlash® Silica Flash Column, petroleum ether/EtOAc with EtOAc from 0~30%, flow rate=35 mL/min) to give PI and P2/P3.

P1:tert-butyl 5-chloro-6-hydroxy-3,4-dihydro-1H-isoquinoline-2-carboxylate (2.8 g, 52.3% yield, white solid). $^1$H NMR (400 MHz, methanol-d$_4$) δ ppm 6.91 (d, J=8.4 Hz, 1H), 6.79 (d, J=8.4 Hz, 1H), 4.46 (s, 2H), 3.64 (t, J=5.7 Hz, 2H), 2.82 (t, J=6.0 Hz, 2H), 1.48 (s, 9H); LCMS (ESI) [M+H−56]$^+$ m/z: calcd 228.1. found 228.0.

P2/P3: a mixture of tert-butyl 5,7-dichloro-6-hydroxy-3,4-dihydro-1H-isoquinoline-2-carboxylate and tert-butyl 5,8-dichloro-6-hydroxy-3,4-dihydro-1H-isoquinoline-2-carboxylate (1.5 g crude, ratio=~3:1, colorless oil).

Step A. tert-butyl 5-chloro-6-(oxazol-5-ylmethoxy)-3,4-dihydro-1H-isoquinoline-2-carboxylate

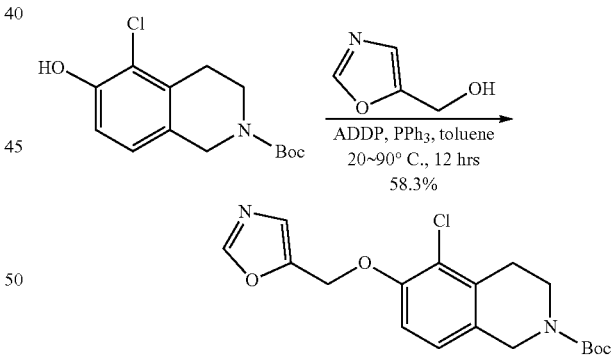

To a solution of tert-butyl 5-chloro-6-hydroxy-3,4-dihydro-1H-isoquinoline-2-carboxylate (0.2 g, 0.71 mmol) in toluene (4 mL) were added oxazol-5-ylmethanol (85 mg, 0.86 mmol), triphenylphosphine (0.3 g, 1.14 mmol). Then ADDP (0.3 g, 1.19 mmol) was added slowly at 20° C. and after addition was complete, the reaction mixture was stirred at 90° C. for 12 hours under nitrogen. The reaction mixture was concentrated under reduced pressure and the residue was purified by flash chromatography (ISCO®; 24 g AgelaFlash® Silica Flash Column, petroleum ether/EtOAc with EtOAc from 0~30%, flow rate=30 mL/min) to afford tert-butyl 5-chloro-6-(oxazol-5-ylmethoxy)-3,4-dihydro-1H-isoquinoline-2-carboxylate (150 mg, 58.3% yield) as colorless oil. ¹H NMR (400 MHz, methanol-d₄) δ ppm 8.25 (s, 1H), 7.25 (s, 1H), 7.10-7.05 (m, 2H), 5.21 (s, 2H), 4.51 (s, 2H), 3.49-3.46 (m, 2H), 2.84 (t, J=6.0 Hz, 2H), 1.49 (s, 9H); LCMS (ESI) [M+H−100]⁺ m/z: calcd 265.1. found 265.0.

N-[(2S)-3-[5-chloro-6-(oxazol-5-ylmethoxy)-3,4-dihydro-1H-isoquinolin-2-yl]-2-hydroxy-propyl]-2-(cyclobutylamino)pyridine-4-carboxamide (Compound 194)

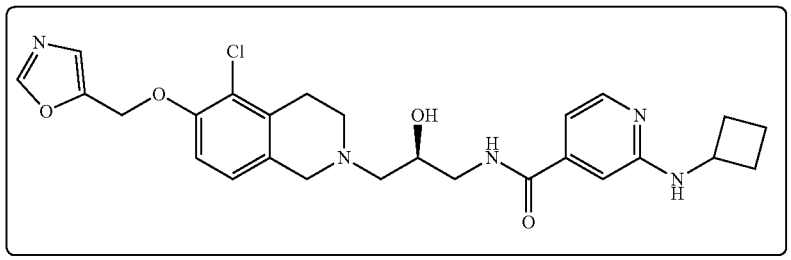 [SMILES: O=C(NC[C@H](O)CN1CCc2c(ccc(OCc3cnco3)c2Cl)C1)c1ccnc(NC2CCC2)c1]

tert-butyl 5-methyl-6-(oxazol-5-ylmethoxy)-3,4-dihydro-1H-isoquinoline-2-carboxylate was converted to N-[(2S)-3-[5-chloro-6-(oxazol-5-ylmethoxy)-3,4-dihydro-1H-isoquinolin-2-yl]-2-hydroxy-propyl]-2-(cyclobutylamino)pyridine-4-carboxamide using reaction conditions outlined in Steps B and Step C from Example IB. The mixture was concentrated under reduced pressure and the residue was purified by preparative HPLC purification (Instrument: Gilson GX-281 Liquid Handler, Gilson 322 Pump, Gilson 156 UV Detector; Column:Waters Xbridge 150×25 mm×5 μm; Mobile phase A: H₂O with 0.05% NH₃—H₂O (v %); Mobile phase B: MeCN; Gradient: B from 45% to 75% in 7.8 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[5-methyl-6-(oxazol-5-ylmethoxy)-3,4-dihydro-1H-isoquinolin-2-yl]propyl]pyridine-4-carboxamide (40 mg, 39.8%) as yellow solid. ¹H NMR (400 MHz, methanol-d₄) δ ppm 8.24 (s, 1H), 7.85 (d, J=5.4 Hz, 1H), 7.20 (s, 1H), 6.88 (s, 2H), 6.78 (s, 1H), 6.69 (d, J=4.8 Hz, 1H), 5.11 (s, 2H), 4.18-4.26 (m, 1H), 4.04-4.12 (m, 1H), 3.68 (s, 2H), 3.47 (d, J=4.5 Hz, 2H), 2.82-2.91 (m, 2H), 2.76 (d, J=5.8 Hz, 2H), 2.59-2.69 (m, 2H), 2.40 (d, J=7.6 Hz, 2H), 2.05 (s, 3H), 1.86-1.98 (m, 2H), 1.71-1.82 (m, 2H); LCMS (ESI) [M+H]⁺ m/z: calcd 492.3. found 492.2; HPLC: 96.88% @ 254 nm; 99.4% ee.

Example 1B4. 2-(cyclobutylamino)-N-[(2S)-2-hydroxy-3-[6-(1H-pyrazol-4-ylmethoxy)-3,4-dihydro-1H-isoquinolin-2-yl]propyl]pyridine-4-carboxamide (Compound 163)

Step A. tert-butyl 6-[(1-tert-butoxycarbonylpyrazol-4-yl)methoxy]-3,4-dihydro-1H-isoquinoline-2-carboxylate

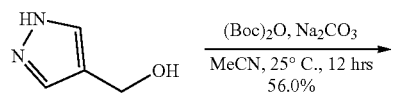

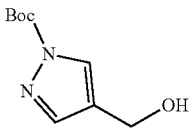 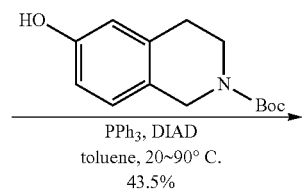

To a solution of 1H-pyrazol-4-ylmethanol (950 mg, 9.68 mmol) in H₂O (5 mL) and MeCN (5 mL) was added Na₂CO₃ (1.14 g, 10.76 mmol). Then tert-butoxycarbonyl tert-butyl carbonate (10.02 mmol, 2.3 mL) was added to the mixture drop-wise. The mixture was stirred at 25° C. for 12 hours. The resulting mixture was diluted with water (5 mL) and the aqueous solution was extracted with DCM (30 mL*3). The organic layer was dried over anhydrous Na₂SO₄, filtered and concentrated under reduced pressure to afford tert-butyl 4-(hydroxymethyl)pyrazole-1-carboxylate (1.2 g, 56.0% yield) as yellow oil. ¹H NMR (400 MHz, methanol-d₄) δ ppm 8.04 (s, 1H), 7.70 (s, 1H), 4.61 (s, 2H), 1.63-1.68 (m, 9H); LCMS (ESI) [2M+Na]⁺ m/z: calcd 419.2. found 419.1.

To a solution of tert-butyl 6-hydroxy-3,4-dihydro-1H-isoquinoline-2-carboxylate (200 mg, 0.80 mmol) and tert-butyl-4-(hydroxymethyl)pyrazole-1-carboxylate (212.02 mg, 0.96 mmol) in toluene (8 mL) were added triphenylphosphine (315.6 mg, 1.20 mmol). The mixture was degassed and backfilled with nitrogen for three times. A solution of ADDP (303.62 mg, 1.20 mmol) in toluene (4 mL) was added to the mixture dropwise at 20° C. Then the mixture was stirred at 90° C. for 16 hours. The resulting mixture was concentrated under reduced pressure and the residue was purified by flash chromatography (ISCO®; 20 g AgelaFlash® Silica Flash Column, petroleum ether/EtOAc with EtOAc from 0-45%, Flow rate: 30 mL/min) to afford tert-butyl-6-[(1-tert-butoxycarbonylpyrazol-4-yl)methoxy]-3,4-dihydro-1H-isoquinoline-2-carboxylate (150 mg, 43.5% yield) as colorless oil. ¹H NMR (400 MHz, methanol-d₄) δ ppm 8.25 (s, 1H), 7.83 (s, 1H), 7.04 (d, J=8.0 Hz, 1H), 6.81-6.86 (m, 1H), 6.80 (d, J=2.5 Hz, 1H), 5.00 (s, 2H), 4.48 (s, 2H), 3.60 (t, J=5.6 Hz, 2H), 2.79-2.83 (m, 2H), 1.64 (s, 9H), 1.49 (s, 9H); LCMS (ESI) [M−200+H]⁺ m/z: calcd 230.1. found 230.1.

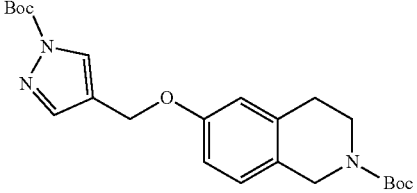

2-(cyclobutylamino)-N-[(2S)-2-hydroxy-3-[6-(1H-pyrazol-4-ylmethoxy)-3,4-dihydro-1H-isoquinolin-2-yl]propyl]pyridine-4-carboxamide (Compound 163)

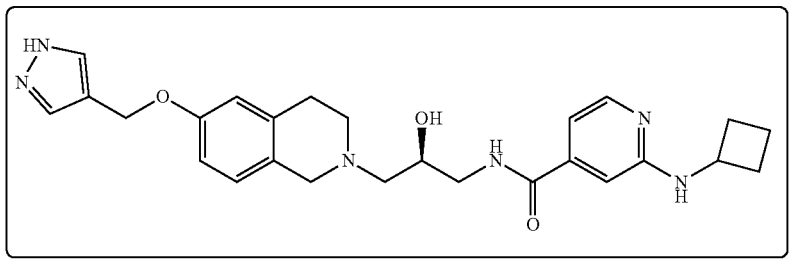 [SMILES: O=C(NC[C@H](O)CN1CCc2cc(OCc3cn[nH]c3)ccc2C1)c1ccnc(NC2CCC2)c1]

tert-butyl-6-[(1-tert-butoxycarbonylpyrazol-4-yl)methoxy]-3,4-dihydro-1H-isoquinoline-2-carboxylate was converted to 2-(cyclobutylamino)-N-[(2S)-2-hydroxy-3-[6-(1H-pyrazol-4-ylmethoxy)-3,4-dihydro-1H-isoquinolin-2-yl]propyl]pyridine-4-carboxamide using reaction conditions outlined in Steps B and Step C from Example 1B. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H$_2$O with 0.05% NH$_3$—H$_2$O (v %); Mobile phase B: MeCN; Gradient: B from 42% to 72% in 9 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[6-(1H-pyrazol-4-ylmethoxy)-3,4-dihydro-1H-isoquinolin-2-yl]propyl]pyridine-4-carboxamide (26 mg, 31.3% yield) as a white solid. $^1$H NMR (400 MHz, methanol-d$_4$) δ ppm 7.89 (d, J=5.4 Hz, 1H), 7.67 (br s, 2H), 6.96 (d, J=8.3 Hz, 1H), 6.71-6.80 (m, 4H), 4.99 (s, 2H), 4.22 (quin, J=7.9 Hz, 1H), 4.08 (quin, J=6.0 Hz, 1H), 3.68 (s, 2H), 3.41-3.53 (m, 2H), 2.80-2.92 (m, 4H), 2.60-2.70 (m, 2H), 2.35-2.45 (m, 2H), 1.86-1.99 (m, 2H), 1.72-1.82 (m, 2H); LCMS (ESI) [M+H]$^+$ m/z: calcd 477.3. found 477.2; HPLC: 98.42% @ 254 nm; 99.2% ee.

Example 1B5. 2-(cyclobutylamino)-N-[(2S)-2-hydroxy-3-[5-methyl-6-[(2-methylpyrazol-3-yl)methoxy]-3N-dihydro-1H-isoquinolin-2-yl]propyl]pyridine-4-carboxamide (Compound 161)

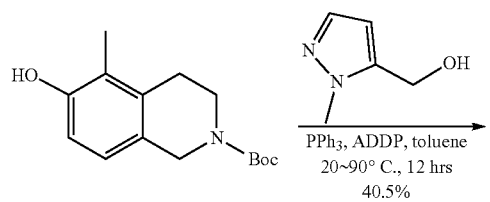
PPh$_3$, ADDP, toluene
20~90° C., 12 hrs
40.5%

-continued

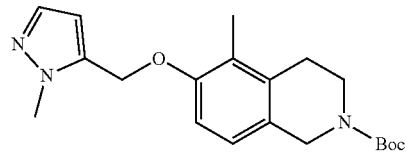

Step A. tert-butyl 5-methyl-6-[(2-methylpyrazol-3-yl)methoxy]-3,4-dihydro-1H-isoquinoline-2-carboxylate. To a solution of tert-butyl 6-hydroxy-5-methyl-3,4-dihydro-1H-isoquinoline-2-carboxylate (150 mg, 0.57 mmol), (2-methylpyrazol-3-yl)methanol (96 mg, 0.86 mmol), PPh$_3$ (225 mg, 0.86 mmol) in toluene (3 mL) was added a solution of ADDP (216 mg, 0.86 mmol) in toluene (5 mL) slowly at 20° C. Then the mixture was stirred at 90° C. for 12 hours. The mixture was combined with another batch and concentrated under reduced pressure to give a crude product, which was purified by flash chromatography (ISCO®; 12 g Agela-Flash® Silica Flash Column, petroleum ether/EtOAc with EtOAc from 0~35%, 30 mL/min) to afford tert-butyl 5-methyl-6-[(2-methylpyrazol-3-yl)methoxy]-3,4-dihydro-1H-isoquinoline-2-carboxylate (110 mg, 40.5% yield) as a colorless oil. $^1$H NMR (400 MHz, methanol-d$_4$) δ ppm 7.42 (d, J=2.0 Hz, 1H), 6.92-6.97 (m, 2H), 6.36 (d, J=2.0 Hz, 1H), 5.12 (s, 2H), 4.49 (s, 2H), 3.90 (s, 3H), 3.63 (t, J=5.6 Hz, 2H), 2.74 (t, J=6.0 Hz, 2H), 2.11 (s, 3H), 1.48 (s, 9H); LCMS (ESI) [M+H–56]$^+$ m/z: calcd 302.2. found 302.1.

443

2-(cyclobutylamino)-N-[(2S)-2-hydroxy-3-[5-methyl-6-[(2-methylpyrazol-3-yl)methoxy]-3,4-dihydro-1H-isoquinolin-2-yl]propyl]pyridine-4-carboxamide (Compound 161)

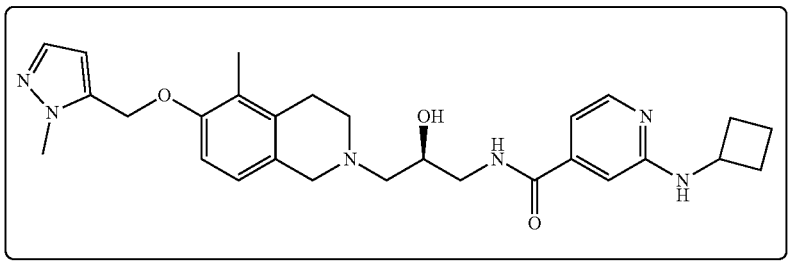 [SMILES: Cc1c(OCc2ccnn2C)ccc2c1CCN(C[C@@H](O)CNC(=O)c1ccnc(NC3CCC3)c1)C2]

tert-butyl 5-methyl-6-[(2-methylpyrazol-3-yl)methoxy]-3,4-dihydro-1H-isoquinoline-2-carboxylate was converted to 2-(cyclobutylamino)-N-[(2S)-2-hydroxy-3-[5-methyl-6-[(2-methylpyrazol-3-yl)methoxy]-3,4-dihydro-1H-isoquinolin-2-yl]propyl]pyridine-4-carboxamide using reaction conditions outlined in Steps B and Step C from Example IB. The crude product, which was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H2O with 0.05% NH3—H2O (v %); Mobile phase B: MeCN; Gradient: B from 27% to 57% in 7.8 min, hold 100% B for 2.5 min; Flow Rate: 25 mL/min; Column Temperature: 30° C.; Wavelength: 220 nm, 254 nm) to give 2-(cyclobutylamino)-N-

444

[(2S)-2-hydroxy-3-[5-methyl-6-[(2-methylpyrazol-3-yl)methoxy]-3,4-dihydro-1H-isoquinolin-2-yl]propyl]pyridine-4-carboxamide (10 mg, 12.8% yield) as a white solid. $^1$H NMR (400 MHz, methanol-$d_4$) δ ppm 7.85 (d, J=5.3 Hz, 1H), 7.42 (d, J=1.8 Hz, 1H), 6.88 (s, 2H), 6.78 (s, 1H), 6.69 (dd, J=5.5, 1.5 Hz, 1H), 6.36 (d, J=2.0 Hz, 1H), 5.11 (s, 2H), 4.22 (quin, J=7.8 Hz, 1H), 4.08 (quin, J=6.0 Hz, 1H), 3.90 (s, 3H), 3.67 (s, 2H), 3.42-3.52 (m, 2H), 2.80-2.91 (m, 2H), 2.72-2.79 (m, 2H), 2.59-2.69 (m, 2H), 2.35-2.44 (m, 2H), 2.06 (s, 3H), 1.85-1.97 (m, 2H), 1.72-1.82 (m, 2H); LCMS (ESI) [M+H]$^+$ m/z: calcd 505.3. found 505.2; HPLC: 98.66% @ 254 nm; 99.3% ee.

Example 1B6. 2-(cyclobutylamino)-N-[(2S)-2-hydroxy-3-[5-methyl-6-(1H-pyrazol-4-ylmethoxy)-3,4-dihydro-1H-isoquinolin-2-yl]propyl]pyridine-4-carboxamide (Compound 254)

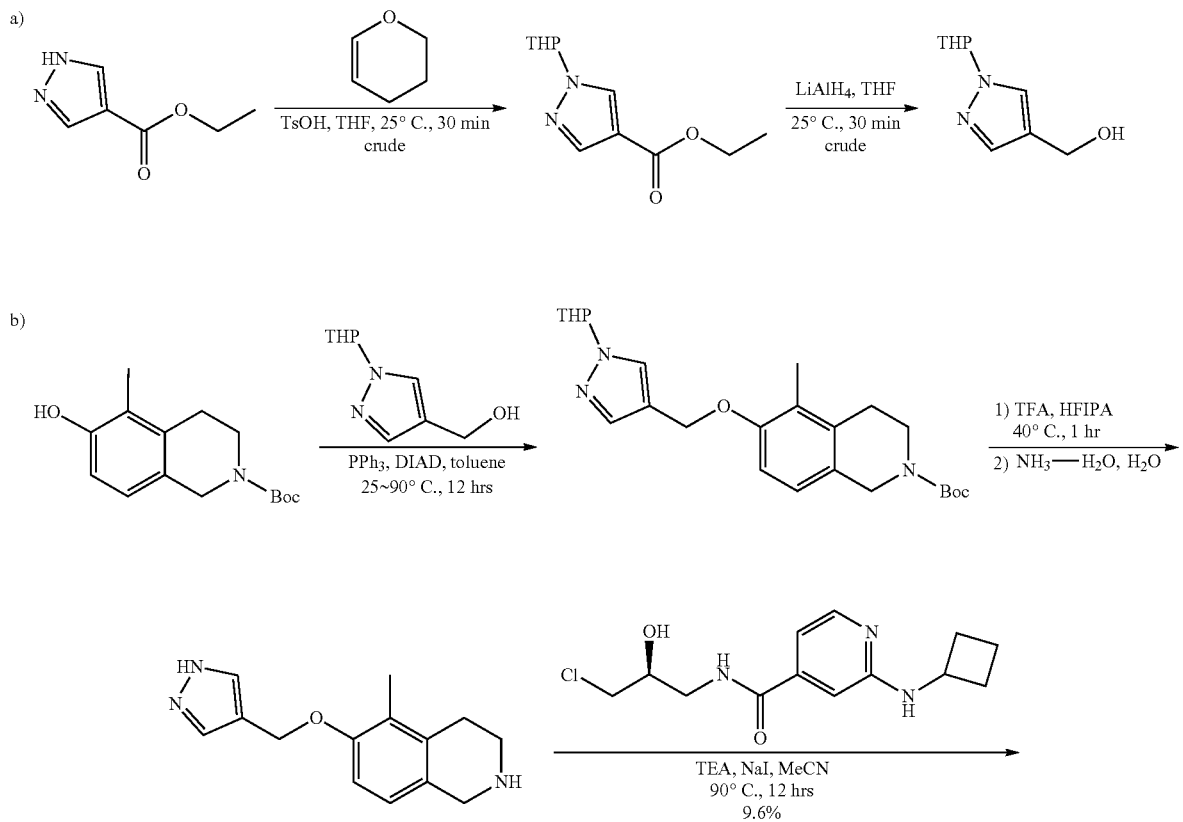

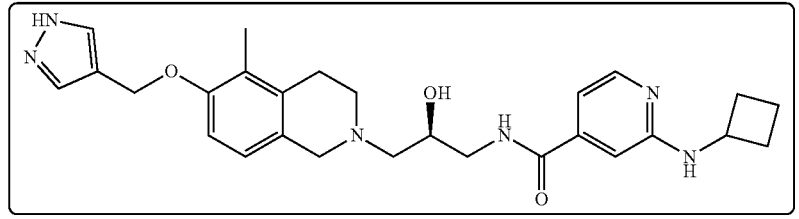

Synthesis of ethyl 1-tetrahydropyran-2-ylpyrazole-4-carboxylate. To a solution of ethyl 1H-pyrazole-4-carboxylate (3 g, 21.4 mmol) and 3,4-dihydro-2H-pyran (3.9 mL, 42.9 mmol) in THF (30 mL) was added 4-methylbenzenesulfonic acid (378 mg, 2.20 mmol). The mixture was stirred at 25° C. for 30 minutes. The resulting mixture was quenched with saturated NaHCO$_3$ aqueous solution and extracted with EtOAc (30 mL*3). The combined organic layers were washed with brine (50 mL), dried over anhydrous Na$_2$SO$_4$, filtered and concentrated under reduced pressure to afford ethyl 1-tetrahydropyran-2-ylpyrazole-4-carboxylate (6.2 g, crude) as yellow oil. The product was directly used on next step without further purification. $^1$H NMR (400 MHz, chloroform-d) δ ppm 8.11 (s, 1H), 7.94 (s, 1H), 5.39 (dd, J=8.4, 3.6 Hz, 1H), 4.29 (q, J=7.3 Hz, 2H), 4.01-4.10 (m, 1H), 3.67-3.75 (m, 1H), 2.04-2.13 (m, 2H), 1.59-1.78 (m, 4H), 1.34 (t, J=7.2 Hz, 3H).

Synthesis of(1-tetrahydropyran-2-ylpyrazol-4-yl)methanol. The suspension of LiAlH$_4$ (1.31 g, 34.4 mmol) in THF (20 mL) was cooled to 0° C. A solution of ethyl 1-tetrahydropyran-2-ylpyrazole-4-carboxylate (6.2 g, 21.3 mmol) in THF (10 mL) was added drop-wise. The mixture was stirred for 30 minutes and then cooled to 0° C. and quenched with H$_2$O (0.5 mL), 10% wt NaOH aqueous solution (0.5 mL) and H$_2$O (1.5 mL). The resulting mixture was stirred for 30 minutes, then filtered and concentrated under reduced pressure to afford (1-tetrahydropyran-2-ylpyrazol-4-yl)methanol (5 g, crude) as colorless oil. $^1$H NMR (400 MHz, chloroform-d) δ ppm 7.62 (s, 1H), 7.54 (s, 1H), 5.35 (dd, J=9.3, 2.8 Hz, 1H), 4.02-4.09 (m, 1H), 3.65-3.73 (m, 1H), 3.65-3.73 (m, 1H), 1.97-2.08 (m, 3H), 1.52-1.73 (m, 6H); LCMS (ESI) [M+H]$^+$ m/z: calcd 183.1. found 183.1.

Synthesis of tert-butyl 5-methyl-6-[(1-tetrahydropyran-2-ylpyrazol-4-yl)methoxy]-3,4-dihydro-1H-isoquinoline-2-carboxylate. To a solution of tert-butyl 6-hydroxy-5-methyl-3,4-dihydro-1H-isoquinoline-2-carboxylate (450 mg, 1.71 mmol) and (1-tetrahydropyran-2-ylpyrazol-4-yl)methanol (900 mg, 4.94 mmol) in toluene (10 mL) was added triphenylphosphine (680 mg, 2.59 mmol). The mixture was degassed and backfilled with nitrogen for three times. A solution of DIAD (513 mg, 2.54 mmol) in toluene (5 mL) was added to the mixture drop-wise at 25° C. and the mixture was stirred at 90° C. for 12 hours. The resulting mixture was concentrated under reduced pressure and the residue was purified by flash chromatography (ISCO®; 12 g*2 AgelaFlash® Silica Flash Column, petroleum ether/EtOAc with EtOAc from 0~50%, Flow rate: 30 mL/min) to afford tert-butyl 5-methyl-6-[(1-tetrahydropyran-2-ylpyrazol-4-yl)methoxy]-3,4-dihydro-1H-isoquinoline-2-carboxylate (650 mg, crude) as white solid. $^1$H NMR (400 MHz, methanol-d$_4$) δ ppm 7.88 (s, 1H), 7.61 (s, 1H), 6.90-6.96 (m, 2H), 5.37-5.42 (m, 1H), 4.99 (s, 2H), 4.50 (br s, 2H), 4.04 (br d, J=12.0 Hz, 2H), 3.73 (td, J=11.0, 2.5 Hz, 2H), 3.64 (t, J=5.6 Hz, 2H), 2.75 (t, J=5.9 Hz, 2H), 2.11 (s, 3H), 2.04 (s, 2H), 1.54-1.81 (m, 6H), 1.50 (s, 9H); LCMS (ESI) [M+Na]$^+$ m/z: calcd 450.2. found 450.2.

5-methyl-6-(1H-pyrazol-4-ylmethoxy)-1,2,3,4-tetrahydroisoquinoline. To a solution of tert-butyl 5-methyl-6-[(1-tetrahydropyran-2-ylpyrazol-4-yl)methoxy]-3,4-dihydro-1H-isoquinoline-2-carboxylate (650 mg, 1.06 mmol) in 1,1,1,3,3,3-Hexafluoro-2-propanol (8 mL) was added TFA (224.2 mg, 1.97 mmol). The mixture was stirred at 40° C. for 1 hour. The resulting mixture was quenched by addition of NH$_3$—H$_2$O (2 mL, 30% wt) and concentrated under reduced pressure. The residue was diluted with DCM (30 mL) and dried over anhydrous Mg$_2$SO$_4$, filtered and concentrated under reduced pressure to afford 5-methyl-6-(1H-pyrazol-4-ylmethoxy)-1,2,3,4-tetrahydroisoquinoline (500 mg, crude) as white gum. LCMS (ESI) [M+H]$^+$ m/z: calcd 244.1. found 244.0; HPLC: 73.97% @ 220 nm.

Synthesis of 2-(cyclobutylamino)-N-[(2S)-2-hydroxy-3-[5-methyl-6-(1H-pyrazol-4-ylmethoxy)-3,4-dihydro-1H-isoquinolin-2-yl]propyl]pyridine-4-carboxamide (Compound 254). To a solution of 5-methyl-6-(1H-pyrazol-4-ylmethoxy)-1,2,3,4-tetrahydroisoquinoline (350 mg, 0.82 mmol, crude), N-[(2S)-3-chloro-2-hydroxy-propyl]-2-(cyclobutylamino)pyridine-4-carboxamide (220 mg, 0.78 mmol), NaI (150 mg, 1.0 mmol) in MeCN (2 mL) was added TEA (250 mg, 2.47 mmol). The mixture was sealed and stirred at 90° C. for 12 hours. The resulting mixture was concentrated under reduced pressure. The residue was purified by flash chromatography (ISCO®; 20 g AgelaFlash® Silica Flash Column, DCM/MeOH with MeOH from 0~8%, Flow rate=30 mL/min) to afford a crude (150 mg) product which was further purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% ammonia hydroxide (v %); Mobile phase B: MeCN; Gradient: B from 30% to 60% in 7.8 min, hold 100% B for 2.5 min; Flow Rate: 25 mL/min; Column Temperature: 30° C.; Wavelength: 220 nm, 254 nm) to afford 2-(cyclobutylamino)-N-[(2S)-2-hydroxy-3-[5-methyl-6-(1H-pyrazol-4-ylmethoxy)-3,4-dihydro-1H-isoquinolin-2-yl]propyl]pyridine-4-carboxamide (35 mg, 9.6% yield) as a white solid. $^1$H NMR (400 MHz, methanol-d$_4$) δ ppm 7.85 (d, J=4.8 Hz, 1H), 7.57-7.75 (m, 2H), 6.87 (s, 2H), 6.78 (d, J=0.6 Hz, 1H), 6.68 (dd, J=5.4, 1.5 Hz, 1H), 5.00 (s, 2H), 4.22 (quin, J=7.9 Hz, 1H), 4.08 (quin, J=6.0 Hz, 1H), 3.69 (s, 2H), 3.47 (d, J=6.0 Hz, 2H), 2.82-2.92 (m, 2H), 2.74-2.79 (m, 2H), 2.61-2.71 (m, 2H), 2.34-2.44 (m, 2H), 2.07 (s, 3H), 1.85-1.96 (m, 2H), 1.69-1.82 (m, 2H); LCMS (ESI) [M+H]$^+$ m/z: calcd 491.3. found 491.2; HPLC: 100% @ 254 nm; 99.4% ee.

Example 1B7. N-[(2S)-3-[5-bromo-6-(oxazol-5-ylmethoxy)-3N-dihydro-1H-isoquinolin-2-yl]-2-hydroxy-propyl]-2-(cyclobutylamino)pyridine-4-carboxamide (Compound 255)

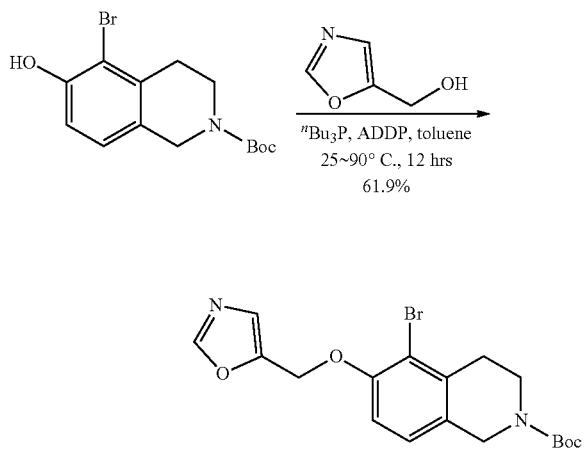 [SMILES: CC(C)(C)OC(=O)N1CCc2c(ccc(O)c2Br)C1 ; OCc1cnco1 ; CC(C)(C)OC(=O)N1CCc2c(ccc(OCc3cnco3)c2Br)C1]

tert-Butyl 5-bromo-6-(oxazol-5-ylmethoxy)-3,4-dihydro-1H-isoquinoline-2-carboxylate. To a solution of tert-butyl 5-bromo-6-hydroxy-3,4-dihydro-1H-isoquinoline-2-carboxylate (300 mg, 0.91 mmol) and oxazol-5-ylmethanol (138.0 mg, 1.39 mmol) in toluene (10 mL) was added n-Bu$_3$P (282.0 mg, 1.39 mmol). The mixture was degassed and backfilled with nitrogen for three times. A solution of (NE)-N-(piperidine-1-carbonylimino)piperidine-1-carboxamide (342.0 mg, 1.36 mmol) in toluene (5 mL) was added to the mixture drop-wise at 25° C. The mixture was stirred at 90° C. for 12 hours. The resulting mixture was combined with another batch and concentrated under reduced pressure. The residue was purified by flash chromatography (ISCO®; 20 g AgelaFlash® Silica Flash Column, petroleum ether/EtOAc with EtOAc from 0~50%, Flow rate: 30 mL/min) to afford tert-butyl 5-bromo-6-(oxazol-5-ylmethoxy)-3,4-dihydro-1H-isoquinoline-2-carboxylate (270 mg, 61.9% yield) as yellow solid. NMR (400 MHz, methanol-d$_4$) δ ppm 8.24 (s, 1H), 7.25 (s, 1H), 7.10-7.15 (m, 1H), 7.01-7.08 (m, 1H), 5.21 (s, 2H), 4.52 (s, 2H), 3.61-3.68 (m, 2H), 2.84 (t, J=6.0 Hz, 2H), 1.49 (s, 9H); LCMS (ESI) [M-100+H]$^+$ m/z: calcd 309.0. found 308.9.

N-[(2S)-3-[5-bromo-6-(oxazol-5-ylmethoxy)-3,4-dihydro-1H-isoquinolin-2-yl]-2-hydroxy-propyl]-2-(cyclobutylamino)pyridine-4-carboxamide tert-butyl 5-bromo-6-(oxazol-5-ylmethoxy)-3,4-dihydro-1H-isoquinoline-2-carboxylate was converted to N-[(2S)-3-[5-bromo-6-(oxazol-5-ylmethoxy)-3,4-dihydro-1H-isoquinolin-2-yl]-2-hydroxy-propyl]-2-(cyclobutylamino)pyridine-4-carboxamide using reaction conditions outlined in Steps B and Step C from Example 1B. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% ammonia hydroxide (v %); Mobile phase B: MeCN; Gradient: B from 35% to 65% in 7.8 min, hold 100% B for 2.5 min; Flow Rate: 25 mL/min; Column Temperature: 30° C.; Wavelength: 220 nm, 254 nm) to afford N-[(2S)-3-[5-bromo-6-(oxazol-5-ylmethoxy)-3,4-dihydro-1H-isoquinolin-2-yl]-2-hydroxy-propyl]-2-(cyclobutylamino)pyridine-4-carboxamide (55 mg, 29.1% yield) as a yellow solid. $^1$H NMR (400 MHz, methanol-d$_4$) δ ppm 8.24 (s, 1H), 7.88 (d, J=5.4 Hz, 1H), 7.24 (s, 1H), 6.96-7.06 (m, 2H), 6.78 (s, 1H), 6.71 (dd, J=5.5, 1.4 Hz, 1H), 5.19 (s, 2H), 4.22 (quin, J=7.8 Hz, 1H), 4.07 (quin, J=6.0 Hz, 1H), 3.69 (s, 2H), 3.47 (qd, J=13.4, 6.0 Hz, 2H), 2.85 (s, 4H), 2.59-2.70 (m, 2H), 2.36-2.45 (m, 2H), 1.86-1.99 (m, 2H), 1.71-1.83 (m, 2H); LCMS (ESI) [M+H]$^+$ m/z: calcd 558.1. found 558.1; HPLC: 94.47% @ 254 nm; 97.1% ee.

Example 1B8. 2-(cyclobutylamino)-N-[(2S)-2-hydroxy-3-[5-iodo-6-(oxazol-5-ylmethoxy)-3N-dihydro-1H-isoquinolin-2-yl]propyl]pyridine-4-carboxamide (Compound 258)

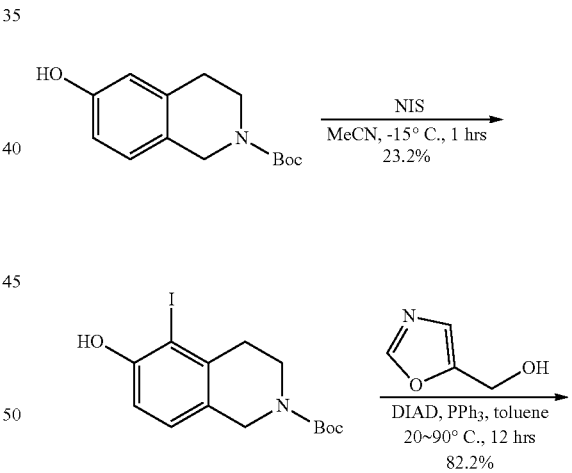

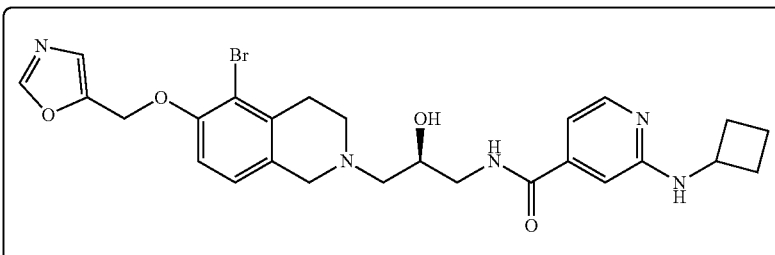

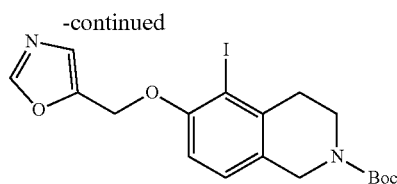

tert-butyl 6-hydroxy-5-iodo-3,4-dihydro-1H-isoquinoline-2-carboxylate. To a solution of tert-butyl 6-hydroxy-3,4-dihydro-1H-isoquinoline-2-carboxylate (2.0 g, 8.02 mmol) in MeCN (10 mL) was added dropwise a solution of NIS (1.8 g, 8.02 mmol) in MeCN (10 mL) at −15° C. The mixture was stirred at −15° C. for 1 hour. The resulting mixture was quenched by addition of saturated $Na_2SO_3$ aqueous solution (20 mL) and extracted with EtOAc (40 mL*3). The combined organic layer was washed with brine (100 mL), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~30%, flow rate=30 mL/min) to afford tert-butyl 6-hydroxy-5-iodo-3,4-dihydro-1H-isoquinoline-2-carboxylate (700 mg, 23.2% yield) as white solid. $^1$H NMR (400 MHz, methanol-$d_4$) δ ppm 6.88-6.97 (m, 1H), 6.71 (d, J=8.3 Hz, 1H), 4.44 (br s, 2H), 3.57-3.60 (m, 2H), 2.76 (br s, 2H), 1.48 (s, 9H); LCMS (ESI) [M+H−100]$^+$ m/z calcd 276.0. found 275.9.

tert-butyl 5-iodo-6-(oxazol-5-ylmethoxy)-3,4-dihydro-1H-isoquinoline-2-carboxylate. To a solution of tert-butyl 6-hydroxy-5-iodo-3,4-dihydro-1H-isoquinoline-2-carboxylate (200 mg, 0.53 mmol) in toluene (5 mL) were added oxazol-5-ylmethanol (55 mg, 0.57 mmol), triphenylphosphine (210 mg, 0.80 mmol) at 20° C. Isopropyl (NE)-N-isopropoxycarbonyl iminocarbamate (160 mg, 0.79 mmol) was added and the reaction mixture was stirred at 90° C. for 12 hours. The resulting mixture was concentrated under reduced pressure and the residue was purified by flash chromatography (ISCO®; 40 g AgelaFlash® Silica Flash Column, petroleum ether/EtOAc with EtOAc from 0~40%, flow rate=30 mF/min) to afford tert-butyl 5-iodo-6-(oxazol-5-ylmethoxy)-3,4-dihydro-1H-isoquinoline-2-carboxylate (200 mg, 82.2% yield) as yellow solid. $^1$H NMR (400 MHz, methanol-$d_4$) δ ppm 8.21-8.27 (m, 1H), 7.26 (s, 1H), 7.13 (d, J=8.4 Hz, 1H), 6.96 (d, J=8.4 Hz, 1H), 5.20 (s, 2H), 4.50 (s, 2H), 3.62 (br t, J=5.9 Hz, 2H), 2.79 (t, J=6.0 Hz, 2H), 1.49 (s, 9H).

2-(cyclobutylamino)-N-[(2S)-2-hydroxy-3-[5-iodo-6-(oxazol-5-ylmethoxy)-3,4-dihydro-1H-isoquinolin-2-yl]propyl]pyridine-4-carboxamide (Compound 258)

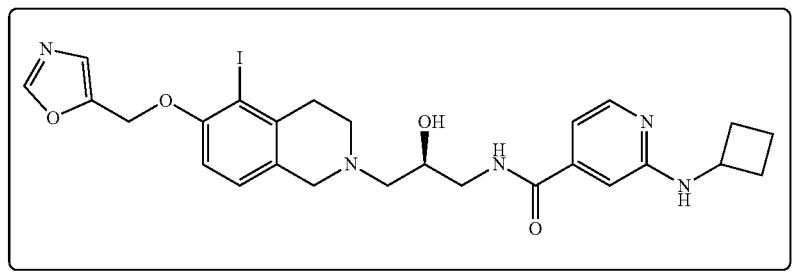 [SMILES: O=C(NC[C@H](O)CN1CCc2c(ccc(OCc3cnco3)c2I)C1)c1ccnc(NC2CCC2)c1]

tert-butyl 5-iodo-6-(oxazol-5-ylmethoxy)-3,4-dihydro-1H-isoquinoline-2-carboxylate was converted to 2-(cyclobutylamino)-N-[(2S)-2-hydroxy-3-[5-iodo-6-(oxazol-5-ylmethoxy)-3,4-dihydro-1H-isoquinolin-2-yl]propyl]pyridine-4-carboxamide using reaction conditions outlined in Steps B and Step C from Example IB. The reaction mixture was concentrated under reduced pressure and the residue was purified by preparative HPFC (Instrument: Gilson GX-281 Liquid Handler, Gilson 322 Pump, Gilson 156 UV Detector; Column: Durashell 150×25 mm×5 μm; Mobile phase A: water (0.05% ammonia hydroxide v/v); Mobile phase B: MeCN; Gradient: B from 35% to 65% in 7.8 min, hold 100% B for 0 min; Flow Rate: 25 mF/min; Column Temperature: 30° C.; Wavelength: 220 nm, 254 nm) to afford 2-(cyclobutylamino)-N-[(2S)-2-hydroxy-3-[5-iodo-6-(oxazol-5-ylmethoxy)-3,4-dihydro-1H-isoquinolin-2-yl]propyl]pyridine-4-carboxamide (2.7 mg, 4.0% yield) as a white solid. $^1$H-NMR (400 MHz, methanol-$d_4$) δ ppm 8.25 (s, 1H), 7.88 (d, J=5.5 Hz, 1H), 7.26 (s, 1H), 7.06 (d, J=8.3 Hz, 1H), 6.91 (d, J=8.5 Hz, 1H), 6.79 (s, 1H), 6.70 (dd, J=5.5, 1.5 Hz, 1H), 5.20 (s, 2H), 4.22 (t, J=7.8 Hz, 1H), 4.05-4.11 (m, 1H), 3.70 (s, 2H), 3.41-3.54 (m, 2H), 2.83 (br dd, J=15.6, 4.8 Hz, 4H), 2.61-2.71 (m, 2H), 2.37-2.46 (m, 2H), 1.86-1.97 (m, 2H), 1.74-1.82 (m, 2H); LCMS (ESI) [M+H]+ m/z: calcd 604.1. found 604.0; HPLC: 100% @ 254 nm; 99.4% ee.

Example 1B9. N-[(2S)-3-[5-chloro-6-(1H-pyrazol-4-ylmethoxy)-3N-dihydro-1H-isoquinolin-2-yl]-2-hydroxy-propyl]-2-(cyclobutylamino)pyridine-4-carboxamide (Compound 280)

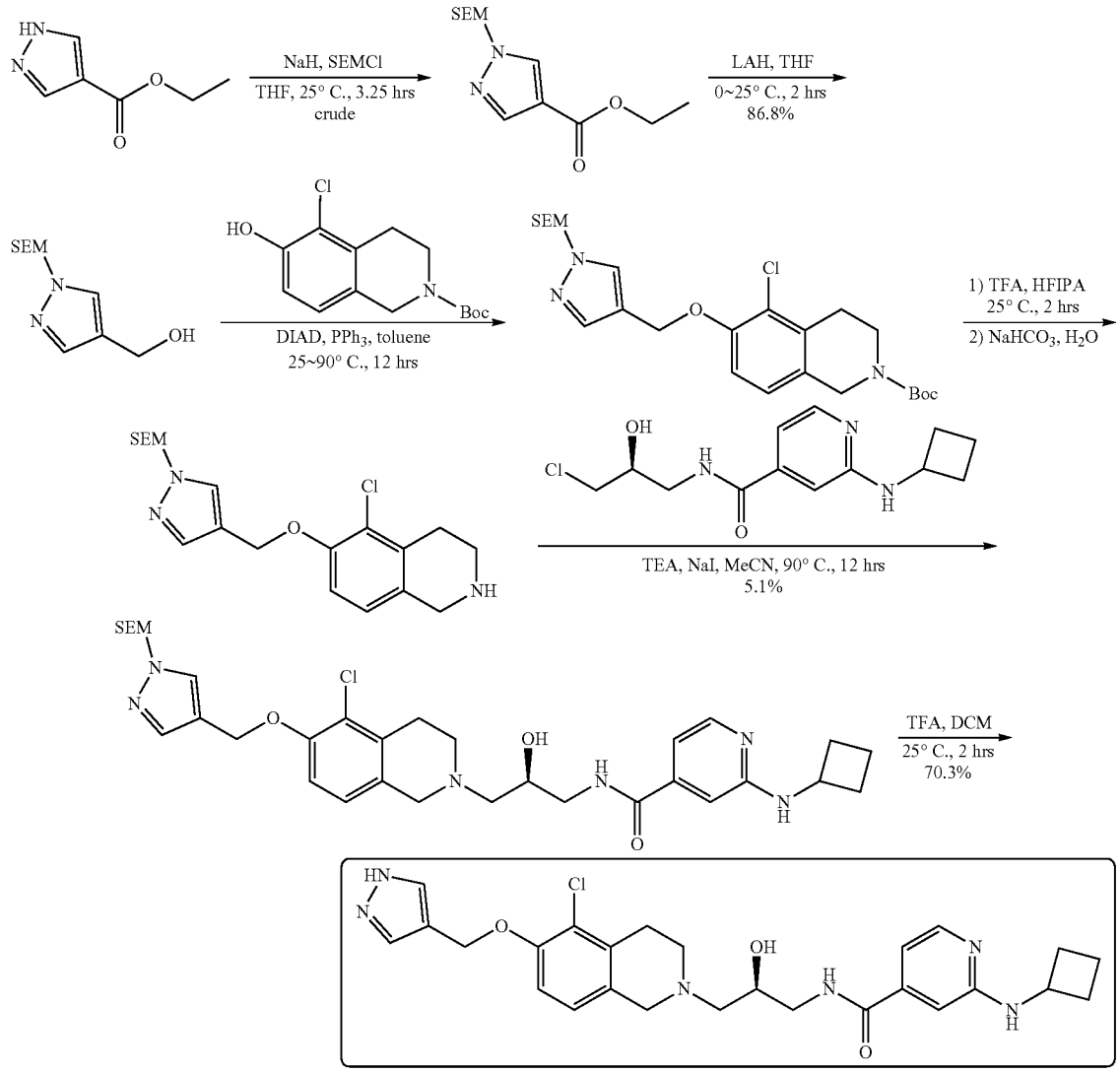

Ethyl 1-(2-trimethylsilylethoxymethyl)pyrazole-4-carboxylate. To a solution of ethyl 1H-pyrazole-4-carboxylate (2.0 g, 14.3 mmol) in THF (30 mL) was added NaH (1.1 g, 28.5 mmol, 60% wt in mineral oil). The mixture was stirred at 0° C. for 15 minutes. 2-(chloromethoxy)ethyl-trimethylsilane (2.6 g, 15.8 mmol) was added to the mixture and stirred at 25° C. for 3 hours. The resulting mixture was quenched by addition of water (15 mL) and extracted with EtOAc (20 mL*3). The combined organic layers were washed with brine (50 mL), dried over anhydrous Na2SO4, filtered and concentrated under reduced pressure to afford ethyl 1-(2-trimethylsilylethoxymethyl)pyrazole-4-carboxylate (4.5 g, crude) as light yellow oil which was used in next step without further purification. 1H NMR (400 MHz, methanol-d4) δ ppm 8.34 (s, 1H), 7.95 (s, 1H), 5.48 (s, 2H), 4.28-4.35 (m, 2H), 3.58-3.67 (m, 2H), 1.37 (t, J=7.0 Hz, 3H), 0.93 (t, J=8.0 Hz, 2H), 0.01 (s, 9H); LCMS (ESI) [M+H]+ m/z: calcd 271.1. found 271.1.

[1-(2-trimethylsilylethoxymethyl)pyrazol-4-yl]methanol. To a suspension of LiAlH4 (950 mg, 25.0 mmol) in THF (30 mL) was added a solution of ethyl 1-(2-trimethylsilylethoxymethyl)pyrazole-4-carboxylate (4.5 g, 16.6 mmol) in THF (20 mL) at 0° C. After the addition was complete, the mixture was allowed to warm to 25° C. and stirred for 2 hours. The resulting mixture was cooled to 0° C. and quenched with H2O (1 mL), NaOH aqueous solution (1 mL, 10% wt) and H2O (3 mL). The resulting mixture was stirred for 30 minutes, then dried over anhydrous Na2SO4, filtered and concentrated under reduced pressure to afford [1-(2-trimethylsilylethoxymethyl)pyrazol-4-yl]methanol (3.3 g, 86.8% yield) as colorless oil. 1H NMR (400 MHz, methanol-d4) δ ppm 7.76 (s, 1H), 7.56 (s, 1H), 5.42 (s, 2H), 4.55 (s, 2H), 3.53-3.61 (m, 2H), 0.89-0.93 (m, 2H), 0.01 (s, 9H); LCMS (ESI) [M+H]+ m/z calcd 229.1, found 229.1.

tert-butyl 5-chloro-6-[[1-(2-trimethylsilylethoxymethyl)pyrazol-4-yl]methoxy]-3,4-dihydro-1H-isoquinoline-2-carboxylate. To a solution of tert-butyl 5-chloro-6-hydroxy-3,4-dihydro-1H-isoquinoline-2-carboxylate (220 mg, 0.78 mmol), [1-(2-trimethylsilylethoxymethyl)pyrazol-4-yl]methanol (177 mg, 0.78 mmol) and triphenylphosphine (305 mg, 1.16 mmol) in toluene (3 mL) was added a solution of isopropyl (NE)-N-isopropoxycarbonyliminocarbamate (235 mg, 1.16 mmol) in toluene (2 mL) slowly at 20° C. under nitrogen and after addition was complete, the mixture was allowed to warm to 90° C. and stir for 12 hours in a sealed tube. The resulting mixture was concentrated under reduced pressure and the residue was purified by flash chromatography (ISCO®; 12 g AgelaFlash® Silica Flash Column, petroleum ether/EtOAc with EtOAc from 0~30%, Flow Rate: 30 mL/min) to afford tert-butyl 5-chloro-6-[[1-(2-trimethylsilylethoxymethyl)pyrazol-4-yl]methoxy]-3,4-dihydro-1H-isoquinoline-2-carboxylate (400 mg, crude) as yellow oil which was used on next step without further purification. ¹H NMR (400 MHz, methanol-d₄) δ ppm 7.87 (s, 1H), 7.65 (s, 1H), 7.04 (s, 2H), 5.44 (s, 2H), 5.10 (s, 2H), 4.49 (br s, 2H), 3.63 (t, J=5.3 Hz, 2H), 3.48-3.59 (m, 2H), 2.83 (t, J=6.0 Hz, 2H), 1.48 (s, 9H), 0.86 (t, J=8.1 Hz, 2H), 0.02 (s, 9H); LCMS (ESI) [M+H−56]+ m/z calcd 438.2. found 438.0.

2-[[4-[(5-chloro-1,2,3,4-tetrahydroisoquinolin-6-yl)oxymethyl]pyrazol-1-yl]methoxy]ethyl-trimethyl-silane. A mixture of tert-butyl 5-chloro-6-[[1-(2-trimethylsilylethoxymethyl)pyrazol-4-yl]methoxy]-3,4-dihydro-1H-isoquinoline-2-carboxylate (400 mg, 0.81 mmol) and TFA (111 mg, 0.97 mmol) in hexafluoroisopropanol (3 mL) was stirred at 25° C. for 2 hours. The residue was quenched by addition of water (20 mL) and washed with DCM (10 mL*2). The aqueous layer was adjusted to pH=7-8 by saturated NaHCO₃ aqueous solution and extracted with DCM (30 mL*3). The combined organic layer was dried over anhydrous Na₂SO₄, filtered and concentrated under reduced pressure to give 2-[[4-[(5-chloro-1,2,3,4-tetrahydroisoquinolin-6-yl)oxymethyl]pyrazol-1-yl]methoxy]ethyl-trimethyl-silane (300 mg, crude) as a yellow oil. ¹H NMR (400 MHz, methanol-d₄) δ ppm 7.87 (s, 1H), 7.63 (s, 1H), 6.94-7.00 (m, 2H), 5.41 (s, 2H), 5.08 (s, 2H), 3.89 (s, 2H), 3.55 (t, J=8.1 Hz, 2H), 3.09 (t, J=6.1 Hz, 2H), 2.75-2.85 (m, 2H), 0.87 (t, J=7.9 Hz, 3H), −0.04 (s, 9H); LCMS (ESI) [M+H]+ m/z: calcd 394.2. found 394.1.

N-[(2S)-3-[5-chloro-6-[[1-(2-trimethylsilylethoxymethyl)pyrazol-4-yl]methoxy]-3,4-dihydro-1H-isoquinolin-2-yl]-2-hydroxy-propyl]-2-(cyclobutylamino)pyridine-4-carboxamidine

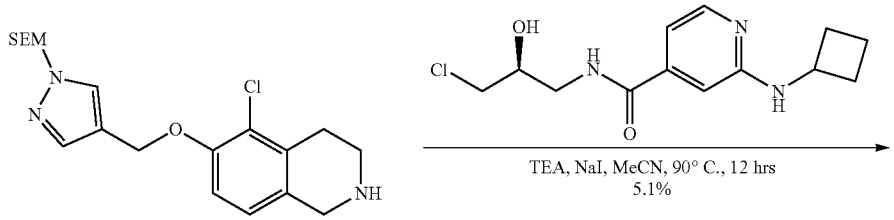

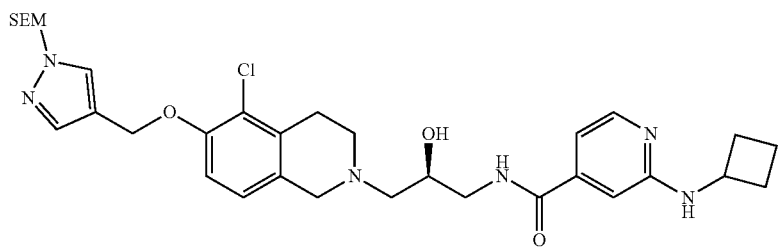

A mixture of 2-[[4-[(5-chloro-1,2,3,4-tetrahydroisoquinolin-6-yl)oxymethyl]pyrazol-1-yl]methoxy]ethyl-trimethyl-silane (300 mg, 0.76 mmol), N-[(2S)-3-chloro-2-hydroxypropyl]-2-(cyclobutylamino)pyridine-4-carboxamide (217 mg, 0.76 mmol), TEA (2.87 mmol, 0.4 mL) and NaI (137 mg, 0.91 mmol) in MeCN (4 mL) was stirred at 90° C. for 12 hours in a sealed tube. The mixture was filtered and concentrated under reduced pressure. The residue was purified by flash chromatography (ISCO®; 12 g of AgelaFlash® Silica Flash Column, DCM/MeOH with MeOH from 0~5%, Flow Rate: 30 mF/min) to afford a crude product which was purified by preparative HPFC (Instrument: Gilson GX-281 Liquid Handler, Gilson 322 Pump, Gilson 156 UV Detector; Column: Waters Xbridge 150×25 mm×5 μm; Mobile phase A: H₂O with 0.05% NH₃—H₂O (v %); Mobile phase B: MeCN; Gradient: B from 50% to 80% in 8 min, hold 100% B for 3 min; Flow Rate: 25 mF/min; Column Temperature: 30° C.; Wavelength: 220 nm, 254 nm) to afford N-[(2S)-3-[5-chloro-6-[[1-(2-trimethylsilylethoxymethyl)pyrazol-4-yl]methoxy]-3,4-dihydro-1H-isoquinolin-2-yl]-2-hydroxy-propyl]-2-(cyclobutylamino)pyridine-4-carboxamide (25 mg, 5.1% yield) as a white solid. ¹H NMR (400 MHz, methanol-d₄) δ ppm 7.85-7.91 (m, 2H), 7.64 (s, 1H), 6.94-7.01 (m, 2H), 6.78 (s, 1H), 6.71 (dd, J=5.5, 1.5 Hz, 1H), 5.42 (s, 2H), 5.08 (s, 2H), 4.23 (quin, J=7.4 Hz, 1H), 4.08 (quin, J=5.9 Hz, 1H), 3.68 (s, 2H), 3.43-3.57 (m, 4H), 2.87 (s, 4H), 2.59-2.69 (m, 2H), 2.31-2.46 (m, 2H), 1.86-1.99 (m, 2H), 1.72-1.83 (m, 2H), 0.83-0.91 (m, 2H), −0.03 (s, 9H); LCMS (ESI) [M+H]+ m/z: calcd 641.3. found 641.2.

tert-butyl N-[(2S)-3-[5-chloro-6-(1H-pyrazol-4-yl-methoxy)-3,4-dihydro-1H-isoquinolin-2-yl]-2-hydroxy-propyl]-2-(cyclobutylamino)pyridine-4-carboxamidine

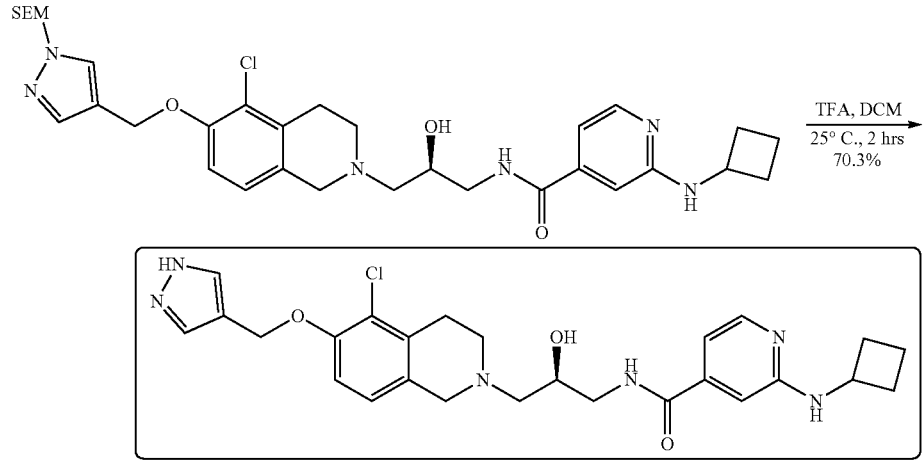

A mixture of N-[(2S)-3-[5-chloro-6-[[1-(2-trimethylsilylethoxymethyl)pyrazol-4-yl]methoxy]-3,4-dihydro-1H-isoquinolin-2-yl]-2-hydroxy-propyl]-2-(cyclobutylamino)pyridine-4-carboxamide (25 mg, 0.04 mmol) and TFA (3 mL) in DCM (5 mL) was stirred at 25° C. for 2 hours. The mixture was concentrated under reduced pressure and the residue was purified by preparative HPLC (Instrument: Gilson GX-215, Gilson 322 Pump, Gilson 156 UV Detector; Column: Xtimate C18 150*25 mm*5 μm; Mobile phase A: water (0.225% FA); Mobile phase B: MeCN; Gradient: B from 0% to 30% in 7 min, hold 100% B for 2 min; Flow Rate: 25 mL/min; Column Temperature: 30° C.; Wavelength: 220 nm, 254 nm) to afford N-[(2S)-3-[5-chloro-6-(1H-pyrazol-4-ylmethoxy)-3,4-dihydro-1H-isoquinolin-2-yl]-2-hydroxy-propyl]-2-(cyclobutylamino)pyridine-4-carboxamide (14 mg, 70.3% yield) as a white solid. $^1$H NMR (400 MHz, methanol-d$_4$) δ ppm 7.99 (d, J=6.0 Hz, 1H), 7.71 (s, 2H), 7.17-7.22 (m, 2H), 7.08 (s, 1H), 6.99 (d, J=5.8 Hz, 1H), 5.17 (s, 2H), 4.49 (s, 2H), 4.34 (d, J=5.6 Hz, 1H), 4.25 (quin, J=7.8 Hz, 1H), 3.71 (br s, 2H), 3.36-3.59 (m, 3H), 3.12-3.31 (m, 3H), 2.44-2.50 (m, 2H), 1.98-2.09 (m, 2H), 1.80-1.90 (m, 2H); LCMS (ESI) [M+H]$^+$ m/z: calcd 511.2. found 511.1, HPLC: 97.79% @ 254 nm; 98.7% ee.

Example 1B10. N-[(2S)-3-[5-bromo-6-[(4-methyloxazol-5-yl)methoxy]-3N-dihydro-1H-isoquinolin-2-yl]-2-hydroxy-propyl]-2-(cyclobutylamino)pyridine-4-carboxamide (Compound 267)

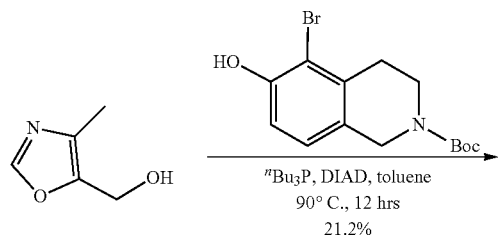

tert-butyl 5-bromo-6-[(4-methyloxazol-5-yl)methoxy]-3,4-dihydro-1H-isoquinoline-2-carboxylate. To a solution of tert-butyl 5-bromo-6-hydroxy-3,4-dihydro-1H-isoquinoline-2-carboxylate (45 mg, 0.14 mmol) in toluene (5 mL) were added (4-methyloxazol-5-yl)methanol (20 mg, 0.18 mmol) and PPh$_3$ (45 mg, 0.222 mmol). The mixture was degassed and backfilled with nitrogen for 3 times and then a solution of isopropyl (NE)-N-isopropoxycarbonyliminocarbamate (42 mg, 0.21 mmol) in toluene (3 mL) was added at 25° C. drop-wise. The mixture was allowed to warm to 90° C. and stirred for 12 hours. The resulting mixture concentrated under reduced pressure. The residue was purified by flash chromatography (ISCO®; 12 g of AgelaFlash® Silica Flash Column, petroleum ether/EtOAc with EtOAc from 0~50%, Flow rate: 30 mL/min) to afford tert-butyl 5-bromo-6-[(4-methyloxazol-5-yl)methoxy]-3,4-dihydro-1H-isoquinoline-2-carboxylate (25 mg) as colorless oil (21.5% yield). $^1$H NMR (400 MHz, methanol-d$_4$) δ ppm 8.16 (s, 1H), 7.14 (d, J=8.0 Hz, 1H), 7.06 (d, J=8.0 Hz, 1H), 5.18 (s, 2H), 4.54 (s, 2H), 3.64-3.68 (m, 2H), 2.86 (t, J=6.1 Hz, 2H), 1.50 (s, 9H); LCMS (ESI) [M-56+H]$^+$ m/z: calcd 367.1. found 367.0.

Steps B and C from Example 1B1 were used to obtain

N-[(2S)-3-[5-bromo-6-[(4-methyloxazol-5-yl)methoxy]-3,4-dihydro-1H-isoquinolin-2-yl]-2-hydroxy-propyl]-2-(cyclobutylamino)pyridine-4-carboxamide

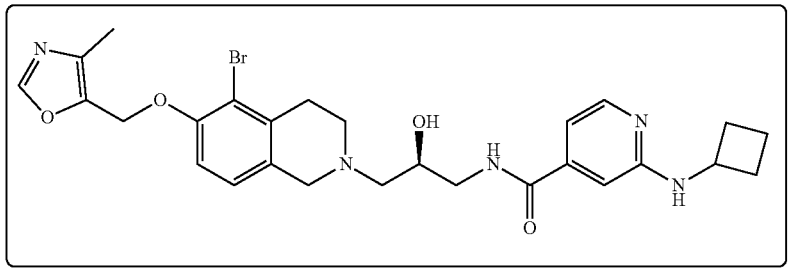 [SMILES: Cc1ncoc1COc1ccc2c(c1Br)CCN(C[C@@H](O)CNC(=O)c1ccnc(NC3CCC3)c1)C2]

tert-butyl 5-bromo-6-[(4-methyloxazol-5-yl)methoxy]-3,4-dihydro-1H-isoquinoline-2-carboxylate was converted to N-[(2S)-3-[5-bromo-6-[(4-methyloxazol-5-yl)methoxy]-3,4-dihydro-1H-isoquinolin-2-yl]-2-hydroxy-propyl]-2-(cyclobutylamino)pyridine-4-carboxamide using reaction conditions outlined in Steps B and Step C from Example IB. The resulting mixture was concentrated under reduced pressure and the residue was purified by HPLC purification (Instrument: Gilson GX-281 Liquid Handler, Gilson 322 Pump, Gilson 156 UV Detector; Column: Waters Xbridge 150×25 mm×5 μm; Mobile phase A: $H_2O$ with 0.05% ammonia hydroxide (v %); Mobile phase B: MeCN; Gradient: B from 27% to 57% in 7.8 min, hold 100% B for 2.5 min; Flow Rate: 25 mL/min; Column Temperature: 30° C.; Wavelength: 220 nm, 254 nm) to afford N-[(2S)-3-[5-bromo-6-[(4-methyloxazol-5-yl)methoxy]-3,4-dihydro-1H-isoquinolin-2-yl]-2-hydroxy-propyl]-2-(cyclobutylamino)pyridine-4-carboxamide (4 mg, 22.7% yield) as a white solid. $^1$H NMR (400 MHz, methanol-$d_4$) δ ppm 8.16 (s, 1H), 7.92 (d, J=5.0 Hz, 1H), 7.07 (d, J=8.0 Hz, 1H), 7.00 (d, J=8.0 Hz, 1H), 6.81 (s, 1H), 6.74 (dd, J=5.5, 1.5 Hz, 1H), 5.17 (s, 2H), 4.20-4.29 (m, 1H), 4.08-4.12 (m, 1H), 3.76 (s, 2H), 3.45-3.56 (m, 2H), 2.90 (br s, 4H), 2.70 (s, 2H), 2.42 (br d, J=8.0 Hz, 2H), 2.20 (s, 3H), 1.94 (t, J=10.5 Hz, 2H), 1.75-1.84 (m, 2H); LCMS (ESI) [M+H]$^+$ m/z: calcd 572.2. found 572.1; HPLC: 98.15% @ 254 nm; 95.1% ee.

Example 1B11. N-[(2S)-3-[7-chloro-6-(oxazol-5-ylmethoxy)-3N-dihydro-1H-isoquinolin-2-yl]-2-hydroxy-propyl]-2-(cyclobutylamino)pyridine-4-carboxamide (Compound 281)

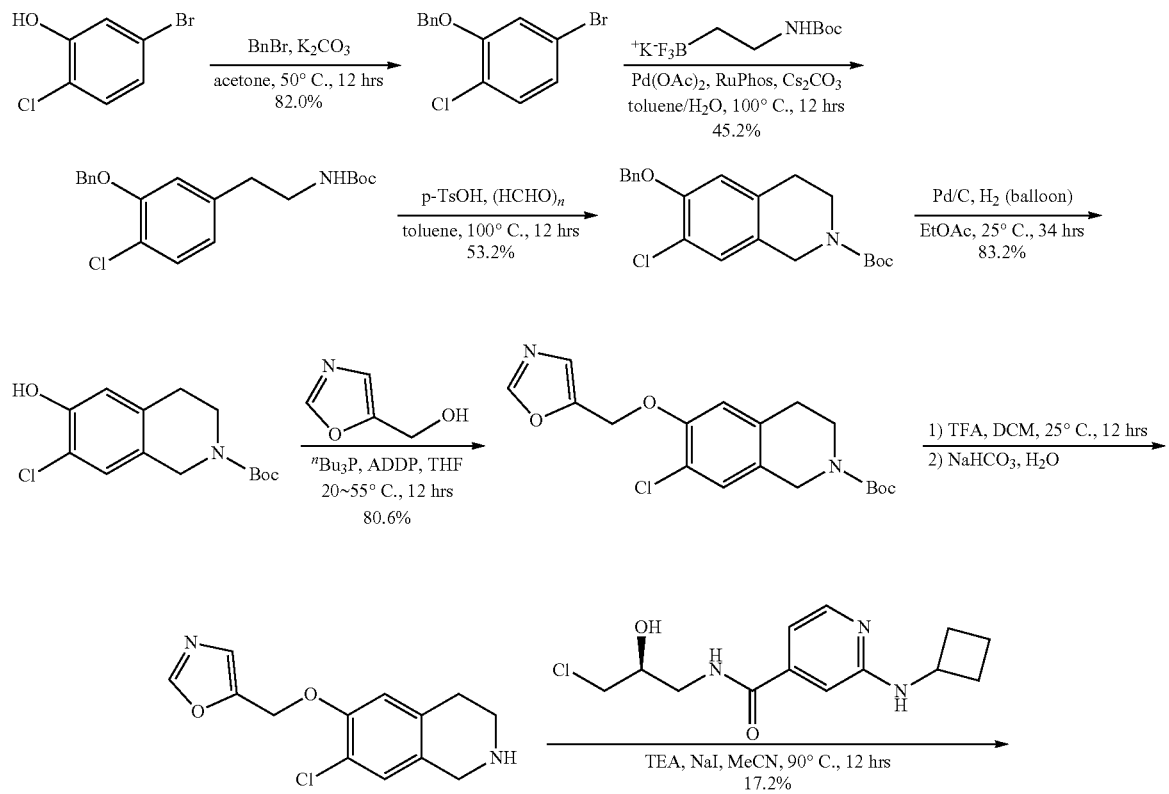

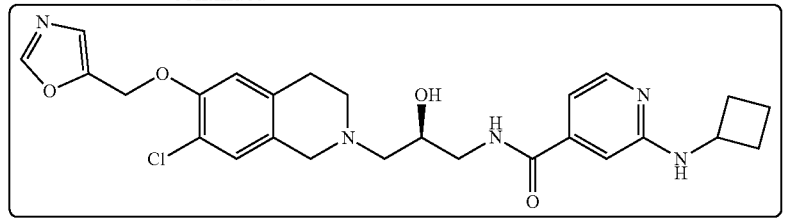

2-benzyloxy-4-bromo-1-chloro-benzene. To a solution of bromomethylbenzene (1.01 g, 5.89 mmol) in acetone (10 mL) were added 5-bromo-2-chloro-phenol (850 mg, 4.10 mmol) and tripotassium; carbonate (1 g, 7.24 mmol). The mixture was stirred at 50° C. for 12 hours. The resulting mixture was filtered and concentrated under reduced pressure. The residue was purified by flash chromatography (ISCO®; 24 g AgelaFlash® Silica Flash Column, petroleum ether/EtOAc with EtOAc from 0-8.6%, Flow rate: 30 mL/min) to afford 2-benzyloxy-4-bromo-1-chloro-benzene (1 g, 82.0% yield) as white solid. ¹H NMR (400 MHz, chloroform-d) δ ppm 7.33-7.49 (m, 5H), 7.26 (s, 1H), 7.13 (d, J=2.0 Hz, 1H), 7.05 (dd, J=8.4, 2.1 Hz, 1H), 5.14 (s, 2H).

tert-butyl N-[2-(3-benzyloxy-4-chloro-phenyl)ethyl]carbamate. To a round bottom flask were added 2-benzyloxy-4-bromo-1-chloro-benzene (1 g, 3.36 mmol), 2-(tert-butoxycarbonylamino)ethyl-trifluoro-boranuide; potassiumhydride (900 mg, 3.58 mmol), Cs₂CO₃ (3.31 g, 10.17 mmol), RuPhos (165 mg, 0.35 mmol), H₂O (5 mL) and toluene (30 mL). The mixture was degassed and backfilled with nitrogen for three times and then stirred for 12 hours at 100° C. under nitrogen. The resulting mixture was dried over anhydrous Na₂SO₄, filtered and concentrated under reduced pressure. The residue was purified by flash chromatography (ISCO®; 20 g AgelaFlash® Silica Flash Column, petroleum ether/EtOAc with EtOAc from 0~22.5%, Flow rate: 30 mL/min) to afford tert-butyl N-[2-(3-benzyloxy-4-chloro-phenyl)ethyl]carbamate (550 mg, 45.2% yield) as yellow solid. ¹H NMR (400 MHz, chloroform-d) δ ppm 7.46-7.50 (m, 2H), 7.40 (t, J=7.3 Hz, 2H), 7.34 (d, J=7.3 Hz, 1H), 7.31 (d, J=8.0 Hz, 1H), 6.82 (s, 1H), 6.75 (d, J=8.0 Hz, 1H), 5.15 (s, 2H), 4.51 (br s, 1H), 3.35 (t, J=6.3 Hz, 2H), 2.76 (t, J=6.8 Hz, 2H), 1.45 (s, 9H); LCMS (ESI) [M+H−56]⁺ m/z: calcd 306.1. found 306.0.

tert-butyl 6-benz.]oxy-7-chloro-3,4-dihydro-1H-isoquinoline-2-carboxylate. To a solution of tert-butyl N-[2-(3-benzyloxy-4-chloro-phenyl)ethyl]carbamate (400 mg, 1.11 mmol) in toluene (40 mL) were added p-TsOH (40.0 mg, 0.23 mmol) and paraformaldehyde (900 mg, 30.0 mmol). The mixture was stirred at 100° C. for 12 hours. The resulting mixture was filtered and concentrated under reduced pressure. The residue was purified by flash chromatography (ISCO®; 20 g AgelaFlash® Silica Flash Column, petroleum ether/EtOAc with EtOAc from 0~12%, Flow rate: 30 mL/min) to afford tert-butyl 6-benzyloxy-7-chloro-3,4-dihydro-1H-isoquinoline-2-carboxylate (220 mg, 53.2% yield) as yellow oil. ¹H NMR (400 MHz, chloroform-d) δ ppm 7.45-7.49 (m, 2H), 7.40 (t, J=7.4 Hz, 2H), 7.31-7.36 (m, 1H), 7.14 (s, 1H), 6.74 (s, 1H), 5.13 (s, 2H), 4.48 (s, 2H), 3.62 (br s, 2H), 2.72-2.79 (m, 2H), 1.49 (s, 9H); LCMS (ESI) [M+H−56]⁺ m/z: calcd 318.2. found 318.0.

tert-butyl 7-chloro-6-hydroxy-3,4-dihydro-1H-isoquinoline-2-carboxylate. To a solution of tert-butyl 6-benzyloxy-7-chloro-3,4-dihydro-1H-isoquinoline-2-carboxylate (190 mg, 0.51 mmol) and AcOH (0.2 mL) in EtOAc (10 mL) was added Pd/C (40 mg, 10% wt of Pd with 50% wt of water). The mixture was degassed and backfilled with hydrogen for three times. Then the mixture was stirred at 25° C. for 34 hours under hydrogen (~15 psi, in balloon). The resulting mixture was filtered and the filtrate was quenched by addition of saturated NaHCO₃ aqueous solution (15 mL) and extracted with EtOAc (20 mL). The combined organic layer was dried over anhydrous Na₂SO₄, filtered and concentrated under reduced pressure to afford tert-butyl 7-chloro-6-hydroxy-3,4-dihydro-1H-isoquinoline-2-carboxylate (120 mg, 83.2% yield) as white solid. ¹H NMR (400 MHz, chloroform-d) δ ppm 7.07 (s, 1H), 6.80 (s, 1H), 4.48 (s, 2H), 3.61 (br s, 2H), 2.77 (t, J=5.1 Hz, 2H), 1.49 (s, 9H); LCMS (ESI) [M+H−56]⁺ m/z: calcd 228.1, found 228.1.

tert-butyl 7-chloro-6-(oxazol-5-ylmethoxy)-3,4-dihydro-1H-isoquinoline-2-carboxylate

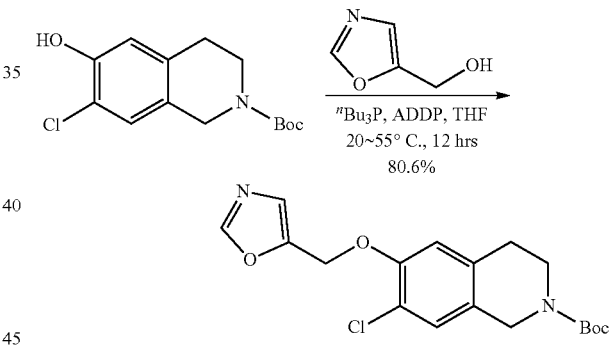

To a solution of oxazol-5-ylmethanol (100.0 mg, 1.01 mmol) and tert-butyl 7-chloro-6-hydroxy-3,4-dihydro-1H-isoquinoline-2-carboxylate (120 mg, 0.42 mmol) in THF (10 mL) were added tributylphosphane (132.0 mg, 0.65 mmol). The mixture was degassed and backfilled with nitrogen for three times. Then a solution of (NE)-N-(piperidine-1-carbonylimino)piperidine-1-carboxamide (155.0 mg, 0.61 mmol) in THF (5 mL) was added drop-wise at 25° C. The mixture was stirred at 55° C. for 12 hours and the resulting mixture was concentrated under reduced pressure. The residue was purified by flash chromatography (ISCO®; 12 g*2 AgelaFlash® Silica Flash Column, petroleum ether/EtOAc with EtOAc from 0~50%, Flow rate: 30 mL/min) to afford tert-butyl 7-chloro-6-(oxazol-5-ylmethoxy)-3,4-dihydro-1H-isoquinoline-2-carboxylate (145 mg, 80.6% yield) as yellow oil. ¹H NMR (400 MHz, chloroform-d) δ ppm 7.94 (s, 1H), 7.19 (s, 1H), 7.15 (s, 1H), 6.80 (s, 1H), 5.14 (s, 2H), 4.51 (s, 2H), 3.65 (br s, 2H), 2.76-2.83 (m, 2H), F51 (s, 9H).

N-[(2S)-3-[7-chloro-6-(oxazol-5-ylmethoxy)-3,4-dihydro-1H-isoquinolin-2-yl]-2-hydroxy-propyl]-2-(cyclobutylamino)pyridine-4-carboxamide. tert-butyl 7-chloro- 6-(oxazol-5-ylmethoxy)-3,4-dihydro-1H-isoquinoline-2-carboxylate was converted to N-[(2S)-3-[7-chloro-6-(oxazol-5-ylmethoxy)-3,4-dihydro-1H-isoquinolin-2-yl]-2-hydroxy-propyl]-2-(cyclobutylamino)pyridine-4-carboxamide using reaction conditions outlined in Steps B and Step C from Example 1B. The mixture was concentrated under reduced pressure to give a crude product, which was purified by preparative HPLC (Instrument: Gilson GX-281 Liquid Handler, Gilson 322 Pump, Gilson 156 UV Detector; Column: Waters Xbridge 150×50 mm×10 μm; Mobile phase A: H$_2$O with 0.05% NH$_3$—H$_2$O (v %); Mobile phase B: MeCN; Gradient: B from 25% to 55% in 8.8 min, hold 100% B for 2 min; Flow Rate: 25 mL/min; Column Temperature: 30° C.; Wavelength: 220 nm, 254 nm) to give N-[(2S)-3-[7-chloro-6-(oxazol-5-ylmethoxy)-3,4-dihydro-1H-isoquinolin-2-yl]-2-hydroxy-propyl]-2-(cyclobutylamino)pyridine-4-carboxamide (15 mg, 17.2% yield) as a yellow dry powder. $^1$H NMR (400 MHz, methanol-d$_4$) δ ppm 8.25 (s, 1H), 7.91 (d, J=5.4 Hz, 1H), 7.25 (s, 1H), 7.08 (s, 1H), 6.95 (s, 1H), 6.79 (s, 1H), 6.75 (d, J=5.4 Hz, 1H), 5.17 (s, 2H), 4.22 (quin, J=7.9 Hz, 1H), 4.07 (quin, J=5.8 Hz, 1H), 3.66 (s, 2H), 3.37-3.56 (m, 2H), 2.78-2.97 (m, 4H), 2.55-2.74 (m, 2H), 2.35-2.45 (m, 2H), 1.88-1.96 (m, 2H), 1.70-1.84 (m, 2H); LCMS (ESI) [M+H]$^+$ m/z: calcd 512.2. found 512.1; HPLC: 99.18% @ 254 nm; 100% ee.

Example 1B12. 2-(cyclobutylamino)-N-[(2S)-2-hydroxy-3-[(4R)-4-hydroxy-6-[(4-methyloxazol-5-yl)methoxy]-3,4-dihydro-1H-isoquinolin-2-yl]propyl]pyridine-4-carboxamide (Compound 505)

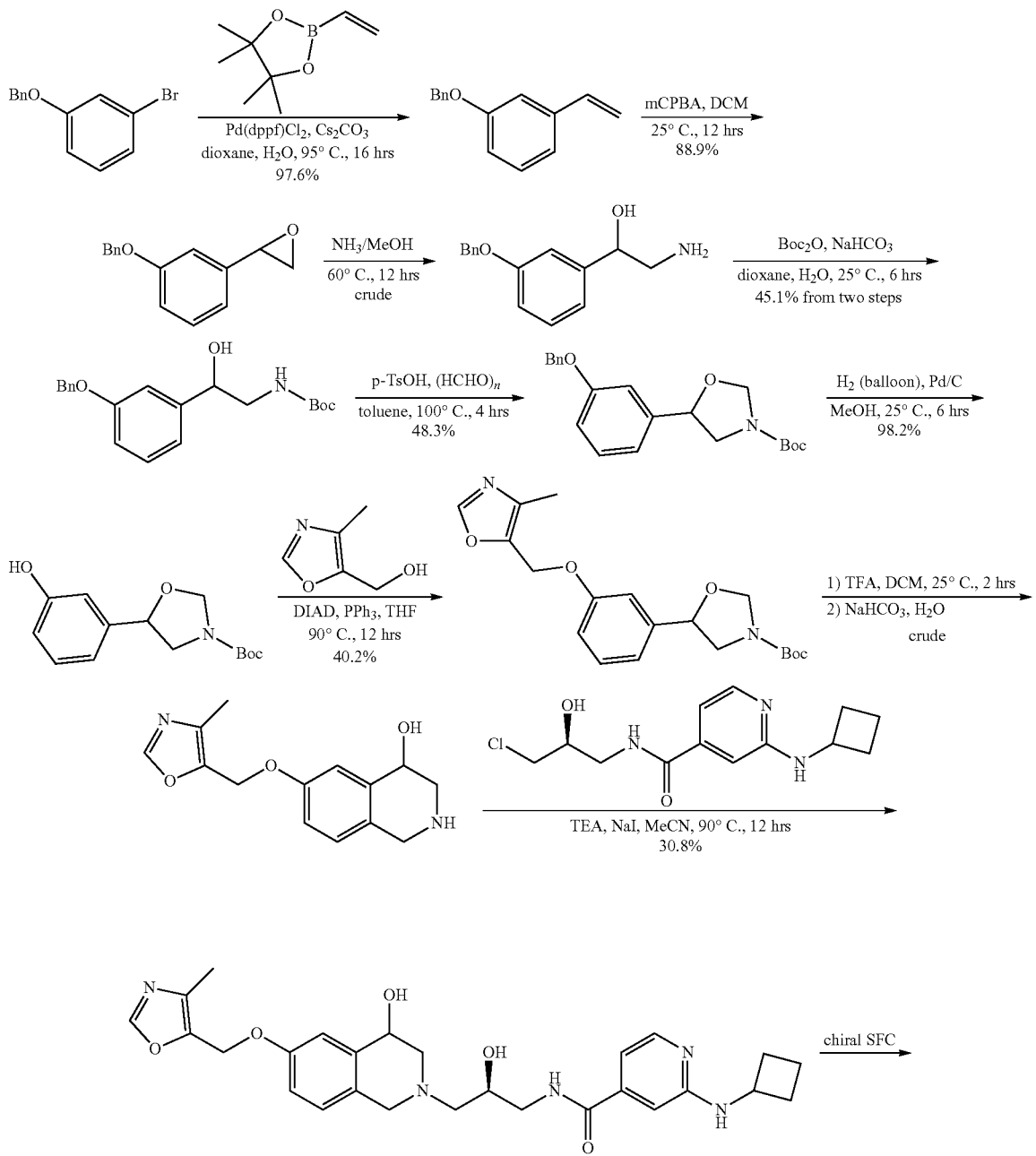

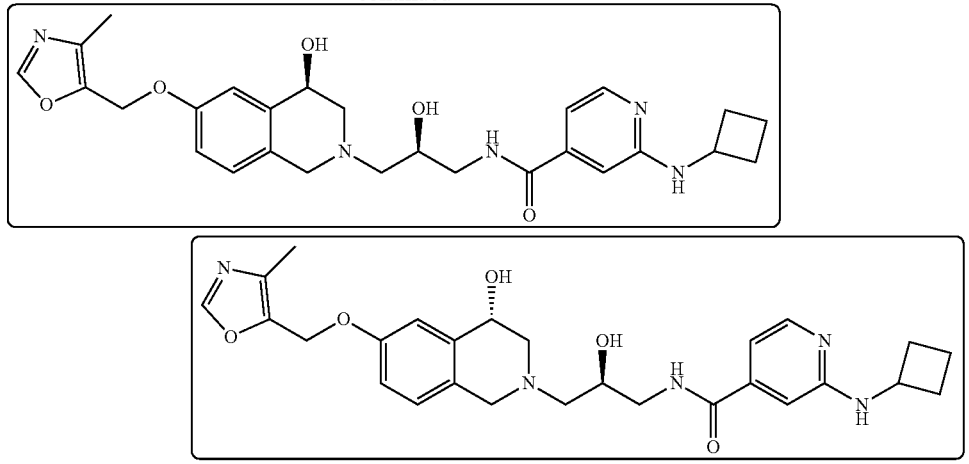

1-benzyloxy-3-vinyl-benzene. To a mixture of 1-benzyloxy-3-bromo-benzene (3 g, 0.011 mol), Pd(dppf)C$_{1-2}$ (1.20 g, 1.64 mmol) and Cs$_2$CO$_3$ (6.0 g, 0.018 mol), dioxane (20 mL) and H$_2$O (5 mL) was added 4,4,5,5-tetramethyl-2-vinyl-1,3,2-dioxaborolane (2.80 g, 0.018 mol), and the reaction was stirred at 95° C. for 16 hours under nitrogen. The resulting mixture was quenched by addition of water (100 mL) and EtOAc (100 mL*3). The combined organic layer was washed with saturated NH$_4$Cl aqueous solution (100 mL*2), dried over anhydrous Na$_2$SO$_4$, filtered and concentrated under reduced pressure to give a crude product which was purified by flash chromatography (ISCO®; 40 g AgelaFlash® Silica Flash Column, petroleum ether/EtOAc with EtOAc from 0~5%, Flow Rate: 30 mL/min) to afford 1-benzyloxy-3-vinyl-benzene (2.34 g, 97.6% yield) as light-yellow liquid. $^1$H NMR (400 MHz, methanol-d$_4$) δ ppm 7.03-7.31 (m, 6H), 6.83-6.93 (m, 2H), 6.73 (dd, J=8.2, 2.4 Hz, 1H), 6.55 (dd, J=17.6, 10.8 Hz, 1H), 5.60 (d, J=17.6 Hz, 1H), 5.07 (d, J=10.8 Hz, 1H), 4.88 (s, 2H); LCMS (ESI) [M+H]$^+$ m/z: calcd 211.1. found 211.1.

2-(3-benzyloxyphenyl)oxirane. A mixture of 1-benzyloxy-3-vinyl-benzene (2.3 g, 0.011 mol) and 3-chlorobenzenecarboperoxoic acid (2.5 g, 0.014 mol) in DCM (20 mL) was stirred at 25° C. for 12 hours. The mixture was concentrated under reduced pressure and the residue was quenched by addition of saturated Na$_2$SO$_3$ aqueous solution (80 mL) and then extracted with DCM (100 mL). The combined organic layer was washed with saturated Na$_2$SO$_3$ aqueous solution (100 mL*5), saturated Na$_2$HCO$_3$ aqueous solution (100 mL*5), dried over anhydrous Na$_2$SO$_4$, filtered and concentrated under reduced pressure to 2-(3-benzyloxyphenyl)oxirane (2.2 g, 88.9% yield) as yellow oil. $^1$H NMR (400 MHz, methanol-d$_4$) δ ppm 7.18-7.39 (m, 6H), 6.84-6.92 (m, 3H), 5.00 (s, 2H), 3.79 (dd, J=4.0, 2.5 Hz, 1H), 3.05 (dd, J=5.5, 4.0 Hz, 1H), 2.71 (dd, J=5.5, 2.5 Hz, 1H).

2-amino-1-(3-benzyloxyphenyl)ethanol. A mixture of 2-(3-benzyloxyphenyl)oxirane (2.1 g, 9.28 mmol) and NH$_3$/MeOH (7 M, 30 mL) was stirred at 60° C. for 12 hours. The mixture was concentrated under reduced pressure to give 2-amino-1-(3-benzyloxyphenyl)ethanol (2.9 g, crude) as yellow liquid which was used in next step directly.

tert-butyl N-[2-(3-benzyloxyphenyl)-2-hydroxy-ethyl]carbamate. A mixture of 2-amino-1-(3-benzyloxyphenyl)ethanol (2.2 g, 9.04 mmol), tert-butoxycarbonyl tert-butyl carbonate (2.20 g, 0.01 mol), NaHCO$_3$ (1.10 g, 13.1 mmol), H$_2$O (6 mL) and dioxane (12 mL) was stirred at 25° C. for 6 hours. The resulting mixture was quenched by addition of water (100 mL) and extracted with DCM (100 mL*3). The combined organic layer was washed with saturated NH$_4$Cl aqueous solution (100 mL*2), dried over anhydrous Na$_2$SO$_4$, filtered and concentrated under reduced pressure to give a crude product which was purified by flash chromatography (ISCO®; 40 g AgelaFlash® Silica Flash Column, petroleum ether/EtOAc with EtOAc from 0~40%, Flow Rate: 30 mL/min) to afford tert-butyl N-[2-(3-benzyloxyphenyl)-2-hydroxy-ethyl]carbamate (1.4 g, 45.1% yield) as yellow solid. $^1$H NMR (400 MHz, methanol-d$_4$) S ppm 7.22-7.38 (m, 6H), 7.04 (br s, 1H), 6.95 (d, J=7.5 Hz, 1H), 6.89 (dd, J=7.9, 2.1 Hz, 1 H), 5.08 (s, 2H), 4.68 (dd, J=7.6, 4.8 Hz, 1H), 3.14-3.29 (m, 2H), 1.42 (s, 9H); LCMS (ESI) [M+Na]$^+$ m/z: calcd 366.2. found 365.9; the regio-chemistry for epoxy opening reaction was confirmed by HMBC with a previously obtained product of known stereochemistry.

tert-butyl 5-(3-benzyloxyphenyl)oxazolidine-3-carboxylate. A mixture of tert-butyl N-[2-(3-benzyloxyphenyl)-2-hydroxy-ethyl]carbamate (1.4 g, 4.08 mmol), paraformaldehyde (448 mg, 0.013 mol) and methyl 4-methylbenzenesulfonate (140 mg, 0.752 mmol) in toluene (60 mL) was stirred at 100° C. for 4 hours. The mixture was concentrated under reduced pressure and the residue was purified by flash chromatography (ISCO®; 24 g AgelaFlash® Silica Flash Column, petroleum ether/EtOAc with EtOAc from 0~12%, Flow Rate: 30 mF/min) to afford tert-butyl 5-(3-benzyloxyphenyl)oxazolidine-3-carboxylate (700 mg, 48.3% yield) as colorless liquid. $^1$H NMR (400 MHz, methanol-d$_4$) δ ppm 7.28-7.46 (m, 6H), 7.05 (s, 1H), 6.95-6.99 (m, 2H), 5.05-5.15 (m, 4H), 4.87 (d, J=4.0 Hz, 1H), 3.85 (dd, J=9.9, 6.4 Hz, 1H), 3.18-3.27 (m, 1H), 1.49 (s, 9H); LCMS (ESI) [M+Na]$^+$ m/z: calcd 378.2. found 378.1.

tert-butyl 5-(3-hydroxyphenyl)oxazolidine-3-carboxylate. A mixture of tert-butyl 5-(3-benzyloxyphenyl)oxazolidine-3-carboxylate (300 mg, 0.844 mmol) and Pd/C (20 mg, 10% wt of Pd with 50% wt) in MeOH (10 mL) was degassed and backfilled with hydrogen for three times and then stirred at 25° C. for 6 hours under hydrogen (~15 psi, in balloon). The mixture was filtered and concentrated under reduced pressure to give tert-butyl 5-(3-hydroxyphenyl)oxazolidine-3-carboxylate (220 mg, 98.2% yield) as colorless oil. $^1$H NMR (400 MHz, DMSO-d$_6$) δ ppm 9.49 (br s, 1H), 7.12-7.21 (m, 1H), 6.69-6.83 (m, 3H), 5.02 (br s, 2H), 4.76-4.80 (m, 1H), 3.79 (ddd, J=9.6, 6.5, 2.6 Hz, 1H), 3.11 (t, J=8.1

Hz, 1H), 1.41 (s, 9H); LCMS (ESI) [M+Na]+ m/z: calcd 288.1. found 288.1; the regio-chemistry of cyclization reaction was confirmed by 2D NMR.

tert-butyl 5-[3-[(4-methyloxazol-5-yl)methoxy]phenyl]oxazolidine-3-carboxylate. To a mixture of (4-methyloxazol-5-yl)methanol (150 mg, 1.33 mmol), tert-butyl 5-(3-hydroxyphenyl)oxazolidine-3-carboxylate (220 mg, 0.829 mmol) and PPh$_3$ (330 mg, 1.26 mmol) in toluene (5 mL) was added isopropyl (NE)-N-isopropoxycarbonyliminocarbamate (220 mg, 1.09 mmol) and the mixture was stirred at 90° C. for 12 hours under nitrogen. The mixture was filtered and concentrated under reduced pressure. The residue was purified by flash chromatography (ISCO®; 12 g AgelaFlash® Silica Flash Column, petroleum ether/EtOAc with EtOAc from 0~35%, Flow Rate: 30 mF/min) to afford tert-butyl 5-[3-[(4-methyloxazol-5-yl)methoxy]phenyl]oxazolidine-3-carboxylate (120 mg, 40.2% yield) as colorless oil. $^1$H NMR (400 MHz, methanol-d$_4$) δ ppm 8.16 (s, 1H), 7.32 (t, J=7.9 Hz, 1H), 6.95-7.08 (m, 3H), 5.05-5.15 (m, 4H), 4.88 (d, J=4.0 Hz, 1H), 3.86 (dd, J=10.0, 6.3 Hz, 1H), 3.23 (t, J=9.0 Hz, 1H), 2.22 (s, 3H), 1.49 (s, 9H); LCMS (ESI) [M+H]+ m/z: calcd 361.2. found 361.1.

6-((4-methyloxazol-5-yl)methoxy)-1,2,3,4-tetrahydroisoquinolin-4-ol. A mixture of tert-butyl 5-[3-[(4-methyloxazol-5-yl)methoxy]phenyl]oxazolidine-3-carboxylate (120 mg, 0.333 mmol) and TFA (0.2 mL, 2.60 mmol) in DCM (2 mL) was stirred at 25° C. for 2 hours. The mixture was concentrated under reduced pressure to give a residue which was dissolved in MeOH (2 mL), followed by addition of NaHCO$_3$ (300 mg). The mixture was stirred 25° C. for 2 hours, then filtered and concentrated under reduced pressure to give 6-[(4-methyloxazol-5-yl)methoxy]-1,2,3,4-tetrahydroisoquinolin-4-ol (200 mg, crude) as yellow oil. LCMS (ESI) [M+H]+ m/z: calcd 261.1. found 260.9.

2-(cyclobutylamino)-N-[(2S)-2-hydroxy-3-[4-hydroxy-6-[(4-methyloxazol-5-yl)methoxy]-3,4-dihydro-1H-isoquinolin-2-yl]propyl]pyridine-4-carboxamide Prepared using reaction conditions outlined in Step C from Example IB. The mixture was filtered and concentrated under reduced pressure to give a crude product which was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% NH$_3$—H$_2$O (v %); Mobile phase B: MeCN; Gradient: B from 18% to 48% in 10.8 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[4-hydroxy-6-[(4-methyloxazol-5-yl)methoxy]-3,4-dihydro-1H-isoquinolin-2-yl]propyl]pyridine-4-carboxamide (30 mg, 30.8% yield) as light yellow solid. $^1$H NMR (400 MHz, methanol-d$_4$) δ ppm 8.04 (s, 1H), 7.82 (t, J=8.5 Hz, 1H), 6.98 (d, J=2.4 Hz, 1H), 6.91 (dd, J=8.5, 3.6 Hz, 1H), 6.76 (d, J=8.4 Hz, 1H), 6.65-6.72 (m, 2H), 4.99 (s, 2H), 4.58 (br s, 1H), 4.13 (quin, J=7.8 Hz, 1H), 3.93-4.01 (m, 1H), 3.57-3.70 (m, 1H), 3.32-3.52 (m, 3H), 2.68-2.85 (m, 2H), 2.51-2.56 (m, 2H), 2.27-2.34 (m, 2H), 2.11 (s, 3H), 1.76-1.89 (m, 2H), 1.68 (br dd, J=7.6, 3.2 Hz, 2H); LCMS (ESI) [M+H]+ m/z: calcd 508.2. found 508.3; HPLC 98.36% @ 254 nm.

2-(cyclobutylamino)-N-[(2S)-2-hydroxy-3-[(4R)-4-hydroxy-6-[(4-methyloxazol-5-yl)methoxy]-3,4-dihydro-1H-isoquinolin-2-yl]propyl]pyridine-4-carboxamide (Compound 505) and 2-(cyclobutylamino)-N-[(2S)-2-hydroxy-3-[(4S)-4-hydroxy-6-[(4-methyloxazol-5-yl)methoxy]-3,4-dihydro-1H-isoquinolin-2-yl]propyl]pyridine-4-carboxamide. 2-(cyclobutylamino)-N-[(2S)-2-hydroxy-3-[4-hydroxy-6-[(4-methyloxazol-5-yl)methoxy]-3,4-dihydro-1H-isoquinolin-2-yl]propyl]pyridine-4-carboxamide (25 mg, 0.049 mmol) was separated by chiral SFC (Instrument: Thar 80; Column: Chiralpak AD 250×50 mm I.D. 10 μm; Mobile phase: supercritical CO$_2$/EtOH (0.1% NH$_3$—H$_2$O, v %)=55/45; Flow Rate: 60 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give PI and P2.

P1: 2-(cyclobutylamino)-N-[(2S)-2-hydroxy-3-[(4R)-4-hydroxy-6-[(4-methyloxazol-5-yl)methoxy]-3,4-dihydro-1H-isoquinolin-2-yl]propyl]pyridine-4-carboxamide was impure and further purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% NH$_3$·H$_2$O (v %); Mobile phase B: MeCN; Gradient: B from 25% to 55% in 8 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[(4R)-4-hydroxy-6-[(4-methyloxazol-5-yl)methoxy]-3,4-dihydro-1H-isoquinolin-2-yl]propyl]pyridine-4-carboxamide (4 mg, single unknown enantiomer, peak 1, retention time=3.138 minute, white solid). $^1$H NMR (400 MHz, methanol-d$_4$) δ ppm 8.16 (s, 1H), 7.95 (d, J=5.3 Hz, 1H), 7.10 (d, J=2.5 Hz, 1H), 7.04 (d, J=8.5 Hz, 1H), 6.89 (dd, J=8.5, 2.5 Hz, 1H), 6.78-6.83 (m, 2H), 5.11 (s, 2H), 4.70 (t, J=4.4 Hz, 1H), 4.26 (quin, J=8.0 Hz, 1H), 4.07-4.14 (m, 1H), 3.79 (d, J=14.6 Hz, 1H), 3.44-3.56 (m, 3H), 2.91-2.97 (m, 1H), 2.82 (dd, J=11.9, 5.1 Hz, 1H), 2.59-2.70 (m, 2H), 2.42 (br d, J=7.8 Hz, 2H), 2.23 (s, 3H), 1.90-1.98 (m, 2H), 1.75-1.84 (m, 2H); LCMS (ESI) [M+H]+ m/z: calcd 508.2. found 508.2; HPLC: 100%@254 nm; 96.5% ee.

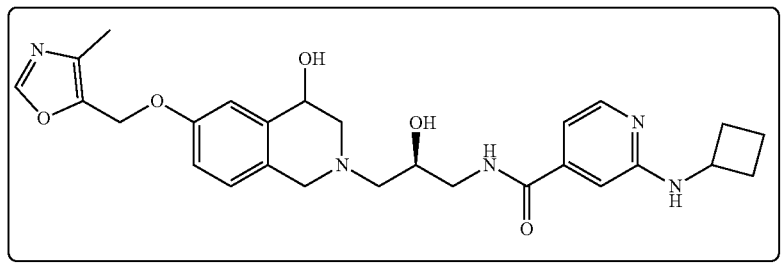 [SMILES: Cc1ncoc1COc1ccc2c(c1)C(O)CN(C[C@@H](O)CNC(=O)c1ccnc(NC3CCC3)c1)C2]

P2: 2-(cyclobutylamino)-N-[(2S)-2-hydroxy-3-[(4S)-4-hydroxy-6-[(4-methyloxazol-5-yl)methoxy]-3,4-dihydro-1H-isoquinolin-2-yl]propyl]pyridine-4-carboxamide was impure and further purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% NH$_3$—H$_2$O (v %); Mobile phase B: MeCN; Gradient: B from 23% to 53% in 8 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[(4S)-4-hydroxy-6-[(4-methyloxazol-5-yl)methoxy]-3,4-dihydro-1H-isoquinolin-2-yl]propyl]pyridine-4-carboxamide (4 mg, single unknown enantiomer, peak 2, retention time=3.461 minute, white solid). $^1$H NMR (400 MHz, methanol-d$_4$) δ ppm 8.04 (s, 1H), 7.82 (d, J=5.3 Hz, 1H), 6.98 (d, J=2.5 Hz, 1H), 6.91 (d, J=8.5 Hz, 1H), 6.76 (dd, J=8.4, 2.6 Hz, 1H), 6.66-6.70 (m, 2H), 4.99 (s, 2H), 4.58 (brt, J=4.5 Hz, 1H), 4.09-4.17 (m, 1H), 3.96 (quin, J=6.1 Hz, 1H), 3.57-3.65 (m, 1H), 3.32-3.50 (m, 3H), 2.76 (t, J=4.5 Hz, 2H), 2.53 (d, J=5.8 Hz, 2H), 2.26-2.33 (m, 2H), 2.11 (s, 3H), 1.77-1.85 (m, 2H), 1.64-1.70 (m, 2H); LCMS (ESI) [M+H]$^+$ m/z: calcd 508.2. found 508.2; HPLC: 100% @ 254 nm; 99.3% ee.

Example 1B13. 2-(cyclobutylamino)-N-[(2S)-3-[8-fluoro-6-(1H-pyrazol-4-ylmethoxy)-3,4-dihydro-1H-isoquinolin-2-yl]-2-hydroxy-propyl]pyridine-4-carboxamide (Compound 596)

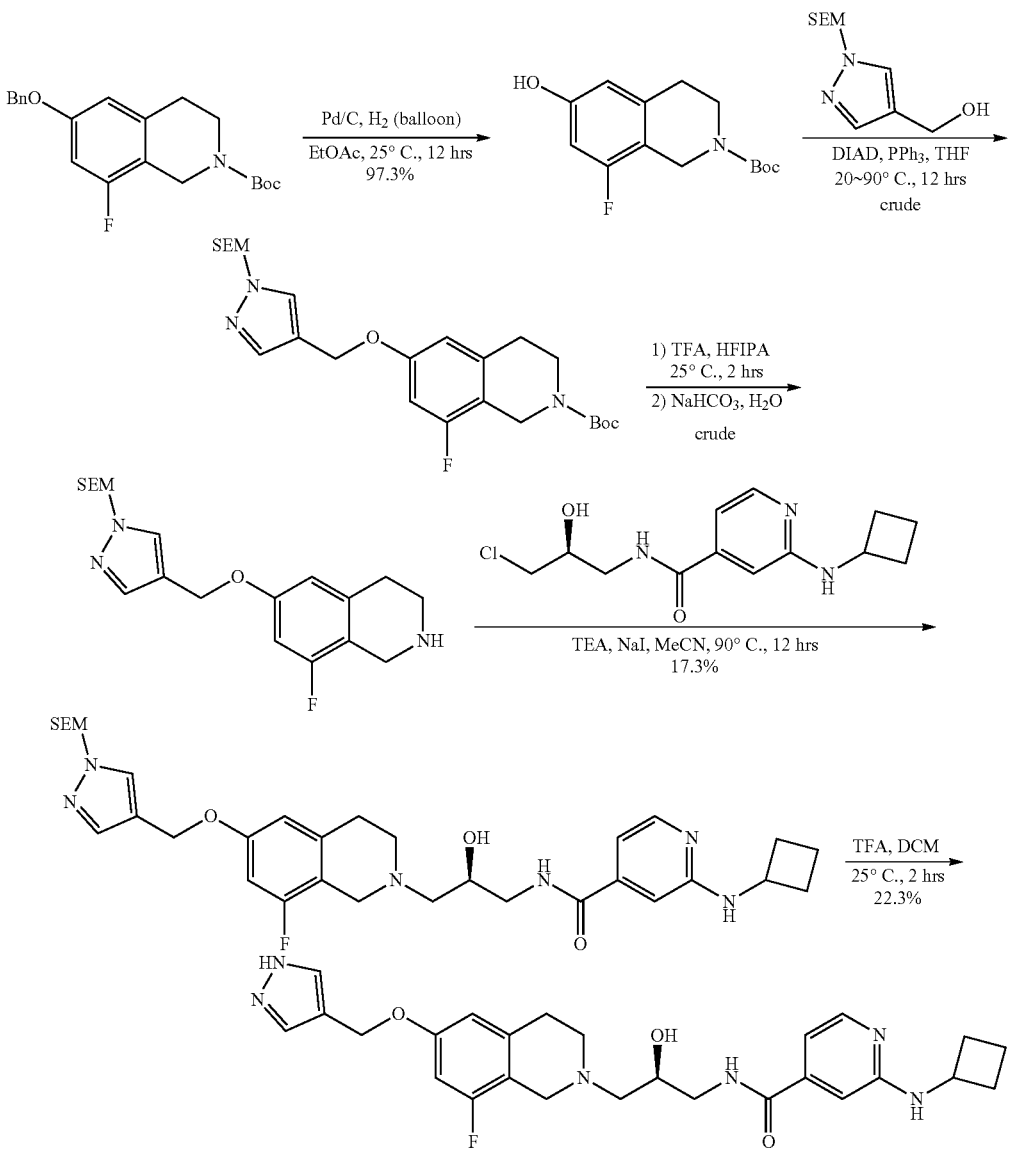

tert-butyl 8-fluoro-6-hydroxy-3,4-dihydro-1H-isoquinoline-2-carboxylate. To a solution of tert-butyl 6-benzyloxy-8-fluoro-3,4-dihydro-1H-isoquinoline-2-carboxylate (450 mg, 1.26 mmol) in EtOAc (5 mL) was added Pd/C (120 mg, 10% wt of Pd with 50% wt of water). The mixture was degassed and backfilled with hydrogen for three times. Then the mixture was stirred at 25° C. for 5 hours under hydrogen (in a balloon). The mixture was filtered and concentrated under reduced pressure to give tert-butyl 8-fluoro-6-hydroxy-3,4-dihydro-1H-isoquinoline-2-carboxylate (320 mg, 95.1% yield) as a yellow oil. $^1$H NMR (400 MHz, methanol-d$_4$) δ ppm 6.30-6.47 (m, 2H), 4.44 (s, 2H), 3.60 (br s, 2H), 2.74 (t, J=5.9 Hz, 2H), 1.49 (s, 9H); $^{19}$F NMR (376 MHz, methanol-d$_4$) δ ppm −121.853, −122.001.

tert-butyl 8-fluoro-6-[[1-(2-trimethylsilylethoxymethyl)pyrazol-4-yl]methoxy]-3,4-dihydro-1H-isoquinoline-2-carboxylate. To a solution of tert-butyl 8-fluoro-6-hydroxy-3,4-dihydro-1H-isoquinoline-2-carboxylate (150 mg, 0.561 mmol), 1-(2-trimethylsilylethoxymethyl)pyrazol-4-yl]methanol (130 mg, 0.569 mmol) and triphenylphosphine (220 mg, 0.839 mmol) in toluene (3 mL) was added a solution of isopropyl (NE)-N-isopropoxycarbonyliminocarbamate (171 mg, 0.846 mmol) in toluene (2 mL) slowly at 20° C. under nitrogen and after addition was complete, the mixture was allowed to warm to 90° C. and stir for 12 hours in a sealed tube. The resulting mixture was concentrated under reduced pressure and the residue was purified by flash chromatography (ISCO®; 12 g AgelaFlash® Silica Flash Column, petroleum ether/EtOAc with EtOAc from 0~30%, Flow Rate: 30 mL/min) to afford tert-butyl 8-fluoro-6-[[1-(2-trimethylsilylethoxymethyl)pyrazol-4-yl]methoxy]-3,4-dihydro-1H-isoquinoline-2-carboxylate (120 mg, crude) as white solid which was used in next step without further purification. $^1$H NMR (400 MHz, methanol-d$_4$) δ ppm 7.88 (s, 1H), 7.63 (s, 1H), 6.58-6.66 (m, 2H), 5.42 (s, 2H), 5.00 (s, 2H), 4.47 (s, 2H), 3.61 (br d, J=4.6 Hz, 2H), 3.54-3.58 (m, 2H), 2.80 (t, J=5.8 Hz, 2H), 1.49 (s, 9H), 0.86-0.89 (m, 2H), −0.05 (s, 9H); $^{19}$F NMR (376 MHz, methanol-d$_4$) δ ppm −120.811, −121.003; LCMS (ESI) [M+H]$^+$ m/z calcd 478.2. found 478.2.

2-[[4-[(8-fluoro-1,2,3,4-tetrahydroisoquinolin-6-yl)oxymethyl]pyrazol-1-yl]methoxy]ethyl-trimethyl-silane. A mixture of tert-butyl 8-fluoro-6-[[1-(2-trimethylsilylethoxymethyl)pyrazol-4-yl]methoxy]-3,4-dihydro-1H-isoquinoline-2-carboxylate (100 mg, 0.209 mmol) and TFA (29 mg, 0.254 mmol) in hexafluoroisopropanol (3 mL) was stirred at 25° C. for 2 hours. The residue was quenched by addition of water (20 mL) and washed with DCM (10 mL*2). The aqueous layer was adjusted to pH=7-8 by saturated NaHCO$_3$ aqueous solution and extracted with DCM (30 mL*3). The combined organic layer was dried over anhydrous Na$_2$SO$_4$, filtered and concentrated under reduced pressure to give 2-[[4-[(8-fluoro-1,2,3,4-tetrahydroisoquinolin-6-yl)oxymethyl]pyrazol-1-yl]methoxy]ethyl-trimethyl-silane (70 mg, crude) as a yellow oil. LCMS (ESI) [M+H]$^+$ m/z: calcd 378.2. found 378.2.

2-(cyclobutylamino)-N-[(2S)-3-[8-fluoro-6-[[1-(2-trimethylsilylethoxymethyl)pyrazol-4-yl]methoxy]-3,4-dihydro-1H-isoquinolin-2-yl]-2-hydroxy-propyl]pyridine-4-carboxamide Prepared using reaction conditions outlined in Step C from Example IB. The mixture was concentrated under reduced pressure and the residue was purified by preparative HPLC (Instrument: Gilson GX-215, Gilson 322 Pump, Gilson 156 UV Detector; Column: Welch Xtimate C18 150*25 mm*5 μm; Mobile phase A: water (0.225% FA); Mobile phase B: MeCN; Gradient: B from 15% to 45% in 9.5 min, hold 100% B for 2 min; Flow Rate: 25 mF/min; Column Temperature: 30° C.; Wavelength: 220 nm, 254 nm) to afford 2-(cyclobutylamino)-N-[(2S)-3-[8-fluoro-6-[[1-(2-trimethylsilylethoxymethyl)pyrazol-4-yl]methoxy]-3,4-dihydro-1H-isoquinolin-2-yl]-2-hydroxy-propyl]pyridine-4-carboxamide (20 mg, 17.3% yield) as a white solid. $^1$H NMR (400 MHz, methanol-d$_4$) δ ppm 7.99 (d, J=5.3 Hz, 1H), 7.91 (s, 1H), 7.66 (s, 1H), 6.82-6.87 (m, 2H), 6.65-6.73 (m, 2H), 5.45 (s, 2H), 5.03 (s, 2H), 4.22-4.28 (m, 2H), 4.06 (s, 2H), 3.48-3.63 (m, 4H), 3.19-3.28 (m, 2H), 2.95-3.09 (m, 4H), 2.37-2.50 (m, 2H), 1.90-2.02 (m, 2H), 1.78-1.88 (m, 2H), 0.81-0.97 (m, 2H), 0.00 (s, 9H).

2-(cyclobutylamino)-N-[(2S)-3-[8-fluoro-6-(1H-pyrazol-4-ylmethoxy)-3,4-dihydro-1H-isoquinolin-2-yl]-2-hydroxy-propyl]pyridine-4-carboxamide. A mixture of 2-(cyclobutylamino)-N-[(2S)-3-[8-fluoro-6-[[1-(2-trimethylsilylethoxymethyl)pyrazol-4-yl]methoxy]-3,4-dihydro-1H-isoquinolin-2-yl]-2-hydroxy-propyl]pyridine-4-carboxamide (17 mg, 0.0272 mmol) and TFA (3 mF) in DCM (5 mF) was stirred at 25° C. for 2 hours. The mixture was concentrated under reduced pressure. The residue was purified by preparative HPFC (Instrument: Gilson GX-215, Gilson 322 Pump, Gilson 156 UV Detector; Column: Welch Xtimate C18 150*25 mm*5 μm; Mobile phase A: water (0.225% FA); Mobile phase B: MeCN; Gradient: B from 5% to 35% in 7.8 min, hold 100% B for 2 min; Flow Rate: 25 mF/min; Column Temperature: 30° C.; Wavelength: 220 nm, 254 nm) to afford 2-(cyclobutylamino)-N-[(2S)-3-[8-fluoro-6-(1H-pyrazol-4-ylmethoxy)-3,4-dihydro-1H-isoquinolin-2-yl]-2-hydroxy-propyl]pyridine-4-carboxamide (3 mg, 22.3% yield) as a white solid. $^1$H NMR (400 MHz, methanol-d$_4$) δ ppm 7.95 (br s, 1H), 7.69 (br s, 2H), 6.75-6.85 (m, 2H), 6.57-6.69 (m, 2H), 5.00 (s, 2H), 4.20-4.28 (m, 1H), 4.14 (br s, 1H), 3.85 (br s, 2H), 3.44-3.53 (m, 2H), 3.03 (br s, 2H), 2.96 (br s, 2H), 2.77-2.88 (m, 2H), 2.41 (br d, J=7.6 Hz, 2H), 1.89-1.97 (m, 2H), 1.72-1.83 (m, 2H); $^{19}$F NMR (376 MHz, methanol-d$_4$) δ ppm −120.811; LCMS (ESI) [M+H]$^+$ m/z: calcd 495.2. found 495.2; HPLC: 95.44% @254 nm; 93.7% ee.

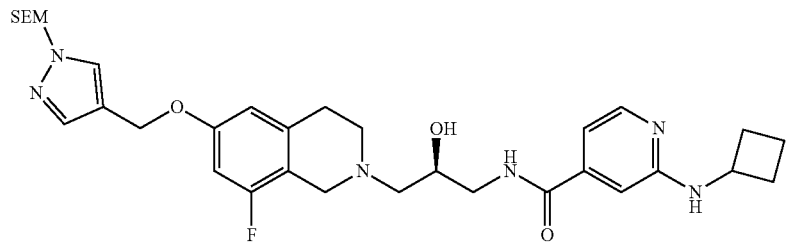 [SMILES: C[Si](C)(C)CCOCn1cc(COc2cc(F)c3c(c2)CCN(C[C@@H](O)CNC(=O)c2ccnc(NC4CCC4)c2)C3)cn1]

Example 1B14. 2-(cyclobutylamino)-N-[(2S)-2-hydroxy-3-[5-iodo-6-[(4-methyloxazol-5-yl)methoxy]-3N-dihydro-1H-isoquinolin-2-yl]propyl]pyridine-4-carboxamide (Compound 268) and 5-[(5-iodo-1,2,3,4-tetrahydroisoquinolin-6-yl)oxymethyl]-4-methyl-oxazole tert-butyl 5-iodo-6-[(4-methyloxazol-5-yl)methoxy]-3,4-dihydro-1H-isoquinoline-2-carboxylate

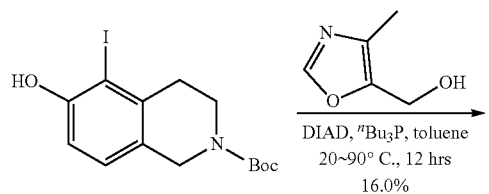

DIAD, $^n$Bu$_3$P, toluene
20~90° C., 12 hrs
16.0%

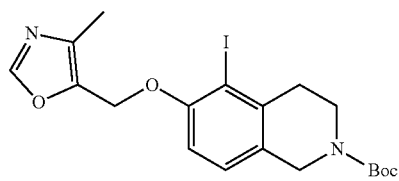

-continued

To a solution of tert-butyl 6-hydroxy-5-iodo-3,4-dihydro-1H-isoquinoline-2-carboxylate (200 mg, 0.533 mmol) in toluene (10 mL) were added (4-methyloxazol-5-yl)methanol (120 mg, 1.06 mmol) and tributylphosphane (162 mg, 0.80 mmol). The mixture was degassed and backfilled with nitrogen for 3 times. Then a solution of isopropyl (NE)-N-isopropoxycarbonyliminocarbamate (160 mg, 0.79 mmol) in toluene (5 mL) was added to the mixture at 25° C. dropwise. The mixture was allowed to warm to 90° C. and stirred for 12 hours. The resulting mixture was combined with another batch and concentrated under reduced pressure. The residue was purified by flash chromatography (ISCO®; 40 g of AgelaFlash® Silica Flash Column, petroleum ether/EtOAc with EtOAc from 0~50%, Flow rate: 30 mL/min) to afford tert-butyl 5-iodo-6-[(4-methyloxazol-5-yl)methoxy]-3,4-dihydro-1H-isoquinoline-2-carboxylate (50 mg, 15.9% yield) as colorless oil. $^1$H NMR (400 MHz, methanol-d$_4$) δ ppm 8.16 (s, 1H), 7.16 (d, J=8.8 Hz, 1H), 6.991 (d, J=8.0 Hz, 1H), 6.99 (d, J=8.3 Hz, 1H), 5.18 (s, 2H), 4.53 (s, 2H), 3.64 (t, J=5.8 Hz, 2H), 2.82 (t, J=5.9 Hz, 2H), 2.22 (s, 3H), 1.51 (s, 9H); LCMS (ESI) [M+H−56]$^+$ m/z: calcd 415.1. found 414.9.

2-(cyclobutylamino)-N-[(2S)-2-hydroxy-3-[5-iodo-6-[(4-methyloxazol-5-yl)methoxy]-3,4-dihydro-1H-isoquinolin-2-yl]propyl]pyridine-4-carboxamide

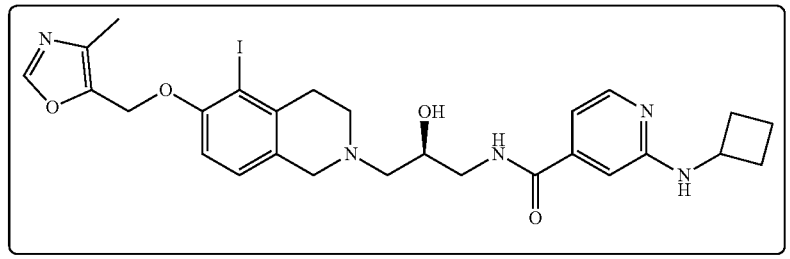 [SMILES: Cc1ncoc1COc1ccc2c(c1I)CCN(C[C@@H](O)CNC(=O)c1ccnc(NC3CCC3)c1)C2]

tert-butyl 5-iodo-6-[(4-methyloxazol-5-yl)methoxy]-3,4-dihydro-1H-isoquinoline-2-carboxylate was converted to 2-(cyclobutylamino)-N-[(2S)-2-hydroxy-3-[5-iodo-6-[(4-methyloxazol-5-yl)methoxy]-3,4-dihydro-1H-isoquinolin-2-yl]propyl]pyridine-4-carboxamide using reaction conditions outlined in Steps B and Step C from Example IB. The mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 µm; Mobile phase A: H$_2$O with 0.05% ammonia hydroxide (v %); Mobile phase B: MeCN; Gradient: B from 36% to 66% in 7.8 min, hold 100% B for 2.5 min; Flow Rate: 25 mL/min; Column Temperature: 30° C.; Wavelength: 220 nm, 254 nm) to afford 2-(cyclobutylamino)-N-[(2S)-2-hydroxy-3-[5-iodo-6-[(4-methyloxazol-5-yl)methoxy]-3,4-dihydro-1H-isoquinolin-2-yl]propyl]pyridine-4-carboxamide (5.2 mg, 12.5% yield) as a white solid. $^1$H NMR (400 MHz, methanol-d$_4$) δ ppm 8.16 (s, 1H), 7.90 (d, J=5.4 Hz, 1H), 7.07 (d, J=8.5 Hz, 1H), 6.92 (d, J=8.4 Hz, 1H), 6.80 (s, 1H), 6.72 (dd, J=5.4, 1.3 Hz, 1H), 5.16 (s, 2H), 4.24 (quin, J=7.9 Hz, 1H), 4.09 (quin, J=5.9 Hz, 1H), 3.71 (s, 2H), 3.43-3.55 (m, 2H), 2.80-2.88 (m, 4H), 2.60-2.72 (m, 2H), 2.37-2.48 (m, 2H), 2.21 (s, 3H), 1.88-2.00 (m, 2H), 1.74-1.83 (m, 2H); LCMS (ESI) [M+H]$^+$ m/z: calcd 618.1. found 618.0; HPLC: 100% @254 nm; 100% ee.

Example 1B15. 2-[(1-acetyl-4-piperidyl)amino]-N-[(2S)-3-[8-fluoro-5-methyl-6-[(4-methyloxazol-5-yl)methoxy]-3,4-dihydro-1H-isoquinolin-2-yl]-2-hydroxy-propyl]pyridine-4-carboxamide (Compound 642)

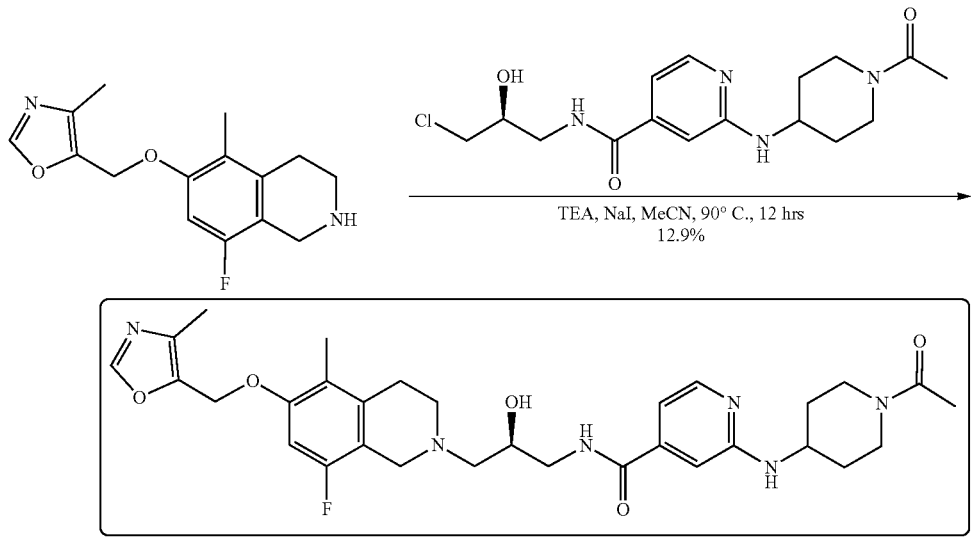

2-[(1-acetyl-4-piperidyl)amino]-N-[(2S)-3-[8-fluoro-5-methyl-6-[(4-methyloxazol-5-yl)methoxy]-3,4-dihydro-1H-isoquinolin-2-yl]-2-hydroxy-propyl]pyridine-4-carboxamide was prepared using reaction conditions outlined in Steps B and Step C from Example IB. The residue was purified by flash chromatography (ISCO®; 4 g AgelaFlash® Silica Flash Column, petroleum ether/EtOAc with EtOAc from 0~50%, Flow rate: 30 mF/min) to afford a crude product which was further purified by preparative HPFC (Instrument: Gilson GX-281 Liquid Handler, Gilson 322 Pump, Gilson 156 UV Detector; Column: Waters Xbridge 150×25 mm×5 pm; Mobile phase A: $H_2O$ with 0.05% ammonia hydroxide (v %); Mobile phase B: MeCN; Gradient: B from 30% to 60% in 7.8 min, hold 100% B for 2.5 min; Flow Rate: 25 mF/min; Column Temperature: 30° C.; Wavelength: 220 nm, 254 nm) to afford the desired product which was still impure. It was purified by chiral SFC (Instrument: Thar80; Column: Daicel Chiralcel OJ (250 mm*30 mm, 10 μm); Mobile phase: supercritical $CO_2$/EtOH (0.1% $NH_3$—$H_2O$, v %)=65/35; Flow Rate: 80 mF/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm to afford 2-[(1-acetyl-4-piperidyl)amino]-N-[(2S)-3-[8-fluoro-5-methyl-6-[(4-methyloxazol-5-yl)methoxy]-3,4-dihydro-1H-isoquinolin-2-yl]-2-hydroxy-propyl]pyridine-4-carboxamide (19.5 mg, 12.9% yield) as white solid. $^1$H NMR (400 MHz, methanol-$d_4$) δ ppm 8.15 (s, 1H), 7.92 (d, J=5.4 Hz, 1H), 6.85 (s, 1H), 6.73-6.76 (m, 1H), 6.73 (s, 1H), 5.07 (s, 2H), 4.42 (br d, J=14.9 Hz, 1H), 4.08 (quin, J=6.0 Hz, 1H), 3.86-4.00 (m, 2H), 3.66 (s, 2H), 3.41-3.54 (m, 2H), 2.80-2.93 (m, 4H), 2.72-2.78 (m, 2H), 2.61-2.72 (m, 2H), 2.19 (s, 3H), 2.12 (s, 3H), 2.00-2.10 (m, 2H), 1.99 (s, 3H), 1.31-1.50 (m, 3H); $^{19}$FNMR (376 MHz, methanol-$d_4$) δ ppm −124.035; LCMS (ESI) [M+H]$^+$ m/z: calcd 595.3. found 595.2; HPFC 100% @ 254 nm; 100% ee.

Example B17. 5-chloro-2-(cyclobutylamino)-N-r(2S)-2-hydroxy-3-[6-[(4-methyloxazol-5-yl)methoxy]-3,4-dihydro-1H-isoquinolin-2-yl]propyl]pyridine-4-carboxamide (Compound 607)

tert-butyl 6-[(4-methyloxazol-5-yl)methoxy]-3,4-dihydro-1H-isoquinoline-2-carboxylate

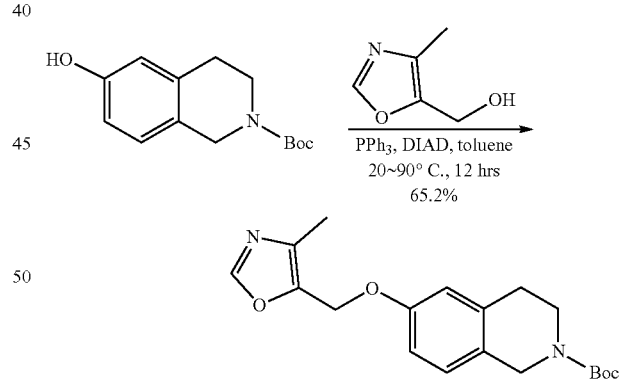

To a solution of tert-butyl 6-hydroxy-3,4-dihydro-1H-isoquinoline-2-carboxylate (500 mg, 2.0 mmol) in toluene (10 mL) were added (4-methyloxazol-5-yl)methanol (250 mg, 2.2 mmol), triphenylphosphine (800 mg, 3.1 mmol) and isopropyl (NE)-N-isopropoxycarbonyliminocarbamate (600 mg, 3.0 mmol). The reaction mixture was stirred at 90° C. for 12 hours. The resulting mixture was quenched by addition of water (30 mL) and extracted with EtOAc (30 mL*3). The combined organic layer was washed with saturated $NH_4Cl$ aqueous solution (30 mL*2), brine (30 mL), dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc from 0~50%, flow rate=30 mL/min) to afford tert-butyl 6-[(4-methyloxazol-5-yl)methoxy]-3,4-dihydro-1H-isoquinoline-2-carboxylate (450 mg, 1.3 mmol, 65.15% yield) as colorless oil. $^1$H NMR (400 MHz, methanol-d$_4$) δ ppm 8.14 (s, 1H), 7.05 (d, J=8.3 Hz, 1H), 6.78-6.87 (m, 2H), 5.07 (s, 2H), 4.49 (br s, 2H), 3.61 (t, J=5.5 Hz, 2H), 2.81 (t, J=5.9 Hz, 2H), 2.20 (s, 3H), 1.49 (s, 9H); LCMS (ESI) [M+H-Boc]$^+$ m/z: calcd 245.1. found 245.1.

2-(cyclobutylamino)-N-[(2S)-2-hydroxy-3-[6-[(4-methyloxazol-5-yl)methoxy]-3,4-dihydro-1H-isoquinolin-2-yl]propyl]pyridine-4-carboxamide

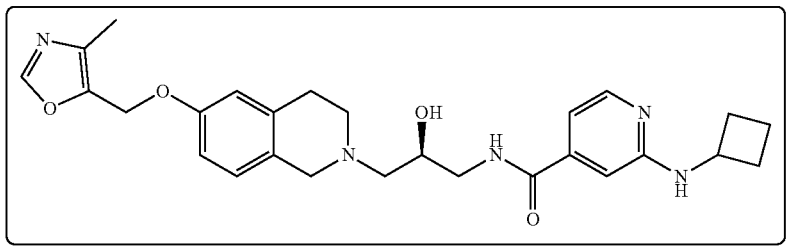 [SMILES: Cc1ncoc1COc1ccc2c(c1)CCN(C[C@@H](O)CNC(=O)c1ccnc(NC3CCC3)c1)C2]

4-methyl-5-(1,2,3,4-tetrahydroisoquinolin-6-yloxymethyl)oxazole was converted to 2-(cyclobutylamino)-N-[(2S)-2-hydroxy-3-[6-[(4-methyloxazol-5-yl)methoxy]-3,4-dihydro-1H-isoquinolin-2-yl]propyl]pyridine-4-carboxamide using reaction conditions outlined in Steps B and Step C from Example IB. The reaction mixture was concentrated under reduced pressure and the residue was purified by preparative HPLC (Instrument: Gilson GX-281 Liquid Handler, Gilson 322 Pump, Gilson 156 UV Detector; Column: Durashell 150×25 mm×5 μm; Mobile phase A: water (0.05% ammonia hydroxide v/v); Mobile phase B: MeCN; Gradient: B from 22% to 52% in 9.5 min, hold 100% B for 2 min; Flow Rate: 25 mL/min; Column Temperature: 30° C.; Wavelength: 220 nm, 254 nm) to afford 2-(cyclobutylamino)-N-[(2S)-2-hydroxy-3-[6-[(4-methyloxazol-5-yl)methoxy]-3,4-dihydro-1H-isoquinolin-2-yl]propyl]pyridine-4-carboxamide (190 mg, 31.47% yield) as a white solid. 15 mg was delivered. $^1$H NMR (400 MHz, methanol-d$_4$) δ ppm 8.14 (s, 1H), 7.90 (d, J=5.5 Hz, 1H), 6.98 (d, J=8.0 Hz, 1H), 6.71-6.81 (m, 4H), 5.06 (s, 2H), 4.23 (t, J=7.9 Hz, 1H), 4.09 (quin, J=5.9 Hz, 1H), 3.69 (s, 2H), 3.43-3.54 (m, 2H), 2.89 (br d, J=5.8 Hz, 2H), 2.80-2.88 (m, 2H), 2.60-2.70 (m, 2H), 2.36-2.46 (m, 2H), 2.21 (s, 3H), 1.85-1.99 (m, 2H), 1.71-1.84 (m, 2H); LCMS (ESI) [M+H]$^+$ m/z: calcd 492.3, found 492.2; HPLC: 100% @ 254 nm; 100% ee.

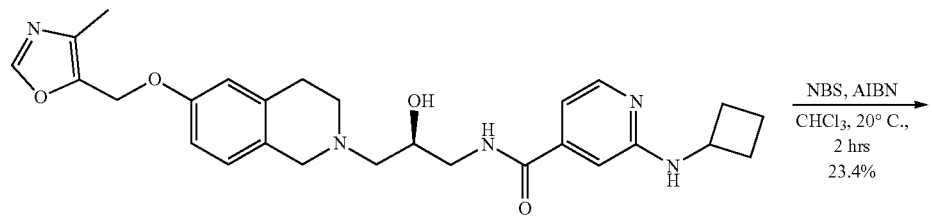

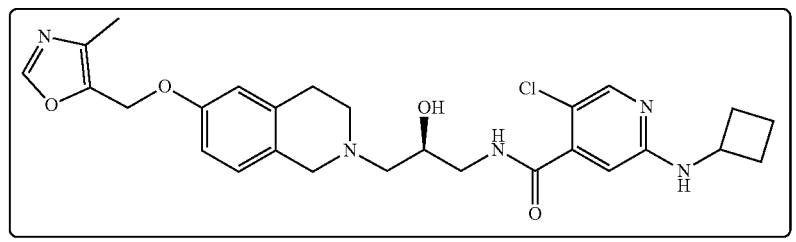

To a solution of 2-(cyclobutylamino)-N-[(2S)-2-hydroxy-3-[6-[(4-methyloxazol-5-yl)methoxy]-3,4-dihydro-1H-isoquinolin-2-yl]propyl]pyridine-4-carboxamide (20 mg, 0.041 mmol) in CHCl$_3$ (1 mL) were added NCS (6 mg, 0.045 mmol) and 2-[(E)-(1-cyano-1-methyl-ethyl)azo]-2-methyl-propanenitrile (3 mg, 0.018 mmol). The reaction mixture was stirred at 20° C. for 2 hours. The reaction mixture was concentrated under reduced pressure and the residue was purified by preparative HPLC (Instrument: Gilson GX-281 Liquid Handler, Gilson 322 Pump, Gilson 156 UV Detector; Column: Durashell 150×25 mm×5 μm; Mobile phase A: water (0.05% ammonia hydroxide v/v); Mobile phase B: MeCN; Gradient: B from 30% to 60% in 9 min, hold 100% B for 2 min; Flow Rate: 25 mL/min; Column Temperature: 30° C.; Wavelength: 220 nm, 254 nm) to afford 5-chloro-2-(cyclobutylamino)-N-[(2S)-2-hydroxy-3-[6-[(4-methyloxazol-5-yl)methoxy]-3,4-dihydro-1H-isoquinolin-2-yl]propyl]pyridine-4-carboxamide (5 mg, 23.4% yield) as a white solid. $^1$H NMR (400 MHz, methanol-d$_4$) δ ppm 8.14 (s, 1H), 7.92-7.96 (m, 1H), 6.98 (d, J=8.1 Hz, 1H), 6.74-6.80 (m, 2H), 6.48 (s, 1H), 5.06 (s, 2H), 4.23 (quin, J=7.8 Hz, 1H), 4.03-4.12 (m, 1H), 3.71 (s, 2H), 3.46 (br dd, J=9.6, 5.8 Hz, 2H), 2.89 (br s, 4H), 2.61-2.76 (m, 2H), 2.33-2.44 (m, 2H), 2.20 (s, 3H), 1.96-2.06 (m, 1H), 1.85-1.95 (m, 2H), 1.72-1.82 (m, 2H); LCMS (ESI) [M+H]$^+$ m/z: calcd 526.2. found 525.9; HPLC: 82.54% @ 254 nm; 100% ee.

Example B18. 2-(cyclobutylamino)-N-[(2S)-3-[8-fluoro-6-[(4-methyloxazol-5-yl)methoxy]-3N-dihydro-1H-isoquinolin-2-yl]-2-hydroxy-propyl]pyridine-4-carboxamide (Compound 506)

tert-butyl 8-fluoro-6-[(4-methyloxazol-5-yl)methoxy]-3,4-dihydro-1H-isoquinoline-2-carboxylate

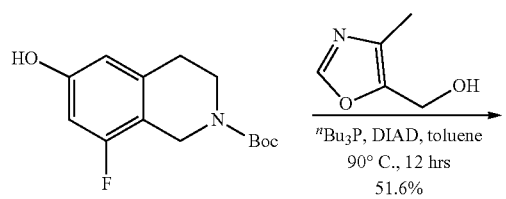

$^n$Bu$_3$P, DIAD, toluene
90° C., 12 hrs
51.6%

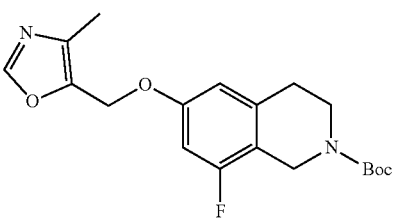

A mixture of (4-methyloxazol-5-yl)methanol (90 mg, 0.796 mmol), tert-butyl 8-fluoro-6-hydroxy-3,4-dihydro-1H-isoquinoline-2-carboxylate (200 mg, 0.748 mmol) and tributylphosphane (227 mg, 1.12 mmol) in toluene (6 mL) was added isopropyl (NE)-N-isopropoxycarbonyliminocarbamate (227 mg, E12 mmol) slowly and the mixture was stirred at 90° C. for 12 hours in a sealed tube. The mixture was concentrated under reduced pressure and then quenched by addition of water (10 mL). The aqueous phase was extracted with EtOAc (10 mL*2) and the combined organic layers were dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0~35%, flow rate=30 mL/min) to afford tert-butyl 8-fluoro-6-[(4-methyloxazol-5-yl)methoxy]-3,4-dihydro-1H-isoquinoline-2-carboxylate (140 mg, 51.6% yield) as a yellow oil. $^1$H NMR (400 MHz, methanol-<k) δ ppm 8.14 (s, 1H), 6.66 (s, 1H), 6.61-6.65 (m, 1H), 5.07 (s, 2H), 4.48 (s, 2H), 3.62 (m, 2H), 2.80 (t, J=5.9 Hz, 2H), 2.21 (s, 3H), E49 (s, 9H); LCMS (ESI) [M+H−56]$^+$ m/z: calcd 307.2. found 307.0.

2-(cyclobutylamino)-N-[(2S)-3-[8-fluoro-6-[(4-methyloxazol-5-yl)methoxy]-3,4-dihydro-1H-isoquinolin-2-yl]-2-hydroxy-propyl]pyridine-4-carboxamide (Compound 506)

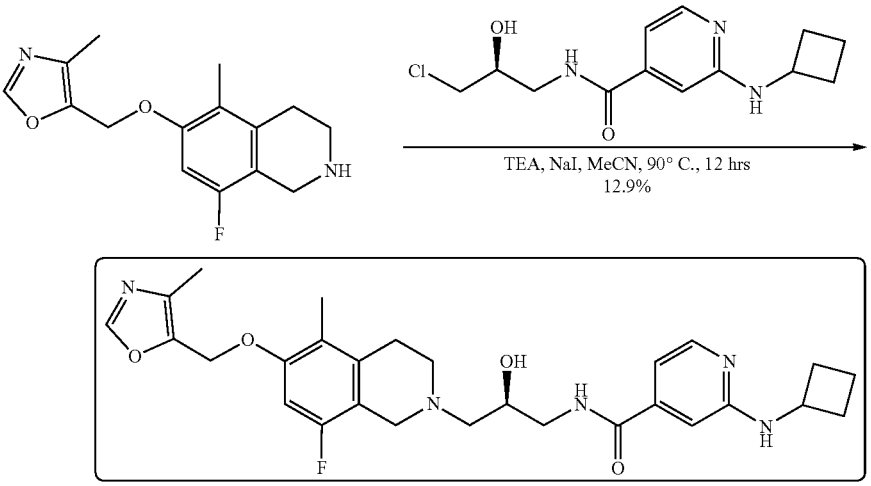

tert-butyl 8-fluoro-6-[(4-methyloxazol-5-yl)methoxy]-3,4-dihydro-1H-isoquinoline-2-carboxylate was converted to 2-(cyclobutylamino)-N-[(2S)-3-[8-fluoro-6-[(4-methyloxazol-5-yl)methoxy]-3,4-dihydro-1H-isoquinolin-2-yl]-2-hydroxy-propyl]pyridine-4-carboxamide using reaction conditions outlined in Steps B and Step C from Example IB. The mixture was concentrated under reduced pressure and the residue was purified by preparative HPLC (Instrument: Gilson GX-281 Liquid Handler, Gilson 322 Pump, Gilson 156 UV Detector; Column: Waters Xbridge BEH C18 150*25 mm*5 μm; Mobile phase A: water (0.05% ammonia hydroxide v/v); Mobile phase B: MeCN; Gradient: B from 27% to 57% in 9.5 min, hold 100% B for 2 min; Flow Rate: 25 mL/min; Column Temperature: 30° C.; Wavelength: 220 nm, 254 nm) to afford 2-(cyclobutylamino)-N-[(2S)-3-[8-fluoro-6-[(4-methyloxazol-5-yl)methoxy]-3,4-dihydro-1H-isoquinolin-2-yl]-2-hydroxy-propyl]pyridine-4-carboxamide (10 mg, 12.9% yield) as a white solid. $^1$H NMR (400 MHz, methanol-$d_4$) δ ppm 8.14 (s, 1H), 7.93 (dd, J=5.4, 0.6 Hz, 1H), 6.79 (s, 1H), 6.76 (dd, J=5.4, 1.5 Hz, 1H), 6.55-6.65 (m, 2H), 5.06 (s, 2H), 4.23 (quin, J=7.8 Hz, 1H), 4.08 (quin, J=6.0 Hz, 1H), 3.66 (s, 2H), 3.39-3.55 (m, 2H), 2.82-2.90 (m, 4H), 2.62-2.71 (m, 2H), 2.36-2.45 (m, 2H), 2.21 (s, 3H), 1.86-1.99 (m, 2H), 1.72-1.83 (m, 2H); $^{19}$F NMR (376 MHz, methanol-$d_4$) δ ppm −120.852; LCMS (ESI) [M+H]$^+$ m/z: calcd 510.2. found 510.2; HPLC: 100%@254 nm; 99.3% ee.

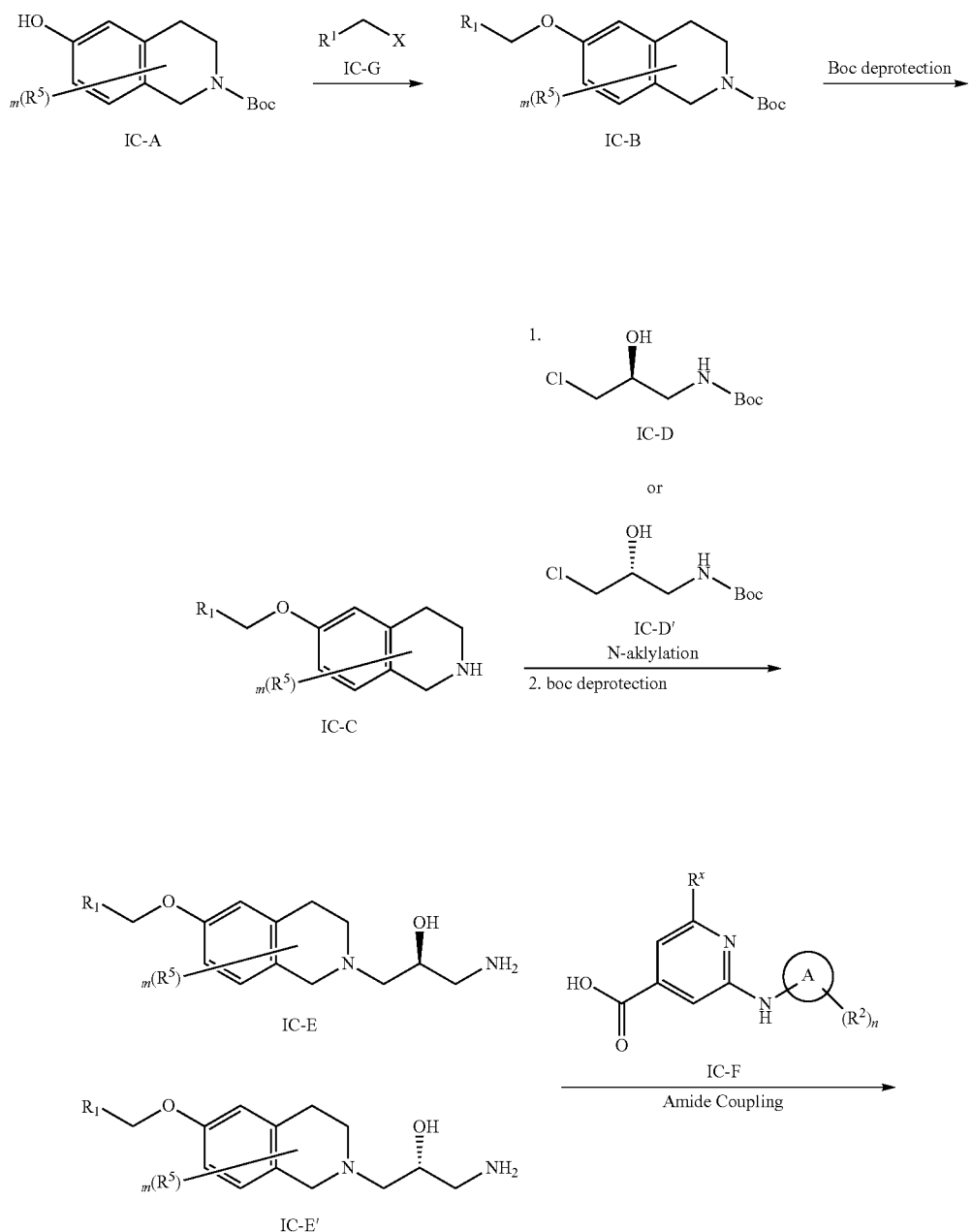

Scheme 1C

481

-continued

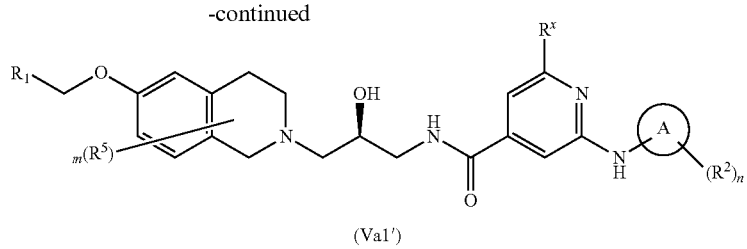

(Va1')

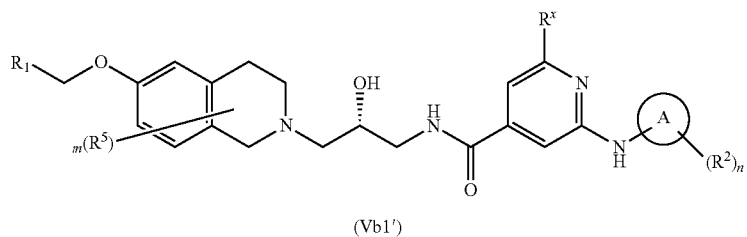

(Vb1')

wherein X is a leaving group and variables $R^5$, $R^x$, $R^1$, $R^2$, m, and n are defined herein. In some embodiments, X is selected from Cl, Br, and I. In some embodiments X is Cl or Br.

General Procedure 1C-A

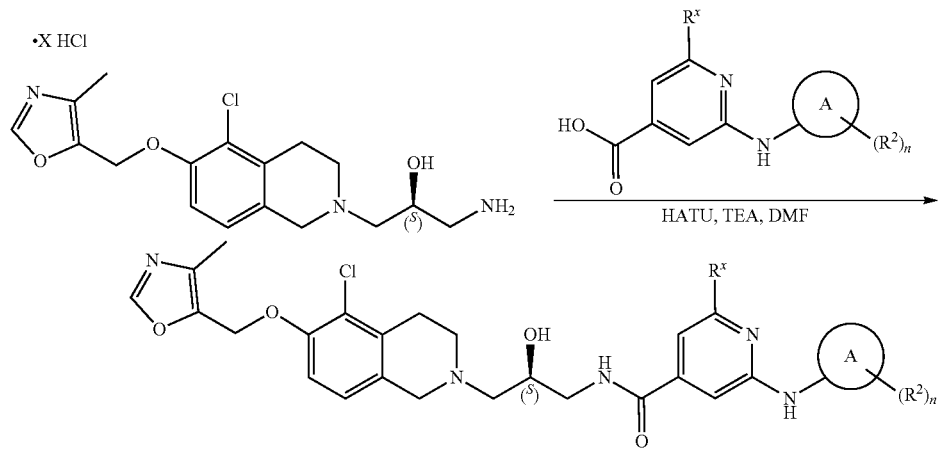

(2S)-1-Amino-3-[5-chloro-6-[(4-methyloxazol-5-yl) methoxy]-3,4-dihydro-1H-isoquinolin-2-yl]propan-2-ol (651 umol, 3HCl) and 2-(cyclobutylamino)pyridine-4-carboxylic acid (651 umol) were mixed in DMF (10 mL). Then, the reaction suspension was cooled to 0° C. and HATU (715.51 umol) followed by triethylamine (3.25 mmol). The reaction mixture was stirred at ambient temperature for 12 hr.

Example 1C1. (S)—N-(3-(5-chloro-6-((4-methyloxazol-5-yl)methoxy)-3,4-dihydroisoquinolin-2 (1H)-yl)-2-hydroxypropyl)-2-(cyclobutylamino) isonicotinamide (Compound 252)

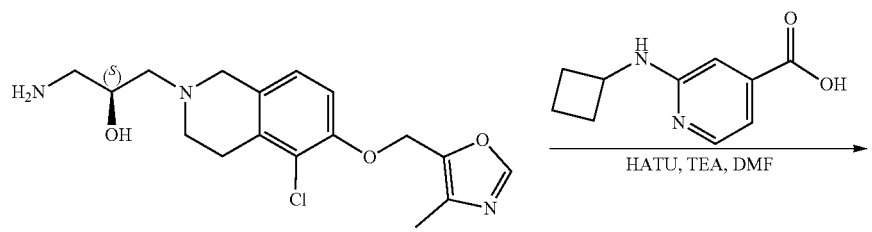

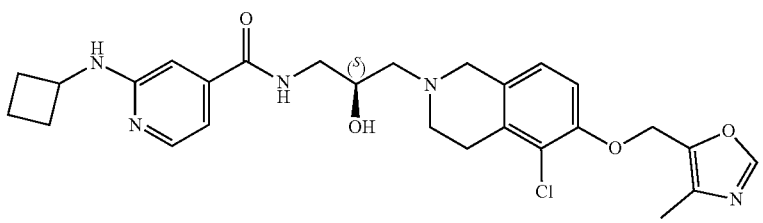

Prepared by general procedure 1C-A. The residue was purified by preparative RP-HPLC with H$_2$O—CH$_3$CN as mobile phase to afford product 1H-[(2S)-3-[5-chloro-6-[(4-methyloxazol-5-yl)methoxy]-3,4-dihydro-1H-isoquinolin-2-yl]-2-hydroxy-propyl]-2-(cyclobutylamino)pyridine-4-carboxamide (89.90 mg, 170.90 umol, 26.27% yield). $^1$H NMR (DMSO-d$_6$, 400 MHz): δ (ppm) 1.66 (m, 2H), 1.85 (m, 2H), 2.14 (s, 3H), 2.26 (m, 2H), 2.70 (m, 3H), 3.19 (m, 2H), 3.37 (m, 3H), 3.60 (m, 2H), 3.88 (m, 1H), 4.25 (m, 1H), 4.84 (d, 1H), 5.19 (s, 2H), 6.74 (ds, 2H), 6.93 (d, 1H), 7.02 (d, 1H), 7.09 (d, 1H), 7.95 (d, 1H), 8.29 (s, 1H), 8.45 (t, 1H). LCMS(ESI): [M+H]$^+$ m/z: calcd 526.2. found 526.2; Rt=0.84 min.

General Procedure IC-B

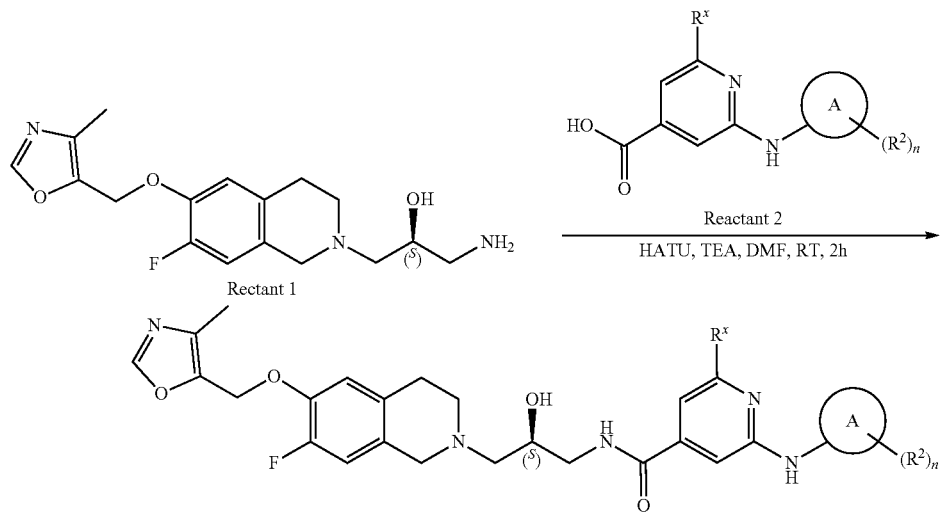

To the solution of Reactant 1 (1.0 equiv, HCl), Reactant 2 (1.0 equiv) and HATU (1.1 equiv) in DMF (1.2 mL) triethylamine (6.0 equiv) was added dropwise. The resulting mixture was stirred at 25° C. for 2 h. After the completion of the reaction, solvent was removed in vacuo and the obtained product was purified by reverse phase HPLC (Device (Mobile Phase, Column): 17_H$_2$O/R1 Sample info: 25-55% ACN 1-9 min water-acetonitrile, flow:30 mL/min (loading pump 4Ll/min acetonitrile) to afford pure product.

Example 1C2. N-[(2S)-3-[7-fluoro-6-[(4-methyloxazol-5-yl)methoxy]-3,4-dihydro-1H-isoquinolin-2-yl]-2-hydroxy-propyl]-2-(3-pyridylamino)pyridine-4-carboxamide (Compound 600)

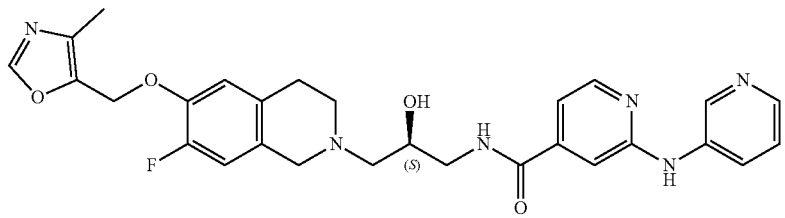

Prepared by general procedure IC-B. Yield: 32.0 mg (26.72%). $^1$H NMR (DMSO-d6, 400 MHz): δ (ppm) 2.14 (s, 3H), 2.70 (m, 2H), 2.75 (m, 2H), 3.22 (m, 1H), 3.31 (m, 2H), 3.43 (m, 1H), 3.54 (m, 2H), 3.90 (m, 1H), 4.86 (d, 1H), 5.15 (s, 2H), 6.91 (d, 1H), 7.02 (d, 1H), 7.11 (d, 1H), 7.26 (s, 1H), 7.29 (dd, 1H), 8.11 (d, 1H), 8.21 (m, 2H), 8.30 (s, 1H), 8.65 (t, 1H), 8.80 (d, 1H), 9.45 (s, 1H). LCMS(ESI): [M+2H]$^+$ m/z: calcd 532.2. found 534.2; Rt=2.68 min.

Example 1C3. 2-[(1-acetyl-4-piperidyl)amino]-N-[(2S)-3-[7-fluoro-6-[(4-methyloxazol-5-yl)methoxy]-3N-dihydro-1H-isoquinolin-2-yl]-2-hydroxy-propyl]-6-[2-methoxyethyl(methyl)amino]pyridine-4-carboxamide (Compound 612)

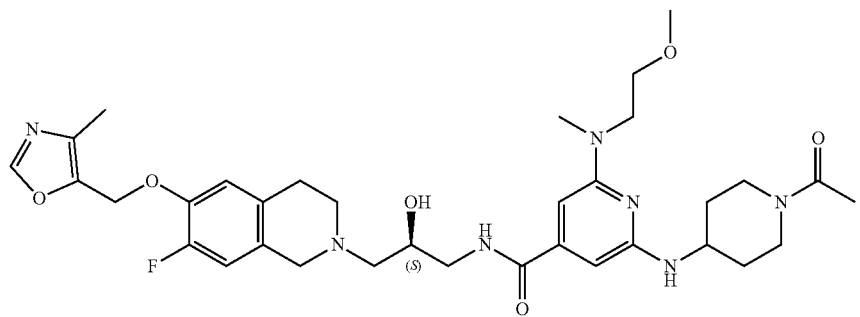

Prepared by general procedure IC-B. Yield: 58.0 mg (26.89%). $^1$H NMR (400 MHz, CDCl$_3$) δ 1.35 (m, 2H), 2.01 (m, 2H), 2.09 (s, 3H), 2.12 (m, 1H), 2.18 (s, 3H), 2.51 (m, 2H), 2.68 (m, 1H), 2.80 (m, 3H), 2.88 (m, 1H), 3.03 (s, 3H), 3.17 (m, 1H), 3.33 (s, 3H), 3.38 (m, 1H), 3.53 (m, 3H), 3.68 (m, 4H), 3.77 (m, 1H), 3.85 (m, 1H), 3.96 (m, 1H), 4.21 (d, 1H), 4.46 (m, 1H), 5.02 (s, 2H), 5.92 (s, 1H), 6.06 (s, 1H), 6.64 (m, 1H), 6.73 (m, 2H), 7.79 (s, 1H). LCMS(ESI): [M+H]$^+$ m/z: calcd 668.2. found 669.2; Rt=2.24 min.

Example 1C4. 2-1(1-acetyl-4-piperidyl)amino]-N-[(2S)-3-[7-fluoro-6-[(4-methyloxazol-5-yl)methoxy]-3N-dihydro-1H-isoquinolin-2-yl]-2-hydroxy-propyl]-6-(1-piperidyl)pyridine-4-carboxamide (Compound 623)

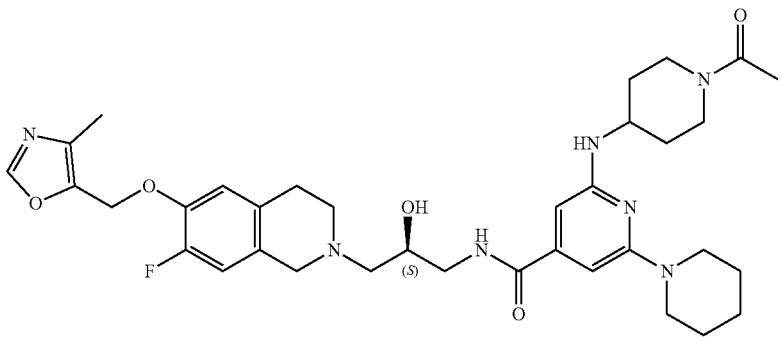

Prepared by general procedure IC-B. Yield: 39.0 mg (13.16%). $^1$H NMR (400 MHz, dmso-d$^6$) δ 1.24 (m, 1H), 1.35 (m, 1H), 1.50 (m, 4H), 1.58 (m, 2H), 1.83 (m, 1H), 1.92 (m, 1H), 1.99 (s, 3H), 2.14 (s, 3H), 2.66 (m, 3H), 2.73 (m, 2H), 2.80 (m, 1H), 3.15 (m, 4H), 3.46 (m, 4H), 3.77 (m, 2H), 3.84 (m, 2H), 4.17 (m, 1H), 4.81 (m, 1H), 5.14 (s, 2H), 6.10 (s, 1H), 6.21 (s, 1H), 6.26 (d, 1H), 6.90 (d, 1H), 7.01 (d, 1H), 8.25 (t, 1H), 8.30 (s, 1H). LCMS(ESI): [M+H]$^+$ m/z: calcd 663.2. found 664.2; Rt=0.98 min.

Example 1C5. 2-(4-acetylpiperazin-1-yl)-6-(cyclobutylamino)-N-[(2S)-3-[7-fluoro-6-[(4-methyloxazol-5-yl)methoxy]-3,4-dihydro-1H-isoquinolin-2-yl]-2-hydroxy-propyl]pyridine-4-carboxamide (Compound 615)

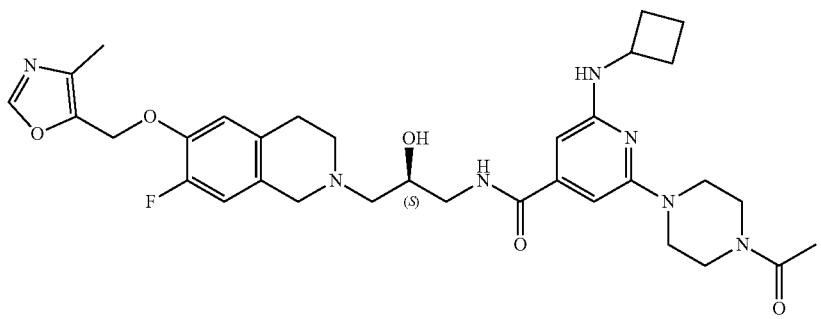

Prepared by general procedure IC-B. Yield: 40.0 mg (18.14%). $^1$H NMR (400 MHz, CDCl$_3$) δ 1.81 (m, 4H), 2.12 (s, 3H), 2.18 (s, 3H), 2.39 (m, 2H), 2.52 (m, 2H), 2.69 (m, 1H), 2.80 (m, 2H), 2.90 (m, 1H), 3.36 (m, 1H), 3.52 (m, 7H), 3.71 (m, 5H), 3.97 (m, 1H), 4.12 (m, 1H), 4.60 (d, 1H), 5.03 (s, 2H), 5.92 (s, 1H), 6.22 (s, 1H), 6.63 (t, 1H), 6.73 (m, 2H), 7.79 (s, 1H). LCMS(ESI): [M+H]$^+$ m/z: calcd 635.2. found 636.4; Rt=1.03 min.

Example 1C6. (S)-2-((1-acetylazetidin-3-yl)amino)-N-(3-(7-fluoro-6-((4-methyloxazol-5-yl)methoxy)-3,4-dihydroisoquinolin-2(1H)-yl-2-hydroxypropyl)-6-(piperidin-1-yl)isonicotinamide (Compound 638)

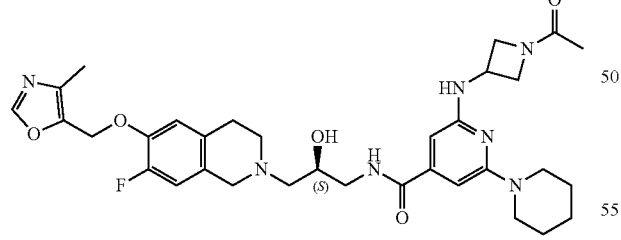

Prepared by general procedure 1C-B. Yield: 21 mg (22%). $^1$H NMR (DMSO-d6, 400 MHz): δ 1.51 (m, 4H), 1.58 (m, 2H), 1.75 (s, 3H), 2.14 (s, 3H), 2.74 (m, 4H), 3.33 (m, 4H), 3.45 (m, 4H), 3.53 (s, 2H), 3.70 (m, 1H), 3.91 (m, 2H), 4.09 (t, 1H), 4.38 (t, 1H), 4.42 (s, 1H), 4.81 (m, 1H), 5.14 (s, 2H), 6.09 (s, 1H), 6.30 (s, 1H), 6.90 (d, 1H), 6.95 (d, 1H), 7.01 (d, 1H), 8.30 (s, 2H). LCMS(ESI): [M+H]$^+$ m/z: calcd 635.7. found 636.4; Rt=1.061 min.

General Procedure IC-C

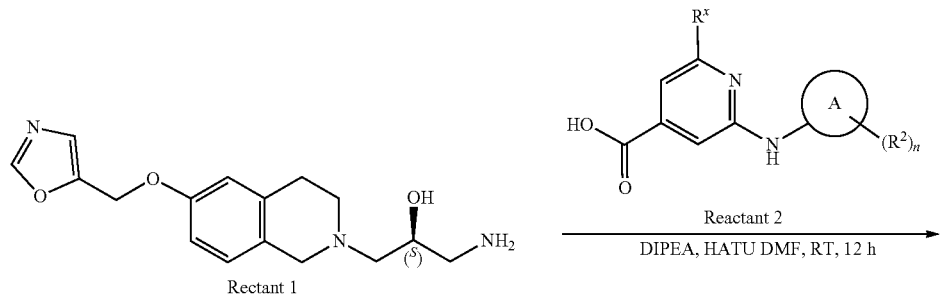

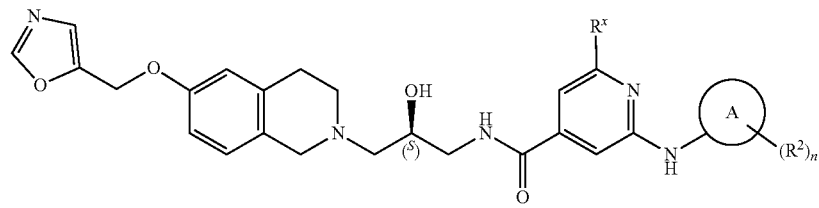

DIPEA (9 equiv) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and $H_2O$-MeOH as a mobile phase) to afford pure product.

Example 1C6. (S)-2-(cyclobutylamino)-6-(4-ethylpiperazin-1-yl)-N-(2-hydroxy-3-(6-(oxazol-5-ylmethoxy)-3,4-dihydroisoquinolin-2(1H)-propyl) isonicotinamide (Compound 286)

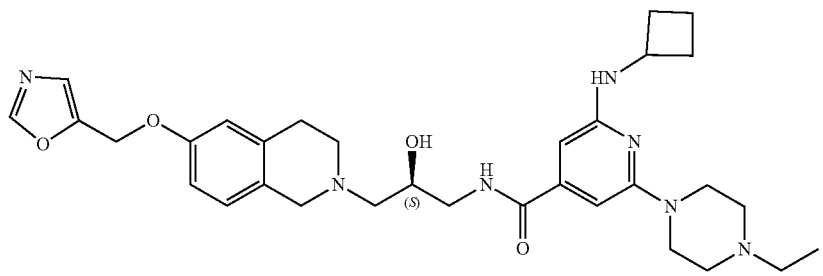

Prepared by general procedure IC-C. Yield: 22.4 mg (31.35%). $^1$H NMR (DMSO-d$_6$, 400 MHz): δ (ppm) 1.08 (t, 3H), 1.71 (t, 2H), 1.88 (m, 2H), 2.29 (m, 2H), 2.36 (m, 2H), 2.43 (m, 5H), 2.75 (m, 2H), 2.83 (m, 2H), 3.18 (m, 2H), 3.44 (m, 5H), 3.59 (s, 2H), 3.87 (m, 1H), 4.23 (m, 1H), 4.56 (d, 1H), 5.05 (s, 2H), 6.04 (s, 1H), 6.08 (d, 1H), 6.18 (s, 1H), 6.71 (m, 2H), 6.92 (d, 1H), 7.16 (s, 1H), 8.04 (t, 1H), 8.15 (s, 1H). LCMS(ESI): [M+H]$^+$ m/z: calcd 589.7. found 491.2; Rt=0.892 min.

Example 1C7. (S)-2-(cxclopentylamino)-N-(2-hydroxy-3-(6-(oxazol-5-ylmethoxy)-3N-dihydroisoquinolin-2(1H)-yl)propyl)isonicotinamide (Compound 407)

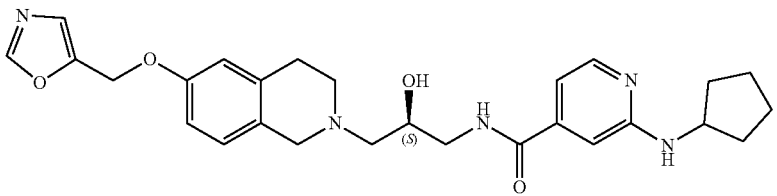

Prepared by general procedure IC-C. Yield: 21 mg (32.05%). $^1$H NMR (400 MHz, DMSO-d$_6$) δ 1.42 (m, 2H), 1.53 (m, 2H), 1.65 (m, 2H), 1.89 (m, 2H), 2.45 (m, 1H), 2.69 (m, 2H), 2.78 (m, 2H), 3.20 (m, 1H), 3.38 (m, 2H), 3.55 (m, 2H), 3.88 (m, 1H), 4.09 (h, 1H), 4.81 (m, 1H), 5.12 (s, 2H), 6.65 (d, 1H), 6.71 (dd, 1H), 6.79 (m, 3H), 6.96 (d, 1H), 7.30 (s, 1H), 7.95 (d, 1H), 8.41 (s, 1H), 8.45 (t, 1H). LCMS(ESI): [M+2H]$^+$ m/z: calcd 491.5. found 492.5; Rt=0.829 min.

Example 1C8. (S)—N-(2-hydroxy-3-(6-(oxazol-5-ylmethoxy)-3N-dihydroisoquinolin-2(1H)-yl)propyl)-2-(pyridin-3-ylamino)isonicotinamide (Compound 399)

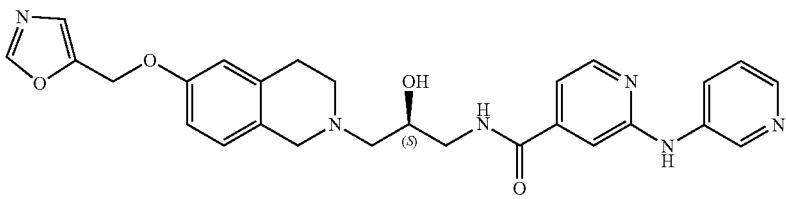

Prepared by general procedure IC-C. Yield: 11.5 mg (18.23%). $^1$H NMR (500 MHz, DMSO-d$_6$+CCl$_4$) δ 2.46 (m, 1H), 2.78 (m, 2H), 2.84 (m, 2H), 2.97 (m, 1H), 3.25 (m, 1H), 3.46 (m, 1H), 3.62 (m, 2H), 3.91 (m, 1H), 4.61 (m, 1H), 5.06 (s, 2H), 6.72 (m, 2H), 6.92 (d, 1H), 7.02 (dd, 1H), 7.16 (m, 2H), 7.26 (s, 1H), 8.02 (dd, 1H), 8.12 (d, 1H), 8.15 (s, 1H), 8.26 (m, 1H), 8.45 (t, 1H), 8.72 (d, 1H), 9.27 (s, 1H). LCMS(ESI): [M+2H]$^+$ m/z: calcd 500.5. found 501.2; Rt=0.713 min.

Example 1C9. (S)-2-(4-acetylpiperazin-1-yl)-6-(cyclobutylamino)-N-(2-hydroxy-3-(6-(oxazol-5-ylmethoxy)-3N-dihydroisoquinolin-2(1H)-yl)propyl)isonicotinamide (Compound 497)

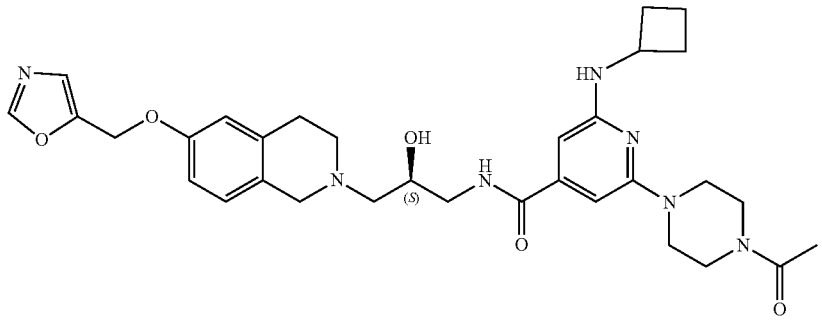

Prepared by general procedure IC-C. Yield: 7 mg (10.18%). 1H NMR (500 MHz, CDCl$_3$) δ 1.77 (m, 2H), 1.86 (m, 2H), 2.15 (s, 3H), 2.42 (m, 2H), 2.55 (m, 1H), 2.63 (m, 1H), 2.74 (m, 1H), 2.93 (m, 3H), 3.41 (m, 2H), 3.52 (m, 2H), 3.56 (m, 2H), 3.59 (d, 3H), 3.72 (m, 3H), 3.80 (m, 1H), 4.02 (m, 1H), 4.16 (m, 1H), 4.61 (d, 1H), 5.06 (s, 2H), 5.95 (s, 1H), 6.26 (s, 1H), 6.70 (t, 1H), 6.73 (s, 1H), 6.79 (d, 1H), 6.96 (d, 1H), 7.16 (s, 1H), 7.91 (s, 1H). LCMS(ESI): [M+H]$^+$ m/z: calcd 603.7. found 608.2; Rt=0.980 min.

Example 1C10. (S)-2-(cyclobutylamino)-N-(2-hydroxy-3-(6-(oxazol-5-ylmethoxy)-3,4-dihydroisoquinolin-2(1H)-yl)propyl-6-(methyl(propyl)amino)isonicotinamide (Compound 415)

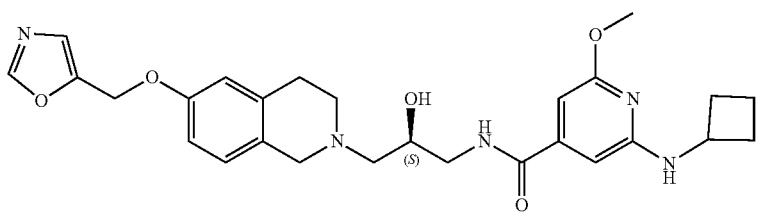

Prepared by general procedure IC-C. Yield: 27.9 mg (43.72%). $^1$H NMR (CDCl$_3$, 500 MHz): δ (ppm) 0.92 (t, 3H), 1.60 (m, 3H), 1.77 (m, 2H), 1.88 (m, 2H), 2.41 (m, 2H), 2.60 (m, 2H), 2.76 (m, 1H), 2.94 (m, 3H), 3.02 (s, 3H), 3.45 (m, 3H), 3.61 (d, 1H), 3.71 (d, 1H), 3.82 (d, 1H), 4.03 (m, 1H), 4.16 (m, 1H), 4.54 (s, 1H), 5.06 (s, 2H), 5.82 (s, 1H), 6.11 (s, 1H), 6.69 (t, 1H), 6.73 (s, 1H), 6.79 (d, 1H), 6.97 (d, 1H), 7.16 (s, 1H), 7.92 (s, 1H). LCMS(ESI): [M+H]$^+$ m/z: calcd 548.6. found 549.2; Rt=0.982 min.

Example 1C11. (S)-2-(cyclobutylamino)-N-(2-hydroxy-3-(6-(oxazol-5-ylmethoxy)-3,4-dihydroisoquinolin-2(1H)-yl)propyl)-6-methoxyisonicotinamide (Compound 310)

Prepared by general procedure IC-C. Yield: 18.9 mg (27.44%). $^1$H NMR (400 MHz, DMSO-de) δ 1.66 (m, 2H), 1.89 (m, 2H), 2.27 (m, 3H), 2.43 (m, 2H), 2.67 (m, 2H), 2.77 (m, 2H), 3.16 (m, 1H), 3.54 (m, 2H), 3.76 (s, 3H), 3.87 (m, 1H), 4.18 (m, 1H), 4.79 (d, 1H), 5.11 (s, 2H), 6.21 (s, 1H), 6.30 (s, 1H), 6.77 (m, 2H), 6.89 (d, 1H), 6.95 (d, 1H), 7.30 (s, 1H), 8.35 (t, 1H), 8.39 (s, 1H). LCMS(ESI): [M+H]$^+$ m/z: calcd 507.6. found 508.2; Rt=1.094 min.

Example 1C12. (S)-2-(cyclobutylamino)-N-(2-hydroxy-3-(6-(oxazol-5-ylmethoxy)-3,4-dihydroisoquinolin-2(1H)-yl)propyl)-6-morpholinoisonicotinamide (Compound 292)

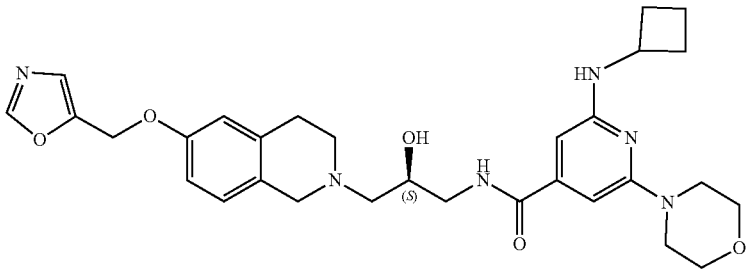

Prepared by general procedure IC-C. Yield: 22.1 mg (33.08%). $^1$H NMR (400 MHz, DMSO-de) δ 1.71 (m, 2H), 1.88 (m, 2H), 2.28 (m, 2H), 2.47 (m, 2H), 2.75 (m, 2H), 2.83 (m, 2H), 3.17 (m, 1H), 3.42 (m, 5H), 3.60 (s, 2H), 3.68 (t, 4H), 3.85 (m, 1H), 4.24 (p, 1H), 4.56 (m, 1H), 5.05 (s, 2H), 6.09 (s, 1H), 6.17 (m, 2H), 6.71 (m, 2H), 6.91 (d, 1H), 7.16 (s, 1H), 8.07 (t, 1H), 8.15 (s, 1H). LCMS(ESI): [M+H]$^+$ m/z: calcd 562.6. found 563.2; Rt=1.053 min.

Example 1C13. (S)-2-(cyclobutylamino)-N-(2-hydroxy-3-(6-(oxazol-5-ylmethoxy)-3,4-dihydroisoquinolin-2(1H)-yl)propyl)-6-(4-propionylpiperazin-1-yl)isonicotinamide(Compound 397)

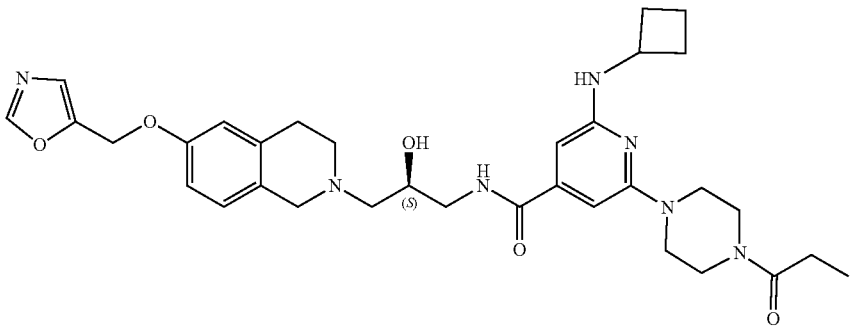

Prepared by general procedure IC-C. Yield: 12.3 mg (19.11%). $^1$H NMR (400 MHz, DMSO-d$_6$+CCl$_4$) δ 1.07 (t, 3H), 1.72 (m, 2H), 1.89 (m, 2H), 2.34 (m, 4H), 2.76 (m, 2H), 2.83 (m, 2H), 3.18 (m, 1H), 3.45 (m, 3H), 3.52 (m, 5H), 3.58 (m, 5H), 3.87 (m, 1H), 4.23 (m, 1H), 4.58 (m, 1H), 5.06 (s, 2H), 6.09 (s, 1H), 6.21 (m, 2H), 6.72 (m, 2H), 6.92 (d, 1H), 7.16 (s, 1H), 8.09 (t, 1H), 8.16 (s, 1H). LCMS(ESI): [M+H]$^+$ m/z: calcd 617.7. found 618.2; Rt=1.073 min.

Example 1C14. (S)-2-(cyclobutylamino)-N-(2-hydroxy-3-(6-(oxazol-5-ylmethoxy)-3,4-dihydroisoquinolin-2(1H)-yl)propyl)-6-(4-methylpiperazin-1-yl)isonicotinamide (Compound

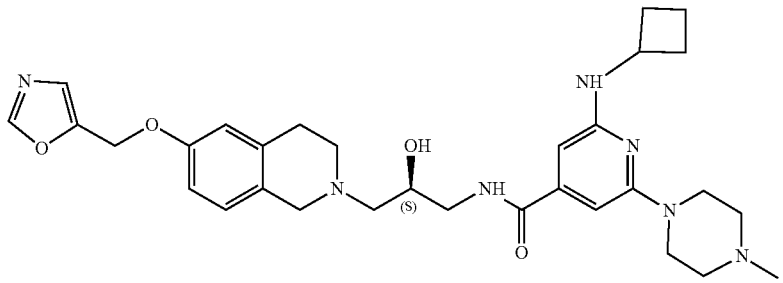

Prepared by general procedure IC-C. Yield: 23.8 mg (36.3%). $^1$H NMR (DMSO-$d_6$, 500 MHz): δ (ppm) 1.69 (m, 2H), 1.87 (m, 2H), 2.24 (s, 3H), 2.29 (m, 2H), 2.39 (m, 4H), 2.54 (m, 2H), 2.76 (m, 2H), 2.83 (m, 2H), 3.17 (m, 1H), 3.43 (m, 5H), 3.61 (s, 2H), 3.86 (m, 1H), 4.23 (m, 1H), 4.57 (s, 1H), 5.05 (s, 2H), 6.04 (s, 1H), 6.08 (d, 1H), 6.18 (s, 1H), 6.71 (m, 2H), 6.92 (d, 1H), 7.15 (s, 1H), 8.06 (t, 1H), 8.15 (d, 1H). LCMS(ESI): [M+H]$^+$ m/z: calcd 575.7; found 576.2; Rt=0.857 min.

Example 1C15. (S)-2-(cyclobutylamino)-N-(2-hydroxy-3-(6-(oxazol-5-ylmethoxy)-3,4-dihydroisoquinolin-2(1H)-yl)propyl)-6-((2-methoxyethyl)(methyl)amino)isonicotinamide (Compound 369)

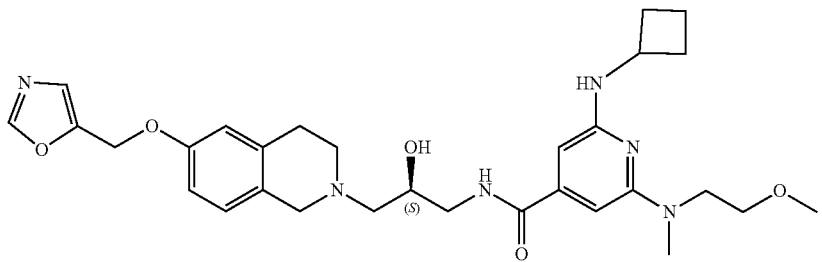

Prepared by general procedure IC-C. Yield: 12.8 mg (26.73%). $^1$H NMR (CDCl$_3$, 500 MHz): δ (ppm) 1.76 (m, 2H), 1.87 (m, 2H), 2.40 (m, 2H), 2.61 (m, 2H), 2.76 (m, 1H), 2.90 (m, 2H), 2.95 (m, 2H), 3.06 (s, 3H), 3.36 (s, 3H), 3.43 (m, 1H), 3.56 (t, 2H), 3.62 (m, 1H), 3.72 (t, 3H), 3.81 (d, 1H), 4.04 (m, 1H), 4.16 (m, 1H), 4.55 (m, 1H), 5.06 (s, 2H), 5.86 (s, 1H), 6.12 (s, 1H), 6.69 (t, 1H), 6.73 (s, 1H), 6.79 (d, 1H), 6.96 (d, 1H), 7.16 (s, 1H), 7.91 (s, 1H). LCMS(ESI): [M+H]$^+$ m/z: calcd 564.6. found 565.2; Rt=0.949 min.

Example 1C16. (S)-2-(cyclobutylamino)-N-(2-hydroxy-3-(6-(oxazol-5-ylmethoxy)-3,4-dihydroisoquinolin-2(1H)-yl)propyl)-6-(piperidin-1-yl)isonicotinamide (Compound 320)

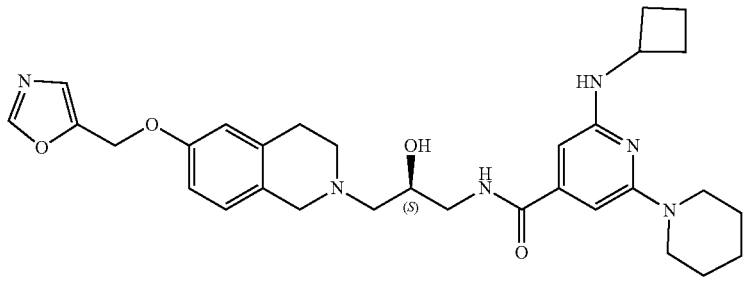

Prepared by general procedure IC-C. Yield: 12.4 mg (16.59%). $^1$H NMR (500 MHz, CDCl$_3$) δ 1.77 (m, 4H), 1.85 (m, 3H), 2.40 (m, 2H), 2.57 (m, 1H), 2.63 (m, 1H), 2.76 (m, 1H), 2.91 (m, 3H), 2.97 (m, 1H), 3.43 (m, 2H), 3.52 (m, 5H), 3.63 (m, 2H), 3.72 (m, 1H), 3.81 (d, 1H), 4.03 (m, 1H), 4.14 (m, 1H), 4.58 (m, 1H), 5.06 (s, 2H), 5.87 (s, 1H), 6.26 (s, 1H), 6.69 (m, 1H), 6.73 (d, 1H), 6.79 (dd, 1H), 6.96 (d, 1H), 7.16 (s, 1H), 7.91 (s, 1H). LCMS(ESI): [M+H]$^+$ m/z: calcd 560.6. found 561.2; Rt=1.018 min.

Example 1C17. (S)-2-(cyclobutylamino)-N-(2-hydroxy-3-(6-(oxazol-5-ylmethoxy)-3,4-dihydroisoquinolin-2(1H)-yl)propyl)-6-(4-isobutyrylpiperazin-1-yl)isonicotinamide (Compound 481)

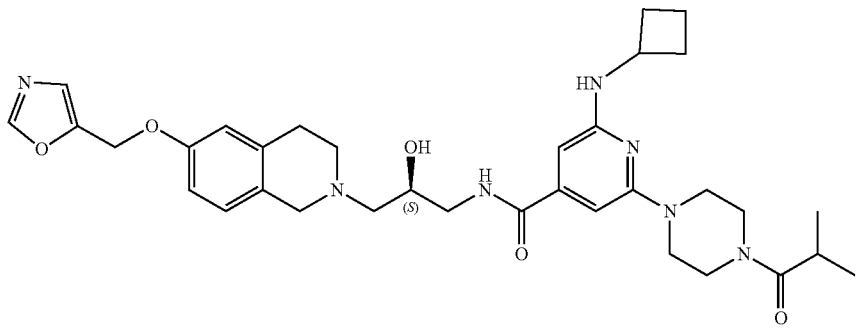

Prepared by general procedure IC-C. Yield: 5.8 mg (10.52%). $^1$H NMR (500 MHz, CDCl$_3$) δ 1.16 (d, 6H), 1.78 (m, 3H), 1.86 (m, 3H), 2.41 (m, 2H), 2.74 (m, 1H), 2.83 (m, 1H), 2.97 (m, 3H), 3.07 (m, 1H), 3.47 (m, 1H), 3.51 (m, 3H), 3.59 (m, 4H), 3.72 (m, 4H), 3.92 (m, 1H), 4.14 (m, 1H), 4.64 (m, 1H), 5.05 (s, 2H), 6.00 (s, 1H), 6.28 (s, 1H), 6.72 (s, 1H), 6.78 (d, 1H), 6.95 (m, 2H), 7.16 (s, 1H), 7.91 (s, 1H). LCMS(ESI): [M+H]$^+$ m/z: calcd 631.7. found 632.2; Rt=1.134 min.

Example 1C18. (S)-2-(cyclobutylamino)-6-(4-ethylpiperazin-1-yl)-N-(2-hydroxy-3-(6-(oxazol-5-ylmethoxy)-3N-dihydroisoquinolin-2(1H)-yl)propyl)isonicotinamide (Compound 286)

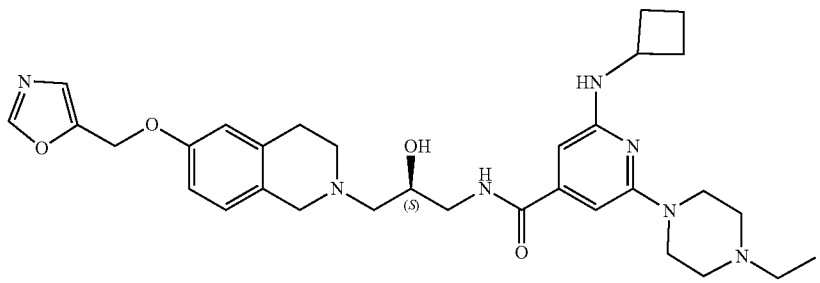

Prepared by general procedure IC-C. Yield: 22.4 mg (31.35%). $^1$H NMR (DMSO-$d_6$, 400 MHz): δ (ppm) 1.08 (t, 3H), 1.71 (t, 2H), 1.88 (m, 2H), 2.29 (m, 2H), 2.36 (m, 2H), 2.43 (m, 5H), 2.75 (m, 2H), 2.83 (m, 2H), 3.18 (m, 2H), 3.44 (m, 5H), 3.59 (s, 2H), 3.87 (m, 1H), 4.23 (m, 1H), 4.56 (d, 1H), 5.05 (s, 2H), 6.04 (s, 1H), 6.08 (d, 1H), 6.18 (s, 1H), 6.71 (m, 2H), 6.92 (d, 1H), 7.16 (s, 1H), 8.04 (t, 1H), 8.15 (s, 1H). LCMS(ESI): [M+H]$^+$ m/z: calcd 589.7. found 491.2; Rt=0.892 min.

Example 1C19. (S)-2-(tert-butyl)-6-(cyclobutylamino)-N-(2-hydroxy-3-(6-(oxazol-5-ylmethoxy)-3,4-dihydroisoquinolin-2(1H)-yl)propyl)isonicotinamide (Compound 308)

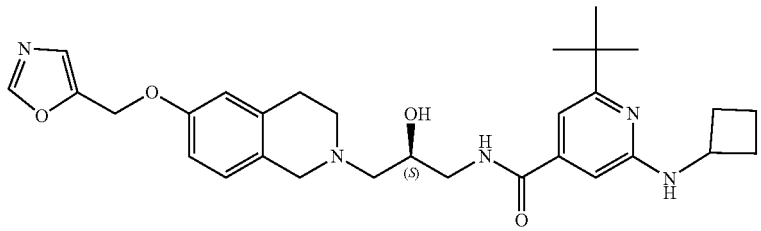

Prepared by general procedure IC-C. Yield: 20.8 mg (28.22%). $^1$H NMR (500 MHz, CDCl$_3$) δ 1.31 (s, 9H), 1.80 (m, 2H), 1.90 (m, 2H), 2.44 (m, 2H), 2.55 (m, 1H), 2.62 (m, 1H), 2.73 (m, 1H), 2.90 (m, 2H), 2.95 (m, 1H), 3.42 (m, 1H), 3.58 (m, 2H), 3.74 (m, 1H), 3.79 (d, 1H), 4.03 (m, 1H), 4.19 (m, 1H), 4.77 (d, 1H), 5.06 (s, 2H), 6.44 (s, 1H), 6.69 (m, 1H), 6.73 (d, 1H), 6.78 (dd, 1H), 6.84 (s, 1H), 6.96 (d, 1H), 7.16 (s, 1H), 7.91 (s, 1H). LCMS(ESI): [M+2H]$^+$ m/z: calcd 533.6. found 534.2; Rt=1.024 min.

Example 1C20. (S)-2-(cyclobutylamino)-N-(2-hydroxy-3-(6-(oxazol-5-ylmethoxy)-3,4-dihydroisoquinolin-2(1H)-yl)propyl)-6-(4-isopropylpiperazin-1-yl)isonicotinamide (Compound 462)

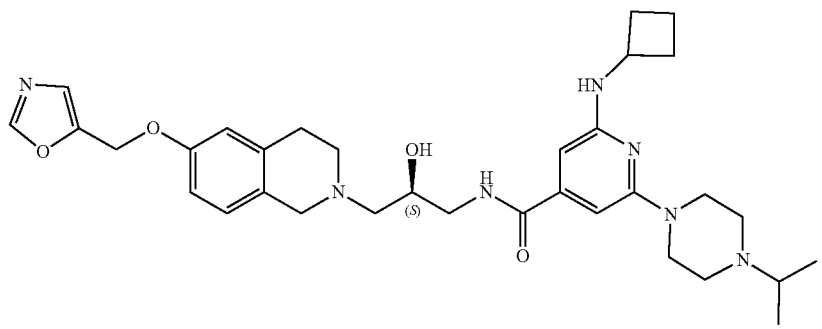

Prepared by general procedure IC-C. Yield: 15.5 mg (23.54%). ¹H NMR (DMSO-d₆, 400 MHz): δ (ppm) 1.04 (d, 6H), 1.70 (m, 2H), 1.89 (m, 2H), 2.31 (m, 2H), 2.54 (m, 4H), 2.67 (m, 1H), 2.79 (m, 4H), 3.19 (d, 3H), 3.43 (m, 4H), 3.60 (m, 2H), 3.75 (m, 1H), 3.88 (m, 1H), 4.22 (m, 1H), 4.56 (d, 1H), 5.05 (s, 2H), 6.04 (m, 2H), 6.17 (s, 1H), 6.70 (m, 2H), 6.92 (d, 1H), 7.16 (s, 1H), 8.04 (t, 1H), 8.15 (s, 1H). LCMS(ESI): [M+H]⁺ m/z: calcd 603.7. found 604.4; Rt=0.908 min.

Example 1C21. (S)-2-(cyclobutylamino)-6-(4-(cyclopropanecarbonyl)piperazin-1-yl)-N-(2-hydroxy-3-(6-(oxazol-5-ylmethoxy)-3N-dihydroisoquinolin-2(1H)-yl)propyl)isonicotinamide (Compound 378)

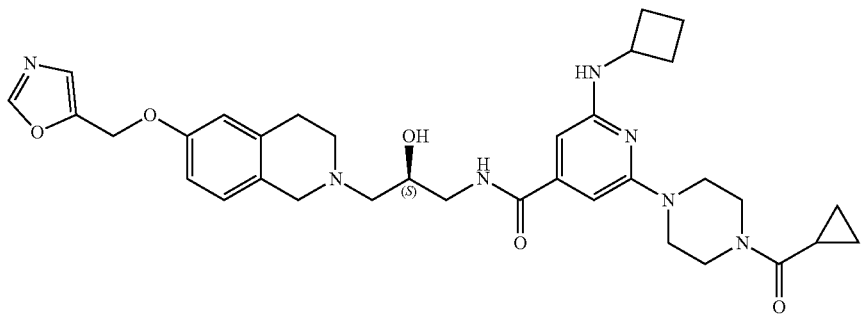

Prepared by general procedure IC-C. Yield: 16.7 mg (27.36%). ¹H NMR (400 MHz, CDCl₃) δ 0.77 (m, 2H), 0.99 (m, 2H), 1.78 (m, 5H), 2.37 (m, 2H), 2.54 (m, 2H), 2.69 (m, 1H), 2.87 (m, 3H), 3.38 (m, 1H), 3.54 (m, 5H), 3.71 (m, 7H), 3.98 (m, 1H), 4.11 (m, 1H), 4.59 (d, 1H), 5.02 (s, 2H), 5.92 (s, 1H), 6.22 (s, 1H), 6.73 (m, 3H), 6.92 (d, 1H), 7.12 (s, 1H), 7.88 (s, 1H). LCMS(ESI): [M+H]⁺ m/z: calcd 629.7. found 630.2; Rt=1.017 min.

Example 1C22. (S)-2-(cyclobutylamino)-6-(ethyl(methyl)amino)-N-(2-hydroxy-3-(6-(oxazol-5-ylmethoxy)-3,4-dihydroisoquinolin-2(1H)-yl)propyl)isonicotinamide (Compound 438)

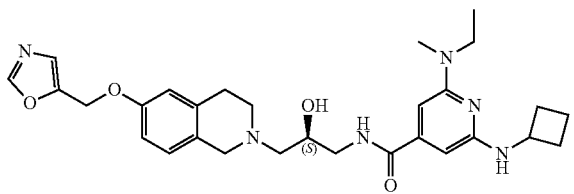

Prepared by general procedure IC-C. Yield: 21.5 mg (37.72%). ¹H NMR (DMSO-d₆, 500 MHz): δ (ppm) 1.10 (t, 3H), 1.69 (m, 2H), 1.87 (m, 2H), 2.29 (m, 2H), 2.55 (m, 2H), 2.77 (m, 2H), 2.84 (m, 2H), 2.94 (s, 3H), 3.19 (m, 1H), 3.42 (m, 1H), 3.53 (q, 2H), 3.62 (m, 2H), 3.88 (m, 1H), 4.23 (m, 1H), 4.62 (s, 1H), 5.05 (s, 2H), 5.93 (s, 2H), 6.00 (s, 1H), 6.70 (s, 1H), 6.72 (d, 1H), 6.92 (d, 1H), 7.16 (s, 1H), 8.01 (t, 1H), 8.15 (s, 1H). LCMS(ESI): [M+H]⁺ m/z: calcd 534.6. found 535.2; Rt=0.925 min.

Example 1C23. (S)-2-(cyclobutylamino)-6-(2-(dimethylamino)ethoxy)-N-(2-hydroxy-3-(6-(oxazol-5-ylmethoxy)-3,4-dihydroisoquinolin-2(1H)-yl)propyl)isonicotinamide (Compound 315)

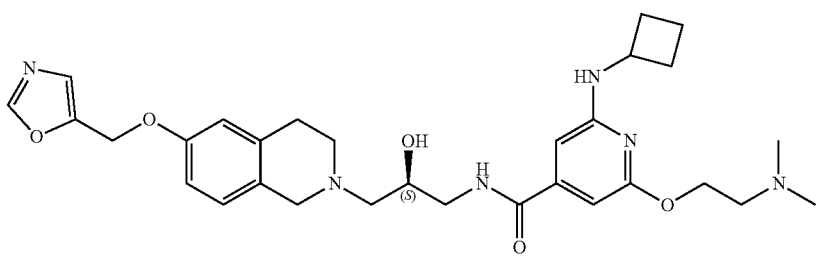

Prepared by general procedure IC-C. Yield: 21.6 mg (26.75%). $^1$H NMR (400 MHz, DMSO-d$_6$+CCl$_4$) δ 1.72 (m, 2H), 1.92 (m, 2H), 2.24 (s, 6H), 2.31 (m, 2H), 2.59 (t, 2H), 2.75 (m, 2H), 2.82 (m, 2H), 3.19 (m, 2H), 3.42 (m, 1H), 3.59 (m, 2H), 3.75 (m, 1H), 3.85 (m, 1H), 4.27 (m, 3H), 4.53 (m, 1H), 5.05 (s, 2H), 6.18 (s, 1H), 6.28 (s, 1H), 6.49 (d, 1H), 6.71 (m, 2H), 6.91 (d, 1H), 7.16 (s, 1H), 8.05 (t, 1H), 8.15 (s, 1H). LCMS(ESI): [M+H]$^+$ m/z: calcd 564.6. found 565.2; Rt=0.865 min.

Example 1C24. (S)-2-(cyclobutylamino)-N-(2-hydroxy-3-(6-(oxazol-5-ylmethoxy)-3,4-dihydroisoquinolin-2(1H)-yl)propyl)-6-isobutylisonicotinamide (Compound 307)

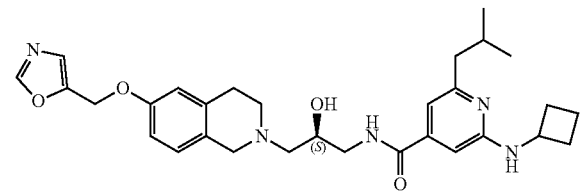

Prepared by general procedure IC-C. Yield: 21.1 mg (28.62%). $^1$H NMR (500 MHz, CDCl$_3$) δ 0.92 (d, 6H), 1.79 (m, 2H), 1.87 (m, 2H), 2.07 (m, 1H), 2.46 (m, 4H), 2.59 (m, 3H), 2.73 (m, 1H), 2.91 (m, 3H), 3.42 (m, 1H), 3.58 (m, 1H), 3.74 (m, 1H), 3.79 (m, 1H), 4.03 (m, 1H), 4.10 (m, 1H), 4.89 (m, 1H), 5.06 (s, 2H), 6.49 (s, 1H), 6.62 (s, 1H), 6.73 (m, 2H), 6.79 (m, 1H), 6.96 (d, 1H), 7.16 (s, 1H), 7.91 (s, 1H). LCMS(ESI): [M+H]$^+$ m/z: calcd 533.6. found 534.2; Rt=0.946 min.

Example 1C25. (S)-2-(4-(tert-butyl)piperazin-1-yl)-6-(cyclobutylamino)-N-(2-hydroxy-3-(6-(oxazol-5-ylmethoxy)-3N-dihydroisoquinolin-2(1H)-yl)propyl) isonicotinamide (Compound 306)

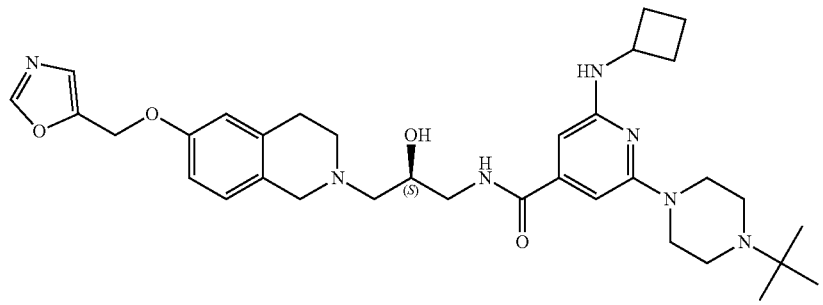

Prepared by general procedure IC-C. Yield: 11 mg (15.97%). $^1$H NMR (500 MHz, DMSO-d$_6$+CCl$_4$) δ 1.07 (s, 9H), 1.70 (m, 2H), 1.91 (m, 2H), 2.29 (m, 2H), 2.57 (m, 4H), 2.78 (m, 3H), 2.84 (m, 2H), 2.93 (m, 1H), 3.16 (m, 1H), 3.42 (m, 5H), 3.62 (m, 2H), 3.87 (m, 1H), 4.23 (h, 1H), 4.60 (m, 1H), 5.05 (s, 2H), 6.05 (m, 2H), 6.18 (m, 1H), 6.71 (m, 2H), 6.92 (d, 1H), 7.16 (s, 1H), 8.05 (m, 1H), 8.15 (s, 1H). LCMS(ESI): [M+H]$^+$ m/z: calcd 617.8. found 619.2; Rt=0.885 min.

Example 1C26. (S)-2-(cyclobutylamino)-N-(2-hydroxy-3-(6-(oxazol-5-ylmethoxy)-3,4-dihydroisoquinolin-2(1H)-yl)propyl-6-(piperazin-1-yl)isonicotinamide (Compound 422)

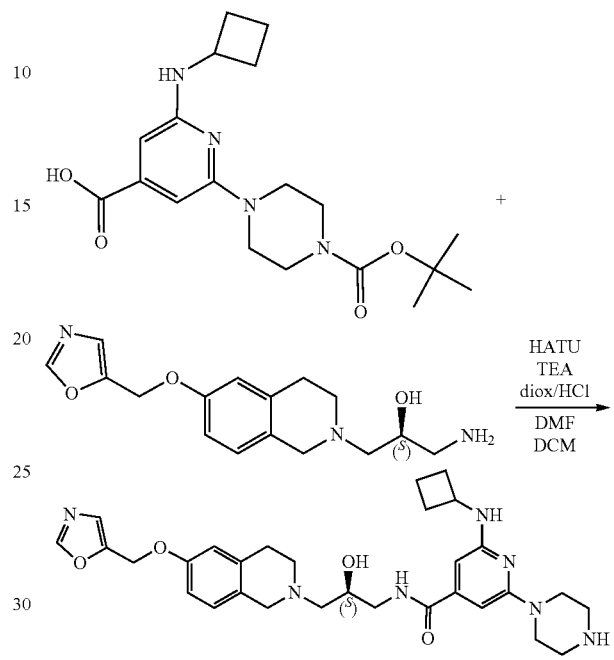

Triethyl amine (241.92 mg, 2.39 mmol, 333.22 uL) was added to a stirred mixture of 2-(4-tert-butoxycarbonylpiperazin-1-yl)-6-(cyclobutylamino)pyridine-4-carboxylic acid (150 mg, 398.46 umol), (2S)-1-amino-3-[6-(oxazol-5-ylmethoxy)-3,4-dihydro-1H-isoquinolin-2-yl]propan-2-ol (164.46 mg, 398.46 umol, 3HCl) and HATU (151.51 mg, 398.46 umol) in DMF (10 mL) at 25° C. The resulting mixture was stirred at 25° C. for 12 hr., and then evaporated in vacuo. The residue was dissolved in dichloromethane (20 mL), Hydrogen chloride solution 4.0M in dioxane (10.50 g, 40.03 mmol, 10 mL, 13.9% purity) was added to a solution, and the resulting suspension was stirred at 25° C. for 24 hr. The reaction mixture was evaporated in vacuo and the residue was purified by reverse phase HPLC (column: XBridgeC18 100×19 mm 5 um) using 30-60% 0-6 min 0.1% NH3-methanol as mobile phase to afford Compound 422

2-(cyclobutylamino)-N-[(2S)-2-hydroxy-3-[6-(oxazol-5-yl-methoxy)-3,4-dihydro-1H-isoquinolin-2-yl]propyl]-6-piperazin-1-yl-pyridine-4-carboxamide (69 mg, 122.85 umol, 30.83% yield). $^1$H NMR (400 MHz, CDCl$_3$): δ (ppm) 1.78 (m, 5H), 2.39 (m, 2H), 2.54 (m, 2H), 2.69 (m, 1H), 2.87 (m, 3H), 2.92 (m, 5H), 3.39 (m, 1H), 3.46 (m, 4H), 3.52 (d, 1H), 3.68 (m, 1H), 3.75 (d, 1H), 3.98 (m, 1H), 4.13 (m, 1H), 4.55 (d, 1H), 5.03 (s, 2H), 5.89 (s, 1H), 6.21 (s, 1H), 6.65 (t, 1H), 6.70 (d, 1H), 6.75 (d, 1H), 6.93 (d, 1H), 7.13 (s, 1H), 7.88 (s, 1H). LCMS(ESI): [M+H]$^+$ m/z: calcd 561.3. found 562.4; Rt=1.919 min.

Prepared by general procedure IC-D. Yield: 33.3 mg (45.19%). $^1$H NMR (400 MHz, DMSO-d$_6$) δ 0.89 (d, 6H), 1.71 (m, 2H), 1.85 (m, 2H), 2.03 (m, 1H), 2.31 (m, 4H), 2.50 (m, 1H), 2.80 (s, 4H), 3.22 (m, 1H), 3.39 (m, 1H), 3.64 (m, 2H), 3.85 (m, 1H), 4.26 (m, 1H), 4.60 (m, 1H), 5.16 (s, 2H), 6.39 (d, 2H), 6.54 (s, 2H), 6.96 (d, 1H), 6.99 (d, 1H), 7.19 (s, 1H), 8.12 (t, 1H), 8.17 (s, 1H). LCMS(ESI): [M+H]$^+$ m/z: calcd 568.1. found 569.2; Rt=0.981 min.

General Procedure 1C-D

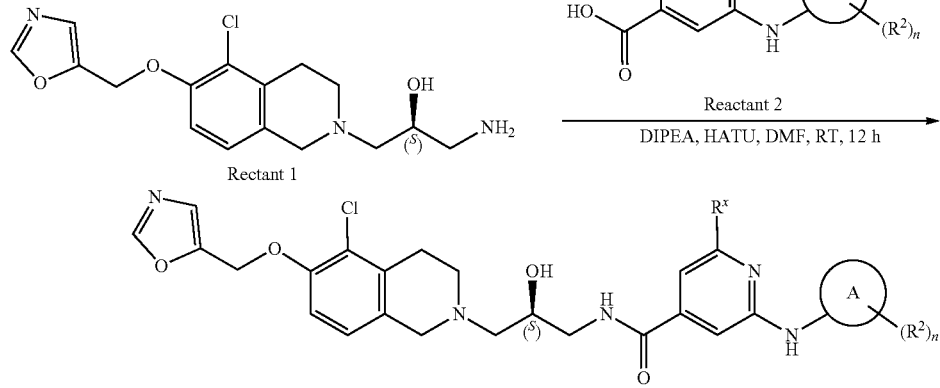

DIPEA (2.5 equiv+E0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (TO mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase) to afford pure product.

Example 1C27. (S)—N-(3-(5-chloro-6-(oxazol-5-ylmethoxy)-3N-dihydroisoquinolin-2(1H)-yl)-2-hydroxypropyl-2-(cyclobutylamino)-6-isobutylisonicotinamide (Compound 287)

Example 1C28. (S)—N-(3-(5-chloro-6-(oxazol-5-ylmethoxy)-3N-dihydroisoquinolin-2(1H)-yl)-2-hydroxypropyl)-2-(cyclobutylamino)-6-morpholinoisonicotinamide (Compound 288)

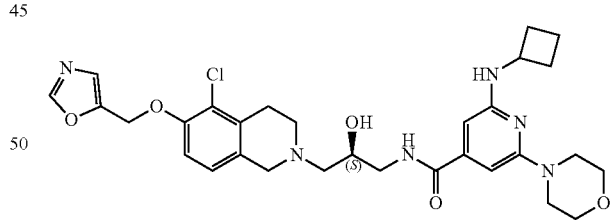

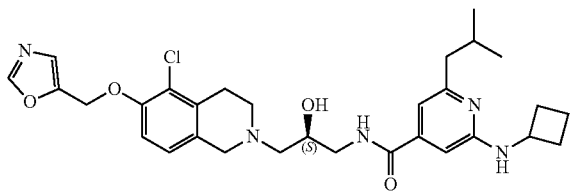

Prepared by general procedure IC-D. Yield: 34.3 mg (47.57%). $^1$H NMR, δ 1.73 (m, 2H), 1.89 (p, 2H), 2.30 (q, 2H), 2.47 (m, 2H), 2.79 (s, 4H), 3.19 (m, 1H), 3.46 (m, 2H), 3.61 (m, 3H), 3.69 (m, 5H), 3.87 (m, 1H), 4.23 (p, 1H), 4.58 (d, 1H), 5.16 (s, 2H), 6.10 (s, 1H), 6.20 (m, 2H), 6.95 (d, 1H), 6.99 (d, 1H), 7.19 (s, 1H), 8.06 (t, 1H), 8.18 (s, 1H), NH is not observed. LCMS(ESI): [M+H]$^+$ m/z: calcd 597.1. found 598.2; Rt=1.087 min.

Example 1C29. (S)—N-(3-(5-chloro-6-(oxazol-5-ylmethoxy)-3N-dihydroisoquinolin-2(1H)-yl)-2-hydroxypropyl)-2-(cyclohexylamino)isonicotinamide (Compound 420)

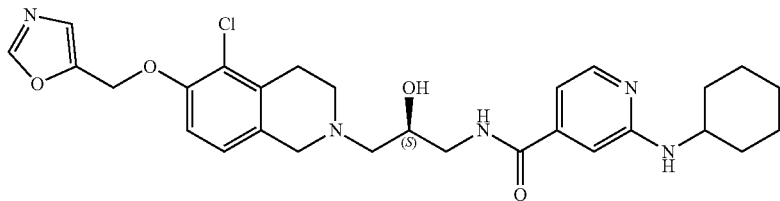

Prepared by general procedure IC-D. Yield: 8.3 mg (13.47%). $^1$H NMR (CDCl$_3$, 500 MHz): δ (ppm) 1.24 (m, 3H), 1.42 (m, 2H), 1.66 (d, 2H), 1.77 (d, 2H), 2.05 (d, 2H), 2.60 (m, 2H), 2.79 (m, 1H), 2.92 (m, 2H), 2.98 (m, 1H), 3.43 (m, 1H), 3.60 (m, 2H), 3.73 (m, 1H), 3.80 (d, 1H), 4.03 (m, 1H), 4.66 (m, 1H), 5.14 (s, 2H), 6.71 (d, 1H), 6.77 (s, 2H), 6.87 (d, 1H), 6.91 (d, 1H), 7.17 (s, 1H), 7.92 (s, 1H), 8.11 (d, 1H). LCMS(ESI): [M+H]$^+$ m/z: calcd 540. found 541.2; Rt=0.885 min.

Example 1C30. (S)—N-(3-(5-chloro-6-(oxazol-5-ylmethoxy)-3,4-dihydroisoquinolin-2(1H)-yl)-2-hydroxypropyl)-2-(cxclopentylamino)isonicotinamide (Compound 382)

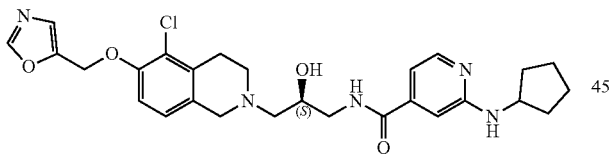

Prepared by general procedure IC-D. Yield: 17.8 mg (28.02%). $^1$H NMR (400 MHz, DMSO-d6) δ 1.41 (m, 2H), 1.53 (m, 2H), 1.67 (m, 2H), 1.89 (m, 2H), 2.73 (m, 4H), 3.21 (m, 2H), 3.37 (m, 2H), 3.58 (m, 2H), 3.88 (m, 1H), 4.09 (m, 1H), 4.83 (d, 1H), 5.24 (s, 2H), 6.66 (d, 1H), 6.70 (d, 1H), 6.80 (s, 1H), 7.02 (d, 1H), 7.12 (d, 1H), 7.33 (s, 1H), 7.95 (d, 1H), 8.42 (m, 2H). LCMS(ESI): [M+H]$^+$ m/z: calcd 526.0. found 527.2; Rt=0.864 min.

Example 1C31. (S)—N-(3-(5-chloro-6-(oxazol-5-ylmethoxy)-3N-dihydroisoquinolin-2(1H)-yl)-2-hydroxypropyl)-2-(cyclobutylamino)-6-(4-propionylpiperazin-1-yl)isonicotinamide (Compound 570)

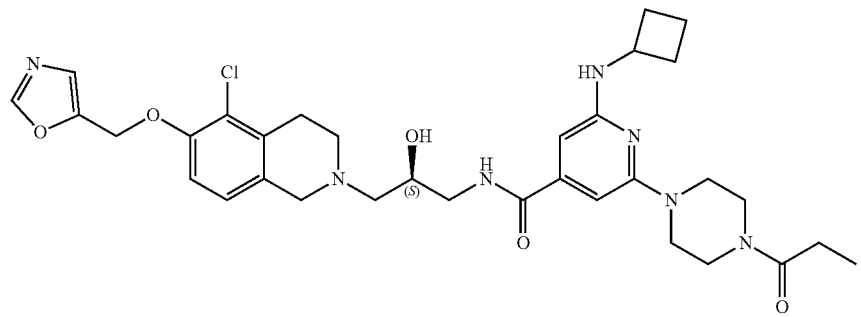

Prepared by general procedure IC-D. Yield: 23.7 mg (36.46%). ¹H NMR (DMSO-d₆, 500 MHz): δ (ppm) 1.07 (t, 3H), 1.70 (m, 2H), 1.89 (m, 2H), 2.32 (m, 4H), 2.81 (m, 4H), 2.98 (m, 2H), 3.18 (m, 1H), 3.43 (m, 3H), 3.54 (m, 6H), 3.65 (m, 2H), 3.88 (m, 1H), 4.24 (m, 1H), 4.66 (s, 1H), 5.17 (s, 2H), 6.11 (s, 1H), 6.24 (d, 2H), 6.96 (m, 1H), 7.01 (d, 1H), 7.20 (s, 1H), 8.10 (t, 1H), 8.18 (s, 1H). LCMS(ESI): [M+H]⁺ m/z: calcd 652.2. found 653.2; Rt=2.847 min.

Example 1C32. (S)—N-(3-(5-chloro-6-(oxazol-5-ylmethoxy)-3N-dihydroisoquinolin-2(1H)-yl)-2-hydroxypropyl)-2-(cyclobutylamino)-6-(4-methylpiperazin-1-yl)isonicotinamide (Compound 419)

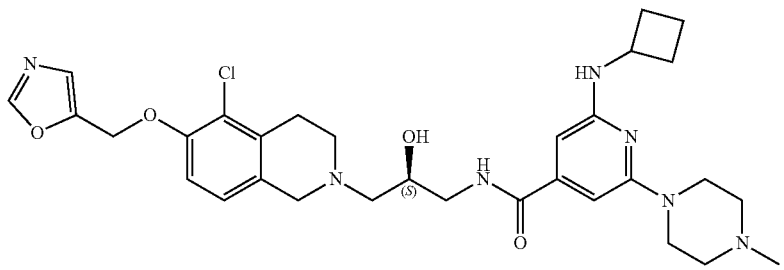

Prepared by general procedure IC-D. Yield: 25.7 mg (41.86%). ¹H NMR (DMSO-d₆, 500 MHz): δ (ppm) 1.69 (m, 2H), 1.88 (m, 2H), 2.24 (s, 3H), 2.30 (m, 2H), 2.39 (m, 4H), 2.45 (m, 2H), 2.79 (m, 4H), 3.14 (m, 1H), 3.43 (m, 5H), 3.61 (m, 2H), 3.86 (s, 1H), 4.23 (m, 1H), 4.58 (d, 1H), 5.16 (s, 2H), 6.05 (s, 1H), 6.12 (d, 1H), 6.19 (s, 1H), 6.94 (d, 1H), 7.00 (d, 1H), 7.19 (s, 1H), 8.03 (t, 1H), 8.17 (s, 1H). LCMS(ESI): [M+2H]⁺ m/z: calcd 610.1. found 611.2; Rt=0.831 min.

Example 1C33. (S)—N-(3-(5-chloro-6-(oxazol-5-ylmethoxy)-3N-dihydroisoquinolin-2(1H)-yl)-2-hydroxypropyl-2-(cyclobutylamino)-6-((2-methoxyethyl)(methyl)amino)isonicotinamide (Compound 345)

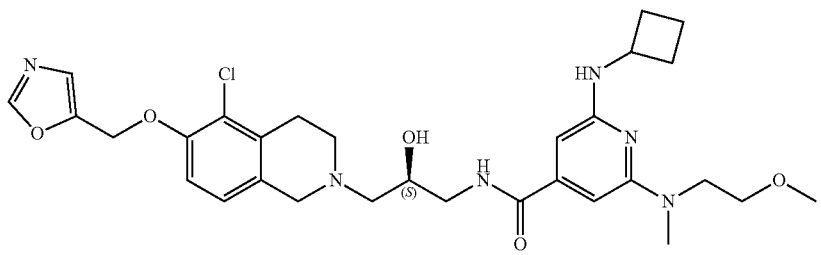

Prepared by general procedure IC-D. Yield: 15.4 mg (31.06%). ¹H NMR (CDCl₃, 400 MHz): δ (ppm) 1.78 (m, 4H), 2.37 (m, 2H), 2.55 (m, 2H), 2.72 (m, 1H), 2.89 (m, 3H), 3.02 (s, 3H), 3.32 (s, 3H), 3.39 (m, 1H), 3.53 (m, 3H), 3.68 (t, 3H), 3.76 (d, 1H), 3.98 (m, 1H), 4.11 (m, 1H), 4.55 (m, 1H), 5.10 (s, 2H), 5.83 (s, 1H), 6.07 (s, 1H), 6.67 (t, 1H), 6.83 (d, 1H), 6.87 (d, 1H), 7.13 (s, 1H), 7.88 (s, 1H), NH is not observed. LCMS(ESI): [M+H]⁺ m/z: calcd 599.1; found 600.2; Rt=0.997 min.

Example 1C34. (S)—N-(3-(5-chloro-6-(oxazol-5-ylmethoxy)-3N-dihydroisoquinolin-2(1H)-yl)-2-hydroxypropyl)-2-(cyclobutylamino)-6-(piperidin-1-yl)isonicotinamide (Compound 305)

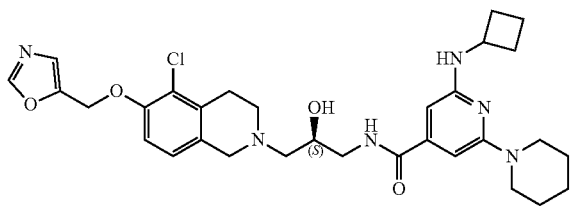

Prepared by general procedure IC-D. Yield: 10.9 mg (16.06%). $^1$H NMR (500 MHz, CDCl$_3$) δ 1.63 (m, 6H), 1.76 (m, 2H), 1.86 (m, 2H), 2.42 (m, 2H), 2.58 (m, 2H), 2.76 (m, 1H), 2.91 (m, 2H), 2.97 (m, 1H), 3.42 (m, 1H), 3.52 (m, 5H), 3.57 (m, 1H), 3.71 (m, 1H), 3.78 (d, 1H), 4.02 (m, 1H), 4.14 (m, 1H), 4.58 (m, 1H), 5.14 (s, 2H), 5.86 (s, 1H), 6.25 (s, 1H), 6.61 (t, 1H), 6.88 (m, 2H), 7.17 (s, 1H), 7.92 (s, 1H). LCMS(ESI): [M+H]$^+$ m/z: calcd 595.1. found 596.2; Rt=1.114 min.

Example 1C35. (S)—N-(3-(5-chloro-6-(oxazol-5-ylmethoxy)-3N-dihydroisoquinolin-2(1H)-yl)-2-hydroxypropyl)-2-(cyclobutylamino)-6-(4-isobutylpiperazin-1-yl)isonicotinamide (Compound 466)

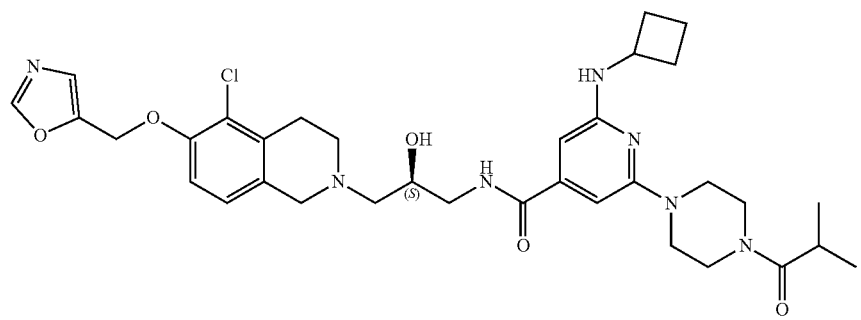

Prepared by general procedure IC-D. Yield: 9.8 mg (15.66%). $^1$H NMR (CDCl$_3$, 500 MHz): δ (ppm) 1.17 (d, 6H), 1.77 (m, 3H), 1.87 (m, 3H), 2.42 (m, 2H), 2.59 (m, 2H), 2.77 (m, 1H), 2.85 (m, 1H), 2.91 (m, 2H), 2.97 (m, 1H), 3.40 (m, 1H), 3.51 (m, 2H), 3.58 (m, 4H), 3.72 (m, 3H), 3.79 (d, 1H), 4.03 (m, 1H), 4.16 (m, 1H), 4.64 (m, 1H), 5.14 (s, 2H), 5.96 (s, 1H), 6.25 (s, 1H), 6.66 (t, 1H), 6.87 (d, 1H), 6.91 (d, 1H), 7.17 (s, 1H), 7.92 (s, 1H). LCMS(ESI): [M+H]$^+$ m/z: calcd 666.2. found 667.2; Rt=1.81 min.

Example 1C36. (S)—N-(3-(5-chloro-6-(oxazol-5-ylmethoxy)-3N-dihydroisoquinolin-2(1H)-yl)-2-hydroxypropyl)-2-(cyclobutylamino)-6-(4-ethylpiperazin-1-yl)isonicotinamide (Compound 299)

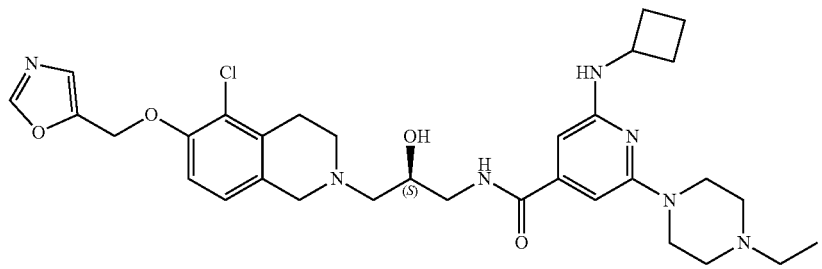

Prepared by general procedure IC-D. Yield: 22.0 mg (30.31%). $^1$H NMR (DMSO-d$_6$, 400 MHz): δ 1.08 (t, 3H), 1.71 (m, 2H), 1.89 (p, 2H), 2.31 (m, 2H), 2.38 (m, 2H), 2.45 (s, 4H), 2.83 (s, 4H), 3.17 (m, 2H), 3.45 (m, 6H), 3.61 (s, 2H), 3.86 (m, 1H), 4.20 (m, 1H), 4.58 (m, 1H), 5.16 (s, 2H), 6.05 (s, 1H), 6.12 (d, 1H), 6.18 (s, 1H), 6.96 (d, 1H), 6.99 (d, 1H), 7.19 (s, 1H), 8.04 (t, 1H), 8.18 (s, 1H). LCMS(ESI): [M+H]$^+$ m/z: calcd 624.2. found 625.2; Rt=0.872 min.

Example 1C38. (S)—N-(3-(5-chloro-6-(oxazol-5-ylmethoxy)-3N-dihydroisoquinolin-2(1H)-yl)-2-hydroxypropyl-2-(cyclobutylamino)-6-(4-isopropylpiperazin-1-yl)isonicotinamide (Compound 566)

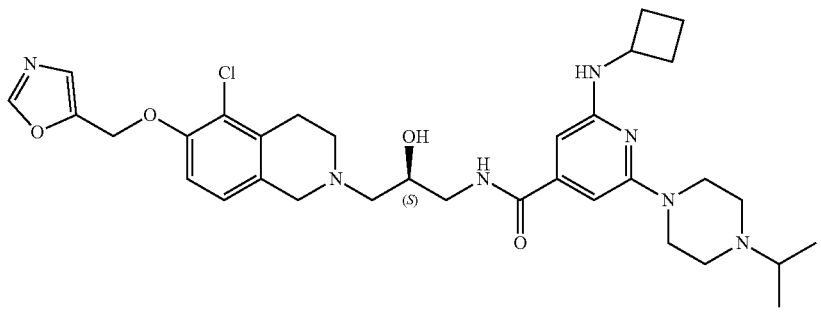

Prepared by general procedure IC-D. Yield: 25.1 mg (38.61%). $^1$H NMR (DMSO-d$_6$, 400 MHz): δ (ppm) 1.04 (d, 6H), 1.70 (m, 2H), 1.88 (m, 2H), 2.30 (m, 2H), 2.46 (m, 4H), 2.69 (m, 1H), 2.79 (s, 3H), 3.17 (m, 4H), 3.44 (m, 4H), 3.61 (s, 2H), 3.77 (m, 1H), 3.86 (m, 1H), 4.23 (q, 1H), 4.60 (m, 1H), 5.16 (s, 2H), 6.04 (s, 1H), 6.12 (d, 1H), 6.18 (s, 1H), 6.95 (d, 1H), 7.00 (d, 1H), 8.04 (t, 1H), 8.10 (s, 1H), 8.18 (s, 1H). LCMS(ESI): [M+H]$^+$ m/z: calcd 638.2; found 639.2; Rt=0.889 min.

Example 1C39. (S)—N-(3-(5-chloro-6-(oxazol-5-ylmethoxy)-3N-dihydroisoquinolin-2(1H)-yl)-2-hydroxypropyl)-2-(cyclobutylamino)-6-(4-(cyclopropanecarbonyl)piperazin-1-yl)isonicotinamide (Compound 571)

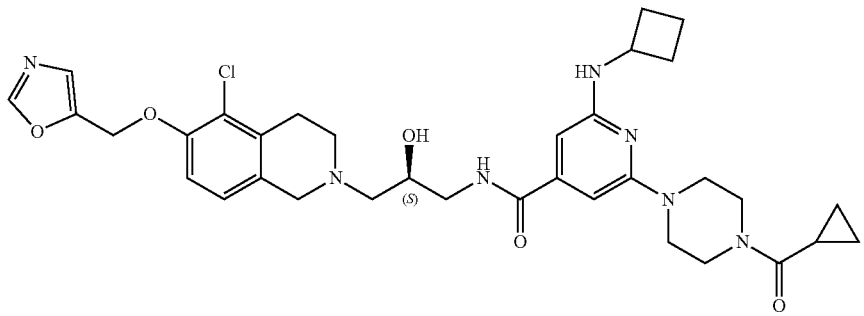

Prepared by general procedure IC-D. Yield: 22.1 mg (34%). $^1$H NMR (DMSO-d$_6$, 400 MHz): δ (ppm) 0.72 (m, 2H), 0.82 (m, 2H), 1.24 (m, 1H), 1.72 (m, 2H), 1.89 (m, 2H), 2.31 (m, 2H), 2.55 (m, 3H), 2.80 (m, 3H), 2.97 (m, 4H), 3.18 (m, 1H), 3.44 (m, 3H), 3.58 (m, 4H), 3.75 (m, 2H), 3.86 (m, 1H), 4.26 (m, 1H), 5.17 (s, 2H), 6.11 (s, 1H), 6.25 (d, 2H), 7.00 (d, 2H), 7.20 (s, 1H), 8.18 (s, 1H). LCMS(ESI): [M+H]$^+$ m/z: calcd 664.2. found 665.2; Rt=1.091 min.

Example 1C40. (S)—N-(3-(5-chloro-6-(oxazol-5-ylmethoxy)-3N-dihydroisoquinolin-2(1H)-yl)-2-hydroxypropyl)-2-(cyclobutylamino)-6-(ethyl(methyl) amino)isonicotinamide (Compound 445)

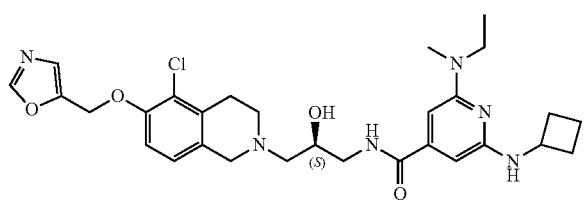

Prepared by general procedure IC-D. Yield: 21.4 mg (36.55%). $^1$H NMR (DMSO-d$_6$, 500 MHz): δ (ppm) 1.10 (t, 3H), 1.71 (m, 2H), 1.89 (m, 2H), 2.30 (m, 2H), 2.80 (m, 4H), 2.95 (s, 3H), 3.17 (m, 1H), 3.42 (m, 1H), 3.54 (q, 3H), 3.62 (m, 2H), 3.87 (m, 1H), 4.23 (m, 1H), 4.61 (m, 1H), 5.16 (s, 2H), 5.97 (m, 3H), 6.95 (d, 1H), 7.00 (d, 1H), 7.19 (s, 1H), 7.98 (m, 1H), 8.17 (d, 1H), NH is not observed. LCMS(ESI): [M+H]$^+$ m/z: calcd 569.1. found 570.2; Rt=0.966 min.

Example 1C41. (S)—N-(3-(5-chloro-6-(oxazol-5-ylmethoxy)-3N-dihydroisoquinolin-2(1H)-yl)-2-hydroxypropyl)-2-(cyclobutylamino)-6-(2-(dimethylamino)ethoxy)isonicotinamide (Compound 329)

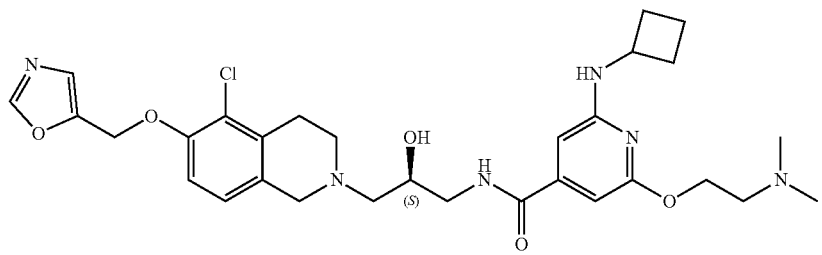

Prepared by general procedure IC-D. Yield: 24.4 mg (33.72%). $^1$H NMR (400 MHz, DMSO-d$_6$+CCl$_4$) δ 1.73 (m, 2H), 1.92 (m, 2H), 2.24 (s, 6H), 2.33 (m, 3H), 2.59 (m, 2H), 2.79 (m, 4H), 3.19 (m, 2H), 3.41 (m, 1H), 3.60 (m, 2H), 3.85 (m, 1H), 4.27 (m, 3H), 4.56 (m, 1H), 5.16 (s, 2H), 6.17 (s, 1H), 6.29 (s, 1H), 6.53 (m, 1H), 6.97 (m, 2H), 7.19 (s, 1H), 8.05 (m, 1H), 8.17 (s, 1H). LCMS(ESI): [M+H]$^+$ m/z: calcd 599.1. found 600.2; Rt=0.902 min.

Example 1C42. (S)-2-(4-(tert-butyl)piperazin-1-yl)-N-(3-(5-chloro-6-(oxazol-5-ylmethoxy)-3N-dihydroisoquinolin-2(1H)-yl)-2-hydroxypropyl)-6-(cyclobutylamino)isonicotinamide (Compound 319)

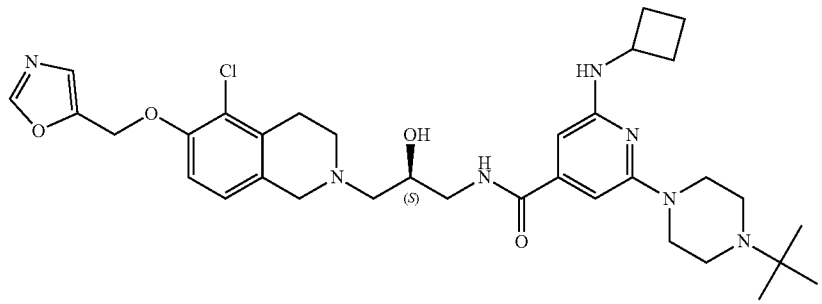

Prepared by general procedure IC-D. Yield: 13.3 mg (18.24%). $^1$H NMR (500 MHz, CDCl$_3$-J) δ 1.11 (s, 9H), 1.76 (m, 2H), 1.87 (m, 2H), 2.41 (m, 2H), 2.58 (m, 3H), 2.65 (m, 4H), 2.75 (m, 1H), 2.90 (m, 2H), 2.95 (m, 1H), 3.41 (m, 1H), 3.55 (m, 5H), 3.71 (m, 1H), 3.77 (d, 1H), 4.01 (m, 1H), 4.14 (h, 1H), 4.60 (d, 1H), 5.14 (s, 2H), 5.91 (s, 1H), 6.23 (s, 1H), 6.61 (t, 1H), 6.87 (d, 1H), 6.91 (d, 1H), 7.17 (s, 1H), 7.92 (s, 1H). LCMS(ESI): [M+H]$^+$ m/z: calcd 652.2. found 653.2; Rt=0.931 min.

Example 1C43. (S)—N-(3-(5-chloro-6-(oxazol-5-ylmethoxy)-3N-dihydroisoquinolin-2(1H)-yl)-2-hydroxypropyl)-2-(cyclobutylamino)-3-fluoroisonicotinamide (Compound 326)

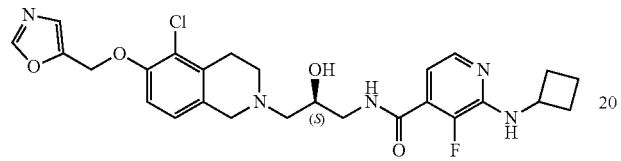

Prepared by general procedure IC-D. Yield: 25.0 mg (37%).

$^1$H NMR (400 MHz, DMSO-d$_6$+CCl$_4$) δ 1.69 (m, 2H), 2.02 (m, 2H), 2.28 (m, 2H), 2.79 (m, 4H), 3.09 (m, 2H), 3.25 (m, 1H), 3.42 (m, 1H), 3.61 (m, 2H), 3.86 (m, 1H), 4.48 (m, 1H), 4.60 (d, 1H), 5.16 (s, 2H), 6.57 (m, 1H), 6.94 (d, 1H), 7.00 (d, 1H), 7.19 (s, 1H), 7.73 (d, 1H), 7.99 (m, 1H), 8.18 (s, 1H). LCMS(ESI): [M+H]$^+$ m/z: calcd 530.0. found 531.2; Rt=1.019 min.

Example 1C44. (S)—N-(3-(5-chloro-6-(oxazol-5-ylmethoxy)-3N-dihydroisoquinolin-2(1H)-yl)-2-hydroxypropyl)-2-(cyclobutylamino)-5-fluoroisonicotinamide (Compound 340)

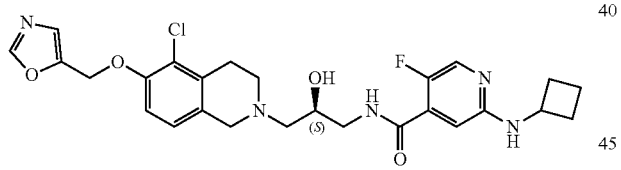

Prepared by general procedure IC-D. Yield: 28.9 mg (38.53%). $^1$H NMR (DMSO-d$_6$, 400 MHz): δ (ppm) 1.70 (m, 2H), 1.88 (m, 2H), 2.30 (m, 2H), 2.54 (m, 2H), 2.79 (m, 4H), 3.26 (m, 1H), 3.46 (m, 1H), 3.61 (m, 2H), 3.86 (m, 1H), 4.22 (q, 1H), 4.63 (m, 1H), 5.16 (s, 2H), 6.66 (d, 2H), 6.93 (d, 1H), 6.99 (d, 1H), 7.19 (s, 1H), 7.82 (s, 1H), 7.87 (t, 1H), 8.18 (s, 1H). LCMS(ESI): [M+H]$^+$ m/z: calcd 530.0. found 531.2; Rt=1.023 min.

Example 1C44. (S)—N-(3-(5-chloro-6-(oxazol-5-ylmethoxy)-3N-dihydroisoquinolin-2(1H)-yl)-2-hydroxypropyl)-2-(cyclobutylamino)-6-methoxyisonicotinamide (Compound 302)

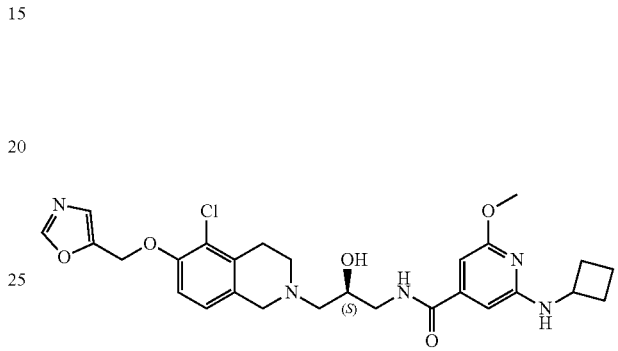

Prepared by general procedure IC-D. Yield: 17.5 mg (26.25%). $^1$H NMR, δ 1.70 (m, 2H), 1.95 (q, 2H), 2.33 (q, 2H), 2.47 (m, 2H), 2.79 (s, 4H), 3.18 (dt, 1H), 3.41 (dt, 1H), 3.60 (m, 2H), 3.80 (s, 3H), 3.86 (m, 1H), 4.25 (h, 1H), 4.58 (s, 1H), 5.16 (s, 2H), 6.15 (s, 1H), 6.29 (s, 1H), 6.51 (d, 1H), 6.93 (d, 1H), 6.98 (d, 1H), 7.19 (s, 1H), 8.11 (t, 1H), 8.18 (s, 1H). LCMS(ESI): [M+2H]$^+$ m/z: calcd 542.0. found 543.2; Rt=1.126 min.

Example 1C45. (S)-2-(4-acetylpiperazin-1-yl)-N-(3-(5-chloro-6-(oxazol-5-ylmethoxy)-3,4-dihydroisoquinolin-2(1H)-yl)-2-hydroxypropyl)-6-(cyclobutylamino)isonicotinamide (Compound 545)

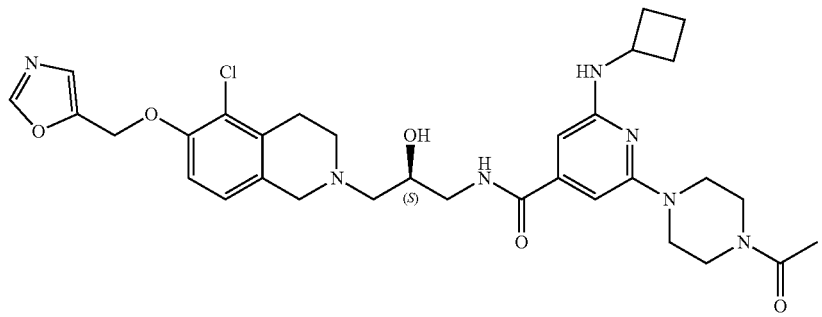

Prepared by general procedure IC-D. Yield: 21.4 mg (32.6%). ¹H NMR (DMSO-d₆, 400 MHz): δ (ppm) 1.66 (m, 2H), 1.86 (m, 2H), 2.04 (s, 3H), 2.25 (m, 2H), 2.43 (m, 2H), 2.72 (m, 4H), 3.17 (d, 2H), 3.40 (m, 2H), 3.50 (m, 6H), 3.57 (s, 2H), 3.88 (m, 1H), 4.19 (m, 1H), 4.82 (d, 1H), 5.23 (s, 2H), 6.11 (s, 1H), 6.25 (s, 1H), 6.60 (d, 1H), 7.01 (d, 1H), 7.11 (d, 1H), 7.33 (s, 1H), 8.29 (t, 1H), 8.42 (s, 1H). LCMS(ESI): [M+H]⁺ m/z: calcd 638.2. found 639.2; Rt=0.999 min.

Example 1C46. (S)—N-(3-(5-chloro-6-(oxazol-5-ylmethoxy)-3N-dihydroisoquinolin-2(1H)-yl)-2-hydroxypropyl)-2-(cyclobutylamino)-6-(methyl(propyl)amino)isonicotinamide (Compound 453)

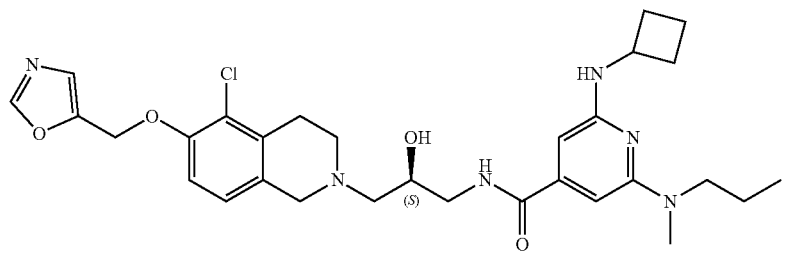

Prepared by general procedure IC-D. Yield: 25.0 mg (35.5%). ¹H NMR (DMSO-d₆, 400 MHz): δ (ppm) 0.91 (t, 3H), 1.58 (m, 2H), 1.70 (m, 2H), 1.88 (m, 2H), 2.29 (m, 2H), 2.80 (m, 5H), 2.96 (s, 3H), 3.17 (m, 1H), 3.43 (m, 4H), 3.63 (m, 2H), 3.87 (m, 1H), 4.23 (m, 1H), 4.60 (m, 1H), 5.16 (s, 2H), 5.94 (s, 1H), 5.97 (m, 2H), 6.95 (d, 1H), 7.00 (d, 1H), 7.19 (s, 1H), 7.96 (t, 1H), 8.18 (s, 1H). LCMS(ESI): [M+2H]⁺ m/z: calcd 583.1. found 584.2; Rt=1.029 min.

Example 1C47. (S)—N-(3-(5-chloro-6-(oxazol-5-ylmethoxy)-3,4-dihydroisoquinolin-2(1H)-yl)-2-hydroxypropyl)-2-(cyclobutylamino)-6-(piperazin-1-yl)isonicotinamide (Compound 464)

(S)—N-(3-(5-chloro-6-(oxazol-5-ylmethoxy)-3,4-dihydroisoquinolin-2(1H)-yl)-2-hydroxypropyl)-2-(cyclobutylamino)-6-(piperazin-1-yl)isonicotinamide (Compound 464)

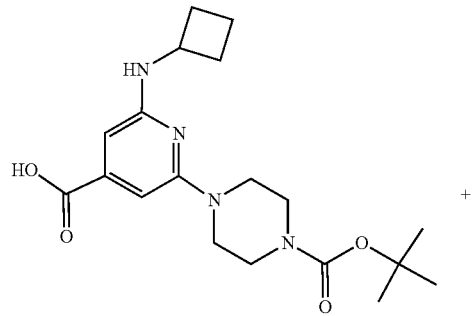

+

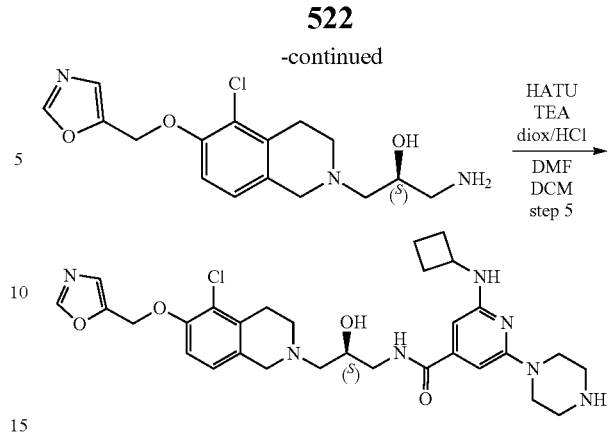

Triethyl amine (241.92 mg, 2.39 mmol, 333.22 uL) was added to a stirred mixture of 2-(4-tert-butoxycarbonylpiperazin-1-yl)-6-(cyclobutylamino)pyridine-4-carboxylic acid (150 mg, 398.46 umol), (2S)-1-amino-3-[5-chloro-6-(oxazol-5-ylmethoxy)-3,4-dihydro-1H-isoquinolin-2-yl]propan-2-ol (178.18 mg, 398.46 umol, 3HCl) and HATU (151.51 mg, 398.46 umol) in DMF (10 mL) at 25° C. The resulting mixture was stirred at 25° C. for 12 hr, and then evaporated in vacuo. The residue was dissolved in dichloromethane (20 mL), hydrogen chloride solution 4.0M in dioxane (10.50 g, 40.03 mmol, 13.13 mL, 13.9% purity) was added to a solution, and the resulting suspension was stirred at 25° C. for 24 hr. The reaction mixture was evaporated in vacuo and the residue was purified by reverse phase HPLC (column: XBridgeC18 100×19 mm 5 um) using 30-60% 0-6 min 0.1% NH₃-methanol as mobile phase to afford Compound 464 N-[(2S)-3-[5-chloro-6-(oxazol-5-ylmethoxy)-3,4-dihydro-1H-isoquinolin-2-yl]-2-hydroxy-propyl]-2-(cyclobutylamino)-6-piperazin-1-yl-pyridine-4-carboxamide (70 mg, 117.43 umol, 29.47% yield). NMR(400 MHz, CDCl₃): δ (ppm) 1.75 (m, 3H), 1.83 (m, 3H), 2.37 (m, 3H), 2.54 (m, 2H), 2.73 (m, 1H), 2.86 (m, 2H), 2.93 (m, 4H), 3.36 (m, 1H), 3.46 (m, 4H), 3.55 (d, 1H), 3.68 (m, 1H), 3.74 (d, 1H), 3.97 (m, 1H), 4.10 (m, 1H), 4.57 (m, 1H), 5.11 (s, 2H), 5.89 (s, 1H), 6.20 (s, 1H), 6.59 (t, 1H), 6.83 (d, 1H), 6.87 (d, 1H), 7.14 (s, 1H), 7.89 (s, 1H). LCMS(ESI): [M+H]⁺ m/z: calcd 596.1. found 597.2; Rt=2.039 min.

General Procedure 1C-E

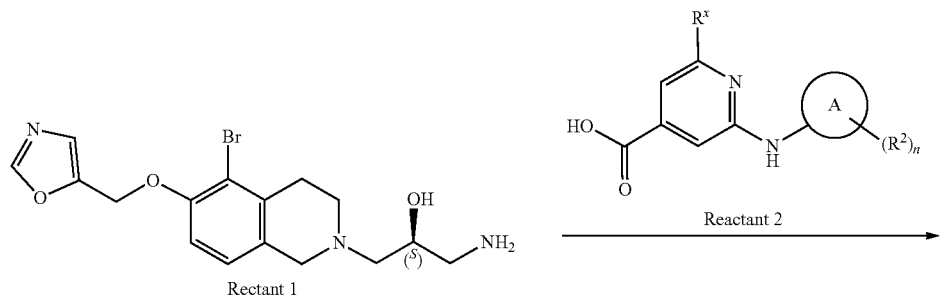

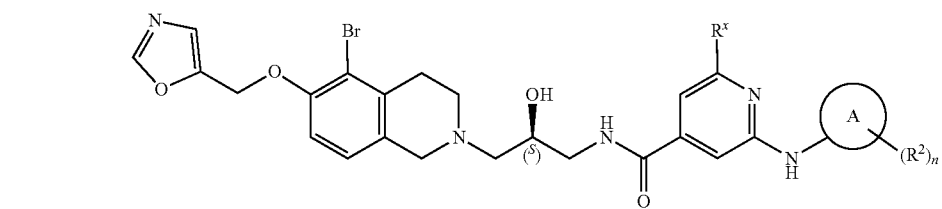

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mF). The reaction mixture was stirred at room temperature overnight. After the completion of the reaction, monitored by LCMS, the resulting suspension was concentrated under reduced pressure. The residue was dissolved in DMSO (1.0 mF) and filtered off. The obtained filtrate was subjected to HPFC (Waters SunFire C18 19*100 5 mkm column and H₂O-MeOH as a mobile phase, Run Time 5 min) to afford pure product.

Example 1C48. (S)—N-(3-(5-bromo-6-(oxazol-5-ylmethoxy)-3N-dihydroisoquinolin-2(1H)-yl)-2-hydroxypropyl)-2-(cyclopentylamino)isonicotinamide (Compound 404)

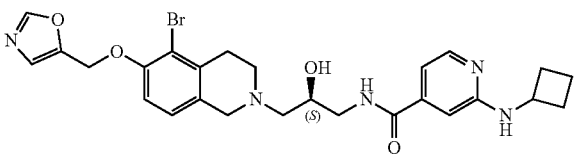

Prepared by general procedure 1C-E. Yield: 19.5 mg (30.0%). ¹H NMR (DMSO-d₆, 400 MHz): δ (ppm) 1.40 (m, 2H), 1.42 (m, 2H), 1.53 (m, 2H), 1.89 (m, 2H), 2.43 (m, 1H), 2.70 (m, 4H), 3.20 (m, 1H), 3.39 (m, 2H), 3.54 (s, 2H), 3.88 (m, 1H), 4.10 (q, 1H), 4.83 (m, 1H), 5.24 (s, 2H), 6.66 (d, 1H), 6.68 (d, 1H), 6.80 (s, 1H), 7.07 (m, 2H), 7.32 (s, 1H), 7.94 (d, 1H), 8.41 (s, 1H), 8.45 (m, 1H). LCMS(ESI): [M+2H]⁺ m/z: calcd 570.4. found 572.1; Rt=0.84 min.

General Procedure IC-F

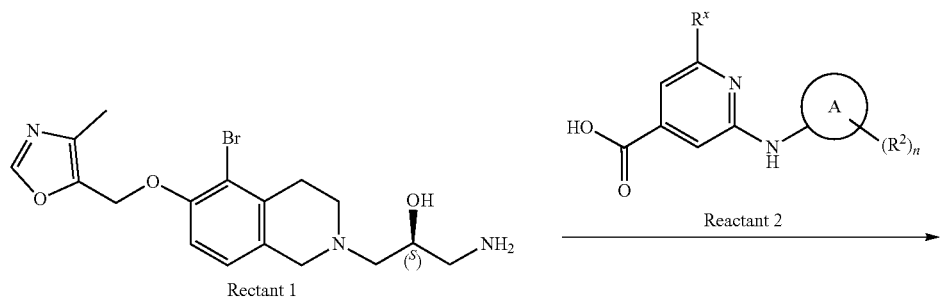

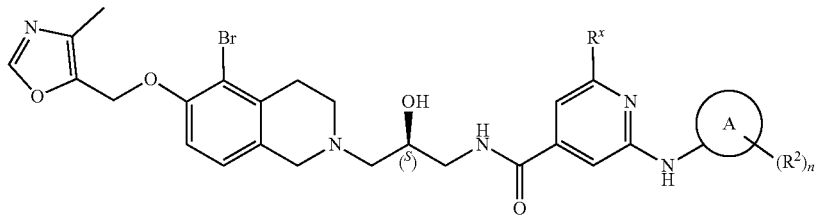

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of solution of HATU (1.05 equiv) in DMF (1.0 mF). The reaction mixture was stirred at room temperature overnight. After the completion of the reaction, monitored by LCMS, the resulting suspension was concentrated under reduced pressure. The residue was dissolved in DMSO (1.0 mF) and filtered off. The obtained filtrate was subjected to HPFC (Waters SunFire C18 19*100 5 mkm column and H₂O-MeOH as a mobile phase) to afford pure product.

Example 1C49. (S)—N-(3-(5-bromo-6-((4-methyl-oxazol-5-yl)methoxy)-3N-dihydroisoquinolin-2(1H)-yl)-2-hydroxypropyl)-2-(cyclohexylamino)isonicotinamide (Compound 346)

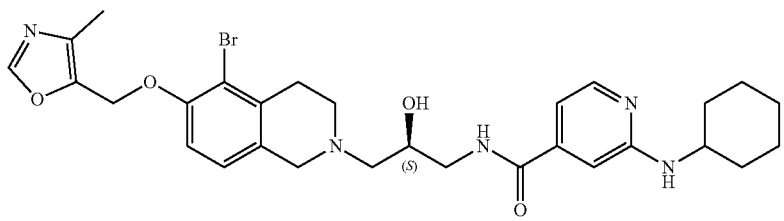

Prepared by general procedure IC-F. Yield: 12.7 mg (16%). ¹H NMR (CDCl₃, 500 MHz): δ (ppm) 1.24 (m, 3H), 1.43 (m, 2H), 1.64 (m, 1H), 1.77 (m, 2H), 2.05 (m, 2H), 2.23 (s, 3H), 2.60 (m, 2H), 2.76 (m, 1H), 2.89 (m, 2H), 2.97 (m, 1H), 3.43 (m, 1H), 3.60 (m, 3H), 3.74 (d, 1H), 3.80 (d, 1H), 4.02 (m, 1H), 4.60 (d, 1H), 5.08 (s, 2H), 6.70 (d, 1H), 6.74 (t, 1H), 6.77 (s, 1H), 6.85 (d, 1H), 6.95 (d, 1H), 7.82 (s, 1H), 8.12 (d, 1H). LCMS(ESI): [M+2H]⁺ m/z: calcd 598.5. found 599.2; Rt=0.907 min.

Example 1C50. (S)—N-(3-(5-bromo-6-((4-methyl-oxazol-5-yl)methoxy)-3,4-dihydroisoquinolin-2(1H)-yl)-2-hydroxypropyl)-2-(cyclopentylamino)isonicotinamide (Compound 350)

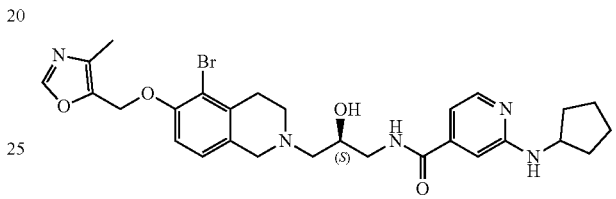

Prepared by general procedure IC-F. Yield: 19.2 mg (25%). ¹H NMR (DMSO-d₆, 400 MHz): δ (ppm) 1.45 (m, 2H), 1.59 (m, 2H), 1.72 (m, 2H), 1.93 (m, 2H), 2.19 (s, 3H), 2.54 (m, 2H), 2.80 (m, 4H), 3.22 (m, 1H), 3.43 (m, 1H), 3.64 (m, 2H), 3.89 (m, 1H), 4.11 (m, 1H), 4.63 (s, 1H), 5.10 (s, 2H), 6.32 (d, 1H), 6.66 (d, 1H), 6.80 (s, 1H), 6.95 (d, 1H), 7.00 (d, 1H), 7.89 (d, 1H), 8.04 (s, 1H), 8.21 (t, 1H). LCMS(ESI): [M+H]⁺ m/z: calcd 584.5. found 586.2; Rt=0.873 min.

General Procedure 1C-G

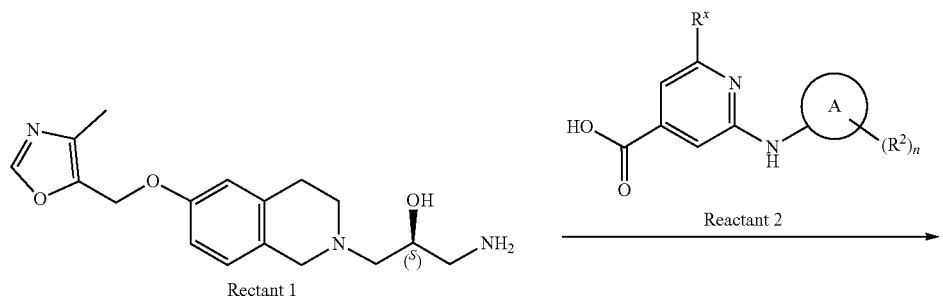

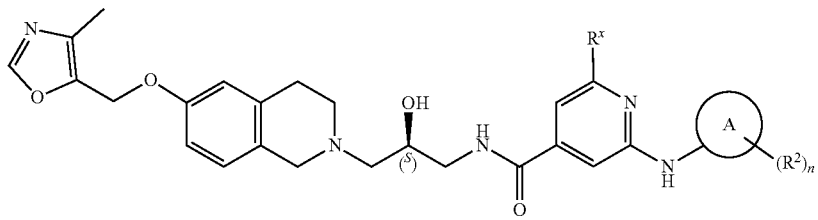

Condition A. DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH-0.1NH$_3$ as a mobile phase) to afford pure product.

Condition B. Reactant 1 and reactant 2 were mixed in DMF (5 mL). The reaction suspension was cooled to 0° C. and HATU followed by TEA were added. The clear solution was stirred at ambient temperature for 1.5 hr at 25° C. then volatiles were evaporated under reduced pressure and recidue was subjected to RP-HPLC to give product.

Example 1C51. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-(morpholin-4-yl)pyridine-4-carboxamide (Compound 384)

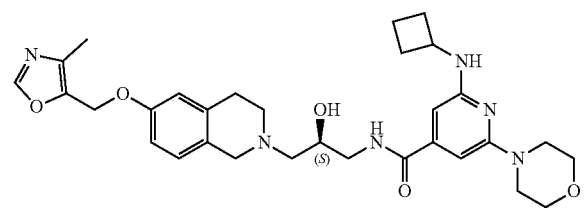

Prepared by general procedure 1C-G, condition A. Yield: 26.8 mg (46.1%). $^1$H NMR (500 MHz, DMSO-d$_6$+CCl$_4$) δ 1.69 (m, 2H), 1.87 (m, 2H), 2.18 (s, 3H), 2.29 (m, 2H), 2.46 (m, 2H), 2.76 (m, 2H), 2.82 (m, 2H), 3.18 (m, 1H), 3.40 (t, 4H), 3.44 (m, 1H), 3.61 (m, 2H), 3.69 (t, 4H), 3.87 (m, 1H), 4.24 (m, 1H), 4.57 (m, 1H), 4.98 (s, 2H), 6.09 (s, 1H), 6.16 (d, 1H), 6.18 (s, 1H), 6.69 (m, 2H), 6.92 (d, 1H), 8.02 (s, 1H), 8.08 (t, 1H). LCMS(ESI): [M+H]$^+$ m/z: calcd 576.3. found 577.2; Rt=1.08 min.

Example 1C52. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-(piperidin-1-yl)pyridine-4-carboxamide (Compound 633)

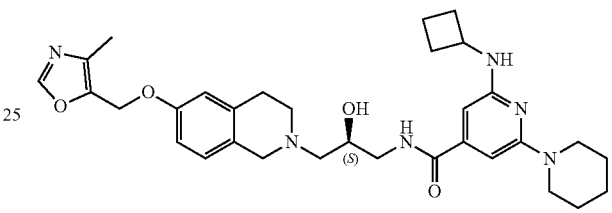

Prepared by general procedure 1C-G, condition A. Yield: 2.9 mg (5.1%). $^1$H NMR (Chloroform-d, 500 MHz) δ (ppm) 1.51 (m, 4H), 1.73 (m, 4H), 2.21 (s, 3H), 2.37 (m, 2H), 2.81 (m, 4H), 3.51 (m, 5H), 5.01 (s, 2H), 5.92 (s, 1H), 6.23 (s, 1H), 6.78 (m, 2H), 6.83 (d, 1H), 7.03 (d, 1H), 7.81 (s, 1H). LCMS(ESI): [M+H]$^+$ m/z: calcd 574.1. found 575.3; Rt=1.02 min.

Example 1C53. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-[4-(propan-2-yl)piperazin-1-yl]pyridine-4-carboxamide (Compound 428)

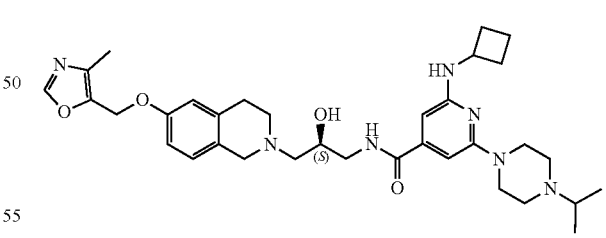

Prepared by general procedure 1C-G, condition A. Yield: 18.0 mg (31.1%). $^1$H NMR (Chloroform-d, 400 MHz): δ (ppm) 1.06 (d, 6H), 1.72 (m, 2H), 1.82 (m, 2H), 2.21 (s, 3H), 2.37 (m, 2H), 2.57 (m, 6H), 2.68 (m, 2H), 2.88 (m, 3H), 3.36 (m, 1H), 3.54 (m, 5H), 3.68 (m, 1H), 3.75 (d, 1H), 3.96 (m, 1H), 4.11 (m, 1H), 4.55 (d, 1H), 4.96 (s, 2H), 5.87 (s, 1H), 6.21 (s, 1H), 6.65 (m, 1H), 6.70 (s, 1H), 6.75 (dd, 1H), 6.93 (d, 1H), 7.79 (s, 1H). LCMS(ESI): [M+2H]$^+$ m/z: calcd 617.3. found 619.3; Rt=0.85 min.

Example 1C54. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-[(2-methoxyethyl(methyl)amino]pyridine-4-carboxamide (Compound 554)

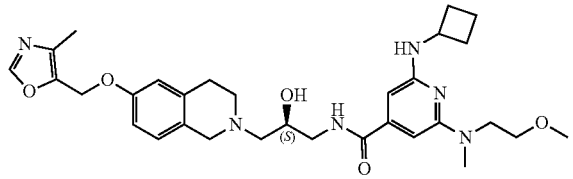

Prepared by general procedure 1C-G, condition A. Yield: 21.0 mg (35.2%). $^1$H NMR (Chloroform-d, 400 MHz): δ (ppm) 1.74 (m, 2H), 1.82 (m, 2H), 2.21 (s, 3H), 2.37 (m, 2H), 2.56 (m, 2H), 2.69 (m, 1H), 2.88 (m, 4H), 3.02 (s, 3H), 3.32 (s, 3H), 3.39 (m, 1H), 3.54 (m, 3H), 3.67 (m, 3H), 3.75 (d, 1H), 3.98 (m, 1H), 4.12 (m, 1H), 4.50 (m, 1H), 4.96 (s, 2H), 5.82 (s, 1H), 6.08 (s, 1H), 6.68 (m, 2H), 6.75 (d, 1H), 6.92 (d, 1H), 7.79 (s, 1H). LCMS(ESI): [M+H]$^+$ m/z: calcd 578.3. found 580.2; Rt=0.98 min.

Example 1C55. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-(2-methylpropyl)pyridine-4-carboxamide (Compound 439)

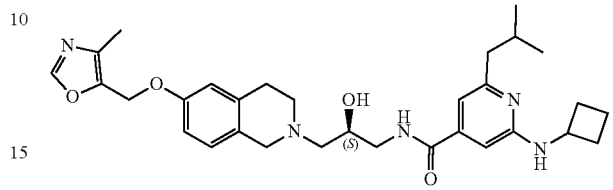

Prepared by general procedure 1C-G, condition A. Yield: 24.8 mg (35.8%). $^1$H NMR (DMSO-d$_6$, 400 MHz): δ (ppm) 0.85 (d, 6H), 1.67 (m, 2H), 1.85 (m, 2H), 1.98 (m, 2H), 2.15 (s, 3H), 2.28 (m, 5H), 2.69 (m, 2H), 2.78 (m, 2H), 3.21 (m, 1H), 3.36 (m, 1H), 3.57 (m, 2H), 3.90 (s, 1H), 4.21 (m, 1H), 4.84 (s, 1H), 5.07 (s, 2H), 6.57 (d, 2H), 6.78 (m, 3H), 6.96 (d, 1H), 8.28 (s, 1H), 8.43 (t, 1H). LCMS(ESI): [M+H]$^+$ m/z: calcd 547.3. found 548.2; Rt=0.94 min.

Example 1C56. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-(4-propanoylpiperazin-1-yl)pyridine-4-carboxamide (Compound 389)

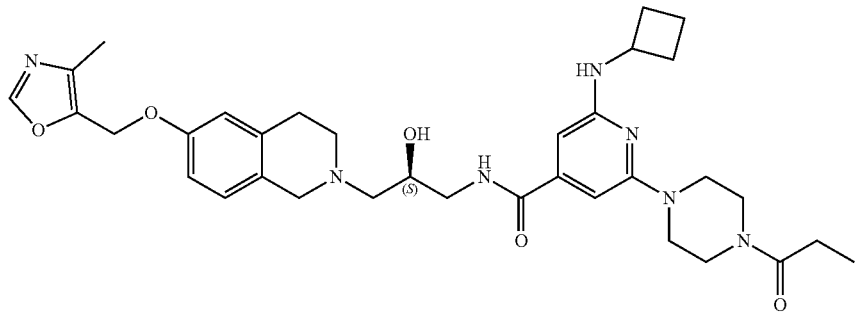

Prepared by general procedure 1C-G, condition A. Yield: 17.6 mg (27.0%). $^1$H NMR (400 MHz, CDCl$_3$) δ 1.15 (t, 3H), 1.78 (m, 4H), 2.20 (s, 3H), 2.36 (m, 4H), 2.53 (m, 2H), 2.70 (m, 1H), 2.89 (m, 3H), 3.36 (m, 1H), 3.52 (m, 8H), 3.68 (m, 3H), 3.76 (m, 1H), 3.98 (m, 1H), 4.12 (m, 1H), 4.58 (d, 1H), 4.96 (s, 2H), 5.92 (s, 1H), 6.22 (s, 1H), 6.69 (m, 1H), 6.75 (m, 2H), 6.92 (d, 1H), 7.79 (s, 1H). LCMS(ESI): [M+H]$^+$ m/z: calcd 631.2. found 632.2; Rt=1.06 min.

Example 1C57. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-[4-(2-methylpropanoyl)piperazin-1-yl]pyridine-4-carboxamide (Compound 463)

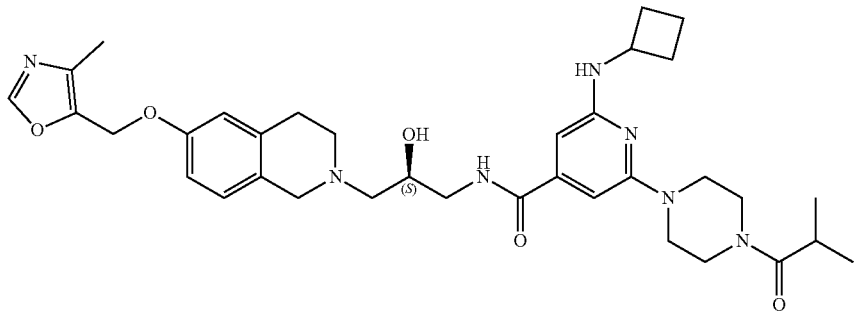

Prepared by general procedure 1C-G, condition A. Yield: 11.0 mg (16.5%). $^1$H NMR (Chloroform-d, 500 MHz): δ (ppm) 1.17 (d, 6H), 1.77 (m, 2H), 1.87 (m, 2H), 2.24 (s, 3H), 2.42 (m, 2H), 2.62 (m, 3H), 2.84 (m, 2H), 2.92 (m, 2H), 2.97 (m, 1H), 3.42 (m, 1H), 3.52 (m, 2H), 3.60 (m, 4H), 3.65 (m, 1H), 3.72 (m, 3H), 3.84 (d, 1H), 4.05 (m, 1H), 4.16 (m, 1H), 4.61 (m, 1H), 5.00 (s, 2H), 5.97 (s, 1H), 6.27 (s, 1H), 6.74 (m, 2H), 6.80 (d, 1H), 6.97 (d, 1H), 7.83 (s, 1H). LCMS (ESI): [M+H]$^+$ m/z: calcd 645.3. found; Rt=min.

Example 1C58. 2-(4-acetylpiperazin-1-yl)-6-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]pyridine-4-carboxamide (Compound 556)

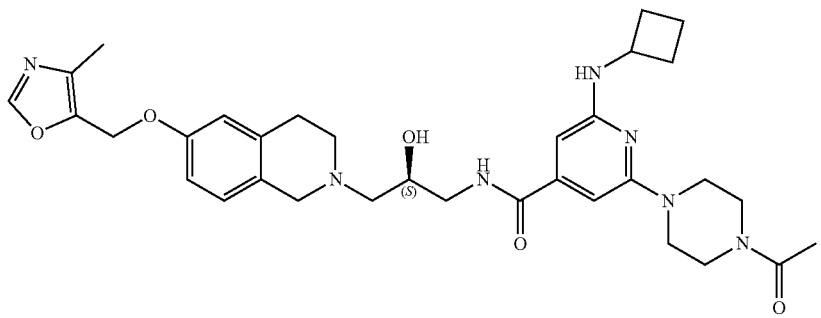

Prepared by general procedure 1C-G, condition A. Yield: 17.5 mg (23.25%). $^1$H NMR (Chloroform-d, 400 MHz): δ (ppm) 1.78 (m, 5H), 2.11 (s, 3H), 2.20 (s, 3H), 2.37 (m, 2H), 2.54 (m, 2H), 2.68 (m, 1H), 2.87 (m, 3H), 3.37 (m, 1H), 3.49 (m, 7H), 3.67 (m, 3H), 3.74 (d, 1H), 3.98 (m, 1H), 4.11 (q, 1H), 4.58 (d, 1H), 4.96 (s, 2H), 5.92 (s, 1H), 6.22 (s, 1H), 6.69 (s, 1H), 6.75 (d, 2H), 6.92 (d, 1H), 7.79 (s, 1H). LCMS(ESI): [M+H]$^+$ m/z: calcd 617.4. found 618.2; Rt=0.97 min.

Example 1C59. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-(4-methylpiperazin-1-yl)pyridine-4-carboxamide (Compound 485)

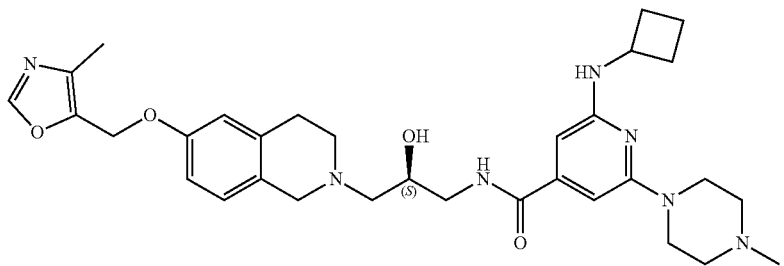

Prepared by general procedure 1C-G, condition A. Yield: 15.5 mg (26.1%). ¹H NMR (400 MHz, DMSO-d₆+CCl₄) δ 1.71 (m, 2H), 1.88 (m, 2H), 2.18 (s, 3H), 2.24 (s, 3H), 2.31 (m, 3H), 2.39 (m, 4H), 2.76 (m, 2H), 2.83 (m, 2H), 3.17 (m, 1H), 3.45 (m, 6H), 3.61 (s, 2H), 3.86 (m, 1H), 4.23 (m, 1H), 4.56 (m, 1H), 4.98 (s, 2H), 6.06 (m, 2H), 6.19 (s, 1H), 6.70 (m, 2H), 6.92 (d, 1H), 8.02 (s, 1H), 8.05 (m, 1H). LCMS (ESI): [M+2H]⁺ m/z: calcd 589.3. found 591.2; Rt=0.87 min.

Example 1C60. 2-(4-tert-butylpiperazin-1-yl)-6-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]pyridine-4-carboxamide (Compound 403)

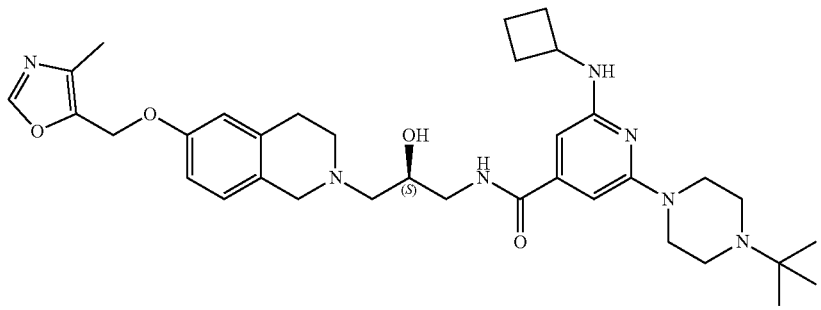

Prepared by general procedure 1C-G, condition A. Yield: 8.1 mg (12.1%). ¹H NMR (500 MHz, CDCl₃) δ 1.11 (s, 9H), 1.77 (m, 3H), 1.87 (m, 2H), 2.24 (s, 3H), 2.41 (m, 2H), 2.55 (m, 3H), 2.65 (m, 3H), 2.73 (m, 1H), 2.91 (m, 3H), 3.41 (m, 1H), 3.56 (m, 5H), 3.71 (m, 1H), 3.79 (m, 1H), 4.01 (m, 1H), 4.14 (m, 1H), 4.58 (d, 1H), 5.00 (s, 2H), 5.91 (s, 1H), 6.24 (s, 1H), 6.65 (m, 1H), 6.73 (s, 1H), 6.79 (d, 1H), 6.96 (d, 1H), 7.82 (s, 1H). LCMS(ESI): [M+H]⁺ m/z: calcd 631.8. found 633.4; Rt=0.93 min.

Example 1C61. 2-(cyclobutylamino)-6-(4-ethylpip-erazin-1-yl)-N-[(2S)-2-hydroxy-3-{6-[(4-methyl-1,3-oxazol-5-yl)methoxy]-1,2,3,4-tetrahydroisoquinolin-2-yl}propyl]pyridine-4-carboxamide (Compound 410)

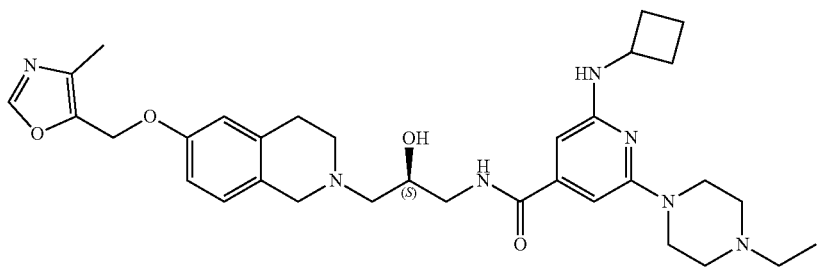

Prepared by general procedure 1C-G, condition A. Yield: 23.7 mg (26.2%). $^1$H NMR (400 MHz, DMSO-d$_6$+CCl$_4$) δ 1.08 (t, 3H), 1.69 (m, 2H), 1.89 (m, 2H), 2.18 (s, 3H), 2.30 (m, 2H), 2.38 (m, 3H), 2.44 (m, 5H), 2.76 (m, 2H), 2.83 (m, 2H), 3.18 (m, 1H), 3.43 (m, 5H), 3.60 (s, 2H), 3.87 (m, 1H), 4.23 (m, 1H), 4.57 (d, 1H), 4.98 (s, 2H), 6.04 (s, 1H), 6.07 (d, 1H), 6.18 (s, 1H), 6.70 (m, 2H), 6.92 (d, 1H), 8.02 (s, 1H), 8.06 (t, 1H). LCMS(ESI): [M+2H]$^+$ m/z: calcd 603.5. found 605.3; Rt=0.88 min.

Example 1C62. 2-(cyclobutylamino)-6-[ethyl(methyl)amino]-N-[(2S)-2-hydroxy-3-{6-[(4-methyl-1,3-oxazol-5-yl)methoxy]-1,2,3,4-tetrahydroisoqui-nolin-2-yl}propyl]pyridine-4-carboxamide (Compound 489)

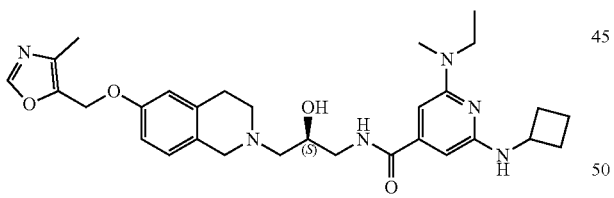

Prepared by general procedure 1C-G, condition A. Yield: 20.0 mg (31.1%). $^1$H NMR (400 MHz, CDCl$_3$) δ 1.09 (t, 3H), 1.77 (m, 5H), 2.20 (s, 3H), 2.37 (m, 2H), 2.54 (m, 2H), 2.68 (m, 1H), 2.86 (m, 3H), 2.96 (s, 3H), 3.39 (m, 1H), 3.53 (m, 3H), 3.66 (m, 1H), 3.74 (m, 1H), 3.97 (m, 1H), 4.12 (m, 1H), 4.51 (m, 1H), 4.96 (s, 2H), 5.79 (s, 1H), 6.08 (s, 1H), 6.73 (m, 3H), 6.92 (d, 1H), 7.79 (s, 1H). LCMS(ESI): [M+H]$^+$ m/z: calcd 548.6. found 549.4; Rt=0.96 min.

Example 1C63. 2-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]-6-[methyl(propyl)amino]pyridine-4-carboxamide (Compound 553)

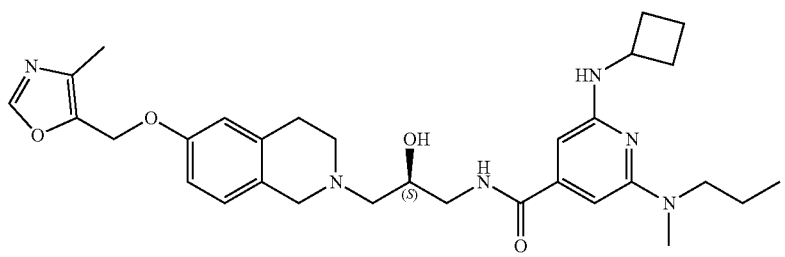

Prepared by general procedure 1C-G, condition A. Yield: 18.0 mg (25.3%). $^1$H NMR (DMSO-d$_6$, 400 MHz): δ (ppm) 0.91 (t, 3H), 1.57 (m, 2H), 1.70 (m, 2H), 1.87 (m, 2H), 2.18 (s, 3H), 2.30 (m, 2H), 2.83 (m, 4H), 2.96 (s, 3H), 3.21 (m, 1H), 3.42 (m, 3H), 3.66 (m, 2H), 3.90 (m, 1H), 4.23 (m, 1H), 4.67 (s, 1H), 4.99 (s, 2H), 5.54 (s, 2H), 5.94 (m, 3H), 6.71 (m, 2H), 6.93 (d, 1H), 8.02 (s, 2H). LCMS(ESI): [M+H]$^+$ m/z: calcd 562.2. found 563.3; Rt=1.04 min.

Example 1C64. 2-(cyclobutylamino)-6-[2-(dimethylamino)ethoxy]-N-[(2S)-2-hydroxy-3-{6-[(4-methyl-1,3-oxazol-5-yl)methoxy]-1,2,3,4-tetrahydroisoquinolin-2-yl}propyl]pyridine-4-carboxamide (Compound 406)

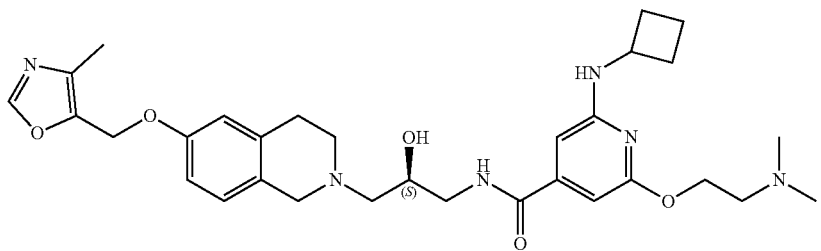

Prepared by general procedure 1C-G, condition A. Yield: 26.3 mg (35.3%). $^1$H NMR (500 MHz, DMSO-d$_6$+CCl$_4$) δ 1.72 (m, 2H), 1.92 (m, 2H), 2.18 (s, 3H), 2.24 (s, 6H), 2.32 (m, 2H), 2.46 (m, 2H), 2.59 (t, 2H), 2.75 (m, 2H), 2.82 (m, 2H), 3.18 (m, 1H), 3.42 (m, 1H), 3.59 (m, 2H), 3.86 (m, 1H), 4.23 (m, 1H), 4.27 (t, 2H), 4.54 (d, 1H), 4.98 (s, 2H), 6.18 (s, 1H), 6.29 (s, 1H), 6.49 (d, 1H), 6.69 (m, 2H), 6.91 (d, 1H), 8.02 (s, 1H), 8.06 (t, 1H). LCMS(ESI): [M+2H]$^+$ m/z: calcd 578.3. found 580.1; Rt=0.87 min.

Example 1C65. 2-(cyclobutylamino)-6-(4-cyclopropanecarbonylpiperazin-1-yl)-N-[(2S)-2-hydroxy-3-{6-[(4-methyl-1,3-oxazol-5-yl)methoxy]-1,2,3,4-tetrahydroisoquinolin-2-yl}propyl]pyridine-4-carboxamide (Compound 455)

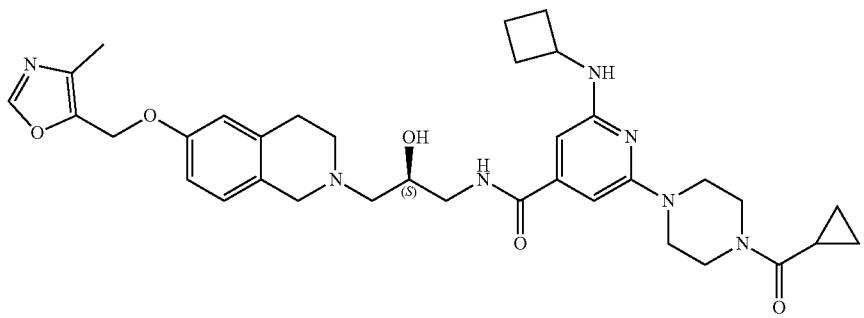

Prepared by general procedure 1C-G, condition A. Yield: 20.9 mg (28.3%). $^1$H NMR (DMSO-d$_6$, 400 MHz): δ (ppm) 0.73 (m, 4H), 1.65 (m, 2H), 1.86 (m, 2H), 2.01 (m, 1H), 2.14 (s, 3H), 2.26 (m, 2H), 2.42 (d, 2H), 2.68 (m, 2H), 2.76 (d, 2H), 3.15 (m, 2H), 3.40 (m, 3H), 3.54 (m, 6H), 3.75 (m, 1H), 3.87 (m, 1H), 4.19 (m, 1H), 4.80 (d, 1H), 5.06 (s, 2H), 6.11 (s, 1H), 6.26 (s, 1H), 6.59 (d, 1H), 6.76 (m, 2H), 6.95 (d, 1H), 8.27 (s, 1H), 8.31 (t, 1H). LCMS(ESI): [M+H]$^+$ m/z: calcd 643.3. found 644.4; Rt=1.03 min.

Example 1C66. 2-[(1-acetylpiperidin-4-yl)amino]-N-[(2S)-2-hydroxy-3-{6-[(4-methyl-1,3-oxazol-5-yl)methoxy]-1,2,3,4-tetrahydroisoquinolin-2-yl}propyl]-6-[(2-methoxyethyl(methyl)amino]pyridine-4-carboxamide (Compound 582)

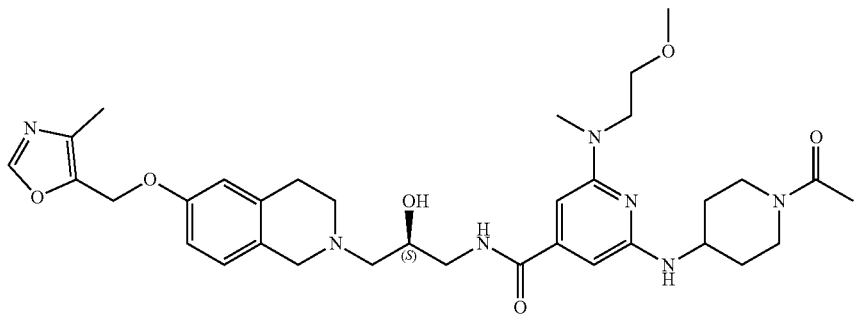

Prepared by general procedure 1C-G, condition A. Yield: 21.7 mg (33.4%). $^1$H NMR (DMSO-d$_6$, 400 MHz): δ (ppm) 1.21 (m, 1H), 1.35 (m, 1H), 1.89 (m, 3H), 2.00 (s, 3H), 2.15 (s, 3H), 2.73 (m, 5H), 2.96 (s, 3H), 3.15 (m, 2H), 3.25 (s, 3H), 3.30 (s, 3H), 3.47 (t, 2H), 3.55 (m, 1H), 3.63 (t, 2H), 3.83 (m, 4H), 4.22 (m, 1H), 5.06 (s, 2H), 6.01 (s, 1H), 6.06 (s, 1H), 6.25 (d, 1H), 6.77 (m, 2H), 6.96 (d, 1H), 8.23 (t, 1H), 8.28 (s, 1H). LCMS(ESI): [M+H]$^+$ m/z: calcd 649.3. found 651.3; Rt=0.81 min.

Example 1C67. 2-[(1-acetylpiperidin-4-yl)amino]-N-[(2S)-2-hydroxy-3-{6-[(4-methyl-1,3-oxazol-5-yl)methoxy]-1,2,3,4-tetrahydroisoquinolin-2-yl}propyl]-6-(4-methylpiperazin-1-yl)pyridine-4-carboxamide (Compound 584)

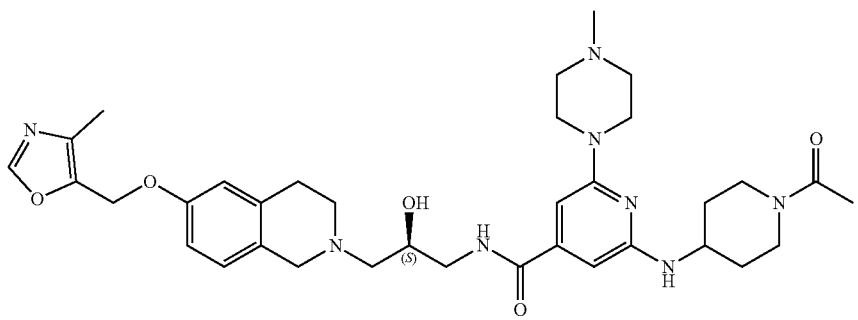

Prepared by general procedure 1C-G, condition A. Yield: 1f mg (11.7%). $^1$H NMR (Chloroform-d, 500 MHz): δ (ppm) 1.38 (m, 2H), 2.04 (m, 1H), 2.11 (s, 5H), 2.23 (s, 3H), 2.37 (m, 3H), 2.62 (s, 3H), 2.90 (m, 6H), 3.21 (m, 1H), 3.40 (m, 1H), 3.59 (m, 6H), 3.71 (m, 1H), 3.80 (d, 3H), 3.88 (m, 1H), 4.02 (m, 1H), 4.27 (d, 1H), 4.49 (d, 1H), 4.99 (s, 2H), 6.02 (s, 1H), 6.24 (s, 1H), 6.71 (m, 2H), 6.78 (d, 1H), 6.95 (d, 1H), 7.82 (s, 1H). LCMS(ESI): [M+2H]$^+$ m/z: calcd 660.3. found 662.4; Rt=0.79 min.

Example 1C68. 2-[(1-acetylpiperidin-4-yl)amino]-N-[(2S)-2-hydroxy-3-{6-[(4-methyl-1,3-oxazol-5-yl)methoxy]-1,2,3,4-tetrahydroisoquinolin-2-yl}propyl]-6-(piperidin-1-yl)pyridine-4-carboxamide (Compound 587)

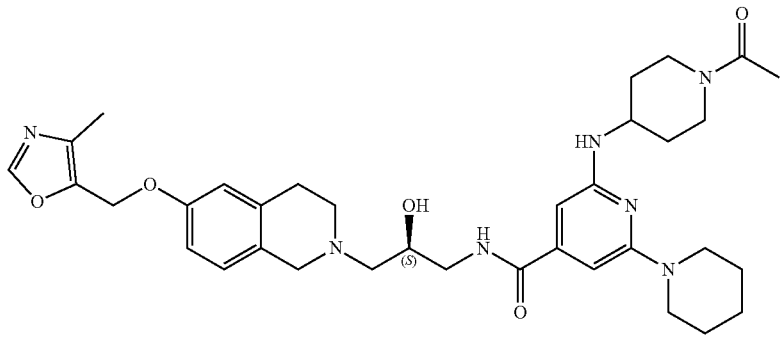

Prepared by general procedure 1C-G, condition A. Yield: 17.7 mg (27.2%). $^1$H NMR (Chloroform-d, 400 MHz): δ (ppm) 1.34 (m, 2H), 1.59 (m, 5H), 2.04 (m, 5H), 2.20 (s, 3H), 2.56 (m, 2H), 2.70 (m, 1H), 2.85 (m, 4H), 3.18 (t, 1H), 3.37 (m, 1H), 3.46 (m, 4H), 3.54 (d, 1H), 3.67 (m, 2H), 3.76 (m, 2H), 3.84 (m, 1H), 3.98 (m, 1H), 4.24 (d, 1H), 4.44 (m, 1H), 4.95 (s, 2H), 5.93 (s, 1H), 6.21 (s, 1H), 6.69 (s, 1H), 6.74 (d, 2H), 6.92 (d, 1H), 7.79 (s, 1H). LCMS(ESI): [M+H]$^+$ m/z: calcd 645.5. found 646.4; Rt=0.88 min.

Example 1C69. 2-(4-acetylpiperazin-1-yl)-6-[(1-acetylpiperidin-4-yl)amino]-N-[(2S)-2-hydroxy-3-{6-[(4-methyl-1,3-oxazol-5-yl)methoxy]-1,2,3,4-tetrahydroisoquinolin-2-yl}propyl]pyridine-4-carboxamide (Compound 594)

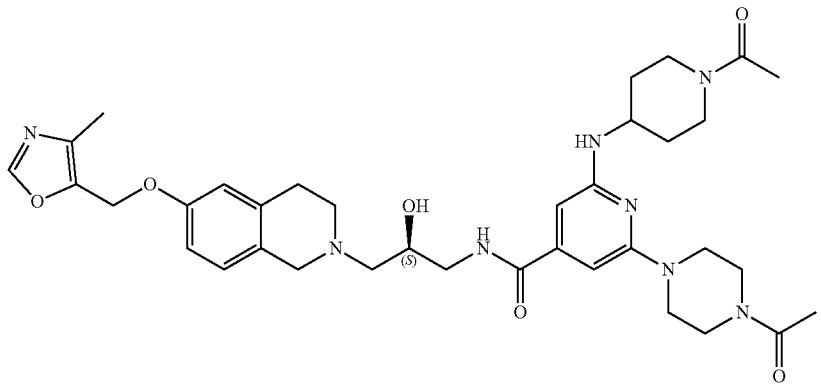

Prepared by general procedure 1C-G, condition A. Yield: 13.1 mg (20.1%). $^1$H NMR (500 MHz, DMSO-d$_6$+CCl$_4$) δ 1.35 (m, 1H), 1.43 (m, 1H), 1.90 (m, 1H), 1.95 (m, 1H), 2.01 (s, 3H), 2.05 (s, 3H), 2.18 (s, 3H), 2.87 (m, 5H), 2.99 (m, 3H), 3.22 (m, 2H), 3.44 (m, 3H), 3.52 (m, 4H), 3.55 (m, 2H), 3.65 (m, 1H), 3.77 (m, 1H), 3.90 (m, 2H), 4.19 (m, 1H), 4.99 (s, 2H), 6.15 (d, 1H), 6.21 (s, 1H), 6.25 (m, 1H), 6.71 (m, 2H), 6.94 (m, 1H), 8.03 (s, 1H), 8.16 (m, 1H). LCMS(ESI): [M+H]$^+$ m/z: calcd 688.1. found 689.4; Rt=0.90 min.

Example 1C69. (S)-2-((1-acetylpiperidin-4-yl)amino)-6-(cyclobutyl(methyl)amino)-N-(2-hydroxy-3-(6-((4-methyloxazol-5-yl)methoxy)-3,4-dihydroisoquinolin-2(1H)-yl)propyl)isonicotinamide (Compound 628)

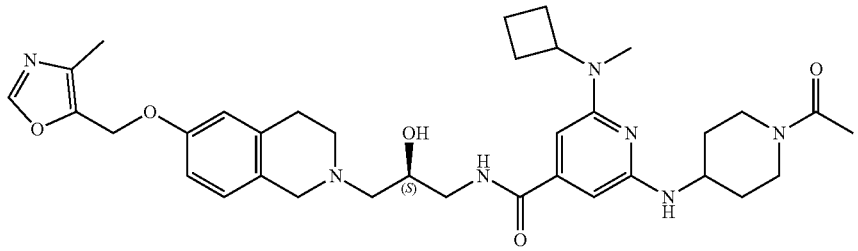

Prepared by general procedure 1C-G, condition A. Yield: 35.7 mg (28%). H NMR (DMSO-$d_6$, 500 MHz): δ (ppm) 1.34 (m, 1H), 1.42 (m, 1H), 1.91 (m, 2H), 2.00 (s, 3H), 2.18 (s, 3H), 2.58 (m, 4H), 2.77 (s, 2H), 2.83 (m, 3H), 2.97 (m, 8H), 3.19 (m, 2H), 3.42 (d, 1H), 3.62 (m, 2H), 3.76 (d, 1H), 3.90 (m, 2H), 4.20 (d, 1H), 4.59 (s, 1H), 4.98 (s, 2H), 5.92 (d, 1H), 6.04 (d, 2H), 6.69 (m, 2H), 6.91 (d, 1H), 8.01 (m, 2H). LCMS(ESI): [M+H]$^+$ m/z: calcd 645.8; found 646.4; Rt=1.001 min.

Example 1C70. (S)-2-((1-acetylpiperidin-4-yl)amino)-6-(dimethylamino)-N-(2-hydroxy-3-(6-((4-methyloxazol-5-yl)methoxy)-3,4-dihydroisoquinolin-2(1H)-yl)propyl)isonicotinamide (Compound 629)

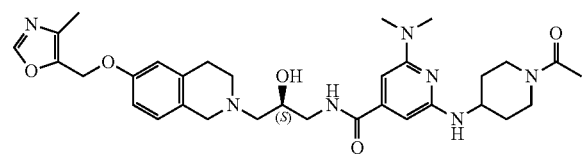

Prepared by general procedure 1C-G, condition A. Yield: 12.6 mg (11%). $^1$H NMR (DMSO-$d_6$, 500 MHz): δ (ppm) 1.34 (m, 1H), 1.44 (m, 1H), 1.66 (m, 2H), 1.93 (m, 2H), 2.00 (s, 3H), 2.16 (m, 7H), 2.76 (m, 1H), 2.84 (d, 2H), 2.91 (s, 3H), 3.19 (t, 2H), 3.42 (m, 1H), 3.60 (m, 2H), 3.77 (d, 1H), 3.89 (m, 2H), 4.19 (d, 1H), 4.58 (s, 1H), 4.71 (m, 1H), 4.98 (s, 2H), 5.92 (d, 1H), 6.02 (s, 1H), 6.06 (s, 1H), 6.69 (m, 2H), 6.92 (d, 1H), 8.00 (m, 1H), 8.02 (s, 1H). LCMS(ESI): [M+H]$^+$ m/z: calcd 605.7. found 606.2; Rt=0.893 min.

Example 1C71. (S)-2-(cyclobutyl)methyl)amino)-6-(cyclobutylamino)-N-(2-hydroxy-3-(6-((4-methyloxazol-5-yl)methoxy)-3,4-dihydroisoquinolin-2(1H)-yl)propyl)isonicotinamide (Compound 635)

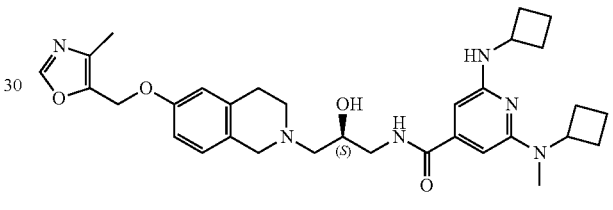

Prepared by general procedure 1C-G, condition A. Yield: 6.2 mg (7%). $^1$H NMR (400 MHz, CDCl$_3$) δ 1.66 (m, 2H), 1.75 (m, 2H), 1.83 (m, 2H), 2.13 (m, 4H), 2.21 (s, 3H), 2.38 (m, 2H), 2.53 (m, 2H), 2.69 (m, 1H), 2.88 (m, 3H), 2.94 (s, 3H), 3.39 (m, 1H), 3.54 (m, 1H), 3.67 (m, 1H), 3.76 (m, 1H), 3.98 (m, 1H), 4.12 (m, 1H), 4.53 (m, 1H), 4.70 (m, 1H), 4.96 (s, 2H), 5.83 (s, 1H), 6.09 (s, 1H), 6.65 (t, 1H), 6.70 (d, 1H), 6.75 (dd, 1H), 6.93 (d, 1H), 7.79 (s, 1H). LCMS(ESI): [M+H]$^+$ m/z: calcd 574.7. found 575.4; Rt=2.454 min.

Example 1C72. (S)-2,6-bis(cyclobutylamino)-N-(2-hydroxy-3-(6-((4-methyloxazol-5-yl)methoxy)-3N-dihydroisoquinolin-2(1H)-yl)propyl)isonicotinamide (Compound 636)

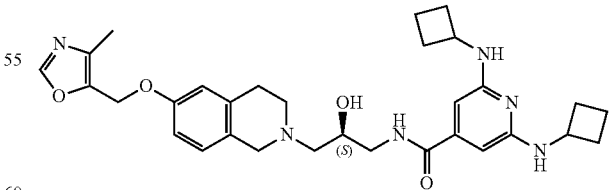

Prepared by general procedure 1C-G, condition A. Yield: 11.5 mg (13.5%). $^1$H NMR (400 MHz, CDCl$_3$) δ 1.75 (m, 9H), 2.21 (s, 3H), 2.37 (m, 4H), 2.52 (m, 1H), 2.57 (m, 1H), 2.69 (m, 1H), 2.86 (m, 3H), 3.38 (m, 1H), 3.54 (d, 1H), 3.66 (m, 1H), 3.75 (d, 1H), 3.98 (m, 1H), 4.06 (m, 2H), 4.56 (m, 2H), 4.96 (s, 2H), 5.87 (s, 2H), 6.70 (m, 2H), 6.75 (dd, 1H), 6.93 (d, 1H), 7.79 (s, 1H). LCMS(ESI): [M+H]+ m/z: calcd 560.7. found 562.2; Rt=2.427 min.

Example 1C73. (S)-2-((1-acetylazetidin-3-yl)amino)-N-(2-hydroxy-3-(6-((4-methyloxazol-5-yl)methoxy)-3N-dihydroisoquinolin-2(1H)-yl)propyl-6-(piperidin-1-yl)isonicotinamide (Compound 634)

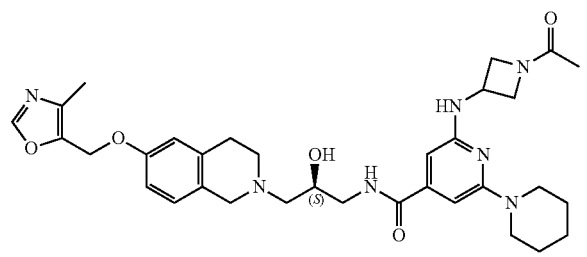

Prepared by general procedure 1C-G, condition A. Yield: 17.9 mg (19%). 1H NMR (400 MHz, DMSO-d6) δ 1.51 (m, 4H), 1.58 (m, 2H), 1.75 (s, 3H), 2.15 (s, 3H), 2.67 (m, 3H), 2.77 (m, 2H), 3.17 (m, 2H), 3.45 (m, 5H), 3.54 (m, 2H), 3.69 (m, 1H), 3.90 (m, 2H), 4.10 (m, 1H), 4.37 (m, 1H), 4.42 (m, 1H), 4.81 (m, 1H), 5.07 (s, 2H), 6.09 (s, 1H), 6.31 (s, 1H), 6.75 (m, 2H), 6.94 (m, 2H), 8.28 (s, 1H), 8.32 (m, 1H). LCMS(ESI): [M+H]+ m/z: calcd 617.7. found 618.4; Rt=1.046 min.

Example 1C74. (S)—N-(2-hydroxy-3-(6-((4-methyloxazol-5-yl)methoxy)-3,4-dihydroisoquinolin-2(1H)-yl)propyl)-2-(pyridin-3-ylamino)isonicotinamide (Compound 581)

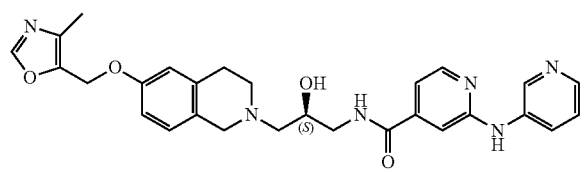

Prepared by general procedure 1C-G, condition A. Yield: 12.3 mg (17%). 1H NMR (400 MHz, CDCl3): δ (ppm) 2.20 (s, 3H), 2.56 (m, 2H), 2.70 (m, 1H), 2.87 (m, 3H), 3.46 (m, 2H), 3.55 (d, 1H), 3.73 (m, 2H), 4.01 (m, 1H), 4.95 (s, 2H), 6.69 (d, 1H), 6.75 (dd, 1H), 6.90 (m, 2H), 7.24 (m, 3H), 7.30 (t, 1H), 7.79 (s, 1H), 8.10 (d, 1H), 8.17 (d, 1H), 8.22 (d, 1H), 8.61 (d, 1H). LCMS(ESI): [M+H]+ m/z: calcd 514.6. found 515.4; Rt=0.771 min.

Example 1C75. (S)-2-((1-acetylpiperidin-4-yl)amino)-N-(2-hydroxy-3-(6-((4-methyloxazol-5-yl)methoxy)-3,4-dihydroisoquinolin-2(1H)-yl)propyl)-5-methoxyisonicotinamide (Compound 597)

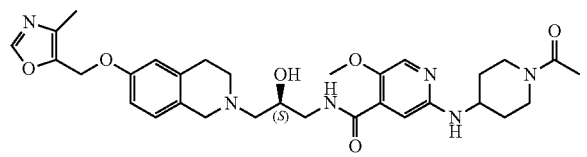

Prepared by general procedure 1C-G, condition B. Yield: 14.2 mg (6.73%). 1H NMR(400 MHz, CDCl3): δ (ppm) 1.35 (m, 2H), 2.09 (m, 5H), 2.21 (s, 3H), 2.53 (m, 2H), 2.68 (m, 1H), 2.85 (m, 4H), 3.20 (t, 1H), 3.40 (m, 1H), 3.54 (d, 1H), 3.76 (m, 5H), 3.92 (s, 3H), 4.00 (m, 1H), 4.26 (d, 1H), 4.48 (d, 1H), 4.96 (s, 2H), 6.70 (s, 1H), 6.75 (dd, 1H), 6.92 (d, 1H), 7.15 (s, 1H), 7.79 (s, 1H), 7.88 (s, 1H), 8.35 (t, 1H). LCMS(ESI): [M+H]+ m/z: calcd 592.7. found 593.4; Rt=2.124 min.

Example 1C76. 2-((1R,5S)-3-oxa-8-azabicyclo[3.2.1]octan-8-yl-6-(cyclobutylamino)-N—((S)-2-hydroxy-3-(6-((4-methyloxazol-5-yl)methoxy)-3N-dihydroisoquinolin-2(1H)-yl)propyl)isonicotinamide (Compound 598)

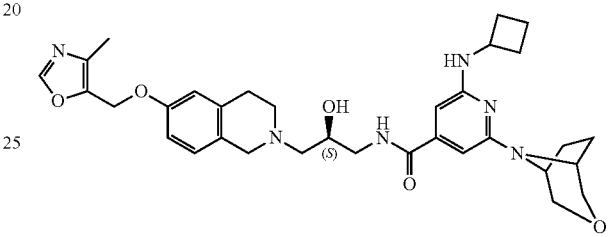

Prepared by general procedure 1C-G, condition B. Yield: 17.5 mg (8.1%). 1H NMR (400 MHz, CDCl3): δ (ppm) 1.73 (m, 2H), 1.82 (m, 2H), 1.92 (m, 2H), 2.01 (m, 2H), 2.21 (s, 3H), 2.36 (m, 2H), 2.57 (m, 2H), 2.71 (m, 1H), 2.89 (m, 3H), 3.37 (m, 1H), 3.54 (m, 4H), 3.68 (m, 1H), 3.78 (m, 3H), 3.99 (m, 1H), 4.09 (m, 1H), 4.36 (s, 2H), 4.57 (d, 1H), 4.96 (s, 2H), 5.87 (s, 1H), 6.16 (s, 1H), 6.73 (m, 3H), 6.93 (d, 1H), 7.79 (s, 1H). LCMS(ESI): [M+H]+ m/z: calcd 602.7. found 603.4; Rt=1.027 min.

Example 1C77. (S)-2-((1-acetylpiperidin-4-yl)amino)-N-(2-hydroxy-3-(6-((4-methyloxazol-5-yl)methoxy)-3,4-dihydroisoquinolin-2(1H)-yl)propyl)-6-methoxyisonicotinamide (Compound 599)

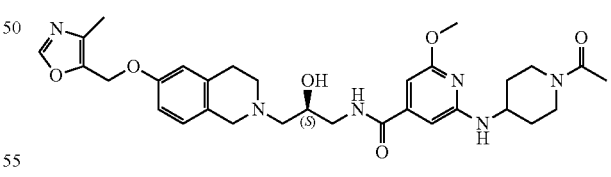

Prepared by general procedure 1C-G, condition B. Yield: 11.4 mg (5.31%). 1H NMR (400 MHz, CDCl3): δ (ppm) 1.38 (m, 2H), 2.09 (m, 5H), 2.21 (s, 3H), 2.55 (m, 2H), 2.70 (m, 1H), 2.88 (m, 5H), 3.19 (t, 1H), 3.38 (m, 1H), 3.54 (d, 1H), 3.68 (m, 1H), 3.75 (d, 1H), 3.83 (m, 5H), 3.98 (m, 1H), 4.41 (d, 1H), 4.48 (d, 1H), 4.96 (s, 2H), 6.22 (s, 1H), 6.29 (s, 1H), 6.73 (m, 3H), 6.92 (d, 1H), 7.79 (s, 1H). LCMS(ESI): [M+H]+ m/z: calcd 592.7. found 593.2; Rt=2.650 min.

General Protocol IC-H

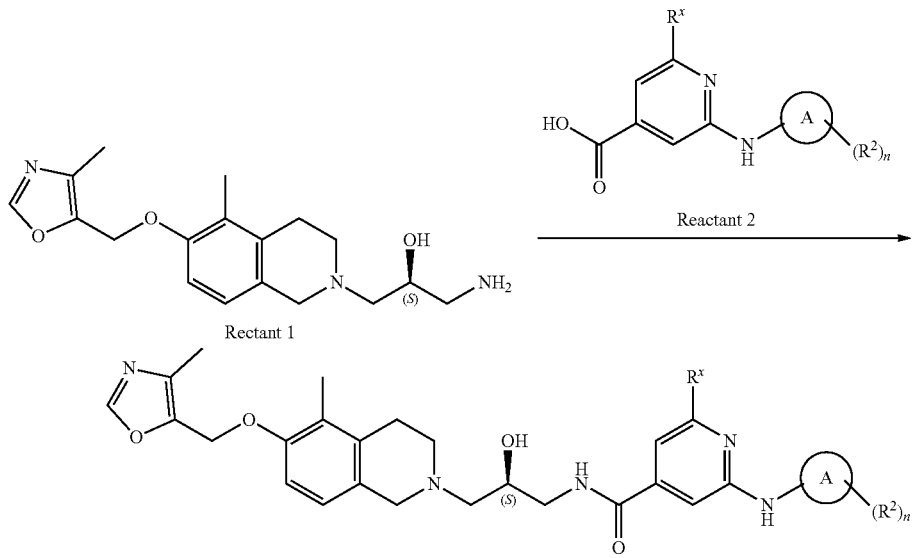

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mF) and filtered off. The obtained filtrate was subjected to HPFC (Waters Sunfire C18 19*100 5 mkm column and $H_2O$-MeOH-$0.1NH_3$ as a mobile phase) to afford pure product.

Example 1C79. (S)-2-(cyclobutylamino)-N-(2-hydroxy-3-[5-methyl-6-((4-methyloxazol-5-yl)methoxy)-3N-dihydroisoquinolin-2(1H)-yl)propyl) isonicotinamide (Compound 272)

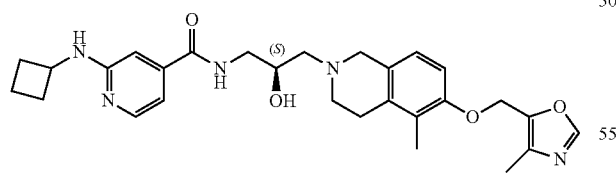

Prepared by general protocol IC-H. $^1$H NMR (Chloroform-d, 400 MHz): δ (ppm) 1.79 (m, 4H), 2.06 (s, 3H), 2.18 (s, 3H), 2.42 (m, 2H), 2.55 (m, 2H), 2.72 (m, 3H), 2.93 (m, 2H), 3.40 (m, 1H), 3.55 (d, 1H), 3.70 (m, 1H), 3.76 (d, 1H), 4.00 (m, 1H), 4.16 (m, 1H), 4.83 (d, 1H), 4.97 (s, 2H), 6.67 (s, 1H), 6.71 (d, 1H), 6.80 (m, 3H), 7.78 (s, 1H), 8.07 (d, 1H). LCMS(ESI): [M+H]$^+$ m/z: calcd 505.2. found 506.2; Rt=0.82 min.

Example 1C80. 2-(cyclopentylamino)-N-[(2S)-2-hydroxy-3-{5-methyl-6-[(4-methyl-1,3-oxazol-5-yl)methoxy]-1,2,3,4-tetrahydroisoquinolin-2-yl}propyl] pyridine-4-carboxamide (Compound 418)

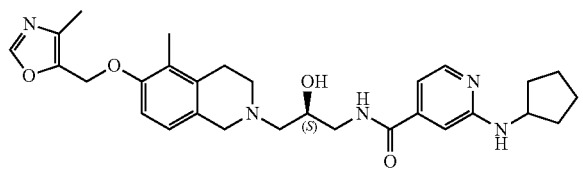

Prepared by general protocol IC-H. Yield: mg 11.8 (17.6%). $^1$H NMR (DMSO-$d_6$, 400 MHz): δ (ppm) 1.46 (m, 2H), 1.58 (m, 2H), 1.72 (m, 2H), 1.93 (m, 2H), 2.02 (s, 3H), 2.16 (s, 3H), 2.55 (m, 2H), 2.70 (m, 2H), 2.78 (m, 2H), 3.23 (m, 1H), 3.41 (d, 1H), 3.61 (m, 2H), 3.88 (m, 1H), 4.11 (m, 1H), 4.58 (s, 1H), 4.99 (s, 2H), 6.29 (d, 1H), 6.62 (d, 1H), 6.80 (m, 3H), 7.84 (d, 1H), 8.01 (s, 1H), 8.25 (t, 1H). LCMS(ESI): [M+H]$^+$ m/z: calcd 519.3. found 520.4; Rt=0.91 min.

Example 1C81. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-(4-propanoylpiperazin-1-yl)pyridine-4-carboxamide (Compound 417)

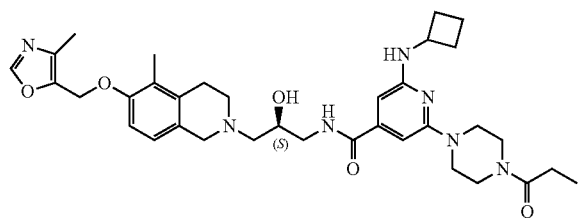

Prepared by general protocol IC-H. Yield: 17.5 mg (23.0%). $^1$H NMR (DMSO-d$_6$, 500 MHz): δ (ppm) 1.06 (t, 3H), 1.70 (m, 2H), 1.89 (m, 2H), 2.01 (s, 3H), 2.15 (s, 3H), 2.30 (m, 2H), 2.34 (q, 2H), 2.69 (m, 2H), 2.79 (m, 2H), 3.19 (m, 1H), 3.42 (m, 3H), 3.51 (m, 4H), 3.56 (m, 2H), 3.60 (m, 1H), 3.88 (m, 1H), 4.23 (m, 1H), 4.58 (s, 1H), 4.98 (s, 2H), 6.09 (s, 1H), 6.19 (d, 1H), 6.22 (s, 1H), 6.81 (s, 2H), 8.01 (s, 1H), 8.11 (t, 1H). LCMS(ESI): [M+H]$^+$ m/z: calcd 645.3. found 646.4; Rt=1.07 min.

Example 1C82. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-(4-methylpiperazin-1-yl)pyridine-4-carboxamide (Compound 503)

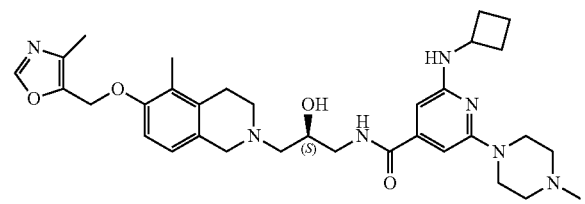

Prepared by general protocol IC-H. Yield: 13.6 mg (19.1%). $^1$H NMR (Chloroform-d, 400 MHz): δ (ppm) 1.73 (m, 2H), 1.82 (m, 2H), 2.05 (s, 3H), 2.18 (s, 3H), 2.30 (s, 3H), 2.36 (m, 3H), 2.45 (t, 4H), 2.52 (m, 2H), 2.71 (m, 3H), 2.91 (m, 1H), 3.37 (m, 1H), 3.51 (t, 4H), 3.66 (m, 1H), 3.74 (d, 1H), 3.98 (m, 1H), 4.12 (m, 1H), 4.56 (d, 1H), 4.96 (s, 2H), 5.89 (s, 1H), 6.22 (s, 1H), 6.70 (t, 1H), 6.78 (d, 1H), 6.82 (d, 1H), 7.24 (s, 1H), 7.78 (s, 1H). LCMS(ESI): [M+H]$^+$ m/z: calcd 603.5. found 605.3; Rt=0.85 min.

Example 1C83. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[methyl(propyl)amino]pyridine-4-carboxamide (Compound 480)

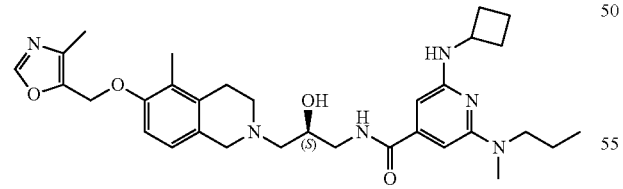

Prepared by general protocol IC-H. Yield: 10.2 mg (17.0%). $^1$H NMR (500 MHz, CDCl$_3$) δ 0.91 (t, 3H), 1.60 (m, 3H), 1.75 (m, 2H), 1.86 (m, 2H), 2.08 (s, 3H), 2.21 (s, 3H), 2.40 (m, 2H), 2.57 (m, 2H), 2.77 (m, 3H), 2.97 (m, 1H), 3.01 (s, 3H), 3.44 (m, 3H), 3.58 (d, 1H), 3.69 (m, 1H), 3.80 (d, 1H), 4.02 (m, 1H), 4.15 (m, 1H), 4.51 (m, 1H), 4.99 (s, 2H), 5.81 (s, 1H), 6.10 (s, 1H), 6.66 (m, 1H), 6.84 (m, 2H), 7.81 (s, 1H). LCMS(ESI): [M+H]$^+$ m/z: calcd 576.3. found 577.4; Rt=1.00 min.

Example 1C84. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-(morpholin-4-yl)pyridine-4-carboxamide (Compound 461)

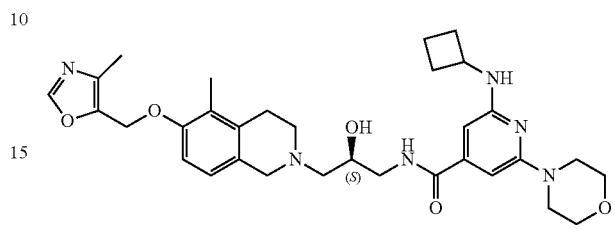

Prepared by general protocol IC-H. Yield: 8.3 mg (13.8%). $^1$H NMR (Chloroform-d, 500 MHz): δ (ppm) 1.75 (m, 2H), 1.85 (m, 2H), 2.08 (s, 3H), 2.21 (s, 3H), 2.41 (m, 2H), 2.62 (m, 2H), 2.79 (m, 3H), 3.00 (m, 1H), 3.42 (m, 1H), 3.48 (t, 4H), 3.63 (d, 1H), 3.70 (m, 1H), 3.79 (t, 4H), 3.84 (d, 1H), 4.04 (m, 1H), 4.15 (m, 1H), 4.60 (m, 1H), 4.99 (s, 2H), 5.96 (s, 1H), 6.24 (s, 1H), 6.75 (m, 1H), 6.82 (d, 1H), 6.86 (d, 1H), 7.81 (s, 1H). LCMS(ESI): [M+H]$^+$ m/z: calcd 590.1. found 591.2; Rt=1.12 min.

Example 1C85. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-(piperidin-1-yl)pyridine-4-carboxamide (Compound 557)

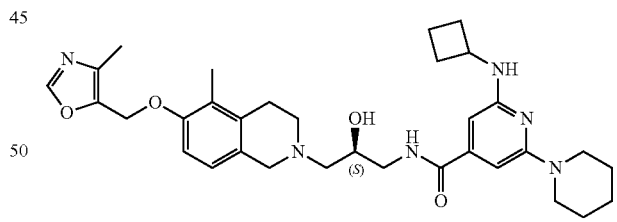

Prepared by general protocol IC-H. Yield: 17.6 mg (25.3%). $^1$H NMR (400 MHz, CDCl$_3$) δ 1.59 (m, 6H), 1.81 (m, 4H), 2.06 (s, 3H), 2.18 (s, 3H), 2.37 (m, 2H), 2.53 (m, 2H), 2.73 (m, 3H), 2.92 (m, 1H), 3.38 (m, 1H), 3.46 (m, 5H), 3.54 (d, 1H), 3.67 (m, 1H), 3.75 (d, 1H), 3.97 (m, 1H), 4.10 (m, 1H), 4.53 (d, 1H), 4.96 (s, 2H), 5.83 (s, 1H), 6.22 (s, 1H), 6.66 (t, 1H), 6.78 (m, 1H), 6.83 (m, 1H), 7.78 (s, 1H). LCMS(ESI): [M+2H]$^+$ m/z: calcd 588.4. found 590.2; Rt=1.08 min.

Example 1C86. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[4-(propan-2-yl)piperazin-1-yl]pyridine-4-carboxamide (Compound 539)

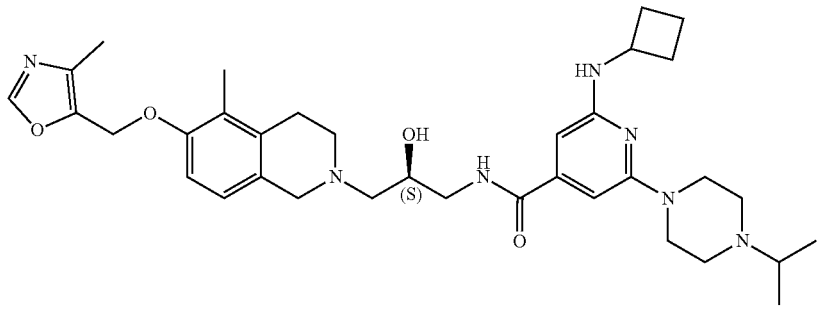

Prepared by general protocol IC-H. Yield: 21.6 mg (30.1%). $^{1}$H NMR (Chloroform-d, 400 MHz): δ (ppm) 1.05 (d, 6H), 1.72 (m, 2H), 1.81 (m, 2H), 2.05 (s, 3H), 2.18 (s, 3H), 2.37 (m, 2H), 2.56 (m, 6H), 2.70 (m, 4H), 2.91 (m, 1H), 3.37 (m, 1H), 3.50 (m, 6H), 3.67 (m, 1H), 3.74 (d, 1H), 3.97 (m, 1H), 4.10 (m, 1H), 4.55 (d, 1H), 4.96 (s, 2H), 5.88 (s, 1H), 6.22 (s, 1H), 6.69 (t, 1H), 6.78 (d, 1H), 6.83 (d, 1H), 7.78 (s, 1H). LCMS(ESI): [M+H]$^{+}$ m/z: calcd 631.1; found 633.4; Rt=0.99 min.

Example 1C87. 2-(cyclobutylamino)-6-(4-ethylpiperazin-1-yl)-N-[(2S)-2-hydroxy-3-{5-methyl-6-[(4-methyl-1,3-oxazol-5-yl)methoxy]-1,2,3,4-tetrahydroisoquinolin-2-yl}propyl]pyridine-4-carboxamide (Compound 394)

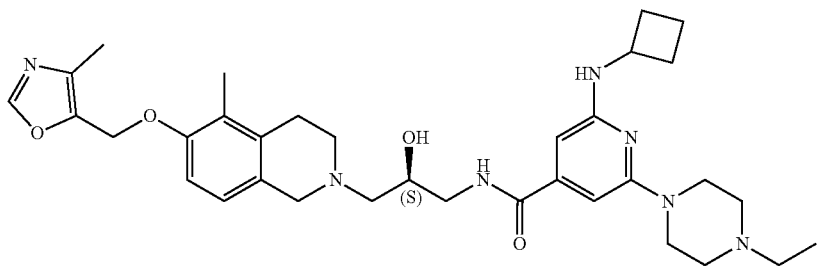

Prepared by general protocol IC-H. Yield: 16.8 mg (21.8%). $^{1}$H NMR (400 MHz, CDCl$_{3}$) δ 1.11 (t, 3H), 1.78 (m, 4H), 2.05 (s, 3H), 2.18 (s, 3H), 2.37 (m, 2H), 2.44 (m, 3H), 2.52 (m, 6H), 2.71 (m, 3H), 2.92 (m, 1H), 3.37 (m, 1H), 3.53 (m, 5H), 3.67 (m, 1H), 3.75 (m, 1H), 3.98 (m, 1H), 4.12 (m, 1H), 4.56 (d, 1H), 4.96 (s, 2H), 5.88 (s, 1H), 6.22 (s, 1H), 6.69 (t, 1H), 6.79 (m, 2H), 7.78 (s, 1H). LCMS(ESI): [M+2H]$^{+}$ m/z: calcd 617.4. found 619.2; Rt=0.91 min.

Example 1C88. 2-(4-acetylpiperazin-1-yl)-6-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]pyridine-4-carboxamide (Compound 502)

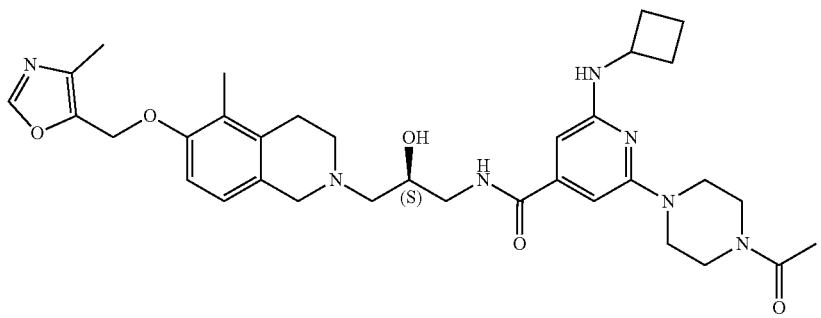

Prepared by general protocol IC-H. Yield: 11.9 mg (17.3%). $^1$H NMR (Chloroform-f 500 MHz): δ (ppm) 1.78 (m, 2H), 1.87 (m, 2H), 2.09 (s, 3H), 2.15 (s, 3H), 2.22 (s, 3H), 2.42 (m, 2H), 2.58 (m, 2H), 2.76 (m, 3H), 2.97 (t, 1H), 3.40 (m, 1H), 3.53 (m, 5H), 3.59 (m, 2H), 3.71 (m, 4H), 3.82 (m, 1H), 4.02 (m, 1H), 4.15 (m, 1H), 4.61 (m, 1H), 5.00 (s, 2H), 5.95 (s, 1H), 6.26 (s, 1H), 6.69 (t, 1H), 6.82 (d, 1H), 6.86 (s, 1H), 7.82 (s, 1H). LCMS(ESI): [M+H]$^+$ m/z: calcd 631.3. found 632.4; Rt=1.03 min.

Example 1C89. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(2-methoxyethyl)(methyl)amino]pyridine-4-carboxamide (Compound 437)

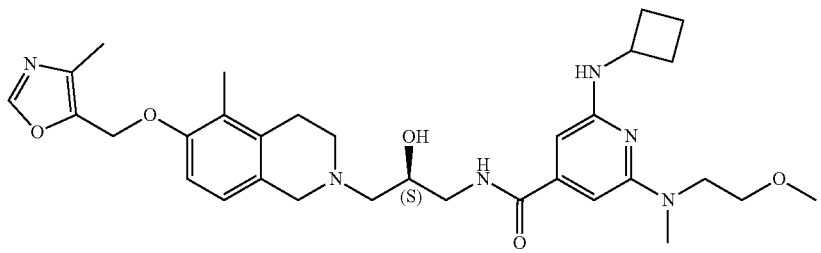

Prepared by general protocol IC-H. Yield: 13.3 mg (21.0%). $^1$H NMR (DMSO-d$_6$, 500 MHz): δ (ppm) 1.70 (m, 2H), 1.87 (m, 2H), 2.02 (s, 3H), 2.16 (s, 3H), 2.29 (m, 2H), 2.68 (m, 2H), 2.78 (m, 2H), 2.98 (s, 3H), 3.20 (m, 1H), 3.29 (s, 3H), 3.41 (m, 1H), 3.49 (t, 2H), 3.60 (m, 2H), 3.65 (t, 2H), 3.86 (m, 1H), 4.22 (m, 1H), 4.99 (s, 2H), 5.95 (s, 1H), 5.98 (m, 2H), 6.81 (s, 2H), 8.02 (s, 2H). LCMS(ESI): [M+H]$^+$ m/z: calcd 592.3. found 593.2; Rt=0.94 min.

Example 1C90. 2-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[4-(2-methylpropanoyl)piperazin-1-yl]pyridine-4-carboxamide (Compound 459)

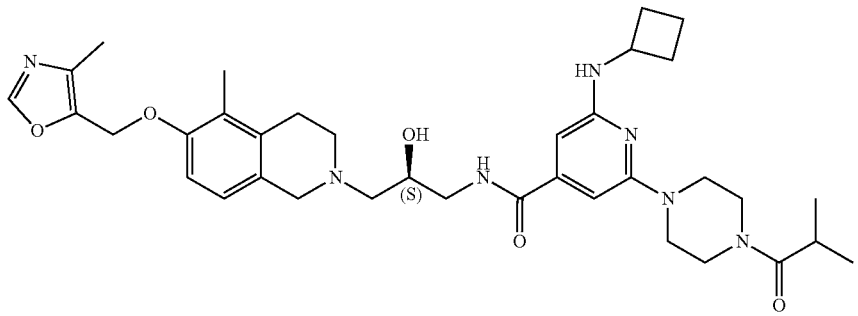

Prepared by general protocol 1-H. Yield: 5.9 mg (9.85%). $^1$H NMR (Chloroform-d, 500 MHz): δ (ppm) 1.17 (d, 6H), 1.81 (m, 5H), 2.09 (s, 3H), 2.22 (s, 3H), 2.42 (d, 2H), 2.59 (m, 2H), 2.78 (m, 3H), 2.84 (m, 1H), 2.98 (m, 1H), 3.41 (m, 1H), 3.52 (m, 2H), 3.60 (m, 5H), 3.72 (m, 3H), 3.82 (d, 1H), 4.03 (m, 1H), 4.16 (m, 1H), 4.61 (d, 1H), 5.00 (d, 2H), 5.96 (s, 1H), 6.26 (s, 1H), 6.72 (t, 1H), 6.82 (d, 1H), 6.87 (d, 1H), 7.82 (s, 1H). LCMS(ESI): [M+H]$^+$ m/z: calcd 659.2. found 660.4; Rt=1.17 min.

Example 1C91. 2-(cyclobutylamino)-6-(4-cyclopropanecarbonylpiperazin-1-yl)-N-[(2S)-2-hydroxy-3-{5-methyl-6-[(4-methyl-1,3-oxazol-5-yl)methoxy]1,2,3,4-tetrahydroisoquinolin-2-yl}propyl]pyridine-4-carboxamide (Compound 411)

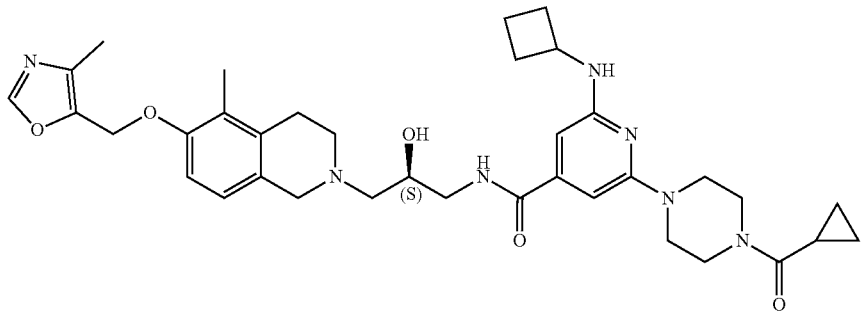

Prepared by general protocol IC-H. Yield: 16.2 mg (24.1%). $^1$H NMR (400 MHz, DMSO-d$_6$+CCl$_4$) δ 0.72 (m, 2H), 0.82 (m, 2H), 1.72 (m, 2H), 1.90 (m, 3H), 2.02 (s, 3H), 2.16 (s, 3H), 2.31 (m, 2H), 2.45 (m, 1H), 2.72 (m, 3H), 2.82 (m, 1H), 3.20 (m, 1H), 3.46 (m, 4H), 3.62 (m, 7H), 3.76 (m, 2H), 3.90 (m, 1H), 4.25 (m, 1H), 4.99 (s, 2H), 6.10 (s, 1H), 6.20 (m, 1H), 6.24 (s, 1H), 6.83 (m, 2H), 8.02 (s, 1H), 8.13 (m, 1H). LCMS(ESI): [M+H]$^+$ m/z: calcd 657.4. found 658.3; Rt=1.11 min.

Example 1C92. 2-(cyclobutylamino)-6-[2-(dimethylamino)ethoxy]-N-[(2S)-2-hydroxy-3-{5-methyl-6-[(4-methyl-1,3-oxazol-5-yl)methoxy]-1,2,3,4-tetrahydroisoquinolin-2-yl}propyl]pyridine-4-carboxamide (Compound 500)

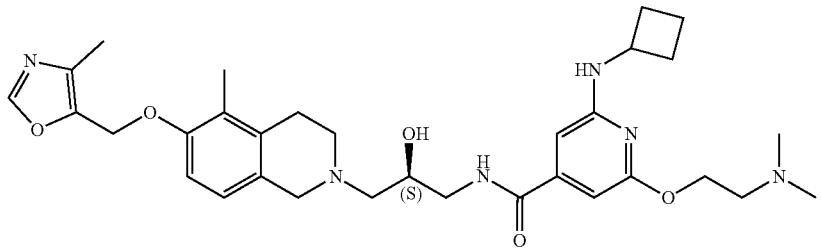

Prepared by general protocol IC-H. Yield: 20.8 mg (32.9%). $^1$H NMR (Chloroform-d, 400 MHz): δ (ppm) 1.74 (m, 2H), 1.83 (m, 3H), 2.05 (s, 3H), 2.18 (s, 3H), 2.29 (s, 6H), 2.40 (m, 2H), 2.51 (m, 2H), 2.65 (t, 2H), 2.71 (m, 3H), 2.91 (m, 1H), 3.37 (m, 1H), 3.53 (d, 1H), 3.65 (m, 1H), 3.74 (d, 1H), 3.96 (m, 1H), 4.12 (m, 1H), 4.31 (t, 2H), 4.68 (d, 1H), 4.96 (s, 2H), 6.20 (s, 1H), 6.26 (s, 1H), 6.69 (t, 1H), 6.78 (d, 1H), 6.83 (d, 1H), 7.78 (s, 1H). LCMS(ESI): [M+2H]$^+$ m/z: calcd 592.3. found 594.2; Rt=0.88 min.

Example 1C93. 2-(cyclobutylamino)-6-[ethyl(methyl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]pyridine-4-carboxamide (Compound 478)

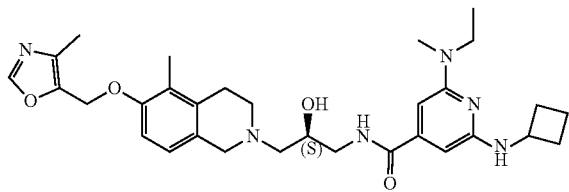

Prepared by general protocol IC-H. Yield: 17.0 mg (23.4%). $^1$H NMR (400 MHz, CDCl$_3$) δ 1.09 (t, 3H), 1.80 (m, 4H), 2.05 (s, 3H), 2.18 (s, 3H), 2.37 (m, 2H), 2.54 (m, 2H), 2.71 (m, 3H), 2.92 (m, 1H), 2.96 (s, 3H), 3.40 (m, 1H), 3.52 (m, 3H), 3.66 (m, 1H), 3.75 (m, 1H), 3.98 (m, 1H), 4.12 (m, 1H), 4.51 (m, 1H), 4.96 (s, 2H), 5.79 (s, 1H), 6.08 (s, 1H), 6.70 (t, 1H), 6.79 (m, 2H), 7.79 (s, 1H). LCMS(ESI): [M+2H]$^+$ m/z: calcd 562.3; found 564.4; Rt=0.98 min.

Example 1C94. 2-(cyclobutylamino)-N-[(2S)-2-hydroxy-3-{5-methyl-6-[(4-methyl-1,3-oxazol-5-yl)methoxy]-1,2,3,4-trihydroisoquinolin-2-yl}propyl]-6-(2-methylpropyl)pyridine-4-carboxamide (Compound 504)

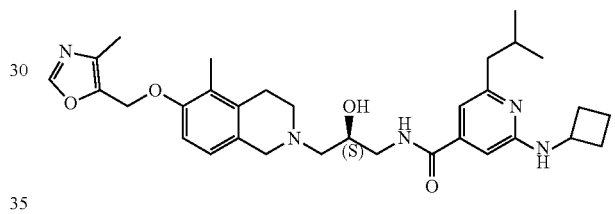

Prepared by general protocol IC-H. Yield: 12.2 mg (20.8%). $^1$H NMR (Chloroform-d, 500 MHz): δ (ppm) 0.92 (d, 6H), 1.79 (m, 2H), 1.89 (m, 2H), 2.09 (d, 4H), 2.22 (s, 3H), 2.45 (m, 4H), 2.59 (m, 2H), 2.77 (m, 3H), 2.98 (m, 1H), 3.42 (m, 1H), 3.54 (m, 1H), 3.59 (d, 1H), 3.73 (m, 1H), 3.81 (d, 1H), 4.03 (m, 1H), 4.12 (m, 1H), 4.88 (m, 1H), 5.00 (s, 2H), 6.50 (s, 1H), 6.62 (s, 1H), 6.73 (t, 1H), 6.82 (d, 1H), 6.86 (d, 1H), 7.82 (s, 1H). LCMS(ESI): [M+H]$^+$ m/z: calcd 561.1. found 562.4; Rt=2.30 min.

Example 1C95. 2-1(1-acetylpiperidin-4-yl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]-6-(piperidin-1-yl)pyridine-4-carboxamide (Compound 595)

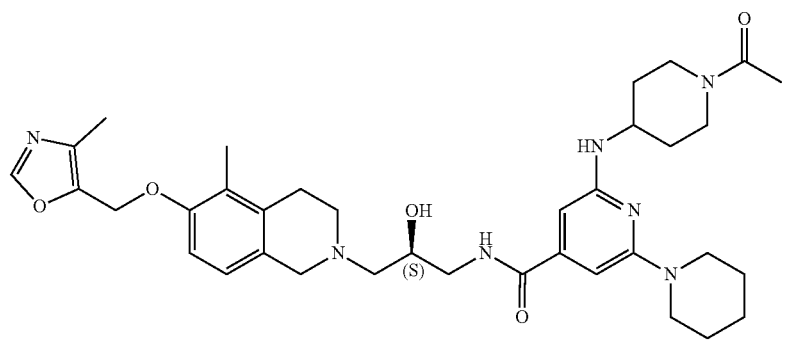

Prepared by general protocol 1-H. Yield: 8.7 mg (13.4%). $^1$H NMR (Chloroform-d, 500 MHz): δ (ppm) 1.39 (m, 2H), 1.63 (m, 7H), 2.08 (m, 4H), 2.12 (s, 4H), 2.22 (s, 3H), 2.64 (m, 2H), 2.81 (m, 2H), 2.87 (m, 2H), 3.03 (m, 1H), 3.22 (m, 1H), 3.43 (m, 1H), 3.51 (m, 4H), 3.66 (m, 1H), 3.73 (m, 1H), 3.81 (d, 1H), 3.86 (m, 2H), 4.06 (s, 1H), 4.25 (s, 1H), 4.48 (m, 1H), 5.00 (s, 2H), 5.98 (s, 1H), 6.25 (s, 1H), 6.75 (t, 1H), 6.82 (d, 1H), 6.87 (d, 1H), 7.82 (s, 1H). LCMS(ESI): [M+H]$^+$ m/z: calcd 659.2. found 660.1; Rt=1.00 min.

Example 1C96. 2-1(1-acetylpiperidin-4-yl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]-6-(4-methylpiperazin-1-yl)pyridine-4-carboxamide (Compound 593)

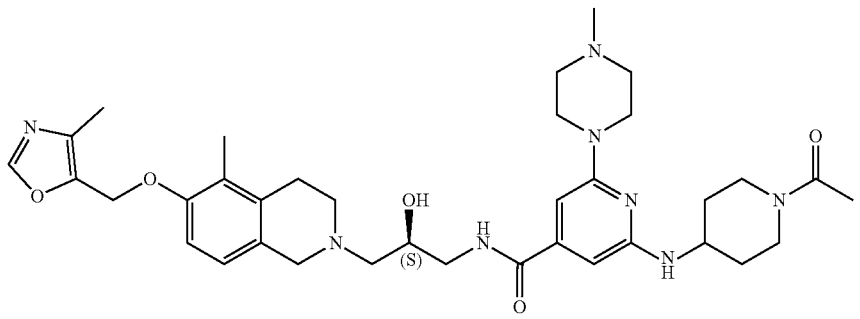

Prepared by general protocol IC-H. Yield: 12.6 mg (19.4%). $^1$H NMR (Chloroform-d, 500 MHz): δ (ppm) 1.38 (m, 3H), 2.08 (s, 5H), 2.11 (s, 5H), 2.20 (s, 3H), 2.35 (s, 3H), 2.50 (m, 4H), 2.57 (m, 2H), 2.75 (m, 3H), 2.85 (m, 1H), 2.95 (m, 1H), 3.21 (m, 1H), 3.39 (m, 1H), 3.55 (m, 4H), 3.71 (m, 1H), 3.79 (m, 2H), 3.86 (m, 1H), 4.01 (m, 1H), 4.26 (m, 1H), 4.50 (m, 1H), 4.99 (s, 2H), 6.01 (s, 1H), 6.23 (s, 1H), 6.69 (t, 1H), 6.80 (d, 1H), 6.85 (d, 1H), 7.81 (s, 1H). LCMS(ESI): [M+H]$^+$ m/z: calcd 674.3. found 676.4; Rt=0.83 min.

Example 1C97. 2-1(1-acetylpiperidin-4-yl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(2-methoxyethyl)(methyl)amino]pyridine-4-carboxamide (Compound 592)

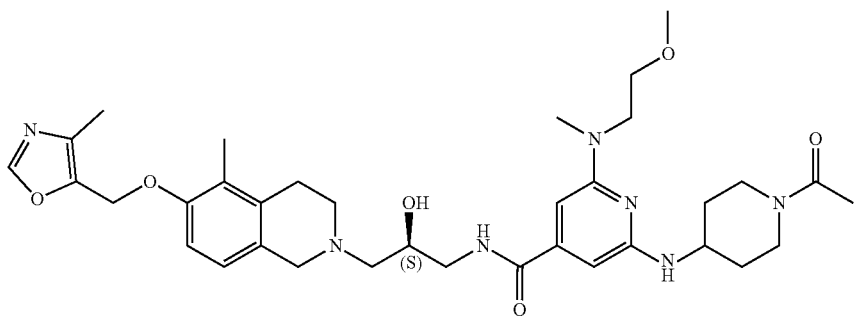

Prepared by general protocol IC-H. Yield: 18.1 mg (27.8%). $^1$H NMR (Chloroform-d, 400 MHz): δ (ppm) 1.34 (m, 2H), 2.06 (d, 8H), 2.17 (s, 3H), 2.53 (m, 2H), 2.71 (m, 3H), 2.81 (m, 1H), 2.91 (m, 1H), 3.02 (s, 3H), 3.16 (t, 1H), 3.32 (s, 3H), 3.37 (m, 1H), 3.52 (m, 3H), 3.66 (m, 3H), 3.76 (m, 2H), 3.85 (m, 1H), 3.97 (m, 1H), 4.21 (m, 1H), 4.46 (m, 1H), 4.96 (s, 2H), 5.27 (s, 1H), 5.91 (s, 1H), 6.06 (s, 1H), 6.79 (m, 3H), 7.78 (s, 1H). LCMS(ESI): [M+H]$^+$ m/z: calcd 663.4. found 664.4; Rt=0.85 min.

Example 1C98. 2-(4-acetylpiperazin-1-yl)-6-[(1-acetylpiperidin-4-yl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]pyridine-4-carboxamide (Compound 590)

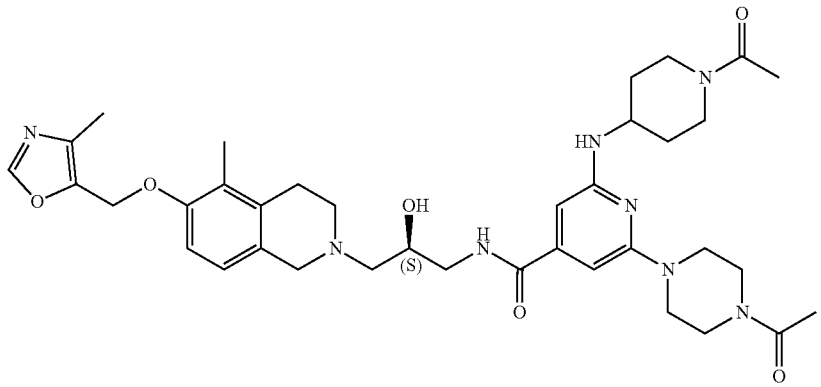

Prepared by general protocol IC-H. Yield: 7.6 mg (11.7%). $^1$H NMR (Chloroform-d, 500 MHz): δ (ppm) 1.38 (m, 3H), 2.08 (s, 4H), 2.13 (s, 7H), 2.21 (s, 3H), 2.59 (m, 2H), 2.77 (m, 3H), 2.88 (m, 1H), 2.97 (m, 1H), 3.20 (m, 1H), 3.40 (m, 1H), 3.54 (m, 8H), 3.71 (m, 3H), 3.83 (m, 3H), 4.02 (m, 1H), 4.29 (d, 1H), 4.49 (d, 1H), 4.99 (s, 2H), 6.05 (s, 1H), 6.25 (s, 1H), 6.81 (d, 1H), 6.86 (d, 1H), 7.81 (s, 1H). LCMS(ESI): [M+H]$^+$ m/z: calcd 702.4. found 703.4; Rt=0.92 min.

Example 1C99. (S)-2-((1-acetylpiperidin-4-yl)amino)-N-(2-hydroxy-3-[5-methyl-6-((4-methyloxazol-5-yl)methoxy)-3,4-dihydroisoquinolin-2(1H)-yl)propyl)-6-methoxyisonicotinamide (Compound 604)

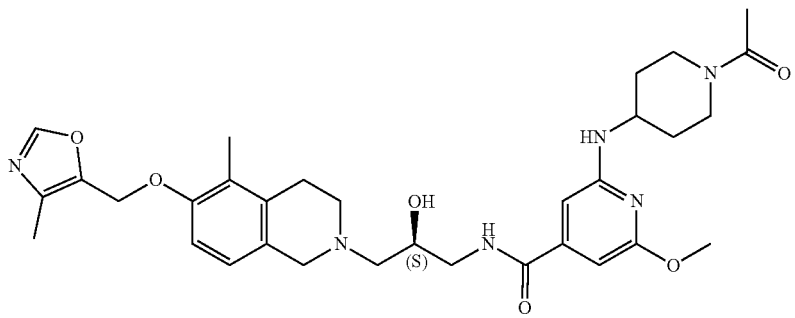

Prepared by general protocol IC-H. Yield: 55.3 mg (19.16%). $^1$H NMR, δ 1.35 (m, 2H), 2.05 (m, 4H), 2.09 (m, 4H), 2.18 (s, 3H), 2.54 (m, 2H), 2.73 (m, 3H), 2.80 (m, 1H), 2.92 (m, 1H), 3.19 (m, 1H), 3.36 (m, 1H), 3.56 (m, 1H), 3.67 (m, 1H), 3.75 (m, 2H), 3.83 (m, 4H), 3.87 (m, 1H), 4.00 (m, 1H), 4.42 (d, 1H), 4.50 (m, 1H), 4.96 (s, 2H), 6.22 (s, 1H), 6.29 (s, 1H), 6.79 (m, 3H), 7.79 (s, 1H). LCMS(ESI): [M+H]$^+$ m/z: calcd 606.4. found 607.4; Rt=2.825 min.

General Procedure IC-1

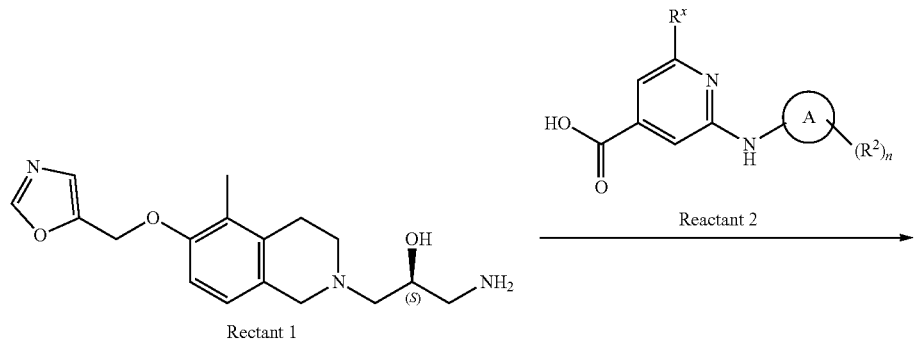

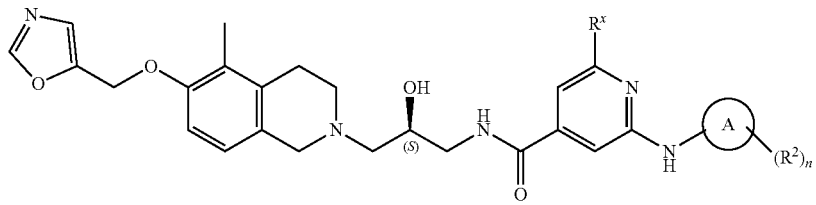

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and $H_2O$-MeOH-0.1$NH_3$ as a mobile phase) to afford pure product.

Example 1C100. 2-(cyclopentylamino)-N-[(2S)-2-hydroxy-3-{5-methyl-6-[(1,3-oxazol-5-yl)methoxy]-1,2,3,4-tetrahydroisoquinolin-2-yl}propyl]pyridine-4-carboxamide (Compound 356)

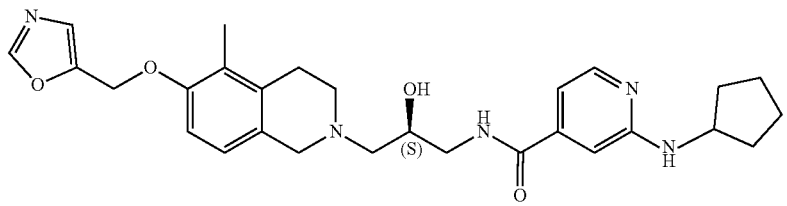

Prepared by general procedure IC-I. Yield: 10.3 mg (13.73%). ¹H NMR (DMSO-d₆, 500 MHz): δ (ppm) 1.47 (m, 2H), 1.57 (m, 2H), 1.65 (m, 2H), 1.74 (m, 2H), 2.05 (m, 2H), 2.10 (s, 3H), 2.59 (m, 2H), 2.77 (m, 3H), 2.96 (m, 1H), 3.43 (m, 1H), 3.59 (d, 1H), 3.72 (m, 1H), 3.79 (d, 1H), 4.03 (m, 2H), 4.69 (d, 1H), 5.05 (s, 2H), 6.72 (d, 1H), 6.79 (m, 3H), 6.85 (d, 1H), 7.13 (s, 1H), 7.91 (s, 1H), 8.10 (d, 1H). LCMS(ESI): [M+H]⁺ m/z: calcd 505.3. found 506.0; Rt=0.807 min.

Example 1C101. N-[(2S)-2-hydroxy-3-{5-methyl-6-[(1,3-oxazol-5-yl)methoxy]-1,2,3,4-tetrahydroisoquinolin-2-yl}propyl]-2-[(pyridin-3-yl)amino]pyridine-4-carboxamide (Compound 531)

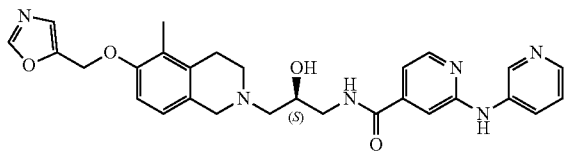

Prepared by general procedure IC-I. Yield: 6.1 mg (9.92%). LCMS(ESI): [M+H]⁺ m/z: calcd 514.2. found 515.2; Rt=0.81 min.

Example 1C102. (S)-2-(4-(cyclopropanecarbonyl)piperazin-1-yl)-N-(2-hydroxy-3-(6-((4-methyloxazol-5-yl)methoxy)-3,4-dihydroisoquinolin-2(1H)-yl)propyl)-6-(spiro[3.3]heptan-2-ylamino)isonicotinamide (Compound 610)

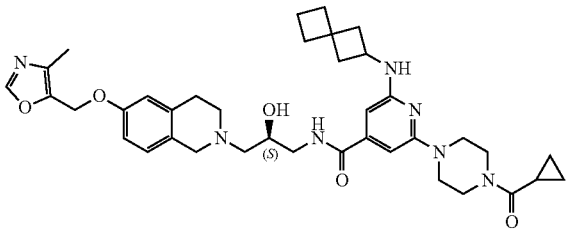

Prepared by general procedure 1C-G, condition B. Yield: 45.5 mg (28.4%). H NMR (400 MHz, CDCl₃) δ 0.77 (m, 2H), 0.99 (m, 2H), 1.80 (m, 5H), 1.91 (m, 2H), 2.04 (m, 2H), 2.21 (s, 3H), 2.48 (m, 3H), 2.58 (m, 1H), 2.69 (m, 1H), 2.87 (m, 3H), 3.37 (m, 1H), 3.51 (m, 2H), 3.58 (m, 3H), 3.72 (m, 7H), 3.95 (m, 2H), 4.53 (d, 1H), 4.96 (s, 2H), 5.91 (s, 1H), 6.21 (s, 1H), 6.69 (m, 2H), 6.75 (m, 1H), 6.92 (1H), 7.79 (s, 1H). LCMS(ESI): [M+H]⁺ m/z: calcd 683.8. found 684.4; Rt=3.190 min.

Example 1C103. (S)-2-(4-(cyclopropanecarbonyl)piperazin-1-yl)-N-(2-hydroxy-3-(6-((4-methyloxazol-5-yl)methoxy)-3,4-dihydroisoquinolin-2(1H)-yl)propyl)-6-(spiro[2.3]hexan-5-ylamino)isonicotinamide (Compound 611)

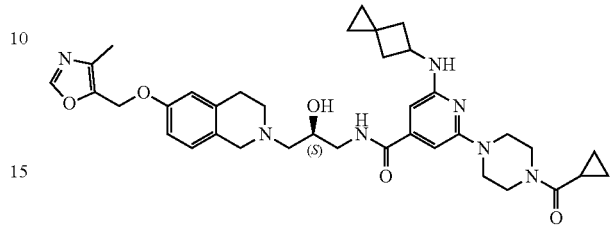

Prepared by general procedure 1C-G, condition B. Yield: 35.5 mg (22.62%). ¹H NMR (400 MHz, CDCl₃) δ 0.40 (m, 2H), 0.49 (m, 2H), 0.78 (m, 2H), 1.00 (m, 2H), 1.75 (m, 1H), 2.12 (m, 2H), 2.21 (s, 3H), 2.39 (m, 2H), 2.51 (m, 1H), 2.59 (m, 1H), 2.70 (m, 1H), 2.87 (m, 2H), 2.92 (m, 1H), 3.37 (m, 1H), 3.54 (m, 4H), 3.61 (m, 2H), 3.74 (m, 6H), 3.98 (m, 1H), 4.31 (m, 1H), 4.68 (d, 1H), 4.96 (s, 2H), 5.94 (s, 1H), 6.24 (s, 1H), 6.69 (m, 2H), 6.76 (m, 1H), 6.93 (d, 1H), 7.79 (s, 1H). LCMS(ESI): [M+H]⁺ m/z: calcd 669.8. found 670.4; Rt=3.010 min.

Example 1C104 (S)-2-((1-acetylpiperidin-4-yl)amino)-6-cyclohexyl-N-(2-hydroxy-3-(6-((4-methyl-oxazol-5-yl)methoxy)-3,4-dihydroisoquinolin-2(1H)-yl)propyl)isonicotinamide (Compound 641)

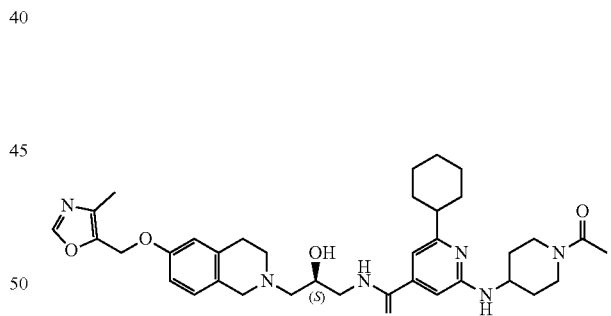

Prepared by general procedure 1C-G, condition B. 41.1 mg (27.4%). ¹H NMR (500 MHz, DMSO-d₆): δ 1.34 (m, 7H), 1.68 (d, 1H), 1.78 (m, 3H), 1.86 (d, 1H), 1.94 (d, 1H), 2.00 (s, 2H), 2.07 (s, 3H), 2.15 (s, 3H), 2.41 (m, 2H), 2.73 (m, 5H), 3.18 (m, 2H), 3.34 (m, 1H), 3.55 (m, 2H), 3.76 (d, 1H), 3.89 (m, 2H), 4.17 (d, 1H), 4.82 (d, 1H), 5.06 (s, 2H), 6.52 (d, 1H), 6.65 (s, 2H), 6.76 (m, 2H), 6.95 (d, 1H), 8.28 (s, 1H), 8.39 (t, 1H). LCMS(ESI): [M+H]⁺ m/z: calcd 644.8. found 645.4; Rt=0.955 min.

General Procedure 1C-J

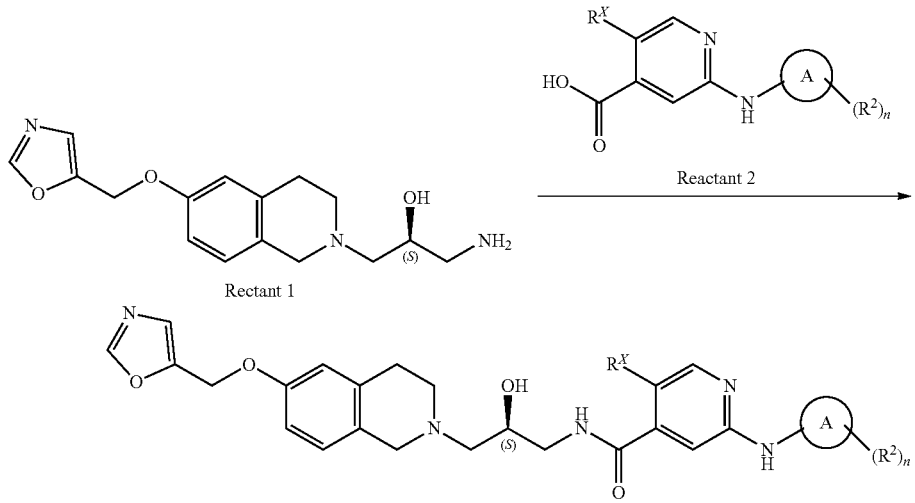

Condition A. DIPEA (5.0 equiv) was added to the solution of reactant 1 (E0 equiv) and reactant 2(1.1 equiv) in DMF (2 mL). The resulting mixture was stirred for 5 min followed by the addition of the solution of EDC (1.05 equiv) in DMF (0.5 mL) and the solution of HOAt (1.05 equiv) in DMF (0.5 mL). The reaction mixture was stirred overnight at room temperature. After the completion of the reaction, monitored by LCMS, the resulting suspension was concentrated under reduced pressure. The residue was dissolved in DMSO (1.0 mL) and filtered off. The obtained filtrate was subjected to HPLC (Waters SunFire C18 19*100 5 mkm column and H2O-MeOH as a mobile phase, RunTime=5 min) to afford pure product.

Condition B. Reactant 1 and reactant 2 were mixed in DMF (5 mL). The reaction suspension was cooled to 0° C. and HATU followed by TEA were added. The clear solution was stirred at ambient temperature for 1.5 hr at 25° C. then volatiles were evaporated under reduced pressure and recidue was subjected to RP-HPLC to give product.

Example 1C105. (S)-2-(cyclobutylamino)-5-fluoro-N-(2-hydroxy-3-(6-(oxazol-5-ylmethoxy)-3A-dihydroisoquinolin-2(1H)-yl)propyl)isonicotinamide (Compound 334)

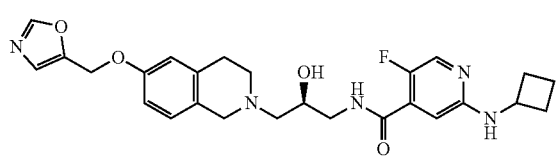 [SMILES: O=C(NC[C@H](O)CN1CCc2cc(OCc3cnco3)ccc2C1)c1cc(NC2CCC2)ncc1F]

Prepared by general procedure IC-J, condition A. Yield 29 mg (39%). ¹H NMR (DMSO-d6, 400 MHz): δ (ppm) 1.70 (m, 2H), 1.86 (m, 2H), 2.30 (m, 2H), 2.54 (m, 2H), 2.76 (m, 2H), 2.83 (m, 2H), 3.24 (m, 1H), 3.47 (d, 1H), 3.59 (m, 2H), 3.87 (m, 1H), 4.22 (q, 1H), 4.61 (m, 1H), 5.05 (s, 2H), 6.66 (d, 2H), 6.71 (m, 2H), 6.90 (d, 1H), 7.16 (s, 1H), 7.83 (d, 1H), 7.88 (m, 1H), 8.16 (s, 1H) LCMS(ESI): [M+H]⁺ m/z: calcd 495.23. found 496.2; Rt=0.984 min.

Example 1C106. (S)—N-(2-hydroxy-3-(6-((4-methyloxazol-5-yl)methoxy)-3,4-dihydroisoquinolin-2(1H)-yl)propyl)-2-(piperidin-1-yl)-6-(pyridin-3-ylamino)isonicotinamide (Compound 601)

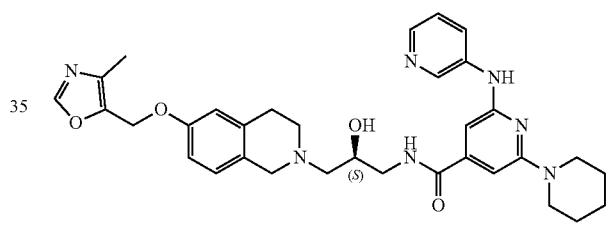

Prepared by general procedure IC-G, condition 2. Yield: 22.8 mg (10.85%). ¹H NMR (400 MHz, CDCl₃): δ (ppm) 1.61 (m, 6H), 2.20 (s, 3H), 2.56 (m, 2H), 2.69 (m, 1H), 2.86 (m, 4H), 3.39 (m, 1H), 3.53 (m, 5H), 3.68 (m, 1H), 3.74 (d, 1H), 3.99 (m, 1H), 4.94 (s, 2H), 6.23 (s, 1H), 6.43 (s, 1H), 6.59 (s, 1H), 6.68 (s, 1H), 6.74 (d, 1H), 6.92 (d, 1H), 6.97 (t, 1H), 7.18 (dd, 1H), 7.79 (s, 1H), 7.86 (d, 1H), 8.17 (d, 1H), 8.66 (d, 1H). LCMS(ESI): [M+H]⁺ m/z: calcd 597.7. found 598.2; Rt=0.920 min.

Example 1C107. (S)-2-(cyclobutylamino)-N-(2-hydroxy-3-(6-((4-methyloxazol-5-yl)methoxy)-3A-dihydroisoquinolin-2(1H)-yl)propyl-5-methoxyisonicotinamide (Compound 602)

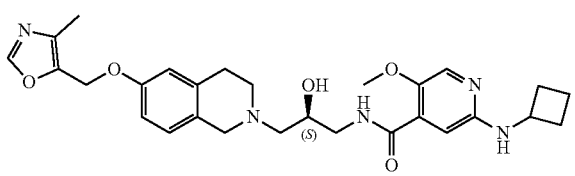

Prepared by general procedure IC-J, condition B. Yield: 59.7 mg (31.91%). $^1$H NMR(400 MHz, CDCl$_3$): δ (ppm) 1.78 (m, 4H), 2.20 (s, 3H), 2.41 (m, 2H), 2.55 (m, 2H), 2.68 (m, 1H), 2.89 (m, 3H), 3.40 (m, 2H), 3.53 (d, 1H), 3.69 (m, 1H), 3.76 (d, 1H), 3.89 (s, 3H), 3.99 (m, 1H), 4.12 (m, 1H), 4.61 (d, 1H), 4.95 (s, 2H), 6.69 (s, 1H), 6.74 (dd, 1H), 6.91 (d, 1H), 7.07 (s, 1H), 7.78 (s, 1H), 7.86 (s, 1H), 8.34 (t, 1H). LCMS(ESI): [M+H]$^+$ m/z: calcd 521.6. found 522.2; Rt=0.834 min.

Example 1C108. 2-((1R,5S)-3-oxa-8-azabicyclo[3.2.1]octan-8-yl)-N—((S)-2-hydroxy-3-(6-((4-methyloxazol-5-yl)methoxy)-3,4-dihydroisoquinolin-2(1H)-yl)propyl)-6-(pyridin-3-ylamino)isonicotinamide (Compound 603)

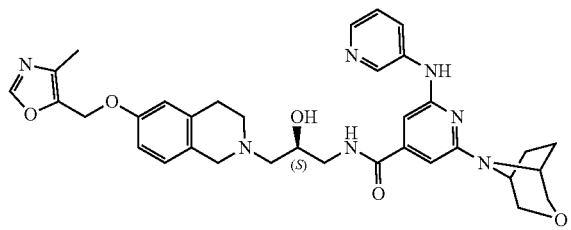

Prepared by general procedure IC-G. Yield: 90.9 mg (41.33%). $^1$H NMR (400 MHz, CDCl$_3$): δ (ppm) 1.96 (m, 2H), 2.05 (m, 2H), 2.20 (s, 3H), 2.55 (m, 2H), 2.74 (m, 1H), 2.88 (m, 3H), 3.40 (m, 1H), 3.56 (m, 3H), 3.67 (m, 1H), 3.79 (m, 3H), 3.99 (m, 1H), 4.36 (m, 2H), 4.94 (s, 2H), 6.27 (s, 1H), 6.36 (s, 1H), 6.59 (m, 1H), 6.69 (m, 1H), 6.94 (m, 2H), 7.17 (m, 1H), 7.79 (m, 2H), 8.20 (d, 1H), 8.69 (s, 1H). LCMS(ESI): [M+H]$^+$ m/z: calcd 625.7. found 626.4; Rt=2.383 min.

Example 1C109. (S)-2-(cyclobutylamino)-5-fluoro-N-(2-hydroxy-3-(6-((4-methyloxazol-5-yl)methoxy)-3,4-dihydroisoquinolin-2(1H)-yl)propyl)isonicotinamide (Compound 614)

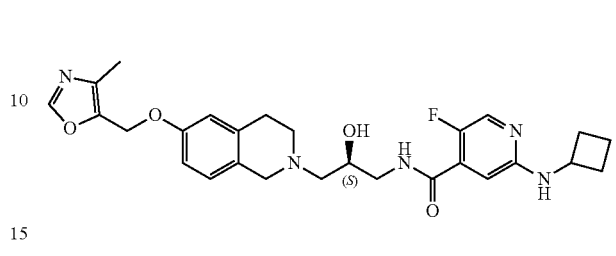

Prepared by general procedure IC-J, condition B. Yield: 11.1 mg (9.3%). $^1$H NMR (400 MHz, CDCl$_3$) δ 1.80 (m, 5H), 2.20 (s, 3H), 2.42 (m, 2H), 2.56 (m, 2H), 2.69 (m, 1H), 2.89 (m, 3H), 3.41 (m, 1H), 3.54 (m, 1H), 3.73 (m, 2H), 4.00 (m, 1H), 4.10 (m, 1H), 4.78 (d, 1H), 4.96 (s, 2H), 6.69 (d, 1H), 6.74 (dd, 1H), 6.86 (d, 1H), 6.92 (d, 1H), 7.19 (m, 1H), 7.79 (s, 1H), 7.99 (d, 1H). LCMS(ESI): [M+H]$^+$ m/z: calcd 509.6. found 510.2; Rt=2.455 min.

Example 1C110. (S)-2-((1-acetylpiperidin-4-yl)amino)-N-(2-hydroxy-3-(6-((4-methyloxazol-5-yl)methoxy)-3,4-dihydroisoquinolin-2(1H)-yl)propyl)-6-isopropylisonicotinamide (Compound 646)

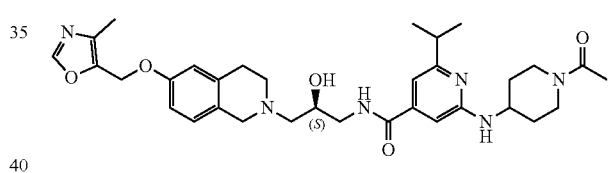

Prepared by general procedure IC-G. Yield: 22 mg (24%). $^1$H NMR (400 MHz, CDCl$_3$) δ 1.20 (d, 6H), 1.36 (m, 2H), 2.03 (m, 2H), 2.08 (s, 3H), 2.14 (m, 1H), 2.20 (s, 3H), 2.52 (m, 1H), 2.58 (m, 1H), 2.70 (m, 1H), 2.85 (m, 5H), 3.20 (m, 1H), 3.37 (m, 1H), 3.54 (d, 1H), 3.68 (m, 1H), 3.74 (m, 2H), 3.87 (m, 1H), 3.99 (m, 1H), 4.45 (m, 1H), 4.51 (d, 1H), 4.96 (s, 2H), 6.54 (s, 1H), 6.64 (s, 1H), 6.69 (d, 1H), 6.74 (dd, 1H), 6.91 (m, 2H), 7.79 (s, 1H). LCMS(ESI): [M+H]$^+$ m/z: calcd 604.7. found 605.4; Rt=0.863 min.

Scheme 1D

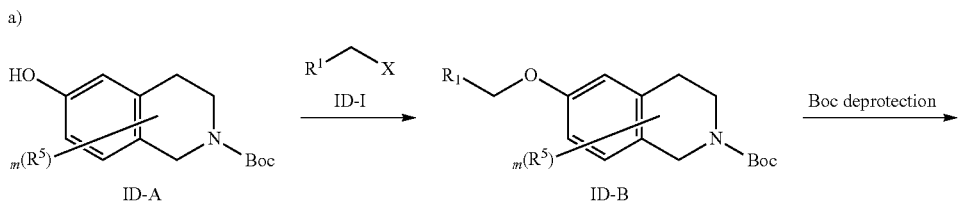

-continued
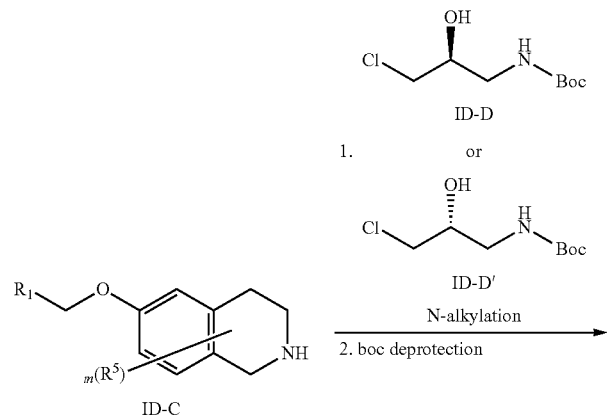
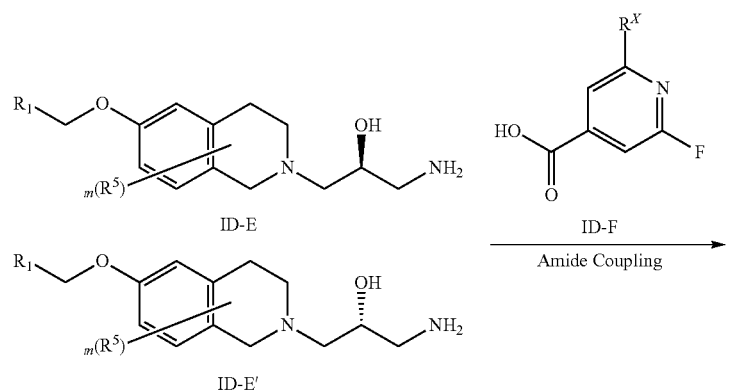
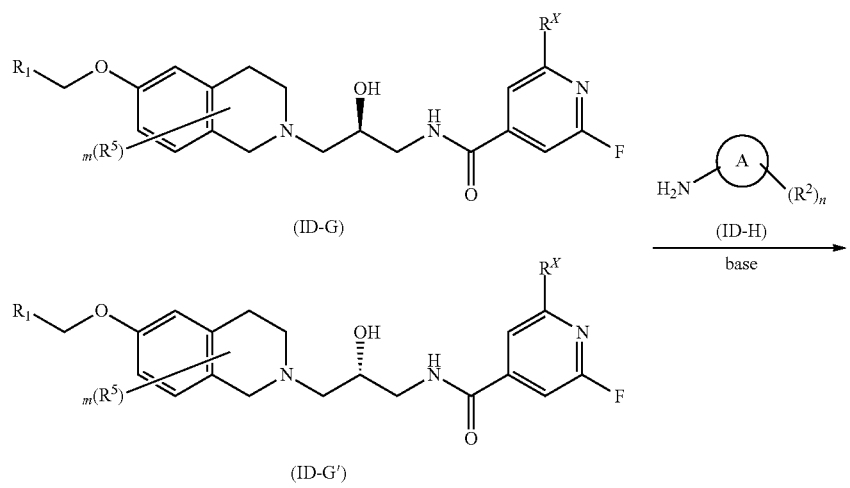

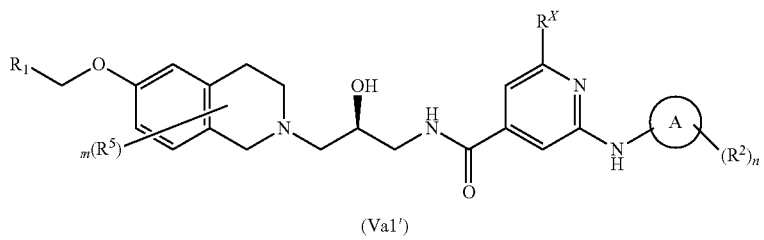
(Va1′)
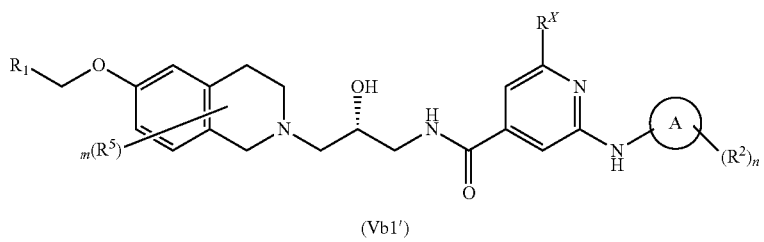
(Vb1′)
wherein X is a leaving group or hydroxy and variables $R^5$, $R^x$, $R^1$, $R^2$, m, and n are defined herein. In some embodiments, X is selected from —OH, Cl, Br, and I. In some embodiments X is Cl or Br. In other embodiments, wherein X is —OH.
General Procedure 1D-A
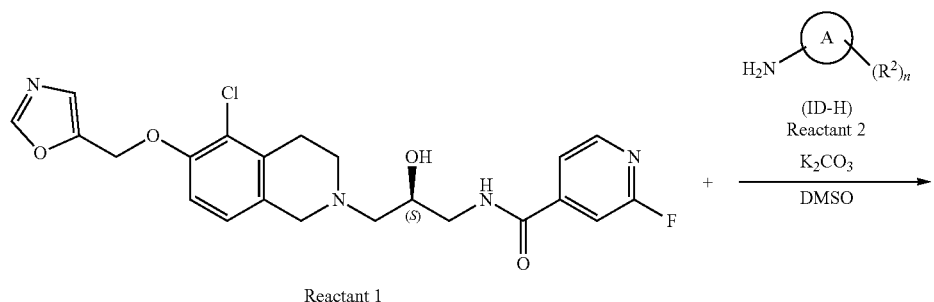
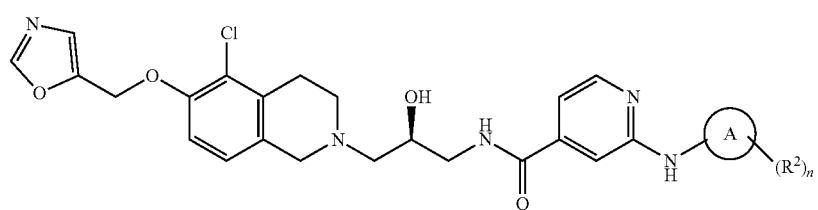

Reactant 1 and reactant 2 were dissolved in DMSO (1.5 ml). Potassium carbonate was added thereto and mixture was stirred at 105° C. for 20 hours. Reaction mixture was subjected to HPLC (column: SunFireC18 100×19 mm 5 um; 40-70% water-methanol, flow: 40 ml/min) affording product.

Example 1D1. (S)—N-(3-(5-chloro-6-(oxazol-5-ylmethoxy)-3N-dihydroisoquinolin-2(1H)-yl)-2-hydroxypropyl)-2-((4-fluorocyclohexyl)amino)isonicotinamide (Compound 311)

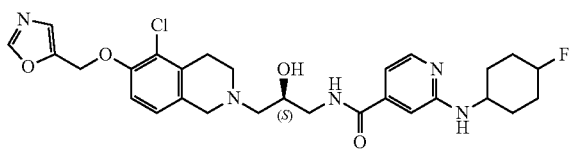

Prepared by general procedure 1D-A. Yield: 16.7 mg (9.19%). $^1$H NMR (400 MHz, CDCl$_3$) δ 1.27 (m, 1H), 1.66 (m, 4H), 1.88 (m, 1H), 2.08 (m, 2H), 2.56 (m, 3H), 2.73 (m, 1H), 2.89 (m, 3H), 3.39 (m, 1H), 3.55 (m, 1H), 3.74 (m, 3H), 3.99 (m, 1H), 4.61 (m, 1H), 4.78 (m, 1H), 5.10 (s, 2H), 6.68 (m, 1H), 6.75 (s, 1H), 6.87 (m, 3H), 7.13 (s, 1H), 7.89 (s, 1H), 8.07 (d, 1H). LCMS(ESI): [M+H]$^+$ m/z: calcd 558.0. found 549.2; Rt=0.869 min.

Example 1D2. (S)—N-(3-(5-chloro-6-(oxazol-5-ylmethoxy)-3,4-dihydroisoquinolin-2(1H)-yl)-2-hydroxypropyl)-2-((1-propionylazetidin-3-yl)amino)isonicotinamide (Compound 426)

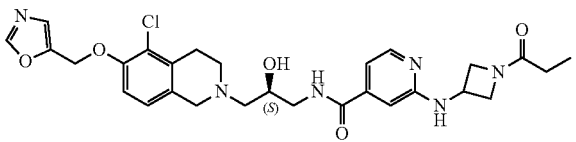

Prepared by general procedure 1-J. Yield: 3.3 mg (2.67%). $^1$H NMR (400 MHz, CDCl$_3$): δ (ppm) 1.11 (t, 3H), 1.57 (m, 1H), 2.10 (q, 2H), 2.57 (m, 2H), 2.75 (m, 1H), 2.91 (m, 3H), 3.41 (m, 1H), 3.55 (d, 1H), 3.68 (m, 1H), 3.73 (m, 1H), 3.86 (m, 2H), 4.00 (m, 1H), 4.38 (m, 1H), 4.47 (m, 1H), 4.61 (m, 1H), 5.11 (s, 3H), 6.78 (m, 2H), 6.86 (m, 2H), 6.94 (m, 1H), 7.14 (s, 1H), 7.89 (s, 1H), 8.10 (d, 1H). LCMS(ESI): [M+H]$^+$ m/z: calcd 569.1. found 570.2; Rt=0.870 min.

Example 1D2. (S)-2-((1-acetylazetidin-3-yl)amino)-N-(3-(5-chloro-6-(oxazol-5-ylmethoxy)-3,4-dihydroisoquinolin-2(1H)-yl)-2-hydroxypropyl)isonicotinamide (Compound 380)

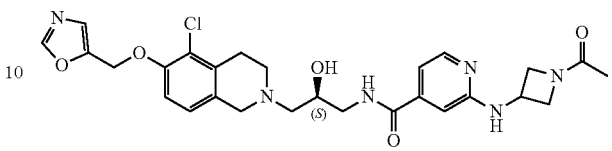

Prepared by general procedure 1D-A. Yield: 2.6 mg (2.16%). $^1$H NMR (400 MHz, CDCl$_3$): δ 1.87 (s, 3H), 2.59 (m, 2H), 2.78 (m, 1H), 2.89 (m, 2H), 2.95 (m, 1H), 3.43 (m, 1H), 3.58 (m, 1H), 3.70 (m, 1H), 3.79 (m, 2H), 3.85 (m, 1H), 3.92 (m, 1H), 4.01 (m, 1H), 4.38 (t, 1H), 4.49 (t, 1H), 4.62 (m, 1H), 5.07 (m, 1H), 5.11 (s, 2H), 6.80 (m, 2H), 6.87 (m, 2H), 6.95 (m, 1H), 7.15 (s, 1H), 7.89 (s, 1H), 8.11 (d, 1H). LCMS(ESI): [M+H]$^+$ m/z: calcd 555.0. found 556.2; Rt=0.830 min.

Example 1D3. (S)—N-(3-(5-chloro-6-(oxazol-5-ylmethoxy)-3,4-dihydroisoquinolin-2(1H)-yl)-2-hydroxypropyl)-2-((1-pivaloylpiperidin-4-yl)amino)isonicotinamide (Compound 432)

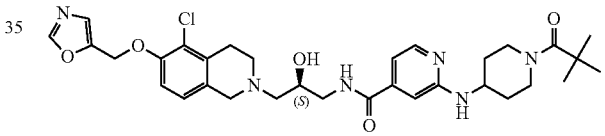

Prepared by general procedure 1D-A. Yield: 20 mg (14.74%). $^1$H NMR (400 MHz, CDCl$_3$): δ (ppm) 1.26 (s, 9H), 1.36 (m, 2H), 2.08 (m, 2H), 2.55 (m, 2H), 2.73 (m, 1H), 2.89 (m, 3H), 3.01 (t, 2H), 3.39 (m, 1H), 3.46 (s, 2H), 3.54 (d, 1H), 3.65 (m, 1H), 3.74 (d, 1H), 3.96 (m, 1H), 4.33 (d, 2H), 4.55 (d, 1H), 5.10 (s, 2H), 6.71 (d, 1H), 6.76 (s, 1H), 6.85 (m, 3H), 7.14 (s, 1H), 7.89 (s, 1H), 8.09 (d, 1H). LCMS(ESI): [M+H]$^+$ m/z: calcd 625.2. found 626.2; Rt=0.929 min.

Example 1D4. (S)—N-(3-(5-chloro-6-(oxazol-5-ylmethoxy)-3N-dihydroisoquinolin-2(1H)-yl)-2-hydroxypropyl)-2-((1-(3-meth ylbutanoyl)piperidin-4-yl)amino)isonicotinamide (Compound 443)

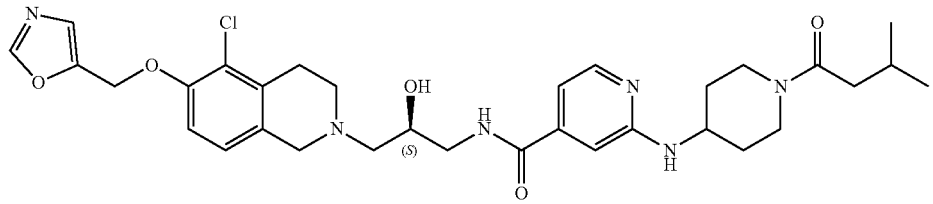

Prepared by general procedure 1D-A. Yield: 14 mg (10.32%). ¹H NMR (400 MHz, CDCl₃): δ (ppm) 0.95 (d, 6H), 1.34 (m, 2H), 2.09 (m, 3H), 2.21 (d, 2H), 2.56 (m, 2H), 2.73 (m, 1H), 2.89 (m, 4H), 3.18 (m, 1H), 3.40 (m, 1H), 3.54 (d, 1H), 3.60 (m, 1H), 3.68 (m, 1H), 3.76 (d, 1H), 3.85 (m, 1H), 3.97 (m, 2H), 4.53 (m, 2H), 5.11 (s, 2H), 6.72 (d, 1H), 6.77 (s, 1H), 6.84 (m, 3H), 7.14 (s, 1H), 7.89 (s, 1H), 8.10 (d, 1H). LCMS(ESI): [M+H]⁺ m/z: calcd 625.2. found 626.2; Rt=0.926 min.

Example 1D5. (S)—N-(3-(5-chloro-6-(oxazol-5-ylmethoxy)-3N-dihydroisoquinolin-2(1H)-yl)-2-hydroxypropyl)-2-((1-(cyclopropanecarbonyl)piperidin-4-yl)amino)isonicotinamide (Compound 366)

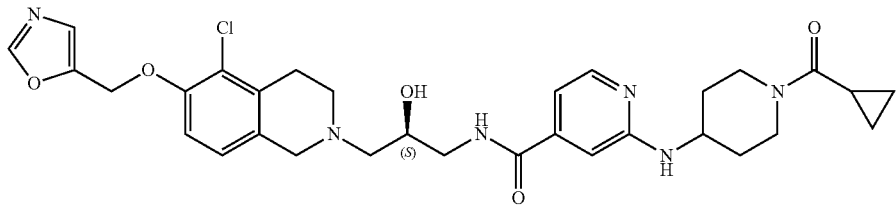

Prepared by general procedure 1D-A. Yield: 17 mg (12.86%). ¹H NMR (400 MHz, CDCl₃): δ (ppm) 0.73 (m, 2H), 0.95 (m, 2H), 1.73 (m, 1H), 1.90 (m, 1H), 2.03 (m, 1H), 2.13 (m, 1H), 2.55 (m, 2H), 2.73 (m, 1H), 2.88 (m, 5H), 3.27 (m, 1H), 3.39 (m, 1H), 3.53 (d, 1H), 3.69 (m, 3H), 3.98 (m, 2H), 4.15 (m, 1H), 4.47 (m, 1H), 4.66 (d, 1H), 5.10 (s, 2H), 6.69 (d, 1H), 6.77 (s, 1H), 6.82 (d, 1H), 6.86 (d, 1H), 6.99 (t, 1H), 7.13 (s, 1H), 7.88 (s, 1H), 8.06 (d, 1H). LCMS(ESI): [M+H]⁺ m/z: calcd 609.1. found 610.2; Rt=1.857 min.

Example 1D6. (S)—N-(3-(5-chloro-6-(oxazol-5-ylmethoxy)-3N-dihydroisoquinolin-2(1H)-yl)-2-hydroxypropyl)-2-((1-isobutylpiperidin-4-yl)amino)isonicotinamide (Compound 452)

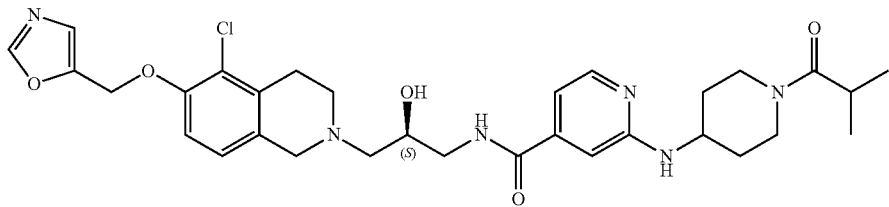

Prepared by general procedure 1D-A. Yield: 8 mg (6.03%). ¹H NMR (400 MHz, CDCl₃): δ (ppm) 1.12 (d, 6H), 1.38 (m, 2H), 2.07 (m, 1H), 2.15 (m, 1H), 2.55 (m, 2H), 2.74 (m, 1H), 2.81 (m, 2H), 2.89 (m, 4H), 3.19 (m, 1H), 3.39 (m, 1H), 3.54 (d, 2H), 3.75 (d, 1H), 3.95 (m, 3H), 4.51 (m, 2H), 5.11 (s, 2H), 6.72 (d, 1H), 6.77 (m, 2H), 6.86 (dd, 2H), 7.14 (s, 1H), 7.89 (s, 1H), 8.11 (d, 1H). LCMS(ESI): [M+H]⁺ m/z: calcd 611.1. found 612.2; Rt=0.885 min.

Example 1D7. (S)-2-((1-butyrylpiperidin-4-yl)amino)-N-(3-(5-chloro-6-(oxazol-5-ylmethoxy)-3,4-dihydroisoquinolin-2(1H)-yl)-2-hydroxypropyl)isonicotinamide (Compound 442)

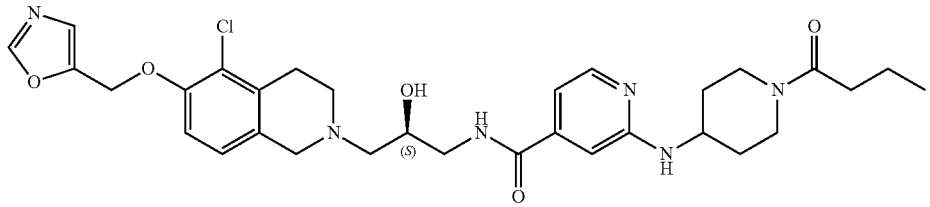

Prepared by general procedure 1D-A. Yield: 12 mg (9.05%). $^1$H NMR (400 MHz, CDCl$_3$): δ (ppm) 0.95 (t, 3H), 1.34 (m, 2H), 1.63 (m, 3H), 2.03 (d, 1H), 2.12 (d, 1H), 2.30 (t, 2H), 2.56 (m, 2H), 2.73 (m, 1H), 2.89 (m, 4H), 3.18 (m, 1H), 3.38 (m, 1H), 3.54 (d, 1H), 3.68 (m, 1H), 3.74 (d, 1H), 3.83 (d, 1H), 3.96 (m, 2H), 4.52 (t, 2H), 5.11 (s, 2H), 6.71 (d, 1H), 6.76 (s, 1H), 6.85 (m, 3H), 7.14 (s, 1H), 7.89 (s, 1H), 8.09 (d, 1H). LCMS(ESI): [M+H]$^+$ m/z: calcd 611.1. found 612.2; Rt=0.886 min.

Example 1D8. (S)-2-((1-butylpiperidin-4-yl)amino)-N-(3-(5-chloro-6-(oxazol-5-ylmethoxy)-3A-dihydroisoquinolin-2(1H)-yl-2-hydroxypropyl)isonicotinamide (Compound 429)

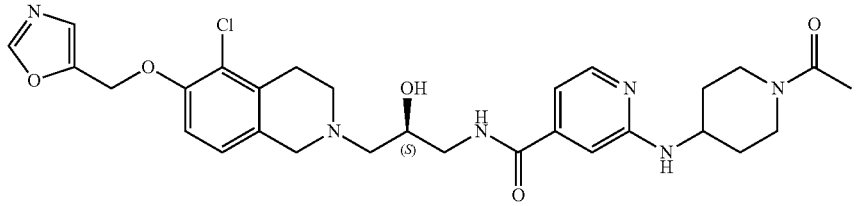

Prepared by general procedure 1D-A. Yield: 9 mg (7.11%). $^1$H NMR (400 MHz, CDCl$_3$): δ (ppm) 1.36 (m, 2H), 2.08 (m, 5H), 2.56 (m, 2H), 2.73 (m, 1H), 2.88 (m, 4H), 3.20 (m, 1H), 3.38 (m, 1H), 3.54 (d, 1H), 3.70 (m, 4H), 3.96 (m, 2H), 4.48 (d, 1H), 4.58 (d, 1H), 5.10 (s, 2H), 6.71 (d, 1H), 6.77 (s, 1H), 6.85 (dd, 2H), 6.92 (t, 1H), 7.13 (s, 1H), 7.89 (s, 1H), 8.08 (d, 1H). LCMS(ESI): [M+H]$^+$ m/z: calcd 583.1. found 584.2; Rt=0.809 min.

Example 1D9. N—((S)-3-(5-chloro-6-(oxazol-5-ylmethoxy)-3N-dihydroisoquinolin-2(1H)-yl)-2-hydroxypropyl)-2-(((1RNS)-4-(trifluoromethyl)cyclohexy)amino)isonicotinamide (Compound 483)

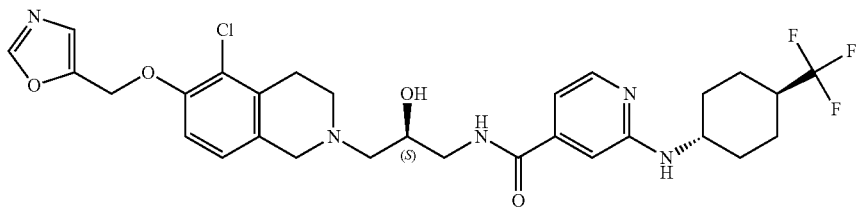

Prepared by general procedure 1D-A. Yield: 26 mg (13.14%). ¹H NMR (400 MHz, CDCl₃) δ 1.15 (m, 2H), 1.46 (m, 2H), 1.98 (m, 3H), 2.20 (m, 2H), 2.54 (m, 2H), 2.72 (m, 1H), 2.89 (m, 3H), 3.38 (m, 1H), 3.53 (m, 1H), 3.65 (m, 2H), 3.73 (m, 2H), 3.98 (m, 1H), 4.49 (d, 1H), 5.10 (s, 2H), 6.69 (d, 1H), 6.72 (s, 1H), 6.85 (m, 2H), 6.90 (m, 1H), 7.13 (s, 1H), 7.89 (s, 1H), 8.07 (d, 1H). LCMS(ESI): [M+H]⁺ m/z: calcd 608.1. found 609.2; Rt=0.947 min.

Example 1D10. N—((S)-3-(5-chloro-6-(oxazol-5-ylmethoxy)-3,4-dihydroisoquinolin-2(1H)-yl)-2-hydroxypropyl)-2-((3-fluorocycloheptyl)amino)isonicotinamide (Compound 322)

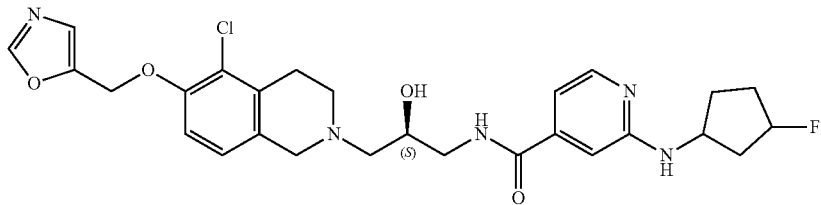

Prepared by general procedure 1D-A. Yield: 25.4 mg (14.35%). ¹H NMR (400 MHz, CDCl₃) δ 1.49 (m, 1H), 1.66 (m, 1H), 2.02 (m, 4H), 2.28 (m, 1H), 2.44 (m, 2H), 2.72 (m, 1H), 2.88 (m, 3H), 3.38 (m, 1H), 3.53 (d, 1H), 3.68 (m, 1H), 3.73 (m, 1H), 3.98 (m, 1H), 4.29 (h, 1H), 4.84 (m, 1H), 5.10 (m, 3H), 6.73 (m, 2H), 6.84 (m, 2H), 6.95 (m, 1H), 7.13 (s, 1H), 7.88 (s, 1H), 8.07 (d, 1H). LCMS(ESI): [M+H]⁺ m/z: calcd 544.0. found 545.2; Rt=0.846 min.

Example 1D11. (S)—N-(3-(5-chloro-6-(oxazol-5-ylmethoxy)-3,4-dihydroisoquinolin-2(1H)-yl)-2-hydroxypropyl)-2-((3,3-difluorocyclobutyl)amino)isonicotinamide (Compound 357)

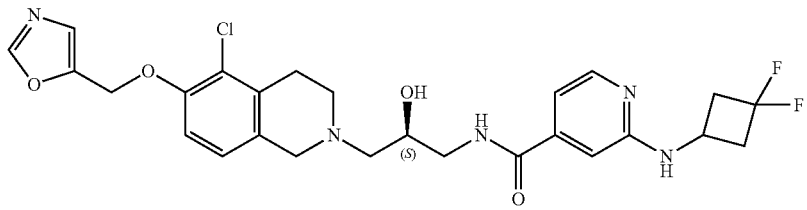

Prepared by general procedure 1D-A. Yield: 14.6 mg (8.19%). ¹H NMR (400 MHz, CDCl₃): δ (ppm) 2.49 (m, 4H), 2.74 (m, 1H), 2.90 (m, 3H), 3.06 (m, 2H), 3.39 (dt, 1H), 3.46 (s, 2H), 3.54 (d, 1H), 3.69 (m, 1H), 4.00 (m, 1H), 4.16 (m, 1H), 4.89 (d, 1H), 5.11 (s, 2H), 6.74 (s, 1H), 6.83 (m, 4H), 7.14 (s, 1H), 7.89 (s, 1H), 8.12 (d, 1H). LCMS(ESI): [M+H]⁺ m/z: calcd 548.0. found 549.2; Rt=0.838 min.

Example 1D12. N—((S)-3-(5-chloro-6-(oxazol-5-ylmethoxy)-3,4-dihydroisoquinolin-2(1H)-yl)-2-hydroxypropyl)-2-((3,3-difluorocyclopentyl)amino)isonicotinamide (Compound 316)

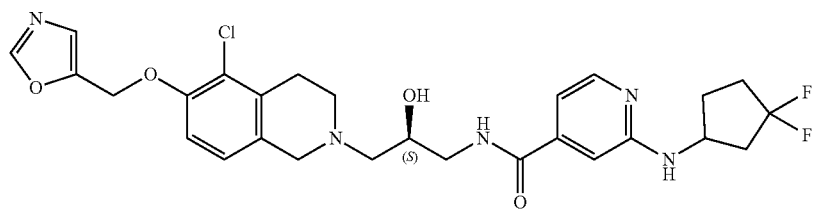

Prepared by general procedure 1D-A. Yield: 15.6 mg (8.53%). $^1$H NMR (400 MHz, CDCl$_3$) δ 1.76 (m, 2H), 1.94 (m, 1H), 2.11 (m, 1H), 2.25 (m, 2H), 2.55 (m, 2H), 2.63 (m, 1H), 2.73 (m, 1H), 2.89 (m, 3H), 3.40 (m, 1H), 3.54 (d, 1H), 3.72 (m, 2H), 3.99 (m, 1H), 4.37 (m, 1H), 4.74 (d, 1H), 5.10 (s, 2H), 6.75 (m, 2H), 6.85 (m, 3H), 7.14 (s, 1H), 7.89 (s, 1H), 8.10 (d, 1H). LCMS(ESI): [M+H]$^+$ m/z: calcd 562.0. found 563.2; Rt=0.912 min.

Example 1D13. (S)—N-(3-(5-chloro-6-(oxazol-5-ylmethoxy)-3,4-dihydroisoquinolin-2(1H)-yl)-2-hydroxypropyl)-2-((3-(difluoromethyl)cyclobutyl)amino)isonicotinamide (Compound 317)

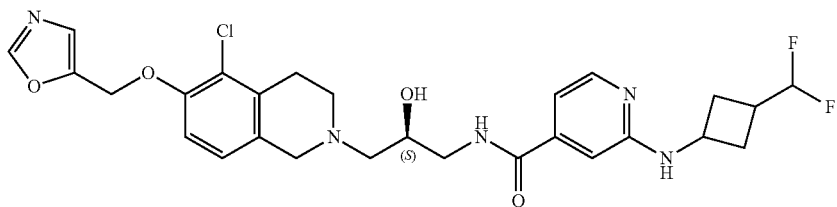

Prepared by general procedure 1D-A. Yield: 12.4 mg (6.78%). $^1$H NMR (400 MHz, CDCl$_3$) δ 1.90 (m, 1H), 2.05 (m, 1H), 2.56 (m, 5H), 2.73 (m, 1H), 2.91 (m, 3H), 3.39 (m, 1H), 3.54 (m, 1H), 3.66 (m, 1H), 3.72 (m, 2H), 3.99 (m, 1H), 4.25 (m, 1H), 4.86 (m, 1H), 5.10 (s, 2H), 5.74 (m, 1H), 6.71 (m, 2H), 6.84 (m, 3H), 7.14 (s, 1H), 7.89 (s, 1H), 8.09 (d, 1H). LCMS(ESI): [M+H]$^+$ m/z: calcd 562.0. found 563.2; Rt=0.888 min.

Example 1D14. (S)—N-(3-(6-((3H-pyrrol-4-yl)methoxy)-5-chloro-3N-dihydroisoquinolin-2(1H)-yl-2-hydroxypropyl-2-((1,1-difluorospiro[2.3]hexan-5-yl)amino)isonicotinamide (Compound 441)

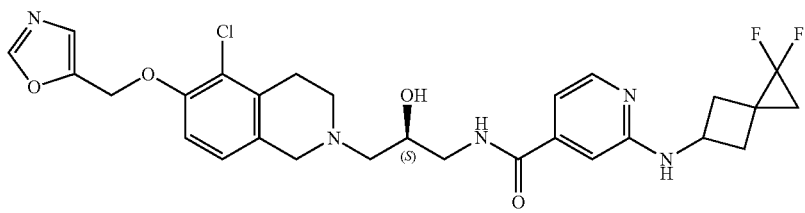

Prepared by general procedure 1D-A. Yield: 22 mg (11.78%). $^1$H NMR (400 MHz, CDCl$_3$): δ (ppm) 1.25 (m, 3H), 2.07 (m, 1H), 2.25 (m, 1H), 2.53 (m, 3H), 2.73 (m, 2H), 2.87 (m, 2H), 2.94 (m, 1H), 3.39 (m, 1H), 3.54 (d, 1H), 3.68 (m, 1H), 3.74 (d, 1H), 3.99 (m, 1H), 4.37 (m, 1H), 4.98 (t, 1H), 5.10 (s, 2H), 6.71 (d, 1H), 6.76 (m, 1H), 6.86 (m, 3H), 7.14 (s, 1H), 7.89 (s, 1H), 8.10 (d, 1H). LCMS(ESI): [M+H]$^+$ m/z: calcd 574.0. found 575.2; Rt=0.899 min.

Example 1D15. N—((S)-3-(5-chloro-6-(oxazol-5-ylmethoxy)-3,4-dihydroisoquinolin-2(1H)-yl)-2-hydroxypropyl-2-((3,3-difluorocyclohexyl)amino)isonicotinamide (Compound 347)

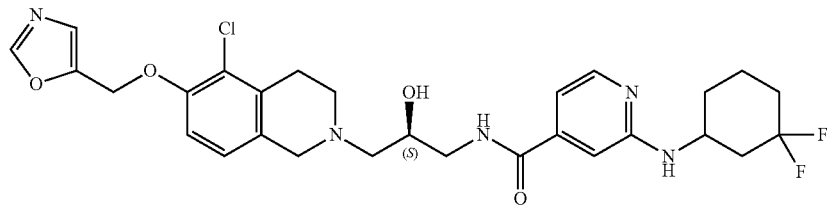

Prepared by general procedure 1D-A. Yield: 6.8 mg (3.63%). $^1$H NMR (400 MHz, CDCl$_3$): δ (ppm) 1.37 (m, 1H), 1.66 (m, 2H), 1.80 (m, 2H), 1.98 (m, 2H), 2.40 (m, 1H), 2.55 (m, 2H), 2.73 (m, 1H), 2.91 (m, 3H), 3.39 (m, 1H), 3.55 (m, 2H), 3.69 (d, 1H), 3.75 (d, 1H), 3.99 (m, 1H), 4.08 (m, 1H), 4.64 (d, 1H), 5.11 (s, 2H), 6.74 (m, 2H), 6.79 (t, 1H), 6.83 (d, 1H), 6.87 (d, 1H), 7.14 (s, 1H), 7.89 (s, 1H), 8.11 (d, 1H). LCMS(ESI): [M+H]$^+$ m/z: calcd 576.0. found 577.2; Rt=0.911 min.

Example 1D16. (S)—N-(3-(5-chloro-6-(oxazol-5-ylmethoxy)-3,4-dihydroisoquinolin-2(1H)-yl)-2-hydroxypropyl)-2-((4N-difluorocyclohexyl)amino)isonicotinamide (Compound 425)

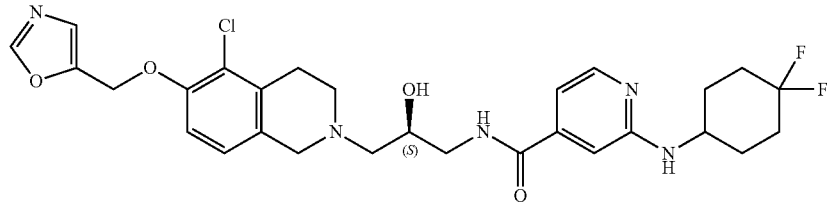

Prepared by general procedure 1D-A. Yield: 26.4 mg (14.08%). $^1$H NMR (400 MHz, CDCl$_3$): δ (ppm) 1.56 (m, 2H), 1.89 (m, 2H), 2.08 (m, 4H), 2.56 (m, 2H), 2.73 (m, 1H), 2.86 (m, 2H), 2.92 (m, 1H), 3.41 (m, 2H), 3.54 (d, 1H), 3.72 (m, 2H), 3.84 (m, 1H), 3.98 (s, 1H), 4.54 (d, 1H), 5.10 (s, 2H), 6.71 (d, 1H), 6.76 (s, 1H), 6.85 (m, 3H), 7.14 (s, 1H), 7.89 (s, 1H), 8.09 (d, 1H). LCMS(ESI): [M+H]$^+$ m/z: calcd 576.0. found 577.2; Rt=0.872 min.

General Procedure 1D-B

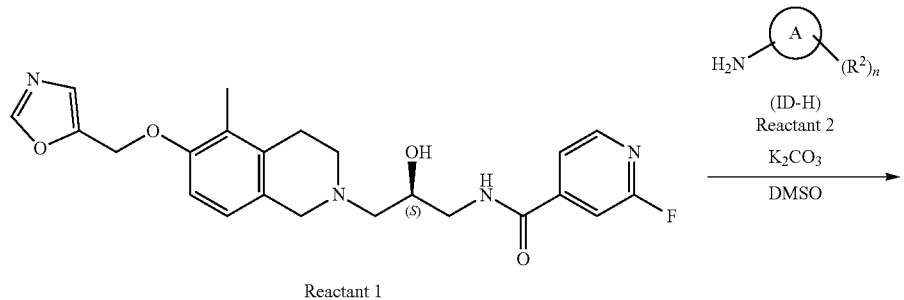

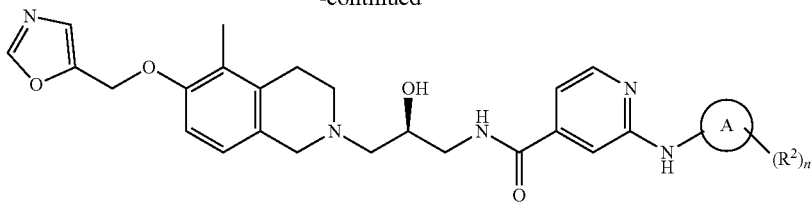

Reactant 1 and reactant 2 were dissolved in DMSO (3 mL). Potassium carbonate, anhydrous, 99% was added thereto and mixture was stirred at 100° C. for 12 hours in sealed tube. Obtained crude product in reaction mixture 3 ml in DMSO was purified by preparative RP-HPLC to afford product.

Example 1D17. (S)—N-(2-hydroxy-3-(5-methyl-6-(oxazol-5-ylmethoxy)-3N-dihydroisoquinolin-2(1H)-yl)propyl)-2-((1-pivaloylpiperidin-4-yl)amino)isonicotinamide (Compound 402)

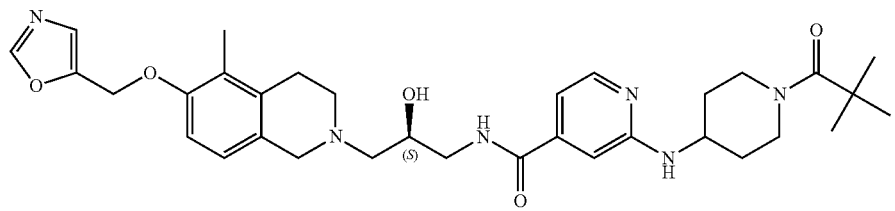

Prepared by general procedure 1D-B. Yield: 11.4 mg (8.3%). $^1$H NMR (400 MHz, CDCl$_3$) δ 1.27 (s, 9H), 1.36 (d, 2H), 2.07 (s, 5H), 2.55 (m, 1H), 2.59 (m, 1H), 2.74 (m, 2H), 2.92 (m, 1H), 3.03 (m, 2H), 3.40 (m, 1H), 3.46 (s, 2H), 3.55 (m, 1H), 3.67 (m, 1H), 3.75 (m, 1H), 3.98 (m, 2H), 4.33 (m, 2H), 4.53 (d, 1H), 5.03 (s, 2H), 6.70 (d, 1H), 6.77 (m, 2H), 6.83 (m, 1H), 6.93 (t, 1H), 7.11 (s, 1H), 7.88 (s, 1H), 8.07 (d, 1H).

Example 1D18. (S)—N-(2-hydroxy-3-(5-methyl-6-(oxazol-5-ylmethoxy)-3N-dihydroisoquinolin-2(1H)-yl)propyl)-2-((1-(3-methylbutanoyl)piperidin-4-yl)amino)isonicotinamide (Compound 447)

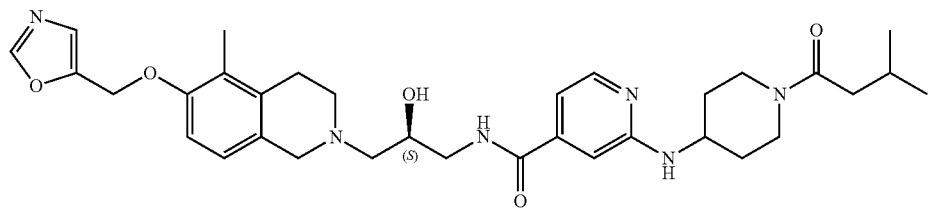

Prepared by general procedure 1D-B. Yield: 19.8 mg (14.13%). $^1$H NMR (CDCl$_3$, 400 MHz): δ (ppm) 0.95 (d, 6H), 1.32 (m, 2H), 2.00 (m, 1H), 2.06 (s, 3H), 2.11 (m, 1H), 2.20 (m, 2H), 2.51 (m, 2H), 2.73 (m, 2H), 2.81 (t, 1H), 2.90 (m, 1H), 3.17 (t, 1H), 3.38 (m, 1H), 3.43 (s, 3H), 3.54 (d, 1H), 3.67 (m, 1H), 3.74 (d, 1H), 3.83 (d, 1H), 3.95 (m, 2H), 4.51 (d, 1H), 4.60 (d, 1H), 5.02 (s, 2H), 6.69 (d, 1H), 6.76 (m, 2H), 6.82 (d, 1H), 7.05 (t, 1H), 7.10 (s, 1H), 7.88 (s, 1H), 8.04 (d, 1H). LCMS(ESI): [M+H]$^+$ m/z: calcd 604.7. found 605.4; Rt=0.868 min.

Example 1D19. (S)—N-(2-hydroxy-3-(5-methyl-6-(oxazol-5-ylmethoxy)-3N-dihydroisoquinolin-2(1H)-yl)propyl)-2-(Y3-(hydroxymethyl)cyclobutyl)amino)isonicotinamide (Compound 487)

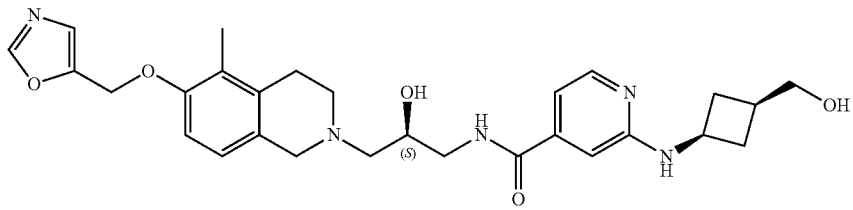

Prepared by general procedure 1D-B. Yield: 25 mg (21.11%). $^1$H NMR (500 MHz, CDCl$_3$) δ 1.76 (m, 4H), 2.10 (s, 3H), 2.30 (m, 1H), 2.58 (m, 4H), 2.78 (m, 3H), 2.98 (m, 1H), 3.42 (m, 1H), 3.62 (m, 3H), 3.74 (m, 1H), 3.81 (m, 1H), 4.04 (m, 1H), 4.12 (m, 1H), 4.85 (m, 1H), 5.06 (s, 2H), 6.79 (m, 3H), 6.86 (d, 1H), 6.92 (m, 1H), 7.14 (s, 1H), 7.91 (s, 1H), 8.11 (d, 1H). LCMS(ESI): [M+H]$^+$ m/z: calcd 521.6. found 523.2; Rt=1.872 min.

Example 1D20. (S)—N-(2-hydroxy-3-(5-methyl-6-(oxazol-5-ylmethoxy)-3N-dihydroisoquinolin-2(1H)-yl)propyl)-2-(spiro[2.3]hexan-5-ylamino)isonicotinamide (Compound 472)

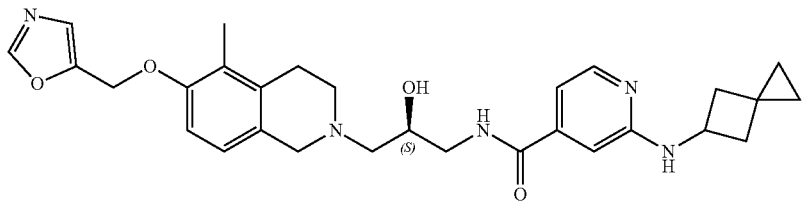

Prepared by general procedure 1D-B. Yield: 22.1 mg (18.81%). $^1$H NMR (500 MHz, CDCl$_3$) δ 0.44 (m, 2H), 0.51 (m, 2H), 2.10 (s, 3H), 2.16 (m, 2H), 2.45 (m, 2H), 2.59 (m, 2H), 2.76 (m, 3H), 2.95 (m, 1H), 3.44 (m, 1H), 3.57 (d, 1H), 3.72 (m, 1H), 3.78 (d, 1H), 4.03 (m, 1H), 4.37 (h, 1H), 5.03 (d, 1H), 5.05 (s, 2H), 6.72 (s, 1H), 6.74 (d, 1H), 6.80 (d, 1H), 6.85 (d, 1H), 6.96 (t, 1H), 7.14 (s, 1H), 7.91 (s, 1H), 8.10 (d, 1H). LCMS(ESI): [M+H]$^+$ m/z: calcd 517.6. found 518.4; Rt=0.879 min.

Example 1D21. (S)—N-(2-hydroxy-3-(5-methyl-6-(oxazol-5-ylmethoxy)-3,4-dihydroisoquinolin-2(1H)-yl)propyl)-2-(spiro[3.3]heptan-2-ylamino)isonicotinamide (Compound 473)

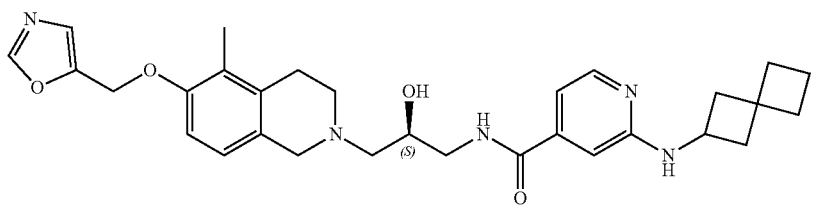

Prepared by general procedure 1D-B. Yield: 14.8 mg (12.26%). $^1$H NMR (500 MHz, CDCl$_3$) δ 1.68 (m, 1H), 1.84 (m, 4H), 1.96 (t, 2H), 2.09 (m, 5H), 2.57 (m, 4H), 2.78 (m, 3H), 2.98 (m, 1H), 3.44 (m, 1H), 3.60 (m, 1H), 3.73 (m, 1H), 3.81 (m, 1H), 4.03 (m, 2H), 4.80 (m, 1H), 5.06 (s, 2H), 6.69 (s, 1H), 6.73 (d, 1H), 6.83 (m, 3H), 7.14 (s, 1H), 7.91 (s, 1H), 8.10 (d, 1H). LCMS(ESI): [M+2H]$^+$ m/z: calcd 531.6. found 533.2; Rt=2.413 min.

Example 1D22. 2-(bicyclo[3.2.0]heptan-6-ylamino)-N—((S)-2-hydroxy-3-(5-methyl-6-(oxazol-5-yl-methoxy)-3,4-dihydroisoquinolin-2(1H)-yl)propyl) isonicotinamide (Compound 486)

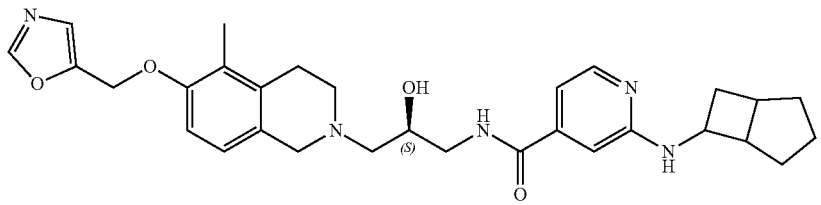

Prepared by general procedure 1D-B. Yield: 22 mg (17.97%). $^1$H NMR (500 MHz, CDCl$_3$) δ 1.54 (m, 4H), 1.82 (m, 3H), 2.01 (m, 2H), 2.10 (s, 3H), 2.57 (m, 3H), 2.78 (m, 4H), 2.98 (m, 1H), 3.44 (m, 1H), 3.60 (m, 2H), 3.73 (m, 1H), 3.81 (m, 1H), 4.04 (m, 1H), 4.95 (m, 1H), 5.06 (s, 2H), 6.63 (m, 1H), 6.75 (m, 1H), 6.82 (m, 3H), 7.14 (s, 1H), 7.91 (s, 1H), 8.11 (d, 1H). LCMS(ESI): [M+H]$^+$ m/z: calcd 531.6. found 533.2; Rt=2.385 min.

Example 1D23. 2-([1,1'-bi(cyclobutan)]-2-ylamino)-N—((S)-2-hydroxy-3-(5-methyl-6-(oxazol-5-yl-methoxy)-3,4-dihydroisoquinolin-2(1H)-yl)propyl) isonicotinamide (Compound 476)

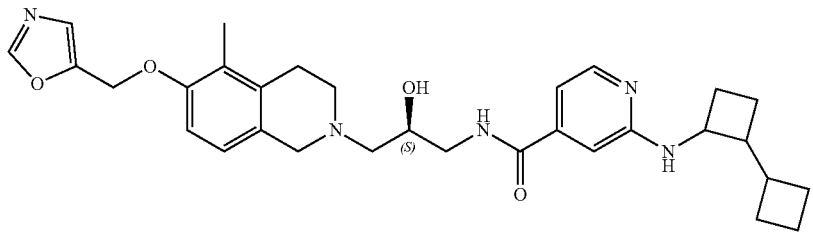

Prepared by general procedure 1D-B. Yield: 9.1 mg (7.19%). $^1$H NMR (500 MHz, CDCl$_3$) δ 1.40 (m, 1H), 1.66 (m, 5H), 1.85 (m, 2H), 1.97 (m, 2H), 2.10 (s, 3H), 2.22 (m, 1H), 2.35 (m, 1H), 2.46 (m, 1H), 2.59 (m, 2H), 2.76 (m, 3H), 2.97 (m, 1H), 3.43 (m, 1H), 3.58 (m, 1H), 3.73 (m, 1H), 3.81 (m, 2H), 4.03 (m, 1H), 4.86 (m, 1H), 5.06 (s, 2H), 6.72 (m, 2H), 6.80 (d, 2H), 6.86 (d, 1H), 7.14 (s, 1H), 7.91 (s, 1H), 8.09 (d, 1H). LCMS(ESI): [M+H]$^+$ m/z: calcd 545.7. found 546.4; Rt=2.549 min.

Example 1D24. (S)—N-(2-hydroxy-3-(5-methyl-6-(oxazol-5-ylmethoxy)-3N-dihydroisoquinolin-2(1H)-yl)propyl)-2-((1-propionylpiperidin-4-yl)amino)isonicotinamide (Compound 496)

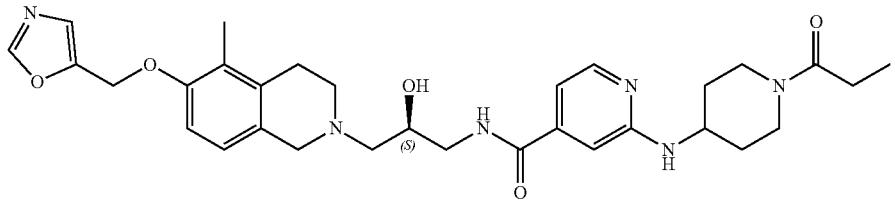

Prepared by general procedure 1D-B. Yield: 9.8 mg (7.37%). $^1$H NMR (400 MHz, CDCl$_3$) δ 1.14 (t, 3H), 1.35 (m, 2H), 2.08 (m, 6H), 2.35 (q, 2H), 2.58 (m, 2H), 2.75 (m, 3H), 2.84 (m, 1H), 2.94 (m, 1H), 3.18 (m, 1H), 3.40 (m, 1H), 3.57 (d, 1H), 3.69 (m, 1H), 3.80 (d, 2H), 3.97 (m, 2H), 4.51 (m, 2H), 5.03 (s, 2H), 6.72 (d, 1H), 6.77 (m, 2H), 6.83 (d, 1H), 6.88 (t, 1H), 7.11 (s, 1H), 7.88 (s, 1H), 8.08 (d, 1H). LCMS(ESI): [M+2H]$^+$ m/z: calcd 576.7. found 577.2; Rt=0.818 min.

Example 1D25. (S)—N-(2-hydroxy-3-(5-methyl-6-(oxazol-5-ylmethoxy)-3,4-dihydroisoquinolin-2(1H)-yl)propyl)-2-((1-propionylazetidin-3-yl)amino)isonicotinamide (Compound 495)

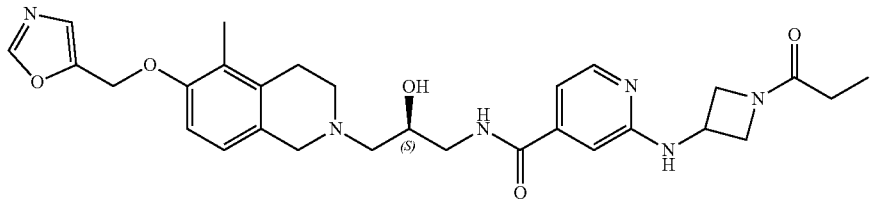

Prepared by general procedure 1D-B. Yield: 8 mg (6.42%). $^1$H NMR (CDCl$_3$, 400 MHz): δ (ppm) 1.10 (t, 3H), 2.10 (m, 5H), 2.60 (m, 2H), 2.76 (m, 3H), 2.92 (m, 1H), 3.48 (m, 1H), 3.60 (m, 2H), 3.75 (d, 1H), 3.88 (m, 2H), 4.01 (m, 1H), 4.37 (m, 1H), 4.46 (m, 1H), 4.62 (m, 1H), 5.03 (s, 2H), 5.44 (m, 1H), 6.69 (t, 1H), 6.77 (d, 1H), 6.83 (m, 2H), 7.12 (s, 1H), 7.30 (m, 1H), 7.89 (s, 1H), 8.00 (t, 1H). LCMS(ESI): [M+H]$^+$ m/z: calcd 548.6. found 549.0; Rt=0.838 min.

Example 1D25. (S)—N-(2-hydroxy-3-(5-methyl-6-(oxazol-5-ylmethoxy)-3N-dihydroisoquinolin-2(1H)-propyl)-2-((1-isobutylazetidin-3-yl)amino)isonicotinamide (Compound 550)

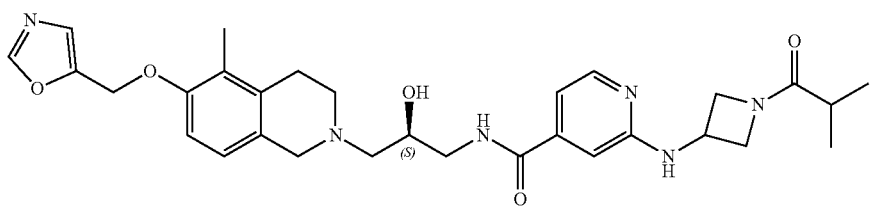

Prepared by general procedure 1D-B. 8.9 mg (6.78%). ¹H NMR (400 MHz, CDCl₃) δ 1.07 (m, 6H), 2.07 (s, 3H), 2.43 (m, 1H), 2.57 (m, 2H), 2.74 (m, 4H), 2.91 (m, 1H), 3.50 (m, 1H), 3.59 (m, 2H), 3.74 (m, 1H), 3.90 (m, 2H), 4.01 (m, 1H), 4.36 (m, 1H), 4.51 (m, 1H), 4.62 (m, 1H), 5.03 (s, 2H), 5.43 (m, 1H), 6.70 (t, 1H), 6.77 (d, 1H), 6.83 (m, 2H), 7.11 (s, 1H), 7.29 (m, 1H), 7.89 (s, 1H), 8.00 (m, 1H). LCMS(ESI): [M+H]⁺ m/z: calcd 562.6. found 563.2; Rt=0.875 min.

Example 1D26. (S)-2-((1-(cyclobutanecarbonyl)piperidin-4-yl)amino)-N-(2-hydroxy-3-(5-methyl-6-(oxazol-5-ylmethoxy)-3N-dihydroisoquinolin-2(1H)-yl)propyl)isonicotinamide (Compound 494)

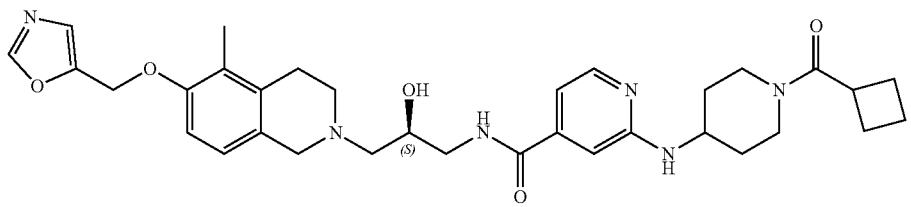

Prepared by general procedure 1D-B. Yield: 8.8 mg (6.29%). ¹H NMR (CDCl₃, 400 MHz): δ (ppm) 1.30 (m, 3H), 1.84 (m, 1H), 1.94 (m, 1H), 2.00 (m, 1H), 2.07 (s, 3H), 2.14 (m, 3H), 2.33 (m, 2H), 2.55 (m, 2H), 2.72 (m, 3H), 2.81 (m, 1H), 2.92 (m, 1H), 3.08 (t, 1H), 3.24 (m, 1H), 3.40 (m, 1H), 3.55 (d, 1H), 3.67 (m, 2H), 3.75 (d, 1H), 3.95 (m, 2H), 4.47 (m, 1H), 4.53 (d, 1H), 5.03 (s, 2H), 6.70 (d, 1H), 6.77 (d, 2H), 6.82 (d, 1H), 6.94 (t, 1H), 7.11 (s, 1H), 7.88 (s, 1H), 8.06 (d, 1H). LCMS(ESI): [M+2H]⁺ m/z: calcd 602.7. found 603.4; Rt=0.901 min.

Example 1D27. (S)-2-((1-butyrylpiperidin-4-yl)amino)-N-(2-hydroxy-3-(5-methyl-6-(oxazol-5-ylmethoxy)-3,4-dihydroisoquinolin-2(1H)-yl)propyl)isonicotinamide (Compound 470)

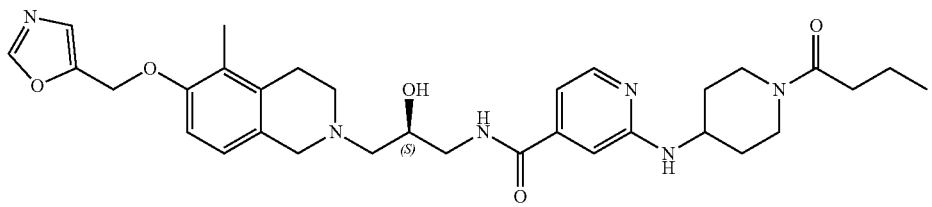

Prepared by general procedure 1D-B. Yield: 7.8 mg (5.64%). ¹H NMR (400 MHz, CDCl₃) δ 0.96 (t, 3H), 1.31 (m, 3H), 1.65 (m, 2H), 2.07 (m, 5H), 2.30 (m, 2H), 2.55 (m, 2H), 2.76 (m, 3H), 2.84 (m, 1H), 2.93 (m, 1H), 3.18 (m, 1H), 3.41 (m, 1H), 3.55 (m, 1H), 3.70 (m, 1H), 3.76 (m, 1H), 3.84 (m, 1H), 3.96 (m, 2H), 4.50 (m, 2H), 5.03 (s, 2H), 6.71 (d, 1H), 6.77 (m, 2H), 6.83 (d, 1H), 6.87 (m, 1H), 7.11 (s, 1H), 7.88 (s, 1H), 8.08 (d, 1H). LCMS(ESI): [M+H]⁺ m/z: calcd 590.7. found 591.4; Rt=1.956 min.

Example 1D28. (S)-2-((1-(cyclopropanecarbonyl)azetidin-3-yl)amino)-N-(2-hydroxy-3-(5-methyl-6-(oxazol-5-ylmethoxy)-3,4-dihydroisoquinolin-2(1H)-yl)propyl)isonicotinamide (Compound 588)

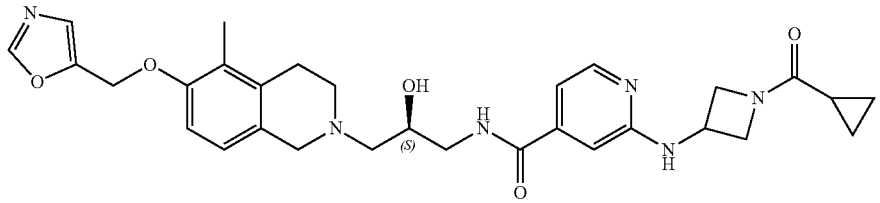

Prepared by general procedure 1D-B. Yield: 17.1 mg (13.43%). $^1$H NMR (CDCl$_3$, 400 MHz): δ (ppm) 0.73 (d, 2H), 0.95 (s, 2H), 1.39 (dd, 1H), 2.07 (s, 3H), 2.60 (d, 3H), 2.77 (d, 3H), 2.92 (m, 1H), 3.51 (m, 1H), 3.60 (m, 2H), 3.75 (m, 1H), 3.89 (m, 1H), 4.02 (m, 2H), 4.36 (m, 1H), 4.64 (m, 2H), 5.03 (s, 2H), 5.61 (m, 1H), 6.67 (t, 1H), 6.77 (d, 1H), 6.83 (d, 1H), 6.88 (s, 1H), 7.11 (s, 1H), 7.41 (m, 1H), 7.89 (s, 1H), 7.98 (m, 1H). LCMS(ESI): [M+H]$^+$ m/z: calcd 560.6. found 561.2; Rt=0.838 min.

Example 1D29. (S)-2-((1-acetylazetidin-3-yl)amino)-N-(2-hydroxy-3-(5-methyl-6-(oxazol-5-ylmethoxy)-3,4-dihydroisoquinolin-2(1H)-yl)propyl)isonicotinamide (Compound 512)

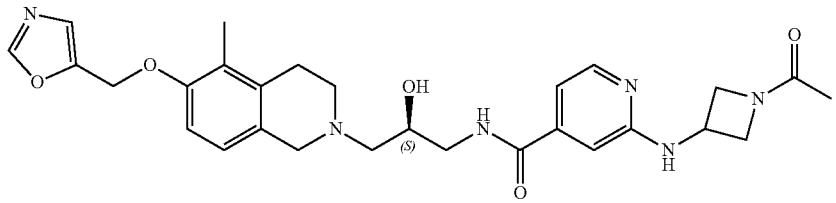

Prepared by general procedure 1D-B. Yield: 11.8 mg (9.47%). $^1$H NMR (400 MHz, CDCl$_3$) δ 1.86 (s, 3H), 2.06 (s, 3H), 2.59 (m, 2H), 2.74 (m, 3H), 2.91 (m, 1H), 3.45 (s, 1H), 3.49 (m, 1H), 3.59 (m, 2H), 3.72 (m, 1H), 3.88 (m, 2H), 4.00 (m, 1H), 4.36 (t, 1H), 4.47 (t, 1H), 4.61 (m, 1H), 5.03 (s, 2H), 5.45 (m, 1H), 6.70 (t, 1H), 6.77 (d, 1H), 6.84 (m, 2H), 7.11 (s, 1H), 7.33 (m, 1H), 7.89 (s, 1H), 7.99 (dd, 1H). LCMS(ESI): [M+H]$^+$ m/z: calcd 534.6. found 535.2; Rt=0.800 min.

Example 1D30. (S)-2-((1-(cyclopropanecarbonyl)piperidin-4-yl)amino)-N-(2-hydroxy-3-(5-methyl-6-(oxazol-5-ylmethoxy)-3N-dihydroisoquinolin-2(1H)-yl)propyl)isonicotinamide (Compound 484)

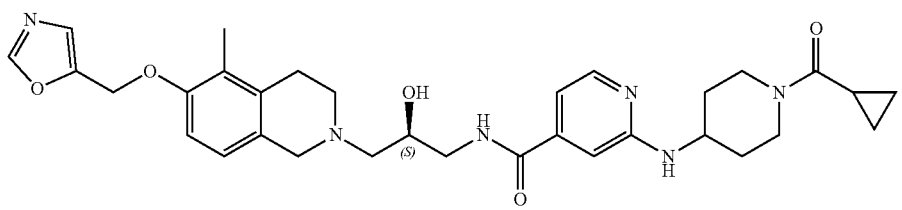

Prepared by general procedure 1D-B. Yield: 8.8 mg (6.58%). $^1$H NMR (400 MHz, CDCl$_3$) δ 0.75 (m, 2H), 0.96 (m, 2H), 1.39 (m, 2H), 1.74 (m, 1H), 2.02 (m, 1H), 2.07 (s, 3H), 2.14 (m, 1H), 2.56 (m, 3H), 2.74 (m, 3H), 2.92 (m, 2H), 3.28 (m, 1H), 3.40 (m, 1H), 3.55 (m, 1H), 3.67 (m, 1H), 3.75 (m, 1H), 3.98 (m, 2H), 4.18 (m, 1H), 4.54 (m, 2H), 5.03 (s, 2H), 6.71 (d, 1H), 6.77 (m, 2H), 6.83 (m, 1H), 6.93 (t, 1H), 7.11 (s, 1H), 7.88 (s, 1H), 8.07 (d, 1H). LCMS(ESI): [M+H]$^+$ m/z: calcd 588.7. found 589.2; Rt=0.827 min.

Example 1D31. (S)—N-(2-hydroxy-3-(5-methyl-6-(oxazol-5-ylmethoxy)-3N-dihydroisoquinolin-2(1H)-yl)propyl-2-((1-isobutylpiperidin-4-yl)amino)isonicotinamide (Compound 427)

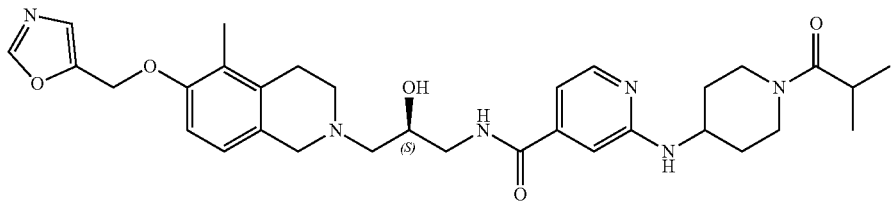

Prepared by general procedure 1D-B. Yield: 8.4 mg (6.08%). $^1$H NMR (CDCl$_3$, 500 MHz): δ (ppm) 1.14 (d, 6H), 1.38 (m, 2H), 2.06 (m, 1H), 2.10 (s, 4H), 2.18 (m, 1H), 2.56 (m, 2H), 2.75 (m, 3H), 2.84 (m, 2H), 2.96 (m, 1H), 3.22 (t, 1H), 3.42 (m, 1H), 3.57 (d, 1H), 3.72 (m, 1H), 3.79 (d, 1H), 3.98 (m, 3H), 4.48 (d, 1H), 4.57 (m, 1H), 5.05 (s, 2H), 6.75 (d, 1H), 6.80 (m, 2H), 6.85 (m, 2H), 7.13 (s, 1H), 7.91 (s, 1H), 8.12 (d, 1H). LCMS(ESI): [M+H]$^+$ m/z: calcd 590.7. found 591.2; Rt=0.827 min.

Example 1D32. (S)—N-(2-hydroxy-3-(5-methyl-6-(oxazol-5-ylmethoxy)-3N-dihydroisoquinolin-2(1H)-yl)propyl)-2-((1-(3-methylbutanoyl)azetidin-3-yl)amino)isonicotinamide (Compound 522)

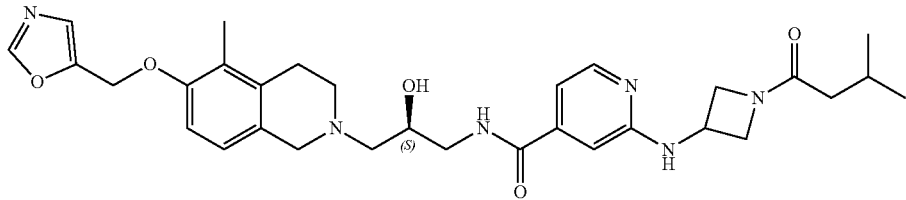

Prepared by general procedure 1D-B. Yield: 13.8 mg (10.54%). $^1$H NMR (400 MHz, CDCl$_3$) δ 0.92 (m, 6H), 1.95 (m, 2H), 2.07 (m, 4H), 2.59 (m, 2H), 2.74 (m, 4H), 2.91 (m, 1H), 3.50 (m, 1H), 3.58 (m, 2H), 3.74 (m, 1H), 3.89 (m, 2H), 4.01 (m, 1H), 4.36 (m, 1H), 4.47 (m, 1H), 4.59 (m, 1H), 5.03 (s, 2H), 5.50 (m, 1H), 6.69 (m, 1H), 6.77 (d, 1H), 6.83 (m, 2H), 7.11 (s, 1H), 7.35 (m, 1H), 7.89 (s, 1H), 7.99 (m, 1H). LCMS(ESI): [M+H]$^+$ m/z: calcd 576.6. found 577.2; Rt=0.920 min.

Example 1D33. (S)—N-(2-hydroxy-3-(5-methyl-6-(oxazol-5-ylmethoxy)-3N-dihydroisoquinolin-2(1H)-yl)propyl)-2-((1-(methylsulfonyl)piperidin-4-yl)amino)isonicotinamide (Compound 386)

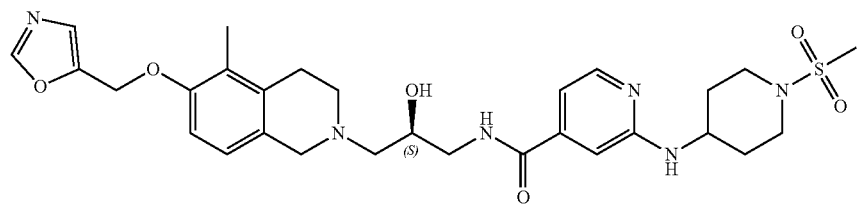

Prepared by general procedure 1D-B. Yield: 15.5 mg (11.4%). ¹H NMR (400 MHz, CDCl₃) δ 1.57 (m, 2H), 2.07 (s, 3H), 2.13 (m, 2H), 2.55 (m, 3H), 2.73 (m, 3H), 2.78 (s, 3H), 2.88 (m, 3H), 3.41 (m, 1H), 3.55 (m, 1H), 3.68 (m, 1H), 3.73 (m, 2H), 3.87 (m, 1H), 3.99 (m, 1H), 4.54 (d, 1H), 5.03 (s, 2H), 6.72 (m, 1H), 6.78 (m, 4H), 7.01 (t, 1H), 7.11 (s, 1H), 7.89 (s, 1H), 8.06 (d, 1H). LCMS(ESI): [M+H]⁺ m/z: calcd 598.7. found 599.2; Rt=0.841 min.

Example 1D34. (S)-2-((1-(cyclobutanecarbonyl)azetidin-3-yl)amino)-N-(2-hydroxy-3-(5-methyl-6-(oxazol-5-ylmethoxy)-3N-dihydroisoquinolin-2(1H)-yl)propyl)isonicotinamide (Compound 586)

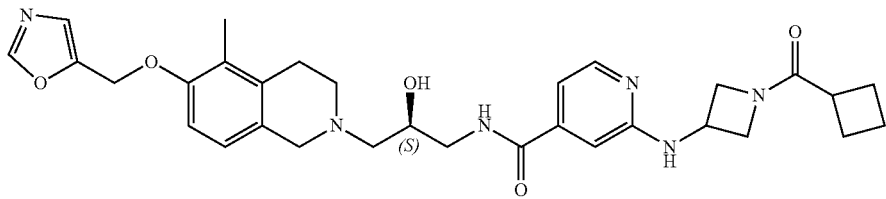

Prepared by general procedure 1D-B. Yield: 5.7 mg (4.23%). ¹H NMR (CDCl₃, 400 MHz): δ (ppm) 1.85 (m, 1H), 1.91 (m, 1H), 2.05 (s, 5H), 2.28 (m, 2H), 2.59 (s, 2H), 2.72 (m, 2H), 2.79 (m, 2H), 2.91 (m, 1H), 3.02 (m, 2H), 3.47 (m, 1H), 3.69 (m, 2H), 3.83 (m, 2H), 4.10 (m, 1H), 4.37 (m, 2H), 4.60 (m, 1H), 5.03 (s, 2H), 5.47 (m, 1H), 6.79 (m, 3H), 6.87 (s, 1H), 7.11 (s, 1H), 7.43 (m, 1H), 7.89 (s, 1H), 8.04 (d, 1H). LCMS(ESI): [M+H]⁺ m/z: calcd 574.6. found 575.2; Rt=0.882 min.

Example 1D35. (S)-2-((1-butyrylazetidin-3-yl)amino)-N-(2-hydroxy-3-(5-methyl-6-(oxazol-5-ylmethoxy)-3,4-dihydroisoquinolin-2(1H)-yl)propyl)isonicotinamide (Compound 551)

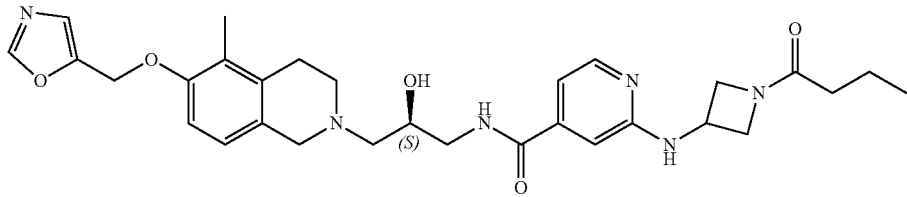

Prepared by general procedure 1D-B. Yield: 14.7 mg (11.23%). ¹H NMR (400 MHz, CDCl₃) δ 0.91 (d, 3H), 1.21 (m, 2H), 1.61 (q, 2H), 2.06 (m, 5H), 2.57 (m, 1H), 2.74 (m, 3H), 2.90 (m, 1H), 3.50 (m, 1H), 3.58 (m, 2H), 3.74 (m, 1H), 3.88 (m, 2H), 4.00 (m, 1H), 4.35 (m, 1H), 4.46 (m, 1H), 4.61 (m, 1H), 5.03 (s, 2H), 5.53 (m, 1H), 6.68 (t, 1H), 6.77 (d, 1H), 6.83 (m, 2H), 7.11 (s, 1H), 7.37 (m, 1H), 7.89 (s, 1H), 7.98 (m, 1H). LCMS(ESI): [M+H]⁺ m/z: calcd 562.6. found 563.2; Rt=0.878 min.

Example 1D36. N—((S)-2-hydroxy-3-(5-methyl-6-(oxazol-5-ylmethoxy)-3,4-dihydroisoquinolin-2(1H)-yl)propyl)-2-(((1r,3S)-3-hydroxycyclobutyl)amino)isonicotinamide (Compound 552)

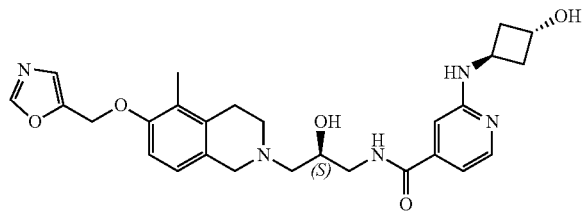

Prepared by general procedure 1D-B. Yield: 46.4 mg (42.13%). $^1$H NMR (500 MHz, DMSO-$d_6$+CCl$_4$) δ 2.04 (s, 3H), 2.16 (m, 6H), 2.71 (m, 2H), 2.80 (m, 2H), 3.25 (m, 1H), 3.41 (m, 1H), 3.62 (m, 2H), 3.89 (m, 1H), 4.20 (m, 1H), 4.29 (m, 1H), 4.61 (m, 1H), 4.67 (d, 1H), 5.07 (s, 2H), 6.60 (d, 1H), 6.67 (d, 1H), 6.72 (s, 1H), 6.83 (m, 2H), 7.15 (s, 1H), 7.86 (d, 1H), 8.16 (s, 1H), 8.31 (br.s, 1H). LCMS(ESI): [M+H]$^+$ m/z: calcd 507.6. found 508.2; Rt=0.705 min.

Example 1D37. N—((S)-2-hydroxy-3-(5-methyl-6-(oxazol-5-ylmethoxy)-3N-dihydroisoquinolin-2(1H)-yl)propyl)-2-(((1r,3S)-3-(hydroxymethyl)cyclobutyl)amino)isonicotinamide (Compound 537)

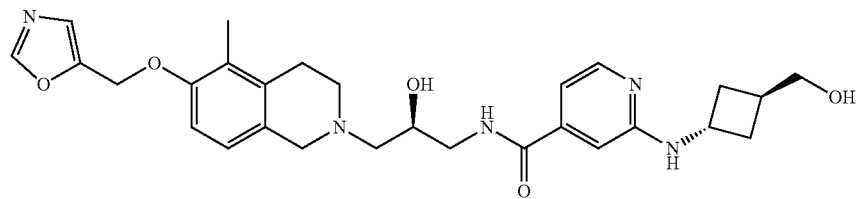 [SMILES: Cc1c(OCc2cnco2)ccc2c1CCN(C[C@@H](O)CNC(=O)c1ccnc(N[C@H]3C[C@H](CO)C3)c1)C2]

Prepared by general procedure 1D-B. Yield: 9.5 mg (8.19%). $^1$H NMR (500 MHz, CDCl$_3$) δ 2.03 (m, 3H), 2.11 (s, 3H), 2.36 (m, 2H), 2.50 (m, 1H), 2.68 (m, 2H), 2.83 (m, 3H), 3.04 (m, 1H), 3.46 (m, 1H), 3.74 (m, 5H), 3.87 (m, 1H), 4.09 (m, 1H), 4.26 (m, 1H), 4.93 (m, 1H), 5.07 (s, 2H), 6.72 (s, 1H), 6.83 (m, 3H), 7.06 (m, 1H), 7.15 (s, 1H), 7.92 (s, 1H), 8.12 (d, 1H). LCMS(ESI): [M+H]$^+$ m/z: calcd 521.3. found 522.4; Rt=0.751 min.

Example 1D38. N-[(2S)-2-hydroxy-3-{5-methyl-6-[(1,3-oxazol-5-yl)methoxy]-1,2,3,4-tetrahydroisoquinolin-2-yl}propyl]-2-{(1s,3s)-3-methoxycyclobutyl]amino}pyridine-4-carboxamide (Compound 535)

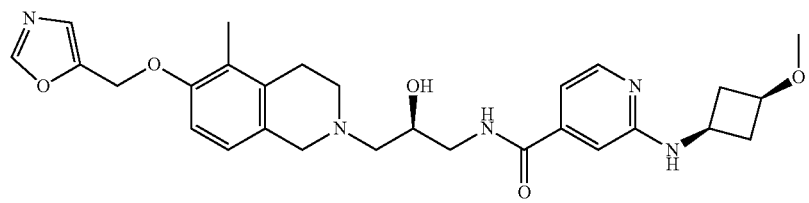 [SMILES: CO[C@H]1C[C@@H](Nc2cc(C(=O)NC[C@H](O)CN3CCc4c(ccc(OCc5cnco5)c4C)C3)ccn2)C1]

Prepared by general procedure 1D-B. Yield: 20.8 mg (18.10%). $^1$H NMR (400 MHz, CDCl$_3$) δ (ppm) 1.78 (m, 2H), 2.07 (s, 3H), 2.55 (m, 2H), 2.73 (m, 3H), 2.83 (m, 2H), 2.92 (m, 1H), 3.23 (s, 3H), 3.45 (m, 2H), 3.54 (d, 1H), 3.66 (m, 2H), 3.75 (d, 1H), 3.83 (m, 1H), 3.99 (m, 1H), 4.81 (d, 1H), 5.03 (s, 2H), 6.71 (m, 2H), 6.77 (d, 1H), 6.83 (d, 1H), 6.92 (t, 1H), 7.11 (s, 1H), 7.88 (s, 1H), 8.06 (d, 1H). LCMS(ESI): [M+H]$^+$ m/z: calcd 521.3. found 522.3; Rt=0.789 min.

Example 1D39. N-[(2S)-2-hydroxy-3-{5-methyl-6-[(1,3-oxazol-5-yl)methoxy]-1,2,3,4-tetrahydroisoquinolin-2-yl}propyl]-2-{[(1r,3r)-3-methoxycyclobutyl]amino}pyridine-4-carboxamide (Compound 591)

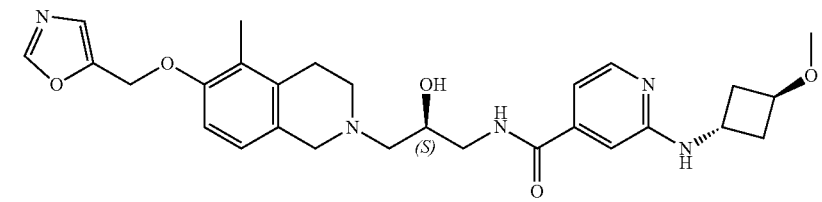

Prepared by general procedure 1D-B. Yield: 20.9 mg (18.47%). $^1$H NMR (400 MHz, CDCl$_3$) δ (ppm) 2.06 (s, 3H), 2.13 (m, 2H), 2.43 (m, 2H), 2.56 (m, 2H), 2.73 (m, 3H), 2.93 (m, 1H), 3.23 (s, 3H), 3.39 (m, 2H), 3.55 (d, 1H), 3.70 (m, 1H), 3.76 (d, 1H), 4.04 (m, 2H), 4.19 (m, 1H), 4.95 (d, 1H), 5.02 (s, 2H), 6.65 (s, 1H), 6.75 (m, 2H), 6.82 (d, 1H), 6.95 (t, 1H), 7.10 (s, 1H), 7.88 (s, 1H), 8.07 (d, 1H). LCMS(ESI): [M+H]$^+$ m/z: calcd 521.3. found 522.2; Rt=0.793 min.

Example 1D40. (S)-2-(bicyclo[1.1.1]pentan-1-ylamino)-N-(2-hydroxy-3-(5-methyl-6-(oxazol-5-ylmethoxy)-3N-dihydroisoquinolin-2(1H)-yl)propyl) isonicotinamide (Compound 514)

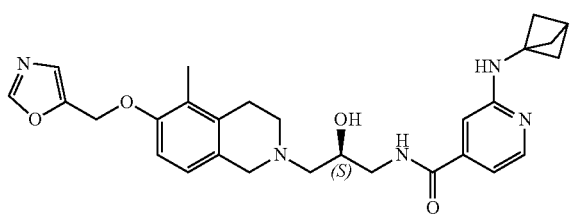

Prepared by general procedure 1D-B. Yield: 19.3 mg (17.35%). $^1$H NMR (400 MHz, CDCl$_3$) δ (ppm) 2.07 (s, 3H), 2.12 (s, 6H), 2.56 (m, 2H), 2.73 (m, 3H), 2.92 (m, 1H), 3.38 (m, 1H), 3.45 (s, 1H), 3.56 (m, 1H), 3.70 (m, 3H), 4.00 (m, 1H), 5.03 (s, 2H), 5.31 (s, 1H), 6.76 (m, 2H), 6.82 (d, 1H), 6.89 (t, 1H), 6.97 (s, 1H), 7.11 (s, 1H), 7.88 (s, 1H), 8.05 (d, 1H). LCMS(ESI): [M+H]$^+$ m/z: calcd 503.3. found 504.2; Rt=0.877 min.

Example 1D41. 2-1(1-acetyl-4-piperidyl)amino]-N-[(2S)-2-hydroxy-3-(5-methyl-6-(oxazol-5-ylmethoxy)-3,4-dihydro-1H-isoquinolin-2-yl]propyl] pyridine-4-carboxamide (Compound 517Compound 517)

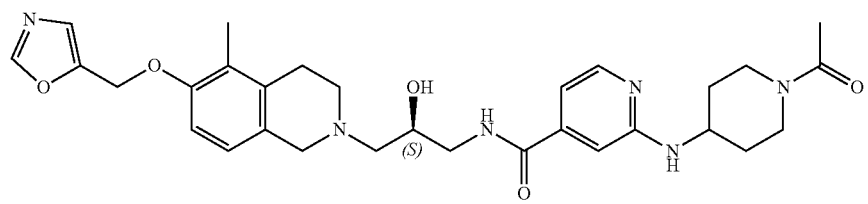

Prepared by general procedure 1D-B. Yield: 14.6 mg (11.96%). $^1$H NMR (500 MHz, CDCl$_3$) δ (ppm) 5 1.35 (q, 2H), 2.07 (m, 7H), 2.55 (tt, 2H), 2.73 (m, 3H), 2.81 (t, 2H), 2.91 (m, 1H), 3.20 (m, 1H), 3.41 (m, 1H), 3.45 (s, 1H), 3.53 (m, 1H), 3.69 (m, 1H), 3.74 (m, 2H), 3.96 (m, 2H), 4.50 (d, 1H), 4.60 (d, 1H), 5.02 (s, 2H), 6.68 (d, 1H), 6.76 (m, 2H), 6.81 (d, 1H), 7.04 (t, 1H), 7.10 (s, 1H), 7.88 (s, 1H), 8.05 (d, 1H). LCMS(ESI): [M+H]$^+$ m/z: calcd 562.3. found 563.2; Rt=0.781 min.

General Procedure 1D-C

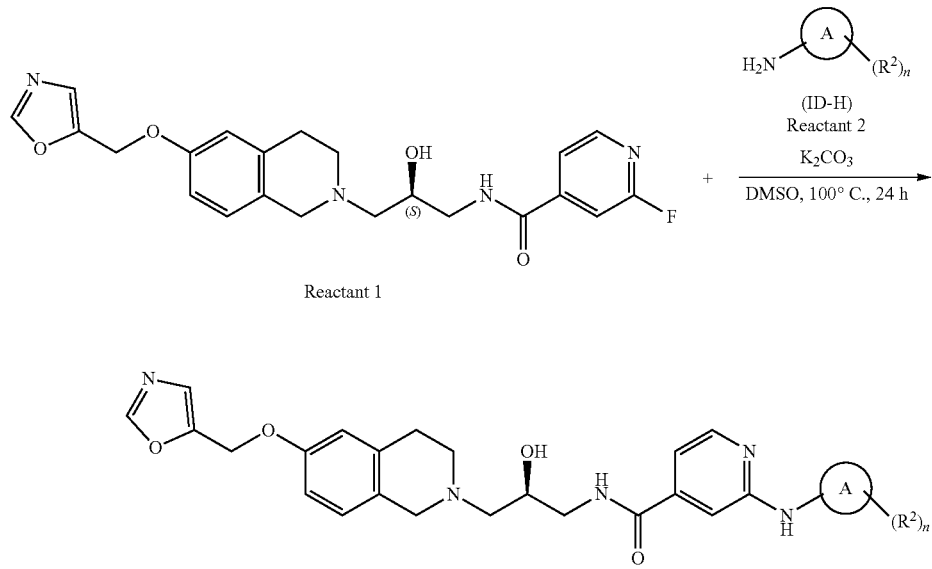

Potassium carbonate (5.0 equiv) was added to the solution of Reactant 1 (3.0 equiv) and Reactant 2 (1.0 equiv) in DMSO (1.5 mL). The reaction mixture was stirred at 100° C. for 24 h. After the completion of the reaction, monitored by NMR, the resulting mixture was subjected to HPLC (column: SunFire C18 100*19 mm 5 um; 40-70% water-methanol, flow: 40 mL/min) to afford pure product.

Example 1D42. N-[(2S)-2-hydroxy-3-[6-(oxazol-5-ylmethoxy)-3,4-dihydro-1H-isoquinolin-2-yl]propyl]-2-[(1-methylsulfonyl-4-piperidyl)amino]pyridine-4-carboxamide (Compound 430)

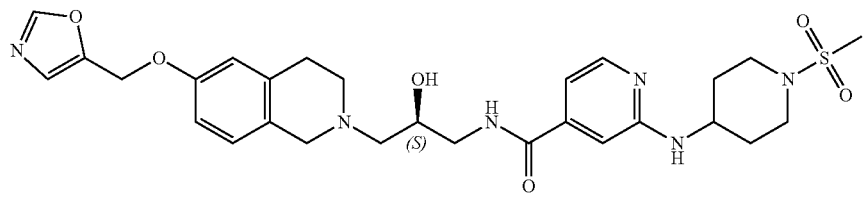

Prepared by general procedure 1D-C. Yield: 7.9 mg (3.8%). $^1$H NMR (Chloroform-d, 400 MHz): δ (ppm) 1.56 (m, 2H), 2.15 (m, 2H), 2.58 (m, 2H), 2.69 (m, 1H), 2.79 (s, 3H), 2.88 (m, 5H), 3.39 (m, 1H), 3.55 (d, 1H), 3.74 (m, 5H), 3.88 (m, 1H), 4.00 (m, 1H), 4.47 (d, 1H), 5.03 (s, 2H), 6.70 (d, 1H), 6.75 (m, 3H), 6.88 (t, 1H), 6.93 (d, 1H), 7.13 (s, 1H), 7.89 (s, 1H), 8.09 (d, 1H). LCMS(ESI): [M+H]$^+$ m/z: calcd 584.2. found 585.4; Rt=1.65 min.

Example 1D43. 2-1(1-acetylazetidin-3-yl)amino]-N-[(2S)-2-hydroxy-3-[6-(oxazol-5-ylmethoxy)-3,4-dihydro-1H-isoquinolin-2-yl]propyl]pyridine-4-carboxamide (Compound 451)

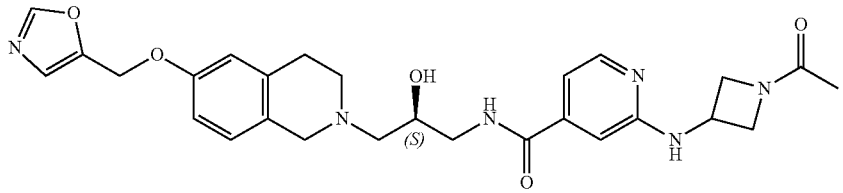

Prepared by general procedure 1D-C. Yield: 20.0 mg 10.9(%). $^1$H NMR (DMSO-d$_6$, 500 MHz): δ (ppm) 1.77 (s, 3H), 2.54 (m, 2H), 2.76 (m, 2H), 2.83 (m, 2H), 3.23 (m, 1H), 3.44 (m, 1H), 3.60 (m, 2H), 3.73 (m, 1H), 3.91 (m, 2H), 4.14 (t, 1H), 4.40 (t, 1H), 4.54 (m, 1H), 4.59 (m, 1H), 5.06 (s, 2H), 6.72 (m, 2H), 6.80 (d, 1H), 6.86 (s, 1H), 6.92 (d, 1H), 7.16 (s, 1H), 7.19 (d, 1H), 7.92 (d, 1H), 8.16 (s, 1H), 8.34 (t, 1H). LCMS(ESI): [M+H]$^+$ m/z: calcd 520.2. found 521.2; Rt=1.62 min.

Example 1D44. N-[(2S)-2-hydroxy-3-[6-(oxazol-5-ylmethoxy)-3,4-dihydro-1H-isoquinolin-2-yl]propyl]-2-[(1-propanoylazetidin-3-yl)amino]pyridine-4-carboxamide (Compound 469)

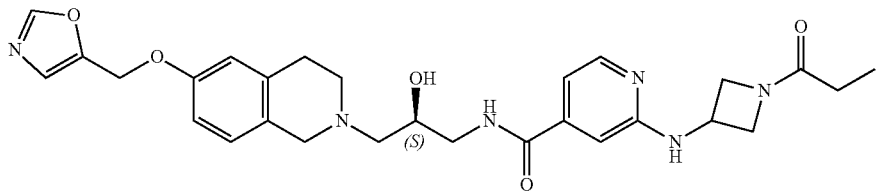

Prepared by general procedure 1D-C. Yield: 8.9 mg (4.7%). $^1$H NMR (400 MHz, CD$_3$OD) δ 1.09 (t, 3H), 2.16 (m, 2H), 2.64 (m, 2H), 2.83 (m, 2H), 2.87 (m, 2H), 3.48 (m, 2H), 3.67 (s, 2H), 3.82 (dd, 1H), 3.99 (dd, 1H), 4.07 (m, 1H), 4.32 (m, 1H), 4.53 (m, 1H), 4.58 (m, 1H), 5.10 (s, 2H), 6.77 (m, 2H), 6.81 (dd, 1H), 6.86 (s, 1H), 6.96 (d, 1H), 7.22 (s, 1H), 7.95 (d, 1H), 8.22 (s, 1H). LCMS(ESI): [M+H]$^+$ m/z: calcd 534.2. found 535.2; Rt=0.78 min.

Example 1D45. N-[(2S)-2-hydroxy-3-[6-(oxazol-5-ylmethoxy)-3,4-dihydro-1H-isoquinolin-2-yl]propyl]-2-[[1-(2-methylpropanoyl)azetidin-3-yl]amino]pyridine-4-carboxamide (Compound 479)

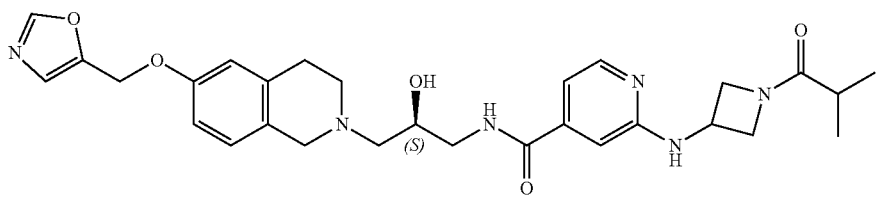

Prepared by general procedure 1D-C. Yield: 6.9 mg (3.6%). ¹H NMR (400 MHz, CDCl₃) δ 1.07 (m, 6H), 1.72 (m, 1H), 2.43 (m, 1H), 2.59 (m, 2H), 2.72 (m, 1H), 2.87 (m, 3H), 3.65 (m, 4H), 3.89 (m, 2H), 4.00 (m, 1H), 4.36 (m, 1H), 4.51 (m, 1H), 4.62 (m, 1H), 5.03 (s, 2H), 5.40 (m, 1H), 6.73 (m, 3H), 6.84 (s, 1H), 6.93 (d, 1H), 7.13 (s, 1H), 7.20 (m, 1H), 7.89 (m, 1H), 8.03 (m, 1H). LCMS(ESI): [M+H]⁺ m/z: calcd 548.2. found 549.4; Rt=0.83 min.

Example 1D46. N-[(2S)-2-hydroxy-3-[6-(oxazol-5-ylmethoxy)-3,4-dihydro-1H-isoquinolin-2-yl]propyl]-2-[[1-(3-methylbutanoyl)azetidin-3-yl]amino]pyridine-4-carboxamide (Compound 474)

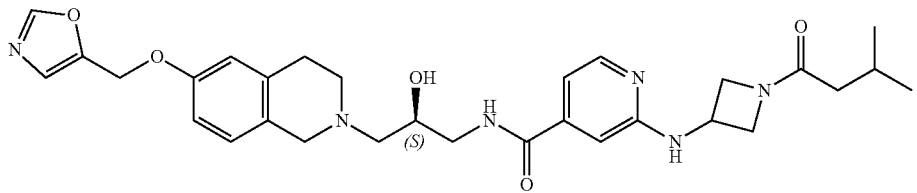

Prepared by general procedure 1D-C. Yield: 15.7 mg (7.9%). ¹H NMR (400 MHz, CDCl₃) δ 0.92 (m, 6H), 2.08 (m, 1H), 2.59 (m, 2H), 2.71 (m, 1H), 2.86 (m, 3H), 3.45 (m, 3H), 3.49 (m, 1H), 3.62 (m, 2H), 3.73 (m, 1H), 3.89 (m, 2H), 4.00 (m, 1H), 4.35 (m, 1H), 4.46 (m, 1H), 4.59 (m, 1H), 5.03 (s, 2H), 5.60 (m, 1H), 6.70 (m, 2H), 6.75 (dd, 1H), 6.86 (s, 1H), 6.92 (d, 1H), 7.13 (s, 1H), 7.36 (m, 1H), 7.89 (m, 1H), 8.00 (d, 1H). LCMS(ESI): [M+H]⁺ m/z: calcd 562.3. found 563.4; Rt=0.88 min.

Example 1D47. 2-[(1-butanoyl-4-piperidyl)amino]-N-[(2S)-2-hydroxy-3-[6-(oxazol-5-ylmethoxy)-3,4-dihydro-1H-isoquinolin-2-yl]propyl]pyridine-4-carboxamide (Compound 431)

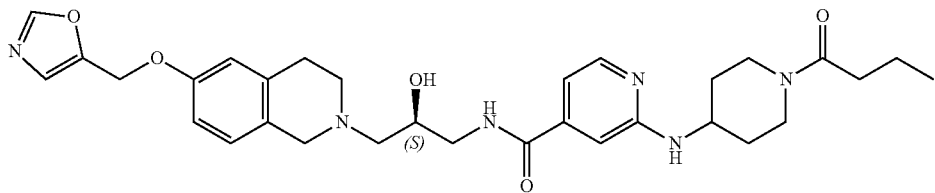

Prepared by general procedure 1D-C. Yield: 42.8 mg (21.1%). ¹H NMR (DMSO-d₆, 500 MHz): δ (ppm) 0.94 (t, 3H), 1.33 (m, 2H), 1.56 (q, 2H), 1.92 (m, 2H), 2.26 (t, 2H), 2.56 (m, 2H), 2.82 (m, 5H), 3.17 (m, 1H), 3.23 (m, 1H), 3.42 (m, 1H), 3.63 (m, 2H), 3.81 (d, 1H), 3.90 (s, 1H), 3.97 (d, 1H), 4.27 (d, 1H), 4.63 (s, 1H), 5.06 (s, 2H), 6.46 (d, 1H), 6.71 (m, 3H), 6.84 (s, 1H), 6.93 (d, 1H), 7.16 (s, 1H), 7.88 (d, 1H), 8.16 (s, 1H), 8.27 (t, 1H). LCMS(ESI): [M+H]⁺ m/z: calcd 576.3. found 577.4; Rt=1.81 min.

Example 1D48. N-[(2S)-2-hydroxy-3-[6-(oxazol-5-ylmethoxy)-3,4-dihydro-1H-isoquinolin-2-yl]propyl]-2-[[1-(2-methylpropanoyl)-4-piperidyl]amino]pyridine-4-carboxamide (Compound 458)

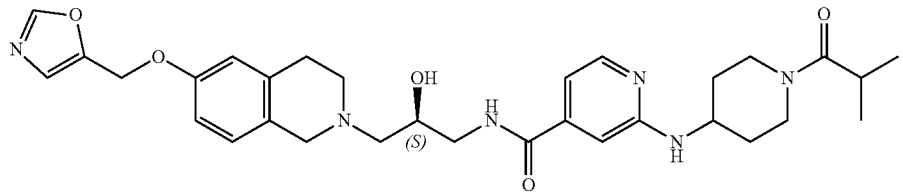

Prepared by general procedure 1D-C. Yield: 23.0 mg (11.3%). $^1$H NMR (DMSO-d$_6$, 400 MHz): δ (ppm) 0.98 (d, 6H), 1.22 (m, 1H), 1.31 (m, 1H), 1.89 (m, 2H), 2.68 (m, 2H), 2.76 (m, 4H), 2.88 (m, 1H), 3.19 (m, 2H), 3.38 (m, 2H), 3.54 (m, 2H), 3.88 (m, 2H), 3.95 (m, 1H), 4.23 (m, 1H), 4.81 (m, 1H), 5.11 (d, 2H), 6.68 (d, 1H), 6.76 (m, 3H), 6.82 (s, 1H), 6.95 (d, 1H), 7.30 (s, 1H), 7.96 (d, 1H), 8.39 (s, 1H), 8.46 (t, 1H). LCMS(ESI): [M+H]$^+$ m/z: calcd 576.3; found 577.4; Rt=1.82 min.

Example 1D49. 2-[[1-(cyclopropanecarbonyl)-4-piperidyl]amino]-N-[(2S)-2-hydroxy-3-[6-(oxazol-5-ylmethoxy)-3,4-dihydro-1H-isoquinolin-2-yl]propyl]pyridine-4-carboxamide (Compound 450)

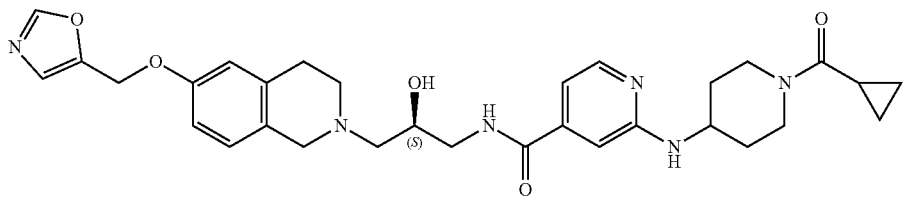

Prepared by general procedure 1D-C. Yield: 21.7 mg (10.7%). $^1$H NMR (Chloroform-d, 400 MHz): δ (ppm) 0.74 (m, 2H), 0.97 (m, 2H), 1.39 (m, 3H), 1.75 (m, 1H), 2.04 (m, 1H), 2.15 (m, 1H), 2.57 (m, 2H), 2.70 (m, 1H), 2.88 (m, 4H), 3.30 (m, 1H), 3.40 (m, 1H), 3.55 (d, 1H), 3.69 (m, 1H), 3.76 (d, 1H), 3.98 (m, 2H), 4.18 (m, 1H), 4.50 (m, 1H), 5.03 (s, 2H), 6.73 (m, 4H), 6.85 (t, 1H), 6.93 (d, 1H), 7.13 (s, 1H), 7.88 (s, 1H), 8.10 (d, 1H). LCMS(ESI): [M+H]$^+$ m/z: calcd 574.3. found 575.4; Rt=1.72 min.

Example 1D50. 2-[[1-(cyclobutanecarbonyl)-4-piperidyl]amino]-N-[(2S)-2-hydroxy-3-[6-(oxazol-5-ylmethoxy)-3N-dihydro-1H-isoquinolin-2-yl]propyl]pyridine-4-carboxamide (Compound 433)

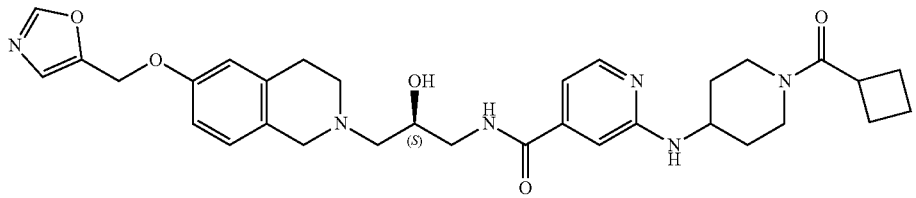

Prepared by general procedure 1D-C. Yield: 28.2 mg (13.6%). $^1$H NMR (DMSO-d6, 500 MHz): δ (ppm) 1.33 (m, 2H), 1.81 (m, 1H), 1.92 (m, 3H), 2.10 (m, 2H), 2.24 (m, 2H), 2.54 (m, 2H), 2.75 (m, 2H), 2.83 (m, 3H), 3.09 (t, 1H), 3.25 (m, 2H), 3.43 (m, 1H), 3.60 (m, 2H), 3.66 (m, 1H), 3.87 (m, 1H), 3.96 (m, 1H), 4.24 (d, 1H), 4.58 (m, 1H), 5.06 (s, 2H), 6.43 (d, 1H), 6.69 (m, 3H), 6.83 (s, 1H), 6.92 (d, 1H), 7.16 (s, 1H), 7.87 (d, 1H), 8.15 (s, 1H), 8.25 (t, 1H). LCMS(ESI): [M+H]$^+$ m/z: calcd 588.3. found; Rt=min.

Example 1D51. N-[(2S)-2-hydroxy-3-[6-(oxazol-5-ylmethoxy)-3,4-dihydro-1H-isoquinolin-2-yl]propyl]-2-[[1-(3-methylbutanoyl)-4-piperidyl]amino]pyridine-4-carboxamide (Compound 446)

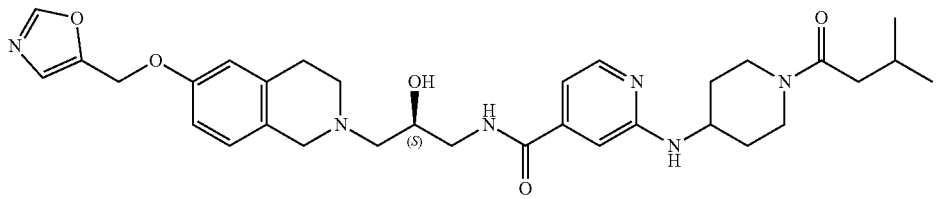

Prepared by general procedure 1D-C. Yield: 29.1 mg (14.0%). $^1$H NMR (DMSO-d6, 400 MHz): δ (ppm) 0.89 (s, 6H), 1.26 (m, 2H), 1.93 (m, 4H), 2.18 (m, 2H), 2.68 (m, 2H), 2.77 (m, 3H), 3.15 (m, 3H), 3.53 (m, 2H), 3.89 (m, 4H), 4.25 (m, 1H), 4.81 (m, 1H), 5.11 (s, 2H), 6.68 (d, 1H), 6.75 (m, 3H), 6.82 (s, 1H), 6.95 (d, 1H), 7.30 (s, 1H), 7.96 (d, 1H), 8.38 (s, 1H), 8.46 (t, 1H). LCMS(ESI): [M+H]$^+$ m/z: calcd 590.3. found 591.2; Rt=1.92 min.

Example 1D52. 2-[[1-(2,2-dimethylpropanoyl)-4-piperidyl]amino]-N-[(2S)-2-hydroxy-3-[6-(oxazol-5-ylmethoxy)-3,4-dihydro-1H-isoquinolin-2-yl]propyl]pyridine-4-carboxamide (Compound 449)

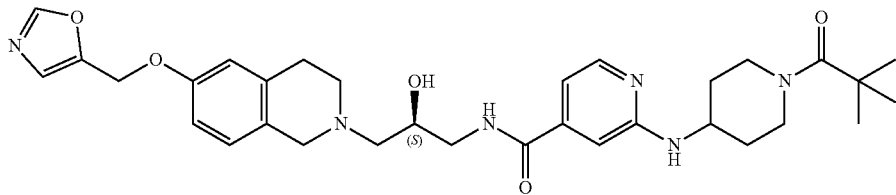

Prepared by general procedure 1D-C. Yield: 28.9 mg (13.9%). $^1$H NMR (DMSO-d6, 400 MHz): δ (ppm) 1.19 (s, 9H), 1.27 (m, 3H), 1.91 (d, 2H), 2.68 (m, 2H), 2.76 (m, 2H), 2.98 (t, 2H), 3.19 (m, 1H), 3.38 (m, 2H), 3.54 (m, 2H), 3.87 (m, 1H), 3.97 (m, 1H), 4.16 (d, 2H), 4.81 (d, 1H), 5.11 (s, 2H), 6.67 (d, 1H), 6.74 (d, 1H), 6.77 (m, 2H), 6.81 (s, 1H), 6.95 (d, 1H), 7.30 (s, 1H), 7.96 (d, 1H), 8.39 (s, 1H), 8.46 (t, 1H). LCMS(ESI): [M+H]$^+$ m/z: calcd 590.3. found 591.2; Rt=1.94 min.

Example 1D53. 2-[(1-acetyl-4-piperidyl)amino]-N-[(2S)-2-hydroxy-3-[6-(oxazol-5-ylmethoxy)-3,4-dihydro-1H-isoquinolin-2-yl]propyl]pyridine-4-carboxamide (Compound 471)

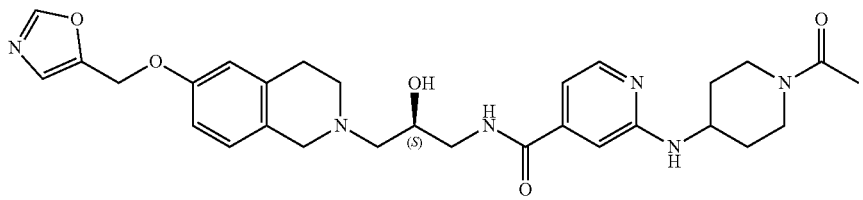

Prepared by general procedure 1D-C. Yield: 20.8 mg (10.8%). $^1$H NMR (400 MHz, CD3OD) δ 1.40 (m, 2H), 1.99 (m, 2H), 2.09 (s, 3H), 2.63 (m, 2H), 2.82 (m, 2H), 2.86 (m, 3H), 3.23 (m, 1H), 3.46 (m, 2H), 3.65 (s, 2H), 3.90 (m, 2H), 4.05 (p, 1H), 4.39 (d, 1H), 5.08 (s, 2H), 6.71 (dd, 1H), 6.75 (m, 2H), 6.82 (s, 1H), 6.95 (d, 1H), 7.20 (s, 1H), 7.89 (d, 1H), 8.20 (s, 1H). LCMS(ESI): [M+H]$^+$ m/z: calcd 548.3. found 549.2; Rt=0.73 min.

Example 1D54. 2-[[1-(cyclobutanecarbonyl)azetidin-3-yl]amino]-N-[(2S)-2-hydroxy-3-[6-(oxazol-5-ylmethoxy)-3,4-dihydro-1H-isoquinolin-2-yl]propyl]pyridine-4-carboxamide (Compound 468)

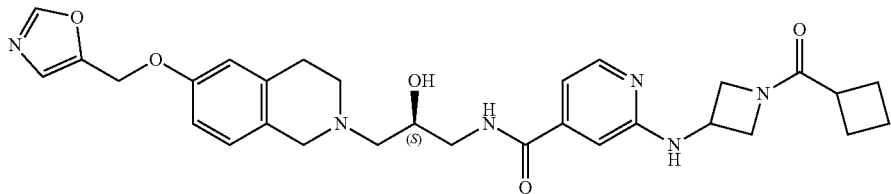

Prepared by general procedure 1D-C. Yield: 10.2 mg (5.2%). $^1$H NMR (500 MHz, DMSO-d6+CCl4) δ 1.84 (m, 1H), 1.93 (m, 1H), 2.05 (m, 2H), 2.19 (p, 2H), 2.79 (m, 2H), 2.85 (m, 2H), 3.04 (m, 3H), 3.24 (m, 1H), 3.44 (m, 1H), 3.63 (m, 2H), 3.73 (dd, 1H), 3.82 (dd, 1H), 3.90 (m, 1H), 4.15 (t, 1H), 4.31 (t, 1H), 4.54 (m, 1H), 4.61 (m, 1H), 5.06 (s, 2H), 6.72 (m, 2H), 6.80 (d, 1H), 6.85 (s, 1H), 6.92 (d, 1H), 7.17 (s, 1H), 7.19 (d, 1H), 7.92 (d, 1H), 8.16 (s, 1H), 8.34 (t, 1H). LCMS(ESI): [M+H]$^+$ m/z: calcd 560.2. found 561.4; Rt=1.94 min.

Example 1D55. 2-1(1-butanoylazetidin-3-yl)amino]-N-[(2S)-2-hydroxy-3-[6-(oxazol-5-ylmethoxy)-3,4-dihydro-1H-isoquinolin-2-yl]propyl]pyridine-4-carboxamide (Compound 434)

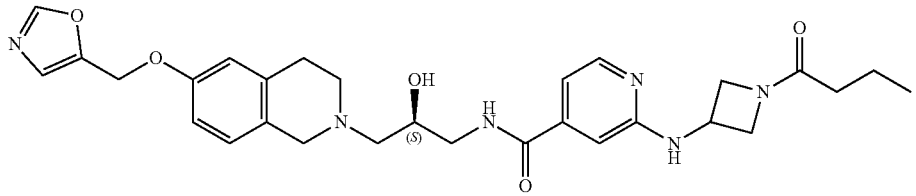

Prepared by general procedure 1D-C. Yield: 4.6 mg (2.4%). $^1$H NMR (Chloroform-d, 400 MHz): δ (ppm) 0.91 (t, 3H), 1.60 (m, 2H), 2.05 (t, 2H), 2.59 (m, 3H), 2.71 (m, 1H), 2.87 (m, 2H), 3.43 (m, 2H), 3.57 (m, 1H), 3.68 (m, 1H), 3.75 (m, 1H), 3.86 (m, 2H), 3.99 (m, 1H), 4.37 (m, 1H), 4.47 (m, 1H), 4.60 (m, 1H), 5.03 (s, 2H), 5.18 (m, 1H), 6.71 (s, 1H), 6.77 (m, 3H), 6.93 (d, 1H), 7.07 (m, 1H), 7.13 (s, 1H), 7.89 (s, 1H), 8.08 (m, 1H). LCMS(ESI): [M+H]$^+$ m/z: calcd 548.3. found 549.4; Rt=0.82 min.

Example 1D56. 2-[[1-(cyclopropanecarbonyl)azetidin-3-yl]amino]-N-[(2S)-2-hydroxy-3-[6-(oxazol-5-ylmethoxy)-3,4-dihydro-1H-isoquinolin-2-yl]propyl]pyridine-4-carboxamide (Compound 563)

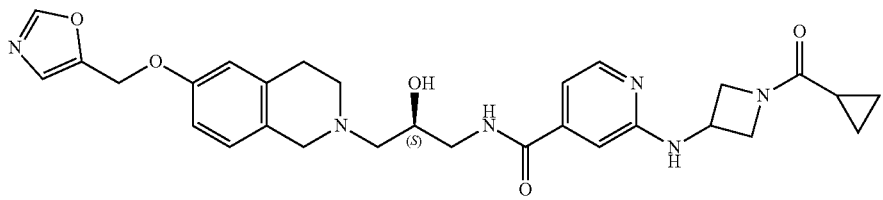

Prepared by general procedure 1D-C. Yield: 15.8 mg (8.2%). $^1$H NMR (DMSO-d$_6$, 500 MHz): δ (ppm) 0.75 (m, 2H), 0.96 (m, 2H), 1.41 (m, 1H), 2.63 (m, 2H), 2.75 (m, 1H), 2.90 (m, 4H), 3.52 (m, 1H), 3.62 (m, 2H), 3.75 (d, 1H), 3.92 (m, 1H), 4.03 (m, 2H), 4.38 (m, 1H), 4.63 (m, 1H), 4.68 (s, 1H), 5.05 (s, 2H), 5.71 (dd, 1H), 6.71 (m, 2H), 6.77 (d, 1H), 6.90 (s, 1H), 6.95 (d, 1H), 7.15 (s, 1H), 7.42 (s, 1H), 7.91 (s, 1H), 8.01 (d, 1H). LCMS(ESI): [M+H]$^+$ m/z: calcd 546.2. found 547.2; Rt=0.82 min.

Example 1D57. N-[(2S)-2-hydroxy-3-[6-(oxazol-5-ylmethoxy)-3,4-dihydro-1H-isoquinolin-2-yl]propyl]-2-[(1-propanoyl-4-piperidyl)amino]pyridine-4-carboxamide (Compound 460)

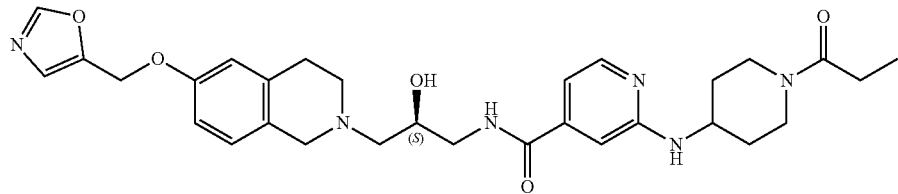

Prepared by general procedure 1D-C. Yield: 21.2 mg (10.7%). $^1$H NMR (Chloroform-d, 400 MHz): δ (ppm) 1.13 (t, 3H), 1.35 (m, 2H), 2.02 (m, 1H), 2.10 (m, 1H), 2.33 (q, 2H), 2.55 (m, 1H), 2.59 (s, 3H), 2.72 (m, 1H), 2.89 (m, 4H), 3.19 (m, 1H), 3.41 (m, 1H), 3.56 (d, 1H), 3.68 (m, 1H), 3.76 (d, 1H), 3.82 (m, 1H), 3.94 (m, 1H), 4.00 (m, 1H), 4.53 (m, 2H), 5.02 (s, 2H), 6.73 (m, 4H), 6.92 (td, 2H), 7.13 (s, 1H), 7.88 (s, 1H), 8.08 (d, 1H). LCMS(ESI): [M+H]$^+$ m/z: calcd 562.3. found 563.4; Rt=0.75 min.

General Procedure 1D-D

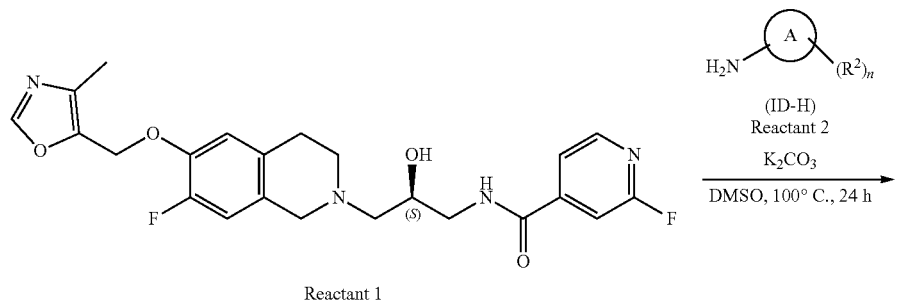

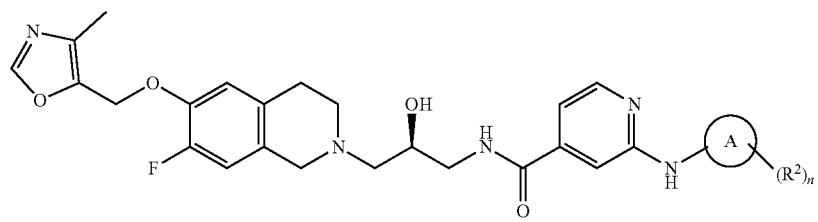

To the solution of Reactant 1 (1.0 equiv) and Reactant 2 (3.0 equiv) in DMSO (1.0 mL) potassium carbonate, anhydrous, 99% (5.0 equiv) was added. The reaction mixture was stirred at 100° C. for 15 h. After the completion of the reaction, the resulting mixture was purified by reverse phase HPLC (Device (Mobile Phase, Column): LC 11 10-40% 0-5 min water-acn, flow: 30 ml/min (loading pump 4 ml/min acn), target mass 581 column: SunFire C18 100×19 mm, 5 um) to give pure product.

Example 1D58. 2-1(1-acetyl-4-piperidyl)amino]-N-[(2S)-3-[7-fluoro-6-[(4-methyloxazol-5-yl)methoxy]-3N-dihydro-1H-isoquinolin-2-yl]-2-hydroxy-propyl]pyridine-4-carboxamide (Compound 625)

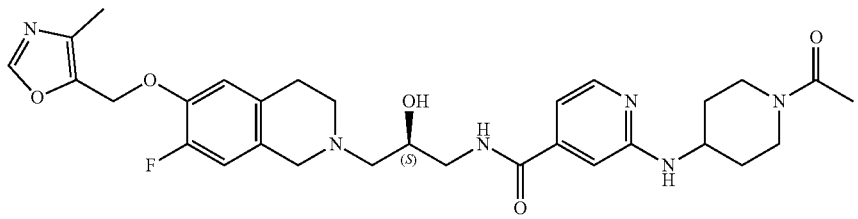

Prepared by general procedure 1D-D. Yield: 10.0 mg (3.97%). $^1$H NMR (400 MHz, CDCl$_3$) δ 1.36 (m, 2H), 2.04 (m, 1H), 2.09 (s, 3H), 2.13 (m, 1H), 2.18 (s, 3H), 2.58 (m, 2H), 2.71 (m, 1H), 2.81 (m, 3H), 2.91 (m, 2H), 3.19 (m, 1H), 3.38 (m, 1H), 3.53 (d, 1H), 3.73 (m, 3H), 3.98 (m, 2H), 4.49 (m, 1H), 4.62 (d, 1H), 5.02 (s, 2H), 6.73 (m, 3H), 6.78 (s, 1H), 6.91 (m, 1H), 7.79 (s, 1H), 8.09 (d, 1H). LCMS(ESI): [M+H]$^+$ m/z: calcd 580.2. found 581.2; Rt=0.74 min.

General Procedure 1D-E

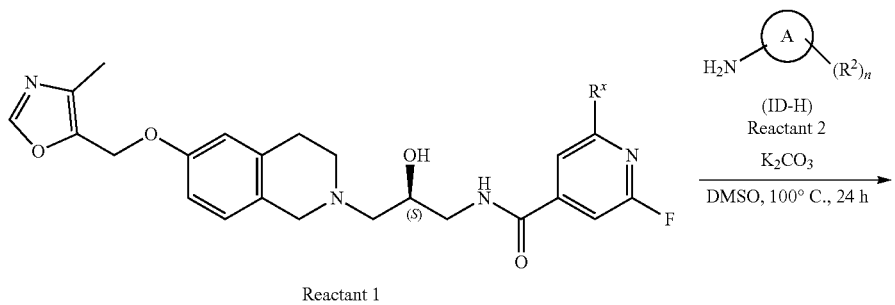

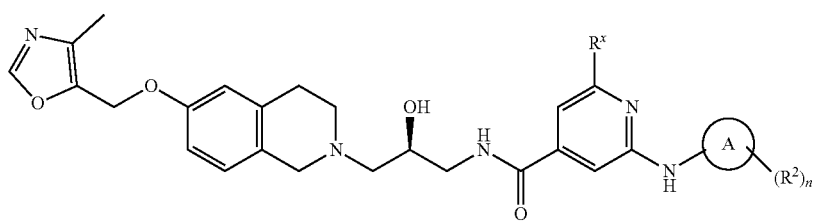

Reactant 1 and reactant 2 were dissolved in DMSO (3 mL). Potassium carbonate, anhydrous, 99% was added thereto and mixture was stirred at 100° C. for 12 hours in sealed tube. Obtained crude product in reaction mixture 3 ml in DMSO was purified by preparative RP-HPLC to afford product.

Example 1D59. (S)—N-(2-hydroxy-3-(6-((4-methyloxazol-5-yl)methoxy)-3,4-dihydroisoquinolin-2(1H)-yl)propyl)-2-(spiro[3.3]heptan-2-ylamino)isonicotinamide (Compound 609)

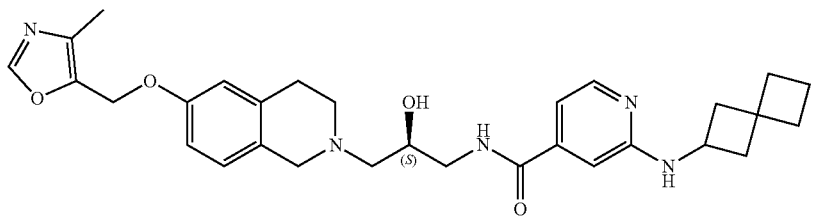

Prepared by general procedure 1D-E. Yield: 17.5 mg (14.26%). $^1$H NMR (400 MHz, CDCl$_3$) δ 1.69 (m, 1H), 1.76 (m, 1H), 1.86 (m, 1H), 1.92 (m, 2H), 1.99 (m, 1H), 2.04 (t, 2H), 2.21 (s, 3H), 2.38 (m, 1H), 2.53 (m, 4H), 2.70 (m, 1H), 2.88 (m, 3H), 3.39 (m, 1H), 3.54 (d, 1H), 3.69 (m, 1H), 3.77 (m, 1H), 3.99 (m, 2H), 4.83 (d, 1H), 4.96 (s, 2H), 6.66 (s, 1H), 6.70 (m, 2H), 6.75 (m, 1H), 6.91 (m, 2H), 7.79 (s, 1H), 8.06 (d, 1H). LCMS(ESI): [M+H]$^+$ m/z: calcd 531.6; found 532.2; Rt=0.931 min.

Example 1D60. (S)—N-(2-hydroxy-3-(6-((4-methyloxazol-5-yl)methoxy)-3,4-dihydroisoquinolin-2(1H)-yl)propyl)-2-(spiro[2.3]hexan-5-ylamino)isonicotinamide (Compound 621)

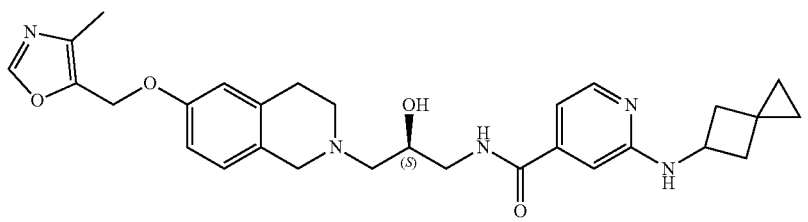

Prepared by general procedure 1D-E. Yield: 25.3 mg (21.53%). $^1$H NMR (400 MHz, CDCl$_3$) δ 0.41 (m, 2H), 0.49 (m, 2H), 2.12 (m, 2H), 2.21 (s, 3H), 2.43 (m, 2H), 2.52 (m, 1H), 2.58 (m, 1H), 2.70 (m, 1H), 2.88 (m, 3H), 3.39 (m, 1H), 3.54 (d, 1H), 3.70 (m, 1H), 3.75 (d, 1H), 3.99 (m, 1H), 4.34 (h, 1H), 4.96 (s, 2H), 4.99 (m, 1H), 6.70 (m, 2H), 6.75 (m, 2H), 6.85 (t, 1H), 6.92 (d, 1H), 7.79 (s, 1H), 8.09 (d, 1H). LCMS(ESI): [M+H]$^+$ m/z: calcd 517.6. found 518.2; Rt=0.881 min.

Example 1D61. (S)-2-((1-acetylpiperidin-4-yl)amino)-N-(2-hydroxy-3-(6-((4-methyloxazol-5-yl)methoxy)-3,4-dihydroisoquinolin-2(1H)-yl)propyl)isonicotinamide (Compound 622)

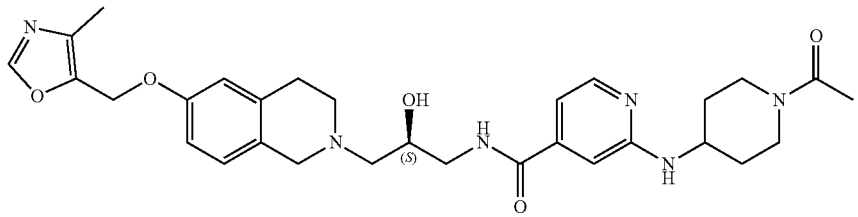

Prepared by general procedure 1D-E. Yield: 10.2 mg (7.98%). $^1$H NMR (400 MHz, CDCl$_3$) δ 1.36 (m, 2H), 2.03 (m, 1H), 2.08 (s, 3H), 2.13 (m, 1H), 2.20 (s, 3H), 2.58 (m, 2H), 2.69 (m, 1H), 2.86 (m, 4H), 3.19 (m, 1H), 3.39 (m, 1H), 3.55 (d, 1H), 3.73 (m, 4H), 3.98 (m, 2H), 4.49 (m, 1H), 4.59 (d, 1H), 4.96 (s, 2H), 6.72 (m, 3H), 6.76 (s, 1H), 6.92 (d, 1H), 6.99 (t, 1H), 7.79 (s, 1H), 8.07 (d, 1H). LCMS(ESI): [M+H]$^+$ m/z: calcd 562.6. found 563.4; Rt=0.778 min.

Example 1D62. (S)-2-((1-(cyclopropanecarbonyl)piperidin-4-yl)amino)-N-(2-hydroxy-3-(6-((4-methyloxazol-5-yl)methoxy)-3,4-dihydroisoquinolin-2(1H)-yl)propyl)isonicotinamide (Compound 624)

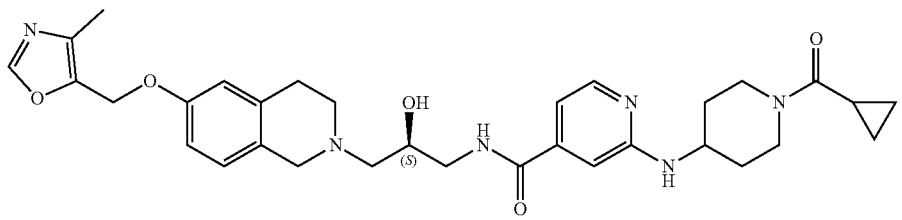

Prepared by general procedure 1D-E. Yield: 6.9 mg (5.08%). $^1$H NMR (400 MHz, CDCl$_3$) δ 0.74 (m, 2H), 0.96 (m, 2H), 1.39 (m, 2H), 1.74 (m, 2H), 2.03 (m, 1H), 2.15 (m, 1H), 2.21 (s, 3H), 2.57 (m, 2H), 2.70 (m, 1H), 2.86 (m, 4H), 3.28 (m, 1H), 3.41 (m, 1H), 3.55 (d, 1H), 3.69 (m, 1H), 3.75 (m, 1H), 3.98 (m, 2H), 4.15 (m, 1H), 4.50 (m, 1H), 4.55 (d, 1H), 4.96 (s, 2H), 6.72 (m, 3H), 6.77 (s, 1H), 6.92 (m, 2H), 7.79 (s, 1H), 8.09 (d, 1H). LCMS(ESI): [M+H]$^+$ m/z: calcd 588.7. found 589.4; Rt=0.827 min.

Example 1D63. N—((S)-2-hydroxy-3-(6-((4-methyloxazol-5-yl)methoxy)-3,4-dihydroisoquinolin-2(1H)-yl)propyl-2-((1-methyl-2-oxopiperidin-4-yl)amino)isonicotinamide (Compound 627)

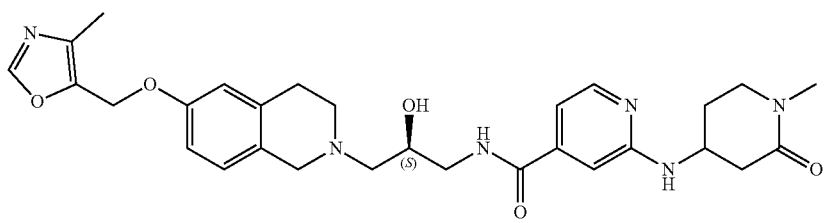

Prepared by general procedure 1D-E. Yield: 4.4 mg (3.46%). ¹H NMR (400 MHz, CDCl₃): δ (ppm) 1.86 (m, 1H), 2.21 (s, 5H), 2.31 (dd, 1H), 2.57 (m, 2H), 2.72 (m, 1H), 2.87 (m, 4H), 2.95 (s, 3H), 3.35 (m, 2H), 3.42 (m, 1H), 3.56 (d, 1H), 3.69 (m, 1H), 3.77 (d, 1H), 4.00 (m, 1H), 4.22 (m, 1H), 4.60 (d, 1H), 4.97 (s, 2H), 6.71 (s, 1H), 6.76 (m, 3H), 6.92 (m, 2H), 7.79 (s, 1H), 8.09 (d, 1H). LCMS(ESI): [M+H]⁺ m/z: calcd 548.6. found 549.4; Rt=1.652 min.

Example 1D64. 2-((1-acetyl-3-methylpiperidin-4-yl)amino)-N—((S)-2-hydroxy-3-(6-((4-methyloxazol-5-yl)methoxy)-3,4-dihydroisoquinolin-2(1H)-yl)propyl)isonicotinamide (Compound 637)

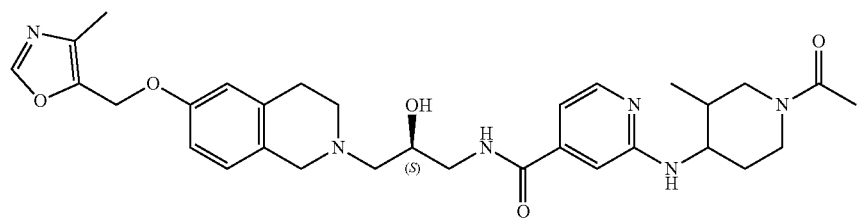

Prepared by general procedure 1D-E. Yield: 2.9 mg (2.21%). ¹H NMR (400 MHz, CDCl₃) δ 0.92 (m, 3H), 1.27 (m, 1H), 1.76 (m, 1H), 2.09 (m, 3H), 2.17 (m, 1H), 2.21 (s, 3H), 2.27 (m, 1H), 2.53 (m, 1H), 2.59 (m, 1H), 2.70 (m, 1H), 2.88 (m, 2H), 3.38 (m, 2H), 3.55 (m, 2H), 3.70 (m, 1H), 3.76 (m, 2H), 3.99 (m, 1H), 4.06 (m, 1H), 4.27 (m, 1H), 4.57 (m, 1H), 4.97 (s, 2H), 6.70 (m, 1H), 6.73 (m, 2H), 6.77 (m, 1H), 6.80 (m, 2H), 6.93 (d, 1H), 7.80 (s, 1H), 8.10 (d, 1H). LCMS(ESI): [M+H]⁺ m/z: calcd 576.7. found 577.4; Rt=1.641 min.

General Procedure 1D-F

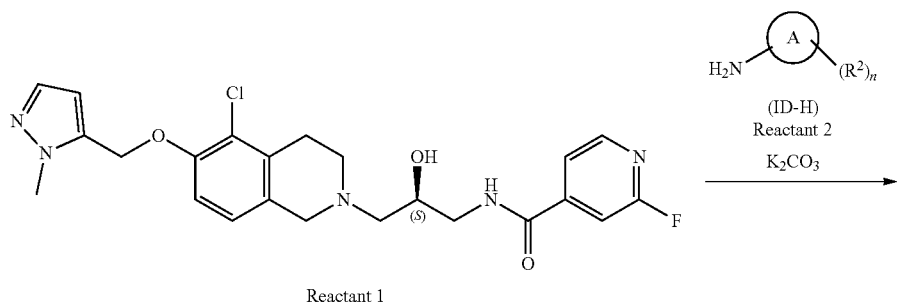

Reactant 1

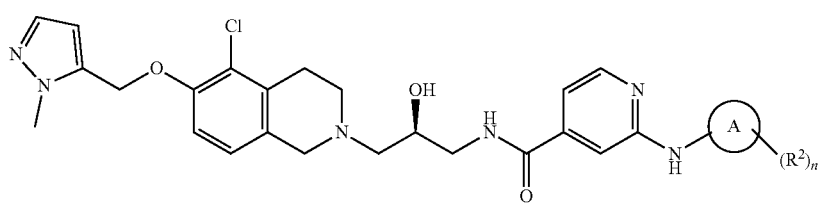

(S)—N-(3-(5-Chloro-6-(((1-methyl-1H-pyrazol-5-yl)methoxy)-3,4-dihydroisoquinolin-2 (1H)-yl)-2-hydroxypropyl)-2-fluoroisonicotinamide (1.0 equiv), corresponding amine (1.0 equiv) and $K_2CO_3$ (3.0 equiv) were mixed together in DMSO (3.0 mL). The resulting mixture was stirred at 100° C. overnight. After all starting material was consumed (as was shown by LCMS), the resulting suspension was concentrated under reduced pressure. The residue was dissolved in DMSO (3.0 mL) and filtered off. The obtained filtrate was subjected to HPLC (Waters Sunfire C18 19*100 5 mkm column and 40-75% $H_2O$+MeOH, flow: 30 mL/min (loading pump 4 mL/min MeOH)).

Example 1D65. (S)—N-(3-(5-chloro-6-(((1-methyl-1H-pyrazol-5-yl)methoxy)-3,4-dihydroisoquinolin-2 (1H)-yl)-2-hydroxypropyl)-2-(cyclopentylamino) isonicotinamide (Compound 275)

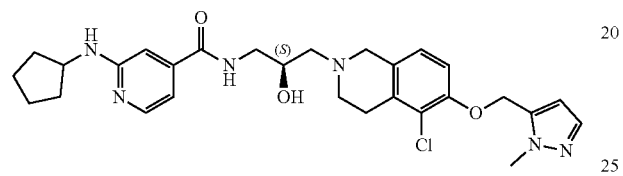

Prepared by general procedure 1D-F. Yield 1.8 mg (26.37%). $^1$H NMR (CDCl$_3$, 400 MHz): δ (ppm) 1.48 (m, 2H), 1.71 (m, 4H), 2.02 (m, 3H), 2.56 (m, 2H), 2.73 (m, 1H), 2.92 (m, 3H), 3.39 (m, 1H), 3.51 (m, 2H), 3.73 (m, 2H), 3.97 (s, 3H), 4.02 (m, 1H), 4.75 (m, 1H), 5.07 (s, 2H), 6.27 (d, 1H), 6.69 (d, 1H), 6.88 (m, 4H), 7.40 (d, 1H), 8.06 (d, 1H). LCMS(ESI): [M+H]$^+$ m/z: calcd 539.1. found 540.2; Rt=0.893 min.

General Procedure 1D-G

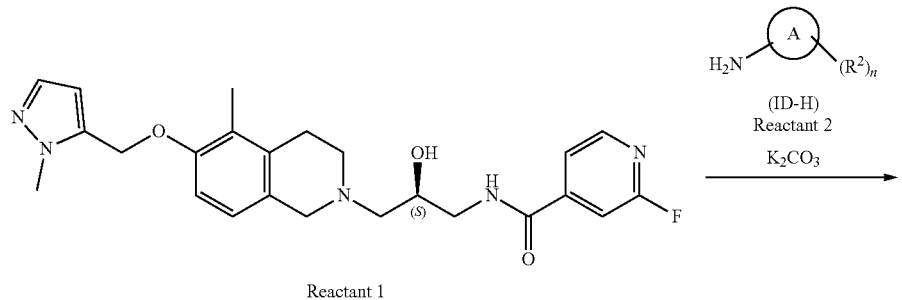

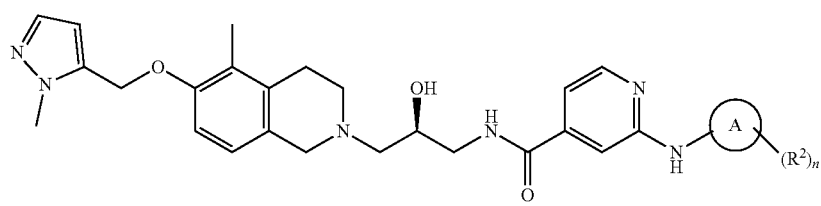

(S)-2-Fluoro-N-(2-hydroxy-3-(5-methyl-6-((1-methyl-1H-pyrazol-5-yl)methoxy)-3,4-dihydroisoquinolin-2(1H)-yl)propyl)isonicotinamide (1.0 equiv), corresponding amine (1.0 equiv) and K₂CO₃ (3.0 equiv) were mixed together in DMSO (3.0 mL). The resulting mixture was stirred at 100° C. overnight. After all starting material was consumed (as was shown by LCMS), the resulting suspension was concentrated under reduced pressure. The residue was dissolved in DMSO (3.0 mL) and filtered off. The obtained filtrate was subjected to HPLC (Waters Sunfire C18 19*100 5 mkm column and 40-75% H₂O+MeOH, flow: 30 mL/min (loading pump 4 mL/min MeOH)).

Example 1D66. (S)-2-(cyclopentylamino)-N-(2-hydroxy-3-(5-methyl-6-((1-methyl-1H-pyrazol-5-yl)methoxy)-3N-dihydroisoquinolin-2(1H)-yl)propyl)isonicotinamide (Compound 277)

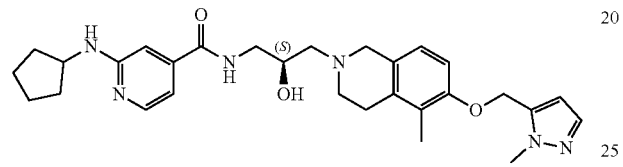

Prepared by general procedure 1D-F. Yield 19.7 mg (15.11%). ¹H NMR (CDCl₃, 400 MHz): δ (ppm) 1.43 (m, 2H), 1.64 (m, 4H), 2.00 (m, 2H), 2.06 (s, 3H), 2.55 (m, 2H), 2.72 (m, 4H), 2.91 (m, 1H), 3.40 (m, 1H), 3.54 (d, 1H), 3.67 (m, 1H), 3.74 (d, 1H), 3.89 (s, 3H), 3.99 (q, 2H), 4.76 (d, 1H), 4.99 (s, 2H), 6.27 (s, 1H), 6.67 (d, 1H), 6.76 (m, 2H), 6.82 (d, 1H), 7.04 (t, 1H), 7.41 (s, 1H), 8.02 (d, 1H). LCMS(ESI): [M+H]⁺ m/z: calcd 518.3. found 519.2; Rt=0.86 min.

Example 1D67. (S)-2-(cyclohexylamino)-N-(2-hydroxy-3-(5-methyl-6-((1-methyl-1H-pyrazol-5-yl)methoxy)-3N-dihydroisoquinolin-2(1H)-yl)propyl)isonicotinamide (Compound 278)

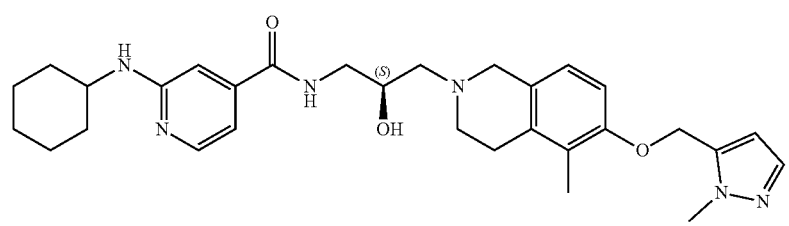

Prepared by general procedure 1D-F. Yield 22.6 mg (19.24%). ¹H NMR (CDCl₃, 400 MHz): δ (ppm) 1.18 (m, 3H), 1.37 (m, 2H), 1.61 (d, 1H), 1.72 (m, 2H), 2.00 (d, 2H), 2.06 (s, 3H), 2.56 (m, 2H), 2.72 (m, 3H), 2.92 (m, 1H), 3.42 (m, 2H), 3.55 (d, 2H), 3.68 (m, 1H), 3.75 (d, 1H), 3.90 (s, 3H), 3.99 (m, 1H), 4.63 (d, 1H), 4.99 (s, 2H), 6.27 (d, 1H), 6.65 (d, 1H), 6.73 (s, 1H), 6.76 (d, 1H), 6.83 (d, 1H), 7.00 (t, 1H), 7.41 (d, 1H), 8.03 (d, 1H). LCMS(ESI): [M+H]⁺ m/z: calcd 532.3. found 533.4; Rt=0.93 min.

Example 1D68. 2-[(1-butanoylazetidin-3-yl)amino]-N-[(2S)-3-[7-fluoro-6-[(4-methyloxazol-5-yl)methoxy]-3,4-dihydro-1H-isoquinolin-2-yl]-2-hydroxy-propyl]pyridine-4-carboxamide (Compound 643)

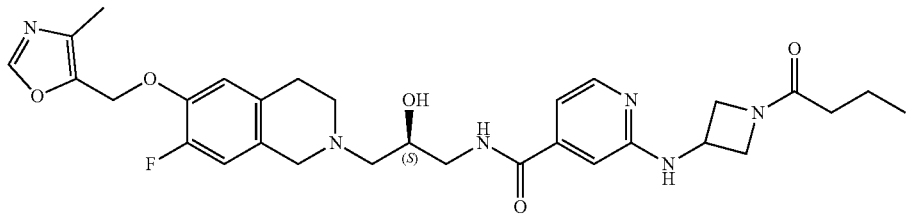

Prepared by general procedure 1D-D. Yield: 3.9 mg (1.54%). $^1$H NMR (400 MHz, CDCl$_3$) δ 0.93 (t, 3H), 1.63 (m, 2H), 2.06 (m, 3H), 2.19 (s, 3H), 2.65 (m, 2H), 2.82 (m, 3H), 2.96 (m, 1H), 3.42 (m, 1H), 3.60 (m, 1H), 3.67 (m, 1H), 3.78 (m, 1H), 3.88 (m, 2H), 4.03 (m, 1H), 4.38 (m, 1H), 4.48 (m, 1H), 4.61 (m, 1H), 5.03 (s, 2H), 5.24 (m, 1H), 6.74 (m, 2H), 6.82 (m, 2H), 7.02 (m, 1H), 7.80 (s, 1H), 8.10 (d, 1H). LCMS(ESI): [M+H]$^+$ m/z: calcd 580.1. found 581.1; Rt=1.92 min.

Example 1D69. 2-(((2R,4S)-1-acetyl-2-methylpiperidin-4-yl)amino)-N—((S)-2-hydroxy-3-(6-((4-methyloxazol-5-yl)methoxy)-3,4-dihydroisoquinolin-2(1H)-yl)propyl)isonicotinamide (Compound 644)

HCl), 2-fluoro-A-[(2S)-2-hydroxy-3-[6-[(4-methyloxazol-5-yl)methoxy]-3,4-dihydro-1H-isoquinolin-2-yl]propyl]pyridine-4-carboxamide (0.3 g, 681.10 umol), potassium carbonate, anhydrous, 99% (753.07 mg, 5.45 mmol, 328.85 uL) in DMSO (6 mL) was stirred at 100° C. for 12 hr in sealed tube. Obtained crude product in reaction mixture 6 ml in DMSO was purified by preparative RP-HPLC with 2-7 MIN 60-100% metanole 0.1 ammonium hydroxyde), 30 ML/MIN as mobile phase to afford product tert-butyl (2R, 4S)-4-[[4-[[(2S)-2-hydroxy-3-[6-[(4-methyloxazol-5-yl)methoxy]-3,4-dihydro-1H-isoquinolin-2-yl]propyl]carbamoyl]-2-pyridyl]amino]-2-methyl-piperidine-1-carboxylate (0.0201 g, 31.67 umol, 4.65% yield). LCMS(ESI): [M+H]$^+$ m/z: calcd 634.7. found 635.4; Rt=0.994 min.

2-(((2P4S)-1-acetyl-2-methylpiperidin-4-yl)amino)-N—((S)-2-hydroxy-3-(6-((4-methyloxazol-5-yl)methoxy)-3,4-dihydroisoquinolin-2(1H)-yl)propyl)isonicotinamide. Hydrogen chloride solution 4.0M in dioxane (160.00 mg, 4.39 mmol, 0.2 mL) was added to a solution of tert-butyl (2R,4S)-4-[[4-[[(2S)-2-hydroxy-3-[6-[(4-methyloxazol-5-yl)methoxy]-3,4-dihydro-1H-isoquinolin-2-yl]propyl]carbamoyl]-2-pyridyl]amino]-2-methyl-piperidine-1-carboxy-

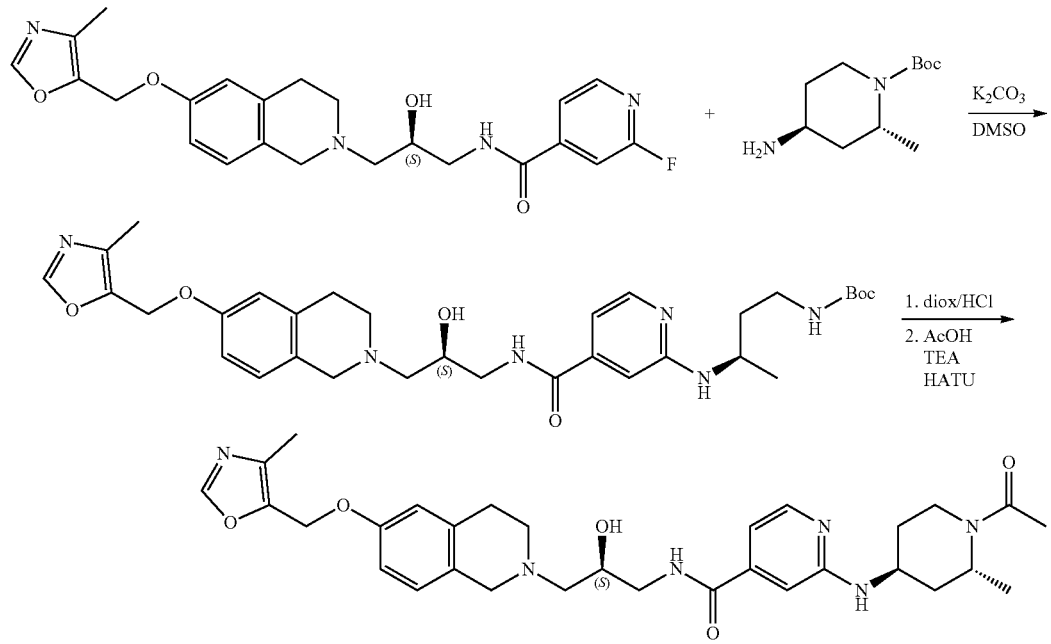

(2R,4S)-tert-butyl 4-((4-(((S)-2-hydroxy-3-(6-((4-methyloxazol-5-yl)methoxy)-3,4-dihydroisoquinolin-2(1H)-yl)propyl)carbamoyl)pyridin-2-yl)amino)-2-methylpiperidine-1-carboxylate. A mixture of tert-butyl (2R,4S)-4-amino-2-methyl-piperidine-1-carboxylate (437.88 mg, 1.75 mmol, late (20.42 mg, 32.17 umol) in DCM (2 mL). The reaction mixture was stirred at 20° C. for 12 hr, then evaporated in vacuo and were mixed with acetic acid (2.90 mg, 48.26 umol, 2.76 uL) in DML (2 mL). The reaction suspension was cooled to 0° C. and HATU (12.23 mg, 32.17 umol) followed by TEA (9.77 mg, 96.52 umol, 13.45 uL) were added and stirred at 20° C. for 12 hr. The reaction mixture was purified by preparative RP-HPLC with 30-80% 0-9.5 min water-methanol(NH₃ 0.1%), flow 30 ml/min as mobile phase to afford product 2-[[(2R,4S)-1-acetyl-2-methyl-4-piperidyl]amino]-N-[(2S)-2-hydroxy-3-[6-[(4-methyloxazol-5-yl)methoxy]-3,4-dihydro-1H-isoquinolin-2-yl]propyl]pyridine-4-carboxamide (0.0074 g, 12.83 umol, 39.89% yield). ¹H NMR (400 MHz, CDCl₃) δ 1.21 (m, 3H), 1.33 (m, 1H), 1.93 (m, 1H), 2.09 (m, 3H), 2.17 (m, 1H), 2.21 (s, 3H), 2.58 (m, 2H), 2.71 (m, 1H), 2.82 (m, 1H), 2.89 (m, 3H), 3.36 (m, 2H), 3.55 (d, 1H), 3.69 (m, 2H), 3.76 (d, 1H), 3.99 (m, 1H), 4.12 (m, 1H), 4.22 (m, 1H), 4.36 (m, 1H), 4.97 (s, 2H), 5.07 (m, 1H), 6.73 (m, 4H), 6.85 (m, 1H), 6.93 (d, 1H), 7.80 (s, 1H), 8.10 (d, 1H). LCMS(ESI): [M+H]⁺ m/z: calcd 576.7. found 577.2; Rt=0.785 min.

Example 1D69. 2-(((1R,3r,5S)-8-acetyl-8-azabicyclo[3.2.1]octan-3-yl)amino)-N—((S)-2-hydroxy-3-(6-((4-methyloxazol-5-yl)methoxy)-3,4-dihydroisoquinolin-2(1H)-yl)propyl)isonicotinamide (Compound 645)

3-[[4-[[(2S)-2-hydroxy-3-[6-[(4-methyloxazol-5-yl)methoxy]-3,4-dihydro-1H-isoquinolin-2-yl]propyl]carbamoyl]-2-pyridyl]amino]-8-azabicyclo[3.2.1]octane-8-carboxylate (0.0501 g, 77.46 umol, 34.12% yield). LCMS (ESI): [M+H]⁺ m/z: calcd 646.7. found 647.2; Rt=1.005 min.

2-[[(1S,5R)-8-acetyl-8-azabicyclo[3.2H]octan-3-yl]amino]-N-[(2S)-2-hydroxy-3-[6-[(4-methyloxazol-5-yl)methoxy]-3,4-dihydro-1H-isoquinolin-2-yl]propyl]pyridine-4-carboxamide. Hydrogen chloride solution 4.0M in dioxane (160.00 mg, 4.39 mmol, 0.2 mL) was added to a solution of tert-butyl (1S,5R)-3-[[4-[[(2S)-2-hydroxy-3-[6-[(4-methyloxazol-5-yl)methoxy]-3,4-dihydro-1H-isoquinolin-2-yl]propyl]carbamoyl]-2-pyridyl]amino]-8-azabicyclo[3.2.1]octane-8-carboxylate (0.0501 g, 77.46 umol) in DCM (2 mL). The reaction mixture was stirred at 20° C. for 12 hr, then evaporated in vacuo and were mixed with acetic acid (6.98 mg, 116.19 umol, 6.65 uL) in DMF (2 mL). The reaction suspension was cooled to 0° C. and HATU (29.45 mg, 77.46 umol) followed by TEA (23.51 mg, 232.38 umol, 32.39 uL) were added and stirred at 20° C. for 12 hr. The reaction mixture was purified by preparative RP-HPLC with

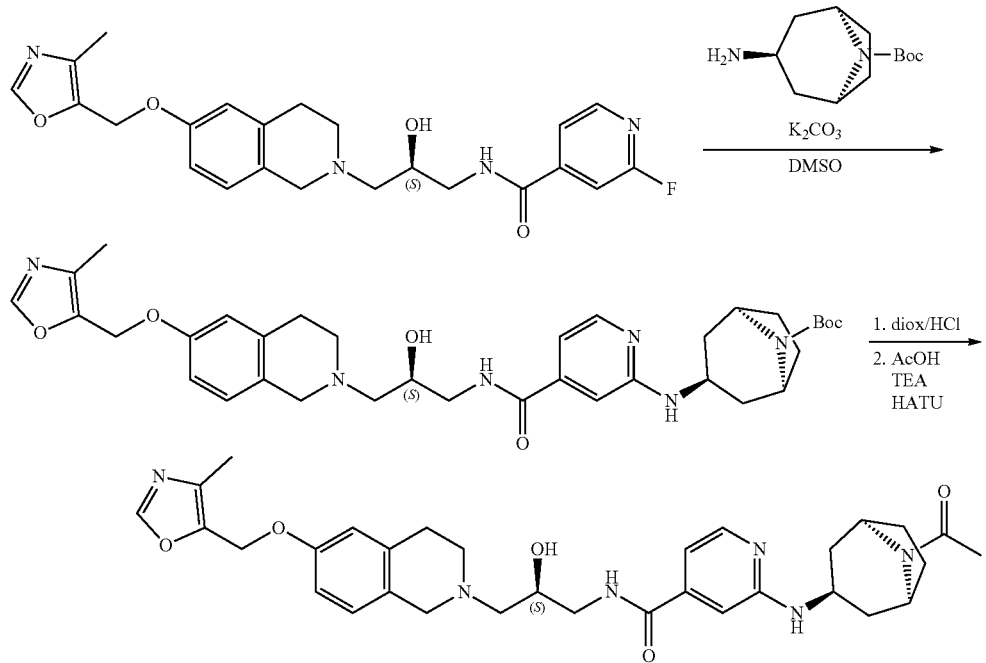

tert-butyl (1S,5R)-3-[[4-[[(2S)-2-hydroxy-3-[6-[(4-methyloxazol-5-yl)methoxy]-3,4-dihydro-1H-isoquinolin-2-yl]propyl]carbamoyl]-2-pyridyl]amino]-H-azabicyclo[3.2.1]octane-8-carboxylate. A mixture of tert-butyl (7S,5R)-3-amino-8-azabicyclo[3.2.1]octane-8-carboxylate (51.38 mg, 227.03 umol), 2-fluoro-N-[(2S)-2-hydroxy-3-[6-[(4-methyloxazol-5-yl)methoxy]-3,4-dihydro-1H-isoquinolin-2-yl]propyl]pyridine-4-carboxamide (0.3 g, 681.10 umol), potassium carbonate, anhydrous, 99% (251.02 mg, 1.82 mmol, 109.62 uL) in DMSO (6 mL) was stirred at 100° C. for 36 hr in sealed tube. Obtained crude product in reaction mixture 6 ml in DMSO was purified by preparative RP-HPLC with 40-70% 0-9.5 min water-methanol(NH₃ 0.1%), flow 30 ml/min as mobile phase to afford product tert-butyl (1S,5R)-

20-70% 0-9.5 min water-methanol(NH₃ 0.1%), flow 30 ml/min as mobile phase to afford product 2-[[(1S,5R)-8-acetyl-8-azabicyclo[3.2.1]octan-3-yl]amino]-N-[(2S)-2-hydroxy-3-[6-[(4-methyloxazol-5-yl)methoxy]-3,4-dihydro-1H-isoquinolin-2-yl]propyl]pyridine-4-carboxamide (0.0083 g, 14.10 umol, 18.20% yield). ¹H NMR (400 MHz, cdcl₃) δ 1.39 (m, 1H), 1.84 (m, 1H), 1.98 (m, 4H), 2.06 (s, 3H), 2.19 (m, 1H), 2.21 (s, 3H), 2.56 (m, 2H), 2.71 (m, 1H), 2.89 (m, 3H), 3.42 (m, 1H), 3.56 (d, 1H), 3.66 (m, 1H), 3.76 (d, 1H), 3.99 (m, 1H), 4.15 (m, 1H), 4.41 (m, 2H), 4.71 (m, 1H), 4.97 (s, 2H), 6.69 (m, 2H), 6.76 (m, 2H), 6.93 (d, 2H), 7.80 (s, 1H), 8.05 (m, 1H). LCMS(ESI): [M+H]⁺ m/z: calcd 588.7. found 589.4; Rt=0.804 min.

Example 1D69. (S)—N-(2-hydroxy-3-(6-((4-methyloxazol-5-yl)methoxy)-3,4-dihydroisoquinolin-2(1H)-yl)propyl)-2-((1-pivaloylpiperidin-4-yl)amino)isonicotinamide (Compound 640)
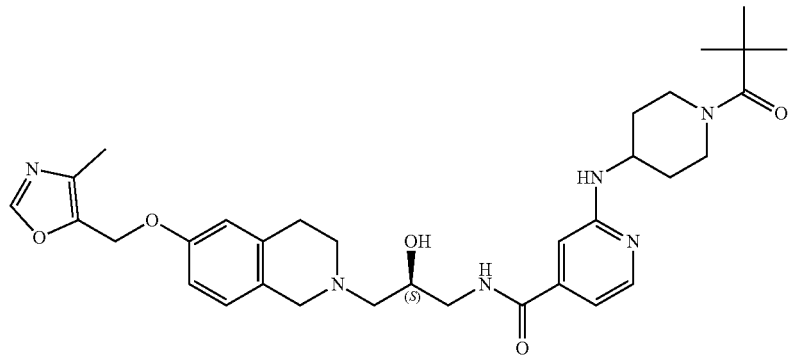
Prepared by general procedure 1D-B. Yield: 9.6 mg (6.8%). $^1$H NMR, δ 1.26 (s, 9H), 1.35 (q, 2H), 2.08 (d, 2H), 2.20 (s, 3H), 2.55 (m, 2H), 2.69 (m, 1H), 2.89 (m, 3H), 3.00 (t, 2H), 3.40 (dt, 1H), 3.45 (s, 2H), 3.54 (m, 1H), 3.72 (m, 2H), 3.98 (m, 2H), 4.33 (d, 2H), 4.57 (d, 1H), 4.96 (s, 2H), 6.71 (m, 2H), 6.76 (s, 1H), 6.93 (m, 2H), 7.79 (s, 1H), 8.07 (d, 1H). LCMS(ESI): [M+H]$^+$ m/z: calcd 604.4. found 605.2; Rt=0.877 min.
Example 2: Synthesis of Compounds of Formula (VIa1') and (VIb1')
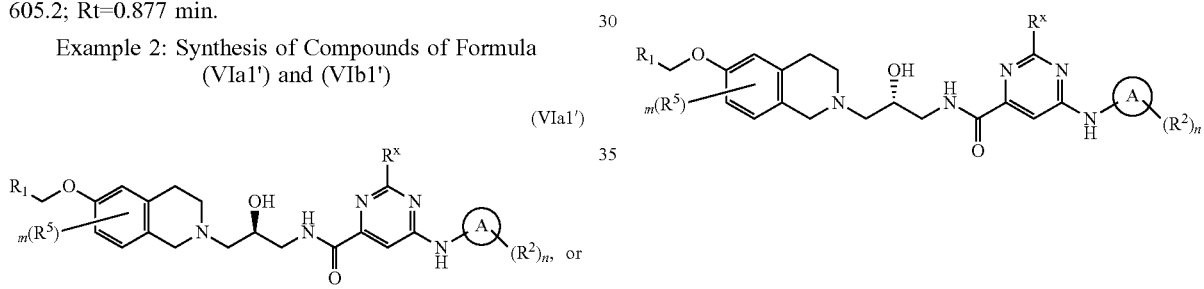
Scheme 2A.
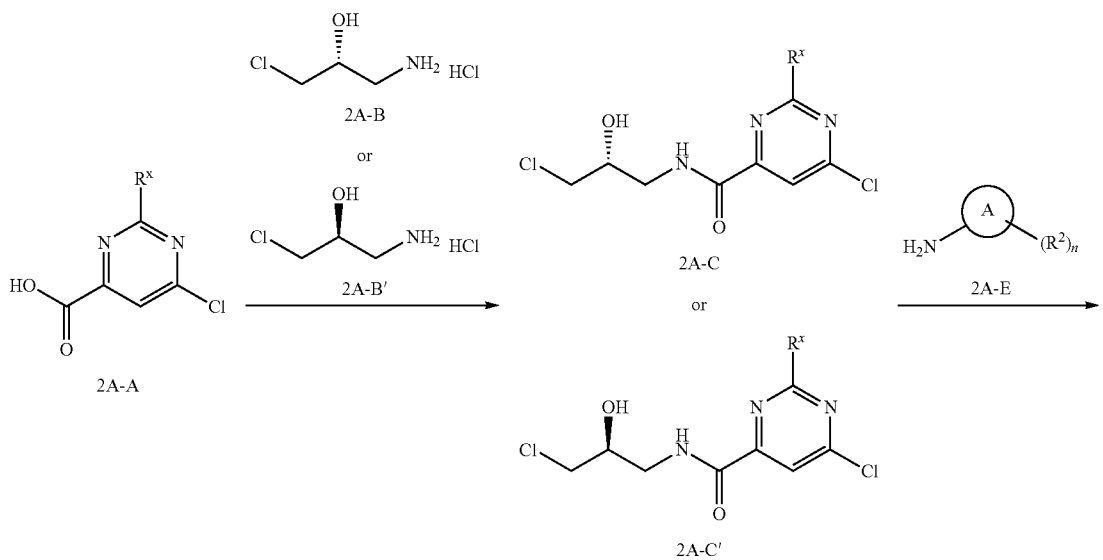

-continued
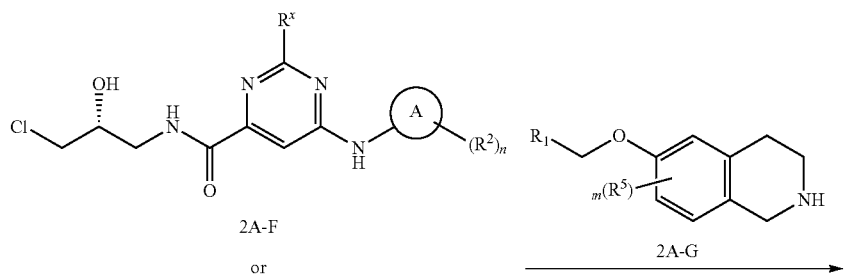
2A-F
or
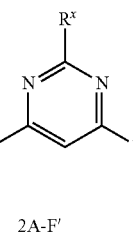
2A-F'
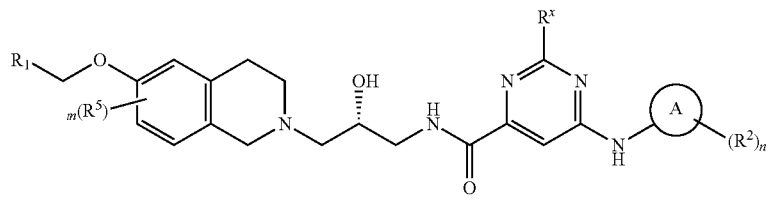
VIa1'
or
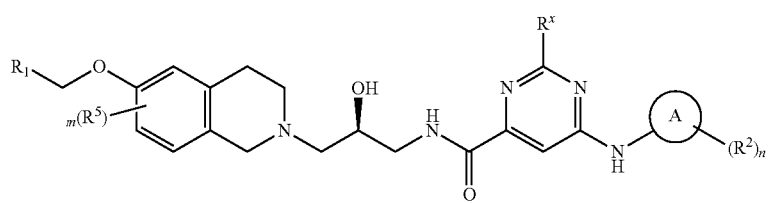
VIab'
wherein variables $R^5$, $R^x$, $R^1$, $R^2$, m, and n are defined herein.
Example 2A1. 6-[(1-acetyl-4-piperidyl)amino]-N-[(2S)-2-hydroxy-3-[6-(oxazol-5-ylmethoxy)-3,4-dihydro-1H-isoquinolin-2-yl]propyl]pyrimidine-4-carboxamide (Compound 135)
a)
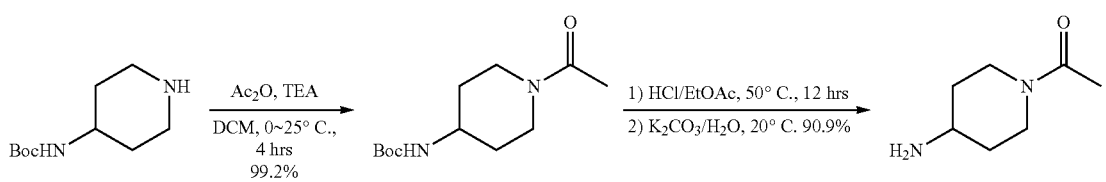

-continued b)

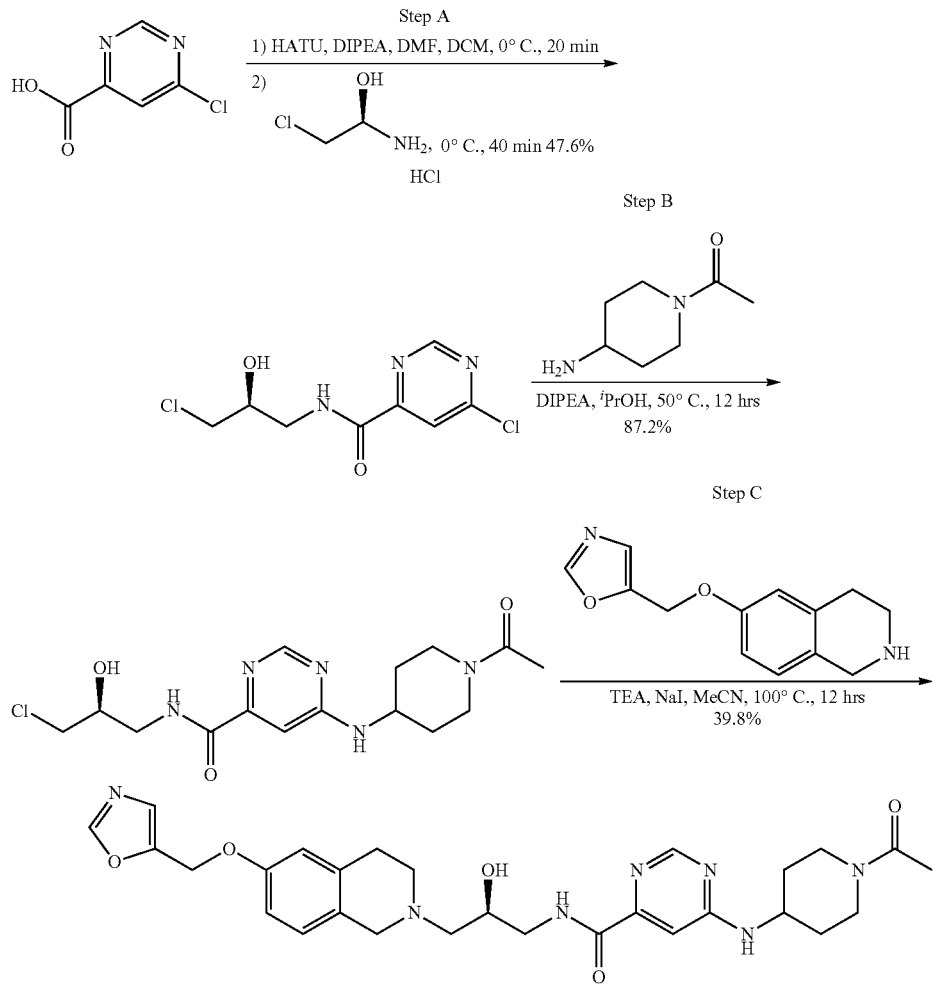

Synthesis of tert-butyl N-(1-acetyl-4-piperidyl)carbamate. To a solution of tert-butyl N-(4-piperidyl)carbamate (5 g, 25.0 mmol) in DCM (80 mL) was added TEA (37.5 mmol, 5.2 mL). Then acetyl acetate (25.0 mmol, 2.4 mL) was added to the mixture dropwise at 0° C. After addition was complete, the mixture was allowed to warm to 25° C. and stirred for 4 hours. The resulting mixture was washed with water (30 mL), saturated NaHCO$_3$ aqueous solution (30 mL*3), dried over anhydrous Na$_2$SO$_4$, filtered and concentrated under reduced pressure to afford tert-butyl N-(1-acetyl-4-piperidyl)carbamate (6 g, 99.18%) as white gum. $^1$H NMR (400 MHz, methanol-d4) δ ppm 4.35 (dd, J=13.4, 1.7 Hz, 1H), 3.76-3.91 (m, 1H), 3.51-3.62 (m, 1H), 3.10-3.22 (m, 1H), 2.70-2.84 (m, 1H), 2.08 (s, 3H), 1.80-1.95 (m, 2H), 1.25-1.46 (m, 11H); LCMS (ESI) [M+H−56]$^+$ m/z: calcd 187.1. found 187.1.

1-(4-amino-1-piperidyl)ethanone. To a solution of tert-butyl N-(1-acetyl-4-piperidyl)carbamate (6 g, 24.8 mmol) in EtOAc (50 mL) was added 4M HCl/EtOAc (100 mL, 0.4 mmol). The mixture was stirred at 50° C. for 12 hours. Saturated K$_2$CO$_3$ aqueous solution (20 mL) was added to the resulting mixture for adjusting the pH=8. The mixture was concentrated under reduced pressure and the residue was extracted with DCM (50 mL). The organic layer was dried over anhydrous Na$_2$SO$_4$, filtered and concentrated under reduced pressure to afford the 1-(4-amino-1-piperidyl)ethanone (3.2 g, 90.9%) as yellow oil. $^1$H NMR (400 MHz, methanol-d4) δ ppm 4.31-4.39 (m, 1H), 3.72-3.85 (m, 1H), 3.00-3.09 (m, 1H), 2.77 (t, J=10.7, 4.2 Hz, 1H), 2.60 (td, J=12.8, 2.8 Hz, 1H), 2.01 (s, 3H), 1.71-1.85 (m, 2H), 1.06-1.27 (m, 2H); LCMS (ESI) [M+H]$^+$ m/z: calcd 143.1. found 143.1.

Example 2A1, Step A. 6-chloro-N-[(2S)-3-chloro-2-hydroxy-propyl]pyrimidine-4-carboxamide. To a solution of 6-chloropyrimidine-4-carboxylic acid (3 g, 19.0 mmol) in DMF (5 mL) and DCM (50 mL) was added HATU (8.6 g, 22.6 mmol), DIPEA (56.8 mmol, 10 mL). The mixture was stirred at 0° C. for 20 minutes and then (2S)-1-amino-3-chloro-propan-2-ol (3 g, 20.55 mmol, HCl salt) was added. The reaction was stirred at 0° C. and carefully monitored by TLC (petroleum ether/EtOAc=1:1, 254 nm) every ten minutes. As the impurity spot (R$_f$=0.25) was observed, the mixture was quenched immediately (~40 minutes) by saturated NH$_4$Cl aqueous solution (30 mL). The organic layer was separated, dried over anhydrous Na$_2$SO$_4$, filtered and concentrated under reduced pressure to give a crude product which was diluted by EtOAc (60 mL), washed with saturated LiCl aqueous solution (25 mL*4). Some product was found in the combined aqueous phase which was extracted with EtOAc (30 mL*3). The combined organic layers were dried over anhydrous Na$_2$SO$_4$, filtered and concentrated under reduced pressure to afford an oil which was purified by flash chromatography (ISCO®; 40 g AgelaFlash® Silica Flash Column, petroleum ether/EtOAc with EtOAc from 0~40%, flow rate=40 mL/min) to afford:

6-chloro-N-[(2S)-3-chloro-2-hydroxy-propyl]pyrimidine-4-carboxamide:

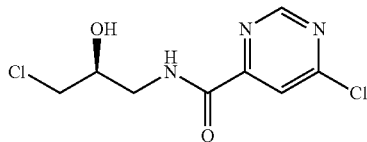 [SMILES: O=C(NC[C@H](O)CCl)c1cc(Cl)ncn1]

(2.25 g, 47.6%) as yellow oil. $^1$H NMR (400 MHz, methanol-d) δ ppm 9.10 (d, J=1.3 Hz, 1H), 8.14 (d, J=1.3 Hz, 1H), 3.99-4.06 (m, 1H), 3.62-3.72 (m, 2H), 3.48-3.61 (m, 2H); LCMS (ESI) [M+H]$^+$ m/z: calcd 250.0. found 250.0.

(R)-6-chloro-N-(3-chloro-2-hydroxypropyl)pyrimidine-4-carboxamide was prepared from (2R)-1-amino-3-chloro-propan-2-ol and 6-chloropyrimidine-4-carboxylic acid using the reaction conditions outlined in Example 2A1, Step C:

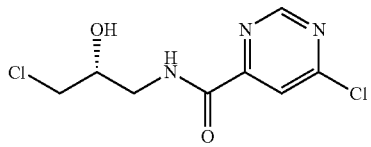 [SMILES: O=C(NC[C@@H](O)CCl)c1cc(Cl)ncn1]

6-chloro-N-[(2R)-3-chloro-2-hydroxy-propyl]pyrimidine-4-carboxamide (2.7 g, 62.2% yield) as a yellow oil. $^1$H NMR (400 MHz, methanol-d$_4$) δ ppm 9.57 (d, J=0.9 Hz, 1H), 8.61 (d, J=1.0 Hz, 1H), 4.40-4.47 (m, 1H), 3.95-4.15 (m, 4H); LCMS (ESI) [M+H]$^+$ m/z: calcd 250.0; found 250.0.

Example 2A1, Step B 6-[(1-acetyl-4-piperidyl)amino]-N-[(2S)-3-chloro-2-hydroxy-propyl]pyrimidine-4-carboxamide). A mixture of 1-(4-amino-1-piperidyl)ethanone (1.7 g, 12.0 mmol), 6-chloro-N-[(2S)-3-chloro-2-hydroxy-propyl]pyrimidine-4-carboxamide (1.5 g, 6.0 mmol), DIPEA (13.0 mmol, 2.3 mL) and i-PrOH (30 mL) was stirred at 50° C. for 12 hours. The mixture was concentrated under reduced pressure and the residue was purified by flash chromatography (ISCO®; 40 g AgelaFlash® Silica Flash Column, DCM/MeOH with MeOH from 0~10%, flow rate=40 mL/min) to afford 6-[(1-acetyl-4-piperidyl)amino]-N-[(2S)-3-chloro-2-hydroxy-propyl]pyrimidine-4-carboxamide (1.86 g, 87.2%) as light-yellow solid. $^1$H NMR (400 MHz, methanol-d) δ ppm 8.48 (s, 1H), 7.12 (s, 1H), 4.45 (br d, J=12.9 Hz, 1H), 4.19-4.23 (m, 1H), 3.91-4.03 (m, 2H), 3.53-3.69 (m, 3H), 3.46 (dd, J=13.8, 7.1 Hz, 1H), 3.32-3.36 (m, 1H), 2.88-2.96 (m, 1H), 2.14 (s, 3H), 2.00-2.12 (m, 2H), 1.41-1.57 (m, 2H); LCMS (ESI) [M+H]$^+$ m/z: calcd 356.1. found 356.1; 100% ee.

Example 2A1, Step C. Synthesis of 6-[(1-acetyl-4-piperidyl)amino]-N-[(2S)-2-hydroxy-3-[6-(oxazol-5-ylmethoxy)-3,4-dihydro-1H-isoquinolin-2-yl]propyl]pyrimidine-4-carboxamide (Compound 135)

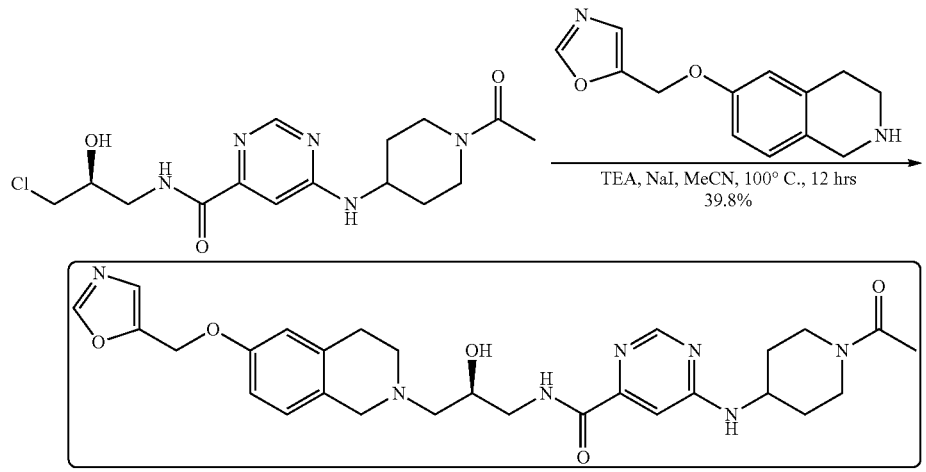

A sealable reaction flask was charged with 6-[(1-acetyl-4-piperidyl)amino]-N-[(2S)-3-chloro-2-hydroxy-propyl]pyrimidine-4-carboxamide (62 mg, 0.174 mmol), 5-(1,2,3,4-tetrahydroisoquinolin-6-yloxymethyl)oxazole (40 mg, 0.174 mmol), TEA (0.717 mmol, 100 uL), NaI (40 mg, 0.267 mmol) and MeCN (1.5 mL). The mixture was sealed and stirred for 12 hours at 100° C. The resulting mixture was concentrated under reduced pressure and the residue was purified by preparative HPLC purification (Instrument: Gilson GX-281 Liquid Handler, Gilson 322 Pump, Gilson 156 UV Detector; Column:Waters Xbridge 150×25 mm×5 µm; Mobile phase A: H$_2$O with 0.05% NH$_3$—H$_2$O (v %); Mobile phase B: MeCN; Gradient: B from 17% to 47% in 7.8 min, hold 100% B for 2.5 min; Flow Rate: 25 mL/min; Column Temperature: 30° C.; Wavelength: 220 nm, 254 nm) to afford 6-[(1-acetyl-4-piperidyl)amino]-N-[(2S)-2-hydroxy-3-[6-(oxazol-5-ylmethoxy)-3,4-dihydro-1H-isoquinolin-2-yl]propyl]pyrimidine-4-carboxamide (38 mg, 39.80% yield) was obtained as off-white solid. $^1$H NMR (400 MHz, methanol-d$_4$) δ ppm 8.26 (s, 1H), 8.24 (s, 1H), 7.23 (s, 1H), 7.07 (s, 1H), 6.95 (d, J=9.3 Hz, 1H), 6.73-6.82 (m, 2H), 5.11 (s, 2H), 4.43 (d, J=13.0 Hz, 1H), 4.15 (s, 1H), 4.06 (quin, J=6.0 Hz, 1H), 3.93 (d, J=14.5 Hz, 1H), 3.66 (s, 2H), 3.44-3.57 (m, 2H), 2.77-2.97 (m, 5H), 2.65 (d, J=6.1 Hz, 2H), 2.12 (s, 3H), 1.97-2.10 (m, 2H), 1.31-1.54 (m, 2H); LCMS (ESI) [M+H]+ m/z: calcd 550.3. found 550.2; HPLC: 95.81% @ 254 nm, 98.6% ee.

Example 2A2. 6-[(1-acetyl-4-piperidyl)amino]-N-[(2S)-2-hydroxy-3-[6-[(2-methylpyrazol-3-yl)methoxy]-3N-dihydro-1H-isoquinolin-2-yl]propyl]pyrimidine-4-carboxamide (Compound 140)

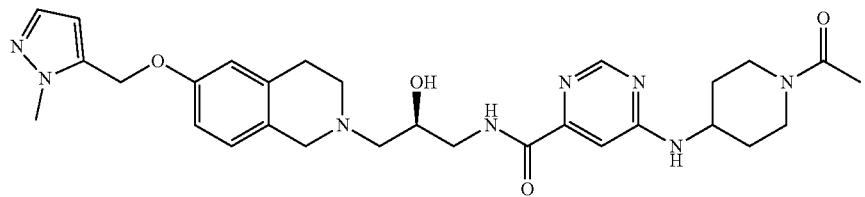 [SMILES: CC(=O)N1CCC(Nc2cc(C(=O)NC[C@H](O)CN3CCc4cc(OCc5ccnn5C)ccc4C3)ncn2)CC1]

6-[(1-acetyl-4-piperidyl)amino]-N-[(2S)-2-hydroxy-3-[6-[(2-methylpyrazol-3-yl)methoxy]-3,4-dihydro-1H-isoquinolin-2-yl]propyl]pyrimidine-4-carboxamide was prepared from (S)-6-((1-acetylpiperidin-4-yl)amino)-N-(3-chloro-2-hydroxypropyl)pyrimidine-4-carboxamide and 6-((1-methyl-1H-pyrazol-5-yl)methoxy)-1,2,3,4-tetrahydroisoquinoline using the conditions outlined in Step E from Example 2A1. The residue was purified by preparative HPLC (Instrument: Gilson GX-281 Liquid Handler, Gilson 322 Pump, Gilson 156 UV Detector; Column: Xtimate C18 150×25 mm×5 μm; Mobile phase A: H₂O with 0.05% NH3-H₂O (v %); Mobile phase B: MeCN; Gradient: B from 20% to 50% in 7.8 min, hold 100% B for 1 min; Flow Rate: 25 mL/min; Column Temperature: 30° C.; Wavelength: 220 nm, 254 nm) to afford 6-[(1-acetyl-4-piperidyl)amino]-N-[(2S)-2-hydroxy-3-[6-[(2-methylpyrazol-3-yl)methoxy]-3,4-dihydro-1H-isoquinolin-2-yl]propyl]pyrimidine-4-carboxamide (28.6 mg, 30.9%) as white solid. ¹H NMR (400 MHz, methanol-d) δ ppm 8.29 (s, 1H), 7.43 (d, J=2.0 Hz, 1H), 7.09 (s, 1H), 6.95-7.00 (m, 1H), 6.78-6.83 (m, 2H), 6.39 (d, J=1.8 Hz, 1H), 5.13 (s, 2H), 4.45 (brd, J=13.8 Hz, 1H), 4.17 (br s, 1H), 4.05-4.11 (m, 1H), 3.92-3.95 (m, 1H), 3.91 (s, 3H), 3.69 (s, 2H), 3.46-3.57 (m, 1H), 2.89-2.96 (m, 3H), 2.82-2.88 (m, 2H), 2.67 (d, J=6.0 Hz, 2H), 2.14 (s, 3H), 1.98-2.12 (m, 2H), 1.38-1.56 (m, 2H); LCMS (ESI) [M+H]+ m/z: calcd 563.3. found 563.2; HPLC: 99.41% @ 254 nm; 98.6% ee.

Example 2A3. 6-[(1-acetyl-4-piperdyl(amino]-N-[(2S)-2-hydroxy-3-[5-methyl-6-[(2-methylpyrazol-3-yl)methoxy]-3,4-dihydro-1H-isoquinolin-2-yl]propyl]pyrimidine-4-carboxamide (Compound 203)

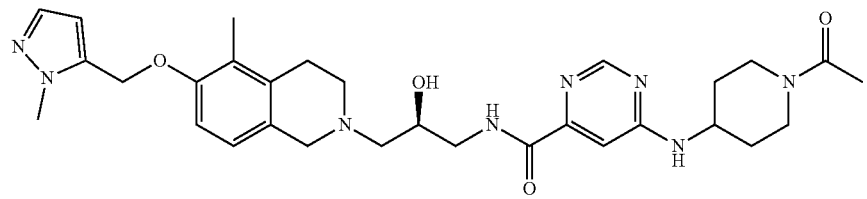 [SMILES: CC(=O)N1CCC(Nc2cc(C(=O)NC[C@H](O)CN3CCc4c(ccc(OCc5ccnn5C)c4C)C3)ncn2)CC1]

6-[(1-acetyl-4-piperidyl)amino]-N-[(2S)-2-hydroxy-3-[5-methyl-6-[(2-methylpyrazol-3-yl)methoxy]-3,4-dihydro-1H-isoquinolin-2-yl]propyl]pyrimidine-4-carboxamide was formed from the reaction of 5-methyl-6-((1-methyl-1H-pyrazol-5-yl)methoxy)-1,2,3,4-tetrahydroisoquinoline and (S)-6-((1-acetylpiperidin-4-yl)amino)-N-(3-chloro-2-hydroxypropyl)pyrimidine-4-carboxamide using the conditions outlined in Step E from Example 2A1. The crude product which was purified preparative HPLC (Instrument: Gilson GX-281 Liquid Handler, Gilson 322 Pump, Gilson 156 UV Detector; Column: Xtimate C18 150×25 mm×5 μm; Mobile phase A: H₂O with 0.05% NH₃—H₂O (v %); Mobile phase B: MeCN; Gradient: B from 23% to 53% in 7.8 min, hold 100% B for 2 min; Flow Rate: 25 mL/min; Column Temperature: 30° C.; Wavelength: 220 nm, 254 nm) to afford 6-[(1-acetyl-4-piperidyl)amino]-N-[(2S)-2-hydroxy-3-[5-methyl-6-[(2-methylpyrazol-3-yl)methoxy]-3,4-dihydro-1H-isoquinolin-2-yl]propyl]pyrimidine-4-carboxamide (21 mg, 43.1% yield) as white solid. $^1$H NMR (400 MHz, methanol-$d_4$) δ ppm 8.25 (s, 1H), 7.42 (d, J=2.0 Hz, 1H), 7.07 (s, 1H), 6.84-6.89 (m, 2H), 6.36 (d, J=2.0 Hz, 1H), 5.11 (s, 2H), 4.43 (br d, J=12.0 Hz, 1H), 4.15 (br s, 1H), 4.03-4.09 (m, 1H), 3.92-3.96 (m, 1H), 3.91 (s, 3H), 3.66 (s, 2H), 3.45-3.55 (m, 2H), 3.24-3.29 (m, 1H), 2.81-2.93 (m, 3H), 2.80 (br s, 2H), 2.64 (d, J=5.8 Hz, 2H), 2.12 (s, 3H), 2.08 (s, 3H), 1.95-2.06 (m, 2H), 1.35-1.54 (m, 2H); LCMS (ESI) [M+H]⁺ m/z: calcd 577.3. found 577.2; HPLC: 100%@254 nm; 97.7% ee.

Example 2A4. 6-[(1-acetyl-4-piperidyl)amino]-N-[(2S)-2-hydroxy-3-[6-(1H-pyrazol-4-ylmethoxy)-3,4-dihydro-1H-isoquinolin-2-yl]propyl]pyrimidine-4-carboxamide (Compound 201))

6-[(1-acetyl-4-piperidyl)amino]-N-[(2S)-2-hydroxy-3-[6-(1H-pyrazol-4-ylmethoxy)-3,4-dihydro-1H-isoquinolin-2-yl]propyl]pyrimidine-4-carboxamide was prepared by the reaction of 6-((1H-pyrazol-4-yl)methoxy)-5-methyl-1,2,3,4-tetrahydroisoquinoline and (S)-6-((1-acetylpiperidin-4-yl)amino)-N-(3-chloro-2-hydroxypropyl)pyrimidine-4-carboxamide using the conditions outlined in Step E from Example 2A1. The residue was purified by preparative HPLC (Instrument: Gilson GX-281 Liquid Handler, Gilson 322 Pump, Gilson 156 UV Detector; Column: Xtimate C18 150×25 mm×5 μm; Mobile phase A: H₂O with 0.05% NH₃—H₂O (v %); Mobile phase B: MeCN; Gradient: B from 20% to 50% in 7.8 min, hold 100% B for 0 min; Flow Rate: 25 mL/min; Column Temperature: 30° C.; Wavelength: 220 nm, 254 nm) to give 6-[(1-acetyl-4-piperidyl)amino]-N-[(2S)-2-hydroxy-3-[6-(1H-pyrazol-4-ylmethoxy)-3,4-dihydro-1H-isoquinolin-2-yl]propyl]pyrimidine-4-carboxamide (6.9 mg, 5.8% yield) as a white dry powder. $^1$H NMR (400 MHz, methanol-$d_4$) δ ppm 8.27 (d, J=0.8 Hz, 1H), 7.67 (s, 2H), 7.07 (s, 1H), 6.93 (d, J=9.3 Hz, 1H), 6.72-6.76 (m, 2H), 4.98 (s, 2H), 4.42 (d, J=13.3 Hz, 1H), 4.15 (s, 1H), 4.06 (quin, J=6.0 Hz, 1H), 3.92 (d, J=14.1 Hz, 1H), 3.65 (s, 2H), 3.44-3.57 (m, 2H), 3.22-3.30 (m, 1H), 2.77-2.94 (m, 5H), 2.64 (d, J=6.0 Hz, 2H), 2.12 (s, 3H), 1.96-2.10 (m, 2H), 1.36-1.53 (m, 2H); LCMS (ESI) [M+H]⁺ m/z: calcd 549.3. found 549.2; HPLC: 95.61% @254 nm; 100% ee.

Example 2A5. 6-[(1-acetyl-4-piperidyl)amino]-N-[(2S)-2-hydroxy-3-[5-methyl-6-(oxazol-5-ylmethoxy)-3,4-dihydro-1H-isoquinolin-2-yl]propyl]pyrimidine-4-carboxamide (Compound 198)

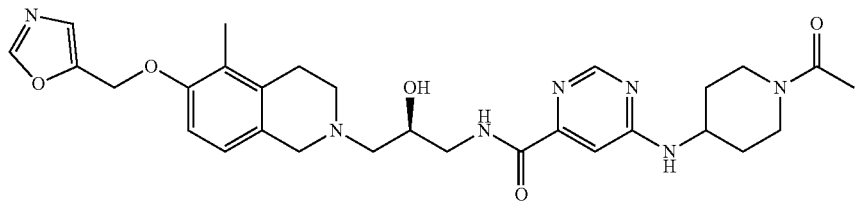

6-[(1-acetyl-4-piperidyl)amino]-N-[(2S)-2-hydroxy-3-[5-methyl-6-(oxazol-5-ylmethoxy)-3,4-dihydro-1H-isoquinolin-2-yl]propyl]pyrimidine-4-carboxamide was prepared from 5%((5-methyl-1,2,3,4-tetrahydroisoquinolin-6-yl)oxy)methyl)oxazole and (S)-6-((1-acetylpiperidin-4-yl)amino)-N-(3-chloro-2-hydroxypropyl)pyrimidine-4-carboxamide using the conditions outlined in Step E from Example 2A1. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H₂O with 0.05% NH₃—H₂O (v %); Mobile phase B: MeCN; Gradient: B from 27% to 57% in 7.8 min, hold 100% B for 0 min; Flow Rate: 25 mL/min; Column Temperature: 30° C.; Wavelength: 220 nm, 254 nm) to afford 6-[(1-acetyl-4-piperidyl)amino]-N-[(2S)-2-hydroxy-3-[5-methyl-6-(oxazol-5-ylmethoxy)-3,4-dihydro-1H-isoquinolin-2-yl]propyl]pyrimidine-4-carboxamide (18 mg, 31.5% yield) as a white solid. $^1$H NMR (400 MHz, methanol-$d_4$) δ ppm 8.24 (s, 2H), 7.20 (s, 1H), 7.07 (s, 1H), 6.86 (s, 2H), 5.11 (s, 2H), 4.43 (d, J=13.1 Hz, 1H), 4.15 (br s, 1H), 4.06 (quin, J=5.9 Hz, 1H), 3.92 (d, J=12.5 Hz, 1H), 3.66 (s, 2H), 3.45-3.55 (m, 2H), 3.23-3.29 (m, 1H), 2.76-2.93 (m,

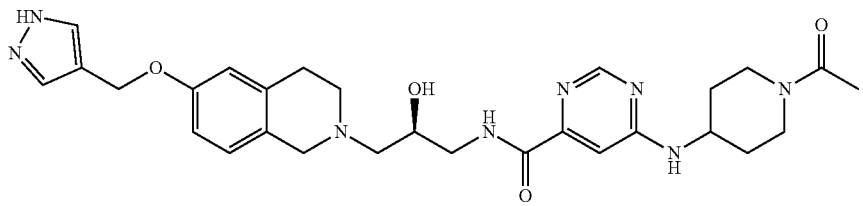 [SMILES: CC(=O)N1CCC(Nc2cc(C(=O)NC[C@H](O)CN3CCc4cc(OCc5cn[nH]c5)ccc4C3)ncn2)CC1]

5H), 2.64 (d, J=5.8 Hz, 2H), 2.12 (s, 3H), 1.96-2.08 (m, 5H), 1.35-1.55 (m, 2H); LCMS (ESI) [M+H]⁺ m/z: calcd 564.3. found 564.2; HPLC: 100%@254 nm; 97.4% ee.

Example 2A6. (S)-6-((1-acetylpiperidin-4-yl)amino)-N-(3-(5-chloro-6-(oxazol-5-ylmethoxy)-3,4-dihydroisoquinolin-2(1H)-yl)-2-hydroxypropyl)pyrimidine-4-carboxamide (Compound 241)

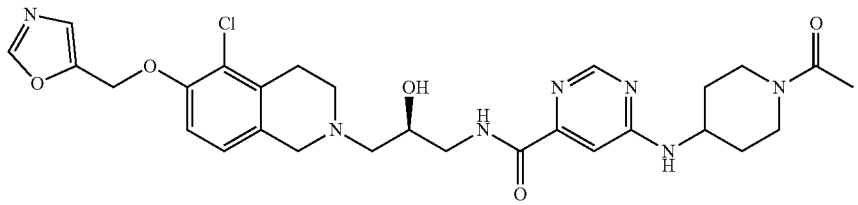 [SMILES: CC(=O)N1CCC(Nc2cc(C(=O)NC[C@H](O)CN3CCc4c(ccc(OCc5cnco5)c4Cl)C3)ncn2)CC1]

(S)-6-((1-acetylpiperidin-4-yl)amino)-N-(3-(5-chloro-6-(oxazol-5-ylmethoxy)-3,4-dihydroisoquinolin-2(1H)-yl)-2-hydroxypropyl)pyrimidine-4-carboxamide was prepared by the reaction of 5-((((5-chloro-1,2,3,4-tetrahydroisoquinolin-6-yl)oxy)methyl)oxazole and (S)-6-((1-acetylpiperidin-4-yl)amino)-N-(3-chloro-2-hydroxypropyl)pyrimidine-4-carboxamide using the conditions outlined in Step E from Example 2A1 The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H₂O with 0.05% NH₃—H₂O (v %); Mobile phase B: MeCN; Gradient: B from 26% to 56% in 7.8 min, hold 100% B for 0 min; Flow Rate: 25 mL/min; Column Temperature: 30° C.; Wavelength: 220 nm, 254 nm) to afford desired product (20 mg, 23.9% yield) which was combined with another batch, dissolved in MeCN and lyophilized to afford 6-[(1-acetyl-4-piperidyl)amino]-N-[(2S)-3-[5-chloro-6-(oxazol-5-ylmethoxy)-3,4-dihydro-1H-isoquinolin-2-yl]-2-hydroxy-propyl]pyrimidine-4-carboxamide (135 mg) as a white solid. ¹H NMR (400 MHz, methanol-d₄) δ ppm 8.22-8.29 (m, 2H), 7.26 (s, 1H), 6.97-7.11 (m, 3H), 5.21 (s, 2H), 4.44 (brd, J=14.6 Hz, 1H), 4.03-4.22 (m, 2H), 3.94 (brd, J=13.1 Hz, 1H), 3.68 (s, 2H), 3.53 (brd, J=5.5 Hz, 2H), 3.25-3.32 (m, 1H), 2.83-2.96 (m, 5H), 2.68 (d, J=5.8 Hz, 2H), 2.15 (s, 3H), 1.98-2.14 (m, 2H), 1.34-1.57 (m, 2H); LCMS (ESI) [M+H]⁺ m/z: calcd 584.2. found 584.1; HPLC: 100% @ 254 nm; 95.4%.

Example 2A7. (S)-6-((1-acetylpiperidin-4-yl)amino)-N-(3-(5-chloro-6-((1-methyl-1H-pyrazol-5-yl)methoxy)-3,4-dihydroisoquinolin-2(1H)-yl)-2-hydroxypropyl)pyrimidine-4-carboxamide (Compound 242)

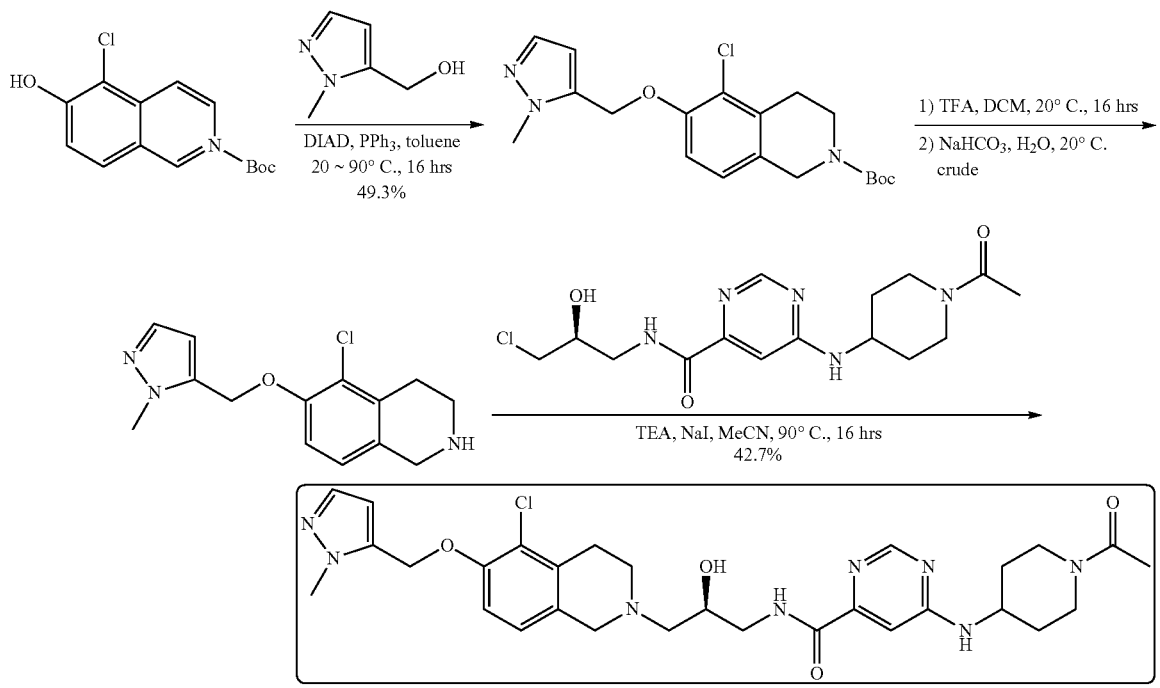

tert-butyl 5-chloro-6-[(2-methylpyrazol-3-yl)methoxy]-3,4-dihydro-1H-isoquinoline-2-carboxylate. To a solution of tert-butyl 5-chloro-6-hydroxy-3,4-dihydro-1H-isoquinoline-2-carboxylate (320 mg, 1.13 mmol), (2-methylpyrazol-3-yl)methanol (152 mg, 1.36 mmol) and triphenylphosphine (442.6 mg, 1.69 mmol) in toluene (10 mL) was added drop-wise isopropyl (NE)-N-isopropoxycarbonyliminocarbamate (341.3 mg, 1.69 mmol) and the reaction mixture was stirred at 90° C. under nitrogen for 16 hours. The mixture was concentrated under reduced pressure and the residue was purified by flash chromatography (ISCO®; 12 g AgelaFlash® Silica Flash Column, petroleum ether/EtOAc with EtOAc from 0~35%, Flow Rate: 30 mF/min) to afford tert-butyl 5-chloro-6-[(2-methylpyrazol-3-yl)methoxy]-3,4-dihydro-1H-isoquinoline-2-carboxylate (210 mg, 49.3% yield) as yellow oil. $^1$H NMR (400 MHz, methanol-$d_4$) δ ppm 7.43 (d, J=1.8 Hz, 1H), 7.07-7.14 (m, 2H), 6.39-6.43 (m, 1H), 5.24 (s, 2H), 4.47-4.57 (m, 2H), 3.89 (s, 3H), 3.67 (t, J=5.8 Hz, 2H), 2.81-2.89 (m, 2H), 1.48-1.52 (m, 9H); LCMS (ESI) [M+H−56]$^+$ m/z: calcd 322.2. found 322.0.

Synthesis of 5-chloro-6-[(2-methylpyrazol-3-yl)methoxy]-1,2,3,4-tetrahydroisoquinoline. The solution of tert-butyl 5-chloro-6-[(2-methylpyrazol-3-yl)methoxy]-3,4-dihydro-1H-isoquinoline-2-carboxylate (190 mg, 0.50 mmol) and TFA (682 mg, 5.98 mmol) in DCM (2 mF) was stirred for 16 hours at 20° C. The mixture was filtered and concentrated under reduced pressure. The residue was quenched by addition of water (10 mF) and washed with DCM (10 mF*3). The aqueous layer was adjusted to pH=7-8 by saturated NaHCO$_3$ aqueous solution. The aqueous layer was extracted with DCM (10 mF*3) and the organic layer was dried over anhydrous Na$_2$SO$_4$, filtered and concentrated under reduced pressure to afford 5-chloro-6-[(2-methylpyrazol-3-yl)methoxy]-1,2,3,4-tetrahydroisoquinoline (100 mg, crude) as yellow solid. LCMS (ESI) [M+H]$^+$ m/z: calcd 278.1. found 278.1.

Synthesis of 6-[(1-acetyl-4-piperidyl)amino]-N-[(2S)-3-[5-chloro-6-[(2-methylpyrazol-3-yl)methoxy]-3,4-dihydro-1H-isoquinolin-2-yl]-2-hydroxy-propyl]pyrimidine-4-carboxamide. A mixture of 5-chloro-6-[(2-methylpyrazol-3-yl)methoxy]-1,2,3,4-tetrahydroisoquinoline (98 mg, 0.35 mmol), 6-[(1-acetyl-4-piperidyl)amino]-N-[(2S)-3-chloro-2-hydroxy-propyl]pyrimidine-4-carboxamide (187 mg, 0.53 mmol), TEA (107 mg, 1.06 mmol), NaI (79 mg, 0.53 mmol) and MeCN (2 mF) was stirred at 90° C. for 16 hours. The mixture was concentrated under reduced pressure and the residue was purified by preparative HPFC (Instrument: Gilson GX-281 Liquid Handler, Gilson 322 Pump, Gilson 156 UV Detector; Column: Durashell 150×25 mm×5 µm; Mobile phase A: H$_2$O with 0.05% NH$_3$—H$_2$O (v %); Mobile phase B: MeCN; Gradient: B from 28% to 58% in 9.5 min, hold 100% B for 0 min; Flow Rate: 25 mL/min; Column Temperature: 30° C.; Wavelength: 220 nm, 254 nm) to afford 6-[(1-acetyl-4-piperidyl)amino]-N-[(2S)-3-[5-chloro-6-[(2-methylpyrazol-3-yl)methoxy]-3,4-dihydro-1H-isoquinolin-2-yl]-2-hydroxy-propyl]pyrimidine-4-carboxamide (90 mg, 42.7% yield) as a white solid. $^1$H NMR (400 MHz, methanol-$d_4$) δ ppm 8.25 (s, 1H), 7.43 (d, J=1.9 Hz, 1H), 6.97-7.10 (m, 3H), 6.40 (d, J=2.0 Hz, 1H), 5.22 (s, 2H), 4.44 (br d, J=13.1 Hz, 1H), 4.03-4.20 (m, 2H), 3.99 (s, 3H), 3.92-3.98 (m, 1H), 3.69 (s, 2H), 3.50-3.57 (m, 2H), 3.24-3.31 (m, 1H), 2.81-2.96 (m, 5H), 2.68 (d, J=6.1 Hz, 2H), 2.15 (s, 3H), 1.98-2.15 (m, 2H), 1.36-1.57 (m, 2H); LCMS (ESI) [M+H]$^+$ m/z: calcd 597.3. found 597.1; HPLC: 100%@254 nm; 96.5% ee.

Example 2A8. 6-[(1-acetyl-4-piperidyl)amino]-N-[(2S)-2-hydroxy-3-[5-methyl-6-(1H-pyrazol-4-ylmethoxy)-3,4-dihydro-1H-isoquinolin-2-yl]propyl]pyrimidine-4-carboxamide (Compound 253)

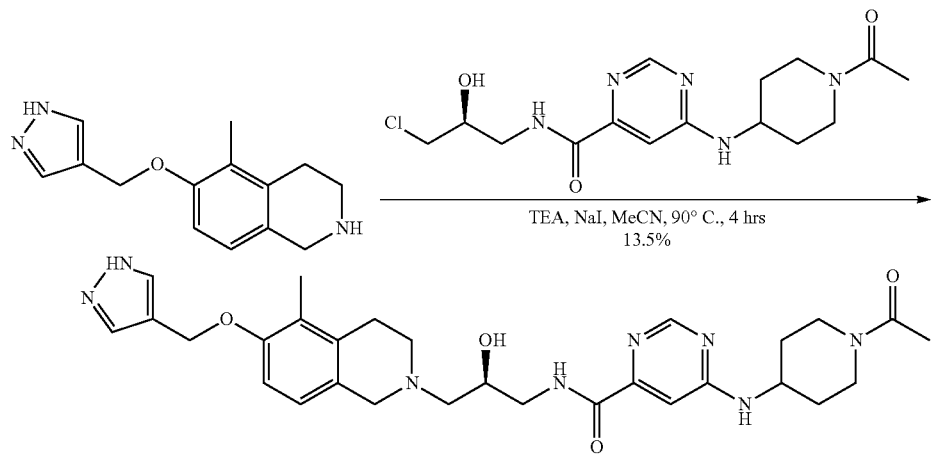

To a solution of 5-methyl-6-(1H-pyrazol-4-ylmethoxy)-1,2,3,4-tetrahydroisoquinoline (45 mg, 0.18 mmol), 6-[(1-acetyl-4-piperidyl)amino]-N-[(2S)-3-chloro-2-hydroxy-propyl]pyrimidine-4-carboxamide (70.0 mg, 0.20 mmol), NaI (35.00 mg, 233.50 umol) in MeCN (2 mL) was added TEA (0.65 mmol, 90 uL), and then the mixture was sealed and stirred at 90° C. for 4 hours. The mixture was concentrated under reduced pressure and the residue was purified with preparative HPLC (Instrument: Gilson GX-281 Liquid Handler, Gilson 322 Pump, Gilson 156 UV Detector; Column: Waters Xbridge 150×25 mm×5 µm; Mobile phase A: H$_2$O with 0.05% NH$_3$—H$_2$O (v %); Mobile phase B: MeCN; Gradient: B from 29% to 29% in 6.5 min, hold 100% B for 1 min; Flow Rate: 25 mL/min; Column Temperature: 30° C.; Wavelength: 220 nm, 254 nm) to afford 6-[(1-acetyl-4-piperidyl)amino]-N-[(2S)-2-hydroxy-3-[5-methyl-6-(1H-pyrazol-4-ylmethoxy)-3,4-dihydro-1H-isoquinolin-2-yl]propyl]pyrimidine-4-carboxamide (14 mg, 13.5% yield) as off-white solid. $^1$H NMR (400 MHz, methanol-$d_4$) δ ppm 8.27 (s, 1H), 7.69 (br s, 2H), 7.08 (s, 1H), 6.85 (s, 2H), 5.00 (s, 2H), 4.43 (d, J=13.1 Hz, 1H), 4.04-4.20 (m, 2H), 3.92 (br d, J=15.3 Hz, 1H), 3.71 (s, 2H), 3.45-3.56 (m, 2H), 3.24-3.29 (m, 1H), 2.85-2.93 (m, 3H), 2.81 (br d, J=5.8 Hz, 2H), 2.66-2.71 (m, 2H), 2.12 (s, 3H), 2.08 (s, 3H), 1.96-2.06 (m, 2H), 1.39-1.55 (m, 2H); LCMS (ESI) [M+H]$^+$ m/z: calcd 563.3. found 563.1; HPLC: 94.87% @ 254 nm; 97.6% ee.

Example 2A9. 6-[(1-acetyl-4-piperidyl)amino]-N-[(2S)-3-[5-chloro-6-(1H-pyrazol-4-ylmethoxy)-3,4-dihydro-1H-isoquinolin-2-yl]-2-hydroxy-propyl]pyrimidine-4-carboxamide (Compound 261)

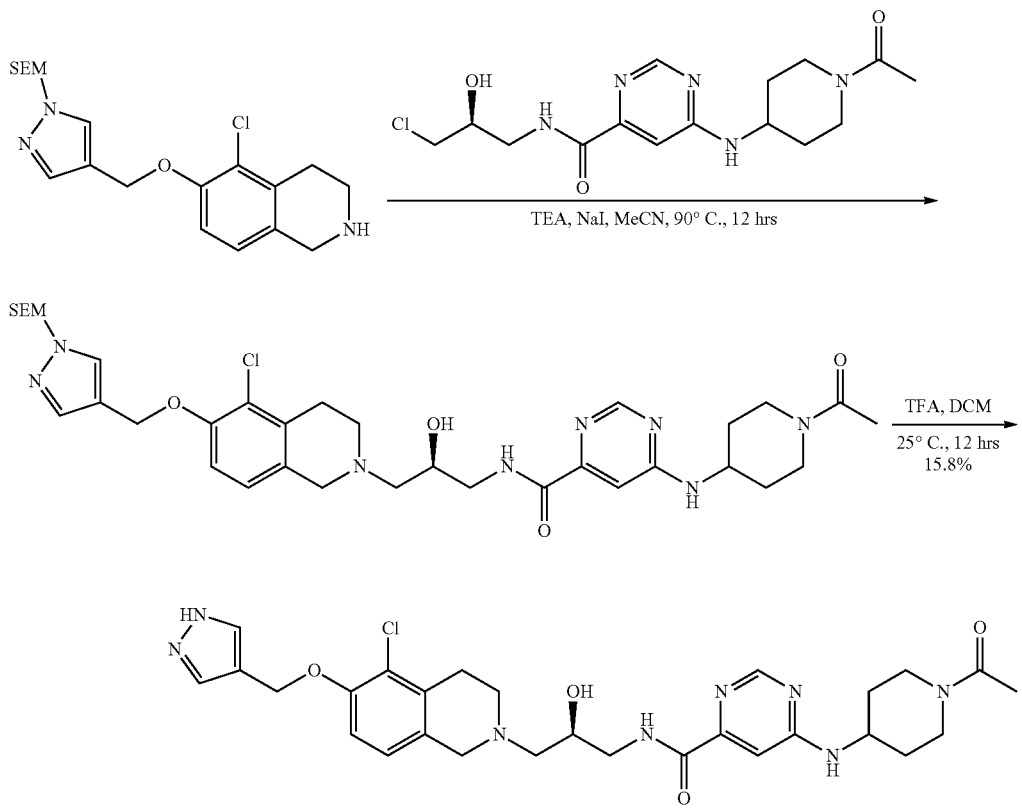

A mixture of 2-[[4-[(5-chloro-1,2,3,4-tetrahydroisoquinolin-6-yl)oxymethyl]pyrazol-1-yl]methoxy]ethyl-trimethylsilane (25 mg, 0.063 mmol), 6-[(1-acetyl-4-piperidyl)amino]-N-[(2S)-3-chloro-2-hydroxy-propyl]pyrimidine-4-carboxamide (30 mg, 0.084 mmol), TEA (35 mg, 0.346 mmol) and NaI (13 mg, 0.087 mmol) and MeCN (1.5 mL) was stirred at 90° C. for 12 hours. The resulting mixture was concentrated under reduced pressure and the residue was purified by flash chromatography (ISCO®; 4 g AgelaFlash® Silica Flash Column, DCM/MeOH with MeOH from 0~7%, Flow Rate: 25 mF/min) to afford 6-[(1-acetyl-4-piperidyl)amino]-N-[(2S)-3-[5-chloro-6-[[1-(2-trimethylsilylethoxymethyl)pyrazol-4-yl]methoxy]-3,4-dihydro-1H-isoquinolin-2-yl]-2-hydroxy-propyl]pyrimidine-4-carboxamide (35 mg, crude) as yellow oil. LCMS (ESI) [M+H]$^+$ m/z calcd 713.2. found 713.3.

6-[(1-acetyl-4-piperidyl)amino]-N-[(2S)-3-[5-chloro-6-(1H-pyrazol-4-ylmethoxy)-3,4-dihydro-1H-isoquinolin-2-yl]-2-hydroxy-propyl[pyrimidine-4-carboxamidine. To a solution of 6-[(1-acetyl-4-piperidyl)amino]-N-[(2S)-3-[5-chloro-6-[[1-(2-trimethylsilylethoxymethyl)pyrazol-4-yl]methoxy]-3,4-dihydro-1H-isoquinolin-2-yl]-2-hydroxy-propyl]pyrimidine-4-carboxamide (43 mg, 60.3 umol) in DCM (4 mF) was added TFA (2 mF). The mixture was stirred at 25° C. for 1.5 hours. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: 10 mM NH$_4$HCO$_3$; Mobile phase B: MeCN; Gradient: B from 20% to 44% in 8 min, hold 100% B for 2 min; Flow Rate: 25 mL/min; Column Temperature: room temperature; Wavelength: 220 nm, 254 nm). The fraction was neutralized by formic acid (0.5 mL), concentrated under reduced pressure and lyophilized for overnight to afford the desired product which contained some HCOONH$_4$. This product was further purified by preparative HPLC (Instrument: Gilson GX-281 Liquid Handler, Gilson 322 Pump, Gilson 156 UV Detector; Column: Xtimate C18 150×25 mm×5 μm; Mobile phase A: H$_2$O with 0.225% FA(v %); Mobile phase B: MeCN; Gradient: B from 8% to 38% in 7 min, hold 100% B for 0 min; Flow Rate: 25 mL/min; Column Temperature: 22° C.; Wavelength: 220 nm, 254 nm) to afford 6-[(1-acetyl-4-piperidyl)amino]-N-[(2S)-3-[5-chloro-6-(1H-pyrazol-4-ylmethoxy)-3,4-dihydro-1H-isoquinolin-2-yl]-2-hydroxy-propyl]pyrimidine-4-carboxamide (5 mg, 27.8% yield, as an off-white solid. $^1$H NMR (400 MHz, methanol-d$_4$) δ ppm 8.32 (s, 1H), 1.11 (s, 2H), 6.97-7.14 (m, 3H), 5.12 (s, 2H), 4.45 (d, J=14.0 Hz, 1H), 4.09-4.27 (m, 2H), 3.86-3.99 (m, 3H), 3.53 (d, J=5.8 Hz, 2H), 3.30 (m, 1H), 3.08 (br s, 2H), 2.80-3.02 (m, 5H), 2.14 (s, 3H), 1.98-2.12 (m, 2H), 1.40-1.62 (m, 2H); LCMS (ESI) [M+H]$^+$ m/z calcd 583.3. found 583.1; HPLC: 97.79% @ 254 nm; 99.3% ee.

Example 2A10, N-[(2S)-2-hydroxy-3-[6-(oxazol-5-ylmethoxy)-3N-dihydro-1H-isoquinolin-2-yl]propyl]-6-[[1-[3-(3-methyldiazirine-3-yl)propanoyl]-4-piperidyl]amino]pyrimidine-4-carboxamide (Compound 363)

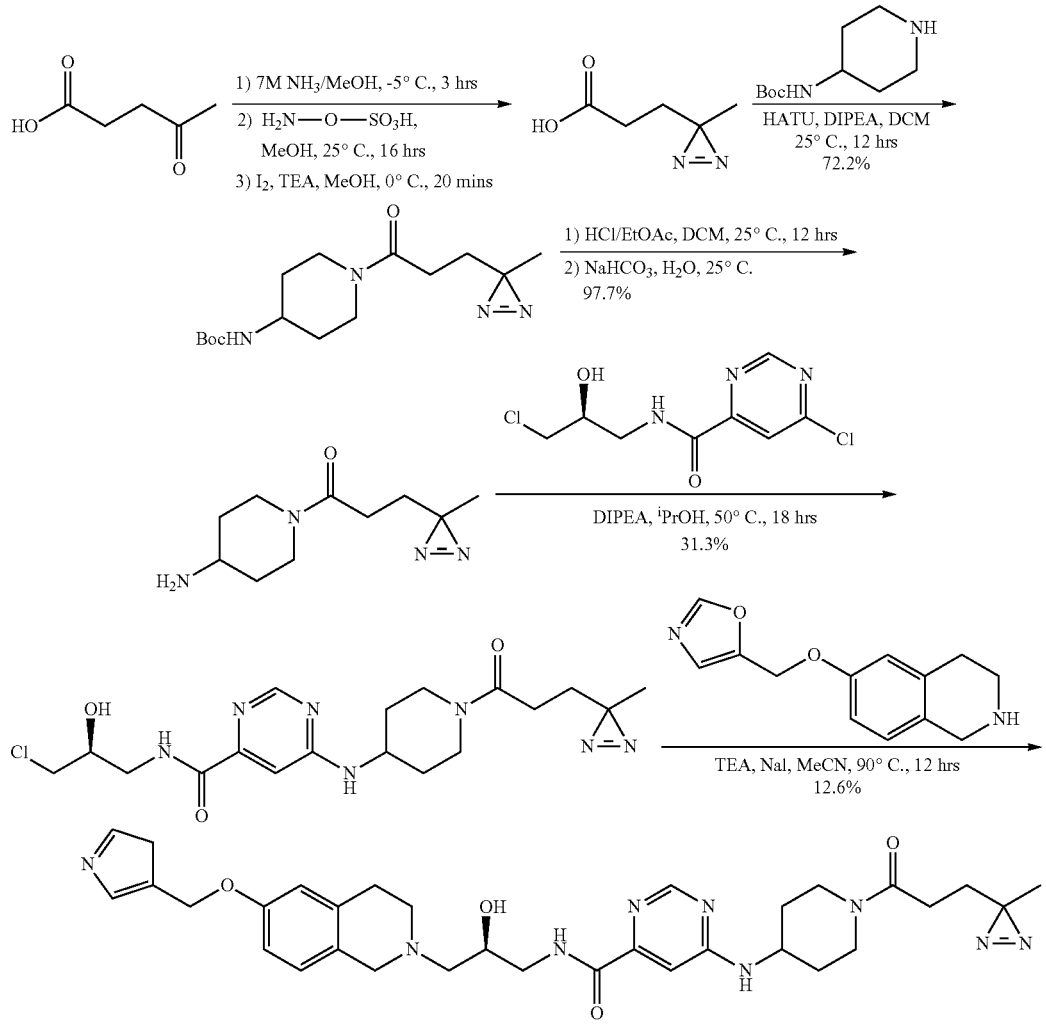

N-](2S)-2-hydroxy-3-[6-(oxazol-5-ylmethoxy)-3,4-dihydro-1H-isoquinolin-2-yl]propyl]-6-[[1-[3-(3-methyldiazirin-3-yl)propanoyl]-4-piperidyl]amino] pyrimidine-4-carboxamide (Compound 363)

3-(3-methyldiazirin-3-yl)propanoic acid. To a round bottom flask were added 4-oxopentanoic acid (3 g, 25.8 mmol) and MeOH (10 mL). The mixture was degassed and backfilled with nitrogen for three times and then 7M $NH_3$/MeOH (7 M, 30 mL) was added to the mixture drop wise at −5° C. The mixture was stirred at −5° C. for 3 hours. Then a solution of hydroxylamine-o-sulfonic acid (3.60 g, 31.8 mmol) in MeOH (10 mL) was added and the mixture was stirred for 16 hours. The suspension was filtered and the filtrate was concentrated under reduced pressure. The residue was dissolved in MeOH (10 mL) and cooled in an ice bath. TEA (6 mL, 43.1 mmol) was added and the solution was allowed to stir for 20 minutes. Iodine (11.7 g, 46.1 mmol) was added until the color remained. The solution was diluted with EtOAc (3 mL) and successively washed with 1M HCl aqueous solution (3 mL), a 10% wt sodium thiosulfate aqueous solution (3 mL), brine (3 mL), and dried over anhydrous $Na_2SO_4$. The organic solvents were removed in vacuum to afford 3-(3-methyldiazirin-3-yl)propanoic acid (2 g, crude) as yellow solid. $^1$H NMR (400 MHz, chloroform-d) δ ppm 2.14-2.21 (m, 2H), 1.70 (t, J=7.8 Hz, 2H), 1.03 (s, 3H).

tert-butyl N-[1-[3-(3-methyldiazirin-3-yl)propanoyl]-4-piperidyl[carbamate. To a solution of 3-(3-methyldiazirin-3-yl)propanoic acid (2 g, 3.12 mmol) and HATU (1.40 g, 3.68 mmol) in DCM (8 mL) were added DIPEA (1.30 g, 10.1 mmol) and tert-butyl N-(4-piperidyl)carbamate (625.2 mg, 3.12 mmol). The mixture was stirred at 25° C. for 12 hours. The resulting mixture was concentrated under reduced pressure and the residue was diluted with EtOAc (100 mL) and washed with saturated $NH_4Cl$ aqueous solution (50 mL*3). The combined organic layer was dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~50%, Flow rate: 30 mL/min) to afford tert-butyl N-[1-[3-(3-methyldiazirin-3-yl)

propanoyl]-4-piperidyl]carbamate (700 mg, 72.2% yield) as white solid. ¹H NMR (400 MHz, methanol-d₄) δ ppm 4.36 (d, J=13.6 Hz, 1H), 3.86 (d, J=13.8 Hz, 1H), 3.52-3.63 (m, 1H), 3.15 (t, J=12.6 Hz, 1H), 2.73-2.86 (m, 1H), 2.26 (t, J=7.6 Hz, 2H), 1.82-1.97 (m, 2H), 1.66 (t, J=7.5 Hz, 2H), 1.44 (s, 9H), 1.24-1.39 (m, 2H), 1.02 (s, 3H); LCMS (ESI) [M+Na]⁺ m/z: calcd 333.1. found 333.1.

1-(4-amino-1-piperidyl)-3-(3-methyldiazirin-3-yl)propan-1-one. To a solution of tert-butyl N-[1-[3-(3-methyldiazirin-3-yl)propanoyl]-4-piperidyl]carbamate (680 mg, 2.19 mmol) in DCM (4 mL) was added 4M HCl/EtOAc (2 mL, 8.0 mmol). The mixture was stirred at 25° C. for 12 hours. The resulting mixture was quenched by addition of saturated NaHCO₃ aqueous solution (5 mL) and stirred at 25° C. for 1 hour. The mixture was dried over anhydrous MgSO₄, filtered and concentrated under reduced pressure to afford 1-(4-amino-1-piperidyl)-3-(3-methyldiazirin-3-yl)propan-1-one (450 mg, 97.7% yield) as yellow oil. ¹H NMR (400 MHz, methanol-d₄) δ ppm 4.51-4.60 (m, 1H), 3.99 (d, J=13.9 Hz, 1H), 3.08-3.19 (m, 1H), 2.66-2.75 (m, 1H), 2.26-2.31 (m, 2H), 1.97-2.05 (m, 2H), 1.64-1.72 (m, 2H), 1.33-1.53 (m, 2H), 1.03 (s, 3H); LCMS (ESI) [M+H−28]⁺ m/z: calcd 183.1. found 183.1.

N-[(2S)-3-chloro-2-hydroxy-propyl]-6-[[1-[3-(3-methyldiazirin-3-yl)propanoyl]-4-piperidyl]amino]pyrimidine-4-carboxamide. A mixture of 1-(4-amino-1-piperidyl)-3-(3-methyldiazirin-3-yl)propan-1-one (320 mg, 1.52 mmol), 6-chloro-N-[(2S)-3-chloro-2-hydroxy-propyl]pyrimidine-4-carboxamide (400 mg, 1.28 mmol), DIPEA (3.67 mmol, 0.64 mL) and ⁱPrOH (5 mL) was stirred at 50° C. for 12 hours. The resulting mixture was concentrated under reduced pressure and the residue was purified by flash chromatography (ISCO®; 20 g AgelaFlash® Silica Flash Column, petroleum ether/EtOAc with EtOAc from 0~50%, Flow rate: 30 mL/min, then DCM/MeOH with MeOH from 0-8%, Flow rate: 30 mL/min) to afford N-[(2S)-3-chloro-2-hydroxy-propyl]-6-[[1-[3-(3-methyldiazirin-3-yl)propanoyl]-4-piperidyl]amino]pyrimidine-4-carboxamide (170 mg, 31.3% yield) as yellow oil. N-[(2S)-3-chloro-2-hydroxy-propyl]-6-[[1-[3-(3-methyldiazirin-3-yl)propanoyl]-4-piperidyl]amino]pyrimidine-4-carboxamide: ¹H NMR (400 MHz, methanol-d₄) δ ppm 8.49 (s, 1H), 7.12 (s, 1H), 4.45 (d, J=11.9 Hz, 1H), 3.96-4.03 (m, 2H), 3.57-3.69 (m, 3H), 3.44-3.50 (m, 2H), 2.92 (t, J=11.1 Hz, 1H), 2.31 (t, J=7.5 Hz, 2H), 2.04-2.16 (m, 2H), 1.68-1.73 (m, 2H), 1.42-1.56 (m, 3H), 1.05 (s, 3H); LCMS (ESI) [M+H]⁺ m/z: calcd 424.2. found 424.1.

N-[(2S)-2-hydroxy-3-[6-(oxazol-5-ylmethoxy)-3,4-dihydro-1H-isoquinolin-2-yl]propyl]-6-[[1-[3-(3-methyldiazirin-3-yl)propanoyl]-4-piperidyl]amino]pyrimidine-4-carboxamide. To a solution of 5-(1,2,3,4-tetrahydroisoquinolin-6-yloxymethyl)oxazole (65.2 mg, 0.283 mmol), TEA (0.430 mmol, 60 uL) and NaI (32.0 mg, 0.213 mmol) in MeCN (1.5 mL) was added N-[(2S)-3-chloro-2-hydroxy-propyl]-6-[[1-[3-(3-methyldiazirin-3-yl)propanoyl]-4-piperidyl]amino]pyrimidine-4-carboxamide (60 mg, 0.142 mmol). The mixture was stirred at 90° C. for 12 hours. The mixture was concentrated under reduced pressure and the residue was purified with preparative HPLC (Instrument: Gilson GX-281 Liquid Handler, Gilson 322 Pump, Gilson 156 UV Detector; Column: Xtimate C18 150×25 mm×5 μm; Mobile phase A: H₂O with 0.10% NH₄HCO₃ (v %); Mobile phase B: MeCN; Gradient: B from 23% to 53% in 8.5 min, hold 100% B for 2 min; Flow Rate: 25 mL/min; Column Temperature: 30° C.; Wavelength: 220 nm, 254 nm) to afford N-[(2S)-2-hydroxy-3-[6-(oxazol-5-ylmethoxy)-3,4-dihydro-1H-isoquinolin-2-yl]propyl]-6-[[1-[3-(3-methyldiazirin-3-yl)propanoyl]-4-piperidyl]amino]pyrimidine-4-carboxamide (11 mg, 12.6% yield) as light-yellow solid. ¹H NMR (400 MHz, methanol-d₄) δ ppm 8.22-8.27 (m, 2H), 7.23 (s, 1H), 7.07 (s, 1H), 6.92-6.97 (m, 1H), 6.74-6.80 (m, 2H), 5.11 (s, 2H), 4.43 (d, J=13.3 Hz, 1H), 4.15 (br s, 1H), 4.01-4.08 (m, 1H), 3.88-3.97 (m, 1H), 3.66 (s, 2H), 3.47-3.56 (m, 2H), 3.20-3.28 (m, 1H), 2.86-2.96 (m, 3H), 2.77-2.86 (m, 2H), 2.65 (d, J=6.1 Hz, 2H), 2.29 (t, J=7.6 Hz, 2H), 1.96-2.12 (m, 2H), 1.65-1.72 (m, 2H), 1.36-1.53 (m, 2H), 1.03 (s, 3H); LCMS (ESI) [M+H]⁺ m/z: calcd 618.3, found 618.2; HPLC: 98.78%@254 nm; 98.1% ee.

Example 2A11. 6-[(1-acetyl-4-piperidyl)amino]-N-[(2S)-3-[8-fluoro-5-methyl-6-[(4-methyloxazol-5-yl)methoxy]-3,4-dihydro-1H-isoquinolin-2-yl]-2-hydroxy-propyl]pyrimidine-4-carboxamide (Compound 618)

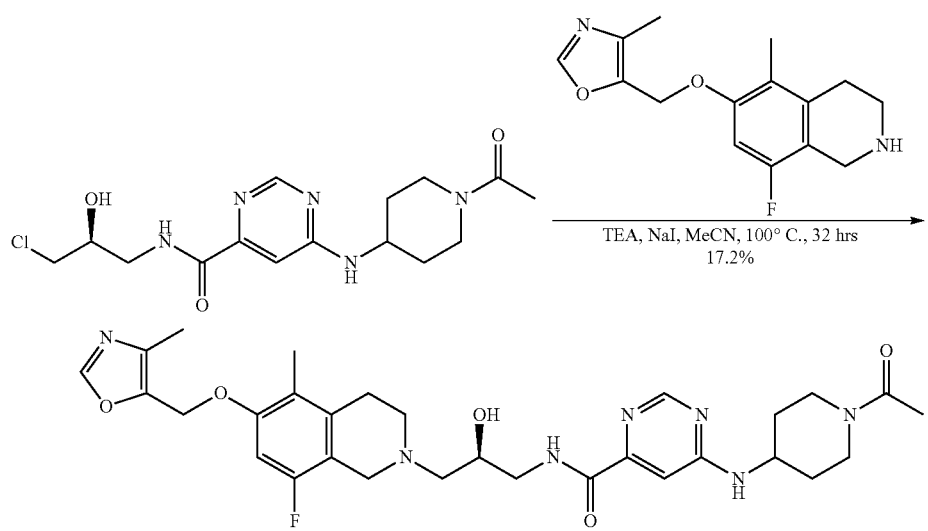

To a solution of 5-[(8-fluoro-5-methyl-1,2,3,4-tetrahydroisoquinolin-6-yl)oxymethyl]-4-methyl-oxazole (40 mg, 0.145 mmol), 6-[(1-acetyl-4-piperidyl)amino]-N-[(2S)-3-chloro-2-hydroxy-propyl]pyrimidine-4-carboxamide 180 mg, 0.506 mmol) in MeCN (1.5 mL) were added NaI (90 mg, 0.60 mmol) and TEA (2.1 mL, 15.2 mmol). The mixture was sealed and stirred at 100° C. for 32 hours. The reaction mixture was concentrated under reduced pressure and the residue was purified with preparative HPLC (Instrument: Gilson GX-281 Liquid Handler, Gilson 322 Pump, Gilson 156 UV Detector; Column: Waters Xbridge BEH C18 150×25 mm×5 μm; Mobile phase A: H$_2$O with 0.225% FA-H$_2$O (v %); Mobile phase B: MeCN; Gradient: B from 5% to 35% in 9.5 min, hold 100% B for 2 min; Flow Rate: 25 mL/min; Column Temperature: 30° C.; Wavelength: 220 nm, 254 nm) to afford 6-[(1-acetyl-4-piperidyl)amino]-N-[(2S)-3-[8-fluoro-5-methyl-6-[(4-methyloxazol-5-yl)methoxy]-3,4-dihydro-1H-isoquinolin-2-yl]-2-hydroxy-propyl]pyrimidine-4-carboxamide (16 mg, 17.2% yield, HCOOH, white solid). NMR (400 MHz, methanol-d$_4$) δ ppm 8.38 (s, 1H), 8.29 (br s, 1H), 8.15 (s, 1H), 7.10 (s, 1H), 6.86 (d, J=11.6 Hz, 1H), 5.11 (s, 2H), 4.43 (brd, J=14.3 Hz, 1H), 4.18-4.26 (m, 1H), 4.14 (s, 2H), 3.93 (br d, J=14.0 Hz, 1H), 3.47-3.57 (m, 2H), 3.32-3.36 (m, 2H), 3.24-3.30 (m, 1H), 3.02-3.14 (m, 2H), 2.96 (br d, J=2.3 Hz, 2H), 2.85-2.93 (m, 1H), 2.20 (s, 3H), 2.12 (s, 3H), 2.06-2.11 (m, 1H), 2.04 (s, 3H), 1.96-2.03 (m, 1H), 1.36-1.56 (m, 2H); $^{19}$FNMR (376 MHz, methanol-d$_4$) δ ppm −122.985; LCMS (ESI) [M+H]$^+$ m/z: calcd 596.3. found 596.2; HPLC: 100%@254 nm; 99.5% ee.

Example 2A12. (S)-6-((1-acetylpiperidin-4-yl)amino)-N-(2-hydroxy-3-[5-methyl-6-((1-methyl-1H-1,2,3-triazol-5-yl)methoxy)-3N-dihydroisoquinolin-2(1H)-yl)propyl]pyrimidine-4-carboxamide (Compound 276)

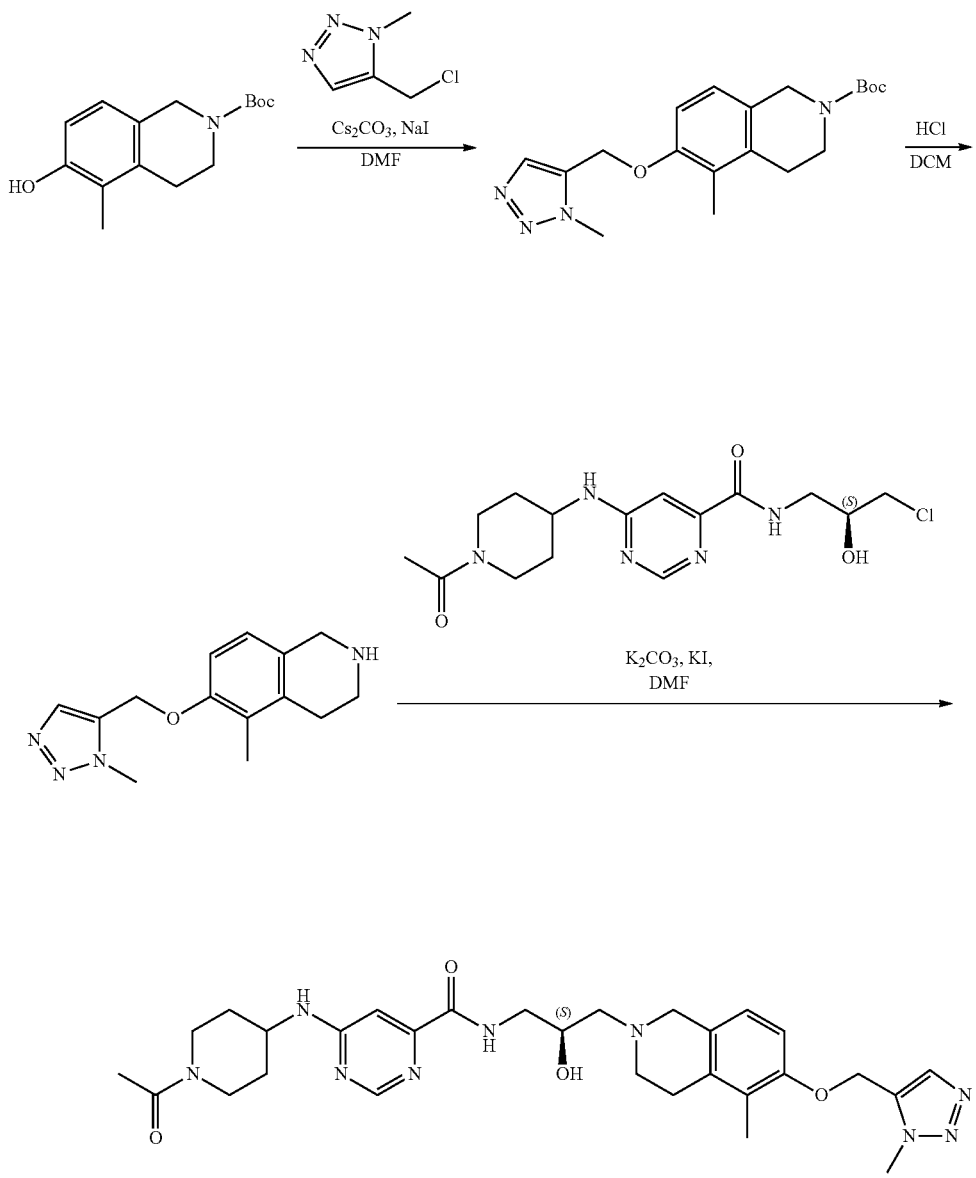

tert-butyl 5-methy-6-((3-methylisoxazol-4-yl)methoxy)-3,4-dihydroisoquinoline-2(1H)-carboxylate. tert-butyl 6-hydroxy-5-methyl-3,4-dihydro-1H-isoquinoline-2-carboxylate (1.1 g, 4.18 mmol), 5-(chloromethyl)-1-methyl-triazole (842.25 mg, 5.01 mmol, HCl), Cesium carbonate (4.08 g, 12.53 mmol) were added to DMF (5 mL). The mixture was stirred at 80° C. for 10 hr and cooled to r.t. MTBE (100 mL) was added and the mixture was extracted with H$_2$O (5*100 mL). The organic phase was separated, dried with Na2SO4 and evaporated in vacuo at 35° C. The residue was purified by HPLC to give tert-butyl 5-methyl-6-[(3-methyltriazol-4-yl)methoxy]-3,4-dihydro-1H-isoquinoline-2-carboxylate (0.3 g, 836.97 umol, 20.04% yield). $^1$H NMR (400 MHz, CDCl$_3$) δ 1.49 (s, 9H), 1.60 (brs, 2H), 2.09 (s, 3H), 2.74 (m, 2H), 3.65 (t, 2H), 4.11 (s, 3H), 4.52 (s, 2H), 5.09 (s, 2H), 6.78 (d, 1H), 6.69 (d, 1H), 7.71 (s, 1H). LCMS(ESI): [M-Boc]$^+$ m/z: calcd 358.2. found 359.2; Rt=1.44 min.

5-methyl-6-((1-methyl-1H-1,2,3-triazol-5-yl)methoxy)-1,2,3,4-tetrahydroisoquinoline. tert-butyl 5-methyl-6-[(3-methyltriazol-4-yl)methoxy]-3,4-dihydro-1H-isoquinoline-2-carboxylate (0.3 g, 836.97 umol) was dissolved in methanol (1 mL) and Hydrogen chloride solution 4.0M in dioxane (2.40 g, 65.82 mmol, 3 mL) was added. The mixture was stirred at 20° C. for 10 hr. The solid formed was filtered, washed with ether (3*10 mL) and dried in vacuo at 35° C. to give 5-methyl-6-[(3-methyltriazol-4-yl)methoxy]-1,2,3,4-tetrahydroisoquinoline (0.21 g, 633.98 umol, 75.75% yield, 2HCl). $^1$H NMR (400 MHz, DMSO-d$_6$) δ 2.04 (s, 3H), 2.85 (m, 2H), 3.33 (m, 2H), 4.04 (s, 3H), 4.15 (s, 2H), 5.29 (s, 2H), 7.06 (m, 2H), 7.79 (s, 1H), 9.43 (brs, 2H). LCMS (ESI): [M+H]$^+$ m/z: calcd 258.15. found 259.0; Rt=0.764 min.

(S)-6-((1-acetylpiperidin-4-yl)amino)-N-(2-hydroxy-3-(5-methyl-6-((1-methyl-1H-1,2,3-triazol-5-yl)methoxy)-3,4-dihydroisoquinolin-2(1H)-yl)propyl)pyrimidine-4-carboxamide. 6-[(1-acetyl-4-piperidyl)amino]-N-[(2S)-3-chloro-2-hydroxy-propyl]pyrimidine-4-carboxamide (270.70 mg, 760.78 umol), 5-methyl-6-[(3-methyltriazol-4-yl)methoxy]-1,2,3,4-tetrahydroisoquinoline (0.21 g, 633.98 umol, 2HCl), Potassium carbonate (262.86 mg, 1.90 mmol, 114.79 uL), Potassium iodide (105.24 mg, 633.98 umol, 33.73 uL) were mixed in DML (5 mL). The mixture was heated at 80° C. for 10 hr while stirring. Then the solvent was evaporated in vacuo at 50° C. The residue was purified by HPLC to give 6-[(1-acetyl-4-piperidyl)amino]-N-[(2S)-2-hydroxy-3-[5-methyl-6-[(3-methyltriazol-4-yl)methoxy]-3,4-dihydro-1H-isoquinolin-2-yl]propyl]pyrimidine-4-carboxamide (4 mg, 6.92 umol, 1.09% yield). NMR (Chloroform-d, 500 MHz): δ (ppm) 1.44 (d, 4H), 2.08 (s, 5H), 2.13 (s, 3H), 2.57 (m, 1H), 2.79 (m, 5H), 2.95 (m, 1H), 3.25 (t, 1H), 3.46 (m, 1H), 3.56 (d, 1H), 3.70 (m, 1H), 3.78 (d, 1H), 3.85 (d, 1H), 4.04 (m, 1H), 4.12 (s, 4H), 4.59 (d, 1H), 5.10 (s, 2H), 6.76 (d, 1H), 6.86 (d, 1H), 7.16 (s, 1H), 7.72 (s, 1H), 8.43 (t, 1H), 8.53 (s, 1H). LCMS(ESI): [M+H]$^+$ m/z: calcd 577.3. found 578.4; Rt=0.807 min.

SCHEME 2B

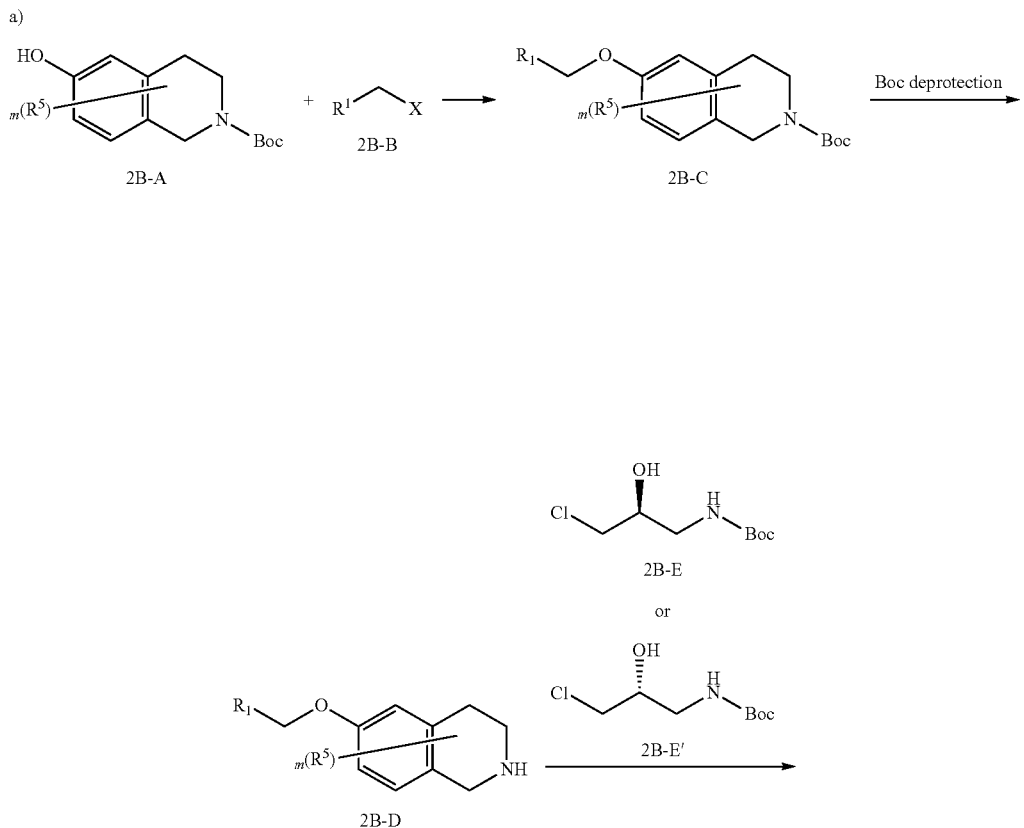

-continued
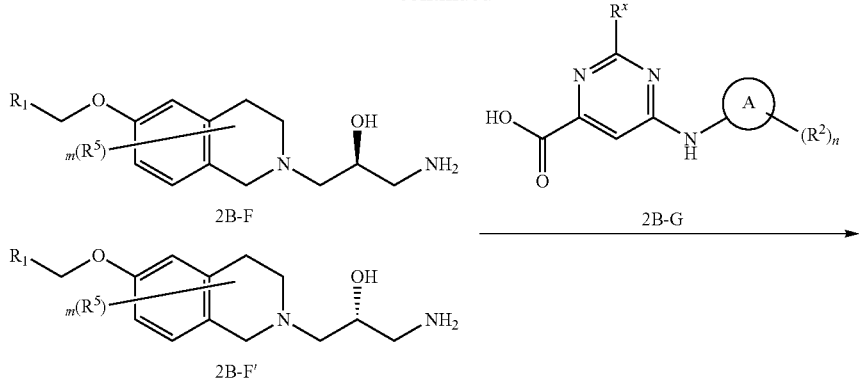
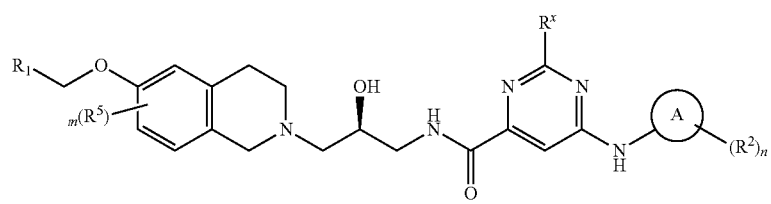
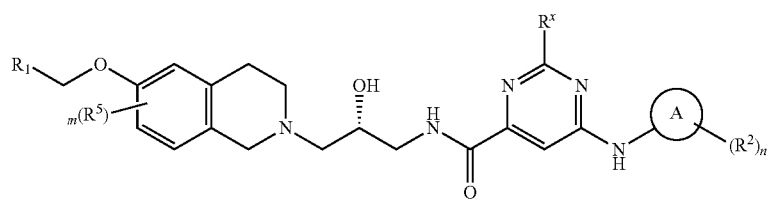
wherein X is a leaving group or hydroxy and variables $R^5$, $R^x$, $R^1$, $R^2$, m, and n are defined herein. In some embodiments, X is selected from —OH, Cl, Br, and I. In some embodiments X is Cl or Br. In other embodiments, wherein X is —OH.
General Procedure 2B-A
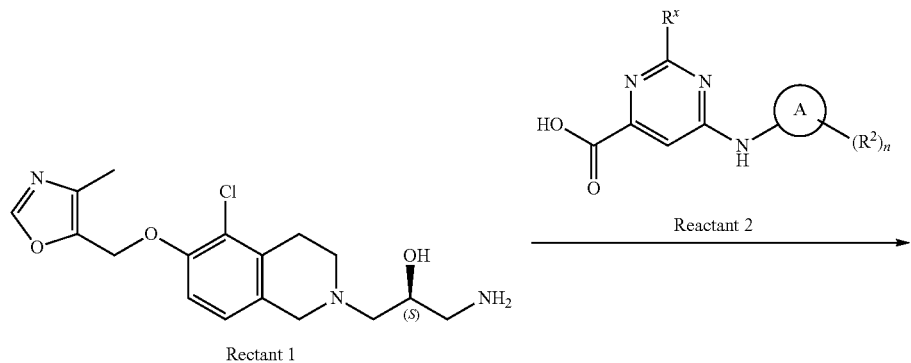

-continued

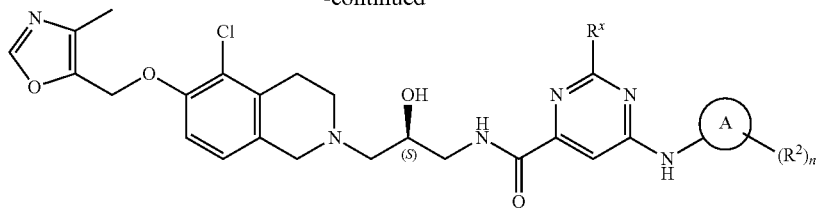

Reactant 1 and Reactant 2 were mixed in DMF (5 mL). The reaction suspension was cooled to 0° C. and HATU followed by DIPEA were added. The clear solution was stirred at ambient temperature for 1.5 hr at 25° C. then volatiles were evaporated under reduced pressure and residue was subjected to RP-HPLC to give products.

Example 2B1. N-[(2S)-3-[5-chloro-6-[(4-methyl-1,3-oxazol-5-yl)methoxy]-1,2,3,4-tetrahydroisoquinolin-2-yl)-2-hydroxypropyl]-6-(cxclopentylamino) pyrimidine-4-carboxamide (Compound 339)

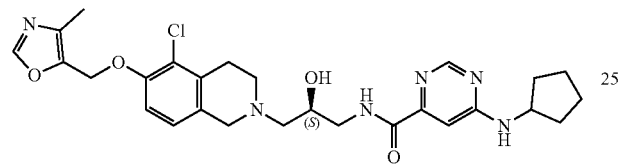

Prepared by general procedure 2B-A. Yield 14.5 mg (19%). $^1$H NMR (DMSO-$d_6$, 400 MHz): δ (ppm) 1.48 (m, 2H), 1.60 (m, 2H), 1.73 (m, 2H), 1.94 (m, 2H), 2.18 (s, 3H), 2.85 (m, 5H), 3.34 (m, 1H), 3.42 (m, 1H), 3.63 (s, 2H), 3.86 (s, 1H), 4.28 (m, 1H), 4.73 (m, 1H), 5.09 (s, 2H), 6.94 (dd, 2H), 7.04 (s, 1H), 7.51 (d, 1H), 8.04 (s, 1H), 8.22 (s, 1H), 8.57 (t, 1H) LCMS(ESI): [M-Boc]$^+$ m/z: calcd 540.3. found 541.2; Rt=1.075 min.

Example 2B2. Synthesis of (S)-6-((1-acetylpiperidin-4-yl)amino)-N-(3-(5-chloro-6-((3-methylisoxazol-4-yl)methoxy)-3N-dihydroisoquinolin-2(1H)-yl)-2-hydroxypropyl)pyrimidine-4-carboxamide (Compound 251)

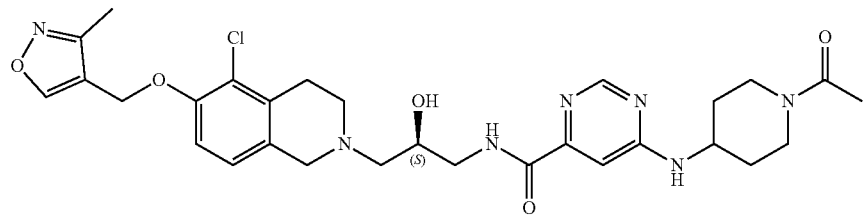

Prepared by general procedure 2B-A. Yield 76.90 mg (20%). $^1$H NMR (CDCl$_3$, 500 MHz) 1.45 (m, 2H), 2.00 (d, 1H), 2.07 (s, 3H), 2.11 (m, 1H), 2.17 (s, 3H), 2.58 (d, 2H), 2.76 (m, 2H), 2.85 (m, 4H), 3.20 (m, 1H), 3.47 (m, 1H), 3.58 (m, 2H), 3.75 (m, 2H), 4.02 (m, 1H), 4.12 (s, 1H), 4.51 (d, 1H), 5.03 (s, 2H), 6.08 (s, 1H), 6.81 (d, 1H), 6.84 (d, 1H), 7.13 (s, 1H), 7.78 (s, 1H), 8.41 (s, 1H), 8.49 (m, 1H). LCMS(ESI): [M+H]$^+$ m/z: calcd 598.2. found 598.2; Rt=0.93 min.

General Procedure 2B-B

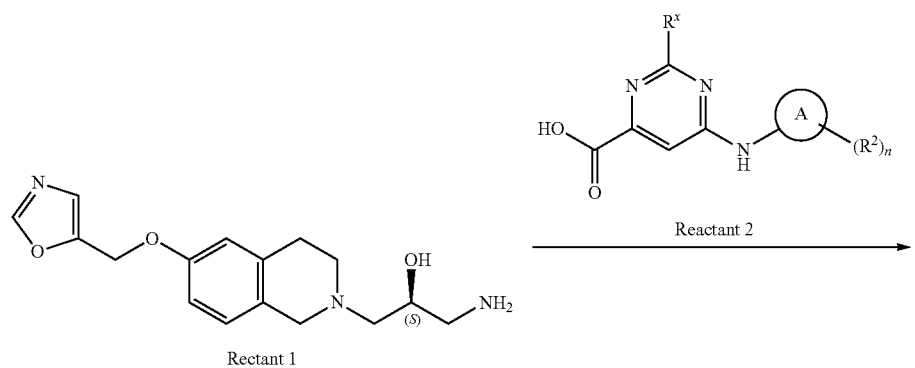

-continued

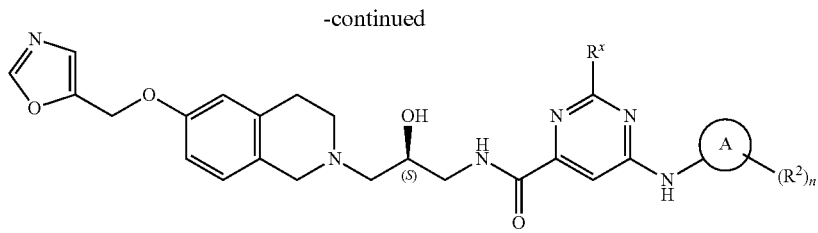

DIPEA (9 equiv) was added to the solution of Reactant 1 (1.0 equiv) and Reactant (1.0 equiv) in DMF (2.0 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mF) and filtered off. The obtained filtrate was subjected to HPFC (Waters Sunfire C18 19*100 5 mkm column and H$_2$O-MeOH as a mobile phase) to afford pure product.

Example 2B3. (S)-2-(ethyl(methyl)amino)-N-(2-hydroxy-3-(6-(oxazol-5-ylmethoxy)-3,4-dihydroisoquinolin-2(1H)-yl)propyl-6-(oxetan-3-ylamino)pyrimidine-4-carboxamide (Compound 289)

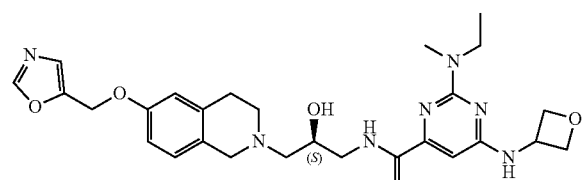

Prepared by general procedure 2B-B. Yield: 21.7 mg (37.86%). $^1$H NMR (DMSO-d$_6$, 400 MHz): δ 1.08 (t, 3H), 2.47 (m, 2H), 2.73 (m, 2H), 2.82 (m, 2H), 3.03 (s, 3H), 3.25 (m, 1H), 3.46 (s, 1H), 3.58 (m, 3H), 3.84 (m, 1H), 4.50 (t, 2H), 4.62 (m, 1H), 4.75 (t, 2H), 4.97 (m, 1H), 5.05 (s, 2H), 6.37 (s, 1H), 6.70 (m, 2H), 6.90 (d, 1H), 7.15 (s, 1H), 7.79 (m, 1H), 8.15 (s, 1H), 8.22 (t, 1H), NH is not observed. LCMS(ESI): [M+H]$^+$ m/z: calcd 537.6. found 538.2; Rt=0.997 min.

Example 2B4. (S)-6-(cyclobutylamino)-N-(2-hydroxy-3-(6-(oxazol-5-ylmethoxy)-3,4-dihydroisoquinolin-2(1H)-yl)propyl)pyrimidine-4-carboxamide (Compound 538)

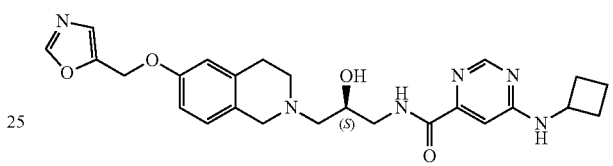

Prepared by general procedure 2B-B. Yield: 17.5 mg (26.47%). LCMS(ESI): [M+H]$^+$ m/z: calcd 478.5. found 479.5; Rt=0.941 min.

Example 2B5. The synthesis of (S)-6-(cyclohexylamino)-N-(2-hydroxy-3-(6-(oxazol-5-ylmethoxy)-3,4-dihydroisoquinolin-2(1H)-yl)propyl)pyrimidine-4-carboxamide (Compound 395)

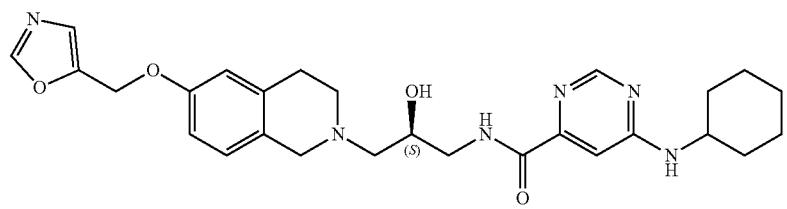

Prepared by general procedure 2B-B. Yield: 7.3 mg (11.66%). $^1$H NMR (500 MHz, CDCl$_3$) δ 1.26 (m, 3H), 1.42 (m, 3H), 1.68 (m, 2H), 1.78 (m, 2H), 2.04 (m, 2H), 2.61 (m, 2H), 2.76 (m, 1H), 2.93 (m, 3H), 3.48 (m, 1H), 3.60 (m, 1H), 3.70 (m, 1H), 3.81 (m, 1H), 4.06 (m, 1H), 5.06 (s, 2H), 5.26 (m, 1H), 6.73 (s, 1H), 6.78 (d, 1H), 6.95 (d, 1H), 7.12 (s, 1H), 7.16 (s, 1H), 7.91 (s, 1H), 8.41 (m, 1H), 8.49 (s, 1H). LCMS(ESI): [M+H]$^+$ m/z: calcd 506.6. found 507.2; Rt=1.007 min.

Example 2B6. (S)-6-(cyclopentylamino)-N-(2-hydroxy-3-(6-(oxazol-5-ylmethoxy)-3,4-dihydroisoquinolin-2(1H)-yl)propyl)pyrimidine-4-carboxamide (Compound 372)

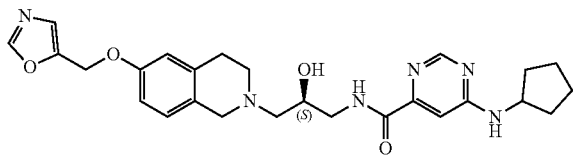

Prepared by general procedure 2B-B. Yield: 17.2 mg (22.93%). $^1$H NMR (CDCl$_3$, 500 MHz): δ (ppm) 1.51 (m, 2H), 1.60 (m, 2H), 1.68 (m, 2H), 1.76 (m, 2H), 2.10 (m, 2H), 2.60 (m, 2H), 2.73 (m, 1H), 2.91 (m, 3H), 3.48 (m, 1H), 3.59 (d, 1H), 3.69 (m, 1H), 3.79 (d, 1H), 4.05 (m, 1H), 5.05 (s, 2H), 5.29 (m, 1H), 6.73 (s, 1H), 6.78 (d, 1H), 6.95 (d, 1H), 7.16 (s, 2H), 7.91 (s, 1H), 8.42 (t, 1H), 8.49 (s, 1H). LCMS(ESI): [M+H]$^+$ m/z: calcd 492.6. found 493.2; Rt=1.013 min.

General Procedure 2B-C

Example 2B7. (S)—N-(3-(5-chloro-6-(oxazol-5-ylmethoxy)-3N-dihydroisoquinolin-2(1H)-yl)-2-hydroxypropyl-2-(ethyl(methyl)amino)-6-(oxetan-3-ylamino)pyrimidine-4-carboxamide (Compound 303)

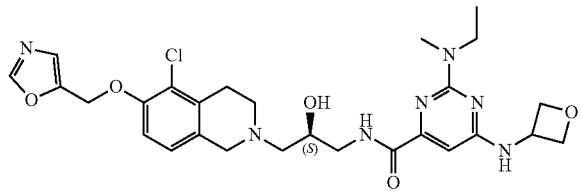

Prepared by general procedure 2B-C. Yield: 26.7 mg (47.43%). $^1$H NMR (400 MHz, DMSO-d$_6$+CCl$_4$) δ 1.12 (t, 3H), 2.76 (m, 4H), 3.03 (m, 5H), 3.24 (m, 1H), 3.44 (m, 1H), 3.59 (m, 4H), 3.83 (m, 1H), 4.51 (t, 2H), 4.66 (m, 1H), 4.75 (t, 2H), 4.95 (m, 1H), 5.16 (s, 2H), 6.37 (s, 1H), 6.93 (d, 1H), 6.98 (d, 1H), 7.19 (s, 1H), 7.78 (m, 1H), 8.17 (s, 1H), 8.22 (t, 1H). LCMS(ESI): [M+H]$^+$ m/z: calcd 572.1. found 573.2; Rt=1.017 min.

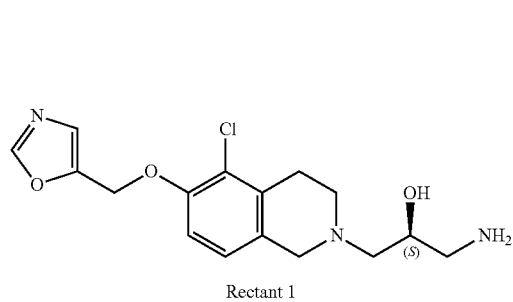

Rectant 1

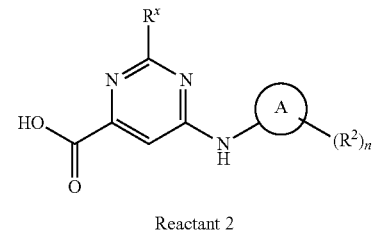

Reactant 2

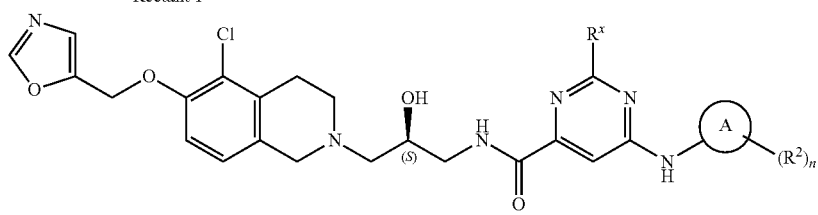

DIPEA (2.5 equiv+E0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (TO mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase) to afford pure product.

Example 2B8. (S)—N-(3-(5-chloro-6-(oxazol-5-ylmethoxy)-3,4-dihydroisoquinolin-2(1H)-yl)-2-hydroxypropyl)-6-(cyclopentylamino)pyrimidine-4-carboxamide (Compound 336)

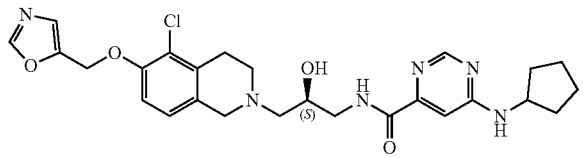

Prepared by general procedure 2B-C. Yield: 41.2 mg (54.93%). $^1$H NMR (DMSO-$d_6$, 400 MHz): δ (ppm) 1.48 (m, 2H), 1.61 (m, 2H), 1.73 (m, 2H), 1.94 (m, 2H), 2.54 (m, 2H), 2.76 (m, 2H), 2.84 (m, 2H), 3.34 (m, 1H), 3.43 (m, 1H), 3.61 (s, 2H), 3.84 (m, 1H), 4.27 (m, 1H), 4.70 (d, 1H), 5.16 (s, 2H), 6.93 (d, 1H), 6.99 (d, 1H), 7.03 (s, 1H), 7.20 (s, 1H), 7.50 (d, 1H), 8.18 (s, 1H), 8.21 (s, 1H), 8.56 (t, 1H). LCMS(ESI): [M+2H]$^+$ m/z: calcd 527.0. found 528.2; Rt=0.996 min.

Example 2B9. (S)—N-(3-(5-chloro-6-(oxazol-5-ylmethoxy)-3,4-dihydroisoquinolin-2(1H)-yl)-2-hydroxypropyl)-6-(cyclobutylamino)pyrimidine-4-carboxamide (Compound 508)

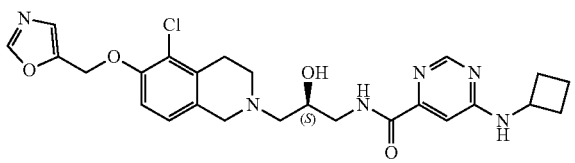

Prepared by general procedure 2B-C. Yield: 37.5 mg (55.4%). $^1$H NMR (400 MHz, DMSO-$d_6$+CCl$_4$) δ 1.75 (m, 2H), 1.96 (m, 2H), 2.33 (m, 2H), 2.76 (m, 1H), 2.83 (m, 2H), 3.44 (m, 2H), 3.61 (m, 2H), 3.85 (m, 1H), 3.99 (m, 1H), 4.48 (m, 2H), 4.70 (d, 1H), 5.17 (s, 2H), 6.94 (d, 1H), 6.98 (d, 1H), 7.20 (s, 1H), 7.77 (s, 1H), 8.18 (s, 1H), 8.56 (s, 1H), NH, NH, OH are not observed. LCMS(ESI): [M+H]$^+$ m/z: calcd 513.0. found 514.2; Rt=0.972 min.

General Procedure 2B-D

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mF). The reaction mixture was stirred at room temperature overnight. After the completion of the reaction, monitored by LCMS, the resulting suspension was concentrated under reduced pressure. The residue was dissolved in DMSO (1.0 mF) and filtered off. The obtained filtrate was subjected to HPFC (Waters SunFire C18 19*100 5 mkm column and H$_2$O-MeOH as a mobile phase, Run Time 5 min) to afford pure product.

Example 2B10. (S)—N-(3-(5-bromo-6-(oxazol-5-ylmethoxy)-3,4-dihydroisoquinolin-2(1H)-yl)-2-hydroxypropyl)-6-(cyclobutylamino)pyrimidine-4-carboxamide (Compound 361)

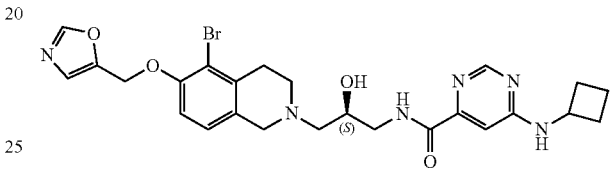

Prepared by general procedure 2B-D. Yield: 22.0 mg (34.0%). $^1$H NMR (400 MHz, dmso+ccl4) δ 1.74 (m, 2H), 1.94 (m, 2H), 2.32 (m, 2H), 2.54 (m, 2H), 2.82 (m, 4H), 3.34 (m, 1H), 3.43 (m, 1H), 3.62 (m, 2H), 3.85 (m, 1H), 4.48 (m, 1H), 4.72 (m, 1H), 5.17 (s, 2H), 6.97 (s, 2H), 7.00 (m, 1H), 7.20 (s, 1H), 7.77 (m, 1H), 8.19 (m, 2H), 8.58 (m, 1H). LCMS(ESI): [M+H]$^+$ m/z: calcd 556.1. found 557.1; Rt=0.98 min.

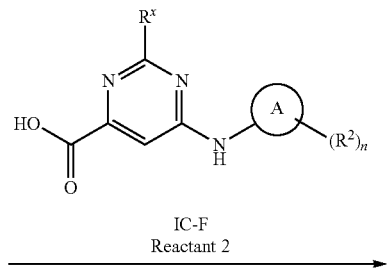

IC-F
Reactant 2

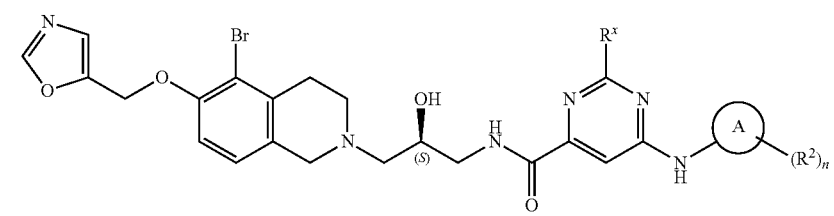

Example 2B11. (S)—N-(3-(5-bromo-6-(oxazol-5-ylmethoxy)-3A-dihydroisoquinolin-2(1H)-yl)-2-hydroxypropyl)-6-(cyclohexylamino)pyrimidine-4-carboxamide (Compound 377)

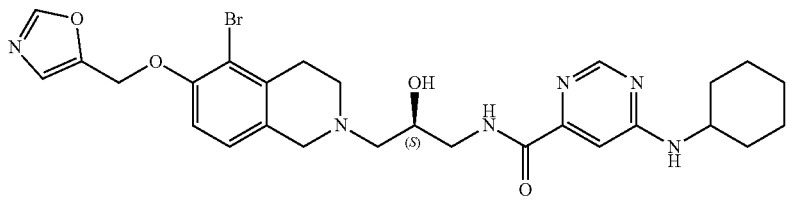

Prepared by general procedure 2B-D. Yield: 21.3 mg (34.0%). $^1$H NMR (Chloroform-d, 500 MHz): δ (ppm) 1.26 (m, 3H), 1.42 (m, 2H), 1.67 (m, 1H), 1.78 (m, 2H), 2.04 (m, 2H), 2.62 (m, 2H), 2.80 (m, 1H), 2.90 (m, 2H), 2.98 (m, 1H), 3.49 (m, 2H), 3.62 (m, 1H), 3.69 (m, 1H), 3.82 (m, 1H), 4.06 (m, 1H), 5.14 (s, 2H), 5.33 (s, 1H), 6.84 (d, 1H), 6.95 (d, 1H), 7.12 (s, 1H), 7.18 (s, 1H), 7.92 (s, 1H), 8.42 (t, 1H), 8.48 (s, 1H). LCMS(ESI): [M+2H]$^+$ m/z: calcd 585.5. found 587.2; Rt=1.05 min.

Example 2B12. (S)—N-(3-(5-bromo-6-(oxazol-5-ylmethoxy)-3N-dihydroisoquinolin-2(1H)-yl)-2-hydroxypropyl)-3-(cyclobutylamino)benzamide (Compound 337)

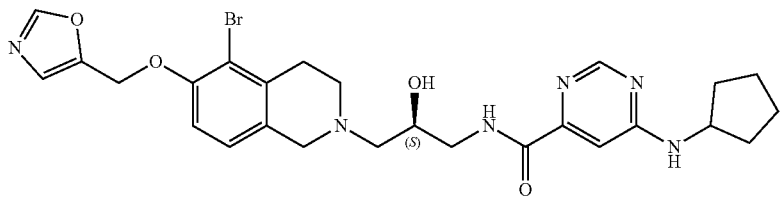

Prepared by general procedure 2B-D. Yield: 28.3 mg (37.0%). $^1$H NMR (DMSO-d$_6$, 400 MHz): δ (ppm) 1.48 (m, 2H), 1.60 (m, 2H), 1.72 (m, 2H), 1.95 (m, 2H), 2.57 (d, 2H), 2.79 (m, 4H), 3.39 (m, 2H), 3.62 (s, 2H), 3.84 (m, 1H), 4.28 (m, 1H), 4.71 (m, 1H), 5.17 (s, 2H), 6.97 (s, 2H), 7.04 (d, 1H), 7.20 (s, 1H), 7.50 (d, 1H), 8.17 (s, 1H), 8.21 (s, 1H), 8.57 (t, 1H). LCMS(ESI): [M+2H]$^+$ m/z: calcd 571.2. found 573.2; Rt=0.99 min.

General Procedure 2B-E

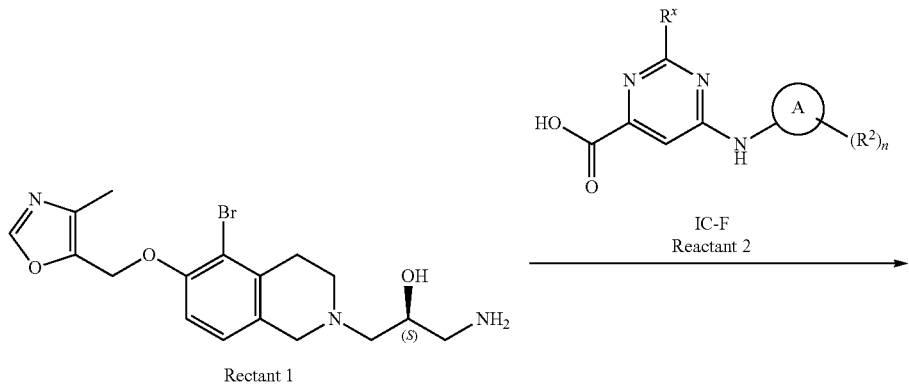

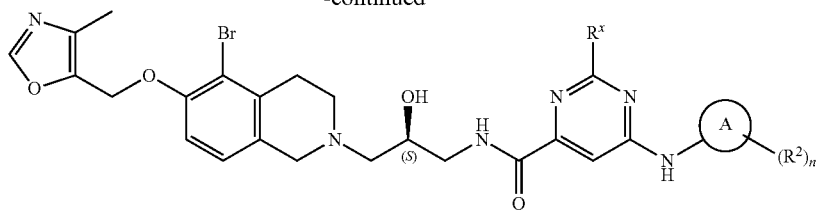

DIPEA (2.5 equiv+E0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mL). The reaction mixture was stirred at room temperature overnight. After the completion of the reaction, monitored by LCMS, the resulting suspension was concentrated under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase) to afford pure product.

Example 2B13. (S)—N-(3-(5-bromo-6-((4-methyl-oxazol-5-yl)methoxy)-3,4-dihydroisoquinolin-2(1H)-yl)-2-hydroxypropyl)-6-(cyclobutylamino)pyrimidine-4-carboxamide (Compound 338)

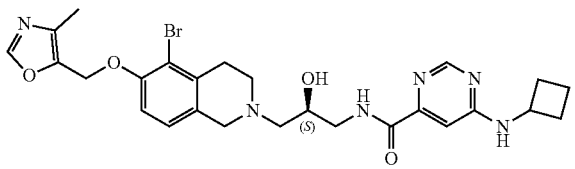

Prepared by general procedure 2B-E. Yield: 30.1 mg (40%). $^1$H NMR (DMSO-d$_6$, 400 MHz): δ (ppm) 1.74 (m, 2H), 1.94 (m, 2H), 2.19 (s, 3H), 2.32 (m, 2H), 2.54 (m, 2H), 2.76 (m, 4H), 3.34 (m, 1H), 3.41 (m, 1H), 3.63 (s, 2H), 3.86 (m, 1H), 4.48 (m, 1H), 4.76 (m, 1H), 5.09 (s, 2H), 6.96 (m, 3H), 7.77 (d, 1H), 8.04 (s, 1H), 8.21 (s, 1H), 8.58 (t, 1H). LCMS(ESI): [M+H]$^+$ m/z: calcd 571.5. found 572.2; Rt=0.996 min.

Example 2B14. The Synthesis of (S)—N-(3-(5-bromo-6-((4-methyloxazol-5-yl)methoxy)-3,4-dihydroisoquinolin-2(1H)-yl)-2-hydroxypropyl)-6-(cyclopentylamino)pyrimidine-4-carboxamide (Compound 358)

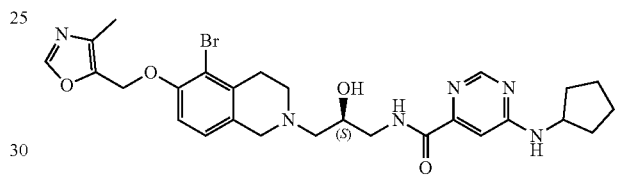

Prepared by general procedure 2B-E. Yield: 31.3 mg (41%). $^1$H NMR (CDCl$_3$, 400 MHz): δ (ppm) 1.48 (m, 2H), 1.65 (m, 2H), 1.71 (m, 3H), 2.06 (m, 2H), 2.19 (s, 3H), 2.55 (d, 2H), 2.71 (m, 1H), 2.87 (m, 3H), 3.42 (m, 1H), 3.54 (d, 1H), 3.66 (m, 2H), 3.74 (d, 1H), 4.00 (m, 1H), 5.04 (s, 2H), 5.29 (s, 1H), 6.80 (d, 1H), 6.90 (d, 1H), 7.12 (s, 1H), 7.79 (s, 1H), 8.40 (t, 1H), 8.45 (s, 1H). LCMS(ESI): [M+H]$^+$ m/z: calcd 585.5. found 586.2; Rt=1.066 min.

General Procedure 2B-F

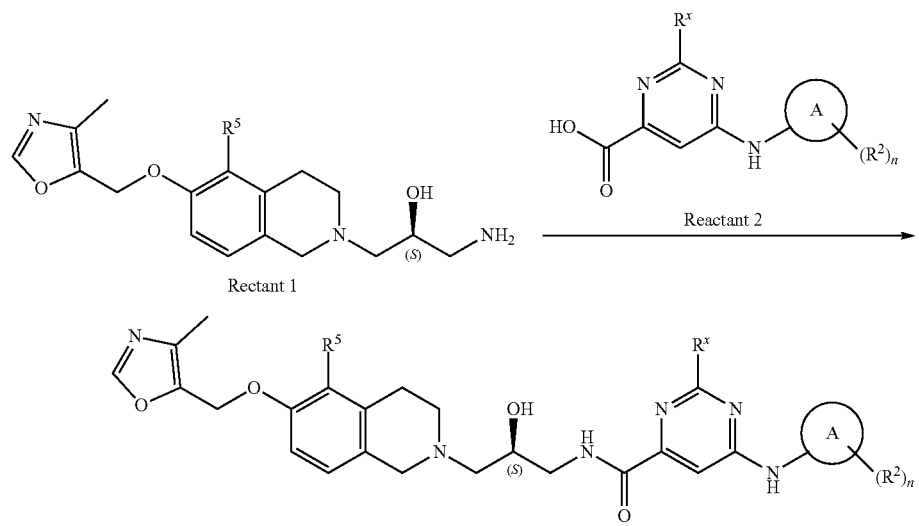

Wherein R[5] is H or CH$_3$.

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mF) and filtered off. The obtained filtrate was subjected to HPFC (Waters Sunfire C18 19*100 5 mkm column and H$_2$O-MeOH-0.1NH$_3$ as a mobile phase) to afford pure product.

Example 2B15. 6-(cyclobutylamino)-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 376)

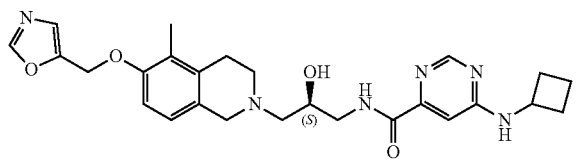

Prepared by general procedure 2B-F. Yield: 36.0 mg (48.0%). $^1$H NMR (CDCl$_3$, 500 MHz): δ (ppm) 1.84 (m, 2H), 1.95 (m, 2H), 2.10 (s, 4H), 2.49 (m, 2H), 2.60 (m, 2H), 2.79 (m, 4H), 2.99 (m, 1H), 3.47 (m, 2H), 3.60 (m, 1H), 3.69 (m, 1H), 3.81 (m, 1H), 4.06 (s, 1H), 5.06 (s, 2H), 5.38 (m, 1H), 6.80 (d, 1H), 6.85 (d, 1H), 7.08 (s, 1H), 7.14 (s, 1H), 7.91 (s, 1H), 8.41 (t, 1H), 8.50 (s, 1H). LCMS(ESI): [M+H]$^+$ m/z: calcd 492.3. found 493.2; Rt=0.974 min.

Example 2B16. 6-(cyclopentylamino)-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 393)

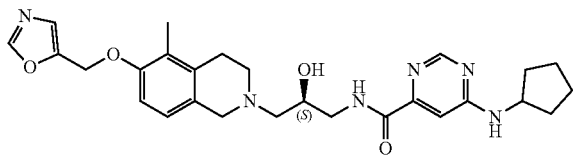

Prepared by general procedure 2B-F. Yield: 7.1 mg (9.47%). $^1$H NMR (500 MHz, CDCl$_3$) δ 1.52 (m, 3H), 1.72 (m, 5H), 2.10 (m, 5H), 2.60 (m, 2H), 2.78 (m, 3H), 2.97 (m, 1H), 3.47 (m, 1H), 3.60 (m, 1H), 3.70 (m, 1H), 3.81 (m, 1H), 4.06 (m, 1H), 5.06 (s, 2H), 5.21 (m, 1H), 6.80 (d, 1H), 6.85 (d, 1H), 7.14 (m, 2H), 7.91 (s, 1H), 8.42 (t, 1H), 8.49 (s, 1H). LCMS(ESI): [M+H]$^+$ m/z: calcd 506.3. found 507.4; Rt=0.97 min.

Example 2B17. 6-(cyclohexylamino)-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 436)

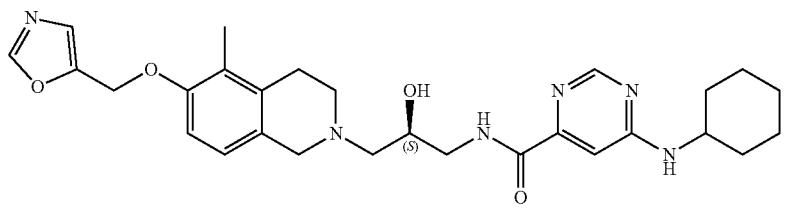

Prepared by general procedure 2B-F. Yield: 9.8 mg (16.4%). $^1$H NMR (CDCl$_3$, 500 MHz): δ (ppm) 1.23 (m, 5H), 1.42 (m, 3H), 1.69 (m, 2H), 1.77 (m, 2H), 2.01 (m, 2H), 2.10 (s, 3H), 2.60 (m, 2H), 2.79 (m, 3H), 2.99 (m, 1H), 3.47 (m, 1H), 3.62 (m, 1H), 3.69 (m, 1H), 3.82 (m, 1H), 4.07 (m, 1H), 5.05 (s, 2H), 6.79 (d, 1H), 6.85 (d, 1H), 7.11 (s, 1H), 7.13 (s, 1H), 7.90 (s, 1H), 8.41 (t, 1H), 8.48 (s, 1H). LCMS(ESI): [M+H]$^+$ m/z: calcd 520.3. found 521.0; Rt=1.035 min.

Example 2B18. 6-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]pyrimidine-4-carboxamide (Compound 371)

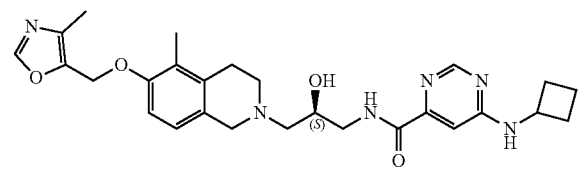

Prepared by general procedure 2B-F. Yield: 8.7 mg (13.3%). $^1$H NMR (Chloroform-d, 500 MHz): δ (ppm) 1.68 (m, 2H), 1.83 (m, 2H), 1.95 (m, 2H), 2.09 (s, 3H), 2.21 (s, 3H), 2.49 (m, 2H), 2.58 (m, 2H), 2.76 (m, 3H), 2.96 (m, 1H), 3.46 (m, 1H), 3.58 (d, 1H), 3.70 (m, 1H), 3.79 (d, 1H), 4.04 (m, 1H), 4.99 (s, 2H), 5.44 (m, 1H), 6.81 (d, 1H), 6.85 (d, 1H), 7.09 (s, 1H), 7.82 (s, 1H), 8.41 (t, 1H), 8.50 (s, 1H). LCMS(ESI): [M+H]$^+$ m/z: calcd 506.3. found 507.0; Rt=0.95 min.

Example 2B19. 6-(cyclopentylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]pyrimidine-4-carboxamide (Compound 367)

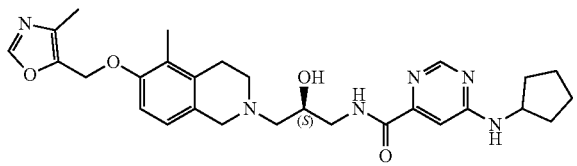

Prepared by general procedure 2B-F. Yield: 7.2 mg (11.1%). ¹H NMR (Chloroform-f 500 MHz): δ (ppm) 1.52 (m, 2H), 1.59 (m, 2H), 1.69 (m, 2H), 1.76 (m, 2H), 2.10 (m, 5H), 2.21 (s, 3H), 2.59 (m, 2H), 2.77 (m, 3H), 2.96 (m, 1H), 3.47 (m, 1H), 3.59 (d, 1H), 3.70 (m, 1H), 3.80 (d, 1H), 4.06 (m, 1H), 4.99 (s, 2H), 5.24 (s, 1H), 6.81 (d, 1H), 6.85 (d, 1H), 7.15 (s, 1H), 7.82 (s, 1H), 8.42 (m, 1H), 8.49 (s, 1H). LCMS(ESI): [M+H]⁺ m/z: calcd 520.2. found 521.0; Rt=0.98 min.

Example 2B20. 6-(cyclohexylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]pyrimidine-4-carboxamide (Compound 368)

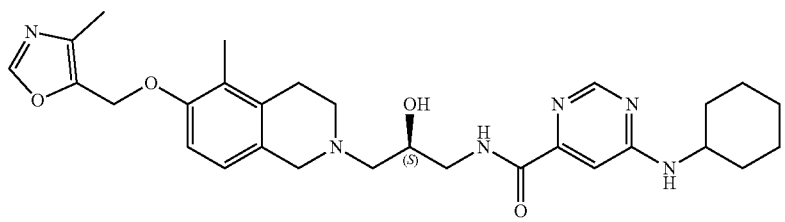

Prepared by general procedure 2B-F. Yield: 4.2 mg (6.3%). ¹H NMR (Chloroform-d, 500 MHz): δ (ppm) 1.25 (m, 3H), 1.42 (m, 2H), 1.60 (m, 2H), 1.67 (m, 2H), 1.79 (m, 2H), 2.04 (d, 2H), 2.09 (s, 3H), 2.21 (s, 3H), 2.59 (m, 2H), 2.77 (m, 3H), 2.96 (m, 1H), 3.47 (m, 1H), 3.60 (m, 1H), 3.69 (m, 1H), 3.80 (m, 1H), 4.05 (m, 1H), 4.99 (s, 2H), 5.18 (m, 1H), 6.81 (d, 1H), 6.85 (d, 1H), 7.12 (s, 1H), 7.82 (s, 1H), 8.41 (t, 1H), 8.49 (s, 1H). LCMS(ESI): [M+H]⁺ m/z: calcd 534.5. found 535.4; Rt=1.15 min.

Example 2B21. 2-[ethyl(methyl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]-6-f(oxetan-3-yl)amino]pyrimidine-4-carboxamide (Compound 477)

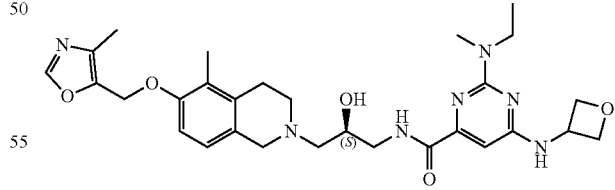

Prepared by general procedure 2B-F. Yield: mg (%). ¹H NMR (500 MHz, CDCl₃) δ 1.14 (t, 3H), 2.08 (s, 3H), 2.21 (s, 3H), 2.57 (m, 2H), 2.76 (m, 3H), 2.97 (m, 1H), 3.10 (s, 3H), 3.43 (m, 1H), 3.62 (m, 4H), 3.79 (m, 1H), 4.03 (m, 1H), 4.60 (t, 2H), 4.98 (m, 5H), 5.06 (m, 1H), 5.16 (m, 1H), 6.46 (s, 1H), 6.82 (m, 2H), 7.81 (s, 1H), 8.33 (t, 1H). LCMS(ESI): [M+H]⁺ m/z: calcd 565.5. found 566.4; Rt=1.06 min.

Example 2B22. (S)-6-((1-acetylpiperidin-4-yl)amino)-N-(2-hydroxy-3-(5-methyl-6-((4-methyloxazol-5-yl)methoxy)-3,4-dihydroisoquinolin-2(1H)-yl)propyl)pyrimidine-4-carboxamide (Compound 274)

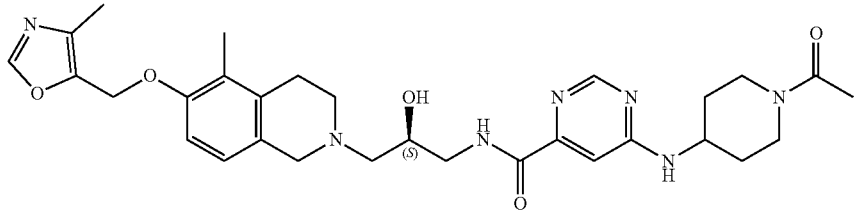

Prepared by general procedure 2B-F. Yield 15 mg (5%). $^1$H NMR (DMSO-d6, 400 MHz): δ (ppm) 1.25 (m, 1H), 1.40 (m, 1H), 1.89 (m, 2H), 2.07 (m, 8H), 2.78 (m, 1H), 2.92 (d, 2H), 3.19 (m, 3H), 3.38 (s, 2H), 3.75 (m, 2H), 4.18 (m, 4H), 4.46 (m, 1H), 5.14 (s, 2H), 5.86 (m, 1H), 7.05 (m, 3H), 7.58 (m, 1H), 7.81 (d, 1H), 8.28 (s, 1H), 8.50 (s, 1H), 8.79 (m, 1H), 9.72 (t, 1H). LCMS(ESI): [M+H]$^+$ m/z: calcd 577.3. found 578.2; Rt=0.89 min.

Example 2B23. (S)-6-((1-acetylpiperidin-4-yl)amino)-N-(2-hydroxy-3-(6-((1-methyl-1H-1,2,3-triazol-5-yl)methoxy)-3,4-dihydroisoquinolin-2(1H)-yl)propyl)pyrimidine-4-carboxamide (Compound 250)

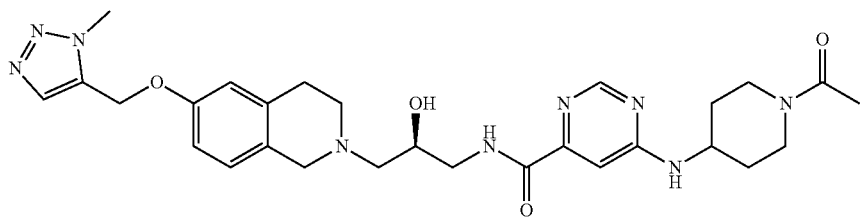 [SMILES: CC(=O)N1CCC(Nc2cc(C(=O)NC[C@H](O)CN3CCc4cc(OCc5cnnn5C)ccc4C3)ncn2)CC1]

6-[(1-Acetyl-4-piperidyl)amino]pyrimidine-4-carboxylic acid (125.09 mg, 473.32 umol) and triethylamine (478.96 mg, 4.73 mmol, 659.72 uL) were dissolved in MeCN (5 mL). HATU (269.96 mg, 709.99 umol) was added and the mixture was stirred for 30 min. Then (2S)-1-amino-3-[6-[(3-methyltriazol-4-yl)methoxy]-3,4-dihydro-1H-isoquinolin-2-yl]propan-2-ol (0.202 g, 473.32 umol, 3HCl) was added and the mixture was stirred for 10 hr at 25° C. Then the solvent was evaporated in vacuo at 35° C. and the residue was purified by HPLC to give 6-[(1-acetyl-4-piperidyl)amino]-N-[(2S)-2-hydroxy-3-[6-[(3-methyltriazol-4-yl)methoxy]-3,4-dihydro-1H-isoquinolin-2-yl]propyl]pyrimidine-4-carboxamide (0.04 g, 70.97 umol, 14.99% yield).

$^1$H NMR (400 MHz, CDCl$_3$) δ (ppm) 1.46 (m, 2H), 2.11 (m, 5H), 2.57 (m, 2H), 2.70 (m, 1H), 2.88 (m, 4H), 3.24 (m, 1H), 3.44 (m, 3H), 3.85 (m, 4H), 4.01 (m, 1H), 4.10 (s, 3H), 4.55 (d, 1H), 5.08 (s, 2H), 5.38 (d, 1H), 6.68 (s, 1H), 6.72 (d, 1H), 6.95 (d, 1H), 7.15 (s, 1H), 7.70 (s, 1H), 8.43 (t, 1H), 8.49 (s, 1H). LCMS(ESI): [M+H]$^+$ m/z: calcd 563.3. found 564.4; Rt=0.83 min.

Example 2B24. (S)-6-((1-acetylpiperidin-4-yl)amino)-N-(2-hydroxy-3-(6-((4-methyloxazol-5-yl)methoxy)-3,4-dihydroisoquinolin-2(1H)-yl)propyl)pyrimidine-4-carboxamide (Compound 219)

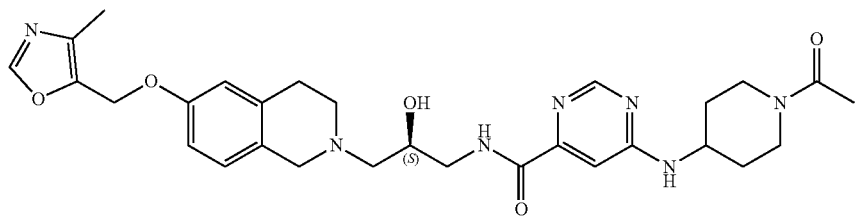

(2S)-1-amino-3-[6-[(4-methyloxazol-5-yl)methoxy]-3,4-dihydro-1H-isoquinolin-2-yl]propan-2-ol (148.04 mg, 466.44 umol, 3HCl) (190.00 mg, 1.01 mmol) and 6-[(1-acetyl-4-piperidyl)amino]pyrimidine-4-carboxylic acid (129.43 mg, 489.76 umol) were mixed in DMF (5 mL). The reaction suspension was cooled to 0° C. and HATU (195.09 mg, 513.08 umol) followed by Triethylamine (235.99 mg, 2.33 mmol, 325.06 uL) were added and stirred at ambient temperature for 24 hr. The reaction mixture was evaporated in vacuo and obtained crude product 0.72 g was purified by preparative RP-HPLC with Methanole as mobile phase to afford product 6-[(1-acetyl-4-piperidyl)amino]-N-[(2S)-2-hydroxy-3-[6-[(4-methyloxazol-5-yl)methoxy]-3,4-dihydro-1H-isoquinolin-2-yl]propyl]pyrimidine-4-carboxamide (65.60 mg, 116.39 umol, 24.95% yield). $^1$H NMR (500 MHz, DMSO-$d_6$+CCl$_4$) δ 1.39 (m, 2H), 1.92 (m, 3H), 2.01 (s, 3H), 2.18 (s, 3H), 2.76 (m, 1H), 2.81 (m, 2H), 2.86 (m, 2H), 3.21 (m, 2H), 3.33 (m, 1H), 3.45 (m, 1H), 3.61 (m, 2H), 3.79 (d, 1H), 3.87 (m, 1H), 4.11 (m, 1H), 4.25 (d, 1H), 4.69 (m, 1H), 4.99 (s, 2H), 6.69 (m, 2H), 6.90 (d, 1H), 7.08 (s, 1H), 7.58 (d, 1H), 8.02 (s, 1H), 8.25 (s, 1H), 8.56 (t, 1H). LCMS(ESI): [M+H]$^+$ m/z: calcd 563.3. found 564.4; Rt=0.897 min.

Example 2B25. (R)-6-((1-acetylpiperidin-4-yl)amino)-N-(2-hydroxy-3-(6-((4-methyloxazol-5-yl)methoxy)-3N-dihydroisoquinolin-2(1H)-yl)propyl)pyrimidine-4-carboxamide (Compound 249)

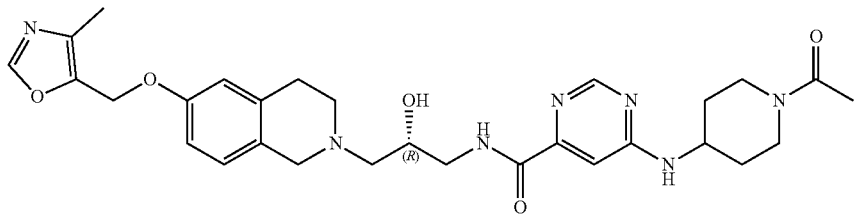

6-[(1-Acetyl-4-piperidyl)amino]pyrimidine-4-carboxylic acid (124.90 mg, 472.62 umol) and (2R)-1-amino-3-[6-[(4-methyloxazol-5-yl)methoxy]-3,4-dihydro-1H-isoquinolin-2-yl]propan-2-ol (150.00 mg, 472.62 umol, 2HCl) were mixed in DMF (15 mL). To the reaction mixture, HATU (179.70 mg, 472.62 umol) and triethylamine (239.12 mg, 2.36 mmol, 329.37 ul) were added at 0° C. The yellow solution was stirred at 25° C. for 12 hr and evaporated in vacuo to obtain crude product (0.3 g). The crude product was purified by reverse phase HPLC to obtain 50 mg (95% by LCMS)-white solid. The second HPLC purification give 6-[(1-acetyl-4-piperidyl)amino]-N-[(2R)-2-hydroxy-3-[6-[(4-methyloxazol-5-yl)methoxy]-3,4-dihydro-1H-isoquinolin-2-yl]propyl]pyrimidine-4-carboxamide (0.027 g, 47.90 umol, 10.14% yield). $^1$H NMR (400 MHz, DMSO-$d_6$) δ (ppm) 1.25 (m, 1H), 1.38 (m, 1H), 1.90 (m, 1H), 2.00 (s, 3H), 2.15 (s, 3H), 2.32 (m, 1H), 2.78 (m, 6H), 3.17 (m, 1H), 3.54 (m, 4H), 3.86 (m, 2H), 4.08 (m, 1H), 4.20 (m, 1H), 4.94 (m, 1H), 5.07 (s, 2H), 6.74 (d, 1H), 6.76 (s, 1H), 6.93 (d, 1H), 7.06 (s, 1H), 7.76 (d, 1H), 8.27 (s, 1H), 8.32 (d, 1H), 8.71 (t, 1H). LCMS(ESI): [M+H]$^+$ m/z: calcd 563.2. found 564.2; Rt=0.89 min.

Example 2B26. 6-(cyclopentylamino)-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 333)

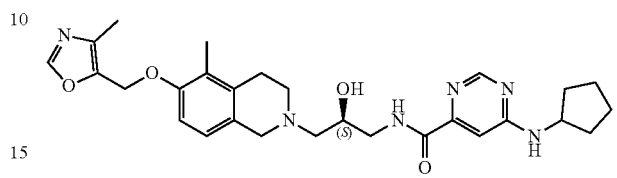

Prepared by general procedure 2B-F. Yield: 28.5 mg (38%). $^1$H NMR (DMSO-$d_6$, 400 MHz): δ (ppm) 1.49 (m, 2H), 1.60 (m, 2H), 1.74 (dd, 2H), 1.95 (m, 2H), 2.18 (s, 3H), 2.75 (m, 2H), 2.85 (m, 2H), 3.05 (m, 2H), 3.31 (m, 1H), 3.45 (m, 1H), 3.59 (m, 2H), 3.84 (m, 1H), 4.28 (m, 1H), 4.67 (s, 1H), 4.99 (s, 2H), 6.69 (m, 2H), 6.90 (d, 1H), 7.04 (m, 1H), 7.51 (d, 1H), 8.03 (s, 1H), 8.23 (s, 1H), 8.54 (t, 1H). LCMS(ESI): [M+H]$^+$ m/z: calcd 506.2. found 507.1; Rt=1.00 min.

Example 2B27. 6-(cyclobutylamino)-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 374)

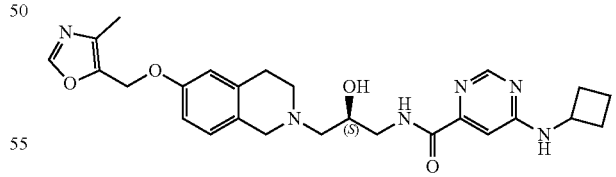

Prepared by general procedure 2B-F. Yield: 18.7 mg (24.9%). $^1$H NMR (Chloroform-d, 500 MHz): δ (ppm) 1.84 (m, 2H), 1.95 (m, 2H), 2.24 (s, 3H), 2.49 (m, 2H), 2.61 (m, 2H), 2.75 (m, 1H), 2.92 (m, 3H), 3.47 (m, 1H), 3.59 (d, 1H), 3.70 (m, 1H), 3.80 (d, 1H), 4.06 (m, 1H), 4.99 (s, 2H), 5.48 (m, 1H), 6.72 (s, 1H), 6.78 (d, 1H), 6.95 (d, 1H), 7.08 (s, 1H), 7.30 (s, 1H), 7.82 (s, 1H), 8.41 (t, 1H), 8.50 (s, 1H). LCMS(ESI): [M+H]$^+$ m/z: calcd 492.3; found 493.2; Rt=0.95 min.

Example 2B27. 6-(cyclohexylamino)-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 388)

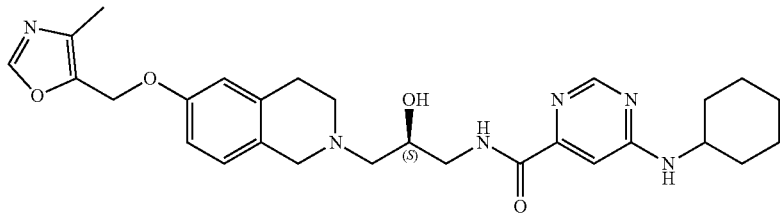

Prepared by general procedure 2B-F. Yield: 7.2 mg (12.56%). $^1$H NMR (500 MHz, CDCl$_3$) δ 1.27 (m, 4H), 1.42 (m, 2H), 1.68 (m, 2H), 1.78 (m, 2H), 2.04 (m, 2H), 2.24 (s, 3H), 2.62 (m, 2H), 2.76 (m, 2H), 2.93 (m, 3H), 3.48 (m, 1H), 3.61 (m, 1H), 3.68 (m, 1H), 3.80 (m, 1H), 4.06 (m, 1H), 4.99 (s, 2H), 5.20 (m, 1H), 6.73 (s, 1H), 6.78 (d, 1H), 6.95 (d, 1H), 7.12 (s, 1H), 7.82 (s, 1H), 8.41 (m, 1H), 8.49 (s, 1H). LCMS(ESI): [M+H]$^+$ m/z: calcd 520.6. found 521.2; Rt=1.01 min.

Example 2B28. 2-[ethyl(methyl)amino]-N-[(2S)-2-hydroxy-3-{6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 457)

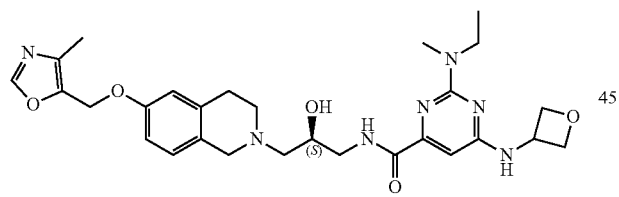

Prepared by general procedure 2B-F. Yield: 30.8 mg (45.0%). $^1$H NMR (DMSO-d$_6$, 400 MHz): δ (ppm) 1.04 (t, 3H), 2.15 (s, 3H), 2.46 (m, 2H), 2.68 (m, 2H), 2.76 (m, 2H), 3.22 (m, 1H), 3.26 (s, 3H), 3.44 (m, 1H), 3.54 (m, 4H), 3.86 (m, 1H), 4.47 (t, 2H), 4.78 (t, 2H), 4.93 (m, 2H), 5.07 (s, 2H), 6.37 (m, 1H), 6.76 (m, 2H), 6.94 (d, 1H), 7.97 (s, 1H), 8.28 (s, 1H), 8.36 (t, 1H). LCMS(ESI): [M+H]$^+$ m/z: calcd 551.4. found 552.4; Rt=0.93 min.

Example 2B29

Example 2B29. N-[(2S)-3-[5-chloro-6-[(4-methyl-1,3-oxazol-5-yl)methoxy]-1,2,3,4-tetrahydroisoquinolin-2-yl]-2-hydroxypropyl]-6-(cyclohexylamino)pyrimidine-4-carboxamide (Compound 501)

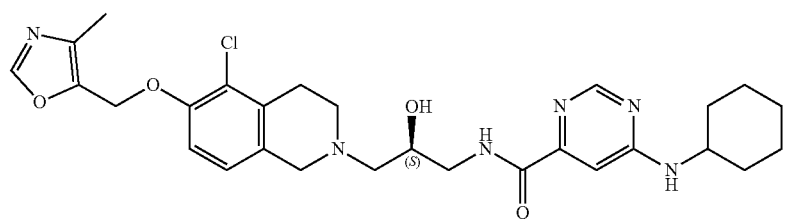

Prepared by general procedure. Yield 13.3 mg (21%). ¹H NMR (Chloroform-d, 500 MHz): δ (ppm) 1.27 (m, 3H), 1.45 (m, 2H), 1.60 (s, 3H), 1.67 (m, 1H), 1.78 (m, 2H), 2.04 (m, 2H), 2.22 (s, 3H), 2.59 (m, 2H), 2.76 (d, 1H), 2.92 (m, 3H), 3.48 (m, 1H), 3.57 (d, 1H), 3.69 (m, 1H), 3.77 (d, 1H), 4.03 (m, 1H), 5.08 (s, 2H), 6.86 (d, 1H), 6.89 (d, 1H), 7.12 (s, 1H), 7.82 (s, 1H), 8.41 (t, 1H), 8.49 (s, 1H). LCMS(ESI): [M-Boc]⁺ m/z: calcd 554.3. found 555.0; Rt=1.071 min.

General Procedure 2B-G

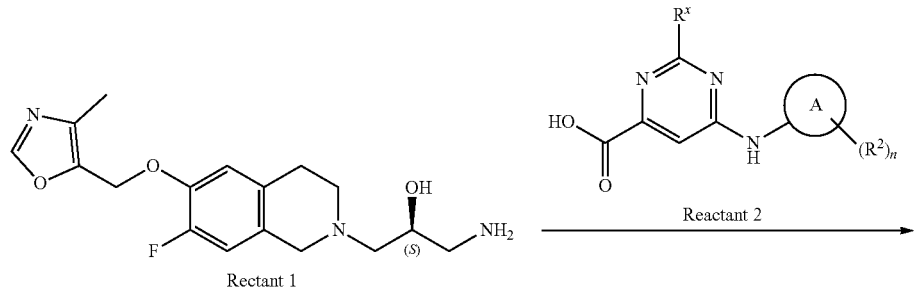

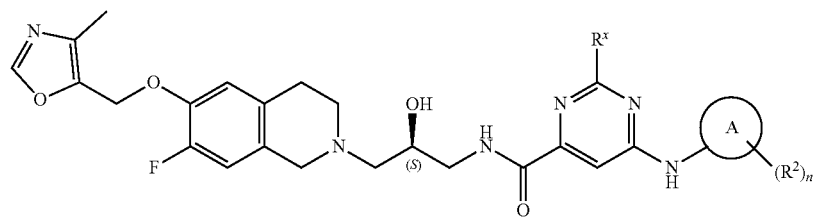

To the solution of Reactant 1 (1.0 equiv, HCl), Reactant 2 (1.0 equiv) and HATU (1.1 equiv) in DMF (1.2 mL) triethylamine (6.0 equiv) was added dropwise. The resulting mixture was stirred at 25° C. for 2 h. After the completion of the reaction, solvent was removed in vacuo and the obtained product was purified by reverse phase HPLC (Device (Mobile Phase, Column): 17_H₂O/R1 Sample info: 25-55% ACN 1-9 min water-acetonitrile, flow:30 mL/min (loading pump 4Ll/min acetonitrile) to afford pure product.

Example 2B30. 6-[(1-acetyl-4-piperidyl)amino]-N-[(2S)-3-[7-fluoro-6-[(4-methyloxazol-5-yl)methoxy]-3N-dihydro-1H-isoquinolin-2-yl]-2-hydroxy-propyl]pyrimidine-4-carboxamide (Compound 576)

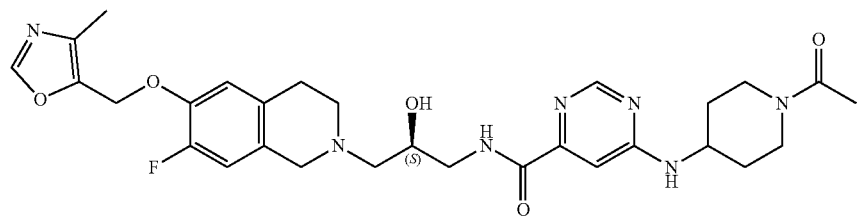

Prepared by general procedure A. Yield: 14.0 mg (16.14%). $^1$H NMR (Chloroform-d, 400 MHz): δ (ppm) 1.23 (s, 2H), 1.44 (m, 2H), 2.09 (m, 5H), 2.17 (s, 3H), 2.57 (m, 2H), 2.70 (m, 2H), 2.80 (m, 1H), 2.88 (m, 1H), 3.21 (m, 1H), 3.45 (m, 2H), 3.52 (d, 1H), 3.62 (m, 1H), 3.70 (d, 1H), 3.82 (d, 1H), 4.01 (m, 1H), 4.54 (d, 1H), 5.02 (s, 2H), 5.64 (s, 1H), 6.72 (m, 2H), 7.13 (s, 1H), 7.79 (s, 1H), 8.46 (s, 2H). LCMS(ESI): [M+H]$^+$ m/z: calcd 581.3. found 582.0; Rt=0.87 min.

as $K_2CO_3$, $Na_2CO_3$, and $Cs_2CO_3$. The reaction may be carried out in the presence of a solvent such as DMSO, i-PrOH, or DMF. The reaction may be heated for example at the reflux temperature of the solvent, or at a temperature in a range of 50° C. to reflux, or in a range of 70° C. to 85° C. Compounds of formula 2C-C may be converted to compounds of formula 2C-D. Examples of conditions known to form esters of formula 2C-D from compounds of formula 2C-C include adding methanol, an amine base such as

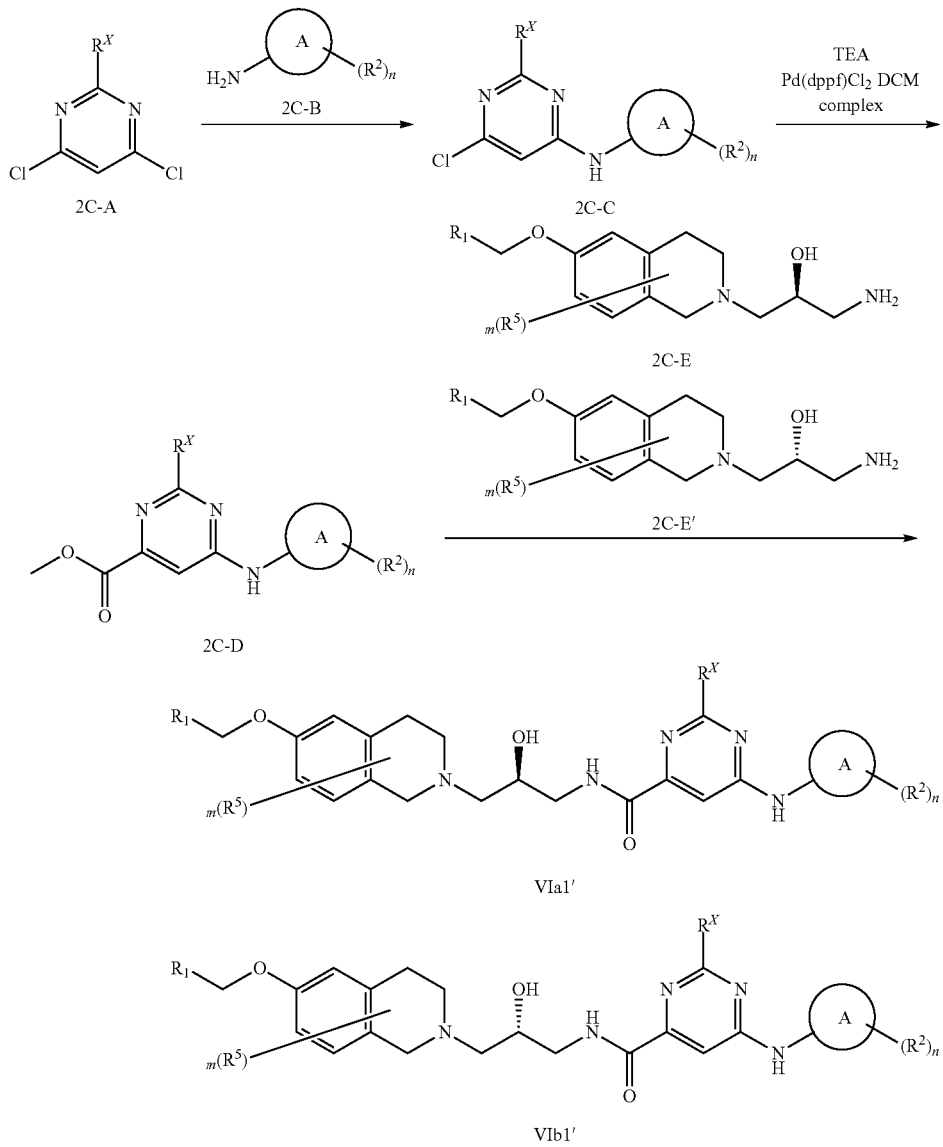

Scheme 2C wherein variables $R^5$, $R^x$, $R^1$, $R^2$, m, and n are defined herein.

As shown in Scheme 2C, compounds of formula (VIa1') or formula (VIb1') can be prepared from compounds of formula 2C-A. Compounds of formula 2C-A can react with amines of formula 2C-B under SNAr conditions form compounds of formula 2C-C or formula 2A-F'. SNAr conditions include but are not limited to adding a base for example an amine base such as TEA or DIPEA, or a carbonate base such triethylamine, a palladium (II) catalyst and CO. Exemplary palladium (II) catalysts include bis(diphenylphosphino)ferrocene)palladium(II) dichloride DCM. The reaction may be carried out under 1 atmosphere of CO or higher. Compounds of formula 2C-D can be coupled with amines of formula 2C-E or 2C-E' to form compounds of formula (VIa1') or (VIb1'). Examples of contemplated conditions include TEA and MeOH.

Example 2C1. (S)-6-((1-acetylazetidin-3-yl)amino)-N-(3-(5-chloro-6-(oxazol-5-ylmethoxy)-3,4-dihydroisoquinolin-2(1H)-yl)-2-hydroxypropyl)-2-isopropylpyrimidine-4-carboxamide (Compound 342)

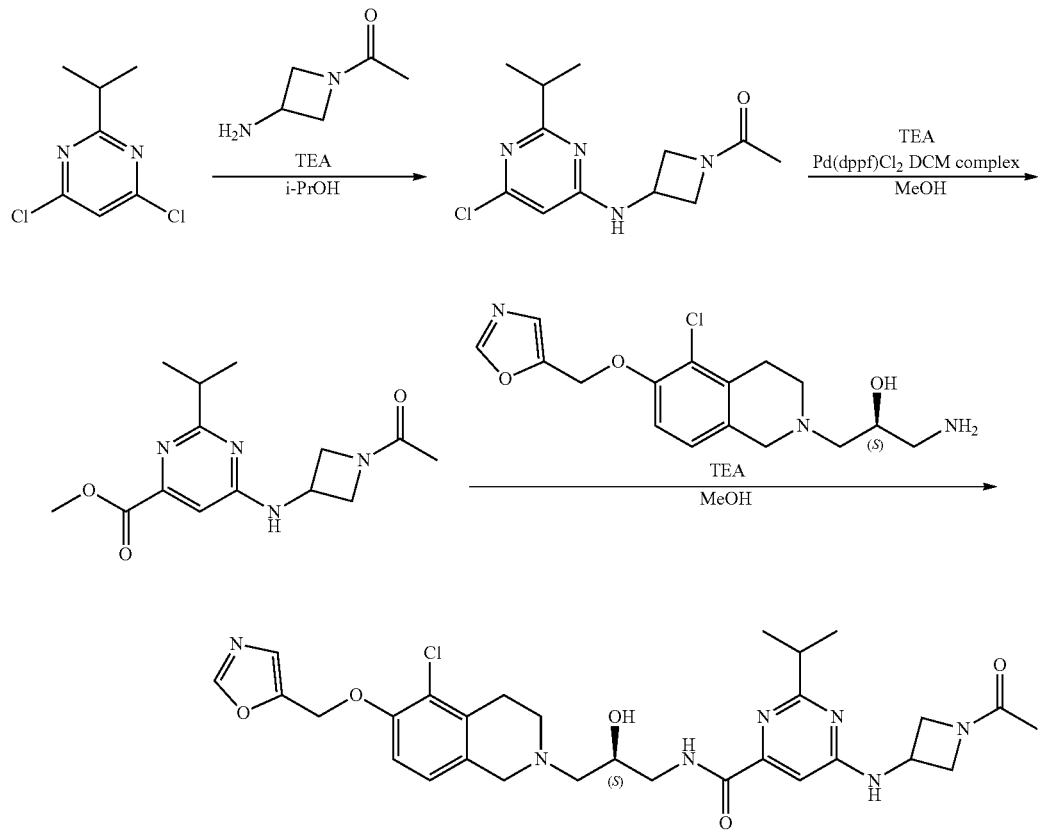

1-(3-((6-chloro-2-isopropylpyrimidin-4-yl)amino)azetidin-1-yl)ethanone. 4,6-Dichloro-2-isopropyl-pyrimidine (4.6 g, 24.08 mmol) and 1-(3-aminoazetidin-1-yl)ethanone (6.02 g, 26.48 mmol, TFA) were mixed in isopropyl alcohol (50 mL). Triethylamine (7.31 g, 72.23 mmol, 10.07 mL) was added and solution was stirred at 82° C. for 20 hr. Then, it was concentrated under reduced pressure, diluted with MTBE (100 ml) and washed successively with water (50 ml) and brine (50 ml). After drying over Na$_2$SO$_4$ it was evaporated in vacuo affording 1-[3-[(6-chloro-2-isopropyl-pyrimidin-4-yl)amino]azetidin-1-yl]ethanone (6.4 g, 23.81 mmol, 98.91% yield).

methyl 6-((1-acetylazetidin-3-yl)amino)-2-isopropylpyrimidine-4-carboxylate. 1-[3-[(6-Chloro-2-isopropyl-pyrimidin-4-yl)amino]azetidin-1-yl]ethanone (2 g, 7.44 mmol) was dissolved in methanol (70 mL). Triethylamine (903.67 mg, 8.93 mmol, 1.24 mL) and (1,1'-bis(diphenylphosphino)ferrocene)palladium(II) dichloride DCM complex (121.55 mg, 148.84 umol) was added thereto. The mixture was stirred at 115° C. for 42 hr under an atmosphere of CO (40 Bar). The solvent was evaporated under reduced pressure. Residue was diluted with ethyl acetate (100 ml) and washed successively with water (60 ml) and brine (60 ml). After drying over Na$_2$SO$_4$ it was evaporated in vacuo affording methyl 6-[(1-acetylazetidin-3-yl)amino]-2-isopropyl-pyrimidine-4-carboxylate (842 mg, crude). $^1$H NMR (400 MHz, CDCl$_3$) δ (ppm) 1.24 (d, 6H), 1.39 (m, 1H), 1.88 (s, 3H), 3.10 (m, 2H), 3.94 (s, 3H), 4.02 (m, 1H), 4.38 (m, 1H), 4.50 (m, 1H), 5.88 (bds, 1H), 6.94 (s, 1H). LCMS(ESI): [M+H]$^+$ m/z: calcd 292.3. found 293.2; Rt=0.790 min.

(S)-6-((1-acetylazetidin-3-yl)amino)-N-(3-(5-chloro-6-(oxazol-5-ylmethoxy)-3,4-dihydroisoquinolin-2(1H)-yl)-2-hydroxypropyl)-2-isopropylpyrimidine-4-carboxamide.

Methyl 6-[(1-acetylazetidin-3-yl)amino]-2-isopropyl-pyrimidine-4-carboxylate (62 mg, 212.09 umol) and (2S)-1-amino-3-[5-chloro-6-(oxazol-5-ylmethoxy)-3,4-dihydro-1H-isoquinolin-2-yl]propan-2-ol (99.58 mg, 222.69 umol, 3HCl) were dissolved in methanol (1.5 mL). Triethylamine (107.31 mg, 1.06 mmol, 147.80 uL) was added thereto. Solution was stirred at 70° C. for 16 hr in a pressure tube. Then, solvent was evaporated in vacuo and residue was subjected to HPLC (SunFire C18 100×19 mm; 50-80% H$_2$O-MeOH; flow rate: 40 ml/min) affording 6-[(1-acetylazetidin-3-yl)amino]-N-[(2S)-3-[5-chloro-6-(oxazol-5-ylmethoxy)-3,4-dihydro-1H-isoquinolin-2-yl]-2-hydroxypropyl]-2-isopropyl-pyrimidine-4-carboxamide (18 mg, 30.10 umol, 14.19% yield). NMR(400 MHz, CDCl$_3$): δ (ppm) 1.23 (d, 6H), 1.88 (s, 3H), 2.58 (m, 2H), 2.74 (m, 1H), 2.90 (m, 4H), 3.49 (m, 1H), 3.55 (d, 1H), 3.65 (m, 1H), 3.75 (d, 1H), 4.00 (m, 4H), 4.38 (m, 1H), 4.49 (t, 1H), 4.73 (m, 1H), 5.10 (s, 2H), 6.21 (s, 1H), 6.82 (d, 1H), 6.86 (d, 1H), 7.04 (s, 1H), 7.14 (s, 1H), 7.89 (s, 1H), 8.53 (t, 1H). LCMS(ESI): [M+H]$^+$ m/z: calcd 598.1; found 599.2; Rt=0.985 min.

Example 2C2. (S)-6-((1-acetylazetidin-3-yl)amino)-N-(2-hydroxy-3-(6-((4-methyloxazol-5-yl)methoxy)-3,4-dihydroisoquinolin-2(1H)-yl)propyl)-2-isopropylpyrimidine-4-carboxamide (Compound 568)

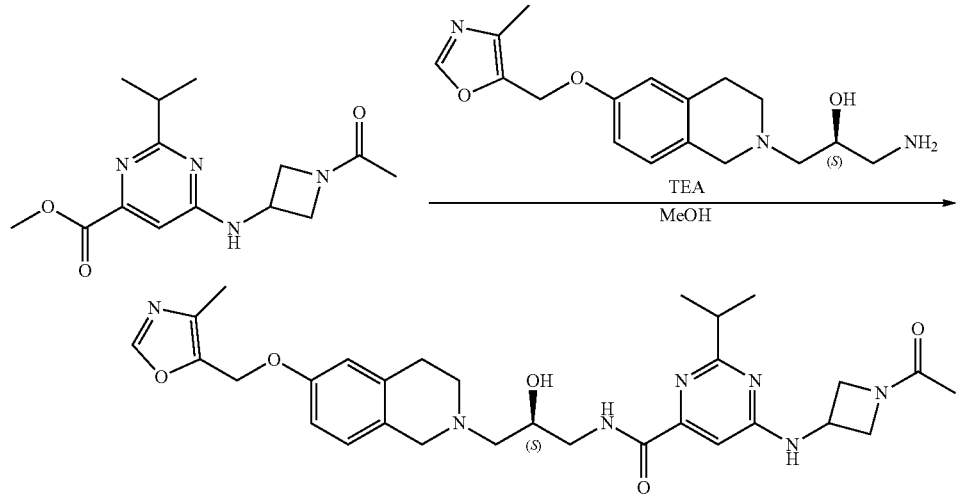

methyl 6-[(1-acetylazetidin-3-yl)amino]-2-isopropyl-pyrimidine-4-carboxylate (68 mg, 232.61 umol) and (2S)-1-amino-3-[6-[(4-methyloxazol-5-yl)methoxy]-3,4-dihydro-1H-isoquinolin-2-yl]propan-2-ol (99.27 mg, 232.61 umol, 3HCl) were dissolved in Methanol (1 mL). Triethylamine (117.69 mg, 1.16 mmol, 162.11 uL) was added thereto. Solution was stirred at 75° C. for 16 hr in a pressure tube. Then, solvent was evaporated in vacuo and residue was subjected to HPLC (column: ACTUS Triart C18 100*20 mm; 20-45% water+NH₃/acetonitrile+NH₃; Flow 30 ml/min) affording 6-[(1-acetylazetidin-3-yl)amino]-N-[(2S)-2-hydroxy-3-[6-[(4-methyloxazol-5-yl)methoxy]-3,4-dihydro-1H-isoquinolin-2-yl]propyl]-2-isopropyl-pyrimidine-4-carboxamide (12 mg, 20.77 umol, 8.93% yield). $^1$H NMR (CDCl₃, 400 MHz): δ (ppm) 1.23 (d, 6H), 1.87 (s, 3H), 2.20 (s, 3H), 2.58 (m, 2H), 2.71 (m, 1H), 2.90 (m, 4H), 3.46 (m, 1H), 3.56 (d, 1H), 3.67 (m, 1H), 3.75 (d, 1H), 4.02 (m, 4H), 4.38 (t, 1H), 4.49 (t, 1H), 4.74 (m, 1H), 4.95 (s, 2H), 6.43 (m, 1H), 6.69 (s, 1H), 6.74 (dd, 1H), 6.91 (d, 1H), 7.06 (s, 1H), 7.79 (s, 1H), 8.54 (t, 1H). LCMS(ESI): [M+H]$^+$ m/z: calcd 577.7. found 578.2; Rt=0.946 min.

Example 2C3. (S)-6-((1-acetylazetidin-3-yl)amino)-N-(2-hydroxy-3-(6-(oxazol-5-ylmethoxy)-3,4-dihydroisoquinolin-2(1H)-yl)propyl)-2-isopropylpyrimidine-4-carboxamide (Compound 349)

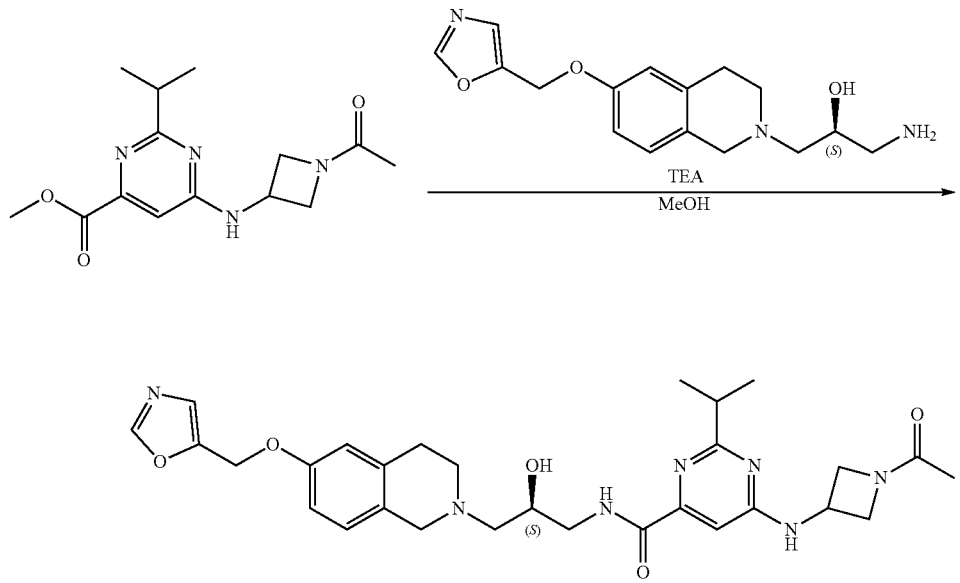

Methyl 6-[(1-acetylazetidin-3-yl)amino]-2-isopropyl-pyrimidine-4-carboxylate (67 mg, 229.19 umol) and (2S)-1-amino-3-[6-(oxazol-5-ylmethoxy)-3,4-dihydro-1H-isoquinolin-2-yl]propan-2-ol (99.33 mg, 240.65 umol, 3HCl) were dissolved in Methanol (1.5 mL). Triethylamine (115.96 mg, 1.15 mmol, 159.72 uL) was added thereto. Solution was stirred at 70° C. for 16 hr in a pressure tube. Then, solvent was evaporated in vacuo and residue was subjected to HPLC (SunFire C18 100×19 mm; 50-80% $H_2O$-MeOH; flow rate: 40 ml/min) affording 6-[(1-acetylazetidin-3-yl)amino]-N-[(2S)-2-hydroxy-3-[6-(oxazol-5-ylmethoxy)-3,4-dihydro-1H-isoquinolin-2-yl]propyl]-2-isopropyl-pyrimidine-4-carboxamide (26 mg, 46.13 umol, 20.13% yield). NMR ($CDCl_3$, 400 MHz): δ (ppm) 1.23 (d, 6H), 1.88 (s, 3H), 2.58 (m, 2H), 2.70 (m, 1H), 2.90 (m, 4H), 3.45 (m, 1H), 3.55 (d, 1H), 3.66 (m, 1H), 3.74 (d, 1H), 4.01 (m, 3H), 4.38 (m, 1H), 4.49 (t, 1H), 4.75 (s, 1H), 5.02 (s, 2H), 6.31 (s, 1H), 6.69 (s, 1H), 6.74 (dd, 1H), 6.91 (d, 1H), 7.05 (s, 1H), 7.12 (s, 1H), 7.88 (s, 1H), 8.54 (t, 1H). LCMS(ESI): $[M+H]^+$ m/z: calcd 563.6. found 564.4; Rt=0.958 min.

Example 2C4. (S)-6-((1-acetylazetidin-3-yl)amino)-N-(2-hydroxy-3-(5-methyl-6-((4-methyloxazol-5-yl)methoxy)-3A-dihydroisoquinolin-2(1H)-yl)propyl)-2-isopropylpyrimidine-4-carboxamide (Compound 575)

Methyl 6-[(1-acetylazetidin-3-yl)amino]-2-isopropyl-pyrimidine-4-carboxylate (66 mg, 225.77 umol) and (2S)-1-amino-3-[5-methyl-6-[(4-methyloxazol-5-yl)methoxy]-3,4-dihydro-1H-isoquinolin-2-yl]propan-2-ol (99.52 mg, 225.77 umol, 3HCl) were dissolved in Methanol (1 mL). Triethylamine (114.23 mg, 1.13 mmol, 157.34 uL) was added thereto. Solution was stirred at 75° C. for 16 hr in a pressure tube. Then, solvent was evaporated in vacuo and residue was subjected to HPLC (column: ACTUS Triart C18 100*20 mm; 20-45% water+$NH_3$/acetonitrile+$NH_3$; Flow 30 ml/min) affording 6-[(1-acetylazetidin-3-yl)amino]-N-[(2S)-2-hydroxy-3-[5-methyl-6-[(4-methyloxazol-5-yl)methoxy]-3,4-dihydro-1H-isoquinolin-2-yl]propyl]-2-isopropyl-pyrimidine-4-carboxamide (14 mg, 23.66 umol, 10.48% yield). $^1$H NMR ($CDCl_3$, 400 MHz): δ (ppm) 1.23 (d, 6H), 1.87 (s, 3H), 2.04 (s, 3H), 2.17 (s, 3H), 2.58 (m, 3H), 2.74 (m, 3H), 2.92 (m, 2H), 3.46 (m, 1H), 3.57 (d, 1H), 3.66 (m, 1H), 3.75 (d, 1H), 4.02 (m, 3H), 4.36 (d, 1H), 4.48 (t, 1H), 4.73 (s, 1H), 4.95 (s, 2H), 6.52 (s, 1H), 6.76 (d, 1H), 6.81 (d, 1H), 7.06 (s, 1H), 7.78 (s, 1H), 8.54 (t, 1H). LCMS(ESI): $[M+H]^+$ m/z: calcd 591.7. found 592.7; Rt=0.985 min.

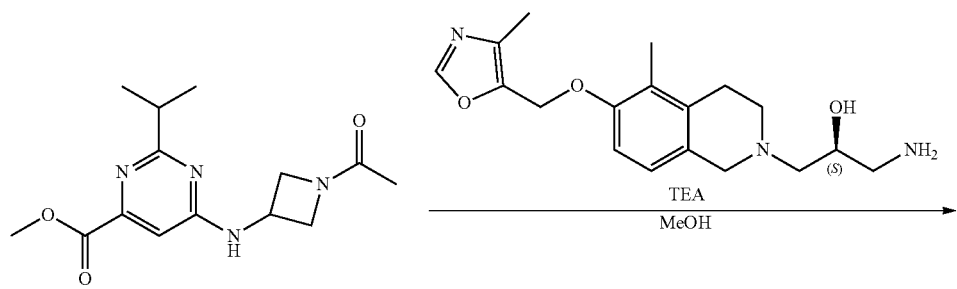

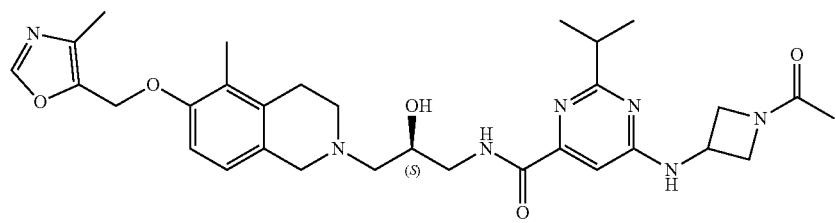

Example 2C5. (S)-6-((1-acetylazetidin-3-yl)amino)-2-(tert-butyl)-N-(3-(5-chloro-6-(oxazol-5-ylmethoxy)-3,4-dihydroisoquinolin-2(1H)-yl)-2-hydroxypropyl)pyrimidine-4-carboxamide (Compound 360)

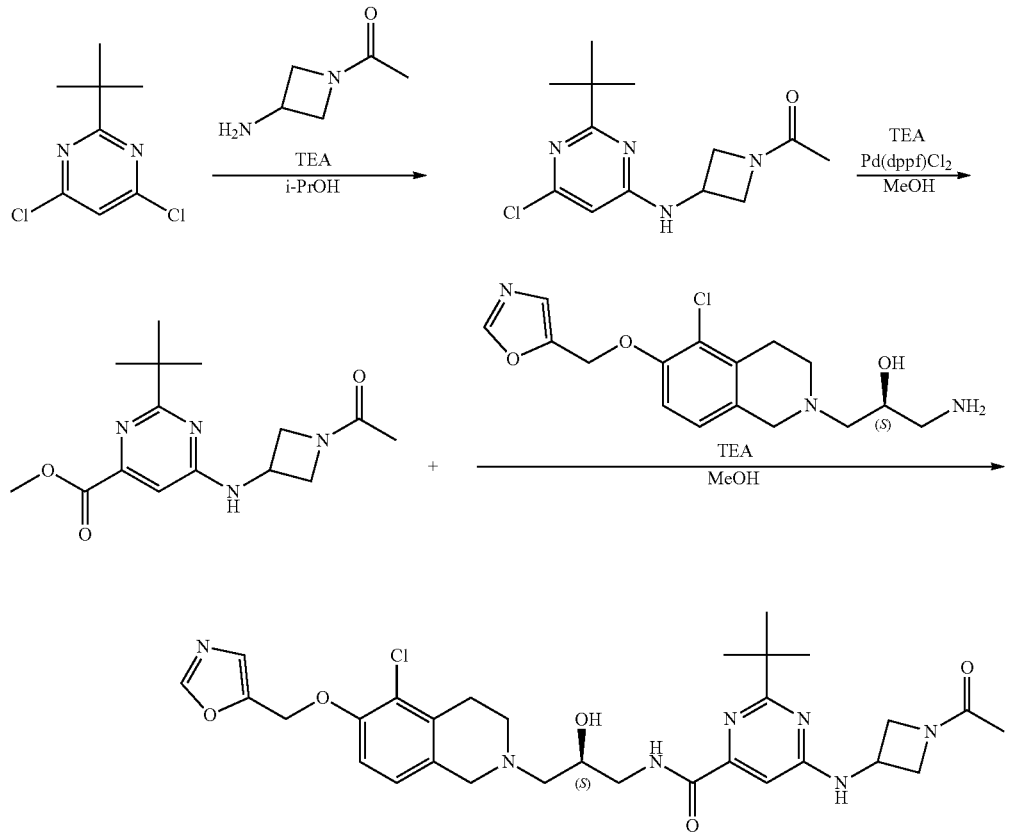

1-(3-((2-(tert-butyl)-6-chloropyrimidin-4-yl)amino)azetidin-1-yl)ethenone. A solution of 2-tert-butyl-4,6-dichloropyrimidine (5 g, 24.38 mmol), 1-(3-aminoazetidin-1-yl)ethanone (6.12 g, 26.82 mmol, CF$_3$COOH) and triethylamine (7.40 g, 73.14 mmol, 10.19 mL) in i-PrOH (50 mL) was heated at 85° C. for 72 hr. The resulting mixture was evaporated in vacuo, the residue was taken up with water (100 ml) and extracted with DCM (3*50 ml). The combined organic layer was washed with brine (2*70 ml), dried over Na$_2$SO$_4$ and evaporated in vacuo to give 1-[3-[(2-tert-butyl-6-chloro-pyrimidin-4-yl)amino]azetidin-1-yl]ethanone (6.2 g, 21.93 mmol, 89.93% yield). $^1$H NMR (500 MHz, DMSO-d$_6$) δ (ppm) 1.32 (s, 9H), 1.91 (s, 3H), 3.93 (m, 1H), 4.02 (m, 1H), 4.39 (m, 1H), 4.51 (m, 1H), 4.65 (m, 1H), 5.57 (bds, 1H), 6.22 (s, 1H). LCMS(ESI): [M+H]$^+$ m/z: calcd 282.8. found 283.2; Rt=1.219 min.

methyl 6-((1-acetylazetidin-3-yl)amino)-2-(tert-butyl)pyrimidine-4-carboxylate. A solution of 1-[3-[(2-tert-butyl-6-chloro-pyrimidin-4-yl)amino]azetidin-1-yl]ethanone (5 g, 17.68 mmol), triethylamine (1.79 g, 17.68 mmol, 2.46 mL) and [1,1'-bis(diphenylphosphino)ferrocene]dichloropalladium(II), complex with dichloromethane (1.44 g, 1.77 mmol) in methanol (200 mL) was heated at 115° C. and 30 atm in autoclave for 72 hr. The resulting mixture was evaporated in vacuo, taken up with water (150 ml) and extracted with DCM (2*100 ml), washed with brine (2*100 ml), dried over Na$_2$SO$_4$ and evaporated in vacuo to obtain methyl 6-[(1-acetylazetidin-3-yl)amino]-2-tert-butyl-pyrimidine-4-carboxylate (4 g, 13.06 mmol, 73.84% yield). $^1$H NMR (400 MHz, CDCl$_3$) δ (ppm) 1.33 (s, 9H), 1.87 (s, 3H), 3.92 (s, 3H), 3.93 (m, 1H), 4.03 (m, 1H), 4.37 (m, 1H), 4.48 (m, 1H), 4.70 (m, 1H), 5.91 (bds, 1H), 6.92 (s, 1H). LCMS(ESI): [M+H]$^+$ m/z: calcd 306.4. found 307.2; Rt=1.002 min.

(S)-6-((1-acetylazetidin-3-yl)amino)-2-(tert-butyl)-N-(3-(5-chloro-6-(oxazol-5-ylmethoxy)-3,4-dihydroisoquinolin-2(1H)-yl)-2-hydroxypropyl)pyrimidine-4-carboxamide. A solution of methyl 6-[(1-acetylazetidin-3-yl)amino]-2-tert-butyl-pyrimidine-4-carboxylate (0.1 g, 326.41 umol), (2S)-1-amino-3-[5-chloro-6-(oxazol-5-ylmethoxy)-3,4-dihydro-1H-isoquinolin-2-yl]propan-2-ol (145.97 mg, 326.41 umol, 3HCl) and triethylamine (132.12 mg, 1.31 mmol, 181.98 uL) in MeOH (3 mL) was heated at 65° C. for 48 hr and evaporated in vacuo to obtain crude product (250 mg). The crude product was puried by reverse phase HPLC (60-70% 0-5 min water-methanol, flow: 30 ml/min (loading pump 4 ml/min methanol) column: SunFire C18 100×19 mm, 5 um) to obtain 6-[(1-acetylazetidin-3-yl)amino]-2-tert-butyl-N-[(2S)-3-[5-chloro-6-(oxazol-5-ylmethoxy)-3,4-dihydro-1H-isoquinolin-2-yl]-2-hydroxy-propyl]pyrimidine-4-carboxamide (0.030 g, 49.01 umol, 15.01% yield). $^1$H NMR (400 MHz, CDCl$_3$): δ (ppm) 1.31 (s, 9H), 1.88 (s, 3H), 2.56 (m, 2H), 2.74 (m, 1H), 2.90 (m, 3H), 3.45 (m, 2H), 3.54 (d, 1H), 3.67 (m, 1H), 3.74 (d, 1H), 4.00 (m, 3H), 4.38 (m, 1H), 4.49 (m, 1H), 4.71 (m, 1H), 5.10 (s, 2H), 5.68 (s, 1H), 6.83 (d, 1H), 6.87 (d, 1H), 7.00 (s, 1H), 7.13 (s, 1H), 7.89 (s, 1H), 8.48 (t, 1H). LCMS(ESI): [M+H]$^+$ m/z: calcd 612.1. found 613.2; Rt=2.595 min.

Example 2C6. (S)-6-((1-acetylazetidin-3-yl)amino)-2-(tert-butyl)-N-(2-hydroxy-3-(6-(oxazol-5-ylmethoxy)-3,4-dihydroisoquinolin-2(1H)-yl)propyl)pyrimidine-4-carboxamide (Compound 379)

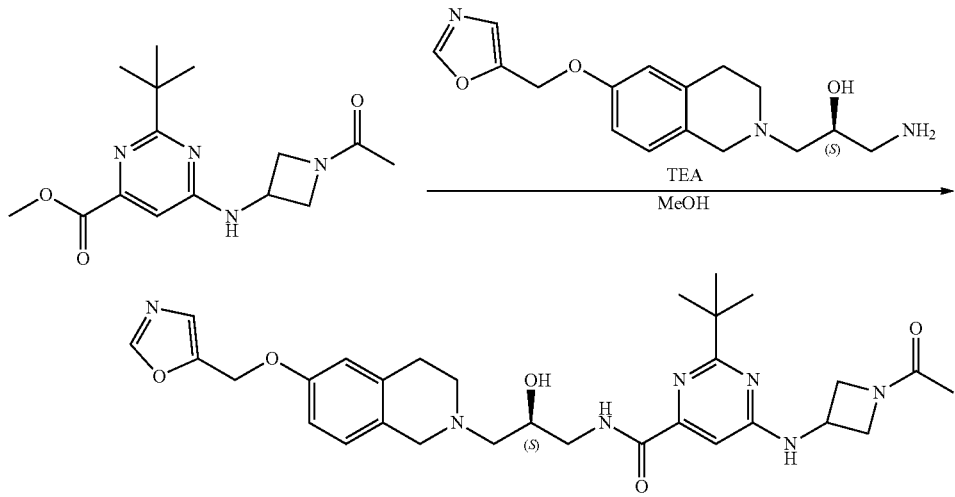

A solution of (2S)-1-amino-3-[6-(oxazol-5-ylmethoxy)-3,4-dihydro-1H-isoquinolin-2-yl]propan-2-ol (0.15 g, 363.43 umol, 3HCl), methyl 6-[(1-acetylazetidin-3-yl)amino]-2-tert-butyl-pyrimidine-4-carboxylate (111.34 mg, 363.43 umol) and Triethylamine (147.10 mg, 1.45 mmol, 202.62 uL) in MeOH (4 mL) was heated at 65° C. for 48 hr and evaporated in vacuo to obtain crude product (300 mg). The crude product was puried by reverse phase HPLC (40-80% 0-6 min water-methanol, flow: 30 ml/min (loading pump 4 ml/min methanol); column: SunFireC18 100×19 mm 5 um) to obtain 6-[(1-acetylazetidin-3-yl)amino]-2-tert-butyl-N-[(2S)-2-hydroxy-3-[6-(oxazol-5-ylmethoxy)-3,4-dihydro-1H-isoquinolin-2-yl]propyl]pyrimidine-4-carboxamide (0.074 g, 128.10 umol, 35.25% yield). $^1$H NMR (400 MHz, DMSO-d6) δ 1.28 (s, 9H), 1.77 (s, 3H), 2.47 (m, 2H), 2.69 (m, 2H), 2.76 (m, 2H), 3.25 (m, 1H), 3.51 (m, 1H), 3.54 (m, 2H), 3.78 (m, 1H), 3.88 (m, 1H), 4.00 (m, 1H), 4.13 (t, 1H), 4.42 (t, 1H), 4.57 (m, 1H), 4.95 (d, 1H), 5.11 (s, 2H), 6.77 (m, 2H), 6.94 (m, 2H), 7.30 (s, 1H), 8.20 (m, 1H), 8.39 (s, 1H), 8.46 (t, 1H). LCMS(ESI): [M+H]$^+$ m/z: calcd 577.7. found 578.7; Rt=2.510 min.

Example 2C7. (S)-6-((1-acetylazetidin-3-yl)amino)-2-(tert-butyl)-N-(2-hydroxy-3-(6-((4-methyloxazol-5-yl)methoxy)-3,4-dihydroisoquinolin-2(1H)-yl)propyl)pyrimidine-4-carboxamide (Compound 564)

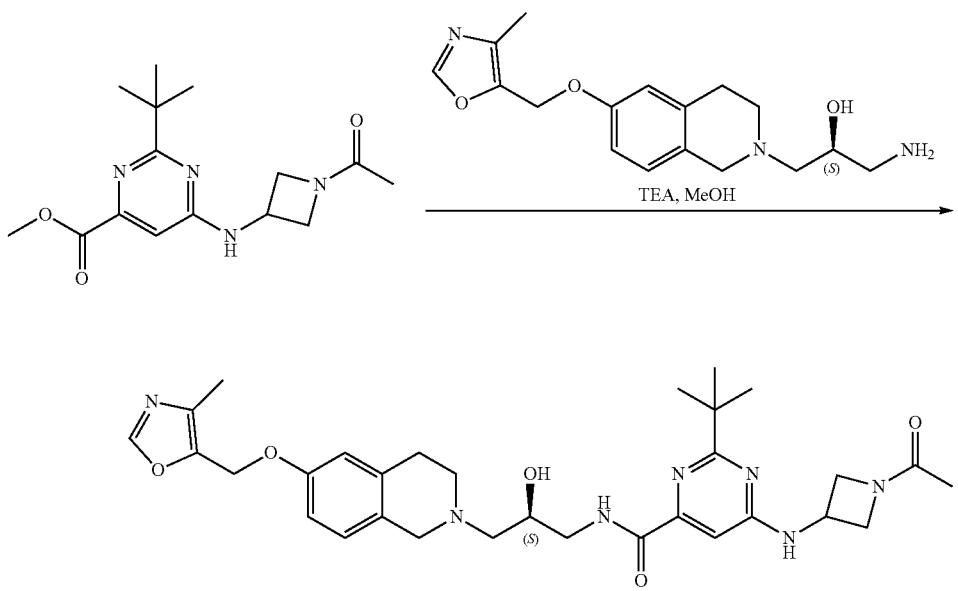

A solution of methyl 6-[(1-acetylazetidin-3-yl)amino]-2-tert-butyl-pyrimidine-4-carboxylate (0.08, 261.13 umol), (2S)-1-amino-3-[6-[(4-methyloxazol-5-yl)methoxy]-3,4-dihydro-1H-isoquinolin-2-yl]propan-2-ol (111.44 mg, 261.13 umol, 3HCl) and Triethylamine (132.12 mg, 1.31 mmol, 181.98 uL) in MeOH (5 mL) was heated at 70° C. for 48 hr and evaporated in vacuo to obtain crude product (300 mg). The crude product was puried by reverse phase HPLC (50-65% 0-6 min water+NH3-methanol+NH3, flow: 30 ml/min (loading pump 4 ml/min methanol+NH3), column: SunFire C18 100×19 mm, 5 um) to obtain 6-[(1-acetylazetidin-3-yl)amino]-2-tert-butyl-N-[(2S)-2-hydroxy-3-[6-[(4-methyloxazol-5-yl)methoxy]-3,4-dihydro-1H-isoquinolin-2-yl]propyl]pyrimidine-4-carboxamide (0.015 g, 25.35 umol, 9.71% yield). $^1$H NMR (CDCl$_3$, 400 MHz): δ (ppm) 1.31 (s, 9H), 1.88 (s, 3H), 2.21 (s, 3H), 2.57 (m, 2H), 2.70 (m, 1H), 2.89 (m, 3H), 3.44 (m, 1H), 3.55 (d, 1H), 3.66 (m, 1H), 3.74 (d, 1H), 4.01 (m, 3H), 4.39 (t, 1H), 4.48 (t, 1H), 4.72 (m, 1H), 4.96 (s, 2H), 6.03 (s, 1H), 6.69 (s, 1H), 6.74 (d, 1H), 6.91 (d, 1H), 7.03 (s, 1H), 7.79 (s, 1H), 8.50 (t, 1H). LCMS(ESI): [M+H]$^+$ m/z: calcd 591.7. found 592.7; Rt=1.039 min.

Example 2C8. (S)-6-((1-acetylazetidin-3-yl)amino)-2-(tert-butyl)-N-(2-hydroxy-3-(5-methyl-6-((4-methyloxazol-5-yl)methoxy)-3,4-dihydroisoquinolin-2(1H)-yl)propyl)pyrimidine-4-carboxamide (Compound 569)

A solution of methyl 6-[(1-acetylazetidin-3-yl)amino]-2-tert-butyl-pyrimidine-4-carboxylate (0.08 g, 261.13 umol), (2S)-1-amino-3-[5-methyl-6-[(4-methyloxazol-5-yl)methoxy]-3,4-dihydro-1H-isoquinolin-2-yl]propan-2-ol (115.10 mg, 261.13 umol, 3HCl) and Triethylamine (132.12 mg, 1.31 mmol, 181.98 uL) in MeOH (5 mL) was heated at 70° C. for 48 hr and evaporated in vacuo to obtain crude product (300 mg). The crude product was puried by reverse phase HPLC (58% 0-6 min water+nh3-methanol+nh3, flow: 30 ml/min (loading pump 4 ml/min methanol+NH3), column: SunFire C18 100×19 mm, 5 um) to obtain 6-[(1-acetylazetidin-3-yl)amino]-2-tert-butyl-N-[(2S)-2-hydroxy-3-[5-methyl-6-[(4-methyloxazol-5-yl)methoxy]-3,4-dihydro-1H-isoquinolin-2-yl]propyl]pyrimidine-4-carboxamide (0.013 g, 21.46 umol, 8.22% yield). NMR (CDCl$_3$, 400 MHz): δ (ppm) 1.31 (s, 9H), 1.88 (s, 3H), 2.05 (s, 3H), 2.18 (s, 3H), 2.55 (m, 2H), 2.71 (m, 3H), 2.93 (m, 1H), 3.45 (m, 2H), 3.55 (d, 1H), 3.69 (m, 1H), 3.75 (d, 1H), 4.02 (m, 3H), 4.39 (m, 1H), 4.50 (m, 1H), 4.71 (m, 1H), 4.96 (s, 2H), 5.91 (s, 1H), 6.77 (d, 1H), 6.82 (d, 1H), 7.02 (s, 1H), 7.78 (s, 1H), 8.49 (t, 1H). LCMS(ESI): [M+H]$^+$ m/z: calcd 605.7. found 606.2; Rt=1.070 min.

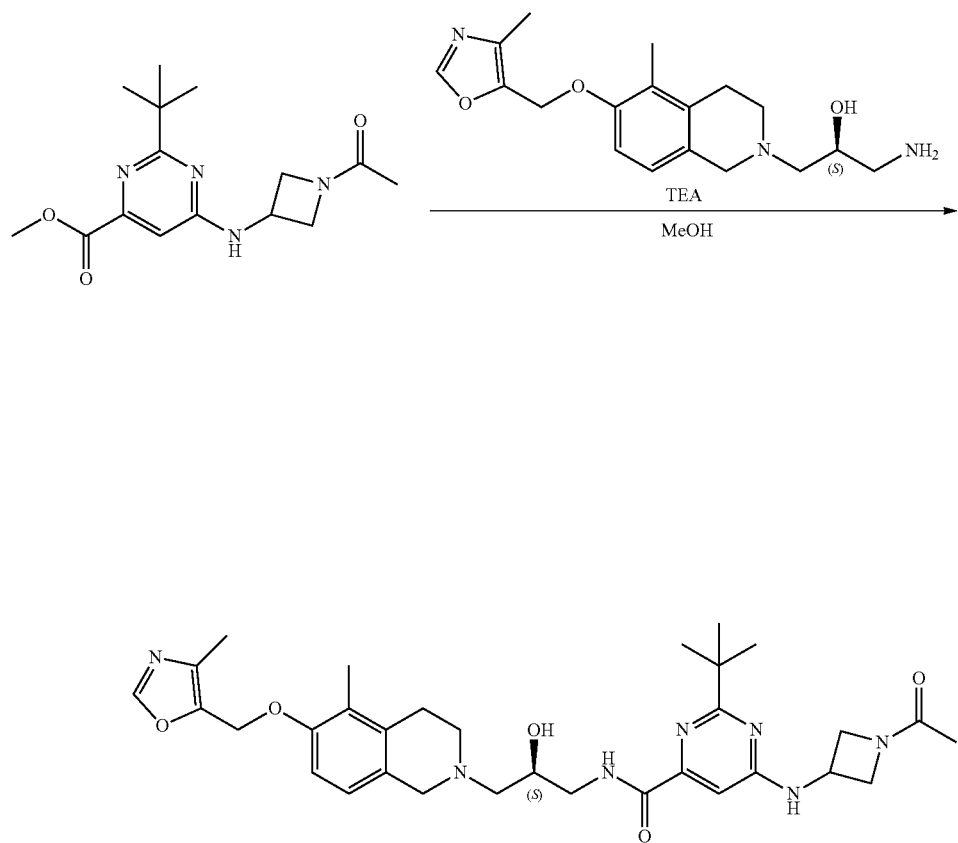

Example 2C9. (S)-2-((1-acetylazetidin-3-yl)amino)-N-(2-hydroxy-3-(6-((4-methyloxazol-5-yl)methoxy)-3,4-dihydroisoquinolin-2(1H)-yl)propyl)-6-(piperidin-1-yl)pyrimidine-4-carboxamide (Compound 608)

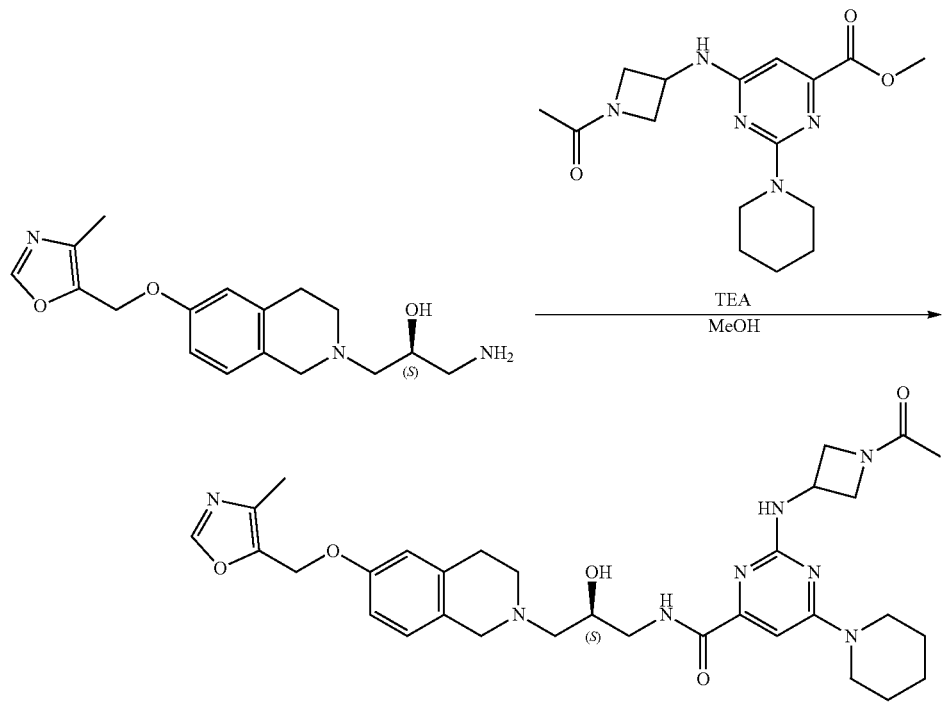

A solution of methyl 6-[(1-acetylazetidin-3-yl)amino]-2-(1-piperidyl)pyrimidine-4-carboxylate (500.00 mg, 1.20 mmol), (2S)-1-amino-3-[6-[(4-methyloxazol-5-yl)methoxy]-3,4-dihydro-1H-isoquinolin-2-yl]propan-2-ol (512.04 mg, 1.20 mmol, 3HCl) and triethylamine (728.46 mg, 7.20 mmol, 1.00 mL) in MeOH (15 mL) was heated at 70° C. for 48 hr in a tightly closed reaction vial, then evaporated in vacuo to obtain crude product (1 g). The crude product was puried by reverse phase HPLC (40/60% 0-5 min water-methanol, flow: 30 ml/min (loading pump 4 ml/min methanol); column: SunFireC18 100×19 mm 5 um) to give Compound 534 6-[(1-acetylazetidin-3-yl)amino]-N-[(2S)-2-hydroxy-3-[6-[(4-methyloxazol-5-yl)methoxy]-3,4-dihydro-1H-isoquinolin-2-yl]propyl]-2-(1-piperidyl)pyrimidine-4-carboxamide (75.1 mg, 121.38 umol, 10.12% yield) and 2-[(1-acetylazetidin-3-yl)amino]-N-[(2S)-2-hydroxy-3-[6-[(4-methyloxazol-5-yl)methoxy]-3,4-dihydro-1H-isoquinolin-2-yl]propyl]-6-(1-piperidyl)pyrimidine-4-carboxamide (27.6 mg, 44.61 umol).

$^1$H NMR(400 MHz, CDCl$_3$): δ (ppm) 1.57 (m, 4H), 1.67 (m, 3H), 1.86 (s, 3H), 2.21 (s, 3H), 2.54 (m, 2H), 2.68 (m, 1H), 2.87 (m, 3H), 3.38 (m, 1H), 3.53 (d, 1H), 3.64 (m, 5H), 3.75 (d, 1H), 3.90 (m, 1H), 3.99 (m, 2H), 4.33 (t, 1H), 4.41 (t, 1H), 4.62 (m, 1H), 4.96 (s, 2H), 5.04 (d, 1H), 6.69 (s, 1H), 6.74 (dd, 1H), 6.82 (s, 1H), 6.92 (d, 1H), 7.79 (s, 1H), 8.24 (t, 1H).

LCMS(ESI): [M+H]$^+$ m/z: calcd 618.7. found 619.4; Rt=2.375 min.

Scheme 2D

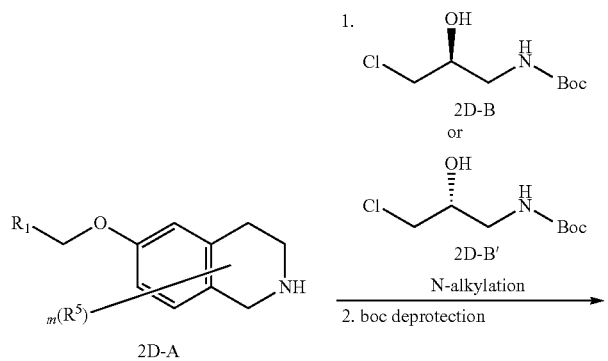

-continued
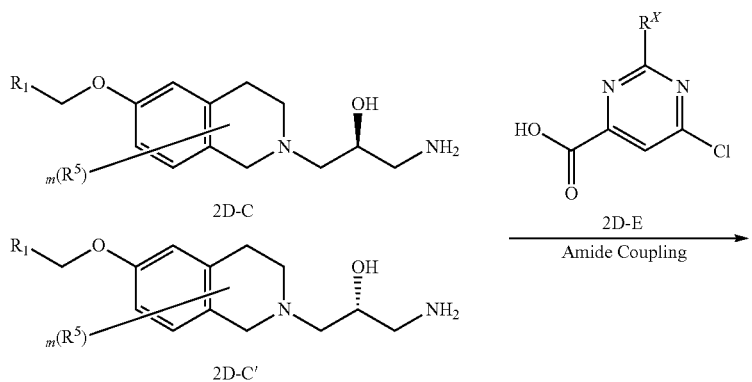
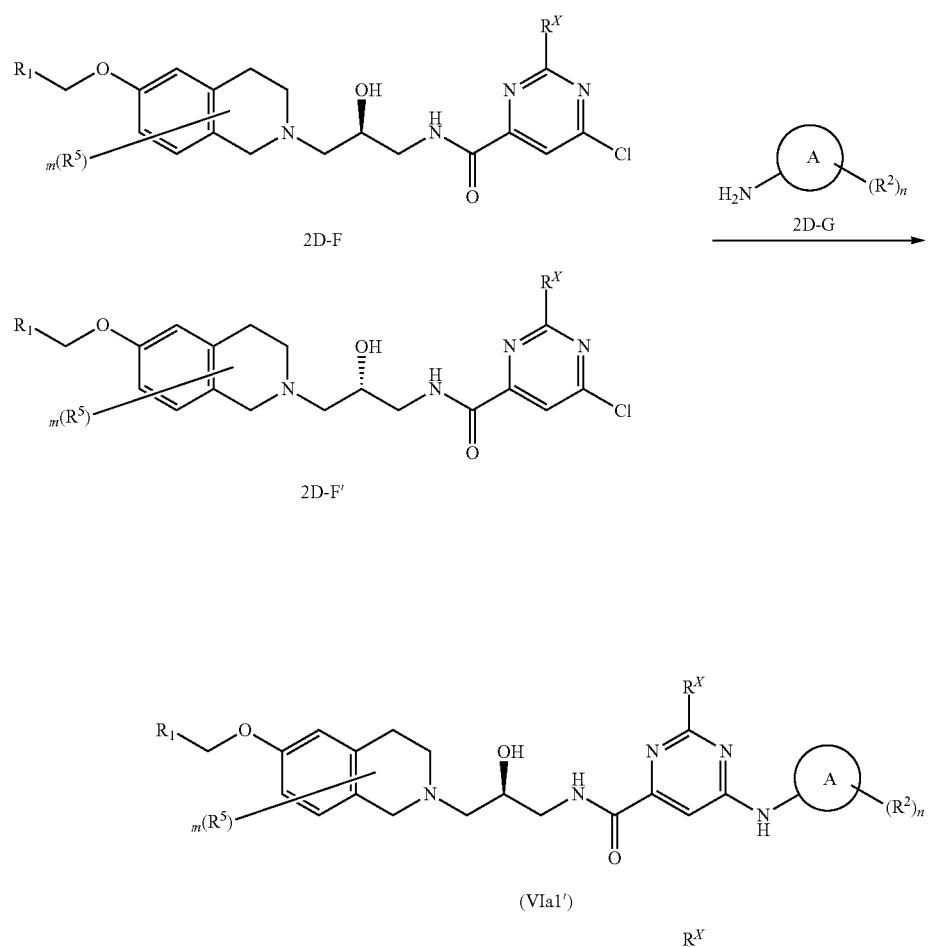
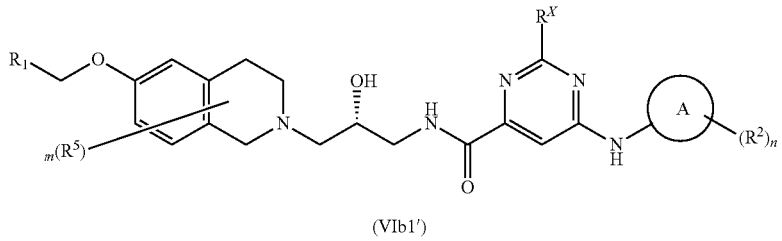

General Procedure 2D-A

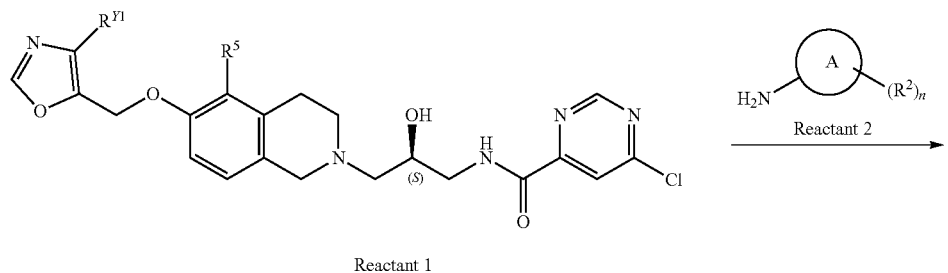

Reactant 1

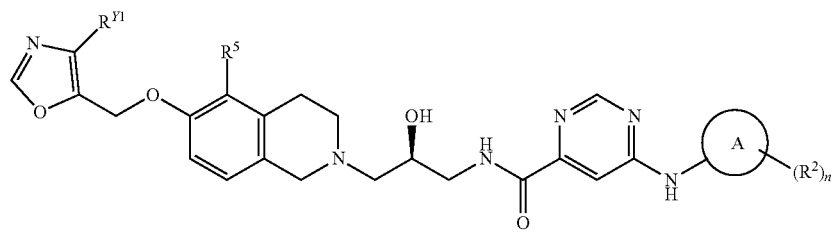

wherein $R^{Y1}$ is H or Me, and $R^5$ is defined herein.

Reactant 1 (1.5 equiv) was added to a solution of Reactant 2 (1.0 equiv) in acetonitrile (5.0 mL). The resulting mixture was stirred for 5 min followed by the addition of TEA (5.0 equiv). The reaction mixture was stirred at 25° C. for 12 h. After the completion of the reaction, the resulting mixture was evaporated in vacuo and the obtained crude product 0.2 g was purified by preparative RP-HPLC with 55-80% 0-9.5 min water-methanol, flow 30 mL/min (loading pump 4 mL/min methanol) as mobile phase to afford products. For Compound 632, Compound 630, Compound 626 corresponding crude mixtures, without any purification were treated with TFA, and then with Ac₂O/TEA. Ac-derivatives were formed clearly which were purified by HPFC to get products Example 2D1. N-[(2S)-2-hydroxy-3-{5-methyl-6-[(1,3-oxazol-5-yl)methoxy]-1,2,3,4-tetrahydroisoquinolin-2-yl}propyl]-6-{[1-(2-methoxyacetyl)azetidin-3-yl]amino}pyrimidine-4-carboxamide (Compound 518)

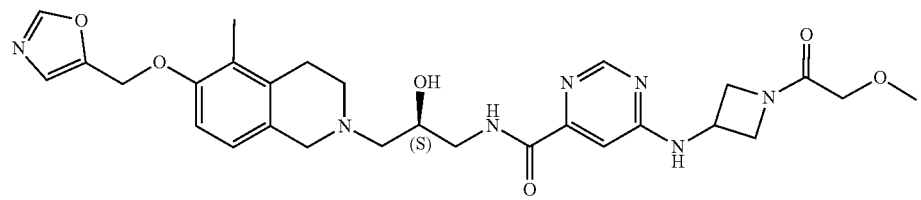

Prepared by general procedure 2D-A. Yield: 6.4 mg (9.85%). ¹H NMR (Chloroform-d, 500 MHz): δ (ppm) 2.11 (s, 3H), 2.68 (m, 2H), 2.71 (m, 4H), 2.84 (m, 1H), 3.07 (s, 3H), 3.40 (m, 1H), 3.49 (m, 2H), 3.68 (m, 1H), 3.72 (s, 3H), 4.16 (m, 2H), 4.50 (m, 1H), 4.68 (m, 1H), 4.72 (m, 1H), 5.06 (s, 2H), 5.95 (m, 1H), 6.81 (d, 1H), 6.86 (d, 1H), 7.14 (s, 1H), 7.21 (s, 1H), 7.92 (s, 1H), 8.48 (t, 1H), 8.55 (s, 1H). LCMS(ESI): [M+H]⁺ m/z: calcd 565.2. found 566.4; Rt=0.91 min.

Example 2D2. N-[(2S)-2-hydroxy-3-{5-methyl-6-[(1,3-oxazol-5-yl)methoxy]-1,2,3,4-tetrahydroisoquinolin-2-yl}propyl]-6-{((1r,4r)-4-(piperidine-1-carbonyl)cyclohexyl]amino}pyrimidine-4-carboxamide (Compound 589)

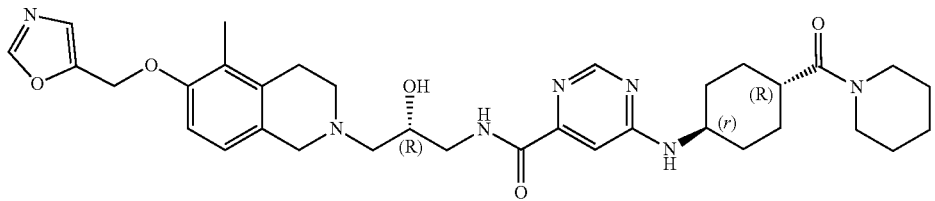

Prepared by general procedure 2D-A. Yield: 3.9 mg (6.0%). ¹H NMR (Chloroform-d, 500 MHz): δ (ppm) 1.26 (m, 2H), 1.53 (m, 4H), 1.65 (m, 5H), 1.75 (m, 2H), 1.84 (m, 2H), 2.10 (s, 3H), 2.21 (m, 2H), 2.50 (m, 1H), 2.62 (m, 2H), 2.78 (m, 3H), 2.99 (m, 1H), 3.44 (m, 3H), 3.56 (m, 2H), 3.68 (m, 2H), 3.83 (m, 1H), 4.05 (m, 1H), 5.05 (s, 2H), 6.79 (d, 1H), 6.85 (d, 1H), 7.11 (m, 1H), 7.13 (s, 1H), 7.91 (s, 1H), 8.40 (t, 1H), 8.50 (s, 1H). LCMS(ESI): [M+H]⁺ m/z: calcd 631.3. found 632.4; Rt=1.03 min.

Example 2D3. N-[(2S)-2-hydroxy-3-{5-methyl-6-[(1,3-oxazol-5-yl)methoxy]-1,2,3,4-tetrahydroisoquinolin-2-yl}propyl]-6-{[(1s,4s)-4-methoxycyclohexyl]amino}pyrimidine-4-carboxamide (Compound 541)

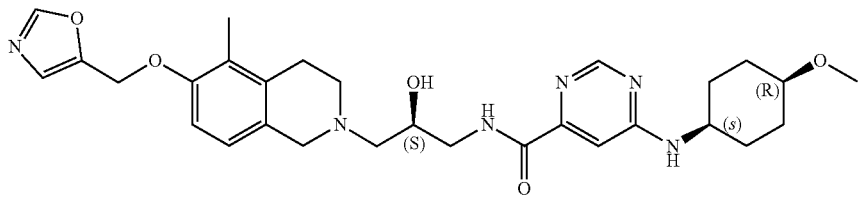

Prepared by general procedure 2D-A. Yield: 10.6 mg (16.3%). ¹H NMR (Chloroform-d, 500 MHz): δ (ppm) 1.58 (m, 8H), 1.65 (m, 2H), 1.81 (m, 2H), 2.10 (s, 3H), 2.69 (m, 1H), 2.83 (m, 3H), 3.05 (m, 1H), 3.41 (m, 4H), 3.43 (m, 1H), 3.48 (m, 2H), 3.51 (m, 2H), 5.05 (s, 2H), 6.80 (d, 1H), 6.85 (d, 1H), 7.09 (s, 1H), 7.13 (s, 1H), 7.91 (s, 1H), 8.40 (m, 1H), 8.49 (s, 1H). LCMS(ESI): [M+H]⁺ m/z: calcd 550.3. found 551.0; Rt=0.96 min.

Example 2D4. N-[(2S)-2-hydroxy-3-{5-methyl-6-[(1,3-oxazol-5-yl)methoxy]-1,2,3,4-tetrahydroisoquinolin-2-yl}propyl]-6-{[(1r,4r)-4-methoxycyclohexyl]amino}pyrimidine-4-carboxamide (Compound 572)

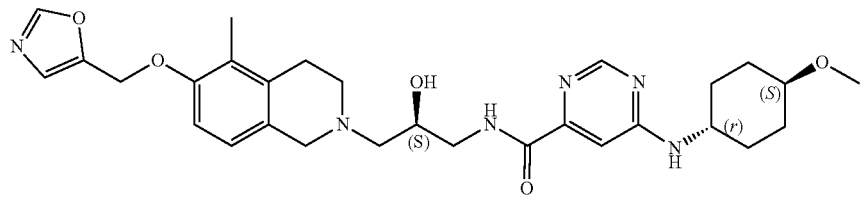

Prepared by general procedure 2D-A. Yield: 9.4 mg (14.46%). $^1$H NMR (Chloroform-d, 500 MHz): δ (ppm) 1.28 (m, 2H), 1.42 (q, 2H), 1.52 (s, 2H), 2.10 (s, 3H), 2.15 (d, 3H), 2.59 (m, 2H), 2.77 (m, 4H), 2.98 (m, 1H), 3.21 (t, 1H), 3.38 (s, 3H), 3.47 (m, 1H), 3.59 (m, 1H), 3.69 (m, 1H), 3.80 (m, 1H), 4.05 (m, 2H), 5.05 (s, 2H), 6.80 (d, 1H), 6.85 (d, 1H), 7.12 (s, 1H), 7.14 (s, 1H), 7.91 (s, 1H), 8.41 (t, 1H), 8.50 (s, 1H). LCMS(ESI): [M+H]$^+$ m/z: calcd 550.6. found 551.2; Rt=0.95 min.

Example 2D5. N-[(2S)-2-hydroxy-3-{5-methyl-6-[(1,3-oxazol-5-yl)methoxy]-1,2,3,4-tetrahydroisoquinolin-2-yl}propyl]-6-{[(1r,4r)-4-(N-methylacetamido)cyclohexyl]amino}pyrimidine-4-carboxamide (Compound 605)

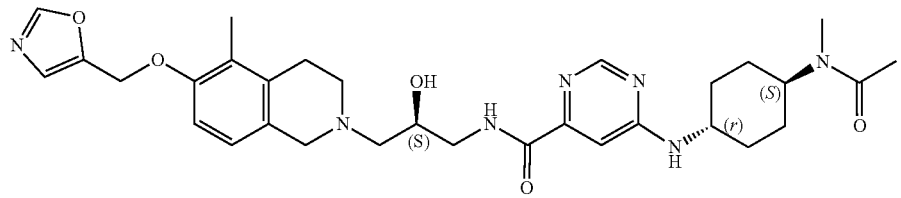

Prepared by general procedure 2D-A. Yield: 7.7 mg (11.84%). $^1$H NMR, δ 1.40 (m, 1H), 1.58 (m, 1H), 1.73 (m, 2H), 2.06 (s, 4H), 2.08 (s, 2H), 2.11 (s, 2H), 2.17 (m, 1H), 2.55 (d, 2H), 2.74 (m, 3H), 2.80 (s, 1H), 2.84 (s, 2H), 2.92 (m, 1H), 3.46 (m, 2H), 3.55 (m, 3H), 3.76 (m, 1H), 4.01 (m, 2H), 4.52 (t, 1H), 5.02 (s, 2H), 5.37 (d, 1H), 6.76 (d, 1H), 6.81 (d, 1H), 7.11 (m, 2H), 7.88 (s, 1H), 8.40 (s, 1H), 8.46 (d, 1H). LCMS(ESI): [M+H]$^+$ m/z: calcd 591.3. found 592.3; Rt=0.85 min.

Example 2D6. N-[(2S)-2-hydroxy-3-{5-methyl-6-[(1,3-oxazol-5-yl)methoxy]-1,2,3,4-tetrahydroisoquinolin-2-yl}propyl]-6-{[1-[(methylcarbamoyl)methyl]piperidin-4-yl}amino)pyrimidine-4-carboxamide (Compound 524)

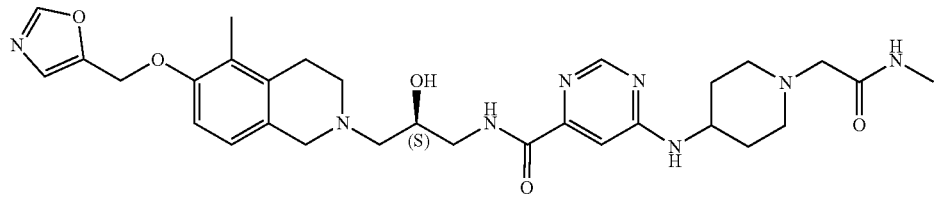

Prepared by general procedure 2D-A. Yield: 11.8 mg (18.15%). ¹H NMR (Chloroform-d, 500 MHz): δ (ppm) 2.01 (m, 5H), 2.39 (m, 2H), 2.65 (m, 2H), 2.83 (m, 4H), 2.87 (m, 5H), 3.04 (s, 3H), 3.45 (m, 1H), 3.70 (m, 3H), 3.88 (m, 2H), 4.11 (m, 1H), 5.05 (s, 2H), 6.80 (d, 1H), 6.85 (d, 1H), 7.12 (m, 3H), 7.91 (s, 1H), 8.41 (t, 1H), 8.51 (s, 1H). LCMS(ESI): [M+H]⁺ m/z: calcd 592.3. found 593.2; Rt=0.75 min.

Example 2D7. N-[(2S)-2-hydroxy-3-{5-methyl-6-[(1,3-oxazol-5-yl)methoxy]-1,2,3,4-tetrahydroisoquinolin-2-yl}propyl]-6-[f(1r,3r)-3-(piperidine-1-carbonyl)cyclobutyl]amino}pyrimidine-4-carboxamide (Compound 526)

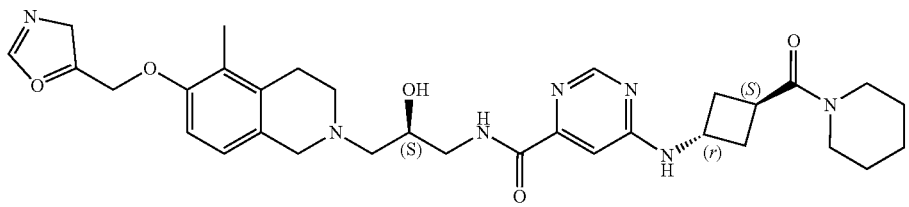

Prepared by general procedure 2D-A. Yield: 9.6 mg (14.76%). ¹H NMR (Chloroform-d, 500 MHz): δ (ppm) 1.56 (m, 2H), 1.82 (m, 4H), 2.12 (m, 6H), 2.51 (m, 2H), 2.65 (m, 4H), 3.02 (m, 1H), 3.22 (m, 3H), 3.61 (m, 6H), 4.10 (m, 4H), 5.05 (s, 2H), 5.42 (m, 1H), 6.73 (d, 1H), 6.78 (d, 1H), 7.12 (s, 1H), 7.83 (s, 1H), 8.32 (t, 1H), 8.52 (s, 1H). LCMS(ESI): [M+H]⁺ m/z: calcd 603.1. found 604.2; Rt=0.92 min.

Example 2D8. N-[(2S)-2-hydroxy-3-{5-methyl-6-[(1,3-oxazol-5-yl)methoxy]-1,2,3,4-tetrahydroisoquinolin-2-yl}propyl]-6-{[(1r,3r)-3-(azetidine-1-carbonyl)cyclobutyl]amino}pyrimidine-4-carboxamide (Compound 519)

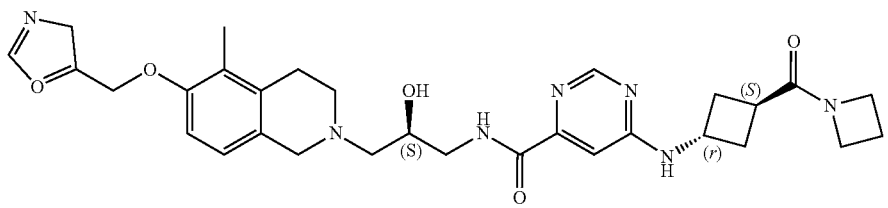

Prepared by general procedure 2D-A. Yield: 6.0 mg (9.23%). ¹H NMR (Chloroform-d, 500 MHz): δ (ppm) 2.03 (m, 3H), 2.12 (m, 2H), 2.26 (m, 2H), 2.60 (m, 2H), 2.76 (m, 5H), 3.01 (m, 2H), 3.46 (m, 5H), 4.12 (m, 5H), 4.41 (m, 1H), 5.06 (s, 2H), 5.42 (m, 1H), 6.71 (d, 1H), 6.79 (d, 1H), 7.03 (s, 1H), 7.21 (s, 1H), 7.81 (s, 1H), 8.43 (t, 1H), 8.52 (s, 1H). LCMS(ESI): [M+H]⁺ m/z: calcd 575.3. found 576.0; Rt=0.88 min.

Example 2D8. N-[(2S)-2-hydroxy-3-{5-methyl-6-[(1,3-oxazol-5-yl)methoxy]-1,2,3,4-tetrahydroisoquinolin-2-yl}propyl]-6-{[1-(3-methylbutanoyl)azetidin-3-yl]amino}pyrimidine-4-carboxamide (Compound 565)

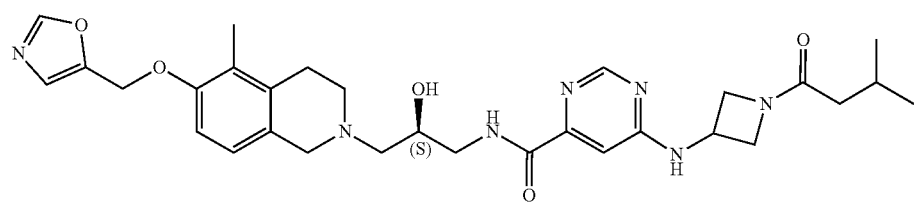

Prepared by general procedure 2D-A. Yield: 9.0 mg (13.84%). ¹H NMR (Chloroform-d, 500 MHz): δ (ppm) 0.97 (m, 6H), 2.00 (s, 2H), 2.11 (s, 3H), 2.15 (m, 1H), 2.69 (m, 2H), 2.84 (m, 3H), 3.05 (m, 1H), 3.49 (m, 2H), 3.70 (m, 2H), 3.87 (m, 1H), 3.99 (m, 2H), 4.14 (m, 1H), 4.43 (m, 1H), 4.55 (m, 1H), 4.75 (m, 1H), 5.06 (s, 2H), 5.99 (s, 1H), 6.81 (d, 1H), 6.86 (d, 1H), 7.14 (s, 1H), 7.22 (s, 1H), 7.92 (s, 1H), 8.49 (t, 1H), 8.54 (s, 1H). LCMS(ESI): [M+H]⁺ m/z: calcd 577.3. found 578.4; Rt=1.03 min.

Example 2D9. 6-[(1-cyclobutanecarbonylazetidin-3-yl)amino]-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 585)

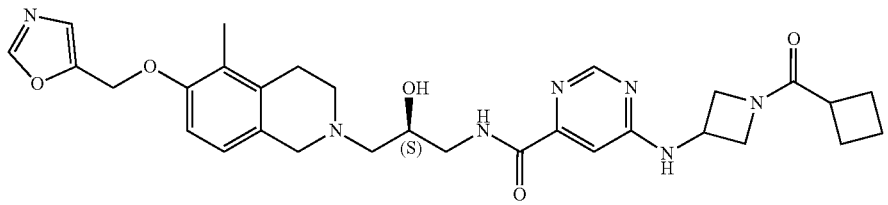

Prepared by general procedure 2D-A. Yield: 2.9 mg (4.46%). ¹H NMR (DMSO-d6, 500 MHz): δ (ppm) 1.83 (m, 1H), 1.94 (m, 1H), 2.05 (s, 5H), 2.18 (m, 2H), 2.41 (m, 1H), 2.75 (m, 4H), 2.97 (s, 4H), 3.33 (m, 1H), 3.45 (m, 1H), 3.59 (m, 2H), 3.77 (m, 1H), 3.86 (m, 2H), 4.17 (m, 1H), 4.35 (m, 1H), 4.68 (m, 1H), 5.06 (s, 2H), 6.81 (m, 2H), 7.09 (m, 1H), 7.14 (s, 1H), 8.15 (s, 1H), 8.24 (m, 2H), 8.61 (t, 1H). LCMS(ESI): [M+H]⁺ m/z: calcd 575.3. found 576.4; Rt=0.94 min.

Example 2D10. N-[(2S)-2-hydroxy-3-{5-methyl-6-[(1,3-oxazol-5-yl)methoxy]-1,2,3,4-tetrahydroisoquinolin-2-yl}propyl]-6-[(1-propanoylazetidin-3-yl)amino]pyrimidine-4-carboxamide (Compound 567)

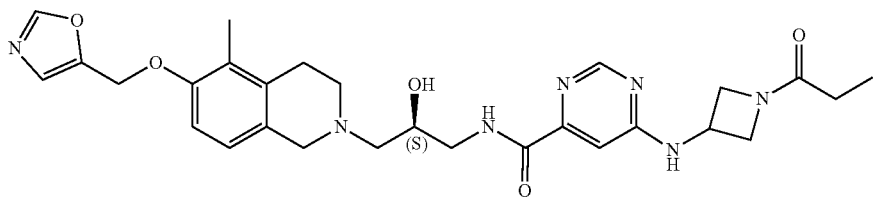

Prepared by general procedure 2D-A. Yield: 5.6 mg (8.61%). ¹H NMR (Chloroform-d, 500 MHz): δ (ppm) 1.14 (t, 3H), 2.11 (s, 3H), 2.15 (q, 2H), 2.71 (m, 2H), 2.86 (m, 4H), 3.06 (m, 1H), 3.49 (m, 2H), 3.70 (m, 2H), 3.90 (m, 1H), 3.99 (m, 2H), 4.15 (m, 1H), 4.43 (m, 1H), 4.54 (m, 1H), 4.77 (s, 1H), 5.06 (s, 2H), 6.81 (d, 1H), 6.86 (d, 1H), 7.14 (s, 1H), 7.22 (s, 1H), 7.92 (s, 1H), 8.50 (t, 1H), 8.54 (s, 1H). LCMS(ESI): [M+H]⁺ m/z: calcd 549.2. found 550.2; Rt=0.95 min.

Example 2D11. 6-[(1-acetylazetidin-3-yl)amino]-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 543)

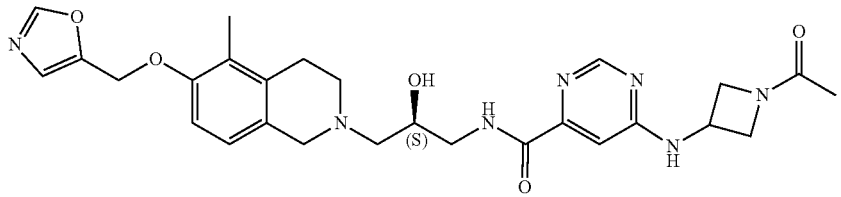

Prepared by general procedure 2D-A. Yield: 9.7 mg (14.92%). $^1$H NMR (Chloroform-d, 500 MHz): 1.92 (s, 3H), 2.11 (s, 3H), 2.72 (m, 2H), 2.86 (m, 3H), 3.08 (m, 1H), 3.47 (m, 2H), 3.70 (m, 2H), 3.97 (m, 2H), 4.02 (m, 1H), 4.16 (m, 1H), 4.43 (m, 1H), 4.46 (m, 1H), 4.57 (m, 1H), 5.06 (s, 2H), 5.97 (m, 1H), 6.81 (d, 1H), 6.86 (d, 1H), 7.14 (s, 1H), 7.22 (s, 1H), 7.92 (s, 1H), 8.49 (t, 1H), 8.55 (s, 1H). LCMS(ESI): [M+H]$^+$ m/z: calcd 535.4. found 536.0; Rt=0.84 min.

Example 2D12. 6-{[1-(2,2-dimethylpropanoyl)piperidin-4-yl]amino}-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 523)

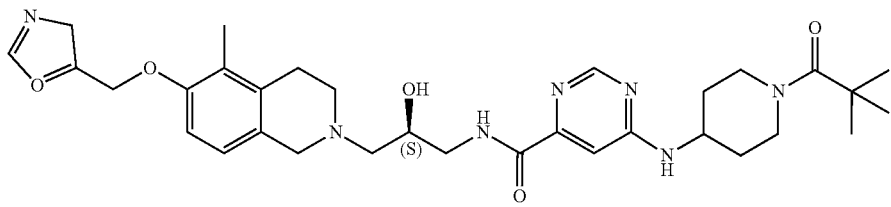

Prepared by general procedure 2D-A. Yield: 8.1 mg (12.46%). $^1$H NMR (Chloroform-d, 500 MHz): 1.31 (m, 9H), 1.45 (m, 2H), 2.11 (s, 3H), 2.14 (m, 1H), 2.69 (m, 2H), 2.86 (m, 3H), 3.03 (m, 3H), 3.49 (m, 2H), 3.69 (m, 2H), 3.91 (m, 2H), 4.11 (m, 2H), 4.39 (m, 2H), 5.06 (s, 2H), 6.82 (d, 1H), 6.85 (d, 1H), 7.14 (s, 2H), 7.92 (s, 1H), 8.43 (t, 1H), 8.53 (s, 1H).

Example 2D13. N-[(2S)-2-hydroxy-3-{5-methyl-6-[(1,3-oxazol-5-yl)methoxy]-1,2,3,4-tetrahydroisoquinolin-2-yl}propyl-6-{[1-(3-methylbutanoyl)piperidin-4-yl]amino}pyrimidine-4-carboxamide (Compound 528)

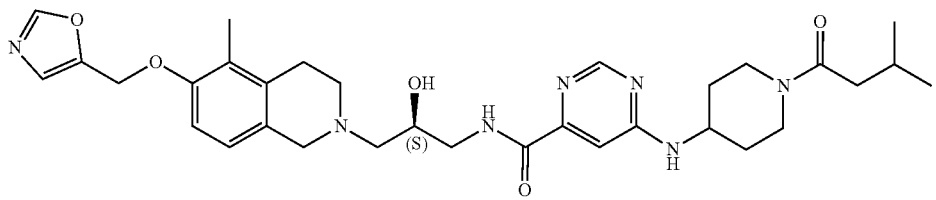

Prepared by general procedure 2D-A. Yield: 11.0 mg (16.92%). ¹H NMR (Chloroform-d, 500 MHz): 0.99 (m, 7H), 1.42 (m, 3H), 2.08 (m, 6H), 2.25 (m, 2H), 2.67 (m, 2H), 2.85 (m, 4H), 3.07 (m, 1H), 3.22 (m, 1H), 3.48 (m, 1H), 3.71 (m, 2H), 3.91 (m, 2H), 4.13 (m, 1H), 4.61 (m, 1H), 5.06 (s, 2H), 6.82 (d, 1H), 6.85 (d, 1H), 7.14 (s, 2H), 7.92 (s, 1H), 8.43 (t, 1H), 8.54 (s, 1H). LCMS(ESI): [M+H]⁺ m/z: calcd 605.3. found 606.2; Rt=1.00 min.

Example 2D14. 6-[(1-cyclobutanecarbonylpiperidin-4-yl)amino]-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 536)

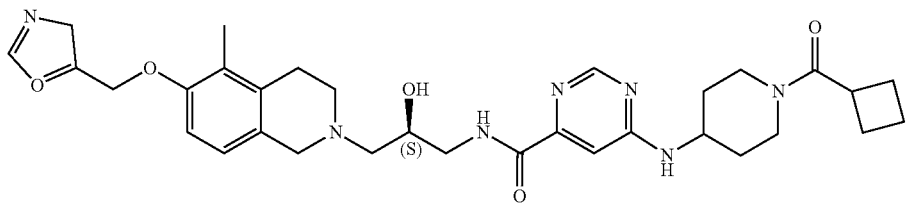

Prepared by general procedure 2D-A. Yield: 11.1 mg (17.07%). ¹H NMR (Chloroform-d, 500 MHz): 1.38 (m, 3H), 1.88 (m, 1H), 1.97 (m, 1H), 1.99 (m, 2H), 2.16 (m, 3H), 2.36 (m, 3H), 2.37 (m, 2H), 2.65 (m, 2H), 2.83 (m, 4H), 3.10 (m, 1H), 3.13 (m, 1H), 3.28 (t, 1H), 3.47 (m, 1H), 3.72 (m, 3H), 3.85 (m, 1H), 4.10 (m, 1H), 4.56 (m, 1H), 5.06 (s, 3H), 6.81 (d, 1H), 6.86 (d, 1H), 7.14 (s, 2H), 7.91 (s, 1H), 8.42 (t, 1H), 8.52 (s, 1H). LCMS(ESI): [M+H]⁺ m/z: calcd 603.1. found 604.2; Rt=0.98 min.

Example 2D15. N-[(2S)-2-hydroxy-3-{5-methyl-6-[(1,3-oxazol-5-yl)methoxy]-1,2,3,4-tetrahydroisoquinolin-2-yl}propyl]-6-{[1-(2-methylpropanoyl)piperidin-4-yl]amino}pyrimidine-4-carboxamide (Compound 520)

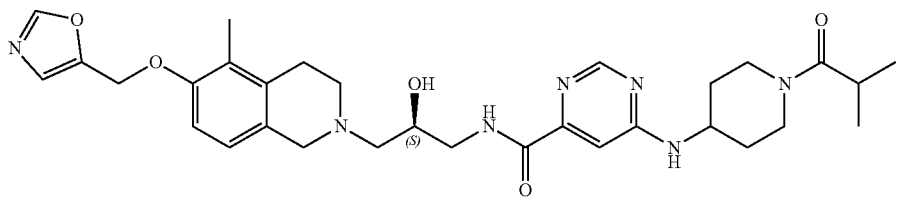

Prepared by general procedure 2D-A. Yield: 8.1 mg (12.46%). ¹H NMR (Chloroform-d, 500 MHz): 1.15 (m, 6H), 1.42 (m, 3H), 2.05 (m, 5H), 2.16 (m, 1H), 2.65 (m, 2H), 2.82 (m, 5H), 3.02 (m, 1H), 3.21 (m, 1H), 3.46 (m, 1H), 3.68 (m, 2H), 3.86 (m, 1H), 3.95 (m, 1H), 4.10 (m, 1H), 4.60 (m, 1H), 5.05 (s, 3H), 6.80 (d, 1H), 6.85 (d, 1H), 7.13 (s, 2H), 7.91 (s, 1H), 8.42 (t, 1H), 8.52 (s, 1H). LCMS(ESI): [M+H]⁺ m/z: calcd 591.4. found 592.3; Rt=0.94 min.

Example 2D16. 6-[(1-butanoylpiperidin-4-yl)amino]-N-[(2S)-2-hydroxy-3-{5-methyl-6-[(1,3-oxazol-5-yl)methoxy]-1,2,3,4-tetrahydroisoquinolin-2-yl}propyl]pyrimidine-4-carboxamide (Compound 560)

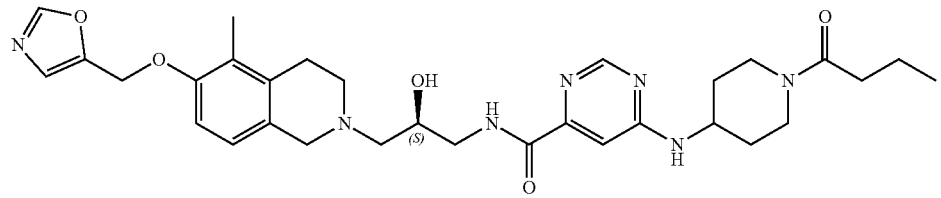

Prepared by general procedure 2D-A. Yield: 7.5 mg (11.53%). ¹H NMR (Chloroform-d, 500 MHz): 0.98 (t, 3H), 1.42 (q, 2H), 1.68 (m, 2H), 2.06 (m, 1H), 2.10 (s, 3H), 2.14 (m, 1H), 2.33 (m, 2H), 2.65 (m, 2H), 2.79 (m, 4H), 2.85 (m, 1H), 3.18 (m, 1H), 3.23 (m 1H), 3.45 (m, 1H), 3.49 (m, 2H), 3.68 (m, 2H), 3.88 (m, 1H), 4.58 (m, 1H), 5.05 (s, 3H), 96.80 (d, 2H), 6.85 (d, 1H), 7.13 (s, 2H), 7.91 (s, 1H), 8.42 (m, 1H), 8.52 (s, 1H). LCMS(ESI): [M+H]⁺ m/z: calcd 591.2. found 592.2; Rt=0.95 min.

Example 2D17. N-[(2S)-2-hydroxy-3-{6-[(4-methyl-1,3-oxazol-5-yl)methoxy]-1,2,3,4-tetrahydroisoquinolin-2-yl}propyl]-6-[(1-methyl-2-oxopiperidin-4-yl)amino]pyrimidine-4-carboxamide (Compound 613)

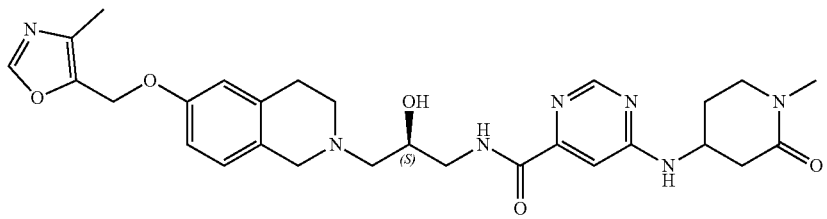

Prepared by general procedure 2D-A. Yield: 5.3 mg (7.07%). ¹H NMR (500 MHz, cdcl₃) δ 1.94 (m, 1H), 2.25 (m, 4H), 2.38 (m, 1H), 2.57 (m, 2H), 2.72 (m, 1H), 2.90 (m, 4H), 3.00 (s, 3H), 3.42 (m, 4H), 3.57 (m, 1H), 3.71 (m, 1H), 3.78 (m, 1H), 4.03 (m, 1H), 4.34 (m, 1H), 4.99 (s, 2H), 5.13 (m, 1H), 6.73 (s, 1H), 6.77 (d, 1H), 6.95 (d, 1H), 7.18 (s, 1H), 7.82 (s, 1H), 8.42 (m, 1H), 8.54 (m, 1H). LCMS(ESI): [M+H]⁺ m/z: calcd 549.2. found 550.2; Rt=0.95 min.

Example 2D18. 6-({2-acetyl-2-azabicyclo[2.2.1]heptan-5-yl}amino)-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 632)

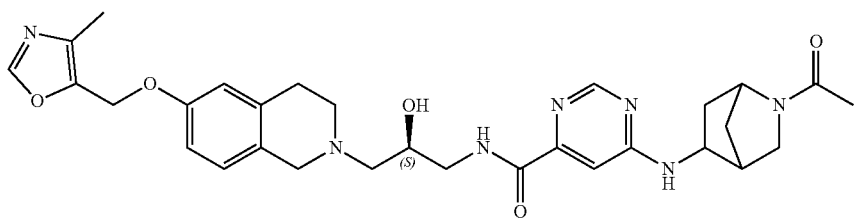

Prepared by general procedure 2D-A. Yield: 7.9 mg (15.8%). ¹H NMR (500 MHz, cdcl3) δ 1.92 (s, 3H), 2.00 (m, 6H), 2.11 (m, 2H), 2.24 (s, 3H), 2.81 (m, 2H), 3.02 (m, 3H), 3.13 (m, 1H), 3.49 (m, 1H), 3.70 (m, 1H), 3.84 (m, 1H), 4.03 (m, 1H), 4.20 (m, 1H), 4.40 (m, 1H), 4.50 (m, 1H), 5.00 (s, 2H), 5.16 (m, 1H), 6.75 (s, 1H), 6.83 (d, 1H), 6.98 (d, 1H), 7.22 (s, 1H), 7.83 (s, 1H), 8.46 (m, 1H), 8.56 (s, 1H). LCMS(ESI): [M+H]⁺ m/z: calcd 575.3. found 576.2; Rt=0.91 min.

Example 2D19. 6-{[(1R,3R,5S)-8-acetyl-8-azabicyclo[3.2.1]octan-3-yl]amino}-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 630)

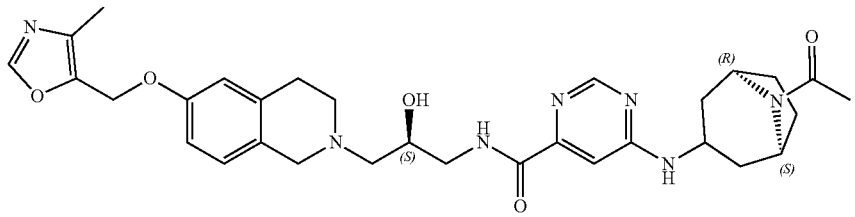

Prepared by general procedure 2D-A. Yield: 15.7 mg (31.4%). $^1$H NMR (Chloroform-d, 400 MHz): δ (ppm) 1.80 (d, 1H), 1.97 (m, 4H), 2.06 (s, 3H), 2.14 (m, 2H), 2.20 (s, 3H), 2.36 (m, 1H), 2.54 (m, 2H), 2.68 (m, 1H), 2.87 (m, 4H), 3.43 (m, 1H), 3.53 (d, 1H), 3.66 (dd, 1H), 3.76 (d, 1H), 4.00 (m, 1H), 4.14 (m, 2H), 4.73 (m, 1H), 4.95 (s, 2H), 5.67 (d, 1H), 6.69 (s, 1H), 6.73 (d, 1H), 6.91 (d, 1H), 7.12 (s, 1H), 7.79 (s, 1H), 8.41 (t, 1H), 8.49 (s, 1H). LCMS(ESI): [M+H]$^+$ m/z: calcd 589.2. found 590.1; Rt=0.83 min.

Example 2D20. 6-{[(2RS,4SR)-1-acetyl-2-methylpiperidin-4-yl]amino}-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 626)

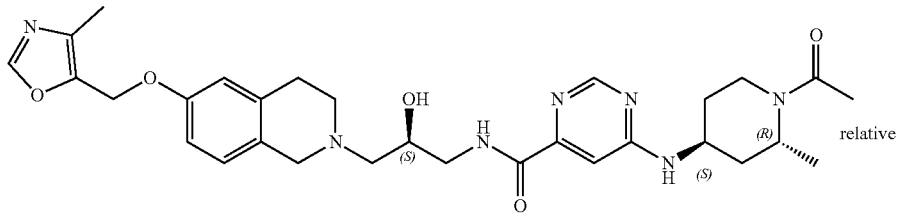

relative

Prepared by general procedure 2D-A and obtained as racemate around piperidine. Yield: 15.7 mg (31.4%). $^1$H NMR (Chloroform-d, 400 MHz): δ (ppm) 1.29 (m, 4H), 1.59 (m, 1H), 1.94 (dd, 1H), 2.09 (d, 3H), 2.20 (s, 3H), 2.56 (m, 2H), 2.69 (m, 1H), 2.86 (m, 4H), 3.42 (m, 2H), 3.54 (d, 1H), 3.65 (m, 2H), 3.75 (d, 1H), 4.01 (m, 1H), 4.38 (m, 2H), 4.96 (s, 3H), 5.39 (m, 1H), 6.69 (s, 1H), 6.74 (dd, 1H), 6.91 (d, 1H), 7.13 (s, 1H), 7.79 (s, 1H), 8.43 (t, 1H), 8.47 (s, 1H). LCMS(ESI): [M+H]$^+$ m/z: calcd 577.3. found 490.2; Rt=0.83 min.

Example 2D21, 6-{[1-(2,2-dimethylpropanoyl)piperidin-4-yl]amino}-N-[(2S)-2-hydroxy-3-{6-[(4-methyl-1,3-oxazol-5-yl)methoxy]-1,2,3,4-tetrahydroisoquinolin-2-yl}propyl]pyrimidine-4-carboxamide (Compound 616)

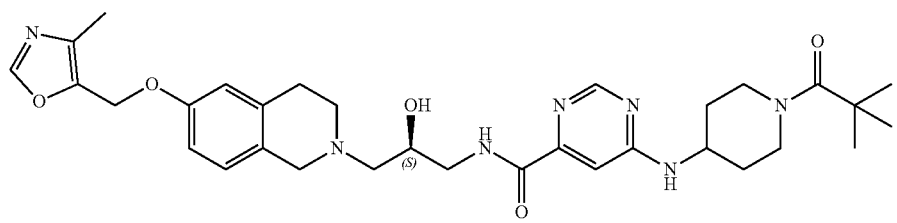

Prepared by general procedure 2D-A. Yield: 5.7 mg (7.6%). ¹H NMR (500 MHz, CDCl₃) δ 1.26 (m, 3H), 1.30 (m, 9H), 1.44 (m, 2H), 2.12 (m, 2H), 2.25 (m, 3H), 2.70 (m, 2H), 2.95 (m, 2H), 3.03 (m, 3H), 3.48 (m, 1H), 3.70 (m, 2H), 3.91 (m, 1H), 4.11 (m, 1H), 4.41 (m, 2H), 5.00 (s, 2H), 5.15 (m, 1H), 6.74 (s, 1H), 6.80 (d, 1H), 6.96 (d, 1H), 7.13 (s, 1H), 7.83 (m, 1H), 8.43 (m, 1H), 8.53 (m, 1H). LCMS(ESI): [M+H]⁺ m/z: calcd 605.3. found 606.4; Rt=1.09 min.

Example 2D22. 6-{[(1R,5S,6R)-3-acetyl-3-azabicyclo[3.1.0]hexan-6-yl]amino}-N-[(2S)-2-hydroxy-3-[6-[(4-methyl-1,3-oxazol-5-yl)methoxy]-1,2,3,4-tetrahydroisoquinolin-2-yl]propyl]pyrimidine-4-carboxamide (Compound 620)

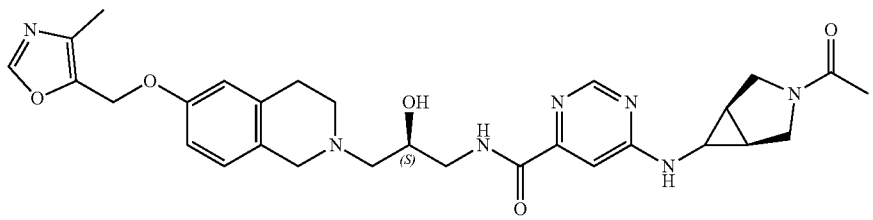

Prepared by general procedure 2D-A. Yield: 2.5 mg (5.0%). ¹H NMR (500 MHz, cdcl3) δ 1.92 (m, 2H), 1.98 (s, 3H), 2.24 (s, 3H), 2.63 (m, 2H), 2.77 (m, 1H), 2.93 (m, 4H), 3.49 (m, 1H), 3.62 (m, 3H), 3.69 (m, 2H), 3.81 (m, 2H), 4.10 (m, 2H), 4.99 (s, 2H), 5.59 (s, 1H), 6.73 (s, 1H), 6.78 (d, 1H), 6.95 (d, 1H), 7.10 (s, 1H), 7.82 (s, 1H), 8.43 (m, 1H), 8.54 (s, 1H). LCMS(ESI): [M+H]⁺ m/z: calcd 561.2. found 562.2; Rt=0.83 min.

Example 2D23. (S)-6-((1-acetylazetidin-3-yl)amino)-N-(2-hydroxy-3-(6-(oxazol-5-ylmethoxy)-3,4-dihydroisoquinolin-2(1H)-yl)propyl)pyrimidine-4-carboxamide (Compound 562)

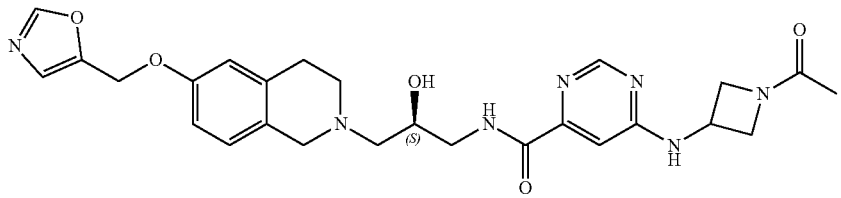

Prepared by general procedure 2D-A. Yield: 3.9 mg (6.0%). ¹H NMR (Chloroform-d, 500 MHz): δ (ppm) 1.91 (s, 3H), 2.68 (m, 2H), 2.83 (m, 1H), 2.98 (m, 3H), 3.49 (m, 2H), 3.68 (m, 2H), 3.86 (m, 1H), 3.99 (m, 2H), 4.11 (m, 1H), 4.44 (m, 1H), 4.56 (m, 1H), 4.77 (m, 1H), 5.06 (s, 2H), 6.00 (s, 1H), 6.74 (s, 1H), 6.79 (d, 1H), 6.96 (d, 1H), 7.16 (s, 1H), 7.23 (s, 1H), 7.92 (s, 1H), 8.50 (t, 1H), 8.54 (s, 1H). LCMS(ESI): [M+H]⁺ m/z: calcd 521.3. found 522.2; Rt=0.80 min.

Example 2D24. (S)-6-((1-acetylpiperidin-4-yl)amino)-N-(3-(5-chloro-6-((4-methyloxazol-5-yl)methoxy)-3,4-dihydroisoquinolin-2(1H)-yl)-2-hydroxypropyl)pyrimidine-4-carboxamide Compound 256

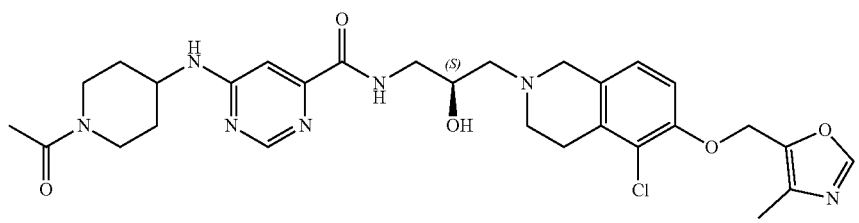

(2S)-1-Amino-3-[5-chloro-6-[(4-methyloxazol-5-yl)methoxy]-3,4-dihydro-1H-isoquinolin-2-yl]propan-2-ol (0.3 g, 650.46 umol, 3HCl) and 6-[(1-acetyl-4-piperidyl)amino]pyrimidine-4-carboxylic acid (171.90 mg, 650.46 umol) were mixed in DMF (10 mL). The reaction suspension was cooled to 0° C. and HATU (272.06 mg, 715.51 umol) followed by triethylamine (329.10 mg, 3.25 mmol, 453.31 uL) were added and stirred at ambient temperature for 12 hr. Then, the reaction mixture was concentrated in vacuo and the obtained crude product 0.88 g was purified by preparative RP-HPLC with H$_2$O—CH$_3$CN as mobile phase to afford product 6-[(1-acetyl-4-piperidyl)amino]-N-[(2S)-3-[5-chloro-6-[(4-methyloxazol-5-yl)methoxy]-3,4-dihydro-1H-isoquinolin-2-yl]-2-hydroxy-propyl]pyrimidine-4-carboxamide (76.90 mg, 128.58 umol, 19.77% yield). NMR (CDCl$_3$, 500 MHz) 1.45 (m, 2H), 2.00 (d, 1H), 2.07 (s, 3H), 2.11 (m, 1H), 2.17 (s, 3H), 2.58 (d, 2H), 2.76 (m, 2H), 2.85 (m, 4H), 3.20 (m, 1H), 3.47 (m, 1H), 3.58 (m, 2H), 3.75 (m, 2H), 4.02 (m, 1H), 4.12 (s, 1H), 4.51 (d, 1H), 5.03 (s, 2H), 6.08 (s, 1H), 6.81 (d, 1H), 6.84 (d, 1H), 7.13 (s, 1H), 7.78 (s, 1H), 8.41 (s, 1H), 8.49 (m, 1H). LCMS(ESI): [M+H]$^+$ m/z: calcd 598.2. found 598.2; Rt=0.93 min.

Example 3-Synthesis of Compounds of Formula (IVa and IVb)

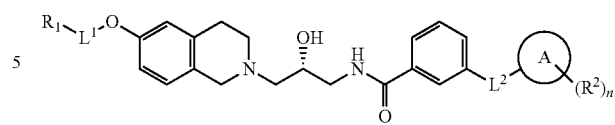
(IVa)

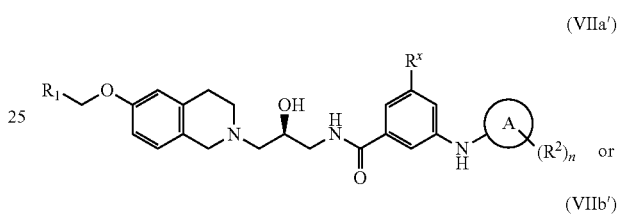
(IVb)

wherein, L$^1$ is a bond or C$_1$-C$_4$-alkylene; R$^1$ is a 4-7 membered heterocycle or a 5-membered heteroaryl substituted with 0-2 instances of R$^4$; R$^4$ is —C$_1$-C$_6$ alkyl; L$^2$ is a bond, Ring A is a heterocycle, 6 membered heteroaryl; n is 0.

Example 3—Synthesis of Compounds of formula (VIIa') and formula (VIIb')

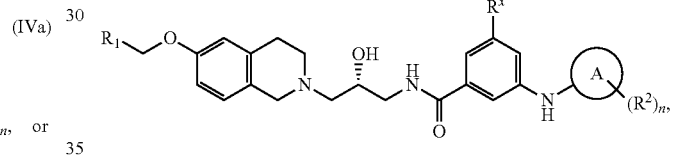
(VIIa')

(VIIb')

SCHEME 3A.

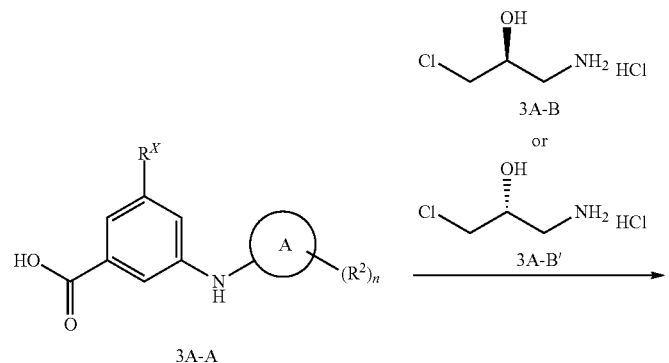

3A-A

-continued

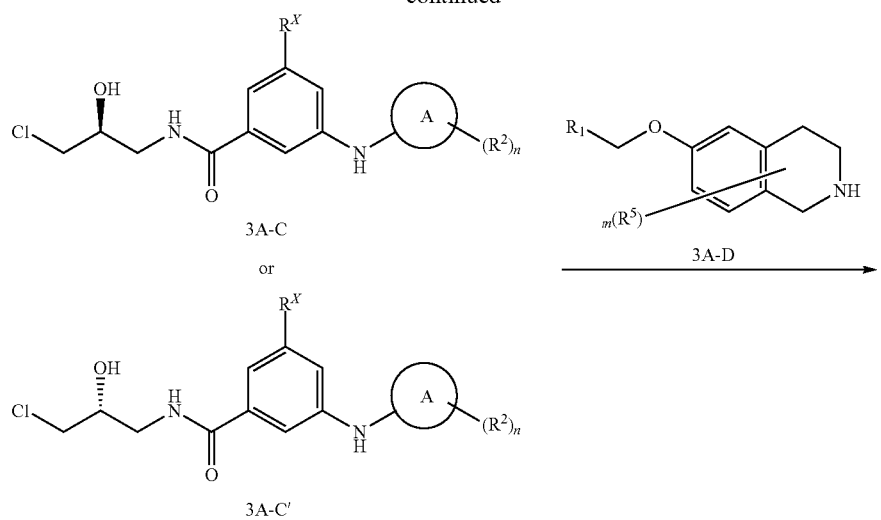

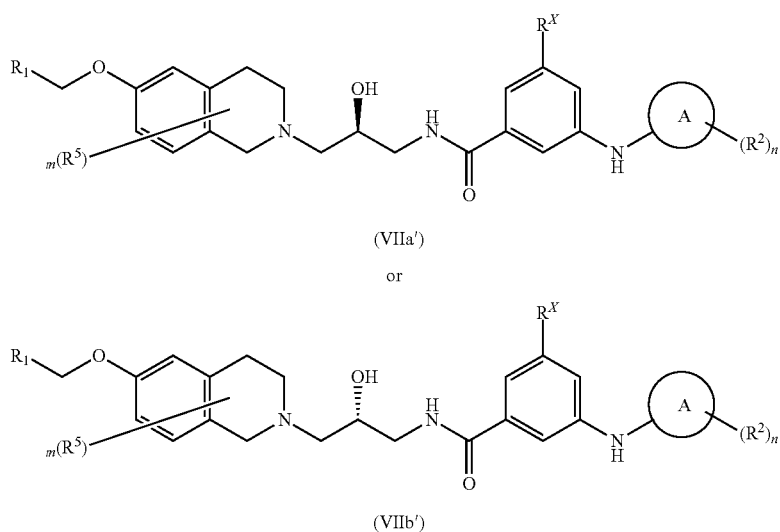

wherein X is a leaving group or hydroxy and variables $R^5$, $R^x$, $R^1$, $R^2$, m, and n are defined herein. In some embodiments, X is selected from —OH, Cl, Br, and I. In some embodiments X is Cl or Br. In other embodiments, wherein X is —OH.

Example 3A1. 3-[(1-acetyl-4-piperidyl)amino]-N-[(2S)-2-hydroxy-3-[6-[(4-methyloxazol-5-yl)methoxy]-3N-dihydro-1H-isoquinolin-2-yl]propyl]-5-(1-piperidyl)benzamide (Compound 631)

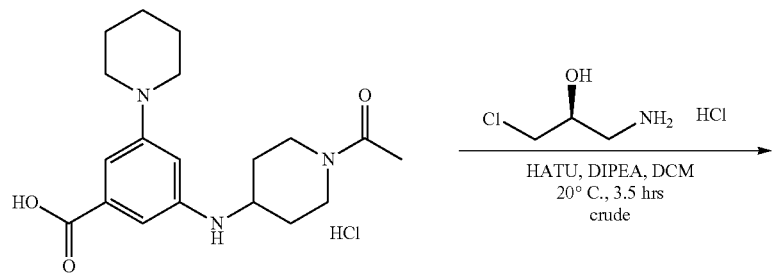

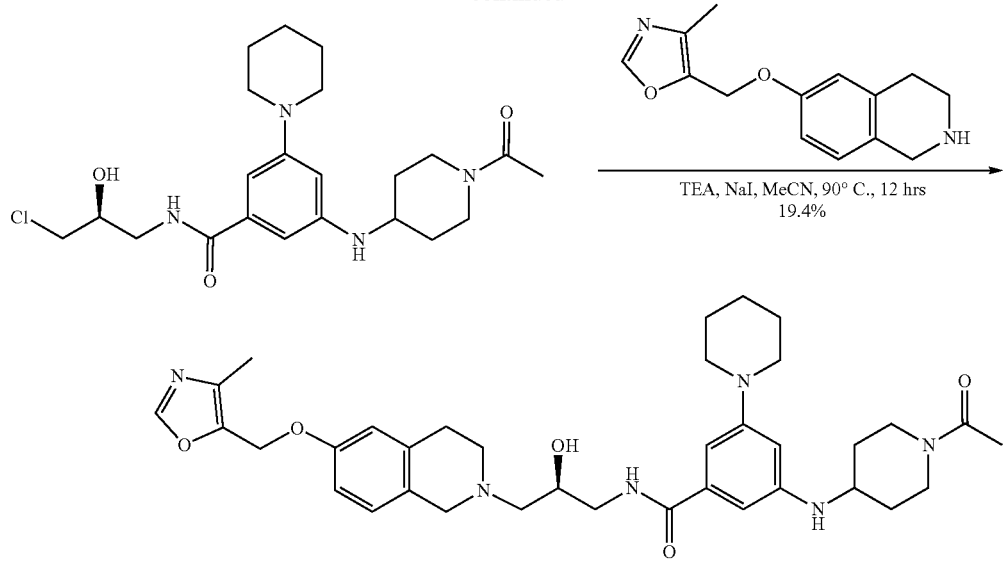

3-[(1-acetyl-4-piperidyl)amino]-N-[(2 S)-3-chloro-2-hydroxy-propyl]-5-(1-piperidyl)benzamide. To a solution of 3-[(1-acetyl-4-piperidyl)amino]-5-(1-piperidyl)benzoic acid (80 mg, 0.209 mmol, HCl salt) and HATU (144 mg, 0.379 mmol) in DCM (4 mL) was added DIEA (280 μL, 1.61 mmol). The mixture was stirred at 20° C. for 30 minutes. Then (2S)-1-amino-3-chloro-propan-2-ol (48 mg, 0.329 mmol, HCl salt) was added and the mixture was stirred at 20° C. for 3 hours. The resulting mixture was quenched by addition of water (10 mL) and extracted with DCM (10 mL*3). The combined organic layer was washed with saturated NH₄Cl aqueous solution (10 mL*2), brine (100 mL), dried over anhydrous Na₂SO₄, filtered and concentrated under reduced pressure. The residue was purified by flash chromatography (ISCO®; 12 g AgelaFlash® Silica Flash Column, DCM/MeOH with MeOH from 0~10%, flow rate=30 mL/min) to afford 3-[(1-acetyl-4-piperidyl) amino]-N-[(2S)-3-chloro-2-hydroxy-propyl]-5-(1-piperidyl)benzamide (30 mg, 32.8 yield) as yellow oil.

3-[(1-acetyl-4-piperidyl)amino]-N-[(2S)-2-hydroxy-3-[6-[(4-methyloxazol-5-yl)methoxy]-3,4-dihydro-1H-isoquinolin-2-yl]propyl]-5-(1-piperidyl)benzamide. To a solution of 3-[(1-acetyl-4-piperidyl)amino]-N-[(2S)-3-chloro-2-hydroxy-propyl]-5-(1-piperidyl)benzamide (20 mg, 45.8 μmol), 4-methyl-5-(1,2,3,4-tetrahydroisoquinolin-6-yloxymethyl)oxazole (16 mg, 65.5 μmol) and NaI (10 mg, 68.7 μmol) in MeCN (2 mL) was added TEA (20 μL, 0.137 mmol). The mixture was stirred at 90° C. for 12 hours. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H₂O with 0.225% PA (v %); Mobile phase B: MeCN; Gradient: B from 0% to 20% in 9.5 min, hold 100% B for 2 min; Flow Rate: 25 mL/min; Column Temperature: 30° C.; Wavelength: 220 nm, 254 nm) to afford 3-[(1-acetyl-4-piperidyl)amino]-N-[(2S)-2-hydroxy-3-[6-[(4-methyloxazol-5-yl)methoxy]-3,4-dihydro-1H-isoquinolin-2-yl]propyl]-5-(1-piperidyl)benzamide (6 mg, 19.4% yield, 0.67PA) as white solid. ¹H NMR (400 MHz, methanol-d₄) δ ppm 8.52 (s, 0.67 H), 8.14 (s, 1H), 7.03 (d, J=8.1 Hz, 1H), 6.79-6.87 (m, 2H), 6.74 (s, 1H), 6.61 (s, 1H), 6.45 (s, 1H), 5.07 (s, 2H), 4.37-4.40 (m, 1H), 4.17 (br s, 1H), 3.92-3.96 (m, 2H), 3.38-3.62 (m, 4H), 3.06-3.20 (m, 6H), 2.78-3.03 (m, 4H), 2.20 (s, 3H), 2.12 (s, 3H), 1.99-2.09 (m, 2H), 1.68-1.72 (m, 4H), 1.60-1.62 (m, 2H), 1.23-1.49 (m, 4H); LCMS (ESI) [M+H]⁺ m/z: calcd 645.4. found 645.3; HPLC: 100% @ 254 nm; 100% ee.

Scheme 3B

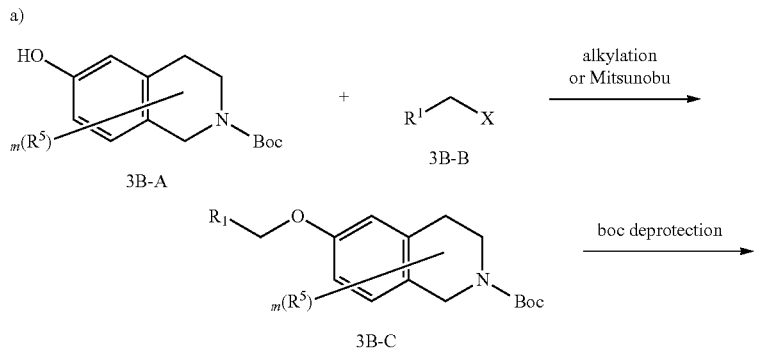

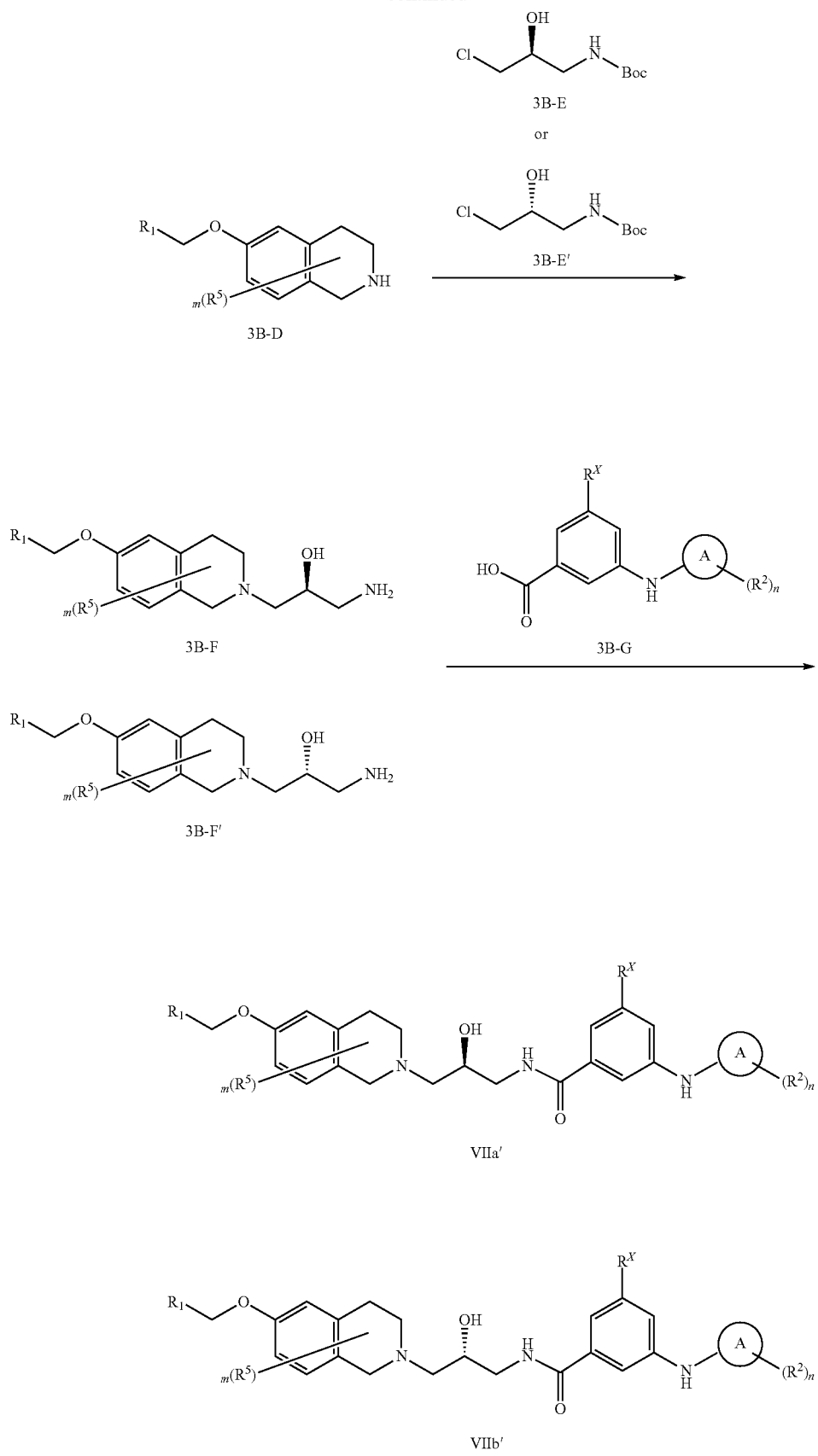

wherein X is a leaving group or hydroxy and variables $R^5$, $R^x$, $R^1$, $R^2$, m, and n are defined herein. In some embodiments, X is selected from —OH, Cl, Br, and I. In some embodiments X is Cl or Br. In other embodiments, wherein X is —OH.

General Procedure 3B-A

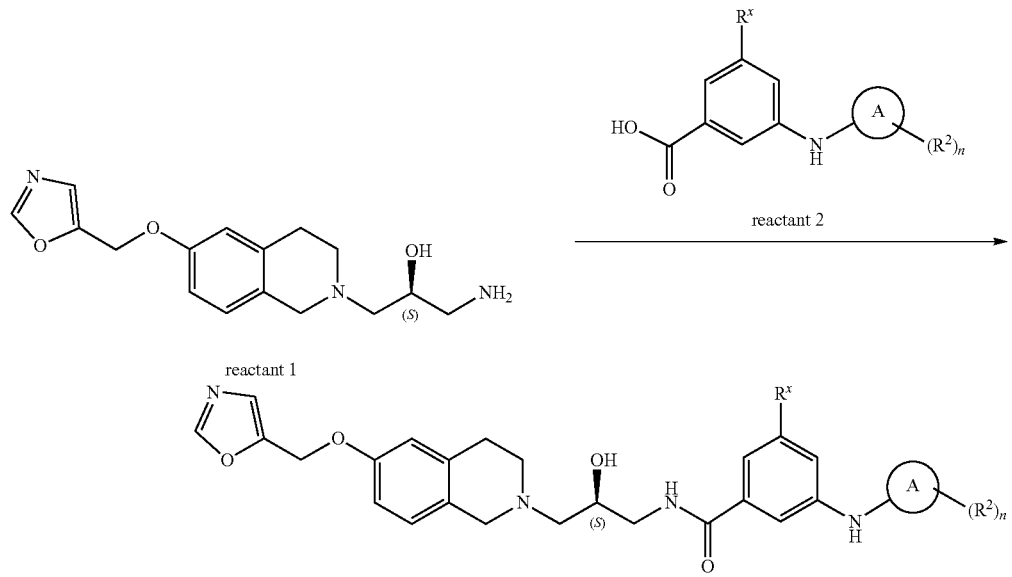

DIPEA (5.0 equiv) was added to the solution of reactant 1 (1.0 equiv) and reactant 2(1.1 equiv) in DMF (2.0 mL). The resulting mixture was stirred for 5 min followed by the addition of the solution of EDC (1.05 equiv) in DMF (0.5 mL) and the solution of HOAt (1.05 equiv) in DMF (0.5 mL). The reaction mixture was stirred overnight at room temperature. After LCMS showed full conversion of starting material, the solvent was removed under reduced pressure. The residue was dissolved in DMSO (1.0 mL) and filtered off. The obtained filtrate was subjected to HPLC (Waters SunFire C18 19*100 5 mkm column and $H_2O$-MeOH as a mobile phase, RunTime=5 min) to afford pure product.

Example 3B1. (S)-3-(cyclobutylamino)-N-(2-hydroxy-3-(6-(oxazol-5-ylmethoxy)-3,4-dihydroisoquinolin 2(1H)-yl)propyl)benzamide (Compound 259)

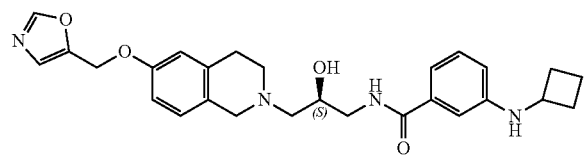

Prepared by general procedure 3B-A. Yield 15.4 mg (15.4%). $^1$H NMR (500 MHz, Chloroform-d) δ 1.83 (m, 4H), 2.45 (m, 2H), 2.57 (dd, 1H), 2.62 (dd, 1H), 2.73 (m, 1H), 2.92 (m, 3H), 3.46 (dt, 1H), 3.56 (m, 2H), 3.71 (ddd, 1H), 3.78 (m, 1H), 3.95 (m, 2H), 4.03 (m, 1H), 5.06 (s, 2H), 6.65 (dd, 1H), 6.73 (m, 2H), 6.79 (dd, 1H), 6.95 (d, 1H), 7.02 (m, 2H), 7.16 (s, 1H), 7.18 (t, 1H), 7.91 (s, 1H). LCMS(ESI): $[M+H]^+$ m/z: calcd 476.1. found 477.2; Rt=0.97 min.

Example 3B2. (S)-3-(Tl-acetylpiperidin-4-yl)amino)-N-(2-hydroxy-3-(6-(oxazol-5-ylmethoxy)-3,4-dihydroisoquinolin-2(1H)-yl)propyl)benzamide (Compound 527)

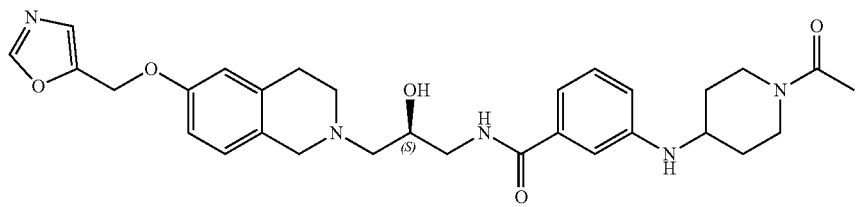

Prepared by general procedure 3B-A. Yield: 11.7 mg (17.99%). $^1$H NMR (DMSO-d$_6$, 500 MHz): δ (ppm) 1.34 (m, 2H), 1.93 (m, 2H), 2.00 (s, 3H), 2.54 (m, 2H), 2.76 (m, 2H), 2.84 (m, 3H), 3.23 (m, 2H), 3.43 (m, 1H), 3.51 (m, 1H), 3.60 (m, 2H), 3.77 (d, 1H), 3.88 (m, 1H), 4.21 (d, 1H), 4.61 (d, 1H), 5.06 (s, 2H), 5.44 (d, 1H), 6.65 (d, 1H), 6.71 (m, 2H), 6.87 (d, 1H), 6.92 (d, 1H), 6.98 (t, 1H), 7.04 (s, 1H), 7.16 (s, 1H), 8.04 (t, 1H), 8.15 (s, 1H). LCMS(ESI): [M+H]$^+$ m/z: calcd 547.6. found 548.2; Rt=0.898 min.

Example 3B3. 3-((1-acetylpyrrolidin-3-yl)amino)-N—((S)-2-hydroxy-3-(6-(oxazol-5-ylmethoxy)-3,4-dihydroisoquinolin-2(1H)-yl)propyl)benzamide (Compound 558)

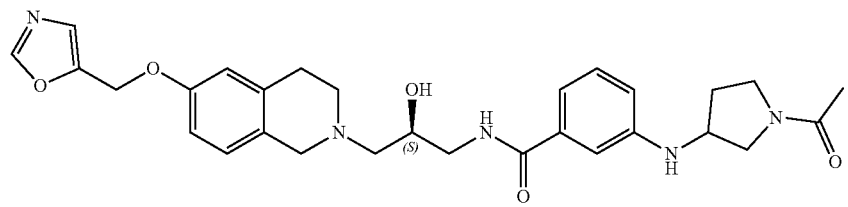

Prepared by general procedure 3B-A. Yield: 21.4 mg (33.78%). $^1$H NMR (400 MHz, DMSO-d$_6$+CCl$_4$) δ 1.96 (m, 4H), 2.19 (m, 1H), 2.76 (m, 2H), 2.84 (m, 2H), 3.27 (m, 4H), 3.45 (m, 3H), 3.61 (m, 3H), 3.88 (m, 1H), 4.05 (m, 1H), 4.63 (m, 1H), 5.06 (s, 2H), 5.87 (dd, 1H), 6.65 (d, 1H), 6.72 (d, 2H), 6.92 (d, 2H), 7.00 (d, 1H), 7.04 (m, 1H), 7.17 (s, 1H), 8.10 (t, 1H), 8.16 (s, 1H). LCMS(ESI): [M+2H]$^+$ m/z: calcd 533.6. found 534.2; Rt=0.879 min.

General Procedure 3B-B

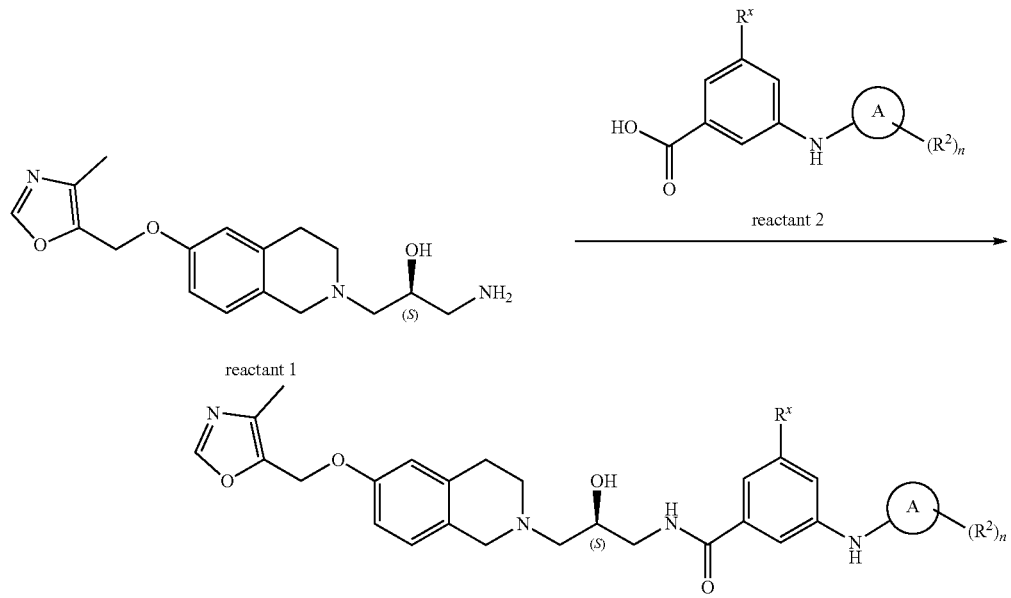

DIPEA (5.0 equiv) was added to the solution of reactant 1 (1.0 equiv) and reactant 2 (1.1 equiv) in DMF (2.0 mL). The resulting mixture was stirred for 5 min followed by the addition of the solution of EDC (1.05 equiv) in DMF (0.5 mL) and the solution of HOAt (1.05 equiv) in DMF (0.5 mL). The reaction mixture was stirred overnight at room temperature. After LCMS showed full conversion of starting material, the solvent was removed under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase, RunTime=5 min) to afford pure product.

Example 3B4. (S)—N-(2-hydroxy-3-(6-((4-methyl-oxazol-5-yl)methoxy)-3N-dihydroisoquinolin-2(1H)-yl)propyl)-3-(oxetan-3-ylamino)benzamide (Compound 262)

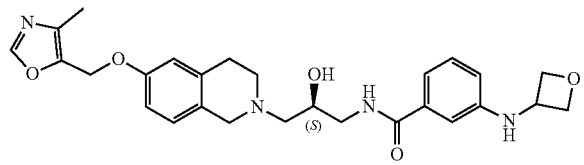

Prepared by general procedure 3B-B. Yield 10.6 mg (10.6%). $^1$H NMR (Chloroform-d, 500 MHz): δ (ppm) 2.24 (s, 3H), 2.61 (m, 2H), 2.74 (m, 1H), 2.92 (m, 3H), 3.45 (m, 2H), 3.59 (d, 1H), 3.73 (m, 1H), 3.80 (d, 1H), 4.02 (m, 1H), 4.28 (m, 1H), 4.53 (t, 2H), 4.68 (m, 1H), 5.02 (m, 4H), 6.63 (d, 1H), 6.76 (m, 3H), 6.96 (d, 1H), 7.00 (s, 1H), 7.07 (d, 1H), 7.21 (t, 1H), 7.82 (s, 1H). LCMS(ESI): [M+H]$^+$ m/z: calcd 492.6. found 493.2; Rt=0.83 min.

Example 3B5. (S)-3-(cyclobutylamino)-N-(2-hydroxy-3-(6-((4-methyloxazol-5-yl)methoxy)-3,4-dihydroisoquinolin-2(1H)-yl)propyl)benzamide (Compound 283)

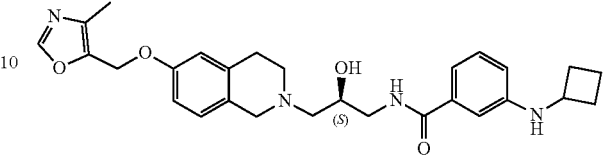

Prepared by general procedure 3B-B. Yield 4.2 mg (4.2%). $^1$H NMR (Chloroform-d, 500 MHz): δ (ppm) 1.82 (m, 5H), 2.24 (s, 3H), 2.46 (m, 2H), 2.61 (m, 2H), 2.75 (m, 1H), 2.93 (m, 4H), 3.46 (m, 1H), 3.60 (m, 1H), 3.73 (m, 1H), 3.80 (m, 1H), 3.97 (m, 1H), 4.04 (m, 1H), 5.00 (s, 2H), 6.66 (d, 1H), 6.73 (s, 2H), 6.78 (d, 1H), 6.96 (d, 1H), 7.01 (m, 2H), 7.17 (t, 1H), 7.82 (s, 1H). LCMS(ESI): [M+H]$^+$ m/z: calcd 490.6. found 491.2; Rt=1.00 min.

General Procedure 3B-C

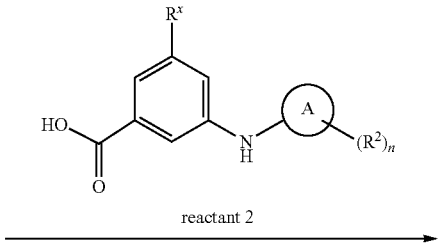

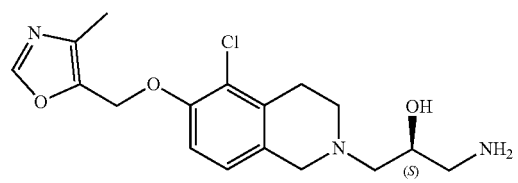

reactant 1 reactant 2

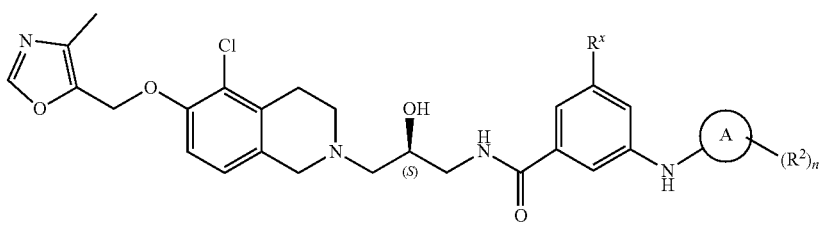

Reactant 1 and Reactant 2 were mixed in DMF (5 mL). The reaction suspension was cooled to 0° C. and HATU followed by DIPEA were added. The clear solution was stirred at ambient temperature for E5 hr at 25° C. then volatiles were evaporated under reduced pressure and residue was subjected to RP-HPLC to give products.

Example 3B6. N-[(2S)-3-{5-chloro-6-[(4-methyl-1,3-oxazol-5-yl)methoxy]-1,2,3,4-tetrahydroisoquinolin-2-yl}-2-hydroxypropyl]-3-(cyclobutylamino)benzamide (Compound 344)

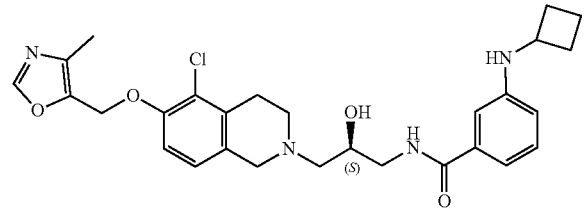

Prepared by general procedure 3B-C. Prepared by general procedure. Yield 29 mg (39%). $^1$H NMR (400 MHz, dmso+ccl4) δ 1.82 (m, 4H), 2.18 (s, 3H), 2.37 (m, 2H), 2.80 (m, 4H), 3.25 (m, 1H), 3.43 (m, 1H), 3.62 (m, 2H), 3.75 (m, 1H), 3.86 (m, 2H), 4.62 (d, 1H), 5.09 (s, 2H), 5.69 (d, 1H), 6.54 (d, 1H), 6.86 (d, 1H), 6.96 (m, 5H), 7.99 (t, 1H), 8.04 (s, 1H). LCMS(ESI): [M-Boc]$^+$ m/z: calcd 524.3. found 525.2; Rt=1.029 min.

Example 3B7. of N-[(2S)-3-[5-chloro-6-[(4-methyl-1,3-oxazol-5-yl)methoxy]-1,2,3,4-tetrahydroisoquinolin-2-yl}-2-hydroxypropyl]-3-[(oxetan-3-yl)amino]benzamide (Compound 490)

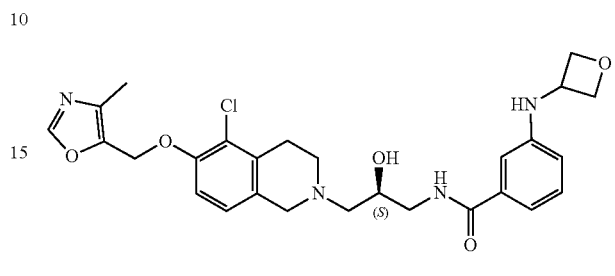

Prepared by general procedure 3B-C. Yield 21 mg (35%). $^1$H NMR (400 MHz, DMSO-d6+CCl4) δ 2.18 (s, 3H), 2.57 (m, 1H), 2.80 (m, 4H), 3.08 (m, 1H), 3.23 (m, 1H), 3.41 (m, 1H), 3.63 (m, 2H), 3.88 (m, 1H), 4.44 (t, 2H), 4.55 (m, 1H), 4.62 (m, 1H), 4.84 (t, 2H), 5.09 (s, 2H), 6.33 (d, 1H), 6.53 (d, 1H), 6.90 (s, 1H), 6.96 (m, 3H), 7.01 (m, 1H), 8.06 (m, 2H). LCMS(ESI): [M-Boc]$^+$ m/z: calcd 526.2. found 527.2; Rt=2.433 min.

General Procedure 3B-D

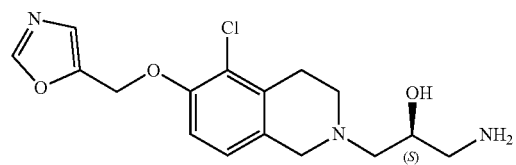

reactant 1

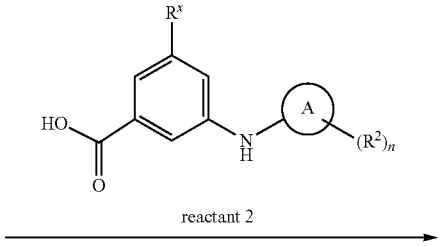

reactant 2

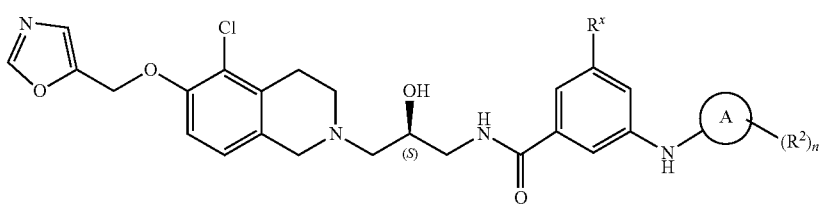

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase) to afford pure product.

Example 3B8. (S)—N-(3-(5-chloro-6-(oxazol-5-ylmethoxy)-3,4-dihydroisoquinolin-2(1H)-yl)-2-hydroxypropyl)-3-(cyclobutylamino)benzamide (Compound 335)

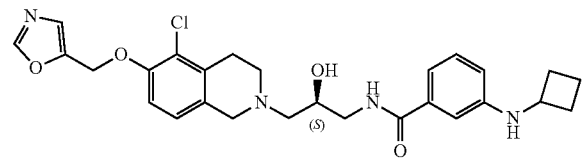

Prepared by general procedure 3B-D. Yield: 36.1 mg (48.13%). $^1$H NMR (DMSO-d$_6$, 400 MHz): δ (ppm) 1.76 (m, 2H), 1.85 (dd, 2H), 2.37 (m, 2H), 2.54 (s, 2H), 2.80 (s, 4H), 3.24 (m, 1H), 3.42 (m, 1H), 3.64 (m, 2H), 3.86 (q, 2H), 4.63 (d, 1H), 5.17 (s, 2H), 5.69 (d, 1H), 6.54 (d, 1H), 6.86 (d, 1H), 6.97 (m, 4H), 7.20 (s, 1H), 7.99 (t, 1H), 8.18 (s, 1H). LCMS(ESI): [M+H]$^+$ m/z: calcd 511.0. found 512.2; Rt=1.081 min.

General Procedure 3B-E

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mL). The reaction mixture was stirred at room temperature overnight. After the completion of the reaction, monitored by LCMS, the resulting suspension was concentrated under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase, Run Time 5 min) to afford pure product.

Example 3B9. (S)—N-(3-(5-bromo-6-(oxazol-5-ylmethoxy)-3,4-dihydroisoquinolin-2(1H)-yl)-2-hydroxypropyl)-3-(cyclobutylamino)benzamide (Compound 348)

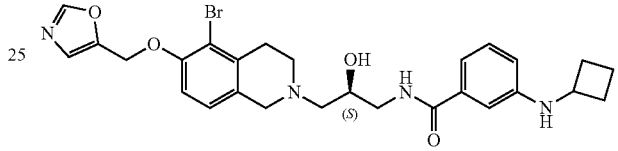

Prepared by general procedure 3B-E. Yield: 24.5 mg (32.0%). $^1$H NMR (400 MHz, dmso+ccl4) δ 1.80 (m, 4H), 2.36 (m, 2H), 2.59 (m, 1H), 2.79 (m, 4H), 3.23 (m, 1H), 3.42 (m, 1H), 3.63 (m, 2H), 3.86 (m, 2H), 4.63 (m, 1H), 5.17 (s, 2H), 5.69 (d, 1H), 6.53 (m, 1H), 6.86 (d, 1H), 6.95 (m, 1H), 6.98 (m, 3H), 7.20 (s, 1H), 7.99 (t, 1H), 8.18 (s, 1H). LCMS(ESI): [M+H]$^+$ m/z: calcd 555.4. found 555.2; Rt=1.06 min.

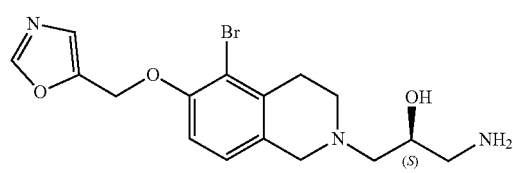

reactant 1

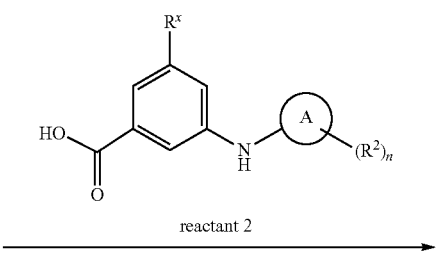

reactant 2

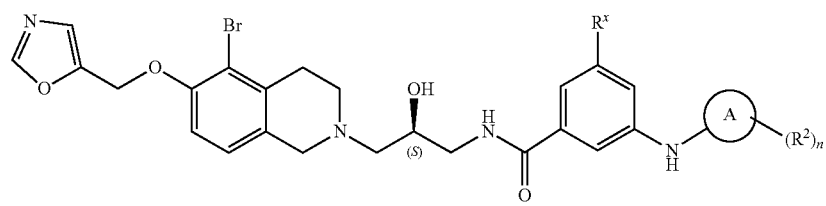

General Procedure 3B-F

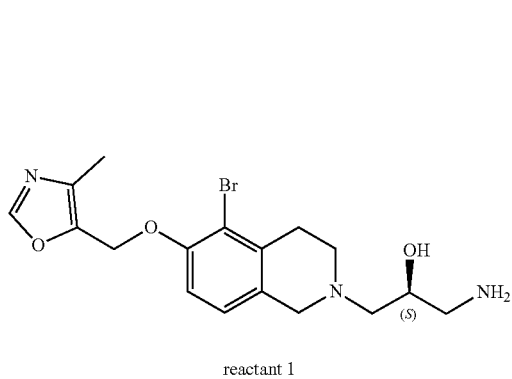

reactant 1

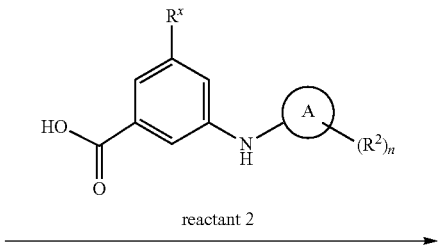

reactant 2

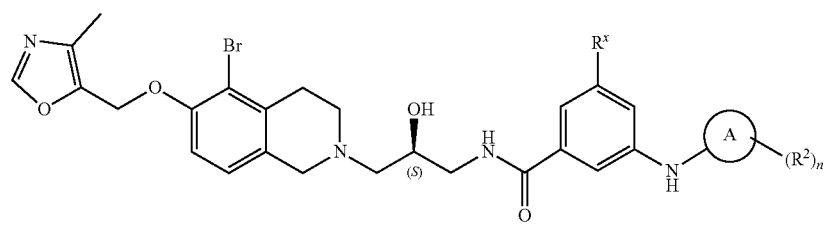

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mL). The reaction mixture was stirred at room temperature overnight. After the completion of the reaction, monitored by LCMS, the resulting suspension was concentrated under reduced pressure. The residue was dissolved in DMSO (1.0 mL) and filtered off. The obtained filtrate was subjected to HPLC (Waters SunFire C18 19*100 5 mkm column and H$_2$O-MeOH as a mobile phase) to afford pure product.

Example 3B10. (S)—N-(3-(5-bromo-6-((4-methyl-oxazol-5-yl)methoxy)-3,4-dihydroisoquinolin-2 (1H)-yl)-2-hydroxypropyl)-3-(cyclobutylamino)benzamide (Compound 354)

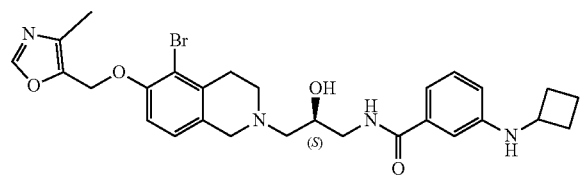

Prepared by general procedure 3B-F. Yield: 21.4 mg (28%). $^1$H NMR (DMSO-d$_6$, 500 MHz): δ (ppm) 1.83 (m, 5H), 2.22 (s, 3H), 2.44 (m, 2H), 2.58 (d, 2H), 2.76 (m, 1H), 2.87 (m, 2H), 2.94 (m, 1H), 3.45 (m, 1H), 3.57 (d, 1H), 3.72 (m, 1H), 3.78 (d, 1H), 3.96 (m, 2H), 4.02 (m, 1H), 5.07 (s, 2H), 6.65 (s, 1H), 6.68 (m, 1H), 6.84 (d, 1H), 6.94 (d, 1H), 6.99 (d, 1H), 7.01 (s, 1H), 7.17 (t, 1H), 7.81 (s, 1H). LCMS(ESI): [M+H]$^+$ m/z: calcd 569.5. found 570.2; Rt=1.149 min.

Example 3B11. (S)—N-(3-(5-bromo-6-((4-methyl-oxazol-5-yl)methoxy)-3,4-dihydroisoquinolin-2 (1H)-yl)-2-hydroxypropyl)-3-(oxetan-3-ylamino) benzamide (Compound 381)

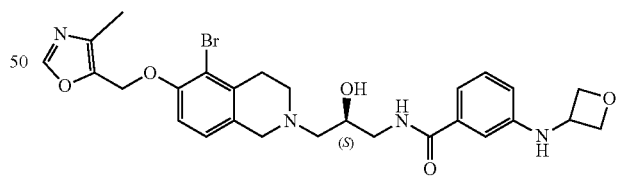

Prepared by general procedure 3B-F. Yield: 7.5 mg (13%). $^1$H NMR (500 MHz, CDCl$_3$) δ 2.23 (s, 3H), 2.62 (m, 2H), 2.80 (m, 1H), 2.90 (m, 2H), 2.99 (m, 1H), 3.46 (m, 1H), 3.55 (m, 1H), 3.62 (m, 1H), 3.74 (m, 1H), 3.82 (m, 1H), 4.05 (m, 1H), 4.29 (m, 1H), 4.53 (t, 2H), 4.68 (m, 1H), 5.03 (t, 2H), 5.09 (s, 2H), 6.63 (d, 1H), 6.77 (m, 1H), 6.85 (d, 1H), 6.95 (d, 1H), 7.00 (s, 1H), 7.06 (d, 1H), 7.22 (t, 1H), 7.82 (s, 1H). LCMS(ESI): [M+H]$^+$ m/z: calcd 571.5; found 572.2; Rt=0.932 min.

General Procedure 3B-G

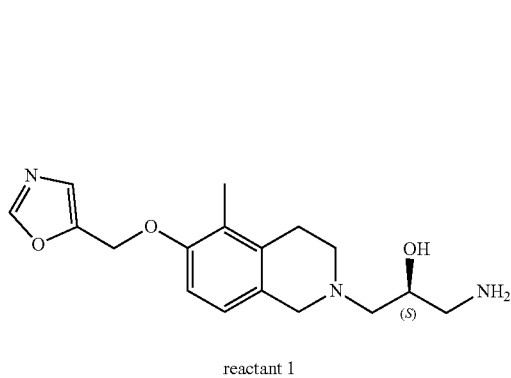

reactant 1

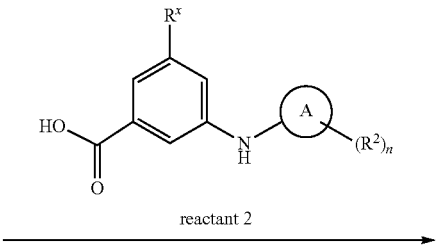

reactant 2

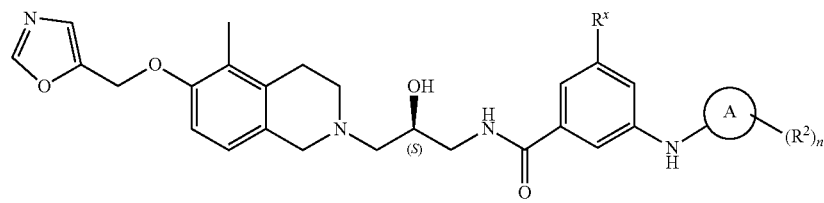

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH-0.1NH$_3$ as a mobile phase) to afford pure product.

Example 3B12. 3-(cyclobutylamino)-N-[(2S)-2-hydroxy-3-{5-methyl-6-[(1,3-oxazol-5-yl)methoxy]-1,2,3,4-tetrahydroisoquinolin-2-yl}propyl]benzamide (Compound 351)

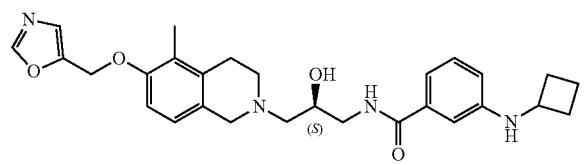

Prepared by general procedure 3B-G. Yield: 23.8 mg (37.73%). $^1$H NMR (DMSO-d$_6$, 400 MHz): δ (ppm) 1.80 (m, 4H), 2.03 (s, 3H), 2.36 (m, 2H), 2.54 (m, 2H), 2.70 (m, 2H), 2.77 (m, 2H), 3.26 (m, 1H), 3.42 (m, 1H), 3.60 (m, 2H), 3.86 (m, 2H), 4.61 (d, 1H), 5.06 (s, 2H), 5.67 (d, 1H), 6.53 (d, 1H), 6.83 (m, 3H), 6.92 (m, 2H), 7.14 (s, 1H), 8.03 (t, 1H), 8.15 (s, 1H). LCMS(ESI): [M+H]$^+$ m/z: calcd 490.3. found 491.2; Rt=0.988 min.

Example 3B13. N-[(2S)-2-hydroxy-3-{5-methyl-6-[(1,3-oxazol-5-yl)methoxy]-1,2,3,4-tetrahydroisoquinolin-2-yl}propyl]-3-[(oxetan-3-yl)amino]benzamide (Compound 424)

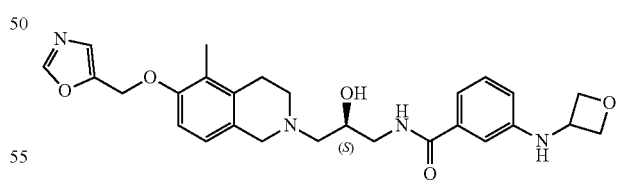

Prepared by general procedure 3B-G. Yield: 12.2 mg (19.6%). $^1$H NMR (CDCl$_3$, 500 MHz): δ (ppm) 2.10 (s, 3H), 2.61 (m, 2H), 2.79 (m, 4H), 2.99 (m, 1H), 3.45 (m, 1H), 3.62 (d, 1H), 3.75 (m, 1H), 3.82 (d, 1H), 4.05 (m, 1H), 4.27 (d, 1H), 4.53 (t, 2H), 4.69 (m, 1H), 5.03 (t, 2H), 5.06 (s, 2H), 6.63 (d, 1H), 6.81 (d, 2H), 6.86 (d, 1H), 7.00 (s, 1H), 7.07 (d, 1H), 7.14 (s, 1H), 7.21 (t, 1H), 7.91 (s, 1H). LCMS(ESI): [M+2H]$^+$ m/z: calcd 492.2. found 493.2; Rt=0.892 min.

Example 3B14. 3-[(1-acetylpiperidin-4-yl)amino]-N-[(2S)-2-hydroxy-3-{5-methyl-6-[(1,3-oxazol-5-yl)methoxy]-1,2,3,4-tetrahydroisoquinolin-2-yl}propyl]benzamide (Compound 529)

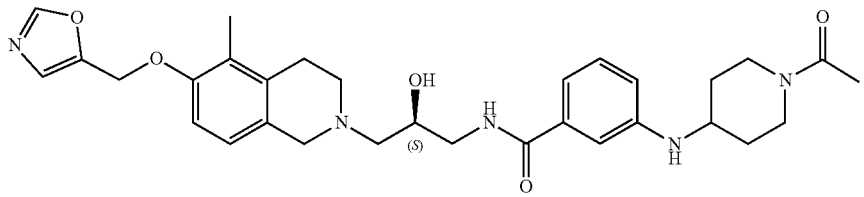

Prepared by general procedure 3B-G. Yield: 17.3 mg (26.8%). $^1$H NMR (DMSO-$d_6$, 400 MHz): δ (ppm) 1.32 (m, 3H), 1.93 (m, 2H), 2.02 (d, 6H), 2.43 (m, 1H), 2.70 (m, 2H), 2.78 (m, 2H), 2.86 (m, 1H), 3.25 (m, 2H), 3.45 (m, 2H), 3.60 (m, 2H), 3.77 (m, 1H), 3.87 (m, 1H), 4.21 (m, 1H), 4.61 (d, 1H), 5.07 (s, 2H), 5.45 (d, 1H), 6.65 (d, 1H), 6.84 (m, 3H), 6.95 (t, 1H), 7.04 (m, 1H), 7.14 (s, 1H), 8.07 (t, 1H), 8.16 (s, 1H) LCMS(ESI): [M+H]$^+$ m/z: calcd 561.3; found 562.2; Rt=0.916 min.

Example 3B15. N-[(2S)-2-hydroxy-3-{5-methyl-6-[(1,3-oxazol-5-yl)methoxy]-1,2,3,4-tetrahydroisoquinolin-2-yl}propyl]-3-[(oxan-4-yl)amino]benzamide (Compound 548)

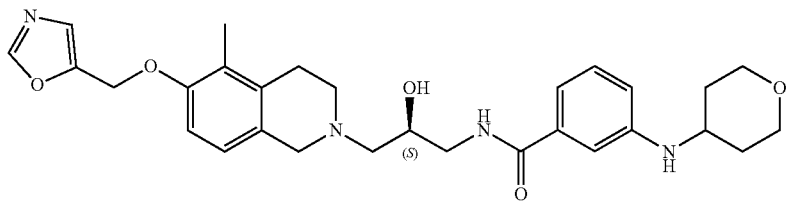

Prepared by general procedure 3B-G. Yield: 18.3 mg (28.3%). $^1$H NMR (DMSO-$d_6$, 400 MHz): δ (ppm) 1.41 (m, 2H), 1.91 (d, 2H), 2.04 (s, 3H), 2.69 (m, 2H), 2.77 (m, 2H), 3.27 (m, 1H), 3.43 (m, 4H), 3.58 (m, 2H), 3.74 (m, 1H), 3.88 (m, 3H), 4.61 (s, 1H), 5.07 (s, 2H), 5.37 (d, 1H), 6.63 (d, 1H), 6.83 (m, 3H), 6.95 (t, 1H), 7.02 (s, 1H), 7.14 (s, 1H), 8.05 (t, 1H), 8.15 (s, 1H). LCMS(ESI): [M+H]$^+$ m/z: calcd 520.3. found 521.2; Rt=0.94 min.

Example 3B16. 3-[(1-acetylpyrrolidin-3-yl)amino]-N-[(2S)-2-hydroxy-3-{5-methyl-6-[(1,3-oxazol-5-yl)methoxy]-1,2,3,4-tetrahydroisoquinolin-2-yl}propyl]benzamide (Compound 525)

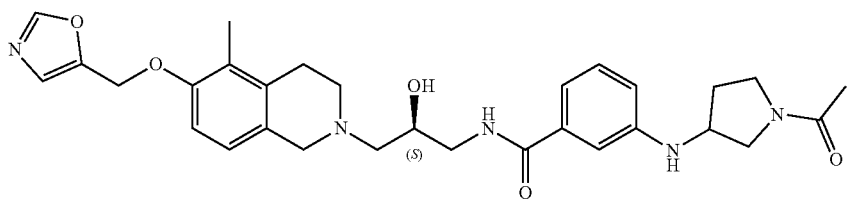

Prepared by general procedure 3B-G. Yield: 8.3 mg (13.47%). $^1$H NMR (500 MHz, CDCl$_3$) δ 1.93 (m, 1H), 2.09 (m, 6H), 2.29 (m, 1H), 2.59 (m, 2H), 2.77 (m, 3H), 2.97 (m, 1H), 3.35 (m, 1H), 3.46 (m, 2H), 3.61 (m, 3H), 3.75 (m, 2H), 3.84 (m, 2H), 4.04 (m, 1H), 4.20 (m, 1H), 5.06 (s, 2H), 6.74 (m, 2H), 6.80 (d, 1H), 6.86 (d, 1H), 7.04 (m, 1H), 7.12 (d, 1H), 7.14 (s, 1H), 7.21 (q, 1H), 7.91 (s, 1H). LCMS(ESI): [M+H]$^+$ m/z: calcd 547.3. found 548.2; Rt=0.905 min.

General Procedure 3B-H

Prepared by general procedure 3B-H. Yield: 4.3 mg (6.8%). $^1$H NMR (Chloroform-d, 500 MHz): δ (ppm) 1.68 (m, 2H), 2.09 (s, 3H), 2.22 (s, 3H), 2.62 (m, 2H), 2.79 (m, 3H), 2.98 (m, 1H), 3.46 (m, 1H), 3.61 (d, 1H), 3.74 (m, 1H), 3.82 (d, 1H), 4.05 (s, 1H), 4.28 (d, 1H), 4.53 (t, 2H), 4.68 (m, 1H), 5.00 (s, 1H), 5.03 (t, 2H), 6.63 (d, 1H), 6.82 (d, 1H), 6.86 (d, 1H), 7.00 (s, 1H), 7.07 (d, 1H), 7.21 (t, 1H), 7.30 (m, 1H), 7.82 (s, 1H). LCMS(ESI): [M+H]$^+$ m/z: calcd 506.5. found 507.1; Rt=0.94 min.

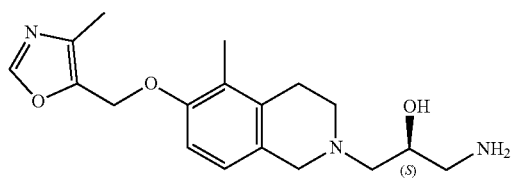

Reactant 1

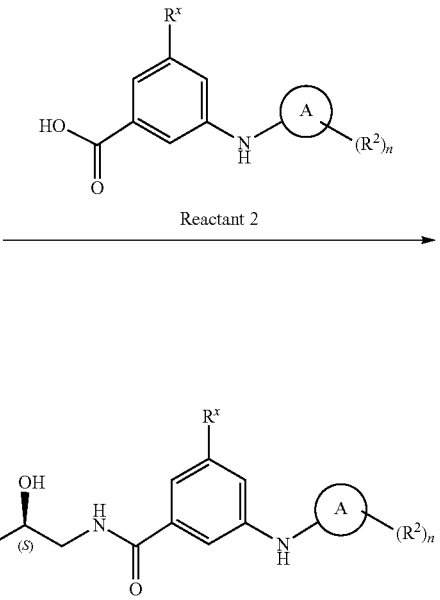

Reactant 2

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH-0.1NH$_3$ as a mobile phase) to afford pure product.

Example 3B17. N-[(2S)-2-hydroxy-3-{5-methyl-6-[(4-methyl-1,3-oxazol-5-yl)methoxy]-1,2,3,4-tetra-hydroisoquinolin-2-yl}propyl]-3-[(oxetan-3-yl)amino]benzamide (Compound 375)

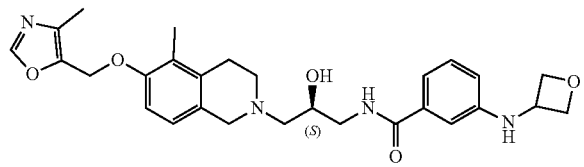

Example 3B18. 3-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]benzamide (Compound 488)

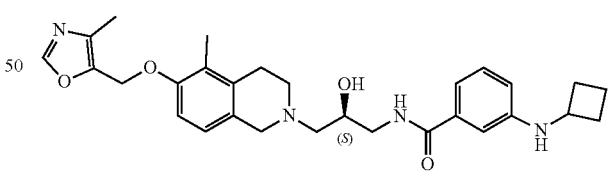

Prepared by general procedure 3B-H. Yield: 23.7 mg (36.5%). $^1$H NMR (500 MHz, CDCl$_3$) δ 1.47 (m, 2H), 1.83 (m, 4H), 2.09 (s, 3H), 2.22 (s, 3H), 2.46 (m, 2H), 2.63 (m, 2H), 2.82 (m, 3H), 3.00 (m, 1H), 3.48 (m, 1H), 3.64 (d, 1H), 3.73 (dt, 1H), 3.84 (d, 1H), 3.97 (m, 1H), 4.06 (m, 1H), 5.00 (s, 2H), 6.66 (d, 1H), 6.75 (m, 1H), 6.84 (m, 2H), 7.01 (m, 2H), 7.18 (t, 1H), 7.82 (s, 1H). LCMS(ESI): [M+H]$^+$ m/z: calcd 504.2. found 505.2; Rt=1.13 min.

Example 4—Synthesis of Compounds of Formula (XIII-a') or Formula (XIII-b')
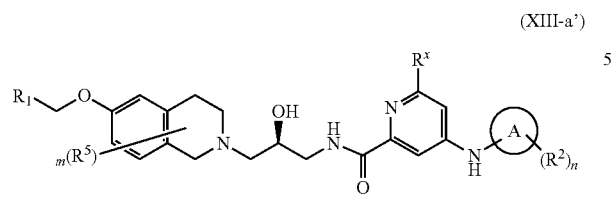
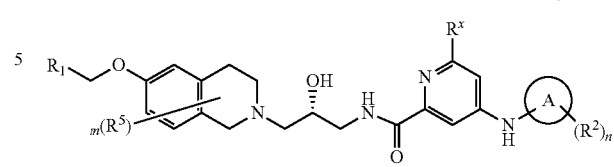
Scheme 4A
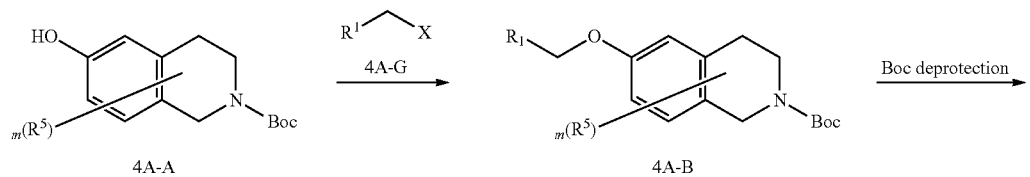
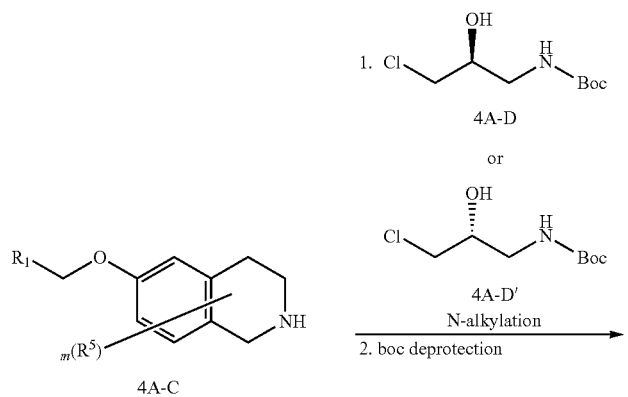
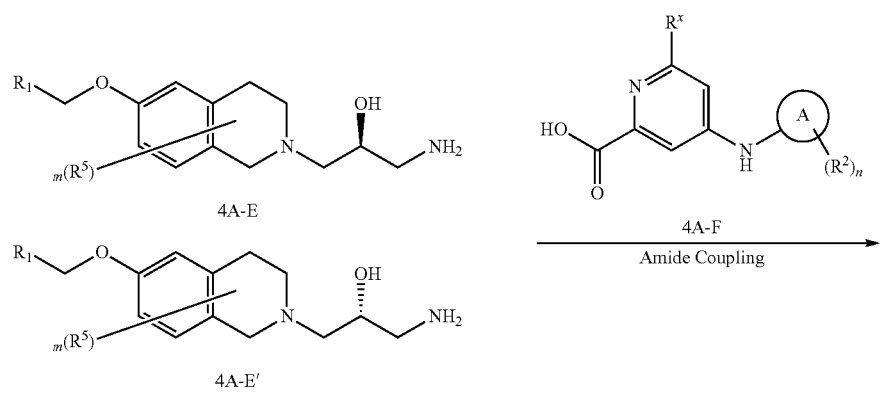

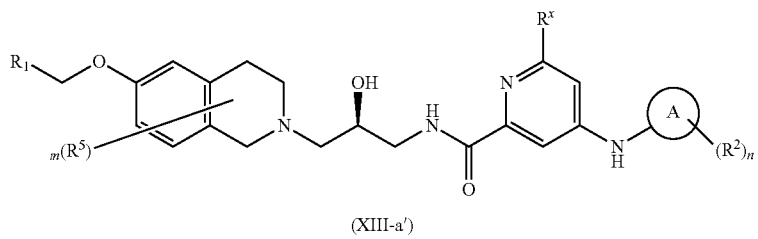

(XIII-a′)

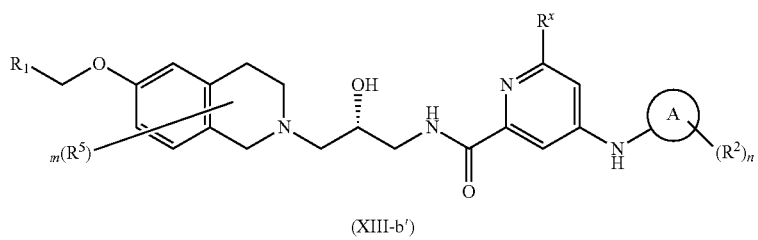

(XIII-b′)

wherein X is a leaving group or hydroxy and variables $R^5$, $R^x$, $R^1$, $R^2$, m, and n are defined herein. In some embodiments, X is selected from —OH, Cl, Br, and I. In some embodiments X is Cl or Br. In other embodiments, wherein X is —OH.

General Procedure 4A-A

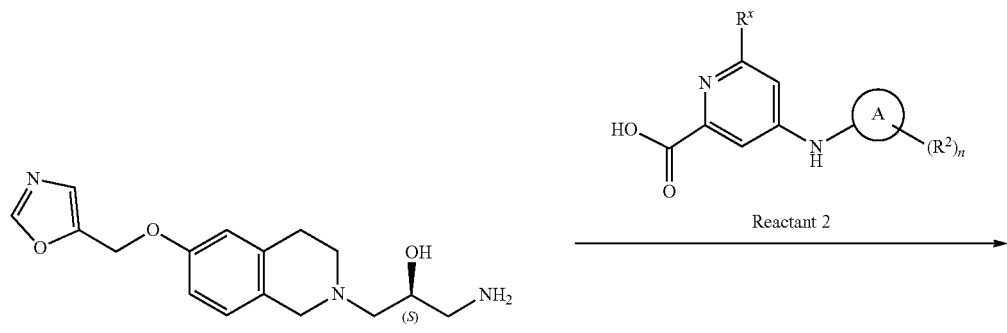

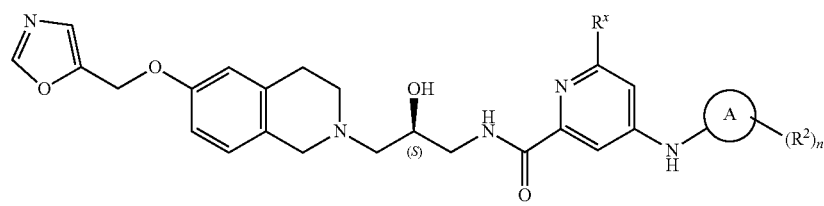

DIPEA (9 equiv) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and $H_2O$-MeOH as a mobile phase) to afford pure product.

Example 4A1. (S)—N-(2-hydroxy-3-(6-(oxazol-5-ylmethoxy)-3,4-dihydroisoquinolin-2(1H)-yl)propyl)-4-((tetrahydro-2H-pyran-4-yl)amino)picolinamide (Compound 511)

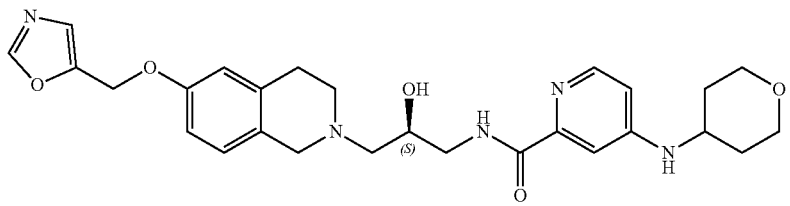

Prepared by general procedure 4A-A. Yield: 9.6 mg (14.72%). $^1$H NMR (CDCl$_3$, 500 MHz): δ (ppm) 1.64 (m, 2H), 2.04 (m, 2H), 2.66 (m, 2H), 2.81 (m, 1H), 2.95 (m, 3H), 3.53 (m, 3H), 3.68 (m, 3H), 3.86 (m, 2H), 4.03 (m, 2H), 4.11 (m, 1H), 4.25 (m, 1H), 5.06 (s, 2H), 6.52 (d, 1H), 6.73 (s, 1H), 6.79 (d, 1H), 6.96 (d, 1H), 7.16 (s, 1H), 7.37 (s, 1H), 7.91 (s, 1H), 8.13 (d, 1H), 8.49 (m, 1H). LCMS(ESI): [M+H]$^+$ m/z: calcd 507.5. found 508.5; Rt=0.704 min.

Example 4A2. (S)-4-((1-acetylpiperidin-4-yl)amino)-N-(2-hydroxy-3-(6-(oxazol-5-ylmethoxy)-3,4-dihydroisoquinolin-2(1H)-yl)propyl)picolinamide (Compound 507)

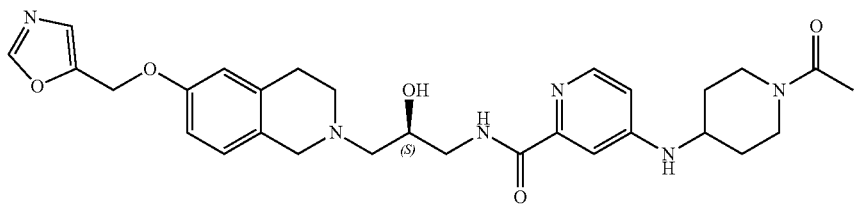

Prepared by general procedure 4A-A. Yield: 17 mg (26.64%). $^1$H NMR (400 MHz, CDCl$_3$) δ 8.47 (t, 1H), 8.08 (d, 1H), 7.87 (s, 1H), 7.34 (d, 1H), 7.12 (s, 1H), 6.90 (d, 1H), 6.73 (dd, 1H), 6.68 (m, 1H), 6.48 (dd, 1H), 5.01 (s, 2H), 4.52 (d, 1H), 4.45 (s, 1H), 4.02 (m, 1H), 3.80 (m, 1H), 3.75 (m, 1H), 3.63 (s, 2H), 3.53 (m, 1H), 3.48 (m, 2H), 3.20 (t, 1H), 2.87 (m, 4H), 2.72 (m, 1H), 2.55 (m, 2H), 2.09 (s, 3H), 2.02 (m, 2H), 1.40 (m, 2H). LCMS(ESI): [M+H]$^+$ m/z: calcd 548.6. found 549.2; Rt=0.760 min.

Example 4A3. (S)-4-(cyclobutylamino)-N-(2-hydroxy-3-(6-(oxazol-5-ylmethoxy)-3,4-dihydroisoquinolin-2(1H)-yl)propyl)picolinamide (Compound 509)

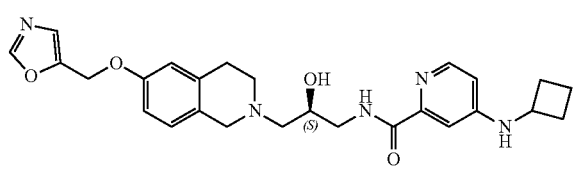

Prepared by general procedure 4A-A. Yield: 16.1 mg (23.99%). $^1$H NMR (400 MHz, DMSO-$d_6$+CCl$_4$) δ 1.81 (m, 2H), 1.93 (m, 2H), 2.39 (m, 2H), 2.59 (m, 2H), 2.79 (m, 1H), 2.89 (m, 2H), 3.31 (m, 1H), 3.45 (m, 2H), 3.65 (m, 3H), 3.92 (m, 2H), 5.07 (s, 2H), 6.42 (m, 1H), 6.72 (m, 2H), 6.91 (m, 2H), 7.17 (m, 2H), 7.91 (d, 1H), 8.16 (s, 1H), 8.53 (s, 1H). LCMS(ESI): [M+H]$^+$ m/z: calcd 477.5. found 478.2; Rt=0.771 min.

General Procedure 4A-B

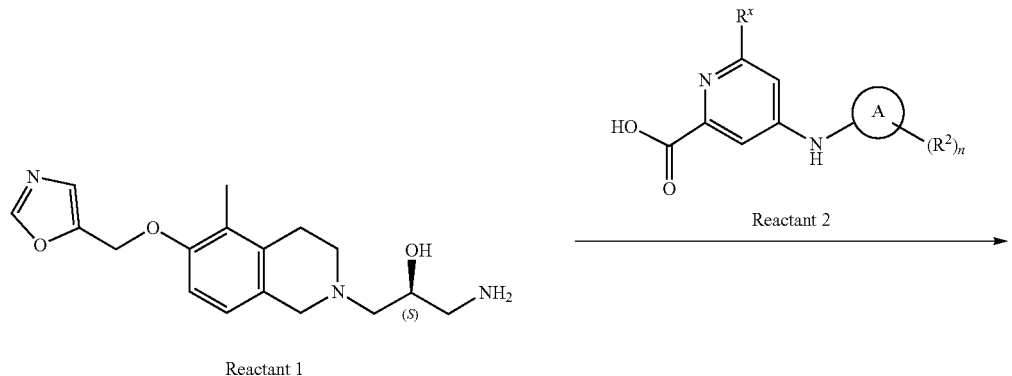

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH-0.1NH$_3$ as a mobile phase) to afford pure product.

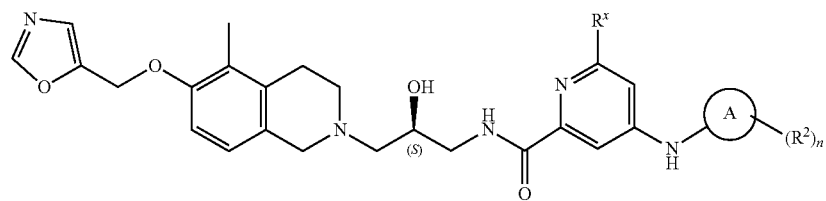

Example 4A4. N-[(2S)-2-hydroxy-3-{5-methyl-6-[(1,3-oxazol-5-yl)methoxy]-1,2,3,4-tetrahydroisoquinolin-2-yl}propyl]-4-[(oxan-4-yl)amino]pyridine-2-carboxamide (Compound 573)

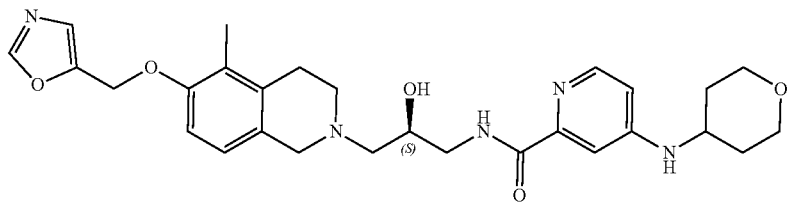

Prepared by general procedure 4A-B. Yield: 14.5 mg (20.1%). $^1$H NMR (CDCl$_3$, 500 MHz): δ (ppm) 1.52 (m, 3H), 2.04 (d, 2H), 2.10 (s, 3H), 2.67 (m, 2H), 2.82 (m, 3H), 3.02 (m, 1H), 3.52 (q, 3H), 3.69 (m, 3H), 3.87 (m, 1H), 4.02 (d, 2H), 4.12 (m, 1H), 4.26 (d, 1H), 5.06 (s, 2H), 6.52 (d, 1H), 6.80 (d, 1H), 6.86 (d, 1H), 7.14 (s, 1H), 7.37 (s, 1H), 7.91 (s, 1H), 8.13 (d, 1H), 8.49 (t, 1H) LCMS(ESI): [M+H]$^+$ m/z: calcd 521.3. found 522.4; Rt=1.673 min.

Example 4A5. 4-1(1-acetylpiperidin-4-yl)amino]-N-[(2S)-2-hydroxy-3-{5-methyl-6-[(1,3-oxazol-5-yl)methoxy]-1,2,3,4-tetrahydroisoquinolin-2-yl}propyl]pyrimidine-2-carboxamide (Compound 559)

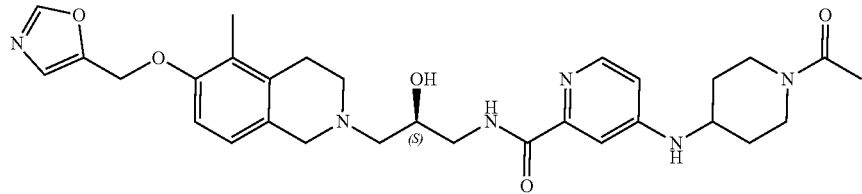

Prepared by general procedure 4A-B. Yield: 12.9 mg (18.8%). $^1$H NMR (500 MHz, CDCl$_3$) δ 1.42 (m, 2H), 2.12 (m, 7H), 2.73 (m, 2H), 2.84 (m, 4H), 3.05 (m, 1H), 3.23 (t, 1H), 3.49 (m, 2H), 3.68 (m, 3H), 3.86 (m, 2H), 4.13 (m, 1H), 4.25 (m, 1H), 4.55 (d, 1H), 5.06 (s, 2H), 6.52 (d, 1H), 6.82 (d, 1H), 6.85 (d, 1H), 7.14 (s, 1H), 7.37 (s, 1H), 7.91 (s, 1H), 8.14 (d, 1H), 8.50 (t, 1H), OH is not observed. LCMS(ESI): [M+H]$^+$ m/z: calcd 562.3. found 5633.3; Rt=0.729 min.

Example 4A6. 4-(cyclobutylamino)-N-[(2S)-2-hydroxy-3-{5-methyl-6-[(1,3-oxazol-5-yl)methoxy]-1,2,3,4-tetrahydroisoquinolin-2-yl}propyl]pyridine-2-carboxamide (Compound 515)

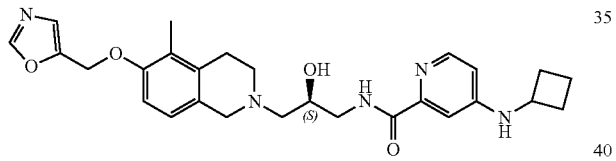

Prepared by general procedure 4A-B. Yield: 23.0 mg (35.0%). $^1$H NMR (DMSO-d$_6$, 400 MHz): δ (ppm) 1.80 (m, 2H), 1.94 (m, 2H), 2.05 (s, 3H), 2.39 (m, 2H), 2.66 (m, 2H), 2.78 (m, 2H), 3.31 (m, 2H), 3.47 (m, 2H), 3.73 (m, 2H), 3.93 (m, 2H), 5.07 (s, 2H), 6.43 (d, 1H), 6.85 (m, 2H), 6.94 (m, 1H), 7.15 (s, 2H), 7.91 (d, 1H), 8.16 (s, 1H), 8.54 (t, 1H). LCMS(ESI): [M+H]$^+$ m/z: calcd 491.3. found 492.2; Rt=0.82 min.

General Procedure 4A-C

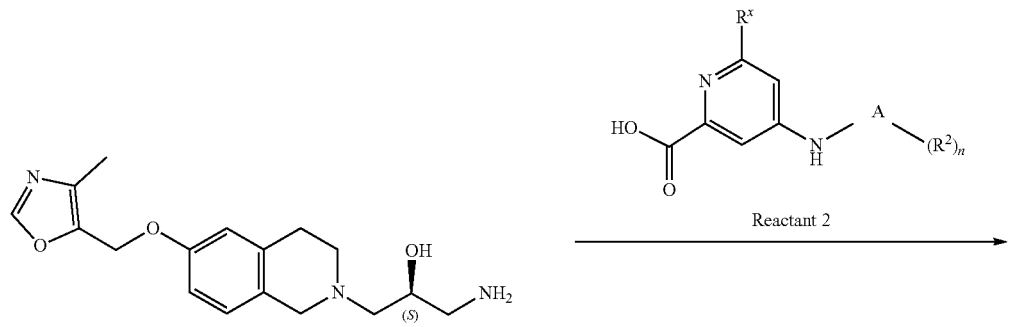

-continued

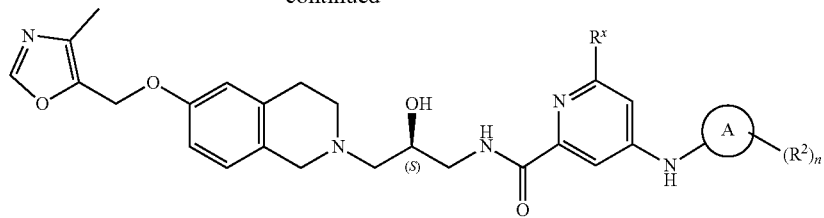

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and $H_2O$-MeOH-0.1$NH_3$ as a mobile phase) to afford pure product.

Example 4A7. 4-(cyclobutylamino)-N-[(2S)-2-hydroxy-3-(6-[(4-methyl-1,3-oxazol-5-yl)methoxy]-1,2,3,4-tetrahydroisoquinolin-2-yl}propyl]pyridine-2-carboxamide (Compound 516)

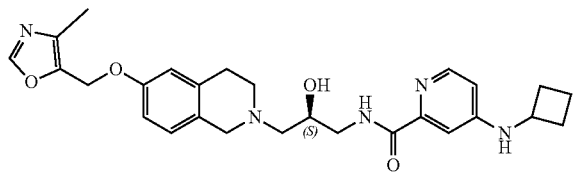

Prepared by general procedure 4A-C. Yield: 4.2 mg (6.75%). $^1$H NMR (Chloroform-d, 500 MHz): δ (ppm) 1.87 (m, 4H), 2.24 (s, 3H), 2.49 (m, 2H), 2.59 (m, 2H), 2.72 (m, 1H), 2.90 (m, 3H), 3.49 (m, 2H), 3.56 (d, 1H), 3.70 (m, 1H), 3.77 (d, 1H), 4.03 (m, 2H), 4.49 (d, 1H), 4.99 (s, 2H), 6.45 (dd, 1H), 6.72 (s, 1H), 6.77 (d, 1H), 6.94 (d, 1H), 7.31 (s, 1H), 7.82 (s, 1H), 8.12 (d, 1H), 8.47 (t, 1H). LCMS(ESI): [M+H]$^+$ m/z: calcd 491.5. found 492.1; Rt=0.79 min.

Example 4A8. 4-(cyclobutylamino)-N-[(2S)-2-hydroxy-3-{5-methyl-6-[(4-methyl-1,3-oxazol-5-yl)methoxy]-1,2,3,4-tetrahydroisoquinolin-2-yl}propyl]pyridine-2-carboxamide (Compound 555)

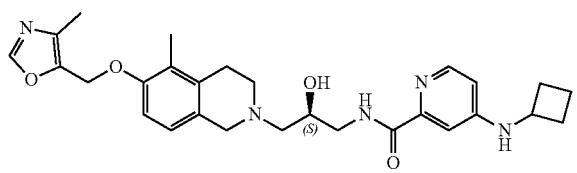

Prepared by general procedure 4A-C. Yield: 15.1 mg (23.1%). $^1$H NMR (Chloroform-d, 400 MHz): δ (ppm) 1.83 (m, 4H), 2.05 (s, 3H), 2.18 (s, 3H), 2.44 (m, 2H), 2.55 (d, 2H), 2.70 (m, 3H), 2.88 (m, 1H), 3.44 (m, 2H), 3.52 (d, 1H), 3.66 (m, 1H), 3.74 (d, 1H), 4.00 (m, 2H), 4.55 (d, 1H), 4.95 (s, 2H), 6.41 (dd, 1H), 6.76 (d, 1H), 6.81 (d, 1H), 7.28 (d, 1H), 7.78 (s, 1H), 8.08 (d, 1H), 8.44 (t, 1H). LCMS(ESI): [M+H]$^+$ m/z: calcd 505.3. found 506.4; Rt=0.83 min.

Example 4A9. (S)-4-(cyclobutylamino)-N-(2-hydroxy-3-(5-methyl-6-((1-methyl-1H-pyrazol-5-yl)methoxy)-3N-dihydroisoquinolin-2(1H)-yl)propyl)picolinamide (Compound 521)

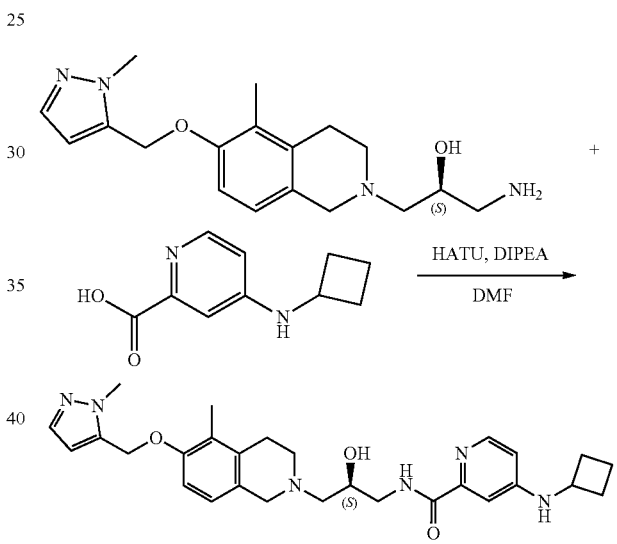

(S)-1-amino-3-(5-methyl-6-((1-methyl-1H-pyrazol-5-yl)methoxy)-3,4-dihydroisoquinolin-2(1H)-yl)propan-2-ol (55 mg, 125.05 umol, 3HCl) and 4-(cyclobutylamino)picolinic acid (26.44 mg, 137.56 umol) were mixed in DMF (1 mL). The reaction suspension was cooled to 0° C. and HATU (49.93 mg, 131.31 umol) followed by DIPEA (113.14 mg, 875.38 umol, 152.48 uL) were added. The clear solution was stirred at ambient temperature for 1.5 hr at 25° C. then volatiles were evaporated under reduced pressure and recidue was subjected to RP-HPLC to give(S)-4-(cyclobutylamino)-N-(2-hydroxy-3-(5-methyl-6-((1-methyl-1H-pyrazol-5-yl)methoxy)-3,4-dihydroisoquinolin-2(1H)-yl)propyl)picolinamide (14.7 mg, 29.13 umol, 23.29% yield). $^1$H NMR (500 MHz, CDCl$_3$) δ (ppm) 1.88 (m, 5H), 2.10 (s, 3H), 2.48 (m, 2H), 2.66 (m, 2H), 2.81 (m, 3H), 3.00 (m, 1H), 3.50 (m, 1H), 3.68 (m, 2H), 3.84 (m, 1H), 3.93 (s, 3H), 4.02 (m, 1H), 4.10 (m, 1H), 4.51 (d, 1H), 5.02 (s, 2H), 6.31 (s, 1H), 6.45 (m, 1H), 6.80 (m, 1H), 6.86 (m, 1H), 7.30 (d, 1H), 7.45 (s, 1H), 8.12 (d, 1H), 8.48 (t, 1H). LCMS(ESI): [M-Boc]$^+$ m/z: calcd 504.3. found 505.4; Rt=0.888 min.

Example 4A1 QMS)-4-(cyclobutylamino)-N-(2-hydroxy-3-(6-((1-methyl-1H-pyrazol-5-yl)methoxy)-3N-dihydroisoquinolin-2(1H)-yl)propyl)picolinamide (Compound 542)

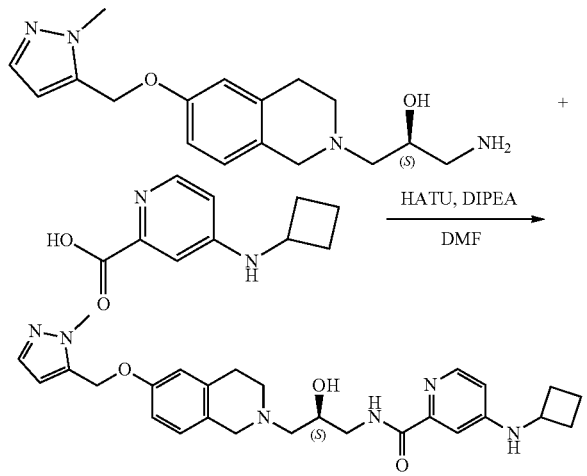

(2S)-1-amino-3-[6-[(2-methylpyrazol-3-yl)methoxy]-3,4-dihydro-1H-isoquinolin-2-yl]propan-2-ol (88 mg, 134.26 umol, 3TFA) and 4-(cyclobutylamino)picolinic acid (28.39 mg, 147.69 umol) were mixed in DMF (1 mF). The reaction suspension was cooled to 0° C. and HATU (53.60 mg, 140.97 umol) followed by DIPEA (12F46 mg, 939.82 umol, 163.70 uF) were added. The clear solution was stirred at ambient temperature for F5 hr at 25° C. then volatiles were evaporated under reduced pressure and recidue was subjected to RP-HPFC to give(S)-4-(cyclobutylamino)-N-(2-hydroxy-3-(6-((1-methyl-1H-pyrazol-5-yl)methoxy)-3,4-dihydroisoquinolin-2(1H)-yl)propyl)picolinamide (8 mg, 16.31 umol, 12.15% yield). $^1$H NMR(Chloroform-d, 500 MHz): δ (ppm) F87 (m, 4H), 2.48 (m, 2H), 2.60 (m, 2H), 2.73 (m, 1H), 2.89 (m, 3H), 3.49 (m, 1H), 3.57 (d, 1H), 3.70 (m, 1H), 3.78 (d, 1H), 3.92 (s, 3H), 4.03 (m, 2H), 4.50 (d, 1H), 5.02 (s, 2H), 6.31 (s, 1H), 6.45 (dd, 1H), 6.72 (s, 1H), 6.77 (dd, 1H), 6.95 (d, 1H), 7.31 (d, 1H), 7.45 (s, 1H), 8.12 (d, 1H), 8.47 (t, 1H). LCMS(ESI): [M+H]$^+$ m/z: calcd 490.3. found 491.2; Rt=0.790 min.

Example 5—Synthesis of Compounds of formula (XIV-a') or formula (XIV-b')

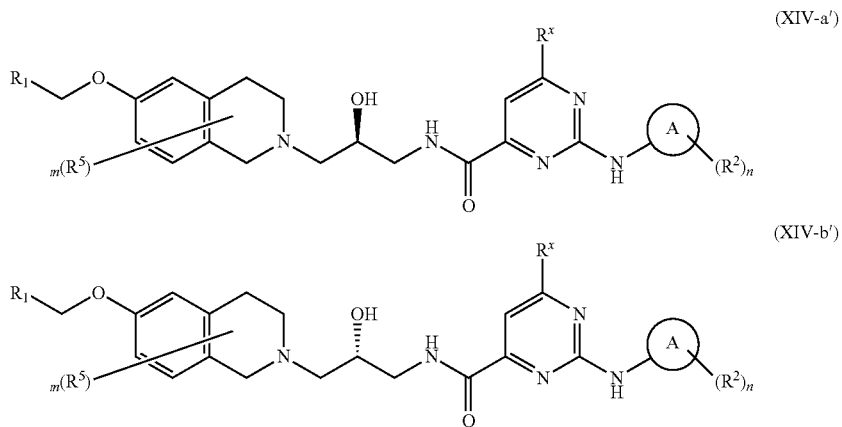

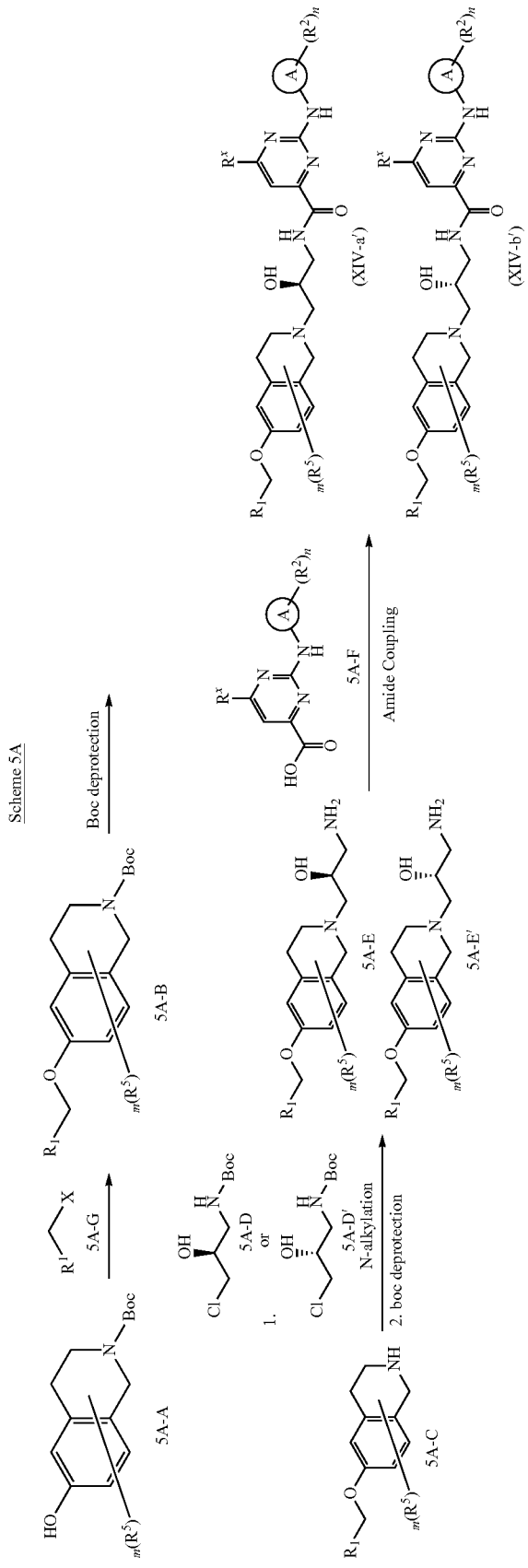

wherein X is a leaving group or hydroxy and variables $R^5$, $R^x$, $R^1$, $R^2$, m, and n are defined herein. In some embodiments, X is selected from —OH, Cl, Br, and I. In some embodiments, X is Cl or Br. In other embodiments, wherein X is —OH.

General Procedure 5A-A

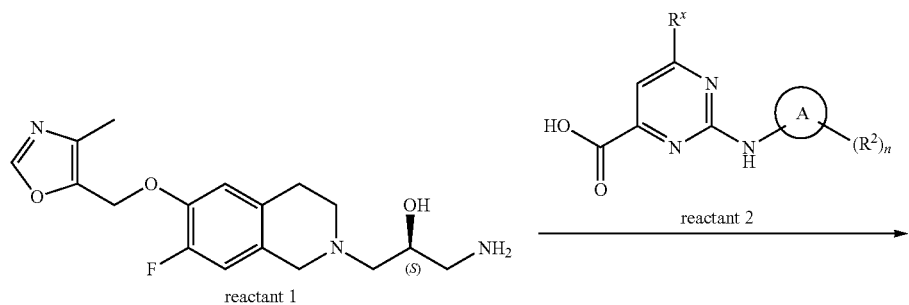

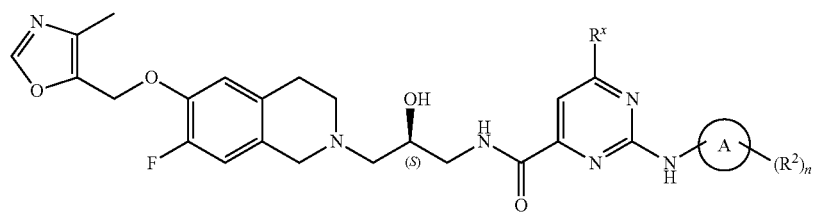

To the solution of Reactant 1 (1.0 equiv, HCl), Reactant 2 (1.0 equiv) and HATU (1.1 equiv) in DMF (1.2 mL) triethylamine (6.0 equiv) was added dropwise. The resulting mixture was stirred at 25° C. for 2 h. After the completion of the reaction, solvent was removed in vacuo and the obtained product was purified by reverse phase HPLC (Device (Mobile Phase, Column): 17_H₂O/R1 Sample info: 25-55% ACN 1-9 min water-acetonitrile, flow: 30 mL/min (loading pump 4Ll/min acetonitrile) to afford pure product.

Example 5A1. 6-[(1-acetylazetidin-3-yl)amino]-N-[(2S)-3-[7-fluoro-6-[(4-methyloxazol-5-yl)methoxy]-3,4-dihydro-1H-isoquinolin-2-yl]-2-hydroxy-propyl]-2-(1-piperidyl)pyrimidine-4-carboxamide (Compound 579)

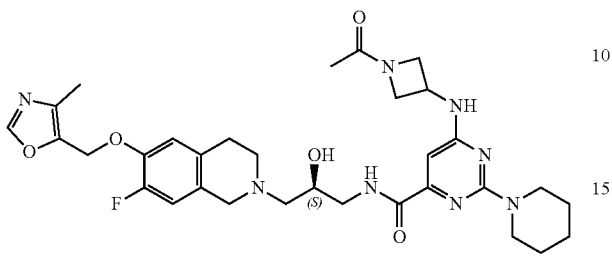

Prepared by general procedure 5A-A. Yield: 9.8 mg (10.32%). $^1$H NMR (Chloroform-d, 400 MHz): δ (ppm) 1.59 (m, 6H), 1.86 (s, 3H), 2.18 (s, 3H), 2.59 (m, 3H), 2.72 (m, 1H), 2.81 (m, 2H), 2.91 (m, 1H), 3.41 (m, 1H), 3.54 (d, 1H), 3.71 (m, 6H), 4.00 (m, 3H), 4.33 (m, 1H), 4.44 (m, 1H), 4.68 (s, 1H), 5.02 (s, 2H), 5.80 (m, 1H), 6.50 (s, 1H), 6.71 (m, 2H), 7.79 (s, 1H), 8.27 (t, 1H). LCMS(ESI): [M+H]$^+$ m/z: calcd 636.3. found 637.2; Rt=1.03 min.

General Procedure 5A-B

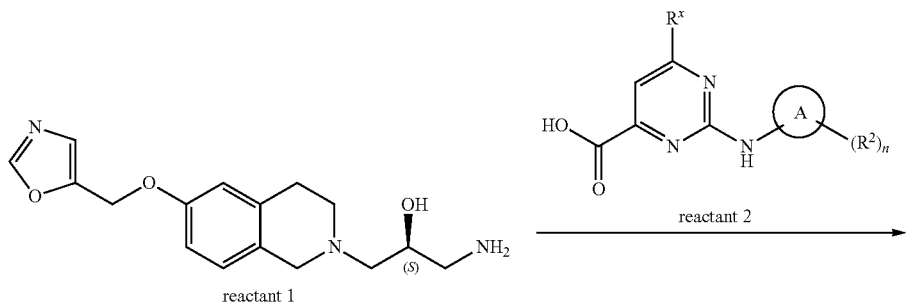

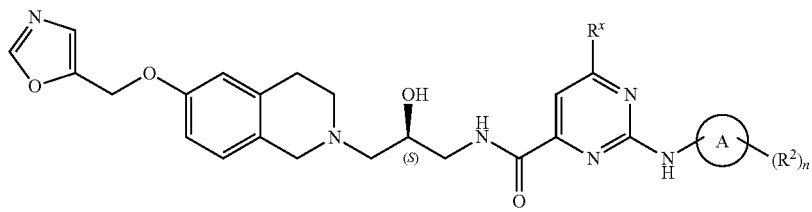

DIPEA (9 equiv) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH as a mobile phase) to afford pure product.

Example 5A2. (S)—N-(2-hydroxy-3-(6-(oxazol-5-ylmethoxy)-3N-dihydroisoquinolin-2(1H)-yl)propyl)-2-(4-isopropylpiperazin-1-yl)-6-(oxetan-3-ylamino)pyrimidine-4-carboxamide (Compound 296)

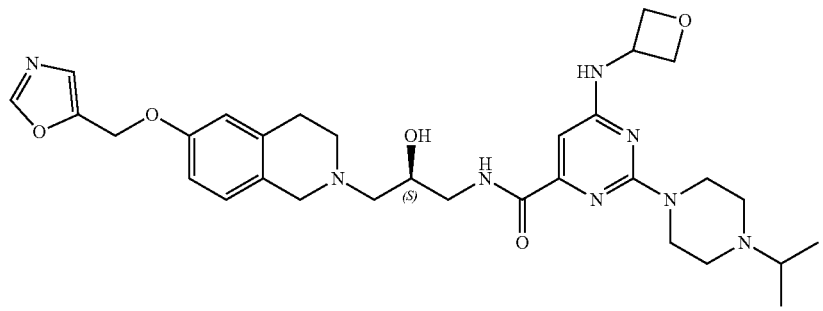

Prepared by general procedure 5A-B. Yield: 14.9 mg (20.68%). $^1$H NMR (DMSO-$d_6$, 400 MHz): δ 1.01 (d, 6H), 2.44 (t, 4H), 2.49 (m, 2H), 2.66 (p, 1H), 2.73 (m, 2H), 2.82 (m, 2H), 3.26 (m, 1H), 3.47 (m, 1H), 3.58 (s, 2H), 3.66 (t, 4H), 3.86 (p, 1H), 4.51 (t, 2H), 4.63 (s, 1H), 4.77 (t, 2H), 4.98 (s, 1H), 5.05 (s, 2H), 6.40 (s, 1H), 6.69 (m, 2H), 6.89 (d, 1H), 7.15 (s, 1H), 7.86 (s, 1H), 8.15 (s, 1H), 8.21 (t, 1H). LCMS(ESI): [M+H]$^+$ m/z: calcd 606.7. found 607.2; Rt=0.752 min.

Example 5A3. (S)-2-(4-(tert-butyl)piperazin-1-yl)-N-(2-hydroxy-3-(6-(oxazol-5-ylmethoxy)-3,4-dihydroisoquinolin-2(1H)-yl)propyl-6-(oxetan-3-ylamino)pyrimidine-4-carboxamide (Compound 373)

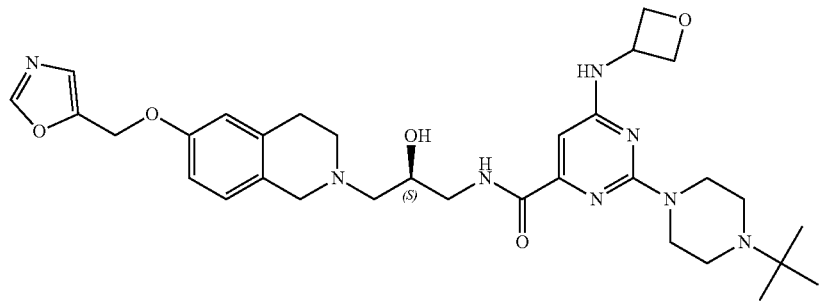

Prepared by general procedure 5A-B. Yield: 17.6 mg (27.86%). $^1$H NMR (DMSO-$d_6$, 400 MHz): δ (ppm) 1.05 (s, 9H), 2.48 (s, 2H), 2.74 (m, 2H), 2.83 (m, 2H), 3.19 (d, 2H), 3.25 (m, 1H), 3.48 (m, 1H), 3.59 (m, 2H), 3.64 (m, 4H), 3.74 (m, 1H), 3.85 (m, 1H), 4.50 (t, 2H), 4.62 (m, 1H), 4.77 (t, 2H), 4.96 (m, 1H), 5.05 (s, 2H), 6.39 (s, 1H), 6.70 (m, 2H), 6.90 (d, 1H), 7.15 (s, 1H), 7.84 (s, 1H), 8.15 (s, 1H), 8.20 (t, 1H). LCMS(ESI): [M+H]$^+$ m/z: calcd 620.7. found 621.2; Rt=0.871 min.

Example 5A4. (S)—N-(2-hydroxy-3-(6-(oxazol-5-ylmethoxy)-3,4-dihydroisoquinolin-2(1H)-yl)propyl)-6-(oxetan-3-ylamino)-2-(piperidin-1-yl)pyrimidine-4-carboxamide (Compound 325)

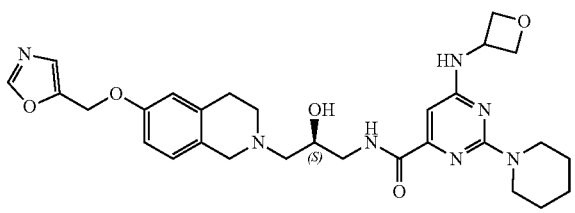

Prepared by general procedure 5A-B. Yield: 26.6 mg (38.95%). $^1$H NMR (500 MHz, CDCl$_3$) δ 1.66 (m, 5H), 2.55 (m, 1H), 2.59 (m, 1H), 2.71 (m, 1H), 2.91 (m, 3H), 3.44 (m, 1H), 3.56 (d, 1H), 3.67 (m, 1H), 3.74 (m, 7H), 4.01 (m, 1H), 4.59 (t, 2H), 4.98 (t, 2H), 5.05 (m, 3H), 5.20 (m, 1H), 6.46 (s, 1H), 6.72 (s, 1H), 6.78 (m, 1H), 6.95 (d, 1H), 7.16 (s, 1H), 7.91 (s, 1H), 8.26 (t, 1H). LCMS(ESI): [M+H]$^+$ m/z: calcd 563.6. found 564.2; Rt=0.997 min.

Example 5A5. (S)-2-(4-acetylpiperazin-1-yl)-N-(2-hydroxy-3-(6-(oxazol-5-ylmethoxy)-3,4-dihydroisoquinolin-2(1H)-yl)propyl-6-(oxetan-3-ylamino)pyrimidine-4-carboxamide (Compound 321)

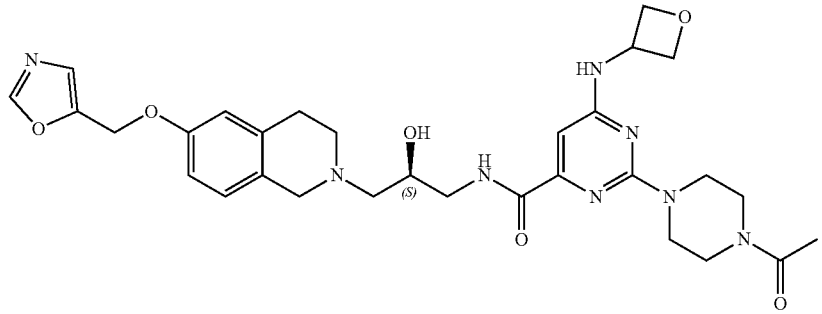

Prepared by general procedure 5A-B. Yield: 18.2 mg (27.51%). $^1$H NMR (400 MHz, DMSO-d$_6$+CCl$_4$) δ 2.04 (s, 3H), 2.74 (m, 2H), 2.82 (m, 2H), 3.26 (d, 1H), 3.46 (d, 7H), 3.58 (m, 2H), 3.66 (m, 2H), 3.71 (m, 2H), 3.86 (m, 1H), 3.99 (m, 1H), 4.50 (t, 2H), 4.78 (t, 2H), 4.98 (m, 1H), 5.05 (s, 2H), 6.46 (m, 1H), 6.71 (m, 2H), 6.90 (d, 1H), 7.16 (s, 1H), 7.97 (m, 1H), 8.15 (s, 1H), 8.26 (t, 1H). LCMS(ESI): [M+H]$^+$ m/z: calcd 606.6. found 607.2; Rt=0.934 min.

Example 5A6. (S)—N-(2-hydroxy-3-(6-(oxazol-5-ylmethoxy)-3N-dihydroisoquinolin-2(1H)-yl)propyl)-2-morpholino-6-(oxetan-3-ylamino)pyrimidine-4-carboxamide(Compound 304)

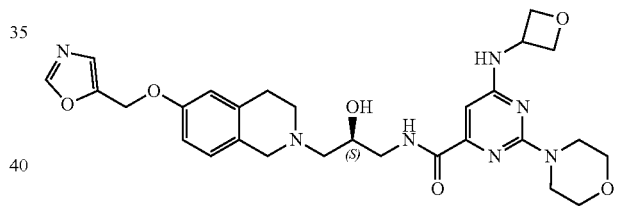

Prepared by general procedure 5A-B. Yield: 12.8 mg (20.75%). $^1$H NMR (500 MHz, CDCl$_3$) δ 1.25 (m, 4H), 1.38 (m, 1H), 2.57 (m, 2H), 2.71 (m, 1H), 2.90 (m, 3H), 3.41 (m, 1H), 3.56 (m, 1H), 3.71 (m, 4H), 3.78 (m, 2H), 4.01 (m, 1H), 4.59 (t, 2H), 4.97 (t, 2H), 5.05 (m, 3H), 5.33 (m, 1H), 6.55 (s, 1H), 6.72 (s, 1H), 6.77 (d, 1H), 6.94 (d, 1H), 7.15 (s, 1H), 7.90 (s, 1H), 8.22 (t, 1H). LCMS(ESI): [M+H]$^+$ m/z: calcd 565.6. found 566.2; Rt=0.979 min.

Example 5A7. (S)-2-(4-ethylpiperazin-1-yl)-N-(2-hydroxy-3-(6-(oxazol-5-ylmethoxy)-3,4-dihydroisoquinolin-2(1H)-yl)propyl-6-(oxetan-3-ylamino)pyrimidine-4-carboxamide (Compound 353)

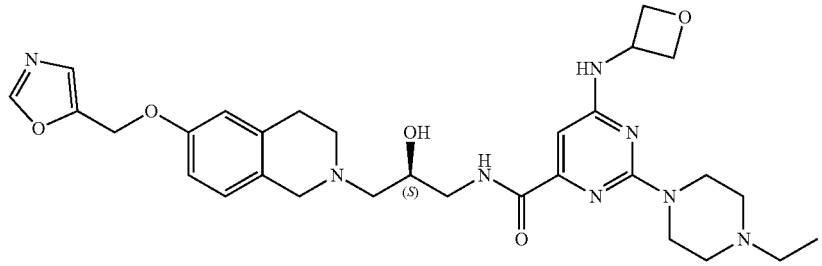

Prepared by general procedure 5A-B. Yield: 4.8 mg (6.82%). ¹H NMR (DMSO-d₆, 500 MHz): δ (ppm) 1.12 (t, 3H), 2.48 (m, 6H), 2.56 (m, 2H), 2.70 (m, 1H), 2.90 (m, 3H), 3.42 (m, 1H), 3.56 (d, 1H), 3.68 (m, 1H), 3.78 (m, 6H), 4.01 (m, 1H), 4.58 (t, 2H), 4.97 (t, 2H), 5.05 (s, 3H), 5.19 (m, 1H), 6.49 (s, 1H), 6.71 (s, 1H), 6.77 (dd, 1H), 6.94 (d, 1H), 7.15 (s, 1H), 7.90 (s, 1H), 8.23 (t, 1H). LCMS(ESI): [M+H]⁺ m/z: calcd 592.7. found 593.2; Rt=0.757 min.

Example 5A8. (S)—N-(2-hydroxy-3-(6-(oxazol-5-ylmethoxy)-3N-dihydroisoquinolin-2(1H)-yl)propyl)-2-((2-methoxyethyl)(methyl)amino)-6-(oxetan-3-ylamino)pyrimidine-4-carboxamide (Compound 295)

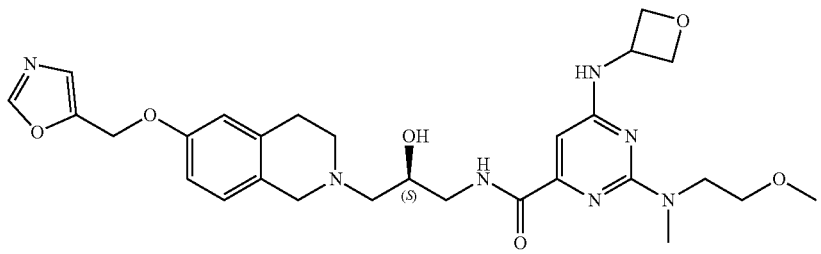

Prepared by general procedure 5A-B. Yield: 14.4 mg (25.53%). ¹H NMR (DMSO-d₆, 400 MHz): δ 2.47 (m, 2H), 2.73 (t, 2H), 2.81 (m, 2H), 3.09 (s, 3H), 3.24 (m, 1H), 3.29 (s, 3H), 3.50 (m, 3H), 3.58 (s, 2H), 3.66 (t, 2H), 3.84 (m, 1H), 4.48 (t, 2H), 4.62 (m, 1H), 4.75 (t, 2H), 4.94 (m, 1H), 5.05 (s, 2H), 6.39 (s, 1H), 6.70 (m, 2H), 6.88 (d, 1H), 7.16 (s, 1H), 7.81 (m, 1H), 8.15 (s, 1H), 8.22 (t, 1H). LCMS(ESI): [M+2H]⁺ m/z: calcd 567.6. found 568.2; Rt=0.950 min.

Example 5A9. (S)—N-(2-hydroxy-3-(6-(oxazol-5-ylmethoxy)-3N-dihydroisoquinolin-2(1H)-yl)propyl)-2-(4-isobutylpiperazin-1-yl)-6-(oxetan-3-ylamino)pyrimidine-4-carboxamide (Compound 313)

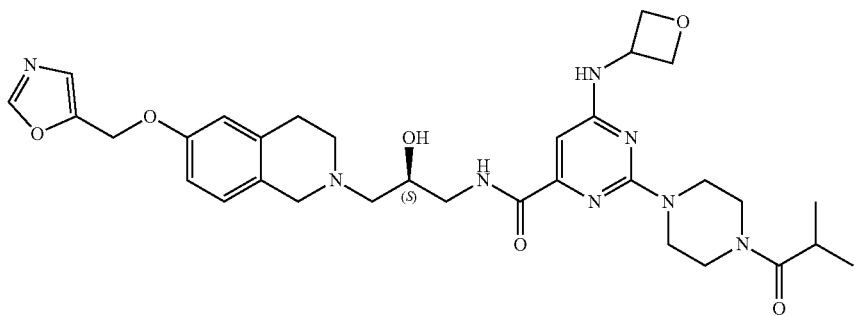

Prepared by general procedure 5A-B. Yield: 11.6 mg (16.76%). ¹H NMR (500 MHz, CDCl₃) δ 1.17 (d, 6H), 2.58 (m, 2H), 2.72 (m, 1H), 2.84 (m, 1H), 2.89 (m, 2H), 2.93 (m, 1H), 3.42 (m, 1H), 3.57 (m, 4H), 3.74 (m, 8H), 4.02 (m, 1H), 4.60 (t, 2H), 4.99 (t, 2H), 5.06 (m, 3H), 5.33 (m, 1H), 6.56 (m, 1H), 6.73 (d, 1H), 6.78 (dd, 1H), 6.95 (d, 1H), 7.16 (s, 1H), 7.91 (s, 1H), 8.21 (t, 1H). LCMS(ESI): [M+H]⁺ m/z: calcd 634.7. found 635.2; Rt=0.989 min.

Example 5A10. (S)-2-(4-(cyclopropanecarbonyl)piperazin-1-yl)-N-(2-hydroxy-3-(6-(oxazol-5-ylmethoxy)-3,4-dihydroisoquinolin-2(1H)-yl)propyl)-6-(oxetan-3-ylamino)pyrimidine-4-carboxamide (Compound 290)

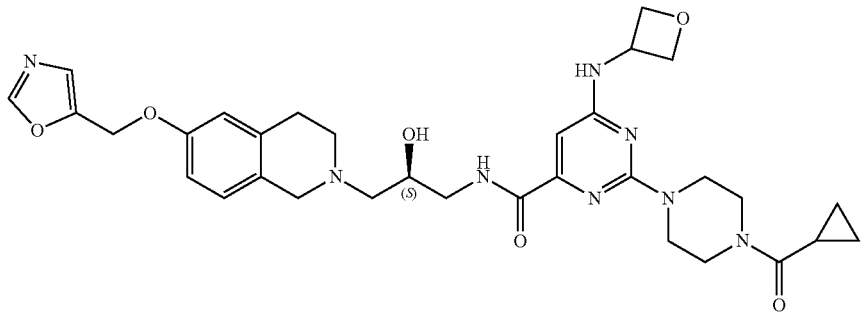

Prepared by general procedure 5A-B. Yield: 18.2 mg (27.61%). $^1$H NMR (DMSO-d$_6$, 400 MHz): δ 0.71 (m, 2H), 0.82 (m, 2H), 1.87 (m, 1H), 2.73 (m, 2H), 2.81 (m, 2H), 3.09 (m, 1H), 3.27 (m, 1H), 3.46 (m, 2H), 3.51 (m, 2H), 3.59 (s, 2H), 3.72 (m, 6H), 3.87 (m, 1H), 4.51 (t, 2H), 4.67 (m, 1H), 4.79 (t, 2H), 5.01 (m, 1H), 5.05 (s, 2H), 6.46 (m, 1H), 6.71 (m, 2H), 6.91 (d, 1H), 7.16 (s, 1H), 7.97 (m, 1H), 8.15 (s, 1H), 8.26 (t, 1H). LCMS(ESI): [M+H]$^+$ m/z: calcd 632.7. found 633.2; Rt=0.935 min.

Example 5A11. (S)—N-(2-hydroxy-3-(6-(oxazol-5-ylmethoxy)-3,4-dihydroisoquinolin-2(1H)-yl)propyl)-2-(methyl(propyl)amino)-6-(oxetan-3-ylamino)pyrimidine-4-carboxamide (Compound 294)

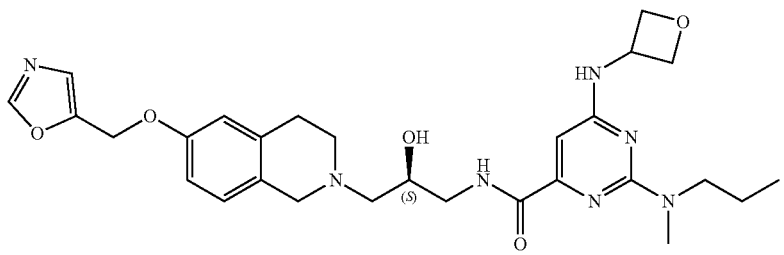

Prepared by general procedure 5A-B. Yield: 18.7 mg (25.43%). $^1$H NMR (DMSO-d$_6$, 400 MHz): δ 0.90 (t, 3H), 1.56 (p, 2H), 2.47 (m, 2H), 2.73 (m, 2H), 2.82 (m, 2H), 3.04 (s, 3H), 3.24 (m, 1H), 3.48 (t, 2H), 3.57 (s, 2H), 3.85 (s, 1H), 4.50 (t, 2H), 4.62 (d, 1H), 4.76 (t, 2H), 4.95 (m, 1H), 5.05 (s, 2H), 6.37 (s, 1H), 6.71 (m, 2H), 6.90 (d, 2H), 7.16 (s, 1H), 7.79 (s, 1H), 8.15 (s, 1H), 8.22 (t, 1H). LCMS(ESI): [M+H]$^+$ m/z: calcd 551.6. found 552.2; Rt=1.039 min.

Example 5A12. (S)—N-(2-hydroxy-3-(6-(oxazol-5-ylmethoxy)-3,4-dihydroisoquinolin-2(1H)-yl)propyl)-6-(oxetan-3-ylamino)-2-(4-propionylpiperazin-1-yl)pyrimidine-4-carboxamide (Compound 309)

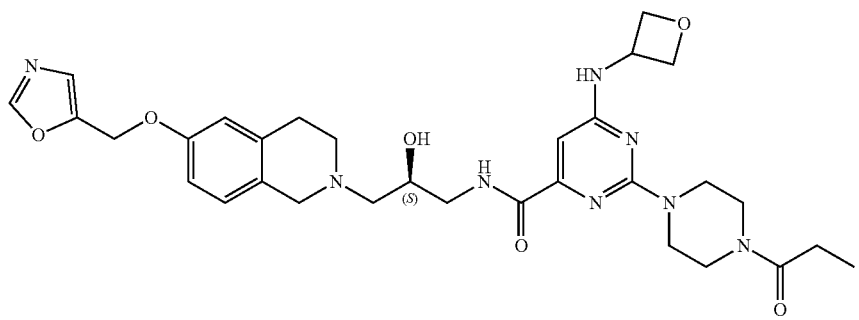

Prepared by general procedure 5A-B. Yield: 23.6 mg (40.23%). $^1$H NMR (500 MHz, CDCl$_3$) δ 1.20 (t, 3H), 2.40 (q, 2H), 2.57 (m, 2H), 2.71 (m, 1H), 2.91 (m, 3H), 3.42 (m, 1H), 3.56 (m, 4H), 3.78 (m, 8H), 4.02 (m, 1H), 4.60 (t, 2H), 4.99 (t, 2H), 5.06 (m, 3H), 5.34 (m, 1H), 6.56 (m, 1H), 6.73 (d, 1H), 6.78 (dd, 1H), 6.95 (d, 1H), 7.16 (s, 1H), 7.91 (s, 1H), 8.20 (t, 1H). LCMS(ESI): [M+2H]$^+$ m/z: calcd 620.7. found 621.2; Rt=0.945 min.

Example 5A13. of (S)-6-((1-acetylazetidin-3-yl)amino)-N-(2-hydroxy-3-(6-(oxazol-5-ylmethoxy)-3,4-dihydroisoquinolin-2(1H)-yl)propyl-2-morpholinopyrimidine-4-carboxamide (Compound 583)

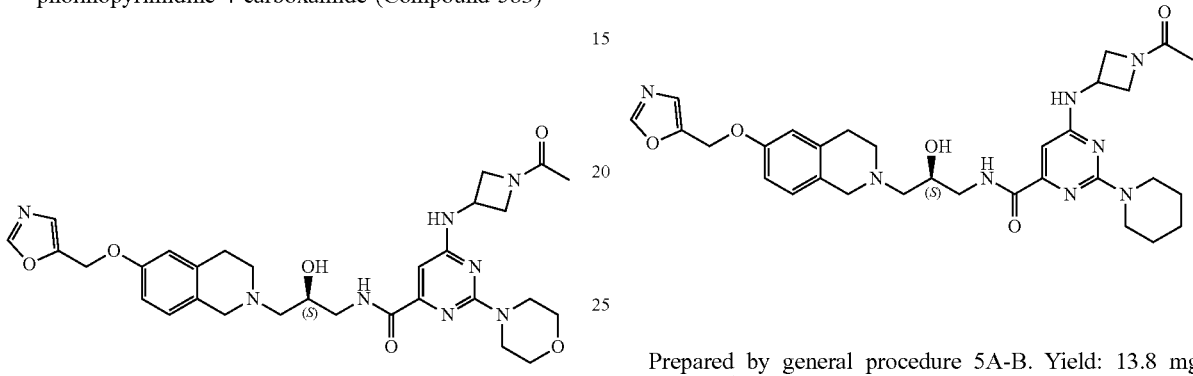

Prepared by general procedure 5A-B. Yield: 15 mg (24.89%). $^1$H NMR (DMSO-d$_6$, 500 MHz): δ (ppm) 1.77 (s, 3H), 2.45 (m, 2H), 2.74 (m, 2H), 2.82 (m, 2H), 3.23 (m, 1H), 3.48 (d, 1H), 3.58 (m, 2H), 3.65 (m, 7H), 3.78 (m, 1H), 3.85 (d, 1H), 3.99 (m, 1H), 4.14 (m, 1H), 4.40 (d, 1H), 4.60 (m, 1H), 4.65 (m, 1H), 5.05 (s, 2H), 6.44 (s, 1H), 6.70 (m, 2H), 6.90 (d, 1H), 7.16 (s, 1H), 7.88 (m, 1H), 8.16 (s, 1H), 8.25 (t, 1H). LCMS(ESI): [M+2H]$^+$ m/z: calcd 606.6. found 607.2; Rt=0.888 min.

Example 5A14. (S)-6-((1-acetylazetidin-3-yl)amino)-N-(2-hydroxy-3-(6-(oxazol-5-ylmethoxy)-3,4-dihydroisoquinolin-2(1H)-yl)propyl)-2-(piperidin-1-yl)pyrimidine-4-carboxamide (Compound 365)

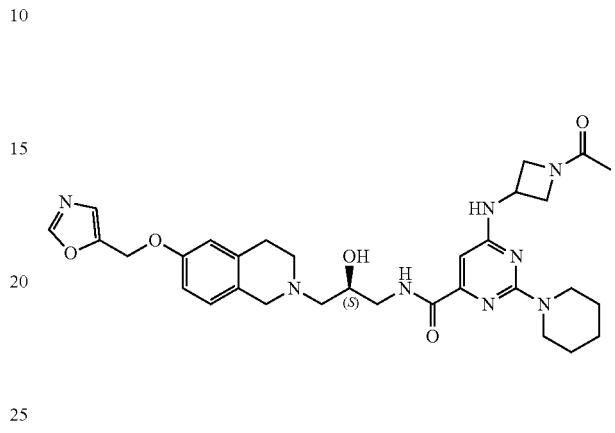

Prepared by general procedure 5A-B. Yield: 13.8 mg (20.93%). $^1$H NMR (CDCl$_3$, 500 MHz): δ (ppm) 1.59 (m, 5H), 1.67 (m, 2H), 1.90 (s, 3H), 2.61 (m, 2H), 2.74 (m, 1H), 2.93 (m, 3H), 3.44 (m, 1H), 3.60 (m, 1H), 3.71 (m, 6H), 3.94 (m, 1H), 4.04 (m, 2H), 4.38 (t, 1H), 4.48 (t, 1H), 4.68 (m, 1H), 5.05 (s, 2H), 5.21 (d, 1H), 6.48 (s, 1H), 6.73 (s, 1H), 6.78 (d, 1H), 6.95 (d, 1H), 7.16 (s, 1H), 7.91 (s, 1H), 8.27 (t, 1H). LCMS(ESI): [M+H]$^+$ m/z: calcd 604.7. found 605.2; Rt=0.967 min.

General Procedure 5A-B

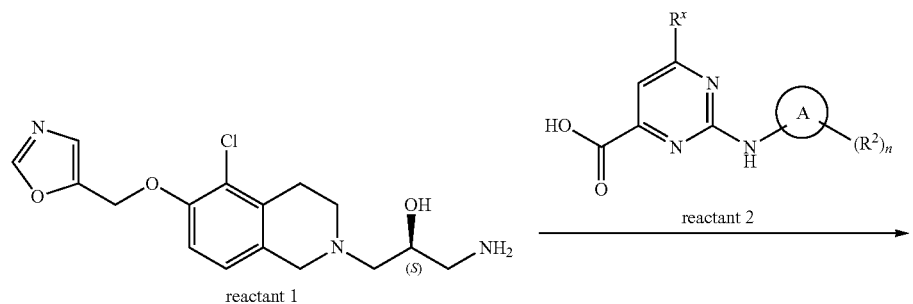

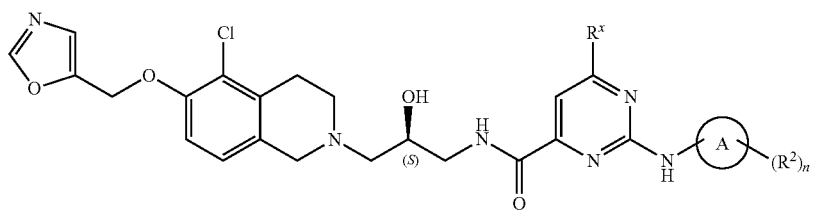

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters SunFire C18 19*100 5 mkm column and $H_2O$-MeOH as a mobile phase) to afford pure product.

Example 5A15. (S)—N-(3-(5-chloro-6-(oxazol-5-ylmethoxy)-3,4-dihydroisoquinolin-2(1H)-yl)-2-hydroxypropyl)-2-(4-methylpiperazin-1-yl)-6-(oxetan-3-ylamino)pyrimidine-4-carboxamide (Compound 285)

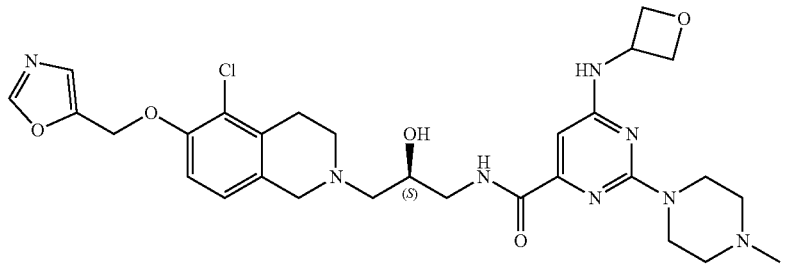

Prepared by general procedure 5A-B. Yield: 15.1 mg (22.03%). $^1$H NMR (DMSO-$d_6$, 400 MHz): δ (ppm) 2.23 (s, 3H), 2.32 (m, 4H), 2.78 (m, 4H), 3.24 (m, 2H), 3.47 (m, 2H), 3.59 (s, 2H), 3.67 (m, 4H), 3.84 (s, 1H), 4.49 (t, 2H), 4.67 (m, 1H), 4.77 (t, 2H), 4.98 (s, 1H), 5.16 (s, 2H), 6.41 (s, 1H), 6.92 (d, 1H), 6.99 (d, 1H), 7.19 (s, 1H), 7.88 (s, 1H), 8.18 (s, 1H), 8.23 (t, 1H). LCMS(ESI): [M+H]$^+$ m/z: calcd 613.1. found 614.2; Rt=0.803 min.

Example 5A16. (S)—N-(3-(5-chloro-6-(oxazol-5-ylmethoxy)-3N-dihydroisoquinolin-2(1H)-yl)-2-hydroxypropyl)-2-(4-isopropylpiperazin-1-yl)-6-(oxetan-3-ylamino)pyrimidine-4-carboxamide (Compound 293)

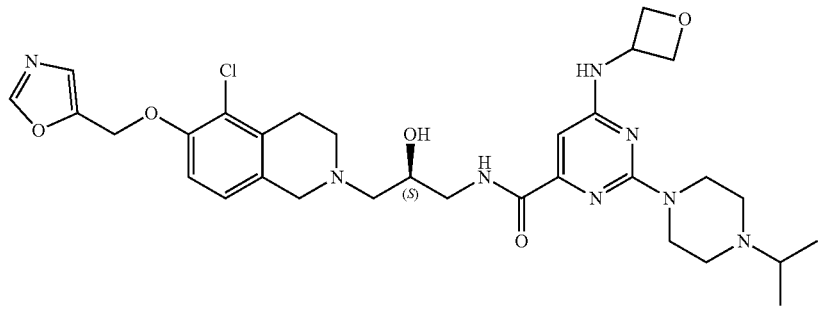

Prepared by general procedure 5A-B. Yield: 17.9 mg (26.56%). ¹H NMR (DMSO-d₆, 400 MHz): δ 2.44 (m, 6H), 2.70 (m, 1H), 2.80 (m, 4H), 3.26 (m, 2H), 3.46 (m, 2H), 3.60 (m, 3H), 3.66 (m, 6H), 3.86 (m, 1H), 4.48 (t, 2H), 4.67 (d, 1H), 4.75 (t, 2H), 4.95 (m, 1H), 5.15 (s, 2H), 6.39 (s, 1H), 6.91 (d, 1H), 7.00 (d, 1H), 7.19 (s, 1H), 7.85 (s, 1H), 8.17 (s, 1H), 8.20 (t, 1H), NH is not observed. LCMS(ESI): [M+H]⁺ m/z: calcd 641.2. found 642.1; Rt=0.791 min.

Example 5A18. (S)—N-(3-(5-chloro-6-(oxazol-5-ylmethoxy)-3N-dihydroisoquinolin-2(1H)-yl)-2-hydroxypropyl)-6-(oxetan-3-ylamino)-2-(piperidin-1-yl)pyrimidine-4-carboxamide (Compound 327)

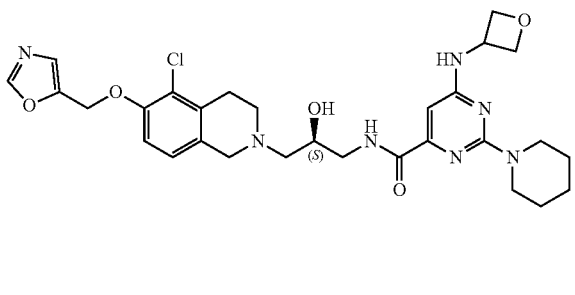

Prepared by general procedure 5A-B. Yield: 10.8 mg (15.53%). ¹H NMR (500 MHz, CDCl₃) δ 1.66 (m, 6H), 2.57 (m, 2H), 2.75 (m, 1H), 2.89 (m, 2H), 2.95 (m, 1H), 3.44 (m, 1H), 3.57 (m, 1H), 3.68 (m, 2H), 3.74 (m, 5H), 4.02 (m, 1H), 4.59 (t, 2H), 4.98 (t, 2H), 5.08 (m, 1H), 5.13 (s, 2H), 5.19 (m, 1H), 6.45 (s, 1H), 6.86 (d, 1H), 6.90 (d, 1H), 7.17 (s, 1H), 7.92 (s, 1H), 8.25 (t, 1H). LCMS(ESI): [M+H]⁺ m/z: calcd 598.1. found 599.2; Rt=1.094 min.

Example 5A19. (S)-2-(4-(tert-butyl)piperazin-1-yl)-N-(3-(5-chloro-6-(oxazol-5-ylmethoxy)-3N-dihydroisoquinolin-2(1H)-yl)-2-hydroxypropyl)-6-(oxetan-3-ylamino)pyrimidine-4-carboxamide (Compound 370)

Prepared by general procedure 5A-B. Yield: 23.6 mg (36.61%). ¹H NMR (DMSO-de, 400 MHz) δ 1.05 (s, 9H), 2.48 (m, 2H), 2.78 (m, 4H), 3.19 (d, 4H), 3.26 (m, 1H), 3.46 (m, 1H), 3.62 (m, 5H), 3.76 (q, 2H), 3.85 (m, 1H), 4.50 (t, 2H), 4.77 (t, 2H), 4.96 (m, 1H), 5.15 (s, 2H), 6.39 (s, 1H), 6.93 (d, 1H), 6.99 (d, 1H), 7.19 (s, 1H), 7.85 (s, 1H), 8.17 (s, 1H), 8.20 (t, 1H). LCMS(ESI): [M+H]⁺ m/z: calcd 655.2. found 656.2; Rt=0.904 min.

Example 5A20. (S)—N-(3-(5-chloro-6-(oxazol-5-ylmethoxy)-3,4-dihydroisoquinolin-2(1H)-yl)-2-hydroxypropyl)-2-morpholino-6-(oxetan-3-ylamino)pyrimidine-4-carboxamide (Compound 298)

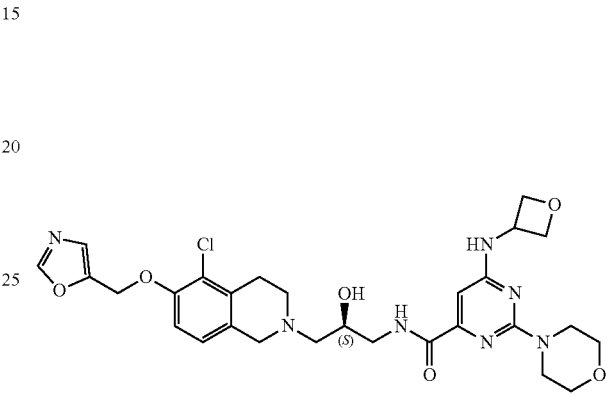

Prepared by general procedure 5A-B. Yield: 17.9 mg (25.17%). ¹H NMR (DMSO-d₆, 400 MHz): δ 2.47 (m, 1H), 2.77 (s, 4H), 3.26 (m, 1H), 3.46 (m, 1H), 3.61 (m, 10H), 3.84 (m, 1H), 4.49 (t, 2H), 4.67 (m, 1H), 4.77 (t, 2H), 4.97 (m, 1H), 5.16 (s, 2H), 6.45 (m, 1H), 6.93 (s, 1H), 6.98 (d, 1H), 7.19 (s, 1H), 7.94 (m, 1H), 8.17 (s, 1H), 8.23 (t, 1H), NH is not observed. LCMS(ESI): [M+H]⁺ m/z: calcd 600.1. found 601.2; Rt=0.928 min.

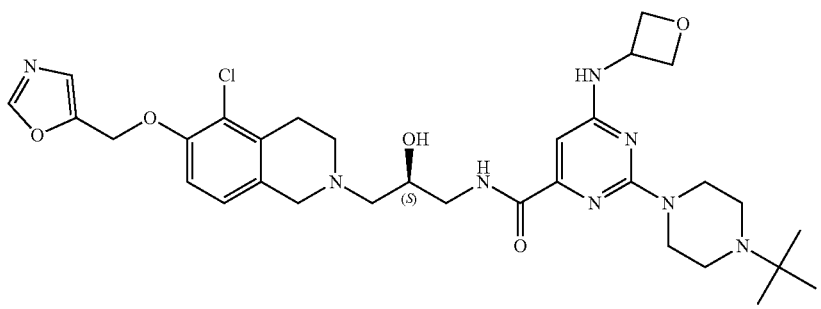

Example 5A21. (S)-2-(4-acetylpiperazin-1-yl)-N-(3-(5-chloro-6-(oxazol-5-ylmethoxy)-3,4-dihydroiso-quinolin-2(1H)-yl)-2-hydroxypropyl)-6-(oxetan-3-ylamino)pyrimidine-4-carboxamide (Compound 300)

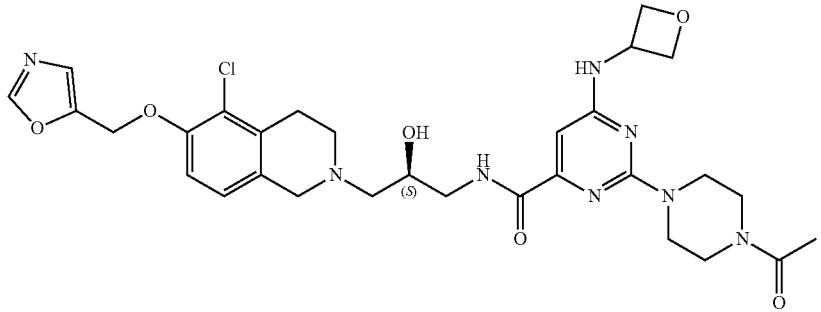

Prepared by general procedure 5A-B. Yield: 24.1 mg (34.31%). $^1$H NMR (400 MHZ, DMSO-$d_6$) δ 2.04 (s, 3H), 2.77 (s, 4H), 3.25 (m, 1H), 3.48 (m, 6H), 3.59 (s, 2H), 3.64 (m, 2H), 3.72 (m, 2H), 3.86 (m, 1H), 4.50 (t, 2H), 4.70 (d, 2H), 4.78 (t, 2H), 4.99 (m, 1H), 5.16 (d, 2H), 6.44 (m, 1H), 6.94 (d, 1H), 6.99 (d, 1H), 7.20 (s, 1H), 7.95 (m, 1H), 8.18 (s, 1H), 8.25 (t, 1H). LCMS(ESI): [M+2H]$^+$ m/z: calcd 641.1. found 642.2; Rt=0.902 min.

Example 5A22. (S)—N-(3-(5-chloro-6-(oxazol-5-ylmethoxy)-3N-dihydroisoquinolin-2(1H)-yl)-2-hydroxypropyl)-2-(4-isobutyrylpiperazin-1-yl)-6-(oxetan-3-ylamino)pyrimidine-4-carboxamide (Compound 323)

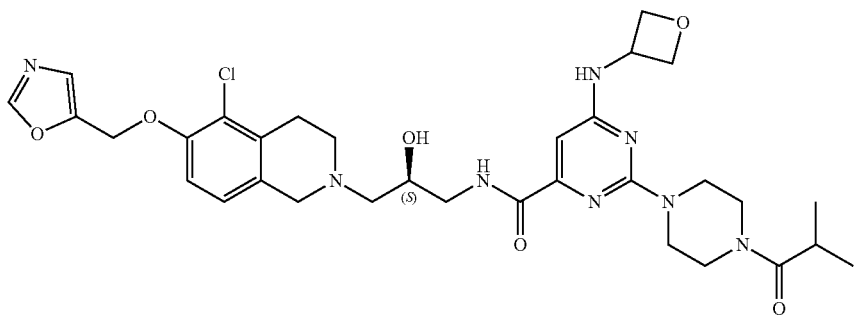

Prepared by general procedure 5A-B. Yield: 20.1 mg (29.85%). $^1$H NMR (400 MHz, DMSO-$d_6$+CCl$_4$) δ 1.06 (d, 6H), 2.81 (m, 5H), 3.27 (m, 1H), 3.49 (m, 6H), 3.60 (m, 2H), 3.71 (m, 5H), 3.86 (m, 1H), 4.50 (t, 2H), 4.70 (m, 1H), 4.79 (t, 2H), 4.97 (m, 1H), 5.16 (s, 2H), 6.46 (m, 1H), 6.93 (d, 1H), 6.98 (d, 1H), 7.19 (s, 1H), 7.97 (m, 1H), 8.17 (s, 1H), 8.25 (m, 1H). LCMS(ESI): [M+H]$^+$ m/z: calcd 669.2. found 670.4; Rt=1.051 min.

Example 5A23. (S)—N-(3-(5-chloro-6-(oxazol-5-ylmethoxy)-3N-dihydroisoquinolin-2(1H)-yl)-2-hydroxypropyl)-6-(oxetan-3-ylamino)-2-(4-propionylpiperazin-1-yl)pyrimidine-4-carboxamide (Compound 318)

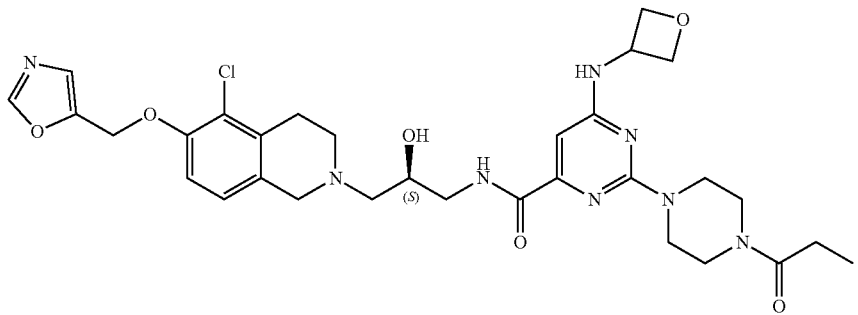

Prepared by general procedure 5A-B. Yield: 20.1 mg (26.9%). $^1$H NMR (400 MHz, DMSO-$d_6$+CCl$_4$) δ 1.07 (t, 3H), 2.34 (m, 2H), 2.78 (m, 4H), 3.14 (m, 2H), 3.28 (m, 1H), 3.48 (m, 5H), 3.60 (m, 2H), 3.65 (m, 2H), 3.71 (m, 2H), 3.86 (m, 1H), 4.51 (t, 2H), 4.70 (m, 1H), 4.78 (t, 2H), 4.99 (m, 1H), 5.16 (s, 2H), 6.45 (m, 1H), 6.93 (d, 1H), 7.00 (d, 1H), 7.19 (s, 1H), 7.96 (m, 1H), 8.18 (s, 1H), 8.25 (m, 1H). LCMS(ESI): [M+H]$^+$ m/z: calcd 655.1. found 656.2; Rt=1.008 min.

Example 5A24. (S)—N-(3-(5-chloro-6-(oxazol-5-ylmethoxy)-3N-dihydroisoquinolin-2(1H)-yl)-2-hydroxypropyl-2-(4-ethylpiperazin-1-yl-6-(oxetan-3-ylamino)pyrimidine-4-carboxamide(Compound 324)

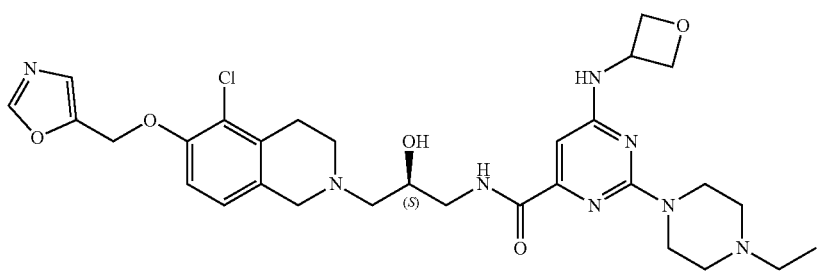

Prepared by general procedure 5A-B. Yield: 12.2 mg (17.4%). $^1$H NMR (500 MHz, Chloroform-d) δ 1.13 (t, 3H), 2.48 (m, 6H), 2.57 (m, 2H), 2.75 (m, 1H), 2.89 (m, 3H), 3.43 (m, 1H), 3.56 (m, 1H), 3.72 (m, 3H), 3.77 (m, 1H), 3.80 (m, 3H), 4.02 (m, 1H), 4.59 (t, 2H), 4.98 (t, 2H), 5.09 (m, 1H), 5.13 (s, 2H), 5.27 (m, 1H), 6.50 (s, 1H), 6.88 (m, 2H), 7.17 (s, 1H), 7.92 (s, 1H), 8.24 (t, 1H). LCMS(ESI): [M+2H]$^+$ m/z: calcd 627.1. found 628.2; Rt=0.797 min.

Example 5A25. (S)—N-(3-(5-chloro-6-(oxazol-5-ylmethoxy)-3N-dihydroisoquinolin-2(1H)-yl)-2-hydroxypropyl)-2-(4-(cyclopropanecarbonyl)piperazin-1-yl)-6-(oxetan-3-ylamino)pyrimidine-4-carboxamide (Compound 297)

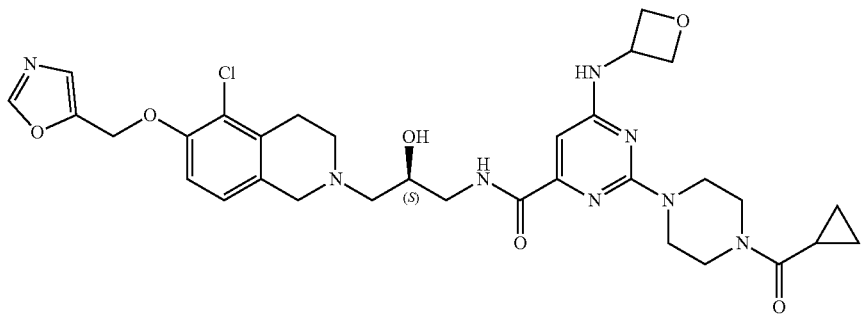

Prepared by general procedure 5A-B. Yield: 21.3 mg (26.94%). $^1$H NMR (400 MHz, DMSO-$d_6$+CCl$_4$) δ 0.72 (m, 2H), 0.82 (m, 2H), 1.88 (m, 1H), 2.76 (s, 4H), 3.07 (m, 1H), 3.28 (m, 1H), 3.49 (m, 3H), 3.60 (s, 2H), 3.71 (m, 7H), 3.86 (m, 1H), 4.51 (t, 2H), 4.71 (d, 1H), 4.79 (t, 2H), 5.00 (m, 1H), 5.15 (s, 2H), 6.45 (m, 1H), 6.94 (d, 1H), 6.98 (d, 1H), 7.19 (s, 1H), 7.95 (m, 1H), 8.17 (s, 1H), 8.26 (q, 1H). LCMS(ESI): [M+H]$^+$ m/z: calcd 667.2. found 668.2; Rt=0.968 min.

Example 5A26. (S)—N-(3-(5-chloro-6-(oxazol-5-ylmethoxy)-3N-dihydroisoquinolin-2(1H)-yl)-2-hydroxypropyl-2-((2-methyoxyethyl)(methyl)amino)-6-(oxetan-3-ylamino)pyrimidine-4-carboxamide (Compound 314)

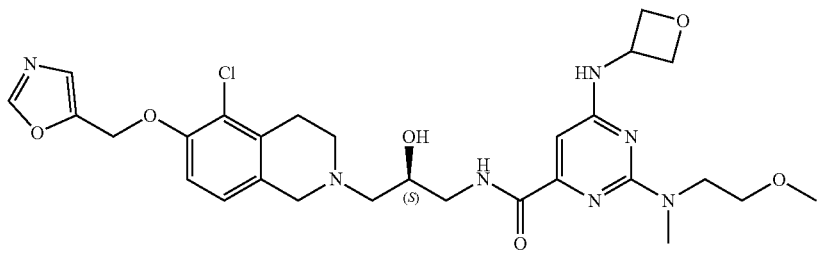

Prepared by general procedure 5A-B. Yield: 16.6 mg (27.4%). $^1$H NMR (400 MHz, DMSO-$d_6$+CCl$_4$) δ 2.77 (m, 4H), 3.09 (s, 3H), 3.25 (m, 2H), 3.29 (s, 3H), 3.48 (m, 3H), 3.59 (m, 2H), 3.67 (m, 2H), 3.74 (m, 1H), 3.83 (m, 1H), 4.49 (t, 2H), 4.66 (d, 1H), 4.76 (t, 2H), 4.94 (m, 1H), 5.16 (s, 2H), 6.39 (m, 1H), 6.92 (d, 1H), 6.99 (d, 1H), 7.19 (s, 1H), 7.81 (m, 1H), 8.17 (s, 1H), 8.21 (m, 1H). LCMS(ESI): [M+H]$^+$ m/z: calcd 602.1. found 603.2; Rt=0.992 min.

Example 5A27. (S)—N-(3-(5-chloro-6-(oxazol-5-ylmethoxy)-3N-dihydroisoquinolin-2(1H)-yl)-2-hydroxypropyl)-2-(methyl(propyl)amino)-6-(oxetan-3-ylamino)pyrimidine-4-carboxamide (Compound 312)

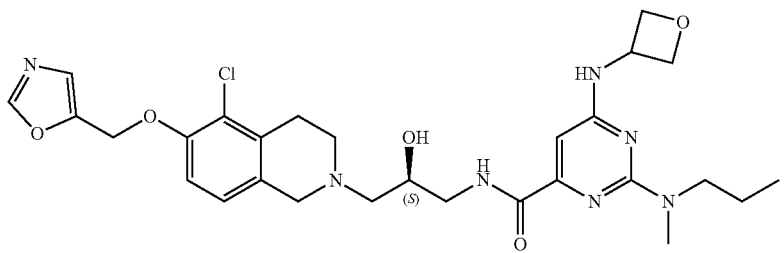

Prepared by general procedure 5A-B. Yield: 9.7 mg (14.23%). $^1$H NMR (500 MHz, Chloroform-d) δ 0.92 (t, 3H), 1.62 (m, 3H), 2.56 (m, 2H), 2.75 (m, 1H), 2.89 (m, 2H), 2.95 (m, 1H), 3.11 (s, 3H), 3.44 (m, 1H), 3.54 (m, 3H), 3.67 (m, 1H), 3.77 (d, 1H), 4.02 (m, 1H), 4.60 (t, 2H), 4.98 (t, 2H), 5.06 (m, 1H), 5.13 (s, 2H), 5.18 (m, 1H), 6.46 (s, 1H), 6.88 (m, 2H), 7.17 (s, 1H), 7.92 (s, 1H), 8.33 (t, 1H). LCMS(ESI): [M+2H]$^+$ m/z: calcd 586.1. found 591.2; Rt=0.87 min.

Example 5A28. S)-6-((1-acetylazetidin-3-yl)amino)-N-(3-(5-chloro-6-(oxazol-5-ylmethoxy)-3A-dihydroisoquinolin-2(1H)-yl)-2-hydroxypropyl)-2-(piperidin-1-yl)pyrimidine-4-carboxamide (Compound 532)

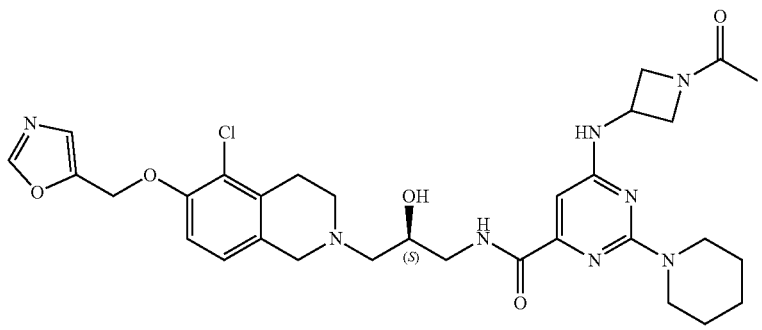

Prepared by general procedure 5A-B. Yield: 8.8 mg (13.38%). $^1$H NMR (500 MHz, CDCl$_3$) δ 1.68 (m, 6H), 1.90 (s, 3H), 2.69 (m, 2H), 2.93 (m, 3H), 3.09 (m, 1H), 3.44 (m, 2H), 3.65 (m, 2H), 3.74 (m, 4H), 3.87 (m, 1H), 3.95 (m, 1H), 4.02 (m, 1H), 4.12 (m, 1H), 4.39 (t, 1H), 4.48 (t, 1H), 4.70 (m, 1H), 5.14 (s, 2H), 5.28 (m, 1H), 6.47 (s, 1H), 6.90 (m, 2H), 7.18 (s, 1H), 7.92 (s, 1H), 8.29 (t, 1H). LCMS(ESI): [M+2H]$^+$ m/z: calcd 639.1. found 640.2; Rt=1.032 min.

Example 5A29. (S)-6-((1-acetylazetidin-3-yl)amino)-N-(3-(5-chloro-6-(oxazol-5-ylmethoxy)-3A-dihydroisoquinolin-2(1H)-yl)-2-hydroxypropyl)-2-morpholinopyrimidine-4-carboxamide (Compound 352)

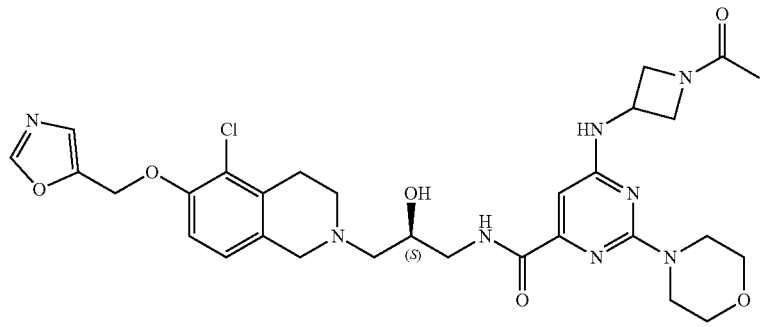

Prepared by general procedure 5A-B. Yield: 13.7 mg (22.2%). $^1$H NMR (DMSO-$d_6$, 500 MHz): δ (ppm) 1.90 (s, 3H), 2.56 (m, 2H), 2.75 (m, 1H), 2.90 (m, 3H), 3.42 (m, 1H), 3.57 (m, 1H), 3.66 (m, 1H), 3.74 (s, 10H), 3.94 (m, 1H), 4.02 (m, 2H), 4.39 (m, 1H), 4.48 (m, 1H), 4.68 (m, 1H), 5.13 (s, 2H), 5.37 (m, 1H), 6.57 (s, 1H), 6.85 (d, 1H), 6.89 (d, 1H), 7.16 (s, 1H), 7.91 (s, 1H), 8.22 (t, 1H). LCMS(ESI): [M+H]$^+$ m/z: calcd 641.1. found 642.2; Rt=0.977 min.

General Procedure 5A-C

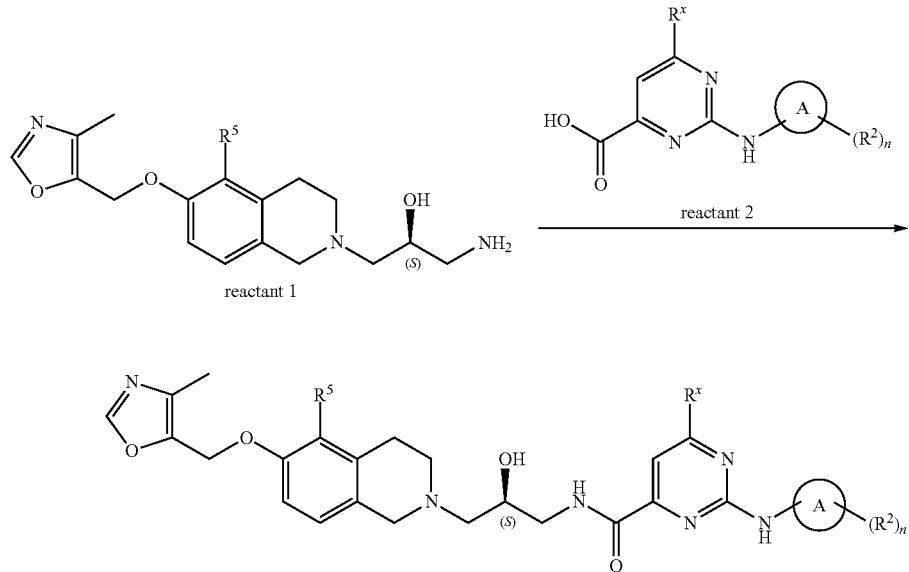

wherein R$^5$ is defined herein.

Conditions 1. Reactant 1 and reactant 2 were mixed in DMF (5 mL). The reaction suspension was cooled to 0° C. and HATU followed by TEA were added. The clear solution was stirred at ambient temperature for 1.5 hr at 25° C. then volatiles were evaporated under reduced pressure and residue was subjected to RP-HPLC to give product.

Conditions 2. DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH-0.1NH$_3$ as a mobile phase) to afford pure product.

Example 5A30. (S)-6-(cyclobutylamino)-N-(2-hydroxy-3-(6-((4-methyloxazol-5-yl)methoxy)-3,4-dihydroisoquinolin-2(1H)-yl)propyl)-2-(piperidin-1-yl)pyrimidine-4-carboxamide (Compound 639)

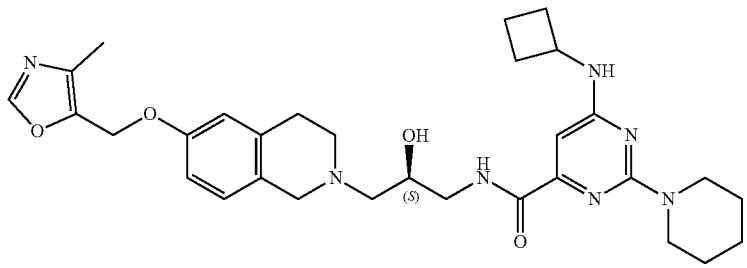

Prepared by general procedure 5A-C, condition 1. Yield: 23.6 mg (18.15%). $^1$H NMR (500 MHz, DMSO-d$_6$): δ 1.47 (m, 4H), 1.57 (m, 2H), 1.68 (m, 2H), 1.88 (m, 2H), 2.15 (s, 3H), 2.25 (m, 2H), 2.50 (m, 1H), 2.67 (m, 2H), 2.76 (m, 2H), 3.21 (m, 1H), 3.41 (m, 2H), 3.53 (s, 2H), 3.67 (m, 4H), 3.85 (m, 1H), 4.36 (m, 1H), 4.93 (d, 1H), 5.07 (s, 2H), 6.30 (s, 1H), 6.75 (m, 2H), 6.94 (d, 1H), 7.55 (m, 1H), 8.28 (s, 1H), 8.35 (m, 1H). LCMS(ESI): [M+H]$^+$ m/z: calcd 575.7. found 576.3; Rt=1.176 min.

Example 5A31. 2-(4-tert-butylpiperazin-1-yl)-N-[(2S)-2-hydroxy-3-(6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 396)

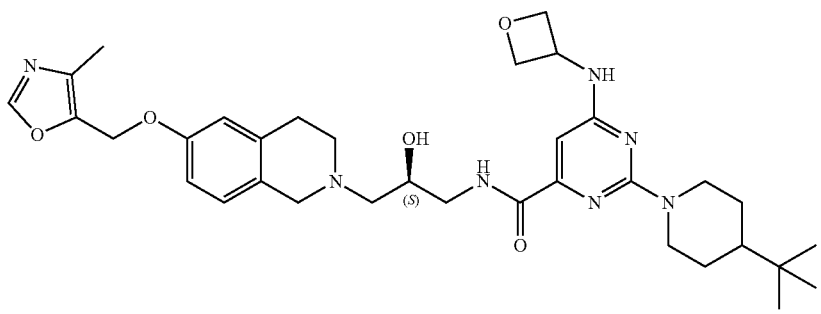

Prepared by general procedure 5A-C, condition 2. Yield: 15.4 mg (21.1%). $^1$H NMR (400 MHz, CDCl$_3$) δ 1.08 (s, 9H), 2.20 (s, 3H), 2.53 (m, 2H), 2.59 (m, 4H), 2.67 (m, 1H), 2.88 (m, 3H), 3.40 (m, 1H), 3.53 (m, 1H), 3.65 (m, 1H), 3.73 (m, 6H), 3.98 (m, 1H), 4.58 (m, 2H), 4.95 (m, 4H), 5.06 (m, 1H), 5.59 (m, 1H), 6.52 (s, 1H), 6.69 (s, 1H), 6.74 (d, 1H), 6.91 (d, 1H), 7.79 (s, 1H), 8.24 (t, 1H). LCMS(ESI): [M+2H]$^+$ m/z: calcd 634.4. found 636.2; Rt=0.81 min.

Example 5A32. 2-(4-cyclopropanecarbonylpiperazin-1-yl)-N-[(2S)-2-hydroxy-3-{6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 400)

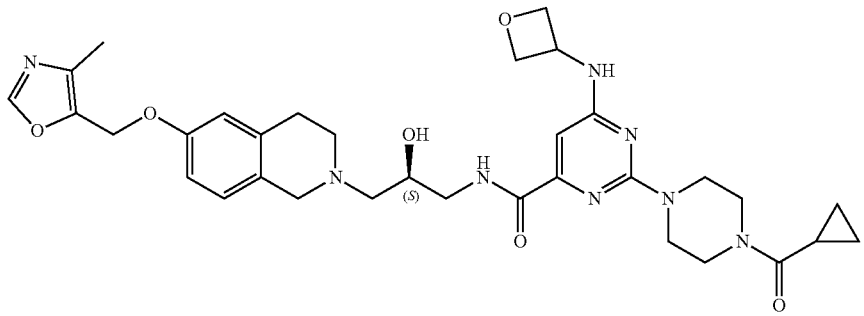

Prepared by general procedure 5A-C, condition 2. Yield: 16.6 mg (23.8%). $^1$H NMR (500 MHz, CDCl$_3$) δ 0.81 (m, 2H), 1.04 (m, 2H), 1.78 (m, 1H), 2.24 (s, 3H), 2.61 (m, 2H), 2.76 (m, 1H), 2.91 (m, 2H), 2.97 (m, 1H), 3.43 (m, 1H), 3.62 (m, 1H), 3.74 (m, 9H), 3.85 (m, 2H), 4.05 (m, 1H), 4.60 (m, 2H), 4.99 (m, 4H), 5.08 (m, 1H), 5.32 (m, 1H), 6.55 (s, 1H), 6.73 (s, 1H), 6.78 (d, 1H), 6.95 (d, 1H), 7.82 (s, 1H), 8.23 (t, 1H). LCMS(ESI): [M+H]$^+$ m/z: calcd 646.3; found 647.0; Rt=0.96 min.

Example 5A33. N-[(2S)-2-hydroxy-3-{6-[(4-methyl-1,3-oxazol-5-yl)methoxy]-1,2,3,4-tetrahydroisoquinolin-2-yl}propyl]-6-[(oxetan-3-yl)amino]-2-(4-propanoylpiperazin-1-yl)pyrimidine-4-carboxamide (Compound 409)

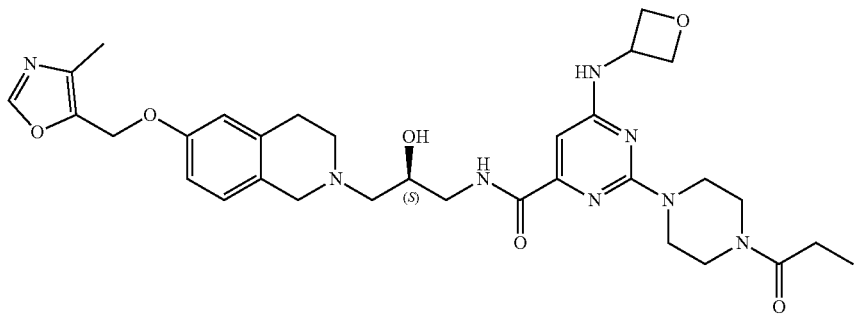

Prepared by general procedure 5A-C, condition 2. Yield: 14.0 mg (17.8%) $^1$H NMR (400 MHz, CDCl$_3$) δ 1.16 (t, 3H), 2.21 (s, 3H), 2.38 (m, 2H), 2.55 (m, 2H), 2.68 (m, 1H), 2.86 (m, 3H), 3.39 (m, 1H), 3.49 (m, 2H), 3.56 (m, 1H), 3.66 (m, 3H), 3.75 (m, 5H), 3.99 (m, 1H), 4.58 (t, 2H), 4.95 (m, 5H), 5.06 (m, 1H), 5.65 (m, 1H), 6.58 (m, 1H), 6.69 (m, 1H), 6.74 (d, 1H), 6.91 (d, 1H), 7.79 (s, 1H), 8.19 (t, 1H). LCMS(ESI): [M+2H]$^+$ m/z: calcd 634.2. found 635.2; Rt=0.96 min.

Example 5A34. N-[(2S)-2-hydroxy-3-{6-[(4-methyl-1,3-oxazol-5-yl)methoxy]-1,2,3,4-tetrahydroisoquinolin-2-yl}propyl]-2-[4-(2-methylpropanoyl)piperazin-1-yl]-6-[(oxetan-3-yl)amino]pyrimidine-4-carboxamide (Compound 454)

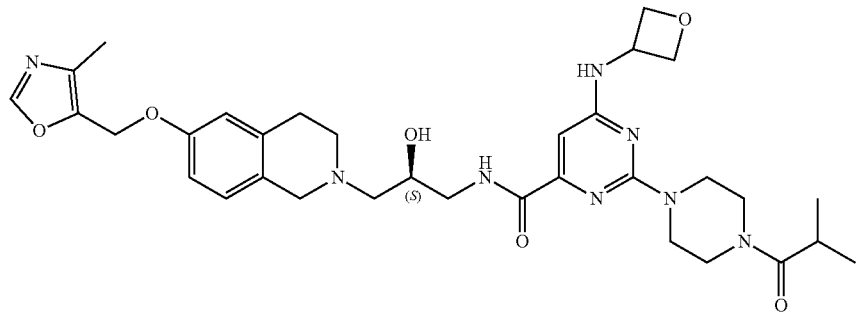

Prepared by general procedure 5A-C, condition 2. Yield: 14.0 mg (22.0%). $^1$H NMR (DMSO-d$_6$, 500 MHz): δ (ppm) 1.06 (d, 6H), 2.18 (s, 3H), 2.74 (m, 2H), 2.83 (m, 3H), 3.25 (m, 2H), 3.47 (m, 1H), 3.51 (m, 4H), 3.59 (s, 2H), 3.69 (m, 5H), 3.86 (s, 1H), 4.50 (t, 2H), 4.67 (s, 1H), 4.78 (t, 2H), 4.98 (s, 3H), 6.45 (s, 1H), 6.68 (m, 2H), 6.90 (d, 1H), 7.97 (s, 1H), 8.02 (s, 1H), 8.25 (t, 1H). LCMS(ESI): [M+H]$^+$ m/z: calcd 648.5. found 649.4; Rt=1.05 min.

Example 5A35. 2-(4-acetylpiperazin-1-yl)-N-[(2S)-2-hydroxy-3-{6-[(4-methyl-E3-oxazol-5-yl)methoxy]-1,2,3,4-tetrahydroisoquinolin-2-yl}propyl]-6-[(oxetan-3-yl)amino]pyrimidine-4-carboxamide (Compound 401)

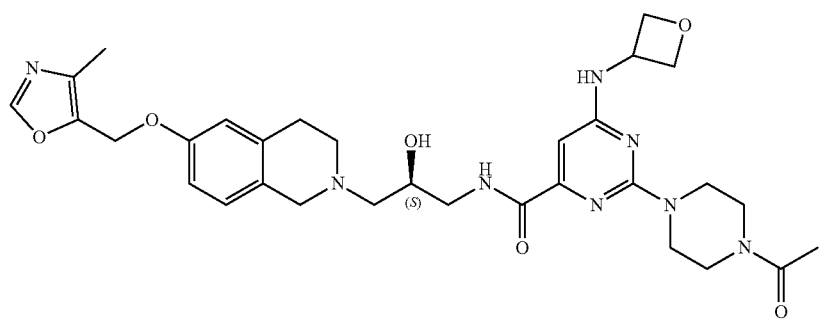

Prepared by general procedure 5A-C, condition 2. Yield: 18.3 mg (27.3%). $^1$H NMR (400 MHz, CDCl$_3$) δ 2.12 (s, 3H), 2.20 (s, 3H), 2.55 (m, 2H), 2.68 (m, 1H), 2.88 (m, 3H), 3.39 (m, 1H), 3.49 (m, 2H), 3.54 (m, 2H), 3.65 (m, 3H), 3.72 (m, 2H), 3.77 (m, 2H), 3.99 (m, 1H), 4.60 (m, 2H), 4.95 (m, 5H), 5.07 (m, 1H), 5.90 (m, 1H), 6.62 (m, 1H), 6.69 (m, 1H), 6.74 (m, 1H), 6.91 (d, 1H), 7.79 (s, 1H), 8.21 (t, 1H). LCMS(ESI): [M+H]$^+$ m/z: calcd 620.2. found 621.3; Rt=0.92 min.

Example 5A36. N-[(2S)-2-hydroxy-3-{6-[(4-methyl-1,3-oxazol-5-yl)methoxy]-1,2,3,4-tetrahydroisoquinolin-2-yl}propyl]-2-(4-methylpiperazin-1-yl)-6-[(oxetan-3-yl)amino]pyrimidine-4-carboxamide (Compound 387)

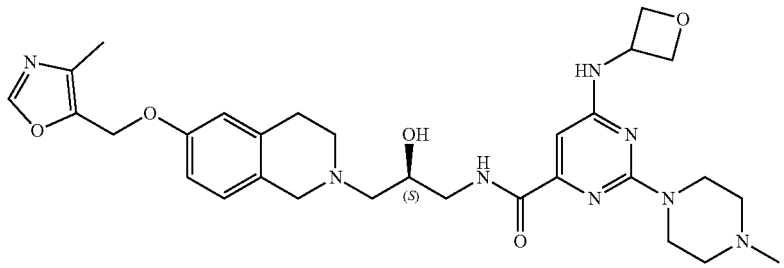

Prepared by general procedure 5A-C, condition 2. Yield: 20.3 mg (35.6%). $^1$H NMR (500 MHz, DMSO-$d_6$+CCl$_4$) δ 2.18 (s, 3H), 2.23 (s, 3H), 2.32 (m, 5H), 2.74 (m, 2H), 2.82 (m, 2H), 3.24 (m, 1H), 3.47 (m, 1H), 3.59 (m, 2H), 3.67 (m, 5H), 3.85 (m, 1H), 4.50 (t, 2H), 4.64 (m, 1H), 4.77 (t, 2H), 4.98 (m, 3H), 6.41 (m, 1H), 6.69 (m, 2H), 6.90 (d, 1H), 7.88 (m, 1H), 8.02 (s, 1H), 8.23 (t, 1H). LCMS(ESI): [M+2H]$^+$ m/z: calcd 592.3. found 594.1; Rt=0.79 min.

Example 5A37. N-[(2S)-2-hydroxy-3-{6-[(4-methyl-1,3-oxazol-5-yl)methoxy]-1,2,3,4-tetrahydroisoquinolin-2-yl}propyl]-6-[(oxetan-3-yl)amino]-2-(piperidin-1-yl)pyrimidine-4-carboxamide (Compound 405)

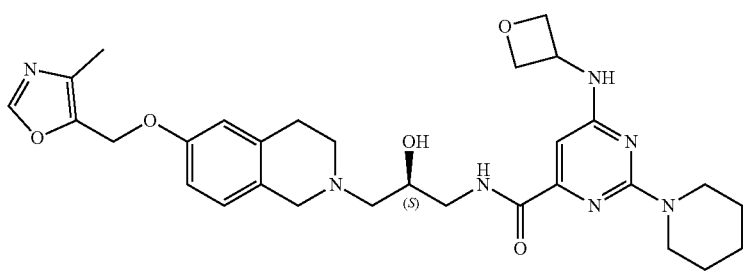

Prepared by general procedure 5A-C, condition 2. Yield: 21.0 mg (28.2%). $^1$H NMR (500 MHz, DMSO-$d_6$+CCl$_4$) δ 1.53 (m, 4H), 1.64 (m, 2H), 2.18 (s, 3H), 2.46 (m, 2H), 2.74 (m, 2H), 2.82 (m, 2H), 3.25 (m, 1H), 3.47 (m, 1H), 3.59 (m, 2H), 3.67 (m, 4H), 3.85 (m, 1H), 4.49 (t, 2H), 4.63 (m, 1H), 4.77 (t, 2H), 4.98 (m, 3H), 6.37 (s, 1H), 6.69 (m, 2H), 6.89 (d, 1H), 7.81 (m, 1H), 8.02 (s, 1H), 8.21 (t, 1H). LCMS (ESI): [M+H]$^+$ m/z: calcd 577.6. found 578.2; Rt=1.09 min.

Example 5A38. 2-(4-ethylpiperazin-1-yl)-N-[(2S)-2-hydroxy-3-(6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 544)

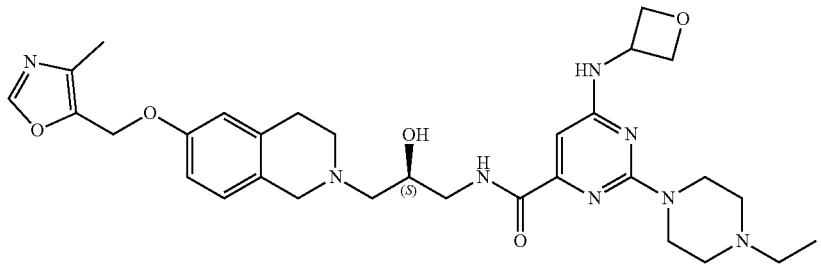

Prepared by general procedure 5A-C, condition 2. Yield: 25.0 mg (38.2%). $^1$H NMR (500 MHz, DMSO-$d_6$+CCl$_4$) δ 1.07 (t, 3H), 2.18 (s, 3H), 2.36 (m, 7H), 2.74 (m, 2H), 2.82 (m, 2H), 3.24 (m, 1H), 3.46 (m, 1H), 3.58 (m, 3H), 3.67 (m, 4H), 3.84 (m, 1H), 4.49 (t, 2H), 4.63 (s, 1H), 4.77 (t, 2H), 4.97 (s, 3H), 6.41 (s, 1H), 6.68 (m, 2H), 6.89 (d, 1H), 7.87 (s, 1H), 8.01 (s, 1H), 8.21 (t, 1H). LCMS(ESI): [M+2H]$^+$ m/z: calcd 606.1. found 608.4; Rt=0.74 min.

Example 5A39. N-[(2S)-2-hydroxy-3-{6-[(4-methyl-1,3-oxazol-5-yl)methoxy]-1,2,3,4-tetrahydroisoquinolin-2-yl}propyl]-2-[methyl(propyl)amino]-6-[(oxetan-3-yl)amino]pyrimidine-4-carboxamide (Compound 390)

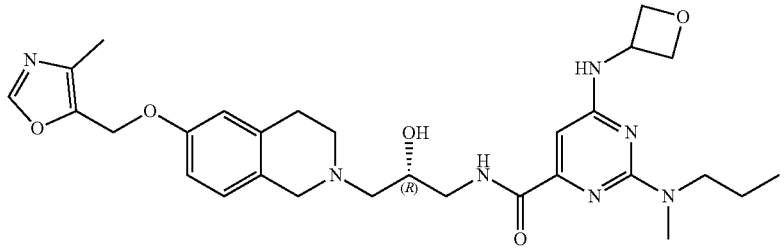

Prepared by general procedure 5A-C, condition 2. Yield: 20.2 mg (29.9%). $^1$H NMR (500 MHz, DMSO-$d_6$+CCl$_4$) δ 0.90 (t, 3H), 1.57 (h, 2H), 2.18 (s, 3H), 2.47 (m, 2H), 2.73 (m, 2H), 2.82 (m, 2H), 3.04 (s, 3H), 3.25 (m, 1H), 3.48 (m, 3H), 3.57 (m, 2H), 3.84 (m, 1H), 4.50 (t, 2H), 4.62 (m, 1H), 4.76 (t, 2H), 4.94 (m, 1H), 4.98 (s, 2H), 6.37 (s, 1H), 6.68 (m, 2H), 6.89 (d, 1H), 7.77 (s, 1H), 8.02 (s, 1H), 8.22 (t, 1H). LCMS(ESI): [M+H]$^+$ m/z: calcd 565.6. found 566.1; Rt=1.04 min.

Example 5A40. N-[(2S)-2-hydroxy-3-{6-[(4-methyl-1,3-oxazol-5-yl)methoxy]-1,2,3,4-tetrahydroisoquinolin-2-yl}propyl]-2-[(2-methoxyethyl)(methyl)amino]-6-[(oxetan-3-yl)amino]pyrimidine-4-carboxamide (Compound 408)

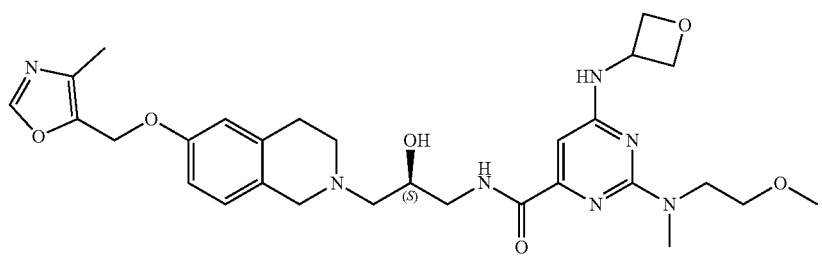

Prepared by general procedure 5A-C, condition 2. Yield: 22.9 mg (41.0%). ¹H NMR (500 MHz, DMSO-d₆+CCl₄) δ 2.18 (s, 3H), 2.46 (m, 2H), 2.74 (m, 2H), 2.82 (m, 2H), 3.10 (s, 3H), 3.25 (m, 1H), 3.29 (s, 3H), 3.49 (m, 3H), 3.58 (m, 2H), 3.68 (t, 2H), 3.84 (m, 1H), 4.50 (t, 2H), 4.63 (m, 1H), 4.76 (t, 2H), 4.93 (m, 1H), 4.98 (s, 2H), 6.40 (m, 1H), 6.68 (m, 2H), 6.89 (d, 1H), 7.82 (m, 1H), 8.02 (s, 1H), 8.22 (m, 1H). LCMS(ESI): [M+H]⁺ m/z: calcd 581.3. found 582.2; Rt=0.98 min.

Example 5A41. N-[(2S)-2-hydroxy-3-{6-[(4-methyl-1,3-oxazol-5-yl)methoxy]-1,2,3,4-tetrahydroisoquinolin-2-yl}propyl]-6-[(oxetan-3-yl)amino]-2-[4-(propan-2-yl)piperazin-1-yl]pyrimidine-4-carboxamide (Compound 492)

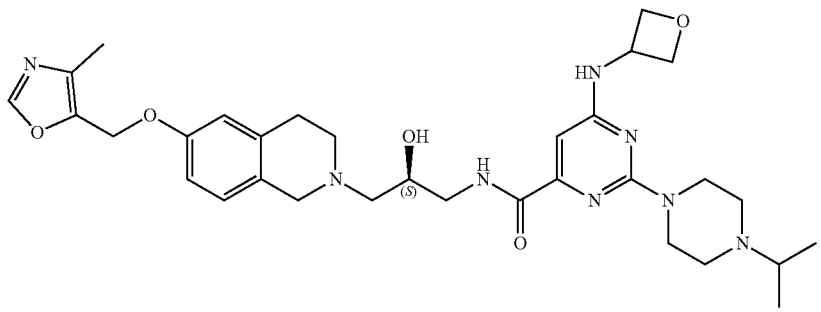

Prepared by general procedure 5A-C, condition 2. Yield: 21.4 mg (30.6%). ¹H NMR (Chloroform-d, 400 MHz): δ (ppm) 1.05 (d, 6H), 2.20 (s, 3H), 2.53 (m, 6H), 2.69 (m, 2H), 2.86 (m, 3H), 3.39 (m, 1H), 3.53 (d, 1H), 3.64 (m, 1H), 3.73 (m, 6H), 3.98 (m, 1H), 4.58 (t, 2H), 4.94 (m, 4H), 5.07 (m, 1H), 5.66 (m, 1H), 6.53 (s, 1H), 6.68 (s, 1H), 6.73 (dd, 1H), 6.91 (d, 1H), 7.79 (s, 1H), 8.24 (t, 1H). LCMS(ESI): [M+H]⁺ m/z: calcd 620.4. found 621.4; Rt=1.81 min.

Example 5A42. 6-[(1-acetylazetidin-3-yl)amino]-N-[(2S)-2-hydroxy-3-{6-[(4-methyl-1,3-oxazol-5-yl)methoxy]-1,2,3,4-tetrahydroisoquinolin-2-yl}propyl]-2-(piperidin-1-yl)pyrimidine-4-carboxamide (Compound 534)

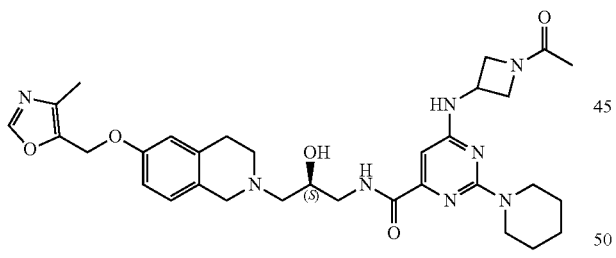

Prepared by general procedure 5A-C, condition 2. Yield: 13.6 mg (20.9%). ¹H NMR (500 MHz, CDCl₃) δ 1.67 (m, 6H), 1.90 (s, 3H), 2.23 (s, 3H), 2.64 (m, 2H), 2.96 (m, 4H), 3.44 (m, 1H), 3.67 (m, 3H), 3.74 (m, 4H), 3.85 (m, 1H), 3.94 (m, 1H), 4.03 (m, 1H), 4.09 (m, 1H), 4.38 (m, 1H), 4.47 (m, 1H), 4.68 (m, 1H), 4.99 (s, 2H), 5.26 (m, 1H), 6.47 (s, 1H), 6.72 (s, 1H), 6.78 (d, 1H), 6.95 (d, 1H), 7.81 (s, 1H), 8.28 (t, 1H). LCMS(ESI): [M+H]⁺ m/z: calcd 618.2; found 619.2; Rt=1.02 min.

Example 5A43. 2-(4-cyclopropanecarbonylpiperazin-1-yl)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 414)

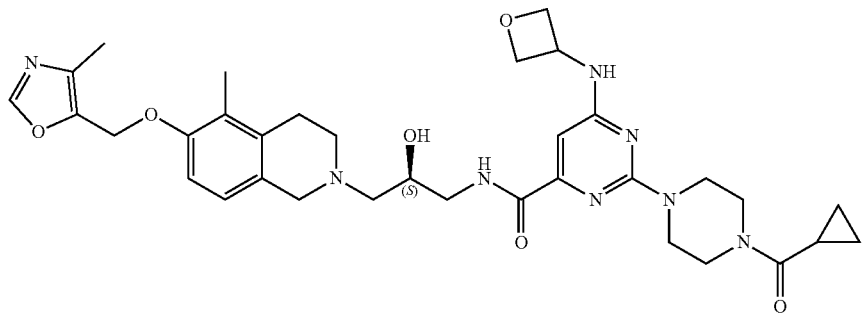

Prepared by general procedure 5A-C, condition 2. Yield: 12.1 mg (16.8%). ¹H NMR (Chloroform-d, 500 MHz): δ (ppm) 0.81 (m, 2H), 1.03 (m, 2H), 1.65 (m, 2H), 1.78 (m, 1H), 2.09 (s, 3H), 2.21 (s, 3H), 2.56 (m, 2H), 2.77 (m, 3H), 2.97 (m, 1H), 3.42 (m, 1H), 3.58 (m, 1H), 3.78 (m, 9H), 4.04 (m, 1H), 4.60 (t, 2H), 4.99 (m, 4H), 5.09 (m, 1H), 5.32 (m, 1H), 6.56 (s, 1H), 6.81 (d, 1H), 6.85 (d, 1H), 7.82 (s, 1H), 8.22 (t, 1H). LCMS(ESI): [M+H]⁺ m/z: calcd 660.3. found 661.0; Rt=0.99 min.

Example 5A44. N-[(2S)-2-hydroxy-3-{5-methyl-6-[(4-methyl-1,3-oxazol-5-yl)methoxy]-1,2,3,4-tetrahydroisoquinolin-2-yl}propyl]-2-(morpholin-4-yl)-6-[(oxetan-3-yl)amino]pyrimidine-4-carboxamide (Compound 423)

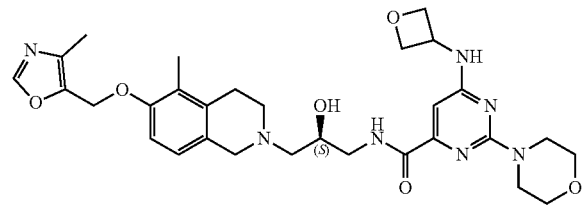

Prepared by general procedure 5A-C, condition 2. Yield: 8.5 mg (11.3%). ¹H NMR (Chloroform-d, 500 MHz): δ (ppm) 2.09 (s, 3H), 2.21 (s, 3H), 2.56 (m, 2H), 2.75 (m, 3H), 2.96 (m, 1H), 3.41 (m, 1H), 3.58 (d, 1H), 3.70 (d, 2H), 3.75 (s, 8H), 4.04 (m, 1H), 4.60 (t, 2H), 4.99 (m, 4H), 5.08 (m, 1H), 5.33 (m, 1H), 6.55 (s, 1H), 6.81 (d, 1H), 6.85 (d, 1H), 7.82 (s, 1H), 8.23 (t, 1H). LCMS(ESI): [M+H]⁺ m/z: calcd 593.4. found 594.2; Rt=0.97 min.

Example 5A45. N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(oxetan-3-yl)amino]-2-(piperidin-1-yl)pyrimidine-4-carboxamide (Compound 391)

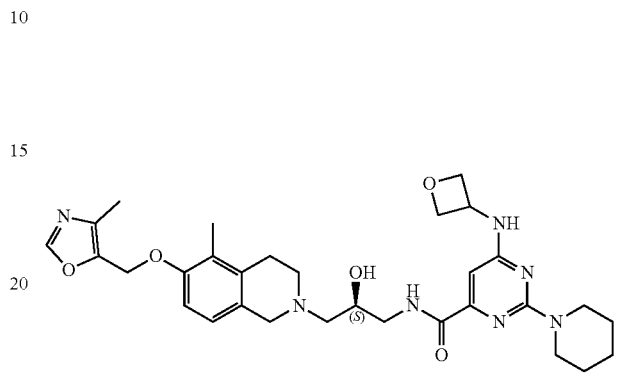

Prepared by general procedure 5A-C, condition 2. Yield: 21.7 mg (32.3%). ¹H NMR (500 MHz, DMSO-d₆+CCl₄) δ 1.53 (m, 4H), 1.63 (m, 2H), 2.01 (s, 3H), 2.16 (s, 3H), 2.47 (m, 2H), 2.68 (m, 2H), 2.75 (m, 2H), 3.26 (m, 1H), 3.47 (m, 1H), 3.58 (m, 2H), 3.66 (m, 4H), 3.85 (m, 1H), 4.49 (t, 2H), 4.62 (m, 1H), 4.77 (t, 2H), 4.98 (s, 3H), 6.37 (m, 1H), 6.79 (s, 2H), 7.81 (m, 1H), 8.01 (s, 1H), 8.21 (t, 1H). LCMS(ESI): [M+H]⁺ m/z: calcd 591.2. found 592.2; Rt=1.09 min.

Example 5A46. N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(oxetan-3-yl)amino]-2-[4-(propan-2-yl)piperazin-1-yl]pyrimidine-4-carboxamide (Compound 444)

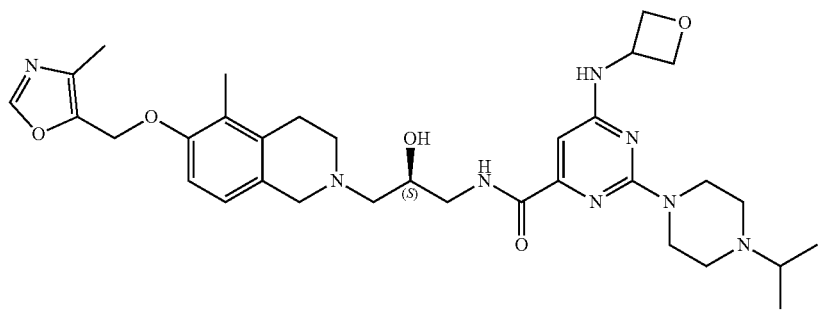

Prepared by general procedure 5A-C, condition 2. Yield: 14.6 mg (19.9%). $^1$H NMR (DMSO-d$_6$, 400 MHz): δ (ppm) 1.02 (d, 6H), 2.02 (s, 3H), 2.16 (s, 3H), 2.45 (m, 7H), 2.68 (m, 2H), 2.76 (m, 2H), 3.24 (m, 1H), 3.47 (m, 1H), 3.62 (m, 6H), 3.85 (m, 1H), 4.49 (t, 2H), 4.63 (s, 1H), 4.77 (t, 2H), 4.98 (s, 3H), 6.39 (s, 1H), 6.80 (s, 2H), 7.88 (d, 1H), 8.01 (s, 1H), 8.22 (t, 1H). LCMS(ESI): [M+2H]$^+$ m/z: calcd 634.4. found 636.4; Rt=0.81 min.

Example 5A47. 2-(4-ethylpiperazin-1-yl)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 385)

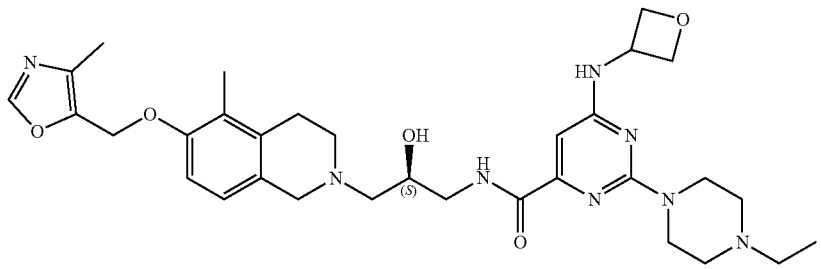

Prepared by general procedure 5A-C, condition 2. Yield: 16.7 mg (24.2%). $^1$H NMR (400 MHz, DMSO-d$_6$+CCl$_4$) δ 0.72 (m, 2H), 0.82 (m, 2H), 1.72 (m, 2H), 1.90 (m, 3H), 2.02 (s, 3H), 2.16 (s, 3H), 2.31 (m, 2H), 2.45 (m, 1H), 2.72 (m, 3H), 2.82 (m, 1H), 3.20 (m, 1H), 3.46 (m, 4H), 3.62 (m, 7H), 3.76 (m, 2H), 3.90 (m, 1H), 4.25 (m, 1H), 4.99 (s, 2H), 6.10 (s, 1H), 6.20 (m, 1H), 6.24 (s, 1H), 6.83 (m, 2H), 8.02 (s, 1H), 8.13 (m, 1H). LCMS(ESI): [M+2H]$^+$ m/z: calcd 620.4. found 622.2; Rt=0.81 min.

Example 5A48. N-[(2K)-2-hydroxy-3-{5-methyl-6-[(4-methyl-1,3-oxazol-5-yl)methoxy]-1,2,3,4-tetrahydroisoquinolin-2-yl}propyl]-2-[methyl(propyl)amino]-6-[(oxetan-3-yl)amino]pyrimidine-4-carboxamide (Compound 465)

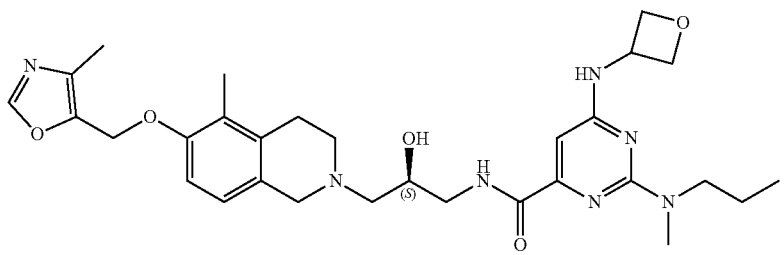

Prepared by general procedure 5A-C, condition 2. Yield: 17.8 mg (24.6%). $^1$H NMR (DMSO-d$_6$, 500 MHz): δ (ppm) 0.90 (t, 3H), 1.56 (m, 2H), 2.01 (s, 3H), 2.16 (s, 3H), 2.47 (m, 2H), 2.68 (m, 2H), 2.74 (m, 2H), 3.03 (s, 3H), 3.26 (m, 1H), 3.47 (m, 3H), 3.57 (m, 2H), 3.84 (m, 1H), 4.50 (t, 2H), 4.61 (m, 1H), 4.76 (t, 2H), 4.94 (s, 1H), 4.98 (s, 2H), 6.37 (s, 1H), 6.79 (m, 2H), 7.77 (s, 1H), 8.01 (s, 1H), 8.22 (t, 1H). LCMS(ESI): [M+H]$^+$ m/z: calcd 579.3; found 580.4; Rt=1.02 min.

Example 5A49. N-[(2S)-2-hydroxy-3-{5-methyl-6-[(4-methyl-1,3-oxazol-5-yl)methoxy]-1,2,3,4-tetrahydroisoquinolin-2-yl}propyl]-2-[(2-methoxyethyl)(methyl)amino]-6-[(oxetan-3-yl)amino]pyrimidine-4-carboxamide (Compound 398)

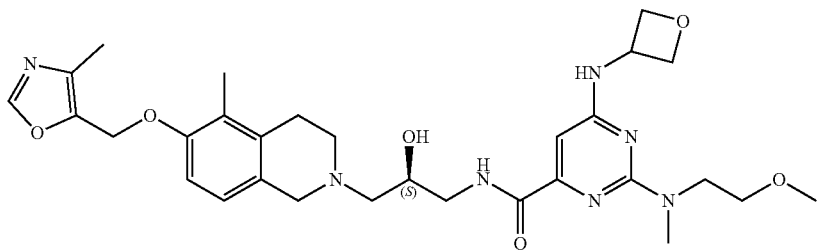

Prepared by general procedure 5A-C, condition 2. Yield: 19.1 mg (28.8%). $^1$H NMR (500 MHz, DMSO-d$_6$+CCl$_4$) δ 2.01 (s, 3H), 2.16 (s, 3H), 2.47 (m, 2H), 2.68 (m, 2H), 2.75 (m, 2H), 3.08 (s, 3H), 3.24 (m, 1H), 3.29 (s, 3H), 3.48 (m, 3H), 3.57 (m, 2H), 3.66 (t, 2H), 3.84 (m, 1H), 4.49 (t, 2H), 4.62 (m, 1H), 4.76 (t, 2H), 4.94 (m, 1H), 4.98 (s, 2H), 6.39 (m, 1H), 6.79 (m, 2H), 7.82 (m, 1H), 8.01 (s, 1H), 8.22 (m, 1H). LCMS(ESI): [M+H]$^+$ m/z: calcd 595.3. found 596.2; Rt=1.01 min.

Example 5A49. N-[(2S)-2-hydroxy-3-{5-methyl-6-[(4-methyl-1,3-oxazol-5-yl)methoxy]-1,2,3,4-tetrahydroisoquinolin-2-yl}propyl]-2-(4-methylpiperazin-1-yl)-6-[(oxetan-3-yl)amino]pyrimidine-4-carboxamide (Compound 456)

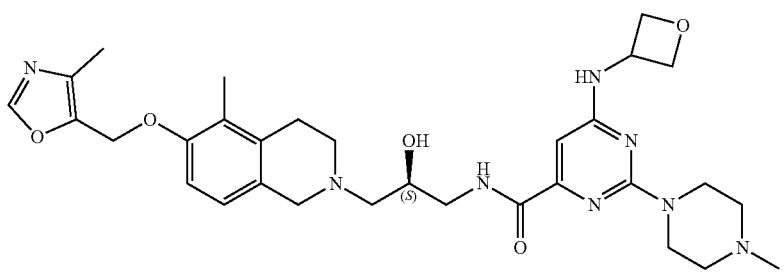

Prepared by general procedure 5A-C, condition 2. Yield: 17.9 mg (25.5%). $^1$H NMR (Chloroform-d, 400 MHz): δ (ppm) 2.05 (s, 3H), 2.17 (s, 3H), 2.31 (s, 3H), 2.42 (m, 4H), 2.53 (m, 2H), 2.72 (m, 3H), 2.91 (t, 1H), 3.40 (m, 1H), 3.53 (d, 1H), 3.66 (m, 1H), 3.73 (m, 5H), 3.98 (m, 1H), 4.58 (t, 2H), 4.95 (m, 4H), 5.06 (m, 1H), 5.64 (m, 1H), 6.54 (s, 1H), 6.77 (d, 1H), 6.81 (d, 1H), 7.78 (s, 1H), 8.23 (t, 1H). LCMS(ESI): [M+2H]$^+$ m/z: calcd 606.1. found 608.2; Rt=0.79 min.

Example 5A50. 2-(4-tert-butylpiperazin-1-yl)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 435)

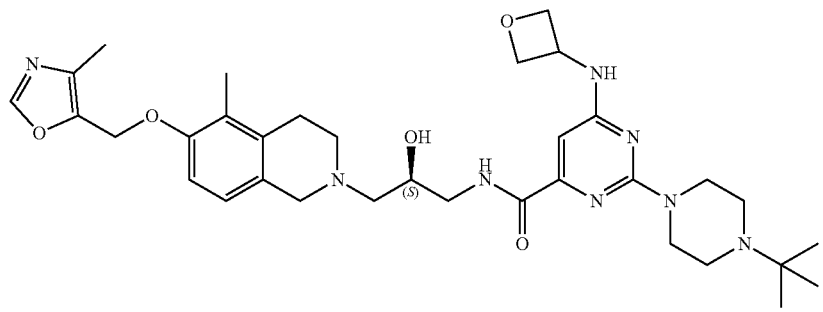

Prepared by general procedure 5A-C, condition 2. Yield: 19.2 mg (26.6%). $^1$H NMR (Chloroform-d, 400 MHz): δ (ppm) 1.07 (s, 9H), 2.05 (s, 3H), 2.17 (s, 3H), 2.52 (m, 2H), 2.58 (m, 4H), 2.72 (m, 3H), 2.91 (m, 1H), 3.40 (m, 1H), 3.53 (d, 1H), 3.65 (m, 1H), 3.74 (m, 6H), 3.98 (m, 1H), 4.58 (t, 2H), 4.95 (m, 4H), 5.06 (s, 1H), 5.59 (d, 1H), 6.52 (s, 1H), 6.77 (d, 1H), 6.81 (d, 1H), 7.78 (s, 1H), 8.24 (t, 1H). LCMS(ESI): [M+2H]$^+$ m/z: calcd 648.4. found 650.4; Rt=0.83 min.

Example 5A51. N-[(2S)-2-hydroxy-3-{5-methyl-6-[(4-methyl-1,3-oxazol-5-yl)methoxy]-1,2,3,4-tetrahydroisoquinolin-2-yl}propyl]-2-[4-(2-methylpropanoyl)piperazin-1-yl]-6-[(oxetan-3-yl)amino]pyrimidine-4-carboxamide (Compound 421)

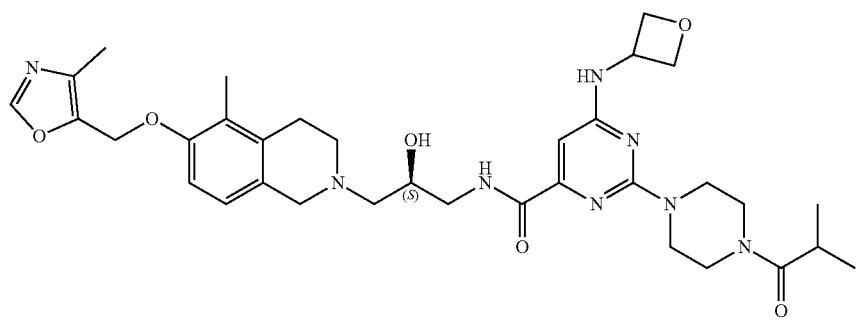

Prepared by general procedure 5A-C, condition 2. Yield: 9.3 mg (15.85%). $^1$H NMR (Chloroform-d, 500 MHz): δ (ppm) 1.17 (d, 6H), 1.68 (m, 3H), 2.09 (s, 3H), 2.21 (s, 3H), 2.60 (m, 2H), 2.78 (m, 3H), 2.85 (m, 1H), 2.99 (m, 1H), 3.42 (m, 1H), 3.59 (m, 3H), 3.70 (m, 3H), 3.79 (m, 4H), 4.05 (m, 1H), 4.60 (t, 2H), 4.99 (m, 3H), 5.10 (m, 1H), 5.33 (m, 1H), 6.56 (s, 1H), 6.81 (d, 1H), 6.85 (d, 1H), 7.82 (s, 1H), 8.22 (t, 1H). LCMS(ESI): [M+H]$^+$ m/z: calcd 662.4. found 663.2; Rt=1.01 min.

Example 5A52. 2-(4-acetylpiperazin-1-yl)-N-[(2S)-2-hydroxy-3-{5-methyl-6-[(4-methyl-1,3-oxazol-5-yl)methoxy]-1,2,3,4-tetrahydroisoquinolin-2-yl}propyl]-6-[(oxetan-3-yl)amino]pyrimidine-4-carboxamide (Compound 499)

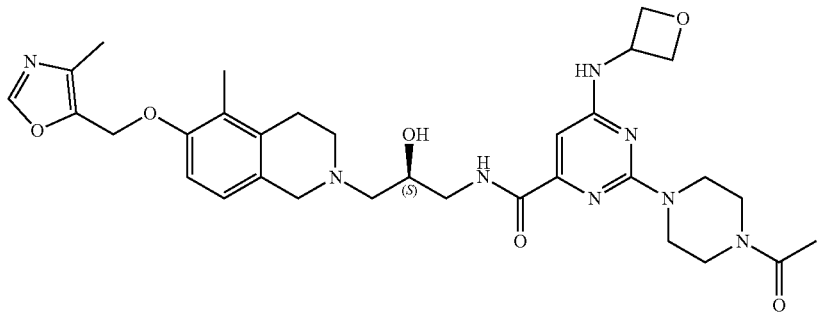

Prepared by general procedure 5A-C, condition 2. Yield: 19.6 mg (26.7%). $^1$H NMR (Chloroform-d, 400 MHz): δ (ppm) 2.05 (s, 3H), 2.12 (s, 3H), 2.17 (s, 3H), 2.52 (m, 2H), 2.70 (m, 3H), 2.92 (t, 1H), 3.39 (m, 1H), 3.51 (m, 3H), 3.64 (m, 3H), 3.75 (m, 6H), 3.99 (m, 1H), 4.59 (t, 2H), 4.95 (m, 4H), 5.07 (s, 1H), 5.85 (s, 1H), 6.61 (s, 1H), 6.79 (dd, 2H), 7.78 (s, 1H), 8.21 (t, 1H). LCMS(ESI): [M+H]$^+$ m/z: calcd 634.2. found 635.4; Rt=0.93 min.

Example 5A53. 6-[(1-acetylazetidin-3-yl)amino]-N-[(2S)-2-hydroxy-3-{5-methyl-6-[(4-methyl-1,3-oxazol-5-yl)methoxy]-1,2,3,4-tetrahydroisoquinolin-2-yl}propyl]-2-(morpholin-4-yl)pyrimidine-4-carboxamide (Compound 574)

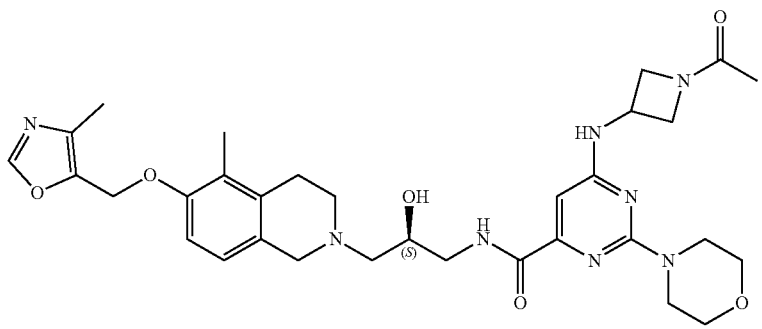

Prepared by general procedure 5A-C, condition 2. Yield: 15.2 mg (23.4%). $^1$H NMR (Chloroform-d, 400 MHz): δ (ppm) 1.86 (s, 3H), 2.04 (s, 3H), 2.17 (s, 3H), 2.54 (m, 2H), 2.72 (m, 4H), 2.91 (m, 1H), 3.44 (m, 1H), 3.54 (d, 1H), 3.62 (m, 1H), 3.70 (m, 9H), 4.01 (m, 3H), 4.34 (m, 1H), 4.44 (m, 1H), 4.70 (m, 1H), 4.96 (s, 2H), 6.29 (s, 1H), 6.62 (s, 1H), 6.77 (d, 1H), 6.81 (d, 1H), 7.78 (s, 1H), 8.26 (t, 1H). LCMS(ESI): [M+H]$^+$ m/z: calcd 634.2. found 635.4; Rt=0.94 min.

Example 5A54. (S)-6-((1-acetylpiperidin-4-yl)amino)-N-(2-hydroxy-3-(6-((4-methyloxazol-5-yl)methoxy)-3N-dihydroisoquinolin-2(1H)-yl)propyl-2-(piperidin-1-yl)pyrimidine-4-carboxamide (Compound 647)

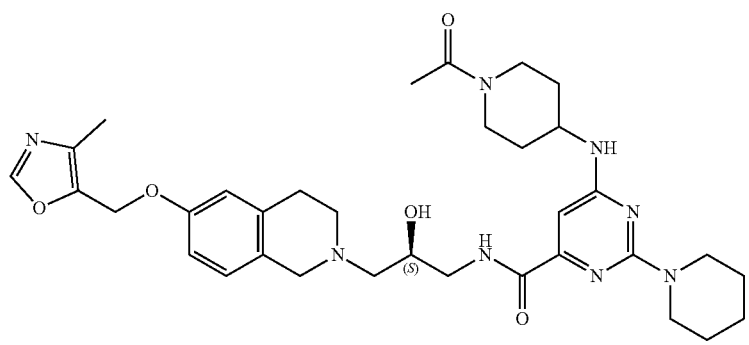

Prepared by general procedure 5A-C, condition 1. Yield: 25 mg (33%). ¹H NMR (400 MHz, CDCl₃) δ 1.43 (m, 2H), 1.59 (m, 4H), 1.65 (m, 2H), 2.04 (m, 1H), 2.12 (s, 3H), 2.14 (m, 1H), 2.23 (s, 3H), 2.57 (m, 2H), 2.71 (m, 1H), 2.88 (m, 4H), 3.22 (m, 1H), 3.43 (m, 1H), 3.56 (m, 1H), 3.66 (m, 1H), 3.73 (m, 5H), 3.79 (m, 1H), 3.83 (m, 1H), 4.01 (m, 2H), 4.51 (m, 1H), 4.99 (s, 2H), 5.01 (m, 1H), 6.48 (s, 1H), 6.71 (d, 1H), 6.77 (dd, 1H), 6.94 (d, 1H), 7.82 (s, 1H), 8.30 (t, 1H). LCMS(ESI): [M+H]⁺ m/z: calcd 646.8. found 647.4; Rt=1.051 min.

Example 6—Synthesis of Compounds of Formula (XII)

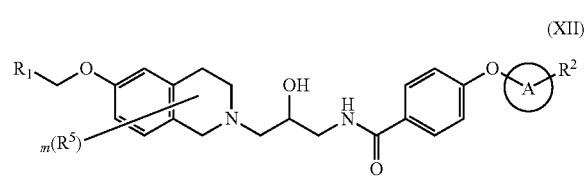

Scheme 6A

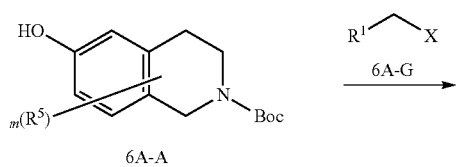

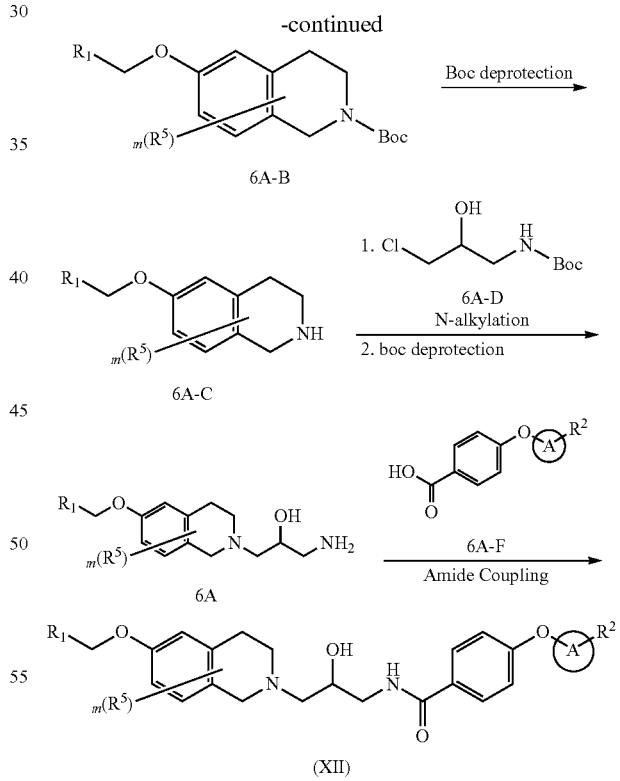

wherein X is a leaving group or hydroxy and variables R⁵, Rˣ, R¹, R², m, and n are defined herein. In some embodiments, X is selected from —OH, Cl, Br, and I. In some embodiments X is Cl or Br. In other embodiments, wherein X is —OH.

General Procedure 6A-A

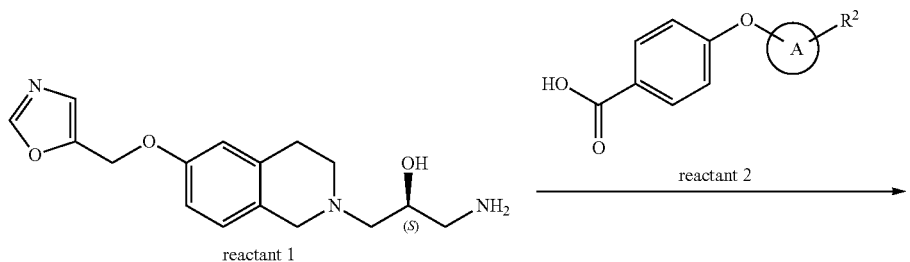

DIPEA (9 equiv) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mF) and filtered off. The obtained filtrate was subjected to HPFC (Waters Sunfire C18 19*100 5 mkm column and H$_2$O-MeOH as a mobile phase) to afford pure product.

Example 6A1. (S)-4-((1-benzylpiperidin-4-yl)oxy)-N-(2-hydroxy-3-(6-(oxazol-5-ylmethoxy)-3,4-dihydroisoquinolin-2(1H)-yl)propyl)benzamide (Compound 291)

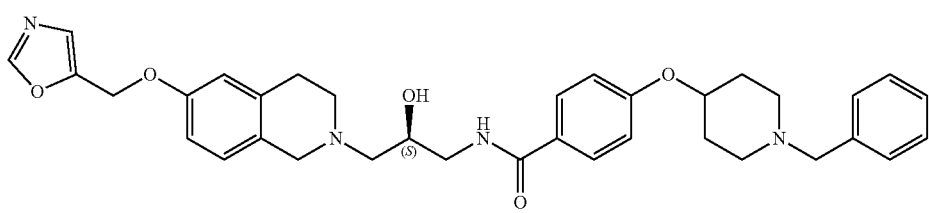

Prepared by general procedure 6A-A. Yield: 13.7 mg (21.05%). $^1$H NMR (DMSO-d$_6$, 400 MHz): δ 1.79 (m, 2H), 1.95 (m, 2H), 2.29 (t, 2H), 2.56 (m, 2H), 2.71 (m, 3H), 2.87 (m, 3H), 3.41 (m, 1H), 3.53 (m, 3H), 3.69 (m, 1H), 3.73 (m, 2H), 3.99 (m, 1H), 4.35 (m, 1H), 5.02 (s, 2H), 6.69 (m, 2H), 6.73 (d, 1H), 6.86 (d, 2H), 6.91 (d, 1H), 7.13 (s, 1H), 7.24 (s, 1H), 7.31 (m, 4H), 7.71 (d, 2H), 7.88 (s, 1H). LCMS (ESI): [M+H]$^+$ m/z: calcd 596.7. found 597.2; Rt=0.887 min.

Example 6A2. of (S)—N-(2-hydroxy-3-(6-(oxazol-5-ylmethoxy)-3,4-dihydroisoquinolin-2(1H)-yl)propyl-4-((1-(pyridin-4-ylmethyl)piperidin-4-yl)oxy)benzamide (Compound 328)

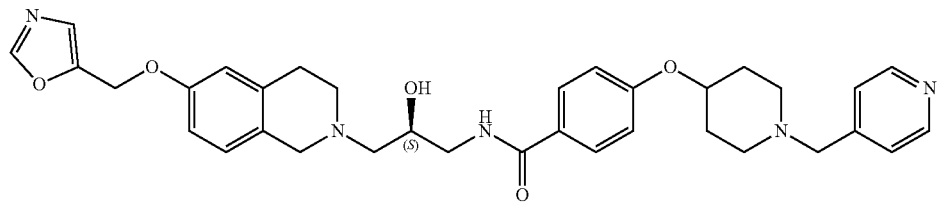

Prepared by general procedure 6A-A. Yield: 10.9 mg (15.36%). $^1$H NMR (400 MHz, CDCl$_3$) δ 1.83 (m, 2H), 1.97 (m, 2H), 2.32 (m, 2H), 2.56 (m, 2H), 2.69 (m, 3H), 2.88 (m, 3H), 3.41 (m, 2H), 3.51 (m, 2H), 3.55 (m, 1H), 3.72 (m, 2H), 3.99 (m, 1H), 4.39 (m, 1H), 5.02 (s, 2H), 6.73 (m, 3H), 6.87 (d, 2H), 6.92 (d, 1H), 7.12 (s, 1H), 7.26 (d, 2H), 7.70 (d, 2H), 7.88 (s, 1H), 8.52 (m, 2H). LCMS(ESI): [M+H]$^+$ m/z: calcd 597.7. found 598.2; Rt=0.783 min.

General Procedure 6A-B

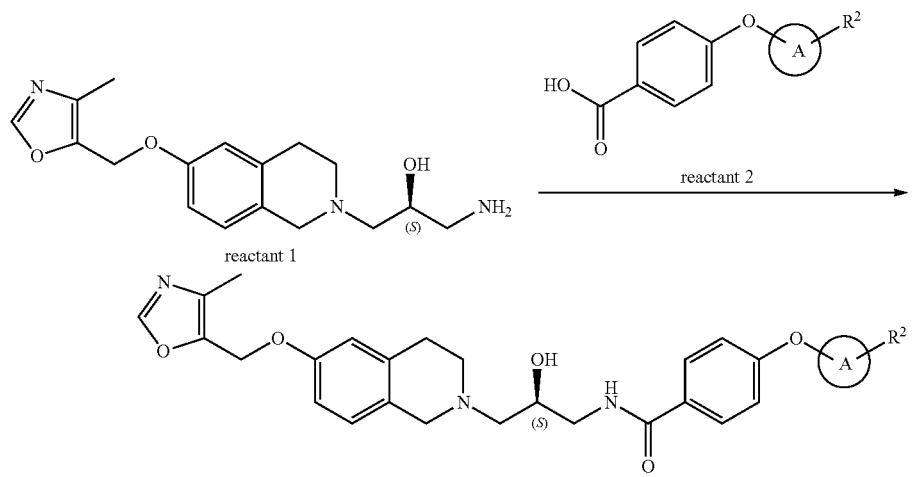

DIPEA (2.5 equiv+1.0 equiv per each acid equiv if amine salt was used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mF) and filtered off. The obtained filtrate was subjected to HPFC (Waters Sunfire C18 19*100 5 mkm column and H$_2$O-MeOH-0.1NH$_3$ as a mobile phase) to afford pure product.

Example 6A3. 4-1(1-benzylpiperidin-4-yl)oxy]-N-[(2S)-2-hydroxy-3-{6-[(4-methyl-1,3-oxazol-5-yl)methoxy]-1,2,3,4-tetrahydroisoquinolin-2-yl}propyl]benzamide (Compound 392)

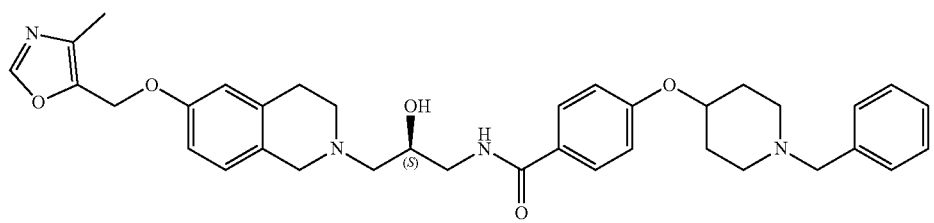

Prepared by general procedure 6A-B. Yield: 7.1 mg (10.8%). $^1$H NMR (500 MHz, CDCl$_3$) δ 1.85 (m, 2H), 2.01 (m, 2H), 2.24 (s, 3H), 2.33 (m, 2H), 2.60 (m, 2H), 2.75 (m, 3H), 2.91 (m, 3H), 3.44 (m, 1H), 3.58 (m, 4H), 3.77 (m, 2H), 4.03 (m, 1H), 4.40 (m, 1H), 5.00 (s, 2H), 6.67 (m, 1H), 6.73 (s, 1H), 6.78 (d, 1H), 6.91 (d, 2H), 6.95 (d, 1H), 7.34 (m, 5H), 7.74 (d, 2H), 7.82 (s, 1H). LCMS(ESI): [M+H]$^+$ m/z: calcd 610.3. found 610.8; Rt=0.89 min.

Example 6A4. N-[(2S)-2-hydroxy-3-{6-[(4-methyl-1,3-oxazol-5-yl)methoxy]-1,2,3,4-tetrahydroisoquinolin-2-yl}propyl]-4-{[1-[(pyridin-4-yl)methyl]piperidin-4-yl}oxy)benzamide (Compound 416)

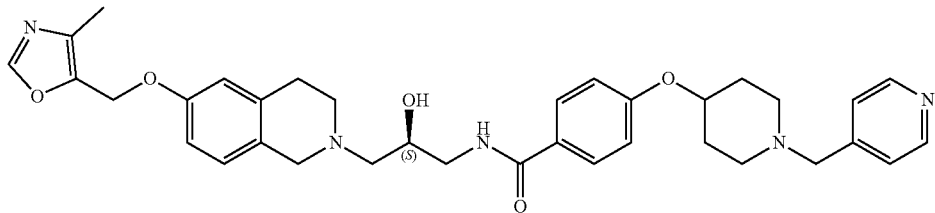

Prepared by general procedure 6A-B. Yield: 13.0 mg (17.8%). $^1$H NMR (Chloroform-d, 500 MHz): δ (ppm) 1.87 (m, 2H), 2.02 (m, 2H), 2.24 (s, 3H), 2.36 (m, 2H), 2.63 (m, 2H), 2.74 (m, 3H), 2.91 (m, 2H), 2.97 (m, 1H), 3.45 (m, 2H), 3.55 (s, 2H), 3.60 (d, 1H), 3.75 (d, 1H), 3.81 (d, 1H), 4.05 (m, 1H), 4.43 (m, 1H), 5.00 (s, 2H), 6.71 (s, 1H), 6.73 (s, 1H), 6.79 (d, 1H), 6.92 (d, 2H), 6.96 (d, 1H), 7.29 (d, 2H), 7.75 (d, 2H), 7.82 (s, 1H), 8.56 (d, 2H). LCMS(ESI): [M+2H]$^+$ m/z: calcd 611.3. found 613.2; Rt=0.74 min.

Example 6A5. N-[(2S)-2-hydroxy-3-{6-[(4-methyl-1,3-oxazol-5-yl)methoxy]-1,2,3,4-tetrahydroisoquinolin-2-yl}propyl]-4-(oxan-4-yloxy)benzamide (Compound 475)

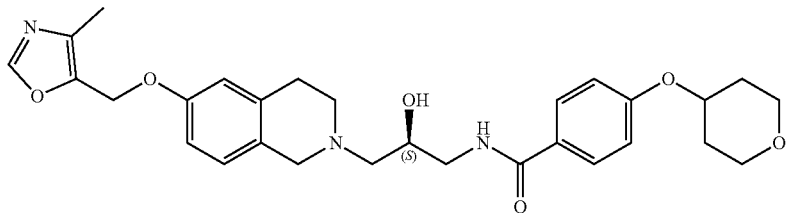

Prepared by general procedure 6A-B. Yield: 20.8 mg (28.8%). $^1$H NMR (400 MHz, DMSO-d$_6$+CCl$_4$) δ 1.67 (m, 2H), 2.00 (m, 2H), 2.19 (s, 3H), 2.84 (m, 1H), 3.18 (m, 3H), 3.35 (m, 1H), 3.42 (m, 1H), 3.51 (m, 3H), 3.87 (m, 3H), 4.10 (m, 4H), 4.61 (m, 1H), 5.02 (s, 2H), 6.77 (m, 2H), 6.89 (d, 2H), 6.94 (d, 1H), 7.01 (m, 1H), 7.81 (m, 2H), 8.38 (m, 1H). LCMS(ESI): [M+H]$^+$ m/z: calcd 521.3. found 522.4; Rt=2.33 min.

Example 6A6. N-[(2S)-2-hydroxy-3-{5-methyl-6-[(4-methyl-1,3-oxazol-5-yl)methoxy]-1,2,3,4-tetrahydroisoquinolin-2-yl}propyl]-4-({1-[(pyridin-4-yl)methyl]piperidin-4-yl}oxy)benzamide (Compound 440)

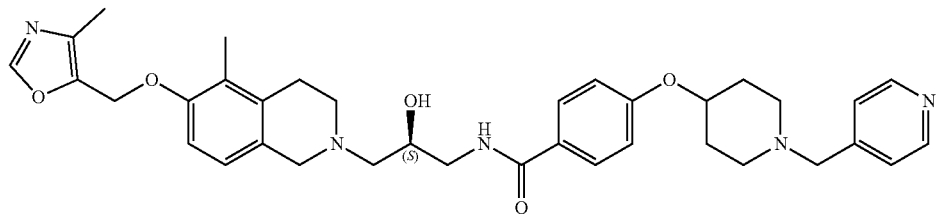

Prepared by general procedure 6A-B. Yield: 11.0 mg (14.6%). $^1$H NMR (DMSO-d$_6$, 500 MHz): δ (ppm) 1.74 (m, 2H), 1.96 (m, 2H), 2.02 (s, 3H), 2.16 (s, 3H), 2.31 (m, 2H), 2.54 (m, 2H), 2.69 (m, 4H), 2.79 (m, 2H), 3.28 (m, 1H), 3.39 (m, 1H), 3.50 (s, 2H), 3.60 (m, 2H), 3.89 (m, 1H), 4.41 (m, 1H), 4.62 (m, 1H), 4.99 (s, 2H), 6.78 (d, 2H), 6.82 (s, 2H), 7.27 (d, 2H), 7.67 (d, 2H), 8.02 (s, 1H), 8.22 (t, 1H), 8.44 (d, 2H). LCMS(ESI): [M+2H]$^+$ m/z: calcd 625.3. found 627.3; Rt=0.79 min.

General Procedure 6A-C

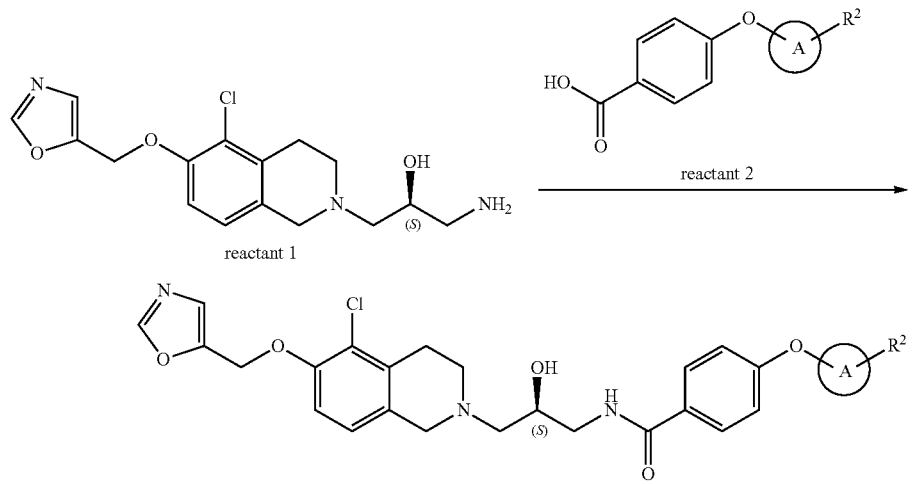

DIPEA (2.5 equiv+1.0 equiv per each acid equiv if amine salt was used) was added to the solution of Reactant 1 (1.0 equiv) and Reactant 2 (1.1 equiv) in DMF (0.5 mL). The resulting mixture was stirred for 5 min followed by the addition of the solution of HATU (1.05 equiv) in DMF (1.0 mF). The reaction mixture was stirred at room temperature overnight. After all starting material was consumed, as was shown by LCMS, the resulting mixture was concentrated under reduced pressure. The residue was dissolved in DMSO (1.0 mF) and filtered off. The obtained filtrate was subjected to HPFC (Waters SunFire C18 19*100 5 mkm column and H$_2$O-MeOH as a mobile phase) to afford pure product.

Example 6A7. (S)—N-(3-(5-chloro-6-(oxazol-5-ylmethoxy)-3,4-dihydroisoquinolin-2(1H)-yl)-2-hydroxypropyl)-4-((tetrahydro-2H-pyran-4-yl)oxy) benzamide (Compound 482)

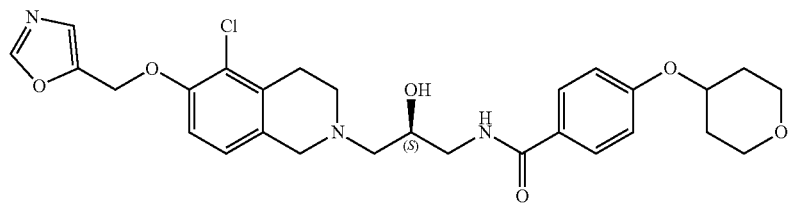

Prepared by general procedure 6A-C. Yield: 19.0 mg (29.57%).

$^1$H NMR (400 MHz, DMSO-d$_6$+CCl$_4$) δ 1.66 (m, 2H), 1.97 (m, 2H), 2.54 (m, 1H), 2.81 (m, 3H), 3.20 (m, 2H), 3.28 (m, 1H), 3.41 (m, 1H), 3.51 (m, 2H), 3.63 (m, 1H), 3.74 (m, 1H), 3.86 (m, 3H), 4.62 (m, 2H), 5.17 (s, 2H), 6.84 (d, 2H), 7.00 (m, 2H), 7.20 (s, 1H), 7.71 (d, 2H), 8.18 (m, 2H). LCMS(ESI): [M+H]$^+$ m/z: calcd 542.0. found 543.2; Rt=0.996 min.

Example 6A8. (S)-4-((1-benzylpiperidin-4-yl)oxy)-N-(3-(5-chloro-6-(oxazol-5-ylmethoxy)-3,4-dihydroisoquinolin-2(1H)-yl)-2-hydroxypropyl)benzamide (Compound 330)

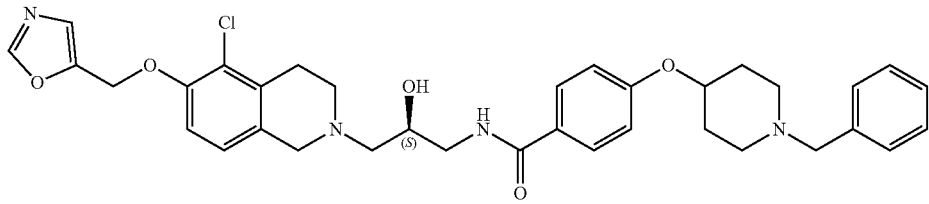

Prepared by general procedure 6A-C. Yield: 12.2 mg (16.62%). $^1$H NMR (500 MHz, CDCl$_3$-d) δ 1.84 (m, 2H), 2.00 (m, 2H), 2.33 (m, 2H), 2.59 (m, 2H), 2.75 (m, 3H), 2.90 (m, 2H), 2.96 (m, 1H), 3.44 (m, 1H), 3.56 (m, 3H), 3.63 (m, 1H), 3.77 (m, 2H), 4.03 (m, 1H), 4.40 (m, 1H), 5.14 (s, 2H), 6.67 (t, 1H), 6.89 (m, 4H), 7.17 (s, 1H), 7.33 (m, 5H), 7.73 (d, 2H), 7.92 (s, 1H). LCMS(ESI): [M+H]$^+$ m/z: calcd 631.2. found 632.2; Rt=0.889 min.

Example 8A9. (S)—N-(3-(5-chloro-6-(oxazol-5-ylmethoxy)-3,4-dihydroisoquinolin-2(1H)-yl)-2-hydroxypropyl)-4-((1-(pyridin-4-ylmethyl)piperidin-4-yl)oxy)benzamide (Compound 301)

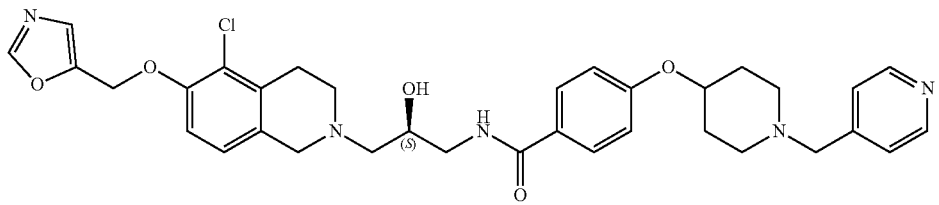

Prepared by general procedure 6A-C. Yield Yield: 12.7 mg (18.33%). $^1$H NMR (400 MHz, DMSO-d$_6$) δ 1.86 (m, 2H), 2.03 (m, 2H), 2.37 (m, 2H), 2.61 (m, 2H), 2.73 (m, 3H), 2.89 (m, 2H), 2.96 (m, 2H), 3.46 (m, 1H), 3.56 (m, 4H), 3.75 (m, 2H), 4.04 (m, 1H), 4.42 (m, 1H), 5.14 (s, 2H), 6.68 (t, 1H), 6.90 (m, 3H), 7.17 (s, 1H), 7.30 (m, 2H), 7.73 (d, 2H), 7.92 (s, 1H), 8.56 (d, 2H). LCMS(ESI): [M+2H]$^+$ m/z: calcd 632.1. found 633.2; Rt=0.775 min.

Example 7—Synthesis of Compounds of Formula (XIa) and Formula (XIb)

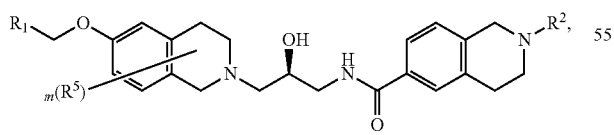

(XIa)

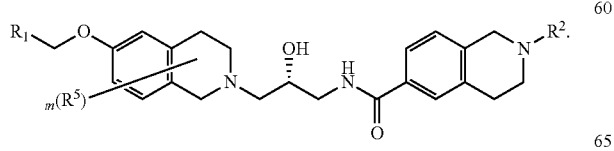

(XIb)

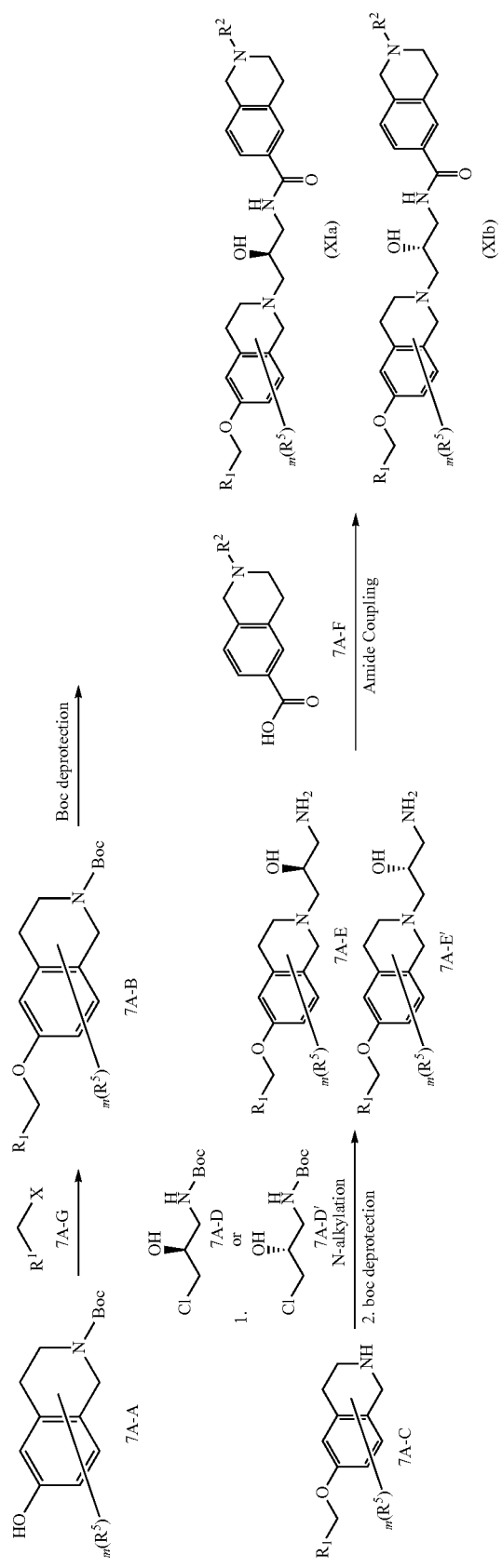

wherein X is a leaving group or hydroxy and variables $R^5$, $R^1$, $R^2$, and m are defined herein. In some embodiments, X is selected from —OH, Cl, Br, and I. In some embodiments X is Cl or Br. In other embodiments, wherein X is —OH.

General Procedure 7-A

Reactant 1 and reactant 2 were mixed in DMF (5 mL). The reaction suspension was cooled to 0° C. and HATU followed by TEA were added. The clear solution was stirred at ambient temperature for 1.5 hr at 25° C. then volatiles were evaporated under reduced pressure and residue was subjected to RP-HPLC to give product.

Example 7-1. (S)—N-(2-hydroxy-3-(6-((4-methyl-oxazol-5-yl)methoxy)-3,4-dihydroisoquinolin-2 (1H)-yl)propyl)-2-(4-methoxybenzoyl)-1,2,3,4-tetra-hydroisoquinoline-6-carboxamide (Compound 498)

Prepared by general procedure 7-A. Yield: 26 mg (10.2%). $^1$H NMR (400 MHz, CDCl$_3$): δ (ppm) 2.20 (s, 3H), 2.55 (m, 2H), 2.69 (m, 1H), 2.86 (m, 2H), 2.91 (m, 2H), 3.42 (m, 1H), 3.54 (d, 1H), 3.74 (m, 4H), 3.83 (s, 4H), 4.01 (m, 1H), 4.80 (s, 2H), 4.96 (s, 2H), 6.70 (s, 1H), 6.74 (d, 1H), 6.80 (t, 1H), 6.92 (d, 4H), 7.11 (s, 1H), 7.42 (d, 2H), 7.56 (d, 1H), 7.60 (s, 1H), 7.79 (s, 1H). LCMS(ESI): [M+H]$^+$ m/z: calcd 610.7. found 611.2; Rt=2.833 min.

Example 7-2. (S)-2-(4-bromobenzoyl)-N-(2-hydroxy-3-(6-((4-methyloxazol-5-yl)methoxy)-3,4-dihydroisoquinolin-2(1H)-yl)propyl-1,2,3,4-tetrahydroisoquinoline-6-carboxamide (Compound 493)

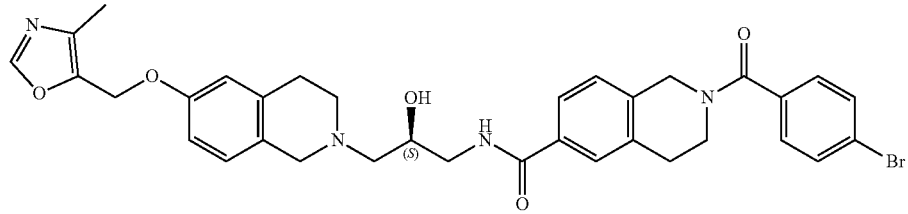

Prepared by general procedure 7-A. Yield: 83 mg (46.49%). $^1$H NMR (400 MHz, CDCl$_3$): δ (ppm) 2.21 (s, 3H), 2.58 (m, 2H), 2.74 (s, 1H), 2.91 (m, 6H), 3.42 (m, 1H), 3.55 (d, 1H), 3.64 (m, 1H), 3.76 (m, 3H), 4.02 (m, 2H), 4.58 (m, 1H), 4.87 (m, 1H), 4.97 (s, 2H), 6.70 (s, 1H), 6.75 (d, 2H), 6.92 (d, 1H), 7.32 (d, 2H), 7.56 (d, 3H), 7.61 (s, 1H), 7.79 (s, 1H). LCMS(ESI): [M+H]$^+$ m/z: calcd 659.6. found 660.2; Rt=3.084 min.

General Procedure 7-B

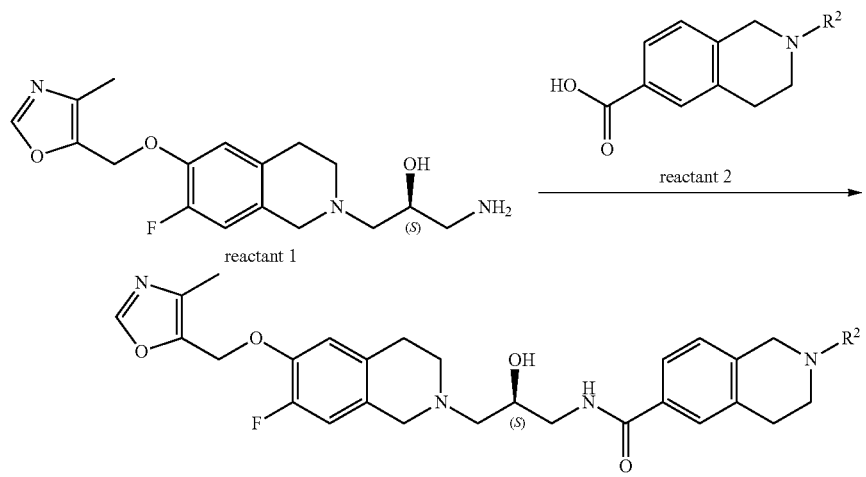

To the solution of Reactant 1 (1.0 equiv, HCl), Reactant 2 (1.0 equiv) and HATU (1.1 equiv) in DMF (1.2 mL) triethylamine (6.0 equiv) was added dropwise. The resulting mixture was stirred at 25° C. for 2 h. After the completion of the reaction, solvent was removed in vacuo and the obtained product was purified by reverse phase HPLC (Device (Mobile Phase, Column): 17_H$_2$O/R1 Sample info: 25-55% ACN 1-9 min water-acetonitrile, flow:30 mL/min (loading pump 4Ll/min acetonitrile) to afford pure product.

Example 7-3. N-[(2S)-3-[7-fluoro-6-[(4-methyloxazol-5-yl)methoxy]-3N-dihydro-1H-isoquinolin-2-yl]-2-hydroxy-propyl]-2-(4-methoxybenzoyl)-3N-dihydro-1H-isoquinoline-6-carboxamide (Compound 577)

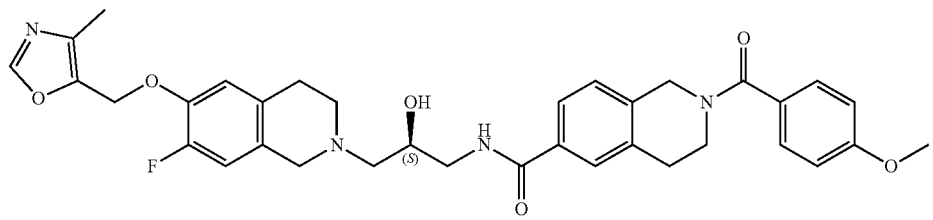

Prepared by general procedure 7-B. Yield: 14.0 mg (14.94%). $^1$H NMR (Chloroform-d, 400 MHz): δ (ppm) 2.59 (s, 4H), 2.62 (m, 1H), 2.76 (m, 1H), 2.82 (m, 2H), 2.93 (m, 3H), 3.43 (m, 2H), 3.57 (d, 1H), 3.73 (m, 3H), 3.82 (s, 4H), 4.03 (m, 1H), 4.79 (s, 2H), 5.02 (s, 2H), 6.72 (dd, 2H), 6.86 (t, 1H), 6.91 (d, 2H), 7.12 (s, 1H), 7.41 (d, 2H), 7.57 (d, 1H), 7.61 (s, 1H), 7.79 (s, 1H). LCMS(ESI): [M+H]$^+$ m/z: calcd 628.2. found 629.3; Rt=2.46 min.

Example 7-4. 2-(4-bromobenzoyl)-N-[(2S)-3-[7-fluoro-6-[(4-methyloxazol-5-yl)methoxy]-3,4-dihydro-1H-isoquinolin-2-yl]-2-hydroxy-propyl]-3,4-dihydro-1H-isoquinoline-6-carboxamide
(Compound 578)

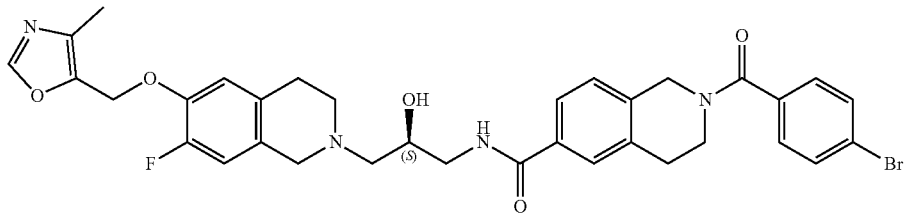

Prepared by general procedure 7-B. Yield: 23.0 mg (22.8%). $^1$H NMR (Chloroform-d, 400 MHz): δ (ppm) 2.19 (s, 3H), 2.55 (m, 2H), 2.71 (m, 1H), 2.80 (m, 2H), 2.90 (m, 3H), 3.43 (m, 3H), 3.52 (d, 1H), 3.61 (s, 1H), 3.71 (d, 2H), 4.01 (m, 1H), 4.58 (m, 1H), 4.86 (m, 1H), 5.02 (s, 2H), 6.70 (d, 1H), 6.73 (d, 1H), 6.87 (t, 1H), 7.18 (s, 1H), 7.31 (d, 2H), 7.55 (d, 3H), 7.60 (s, 1H), 7.78 (s, 1H). LCMS(ESI): [M+2H]$^+$ m/z: calcd 677.1. found 679.2; Rt=1.12 min.

General Procedure 7-C

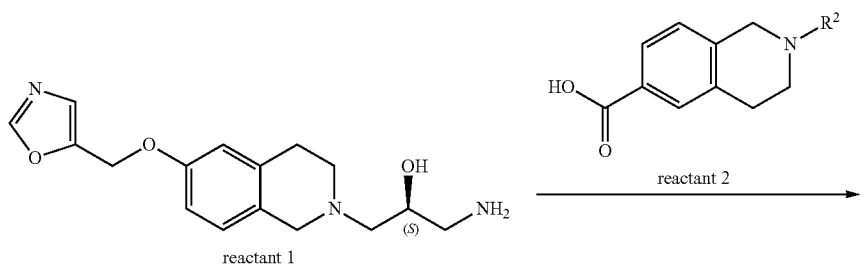

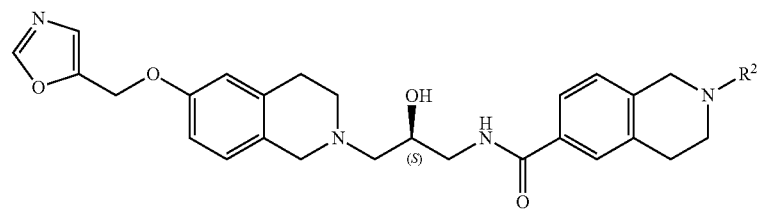

DIPEA (9 equiv) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and H$_2$O-MeOH as a mobile phase) to afford pure product.

Example 7-5. (S)—N-(2-hydroxy-3-(6-(oxazol-5-ylmethoxy)-3,4-dihydroisoquinolin-2(1H)-yl)propyl)-2-(4-methoxybenzoyl)-1,2,3,4-tetrahydroisoquinoline-6-carboxamide (Compound 547)

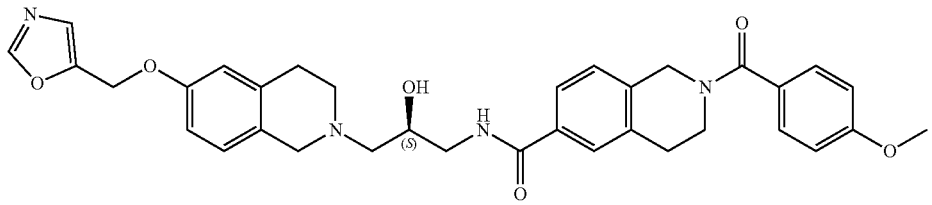

Prepared by general procedure 7-C. Yield: 21.4 mg (31.49%). $^1$H NMR (400 MHz, CDCl$_3$) δ 2.56 (m, 2H), 2.70 (m, 1H), 2.89 (m, 6H), 3.42 (m, 1H), 3.55 (d, 1H), 3.73 (m, 4H), 3.82 (s, 3H), 4.01 (m, 1H), 4.78 (m, 2H), 5.02 (s, 2H), 6.69 (m, 1H), 6.74 (m, 1H), 6.86 (m, 1H), 6.91 (d, 4H), 7.12 (s, 1H), 7.41 (m, 2H), 7.55 (d, 1H), 7.59 (s, 1H), 7.88 (s, 1H). LCMS(ESI): [M+H]$^+$ m/z: calcd 596.6. found 597.2; Rt=1.031 min.

Example 7-6. (S)—N-(2-hydroxy-3-(6-(oxazol-5-ylmethoxy)-3,4-dihydroisoquinolin-2(1H)-yl)propyl)-2-(4-methoxybenzoyl-1,2,3,4-tetrahydroisoquinoline-6-carboxamide (Compound 547)

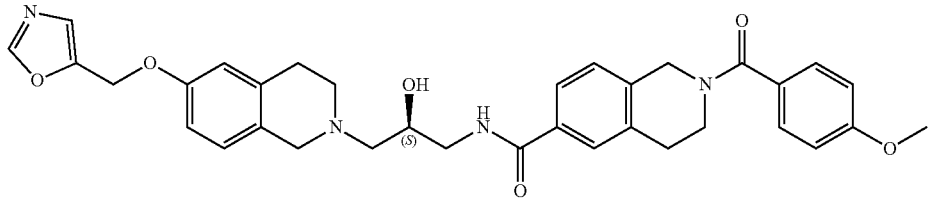

Prepared by general procedure 7-C. Yield: 21.4 mg (31.49%). $^1$H NMR (400 MHz, CDCl$_3$) δ 2.56 (m, 2H), 2.70 (m, 1H), 2.89 (m, 6H), 3.42 (m, 1H), 3.55 (d, 1H), 3.73 (m, 4H), 3.82 (s, 3H), 4.01 (m, 1H), 4.78 (m, 2H), 5.02 (s, 2H), 6.69 (m, 1H), 6.74 (m, 1H), 6.86 (m, 1H), 6.91 (d, 4H), 7.12 (s, 1H), 7.41 (m, 2H), 7.55 (d, 1H), 7.59 (s, 1H), 7.88 (s, 1H). LCMS(ESI): [M+H]$^+$ m/z: calcd 596.6. found 597.2; Rt=1.031 min.

Example 7-7. (S)-2-(4-bromobenzoyl)-N-(2-hydroxy-3-(6-(oxazol-5-ylmethoxy)-3,4-dihydroisoquinolin-2(1H)-yl)propyl-1,2,3,4-tetrahydroisoquinoline-6-carboxamide (Compound 561)

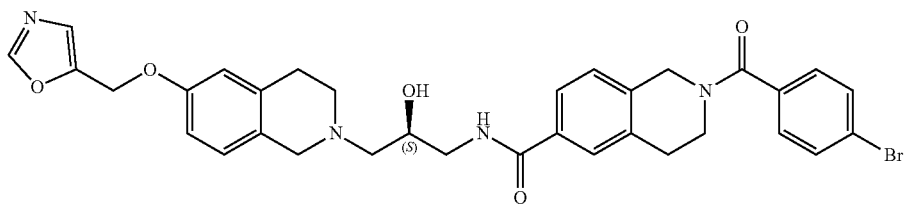

Prepared by general procedure 7-C. Yield: 21.4 mg (33.37%). $^1$H NMR (400 MHz, DMSO-$d_6$) δ 2.53 (s, 2H), 2.76 (m, 2H), 2.84 (m, 4H), 2.97 (m, 2H), 3.27 (m, 1H), 3.42 (m, 1H), 3.61 (m, 3H), 3.88 (m, 1H), 4.60 (m, 2H), 4.73 (m, 1H), 5.05 (m, 2H), 6.71 (m, 2H), 6.90 (d, 1H), 7.16 (s, 1H), 7.38 (d, 2H), 7.59 (m, 4H), 8.16 (s, 1H), 8.28 (t, 1H). LCMS(ESI): [M+H]$^+$ m/z: calcd 645.5. found 646.2; Rt=1.097 min.

General Procedure 7-D

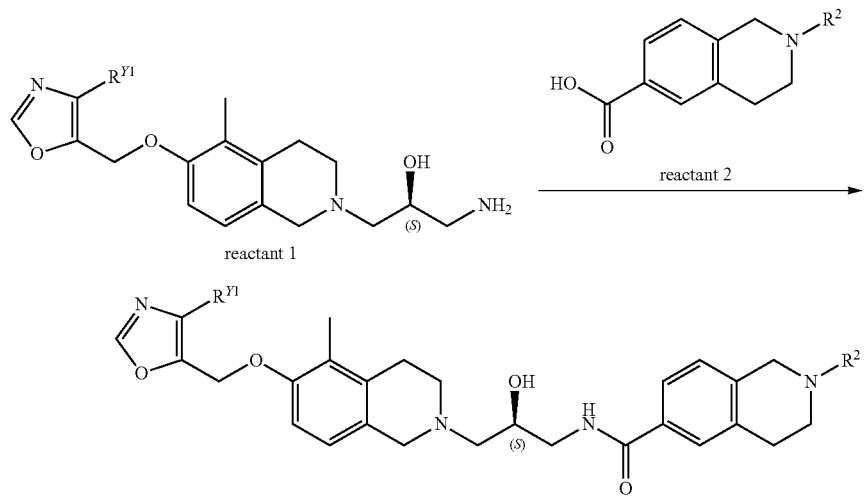

wherein $R^{Y1}$ is H or $CH_3$.

DIPEA (2.5 equiv+1.0 equiv per each acid equiv if amine salt used) was added to the solution of Reactant 1 (1.0 equiv) and Reactant 2 (1.0 equiv) in DMF (2.0 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters Sunfire C18 19*100 5 mkm column and $H_2O$-MeOH-0.1$NH_3$ as a mobile phase) to afford pure product.

Example 7-8. 2-(4-bromobenzoyl-N-[(2S)-2-hydroxy-3-{5-methyl-6-[(4-methyl-1,3-oxazol-5-yl)methoxy]-1,2,3,4-tetrahydroisoquinolin-2-yl}propyl]-1,2,3,4-tetrahydroisoquinoline-6-carboxamide (Compound 530)

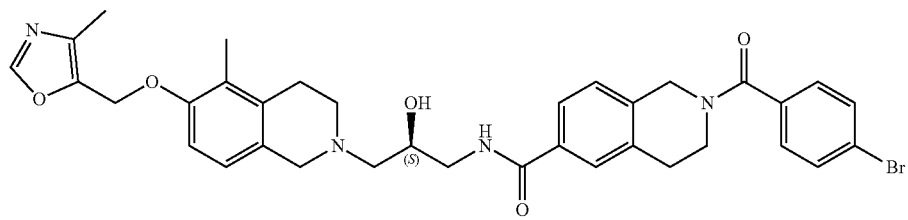

Prepared by general procedure 7-D. Yield: 9.2 mg (14.0%). $^1$H NMR (500 MHz, CDCl$_3$) δ 2.10 (s, 3H), 2.22 (s, 3H), 2.73 (m, 2H), 2.86 (m, 2H), 2.95 (m, 3H), 3.11 (m, 1H), 3.50 (s, 2H), 3.63 (m, 2H), 3.78 (m, 2H), 3.96 (m, 2H), 4.14 (m, 1H), 4.62 (m, 1H), 4.92 (m, 1H), 5.01 (s, 2H), 6.85 (d, 1H), 6.87 (d, 1H), 7.06 (m, 1H), 7.34 (s, 2H), 7.59 (d, 3H), 7.67 (s, 1H), 7.82 (s, 1H). LCMS(ESI): [M+H]+ m/z: calcd 673.5. found 674.2; Rt=1.18 min.

Example 7-9. N-[(2S)-2-hydroxy-3-{5-methyl-6-[(4-methyl-1,3-oxazol-5-yl)methoxy]-1,2,3,4-tetrahydroisoquinolin-2-yl}propyl]-2-(4-methoxybenzoyl)-1,2,3,4-tetrahydroisoquinoline-6-carboxamide (Compound 533)

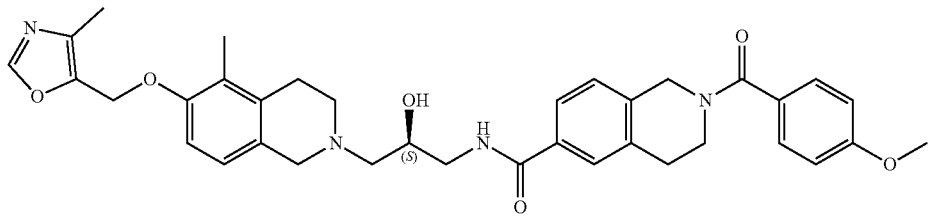

Prepared by general procedure 7-D. Yield: 9.0 mg (14.1%).

$^1$H NMR (500 MHz, CDCl$_3$) δ 2.11 (s, 3H), 2.24 (s, 3H), 2.71 (m, 2H), 2.84 (m, 2H), 2.94 (m, 3H), 3.12 (m, 1H), 3.48 (m, 2H), 3.77 (m, 3H), 3.86 (m, 3H), 3.95 (m, 2H), 4.13 (m, 1H), 4.82 (m, 2H), 5.00 (s, 2H), 6.72 (m, 2H), 6.84 (d, 1H), 6.87 (d, 1H), 6.94 (d, 2H), 7.46 (d, 2H), 7.63 (d, 1H), 7.66 (s, 1H), 7.82 (s, 1H).

LCMS(ESI): [M+H]+ m/z: calcd 624.2. found 625.4; Rt=1.11 min.

Example 7-10. (4-bromobenzoyl)-N-[(2S)-2-hydroxy-3-{5-methyl-6-[(1,3-oxazol-5-yl)methoxy]-1,2,3,4-tetrahydroisoquinolin-2-yl}propyl]-1,2,3,4-tetrahydroisoquinoline-6-carboxamide (Compound 546)

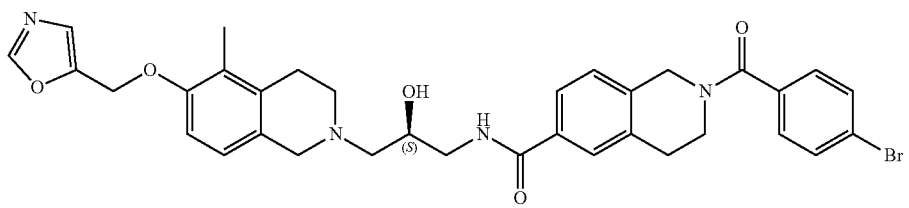

Prepared by general procedure 7-D. Yield: 12.2 mg (20.24%). $^1$H NMR (CDCl$_3$, 500 MHz): δ (ppm) 2.11 (s, 3H), 2.65 (m, 2H), 2.88 (m, 5H), 3.05 (m, 1H), 3.47 (m, 2H), 3.69 (m, 3H), 3.78 (m, 1H), 3.88 (d, 1H), 4.00 (m, 1H), 4.10 (m, 1H), 4.60 (m, 1H), 4.92 (m, 1H), 5.06 (s, 2H), 6.82 (d, 1H), 6.87 (d, 1H), 6.97 (t, 1H), 7.14 (s, 1H), 7.35 (d, 2H), 7.60 (m, 3H), 7.65 (s, 1H), 7.92 (s, 1H) LCMS(ESI): [M+3H]+ m/z: calcd 658.2. found 661.0; Rt=1.11 min.

Example 7-11. N-[(2S)-2-hydroxy-3-{5-methyl-6-[(1,3-oxazol-5-yl)methoxy]-1,2,3,4-tetrahydroisoquinolin-2-yl}propyl]-2-(4-methoxybenzoyl)-1,2,3,4-tetrahydroisoquinoline-6-carboxamide (Compound 540)

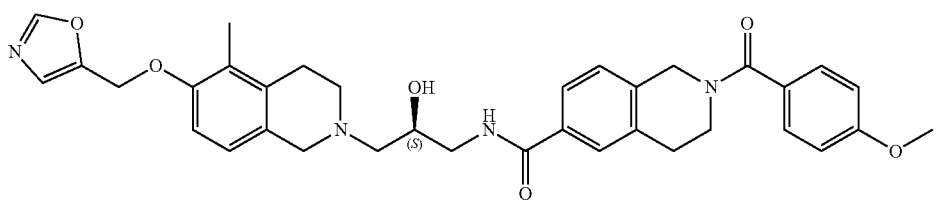

Prepared by general procedure 7-D. Yield: 9.1 mg (14.45%). $^1$H NMR (500 MHz, CDCl$_3$) δ 2.11 (s, 3H), 2.72 (m, 2H), 2.84 (m, 2H), 2.96 (m, 3H), 3.08 (m, 1H), 3.52 (m, 2H), 3.80 (m, 4H), 3.87 (s, 3H), 3.93 (m, 1H), 4.13 (m, 1H), 4.83 (s, 2H), 5.07 (s, 2H), 6.83 (d, 1H), 6.87 (d, 1H), 6.95 (d, 2H), 7.04 (s, 1H), 7.14 (s, 1H), 7.46 (d, 2H), 7.61 (m, 1H), 7.66 (s, 1H), 7.92 (s, 1H), NH is not observed. LCMS(ESI): [M+2H]$^+$ m/z: calcd 610.3. found 611.0; Rt=1.038 min.
Example 8. Synthesis of Compounds of Formula (XVa) and Formula (XVb)
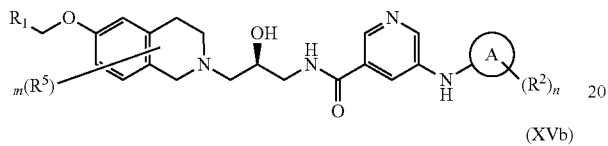
(XVa)
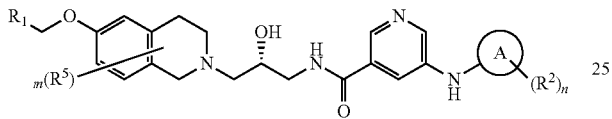
(XVb)

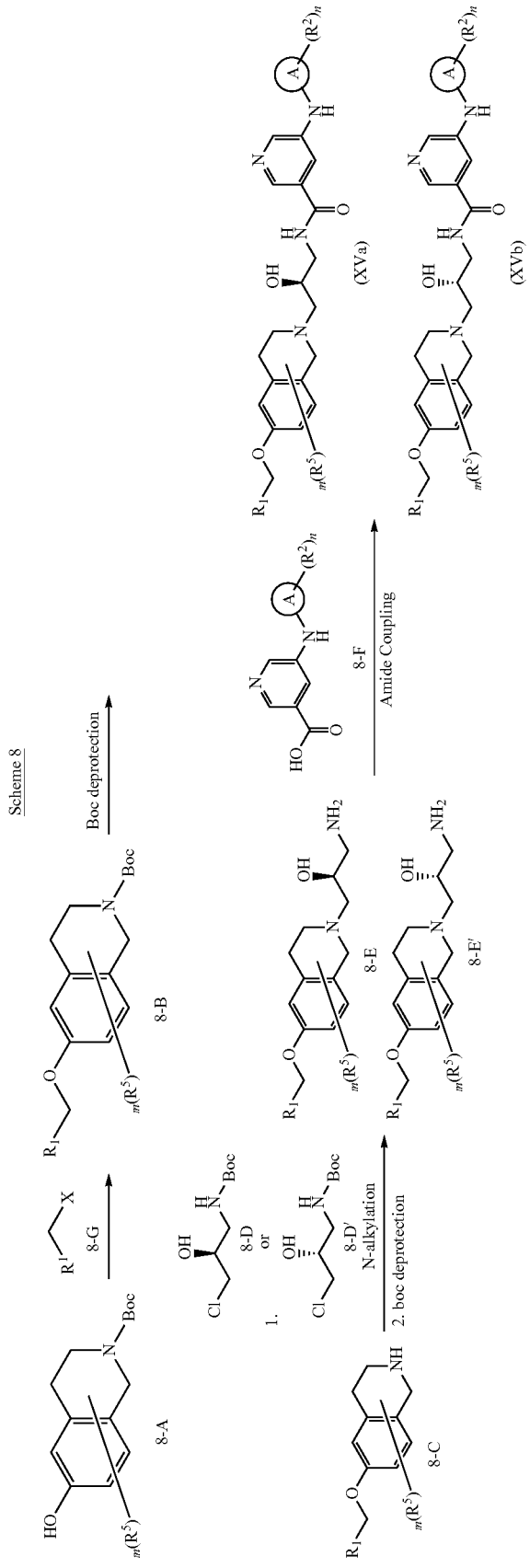

wherein X is a leaving group or hydroxy and variables $R^5$, $R^x$, $R^1$, $R^2$, m, and n are defined herein. In some embodiments, X is selected from —OH, Cl, Br, and I. In some embodiments X is Cl or Br. In other embodiments, wherein X is —OH.

General Procedure 8-A

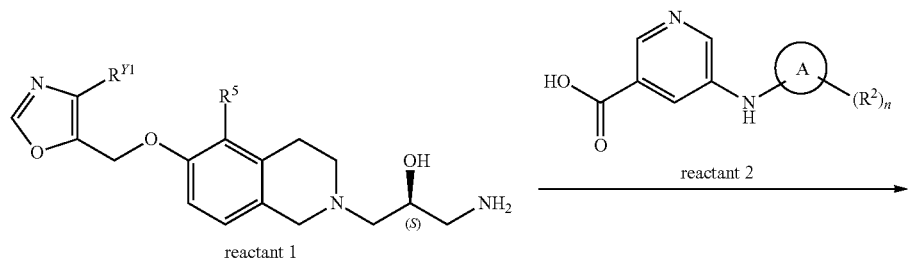

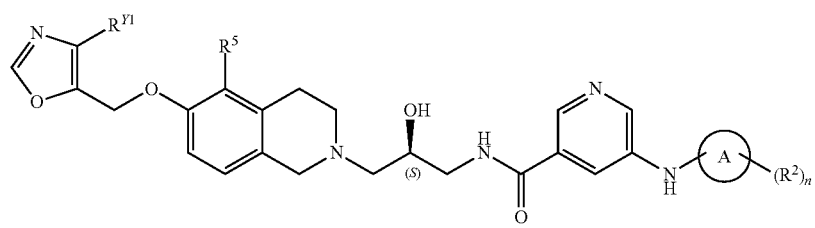

Wherein $R^{Y1}$ is H or $CH_3$, and $R^5$ is defined herein.

Condition 1. DIPEA (5.0 equiv) was added to the solution of reactant 1 (1.0 equiv) and reactant 2 (1.1 equiv) in DMF (2.0 mL). The resulting mixture was stirred for 5 min followed by the addition of the solution of EDC (1.05 equiv) in DMF (0.5 mL) and the solution of HOAt (1.05 equiv) in DMF (0.5 mL). The reaction mixture was stirred overnight at room temperature. After LCMS showed full conversion of starting material, the solvent was removed under reduced pressure. The residue was dissolved in DMSO (1.0 mL) and filtered off. The obtained filtrate was subjected to HPLC (Waters SunFire C18 19*100 5 mkm column and H₂O-MeOH as a mobile phase, RunTime=5 min) to afford pure product.

Condition 2. DIPEA (2.5 equiv+1.0 equiv per each acid equiv if amine salt was used) was added to the solution of Reactant 1 (1.0 equiv) and Reactant 2(1.1 equiv) in DMF (0.5 mL). The resulting mixture was stirred for 5 min followed by the addition of the solution of HATU (1.05 equiv) in DMF (1.0 mL). The reaction mixture was stirred at room temperature overnight. After all starting material was consumed, as was shown by LCMS, the resulting mixture was concentrated under reduced pressure. The residue was dissolved in DMSO (1.0 mL) and filtered off. The obtained filtrate was subjected to HPLC (Waters SunFire C18 19*100 5 mkm column and H₂O-MeOH as a mobile phase) to afford pure product.

Example 8-1. (S)-5-(cyclobutylamino)-N-(2-hydroxy-3-(6-(oxazol-5-ylmethoxy)-3N-dihydroisoquinolin-2(1H)-yl)propyl)nicotinamide (Compound 270)

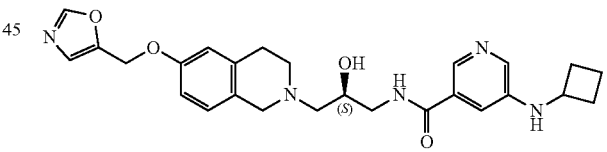

Prepared according to general procedure 8-A, condition 1. Yield 12.0 mg (12.0%). $^1$H NMR (400 MHz, DMSO-$d_6$) δ (ppm). LCMS(ESI): [M+H]⁺ m/z: calcd 478.1. found 479.2; Rt=0.86 min.

Example 8-2. (S)-5-(cyclobutylamino)-N-(2-hydroxy-3-(6-((4-methyloxazol-5-yl)methoxy)-3N-dihydroisoquinolin-2(1H)-yl)propyl)nicotinamide (Compound 271)

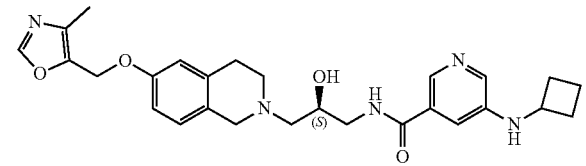

Prepared according to general procedure 8-A, condition 2. Yield 13.1 mg (13.1%). $^1$H NMR (Chloroform-d, 500 MHz): δ (ppm) 1.85 (m, 4H), 2.24 (s, 3H), 2.48 (m, 2H), 2.59 (m, 3H), 2.74 (m, 1H), 2.91 (m, 3H), 3.45 (m, 1H), 3.57 (d, 1H), 3.75 (m, 1H), 3.82 (d, 1H), 3.97 (m, 1H), 4.03 (m, 2H), 5.00 (s, 2H), 6.73 (s, 2H), 6.79 (d, 1H), 6.96 (d, 1H), 7.24 (s, 1H), 7.82 (s, 1H), 8.06 (d, 1H), 8.26 (s, 1H). LCMS(ESI): [M+H]$^+$ m/z: calcd 491.6. found 492.4; Rt=0.83 min.

Example 8-3. (S)-5-((1-acetylpiperidin-4-yl)amino)-N-(2-hydroxy-3-(6-(oxazol-5-ylmethoxy)-3,4-dihydroisoquinolin-2(1H)-yl)propyl)nicotinamide (Compound 549)

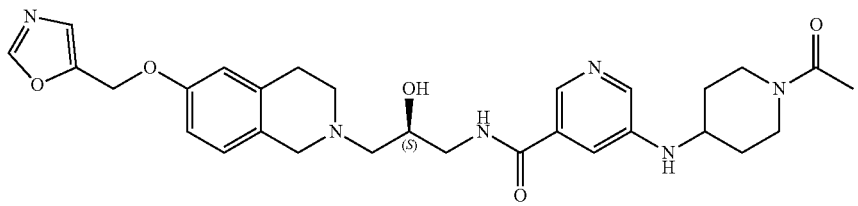

Prepared according to general procedure 8-A, condition 1. Yield: 31.6 mg (46.61%). $^1$H NMR (DMSO-d$_6$, 400 MHz): δ (ppm) 1.37 (m, 2H), 1.95 (m, 2H), 2.02 (s, 3H), 2.76 (m, 2H), 2.83 (m, 2H), 3.20 (m, 3H), 3.49 (m, 3H), 3.60 (m, 2H), 3.78 (m, 1H), 3.90 (m, 1H), 4.22 (m, 1H), 4.57 (m, 1H), 5.06 (s, 2H), 5.80 (m, 1H), 6.71 (m, 2H), 6.92 (m, 1H), 7.16 (s, 1H), 7.27 (s, 1H), 8.01 (m, 1H), 8.15 (m, 2H), 8.23 (t, 1H). LCMS(ESI): [M+H]$^+$ m/z: calcd 548.6. found 549.2; Rt=0.749 min.

Example 8-4. N—((S)-2-hydroxy-3-(6-(oxazol-5-ylmethoxy)-3,4-dihydroisoquinolin-2(1H)-yl)propyl)-5-((tetrahydrofuran-3-yl)amino)nicotinamide (Compound 355)

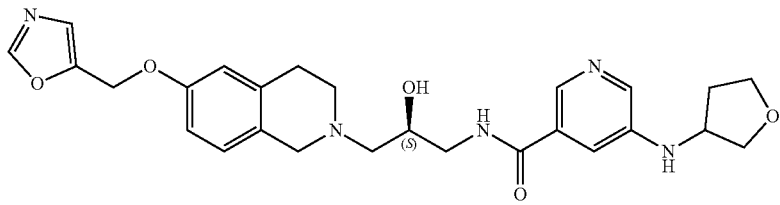

Prepared according to general procedure 8-A, condition 1. Yield: 27 mg (36%). $^1$H NMR (DMSO-d$_6$, 400 MHz): δ (ppm) 1.82 (m, 1H), 2.22 (m, 1H), 2.76 (m, 2H), 2.83 (m, 2H), 3.19 (m, 2H), 3.50 (m, 1H), 3.59 (m, 3H), 3.76 (m, 2H), 3.89 (m, 3H), 4.03 (m, 1H), 4.56 (s, 1H), 5.05 (s, 2H), 6.11 (d, 1H), 6.71 (m, 2H), 6.91 (d, 1H), 7.16 (s, 1H), 7.24 (s, 1H), 7.99 (d, 1H), 8.16 (m, 2H), 8.26 (t, 1H). LCMS(ESI): [M+2H]$^+$ m/z: calcd 493.5. found 494.2; Rt=0.709 min.

Example 8-5. (S)—N-(2-hydroxy-3-(6-(oxazol-5-ylmethoxy)-3,4-dihydroisoquinolin-2(1H)-yl)propyl-5-((tetrahydro-2H-pyran-4-yl)amino)nicotinamide (Compound 383)

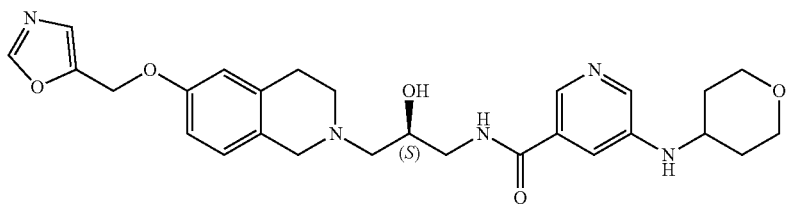

Prepared according to general procedure 8-A, condition 1. Yield: 31.2 mg (42.28%). $^1$H NMR (400 MHz, CDCl$_3$) δ 1.46 (m, 2H), 2.00 (m, 2H), 2.55 (m, 2H), 2.71 (m, 1H), 2.87 (m, 3H), 3.39 (m, 1H), 3.50 (m, 5H), 3.74 (m, 2H), 3.82 (m, 1H), 4.00 (m, 3H), 5.02 (s, 2H), 6.69 (m, 1H), 6.74 (m, 1H), 6.91 (m, 2H), 7.12 (s, 1H), 7.30 (m, 1H), 7.88 (s, 1H), 8.07 (d, 1H), 8.23 (s, 1H). LCMS(ESI): [M+H]$^+$ m/z: calcd 507.6. found 508.2; Rt=0.808 min.

Example 8-6. 5-[(1-acetylpiperidin-4-yl)amino]-N-[(2S)-2-hydroxy-3-{5-methyl-6-[(1,3-oxazol-5-yl)methoxy]-1,2,3,4-tetrahydroisoquinolin-2-yl}propyl]pyridine-3-carboxamide (Compound 606)

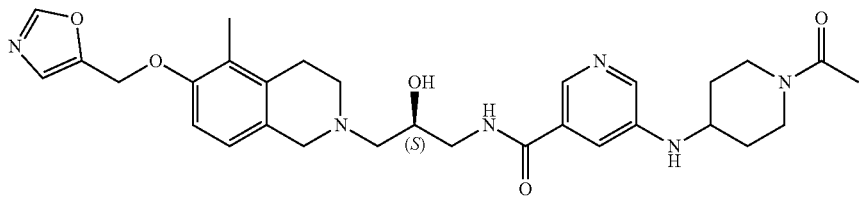

Prepared according to general procedure 8-A, condition 2. Yield: 7.8 mg (12.32%). $^1$H NMR (400 MHz, CDCl$_3$) δ 1.39 (m, 2H), 2.10 (m, 5H), 2.13 (m, 4H), 2.58 (m, 2H), 2.82 (m, 4H), 2.98 (m, 1H), 3.22 (t, 1H), 3.43 (m, 1H), 3.60 (d, 2H), 3.82 (m, 4H), 4.05 (m, 1H), 4.54 (m, 1H), 5.05 (s, 2H), 6.79 (m, 2H), 6.85 (d, 1H), 7.13 (s, 1H), 7.35 (s, 1H), 7.91 (s, 1H), 8.11 (d, 1H), 8.27 (s, 1H). LCMS(ESI): [M+2H]$^+$ m/z: calcd 562.3. found 563.3; Rt=0.801 min.

Example 8-7. N-[(2S)-2-hydroxy-3-{5-methyl-6-[(1,3-oxazol-5-yl)methoxy]-1,2,3,4-tetrahydroisoquinolin-2-yl}propyl]-5-f(oxolan-3-yl)amino]pyridine-3-carboxamide (Compound 510)

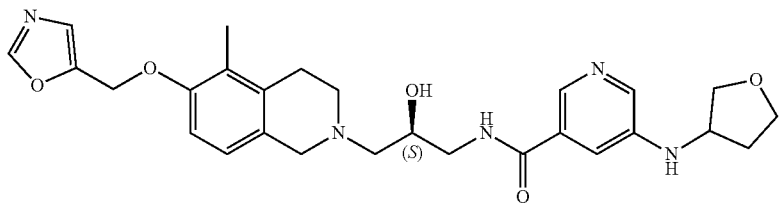

Prepared according to general procedure 8-A, condition 2. Yield: 7.3 mg (10.96%). $^1$H NMR (CDCl$_3$, 500 MHz): δ (ppm) 1.90 (m, 2H), 2.11 (s, 3H), 2.33 (m, 1H), 2.66 (m, 2H), 2.85 (m, 3H), 3.05 (m, 1H), 3.46 (m, 1H), 3.67 (m, 1H), 3.76 (m, 2H), 3.88 (m, 2H), 4.00 (m, 3H), 4.11 (m, 1H), 4.16 (m, 1H), 5.06 (s, 2H), 6.81 (d, 1H), 6.87 (d, 1H), 6.92 (t, 1H), 7.14 (s, 1H), 7.35 (s, 1H), 7.91 (s, 1H), 8.12 (s, 1H), 8.32 (s, 1H). LCMS(ESI): [M+H]$^+$ m/z: calcd 507.3. found 508.2; Rt=0.774 min.

Example 8-8. N—((S)-3-(5-chloro-6-(oxazol-5-ylmethoxy)-3N-dihydroisoquinolin-2(1H)-yl)-2-hydroxypropyl)-5-((tetrahydrofuran-3-yl)amino)nicotinamide (Compound 359)

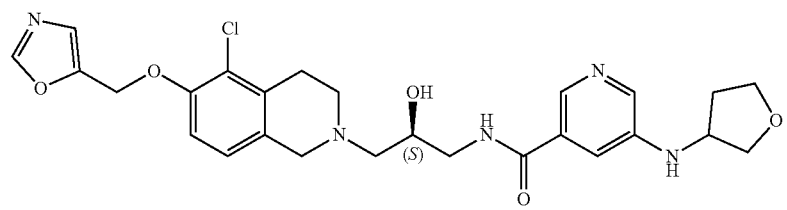

Prepared by general procedure 8-A, condition 2. Yield: 28.0 mg (37.33%). $^1$H NMR(DMSO-$d_6$, 400 MHz): δ (ppm) 1.75 (m, 1H), 2.20 (m, 1H), 2.46 (m, 2H), 2.72 (s, 4H), 3.17 (m, 1H), 3.43 (m, 1H), 3.52 (m, 1H), 3.57 (s, 2H), 3.73 (m, 1H), 3.81 (m, 1H), 3.89 (m, 2H), 4.02 (m, 1H), 4.84 (d, 1H), 5.23 (s, 2H), 6.29 (d, 1H), 7.01 (d, 1H), 7.11 (d, 1H), 7.25 (s, 1H), 7.33 (s, 1H), 8.06 (s, 1H), 8.20 (s, 1H), 8.41 (s, 1H), 8.47 (t, 1H). LCMS(ESI): [M+2H]$^+$ m/z: calcd 528.0. found 529.2; Rt=0.795 min.

Example 9

Example 9-1. (S)—N-(3-(6-((1H-1,2,3-triazol-5-yl)methoxy)-5-chloro-3N-dihydroisoquinolin-2(1H)-yl)-2-hydroxypropyl)-2-(cyclobutylamino)isonicotinamide (Compound 269)

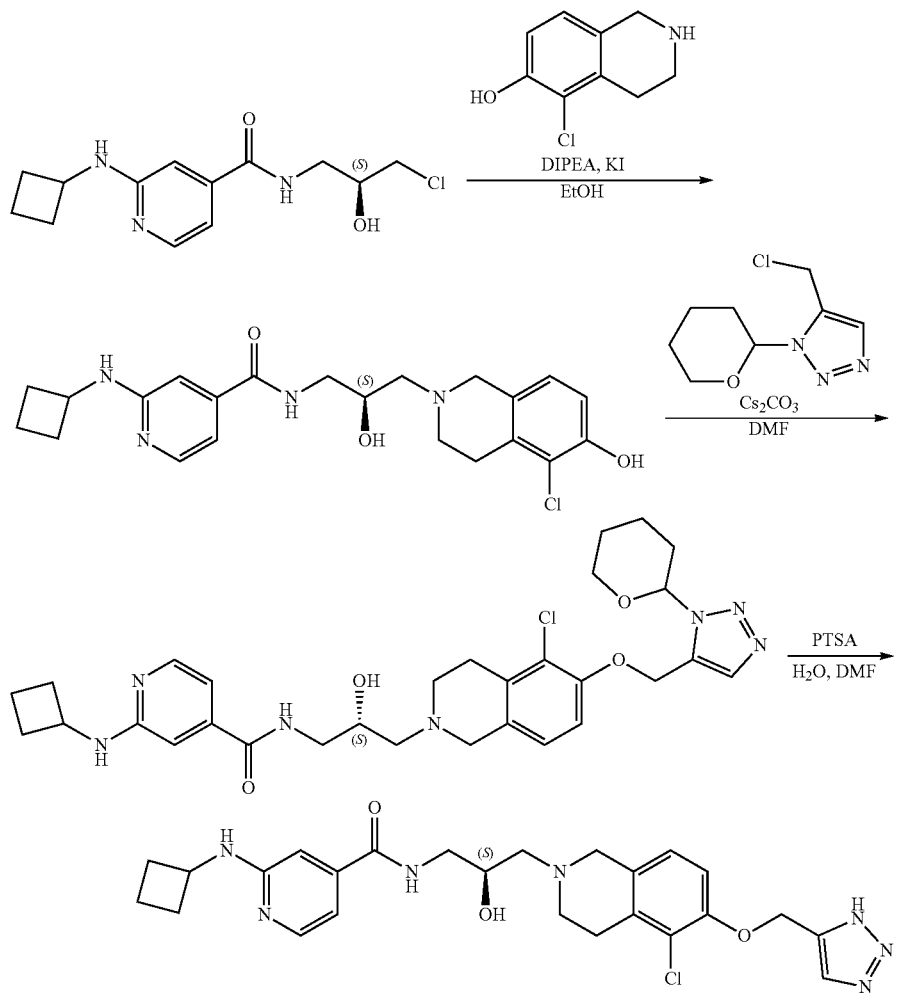

(S)—N-(3-(5-chloro-6-hydroxy-3,4-dihydroisoquinolin-2(1H)-yl)-2-hydroxypropyl)-2-(cyclobutylamino)isonicotinamide. 5-Chloro-1,2,3,4-tetrahydroisoquinolin-6-ol (277.72 mg, 1.51 mmol, HCl), N-[(2S)-3-chloro-2-hydroxypropyl]-2-(cyclobutylamino)pyridine-4-carboxamide (0.63 g, 2.22 mmol), DIPEA (2.39 g, 18.50 mmol, 3.22 mL), KI (307.13 mg, 1.85 mmol, 98.44 uL) were stirred in ethanol (10 mL) at 60° C. for 10. After the completion of the reaction (monitored by LCMS), the solvent was evaporated in vacuo. The residue was purified by HPLC (40-60% 0-6 min water-methanol, flow: 30 ml/min (loading pump 4 ml/min methanol), target mass 431 column: SunFire C18 100*19 mm, 5 um) to give A-[(2S)-3-(5-chloro-6-hydroxy-3,4-dihydro-1H-isoquinolin-2-yl)-2-hydroxy-propyl]-2-(cyclobutylamino)pyridine-4-carboxamide (0.2 g, 464.12 umol, 25.08% yield). $^1$H NMR (500 MHz, CDCl$_3$) δ (ppm) 1.79 (m, 2H), 1.88 (m, 2H), 2.44 (m, 2H), 2.60 (m, 2H), 2.77 (m, 1H), 2.86 (m, 2H), 2.95 (m, 1H), 3.43 (m, 1H), 3.48 (m, 1H), 3.57 (m, 1H), 3.73 (m, 2H), 4.01 (m, 1H), 4.17 (m, 1H), 4.88 (m, 1H), 6.70 (s, 1H), 6.73 (d, 1H), 6.81 (d, 1H), 6.85 (m, 2H), 8.10 (d, 1H). LCMS(ESI): [M+H]$^+$ m/z: calcd 431.2. found 431.2; Rt=0.71 min.

N-((2S)-3-(5-chloro-6-((1-(tetrahydro-2H-pyran-2-yl)-1H-1,2,3-triazol-5-yl)methoxy)-3,4-dihydroisoquinolin-2(1H)-yl)-2-hydroxypropyl)-2-(cyclobutylamino)isonicotinamide. N-[(2S)-3-(5-Chloro-6-hydroxy-3,4-dihydro-1H-isoquinolin-2-yl)-2-hydroxy-propyl]-2-(cyclobutylamino)pyridine-4-carboxamide (115.47 mg, 267.96 umol), 5-(chloromethyl)-1-tetrahydropyran-2-yl-triazole (64.84 mg, 321.55 umol) and cesium carbonate (130.96 mg, 401.94 umol) were mixed in DMF (1.5 mL) and heated at 80° C. for 10 hr while stirring. This reaction mixture was used on the next step.

(S)—N-(3-(6-((1H-1,2,3-triazol-5-yl)methoxy)-5-chloro-3,4-dihydroisoquinolin-2(1H)-yl)-2-hydroxypropyl)-2-(cyclobutlyamino)isonicotinamide. To the reaction mixture from the previous step, H₂O (2 mL) and PTSA (459.30 mg, 2.67 mmol) were added. The resulting mixture was stirred at 25° C. for 10 hr. Then, the solvents were evaporated in vacuo at 50° C. and the residue was purified by HPLC (30-50% 0-5 min water-methanol, flow: 30 ml/min (loading pump 4 ml/min methanol) target mass 513 column: SunFireC18 100×19 mm 5 um) to give N-[(2S)-3-[5-chloro-6-(1H-tri-azol-5-ylmethoxy)-3,4-dihydro-1H-isoquinolin-2-yl]-2-hy-droxy-propyl]-2-(cyclobutylamino)pyridine-4-carboxamide (60 mg, 117.19 umol, 43.94% yield). ¹H NMR (DMSO-d₆, 400 MHz): δ (ppm) 1.65 (m, 2H), 1.86 (m, 2H), 2.26 (m, 2H), 2.44 (m, 2H), 2.72 (m, 3H), 3.21 (m, 1H), 3.38 (m, 1H), 3.55 (m, 2H), 3.89 (m, 1H), 4.25 (m, 2H), 4.51 (s, 2H), 5.21 (s, 2H), 6.75 (ds, 2H), 6.94 (d, 1H), 6.99 (d, 1H), 7.14 (d, 1H), 7.81 (s, 1H), 7.95 (d, 1H), 8.49 (t, 1H). LCMS(ESI): [M+H]⁺ m/z: calcd 512.2. found 512.2; Rt=0.75 min.

Example 9-2. (S)—N-(3-(6-((1H-1,2,3-triazol-5-yl)methoxy)-5-chloro-3N-dihydroisoquinolin-2(1H)-yl)-2-hydroxypropyl)-6-((1-acetylpiperidin-4-yl)amino)pyrimidine-4-carboxamide (Compound 343)

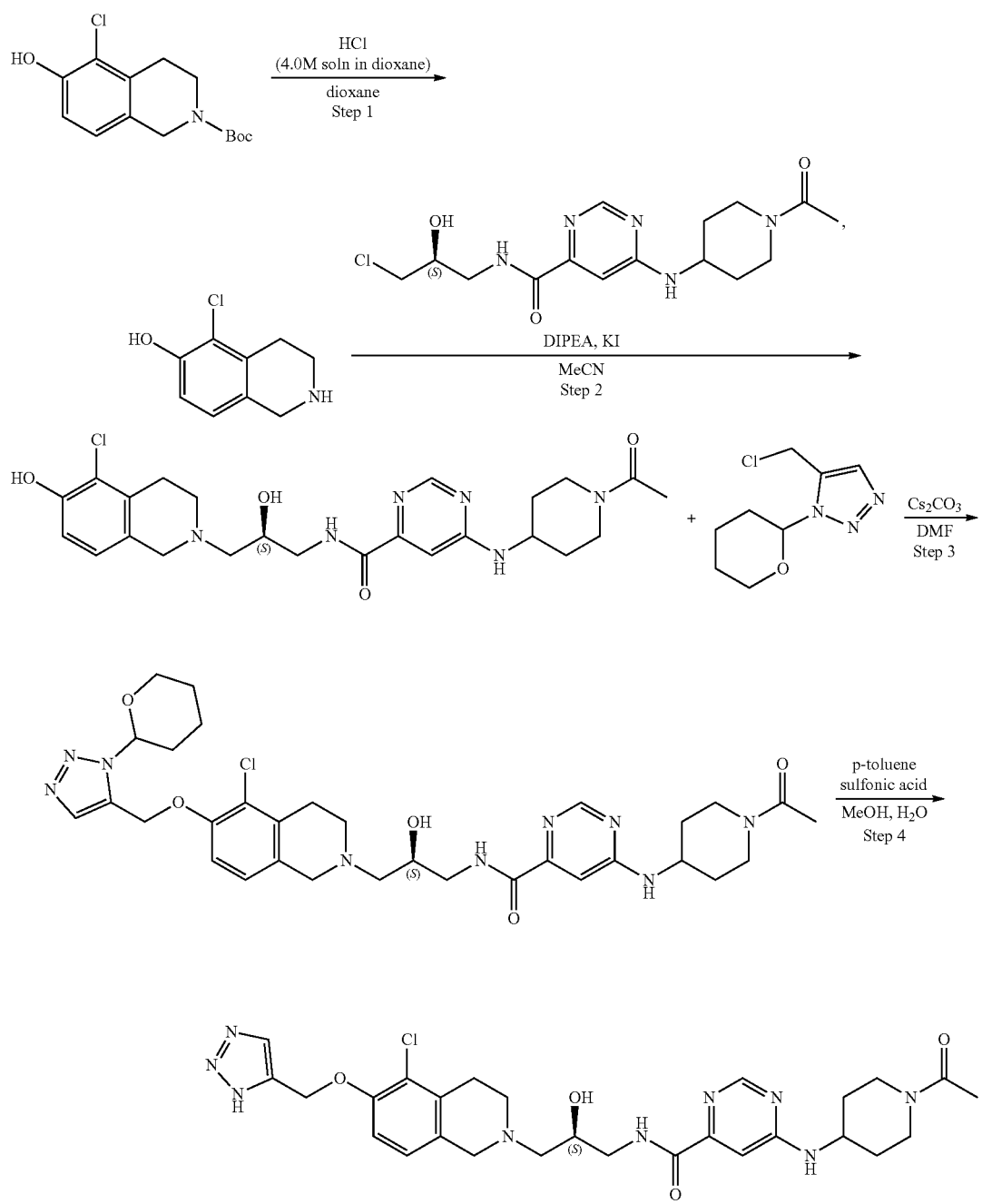

EN-TG2-680

5-chloro-1,2,3,4-tetrahydroisoquinolin-6-ol. tert-Butyl 5-chloro-6-hydroxy-3,4-dihydro-1H-isoquinoline-2-carboxylate (0.5 g, 1.76 mmol) was dissolved in dioxane (1.0 mL) and hydrogen chloride solution 4.0M in dioxane (4.00 g, 109.71 mmol, 5 mL) was added. The reaction mixture was stirred at 20° C. for 10 h. The formed solid was filtered on and dried in vacuo at 40° C. to give 5-chloro-1,2,3,4-tetrahydroisoquinolin-6-ol (0.37 g, 1.68 mmol, 95.40% yield, HCl). NMR (DMSO-de, 500 MHz): δ 2.91 (t, 2H), 3.39 (t, 2H), 4.14 (s, 2H), 6.94 (d, 1H), 7.02 (d, 1H), 9.45 (m, 2H), 10.32 (s, 1H). LCMS(ESI): [M+H]$^+$ m/z: calcd 183.0. found 184.0; Rt=0.42 min.

6-[(1-acetyl-4-piperidyl)amino]-N-[(2S)-3-(5-chloro-6-hydroxy-3,4-dihydro-1H-isoquinolin-2-yl)-2-hydroxy-propyl]pyrimidine-4-carboxamide.6-[(1-Acetyl-4-piperidyl) amino]-N-[(2S)-3-chloro-2-hydroxy-propyl]pyrimidine-4-carboxamide (0.15 g, 421.56 umol), 5-chloro-1,2,3,4-tetrahydroisoquinolin-6-ol (278.35 mg, 1.26 mmol, HCl), N,N-diisopropylethylamine (544.84 mg, 4.22 mmol, 734.29 uL), potassium iodide (139.96 mg, 843.13 umol, 44.86 uL) were mixed in MeCN (50 mL) and heated at 80° C. for 30 h. After the completion of the reaction, the resulting mixture was cooled to r.t. and the solvent was evaporated in vacuo at 40° C. The residue was purified by HPLC (20-60% R1 0-5 min 30 mL/min (loading pump 4 mL/min R1) SIM 504+ column: SunFireC18 100*19 mm) to give 6-[(1-acetyl-4-piperidyl)amino]-N-[(2S)-3-(5-chloro-6-hydroxy-3,4-dihydro-1H-isoquinolin-2-yl)-2-hydroxy-propyl]pyrimidine-4-carboxamide (0.02 g, 39.76 umol, 9.43% yield). $^1$H NMR (500 MHz, Chloroform-d) δ 1.43 (m, 2H), 2.07 (m, 1H), 2.13 (m, 3H), 2.57 (m, 2H), 2.75 (m, 1H), 2.87 (m, 3H), 2.94 (m, 1H), 3.25 (m, 1H), 3.46 (m, 2H), 3.60 (m, 2H), 3.68 (m, 1H), 3.73 (m, 1H), 3.83 (m, 1H), 4.03 (m, 1H), 4.16 (s, 1H), 4.60 (m, 1H), 5.07 (br.s, 1H), 5.52 (br.s, 1H), 6.84 (s, 2H), 7.15 (s, 1H), 8.41 (t, 1H), 8.52 (s, 1H). LCMS(ESI): [M+H]$^+$ m/z: calcd 502.2. found 503.2; Rt=0.79 min.

6-((1-acetylpiperidin-4-yl)amino)-N-((2S)-3-(5-chloro-6-((1-(tetrahydro-2H-pyran-2-yl)-1H-1,2,3-triazol-5-yl) methoxy)-3,4-dihydroisoquinolin-2(1H)-yl)-2-hydroxypropyl)pyrimidine-4-carboxamide (5)-6-((1-Acetylpiperidin-4-yl)amino)-N-(3-(5-chloro-6-hydroxy-3,4-dihydroisoquinolin-2(1H)-yl)-2-hydroxypropyl)pyrimidine-4-carboxamide (50 mg, 99.41 umol), cesium carbonate (64.78 mg, 198.81 umol) were mixed in DMF (2 mL) and 5-(chloromethyl)-1-tetrahydropyran-2-yl-triazole (30.07 mg, 149.11 umol) was added. The reaction mixture was stirred at 80° C. for 10 h. LCMS analysis of the reaction mixture showed 29% of product. The mixture was used as is on the next step. LCMS(ESI): [M+H]$^+$ m/z: calcd 667.3. found 668.2; Rt=1.04 min.

6-[(1-acetyl-4-piperidyl)amino]-N-[(2S)-3-[5-chloro-6-(1H-triazol-5-ylmethoxy)-3,4-dihydro-1H-isoquinolin-2-yl]-2-hydroxy-propyl]pyrimidine-4-carboxamide. 4-Methylbenzene-1-sulfonic acid hydrate (200 mg, 1.05 mmol, 161.29 uL) was added to a solution of 6-[(1-acetyl-4-piperidyl)amino]-N-[(2S)-3-[5-chloro-6-[(3-tetrahydropyran-2-yltriazol-4-yl)methoxy]-3,4-dihydro-1H-isoquinolin-2-yl]-2-hydroxy-propyl]pyrimidine-4-carboxamide (20 mg, 29.93 umol) (crude mixture from previous step in 2.0 ml of DMF) in a mixture of methanol (1.0 mL) and water (1.0 mL). The resulting mixture was stirred at 25° C. for 3 hr, then evaporated in vacuo and twice purified by reverse phase HPLC (column: SunFireC18 100*19 mm 5 um) using water/acetonitrile as mobile phase for first HPLC, and water/methanol for second HPLC to afford Compound 343 6-[(1-acetyl-4-piperidyl)amino]-N-[(2S)-3-[5-chloro-6-(1H-triazol-5-ylmethoxy)-3,4-dihydro-1H-isoquinolin-2-yl]-2-hydroxy-propyl]pyrimidine-4-carboxamide (6 mg, 10.27 umol, 34.32% yield) as beige solid. $^1$H NMR (500 MHz, CDCl$_3$) δ 1.45 (m, 2H), 2.08 (m, 2H), 2.14 (s, 3H), 2.18 (m, 2H), 2.59 (m, 2H), 2.78 (m, 1H), 2.84 (m, 2H), 2.92 (m, 3H), 3.25 (m, 1H), 3.48 (m, 2H), 3.58 (m, 1H), 3.69 (m, 1H), 3.76 (m, 1H), 3.86 (m, 1H), 4.04 (m, 1H), 4.58 (m, 1H), 5.30 (s, 2H), 6.89 (m, 2H), 7.15 (s, 1H), 7.84 (s, 1H), 8.46 (t, 1H), 8.51 (s, 1H). LCMS(ESI): [M+H]$^+$ m/z: calcd 583.2. found 584.2; Rt=0.89 min.

Example 9-3. (S6-((I H-1,2,3-triazol-5-yl)methoxy)-5-methyl-3,4-dihydroisoquinolin-2(1H)-yl)-2-hydroxypropyl)-2-(cyclobutylamino)isonicotinamide (Compound 273)

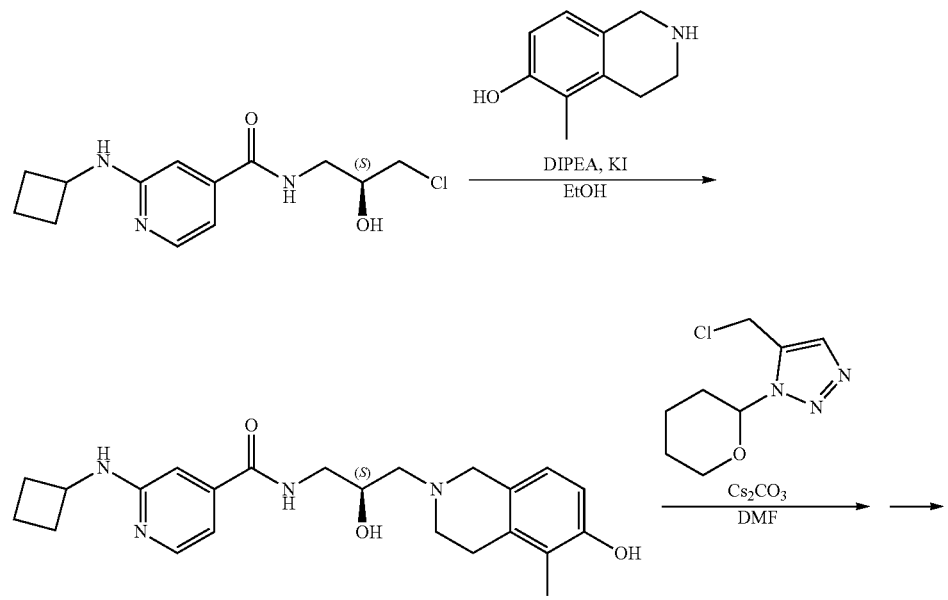

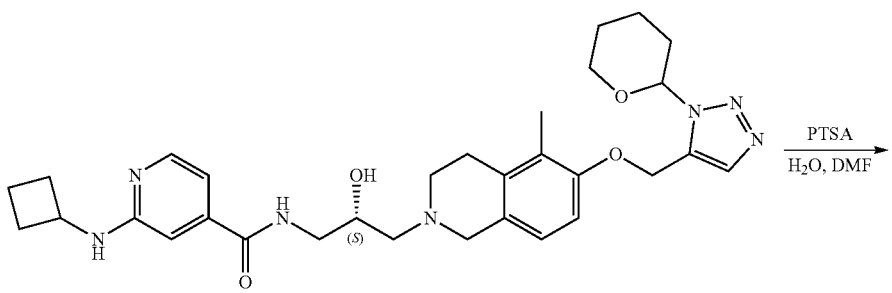

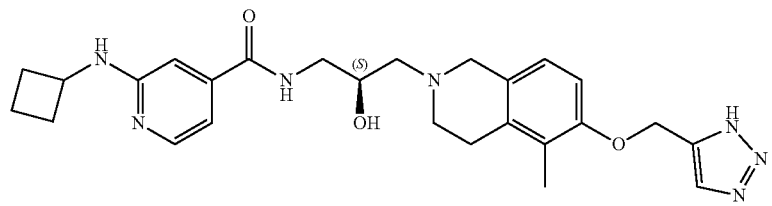

(S)-2-(cyclobutylamino)-N-(2-hydroxy-3-(6-hydroxy-5-methyl-3,4-dihydroisoquinolin-2(1H)-yl)propyl)isonicotinamide. 5-Methyl-1,2,3,4-tetrahydroisoquinolin-6-ol (0.25 g, 1.53 mmol), N-[(2S)-3-chloro-2-hydroxy-propyl]-2-(cyclobutylamino)pyridine-4-carboxamide (521.55 mg, 1.84 mmol), DIPEA (989.79 mg, 7.66 mmol, 1.33 mL), KI (254.26 mg, 1.53 mmol, 81.50 uL) were stirred in ethanol (10 mL) at 60° C. for 10 hr. After the completion of the reaction (monitored by LCMS), the solvent was evaporated in vacuo. The obtained residue was purified by HPLC (40-60% 0-6 min water-methanol, flow: 30 ml/min (loading pump 4 ml/min methanol), target mass 411 column: SunFire C18 100×19 mm, 5 um) to give 2-(cyclobutylamino)-N-[(2S)-2-hydroxy-3-(6-hydroxy-5-methyl-3,4-dihydro-1H-isoquinolin-2-yl)propyl]pyridine-4-carboxamide (0.11 g, 267.96 umol, 17.49% yield). This compound was used on the next step without NMR. LCMS(ESI): [M+H]⁺ m/z: calcd 410.2; found 411.2; Rt=0.70 min.

2-(cyclobutylamino)-N-((2S)-2-hydroxy-3-(5-methyl-6-((1-(tetrahydro-2H-pyran-2-yl)-1H-1,2,3-triazol-5-yl)methoxy)-3,4-dihydroisoquinolin-2(1H)-yl)propyl)isonicotinamide. 2-(cyclobutylamino)-A-[(2S)-2-hydroxy-3-(6-hydroxy-5-methyl-3,4-dihydro-1H-isoquinolin-2-yl)propyl]pyridine-4-carboxamide (0.11 g, 267.96 umol), 5-(chloromethyl)-1-tetrahydropyran-2-yl-triazole (64.84 mg, 321.55 umol), cesium carbonate (130.96 mg, 401.94 umol) were mixed in DMF (1.5 mL) and stirred at 80° C. for 10 hr. This reaction mixture was used on the next step.

(S)—N-(3-(6-((1H-1,2,3-triazol-5-yl)methoxy)-5-methyl-3,4-dihydroisoquinolin-2(1H)-yl)-2-hydroxypropyl)-2-(cyclobutylamino)isonicotinamide. To the reaction mixture from the previous step H₂O (2 mL) and PTSA (448.67 mg, 2.61 mmol) were added. The resulting mixture was stirred at 25° C. for 10 hr. When LCMS showed no starting material, the solvents were evaporated in vacuo at 50° C. and the residue was purified by HPLC (30-50% 0-5 min water-methanol, flow: 30 ml/min (loading pump 4 ml/min methanol) target mass 491 column: SunFireC18 100*19 mm 5 um) to give 2-(cyclobutylamino)-A-[(2S)-2-hydroxy-3-[5-methyl-6-(1H-triazol-5-ylmethoxy)-3,4-dihydro-1H-isoquinolin-2-yl]propyl]pyridine-4-carboxamide (9 mg, 18.31 umol, 7.03% yield). ¹H NMR (Chloroform-d, 500 MHz): δ (ppm) 1.78 (m, 3H), 1.89 (m, 3H), 2.12 (s, 3H), 2.45 (m, 2H), 2.59 (m, 2H), 2.76 (m, 3H), 2.96 (m, 1H), 3.45 (m, 1H), 3.58 (d, 1H), 3.72 (m, 1H), 3.78 (d, 1H), 4.04 (m, 1H), 4.17 (m, 1H), 4.93 (d, 1H), 5.22 (s, 2H), 6.72 (s, 2H), 6.83 (dd, 2H), 7.00 (t, 1H), 7.77 (s, 1H), 8.06 (d, 1H). LCMS(ESI): [M+H]⁺ m/z: calcd 491.2. found 492.4; Rt=0.71 min.

Example 9-4. (S)—N-(3-(6-((1H-1,2,3-triazol-5-yl)methoxy)-3,4-dihydroisoquinolin-2(1H)-yl)-2-hydroxypropyl)-6-((1-acetylpiperidin-4-yl)amino)pyrimidine-4-carboxamide (Compound 257)

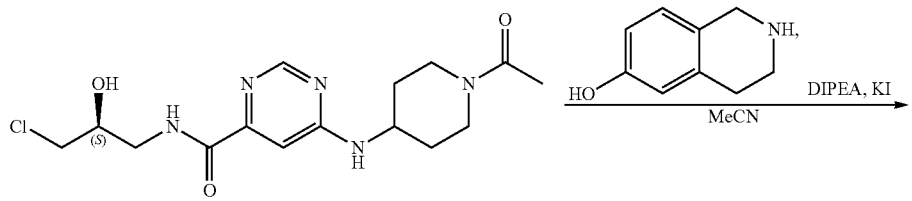

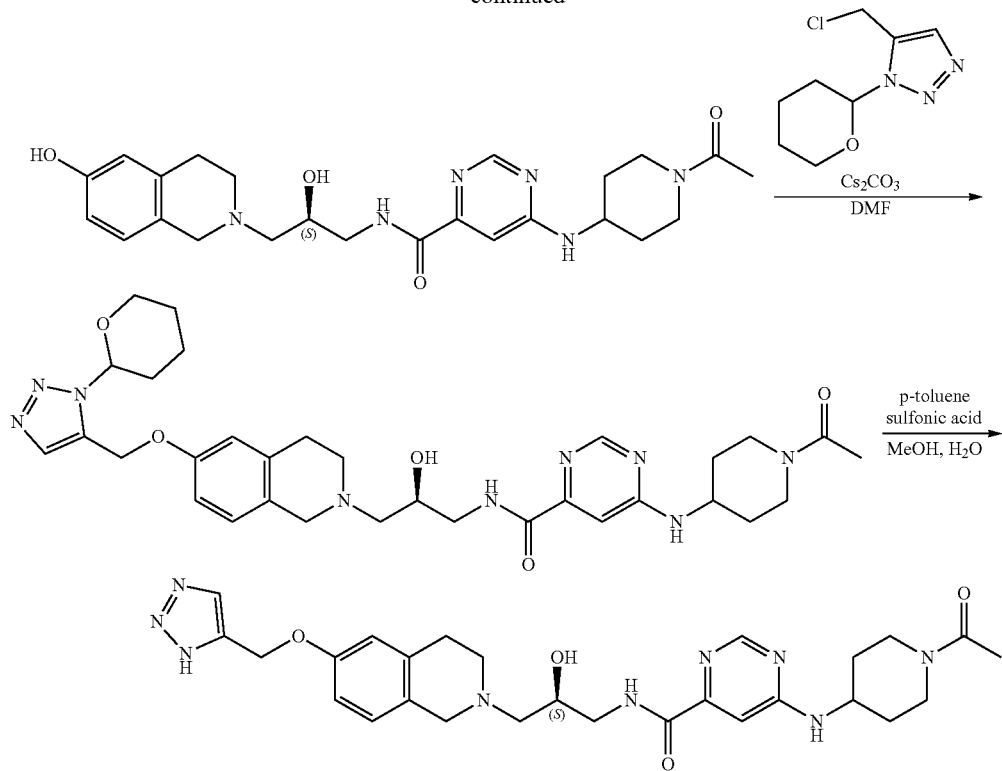

EN-TG2-682

6-[(1-acetyl-4-piperidyl)amino]-N-[(2S)-2-hydroxy-3-(6-hydroxy-3,4-dihydro-1H-isoquinolin-2-yl)propyl[pyrimidine-4-carboxamide. 6-[(1-acetyl-4-piperidyl)amino]-N-[(2S)-3-chloro-2-hydroxy-propyl]pyrimidine-4-carboxamide (0.27 g, 758.81 umol), 1,2,3,4-tetrahydroisoquinolin-6-ol (135.85 mg, 910.58 umol), AA-diisopropylethylamine (196.14 mg, 1.52 mmol, 264.34 uL), potassium iodide (188.95 mg, 1.14 mmol, 60.56 uL) were mixed in MeCN (50 mL) and heated at 80° C. for 10 hr while stirring. The reaction completion was monitored by LCMS every 10 hr 1,2,3,4-tetrahydroisoquinolin-6-ol (135.85 mg, 910.58 umol) and N,N-diisopropylethylamine (196.14 mg, 1.52 mmol, 264.34 uL) were added after 10 and 20 hr of heating. And 76% of product and 7% of starting chloride was obtained in reaction mixture after 30 hr of heating. The solvent was evaporated in vacuo at 40° C. The residue was purified by HPLC to give 6-[(1-acetyl-4-piperidyl)amino]-N-[(2S)-2-hydroxy-3-(6-hydroxy-3,4-dihydro-1H-isoquinolin-2-yl)propyl]pyrimidine-4-carboxamide (0.2 g, 426.85 umol, 56.25% yield). $^1$H NMR (DMSO-$d_6$, 400 MHz): δ 1.28 (m, 1H), 1.38 (m, 1H), 1.91 (m, 2H), 2.00 (s, 3H), 2.46 (m, 2H), 2.72 (m, 6H), 3.16 (m, 2H), 3.42 (m, 1H), 3.48 (m, 2H), 3.78 (m, 1H), 3.86 (m, 1H), 4.09 (m, 1H), 4.21 (m, 1H), 4.93 (m, 1H), 6.48 (s, 1H), 6.49 (d, 1H), 6.79 (d, 1H), 7.06 (s, 1H), 7.75 (d, 1H), 8.31 (m, 1H), 8.72 (t, 1H). LCMS(ESI): [M+H]$^+$ m/z: calcd 468.2. found 469.2; Rt=0.76 min.

6-((1-acetylpiperidin-4-yl)amino)-N-((2S)-2-hydroxy-3-(6-((1-(tetrahydro-2H-pyran-2-yl)-1H-1,2,3-triazol-5-yl)methoxy)-3,4-dihydroisoquinolin-2(1H)-yl)propyl)pyrimidine-4-carboxamide. 6-[(1-Acetyl-4-piperidyl)amino]-N-[(2S)-2-hydroxy-3-(6-hydroxy-3,4-dihydro-1H-isoquinolin-2-yl)propyl]pyrimidine-4-carboxamide (99.57 mg, 212.51 umol), 5-(chloromethyl)-1-tetrahydropyran-2-yl-triazole (51.42 mg, 255.01 umol), cesium carbonate (103.86 mg, 318.77 umol) were heated in DMF (3.0 mL) at 80° C. for 10 hr while stirring. Then, the solvent was evaporated in vacuo at 50° C. and the residue was used on the next step as is. LCMS(ESI): [M-THP]$^+$ m/z: calcd 549.2. found 550.4; Rt=1.04 min.

6-[(1-acetyl-4-piperidyl)amino]-N-[(2S)-2-hydroxy-3-[6-(1H-triazol-5-ylmethoxy)-3,4-dihydro-1H-isoquinolin-2-yl]propyl]pyrimidine-4-carboxamide. 6-[(1-Acetyl-4-piperidyl)amino]-N-[(2S)-2-hydroxy-3-[6-[(3-tetrahydropyran-2-yltriazol-4-yl)methoxy]-3,4-dihydro-1H-isoquinolin-2-yl]propyl]pyrimidine-4-carboxamide (134.57 mg, 212.35 umol) was dissolved in mixture of H$_2$O (3.0 mL) and ethanol (3.0 mL). 4-Methylbenzene-1-sulfonic acid hydrate (403.92 mg, 2.12 mmol, 325.74 uL) was added. The mixture was stirred at 25° C. for 10 hr. Then, the solvents were evaporated in vacuo at 40° C. The residue was purified by HPLC (20-65% R1 0-5 min 30 ml/min (loading pump 4 mL/min R1) SIM 550+column: SunFireC18 100*19 mm sample with TEA) to give 6-[(1-acetyl-4-piperidyl)amino]-N-[(2S)-2-hydroxy-3-[6-(1H-triazol-5-ylmethoxy)-3,4-dihydro-1H-isoquinolin-2-yl]propyl]pyrimidine-4-carboxamide (105 mg, 19E04 umol, 89.97% yield). $^1$H NMR (400 MHz, Chloroform-d) δ 1.42 (m, 2H), 2.04 (m, 1H), 2.11 (s, 4H), 2.56 (m, 2H), 2.69 (m, 1H), 2.83 (m, 4H), 3.22 (t, 1H), 3.43 (m, 1H), 3.53 (d, 1H), 3.66 (m, 1H), 3.73 (d, 1H), 3.82 (d, 1H), 4.00 (m, 1H), 4.55 (d, 1H), 5.17 (s, 2H), 5.25 (m, 1H), 6.71 (s, 1H), 6.75 (d, 1H), 6.89 (d, 1H), 7.13 (s, 1H), 7.74 (s, 1H), 8.44 (m, 1H), 8.48 (s, 1H) OH, NH are not observed. LCMS(ESI): [M+H]$^+$ m/z: calcd 549.3. found 550.4; Rt=0.85 min.

Example 9-5. (S)-2-(cyclobutylamino)-N-(2-hydroxy-3-(5-methyl-6-((3-methylisoxazol-4-yl)methoxy)-3N-dihydroisoquinolin-2(1H)-propyl) isonicotinamide (Compound 263)

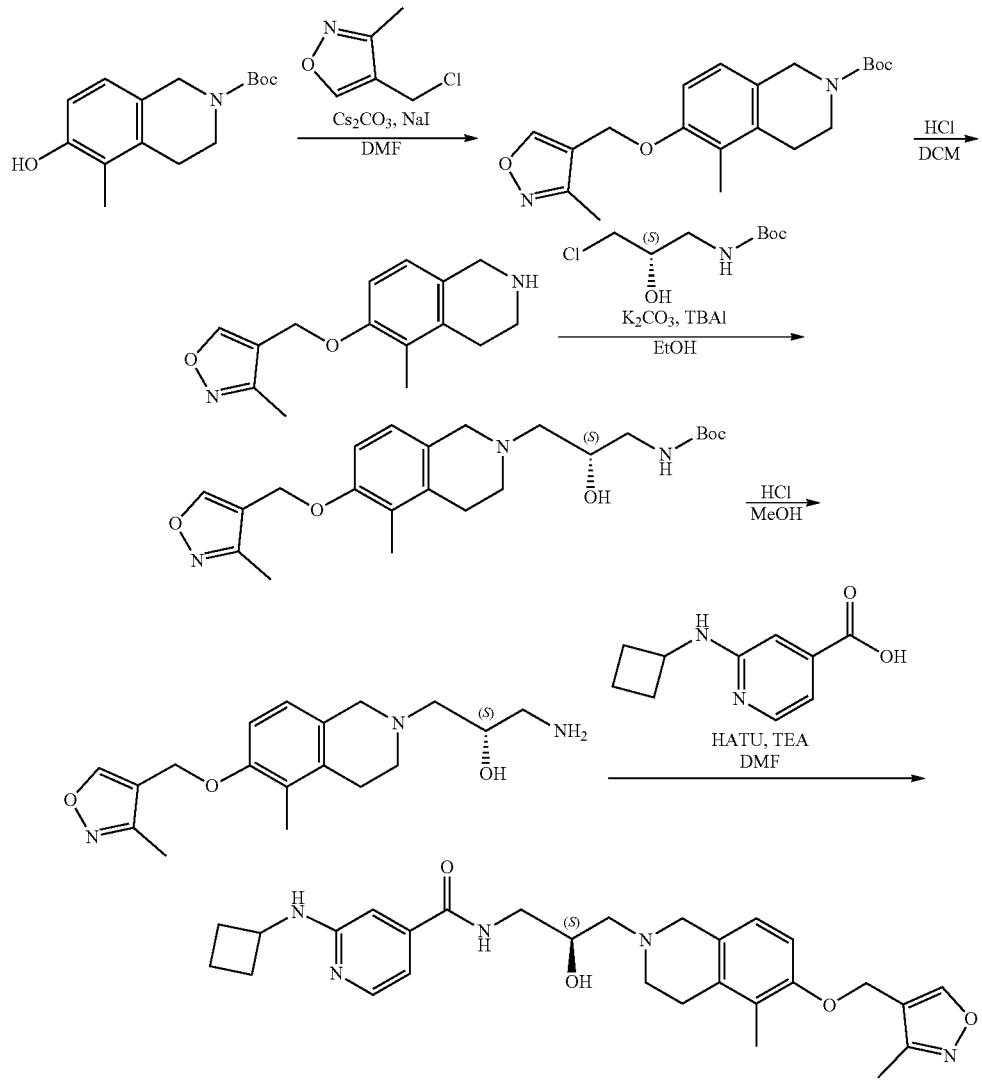

tert-butyl 5-methyl-6-((3-methylisoxazol-4-yl)methoxy)-3,4-dihydroisoquinoline-2(1H)-carboxylate. 4-(Chloromethyl)-3-methyl-isoxazole (1.20 g, 9.11 mmol) was added to the mixture of tert-butyl 6-hydroxy-5-methyl-3,4-dihydro-1H-isoquinoline-2-carboxylate (2 g, 6.08 mmol), cesium carbonate (2.97 g, 9.11 mmol) and sodium iodide (182.15 mg, 1.22 mmol) in DMF (25 mL). The reaction was stirred at 45° C. for 12 hr. The mixture was quenching with H₂O (100 mL). The aqueous layer was extracted with MTBE (2*100 mL). The combined organic layers were washed with water (2*30 mL) and brine, dried over Na₂SO₄ and concentrated in vacuo to afford tert-butyl 5-methyl-6-[(3-methylisoxazol-4-yl)methoxy]-3,4-dihydro-1H-isoquinoline-2-carboxylate (2.8 g, crude) which was used without purification. $^1$H NMR (400 MHz, CDCl$_3$) δ 1.49 (s, 9H), 2.11 (s, 3H), 2.36 (s, 3H), 2.74 (t, 2H), 3.65 (t, 2H), 4.53 (s, 2H), 4.88 (s, 2H), 6.79 (d, 1H), 6.94 (d, 1H), 8.37 (s, 1H). LCMS(ESI): [M-Boc]$^+$ m/z: calcd 258.2; found 259.2; Rt=0.82 min.

3-methyl-4-(((5-methyl-1,2,3,4-tetrahydroisoquinolin-6-yl)oxy)methyl)isoxazole. Hydrogen chloride solution 4.0M in dioxane (16.28 g, 62.49 mmol, 15.50 mL, 14% purity) was carefully added at r.t. to a solution of tert-butyl 5-methyl-6-[(3-methylisoxazol-4-yl)methoxy]-3,4-dihydro-1H-isoquinoline-2-carboxy late (2.8 g, 6.25 mmol) in DCM (35 mL). The reaction mixture was then stirred for 12 hr at r.t. and the solvents were evaporated in vacuo to give 3-methyl-4-[(5-methyl-1,2,3,4-tetrahydroisoquinolin-6-yl) oxymethyl]isoxazole (2 g, crude, 2HCl) which was used without purification. $^1$H NMR (400 MHz, DMSO-d$_6$) δ 2.00 (s, 3H), 2.26 (s, 3H), 2.84 (m, 2H), 3.32 (m, 2H), 4.14 (s, 2H), 4.99 (s, 2H), 7.03 (s, 2H), 8.90 (s, 1H), 9.45 (s, 2H). LCMS(ESI): [M+H]$^+$ m/z: calcd 258.2. found 259.1; Rt=0.81 min.

(S)-tert-butyl (2-hydroxy-3-(5-methyl-6-((3-methylisoxazol-4-yl)methoxy)-3,4-dihydroisoquinolin-2(1H)-yl)propyl) carbamate. 3-Methyl-4-[(5-methyl-1,2,3,4-tetrahydroisoquinolin-6-yl)oxymethyl]isoxazole (2 g, 4.83 mmol, 2HCl), potassium carbonate (2.34 g, 16.91 mmol, 1.02 mL) and tetrabutylammonium iodide (178.42 mg, 483.04 umol) were mixed together in EtOH (40 mL). The resulting suspension was stirred at r.t. for 10 min., then tert-butyl N-[(2S)-3-chloro-2-hydroxy-propyl]carbamate (1.42 g, 6.76 mmol) was added in one portion and the reaction mixture was stirred at 50° C. for 24 hr, cooled down and concentrated in vacuo. The residue was suspended in MTBE (100 mL) and filtered. The filtercake was washed with MTBE (3*100 mL) and discarded. The filtrate was evaporated in vacuo to leave the residue tert-butyl N-[(2S)-2-hydroxy-3-[5-methyl-6-[(3-methylisoxazol-4-yl)methoxy]-3,4-dihydro-1H-isoquinolin-2-yl]propyl]carbamate (3 g, crude). $^1$H NMR (400 MHz, DMSO-$d_6$) δ 1.35 (s, 9H), 1.99 (s, 3H), 2.26 (s, 3H), 2.40 (s, 2H), 2.63 (m, 4H), 2.87 (m, 2H), 3.03 (m, 1H), 3.49 (m, 1H), 3.69 (m, 1H), 4.60 (m, 1H), 4.93 (s, 2H), 6.62 (m, 1H), 6.86 (m, 2H), 8.87 (s, 1H). LCMS(ESI): [M+H]$^+$ m/z: calcd 431.2. found 432.2; Rt=1.09 min.

(S)-1-amino-3-(5-methyl-6-((3-methylisoxazol-4-yl)methoxy)-3,4-dihydroisoquinolin-2(1H)-yl)propan-2-ol. Hydrogen chloride solution 4.0M in dioxane (12.67 g, 48.66 mmol, 12.07 mL, 14% purity) was carefully added at r.t. to a solution of tert-butyl N-[(2S)-2-hydroxy-3-[5-methyl-6-[(3-methylisoxazol-4-yl)methoxy]-3,4-dihydro-1H-isoquinolin-2-yl]propyl]carbamate (3 g, 4.87 mmol) in MeOH (30 mL). The reaction mixture was then stirred for 12 hr at r.t. and the solvents were evaporated in vacuo to give (2S)-1-amino-3-[5-methyl-6-[(3-methylisoxazol-4-yl)methoxy]-3,4-dihydro-1H-isoquinolin-2-yl]propan-2-ol (2.4 g, crude, 3HCl). $^1$H NMR (400 MHz, DMSO-$d_6$) δ (ppm) 1.10 (m, 2H), 2.05 (s, 3H), 2.27 (s, 3H), 3.40 (m, 1H), 3.56 (m, 3H), 3.74 (m, 1H), 4.32 (m, 2H), 4.46 (m, 1H), 5.01 (s, 2H), 7.04 (m, 2H), 8.20 (m, 3H), 8.91 (s, 1H), 10.78 (m, 1H). LCMS(ESI): [M+H]$^+$ m/z: calcd 331.2. found 332.2; Rt=0.71 min.

(S)-2-(cyclobutylamino)-N-(2-hydroxy-3-(5-methyl-6-((3-methylisoxazol-4-yl)methoxy)-3,4-dihydroisoquinolin-2(1H)-yl)propyl)isonicotinamide. (2S)-1-Amino-3-[5-methyl-6-[(3-methylisoxazol-4-yl)methoxy]-3,4-dihydro-1H-isoquinolin-2-yl]propan-2-ol (0.5 g, 1.13 mmol, 3HCl) and 2-(cyclobutylamino)pyridine-4-carboxylic acid (347.37 mg, 1.13 mmol, CF$_3$CO$_2$H) were mixed in DML (10 mL). The reaction suspension was cooled to 0° C. and HATU (431.30 mg, 1.13 mmol) followed by TEA (1.03 g, 10.21 mmol, 1.42 mL) were added. The clear solution was stirred at ambient temperature for 12 h, then volatiles were evaporated under reduced pressure and residue (1 g) was subjected to RP HPLC (column: XBridge Prep C18 OBD 100×19 mm 5 um, H$_2$O-MeOH as mobile phase) to give Compound 263 2-(cyclobutylamino)-N-[(2S)-2-hydroxy-3-[5-methyl-6-[(3-methylisoxazol-4-yl)methoxy]-3,4-dihydro-1H-isoquinolin-2-yl]propyl]pyridine-4-carboxamide (0.04 g, 79.11 umol, 6.97% yield). $^1$H NMR (500 MHz, Chloroform-d) δ 1.74 (m, 2H), 1.83 (m, 2H), 2.05 (s, 3H), 2.32 (s, 3H), 2.39 (m, 2H), 2.55 (m, 2H), 2.73 (m, 3H), 2.91 (m, 1H), 3.40 (m, 2H), 3.54 (d, 1H), 3.67 (m, 1H), 3.72 (m, 1H), 3.99 (m, 1H), 4.12 (h, 1H), 4.84 (s, 2H), 5.00 (d, 1H), 6.67 (m, 2H), 6.73 (d, 1H), 6.81 (d, 1H), 7.14 (t, 1H), 8.00 (d, 1H), 8.33 (s, 1H). LCMS(ESI): [M+H]$^+$ m/z: 505.27 calcd; 506.4 found; Rt=0.844 min.

Example 9-6. (S)-6-((1-acetylpiperidin-4-yl)amino)-N-(2-hydroxy-3-(5-methyl-6-((3-methylisoxazol-4-yl)methoxy)-3N-dihydroisoquinolin-2(1H)-yl)propyl)pyrimidine-4-carboxamide (Compound 264)

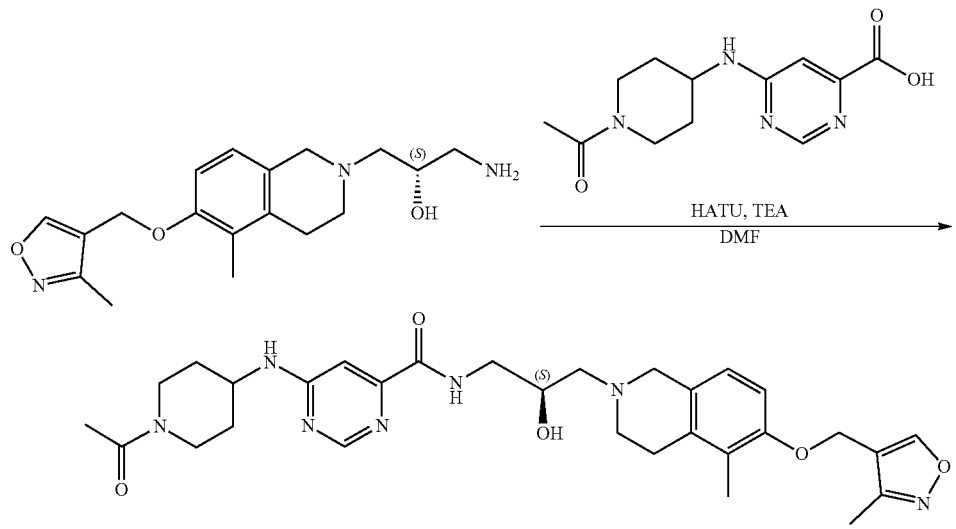

(2S)-1-Amino-3-[5-methyl-6-[(3-methylisoxazol-4-yl)methoxy]-3,4-dihydro-1H-isoquinolin-2-yl]propan-2-ol (500.00 mg, 1.13 mmol, 3HCl) and 6-[(1-acetyl-4-piperidyl)amino]pyrimidine-4-carboxylic acid (299.78 mg, 1.13 mmol) were mixed in DMF (10 mL). The reaction suspension was cooled to 0° C. and HATU (431.30 mg, 1.13 mmol) followed by TEA (1.03 g, 10.21 mmol, 1.42 mL) were added. The obtained clear solution was stirred at ambient temperature for 12 hr, then volatiles were evaporated under reduced pressure and recidue (1 g) was subjected to RP HPLC (H$_2$O-ACN as mobile phase) to give Compound 264 6-[(1-acetyl-4-piperidyl)amino]-N-[(2S)-2-hydroxy-3-(5-methyl-6-[(3-methylisoxazol-4-yl)methoxy]-3,4-dihydro-1H-isoquinolin-2-yl]propyl]pyrimidine-4-carboxamide (0.098 g, 169.65 umol, 14.96% yield). $^1$H NMR (400 MHz, DMSO-$d_6$) δ (ppm) 1.10 (m, 2H), 1.85 (m, 2H), 2.05 (s, 6H), 2.27 (s, 3H), 2.50 (m, 4H), 2.60-2.80 (m, 5H), 3.16 (d, 1H), 3.40 (m, 1H), 3.56 (m, 2H), 3.86 (m, 2H), 4.09 (s, 1H) 4.23 (m, 1H), 4.94 (s, 2H), 6.84 (dd, 2H), 7.06 (s, 1H), 7.76 (d, 1H), 8.30 (s, 1H), 8.70 (t, 1H), 8.88 (s, 1H). LCMS(ESI): [M+H]$^+$ m/z: calcd 577.3; found 578.2; Rt=0.89 min.

Example 9-7. 5-chloro-2-(cyclobutylamino)-N-[(2S)-2-hydroxy-3-[6-(oxazol-5-ylmethoxy)-3N-dihydro-1H-isoquinolin-2-yl]propyl]pyridine-4-carboxamide (Compound 284)

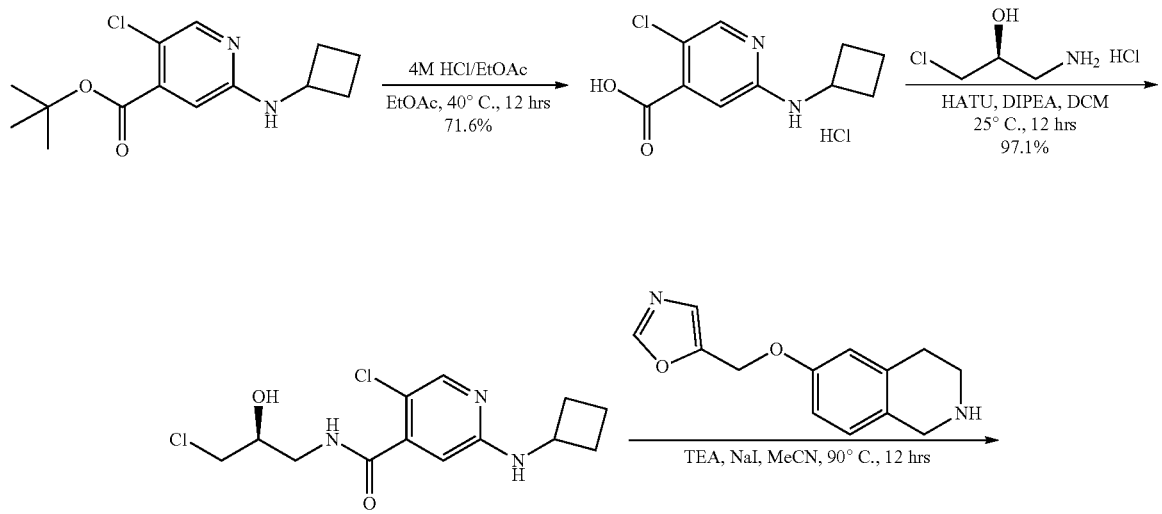

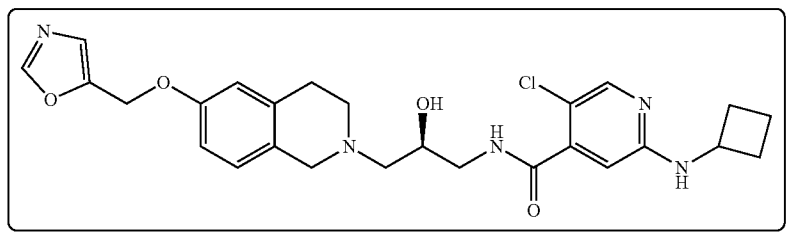

tert-butyl 2-(cyclobutylamino)pyridine-4-carboxylate. To a solution of tert-butyl 2-fluoropyridine-4-carboxylate (1 g, 5.07 mmol) and cyclobutanamine (11.71 mmol, 1 mL) in NMP (20 mL) was added K$_2$CO$_3$ (2.10 g, 15.21 mmol). The mixture was stirred at 100° C. for 12 hours and the resulting mixture was diluted with EtOAc (200 mL), washed with saturated NH$_4$Cl aqueous solution (80 mL*4), brine (100 mL), dried over anhydrous Na$_2$SO$_4$, filtered and concentrated under reduced pressure. The residue was purified by flash chromatography (ISCO®; 20 g AgelaFlash® Silica Flash Column, Petroleum ether/EtOAc with EtOAc from 0-15%, Flow rate: 30 mL/min) to afford tert-butyl 2-(cyclobutylamino)pyridine-4-carboxylate (800 mg, 63.5% yield) as yellow solid. $^1$H NMR (400 MHz, methanol-d$_4$) δ ppm 8.02 (d, J=5.5 Hz, 1H), 6.97 (s, 1H), 6.94 (dd, J=5.4, 1.4 Hz, 1H), 4.28 (quin, J=7.8 Hz, 1H), 2.37-2.49 (m, 2H), 1.89-2.00 (m, 2H), 1.74-1.86 (m, 2H), 1.60 (s, 9H); LCMS (ESI) [M+H]$^+$ m/z: calcd 249.2. found 249.0.

tert-butyl 5-chloro-2-(cyclobutylamino)pyridine-4-carboxylate. To a solution of tert-butyl 2-(cyclobutylamino)pyridine-4-carboxylate (150 mg, 0.60 mmol) in MeCN (10 mL) was added 1-chloropyrrolidine-2,5-dione (83 mg, 0.62 mmol) in batches. The mixture was stirred at 50° C. for 6 hours. The resulting mixture was combined with another two batches. The mixture was quenched by addition of water (100 mL) and extracted with EtOAc (100 mL*3). The combined organic layer was dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~10%, Flow rate: 30 mL/min) to afford tert-butyl 5-chloro-2-(cyclobutylamino)pyridine-4-carboxylate (300 mg, 65.9% yield) as yellow gum. $^1$H NMR (400 MHz, DMSO-d$_6$) δ ppm 8.04 (s, 1H), 7.28 (d, J=7.3 Hz, 1H), 6.64 (s, 1H), 4.24 (quin, J=7.8 Hz, 1H), 2.22-2.30 (m, 2H), 1.79-1.90 (m, 2H), 1.60-1.73 (m, 2H), 1.53 (s, 9H); regiochemistry was confirmed by HMBC.

5-chloro-2-(cyclobutylamino)pyridine-4-carboxylic acid. To a solution of tert-butyl 5-chloro-2-(cyclobutylamino)pyridine-4-carboxylate (300 mg, 1.06 mmol) in EtOAc (10 mL) was added 4M HCl/EtOAc (10 mL). The mixture was stirred at 40° C. for 12 hours. The precipitate was collected by filtration, washed with EtOAc (5 mL*3) and dried under reduced pressure to afford 5-chloro-2-(cyclobutylamino)pyridine-4-carboxylic acid (200 mg, 71.6% yield, HCl salt) as white solid. $^1$H NMR (400 MHz, methanol-$d_4$) δ ppm 8.01 (s, 1H), 7.32 (s, 1H), 4.19 (quin, J=7.7 Hz, 1H), 2.49-2.58 (m, 2H), 2.07-2.20 (m, 2H), 1.84-1.97 (m, 2H).

5-chloro-N-[(2S)-3-chloro-2-hydroxy-propyl]-2-(cyclobutylamino)pyridine-4-carboxamide. To a solution of 5-chloro-2-(cyclobutylamino)pyridine-4-carboxylic acid (180 mg, 0.68 mmol, HCl salt) and HATU (270 mg, 0.71 mmol) in DCM (5 mL) were added DIPEA (3.44 mmol, 600 μL) and (2S)-1-amino-3-chloro-propan-2-ol (100 mg, 0.68 mmol, HCl salt). The mixture was stirred at 25° C. for 12 hours. The resulting mixture was combined with another batch and concentrated under reduced pressure. The residue was diluted with EtOAc (100 mL) and washed with saturated NH$_4$Cl aqueous solution (30 mL*2), brine (20 mL), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~50%, Flow rate: 30 mL/min) to afford 5-chloro-N-[(2S)-3-chloro-2-hydroxy-propyl]-2-(cyclobutylamino)pyridine-4-carboxamide (235 mg, 97.1% yield) as yellow solid. $^1$H NMR (400 MHz, methanol-$d_4$) δ ppm 7.94 (s, 1H), 6.49 (s, 1H), 4.23 (quin, J=7.9 Hz, 1H), 3.99 (quin, J=5.5 Hz, 1H), 3.65-3.71 (m, 1H), 3.50-3.61 (m, 2H), 3.40-3.47 (m, 1H), 2.38 (brd, J=7.5 Hz, 2H), 1.85-1.98 (m, 2H), 1.72-1.82 (m, 2H); LCMS (ESI) [M+H]$^+$ m/z: calcd 318.2. found 318.0.

5-chloro-2-(cyclobutylamino)-N-[(2S)-2-hydroxy-3-[6-(oxazol-5-ylmethoxy)-3,4-dihydro-1H-isoquinolin-2-yl]propyl]pyridine-4-carboxamide. To a solution of 5-chloro-N-[(2S)-3-chloro-2-hydroxy-propyl]-2-(cyclobutylamino)pyridine-4-carboxamide (100 mg, 0.31 mmol), 5-(1,2,3,4-tetrahydroisoquinolin-6-yloxymethyl)oxazole (75 mg, 0.33 mmol), TEA (100 mg, 0.10 mmol) in MeCN (2 mL) was added NaI (60 mg, 0.40 mmol). The mixture was stirred at 90° C. for 12 hours. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% ammonia hydroxide (v %); Mobile phase B: MeCN; Gradient: B from 27% to 57% in 7.8 min, hold 100% B for 2.5 min; Flow Rate: 25 mL/min; Column Temperature: 30° C.; Wavelength: 220 nm, 254 nm) to afford 5-chloro-2-(cyclobutylamino)-N-[(2S)-2-hydroxy-3-[6-(oxazol-5-ylmethoxy)-3,4-dihydro-1H-isoquinolin-2-yl]propyl]pyridine-4-carboxamide (65 mg, 40.4% yield) as yellow solid. $^1$H NMR (400 MHz, methanol-$d_4$) δ ppm 8.23 (s, 1H), 7.92 (s, 1H), 7.22 (s, 1H), 6.97 (d, J=8.3 Hz, 1H), 6.74-6.81 (m, 2H), 6.48 (s, 1H), 5.10 (s, 2H), 4.22 (quin, J=7.8 Hz, 1H), 4.00-4.09 (m, 1H), 3.68 (s, 2H), 3.39-3.52 (m, 2H), 2.82-2.89 (m, 4H), 2.61-2.72 (m, 2H), 2.33-2.39 (m, 2H), 1.85-1.97 (m, 2H), 1.71-1.80 (m, 2H); LCMS (ESI) [M+H]$^+$ m/z: calcd 512.0. found 512.1; HPLC: 100% @ 254 nm; 100% ee.

Example 9-8. (S)-1-((4-(3-bromothiophen-2-yl)pyrimidin-2-yl)amino)-3-(6-(oxazol-5-ylmethoxy)-3,4-dihydroisoquinolin-2(1H)-yl)propan-2-ol (Compound 331)

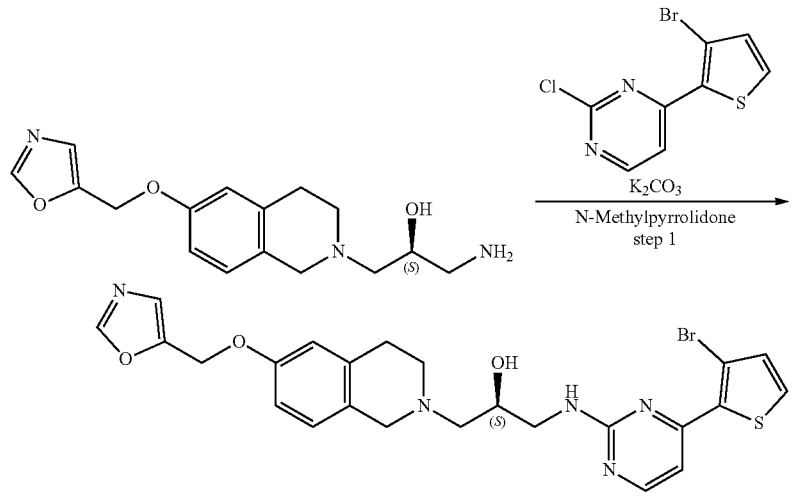

EN-TG2-1532

(2S)-1-Amino-3-[6-(oxazol-5-ylmethoxy)-3,4-dihydro-1H-isoquinolin-2-yl]propan-2-ol (225 mg, 545.14 umol, 3HCl), 4-(3-bromothiophen-2-yl)-2-chloropyrimidine (152.21 mg, 552.37 umol) and potassium carbonate, anhydrous, 99% (452.06 mg, 3.27 mmol, 197.41 uL) were mixed together in N-methylpyrrolidone (2.5 mL). The resulting mixture was stirred under argon at 115° C. for 12 hr, then N-methylpyrrolidone was removed under redused pressure (1 mm. Hg) and the residue was purified by reverse phase HPLC (column: SunFireC18 100×19 mm 5 um) using water/methanol as mobile phase (60-85% methanol) to afford Compound 331 (2S)-1-[[4-(3-bromo-2-thienyl)pyrimidin-2-yl]amino]-3-[6-(oxazol-5-ylmethoxy)-3,4-dihydro-1H-isoquinolin-2-yl]propan-2-ol (73 mg, 134.58 umol, 24.69% yield) as beige solid. $^1$H NMR (500 MHz, DMSO-$d_6$) δ 2.55 (m, 1H), 2.69 (m, 2H), 2.77 (m, 2H), 3.29 (m, 2H), 3.55 (m, 3H), 3.95 (m, 1H), 4.72 (m, 1H), 5.11 (s, 2H), 6.76 (m, 1H), 6.78 (m, 1H), 6.93 (d, 1H), 7.12 (m, 1H), 7.22 (m, 1H), 7.29 (s, 1H), 7.41 (d, 1H), 7.76 (m, 1H), 8.38 (m, 2H). LCMS(ESI): [M-Boc]⁺ m/z: calcd 542.5. found 544.0; Rt=1.104 min.

Example 9-9. 2-(cyclobutylamino)-N-[(2S)-2-hydroxy-3-[2-(oxazol-5-ylmethoxy)-7,8-dihydro-5H-1,6-naphthyridin-6-yl]propyl]pyridine-4-carboxamide (Compound 413)

added in portions at 0° C. The resulting mixture was stirred at 40° C. for 12 hours. The resulting mixture was quenched by addition of NH₄Cl (100 mL) and extracted with EtOAc (100 mL*3). The combined organic layer was washed with brine (100 mL), dried over anhydrous Na₂SO₄, filtered and concentrated under reduced pressure to give 6-benzyl-1,5,7,8-tetrahydro-1,6-naphthyridin-2-one (850 mg, crude) as a yellow solid which was used next step without further purification.

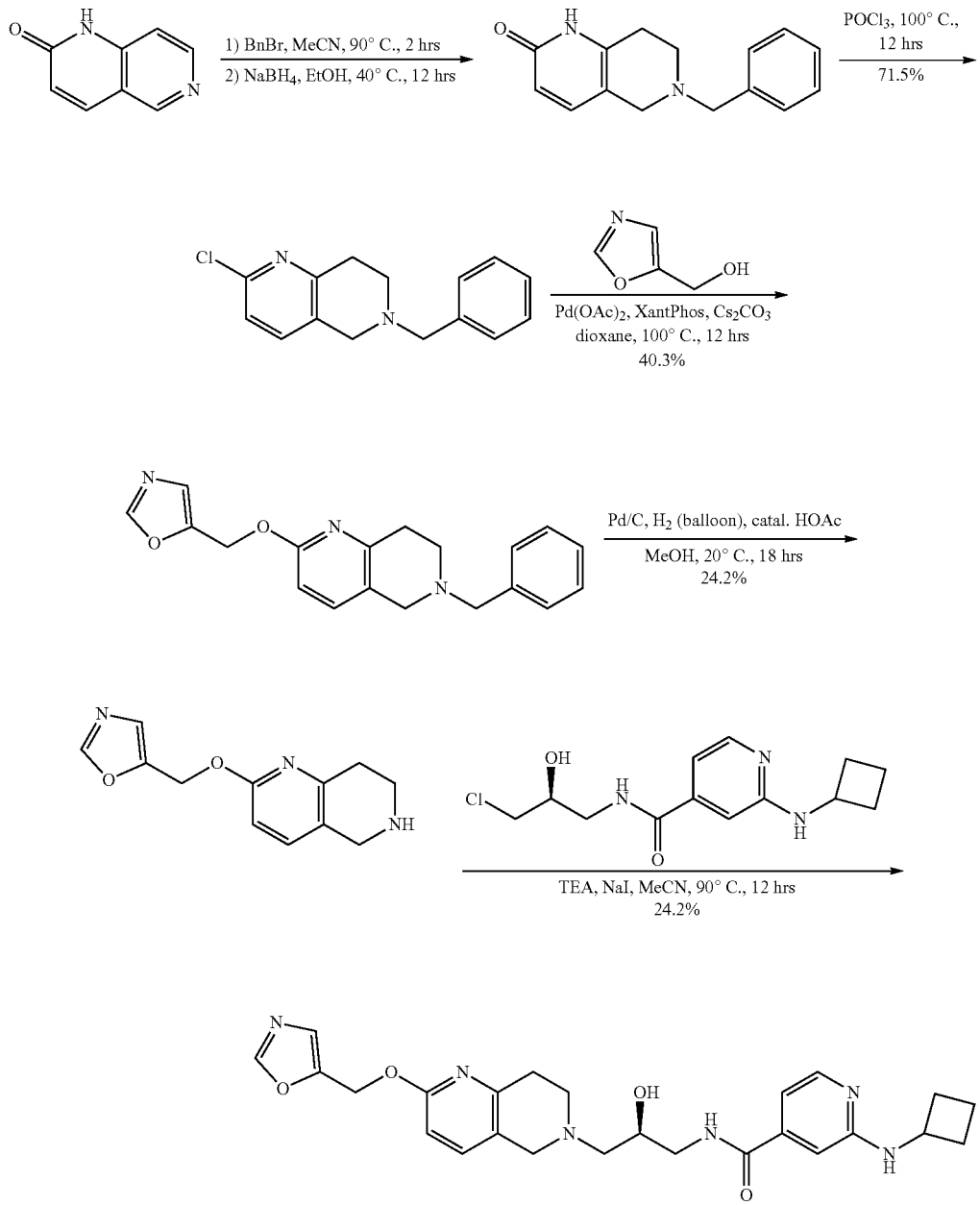

6-benzl]-2-chloro-7,8-dihydro-5H-1,6-naphthyridine. A mixture of 1H-1,6-naphthyridin-2-one (500 mg, 3.42 mmol) and bromomethylbenzene (720 mg, 4.21 mmol) in MeCN (10 mL) was stirred at 90° C. for 2 hours. The resulting mixture was cooled to 20° C. and concentrated under reduced pressure to remove MeCN. The residue was dissolved in EtOH (10 mL) and NaBH₄ (1 g, 26.4 mmol) was 6-benzyl-2-chloro-7,8-dihydro-5H-1,6-naphthyridine. A mixture of 6-benzyl-1,5,7,8-tetrahydro-1,6-naphthyridin-2-one (1 g, 4.16 mmol) in POCl₃ (10 mL) was stirred at 100° C. for 12 hours. The mixture was quenched by poured into ice/water (30 mL). The mixture was washed with EtOAc (30 mL*2) and the aqueous phase was adjusted pH=9 with saturated NaOH aqueous solution, then extracted with EtOAc (50 mL*3). The combined organic layer was washed with brine (100 mL*3), dried over anhydrous Na$_2$SO$_4$, filtered and concentrated under reduced pressure to give 6-benzyl-2-chloro-7,8-dihydro-5H-1,6-naphthyridine (770 mg, 71.5% yield) as a brown oil, which was directly used without further purification. LCMS (ESI) [M+H]$^+$ m/z: calcd 259.1. found 259.0.

5-[(6-benzyl)]-7,8-dihydro-5H-1,6-naphthyridin-2-yl)oxymethyl]oxazole. A mixture of 6-benzyl-2-chloro-7,8-dihydro-5H-1,6-naphthyridine (600 mg, 2.32 mmol), oxazol-5-ylmethanol (345 mg, 3.48 mmol), Pd(OAc)$_2$ (26 mg, 0.116 mmol), XantPhos (135 mg, 0.233 mmol) and dioxane (10 mL) was stirred at 100° C. for 12 hours under nitrogen. The resulting mixture was filtered, diluted with H$_2$O (30 mL) and extracted with EtOAc (30 mL*3). The combined organic layer was washed with brine (100 mL*2), dried over anhydrous Na2SO4, filtered and concentrated under reduced pressure to give a crude product, which was purified by flash chromatography (ISCO®; 24 g AgelaFlash® Silica Flash Column, petroleum ether/EtOAc with EtOAc from 0~35%, 30 mL/min) to afford 5-[(6-benzyl-7,8-dihydro-5H-1,6-naphthyridin-2-yl)oxymethyl]oxazole (300 mg, 40.3% yield) as a colorless oil. $^1$H NMR (400 MHz, methanol-d$_4$) δ ppm 8.20 (s, 1H), 7.28-7.42 (m, 6H), 7.20 (s, 1H), 6.58 (d, J=8.4 Hz, 1H), 52H), 3.56 (s, 2H) 0.38 (s, 2H), 3.73 (s, 2.89-2.94 (m, 2H), 2.82-2.86 (m, 2H); LCMS (ESI) [M+H]$^+$ m/z: calcd 322.1. found 322.1.

5-(5,6,7,8-tetrahydro-[6-naphthyridin-2-yloxymethyl)oxazole. To a solution of 5-[(6-benzyl-7,8-dihydro-5H-1,6-naphthyridin-2-yl)oxymethyl]oxazole (230 mg, 0.716 mmol) in MeOH (10 mL) were added Pd/C (20 mg, 10% wt of Pd with 50% wt of water) and HOAc (2 drops) under nitrogen atmosphere. The suspension was degassed and purged with hydrogen for 3 times. The mixture was stirred for 18 hours under hydrogen (note: the reaction mixture was monitored by LCMS every 3 hours in order to avoid over reduction). The mixture was filtered and the filtrate was concentrated under reduced pressure to give a crude product which was purified by preparative TLC (silica, DCM/MeOH=10:1, 254 nm) to afford 5-(5,6,7,8-tetrahydro-1,6-naphthyridin-2-yloxymethyl)oxazole (40 mg, 24.2% yield) as a colorless oil. LCMS (ESI) [M+H]$^+$ m/z: calcd 232.1. found 232.1. (50 mg of 5-[(6-benzyl-7,8-dihydro-5H-1,6-naphthyridin-2-yl)oxymethyl]oxazole was recovered).

2-(cyclobutylamino)-N-[(2S)-2-hydroxy-3-[(oxazol-5-ylmethoxy)-7,8-dihydro-5H-1,6-naphthyridin-6-yl]propyl]pyridine-4-carboxamide. A mixture of 5-(5,6,7,8-tetrahydro-1,6-naphthyridin-2-yloxymethyl)oxazole (20 mg, 0.0865 mmol), N-[(2S)-3-chloro-2-hydroxy-propyl]-2-(cyclobutylamino)pyridine-4-carboxamide (30 mg, 0.106 mmol), TEA (27 mg, 0.267 mmol) and NaI (20 mg, 0.133 mmol) in MeCN (1 mL) was stirred at 90° C. for 12 hours in a sealed tube. The mixture was concentrated under reduced pressure to give a crude product, which was purified by preparative HPLC (Instrument: Gilson GX-281 Liquid Handler, Gilson 322 Pump, Gilson 156 UV Detector; Column: Waters Xbridge 150×50 mm×10 μm; Mobile phase A: H$_2$O with 0.05% NH$_3$—H$_2$O (v %); Mobile phase B: MeCN; Gradient: B from 21% to 61% in 8 min, hold 100% B for 2 min; Flow Rate: 25 mL/min; Column Temperature: 30° C.; Wavelength: 220 nm, 254 nm) to give 2-(cyclobutylamino)-N-[(2S)-2-hydroxy-3-[2-(oxazol-5-ylmethoxy)-7,8-dihydro-5H-1,6-naphthyridin-6-yl]propyl]pyridine-4-carboxamide (10 mg, 24.2% yield) as a white dry powder. $^1$H NMR (400 MHz, methanol-d$_4$) δ ppm 8.21 (s, 1H), 7.92 (d, J=5.4 Hz, 1H), 7.36 (d, J=8.4 Hz, 1H), 7.21 (s, 1H), 6.80 (s, 1H), 6.76 (d, J=5.4 Hz, 1H), 6.59 (d, J=8.3 Hz, 1H), 5.39 (s, 2H), 4.23 (quin, J=7.8 Hz, 1H), 4.08 (quin, J=5.9 Hz, 1H), 3.67 (s, 2H), 3.49-3.57 (m, 1H), 3.38-3.46 (m, 1H), 2.92 (s, 4H), 2.62-2.71 (m, 2H), 2.36-2.45 (m, 2H), 1.87-1.98 (m, 2H), 1.72-1.83 (m, 2H); LCMS (ESI) [M+H]$^+$ m/z: calcd 479.2. found 479.2; HPLC: 99.87%@254 nm; 99.5% ee.

Example 9-10. 6-[(1-acetyl-4-piperidyl)amino]-N-[(2S)-2-hydroxy-3-[2-(oxazol-5-ylmethoxy)-7,8-dihydro-5H-1,6-naphthyridin-6-yl]propyl]pyrimidine-4-carboxamide (Compound 412)

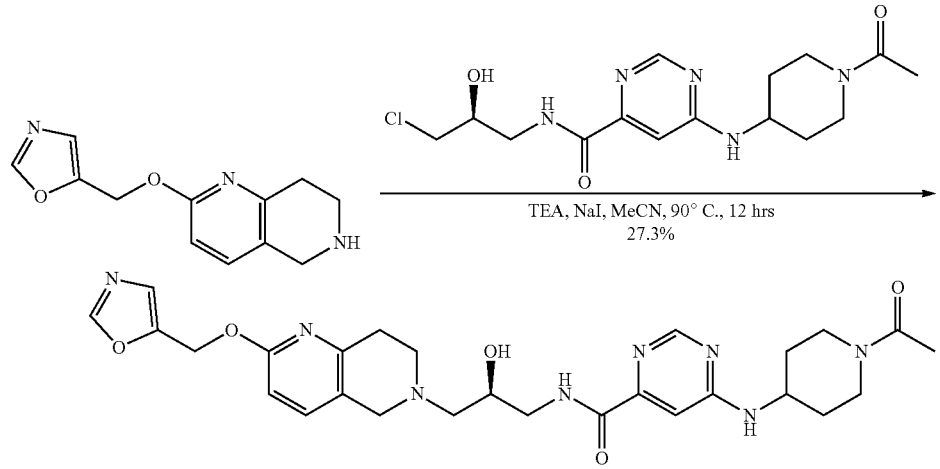

A mixture of 5-(5,6,7,8-tetrahydro-1,6-naphthyridin-2-yloxymethyl)oxazole (20 mg, 0.0865 mmol), 6-[(1-acetyl-4-piperidyl)amino]-N-[(2S)-3-chloro-2-hydroxy-propyl]pyrimidine-4-carboxamide (40 mg, 0.112 mmol), TEA (27 mg, 0.267 mmol) and NaI (20 mg, 0.133 mmol) in MeCN (2 mL) was stirred at 90° C. for 12 hours in a sealed tube. The mixture was concentrated under reduced pressure to give a crude product, which was purified by preparative HPLC (Instrument: Gilson GX-281 Liquid Handler, Gilson 322 Pump, Gilson 156 UV Detector; Column: Waters Xbridge 150×50 mm×10 μm; Mobile phase A: H$_2$O with 0.05% NH$_3$—H$_2$O (v %); Mobile phase B: MeCN; Gradient: B from 12% to 42% in 9.5 min, hold 100% B for 2 min; Flow Rate: 25 mL/min; Column Temperature: 30° C.; Wavelength: 220 nm, 254 nm) to give 6-[(1-acetyl-4-piperidyl)amino]-N-[(2S)-2-hydroxy-3-[2-(oxazol-5-ylmethoxy)-7,8-dihydro-5H-1,6-naphthyridin-6-yl]propyl]pyrimidine-4-carboxamide (13 mg, 27.3% yield) as a white dry powder. $^1$H NMR (400 MHz, methanol-$d_4$) δ ppm 8.24 (s, 1H), 8.22 (s, 1H), 7.35 (d, J=8.4 Hz, 1H), 7.23 (s, 1H), 7.07 (s, 1H), 6.58 (d, J=8.4 Hz, 1H), 5.40 (s, 2H), 4.43 (d, J=13.3 Hz, 1H), 4.16 (s, 1H), 4.05 (quin, J=6.0 Hz, 1H), 3.93 (d, J=15.1 Hz, 1H), 3.66 (s, 2H), 3.52 (d, J=5.8 Hz, 2H), 3.23-3.30 (m, 1H), 2.85-2.99 (m, 5H), 2.68 (d, J=6.1 Hz, 2H), 2.12 (s, 3H), 1.97-2.11 (m, 2H), 1.36-1.54 (m, 2H); LCMS (ESI) [M+H]$^+$ m/z: calcd 551.3. found 551.2; HPLC: 99.22%@254 nm; 95.6% ee.

Example 9-11. 2-(cyclobutylamino)-N-[(2S)-2-hydroxy-3-[2-[(4-methyloxazol-5-yl)methoxy]-7,8-dihydro-5H-1,6-naphthyridin-6-yl]propyl]pyridine-4-carboxamide (Compound 467)

6-benzyl-1,5,7,8-tetrahydro-1,6-naphthyridin-2-one. A mixture of 1H-1,6-naphthyridin-2-one (3 g, 20.5 mmol) and bromomethylbenzene (3 mL, 25.3 mmol) in MeCN (15 mL) was stirred at 90° C. for 2 hours. The resulting mixture was cooled to 20° C. and concentrated under reduced pressure to remove MeCN. The residue was diluted with EtOH (15 mL), followed by addition of NaBH$_4$ (4 g*3, 0.106 mol) in portions at 0° C. The resulting mixture was stirred at 20° C. for 36 hours. The reaction mixture was adjusted to pH=9 with 2 N HCl aqueous solution and concentrated under reduced pressure. Water (20 mL) was added and extracted with EtOAc (50 mL*2). The organic layers was combined and dried over anhydrous Na2SO4, concentrated under reduced pressure to give crude product. The residue was purified by flash chromatography (ISCO®; 40 g Agela-Flash® Silica Flash Column, EtOAc/MeOH with MeOH from 0~10%, flow rate=30 mL/min) to afford 6-benzyl-1,5,7,8-tetrahydro-1,6-naphthyridin-2-one (2.7 g, 54.7% yield) as light-yellow solid. $^1$H NMR (400 MHz, methanol-$d_4$) δ ppm 7.25-7.40 (m, 6H), 6.34 (d, J=9.3 Hz, 1H), 3.70 (s, 2H),

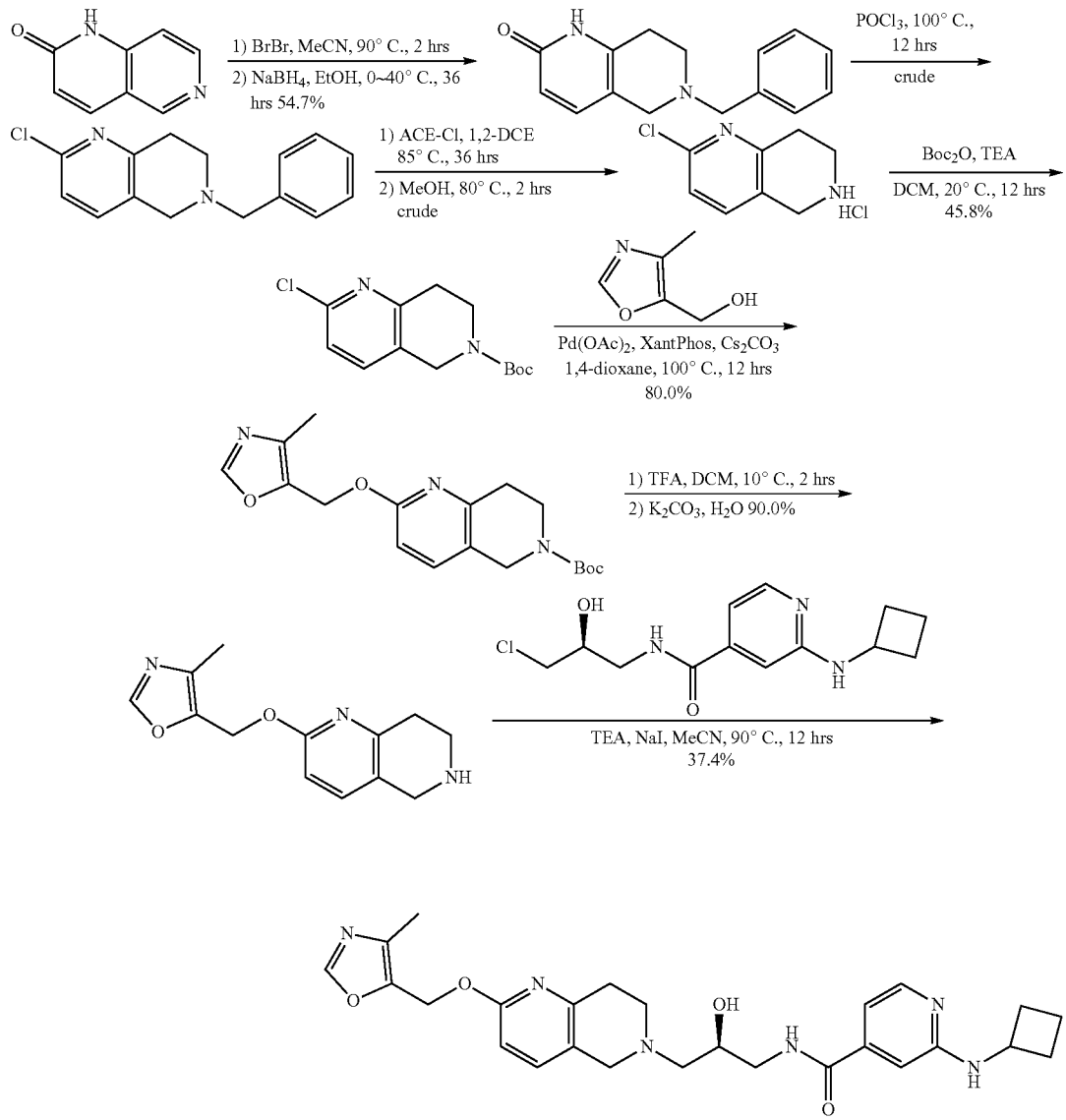

3.39 (s, 2H), 2.74-2.79 (m, 2H), 2.68-2.73 (m, 2H); LCMS (ESI) [M+H]+ calcd 241.1. found 241.1.

6-benzyl-2-chloro-7,8-dihydro-5H-1,6-naphthyridine. A mixture of 6-benzyl-1,5,7,8-tetrahydro-1,6-naphthyridin-2-one (2 g, 8.32 mmol) in POCl$_3$ (10 mL) was stirred at 100° C. for 12 hours. The mixture was quenched by pouring into ice/water (30 mL) and then washed with EtOAc (30 mL*2). The aqueous phase was adjusted to pH=9 with saturated K$_2$CO$_3$ aqueous solution and extracted with EtOAc (50 mL*3). The combined organic layer was washed with brine (20 mL*3), dried over anhydrous Na$_2$SO$_4$, filtered and concentrated under reduced pressure to give 6-benzyl-2-chloro-7,8-dihydro-5H-1,6-naphthyridine (2.4 g, crude) as a brown oil, which was directly used without further purification. $^1$H NMR (400 MHz, methanol-d$_4$) δ ppm 7.51-7.70 (m, 6H), 7.37 (d, J=8.0 Hz, 1H), 4.55 (s, 2H), 4.45 (s, 2H), 3.22-3.31 (m, 4H); LCMS (ESI) [M+H]+ m/z: calcd 259.1. found 259.0.

2-chloro-5,6,7,8-tetrahydro-1,6-naphthyridine. To a mixture of 6-benzyl-2-chloro-7,8-dihydro-5H-1,6-naphthyridine (2.2 g, 8.50 mmol) in 1,2-DCE (20 mL) was added 1-chloroethyl carbonochloridate (1.4 mL*3, 12.8 mmol) every 12 hours and the resulting mixture was stirred at 85° C. for 36 hours. The resulting mixture was concentrated under reduced pressure to give a crude product, which was dissolved in methanol (30 mL) and stirred for 2 hours at 80° C. The resulting mixture was concentrated under reduced pressure to removed some methanol and filtered. The filtered cake was dried to afford 2-chloro-5,6,7,8-tetrahydro-1,6-naphthyridine (1.5 g, crude, HCl salt) as a brown solid, which was used directly in the next step.

tert-butyl 2-chloro-7,8-dihydro-5H-1,6-napthyridine-6-carboxylate. To a mixture of 2-chloro-5,6,7,8-tetrahydro-1,6-naphthyridine (1.5 g, 7.31 mmol, HCl salt) in DCM (10 mL) was added (Boc)$_2$O (2.38 g, 10.9 mmol) and TEA (3 mL, 21.8 mmol). The resulting mixture was stirred at 20° C. for 12 hours. The resulting mixture was quenched by addition of water (20 mL) and extracted with DCM (20 mL*3). The combined organic layer was washed with brine (20 mL), dried over anhydrous Na$_2$SO$_4$, filtered and concentrated under reduced pressure. The residue was purified by flash chromatography (ISCO®, 20 g AgelaFlash® Silica Flash Column, petroleum ether/EtOAc with EtOAc from 0~35%, flow rate=30 mL/min) to afford tert-butyl 2-chloro-7,8-dihydro-5H-1,6-naphthyridine-6-carboxylate (900 mg, 45.8% yield) as white solid. $^1$H NMR (400 MHz, methanol-d$_4$) δ ppm 7.60 (d, J=8.1 Hz, 1H), 7.28 (d, J=8.3 Hz, 1H), 4.58 (s, 2H), 3.74 (t, J=5.8 Hz, 2H), 2.90 (t, J=5.9 Hz, 2H), 1.49 (s, 9H); LCMS (ESI) [M+H]+ m/z: calcd 269.1. found 268.9.

tert-butyl 2-[(4-methyloxazol-5-yl)methoxy]-7,8-dihydro-5H-1,6-naphthyridine-6-carboxylate. A mixture of tert-butyl 2-chloro-7,8-dihydro-5H-1,6-naphthyridine-6-carboxylate (350 mg, 1.30 mmol), (4-methyloxazol-5-yl)methanol (192 mg, 1.70 mmol), Pd(OAc)$_2$ (15 mg, 0.067 mmol), XantPhos (76 mg, 0.131 mmol), Cs$_2$CO$_3$ (1.27 g, 3.91 mmol) in 1,4-dioxane (10 mL) was heated at 100° C. for 12 hours under nitrogen. The resulting mixture was filtered and the filtrate was diluted with water (30 mL) and extracted with EtOAc (30 mL*3). The combined organic layer was dried over anhydrous Na$_2$SO$_4$, filtered and concentrated under reduced pressure to give a crude product, which was purified by flash chromatography (ISCO®; 24 g AgelaFlash® Silica Flash Column, petroleum ether/EtOAc with EtOAc from 0-26%, 35 mL/min) to afford tert-butyl 2-[(4-methyloxazol-5-yl)methoxy]-7,8-dihydro-5H-1,6-naphthyridine-6-carboxylate (360 mg, 80.0% yield) as a yellow oil. $^1$H NMR (400 MHz, methanol-d$_4$) δ ppm 8.10 (s, 1H), 7.43 (d, J=8.4 Hz, 1H), 6.63 (d, J=8.5 Hz, 1H), 5.36 (s, 2H), 4.49 (s, 2H), 3.72 (t, J=5.6 Hz, 2H), 2.86 (t, J=5.9 Hz, 2H), 2.26 (s, 3H), 1.49 (s, 9H); LCMS (ESI) [M+H]+ m/z: calcd 346.2. found 346.1.

4-methyl-5-(5,6,7,8-tetrahydro-1,6-naphthyridin-2-yloxymethyl)oxazole. To a solution of tert-butyl 2-[(4-methyloxazol-5-yl)methoxy]-7,8-dihydro-5H-1,6-naphthyridine-6-carboxylate (360 mg, 1.04 mmol) in DCM (10 mL) was added TFA (1 mL). The mixture was stirred at 10° C. for 2 hours. The mixture was concentrated under reduced pressure to give a crude product, which was diluted with H$_2$O (20 mL). The aqueous phase was adjusted to pH=8 with saturated K$_2$CO$_3$ aqueous solution, and extracted with DCM (20 mL*2). The combined organic layer was dried over anhydrous Na$_2$SO$_4$, filtered and concentrated under reduced pressure to give 4-methyl-5-(5,6,7,8-tetrahydro-1,6-naphthyridin-2-yloxymethyl)oxazole (230 mg, 90.0% yield) as a yellow oil. 210 mg of this crude product was used in next step directly. The rest 10 mg was further purified by preparative HPLC (Instrument: Gilson GX-281 Liquid Handler, Gilson 322 Pump, Gilson 156 UV Detector; Column: Waters Xbridge 150×50 mm×10 μm; Mobile phase A: H$_2$O with 0.05% NH$_3$—H$_2$O (v %); Mobile phase B: MeCN; Gradient: B from 24% to 54% in 7.8 min, hold 100% B for 2 min; Flow Rate: 25 mL/min; Column Temperature: 30° C.; Wavelength: 220 nm, 254 nm) to give 4-methyl-5-(5,6,7,8-tetrahydro-1,6-naphthyridin-2-yloxymethyl)oxazole (4 mg, 40.0% yield) as a white dry powder. $^1$H NMR (400 MHz, methanol-d$_4$) δ ppm 8.10 (s, 1H), 7.35 (d, J=8.4 Hz, 1H), 6.58 (d, J=8.4 Hz, 1H), 5.35 (s, 2H), 3.88 (s, 2H), 3.15 (t, J=6.1 Hz, 2H), 2.85 (t, J=6.0 Hz, 2H), 2.27 (s, 3H); LCMS (ESI) [M+H]+ m/z: calcd 246.1. found 246.1; HPLC: 99.57%@220 nm.

2-(cyclobutylamino)-N-[(2S)-2-hydroxy-3-[2-[(4-methyloxazol-5-yl)methoxy]-7,8-dihydro-5H-1,6-naphthyridin-6-][propyl[pyridine-4-carboxamide. A mixture of 4-methyl-5-(5,6,7,8-tetrahydro-1,6-naphthyridin-2-yloxymethyl)oxazole (20 mg, 0.0815 mmol), N-[(2S)-3-chloro-2-hydroxy-propyl]-2-(cyclobutylamino)pyridine-4-carboxamide (30 mg, 0.106 mmol), TEA (25 mg, 0.247 mmol) and NaI (19 mg, 0.127 mmol) in MeCN (1 mL) was stirred at 90° C. for 12 hours. The mixture was concentrated under reduced pressure to give a crude product, which was purified by preparative HPLC (Instrument: Gilson GX-281 Liquid Handler, Gilson 322 Pump, Gilson 156 UV Detector; Column: Waters Xbridge 150×50 mm×10 μm; Mobile phase A: H$_2$O with 0.05% NH$_3$—H$_2$O (v %); Mobile phase B: MeCN; Gradient: B from 25% to 55% in 9.5 min, hold 100% B for 2 min; Flow Rate: 25 mL/min; Column Temperature: 30° C.; Wavelength: 220 nm, 254 nm) to give 2-(cyclobutylamino)-N-[(2S)-2-hydroxy-3-[2-[(4-methyloxazol-5-yl)methoxy]-7,8-dihydro-5H-1,6-naphthyridin-6-yl]propyl]pyridine-4-carboxamide (15 mg, 37.4% yield) as a white dry powder. $^1$H NMR (400 MHz, methanol-d$_4$) δ ppm 8.11 (s, 1H), 7.91 (d, J=5.3 Hz, 1H), 7.35 (d, J=8.5 Hz, 1H), 6.80 (s, 1H), 6.76 (dd, J=5.4, 1.4 Hz, 1H), 6.57 (d, J=8.3 Hz, 1H), 5.35 (s, 2H), 4.23 (quin, J=7.8 Hz, 1H), 4.07 (quin, J=5.9 Hz, 1H), 3.67 (s, 2H), 3.49-3.56 (m, 1H), 3.38-3.45 (m, 1H), 2.92 (s, 4H), 2.61-2.71 (m, 2H), 2.36-2.44 (m, 2H), 2.27 (s, 3H), 1.87-1.98 (m, 2H), 1.72-1.82 (m, 2H); LCMS (ESI) [M+H]+ m/z: calcd 493.2. found 493.2; HPLC: 99.73%@254 nm; 99.4% ee.

Example 9-12. 2-[(1-acetyl-4-piperidyl)amino]-N-[(2S)-2-hydroxy-3-[2-[(4-methyloxazol-5-yl)methoxy]-7,8-dihydro-5H-1,6-naphthyridin-6-yl]propyl]pyridine-4-carboxamide (Compound 617)
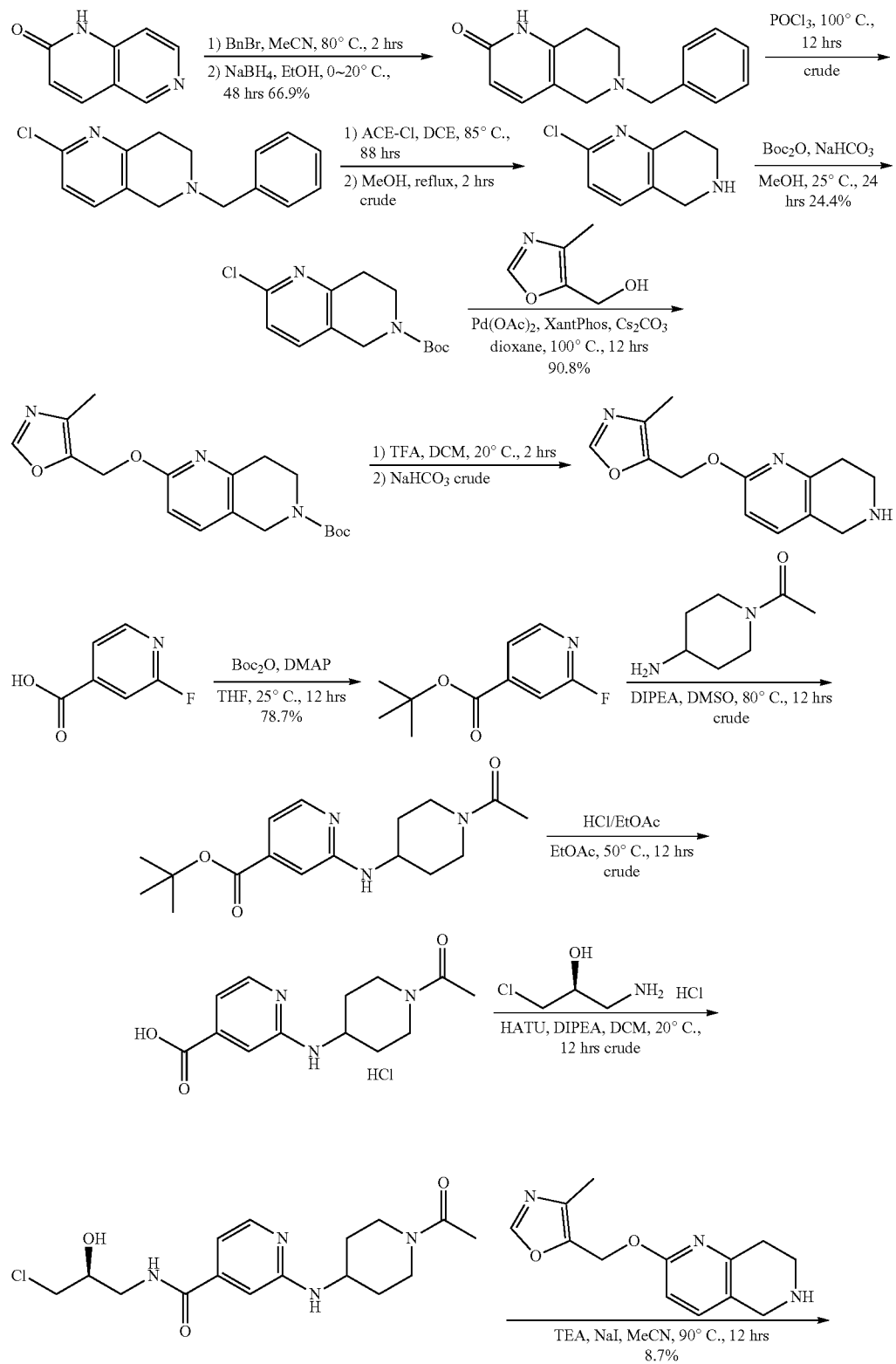

-continued

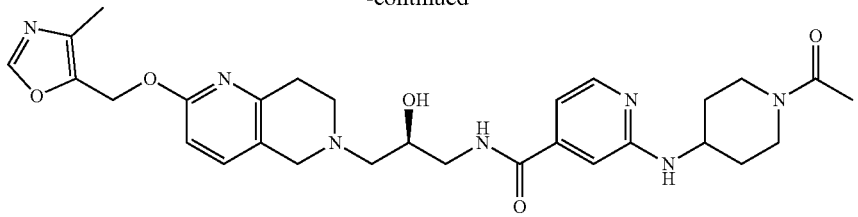

6-benzyl-1,5,7,8-tetrahydro-1,6-naphthyridin-2-one. A mixture of 1H-1,6-naphthyridin-2-one (2.0 g, 13.7 mmol) and bromomethylbenzene (2 mL, 16.8 mmol) in MeCN (15 mL) was stirred at 80° C. for 2 hours. The resulting mixture was cooled to 20° C. and concentrated under reduced pressure to remove MeCN. The residue was dissolved in EtOH (150 mL) and NaBH$_4$ (6 g, 0.159 mol) was added at 0° C. The resulting mixture was stirred at 20° C. for 48 hours. The reaction mixture was diluted with water (50 mL) and the precipitate was collected by filtration, washed with water (10 mL*3) to 6-benzyl-1,5,7,8-tetrahydro-1,6-naphthyridin-2-one (2.2 g, 66.9% yield) as yellow solid. $^1$H NMR (400 MHz, methanol-d$_4$) δ ppm 7.28-7.40 (m, 6H), 6.35 (d, J=9.3 Hz, 1H), 3.71 (s, 2H), 3.39 (s, 2H), 2.75-2.80 (m, 2H), 2.72 (br d, J=5.3 Hz, 2H); LCMS (ESI) [M+H]$^+$ calcd 241.1. found 241.0.

6-benzl]-2-chloro-7,8-dihydro-5H-1,6-naphthyridine. A mixture of 6-benzyl-1,5,7,8-tetrahydro-1,6-naphthyridin-2-one (2.0 g, 8.32 mmol) in POCl$_3$ (53.6 g, 0.350 mmol) was stirred for 12 hours at 100° C. under nitrogen. The resulting mixture was poured into ice-water (50 mL) and adjusted pH to 7 with saturated NaHCO$_3$ aqueous solution. The resulting mixture was extracted with EtOAc (100 mL*3) and the combined organic layer was washed with saturated NH$_4$Cl aqueous solution (100 mL*2), brine (100 mL), dried over anhydrous Na$_2$SO$_4$, filtered and concentrated under reduced pressure to 6-benzyl-2-chloro-7,8-dihydro-5H-1,6-naphthyridine (2.2 g, crude) as brown solid. $^1$H NMR (400 MHz, methanol-d$_4$) δ ppm 7.60-7.69 (m, 2H), 7.51-7.55 (m, 2H), 7.37 (d, J=8.0 Hz, 1H), 7.18-7.25 (m, 1H), 7.09-7.17 (m, 1H), 4.56 (s, 2H), 4.46 (s, 2H), 3.89 (br s, 1H), 3.57 (br s, 1H), 3.14-3.31 (m, 2H); LCMS (ESI) [M+H]$^+$ calcd 259.1. found 259.0.

2-chloro-5,6,7,8-tetrahydro-1,6-naphthyridine. To a mixture of 6-benzyl-2-chloro-7,8-dihydro-5H-1,6-naphthyridine (2.0 g, 7.73 mmol) in 1,2-dichloromethane (20 mL) was added 1-chloroethyl carbonochloridate (1.4 mL, 12.8 mmol). The resulting mixture was stirred at 85° C. for 88 hours. The resulting mixture was concentrated under reduced pressure and the residue was dissolved in MeOH (10 mL). The mixture was heated to 85° C. and stirred for 2 hours. The mixture was concentrated under reduced pressure to afford to a mixture (1.2 g, crude) of 2-chloro-5,6,7,8-tetrahydro-1,6-naphthyridine and 6-benzyl-2-chloro-7,8-dihydro-5H-1,6-naphthyridine as a brown solid which was used directly in the next step.

tert-butyl 2-chloro-7,8-dihydro-5H-1,6-naphthyridine-6-carboxylate. To a mixture(1.2 g, crude) of 2-chloro-5,6,7,8-tetrahydro-1,6-naphthyridine and 6-benzyl-2-chloro-7,8-dihydro-5H-1,6-naphthyridine in MeOH (10 mL) were added tert-butoxycarbonyl tert-butyl carbonate (2 mL, 8.71 mmol) and NaHCO$_3$ (2.40 g, 28.6 mmol) and the mixture was stirred for 24 hours at 20° C. under nitrogen. The resulting mixture was concentrated under reduced pressure and the residue was purified by flash chromatography (ISCO®; 24 g AgelaFlash® Silica Flash Column, petroleum ether/EtOAc with EtOAc from 0~30%, Flow Rate: 30 mL/min) to afford tert-butyl 2-chloro-7,8-dihydro-5H-1,6-naphthyridine-6-carboxylate (790 mg, 41.3% yield) as yellow solid. $^1$H NMR (400 MHz, methanol-d$_4$) δ ppm 7.60 (d, J=8.1 Hz, 1H), 7.28 (d, J=8.1 Hz, 1H), 4.59 (br s, 2H), 3.74 (t, J=5.9 Hz, 2H), 2.91 (t, J=5.9 Hz, 2H), 1.49 (s, 9H); LCMS (ESI) [M+H]$^+$ calcd 269.1. found 269.1.

tert-butyl 2-[(4-methyloxazol-5-yl)methoxy]-7,8-dihydro-5H-1,6-naphthyridine-6-carboxylate. To a mixture of tert-butyl 2-chloro-7,8-dihydro-5H-1,6-naphthyridine-6-carboxylate (300 mg, 1.12 mmol) and (4-methyloxazol-5-yl)methanol (195 mg, 1.72 mmol) in dioxane (10 mL) were added Pd(OAc)$_2$ (12.0 mg, 0.053 mmol), XantPhos (66.0 mg, 0.11 mmol) and Cs$_2$CO$_3$ (1.1 g, 3.38 mmol) and the mixture was stirred at 100° C. for 12 hours under nitrogen. The resulting mixture was filtered and the filtrate was diluted with H$_2$O (10 mL), extracted with EtOAc (10 mL*3). The combined organic layer was washed with brine (20 mL*2), dried over anhydrous Na2SO4, filtered and concentrated under reduced pressure to give a crude product, which was purified by flash chromatography (ISCO®; 24 g Agela-Flash® Silica Flash Column, petroleum ether/EtOAc with EtOAc from 0~25%, 30 mL/min) to afford tert-butyl 2-[(4-methyloxazol-5-yl)methoxy]-7,8-dihydro-5H-1,6-naphthyridine-6-carboxylate (350 mg, 90.8% yield) as a colorless oil. $^1$H NMR (400 MHz, methanol-d$_4$) δ ppm 8.10 (s, 1H), 7.43 (d, J=8.4 Hz, 1H), 6.63 (d, J=8.4 Hz, 1H), 5.36 (s, 2H), 4.49 (s, 2H), 3.72 (br t, J=5.8 Hz, 2H), 2.86 (t, J=5.9 Hz, 2H), 2.26 (s, 3H), 1.49 (s, 9H).

4-methyl-5-(5,6,7,8-tetrahydro-1,6-naphthyridin-2-yloxymethyl)oxazole. To a mixture of tert-butyl 2-[(4-methyloxazol-5-yl)methoxy]-7,8-dihydro-5H-1,6-naphthyridine-6-carboxylate (200 mg, 0.58 mmol) in DCM (1 mL) was added TFA (0.2 mL) and the mixture was stirred for 2 hours at 20° C. under nitrogen. The resulting mixture was adjusted pH to 7 with NaHCO$_3$ solid and then filtered and concentrated under reduced pressure to afford 4-methyl-5-(5,6,7,8-tetrahydro-1,6-naphthyridin-2-yloxymethyl)oxazole (350 mg, crude) as yellow oil, which was used in next step directly without further purification.

tert-butyl 2-fluoropyridine-4-carboxylate. To a solution of 2-fluoropyridine-4-carboxylic acid (10 g, 70.8 mmol) in THF (80 mL) was added DMAP (17 g, 0.139 mol). A solution of di-tert-butyl dicarbonate (24 mL, 0.105 mol) in THF (40 mL) was added drop-wise and the mixture was stirred at 25° C. for 12 hours. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 80 g AgelaFlash® Silica Flash Column, petroleum ether/EtOAc with EtOAc from 0~10%, Flow Rate: 30 mL/min) to afford tert-butyl 2-fluoropyridine-4-carboxylate (11 g, 78.7% yield) as colorless liquid. $^1$H NMR (400 MHz, methanol-$d_4$) δ ppm 8.35 (d, J=5.0 Hz, 1H), 7.67-7.81 (m, 1H), 7.39-7.55 (m, 1H), 1.61 (s, 9H).

tert-butyl 2-[(1-acetyl-4-piperidyl)amino]pyridine-4-carboxylate. To a mixture of tert-butyl 2-fluoropyridine-4-carboxylate (3.0 g, 15.2 mmol) and 1-(4-amino-1-piperidyl)ethanone (3.0 g, 21.1 mmol) in DMSO (30 mL) was added DIPEA (7.5 mL, 43.1 mmol) and the mixture was stirred for 12 hours at 90° C. under nitrogen. The resulting mixture was quenched by addition of water (50 mL) and extracted with EtOAc (50 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 40 g AgelaFlash® Silica Flash Column, DCM/MeOH with MeOH from 0-5.3%, Flow Rate: 30 mL/min) to afford tert-butyl 2-[(1-acetyl-4-piperidyl)amino]pyridine-4-carboxylate (1.84 g, crude) as yellow solid. LCMS (ESI) [M+H]$^+$ calcd 320.2. found 320.1.

2-[(1-acetyl-4-piperidyl)amino]pyridine-4-carboxylic acid. A mixture of tert-butyl 2-[(1-acetyl-4-piperidyl)amino]pyridine-4-carboxylate (1.84 g, 5.76 mmol) in 4M HCl/EtOAc (40 mL) was stirred for 12 hours at 50° C. under nitrogen. The precipitate was collected by filtration and dried to afford 2-[(1-acetyl-4-piperidyl)amino]pyridine-4-carboxylic acid (1.1 g, crude) as white solid.

2-[(1-acetyl-4-piperidyl)amino]-N-[(2S)-3-chloro-2-hydroxy-propyl]pyridine-4-carboxamide. To a mixture of 2-[(1-acetyl-4-piperidyl)amino]pyridine-4-carboxylic acid (900 mg, 3.42 mmol) and (2S)-1-amino-3-chloro-propan-2-ol (603 mg, 4.13 mmol, HCl) in DCM (5 mL) were added HATU (1.62 g, 4.26 mmol) and DIPEA (1.8 mL, 10.3 mmol) and the mixture was stirred for 12 hours at 20° C. under nitrogen. The resulting mixture was quenched by addition of water (10 mL) and extracted with EtOAc (20 mL*3). The combined organic layer was washed with saturated NH$_4$Cl aqueous solution (20 mL*2), brine (30 mL), dried over anhydrous Na$_2$SO$_4$, filtered and concentrated under reduced pressure to afford 2-[(1-acetyl-4-piperidyl)amino]-N-[(2S)-3-chloro-2-hydroxy-propyl]pyridine-4-carboxamide (700 mg, crude) as yellow oil.

2-[(1-acetyl-4-piperidyl)amino]-N-[(2S)-2-hydroxy-3-[2-[(4-methyloxazol-5-yl)methoxy]-7,8-dihydro-5H-[6-naphthyridin-6-yl]propyl]pyridine-4-carboxamide. To a mixture of 4-methyl-5-(5,6,7,8-tetrahydro-1,6-naphthyridin-2-yloxymethyl)oxazole (40 mg, 0.16 mmol) and 2-[(1-acetyl-4-piperidyl)amino]-N-[(2S)-3-chloro-2-hydroxy-propyl]pyridine-4-carboxamide (72 mg, 0.20 mmol) in MeCN (3 mL) were added NaI (25 mg, 0.17 mmol) and TEA (0.08 mL, 0.57 mmol) and the mixture was stirred for 12 hours at 90° C. under nitrogen. The resulting mixture was concentrated under reduced pressure and the residue was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% 0.05% ammonia hydroxide (v %); Mobile phase B: MeCN; Gradient: B from 15% to 45% in 9.5 min, hold 100% B for 2.5 min; Plow Rate: 25 mL/min; Column Temperature: 30° C.; Wavelength: 220 nm, 254 nm) to afford a crude product (~15 mg) which was impure. This crude product was further purified by chiral SPC (Instrument: Berger, Multigr AM-II; Column: Chiralpak AD 250× 30 mm I.D. 20 μm; Mobile phase: supercritical CO$_2$/EtOH (0.1% NH$_3$—H$_2$O, v %)=60/40; Plow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford 2-[(1-acetyl-4-piperidyl)amino]-N-[(2S)-2-hydroxy-3-[2-[(4-methyloxazol-5-yl)methoxy]-7,8-dihydro-5H-1,6-naphthyridin-6-yl]propyl]pyridine-4-carboxamide (8 mg, 8.7% yield) as white solid. $^1$H NMR (400 MHz, methanol-$d_4$) δ ppm 8.10 (s, 1H), 7.94 (d, J=5.5 Hz, 1H), 7.35 (d, J=8.4 Hz, 1H), 6.86 (s, 1H), 6.74-6.77 (m, 1H), 6.57 (d, J=8.3 Hz, 1H), 5.35 (s, 2H), 4.42 (brd, J=11.9 Hz, 1H), 4.02-4.12 (m, 1H), 3.86-4.01 (m, 2H), 3.66 (s, 2H), 3.40-3.56 (m, 4H), 2.92 (s, 3H), 2.85-2.91 (m, 2H), 2.61-2.69 (m, 2H), 2.27 (s, 3H), 2.12 (s, 3H), 1.97-2.09 (m, 2H), 1.26-1.50 (m, 2H); LCMS (ESI) [M+H]$^+$ m/z: calcd 564.3. found 564.2; HPLC: 98.33%@254 nm; 100% ee.

Example 9-13. (S)-6-((1-acetylpiperidin-4-yl)amino)-N-(2-hydroxy-3-(6-((3-methylisoxazol-4-yl)methoxy)-3N-dihydroisoquinolin-2(1H)-yl)propyl)pyrimidine-4-carboxamide (Compound 233)

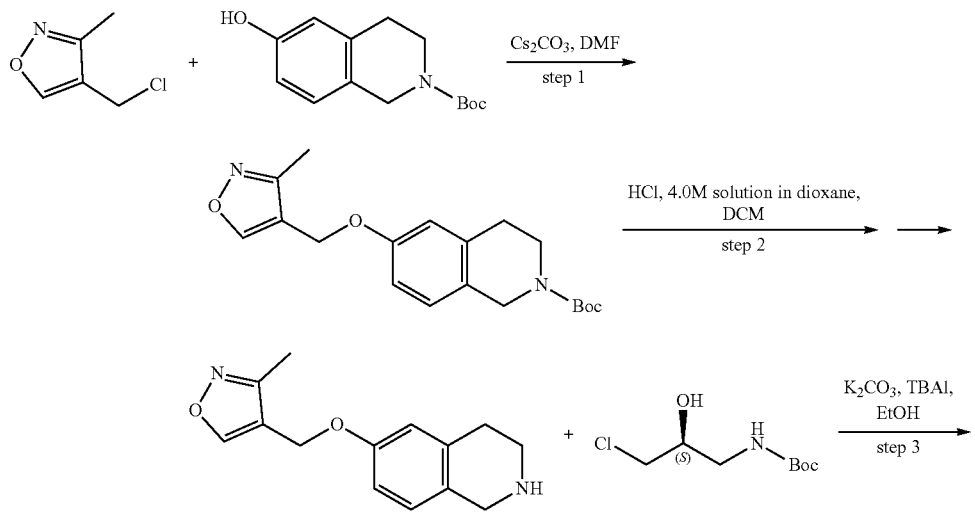

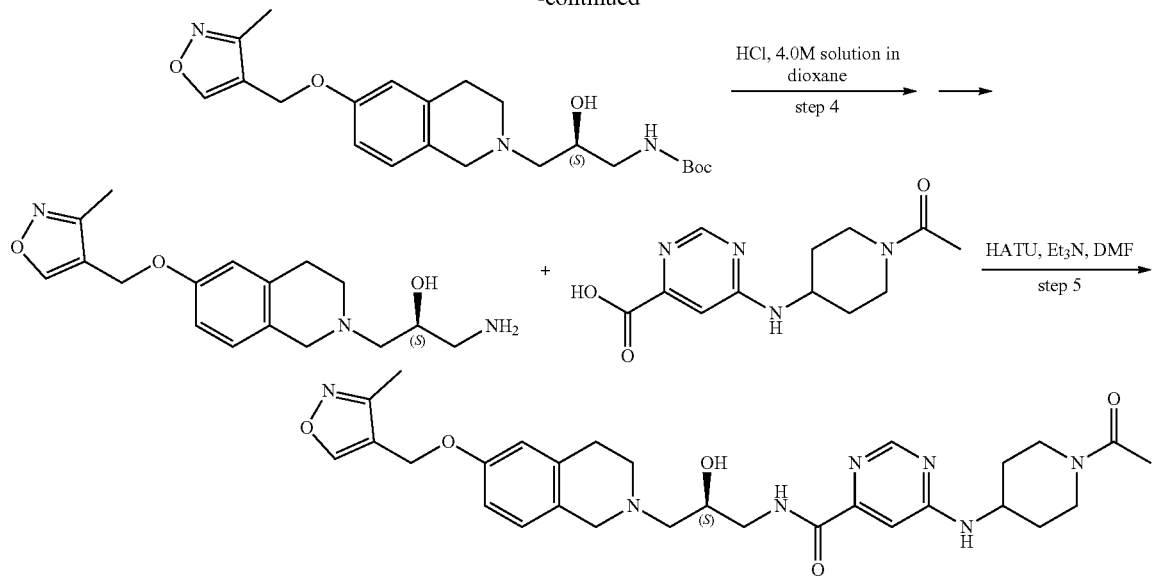

tert-butyl 6-((3-methylisoxazol-4-yl)methoxy)-3,4-dihydroisoquinoline-2(1H)-carboxylate. To a solution of tert-butyl 6-hydroxy-3,4-dihydro-1H-isoquinoline-2-carboxylate (2 g, 8.02 mmol) in dimethylformamide (30 ml) was added cesium carbonate (7.84 g, 24.07 mmol), followed by 4-(chloromethyl)-3-methyl-isoxazole (1.27 g, 9.63 mmol). The reaction mixture was stirred at 45° C. for 14 hr. The reaction mixture was cooled down, poured into water (100 ml) and extracted with EtOAc (3*25 ml). The combined organic extracts were washed with brine(2*10 ml), dried over sodium sulphate and evaporated in vacuo to afford product tert-butyl 6-[(3-methylisoxazol-4-yl)methoxy]-3,4-dihydro-1H-isoquinoline-2-carboxylate (2.6 g, 7.55 mmol, 94.10% yield). $^1$H NMR (500 MHz, CDCl$_3$) δ (ppm) 1.48 (s, 9H), 2.34 (s, 3H), 2.80 (m, 2H), 3.62 (m, 2H), 4.12 (s, 2H), 4.88 (s, 2H), 6.71 (s, 1H), 6.78 (d, 1H), 7.03 (d, 1H), 7.26 (s, 1H), 8.36 (s, 1H). LCMS(ESI): [M-Boc]$^+$ m/z: calcd 344.1. found 245.0; Rt=1.51 min.

3-methyl-4-(((1,2,3,4-tetrahydroisoquinolin-6-yl)oxy)methyl)isoxazole. Hydrogen chloride solution 4.0M in dioxane (2.40 g, 65.82 mmol, 3 ml) was added to a solution of tert-butyl 6-[(3-methylisoxazol-4-yl)methoxy]-3,4-dihydro-1H-isoquinoline-2-carboxylate (2.6 g, 7.55 mmol) in DCM (30 ml). The reaction mixture was stirred at 28° C. for 12 hr, then evaporated and added to MTBE (15 ml) the resulting precipitate was filtered off, washed with MTBE (40 ml) and dried to afford 3-methyl-4-(1,2,3,4-tetrahydroisoquinolin-6-yloxymethyl)isoxazole (1.5 g, 5.34 mmol, 70.77% yield, HCl). $^1$H NMR (500 MHz, DMSO-d$_6$) δ (ppm) 2.25 (s, 3H), 2.97 (m, 2H), 3.29 (m, 3H), 4.14 (s, 2H), 4.98 (s, 2H), 6.88 (s, 1H), 6.90 (d, 1H), 7.13 (d, 1H), 8.90 (s, 1H), 9.55 (s, 1H). LCMS(ESI): [M-Boc]$^+$ m/z: calcd 344.1. found 245.0; Rt=1.51 min.

(S)-tert-butyl (2-hydroxy-3-(6-((3-methylisoxazol-4-yl)methoxy)-3,4-dihydroisoquinolin-2(1H)-yl)propyl)carbamate. A mixture of tert-butyl N-[(2 S)-3-chloro-2-hydroxypropyl]carbamate (336.07 mg, 1.60 mmol), 3-methyl-4-(1,2,3,4-tetrahydroisoquinolin-6-yloxymethyl)isoxazole (0.3 g, 1.07 mmol, HCl), potassium carbonate, anhydrous, 99% (354.44 mg, 2.56 mmol, 154.78 uL), tetra-n-butylammonium iodide (118.41 mg, 320.57 umol) in EtOH (10 ml) was stirred at 65° C. for 24 hr in sealed tube. The reaction mixture was filtered off and solution was evaporated in vacuo to afford crude product tert-butyl N-[(2S)-2-hydroxy-3-[6-[(3-methylisoxazol-4-yl)methoxy]-3,4-dihydro-1H-isoquinolin-2-yl]propyl]carbamate (0.38 g, 910.19 umol, 85.18% yield). $^1$H NMR (500 MHz, CDCl$_3$) δ (ppm) 1.41 (m, 9H), 2.36 (s, 3H), 2.48 (m, 2H), 2.68 (m, 1H), 2.75 (m, 3H), 3.10 (m, 1H), 3.87 (m, 4H), 3.90 (m, 1H), 4.90 (s, 2H), 5.03 (m, 1H), 6.69 (s, 1H), 6.75 (d, 1H), 6.96 (d, 1H), 8.36 (s, 1H). LCMS(ESI): [M+H]$^+$ m/z: calcd 417.2. found 418.2; Rt=1.03 min.

(S)-1-amino-3-(6-((3-methylisoxazol-4-yl)methoxy)-3,4-dihydro isoquinolin-2(1H)-yl)propan-2-ol. Hydrogen chloride solution 4.0M in dioxane (800.00 mg, 21.94 mmol, 1 mL) was added to a solution of tert-butyl N-[(2S)-2-hydroxy-3-[6-[(3-methylisoxazol-4-yl)methoxy]-3,4-dihydro-1H-isoquinolin-2-yl]propyl]carbamate (300.00 mg, 718.57 umol) in DCM (5 mL). The reaction mixture was stirred at 25° C. for 24 hr, then evaporated and added CH$_3$CN (4 mL) the resulting precipitate was filtered off, washed with CH$_3$CN (4 ml), dried and obtained crude product 0.3 g was purified by preparative RP-HPLC with CH3CN as mobile phase to afford product (2S)-1-amino-3-[6-[(3-methylisoxazol-4-yl)methoxy]-3,4-dihydro-1H-isoquinolin-2-yl]propan-2-ol (0.1854 g, 584.15 umol, 81.29% yield). $^1$H NMR (500 MHz, D$_2$O) δ (ppm) 2.14 (s, 3H), 2.86 (m, 5H), 3.09 (m, 3H), 3.87 (m, 2H), 4.21 (m, 1H), 4.83 (s, 2H), 6.72 (s, 1H), 6.75 (d, 1H), 6.97 (d, 1H), 8.44 (s, 1H). LCMS(ESI): [M+H]$^+$ m/z: calcd 317.1. found 318.2; Rt=0.67 min.

(S)-6-((1-acetylpiperidin-4-yl)amino)-N-(2-hydroxy-3-(6-((3-methylisoxazol-4-yl)methoxy)-3,4-dihydroisoquinolin-2(1H)-yl)propyl)pyrimidine-4-carboxamide. (2S)-1-amino-3-[6-[(3-methylisoxazol-4-yl)methoxy]-3,4-dihydro-1H-isoquinolin-2-yl]propan-2-ol (0.1854 g, 475.01 umol, 2HCl) (190.00 mg, 1.01 mmol) and 6-[(1-acetyl-4-piperidyl)amino]pyrimidine-4-carboxylic acid (138.09 mg, 522.52 umol) were mixed in DMF (5 mL). The reaction suspension was cooled to 0° C. and HATU (198.68 mg, 522.52 umol) followed by Triethylamine (240.33 mg, 2.38 mmol, 331.04 uL) were added and stirred at ambient temperature for 24 hr. The reaction mixture was evaporated in vacuo and obtained crude product 0.66 g was purified by preparative RP-HPLC with CH3CN as mobile phase to afford product 6-[(1-acetyl- 4-piperidyl)amino]-N-[(2S)-2-hydroxy-3-[6-[(3-methyl-isoxazol-4-yl)methoxy]-3,4-dihydro-1H-isoquinolin-2-yl]propyl]pyrimidine-4-carboxamide (0.253 g, 448.86 umol, 94.49% yield) NMR(DMSO-$d_6$, 500 MHz): δ (ppm) 1.25 (m, 2H), 1.37 (m, 2H), 1.89 (m, 3H), 2.00 (s, 3H), 2.26 (s, 3H), 2.74 (m, 5H), 3.18 (d, 1H), 3.26 (m, 1H), 3.41 (m, 1H), 3.54 (m, 2H), 3.78 (m, 1H), 3.87 (m, 1H), 4.08 (m, 1H), 4.22 (m, 1H), 4.94 (s, 2H), 6.76 (m, 2H), 6.94 (d, 1H), 7.06 (s, 1H), 7.76 (d, 1H), 8.33 (s, 1H), 8.71 (t, 1H), 8.88 (s, 1H). LCMS(ESI): [M+H]$^+$ m/z: calcd 563.3. found 564.2; Rt=0.907 min.

Example 9-14. 6-[(1-acetyl-4-piperidyl)amino]-N-[(2S)-2-hydroxy-3-[2-[(4-methyloxazol-5-yl)methoxy]-7,8-dihydro-5H-1,6-naphthyridin-6-yl]propyl]pyrimidine-4-carboxamide (Compound 491)

mmol) and TEA (90 uL, 0.646 mmol). The mixture was sealed and stirred at 90° C. for 12 hours. The mixture was concentrated under reduced pressure and the residue was purified with preparative HPLC (Instrument: Gilson GX-281 Liquid Handler, Gilson 322 Pump, Gilson 156 UV Detector; Column: Xtimate C18 150×25 mm×5 μm; Mobile phase A: H$_2$O with 0.1% NH$_4$HCO$_3$ (v %); Mobile phase B: MeCN; Gradient: B from 11% to 41% in 11.5 min, hold 100% B for 2 min; Flow Rate: 25 mL/min; Column Temperature: 30° C.; Wavelength: 220 nm, 254 nm) to afford 6-[(1-acetyl-4-piperidyl)amino]-N-[(2S)-2-hydroxy-3-[2-[(4-methyloxazol-5-yl)methoxy]-7,8-dihydro-5H-1,6-naphthyridin-6-yl]propyl]pyrimidine-4-carboxamide (30 mg, 26.1% yield) as white solid. $^1$H NMR (400 MHz, methanol-$d_4$) δ ppm 8.22 (s, 1H), 8.12 (s, 1H), 7.32 (d, J=8.4 Hz, 1H), 7.06 (s, 1H), 6.55 (d, J=8.4 Hz, 1H), 5.36 (s, 2H), 4.43 (d, J=13.0 Hz, 1H), 4.15 (br s, 1H), 4.02-4.08 (m, 1H), 3.92 (d,

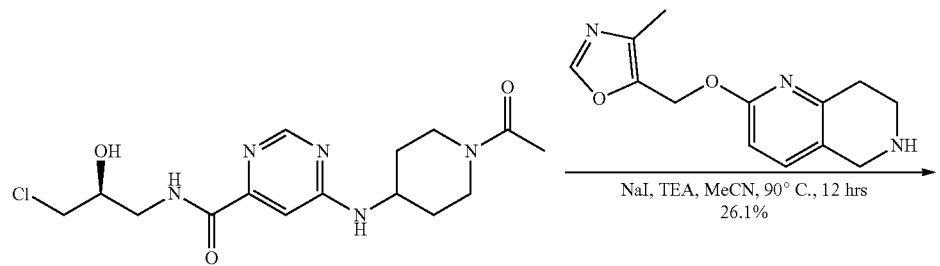

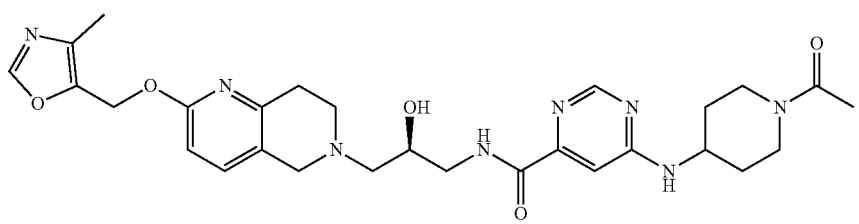

To a solution of 4-methyl-5-(5,6,7,8-tetrahydro-1,6-naphthyridin-2-yloxymethyl)oxazole (50 mg, 0.204 mmol), 6-[(1-acetyl-4-piperidyl)amino]-N-[(2S)-3-chloro-2-hydroxy-propyl]pyrimidine-4-carboxamide (80 mg, 0.225 mmol) in MeCN (1.5 mL) were added NaI (40 mg, 0.267

J=14.5 Hz, 1H), 3.64 (s, 2H), 3.52 (d, J=5.8 Hz, 2H), 3.24-3.30 (m, 1H), 2.85-2.98 (m, 5H), 2.68 (d, J=6.1 Hz, 2), 2.27 (s, 3H), 2.12 (s, 3H), 1.96-2.10 (m, 2H), 1.36-1.54 (m, 2H); LCMS (ESI) [M+H]$^+$ m/z: calcd 565.3. found 565.2; HPLC: 100%@254 nm; 97.7% ee.

Example 9-15. 3-[(1-acetyl-4-piperidyl)amino]-N-[(2S)-2-hydroxy-3-[6-[(4-methyloxazol-5-yl)methoxy]-3N-dihydro-1H-isoquinolin-2-yl]propyl]-5-[2-methoxyethyl(methyl)amino]benzamide (Compound 649) and 3-[(1-acetyl-4-piperidyl)amino]-N-[(2R)-2-hydroxy-3-[6-[(4-methyloxazol-5-yl)methoxy]-3N-dihydro-1H-isoquinolin-2-yl]propyl]-5-[2-methoxyethyl(methyl)amino]benzamide (Compound 648)
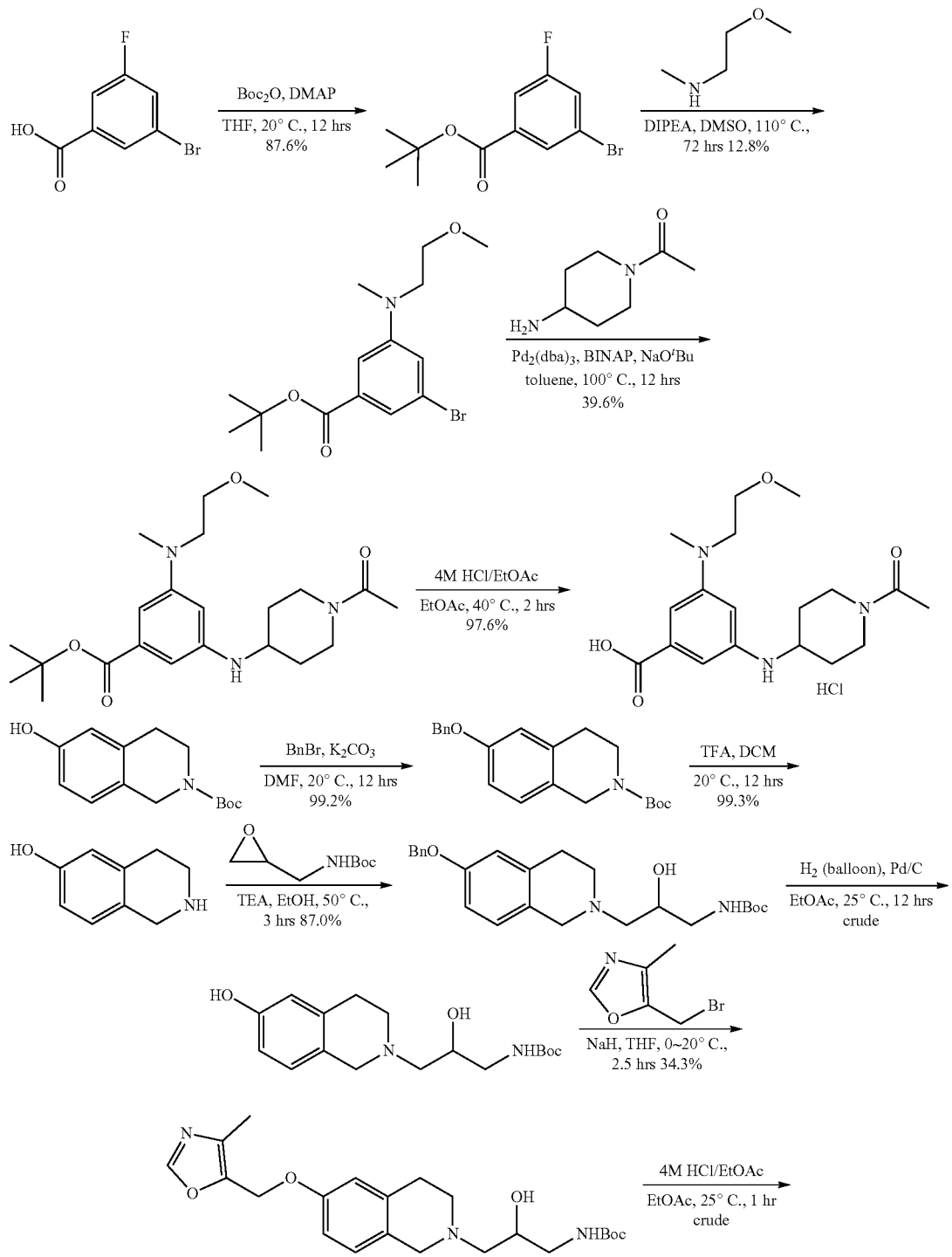

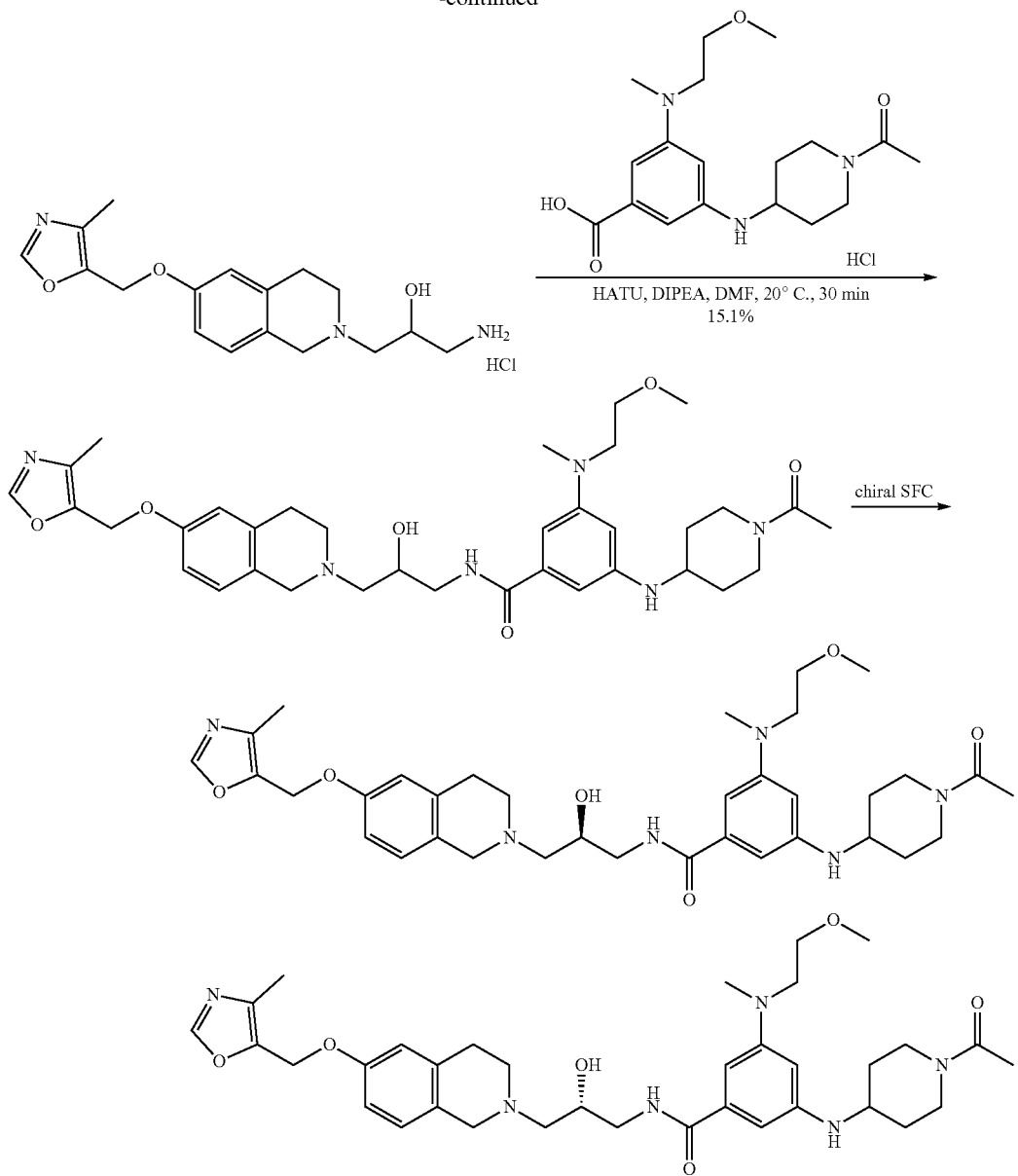

tert-butyl 6-benzl]oxy-3,4-dihydro-1H-isoquinoline-2-carboxylate. To a solution of tert-butyl 6-hydroxy-3,4-dihydro-1H-isoquinoline-2-carboxylate (2 g, 8.02 mmol) in DMF (20 mL) were added K$_2$CO$_3$ (2.22 g, 16.0 mmol) and bromomethylbenzene (1.37 g, 8.02 mmol). The mixture was stirred at 20° C. for 12 hours. The resulting mixture was diluted with EtOAc (300 mL). The organic layer was washed with brine (30 mL*4), dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0-5.5%, Flow rate: 30 mL/min) to afford tert-butyl 6-benzyloxy-3,4-dihydro-1H-isoquinoline-2-carboxylate (2.7 g, 99.2% yield) as colorless oil. $^1$H NMR (400 MHz, methanol-<k) δ ppm 7.40-7.44 (m, 2H), 7.33-7.38 (m, 2H), 7.27-7.32 (m, 1H), 7.02 (d, J=8.4 Hz, 1H), 6.81-6.84 (m, 1H), 6.79 (d, J=2.4 Hz, 1H), 5.05 (s, 2H), 4.47 (br s, 2H), 3.59 (t, J=5.8 Hz, 2H), 2.78 (t, J=5.9 Hz, 2H), 1.49 (s, 9H); LCMS (ESI) [M+H−56]$^+$ m/z: calcd 284.2, found 284.1.

tert-butyl 6-benzyloxy-3,4-dihydro-1H-isoquinoline-2-carboxylate. To a solution of tert-butyl 6-benzyloxy-3,4-dihydro-1H-isoquinoline-2-carboxylate (200 mg, 0.589 mmol) in DCM (5 mL) was added TFA (0.5 mL, 6.49 mmol). The mixture was stirred at 20° C. for 12 hours. The resulting mixture was quenched by addition of saturated NaHCO$_3$ aqueous solution (10 mL) and extracted with DCM (20 mL*3). The combined organic layer was dried over anhydrous Na$_2$SO$_4$, filtered and concentrated under reduced pressure to afford 6-benzyloxy-1,2,3,4-tetrahydroisoquinoline (140 mg, 99.3% yield) as yellow gum. $^1$H NMR (400 MHz, methanol-d$_4$) δ ppm 7.39-7.44 (m, 2H), 7.33-7.38 (m, 2H), 7.26-7.32 (m, 1H), 6.95 (d, J=8.4 Hz, 1H), 6.76-6.80 (m, 1H), 6.74 (d, J=2.4 Hz, 1H), 5.04 (s, 2H), 3.91 (s, 2H), 3.04-3.10 (m, 2H), 2.81 (t, J=6.0 Hz, 2H).

tert-butyl N-[3-(6-benzyloxy-3,4-dihydro-1H-isoquinolin-2-yl)-2-hydroxy-propyl]carbamate To a solution of tert-butyl N-(oxiran-2-ylmethyl)carbamate (300 mg, 1.73 mmol) in EtOH (10 mL) were added 6-benzyloxy-1,2,3,4-tetrahydroisoquinoline (140 mg, 0.585 mmol) and TEA (170 mg, 1.68 mmol). The mixture was stirred at 50° C. for 3 hours. The resulting mixture was concentrated under reduced pressure and the residue was purified by flash chromatography (ISCO®; 24 g AgelaFlash® Silica Flash Column, petroleum ether/EtOAc with EtOAc from 0-100%, Flow rate: 30 mL/min) to afford tert-butyl N-[3-(6-benzyloxy-3,4-dihydro-1H-isoquinolin-2-yl)-2-hydroxy-propyl]carbamate (210 mg, 87.0% yield) as yellow oil. $^1$H NMR (400 MHz, methanol-$d_4$) δ ppm 7.41-7.46 (m, 2H), 7.35-7.40 (m, 2H), 7.29-7.34 (m, 1H), 6.97 (d, J=8.4 Hz, 1H), 6.77-6.81 (m, 1H), 6.76 (d, J=2.3 Hz, 1H), 5.06 (s, 2H), 3.93 (dt, J=11.9, 5.9 Hz, 1H), 3.66 (d, J=2.0 Hz, 2H), 3.17-3.24 (m, 1H), 3.05-3.12 (m, 1H), 2.87-2.93 (m, 2H), 2.80-2.86 (m, 2H), 2.52-2.64 (m, 2H), 1.46 (s, 9H); LCMS (ESI) [M+H]$^+$ m/z: calcd 413.2. found 413.0.

tert-butyl N-[2-hydroxy-3-(6-hydroxy-3,4-dihydro-1H-isoquinolin-2-yl)propyl]carbamate. To a round bottom flask were added tert-butyl N-[3-(6-benzyloxy-3,4-dihydro-1H-isoquinolin-2-yl)-2-hydroxy-propyl]carbamate (190 mg, 0.460 mmol), Pd/C (20 mg, 10% wt of Pd with 50% wt of water) and EtOAc (3 mL). The mixture was degassed and backfilled with hydrogen for three times and then stirred for 12 hours at 25° C. under hydrogen (in balloon, ~15 psi). The resulting mixture was filtered and concentrated under reduced pressure to afford tert-butyl N-[2-hydroxy-3-(6-hydroxy-3,4-dihydro-1H-isoquinolin-2-yl)propyl]carbamate (200 mg, crude) as yellow oil. $^1$H NMR (400 MHz, methanol-$d_4$) δ ppm 6.85 (d, J=8.3 Hz, 1H), 6.56 (dd, J=8.3, 2.4 Hz, 1H), 6.53 (d, J=2.4 Hz, 1H), 3.84-3.98 (m, 1H), 3.57-3.68 (m, 2H), 3.14-3.22 (m, 1H), 3.02-3.10 (m, 1H), 2.77-2.88 (m, 4H), 2.48-2.61 (m, 2H), E44 (s, 9H); LCMS (ESI) [M+H]$^+$ m/z: calcd 323.2. found 323.1.

tert-butyl N-[2-hydroxy-3-[6-[(4-methyloxazol-5-yl)methoxy]-3,4-dihydro-1H-isoquinolin-2-yl]propyl[carbamate. To a solution of tert-butyl N-[2-hydroxy-3-(6-hydroxy-3,4-dihydro-1H-isoquinolin-2-yl)propyl]carbamate (90 mg, 0.279 mmol) in THF (3 mL) was added NaH (35 mg, 0.875 mmol, 60% wt in mineral oil). The mixture was stirred at 0° C. for 30 minutes. Then 5-(bromomethyl)-4-methyl-oxazole (100 mg, 0.568 mmol) was added and the mixture was stirred at 20° C. for 2 hours. The resulting mixture was quenched by addition of saturated NH$_4$Cl aqueous solution (5 mL) and extracted with EtOAc (20 mL*3). The combined organic layer was washed with brine (100 mL), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0-100% for 25 minutes, then DCM/MeOH with MeOH from 0-8%, Flow rate: 30 mL/min) to afford tert-butyl N-[2-hydroxy-3-[6-[(4-methyl-oxazol-5-yl)methoxy]-3,4-dihydro-1H-isoquinolin-2-yl]propyl]carbamate (40 mg, 34.3% yield) as yellow oil. LCMS (ESI) [M+H]$^+$ m/z: calcd 418.2. found 418.2.

1-amino-3-[6-[(4-methyloxazol-5-yl)methoxy]-3,4-dihydro-1H-isoquinolin-2-yl]propan-2-ol. To a solution of tert-butyl N-[2-hydroxy-3-[6-[(4-methyloxazol-5-yl)methoxy]-3,4-dihydro-1H-isoquinolin-2-yl]propyl]carbamate (65 mg, 0.156 mmol) in EtOAc (3 mL) was added 4M HCl/EtOAc (1 mL, 4 mmol). The mixture was stirred at 25° C. for 1 hour. The resulting mixture was concentrated under reduced pressure to afford 1-amino-3-[6-[(4-methyloxazol-5-yl)methoxy]-3,4-dihydro-1H-isoquinolin-2-yl]propan-2-ol (60 mg, HCl salt, crude) as white solid. LCMS (ESI) [M+H]$^+$ m/z: calcd 318.2. found 318.1.

3-[(1-acetyl-4-piperidyl)amino]-N-[2-hydroxy-3-[6-[(4-methyloxazol-5-yl)methoxy]-3,4-dihydro-1H-isoquinolin-2-yl]propyl]-5-[2-methoxyethyl(methyl)amino[benzamide. To a solution of 3-[(1-acetyl-4-piperidyl)amino]-5-[2-methoxyethyl(methyl)amino]benzoic acid (55 mg, 0.143 mmol, HCl) in DMF (2 mL) were added HATU (55. mg, 0.144 mmol) and DIPEA (111 mg, 0.861 mmol). Then 1-amino-3-[6-[(4-methyloxazol-5-yl)methoxy]-3,4-dihydro-1H-isoquinolin-2-yl]propan-2-ol (60 mg, 0.169 mmol, HCl) was added and the mixture was stirred at 20° C. for 30 minutes. The residue was purified by flash chromatography (ISCO®; 12 g AgelaFlash® Silica Flash Column, DCM/MeOH with MeOH from 0~10%, Flow rate: 30 mL/min) to afford the crude product (batch 1, 40 mg) as yellow oil and crude product (batch 2, 50 mg) as yellow oil. The crude product (batch 1) was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% ammonia hydroxide (v %); Mobile phase B: MeCN; Gradient: B from 35% to 65% in 7.8 min, hold 100% B for 2.5 min; Flow Rate: 25 mL/min; Column Temperature: 30° C.; Wavelength: 220 nm, 254 nm) and the crude product (batch 2, 50 mg) was purified by preparative HPLC (Instrument: Gilson GX-281 Liquid Handler, Gilson 322 Pump, Gilson 156 UV Detector; Column: Waters Xbridge 150×25 mm×5 μm; Mobile phase A: H$_2$O with 0.05% ammonia hydroxide (v %); Mobile phase B: MeCN; Gradient: B from 23% to 53% in 7.8 min, hold 100% B for 2.5 min; Flow Rate: 25 mL/min; Column Temperature: 30° C.; Wavelength: 220 nm, 254 nm). The fractions were combined and lyophilized to afford to afford 3-[(1-acetyl-4-piperidyl)amino]-N-[2-hydroxy-3-[6-[(4-methyloxazol-5-yl)methoxy]-3,4-dihydro-1H-isoquinolin-2-yl]propyl]-5-[2-methoxyethyl(methyl)amino]benzamide (14 mg, 15.1% yield) as white solid. $^1$H NMR (400 MHz, methanol-$d_4$) δ ppm 8.14 (s, 1H), 6.99 (d, J=8.4 Hz, 1H), 6.74-6.82 (m, 2H), 6.53 (s, 1H), 6.46 (s, 1H), 6.23 (s, 1H), 5.07 (s, 2H), 4.40 (br d, J=14.0 Hz, 1H), 4.08-4.15 (m, 1H), 3.92 (br d, J=13.6 Hz, 1H), 3.71 (s, 2H), 3.49-3.62 (m, 6H), 3.44 (dd, J=13.6, 6.4 Hz, 1H), 3.36 (s, 3H), 3.27 (br d, J=10.8 Hz, 1H), 2.96 (s, 3H), 2.83-2.94 (m, 5H), 2.62-2.75 (m, 1H), 2.19-2.23 (m, 1H), 2.21 (s, 2H), 2.01-2.15 (m, 5H), 1.30-1.47 (m, 1H); LCMS (ESI) [M+H]$^+$ m/z: calcd 649.4. found 649.3; HPLC: 96.13%@254 nm; racemic.

2-[(1-acetyl-4-piperidyl)amino]-N-[(2S)-2-hydroxy-3-[6-[(4-methyloxazol-5-yl)methoxy]-3,4-dihydro-1H-isoquinolin-2-yl]propyl]-5-[2-methoxyethyl(methyl)amino]benzamide and 3-[(1-acetyl-4-piperidyl)amino]-N-[(2R)-2-hydroxy-3-[6-[(4-methyloxazol-5-yl)methoxy]-3,4-dihydro-1H-isoquinolin-2-yl]propyl]-5-[2-methoxyethyl(methyl)amino]benzamide. 3-[(1-acetyl-4-piperidyl)amino]-N-[2-hydroxy-3-[6-[(4-methyloxazol-5-yl)methoxy]-3,4-dihydro-1H-isoquinolin-2-yl]propyl]-5-[2-methoxyethyl(methyl)amino]benzamide (14 mg, 21.6 umol) was separated by chiral SFC (Instrument: Thar80; Column: Daicel Chiralcel OJ (250 mm*30 mm, 10 μm); Mobile phase: supercritical CO$_2$/EtOH (0.1% NH$_3$—H$_2$O, v %)=50/50; Flow Rate: 80 mF/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm to afford A and B.

A: 3-[(1-acetyl-4-piperidyl)amino]-N-[(2S)-2-hydroxy-3-[6-[(4-methyloxazol-5-yl)methoxy]-3,4-dihydro-1H-isoquinolin-2-yl]propyl]-5-[2-methoxyethyl(methyl)amino]benzamide (5.2 mg, single unknown enantiomer, peak 1, retention time: 1.498 min, yellow solid). $^1$H NMR (400 MHz, methanol-d$_4$) δ ppm 8.13 (s, 1H), 6.97 (d, J=8.3 Hz, 1H), 6.73-6.79 (m, 2H), 6.51 (s, 1H), 6.44 (s, 1H), 6.21 (s, 1H), 5.05 (s, 2H), 4.38 (br d, J=13.3 Hz, 1H), 4.09 (quin, J=6.0 Hz, 1H), 3.90 (br d, J=13.8 Hz, 1H), 3.62-3.72 (m, 2H), 3.46-3.59 (m, 7H), 3.38-3.45 (m, 1H), 3.34 (s, 3H), 3.22-3.29 (m, 1H), 2.94 (s, 3H), 2.77-2.91 (m, 5H), 2.57-2.70 (m, 2H), 2.19 (s, 3H), 1.97-2.14 (m, 6H), 1.32-1.44 (m, 2H); LCMS (ESI) [M+H]$^+$ m/z: calcd 649.4. found 649.2; HPFC: 100%@254 nm; 100% ee.

B: 3-[(1-acetyl-4-piperidyl)amino]-N-[(2R)-2-hydroxy-3-[6-[(4-methyloxazol-5-yl)methoxy]-3,4-dihydro-1H-isoquinolin-2-yl]propyl]-5-[2-methoxyethyl(methyl)amino] benzamide (6 mg, single unknown enantiomer, peak 2, retention time=2.221 min, yellow solid). $^1$H NMR (400 MHz, methanol-d$_4$) δ ppm 8.03 (s, 1H), 6.87 (d, J=8.3 Hz, 1H), 6.63-6.69 (m, 2H), 6.41 (s, 1H), 6.34 (s, 1H), 6.11 (s, 1H), 4.95 (s, 2H), 4.28 (br d, J=14.8 Hz, 1H), 3.99 (br t, J=5.9 Hz, 1H), 3.80 (brd, J=14.1 Hz, 1H), 3.58 (s, 2 H), 3.36-3.49 (m, 7H), 3.28-3.35 (m, 1H), 3.24 (s, 3H), 3.12-3.19 (m, 1H), 2.84 (s, 3H), 2.68-2.81 (m, 5H), 2.48-2.60 (m, 2H), 2.09 (s, 3H), 2.01 (s, 3H), 1.89-1.98 (m, 2H), 1.24-1.32 (m, 2H); LCMS (ESI) [M+H]$^+$ m/z: calcd 649.4. found 649.2; HPLC: 95.33%@254 nm; 99.0% ee.

tert-butyl 3-[(1-acetyl-4-piperidyl)amino]-5-[2-methoxyethyl(methyl)amino]benzoate. To a mixture of tert-butyl 3-bromo-5-[2-methoxyethyl(methyl)amino]benzoate (300 mg, 0.871 mmol) and 1-(4-amino-1-piperidyl)ethanone (200 mg, 1.41 mmol) in toluene (10 mL) were added Pd$_2$(dba)$_3$ (160 mg, 0.174 mmol), BINAP (220 mg, 0.353 mmol) and NaO$^t$Bu (168 mg, 1.75 mmol). The resulting mixture was degassed and backfilled with nitrogen for three times and then stirred at 100° C. for 12 hours under nitrogen. The resulting mixture was filtered and the filtrated was diluted with EtOAc (50 mL). The organic layer was washed saturated NH$_4$Cl aqueous solution (10 mL*3), brine (10 mL), dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0-100%, Flow rate: 30 mL/min) to afford tert-butyl 3-[(1-acetyl-4-piperidyl)amino]-5-[2-methoxyethyl(methyl)amino]benzoate (140 mg, 39.6% yield) as yellow oil. $^1$H NMR (400 MHz, methanol-d$_4$) δ ppm 6.69-6.71 (m, 1H), 6.65 (d, J=1.6 Hz, 1H), 6.28 (t, J=2.2 Hz, 1H), 4.33-4.42 (m, 1H), 3.91 (br d, J=14.0 Hz, 1H), 3.47-3.61 (m, 7H), 3.35 (s, 3H), 2.96-2.99 (m, 1H), 2.95 (s, 3H), 2.11 (s, 3H), 1.57 (s, 9H), 1.29-1.47 (m, 3H); LCMS (ESI) [M+H]$^+$ m/z: calcd 406.3. found 406.2.

3-[(1-acetyl-4-piperidyl)amino]-5-[2-methoxyethyl (methyl)amino]benzoic acid. To a solution of tert-butyl 3-[(1-acetyl-4-piperidyl)amino]-5-[2-methoxyethyl(methyl) amino]benzoate (140 mg, 0.345 mmol) in EtOAc (3 mL) was added 4M HCl/EtOAc (5 mL, 20 mmol). The mixture was stirred at 40° C. for 2 hours. The precipitate was collected by filtration, washed with EtOAc (5 mL*3) and dried under reduced pressure to afford 3-[(1-acetyl-4-piperidyl)amino]-5-[2-methoxyethyl(methyl)amino]benzoic acid (130 mg, 97.6% yield, HCl) as yellow solid. LCMS (ESI) [M+H]$^+$ m/z: calcd 350.2. found 350.1.

Example 10. PRMT5 Cooperativity Assay

PRMT5 inhibitor potency and cooperativity in the absence and presence of cofactors SAM, SAH or MTA was assessed at equilibrium by measuring the dose dependent displacement of a fixed concentration of C-terminal 5'-T AMR A labeled peptide from Prmt5, utilizing fluorescent anisotropy as a signal. Two peptides were utilized for these studies:

Me0: Ac-SGRGKGGKGLGKGGAKRHRKV-K(5-TAMRA)-NH2
Me2: Ac-SGR(Sym Me2)GKGGKGLGKGGAKRHRKV-K (5-TAMRA)-NH2

Peptide Me0 was used to determine the affinity of compounds in the absence of cofactor. Peptide Me2 was used to determine the affinity of compounds in the presence of 50 µM cofactor.

Study Compounds and Reference Compounds:
    Study compounds are dissolved in DMSO starting with a stock concentration of 10 mM
    Reference compound1: EPZ015666 (GSK3235025) (SelleckChem, cat #S7748-5mgs, 10 mM in DMSO)
    Reference compound2: (S)-2-(cyclobutylamino)-N-(3-(8, 9-dihydro-[1,3]dioxolo[4,5-f]isoquinolin-7(6H)-yl)-2-hydroxypropyl)isonicotinamide (Tango, 10 mM in DMSO)

Assay Conditions:
    Study compound and reference compound concentration: 3-fold serial dilution from 125 µM
    Each assay plate contains the above two reference compounds
    DMSO concentration in each well: 1.25% DMSO
    Compound IC$_{50}$ was determined in 4 assay conditions:
      1. 50 µM Cofactor SAM+25 nM Me2+100 nM PRMT5
      2. 50 µM Cofactor MTA+25 nM Me2+50 nM PRMT5
      3. 50 µM Cofactor MTA+25 nM Me0+25 nM PRMT5
      4. No cofactor+25 nM Me2+100 nM PRMT5

Materials:

| Reagents | Vendor |
|---|---|
| Bicine pH 8.0, 0.5M | Alfa Aesar, Cat# A14957 |
| Sodium Chloride, 5M | Sigma-Aldrich, Cat# S5150 |
| Tween-20, 10% | Sigma-Aldrich, Cat# 11332465001 |
| DL-Dithiothreitol or DTT, 0.5M in water | Sigma-Aldrich, Cat# 43816 |
| PRMT5:MEP50, 51 µM; Storage Buffer 50 mM Tris, 250 mM NaCl, 1 mM TCEP, pH 8.0 | Viva custom protein |
| Me0-PEP21, Unmethylated Peptide, 1.9 mM in water | Anaspec custom order |
| Me2-PEP21-sDMA, Dimethylated Peptide, 1.9 mM in water | Anaspec custom order |
| Dimethyl Sulfoxide | Sigma-Aldrich, Cat# D8418-1L |
| S-adenosyl methionine (SAM), 32 mM | CAYMAN CHEMICAL, Cat# 0461501-31 |
| 5-Deoxy-5-methyladenosine (MTA), 25 mM | EMD Millipore, Cat# 260585 |

Preparation of Cofactor Solutions
    SAM was dissolved in distilled deionized water to make a 32 mM solution, which was stored at −20° C. and discarded after one freeze-thaw cycle
    MTA—was dissolved in distilled deionized water to make 2.5 mM stock solution. Gentle heating 37° C. for 1 minute was used as necessary to fully solubilize. The solution was stored at −20° C. and used over multiple freeze-thaw cycles Plates:

| Plate | Vendor | Application |
|---|---|---|
| Greiner 384-well flat-bottom clear, polypropylene plates | Greiner, Cat#781201 or Cat#781280 | Compound dilution |
| ECHO LDV 384-well plate | Labcyte, Cat# LP-0200 | Compound dilution |
| Greiner 384-well Black, polypropylene plates | Greiner, Cat# 781076 | Assay plate |

Instrumentation:

| Instrument | Application |
|---|---|
| Echo (Labcyte # 555) | Compound dilution |
| Perkin Elmer Envision, Cat# 2104 | Plate reader, FP TAMRA, Ex540/Em590 |

Reagent Preparation:
Prepare Compound Dilution in Assay Plate:
 9 μL of 10 mM compound in DMSO was prepared
 A 10-point, 3-fold dilution, top working concentration at 125 μM was prepared as detailed in Table 2.
 4 copies of compound plate were generated for the four assay conditions

TABLE 2

| Point | Plate type | Source (mM) | Transfer (nL) | Backfill DMSO (nL) | Final Concentration (uM) |
|---|---|---|---|---|---|
| 1 | Source plate 1 | 10 | 187.5 | 0 | 1,250 |
| 2 | Source plate 1 | 10 | 62.5 | 125 | 416.7 |
| 3 | Inter plate 1 | 1.534 | 135 | 52.5 | 138.9 |
| 4 | Inter plate 1 | 1.534 | 45 | 142.5 | 46.3 |
| 5 | Inter plate 1 | 1.534 | 15 | 172.5 | 15.43 |
| 6 | Inter plate 1 | 1.534 | 5 | 182.5 | 5.144 |
| 7 | Inter plate 2 | 0.01905 | 135 | 52.5 | 1.715 |
| 8 | Inter plate 2 | 0.01905 | 45 | 142.5 | 0.5716 |
| 9 | Inter plate 2 | 0.01905 | 15 | 172.5 | 0.01905 |
| 10 | Inter plate 2 | 0.01905 | 5 | 182.5 | 0.006351 |

The compound concentration of source plate 1 is 10 mM
The compound concentration of Inter plate 1 is 1.534 mM, which is prepared by transferring 1.2 μL of 10 mM compound to 6.576 μL DMSO
The compound concentration of Inter plate 2 is 0.01905 mM, which is prepared by transferring 15 nL of 0.1 mM compound to 7.858 μL DMSO
187.5 nL of DMSO was dispensed in columns 1,12, 13 & 24 for the control reaction, 187.5 nL of compound dilutions in columns 3 to 22 in the assay plate shown in table 3

TABLE 3

| | 1 | 2 3 4 5 6 7 8 9 10 11 | 12 | 13 | 14 15 16 17 18 19 20 21 22 | 23 | 24 |
|---|---|---|---|---|---|---|---|
| A | min control | cpd 1, 10 dose, 3-fold, top = 125 uM | max control | min control | cpd 17, 10 dose, 3-fold, top = 125 uM | | max control |
| B | (100% Inh) | cpd 2, 10 dose, 3-fold, top = 125 uM | (100% Inh) | (100% Inh) | cpd 18, 10 dose, 3-fold, top = 125 uM | | (100% Inh) |
| C | | cpd 3, 10 dose, 3-fold, top = 125 uM | | | cpd 19, 10 dose, 3-fold, top = 125 uM | | |
| D | | cpd 4, 10 dose, 3-fold, top = 125 uM | | | cpd 20, 10 dose, 3-fold, top = 125 uM | | |
| E | | cpd 5, 10 dose, 3-fold, top = 125 uM | | | cpd 21, 10 dose, 3-fold, top = 125 uM | | |
| F | | cpd 6, 10 dose, 3-fold, top = 125 uM | | | cpd 22, 10 dose, 3-fold, top = 125 uM | | |
| G | | cpd 7, 10 dose, 3-fold, top = 125 uM | | | cpd 23, 10 dose, 3-fold, top = 125 uM | | |
| H | | cpd 8, 10 dose, 3-fold, top = 125 uM | | | cpd 24, 10 dose, 3-fold, top = 125 uM | | |
| I | | cpd 9, 10 dose, 3-fold, top = 125 uM | | | cpd 25, 10 dose, 3-fold, top = 125 uM | | |
| J | | cpd 10, 10 dose, 3-fold, top = 125 uM | | | cpd 26, 10 dose, 3-fold, top = 125 uM | | |
| K | | cpd 11, 10 dose, 3-fold, top = 125 uM | | | cpd 27, 10 dose, 3-fold, top = 125 uM | | |
| L | | cpd 12, 10 dose, 3-fold, top = 125 uM | | | cpd 28, 10 dose, 3-fold, top = 125 uM | | |
| M | | cpd 13, 10 dose, 3-fold, top = 125 uM | | | cpd 29, 10 dose, 3-fold, top = 125 uM | | |
| N | | cpd 14, 10 dose, 3-fold, top = 125 uM | | | cpd 30, 10 dose, 3-fold, top = 125 uM | | |
| O | | cpd 15, 10 dose, 3-fold, top = 125 uM | | | cpd 31, 10 dose, 3-fold, top = 125 uM | | |
| P | | cpd 16, 10 dose, 3-fold, top = 125 uM | | | cpd 32, 10 dose, 3-fold, top = 125 uM | | |

The assay buffer was freshly prepared: 30 mM Bicine pH 8, 0.003% Tween 20, 1.5 mM DTT, and 150 mM NaCl Preparation of the four assay samples:
  RMT5 was thawed on ice; Me2, Me0, SAM and MTA were thawed at room temperature. The peptide stock was diluted to 7 µM in ddH₂O.
  SAM Me2 assay samples:
    3×SAM (cofactor): 150 µM SAM (Cayman) in assay buffer was prepared.
    1.5×PRMT5/Me2 (Max control): 150 nM PRMT5, and 37.5 nM Me2 in assay buffer was prepared.
    1.5×Me2 (Min control): 37.5 nM Me2 in assay buffer was prepared,
  Apo-Me0 assay samples:
    3× No Cofactor: assay buffer only was prepared
    1.5×PRMT5/Me0 (Max control): 150 nM PRMT5, and 37.5 nM Me2 in assay buffer was prepared.
    1.5×Me0 (Min control): 37.5 nM Me2 in assay buffer was prepared
  MTA-Me0 assay samples:
    3×MTA (cofactor): 150 uM MTA in assay buffer was prepared.
    1.5×PRMT5/Me0 (Max control): 37.5 nM PRMT5, and 37.5 nM Me0 in assay buffer was prepared.
    1.5×Me0 (Min control): 37.5 nM Me0 in assay buffer was prepared.
  MTA-Me2 assay samples:
    3×MTA (cofactor): 150 uM MTA in assay buffer was prepared.
    1.5×PRMT5/Me2 (Max control): 75 nM PRMT5, and 37.5 nM Me0 in assay buffer was prepared.
    1.5×Me2 (Min control): 37.5 nM Me0 in assay buffer was prepared.

Assay Procedure:
  Above reagents were prepared
  5 µL 3× cofactor solution was dispensed to wells in all columns by 16-channel electronic pipettes
  Assay plate containing compound was spinned 60 sec at 1000 rpm
  10 µL Min control (peptide) solution was dispensed to the wells (columns1&13) by 16-channel electronic pipettes
  10 µL enzyme (1.5× enzyme/peptide) solution was dispensed to the wells (columns 2-12& 14-24) by 16-channel electronic pipettes
  Assay plate containing compound was spinned 60 sec at 1000 rpm, and incubated at 23° C. for 30 min
  Procedure was repeated for other three assay conditions and all plates were incubated for 30 min
  Assay plate was read on Envision instrument Data Analysis
  Fluorescence polarization is normalized to calculate % inhibition.

$$\% \text{ inhibition} - i = \left(1 - \frac{i - P}{\text{Prmt5\_P} - P}\right) * 100 \quad \text{Equation 1}$$

Where:
% inhibition-i is the percentage inhibition at a given concentration of inhibitor
i is the Fluorescent anisotropy at a given inhibitor concentration
P is the anisotropy signal given by the peptide alone and represents the minimum signal
Prmt5_P is the anisotropy signal given by the Prmt5 and peptide complex in the presence of DMSO, representing the maximum fluorescent anisotropy signal
  % inhibition data were fit with a 4-parameter logistic model. Bottom and Top were fixed to 0% and 100%, respectively. $IC_{50}$ values are reported.
  The Ki can be calculated from the $IC_{50}$ using the Cheng-Prussof equation:

$$IC_{50} = Ki \times \left(1 + \frac{[\text{Peptide}]}{Kd, \text{Peptide}}\right)$$

For the assay performed in the presence of SAM, the Me2 peptide binding affinity to PRMT5 in the presence of SAM was determined to be 50 nM, and the peptide concentration is 25 nM, therefore $IC_{50}=Ki\times1.5$
  For the assay performed in the presence of MTA, the Me0 peptide binding affinity to PRMT5 in the presence of MTA was determined to be 2 nM, and the peptide concentration is 25 nM, therefore $IC_{50}=Ki\times13.5$ Envision® Set Up:
  Mirror (Barcode 682)
  Filter (Barcode 245)
  Filter (Barcode 246)
  Filter (Barcode 132)

The data for this example is shown in Table 1a, Columns 3-6.

Example 11—Cellular Assay—SDMA In-Cell Western Protocol

A HAP1 MTAP-isogenic cell line pair was acquired from Horizon Discovery (HZGHC004894c005) and maintained in DMEM (ThermoFisher 11965)+10% FBS (Gemini 100-500) in a humidified, 10% CO2 tissue culture incubator. The SAM-cooperative PRMT5 inhibitor, GSK3326595, was sourced from SelleckChem and maintained as a 10 mM DMSO stock. All test compounds are maintained as 10 mM DMSO stocks.

On Day 0, MTAP-intact or MTAP-deleted cells are seeded in a 384-well plate, and incubated in a humidified, 10% $CO_2$ tissue culture incubator for 16-24 hours. On Day 1, the test compounds are dispensed to wells at defined concentrations using a Tecan D300e digital dispenser (n=4), and the volume of DMSO is normalized to highest class volume. Each plate includes wells dosed with defined concentrations of GSK33226595 as a plate control. The compounds are incubated with cells for 24 hours in a humidified, 10% $CO_2$ tissue culture incubator.

On Day 2, the compound-treated cells are fixed with a final concentration of 4% formaldehyde. The cells are then washed/permeabilized with IX PBS+0.1% Triton X-100, and then blocked with 5% goat serum/1×TBS. The fixed cells are then incubated overnight at 4° C. with a primary SDMA antibody cocktail (Cell Signaling 13222).

On Day 3, the cells are washed with 1×PBS+0.1% Triton X-100, and then incubated at room temperature for 1 hour with a NIR fluorescent secondary antibody cocktail that also contains DRAQ5 (LiCor 926-32211 and VWR 10761-508). The cells are washed with 1×PBS+0.1% Triton X-100, and then washed again with $ddH_{2O}$. The plates are then imaged using a NIR fluorescent imager (LiCor Odyssey).

For data analysis, the SDMA signal is normalized to the DRAQ5 signal. Assay background is determined by the signal from wells treated with 10 µM GSK3326595, and subtracted from every well. The data are plotted as % of the DMSO control wells for the MTAP-intact and the MTAP-deleted cell lines independently, with a 4-parameter fit non-linear regression model constrained to 0 (GraphPad Prism).

The data obtained in this experiment is presented in Table 1a, columns 7-9.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein.

The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a methylthioadenosine phosphorylase-deficient (MTAP-deficient) and/or a methylthioadenosine-accumulating (MTA-accumulating) cancer selected from the group consisting of glioblastoma, malignant peripheral nerve sheath tumors (MPNST), esophageal cancer, bladder cancer, pancreatic cancer, mesothelioma, melanoma, non-small cell lung cancer, astrocytoma, diffuse large B-cell lymphoma (DLBCL), leukemia, head and neck cancer, myxofibrosarcoma, cholangiosarcoma, cancer of the brain, stomach cancer, kidney cancer, breast cancer, cancer of the endometrium, urinary tract cancer, liver cancer, soft tissue cancer, pleura cancer, large intestine cancer and sarcoma in a subject in need thereof by administering to the subject a therapeutically effective amount of a compound or a pharmaceutically acceptable salt thereof wherein the compound is of formula (I)

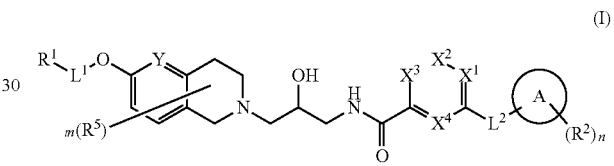

wherein
$X^1$, $X^2$, $X^3$ and $X^4$ are each independently N or $CR^x$;
Y is N, CH or $CR^5$;
$L^1$ is a bond or $C_1$-$C_4$-alkylene substituted with 0-2 instances of $R^6$;
$L^2$ is a bond, —NH— or —O—;
Ring A is a carbocycle, heterocycle, 5-6 member monocyclic heteroaryl or a monocyclic aryl;
$R^1$ is a 3-7 membered carbocycle, a 4-7 membered heterocycle or a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)$OR^3$, —$CH_2$C(=O)$R^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$;
each $R^3$ is independently selected from H, $C_1$-$C_6$ alkyl, $C_1$-$C_6$ heteroalkyl, $C_3$-$C_7$ carbocyclyl, $C_3$-$C_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N (R³)₂, —S(=O)R³, —S(=O)₂R³, —SR³, —S(=O)(=NR³)R³, —NRS(=O)₂R³ and —S(=O)₂N(R³)₂;

each R^x is independently selected from hydrogen, halo, —CN, —C₁-C₆ alkyl, —C₁-C₆ heteroalkyl, —C₁-C₆ haloalkyl, —C₃-C₉ carbocyclyl, —C₃-C₉ heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NRS(=O)₂R³ and —S(=O)₂N(R³)₂ wherein each alkyl, carbocyclyl, heterocyclyl, heterocyclylalkyl, cycloalkylalkyl is optionally substituted;

each R⁵ is independently selected from =O, halo, —CN, —C₁-C₆ alkyl, —C₁-C₆ heteroalkyl, —C₁-C₆ haloalkyl, —C₃-C₉ carbocyclyl, —C₃-C₉ heterocyclyl, C₆-C₁₀ aryl, C₅-C₁₀ heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a —C₃-C₉ heterocyclyl;

each R⁶ is independently selected from halo, —C₁-C₄ alkyl, —C₁-C₄ haloalkyl, —OC₁-C₄ alkyl, —OC₁-C₄ haloalkyl, or two R⁶ can be taken together with the atoms to which they are attached to form a C₃-C₇ carbocycle or a C₃-C₇ heterocycle;

m is 0, 1, 2 or 3; and n is 0, 1, 2 or 3.

2. The method of claim 1 wherein the compound has structure (Ia)

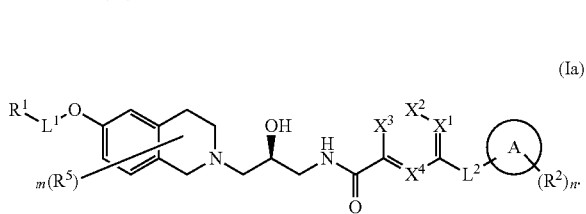

(Ia)

3. The method of claim 2 wherein the compound has structure (IIa)

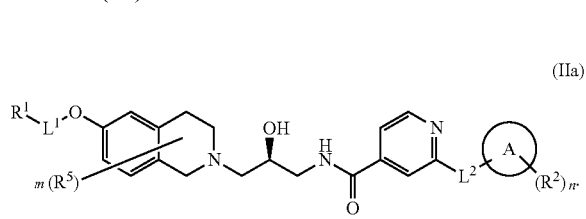

(IIa)

4. The method of claim 2 wherein the compound has structure (IVa)

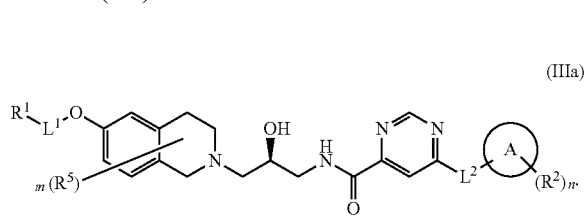

(IIIa)

5. The method of claim 2 wherein the compound has structure (IVa)

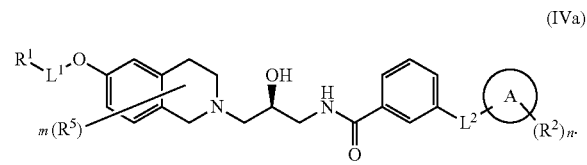

(IVa)

6. The method of claim 2 wherein the compound has structure (Va1')

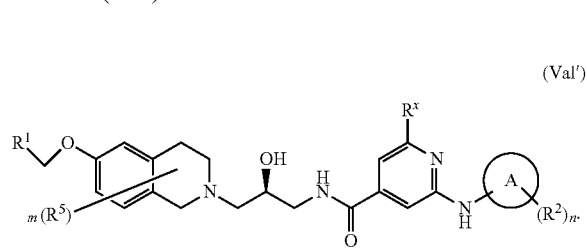

(Va1')

7. The method of claim 6 wherein R^x is H, N(R³)₂, NHR³, N(CH₃)R³, OR³, C₁-C₆ alkyl, optionally substituted —C₃-C₉ carbocyclyl or optionally substituted —C₃-C₉ heterocyclyl.

8. The method of claim 2 wherein the compound has structure (VIa1')

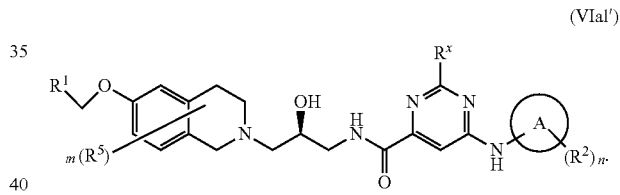

(VIa1')

9. The method of claim 8 wherein R^x is H, N(R³)₂, NHR³, N(CH₃)R³, OR³, C₁-C₆ alkyl, optionally substituted —C₃-C₉ carbocyclyl or optionally substituted —C₃-C₉ heterocyclyl.

10. The method of claim 2 wherein the compound has structure (VIIa1)

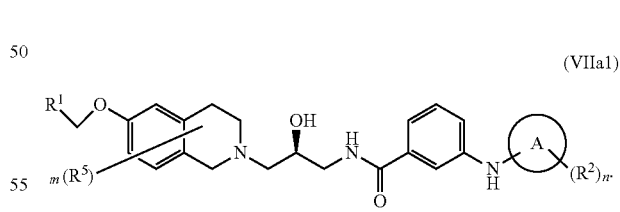

(VIIa1)

11. A method of treating a methylthioadenosine phosphorylase-deficient (MTAP-deficient) and/or a methylthioadenosine-accumulating (MTA-accumulating) cancer selected from the group consisting of glioblastoma, malignant peripheral nerve sheath tumors (MPNST), esophageal cancer, bladder cancer, pancreatic cancer, mesothelioma, melanoma, non-small cell lung cancer, astrocytoma, diffuse large B-cell lymphoma (DLBCL), leukemia, head and neck cancer, myxofibrosarcoma, cholangiosarcoma, cancer of the brain, stomach cancer, kidney cancer, breast cancer, cancer of the endometrium, urinary tract cancer, liver cancer, soft tissue cancer, pleura cancer, large intestine cancer and sarcoma in a subject in need thereof by administering to the subject a therapeutically effective amount of a compound or a pharmaceutically acceptable salt thereof wherein the compound is of formula (XI)

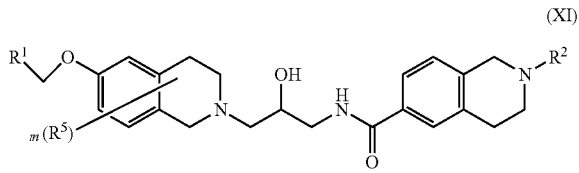

(XI)

wherein:
R$^1$ is a 3-7 membered carbocycle, a 4-7 membered heterocycle or a 5-6 membered heteroaryl substituted with 0-3 instances of R$^4$;
each R$^2$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, heterocyclylalkyl, cycloalkylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ and —S(=O)$_2$N(R$^3$)$_2$;
each R$^3$ is independently selected from H, C$_1$-C$_6$ alkyl, C$_3$-C$_7$ carbocyclyl, C$_3$-C$_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each R$^4$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, heterocyclylalkyl, cycloalkylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ and —S(=O)$_2$N(R$^3$)$_2$;
each R$^5$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, C$_6$-C$_{10}$ aryl, C$_5$-C$_{10}$ heteroaryl, cycloalkylalkyl, heterocyclylalkyl, arylalkyl, heteroarylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$, —S(=O)$_2$N(R$^3$)$_2$, or two R$^5$ can be taken together with the atoms to which they are attached to form a —C$_3$-C$_9$ carbocyclyl or a —C$_3$-C$_9$ heterocyclyl; and
m is 0, 1, 2 or 3.

12. A method of treating a methylthioadenosine phosphorylase-deficient (MTAP-deficient) and/or a methylthioadenosine-accumulating (MTA-accumulating) cancer selected from the group consisting of glioblastoma, malignant peripheral nerve sheath tumors (MPNST), esophageal cancer, bladder cancer, pancreatic cancer, mesothelioma, melanoma, non-small cell lung cancer, astrocytoma, diffuse large B-cell lymphoma (DLBCL), leukemia, head and neck cancer, myxofibrosarcoma, cholangiosarcoma, cancer of the brain, stomach cancer, kidney cancer, breast cancer, cancer of the endometrium, urinary tract cancer, liver cancer, soft tissue cancer, pleura cancer, large intestine cancer and sarcoma in a subject in need thereof by administering to the subject a therapeutically effective amount of a compound or a pharmaceutically acceptable salt thereof wherein the compound is of formula (XII)

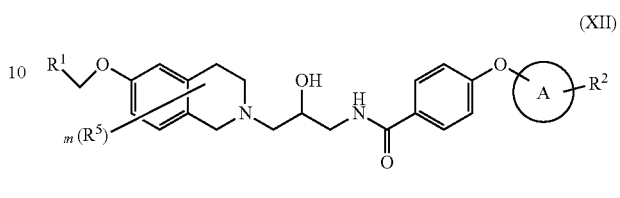

(XII)

wherein
Ring A is a carbocycle, heterocycle, 5-6 member monocyclic heteroaryl or a monocyclic aryl;
R$^1$ is a 3-7 membered carbocycle, a 4-7 membered heterocycle or a 5-6 membered heteroaryl substituted with 0-3 instances of R$^4$;
each R$^2$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, heterocyclylalkyl, heteroarylalkyl, arylalkyl, cycloalkylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ and —S(=O)$_2$N(R$^3$)$_2$;
each R$^3$ is independently selected from H, C$_1$-C$_6$ alkyl, C$_3$-C$_7$ carbocyclyl, C$_3$-C$_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each R$^4$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, heterocyclylalkyl, cycloalkylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ and —S(=O)$_2$N(R$^3$)$_2$;
each R$^5$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, —C$_3$-C$_9$ heterocyclyl, C$_6$-C$_{10}$ aryl, C$_5$-C$_{10}$ heteroaryl, cycloalkylalkyl, heterocyclylalkyl, arylalkyl, heteroarylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$, —S(=O)$_2$N(R$^3$)$_2$, or two R$^5$ can be taken together with the atoms to which they are attached to form a —C$_3$-C$_9$ carbocyclyl or a —C$_3$-C$_9$ heterocyclyl; and
m is 0, 1, 2 or 3.

13. The method of claim 2 wherein R$^1$ is selected from:

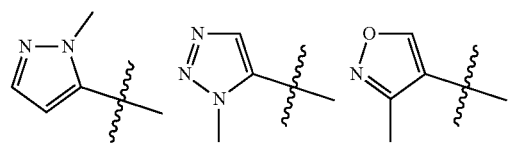

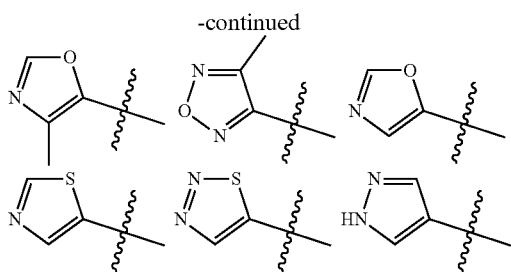

14. The method of claim 2 wherein ring A is piperidinyl, pyrrolidinyl, oxetanyl, tetrahydrofuranyl, azetidinyl, tetrahydropyranyl, 1,4-dioxan-2-yl or morpholinyl.

15. The method of claim 2 wherein ring A is cyclopropyl, cyclobutyl, cyclopentyl, cyclohexyl, cycloheptyl, spiro[2.3]hexyl, spiro[3.3]heptyl.

16. The method of claim 2 wherein n is 1, $R^2$ is —C(=O)$R^3$ and $R^3$ is $C_1$-$C_6$ alkyl or $C_3$-$C_7$ carbocyclyl.

17. The method of claim 1 wherein the compound is selected from:

| Nr. | Structure |
|---|---|
| 161 | 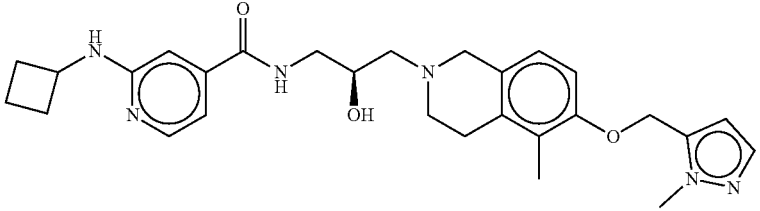 |
| 163 | 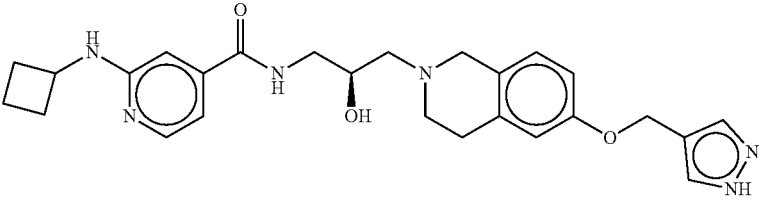 |
| 179 | 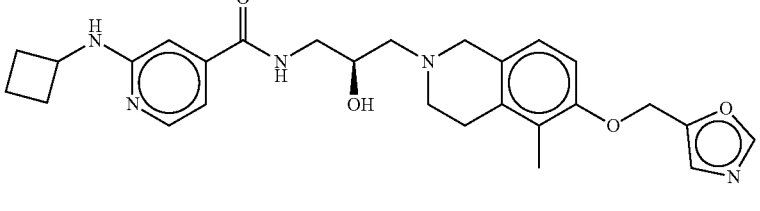 |
| 194 | 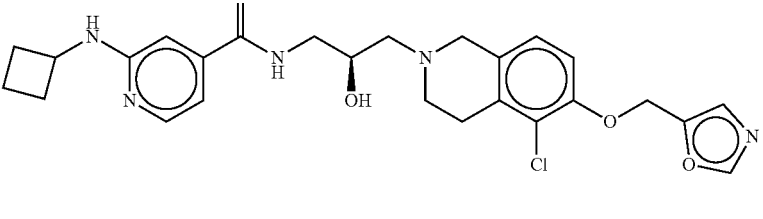 |
| 198 | 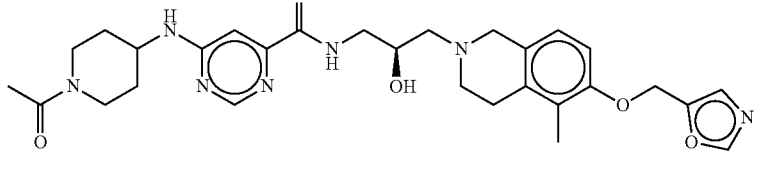 |
| 201 | 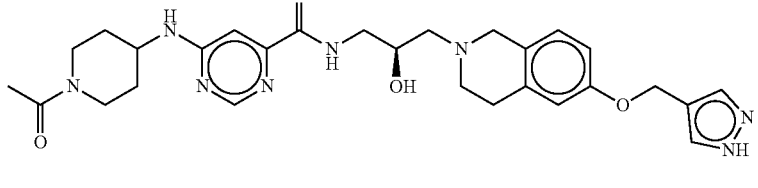 |
| 203 | 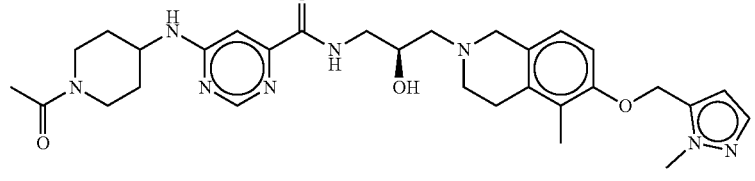 |

| Nr. | Structure |
|---|---|
| 207 | 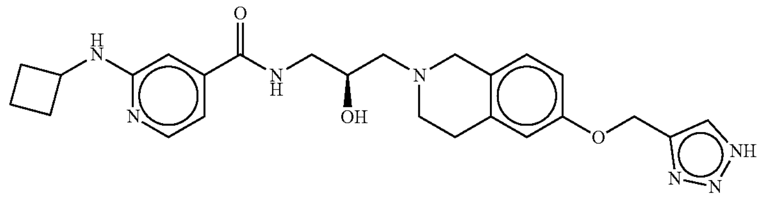 |
| 219 | 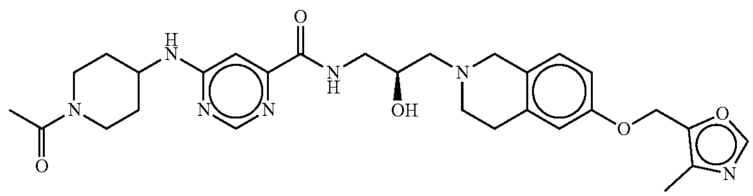 |
| 233 | 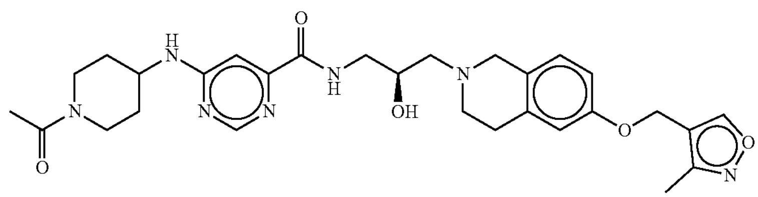 |
| 241 | 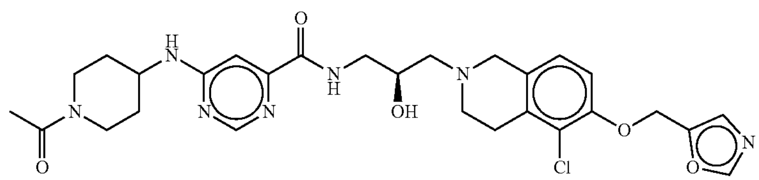 |
| 242 | 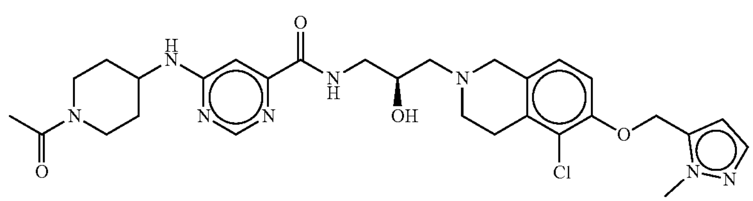 |
| 249 | 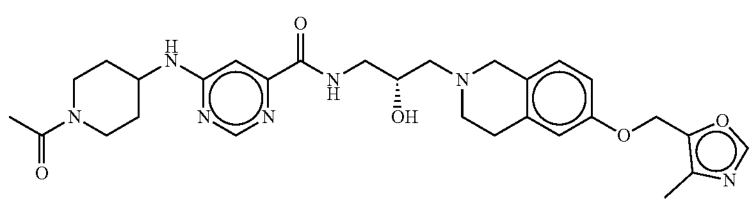 |
| 250 | 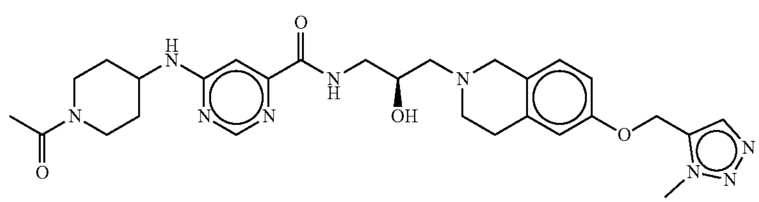 |
| 251 | 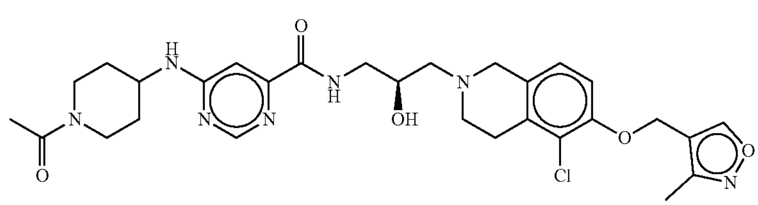 |

| Nr. | Structure |
| --- | --- |
| 252 | 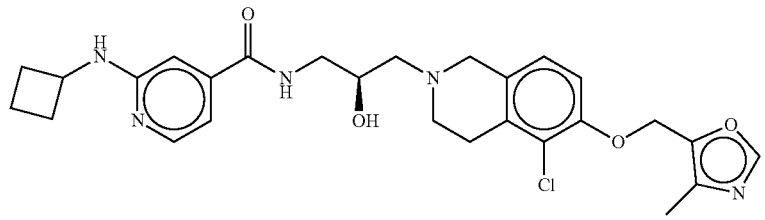 |
| 253 | 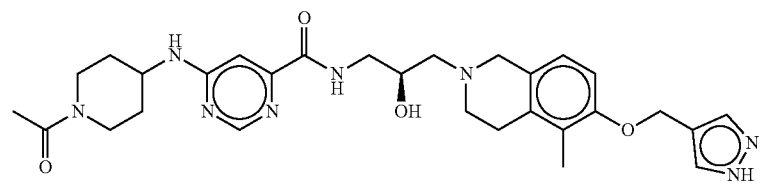 |
| 254 | 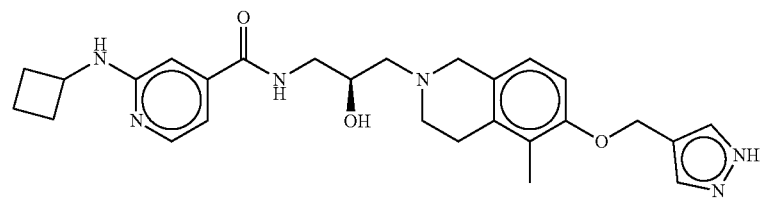 |
| 255 | 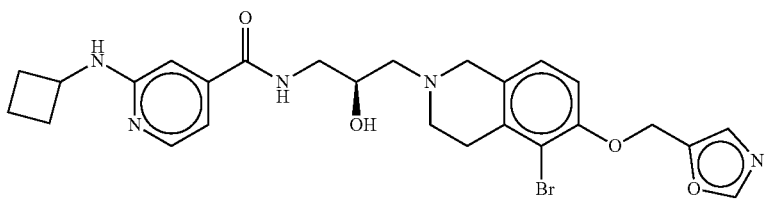 |
| 256 | 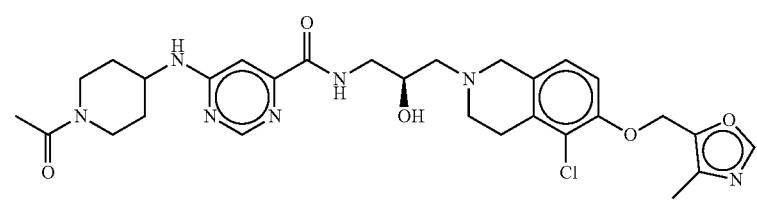 |
| 257 | 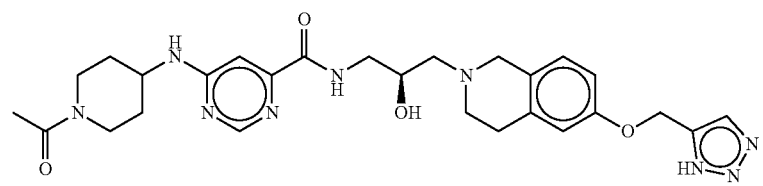 |
| 258 | 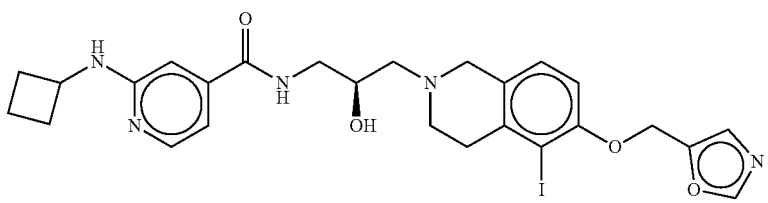 |

-continued

| Nr. | Structure |
|---|---|
| 259 | 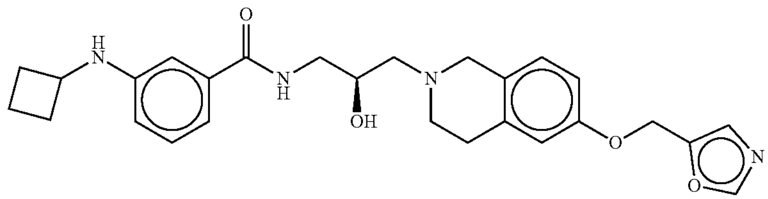 |
| 260 | 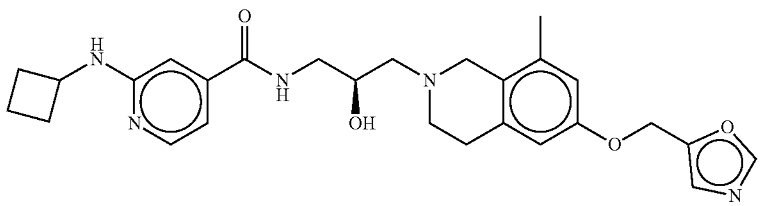 |
| 261 | 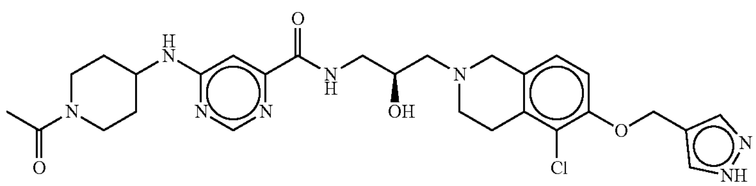 |
| 262 | 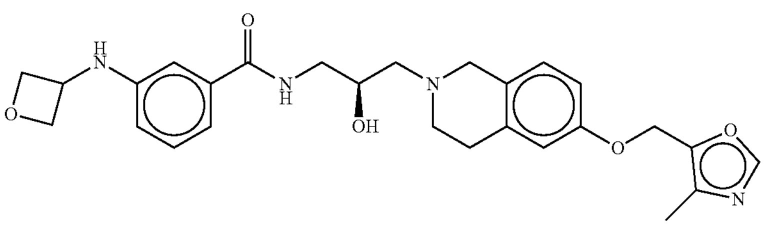 |
| 263 | 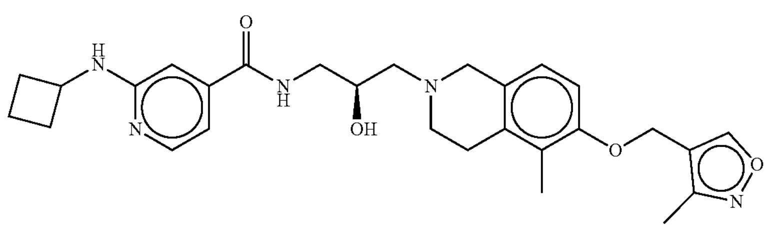 |
| 264 | 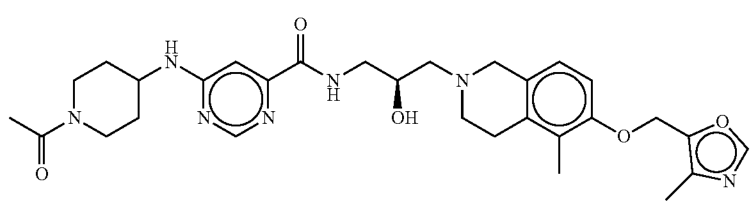 |
| 265 | 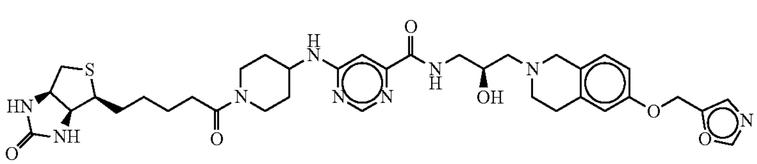 |

| Nr. | Structure |
|---|---|
| 266 | 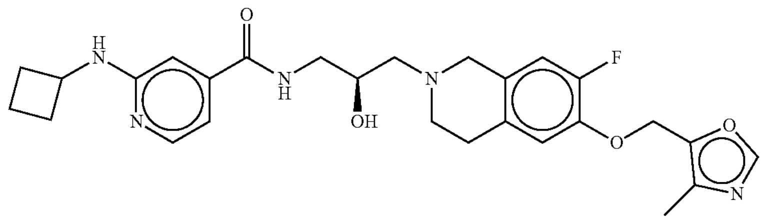 |
| 267 | 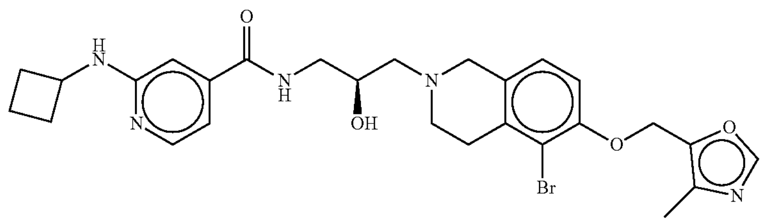 |
| 268 | 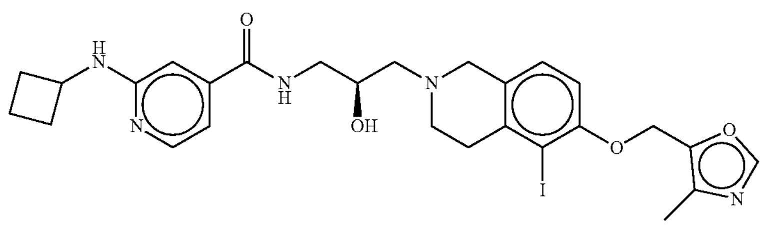 |
| 269 | 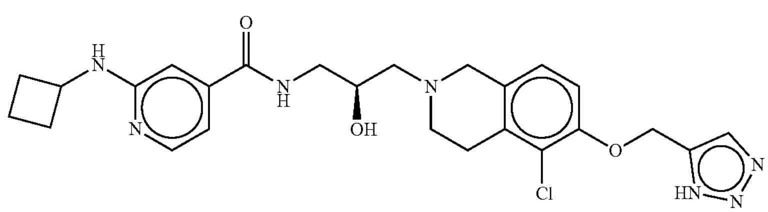 |
| 270 | 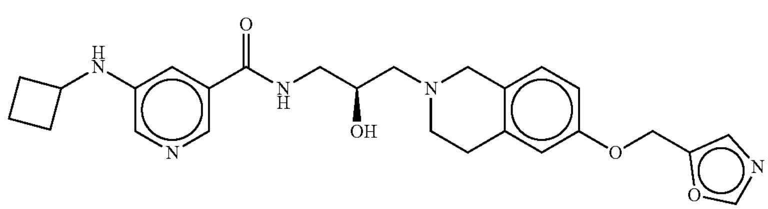 |
| 271 | 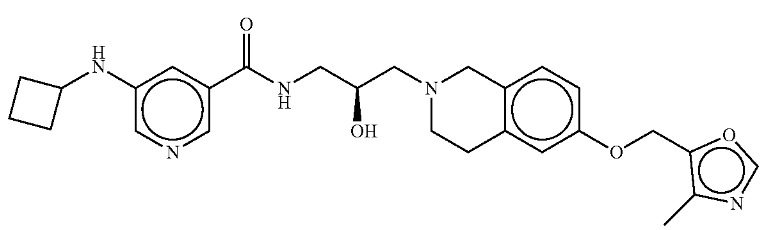 |
| 272 | 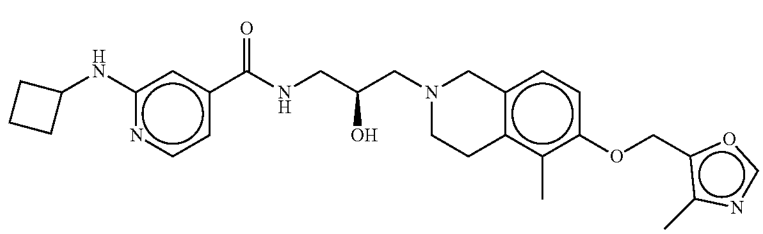 |

-continued
| Nr. | Structure |
|---|---|
| 273 | 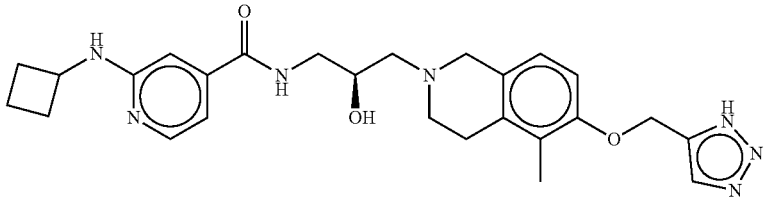 |
| 274 | 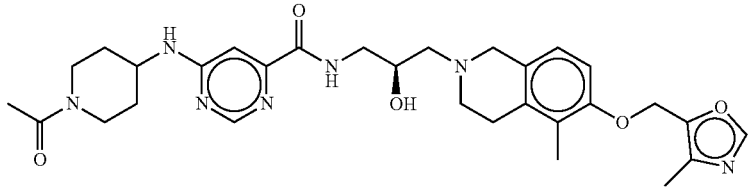 |
| 275 | 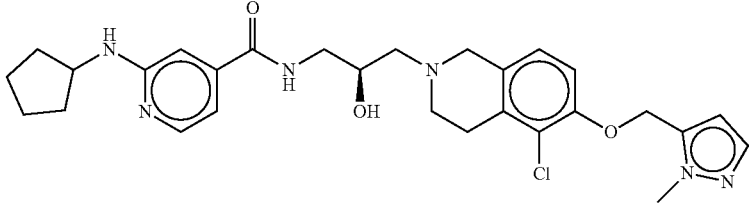 |
| 276 | 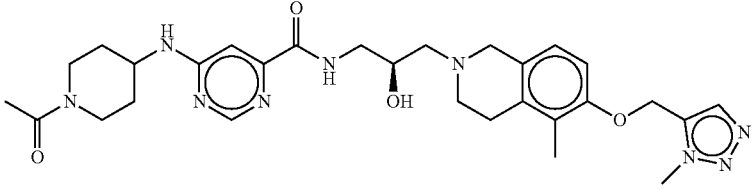 |
| 277 | 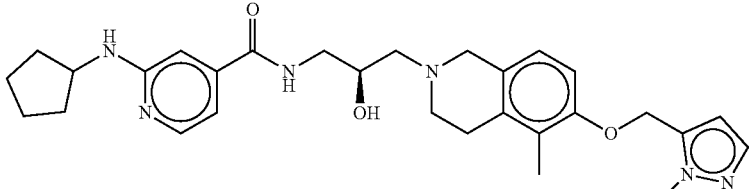 |
| 278 | 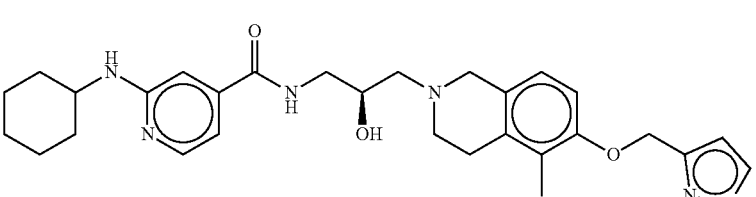 |
| 279 | 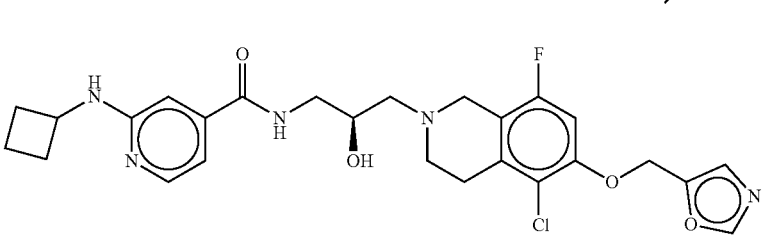 |

-continued

| Nr. | Structure |
|---|---|
| 280 | 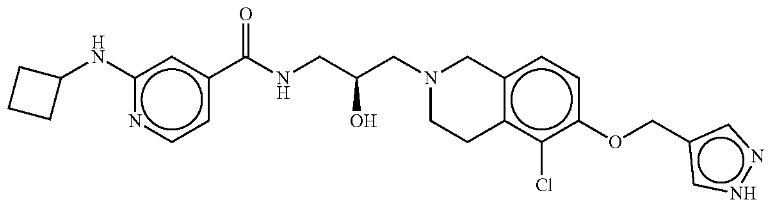 |
| 281 | 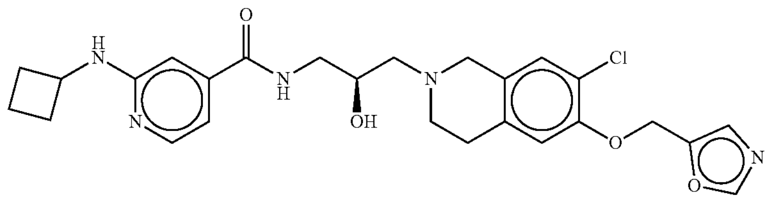 |
| 282 | 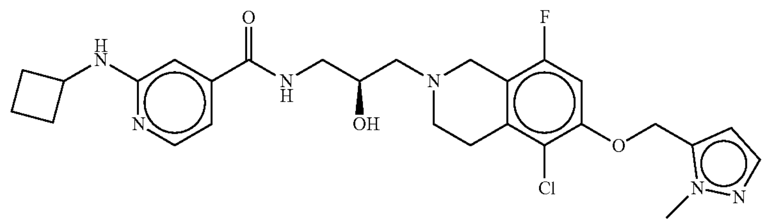 |
| 283 | 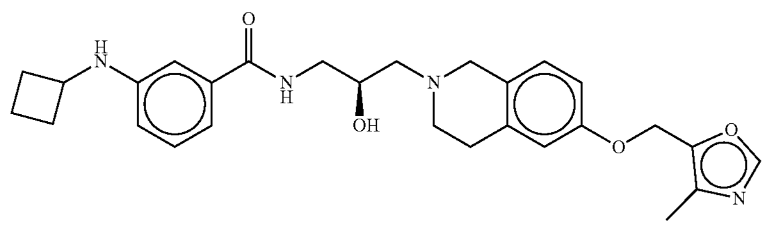 |
| 284 | 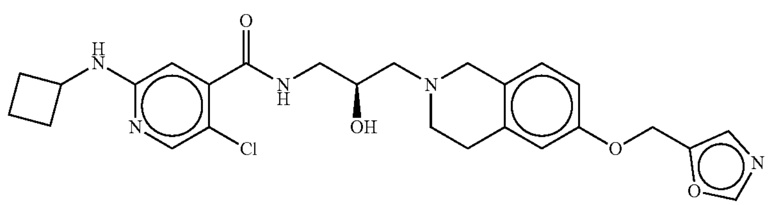 |
| 285 | 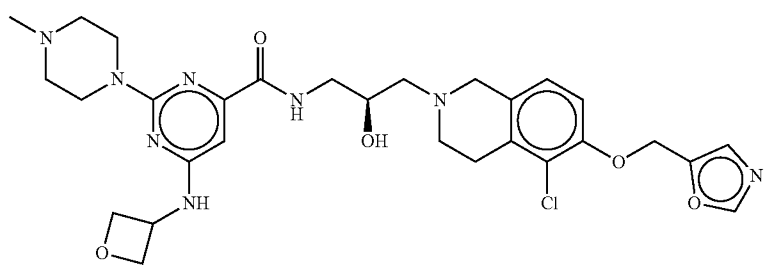 |
| 286 | 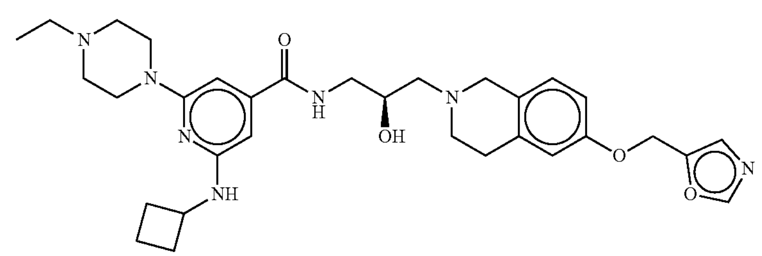 |

| Nr. | Structure |
|---|---|
| 287 | 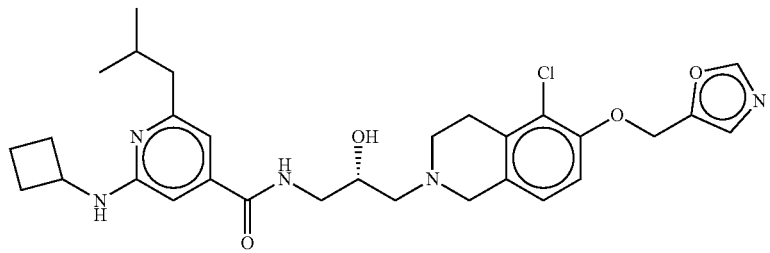 |
| 288 | 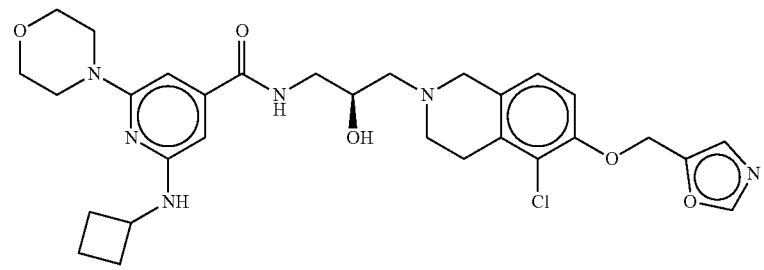 |
| 289 | 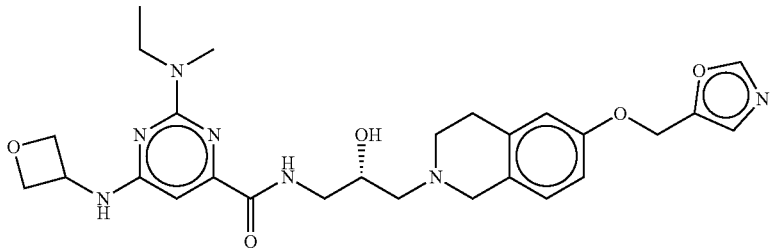 |
| 290 | 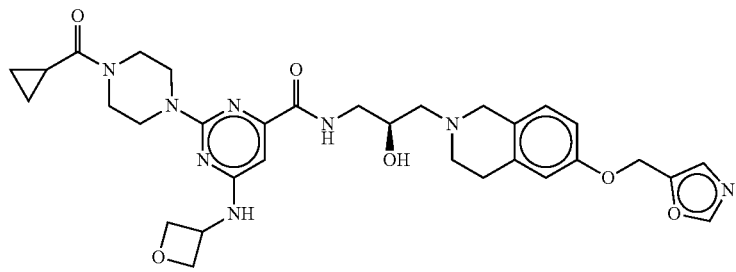 |
| 292 | 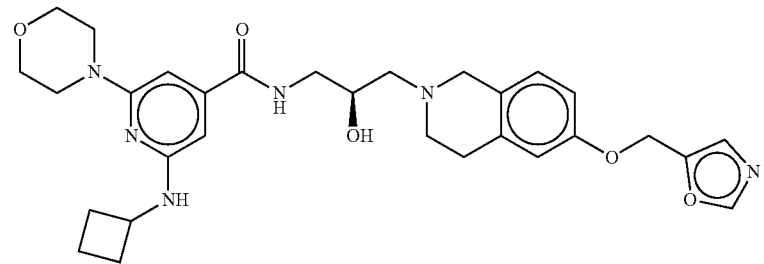 |

| Nr. | Structure |
|---|---|
| 293 | 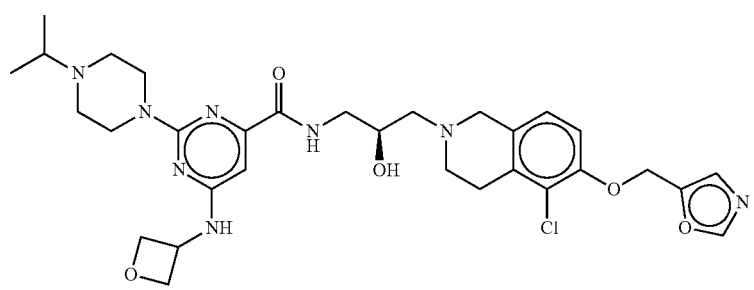 |
| 294 | 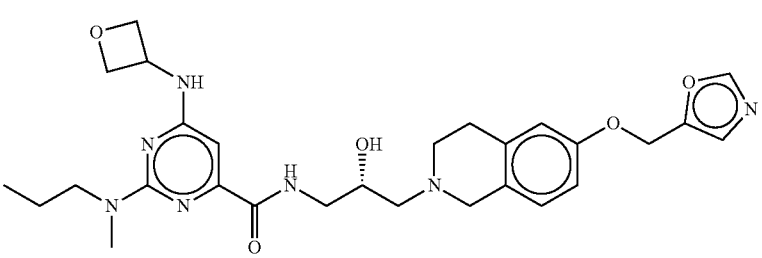 |
| 295 | 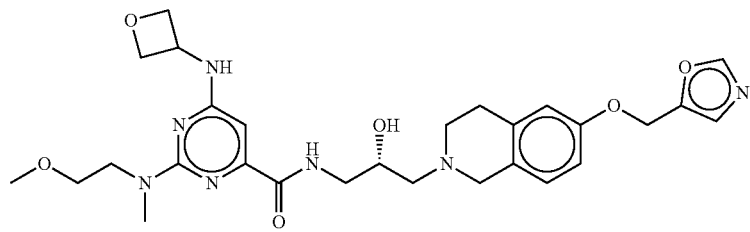 |
| 296 | 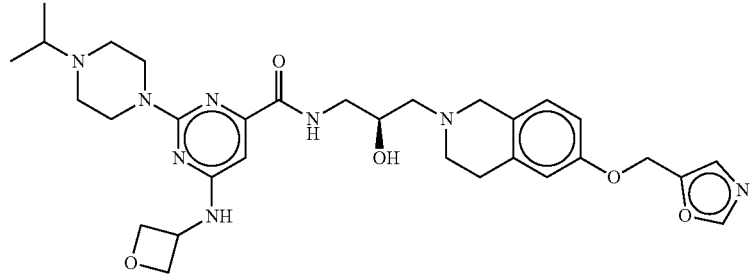 |
| 297 | 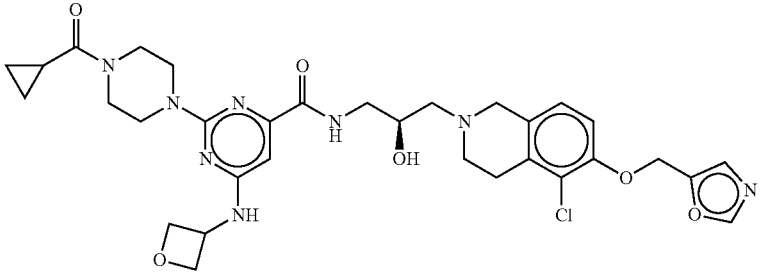 |

| Nr. | Structure |
|---|---|
| 298 | 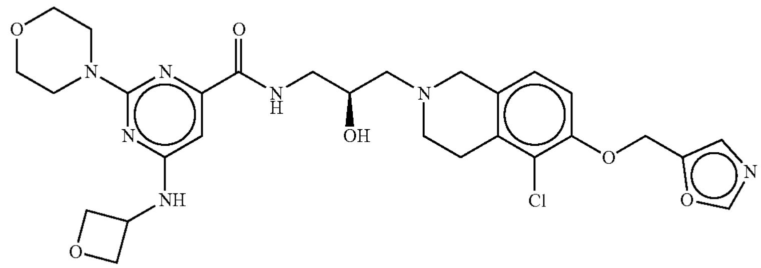 |
| 299 | 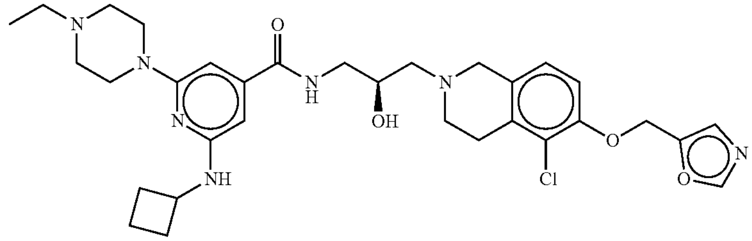 |
| 300 | 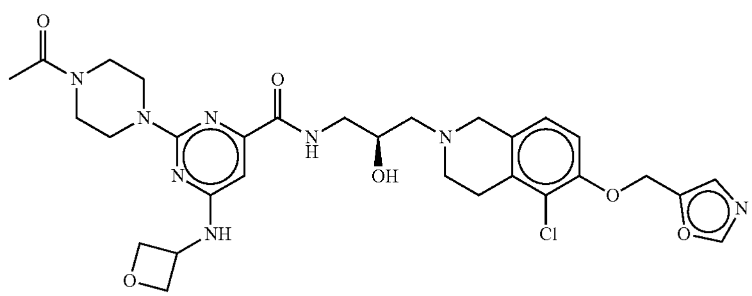 |
| 302 | 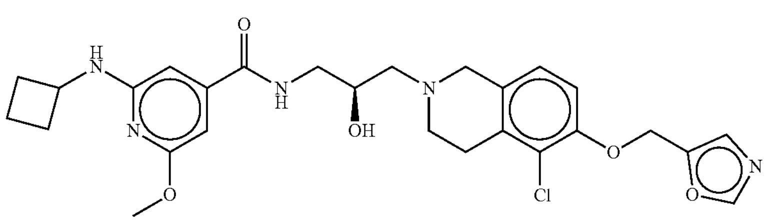 |
| 303 | 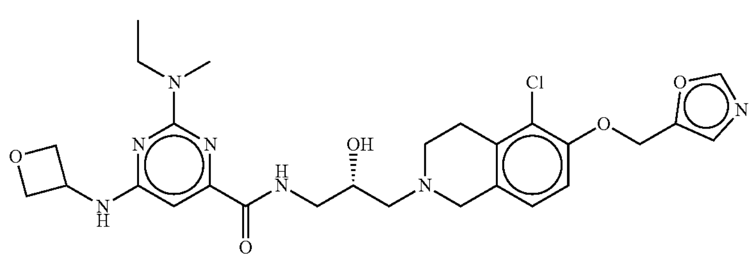 |
| 304 | 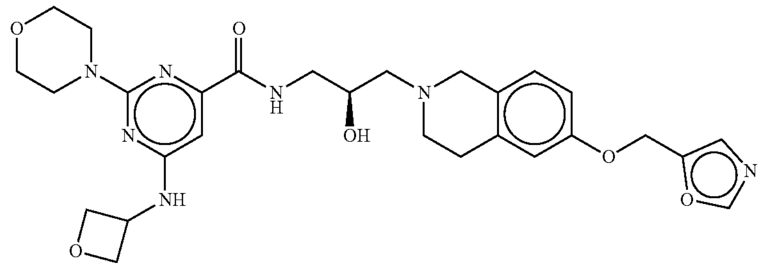 |

| Nr. | Structure |
|---|---|
| 305 | 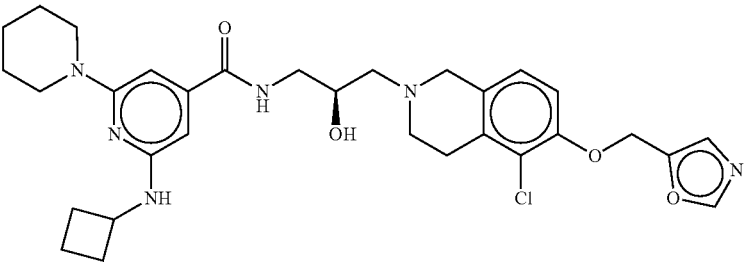 |
| 306 | 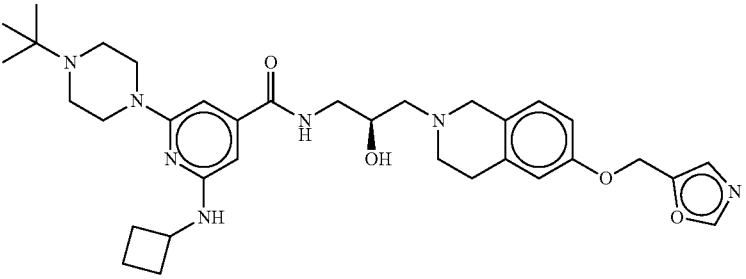 |
| 307 | 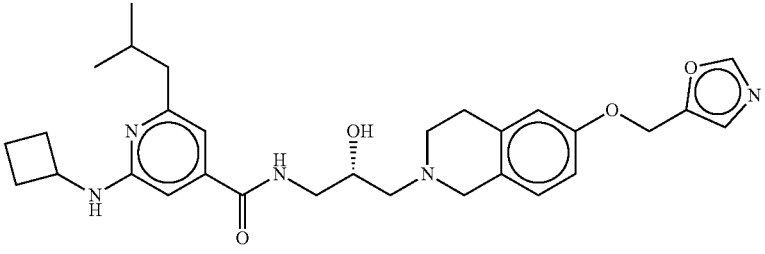 |
| 308 | 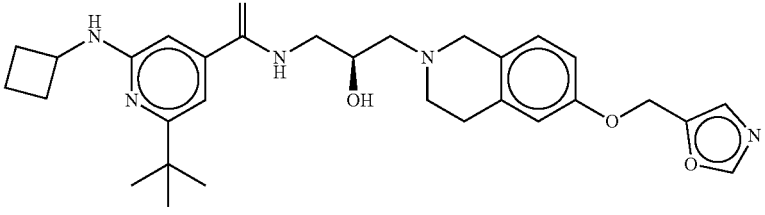 |
| 309 | 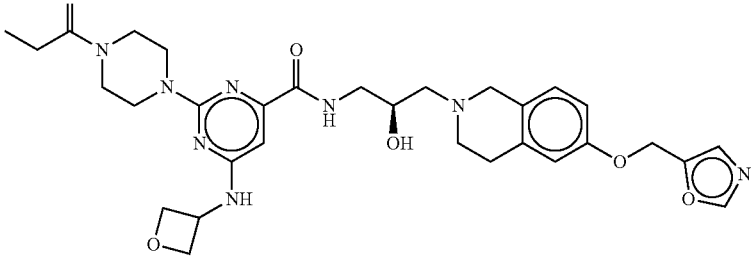 |
| 310 | 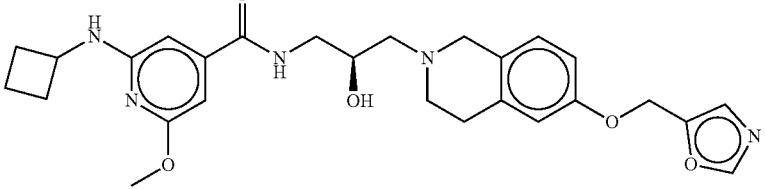 |

| Nr. | Structure |
|---|---|
| 311 | 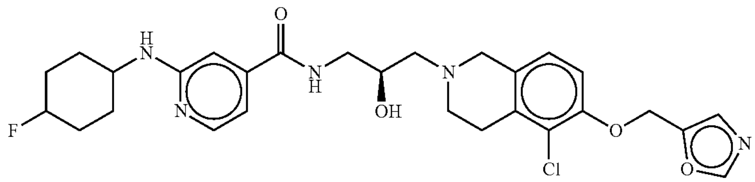 |
| 312 | 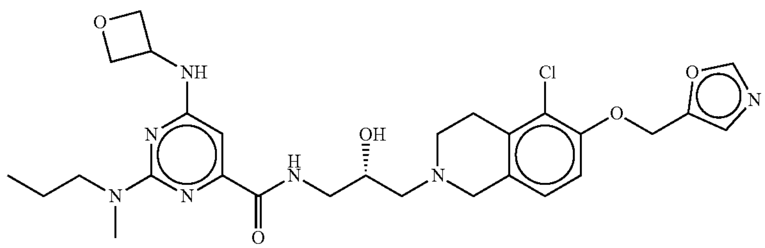 |
| 313 | 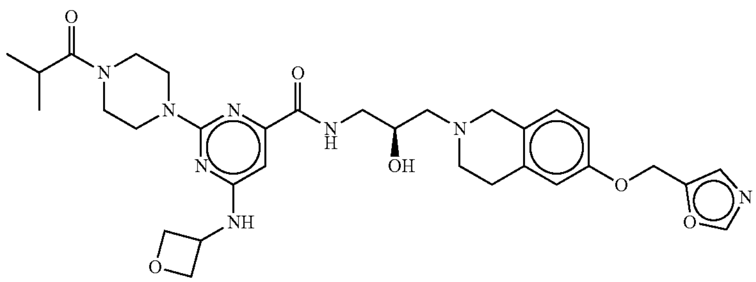 |
| 314 | 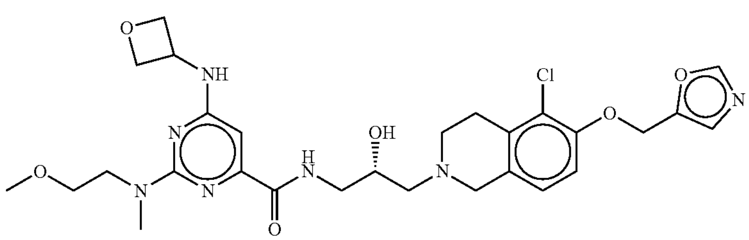 |
| 315 | 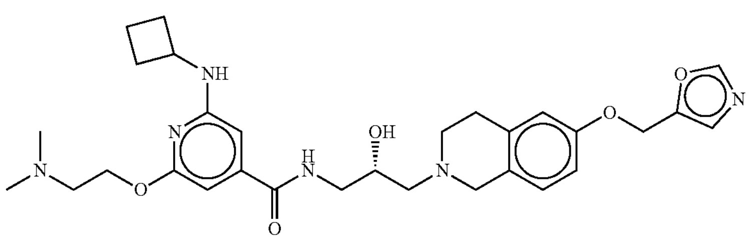 |
| 316 | 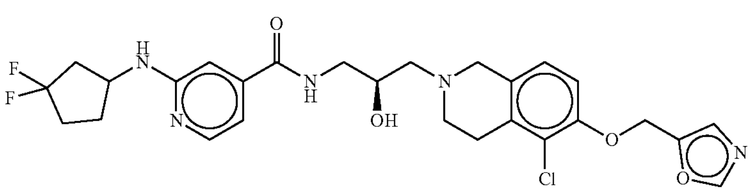 |
| 317 | 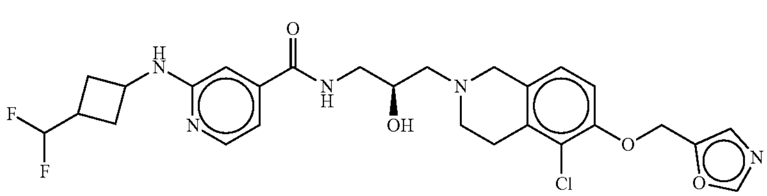 |

-continued
| Nr. | Structure |
|---|---|
| 318 | 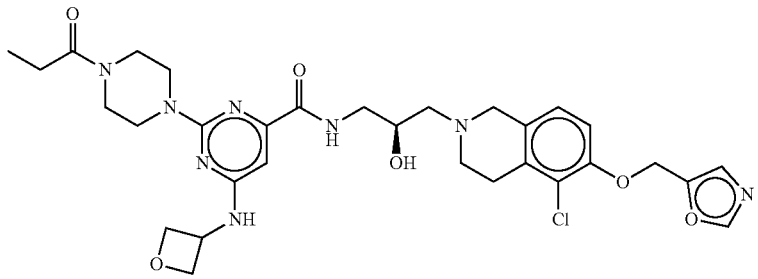 |
| 319 | 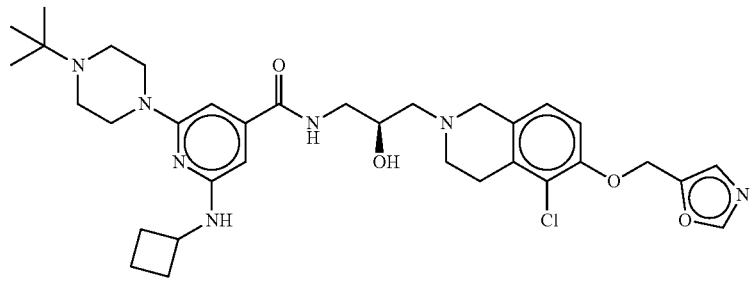 |
| 320 | 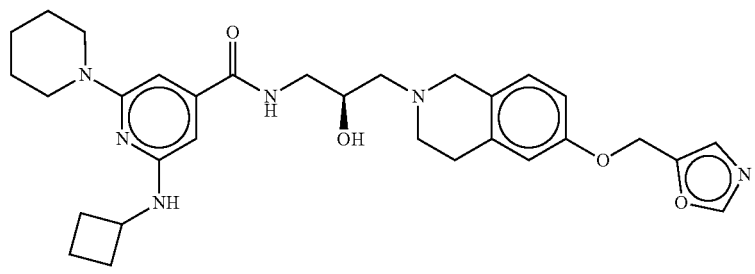 |
| 321 | 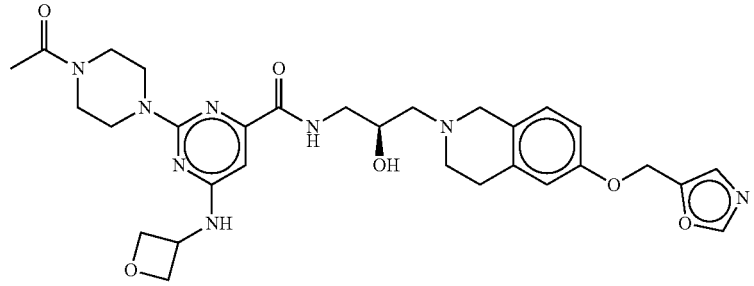 |
| 322 | 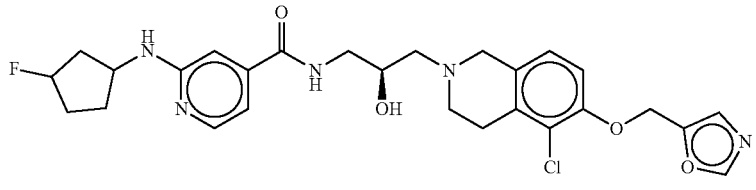 |
| 323 | 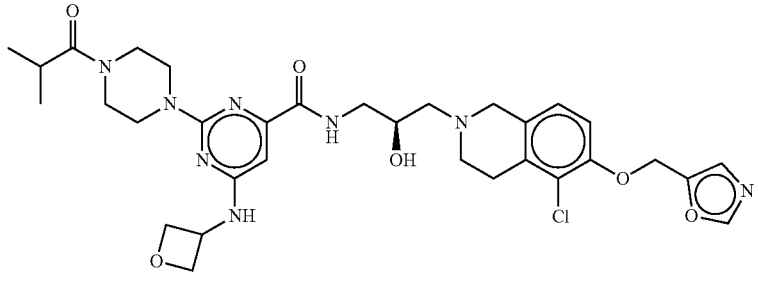 |

| Nr. | Structure |
|---|---|
| 324 | 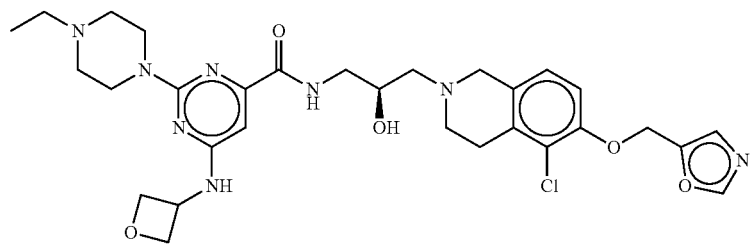 |
| 325 | 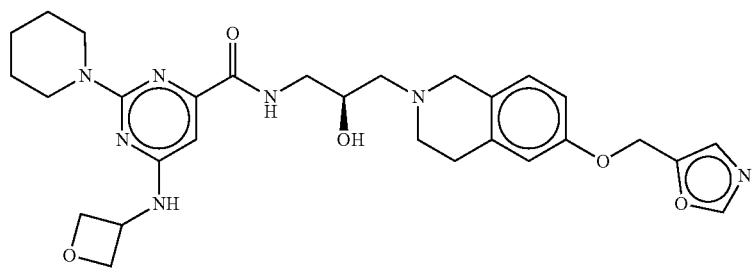 |
| 326 | 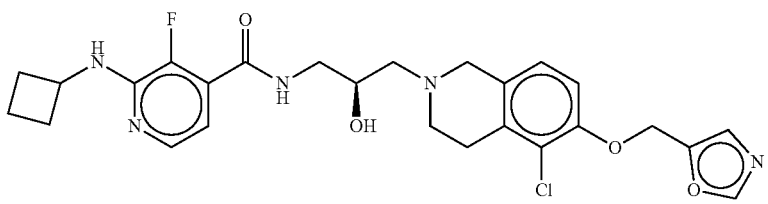 |
| 327 | 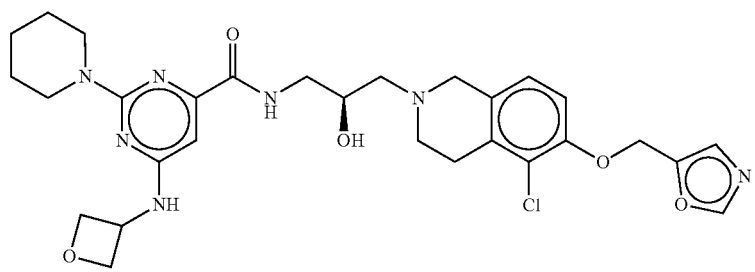 |
| 329 | 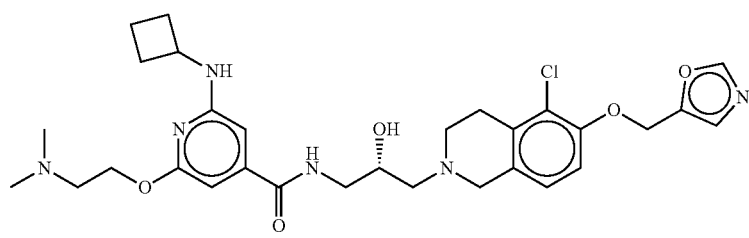 |
| 331 | 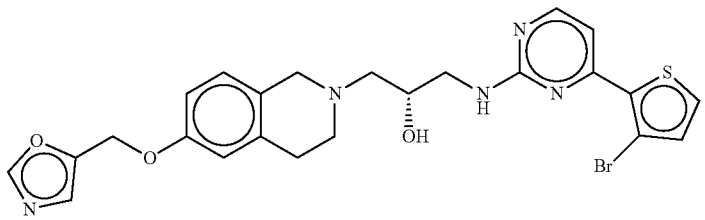 |

| Nr. | Structure |
|---|---|
| 332 | 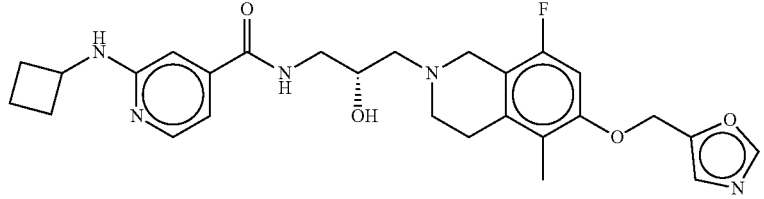 |
| 333 | 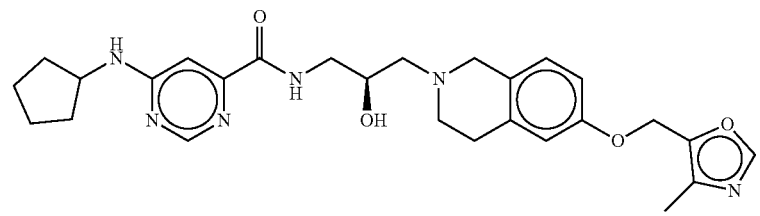 |
| 334 | 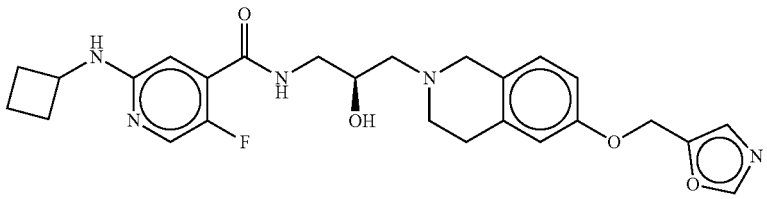 |
| 335 | 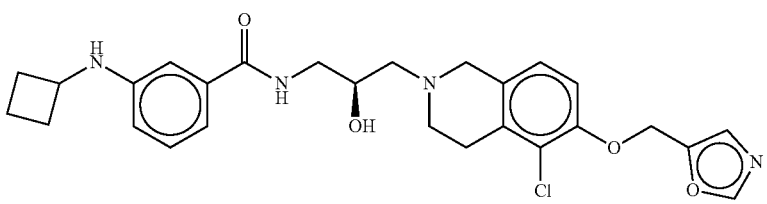 |
| 336 | 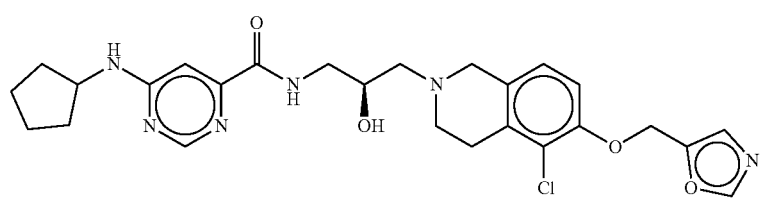 |
| 337 | 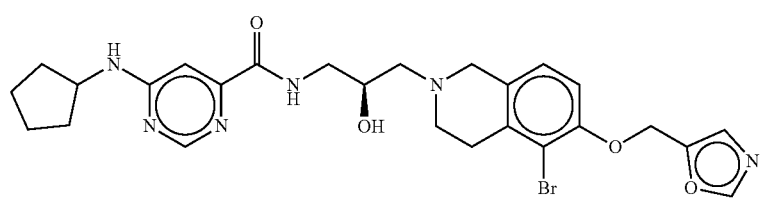 |
| 338 | 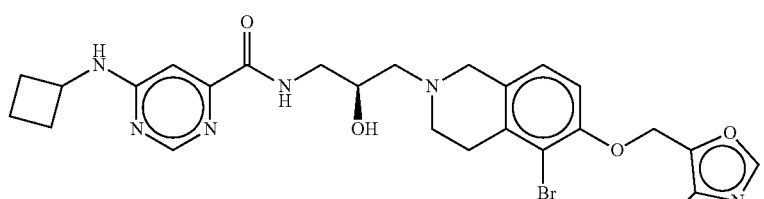 |

| Nr. | Structure |
|---|---|
| 339 | 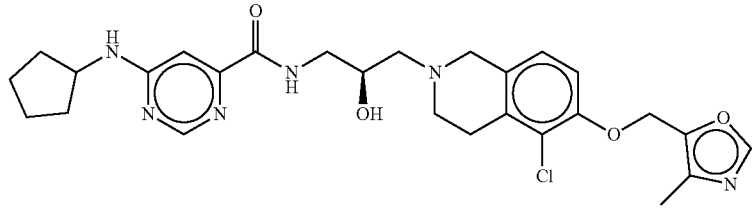 |
| 340 | 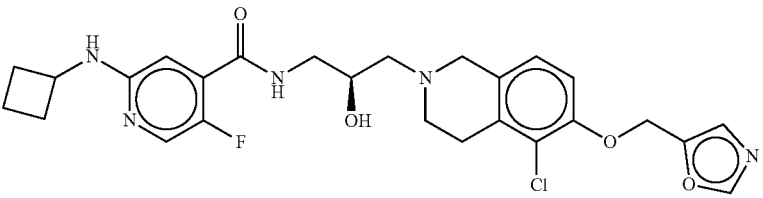 |
| 341 | 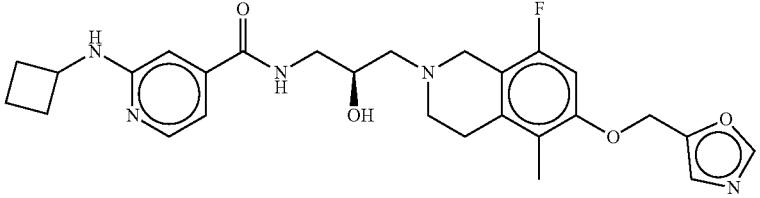 |
| 342 | 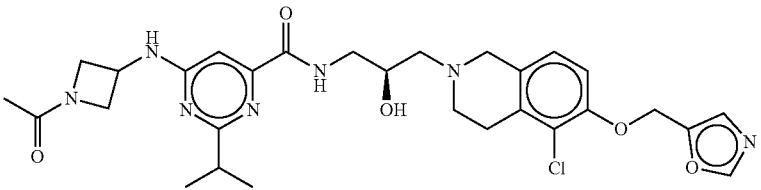 |
| 343 | 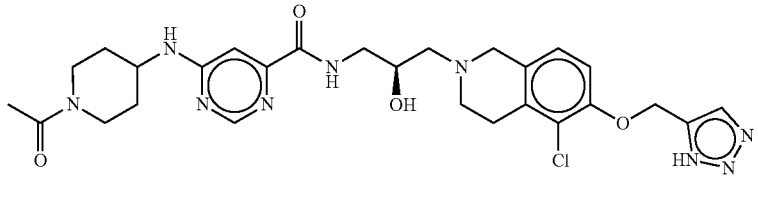 |
| 344 | 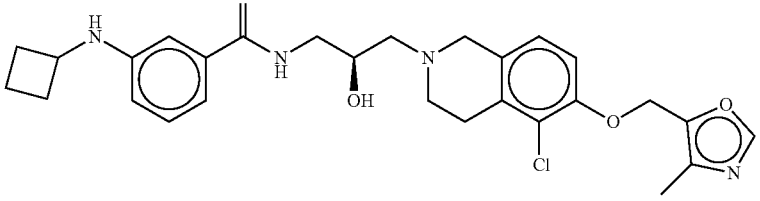 |
| 345 | 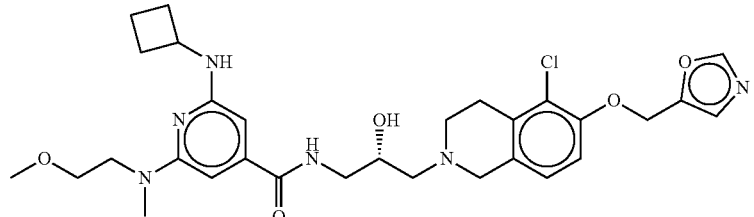 |

-continued
| Nr. | Structure |
|---|---|
| 346 | 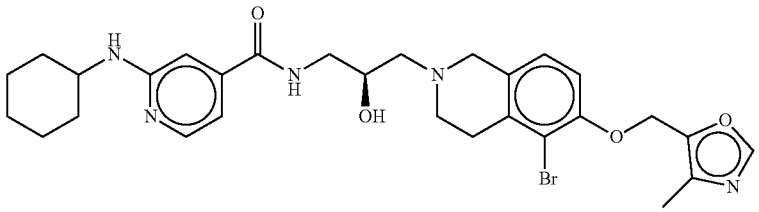 |
| 347 | 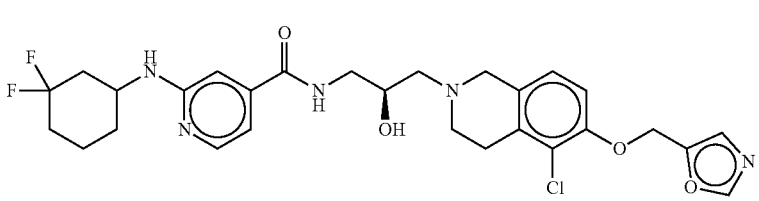 |
| 348 | 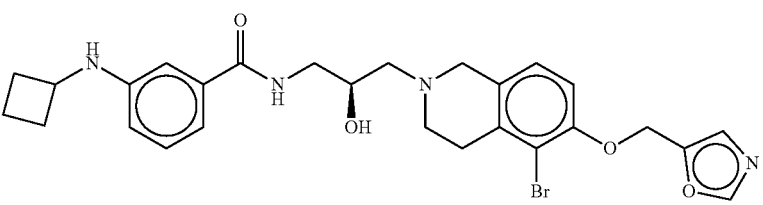 |
| 349 | 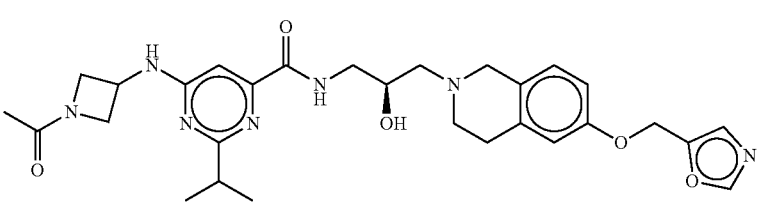 |
| 350 | 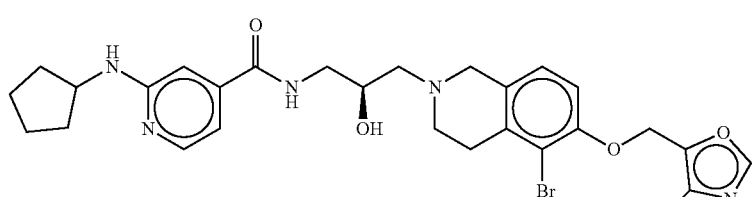 |
| 351 | 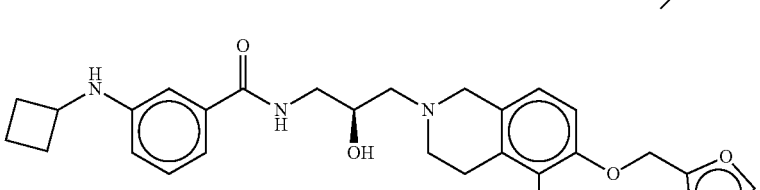 |
| 352 | 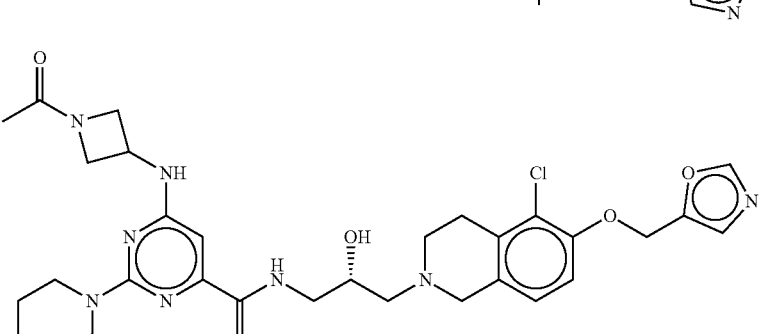 |

| Nr. | Structure |
|---|---|
| 353 | ![Structure 353] |
| 354 | ![Structure 354] |
| 355 | ![Structure 355] |
| 356 | ![Structure 356] |
| 357 | ![Structure 357] |
| 358 | ![Structure 358] |
| 359 | ![Structure 359] |

| Nr. | Structure |
|---|---|
| 360 | 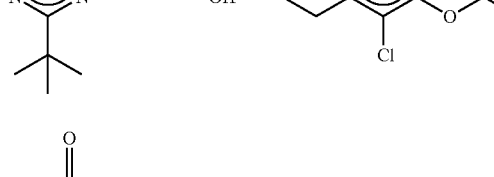 |
| 361 | 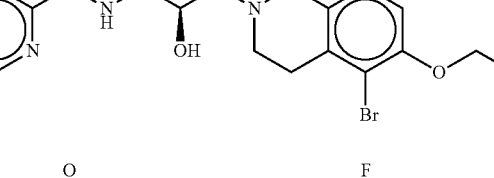 |
| 362 | 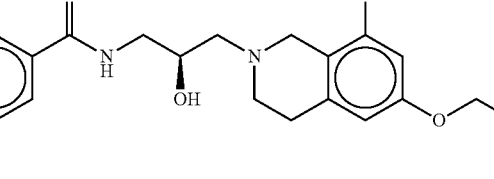 |
| 363 | 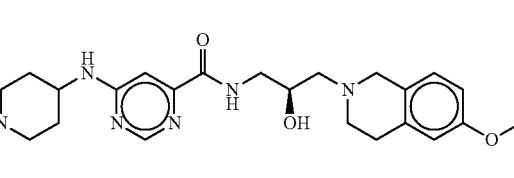 |
| 364 | 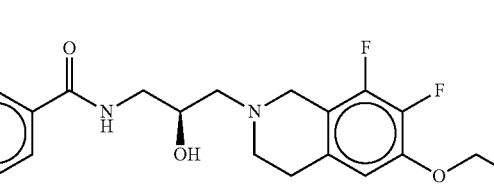 |
| 365 | 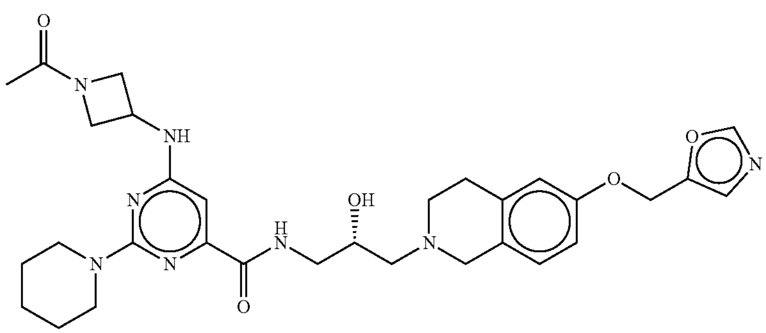 |
| 366 | 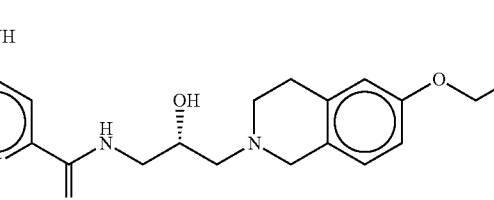 |

| Nr. | Structure |
|---|---|
| 367 | 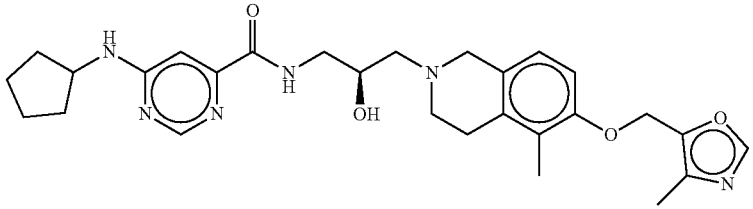 |
| 368 | 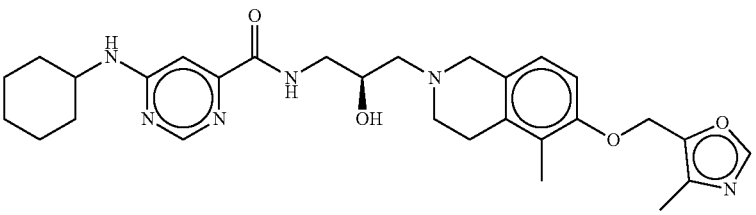 |
| 369 | 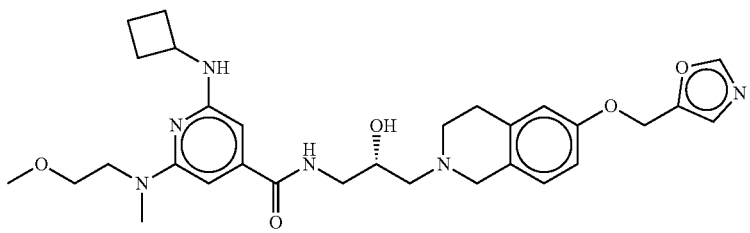 |
| 370 | 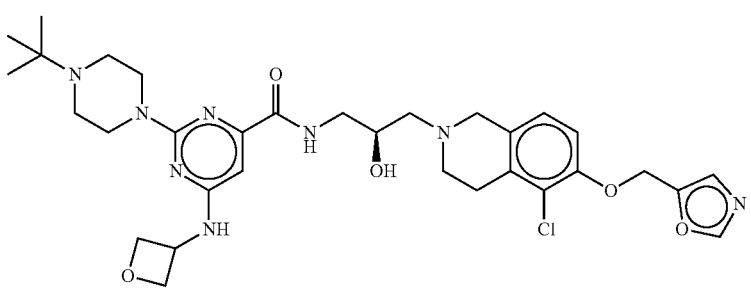 |
| 371 | 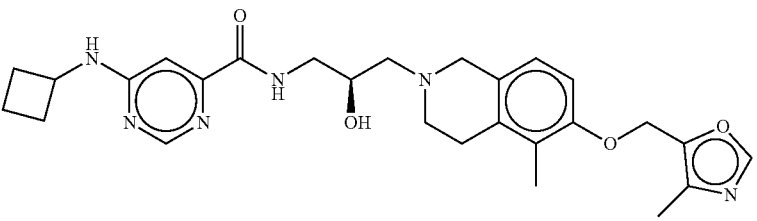 |
| 372 | 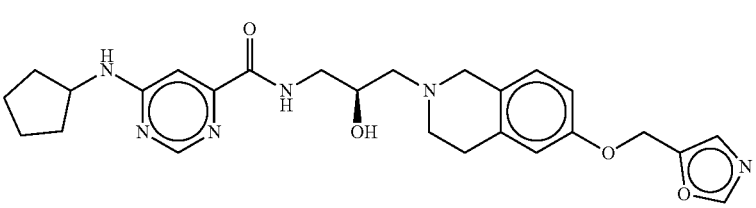 |

| Nr. | Structure |
|---|---|
| 373 | 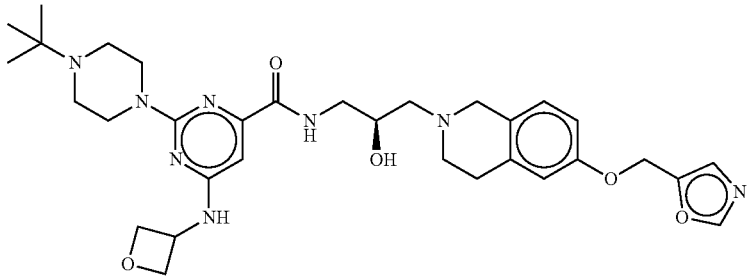 |
| 374 | 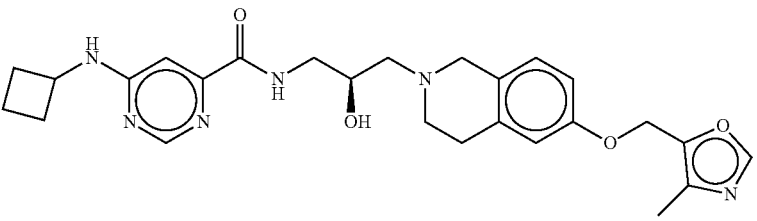 |
| 375 | 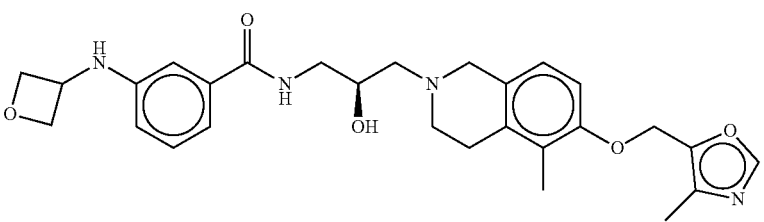 |
| 376 | 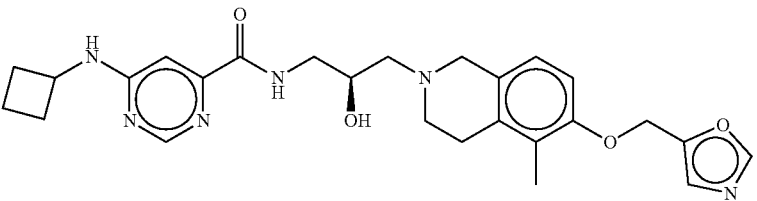 |
| 377 | 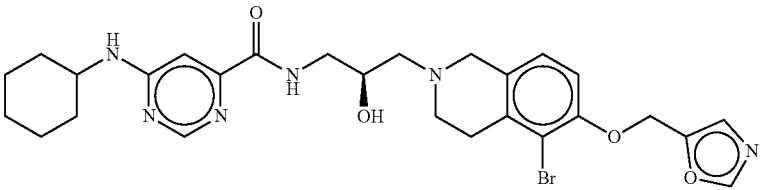 |
| 378 | 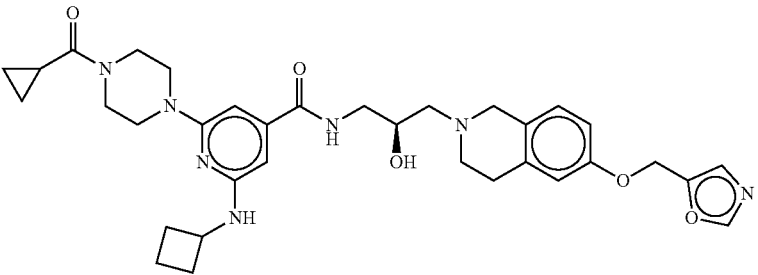 |

| Nr. | Structure |
|---|---|
| 379 | 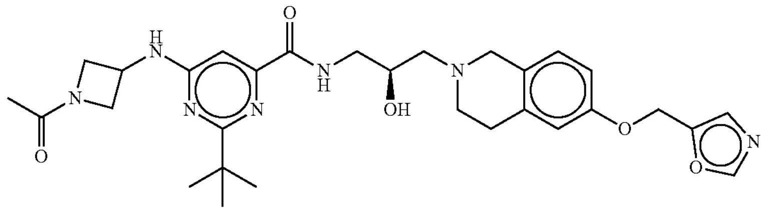 |
| 380 | 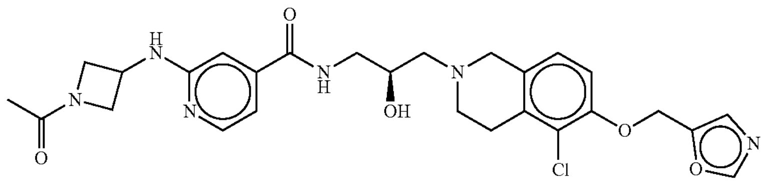 |
| 381 | 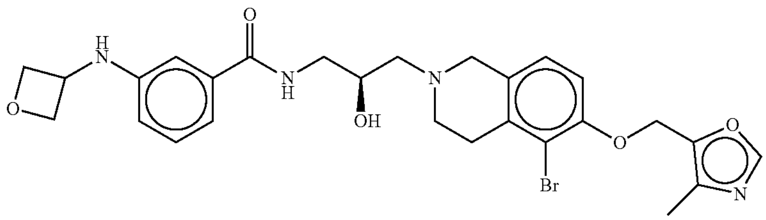 |
| 382 | 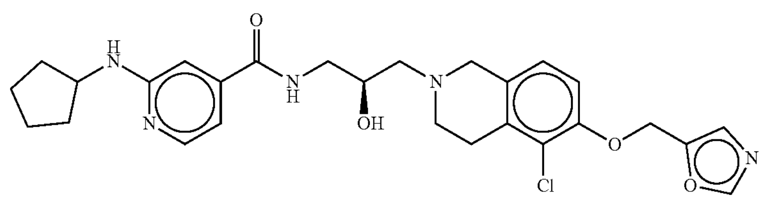 |
| 383 | 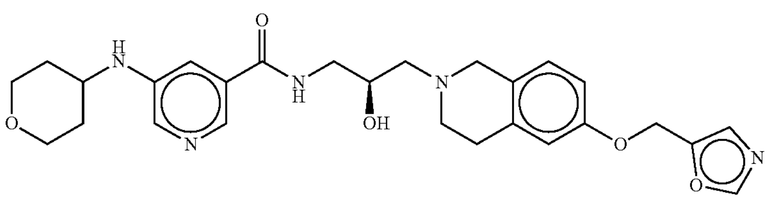 |
| 384 | 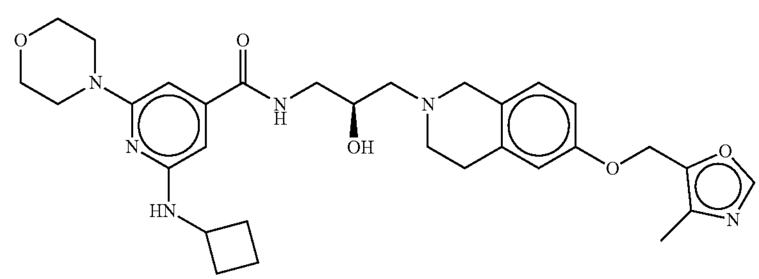 |
| 385 | 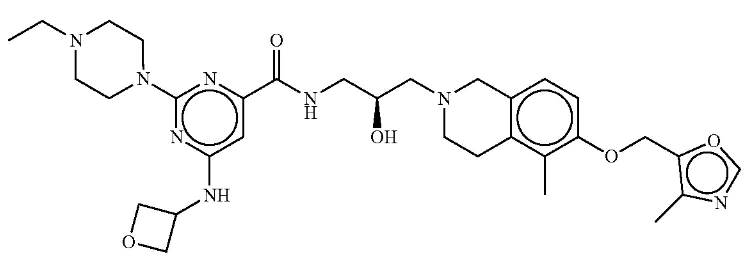 |

| Nr. | Structure |
|---|---|
| 386 | 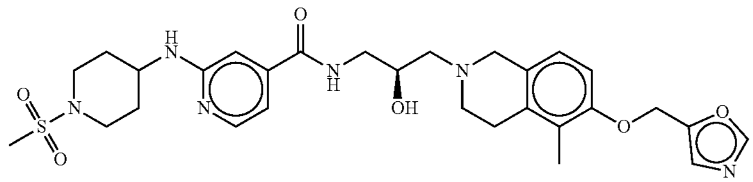 |
| 387 | 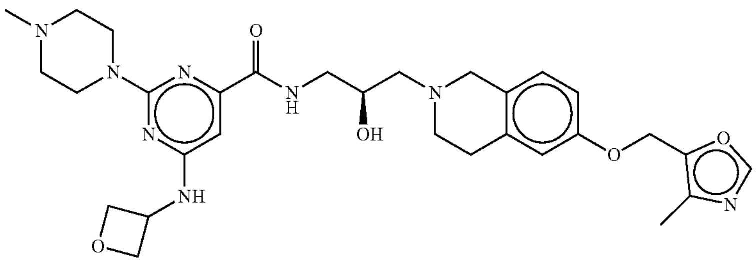 |
| 388 | 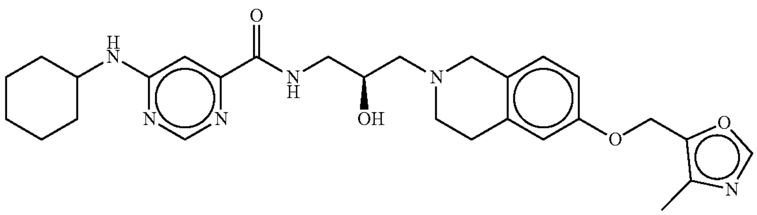 |
| 389 | 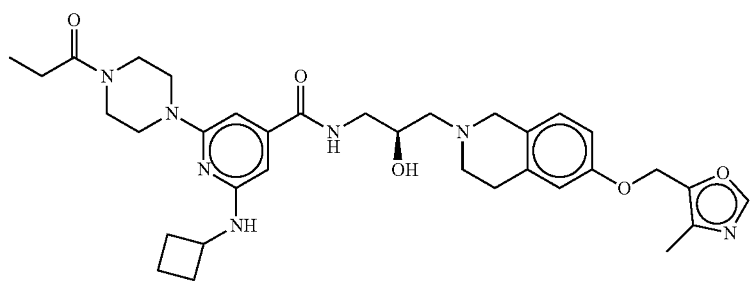 |
| 390 | 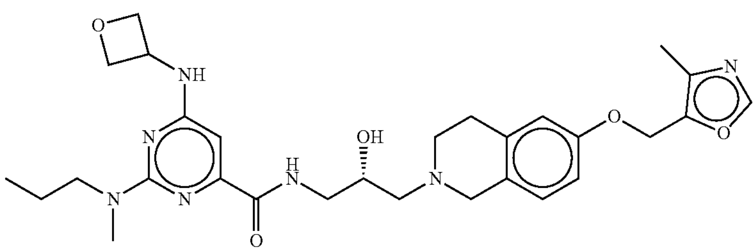 |
| 391 | 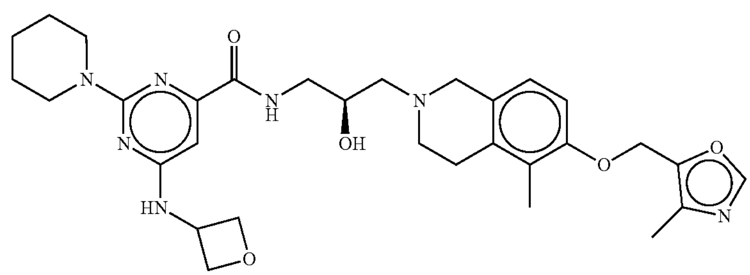 |

| Nr. | Structure |
|---|---|
| 393 | 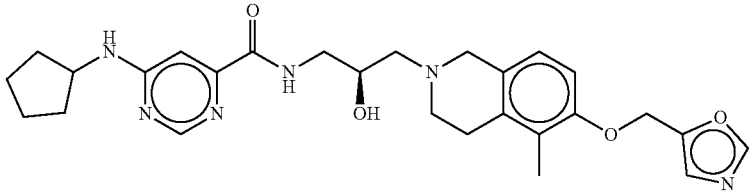 |
| 394 | 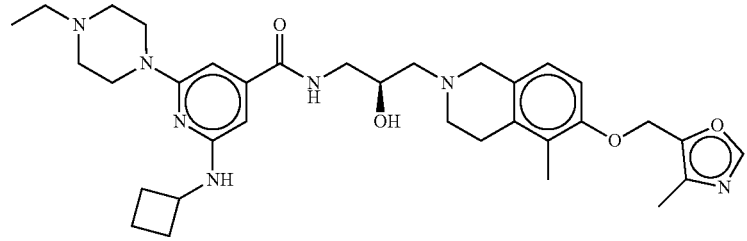 |
| 395 | 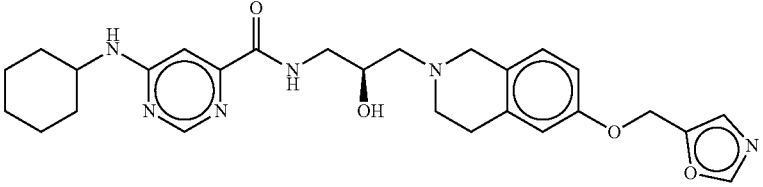 |
| 396 | 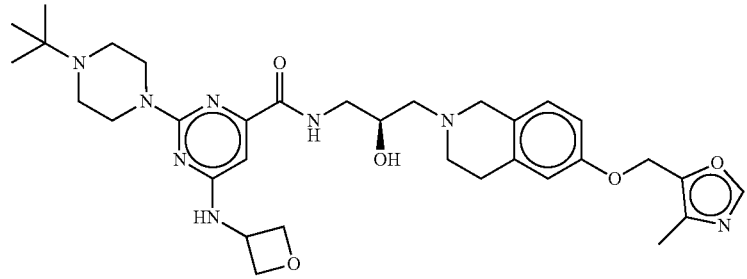 |
| 397 | 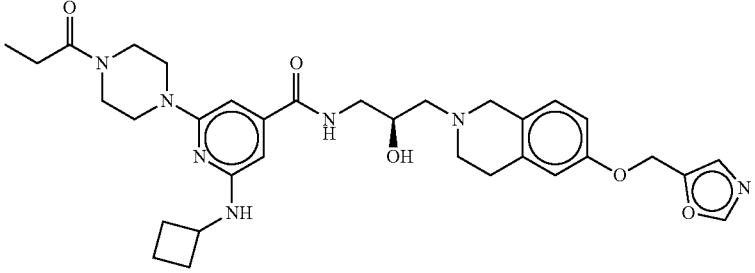 |
| 398 | 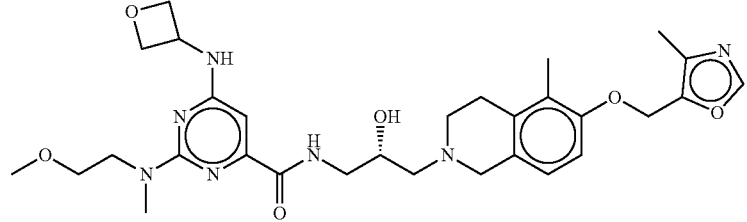 |

| Nr. | Structure |
|---|---|
| 399 | 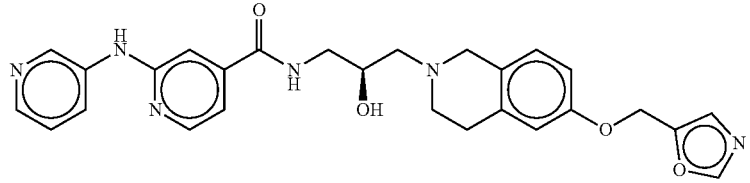 |
| 400 | 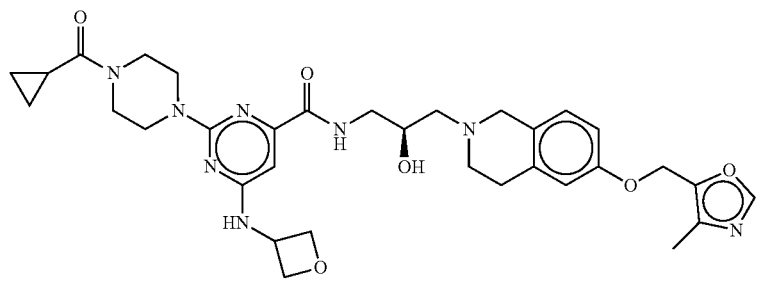 |
| 401 | 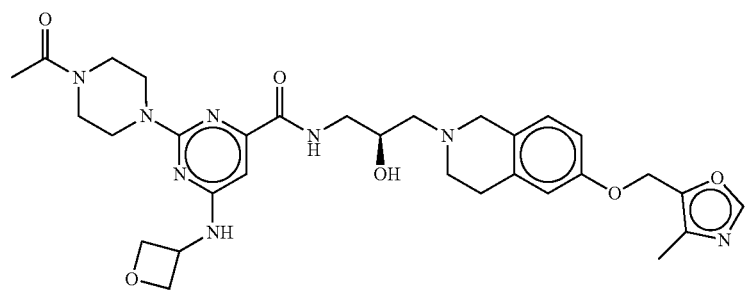 |
| 402 | 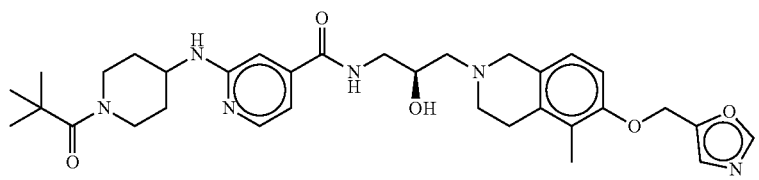 |
| 403 | 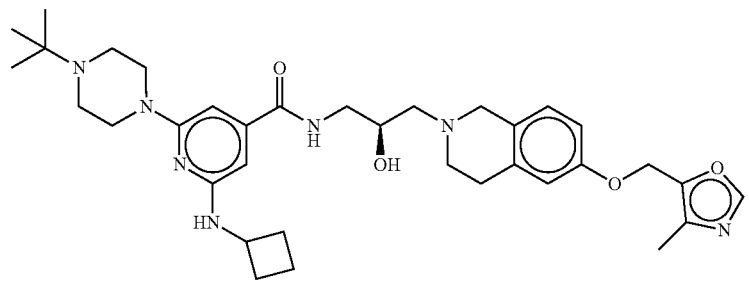 |
| 404 | 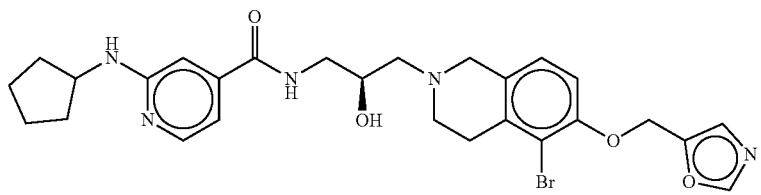 |

| Nr. | Structure |
|---|---|
| 405 | 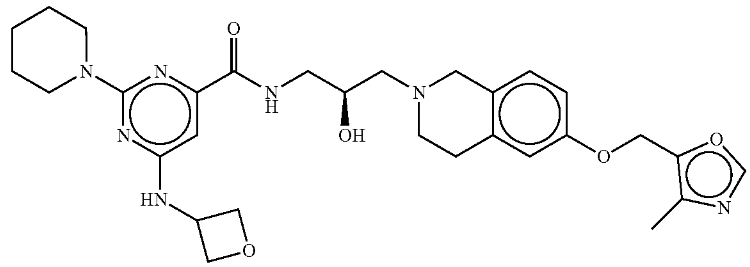 |
| 406 | 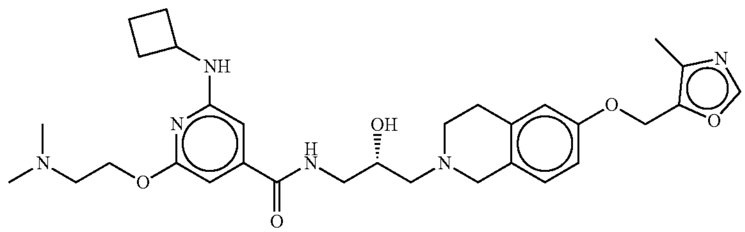 |
| 407 | 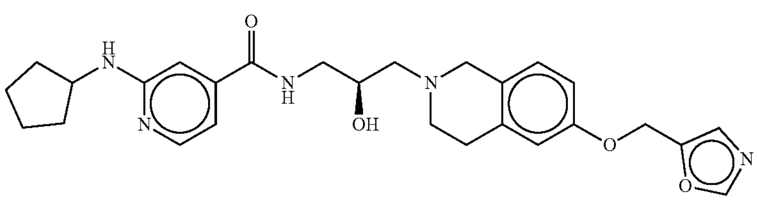 |
| 408 | 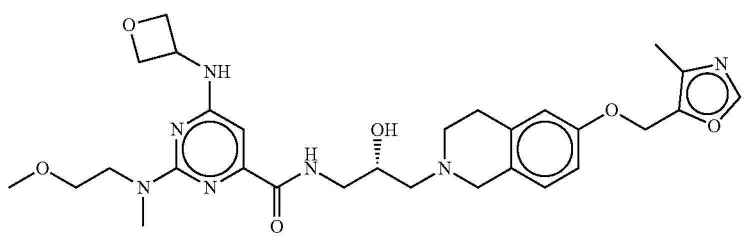 |
| 409 | 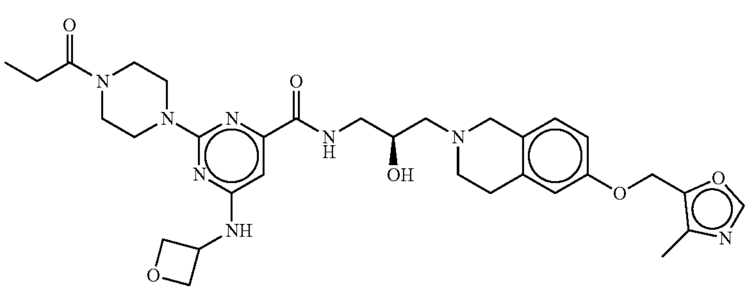 |
| 410 | 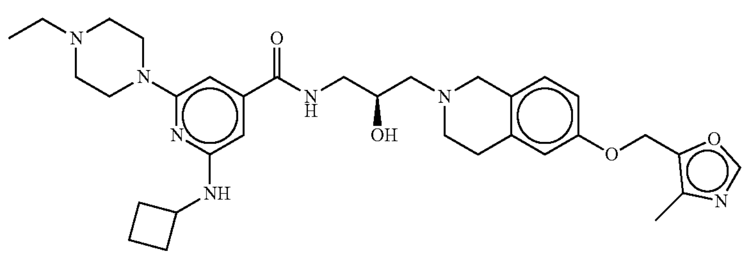 |

| Nr. | Structure |
|---|---|
| 411 | 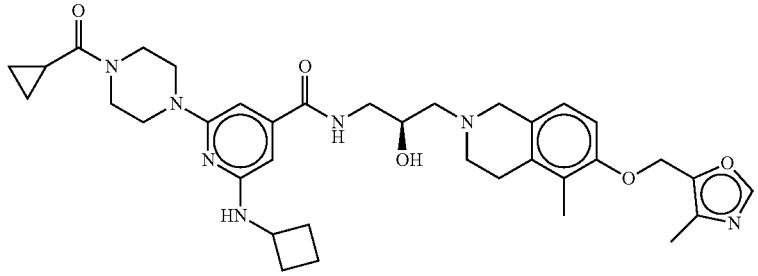 |
| 412 | 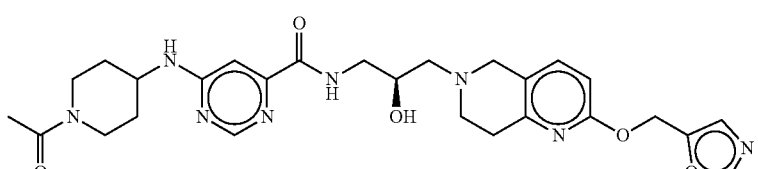 |
| 413 | 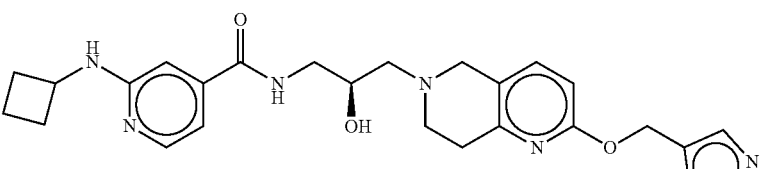 |
| 414 | 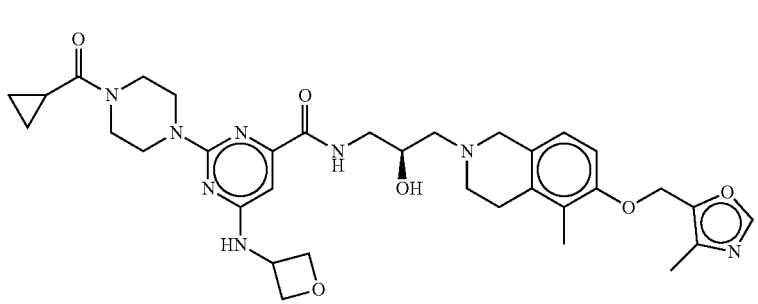 |
| 415 | 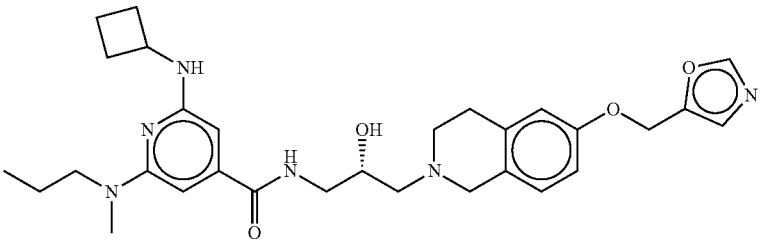 |
| 417 | 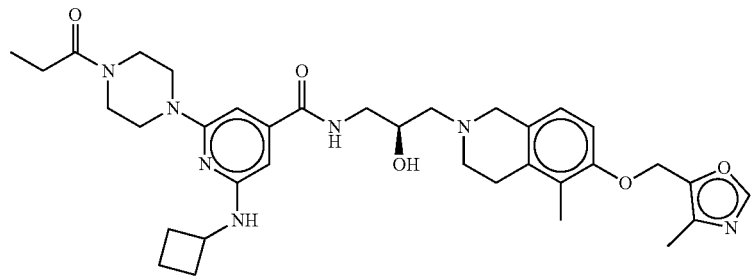 |

| Nr. | Structure |
|---|---|
| 418 | 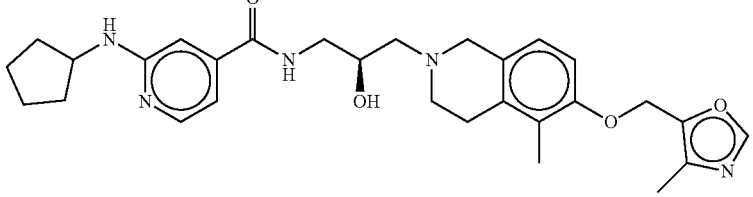 |
| 419 | 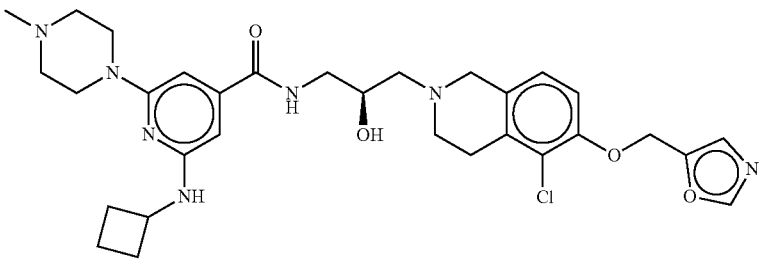 |
| 420 | 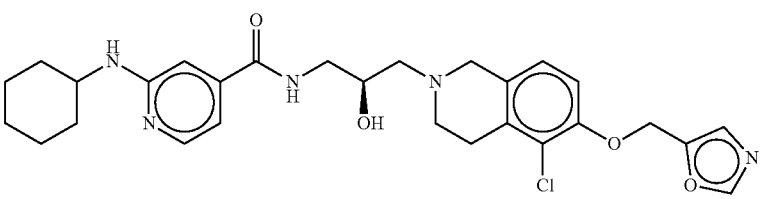 |
| 421 | 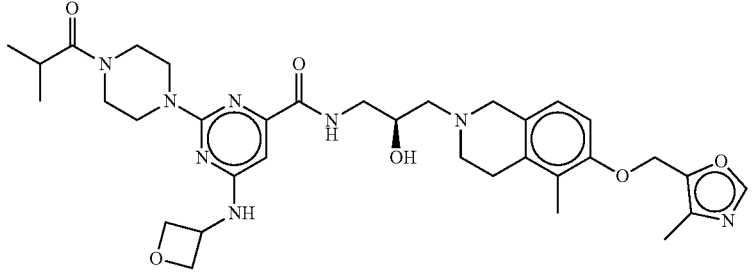 |
| 422 | 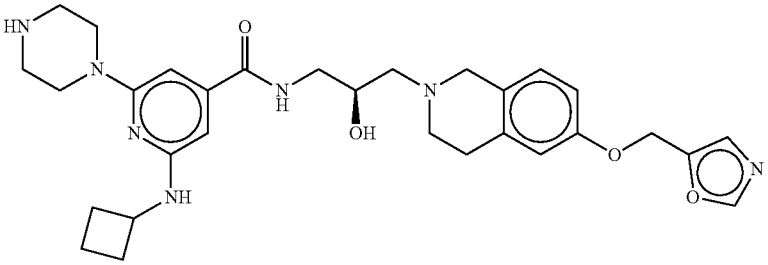 |
| 423 | 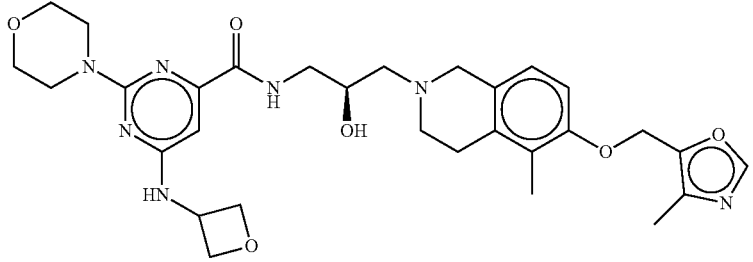 |

| Nr. | Structure |
|---|---|
| 424 | 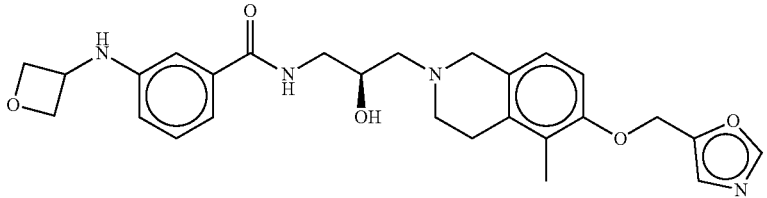 |
| 425 | 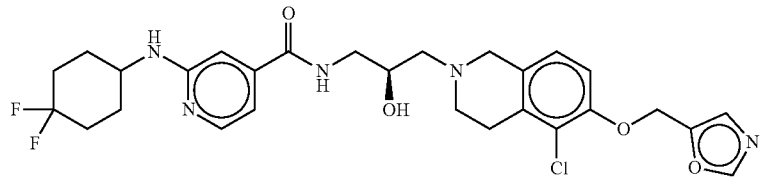 |
| 426 | 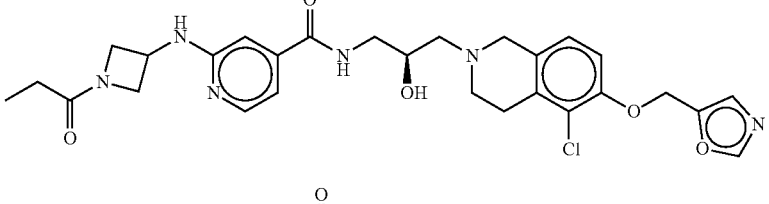 |
| 427 | 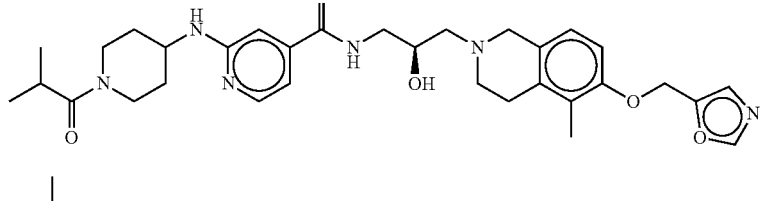 |
| 428 | 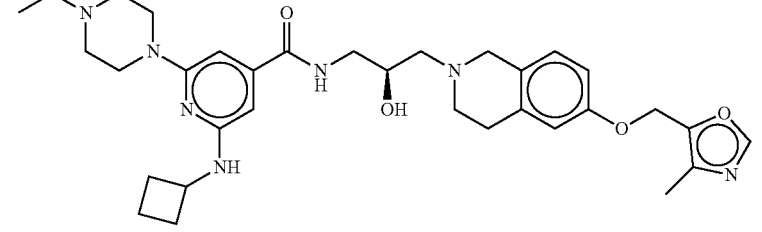 |
| 429 | 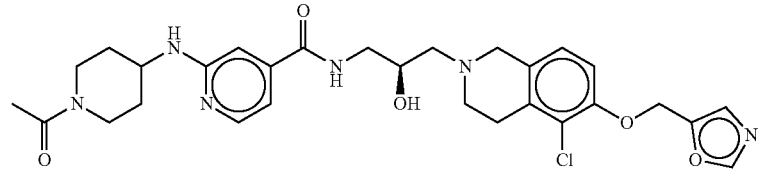 |
| 430 | 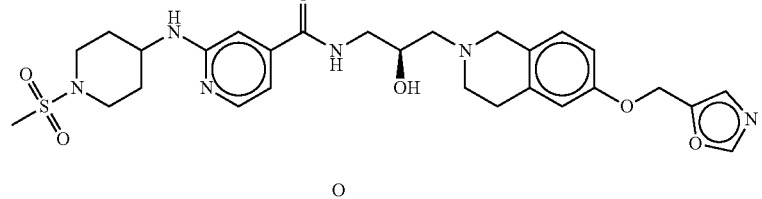 |
| 431 | 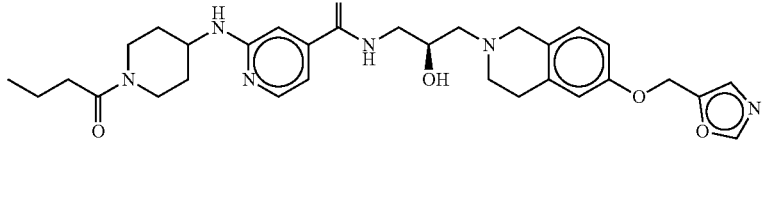 |

| Nr. | Structure |
|---|---|
| 432 | 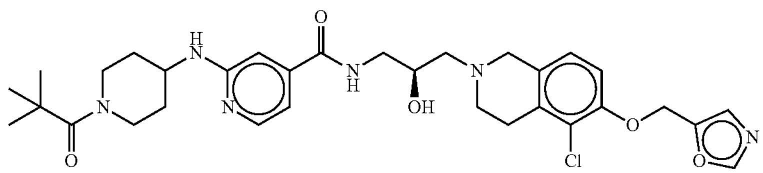 |
| 433 | 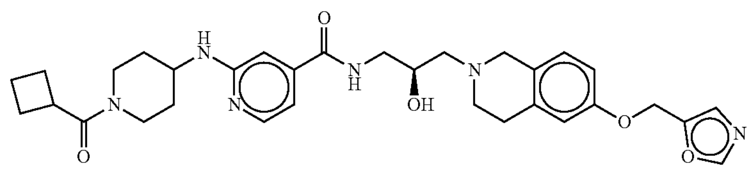 |
| 434 | 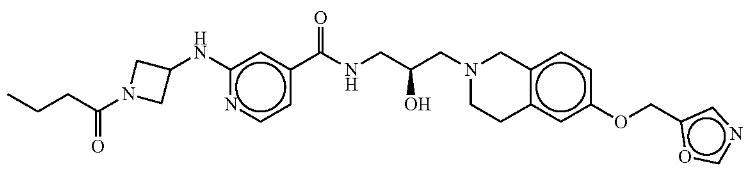 |
| 435 | 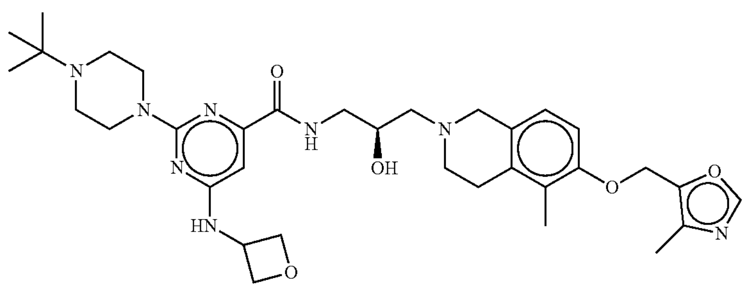 |
| 436 | 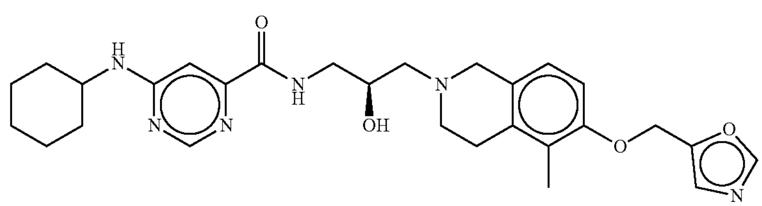 |
| 437 | 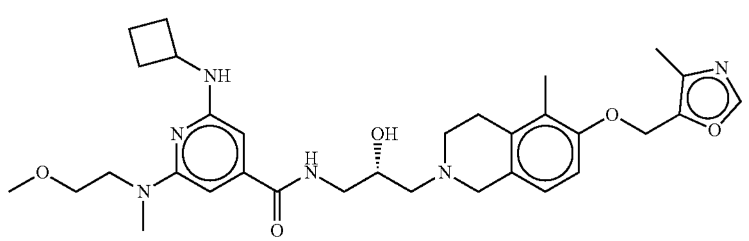 |
| 438 | 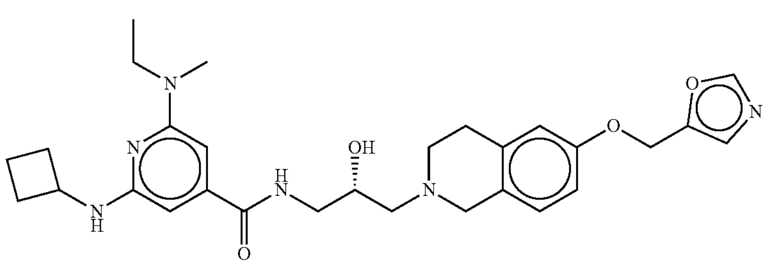 |

| Nr. | Structure |
|---|---|
| 439 | 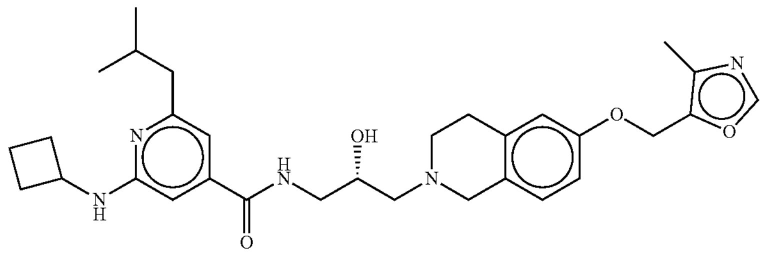 |
| 441 | 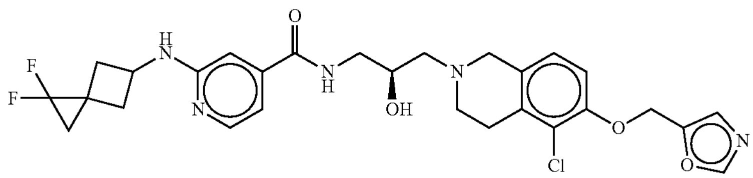 |
| 442 | 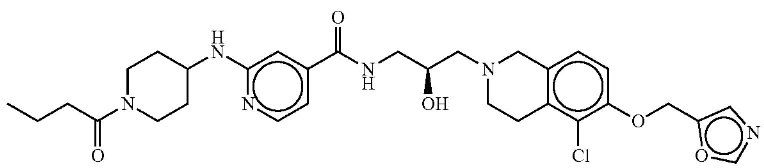 |
| 443 | 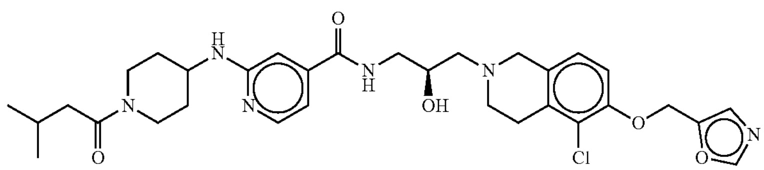 |
| 444 | 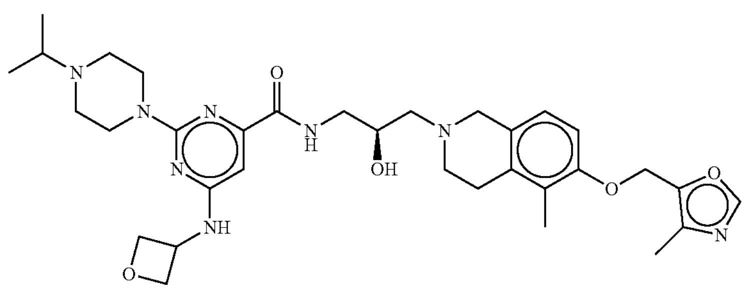 |
| 445 | 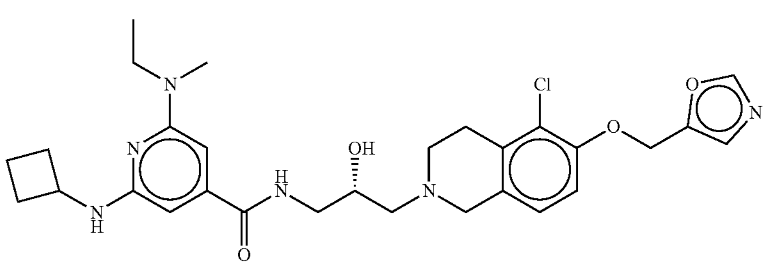 |
| 446 | 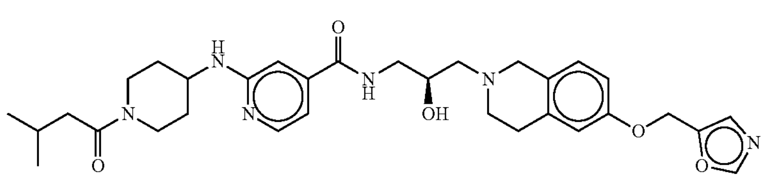 |

-continued

| Nr. | Structure |
|---|---|
| 447 | 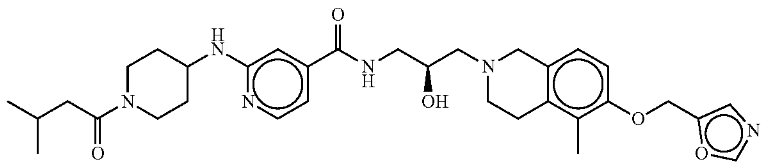 |
| 448 | 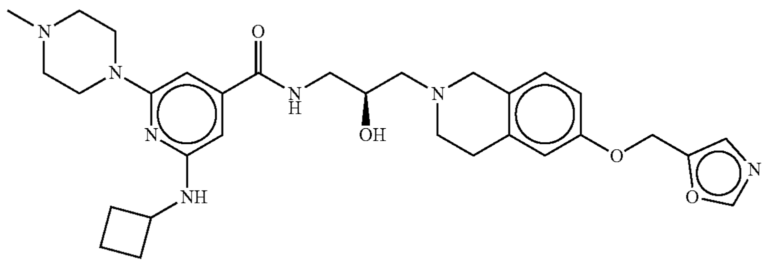 |
| 449 | 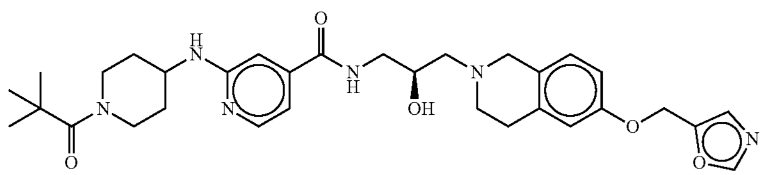 |
| 450 | 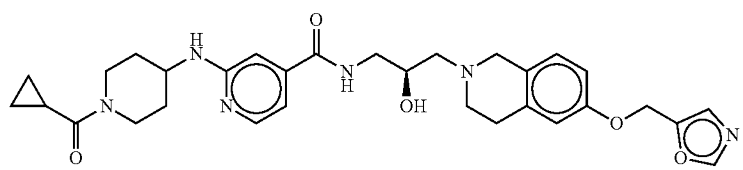 |
| 451 | 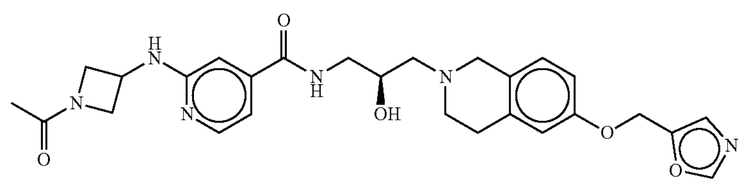 |
| 452 | 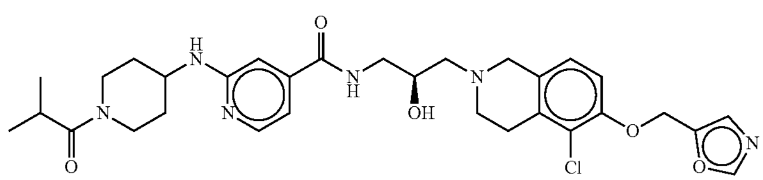 |
| 453 | 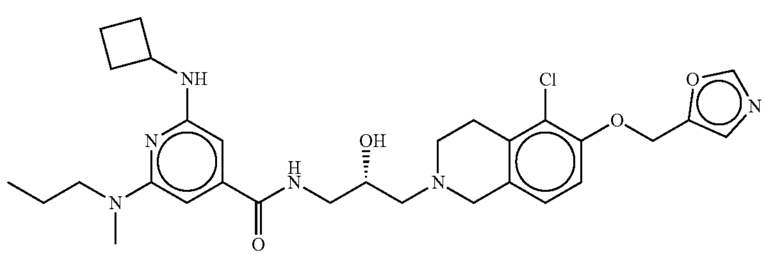 |

| Nr. | Structure |
|---|---|
| 454 | 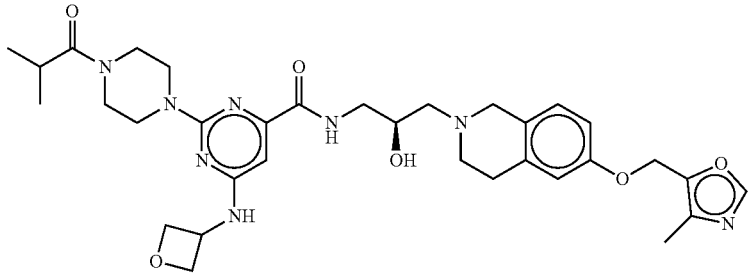 |
| 455 | 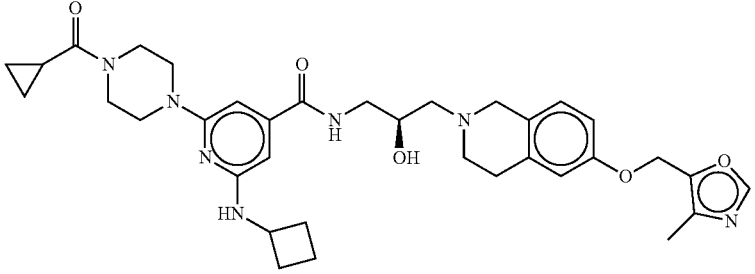 |
| 456 | 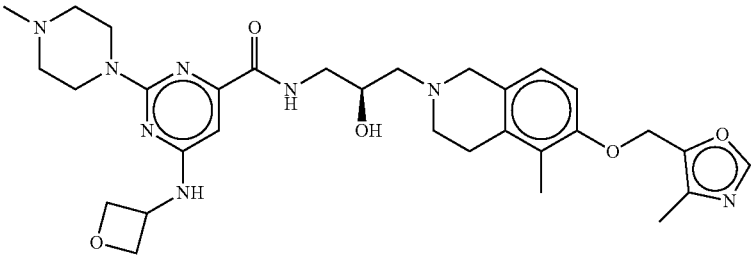 |
| 457 | 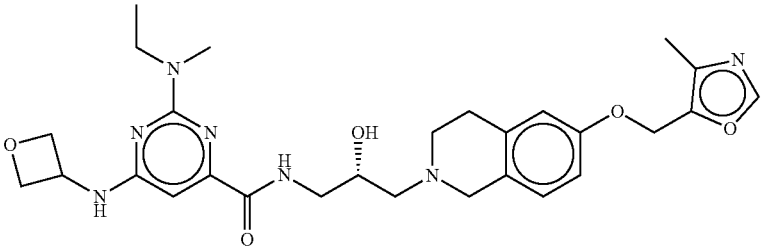 |
| 458 | 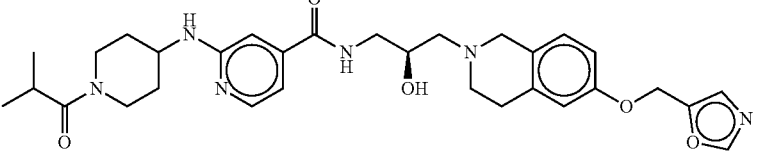 |
| 459 | 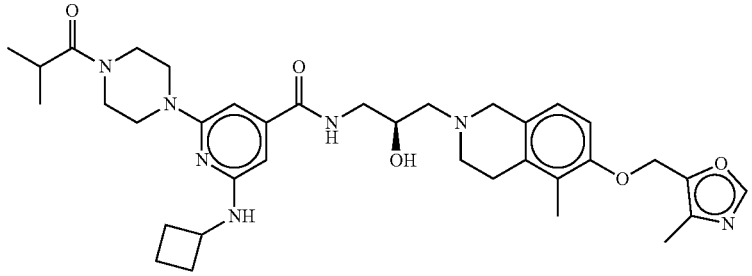 |

-continued

| Nr. | Structure |
|---|---|
| 460 | 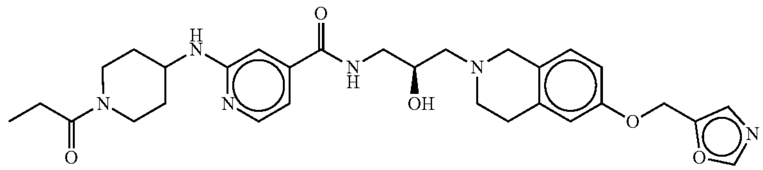 |
| 461 | 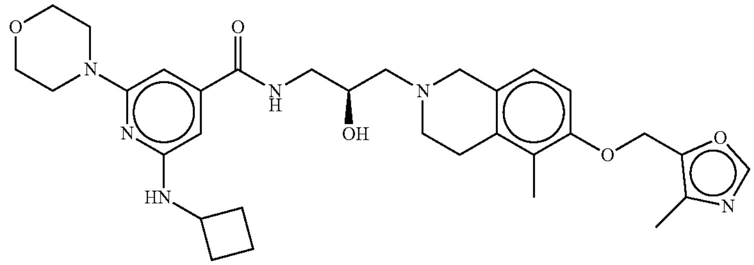 |
| 462 | 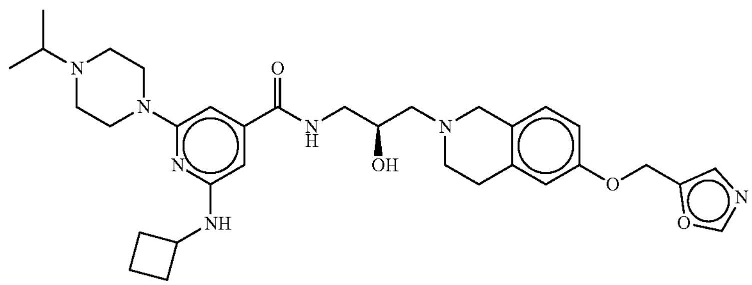 |
| 463 | 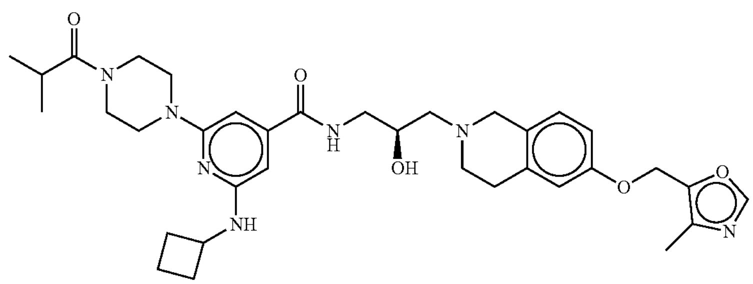 |
| 464 | 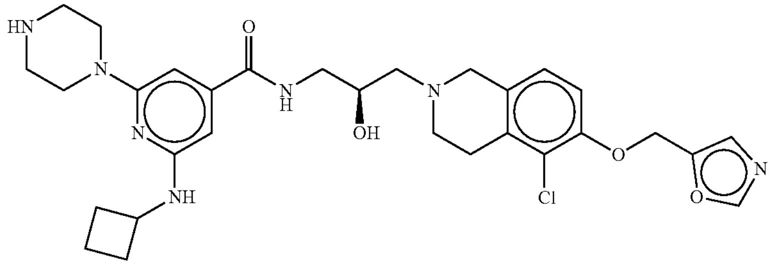 |
| 465 | 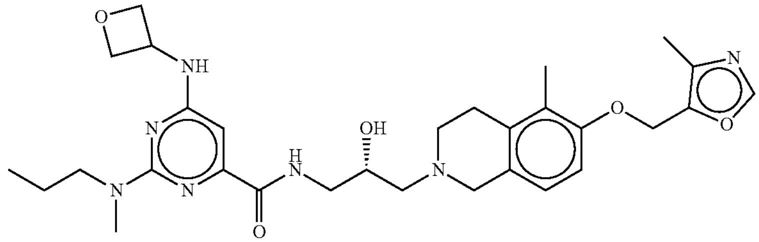 |

-continued

| Nr. | Structure |
|---|---|
| 466 | 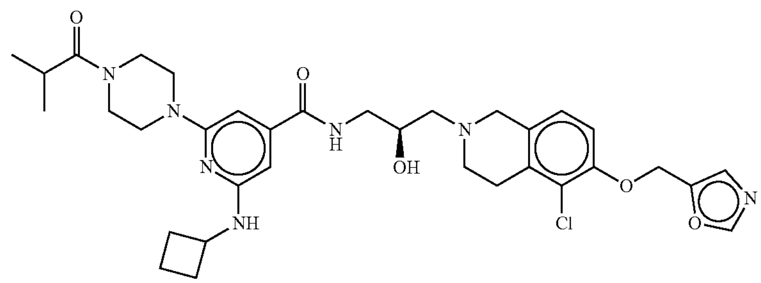 |
| 467 | 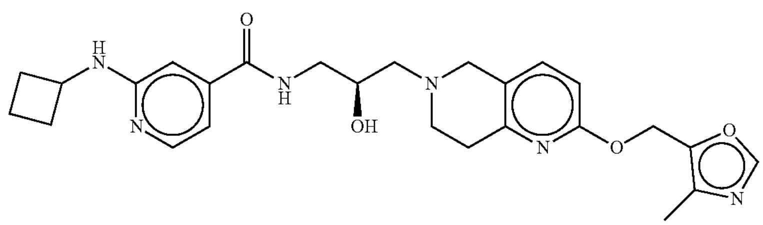 |
| 468 | 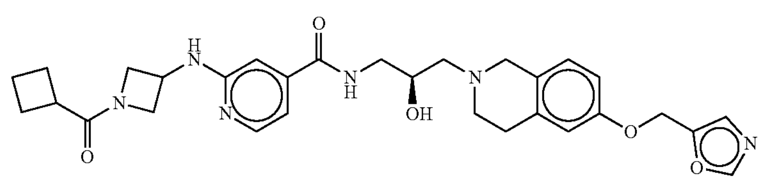 |
| 469 | 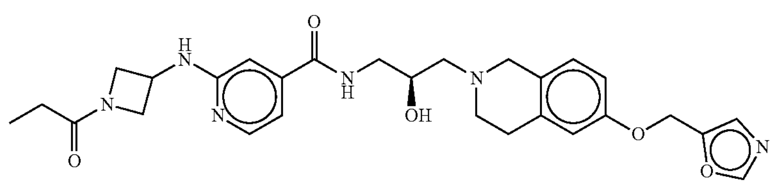 |
| 470 | 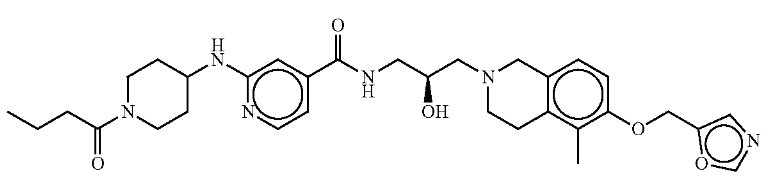 |
| 471 | 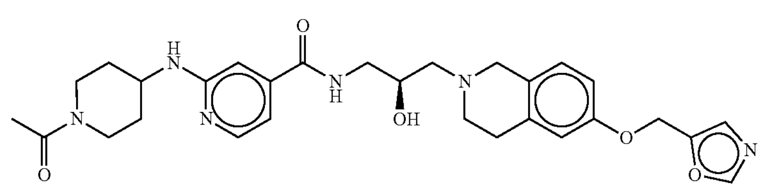 |
| 472 | 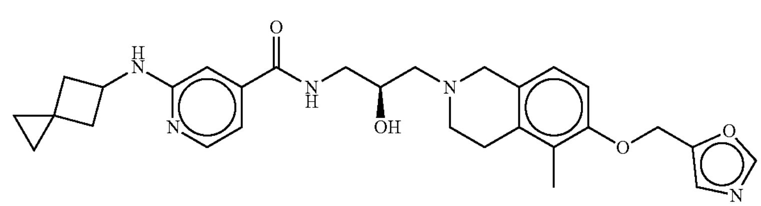 |

| Nr. | Structure |
|---|---|
| 473 | 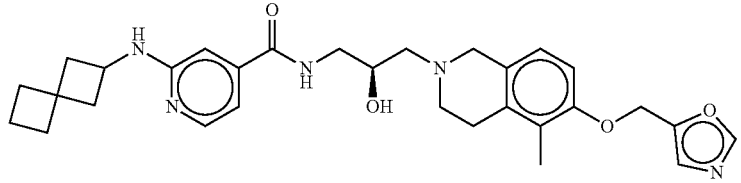 |
| 474 | 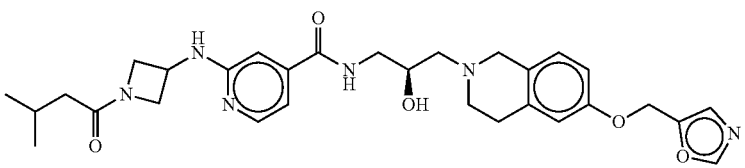 |
| 476 | 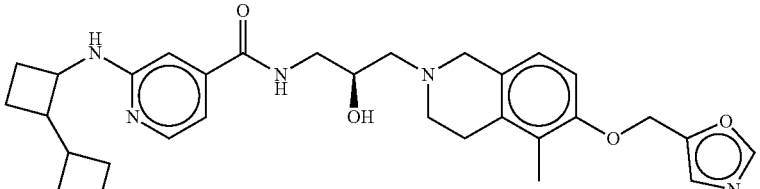 |
| 477 | 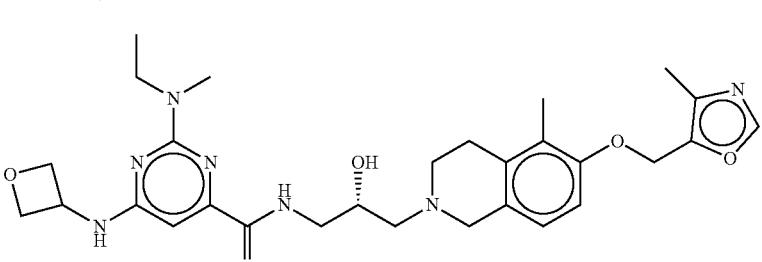 |
| 478 | 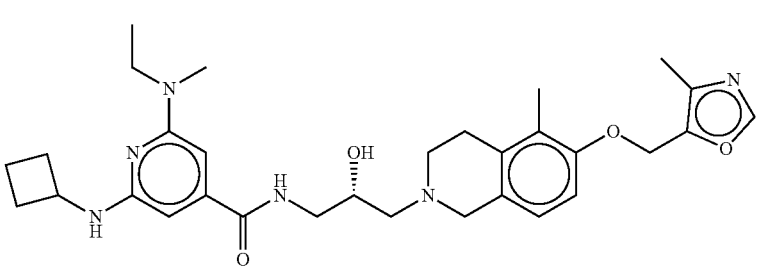 |
| 479 | 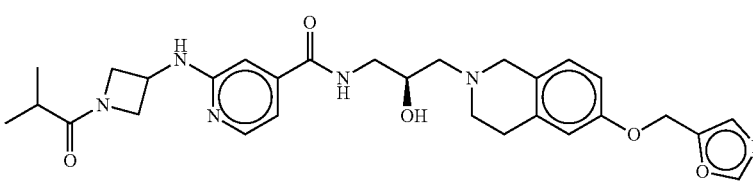 |
| 480 | 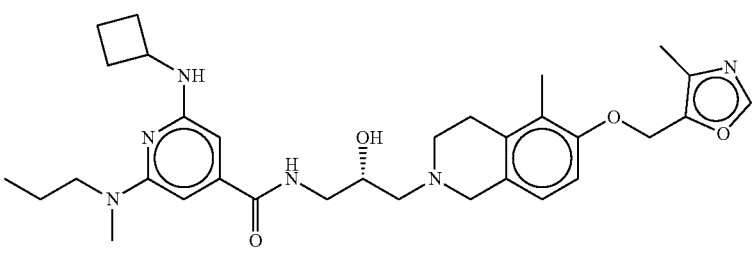 |

| Nr. | Structure |
|---|---|
| 481 | 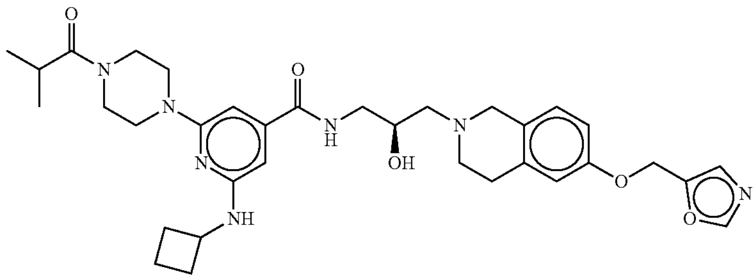 |
| 483 | 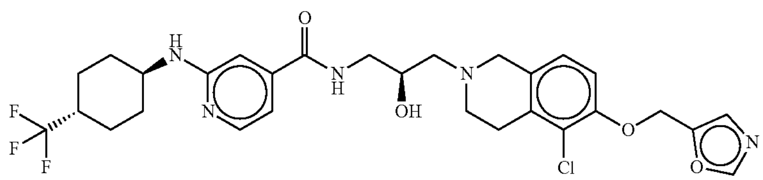 |
| 484 | 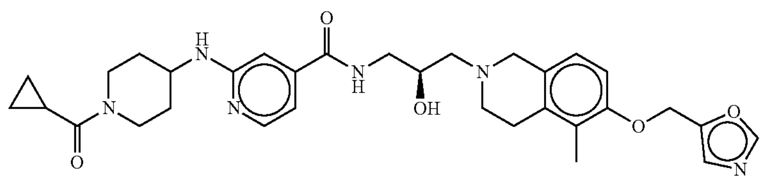 |
| 485 | 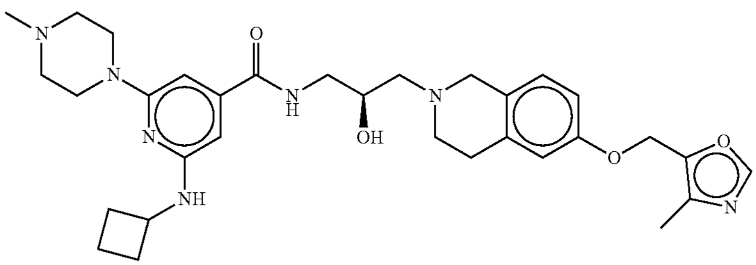 |
| 486 | 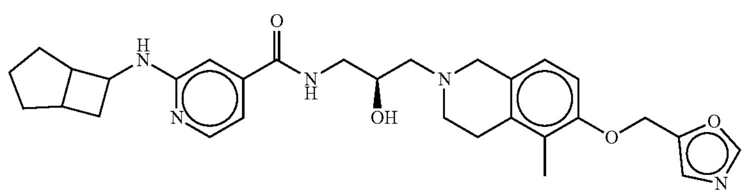 |
| 487 | 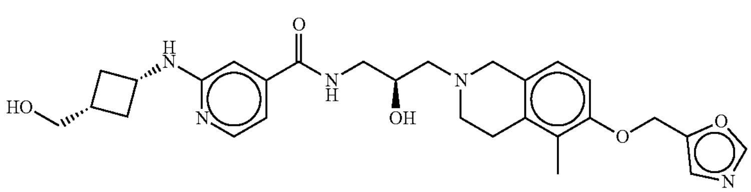 |
| 488 | 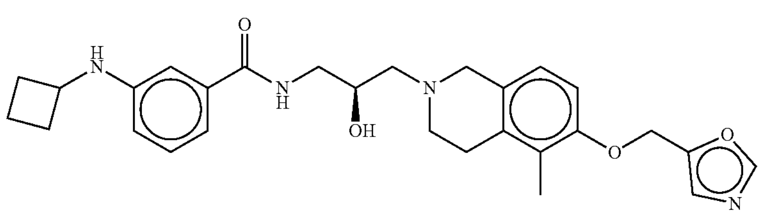 |

| Nr. | Structure |
|---|---|
| 489 | 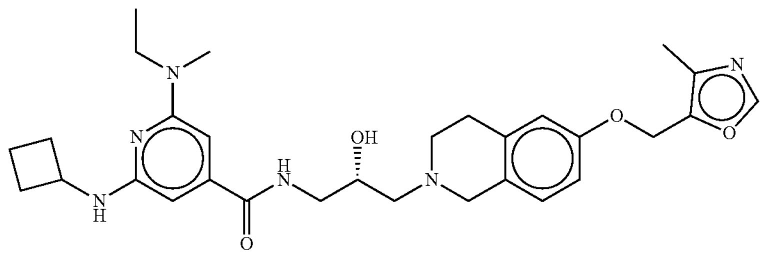 |
| 490 | 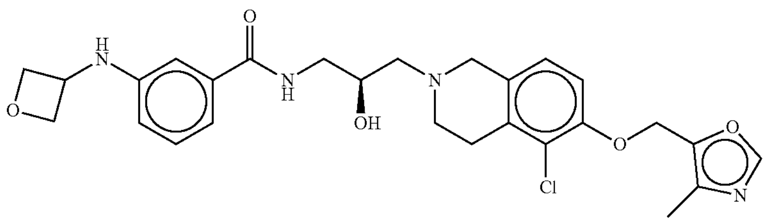 |
| 491 | 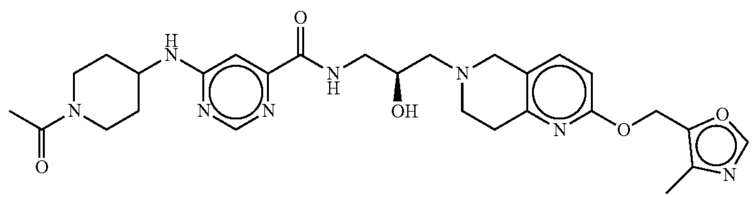 |
| 492 | 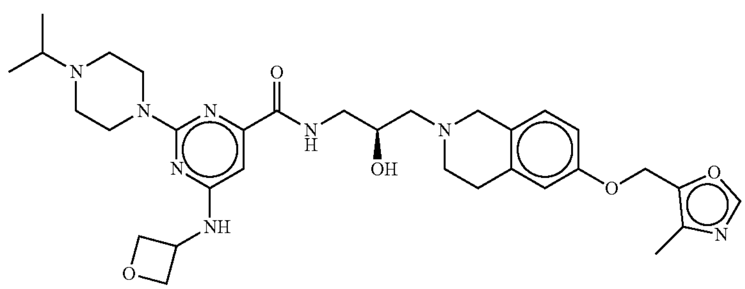 |
| 494 | 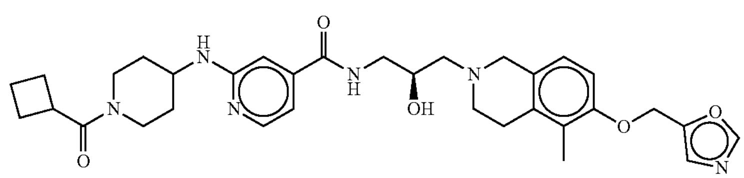 |
| 495 | 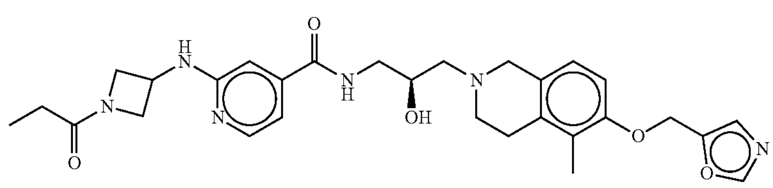 |
| 496 | 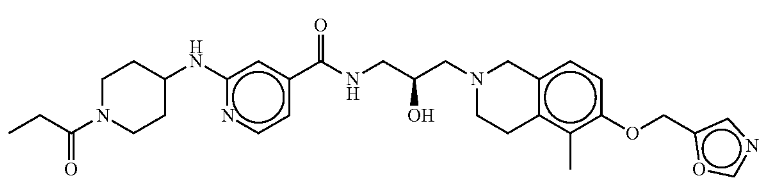 |

-continued
| Nr. | Structure |
|---|---|
| 497 | 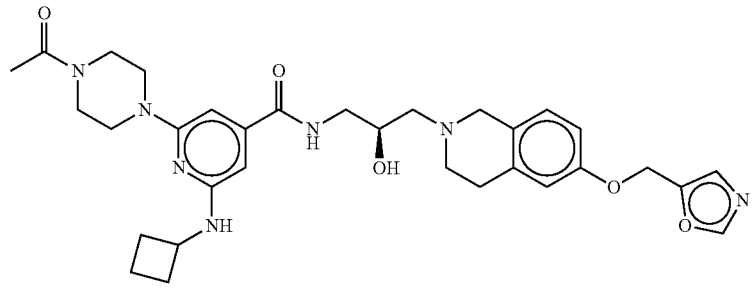 |
| 499 | 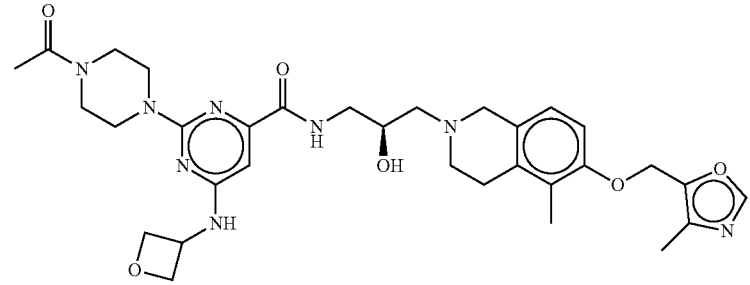 |
| 500 | 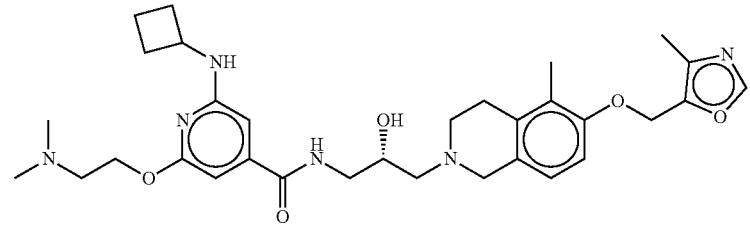 |
| 501 | 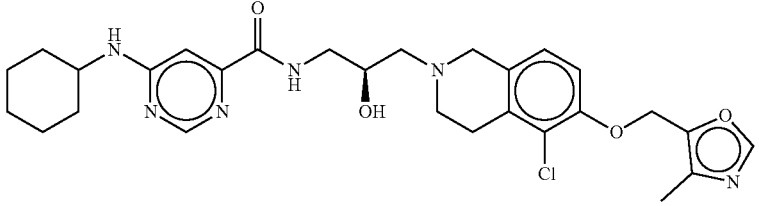 |
| 502 | 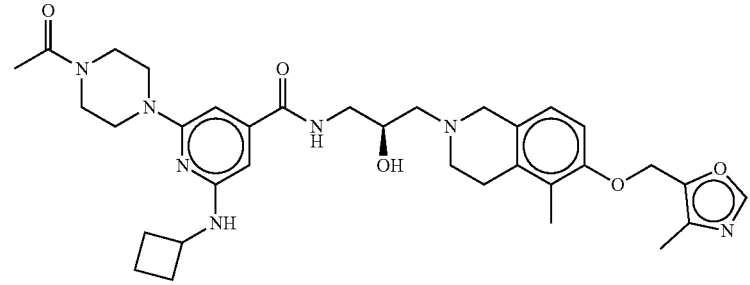 |
| 503 | 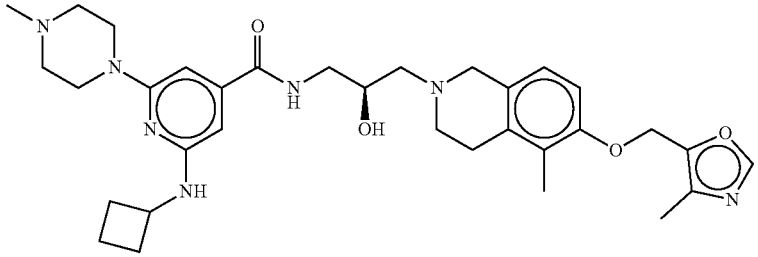 |

| Nr. | Structure |
|---|---|
| 504 | 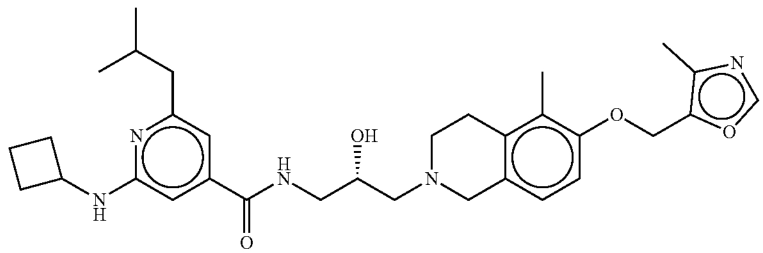 |
| 505* | 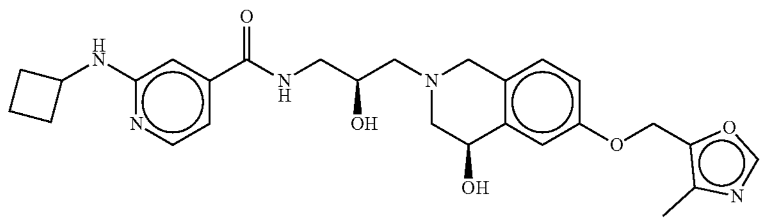 |
| 506 | 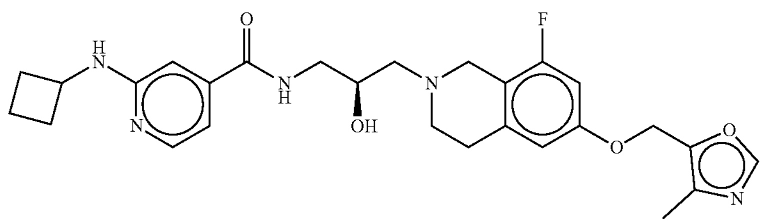 |
| 507 | 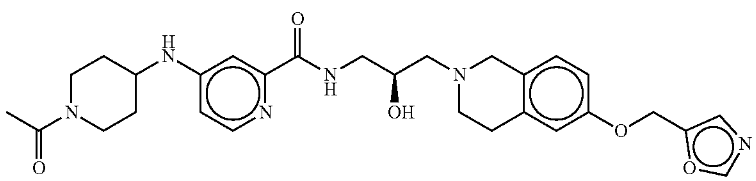 |
| 508 | 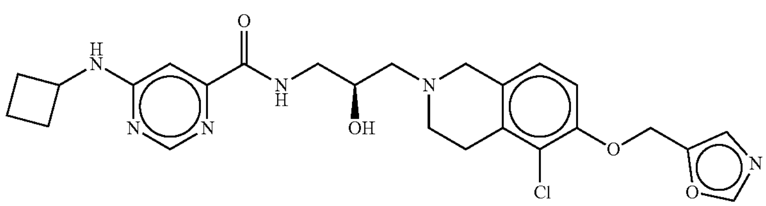 |
| 509 | 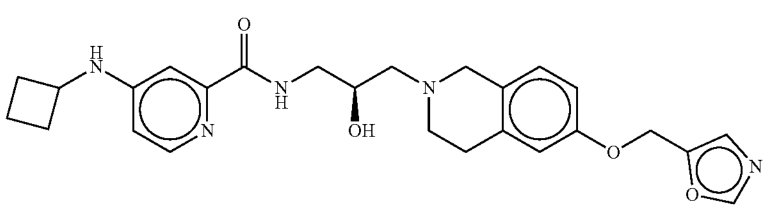 |
| 510 | 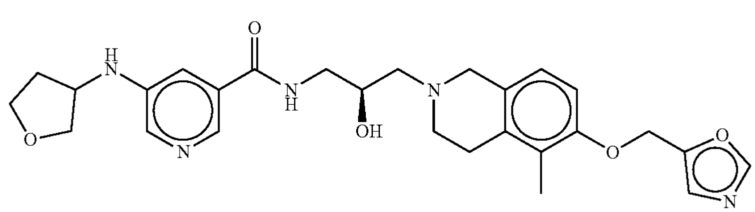 |

-continued
| Nr. | Structure |
|---|---|
| 511 | 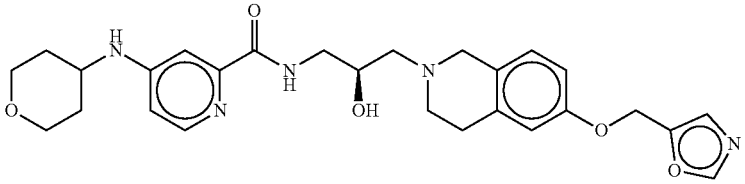 |
| 512 | 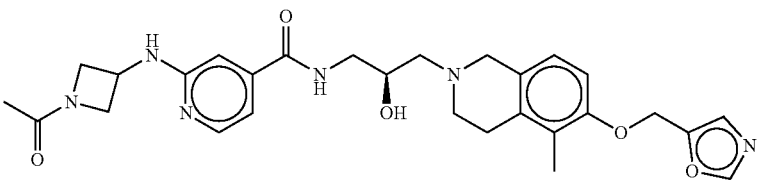 |
| 513 | 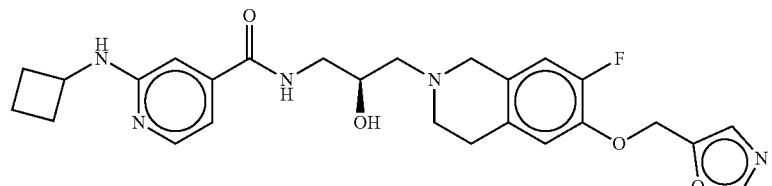 |
| 514 | 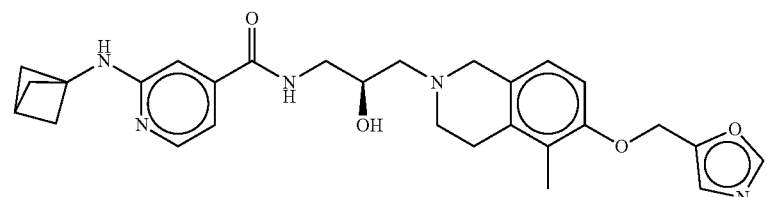 |
| 515 | 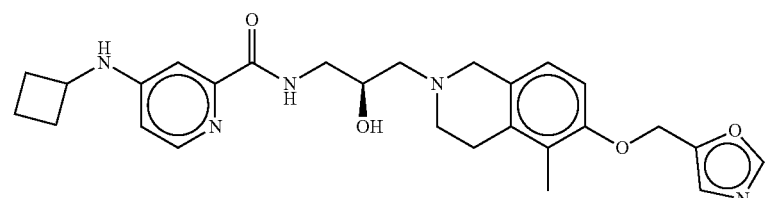 |
| 516 | 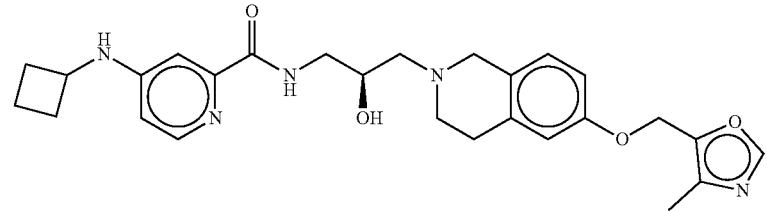 |
| 517 | 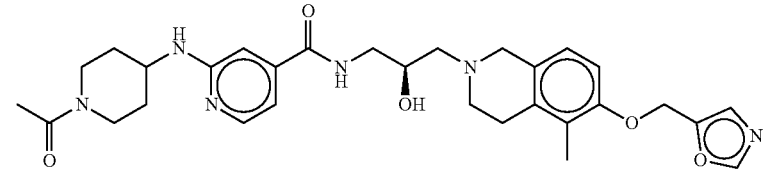 |
| 518 | 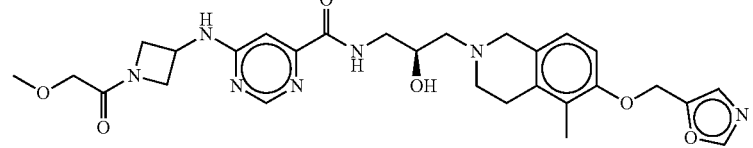 |

-continued

| Nr. | Structure |
|---|---|
| 519 | 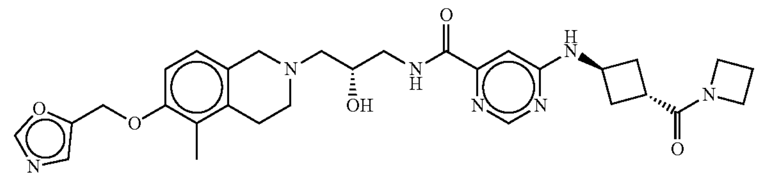 |
| 520 | 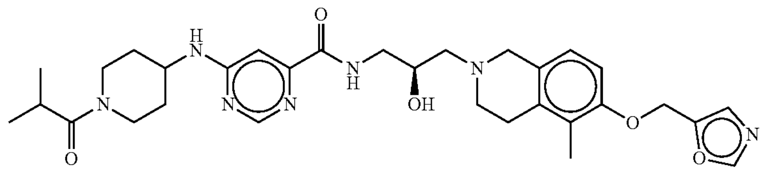 |
| 521 | 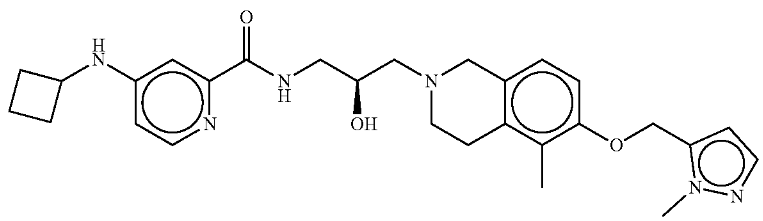 |
| 522 | 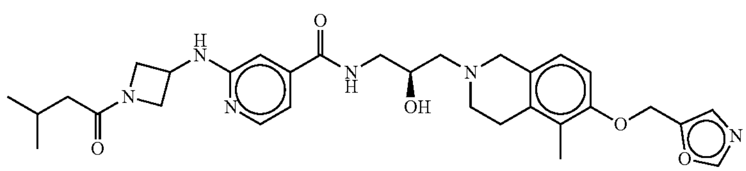 |
| 523 | 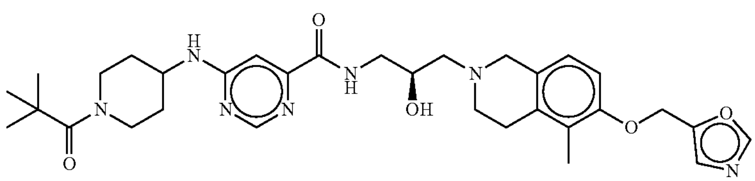 |
| 524 | 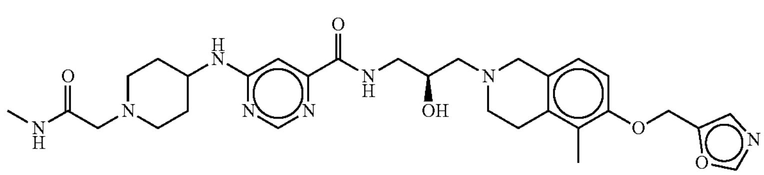 |
| 525 | 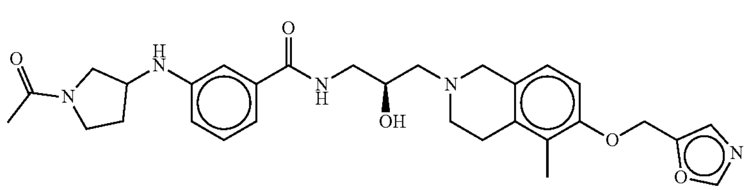 |
| 526 | 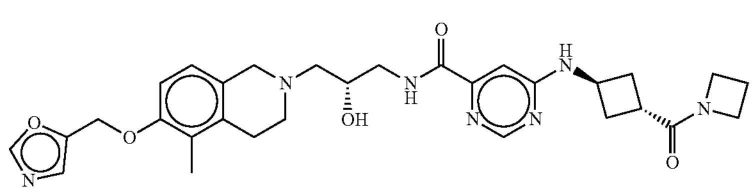 |

US 11,986,471 B2
-continued
| Nr. | Structure |
|---|---|
| 527 | 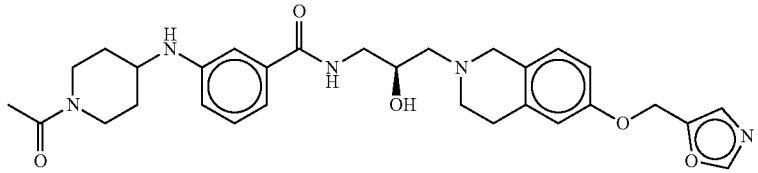 |
| 528 | 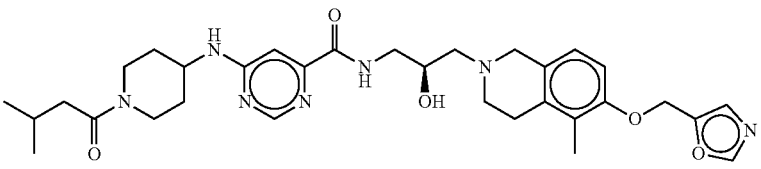 |
| 529 | 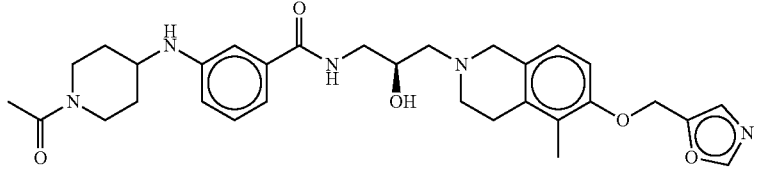 |
| 530 | 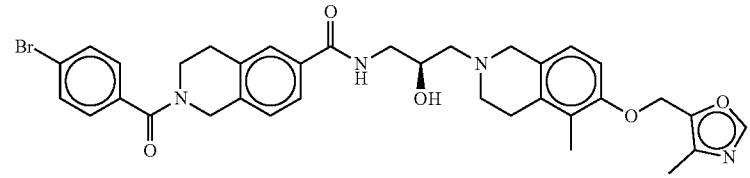 |
| 531 | 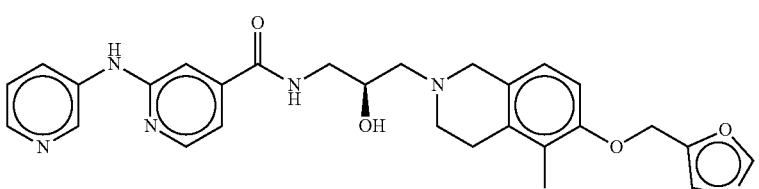 |
| 532 | 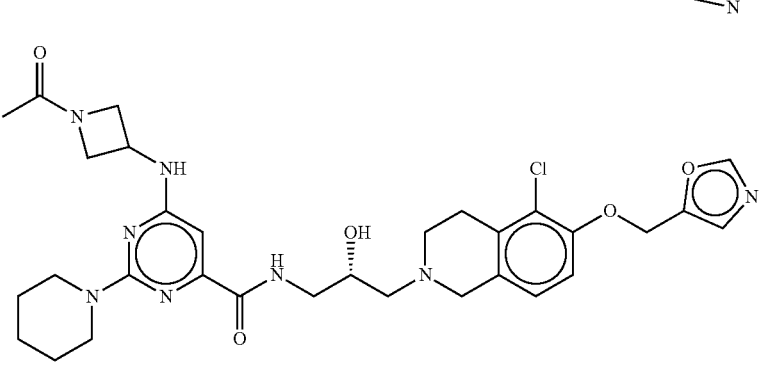 |
| 534 | 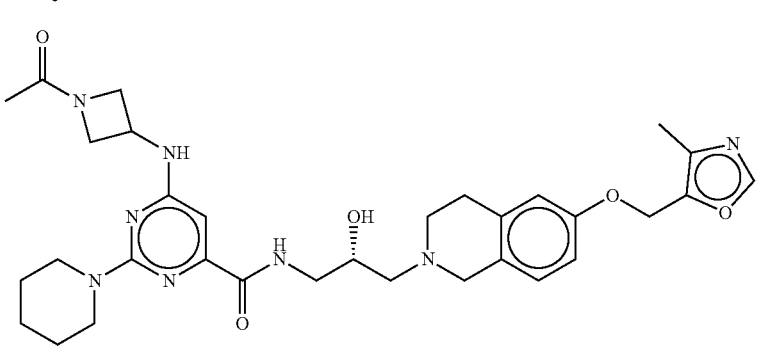 |

-continued
| Nr. | Structure |
|---|---|
| 535 | 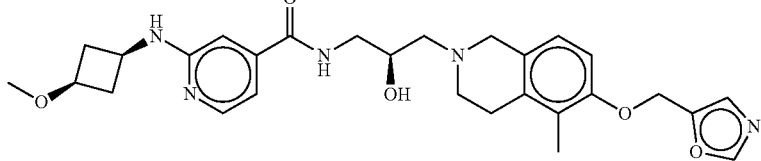 |
| 536 | 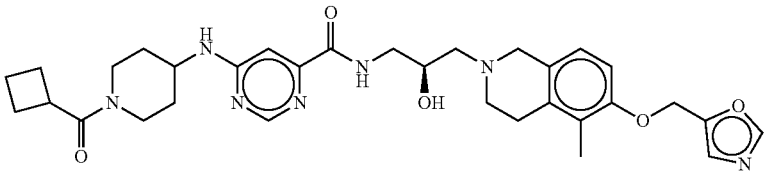 |
| 537 | 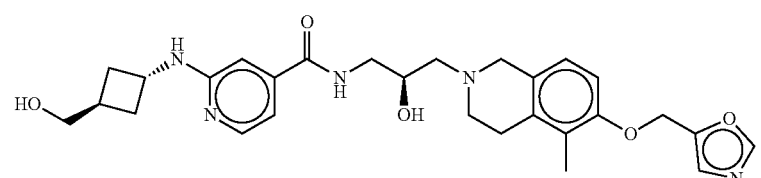 |
| 538 | 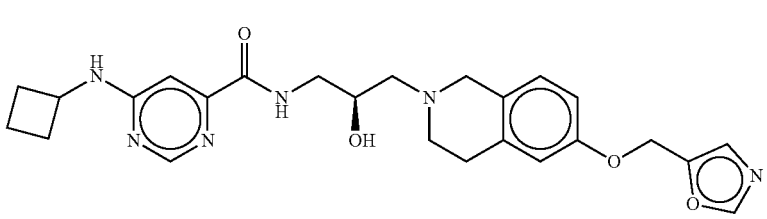 |
| 539 | 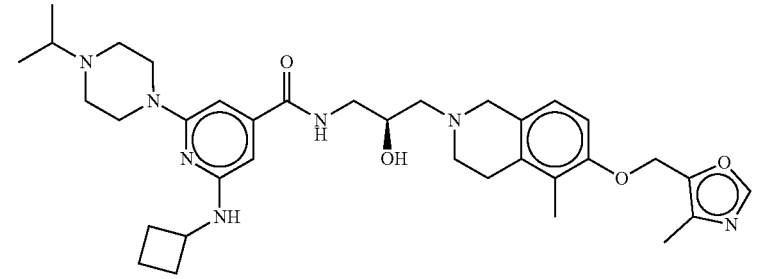 |
| 541 | 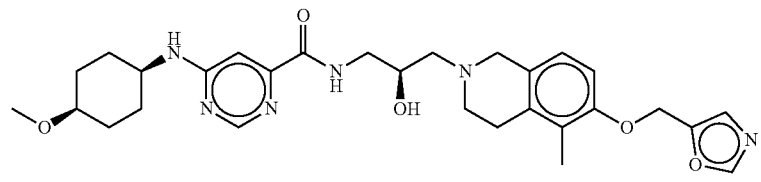 |
| 542 | 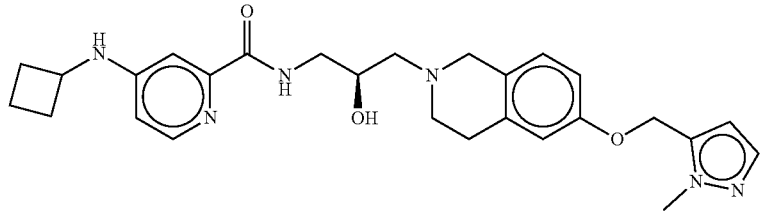 |

| Nr. | Structure |
|---|---|
| 543 | 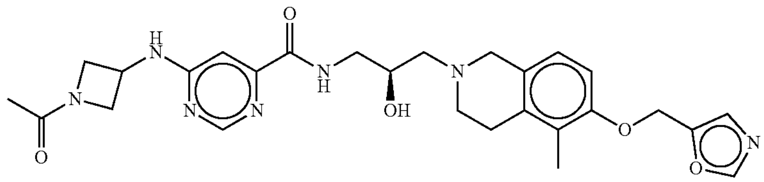 |
| 544 | 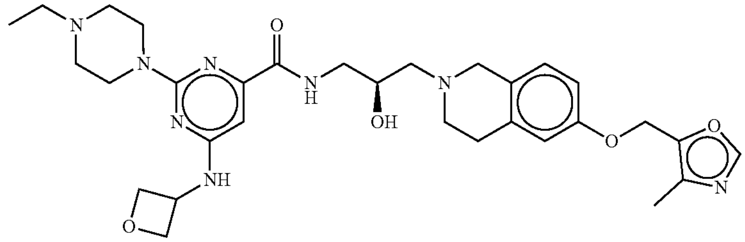 |
| 545 | 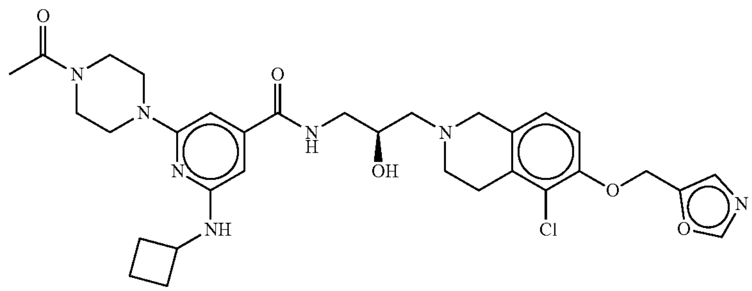 |
| 548 | 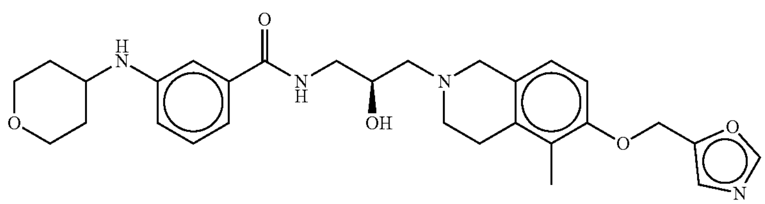 |
| 549 | 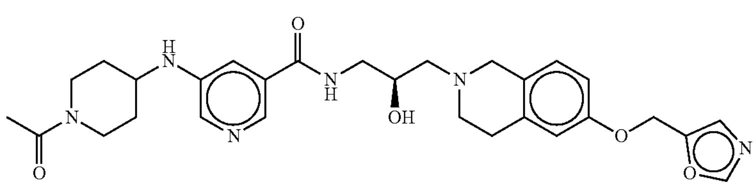 |
| 550 | 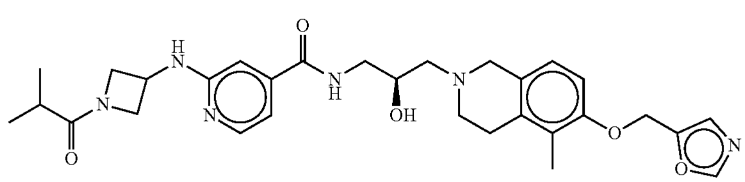 |
| 551 | 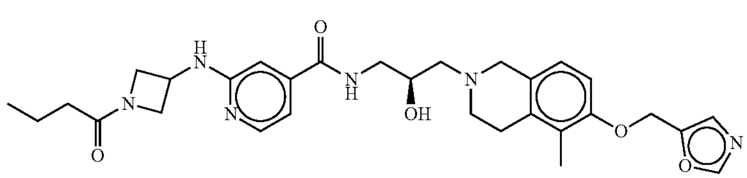 |

-continued

| Nr. | Structure |
|---|---|
| 552 | 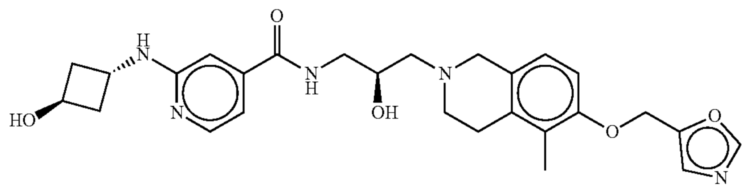 |
| 553 | 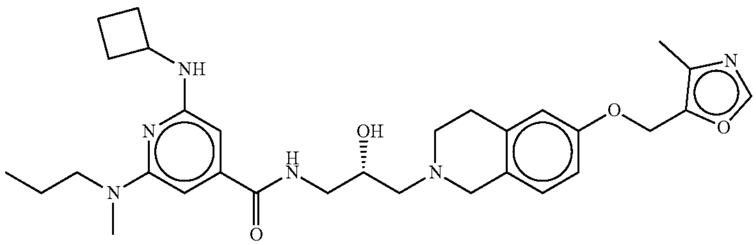 |
| 554 | 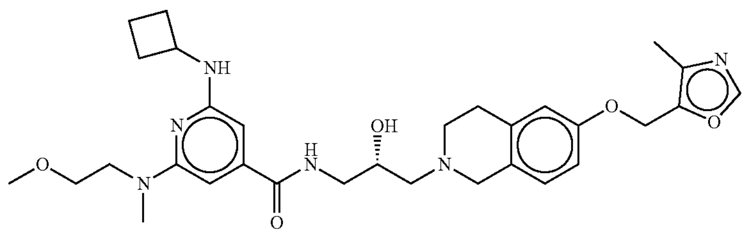 |
| 555 | 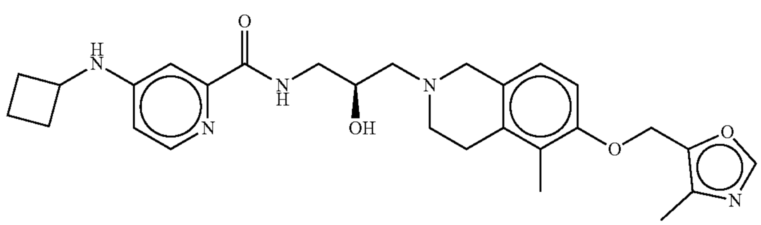 |
| 556 | 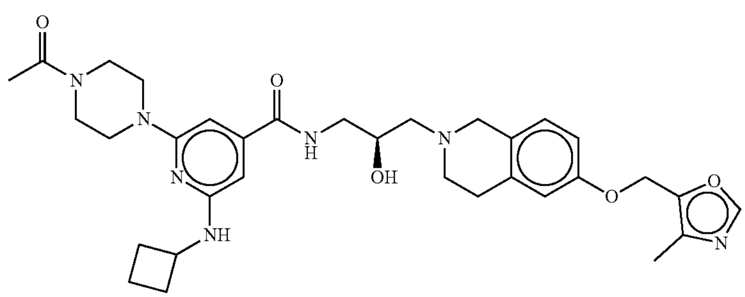 |
| 557 | 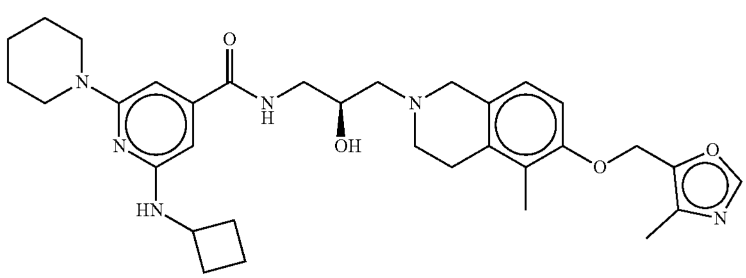 |

-continued
| Nr. | Structure |
|---|---|
| 558 | 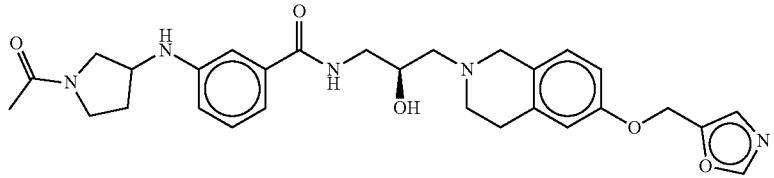 |
| 559 | 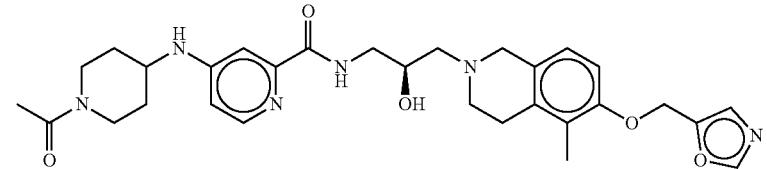 |
| 560 | 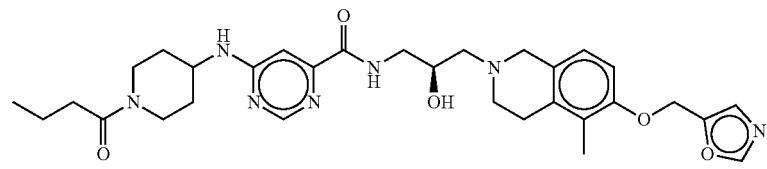 |
| 562 | 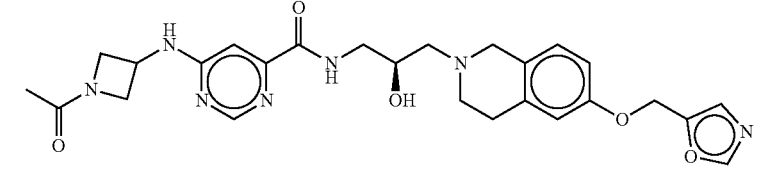 |
| 563 | 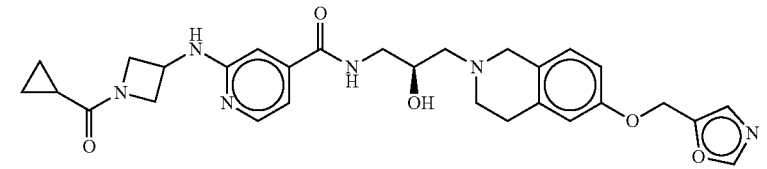 |
| 564 | 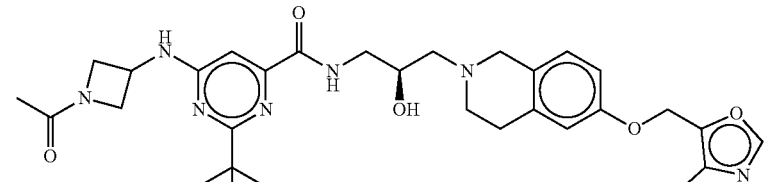 |
| 565 | 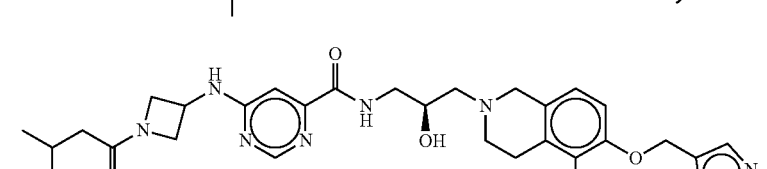 |
| 566 | 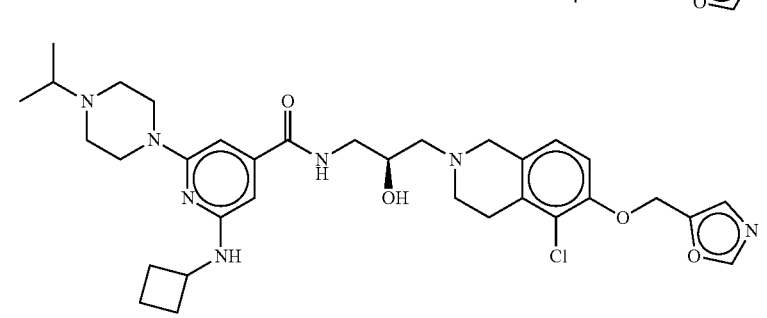 |

| Nr. | Structure |
|---|---|
| 567 | 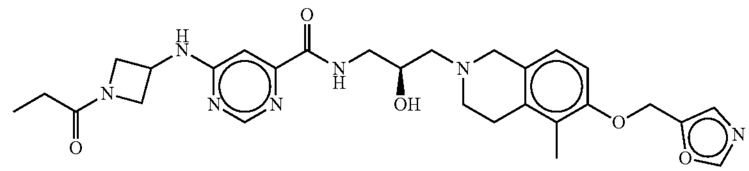 |
| 568 | 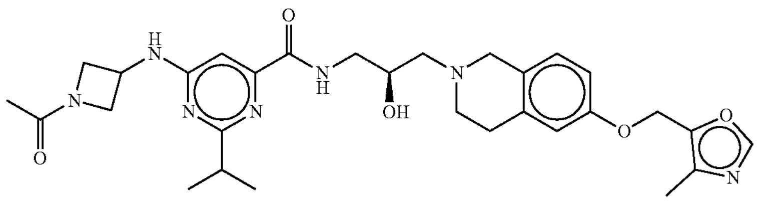 |
| 569 | 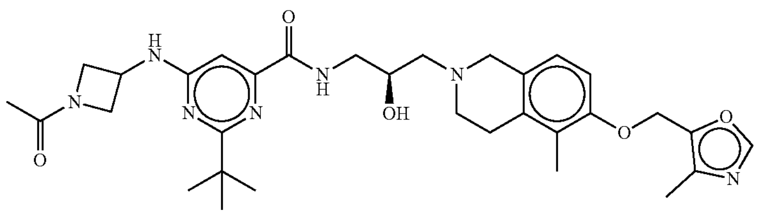 |
| 570 | 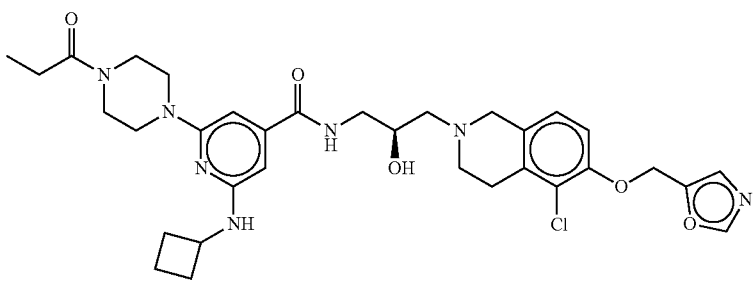 |
| 571 | 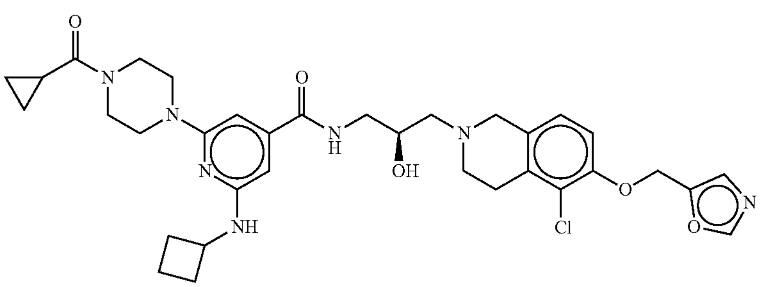 |
| 572 | 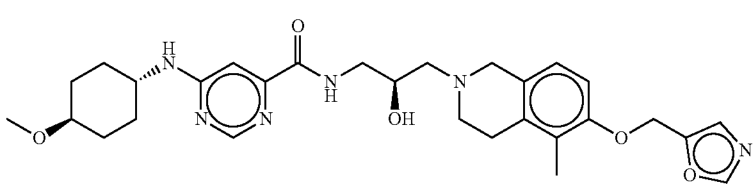 |
| 573 | 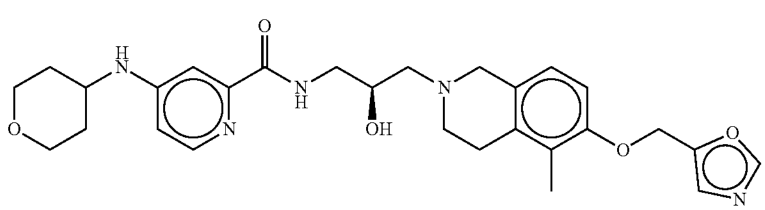 |

| Nr. | Structure |
|---|---|
| 574 | 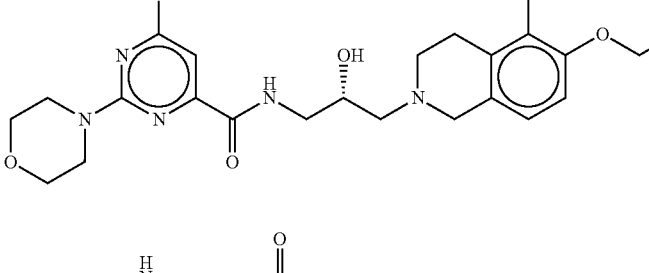 |
| 575 | 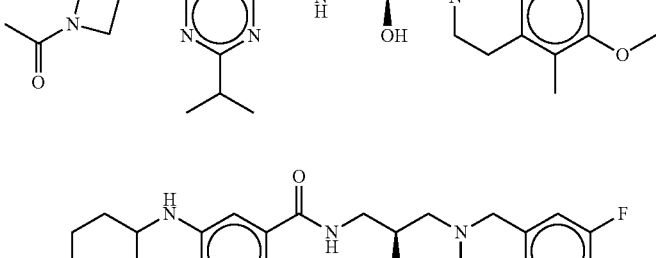 |
| 576 | 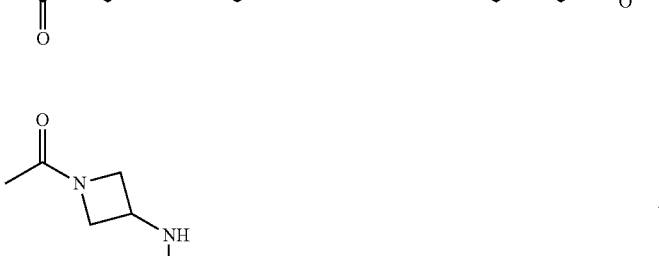 |
| 579 | 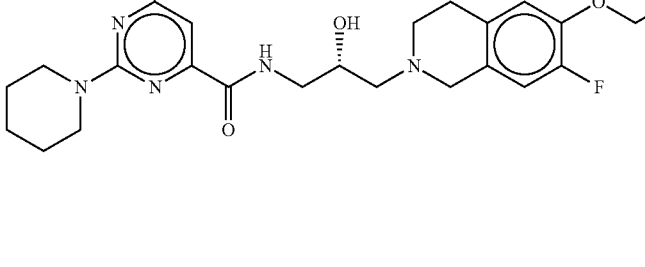 |
| 580 | 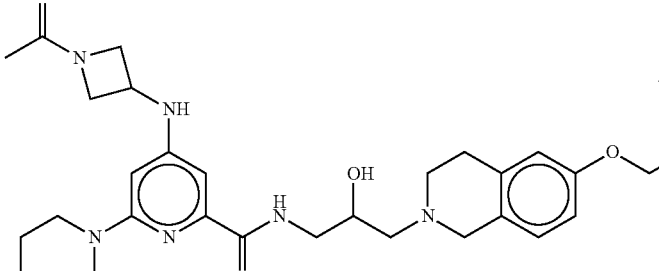 |

| Nr. | Structure |
|---|---|
| 581 | 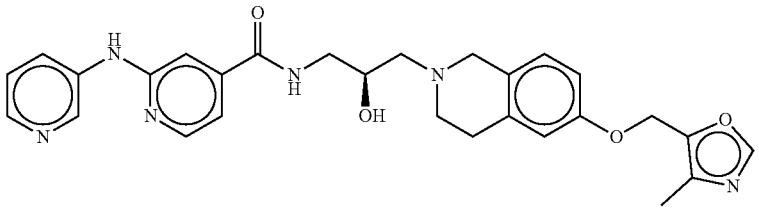 |
| 582 | 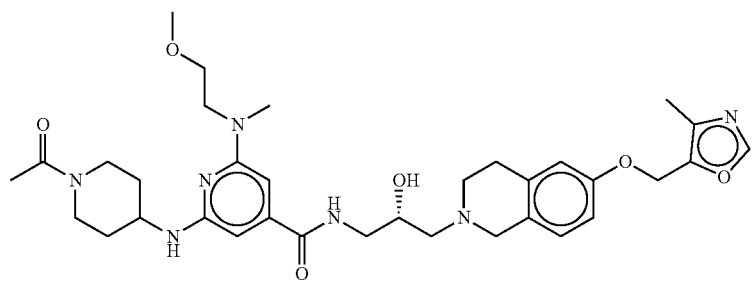 |
| 583 | 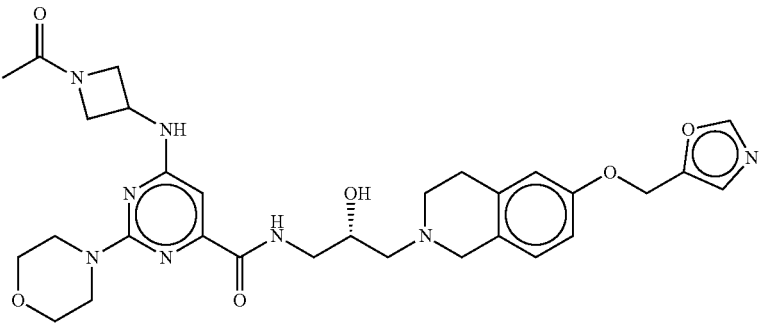 |
| 584 | 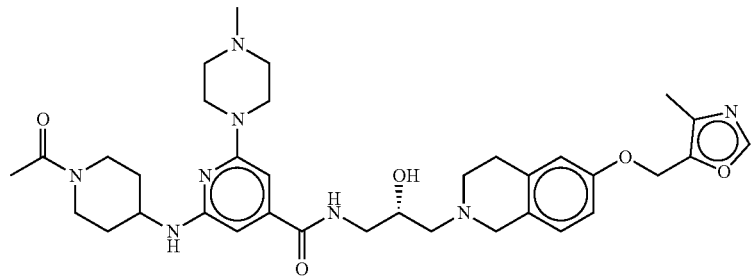 |
| 585 | 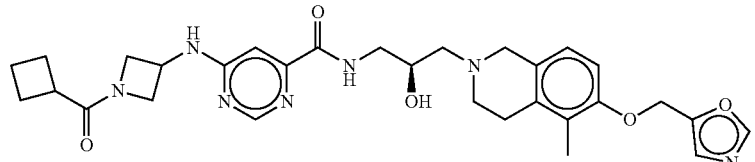 |
| 586 | 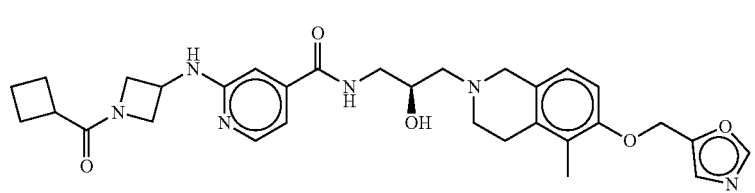 |

| Nr. | Structure |
|---|---|
| 587 | 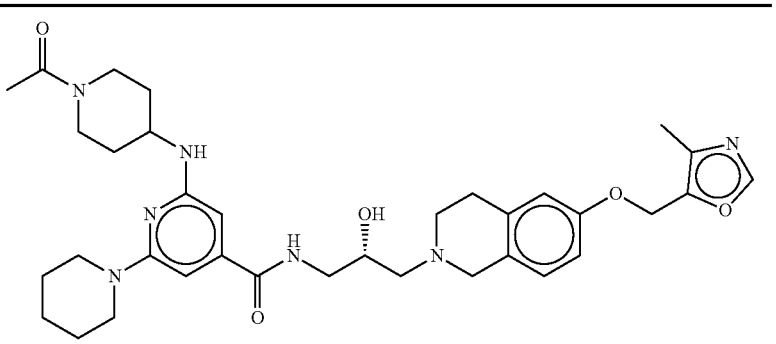 |
| 588 | 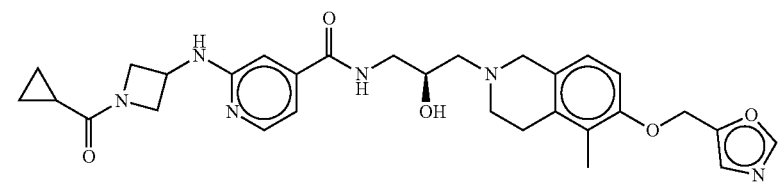 |
| 589 | 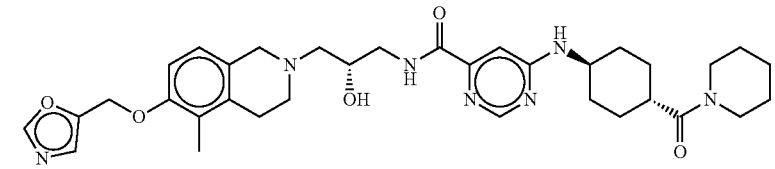 |
| 590 | 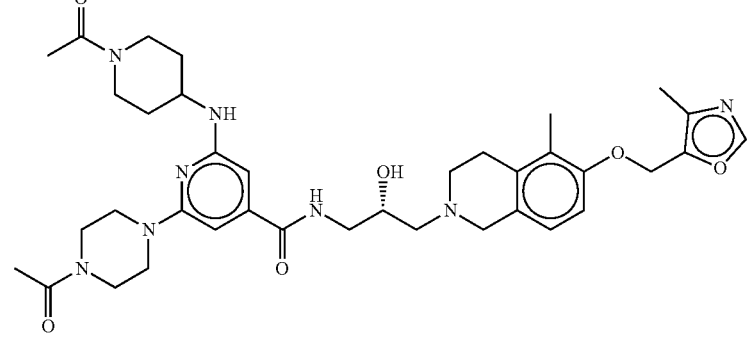 |
| 591 | 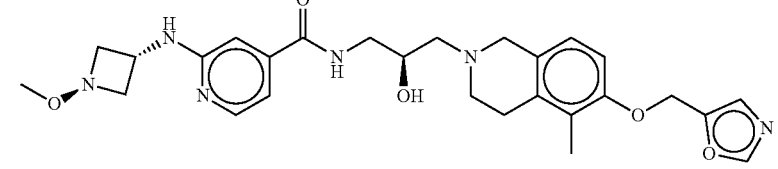 |
| 592 | 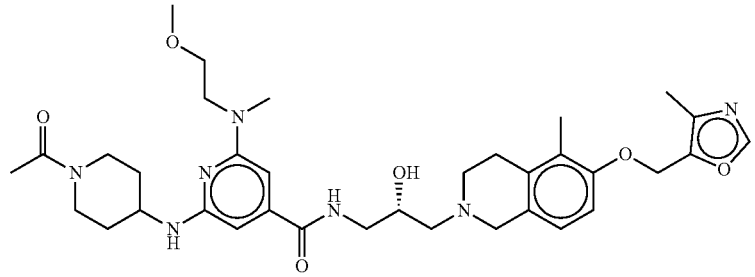 |

| Nr. | Structure |
| --- | --- |
| 593 | 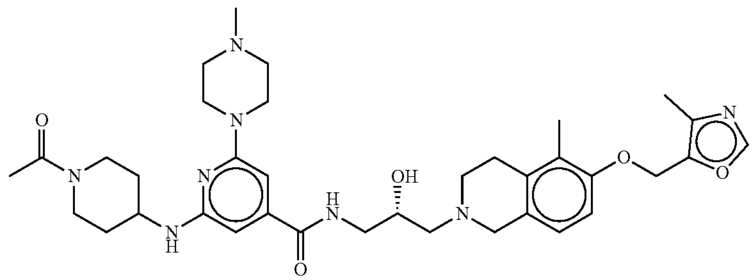 |
| 594 | 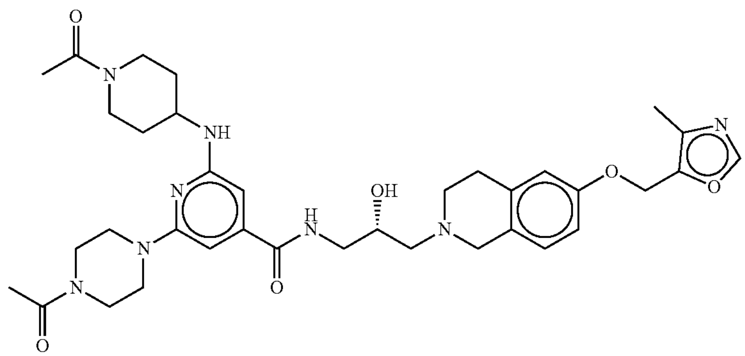 |
| 595 | 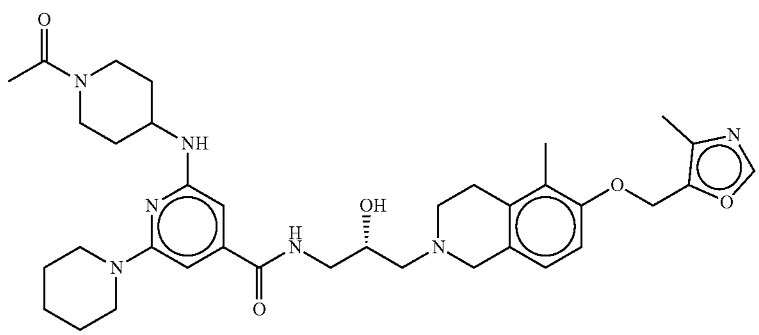 |
| 596 | 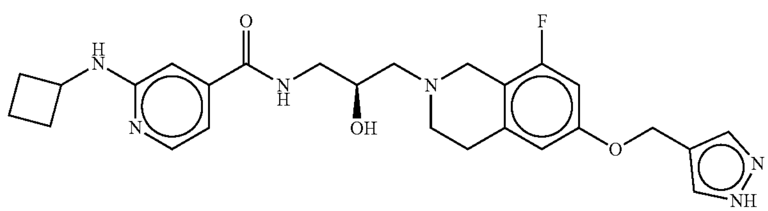 |
| 597 | 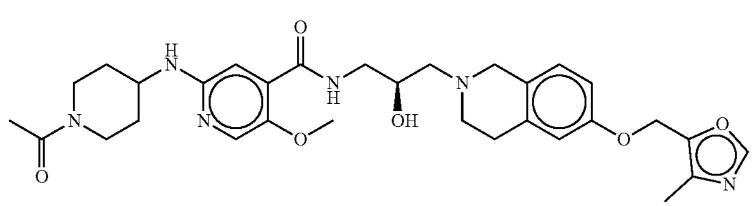 |

| Nr. | Structure |
|---|---|
| 598 | 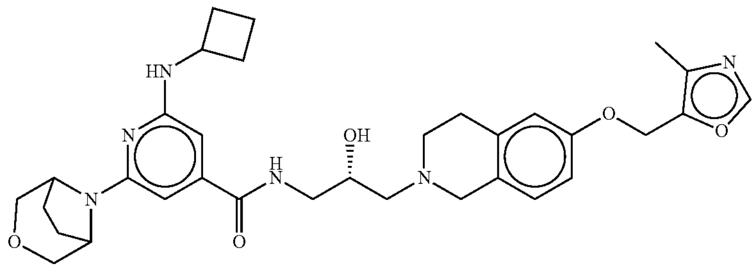 |
| 599 | 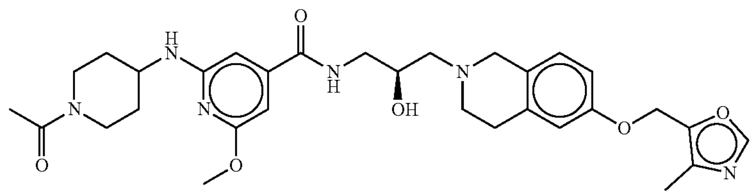 |
| 600 | 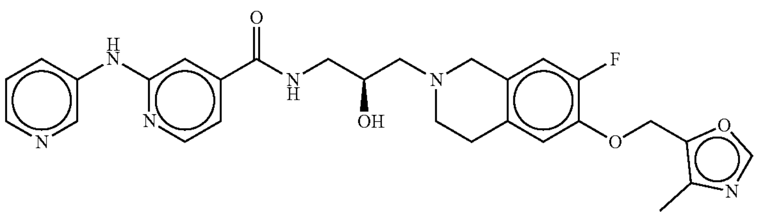 |
| 601 | 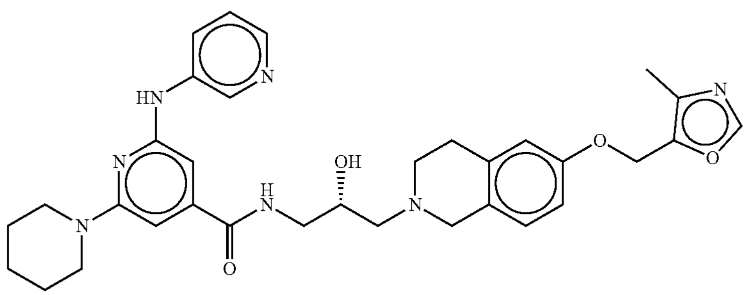 |
| 602 | 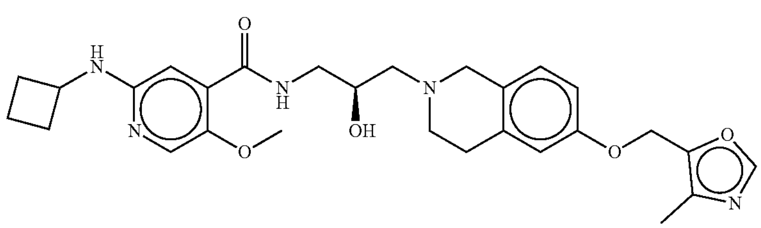 |
| 603 | 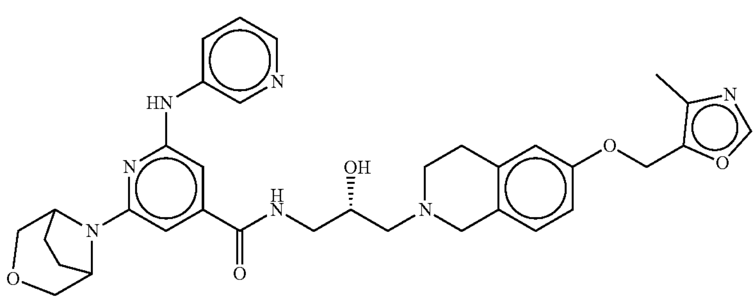 |

| Nr. | Structure |
|---|---|
| 604 | 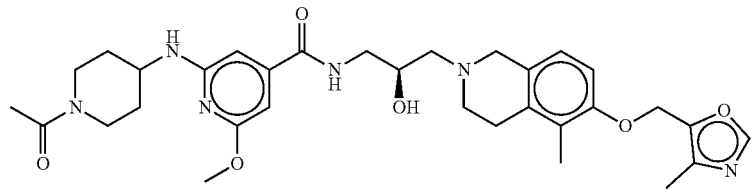 |
| 605 | 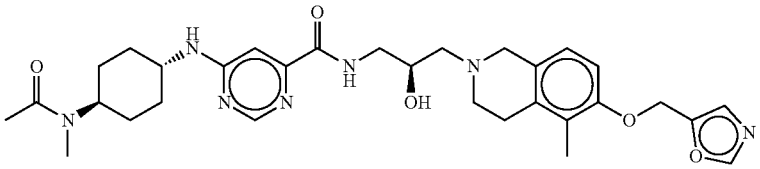 |
| 606 | 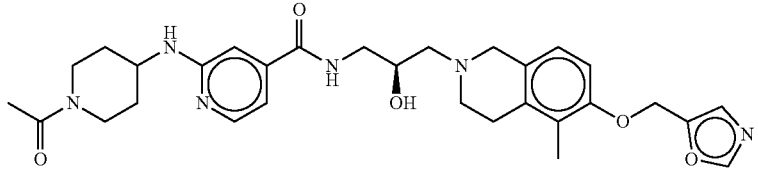 |
| 607 | 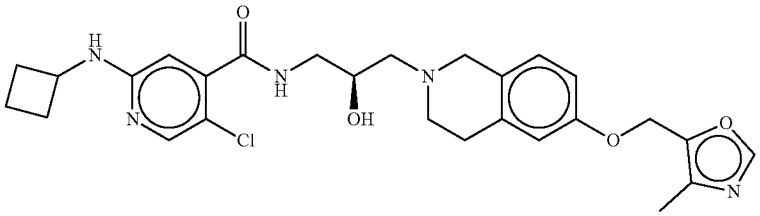 |
| 608 | 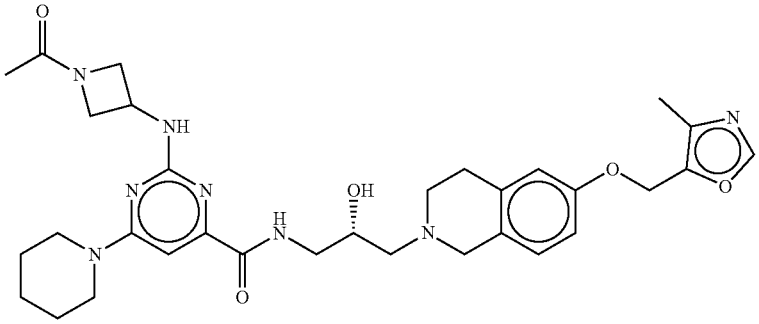 |
| 609 | 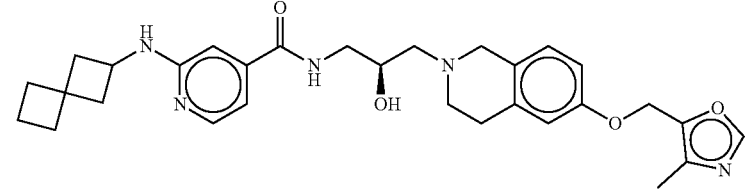 |

| Nr. | Structure |
|---|---|
| 610 | 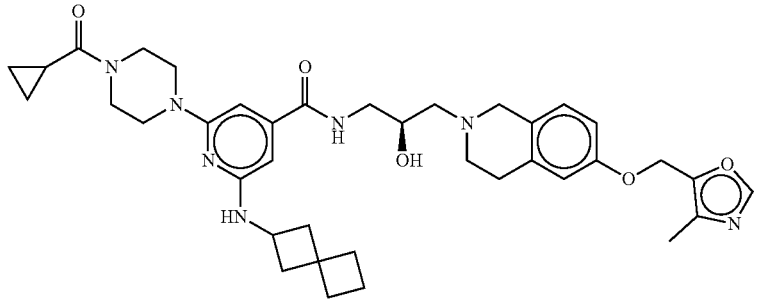 |
| 611 | 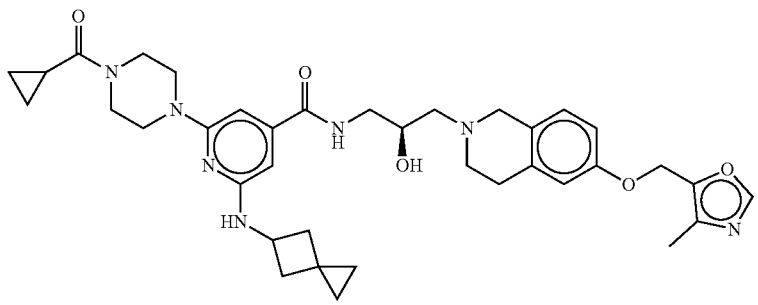 |
| 612 | 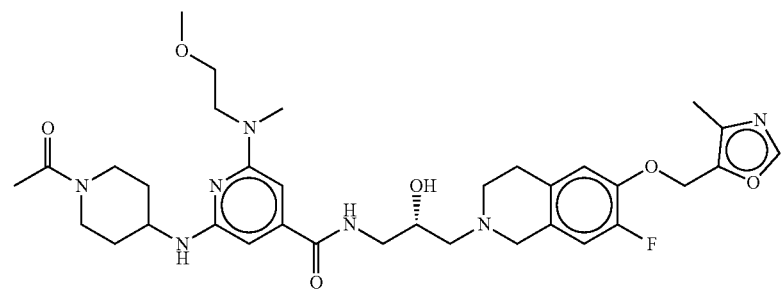 |
| 613 | 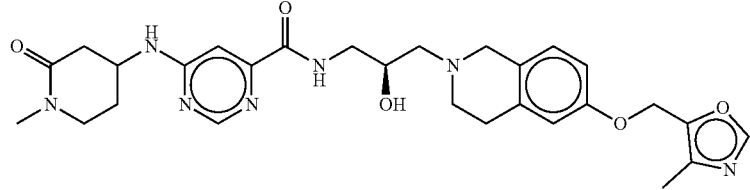 |
| 614 | 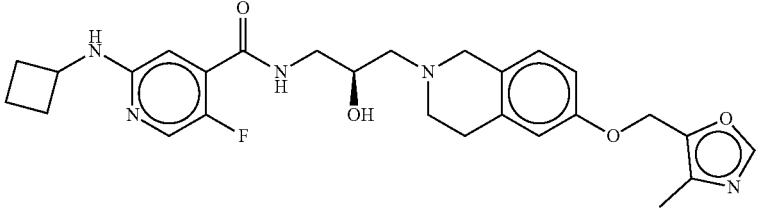 |

-continued
| Nr. | Structure |
|---|---|
| 615 | 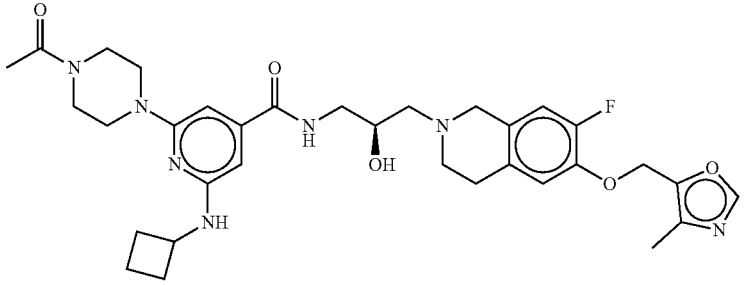 |
| 616 | 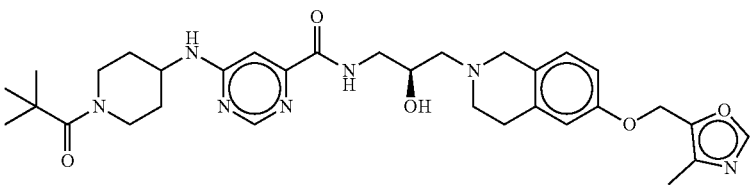 |
| 617 | 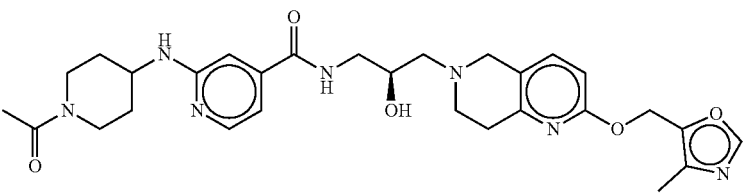 |
| 618 | 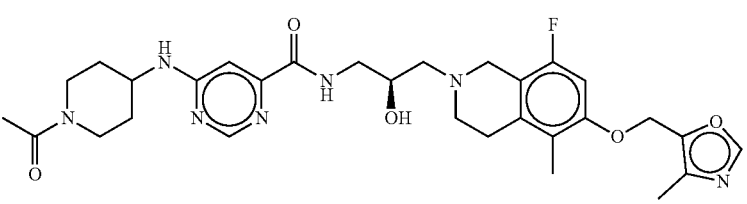 |
| 619 | 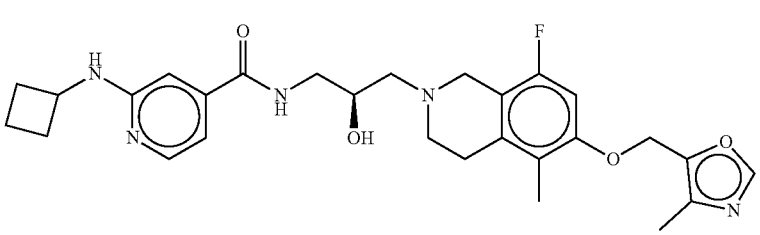 |
| 620 | 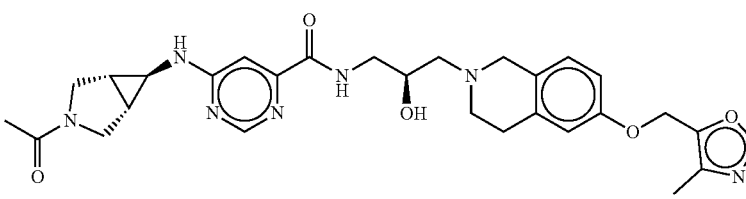 |
| 621 | 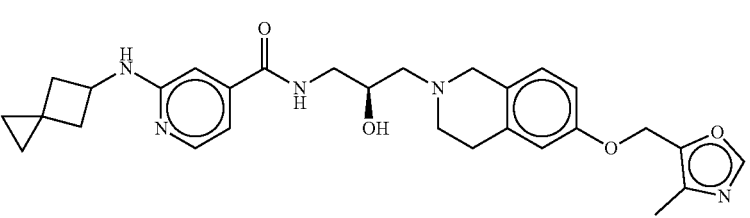 |

-continued

| Nr. | Structure |
|---|---|
| 622 | 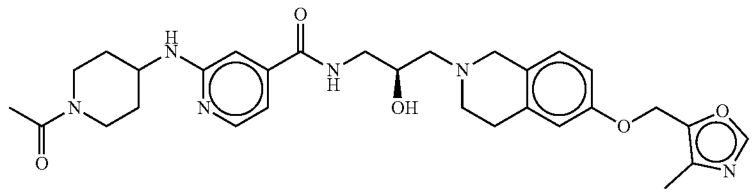 |
| 623 | 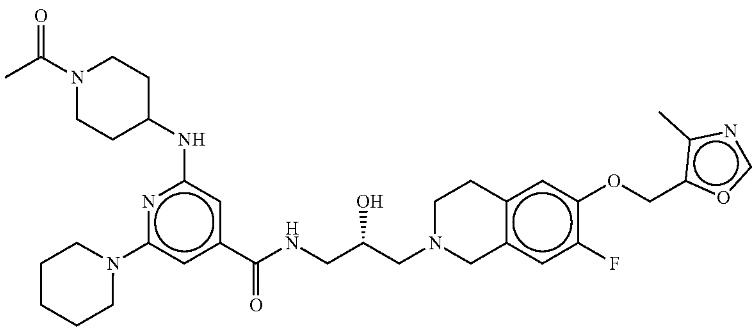 |
| 624 | 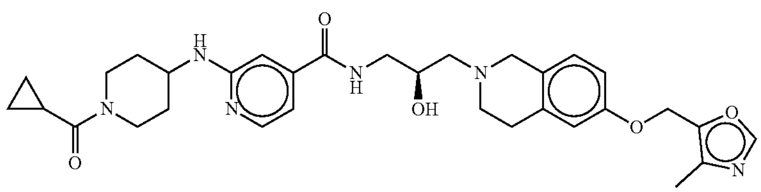 |
| 625 | 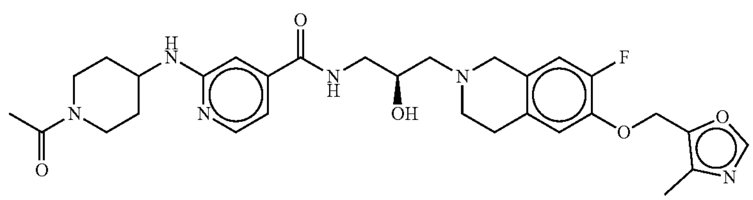 |
| 626 | 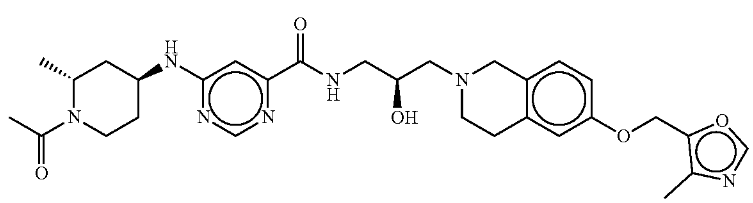 |
| 627 | 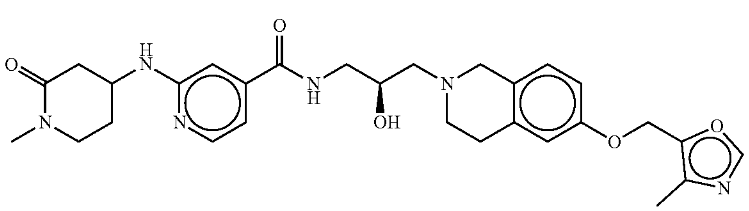 |
| 628 | 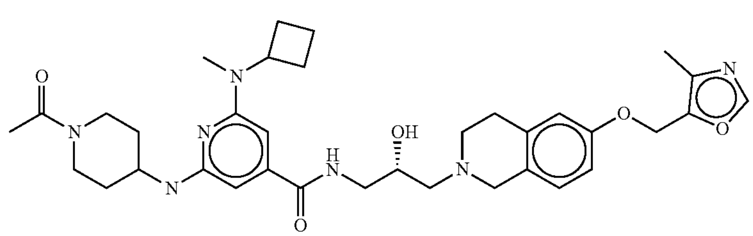 |

| Nr. | Structure |
|---|---|
| 629 | 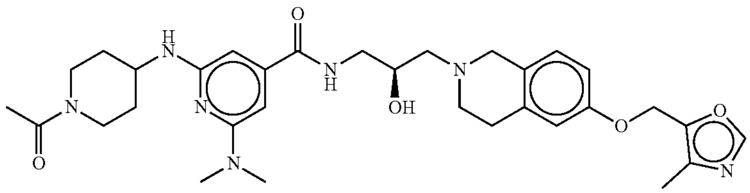 |
| 630 | 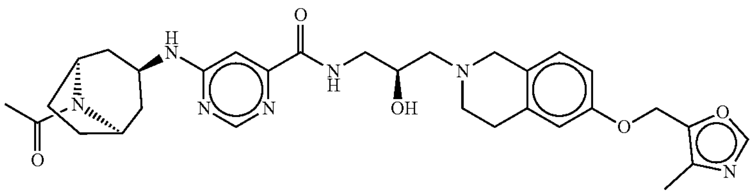 |
| 631 | 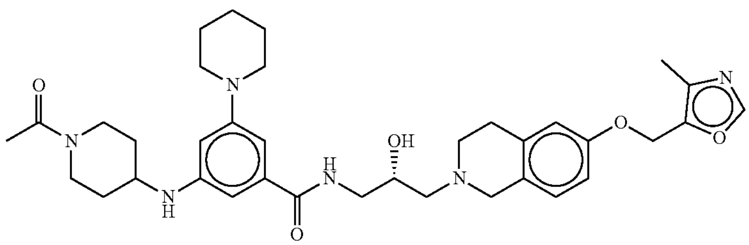 |
| 632 | 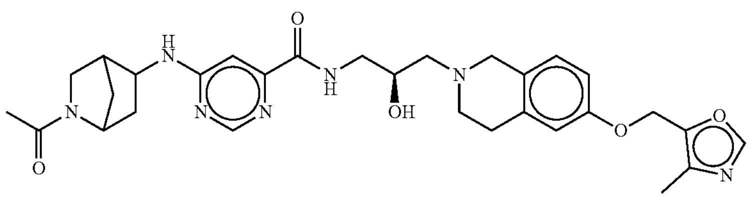 |
| 633 | 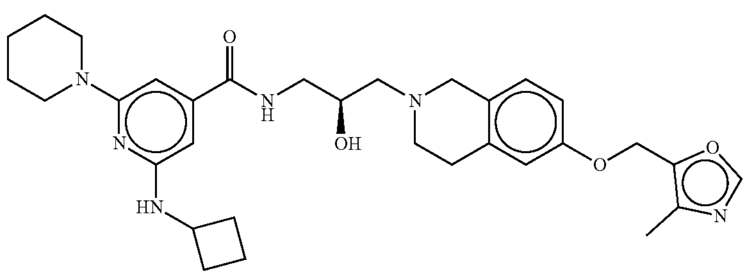 |
| 634 | 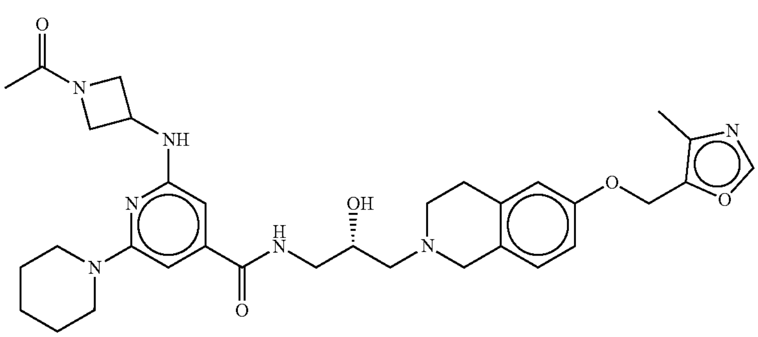 |

-continued

| Nr. | Structure |
|---|---|
| 635 | 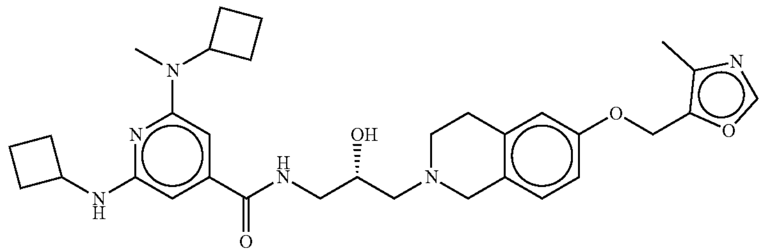 |
| 636 | 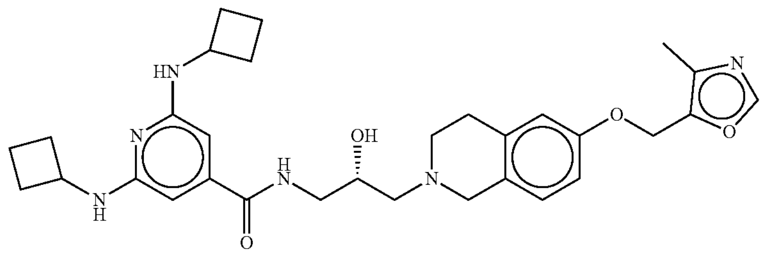 |
| 637 | 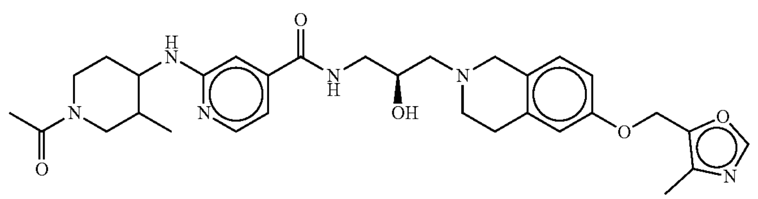 |
| 638 | 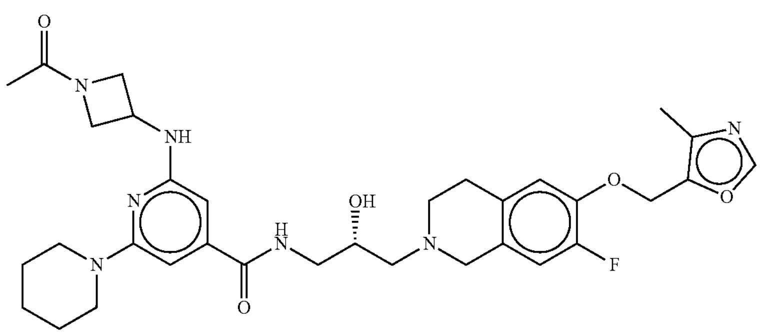 |
| 639 | 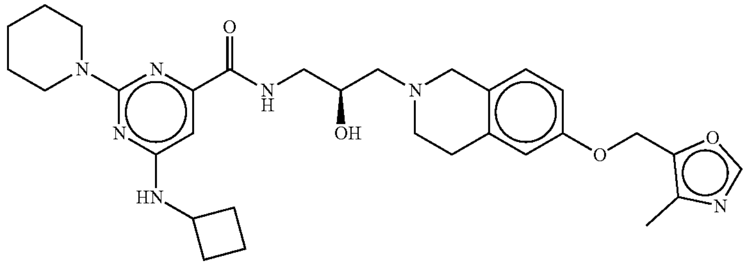 |
| 640 | 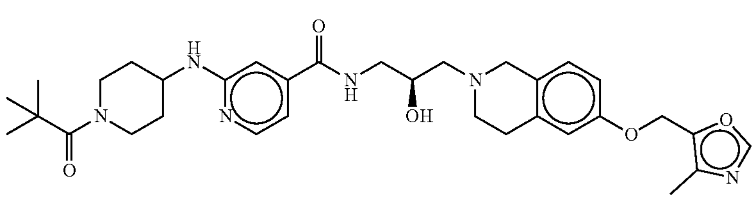 |

-continued
| Nr. | Structure |
|---|---|
| 641 | 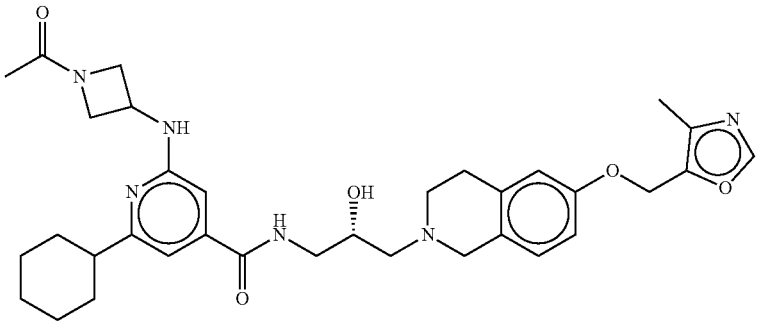 |
| 642 | 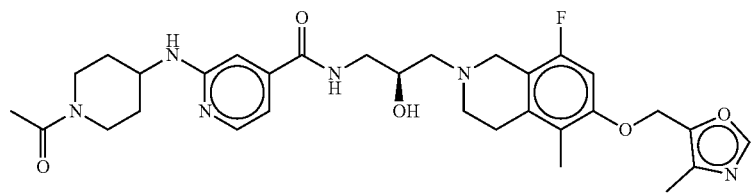 |
| 643 | 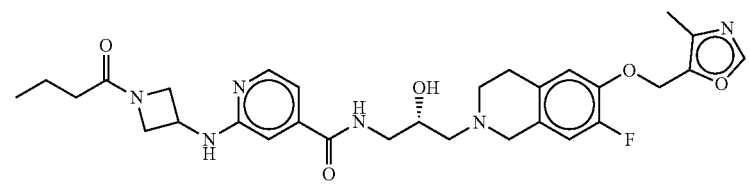 |
| 644 | 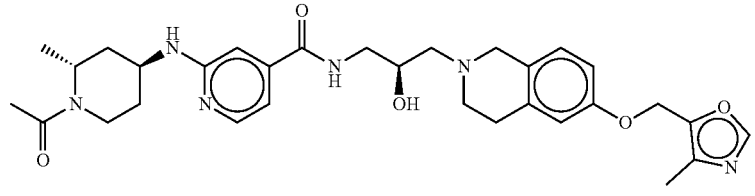 |
| 645 | 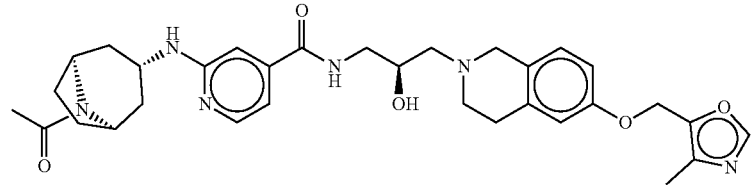 |
| 646 | 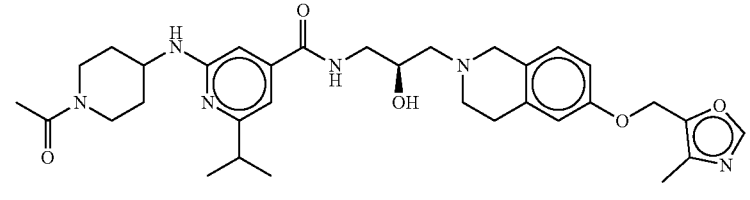 |

-continued

| Nr. | Structure |
|---|---|
| 647 | 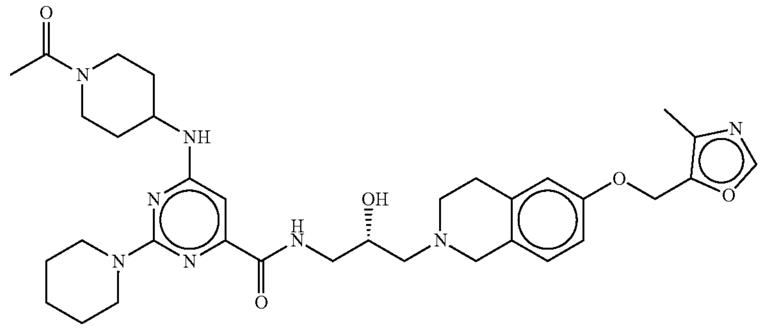 |
| 648** | 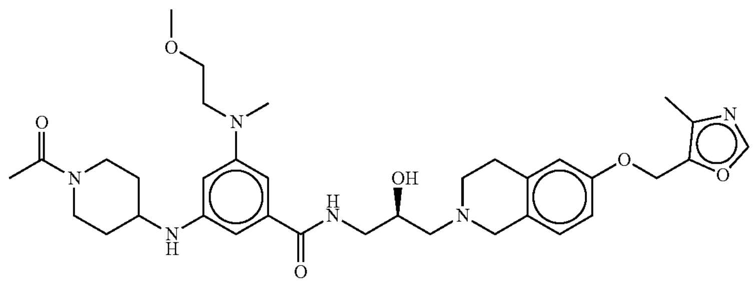 |
| 649** | 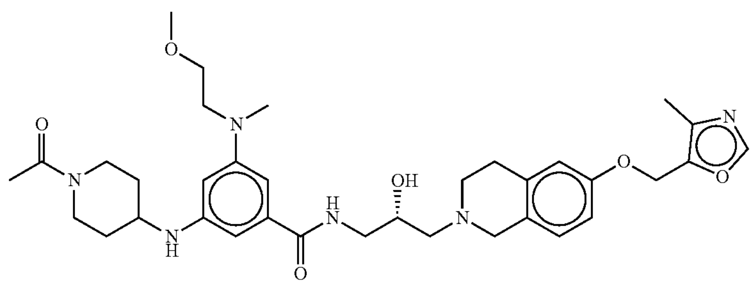 |
| 650 | 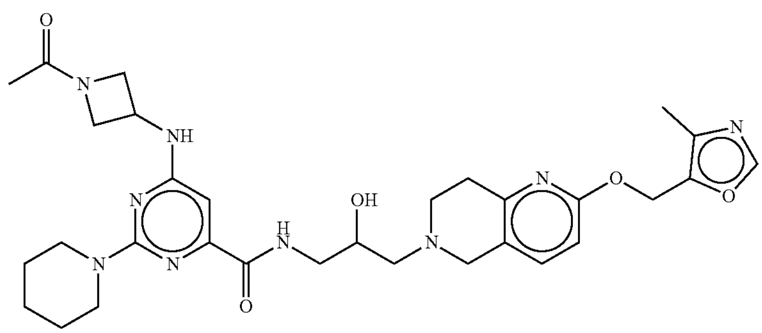 |
| 651 | 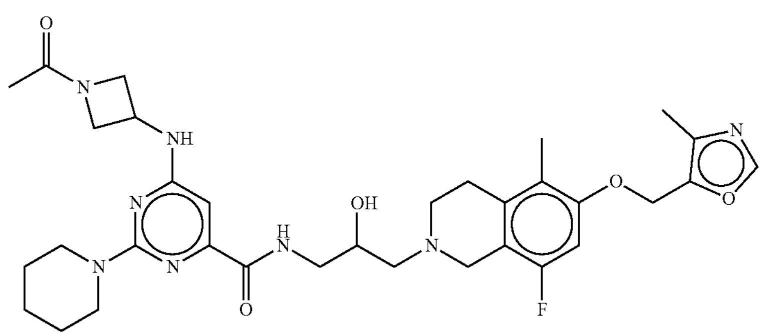 |

-continued

| Nr. | Structure |
|---|---|
| 652 | 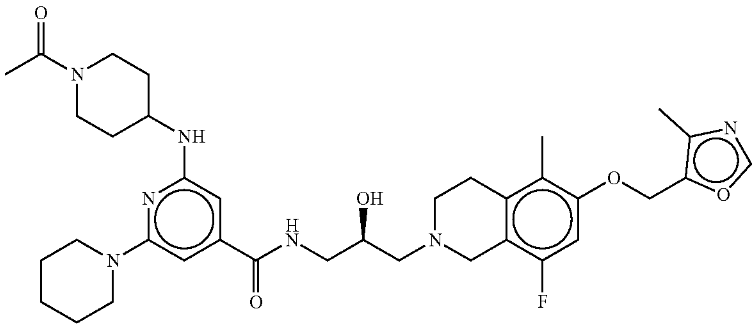 |
| 653 | and |
| 654 | 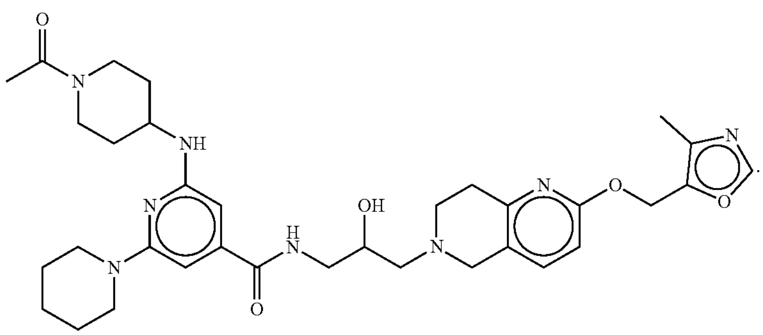 |

18. The method of claim 12 wherein the compound is selected form:

| Nr. | Structure |
|---|---|
| 291 | 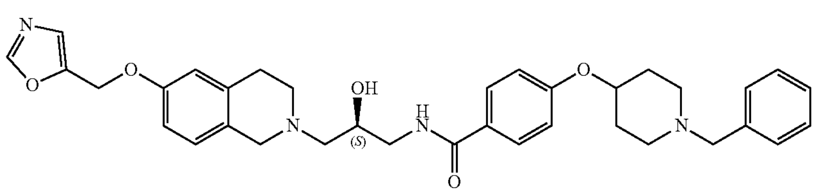 |
| 301 | 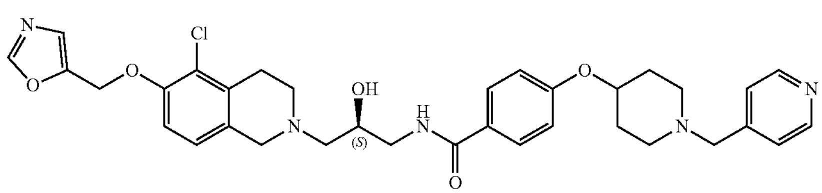 |

-continued
| Nr. | Structure |
|---|---|
| 328 | 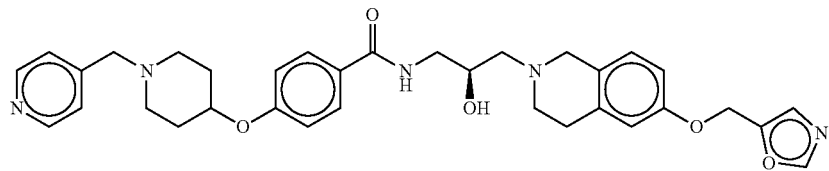 |
| 330 | 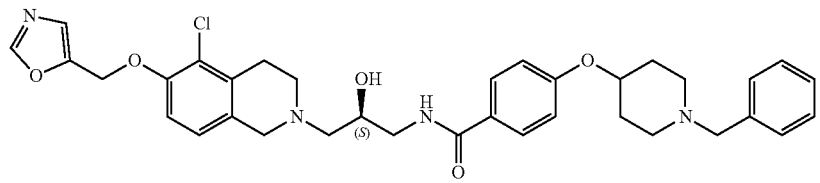 |
| 392 | 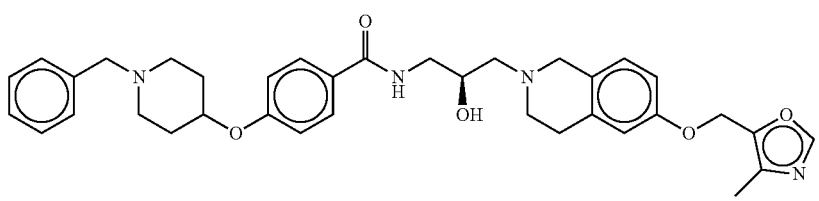 |
| 416 | 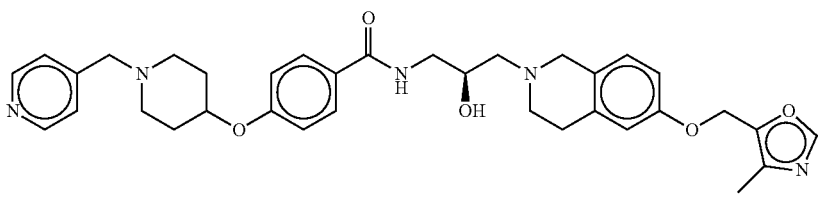 |
| 440 | 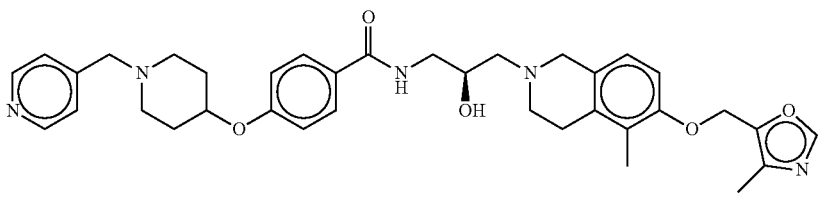 |
| 475 | 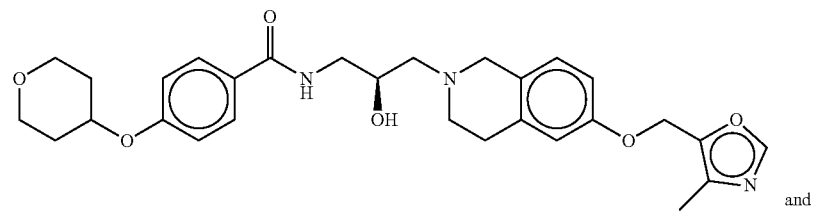 and |
| 482 | 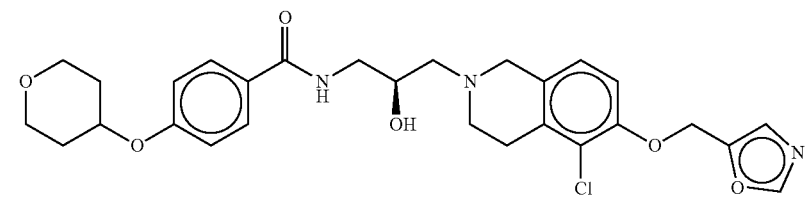 |

19. A method of claim 11 wherein the compound is selected from:

| Nr. | Structure |
| --- | --- |
| 493 | 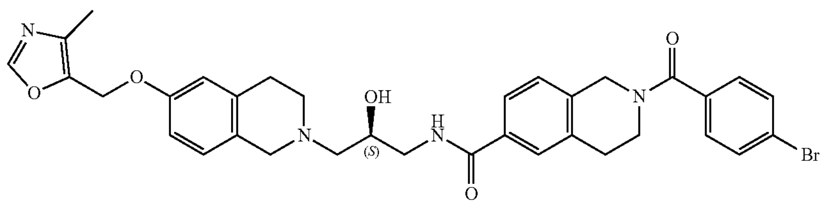 |
| 498 | 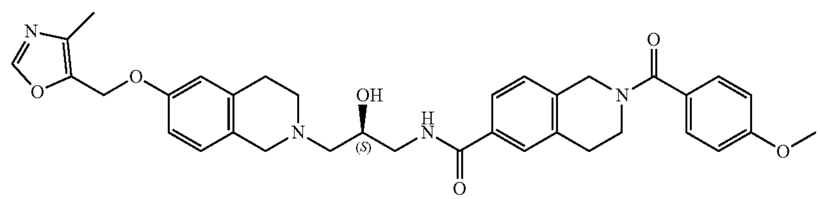 |
| 530 | 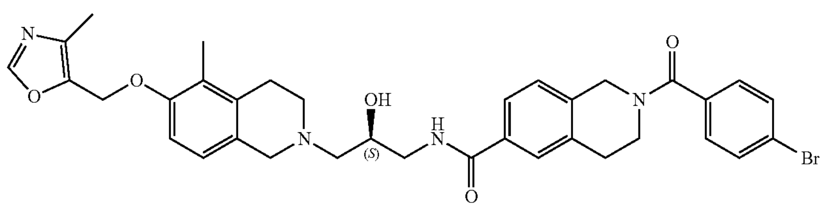 |
| 533 | 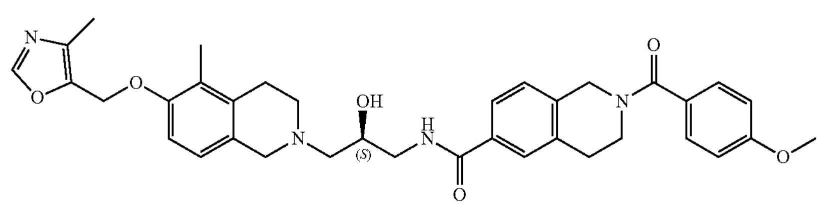 |
| 540 | 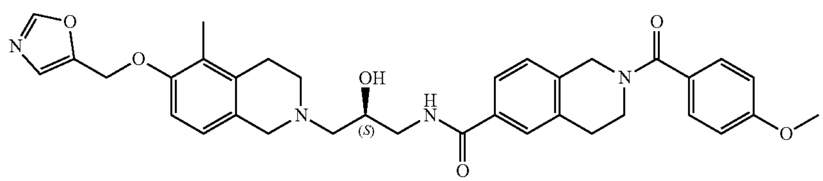 |
| 546 | 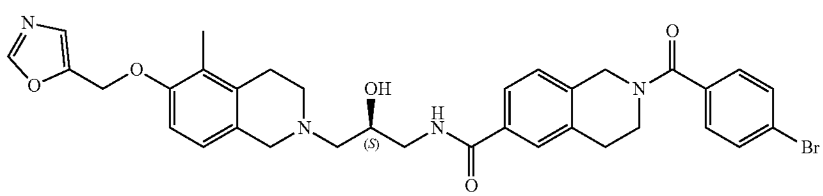 |
| 547 | 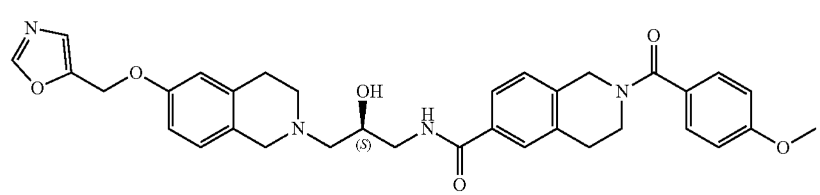 |

| Nr. | Structure |
|---|---|
| 561 | [chemical structure] |
| 577 | [chemical structure] and |
| 578 | [chemical structure] |

20. The method of claim 1 wherein the cancer is glioblastoma, malignant peripheral nerve sheath tumors (MPNST), esophageal squamous cell carcinoma, esophageal adenocarcinoma, bladder urothelial carcinoma, pancreatic cancer pancreatic adenocarcinoma, mesothelioma, melanoma, lung squamous cancer, lung adenocarcinoma, astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, kidney cancer, breast cancer, endometrium cancer, urinary tract cancer, liver cancer, soft tissue cancer, pleura cancer or large intestine cancer.

* * * * *